United States Patent
Marx et al.

(10) Patent No.: US 11,548,888 B2
(45) Date of Patent: Jan. 10, 2023

(54) KRAS G12C INHIBITORS

(71) Applicants: Mirati Therapeutics, Inc., San Diego, CA (US); Array BioPharma, Inc., Boulder, CO (US)

(72) Inventors: Matthew Arnold Marx, San Diego, CA (US); James Gail Christensen, San Diego, CA (US); Christopher Ronald Smith, San Diego, CA (US); John P Fischer, Boulder, CO (US); Aaron Craig Burns, San Diego, CA (US)

(73) Assignees: Mirati Therapeutics, Inc., San Diego, CA (US); Array BioPharma Inc., Boulder, CO (US)

(*) Notice: Subject to any disclaimer, the term of this patent is extended or adjusted under 35 U.S.C. 154(b) by 0 days.

(21) Appl. No.: 16/917,128

(22) Filed: Jun. 30, 2020

(65) Prior Publication Data

US 2020/0331911 A1  Oct. 22, 2020

Related U.S. Application Data

(63) Continuation-in-part of application No. PCT/US2020/012906, filed on Jan. 9, 2020.

(60) Provisional application No. 62/790,757, filed on Jan. 10, 2019.

(51) Int. Cl.
*C07D 471/04* (2006.01)
*C07D 519/00* (2006.01)
*A61P 35/00* (2006.01)

(52) U.S. Cl.
CPC ............ *C07D 471/04* (2013.01); *A61P 35/00* (2018.01); *C07D 519/00* (2013.01)

(58) Field of Classification Search
CPC ...... C07D 471/04; C07D 519/00; A61P 35/00
See application file for complete search history.

(56) References Cited

U.S. PATENT DOCUMENTS

| | | | |
|---|---|---|---|
| 8,163,763 B2 | 4/2012 | Bergeron et al. |
| 8,426,401 B2 | 4/2013 | Bian et al. |
| 9,562,019 B2 | 2/2017 | Djaballah et al. |
| 9,840,516 B2 | 12/2017 | Li et al. |
| 10,125,134 B2 | 11/2018 | Blake et al. |
| 2003/0191143 A1 | 10/2003 | Pitts et al. |
| 2010/0081654 A1 | 4/2010 | Stockwell et al. |
| 2011/0269244 A1 | 11/2011 | Petter et al. |
| 2013/0029978 A1 | 1/2013 | Kamino et al. |
| 2014/0288045 A1 | 9/2014 | Ren et al. |
| 2015/0175558 A1 | 6/2015 | Stockwell et al. |
| 2015/0239900 A1 | 8/2015 | Li et al. |
| 2016/0031898 A1 | 2/2016 | Ren et al. |
| 2016/0108019 A1 | 4/2016 | Li et al. |
| 2016/0166571 A1 | 6/2016 | Janes et al. |
| 2016/0229836 A1 | 8/2016 | Stockwell et al. |
| 2016/0264627 A1 | 9/2016 | Henning et al. |
| 2016/0297774 A1 | 10/2016 | Li et al. |
| 2017/0022184 A1 | 1/2017 | Li et al. |
| 2017/0115303 A1 | 4/2017 | Cravatt et al. |
| 2017/0190672 A1 | 7/2017 | Mani et al. |
| 2017/0197945 A1 | 7/2017 | Li et al. |
| 2018/0015087 A1 | 1/2018 | Liu et al. |
| 2018/0118757 A1 | 5/2018 | Li et al. |
| 2018/0118761 A1 | 5/2018 | Sebti et al. |
| 2018/0127396 A1 | 5/2018 | Li et al. |
| 2018/0141927 A1 | 5/2018 | Li et al. |
| 2018/0155348 A1 | 6/2018 | Li et al. |
| 2018/0162812 A1 | 6/2018 | Ren et al. |
| 2018/0177767 A1 | 6/2018 | Lanman et al. |
| 2018/0194748 A1 | 7/2018 | Li et al. |
| 2018/0201610 A1 | 7/2018 | Tao et al. |
| 2018/0273515 A1 | 9/2018 | Li et al. |
| 2018/0273523 A1 | 9/2018 | Li et al. |
| 2018/0273577 A1 | 9/2018 | Revenko et al. |
| 2018/0282307 A1 | 10/2018 | Li et al. |
| 2018/0282308 A1 | 10/2018 | Li et al. |
| 2018/0289683 A1 | 10/2018 | McCormick et al. |
| 2020/0262837 A1 | 8/2020 | Marx et al. |
| 2020/0399297 A1 | 12/2020 | Campbell et al. |

FOREIGN PATENT DOCUMENTS

| | | |
|---|---|---|
| WO | 02/053558 A1 | 7/2002 |
| WO | 02/087513 A2 | 11/2002 |
| WO | 2007/146122 A2 | 12/2007 |
| WO | 2008/009078 A2 | 1/2008 |
| WO | 2009/047255 A1 | 4/2009 |
| WO | 2010/014939 A1 | 2/2010 |
| WO | 2010/120996 A1 | 10/2010 |
| WO | 2013/155223 A1 | 10/2013 |
| WO | 2014/143659 A1 | 9/2014 |
| WO | 2014/152588 A1 | 9/2014 |
| WO | 2016/049568 A1 | 3/2015 |
| WO | 2015/054572 A1 | 4/2015 |
| WO | 2016/025650 A1 | 2/2016 |
| WO | 2016/044772 A1 | 3/2016 |
| WO | 2016/049565 A1 | 3/2016 |
| WO | 2016/164675 A1 | 10/2016 |
| WO | 2016/168540 A1 | 10/2016 |
| WO | 2017/058728 A1 | 4/2017 |
| WO | 2017/058768 A1 | 4/2017 |
| WO | 2017/058792 A1 | 4/2017 |
| WO | 2017/058805 A1 | 4/2017 |
| WO | 2017/058807 A1 | 4/2017 |
| WO | 2017/058902 A1 | 4/2017 |
| WO | 2017/058915 A1 | 4/2017 |
| WO | 2017/070256 A2 | 4/2017 |

(Continued)

OTHER PUBLICATIONS

Downward, J., "Targeting RAS signalling pathways in cancer therapy." Nature Reviews Cancer 3.1 (2003): 11-22.*

(Continued)

*Primary Examiner* — John M Mauro
(74) *Attorney, Agent, or Firm* — Wood, Phillips, Katz, Clark & Mortimer

(57) ABSTRACT

The present invention relates to compounds that inhibit KRas G12C. In particular, the present invention relates to compounds that irreversibly inhibit the activity of KRas G12C, pharmaceutical compositions comprising the compounds and methods of use therefor.

9 Claims, No Drawings

(56) References Cited

FOREIGN PATENT DOCUMENTS

| | | |
|---|---|---|
| WO | 2017/079864 A1 | 5/2017 |
| WO | 2017/080980 A1 | 5/2017 |
| WO | 2017/087528 A1 | 5/2017 |
| WO | 2017/100546 A1 | 6/2017 |
| WO | 2018/064510 A1 | 4/2018 |
| WO | 2018/068017 A1 | 4/2018 |
| WO | 2018/102452 A2 | 6/2018 |
| WO | 2018/102453 A1 | 6/2018 |
| WO | 2018/112420 A1 | 6/2018 |
| WO | 2018/115380 A1 | 6/2018 |
| WO | 2018/119183 A2 | 6/2018 |
| WO | 2018/140512 A1 | 8/2018 |
| WO | 2018/140513 A1 | 8/2018 |
| WO | 2018/140514 A1 | 8/2018 |
| WO | 2018/140598 A1 | 8/2018 |
| WO | 2018/140599 A1 | 8/2018 |
| WO | 2018/140600 A1 | 8/2018 |
| WO | 2018/143315 A1 | 8/2018 |
| WO | 2018/195439 A2 | 10/2018 |
| WO | 2019/051291 A1 | 3/2019 |
| WO | 202063594 | 4/2020 |
| WO | 202098488 | 5/2020 |
| WO | 202027202 | 8/2020 |
| WO | 2020163598 | 8/2020 |
| WO | 2020165670 | 8/2020 |
| WO | 2020169838 | 8/2020 |
| WO | 2020171499 | 8/2020 |
| WO | 2020172332 | 8/2020 |
| WO | 2020176693 | 9/2020 |
| WO | 2020176963 | 9/2020 |
| WO | 2020177629 | 9/2020 |
| WO | 2020178282 | 9/2020 |
| WO | 2020181142 | 9/2020 |
| WO | 2020198125 | 10/2020 |
| WO | 2020204359 | 10/2020 |
| WO | 2020205473 | 10/2020 |
| WO | 2020205486 | 10/2020 |
| WO | 2020212895 | 10/2020 |
| WO | 2020214537 | 10/2020 |
| WO | 2020221239 | 11/2020 |
| WO | 2020230028 | 11/2020 |
| WO | 2020230091 | 11/2020 |
| WO | 2020231806 | 11/2020 |
| WO | 2020231808 | 11/2020 |
| WO | 2020232130 | 11/2020 |
| WO | 2020233592 | 11/2020 |
| WO | 2020234103 | 11/2020 |
| WO | 2020236940 | 11/2020 |
| WO | 2020236947 | 11/2020 |
| WO | 2020236948 | 11/2020 |
| WO | 2020247914 | 12/2020 |
| WO | 2020252336 | 12/2020 |
| WO | 2020252353 | 12/2020 |
| WO | 2021000885 | 1/2021 |
| WO | 2021023154 | 2/2021 |
| WO | 2021023247 | 2/2021 |
| WO | 2021027911 | 2/2021 |
| WO | 2021027943 | 2/2021 |
| WO | 2021031952 | 2/2021 |
| WO | 2021034992 | 2/2021 |
| WO | 2021037018 | 3/2021 |
| WO | 2021041671 | 3/2021 |
| WO | 2021043322 | 3/2021 |
| WO | 2021045279 | 3/2021 |
| WO | 2021050732 | 3/2021 |
| WO | 2021051034 | 3/2021 |
| WO | 2021052499 | 3/2021 |
| WO | 2021055728 | 3/2021 |
| WO | 2021057832 | 4/2021 |
| WO | 2021058018 | 4/2021 |
| WO | 2021061515 | 4/2021 |
| WO | 2021061749 | 4/2021 |
| WO | 2021063346 | 4/2021 |
| WO | 2021068898 | 4/2021 |
| WO | 2021075147 | 4/2021 |
| WO | 2021076655 | 4/2021 |
| WO | 2021078285 | 4/2021 |
| WO | 2021078312 | 4/2021 |
| WO | 2021080359 | 4/2021 |
| WO | 2021081212 | 4/2021 |
| WO | 2021083167 | 5/2021 |
| WO | 2021084765 | 5/2021 |
| WO | 2021085653 | 5/2021 |
| WO | 2021086833 | 5/2021 |
| WO | 2021088458 | 5/2021 |
| WO | 2021088938 | 5/2021 |
| WO | 2021091956 | 5/2021 |
| WO | 2021091967 | 5/2021 |
| WO | 2021091982 | 5/2021 |
| WO | 2021093758 A1 | 5/2021 |
| WO | 2021104431 A1 | 6/2021 |
| WO | 2021106230 A1 | 6/2021 |
| WO | 2021106231 A1 | 6/2021 |
| WO | 2021107160 A1 | 6/2021 |
| WO | 2021108683 A1 | 6/2021 |
| WO | 2021109737 A1 | 6/2021 |
| WO | 2021113595 A1 | 6/2021 |
| WO | 2021120045 A1 | 6/2021 |
| WO | 2021121330 A1 | 6/2021 |
| WO | 2021121367 A1 | 6/2021 |
| WO | 2021121371 A1 | 6/2021 |
| WO | 2021121397 A1 | 6/2021 |
| WO | 2021126120 A1 | 6/2021 |
| WO | 2021126799 A1 | 6/2021 |
| WO | 2021127404 A1 | 6/2021 |
| WO | 2021129820 A1 | 7/2021 |
| WO | 2021129824 A1 | 7/2021 |
| WO | 2021139678 A1 | 7/2021 |
| WO | 2021139748 A1 | 7/2021 |
| WO | 2021141628 A1 | 7/2021 |
| WO | 2021142252 A1 | 7/2021 |
| WO | 2021143693 A1 | 7/2021 |
| WO | 2021145520 A1 | 7/2021 |
| WO | 2021145521 A1 | 7/2021 |
| WO | 2021147965 A1 | 7/2021 |
| WO | 2021147967 A1 | 7/2021 |
| WO | 2021150613 A1 | 7/2021 |
| WO | 2021152149 A1 | 8/2021 |
| WO | 2021168193 A1 | 8/2021 |
| WO | 2021169963 A1 | 9/2021 |
| WO | 2021169990 A1 | 9/2021 |
| WO | 2021173923 A1 | 9/2021 |
| WO | 2021175199 A1 | 9/2021 |
| WO | 2021177721 A1 | 9/2021 |
| WO | 2021178740 A2 | 9/2021 |
| WO | 2021178741 A1 | 9/2021 |
| WO | 2021180181 A1 | 9/2021 |
| WO | 2021185233 A1 | 9/2021 |
| WO | 2021190467 A2 | 9/2021 |
| WO | WO-2021169990 A1 * | 9/2021 |
| WO | 2021197499 A1 | 10/2021 |
| WO | 2021203768 A1 | 10/2021 |
| WO | 2021207172 A1 | 10/2021 |
| WO | 2021211864 A1 | 10/2021 |
| WO | 2021215544 A1 | 10/2021 |
| WO | 2021216770 A1 | 10/2021 |
| WO | 2021217019 A1 | 10/2021 |
| WO | 2021090855 A1 | 11/2021 |
| WO | 2021218110 A1 | 11/2021 |
| WO | 2021219072 A1 | 11/2021 |
| WO | 2021219090 A2 | 11/2021 |
| WO | 2021219091 A1 | 11/2021 |
| WO | 2021228161 A1 | 11/2021 |
| WO | 2021231526 A1 | 11/2021 |
| WO | 2021236475 A1 | 11/2021 |
| WO | 2021239058 A1 | 12/2021 |
| WO | 2021243280 A1 | 12/2021 |
| WO | 2021244603 A1 | 12/2021 |
| WO | 2021245051 A1 | 12/2021 |
| WO | 2021245055 A1 | 12/2021 |
| WO | 2021245499 A1 | 12/2021 |
| WO | 2021248079 A1 | 12/2021 |
| WO | 2021248082 A1 | 12/2021 |

(56) References Cited

FOREIGN PATENT DOCUMENTS

| WO | 2021248083 A1 | 12/2021 |
|---|---|---|
| WO | 2021248090 A1 | 12/2021 |
| WO | 2021248095 A1 | 12/2021 |
| WO | 2021249563 A1 | 12/2021 |
| WO | 2021252339 A1 | 12/2021 |
| WO | 2021257828 A1 | 12/2021 |
| WO | 2021259331 A1 | 12/2021 |
| WO | 2022002102 A1 | 1/2022 |
| WO | 2022015375 A1 | 1/2022 |
| WO | 2022017339 A1 | 1/2022 |
| WO | 2022028346 A1 | 2/2022 |
| WO | 2022028492 A1 | 2/2022 |
| WO | 2022031678 A1 | 2/2022 |
| WO | 2022036176 A1 | 2/2022 |

OTHER PUBLICATIONS

Bauer, R. A., "Covalent inhibitors in drug discovery: from accidental discoveries to avoided liabilities and designed therapies." Drug discovery today 20.9 (2015): 1061-1073.*

Abuabara, K., "Cause-specific mortality in patients with severe psoriasis: a population-based cohort study in the UK." British Journal of Dermatology 163.3 (2010): 586-592.*

Lee, W. J., "Heat shock protein 90 inhibitor decreases collagen synthesis of keloid fibroblasts and attenuates the extracellular matrix on the keloid spheroid model." Plastic and reconstructive surgery 136.3 (2015): 328e-337e.*

Ostrem, J. M., "K-Ras (G12C) inhibitors allosterically control GTP affinity and effector interactions." Nature 503.7477 (2013): 548-551.*

WO-2021169990-A1; (2021) ProQuest English machine translation p. 1-92.*

Figueras, A. et al., "The impact of KRAS mutations on VEGF-A production and tumour vascular network", BMC Cancer 2013, 13:125.

Janes, M. et al., "Targeting KRAS Mutant Cancers with a Covalent G12C-Specific Inhibitor", 2018, Cell 172, 578-589, Jan. 25, 2018, Elsevier Inc.

Matikas, A. et al., "Targeting KRAS mutated non-small cell lung cancer: A history of failures and a future of hope for a diverse entity", Cretical Reviews in Oncology/Hematology 110 (2017) 1-12, Elsevier Ireland Ltd.

McCormick, F., "Targeting KRAS Directly", Annual Review of Cancer Biology, 2018, 2:81, 81-90.

Misalee, S. et al., KRAS G12C NSCLC models are sensitive to direct targeting of KRAS in combination with PI3K Inhibition, Downloaded from clincancerres.aacrjournals.org on Oct. 22, 2018. © 2018 American Association for Cancer Research.

Nabet, B. et al., "It Takes Two To Target: A Study in KRAS Dimerization", pubs.acs.org/biochemistry, DOI: 10.1021.

O'Bryan, J., "Pharmacological Targeting of RAS: Recent Success with Direct Inhibitors", Pharmacological Research (2018), https://doi.org/10.1016/j.phrs.2018.10.021.

Ross, S. et al., "Targeting KRAS-dependent tumors with AZD4785, a high-affinity therapeutic antisense oligonucleotide inhibitor of KRAS", Sci. Transl. Med. 9, eaal5253 (2017) Jun. 14, 2017.

Ruess, D. et al., "Mutant KRAS-driven cancers depend on PTPN11/SHP2 phosphatase", Nature Medicine, Letters, https://doi org/10.1038/s41591-018-0024-8.

Simanshu, D. et al., "RAS Proteins and Their Regulators in Human Disease", Cell 170, 17-33, Jun. 29, 2017.

Suzawa, K., et al., "Activation of KRAS mediates resistance to targeted therapy in MET exon 14 mutant non-small cell lung cancer", Author Manuscript Published OnlineFirst on Oct. 23, 2018; DOI: 10.1158/1078-0432.CCR-18-1640, Downloaded from clincancer-res.aacrjournals.org on Oct. 29, 2018 © 2018 American Association for Cancer Research.

Wijeratne, A. et al., "Chemical Proteomic Characterization of a covalent KRASG12C inhibitor", ACS Med. Chem. Ltter., DOI: 10.1021/acsmedchemlett.8b00110, May 21, 2018.

Wood, K. et al., "Prognostic and Predictive Value in KRAS in Non-Small-Cell Lung Cancer A Review", JAMA Oncol. 2016:2(6), 805-812, Apr. 21, 2016.

Yen, I. et al., "Pharmacological Induction of RAS-GTP Confers RAF Inhibitor Sensitivity in KRAS Mutant Tumors", Cancer Cell 34, 611-625, Oct. 8, 2018, Elsevier Inc.

Ziemke, E. et al., "Sensitivity of KRAS-Mutant Colorectal Cancers to Combination Therapy That Cotargets MEK and CDK4/6", Clin Cancer Res; 22(2) Jan. 15, 2016.

Ambrogio, C. et al., "KRAS Dimerization Impacts MEK Inhibitor Sensitivity and Oncogenic Activity of Mutant KRAS", Cell 172, 1-12, Feb. 8, 2018, Elsevier Inc.

Hansen, R. et al., "An Internally Controlled Quantitative Target Occupancy Assay for Covalent Inhibitors", Scientific Reports, 8:14312 (2018), DOI: 10.1038/s41598-018-32683-w.

Pantar, T. et al., "Assessment of mutation probabilities of KRAS G12 missense mutants and their long-timescale dynamics by atomistic molecular simulations and Markov state modeling", PLOS Computational Biology, Sep. 10, 2018.

Skoulidis, F. et al., "STK11/LKB1 Mutations and PD-1 Inhibitor Resistance in KRAS-Mutant Lung Adenocarcinoma", Downloaded from cancerdiscovery.aacrjournals.org on May 21, 2018. © 2018 American Association for Cancer Research.

Yuan, T. et al., "Differential Effector Engagement by Oncogenic KRAS", Cell Reports 22, 1889-1902, Feb. 13, 2018, Cell Press.

Calles, et al., "Immunohistochemical Loss of LKB1 Is a Biomarker for MOre Aggressive Biology in KRAS-Mutant Lung Adenocarcinoma", Clin Cancer Res. 2015. 21(12).

Torralvo et al., "The Activity of Immune Checkpoint Inhibition in KRAS Mutated Non-small Cell Lung Cancer: A Single Centre Experience", Cancer Genomics & Proteomics, 2019. 16: 577-582.

Sung, Y. et al., "Mutagenesis of the H-ras p21 at Glycine-60 Residue Disrupts GTP-Induced Conformational Change", Biochemistry 1995, 34, 3470-3477, American Chemical Society.

Tape, C. et al., "Oncogenic KRAS Regulates Tumor Cell Signaling via Stromal Reciprocation", Cell 165, 1-11May 5, 2016.

Thierry, A. et al., "Clinical validation of the detection of KRAS and BRAF mutations from circulating tumor DNA", Nature Medicine, vol. 20, No. 4, pp. 430-436, Apr. 2014.

Tran, E. et al., "T-Cell Transfer Therapy Targeting Mutant KRAS in Cancer", N Engl J Med 2016;375:2255-62., Dec. 8, 2016; DOI: 10.1056/NEJMoa1609279.

Wang, Y. et al., "Targeting Mutant KRAS for Anticancer Therapeutics: A Review of Novel Small Molecule Modulators", J. Med. Chem. 2013, 56, 5219-5230, dx.doi.org/10.1021/jm3017706; 2013 American Chemical Society, ACS Publications.

Wang, Y. et al., "Ezh2 Acts as a Tumor Suppressor in Kras-driven Lung Adenocarcinoma", International Journal of Biological Sciences 2017; 13(5): 652-659. doi: 10 7150/ijbs.19108.

Welsch, M. et al., "Multivalent Small-Molecule Pan-RAS Inhibitors", Welsch et al., 2017, Cell 168, 878-889 Feb. 23, 2017; 2017 Elsevier Inc. http://dx.doi.org/10.1016/j.cell.2017.02.006.

Winter, J. et al., "Small Molecule Binding Sites on the Ras:SOS Complex Can Be Exploited for Inhibition of Ras Activation", J. Med. Chem. 2015, 58, 2265-2274; DOI: 10.1021/jm501660t; 2015 American Chemical Society, ACS Publications.

Wood, K. et al., "Reply" Comments & Response, Letters JAMA Oncology Published online Jul. 21, 2016, American Medical Association.

Xiong, Y. et al., "Development of covalent guanosine mimetic inhibitors of G12C KRAS", ACS Med. Chem. Lett., Just Accepted Manuscript • DOI: 10.1021/acsmedchemlett.6b00373 • Publication Date (Web): Nov. 30, 2016 Downloaded from http://pubs.acs.org on Dec. 1, 2016.

Xiong, Y. et al., "Covalent Guanosine Mimetic Inhibitors of G12C KRAS" ACS Med. Chem. Lett. 2017, 8, 61-66, DOI: 10.1021/acsmedchemlett.6b00373; 2016 American Chemical Society, ACS Publications.

Janes et al., "Targeting KRAS Mutant Cancers with a Covalent G12C-Specific Inhibitor", Cell 172, 578-589, Jan. 25, 2018.

(56) References Cited

OTHER PUBLICATIONS

Singh et al., "A Gene Expression Signature Associated with K-Ras Addiction" Reveals Regulators of EMT and Tumor Cell Survival, Cancer Cell 15, p. 489-500, Jun. 2, 2009.
Stephen et al., "Dragging Ras Back in the Ring", Cancer Cell 25, p. 272, Mar. 17, 2014.
Zhu et al., "Inhibition of KRAS-driven tumorigenicity by interruption of an autocrine cytokine circuit", doi:10.1158/2159-8290.CD-13-0646; Cancer Discovery Published OnlineFirst Jan. 20, 2014.
Simanshu et al., "RAS Proteins and Their Regulators in Human Disease", Cell 170, p. 17, Jun. 29, 2017.
Pacold et al., "Crystal Structure and Functional Analysis of Ras Binding to Its Effector Phosphoinositide 3-Kinase gamma", Cell, vol. 103, p. 931-943, Dec. 8, 2000.
Lech-Gustav et al., "The Renaissance of Ras", ACS Chem. Biol., 2014, 9, 2447-2458.
Karachaliou et al., "KRAS Mutations in Lung Cancer", Clinical Lung Cancer, vol. 14, No. 3, p. 2015-14, 2013.
Schwartz et al., "Covalent EGFR inhibitor analysis reveals importance of reversible interactions to potency and mechanisms of drug resistance", PNAS, vol. 111, No. 1, p. 173-178, Jan. 7, 2014.
Sun et al., "A method for the second-site screening of K-Ras in the presence of a covalently attached first-site ligand", J. Biomol. NMR (2014) vol. 60 p. 11-14.
Kyriakis, J., "Thinking Outside the Box about Ras", J. Biol. Chem. 2009, 284:10993-10994, published online Dec. 17, 2008.
Sunaga et al., "Knockdown of Oncogenic KRAS in Non-Small Cell Lung Cancers Suppresses Tumor Growth and Sensitizes Tumor Cells to Targeted Therapy", Mol. Cancer Ther. 2011; 10:336-346.
Serafimova et al., "Reversible targeting of noncatalytic cysteines with chemically tuned electrophiles", Nat Chem Biol.; 8(5):471-476. doi:10.1038/nchembio.925.
Walker et al., "Structural insights into phosphoinositide 3-kinase catalysis and signalling", Nature vol. 402, p. 18 Nov. 1999; www.nature.com.
Barbie et al., "Systematic RNA interference reveals that oncogenic KRAS-driven cancers require TBK1", Nature, vol. 162, p. 108, Nov. 5, 2009; doi:10.1038/nature08460.
Zimmermann et al., "Small molecule inhibition of the KRAS-PDEdelta interaction impairs oncogenic KRAS signalling", Nature, vol. 497, p. 638, May 30, 2013.
Karnoub et al., "Ras oncogenes: split personalities", Nature Reviews, molecular Cell Biology, vol. 9, Jul. 2008 p. 517.
Nassar et al., "Ras/Rap effector specificity determined by charge reversal", Nature Structural Biology, vol. 3, No. 8, Aug. 1996.
De Rooij et al., "Minimal Ras-binding domain of Raf1 can be used as an activation-specific probe for Ras", Oncogene (1997) 14, 623-625, 1997 Stockton Press.
Cox et al., "The dark side of RAs: regulation of apoptosis", Oncogene (2003) 22, 8999-9006, 2003 Nature Publishing Group.
Tanaka et al., "Interfering with RAS-effector protein interactions prevent RAS-dependent tumour initiation and causes stop start control of cancer growth", Oncogene (2010) 29, 6064-6070, 2010 Macmillan Publishers Limited.
Grant et al., "Novel Allosteric Sites on Ras for Lead Generation", PLOS ONE, vol. 6, Issue 10, Oct. 2011.
Maegley et al., "Ras-catalyzed hydrolysis of GTP: A new perspective from model studies", Proc. Natl. Acad. Sci. USA, vol. 93, pp. 8160-8166, Aug. 1996.
Ahmadian et al., "Guanosine triphosphatase stimulation of oncogenic Ras mutants", Proc. Natl. Acad. Sci. USA, vol. 96, pp. 7065-7070, Jun. 1999.
Kiel et al., "Electrostatically optimized Ras-binding Ral guanine dissociation stimulator mutants increase the rate of association by stabilizing the encounter complex", PNAS, vol. 101, No. 25, p. 9223-9228, Jun. 22, 2004.
Kotting et al., "The GAP arginine finger movement into the catalytic site of Ras increases the activation entropy", PNAS, vol. 105, No. 17, p. 6260-6265, Apr. 29, 2008.

Shaw et al., "Selective killing of K-ras mutant cancer cells by small molecule inducers of oxidative stress", PNAS, vol. 108, No. 21, p. 8773-8778, May 24, 2011.
Ischenko et al., "Direct reprogramming by oncogenic Ras and Myc", PNAS early edition 1, 2013.
Smith et al., "NMR-based functional profiling of RASopathies and oncogenic RAS mutations", PNAS, vol. 110, No. 12, p. 4574-4579, Mar. 19, 2013.
Shima, et al., "In silico discovery of small-molecule Ras inhibitors that display antitumor activity by blocking the Ras-effector interaction", PNAS, vol. 110, No. 20, p. 8182-8187, May 14, 2013.
Burns et al., "Approach for targeting Ras with small molecules that activate SOS-mediated nucleotide exchange", PNAS, vol. 111, No. 9, p. 3401-3406, Mar. 4, 2014.
Zeng et al., "Design of inhibitors of Ras-Raf interaction using a computational combinatorial algorithm", Protein Engineering, vol. 14, No. 1, p. 39-45, 2001.
Schehfzek et al., "The Ras-RasGAP Complex: Structural Basis for GTPAse Activation and Its Loss in Oncogenic Ras Mutants", Science, vol. 277, Jul. 18, 1997.
Taylor et al., "Protein Kinases: Evolution of Synamic Regulatory Proteins", Trends Biochem Sci. Feb. 2011; 36(2): 65-77. doi:10.1016/j.tibs.2010.09.006.
Fell et al. 'Discovery of Tetrahydropyridopyrimidines as Irreversible Covalent Inhibitors of KRAS-G12C with In Vivo Activity', ACS Medicinal Chemistry Letters, Nov. 7, 2018 (Nov. 7, 2018), vol. 9, pp. 1230-1234.
International Search Report and Written Opinion for corresponding PCT application No. PCT/US18/61060 dated Feb. 7, 2019.
Martin, James S. et al., "Characterising covalent warhead reactivity", Bioorganic & Medicinal Chemistry, 27 (2019) 2066-2074.
Palkowitz, Maximilian D. et al., "Synthesis of Diverse N-Acryloyl Azetidines and Evaluation of Their Enhanced Thiol Reactivities", ACS Publications Mar. 16, 2017, 9, 9, 2270-2273.
International Search Report and Written Opinion for PCT Application No. PCT/US2020/012906.
Blake et al., "Discovery of 5,6,7,8-tetrahydropyrido[3,4-d]pyrimidine inhibitors of Erk2" Bioorganic & Medicinal Chemistry Letters, Jun. 15, 2014, vol. 24, p. 2635-2639; p. 2635, Figure 1, p. 2637, right col. Para 2.
Ambrogio, C. et al., "Combined inhibition of DDR1 and Notch signaling is a therapeutic strategy for KRAS-driven lung adenocarcinoma", Nature Medicine, vol. 22, No. 3, pp. 270-279, Mar. 2016.
Araki, M. et al., "Solution Structure of the State 1 Conformer of GTP-bound H-Ras Protein and Distinct Dynamic Properties between the State 1 and State 2 Conformers" The Journal of Biological Chemistry vol. 286, No. 45, pp. 39644-39653, Nov. 11, 2011.
Broutin, S. et al., "Insights into significance of combined inhibition of MEK and m-TOR signalling output in KRAS mutant non-small-cell lung cancer", British Journal of Cancer (2016), 1-4 | doi: 10.1038/bjc.2016.220.
Burgess, M. et al., "KRAS Allelic Imbalance Enhances Fitness and Modulates MAP Kinase Dependence in Cancer", Cell 168, 817-829, Feb. 23, 2017, Elsevier Inc.
Cammarata, M. et al., "Impact of G12 Mutations on the Structure of K-Ras Probed by Ultraviolet Photodissociation Mass Spectrometry", . Am. Chem. Soc., 2016, 138 (40), pp. 13187-13196.
Costa-Cabral, S. et al., "CDK1 Is a Synthetic Lethal Target for KRAS Mutant Tumours", PLOS ONE | DOI:10.1371/journal.pone.0149099 Feb. 16, 2016.
Cully, "Closing the door on KRAS-mutant lung cancer", Nature Reviews Drug Discovery | Published online Nov. 3, 2016; doi:10.1038/nrd.2016.216, MacMillan Publishers.
Dharmaiah, S. et al., "Structural basis of recognition of farnesylated and methylated KRAS4b by PDEσ", E6766-E6775, PNAS, Published online Oct. 17, 2016.
Fiala, O. et al., "The dominant role of G12C over other KRAS mutation types in the negative prediction of efficacy of epidermal growth factor receptor tyrosine kinase inhibitors in nonsmall cell lung cancer", Cancer Genetics 206 (2013) 26-31.

(56) References Cited

OTHER PUBLICATIONS

Ford, B. et al., "Structure of the G60A Mutant of Ras Implications for the Dominant Negative Effect", J. Biol. Chem., vol. 280, No. 27, Issue of Jul. 8, pp. 25697-25705, 2005.
Hall, B. et al., "The structural basis for the transition from Ras-GTP to Ras-GDP", PNAS, vol. 99, No. 19, pp. 12138-12142, Sep. 17, 2002.
Hunter, J. et al., "In situ selectivity profiling and crystal structure of SML-8-73-1, an active site inhibitor of oncogenic K-Ras G12C", PNAS, vol. 111, No. 24, pp. 8895-8900, Jun. 17, 2014.
Ihle, N. et al., "Effect of KRAS Oncogene Substitutions on Protein Behavior: Implications for Signaling and Clinical Outcome", JNCI, Oxford Journals, vol. 104, Issue 3, Feb. 8, 2012.
Jarvis, L., "Have drug hunters finally cracked KRas?", c&en, vol. 94, Issue 23, pp. 28-33, Jun. 6, 2016.
Kamerkar, S. et al., "Exosomes facilitate therapeutic targeting of oncogenic KRAS in pancreatic cancer", Nature 546, 498-503 (Jun. 22, 2017) doi:10.1038/nature22341.
Kaufman, J. et al., "Treatment of KRAS-Mutant Non-Small Cell Lung Cancer The End of the Beginning for Targeted Therapies", JAMA May 9, 2017 vol. 317, No. 18.
Kerr, E. et al., "Mutant Kras copy number defines metabolic reprogramming and therapeutic susceptibilities", Nature 531, 110-113, (Mar. 3, 2016) doi:10.1038/nature16967.
Kim, J. et al., "CPS1 maintains pyrimidine pools and DNA synthesis in KRAS/LKB1-mutant lung cancer cells", Nature 546, 168-172, (Jun. 1, 2017) doi:10.1038/nature22359.
Kim, J. et al., "XPO1-dependent nuclear export is a druggable vulnerability in KRAS-mutant lung cancer", Nature 538, 114-117 (Oct. 6, 2016) doi:10.1038/nature19771.
Kitai, H. et al., "Key roles of EMT for adaptive resistance to MEK inhibitor in KRAS mutant lung cancer", SSN: 2154-1248 (Print) 2154-1256 (Online) Journal homepage: http://www.tandfonline.com/loi/ksgt20.
Kosloff, M. et al., "GTPase Catalysis by Ras and Other G-proteins: Insights from Substrate Directed SuperImposition", J. Mol. Biol. (2003) 331, 1157-1170, doi: 10.1016/80022-2836(03)00847-7.
Ledford, H., "Thirty years of pursuit have failed to yield a drug to take on one of the deadliest families of cancer-causing proteins. Now some researchers are taking another shot." The RAS Renaissance, Nature, vol. 520, 278-280, Apr. 16, 2015.
Lim, S. et all., "Therapeutic Targeting of Oncogenic K-Ras by a Covalent Catalytic Site Inhibitor", Angew. Chem. Int. Ed. 2014, 53, 199-204.
Loncle, C. et al., "The pancreatitis-associated protein VMP1, a key regulator of inducible autophagy, promotes KrasG12D-mediated pancreatic cancer initiation", Cell Death and Disease (2016) 7, e2295; doi:10.1038/cddis.2016.202 Official journal of the Cell Death Differentiation Association.
Manchado, E. et al., "A combinatorial strategy for treating KRAS-mutant lung cancer", Nature 534, 647-651 (Jun. 30, 2016) doi:10.1038/nature18600.
Maurer, T. et al., "Small-molecule ligands bind to a distinct pocket in Ras and inhibit SOS-mediated nucleotide exchange activity", PNAS, Apr. 3, 2012, vol. 109, No. 14, pp. 5299-5304.
Muller, M. et al., "Nucleotide based covalent inhibitors of KRas can only be efficient in vivo if they bind reversibly with GTP-like affinity", Scientific Reports, 7: 3687 | DOI:10.1038/s41598-017-03973-6.
Nadal, E. et al., "Abstract C141: KRAS G12C mutation is prognostic of poor outcome in resected lung adenocarcinomas and predictive of poor response to MEK inhibition in vitro", Mol Cancer Ther Nov. 12, 2013; C141; doi: 10.1158/1535-7163.TARG-13-C141.
Nussinov, R. et al., "Independent and core pathways in oncogenic KRAS signaling", Journal: Expert Review of Proteomics, DOI: 10.1080/14789450.2016.1209417, Published by Taylor & Francis.
Ostrem, J. et al., "Direct small-molecule inhibitors of KRAS: from structural insights to mechanism-based design", Nature Reviews Drug Discovery 15, 771-785 (2016) doi:10.1038/nrd.2016.139.
Ostrem, J. et al., "K-Ras(G12C) inhibitors allosterically control GTP affinity and effector interactions", Nature, vol. 503: 548, Nov. 28, 2013.
Papke, B. et al., "Drugging RAS: Know the enemy", Science 355, 1158-1163 (2017) Mar. 17, 2017.
Park, K. et al., "The HSP90 inhibitor, NVP-AUY922, sensitizes KRAS-mutant non-small cell lung cancer with intrinsic resistance to MEK inhibitor, trametinib", Cancer Letters 372 (2016) 75-81.
Patricelli, M. et al., "Selective Inhibition of Oncogenic KRAS Output with Small Molecules Targeting the Inactive State", OnlineFirst on Jan. 6, 2016; DOI: 10.1158/2159-8290.CD-15-1105.
Perara, D. et al., "Oncogenic KRAS triggers MAPK-dependent errors in mitosis and MYC-dependent sensitivity to anti-mitotic agents", Scientific Reports, 6:29741, DOI: 10.1038/srep29741.
Renaud, S. et al., "KRAS in Non-Small-Cell Lung Cancer: Oncogenic Addiction and Epidermal Growth Factor Receptor Tyrosine Kinase Inhibitors", JAMA Oncology Published online Jul. 21, 2016.
Riquelme, E. et al., "Modulation of EZH2 expression by MEK-ERK or PI3K-AKT signaling in lung cancer is dictated by different KRAS oncogene mutations", Author Manuscript Published OnlineFirst on Dec. 16, 2015; DOI: 10.1158/0008-5472.CAN-15-1141, American Association for Cancer Research.
Rudoni, S. et al., "Role of guanine nucleotides in the regulation of the Ras/cAMP pathway in *Saccharomyces cerevisiae*". Biochimica et Biophysica Acta 1538 (2001) 181^189.
Samatar, A. et al., "Targeting RAS-ERK signalling in cancer: promises and challenges", Nature Reviews Drug Discovery, vol. 13, pp. 928-942, Dec. 2014.
Sautier, B. et al., "Latest advances towards Ras inhibition—A medicinal chemistry perspective", Angewandte Chemie International Edition, 10.1002/anie.201608270.
Serresi, M. et al., "Polycomb Repressive Complex 2 Is a Barrier to KRAS-Driven Inflammation and Epithelial-Mesenchymal Transition in Non-Small-Cell Lung Cancer", Cancer Cell 29, 17-31, Jan. 11, 2016, 2016 Elsevier Inc. 17.
Shima, F. et al., "Structural Basis for Conformational Dynamics of GTP-bound Ras Protein", The Journal of Biological Chemistry, vol. 285, No. 29, pp. 22696-22705, Jul. 16, 2010.
Shipman, L., "Putting the brakes on KRAS-G12C nucleotide cycling", Nature Reviews Cancer, Published online Feb. 19, 2016; doi:10.1038/nrc.2016.13.
Spoerner, M. et al., "Dynamic properties of the Ras switch I region and its importance for binding to effectors", PNAS, vol. 98, No. 9, pp. 4944-4949, Apr. 24, 2001.
Sun, Q. et al., "Discovery of Small Molecules that Bind to K-Ras and Inhibit Sos-Mediated Activation**", Angew. Chem. Int. Ed. 2012, 51, 1-5, 2012 Wiley-VCH Verlag GmbH & Co. KGaA, Weinheim.
Sun, Q., et al., "A method for the second-site screening of K-Ras in the presence of a covalently attached first-site ligand", J Biomol NMR (2014) 60:11-14 DOI 10.1007/s10858-014-9849-8.
Sunaga, N. et al., "Oncogenic KRAS-induced epiregulin overexpression contributes to aggressive phenotype and is a promising therapeutic target in non-small-cell lung cancer", Oncogene (2013) 32, 4034-4042& 2013 Macmillan Publishers Limited.

\* cited by examiner

KRAS G12C INHIBITORS

FIELD OF THE INVENTION

The present invention relates to compounds that inhibit KRas G12C. In particular, the present invention relates to compounds that irreversibly inhibit the activity of KRas G12C, pharmaceutical compositions comprising the compounds and methods of use therefor.

BACKGROUND OF THE INVENTION

Kirsten Rat Sarcoma 2 Viral Oncogene Homolog ("KRas") is a small GTPase and a member of the Ras family of oncogenes. KRas serves a molecular switch cycling between inactive (GDP-bound) and active (GTP-bound) states to transduce upstream cellular signals received from multiple tyrosine kinases to downstream effectors to regulate a wide variety of processes, including cellular proliferation (e.g., see Alamgeer et al., (2013) Current Opin Pharmcol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas and downstream signaling have been reported in 25-30% of lung adenocarcinomas. (e.g., see Samatar and Poulikakos (2014) Nat Rev Drug Disc 13(12): 928-942 doi: 10.1038/nrd428). Single nucleotide substitutions that result in missense mutations at codons 12 and 13 of the KRas primary amino acid sequence comprise approximately 40% of these KRas driver mutations in lung adenocarcinoma, with a G12C transversion being the most common activating mutation (e.g., see Dogan et al., (2012) Clin Cancer Res. 18(22):6169-6177, published online 2012 Sep. 26. doi: 10.1158/1078-0432.CCR-11-3265).

The well-known role of KRAs in malignancy and the discovery of these frequent mutations in KRas in various tumor types made KRas a highly attractable target of the pharmaceutical industry for cancer therapy.

Despite many failed efforts to target KRas, compounds that inhibit KRas activity are still highly desirable and under investigation, including those that disrupt effectors such as guanine nucleotide exchange factors (e.g., see Sun et al., (2012) Agnew Chem Int Ed Engl. 51(25):6140-6143 doi: 10.1002/anie201201358) as well target KRas G12C (e.g., see Ostrem et al., (2013) Nature 503:548-551). Clearly there remains a continued interest and effort to develop inhibitors of KRas, particularly inhibitors of activating KRas mutants, including KRas G12C.

Thus, there is a need to develop new KRas G12C inhibitors that demonstrate sufficient efficacy, stability and/or safety for treating KRas G12C-mediated cancer. The compounds and compositions of the present invention advantageously overcome one or more of the previous shortcomings by providing selective KRas G12C inhibitors.

SUMMARY OF THE INVENTION

In one aspect of the invention, compounds are provided that inhibit KRas G12C activity. In certain embodiments, the compounds are represented by Formula (I):

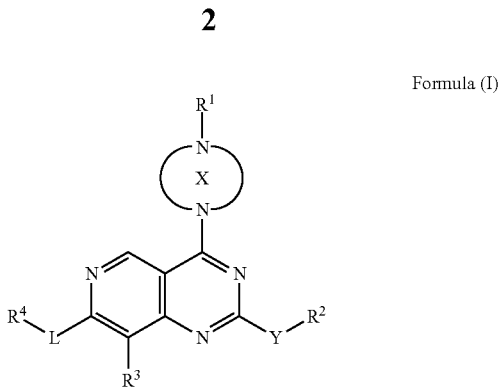

Formula (I)

or a pharmaceutically acceptable salt thereof, wherein:
X is a 4-12 membered saturated or partially saturated monocyclic, bridged, spirocyclic or fused bicyclic ring, wherein the saturated or partially saturated monocyclic ring is optionally substituted with one or more $R^8$;
Y is a bond, O, S or $NR^5$;
$R^1$ is —C(O)C($R^A$)═C($R^B$)$_p$ or —SO$_2$C($R^A$)═C($R^B$)$_p$;
$R^2$ is hydrogen, alkyl, alkoxy, hydroxyalkyl, dihydroxyalkyl, alkylaminylalkyl, dialkylaminylalkyl, —Z—NR$^5$SO$_2$C1-C3 alkyl, haloalkyl, —Z—NR$^5$R$^{10}$, cycloalkyl, heterocyclyl, heterocyclylalkyl, aryl, aralkyl, heteroaryl, or heteroarylalkyl, wherein each of the Z, heterocyclyl, heterocyclylalkyl, aryl, heteroaryl, and heteroarylalkyl may be optionally substituted with one or more $R^9$;
Z is C1-C4 alkylene;
$R^3$ is independently hydrogen, halogen, C1-C3 alkyl, oxo, CN, —O-haloalkyl or —OR$^5$;
L is a bond, —C(O)—, or C1-C3 alkylene;
$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more substituents independently selected from $R^6$, $R^7$ and $R^9$;
each $R^5$ is independently hydrogen or C1-C3 alkyl;
$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;
each $R^7$ is independently halogen, hydroxyl, C1-C6 alkyl, C2-C4 alkynyl, cycloalkyl, alkoxy, haloalkyl, amino, cyano, heteroalkyl, hydroxyalkyl or Q-haloalkyl, wherein Q is O or S;
each $R^8$ is oxo, C1-C3 alkyl, C2-C4 alkynyl, heteroalkyl, cyano, —C(O)OR$^5$, —C(O)N(R$^5$)$_2$, —N(R$^5$)$_2$, or haloC1-C3 alkyl, wherein the C1-C3 alkyl may be optionally substituted with cyano, halogen, —OR$^5$, —N(R$^5$)$_2$, or heteroaryl;
each $R^9$ is independently hydrogen, oxo, acyl, hydroxyl, hydroxyalkyl, cyano, —N(R$^5$)$_2$ halogen, C1-C6 alkyl, aralkyl, haloalkyl, heteroalkyl, cycloalkyl, heterocyclyl, heterocyclylalkyl, alkoxy, dialkylaminyl, dialkylamidoalkyl, or dialkylaminylalkyl, wherein the C1-C6 alkyl may be optionally substituted with cycloalkyl;
each $R^{10}$ is independently hydrogen, acyl, C1-C3 alkyl, heteroalkyl or hydroxyalkyl;
$R^A$ is absent, hydrogen, deuterium, cyano, halogen, C1-C-3 alkyl, haloalkyl, heteroalkyl, —C(O)N(R$^5$)$_2$, or hydroxyalkyl;
each $R^B$ is independently hydrogen, deuterium, cyano, C1-C3 alkyl, hydroxyalkyl, heteroalkyl, C1-C3 alkoxy, halogen, haloalkyl, —ZNR⁵R¹¹, wherein R¹¹ is haloalkyl; —C(O)N(R⁵)₂, —NHC(O)C1-C3 alkyl, —CH₂NHC(O)C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more R⁷;

p is one or two; and wherein, when ≡ is a triple bond then $R^A$ is absent, $R^B$ is present and p equals one, or when ═ is a double bond then $R^A$ is present, $R^B$ is present and p equals two, or $R^A$, $R^B$ and the carbon atoms to which they are attached form a 5-8 membered partially saturated cycloalkyl optionally substituted with one or more R⁷.

Also included are compounds of Formula I having the Formula I-A:

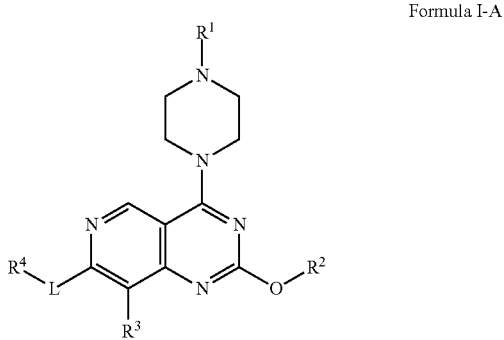

Formula I-A where R¹, R³, R⁴, R⁸, and L are as defined for Formula I, R² is heterocyclylalkyl optionally substituted with one or more R⁹, and the piperazinyl ring is optionally substituted with one or more R⁸, where R⁸ is as defined for Formula I.

In another aspect of the invention, pharmaceutical compositions are provided comprising a therapeutically effective amount of a compound of the present invention or a pharmaceutically acceptable salt thereof and a pharmaceutically acceptable excipient.

In yet another aspect of the invention, methods for inhibiting KRas G12C activity in a in a cell, comprising contacting the cell with a compound of Formula I and Formula I-A. In one embodiment, the contacting is in vitro. In one embodiment, the contacting is in vivo.

Also provided herein is a method of inhibiting cell proliferation, in vitro or in vivo, the method comprising contacting a cell with an effective amount of a compound of Formula I and Formula I-A, or a pharmaceutically acceptable salt thereof, or a pharmaceutical composition thereof as defined herein.

Also provided are methods for treating cancer in a patient comprising administering a therapeutically effective amount of a compound or pharmaceutical composition of the present invention or a pharmaceutically acceptable salt thereof to a patient in need thereof.

Also provided herein is a method of treating a KRas G12C-associated disease or disorder in a patient in need of such treatment, the method comprising administering to the patient a therapeutically effective amount of a compound of Formula I and Formula I-A, or a pharmaceutically acceptable salt or solvate thereof, or a pharmaceutical composition thereof as defined herein.

Also provided herein is a compound of Formula I and Formula I-A, or a pharmaceutically acceptable salt or solvate thereof, or a pharmaceutical composition thereof as defined herein for use in therapy.

Also provided herein is a compound of Formula I and Formula I-A, or a pharmaceutically acceptable salt or solvate thereof or a pharmaceutical composition thereof as defined herein for use in the treatment of cancer.

Also provided herein is a compound of Formula I and Formula I-A, or a pharmaceutically acceptable salt or solvate thereof for use in the inhibition of KRas G12C.

Also provided herein is a compound of Formula I and Formula I-A, or a pharmaceutically acceptable salt or solvate thereof or a pharmaceutical composition thereof as defined herein, for use in the treatment of a KRas G12C-associated disease or disorder.

Also provided herein is the use of a compound of Formula I and Formula I-A, or a pharmaceutically acceptable salt or solvate thereof, as defined herein in the manufacture of a medicament for the treatment of cancer.

Also provided herein is a use of a compound of Formula I and Formula I-A, or a pharmaceutically acceptable salt or solvate thereof, as defined herein in the manufacture of a medicament for the inhibition of activity of KRas G12C.

Also provided herein is the use of a compound of Formula I and Formula I-A, or a pharmaceutically acceptable salt or solvate thereof, as defined herein, in the manufacture of a medicament for the treatment of a KRas G12C-associated disease or disorder.

Also provided herein is a method for treating cancer in a patient in need thereof, the method comprising (a) determining that the cancer is associated with a KRas G12C mutation (e.g., a KRas G12C-associated cancer); and (b) administering to the patient a therapeutically effective amount of a compound of Formula I and Formula I-A, or a pharmaceutically acceptable salt thereof, or a pharmaceutical composition thereof.

Also provided herein is a process for preparing a compound of Formula I and Formula I-A, or a pharmaceutically acceptable salt or solvate thereof.

Also provided herein is a compound of Formula I and Formula I-A, or a pharmaceutically acceptable salt thereof obtained by a process of preparing the compound as defined herein.

DETAILED DESCRIPTION OF THE INVENTION

The present invention relates to inhibitors of KRas G12C. In particular, the present invention relates to compounds that irreversibly inhibit the activity of KRas G12C, pharmaceutical compositions comprising a therapeutically effective amount of the compounds and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12C" refers to a mutant form of a mammalian KRas protein that contains an amino acid substitution of a cysteine for a glycine at amino acid position 12. The assignment of amino acid codon and residue positions for human KRas is based on the amino acid sequence identified by UniProtKB/Swiss-Prot P01116: Variant p.Gly12Cys.

As used herein, a "KRas G12C inhibitor" refers to compounds of the present invention that are represented by formulae (I) as described herein. These compounds are capable of negatively modulating or inhibiting all or a portion of the enzymatic activity of KRas G12C. The KRas G12C inhibitors of the present invention interact with and irreversibly bind to KRas G12C by forming a covalent adduct with the sulfhydryl side chain of the cysteine residue at position 12 resulting in the inhibition of the enzymatic activity of KRas G12C.

A "KRas G12C-associated disease or disorder" as used herein refers to diseases or disorders associated with or mediated by or having a KRas G12C mutation. A non-limiting example of a KRas G12C-associated disease or disorder is a KRas G12C-associated cancer.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12C mutation (e.g., as determined using a regulatory agency-approved, e.g., FDA-approved, assay or kit). In some embodiments, the subject has a tumor that is positive for a KRas G12C mutation (e.g., as determined using a regulatory agency-approved assay or kit). The subject can be a subject with a tumor(s) that is positive for a KRas G12C mutation (e.g., identified as positive using a regulatory agency-approved, e.g., FDA-approved, assay or kit). The subject can be a subject whose tumors have a KRas G12C mutation (e.g., where the tumor is identified as such using a regulatory agency-approved, e.g., FDA-approved, kit or assay). In some embodiments, the subject is suspected of having a KRas G12C gene-associated cancer. In some embodiments, the subject has a clinical record indicating that the subject has a tumor that has a KRas G12C mutation (and optionally the clinical record indicates that the subject should be treated with any of the compositions provided herein).

The term "pediatric patient" as used herein refers to a patient under the age of 16 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman RE, Kliegman R, Arvin AM, Nelson WE. Nelson Textbook of Pediatrics, 15th Ed. Philadelphia: W.B. Saunders Company, 1996; Rudolph A M, et al. Rudolph's Pediatrics, 21st Ed. New York: McGraw-Hill, 2002; and Avery MD, First LR. Pediatric Medicine, 2nd Ed. Baltimore: Williams & Wilkins; 1994.

In some embodiments of any of the methods or uses described herein, an assay is used to determine whether the patient has KRas G12C mutation using a sample (e.g., a biological sample or a biopsy sample (e.g., a paraffin-embedded biopsy sample) from a patient (e.g., a patient suspected of having a KRas G12C-associated cancer, a patient having one or more symptoms of a KRas G12C-associated cancer, and/or a patient that has an increased risk of developing a KRas G12C-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

The term "amino" refers to —$NH_2$;

The term "acyl" refers to —$C(O)CH_3$.

The term "alkyl" as employed herein refers to straight and branched chain aliphatic groups having from 1 to 12 carbon atoms, 1-8 carbon atoms 1-6 carbon atoms, or 1-3 carbon atoms which is optionally substituted with one, two or three substituents. Examples of alkyl groups include, without limitation, methyl, ethyl, propyl, isopropyl, butyl, isobutyl, sec-butyl, tert-butyl, pentyl, and hexyl.

The term "haloalkyl" refers to an alkyl chain as defined herein above, in which one or more hydrogen has been replaced by a halogen. Examples of haloalkyls are trifluoromethyl, difluoromethyl and fluoromethyl.

The term "haloalkyloxy" refers to —O-haloalkyl.

An "alkylene," group is an alkyl group, as defined hereinabove, that is positioned between and serves to connect two other chemical groups. Exemplary alkylene groups include, without limitation, methylene, ethylene, propylene, and butylene.

The term "alkoxy" refers to —OC1-C6 alkyl.

The term "cycloalkyl" as employed herein includes saturated and partially unsaturated cyclic hydrocarbon groups having 3 to 12 carbons, for example 3 to 8 carbons, and as a further example 3 to 6 carbons, wherein the cycloalkyl group additionally is optionally substituted. Examples of cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are replaced by a heteroatom selected from the group consisting of O, S, and N.

As used herein, the term "hydroxyalkyl" refers to an alkyl chain, as defined herein above, wherein one hydrogen atom is replaced with a hydroxyl group.

The term "dihydroxyalkyl" refers to an alkyl group as defined herein wherein two carbon atoms are each substituted with a hydroxyl group.

The term "alkylaminyl" refers to —$NR^x$-alkyl, wherein $R^x$ is hydrogen.

The term "dialkylaminyl" refers to —$N(R^y)_2$, wherein each $R^y$ is independently C1-C3 alkyl.

The term "alkylaminylalkyl" refers to -alkyl-$NR^x$-alkyl, wherein $R^x$ is hydrogen.

The term "dialkylaminylalkyl" refers to -alkyl-$N(R^y)_2$, wherein each $R^y$ is independently C1-C4 alkyl, wherein the alkyl of the-alkyl-$N(R^y)_2$ is an alkyl group as defined hereinabove and may be optionally substituted with hydroxy or hydroxyalkyl.

An "aryl" group is a $C_6$-$C_{14}$ aromatic moiety comprising one to three aromatic rings, which is optionally substituted. As one embodiment, the aryl group is a $C_6$-$C_{10}$ aryl group.

Examples of aryl groups include, without limitation, phenyl, naphthyl, anthracenyl, fluorenyl, and dihydrobenzofuranyl. An "aryl" group may be optionally include one aromatic ring fused to a heterocyclyl.

An "aralkyl" or "arylalkyl" group comprises an aryl group covalently linked to an alkyl group as defined herein above, either of which may independently be optionally substituted or unsubstituted. An example of an aralkyl group is $(C_1\text{-}C_6)$alkyl$(C_6\text{-}C_{10})$aryl, including, without limitation, benzyl, phenethyl, and naphthylmethyl. An example of a substituted aralkyl is wherein the alkyl group is substituted with hydroxyalkyl.

A "heterocyclyl" or "heterocyclic" group is a ring structure having from about 3 to about 12 atoms, for example 4 to 8 atoms, wherein one or more atoms are selected from the group consisting of N, O, and S, the remainder of the ring atoms being carbon. The heterocyclyl may be a monocyclic, a bicyclic, a spirocyclic or a bridged ring system. The heterocyclic group is optionally substituted with $R^7$ on carbon or nitrogen at one or more positions, wherein $R^7$ is as defined for Formula I. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, thiazolidinyl, dithianyl, trithianyl, dioxolanyl, oxazolidinyl, oxazolidinonyl, decahydroquinolinyl, piperidonyl, 4-piperidinonyl, thiomorpholinyl, thiomorpholinyl 1,1 dioxide, hexahydrofuro[3.2-b]furanyl, (3R, 3aR, 6R, 6aR)-hydroxyhexahydrofuro[3.2-b]furanyl, morpholinyl, oxazepanyl, and azabicyclohexanes, azabicycloheptanes and oxa azabiocycloheptanes, including diazabicyclo[3.2.0]heptan-6-yl, diazabicyclo[3.2.0]heptan-2-yl, diazabicyclo[3.2.1]octan-8-yl or diazabicyclo[3.2.1]octan-3-yl. Specifically excluded from the scope of this term are compounds having adjacent annular 0 and/or S atoms.

The term "heterocyclylalkyl" refers to a heterocyclyl group as defined herein covalently linked to an alkyl group as defined hereinabove wherein the radical is on the alkyl group, wherein the alkyl group of the heterocyclylalkyl may be optionally substituted with hydroxy or hydroxyalkyl.

As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from one to three heteroatoms per ring selected from the group consisting of N, O, and S. Examples of heteroaryl groups include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1, 2,5-thiadiazinyl, 1,2,3-thiadiazolyl, 1,2,4-thiadiazolyl, 1,2, 5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "heteroarylalkyl" group comprises a heteroaryl group covalently linked to an alkyl group, wherein the radical is on the alkyl group, either of which is independently optionally substituted or unsubstituted. Examples of heteroarylalkyl groups include a heteroaryl group having 5, 6, 9, or 10 ring atoms bonded to a C1-C6 alkyl group. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent annular 0 and/or S atoms.

As used herein, "an effective amount" of a compound is an amount that is sufficient to negatively modulate or inhibit the activity of KRas G12C. Such amount may be administered as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of KRas G12C. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

As used herein, the term "about" when used to modify a numerically defined parameter (e.g., the dose of the KRAS inhibitor detailed herein or a pharmaceutically acceptable salt thereof, or the length of treatment time described herein) means that the parameter may vary by as much as 10% below or above the stated numerical value for that parameter. For example, a dose of about 5 mg/kg may vary between 4.5 mg/kg and 5.5 mg/kg. "About" when used at the beginning of a listing of parameters is meant to modify each parameter. For example, about 0.5 mg, 0.75 mg or 1.0 mg means about 0.5 mg, about 0.75 mg or about 1.0 mg. Likewise, about 5% or more, 10% or more, 15% or more, 20% or more, and 25% or more means about 5% or more, about 10% or more, about 15% or more, about 20% or more, and about 25% or more.

Compounds

In one aspect of the invention, compounds are provided represented by formula (I):

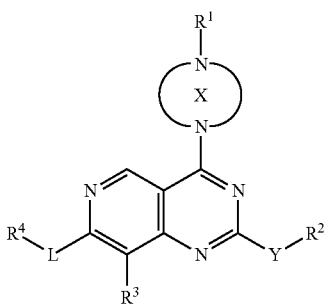

Formula (I)

or a pharmaceutically acceptable salt thereof, wherein:

X is a 4-12 membered saturated or partially saturated monocyclic, bridged, spirocyclic or fused bicyclic ring, wherein the saturated or partially saturated monocyclic ring is optionally substituted with one or more $R^8$;

Y is a bond, O, S or $NR^5$;

$R^1$ is $-C(O)C(R^A)\!=\!\!=\!\!=\!C(R^B)_p$ or $SO_2C(R^A)\!=\!\!=\!\!=\!C(R^B)_p$;

$R^2$ is hydrogen, alkyl, alkoxy, hydroxyalkyl, dihydroxyalkyl, alkylaminylalkyl, dialkylaminylalkyl, $-Z-NR^5SO_2C1$-C3 alkyl, $-Z-NR^5R^{10}$, cycloalkyl, heterocyclyl, heterocyclylalkyl, aryl, aralkyl, heteroaryl, or heteroarylalkyl, wherein each of the Z, heterocyclyl, heterocyclylalkyl, aryl, heteroaryl, and heteroarylalkyl may be optionally substituted with one or more $R^9$;

Z is C1-C4 alkylene;

each $R^3$ is independently C1-C3 alkyl, halogen, CN, —O-haloalkyl or $-OR^5$;

L is a bond, —C(O)—, or C1-C3 alkylene;

$R^4$ is hydrogen, cycloalkyl, heterocyclyl, aryl, aralkyl or heteroaryl, wherein each of the cycloalkyl, heterocyclyl, aryl, aralkyl and heteroaryl may be optionally substituted with one or more substituents independently selected from $R^6$, $R^7$ and $R^9$;

each $R^5$ is independently hydrogen or C1-C3 alkyl;

$R^6$ is cycloalkyl, heterocyclyl, heterocyclylalkyl, aryl, or heteroaryl, wherein each of the cycloalkyl, heterocyclyl, aryl, or heteroaryl may be optionally substituted with one or more $R^7$;

each $R^7$ is independently halogen, hydroxyl, C1-C6 alkyl, C2-C4 alkynyl, cycloalkyl, alkoxy, haloalkyl, amino, cyano, heteroalkyl, hydroxyalkyl or Q-haloalkyl, wherein Q is O or S;

each $R^8$ is oxo, C1-C3 alkyl, C2-C4 alkynyl, heteroalkyl, cyano, $-C(O)OR^5$, $-C(O)N(R^5)_2$, $-N(R^5)_2$, or haloC1-C3 alkyl, wherein the C1-C3 alkyl may be optionally substituted with cyano, halogen, $-OR^5$, $-N(R^5)_2$, or heteroaryl;

each $R^9$ is independently hydrogen, oxo, acyl, hydroxyl, hydroxyalkyl, cyano, $-N(R^5)_2$ halogen, C1-C6 alkyl, aralkyl, haloalkyl, heteroalkyl, cycloalkyl, heterocyclyl, heterocyclylalkyl, alkoxy, dialkylaminyl, dialkylamidoalkyl, or dialkylaminylalkyl, wherein the C1-C6 alkyl may be optionally substituted with cycloalkyl;

each $R^{10}$ is independently hydrogen, acyl, C1-C3 alkyl, heteroalkyl or hydroxyalkyl;

$R^A$ is absent, hydrogen, deuterium, cyano, halogen, C1-C3 alkyl, haloalkyl, heteroalkyl, $-C(O)N(R^5)_2$, or hydroxyalkyl;

each $R^B$ is independently hydrogen, deuterium, cyano, C1-C3 alkyl, hydroxyalkyl, heteroalkyl, C1-C3 alkoxy, halogen, haloalkyl, $-ZNR^5R^{11}$, wherein $R^{11}$ is haloalkyl, $-C(O)N(R^5)_2$, $-NHC(O)C1$-C3 alkyl, $-CH_2NHC(O)C1$-C3 alkyl, heteroaryl, heteroarylalkyl, dialkylaminylalkyl, or heterocyclylalkyl, wherein the heterocyclyl portion is substituted with one or more substituents independently selected from halogen, hydroxyl, alkoxy and C1-C3 alkyl, and wherein the heteroaryl or the heteroaryl portion of the heteroarylalkyl is optionally substituted with one or more $R^1$;

p is one or two; and wherein, when $\!=\!\!=\!\!=\!$ is a triple bond then $R^A$ is absent, $R^B$ is present and p equals one;

or when $\!=\!\!=\!\!=\!$ is a double bond then $R^A$ is present, $R^B$ is present and p equals two, or $R^A$, $R^B$ and the carbon atoms to which they are attached form a 5-8 membered partially saturated cycloalkyl optionally substituted with one or more $R^7$.

In certain embodiments, $R^1$—X is:

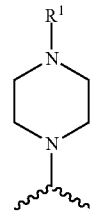

wherein $R^1$ is as defined for Formula I and the piperazinyl ring is optionally substituted with one or more $R^8$, where $R^8$ is as defined for Formula I. In certain embodiments, $R^8$ is C1-C3 alkyl wherein the alkyl is optionally substituted with cyano or $OR^5$, or $-C(O)N(R^5)_2$, wherein each $R^5$ is independently hydrogen or C1-C3 alkyl. In certain embodiments, $R^8$ is heteroalkyl, C2-C4 alkynyl, or C1-C3alkyl optionally substituted with $-OR^5$, cyano or heteroaryl. In certain embodiments, $R^8$ is $C_1$-C3 alkyl optionally substituted with cyano. In certain embodiments, $R^8$ is cyano.

In one embodiment, $R^1$ is $-SO_2C(R^A)\!=\!\!=\!\!=\!C(R^B)_p$, wherein $\!=\!\!=\!\!=\!$ is a double bond, p is two, and $R^A$, $R^B$ and p are as defined for Formula I.

In particular embodiments, $R^1$ is $-C(O)C(R^A)\!=\!\!=\!\!=\!C(R^B)_p$ where $R^A$, $R^B$ and p are as defined for Formula I. In one embodiment, $R^1$ is $-C(O)C(R^A)\!=\!\!=\!\!=\!C(R^B)_p$, wherein $\!=\!\!=\!\!=\!$ is a triple bond and $R^A$ is absent, p is one and $R^B$ is as defined for Formula I. In one embodiment, $R^1$ is $-C(O)C(R^A)\!=\!\!=\!\!=\!C(R^B)_p$, wherein $\!=\!\!=\!\!=\!$ is a triple bond and $R^A$ is absent, p is one and $R^B$ is hydroxyalkyl.

In one embodiment, $R^1$ is $-C(O)C(R^A)\!=\!\!=\!\!=\!C(R^B)_p$, wherein $\!=\!\!=\!\!=\!$ is a double bond, p is two, and $R^A$, $R^B$ and p are as defined for Formula I. In one embodiment, $R^1$ is $-C(O)C(R^A)\!=\!\!=\!\!=\!C(R^B)_p$, wherein $\!=\!\!=\!\!=\!$ is a double bond, $R^A$ is hydrogen or C1-C3 alkyl, p is two, and at least one $R^B$ is deuterium, cyano, C1-C3 alkyl, hydroxyalkyl, heteroalkyl, C1-C3 alkoxy, halogen, haloalkyl, $-ZNR^5R^{11}$, $-C(O)N(R^5)_2$, $-NHC(O)C1$-C3 alkyl, $-CH_2NHC(O)C1$-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$. In one embodiment, when ══ is a double bond, the double bond is in the E configuration. In one embodiment, the double bond is in the Z configuration.

In certain embodiments, $R^1$ is —C(O)C($R^4$)══C($R^B$)$_p$, wherein ══ is a double bond, p is two, one $R^B$ is heterocyclylalkyl substituted with one or more substituents independently selected from halogen, hydroxyl, alkoxy or C1-C3 alkyl and the other $R^B$ is hydrogen. In one embodiment, the heterocyclyl portion of the heterocyclylalkyl is azetidinyl substituted with a halogen. In certain embodiments, the halogen is fluorine. In one embodiment, the heterocyclyl portion of the heterocyclylalkyl is pyrrolidinyl substituted with one or more halogen. In certain embodiments, the halogen-substituted pyrrolidinyl is fluoropyrrolidinyl or difluoropyrrolidinyl.

In certain embodiments, $R^1$ is —C(O)C($R^4$)══C($R^B$)$_p$, wherein ══ is a double bond and p is two, wherein one $R^B$ is halogen and the other $R^B$ is hydrogen. In one embodiment, the halogen is chlorine.

In certain embodiments, $R^1$ is —C(O)C($R^4$)══C($R^B$)$_p$, wherein ══ is a double bond and p is two, wherein one $R^B$ is haloalkyl and the other $R^B$ is hydrogen. In one embodiment, the haloalkyl is chloromethyl, fluoromethyl, difluoromethyl or trifluoromethyl.

In certain embodiments, $R^1$ is —C(O)C($R^4$)══C($R^B$)$_p$, wherein ══ is a double bond and p is two, wherein one $R^B$ is heteroalkyl and the other $R^B$ is hydrogen. In one embodiment, the heteroalkyl is methoxymethyl.

In certain embodiments, $R^1$ is —C(O)C($R^4$)══C($R^B$)$_p$, wherein ══ is a double bond and p is two, wherein one $R^B$ is —ZN$R^5R^{11}$, wherein Z is methylene, $R^5$ is methyl and $R^{11}$ is trifluoromethyl or 2,2,2-trifluoroethyl, and the other $R^B$ is hydrogen.

In certain embodiments, $R^1$ is —C(O)C($R^4$)══C($R^B$)$_p$, wherein ══ is a double bond and p is two, wherein one $R^B$ is hydroxyalkyl and the other $R^B$ is hydrogen.

In certain embodiments, $R^1$ is —C(O)C($R^4$)══C($R^B$)$_p$, wherein ══ is a double bond and p is two, wherein one $R^B$ is heteroaryl optionally substituted with one or more $R^7$ and the other $R^B$ is hydrogen. In one embodiment, the heteroaryl is pyrrolyl, imidazolyl, pyrazolyl, triazolyl, pyridyl, pyridazinyl, pyrimidinyl, pyrazinyl or triazinyl, each substituted with one or more $R^7$.

In certain embodiments, $R^1$ is —C(O)C($R^4$)══C($R^B$)$_p$, wherein ══ is a double bond and p is two, wherein one $R^B$ is heteroarylalkyl optionally substituted with one or more $R^7$, and the other $R^B$ is hydrogen. In one embodiment, the heteroaryl portion of the heteroarylalkyl is pyrrolyl, imidazolyl, pyrazolyl, triazolyl, pyridyl, pyridazinyl, pyrimidinyl, pyrazinyl or triazinyl, each optionally substituted with one or more $R^7$. In one embodiment, the one or more $R^7$ is C1-C3 alkyl.

In certain embodiments, $R^1$ is —C(O)C($R^4$)══C($R^B$)$_p$, wherein ══ is a double bond and p is two, wherein one $R^B$ is —C(O)N($R^5$)$_2$ and the other $R^B$ is hydrogen. In one embodiment, each $R^5$ is hydrogen. In one embodiment, each $R^5$ is C1-C3 alkyl.

In certain embodiments, $R^1$ is —C(O)C($R^4$)══C($R^B$)$_p$, wherein ══ is a double bond and p is two, wherein one $R^B$ is —NHC(O)C1-C3 alkyl or —CH$_2$NHC(O)C1-C3 alkyl and the other $R^B$ is hydrogen. In one embodiment, the C1-C3 alkyl is methyl.

In one embodiment, $R^1$ is —C(O)C($R^4$)══C($R^B$)$_p$ wherein ══ is a double bond, wherein $R^4$ is deuterium, cyano, halogen, C1-C-3 alkyl, haloalkyl, heteroalkyl, —C(O)N($R^5$)$_2$, or hydroxyalkyl, p is two, and each $R^B$ is hydrogen. In one embodiment, $R^4$ is halogen. In one embodiment, the halogen is fluorine or chlorine. In one embodiment, $R^4$ is haloalkyl. In one embodiment, the haloalkyl is trifluoromethyl. In one embodiment, $R^4$ is cyano. In one embodiment, $R^4$ is heteroalkyl. In one embodiment, the heteroalkyl is methoxy. In one embodiment, $R^4$ is hydroxyalkyl.

In one embodiment, $R^1$ is —C(O)C($R^4$)══C($R^B$)$_p$, wherein ══ is a double bond, and $R^4$ is deuterium, p is two and at least one $R^B$ is deuterium.

In one embodiment, $R^1$ is —C(O)C($R^4$)══C($R^B$)$_p$, wherein ══ is a double bond, p is two, $R^4$ is hydrogen, p is two and each $R^B$ is hydrogen.

In one embodiment, $R^1$ is —C(O)C($R^4$)══C($R^B$)$_p$, wherein ══ is a double bond and p is two, one $R^B$ is hydrogen and $R^4$ and one $R^B$ and the carbon atoms to which they are attached form a 5-8 membered partially saturated cycloalkyl substituted with oxo.

In one embodiment, $R^1$ is —C(O)C($R^4$)══C($R^B$)$_p$, wherein ══ is a double bond and p is two, one $R^B$ is hydrogen, the second $R^B$ is dialkylaminylalkyl, and $R^4$ is halogen.

In one embodiment, Y is O or $NR^5$ and $R^2$ is selected from the group consisting of alkyl, hydroxyalkyl, dihydroxyalkyl, alkylaminylalkyl, dialkylaminylalkyl, heterocyclyl, heterocyclylalkyl, —$NR^5SO_2$C1-C3 alkyl, haloalkyl and heteroaryl. In one embodiment, Y is O and $R^2$ is hydroxyalkyl, dihydroxyalkyl, alkylaminylalkyl, or dialkylaminylalkyl, wherein the alkylaminylalkyl or dialkylaminylalkyl is optionally substituted with one or more $R^9$. In one embodiment, the optionally substituted alkylaminylalkyl or dialkylaminylalkyl is independently selected from methylaminylpropan-2-yl, dimethylaminylethyl, methylethylaminylethyl, dimethylaminylpropanyl, dimethylaminylpropan-2-yl, dimethylaminylbutanyl, dimethylaminylbutan-2-yl, 2-dimethylaminylpropanol, or diethylaminylethyl. In one embodiment, Y is O or $NR^5$ and $R^2$ is heterocyclyl or heterocyclylalkyl optionally substituted with one or more $R^9$. Nonlimiting examples of one or more $R^9$ when $R^2$ is heterocyclyl or heterocyclylalkyl include C1-C3 alkyl, acyl, oxo, cyano, alkoxy, cycloalkyl, cycloalkylmethyl, halogen, and hydroxyl. Nonlimiting examples of the heterocyclyl portion when $R^2$ is heterocyclyl or heterocyclylalkyl each optionally substituted with one or more $R^9$ include azetidinyl, C1-C4 alkyl-substituted azetidinyl (e.g., methylazetidinyl, ethyl-azetidinyl, isopropylazetidinyl, or tert-butylazetidinyl), halo-substituted azetidinyl (e.g., difluoroazetidinyl), dimethylaminyl-substituted azetidinyl, cycloalkyl-substituted azetidinyl (e.g., cyclopropyl), C1-C4 alkyl-disubstituted azetidinyl (e.g., dimethylazetidinyl), azetidinyl substituted with two C1-C4 alkyl and alkoxy, oxetanyl, C1-C4 alkyl-substituted oxetanyl (e.g., methyloxetanyl), tetrahydropyran, pyrrolidinyl, C1-C3 alkyl-substituted pyrrolidinyl (e.g., methylpyrrolidinyl, dimethylpyrrolidinyl, and isopropylpyrrolidinyl), cycloalkylpyrrolidinyl (e.g., cyclopropylpyrrolidinyl and cyclobutylpyrrolidinyl) cycloalkylalkylpyrrolidinyl, hydroxypyrrolindinyl, halo-substituted pyrrolidinyl (e.g., fluoropyrrolidinyl and difluoropyrrolidinyl), haloalkyl-substituted pyrrolidinyl (e.g., fluoroethylpyrrolidinyl and difluoroethylpyrrolidinyl), pyrrolidinyl substituted with one or more substituted independently selected from halogen and C1-C6 alkyl (e.g., N-methyl-3,3-difluoropyrrolidinyl, N-methyl-3-fluoropyrrolidinyl, methoxyethylpyrrolidinyl, (N-methyl)methoxypyrrolidinyl, piperazinyl, dimethylaminylpyrrolidinyl, morpholinyl, methylmorpholinyl, 1,4-oxazepanyl, 1,4-oxazinyl, piperdinyl, C1-C3 alkyl-substituted piperidinyl (e.g., methylpiperidinyl), acylpiperdinyl, cyanopiperdinyl, cycloalkylpiperdinyl, halopiperdinyl (e.g., fluoropiperdinyl), dihalopiperdinyl (e.g., difluoropiperdinyl), alkoxypiperdinyl, heterocyclyl-substituted piperdinyl (e.g., tertrahydropyranyl), piperidonyl, thiomorpholinyl-1,1-dioxide, hexahydrofuro[3.2-b]furanyl, (3R, 3aR, 6R, 6aR)-hydroxyhexahydrofuro[3.2-b]furanyl, 3-azabicyclo[3.1.0]hexanyl (e.g., (1S, 2S, 5R)-azabicyclo[3.1.0]hexanyl and (1R, 2S, 5S-azabicyclo[3.1.0]hexanyl), oxa-5-azabicyclo[2.2.1]heptan-5-yl, and 2-methyl-azabicyclo[2.2.1]heptan-2-yl, azabicyclo[2.2.1]heptan-2-yl.

In one embodiment, the heterocyclyl portion when $R^2$ is heterocyclyl or heterocyclylalkyl is tetrahydropyrazinyl optionally substituted with one or more $R^9$. In one embodiment, the tetrahydropyrazinyl is substituted with one $R^9$, wherein $R^9$ is halogen, hydroxyalkyl or haloalkyl.

In one embodiment wherein $R^2$ is heterocyclylalkyl optionally substituted with one or more $R^9$, the alkyl portion of the heterocyclylalkyl is C1-C3 alkyl. In one embodiment the alkyl portion is methylene. In one embodiment the alkyl portion is ethylene. In one embodiment the alkyl portion is propylene.

In one embodiment, Y is O and $R^2$ is heteroarylalkyl optionally substituted with one or more $R^9$. In one embodiment, the heteroaryl portion of the heteroarylalkyl is pyridinyl, imidazolyl, pyrazolyl, pyrrolopyrimdinyl and tetrahydroisoquinolinyl, each optionally substituted with one ore more $R^9$.

In one embodiment, Y is O and $R^2$ is aralkyl optionally substituted with one or more $R^9$. In one embodiment, the aryl portion of the aralkyl is phenyl. In one embodiment, the phenyl is substituted with a single $R^9$, wherein $R^9$ is amino.

In one embodiment, Y is O and $R^2$ is —$ZR^5R^{10}$. In one embodiment, $R^5$ is C1-C3 alkyl and $R^{10}$ is independently selected from acyl, hydroxyalkyl or alkoxy.

In one embodiment, Y is O and $R^2$ is —$NR^5SO_2C1$-C3 alkyl. In one embodiment, $R^5$ is hydrogen and the C1 C3 alkyl is methyl.

In one embodiment, Y is O and $R^2$ is haloalkyl. In one embodiment, the haloalkyl is 1,1,1-trifluoropropyl In one embodiment, Y is a bond and $R^2$ is hydrogen, alkyl, haloalkyl, alkoxy, cycloalkyl, —$NR^5SO_2C1$-C3 alkyl, heterocyclyl or aryl, wherein said heterocyclyl and aryl are optionally substituted with one or more $R^9$.

In one embodiment, Y is a bond and $R^2$ is hydrogen.

In one embodiment, Y is a bond and $R^2$ is alkyl. In one embodiment, the alkyl is a C1-C3 alkyl. In one embodiment, the C1-C3 alkyl is methyl.

In one embodiment, Y is a bond and $R^2$ is haloalkyl. In one embodiment, the haloalkyl is trifluormethyl.

In one embodiment, Y is a bond and $R^2$ is alkoxy. In one embodiment, the alkoxy is methoxy.

In one embodiment, Y is a bond and $R^2$ is cycloalkyl. In one embodiment, the cycloalkyl is cyclopropyl. In one embodiment, Y is a bond and $R^2$ is heterocyclyl optionally substituted with one or more $R^9$. In one embodiment, Y is a bond and $R^2$ is heterocyclyl optionally substituted with methyl, halogen or dimethylamino. Nonlimiting examples of $R^2$ heterocyclyls include azetidinyl, piperidinyl, piperazinyl, morpholinyl, and pyrrolidinyl.

In one embodiment, Y is a bond and $R^2$ is aryl optionally substituted with one or more $R^9$. In one embodiment, the aryl is phenyl substituted with heterocyclylalkyl.

In certain other embodiments when X is a monocyclic ring, $R^4$ is aryl. In one embodiment, $R^4$ is selected from the group consisting of phenyl and naphthyl and is optionally substituted with one or more $R^6$, $R^7$ or $R^9$. Examples of $R^7$ substituents include halogen, hydroxyl, C1-C6 alkyl (e.g., C1-C3 alkyl), cycloalkyl, haloalkyl, Q-haloalkyl, amino, cyano, hydroxyalkyl and alkoxy. In one embodiment, the aryl is phenyl substituted with one or more $R^7$ groups independently selected from halogen, hydroxyl, C1-C3 alkyl, haloalkyl, Q-haloalkyl, and alkoxy. In one embodiment, the aryl is phenyl substituted with one or more $R^7$ groups independently selected from halogen, haloalkyl, methyl, isopropyl, methoxy, Q-haloalkyl and hydroxyl. In one embodiment, the aryl is phenyl substituted with one or more $R^7$ groups independently selected from methyl, trifluoromethyl, 2,2,2-trifluoroethyl, hydroxyl, trifluoromethoxy, hydroxyl, fluoro, chloro, isopropyl, amino, cyclopropyl and trifluoromethylthio. In one embodiment, the aryl is phenyl substituted with one to three $R^7$ groups independently selected from amino, hydroxyl, cyclopropyl, fluorine and chlorine. In one embodiment, the aryl is phenyl substituted with hydroxyl and C1-C3 alkyl or two C1-C3 alkyl. In one embodiment, the aryl is phenyl substituted with chloro and cyclopropyl. In one embodiment, the aryl is phenyl substituted with Q-haloalkyl and hydroxyl or fluorine. In one embodiment, the aryl is phenyl substituted with amino, two chlorines and fluorine.

In one embodiment, $R^4$ is aryl wherein aryl is naphthyl optionally substituted with one or more $R^7$. In one embodiment, the aryl is naphthyl substituted with one or more $R^7$ groups independently selected from halogen, hydroxyl, C3 alkyl, C2-C4 alkynyl, haloalkyl, Q-haloalkyl, and alkoxy. In one embodiment, the aryl is naphthyl substituted with one or more $R^7$ groups independently selected from halogen, haloalkyl, methyl, isopropyl, methoxy, Q-haloalkyl and hydroxyl. In one embodiment, $R^4$ is naphthyl optionally substituted with one or more $R^7$ substituents independently selected from hydroxyl, halogen, C1-C3 alkyl, C2-C4 alkynyl, amino, and haloalkyl. In one embodiment, $R^4$ is naphthyl optionally substituted with one to three $R^7$ substituents independently selected from difluoromethyl, methyl, hydroxyl, amino, ethynyl, 2-propynyl, fluoro, and chloro.

In one embodiment, the aryl is naphthyl optionally substituted with one or more halogen. In one embodiment, the aryl is naphthyl optionally substituted with chloro. In one embodiment, the aryl is naphthyl substituted with chloro and fluoro. In one embodiment, the aryl is naphthyl substituted with C1-C6 alkyl. In one embodiment, the aryl is naphthyl substituted with C2-C4 alkynyl. In one embodiment, the aryl is naphthyl substituted with hydroxyl. In one embodiment, the aryl is naphthyl substituted with hydroxyl and trifluoromethyl or C1-C3 alkyl. In one embodiment, the aryl is naphthyl substituted with hydroxyl. In one embodiment, the aryl is naphthyl which is unsubstituted.

In one embodiment, $R^4$ is heteroaryl optionally substituted with one or more $R^7$. In one embodiment, $R^4$ is heteroaryl optionally substituted with one or more $R^7$ independently selected from halogen, hydroxyl, C3 alkyl, haloalkyl, Q-haloalkyl, alkoxy and amino. In one embodiment, $R^4$ is indoyl, indazolyl, quinolinyl, isoquinolinyl, pyridinyl or benzo[d]thiazolyl optionally substituted with one or more $R^7$. In one embodiment, $R^4$ is indoyl, indazolyl, quinolinyl, isoquinolinyl, pyridinyl or benzo[d]thiazolyl optionally substituted with one or more $R^7$ independently selected from halogen, hydroxyl, C1-C3 alkyl, C2-C4 alkynyl, haloalkyl, Q-haloalkyl, alkoxy and amino.

In yet other embodiments, $R^4$ is heteroaryl, optionally an indoyl or an indazolyl, each of which may be substituted with one or more $R^7$. In one embodiment, $R^4$ is heteroaryl optionally substituted with one or more $R^7$ substituents independently selected from the group consisting of halogen, hydroxyl, C1-C3 alkyl, C2-C4 alkynyl, haloalkyl, Q-haloalkyl and alkoxy. In one embodiment, the $R^4$ heteroaryl is indazolyl optionally substituted with one or two $R^7$ independently selected from alkoxy, haloalkyl, halogen and C1-C6 alkyl. In other embodiments, the $R^4$ heteroaryl is a quinolinyl or isoquinolinyl, each optionally substituted with one or more $R^7$. In one embodiment, the $R^4$ heteroaryl is a quinolinyl or isoquinolinyl, each optionally substituted with one or more $R^7$ independently selected from amino, C1-C3 alkyl, halogen and hydroxyl. In one embodiment, the $R^4$ heteroaryl is a quinolinyl or isoquinolinyl, each optionally substituted with one or more $R^7$ independently selected from methyl, chlorine, hydroxyl and amino. In one embodiment, the $R^4$ heteroaryl is a quinolinyl or isoquinolinyl, each optionally substituted with methyl or chlorine. In one embodiment, the $R^4$ heteroaryl is a pyridinyl optionally substituted with one or more $R^7$. In one embodiment, the $R^4$ heteroaryl is pyridinyl optionally substituted with one or more $R^7$ independently selected from C1-C3 alkyl, halogen and haloalkyl. In other embodiments, the $R^4$ heteroaryl is benzo[d]thiazolyl optionally substituted with one or more $R^7$, such as hydroxyl, one or two C1-C3 alkyl, or hydroxyl and one or two C1-C3 alkyl. In one embodiment, the $R^4$ heteroaryl is indoyl optionally substituted with one or more $R^7$. In one embodiment, the $R^4$ heteroaryl is indoyl optionally substituted with one or two $R^7$ independently selected from hydroxyl and C1-C3 alkyl.

In one embodiment, where X is a monocyclic ring, $R^4$ is aralkyl. In certain embodiments, the aralkyl is benzyl. In other embodiments, the alkyl of the benzyl group is optionally substituted with hydroxyalkyl.

In one embodiment, L is a bond.

In one embodiment, $R^3$ is C1-C3 alkyl. In one embodiment, the C1-C3 alkyl is methyl.

In one embodiment, $R^3$ is halogen. In one embodiment, the halogen is fluorine or chlorine.

In one embodiment, $R^3$ is —$OR^5$, wherein $R^5$ is hydrogen.

In one embodiment, $R^3$ is —O-haloalkyl. In one embodiment, the haloalkyl is 1,1,1-trifluroethyl.

In one embodiment, $R^8$ is heteroalkyl, C2-C4 alkynyl or C1-C3 alkyl optionally substituted with —$OR^5$, cyano or heteroaryl. In one embodiment, $R^8$ is methyl, cyanomethyl, methoxymethyl, or hydroxymethyl. In one embodiment, $R^8$ is methyl. In one embodiment, $R^8$ is cyanomethyl. In one embodiment, $R^8$ is hydroxymethyl.

In one embodiment, Formula I includes compounds having the Formula I-A:

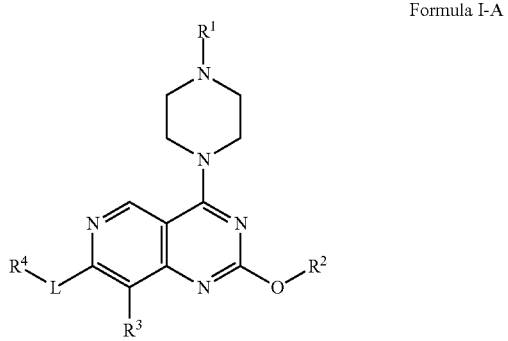

Formula I-A and $R^1$, $R^3$, $R^4$, $R^9$, and L are as defined for Formula I, $R^2$ is heterocyclylalkyl optionally substituted with one or more $R^9$, and the piperidinyl ring is optionally substituted with one or more $R^8$, where $R^8$ is as defined for Formula I. In one embodiment, the heterocyclyl portion of the $R^2$ heterocyclylalkyl is a monocyclic, bicyclic, or bridged ring system having one or two ring heteroatoms independently selected from N and O. In one embodiment, $R^2$ heterocyclyl is azetidinyl, pyrrolidinyl, piperidinyl, piperazinyl, morpholinyl, oxetanyl, 1,4-oxazepanyl, tetrahydropyrazinyl, thiomorpholinyl-1,1-dioxide, hexahydrofuro[3.2-b]furanyl, (3R, 3aR, 6R, 6aR)-hydroxyhexahydrofuro[3.2-b]furanyl, 3-azabicyclo[3.1.0]hexanyl, 2-oxa-5-azabicyclo[2.2.1]heptan-5-yl, and azabicyclo[2.2.1]heptan-2-yl, optionally substituted with one or more $R^9$. In one embodiment, each $R^9$ is selected from acyl, oxo, halogen, cyano, C1-C3 alkyl, alkoxy, hydroxyalkyl, heteroalkyl, cycloalkyl, aralkyl and dialkylamidoalkyl. In one embodiment, L is a bond. In one embodiment, $R^4$ is aryl or heteroaryl, each of which is optionally substituted with one or more $R^6$ or $R^7$. In one embodiment, $R^4$ is aryl or heteroaryl, each of which is optionally substituted with one or more $R^7$. In one embodiment, each $R^7$ is independently selected from hydroxyl, amino, halogen, C1-C3 alkyl, C2-C4-alkynyl, haloalkyl, Q-haloalkyl, cycloalkyl and alkoxy. In one embodiment, the aryl is phenyl substituted with one or more $R^7$ groups independently selected from halogen, hydroxyl, C1-C3 alkyl, haloalkyl, Q-haloalkyl, and alkoxy. In one embodiment, the aryl is phenyl substituted with one or more $R^7$ groups independently selected from halogen, haloalkyl, methyl, isopropyl, methoxy, Q-haloalkyl and hydroxyl. In one embodiment, the aryl is phenyl substituted with one or more $R^7$ groups independently selected from methyl, trifluoromethyl, 2,2,2-trifluoroethyl, hydroxyl, trifluoromethoxy, hydroxyl, fluoro, chloro, isopropyl, cyclopropyl and trifluoromethylthio. In one embodiment, the aryl is phenyl substituted with one to three $R^7$ groups independently selected from hydroxyl, fluorine and chlorine. In one embodiment, the aryl is phenyl substituted with hydroxyl and C1-C3 alkyl or two C1-C3 alkyl. In one embodiment, the aryl is phenyl substituted with Q-haloalkyl and hydroxyl or fluorine. In one embodiment, the aryl is naphthyl substituted with one or more $R^7$ groups independently selected from halogen, hydroxyl, C1-C3 alkyl, C2-C4-alkynyl, haloalkyl, Q-haloalkyl, and alkoxy. In one embodiment, the aryl is naphthyl substituted with one or more $R^7$ groups independently selected from halogen, haloalkyl, methyl, isopropyl, methoxy, Q-haloalkyl and hydroxyl. In one embodiment, $R^4$ is naphthyl optionally substituted with one or more $R^7$ substituents independently selected from hydroxyl, halogen, C1-C3 alkyl, C2-C4-alkynyl, amino, and haloalkyl. In one embodiment, $R^4$ is naphthyl optionally substituted with one to three $R^7$ substituents independently selected from difluoromethyl, methyl, hydroxyl, amino, fluoro, and chloro. In one embodiment, the aryl is naphthyl optionally substituted with one or more halogen. In one embodiment, the aryl is naphthyl substituted with hydroxyl and trifluoromethyl or C1-C3 alkyl. In one embodiment, the aryl is naphthyl substituted with hydroxyl. In one embodiment, the aryl is naphthyl substituted with ethynyl or 2-propynyl. In one embodiment, $R^4$ is heteroaryl, wherein the heteroaryl is indazolyl optionally substituted with one or two $R^7$ independently selected from alkoxy, haloalkyl, and C1-C6 alkyl. In one embodiment, $R^4$ is heteroaryl, wherein the heteroaryl is quinolinyl or isoquinolinyl, each optionally substituted with one or more $R^7$. In one embodiment, $R^4$ is heteroaryl, wherein the heteroaryl is quinolinyl or isoquinolinyl, each optionally substituted with one or more amino, C1-C3 alkyl, C2-C4 alkynyl, halogen or hydroxyl. In one embodiment, the $R^4$ heteroaryl is a pyridinyl optionally substituted with one or more $R^7$. In one embodiment, the $R^4$ heteroaryl is pyridinyl optionally substituted with one or more $R^7$ independently selected from C1-C3 alkyl, halogen and haloalkyl. In one embodiment, the $R^4$ heteroaryl is benzo[d]thiazolyl optionally substituted with one or more $R^7$, such as hydroxyl, one or two C1-C3 alkyl, or hydroxyl and one or two C1-C3 alkyl. In one embodiment, the $R^4$ heteroaryl is indolyl optionally substituted with one or more $R^7$. In one embodiment, the $R^4$ heteroaryl is indolyl optionally substituted with one or two $R^7$ independently selected from hydroxyl, halogen and C1-C3 alkyl. In one embodiment, $R^H$ is trifluoromethyl. In one embodiment, the piperidinyl ring is unsubstituted. In one embodiment, the piperidinyl ring is substituted with one $R^8$. In one embodiment, $R^8$ is C1-C3 alkyl optionally substituted with cyano, hydroxyl or methoxy. In one embodiment, $R^8$ is methyl, cyanomethyl, hydroxymethyl or methoxymethyl. In one embodiment, $R^8$ is cyano.

In particular embodiments, $R^1$ is —C(O)C($R^A$)═══C($R^B$)$_p$ where $R^A$, $R^B$ and p are as defined for Formula I. In one embodiment, $R^1$ is —C(O)C($R^A$)═══C($R^B$)$_p$, wherein ═══ is a triple bond and $R^A$ is absent, p is one and $R^B$ is hydroxyalkyl.

In one embodiment, $R^1$ is —C(O)C($R^A$)═══C($R^B$)$_p$, wherein ═══ is a double bond, p is two, and $R^A$, $R^B$ and p are as defined for Formula I. In one embodiment, $R^1$ is —C(O)C($R^A$)═══C($R^B$)$_p$, wherein ═══ is a double bond, $R^A$ is hydrogen or C1-C3 alkyl, p is two, and at least one $R^B$ is deuterium, cyano, C1-C3 alkyl, hydroxyalkyl, heteroalkyl, C1-C3 alkoxy, halogen, haloalkyl, —ZNR$^5$R$^{11}$, —C(O)N(R$^5$)$_2$, —NHC(O)C1-C3 alkyl, —CH$_2$NHC(O)C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more $R^7$. In one embodiment, when ═══ is a double bond, the double bond is in the E configuration. In one embodiment, the double bond is in the Z configuration.

In certain embodiments, $R^1$ is —C(O)C($R^A$)═══C($R^B$)$_p$, wherein ═══ is a double bond, p is two, one $R^B$ is heterocyclylalkyl substituted with one or more substituents independently selected from halogen, hydroxyl, alkoxy or C1-C3 alkyl and the other $R^B$ is hydrogen. In one embodiment, the heterocyclyl portion of the heterocyclylalkyl is azetidinyl substituted with a halogen. In certain embodiments, the halogen is fluorine. In one embodiment, the heterocyclyl portion of the heterocyclylalkyl is pyrrolidinyl substituted with one or more halogen. In certain embodiments, the halogen-substituted pyrrolidinyl is fluoropyrrolidinyl or difluoropyrrolidinyl.

In certain embodiments, $R^1$ is —C(O)C($R^A$)═══C($R^B$)$_p$, wherein ═══ is a double bond and p is two, wherein one $R^B$ is halogen and the other $R^B$ is hydrogen. In one embodiment, the halogen is chlorine.

In certain embodiments, $R^1$ is —C(O)C($R^A$)═══C($R^B$)$_p$, wherein ═══ is a double bond and p is two, wherein one $R^B$ is haloalkyl and the other $R^B$ is hydrogen. In one embodiment, the haloalkyl is chloromethyl, fluoromethyl, difluoromethyl or trifluoromethyl.

In certain embodiments, $R^1$ is —C(O)C($R^A$)═══C($R^B$)$_p$, wherein ═══ is a double bond and p is two, wherein one $R^B$ is heteroalkyl and the other $R^B$ is hydrogen. In one embodiment, the heteroalkyl is methoxymethyl.

In certain embodiments, $R^1$ is —C(O)C($R^A$)═══C($R^B$)$_p$, wherein ═══ is a double bond and p is two, wherein one $R^B$ is —ZNR$^5$R$^{11}$, wherein Z is methylene, R$^5$ is methyl and R$^{11}$ is trifluoromethyl or 2,2,2-trifluoroethyl, and the other $R^B$ is hydrogen.

In certain embodiments, $R^1$ is —C(O)C($R^A$)═══C($R^B$)$_p$, wherein ═══ is a double bond and p is two, wherein one $R^B$ is hydroxyalkyl and the other $R^B$ is hydrogen.

In certain embodiments, $R^1$ is —C(O)C($R^A$)═══C($R^B$)$_p$, wherein ═══ is a double bond and p is two, wherein one $R^B$ is heteroaryl optionally substituted with one or more $R^7$ and the other $R^B$ is hydrogen. In one embodiment, the heteroaryl is pyrrolyl, imidazolyl, pyrazolyl, triazolyl, pyridyl, pyridazinyl, pyrimidinyl, pyrazinyl or triazinyl, each substituted with one or more $R^7$.

In certain embodiments, $R^1$ is —C(O)C($R^A$)═══C($R^B$)$_p$, wherein ═══ is a double bond and p is two, wherein one $R^B$ is heteroarylalkyl optionally substituted with one or more $R^7$, and the other $R^B$ is hydrogen. In one embodiment, the heteroaryl portion of the heteroarylalkyl is pyrrolyl, imidazolyl, pyrazolyl, triazolyl, pyridyl, pyridazinyl, pyrimidinyl, pyrazinyl or triazinyl, each optionally substituted with one or more $R^7$. In one embodiment, the one or more $R^7$ is C1-C3 alkyl.

In certain embodiments, $R^1$ is —C(O)C($R^A$)═══C($R^B$)$_p$, wherein ═══ is a double bond and p is two, wherein one $R^B$ is —C(O)N(R$^5$)$_2$ and the other $R^B$ is hydrogen. In one embodiment, each R$^5$ is hydrogen. In one embodiment, each R$^5$ is C1-C3 alkyl.

In certain embodiments, $R^1$ is —C(O)C($R^A$)═══C($R^B$)$_p$, wherein ═══ is a double bond and p is two, wherein one $R^B$ is —NHC(O)C1-C3 alkyl or —CH$_2$NHC(O)C1-C3 alkyl and the other R$^B$ is hydrogen. In one embodiment, the C1-C3 alkyl is methyl.

In one embodiment of Formula I-A, R$^1$ is —C(O)C(R$^A$)=C(R$^B$)$_p$, wherein R$^A$ is deuterium, cyano, halogen, C1-C-3 alkyl, haloalkyl, heteroalkyl, —C(O)N(R$^5$)$_2$, or hydroxyalkyl, p is two, each R$^B$ is hydrogen. In one embodiment, R$^A$ is halogen. In one embodiment, the halogen is fluorine or chlorine. In one embodiment, R$^A$ is haloalkyl. In one embodiment, the haloalkyl is trifluoromethyl. In one embodiment, R$^A$ is cyano. In one embodiment, R$^A$ is heteroalkyl. In one embodiment, the heteroalkyl is methoxy. In one embodiment, R$^A$ is hydroxyalkyl.

In one embodiment of Formula I-A, R$^1$ is —C(O)C(R$^A$)⸺C(R$^B$)$_p$, wherein ⸺ is a double bond and R$^A$ is deuterium, p is two and at least one R$^B$ is deuterium.

In one embodiment of Formula I-A, R$^1$ is —C(O)C(R$^A$)⸺C(R$^B$)$_p$, wherein ⸺ is a double bond and p is two, one R$^B$ is hydrogen and R$^A$ and one R$^B$ and the carbon atoms to which they are attached form a 5-8 membered partially saturated cycloalkyl substituted with oxo.

In one embodiment of Formula I-A, R$^1$ is —C(O)C(R$^A$)⸺C(R$^B$)$_p$, wherein ⸺ is a double bond and p is two, one R$^B$ is hydrogen, the second R$^B$ is dialkylaminylalkyl, and R$^A$ is halogen.

In one embodiment of Formula I, X is a saturated bridged ring system. Nonlimiting examples of bridged ring systems include diazabicycloheptanes and diazabicyclooctanes. In certain embodiments, when X is a saturated bridged ring system, R$^1$ is —C(O)CH═CH$_2$. In one embodiment, the bridged ring system is substituted with one or two groups independently selected from R$^8$, where R$^8$ is as defined for Formula I. In one embodiment, the bridged ring system is unsubstituted. In one embodiment, the bridged ring system is diazabicyclo[3.2.0]heptan-6-yl, diazabicyclo[3.2.0]heptan-2-yl, diazabicyclo[3.2.1]octan-8-yl or diazabicyclo[3.2.1]octan-3-yl.

In one embodiment of Formula I, R$^1$—X is:

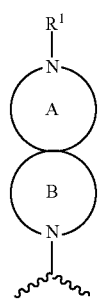

wherein A and B are a spirocyclic ring system, wherein A and B are the same or different and independently represent a 4-6 membered saturated ring system, wherein the rings are optionally substituted with one or more independently selected R$^8$, wherein R$^8$ is as defined for Formula I. In certain embodiments, rings A and B are unsubstituted.

In certain embodiments when A and B represent a spirocyclic ring system, R$^1$ is —C(O)CH═CH$_2$.

In one embodiment when A and B represent a spirocyclic ring system, R$^1$ is —C(O)C(R$^A$)⸺C(R$^B$)$_p$, wherein ⸺ is a double bond and R$^A$ is hydrogen or C1-C3 alkyl, p is two and at least one R$^B$ is deuterium, cyano, C1-C3 alkyl, hydroxyalkyl, heteroalkyl, C1-C3 alkoxy, halogen, haloalkyl, —ZNR$^5$R$^{11}$, —C(O)N(102, —NHC(O)C1-C3 alkyl, —CH$_2$NHC(O)C1-C3 alkyl, heteroaryl, heteroarylalkyl, dialkylaminylalkyl, or heterocyclylalkyl wherein the heterocyclyl portion is substituted with one or more substituents independently selected from halogen, hydroxyl, alkoxy and C1-C3 alkyl, wherein the heteroaryl or the heteroaryl portion of the heteroarylalkyl is optionally substituted with one or more R$^7$. In one embodiment, when ⸺ is a double bond, the double bond is in the E configuration. In one embodiment, the double bond is in the Z configuration.

In one embodiment when A and B represent a spirocyclic ring system, R$^1$ is —C(O)C(R$^A$)═C(R$^B$)$_p$, wherein R$^A$ is deuterium, cyano, halogen, C1-C-3 alkyl, haloalkyl, heteroalkyl, —C(O)N(R$^5$)$_2$, or hydroxyalkyl, p is two, each R$^B$ is hydrogen. In one embodiment, R$^A$ is halogen. In one embodiment, the halogen is fluorine or chlorine. In one embodiment, R$^A$ is haloalkyl. In one embodiment, the haloalkyl is trifluoromethyl. In one embodiment, R$^A$ is cyano. In one embodiment, R$^A$ is heteroalkyl. In one embodiment, the heteroalkyl is methoxy. In one embodiment, R$^A$ is hydroxyalkyl.

In one embodiment, the spirocyclic ring system is unsubstituted. Non-limiting examples of spirocyclic ring systems include:

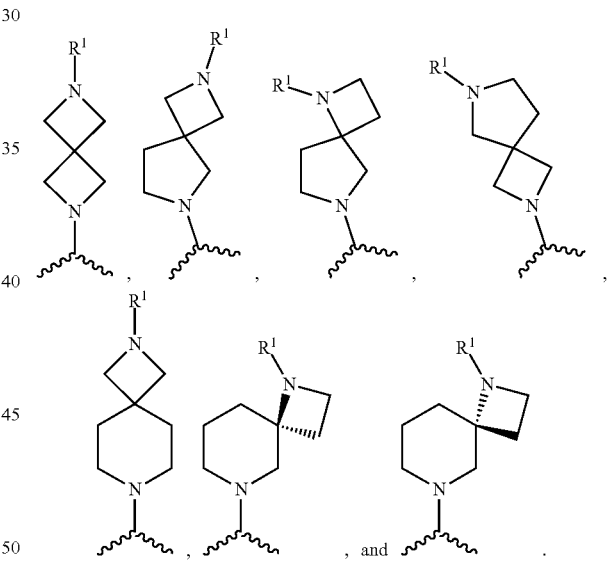

In one embodiment of Formula I when A and B represent a spirocyclic ring system, R$^2$ is selected from the group consisting of hydrogen (wherein Y is a bond), hydroxyalkyl, dialkylaminylalkyl, heterocyclyl and heterocyclylalkyl, wherein each of the heterocyclyl or heterocyclylalkyl are independently optionally substituted with R$^9$. In another embodiment, R$^2$ is heterocyclyl and heterocyclylalkyl, wherein each of the heterocyclyl or heterocyclylalkyl are independently optionally substituted with one or more R$^9$. In certain embodiments, R$^2$ is dialkylaminylalkyl optionally substituted with one or more R$^9$. Non-limiting examples include dimethylaminylethyl, dimethylaminylpropanyl, dimethylaminylpropan-2-yl, dimethylaminylbutanyl, dimethylaminylbutan-2-yl, 2-dimethylaminylpropanol, or diethylaminylethyl.

In one embodiment when A and B represent a spirocyclic ring system, Y is O and $R^2$ is selected from the group consisting of hydroxyalkyl, dialkylaminylalkyl, heterocyclyl, heterocyclylalkyl, and $-ZR^5R^{10}$, wherein $R^5$ and $R^{10}$ are as defined for Formula I. In one embodiment, the heterocyclyl is piperdinyl substituted with one $R^9$, wherein $R^9$ is heterocyclyl.

In one embodiment when A and B represent a spirocyclic ring system, Y is O and $R^2$ is selected from the group consisting of hydroxyalkyl, dialkylaminylalkyl, heterocyclyl and heterocyclylalkyl, wherein each of the heterocyclyl or heterocyclylalkyl are independently optionally substituted with $R^9$. In another embodiment, $R^2$ is heterocyclyl and heterocyclylalkyl, wherein each of the heterocyclyl or heterocyclylalkyl are independently optionally substituted with one or more $R^9$. Non-limiting examples of $R^9$ include acyl, oxo, halogen, cyano, C1-C6 alkyl, alkoxy, hydroxyalkyl, heteroalkyl, heterocyclyl, cycloalkyl, aralkyl or dialkylamidoalkyl. In certain embodiments, $R^2$ is dialkylaminylalkyl optionally substituted with one or more $R^9$. Non-limiting examples include dimethylaminylethyl, dimethylaminylpropanyl, dimethylaminylpropan-2-yl, dimethylaminylbutanyl, dimethylaminylbutan-2-yl, 2-dimethylaminylpropanol, or diethylaminylethyl.

In one embodiment of Formula I when A and B represent a spirocyclic ring system, $R^4$ is aryl optionally substituted with one or more $R^6$ or $R^7$. In one embodiment, $R^4$ is phenyl or naphthyl optionally substituted with one or more $R^6$ or $R^7$. In one embodiment, $R^4$ is phenyl or naphthyl optionally substituted with one or more $R^7$. In one embodiment, $R^4$ is phenyl or naphthyl optionally substituted with one or more $R^7$ substituents independently selected from halogen, hydroxyl, C1-C3alkyl, cycloalkyl, alkoxy, haloalkyl, or Q-haloalkyl wherein Q is O or S. In one embodiment, $R^4$ is phenyl or naphthyl optionally substituted with one or more $R^7$ substituents independently selected from methyl, trifluoromethyl, hydroxyl, trifluoromethoxy, hydroxyl, fluoro, chloro, isopropyl, cyclopropyl and methylthio.

In one embodiment when A and B represent a spirocyclic ring system, $R^4$ is isoquinolinyl which is optionally substituted with amino, C1-C3 alkyl or halogen. In one embodiment, $R^4$ is aralkyl. In certain embodiments, the aralkyl is benzyl. In one embodiment, the aralkyl is benzyl wherein the alkyl portion is substituted with hydroxyl or hydroxyalkyl.

In one embodiment, X is a fused bicyclic ring system. In one embodiment, $R^1-X$ is:

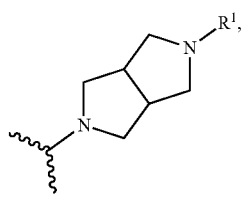

Nonlimiting examples of compounds of Formula I and Formula I-A are selected from the group consisting of:

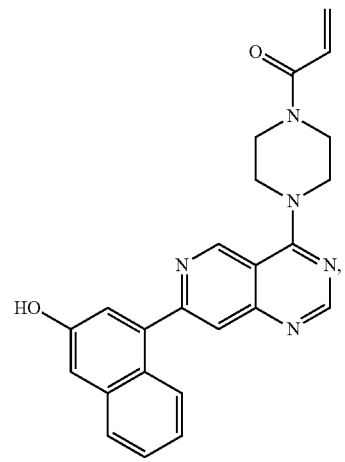

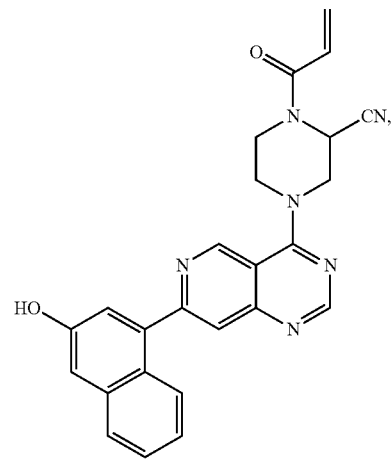

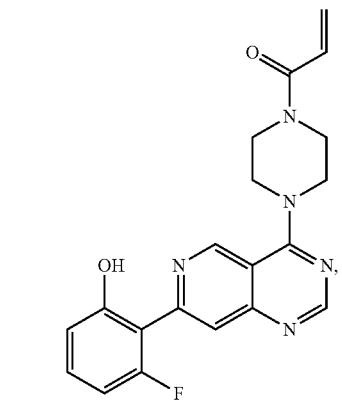

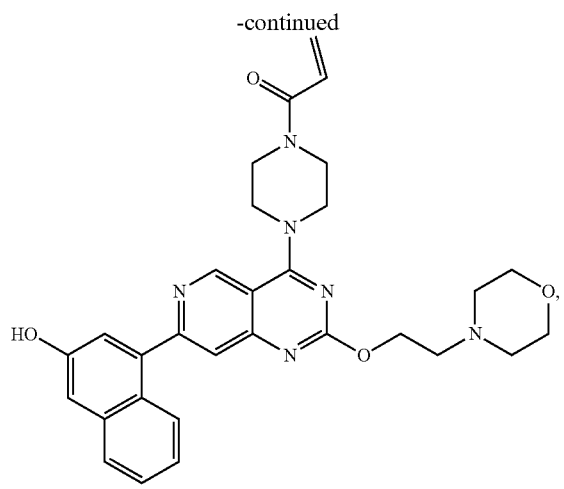
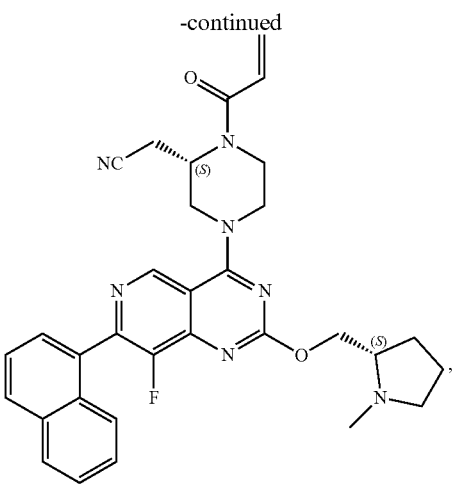
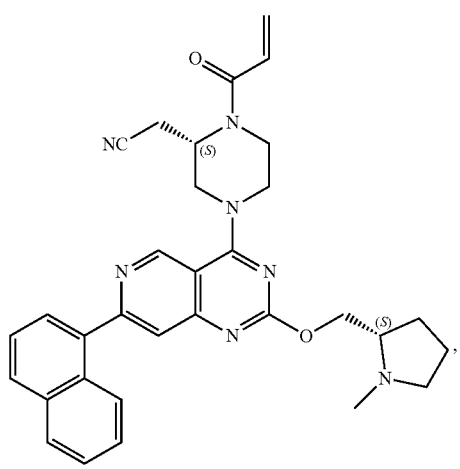
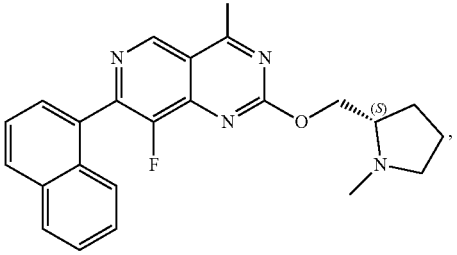
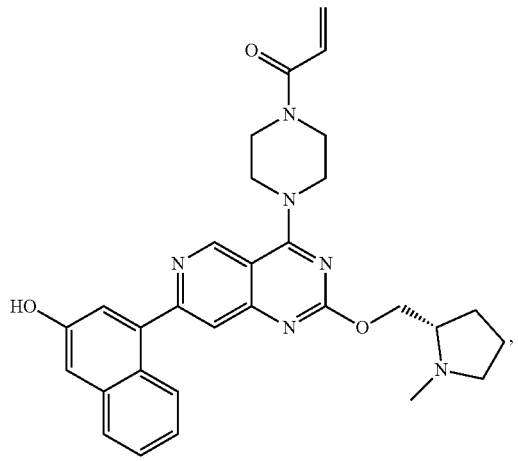
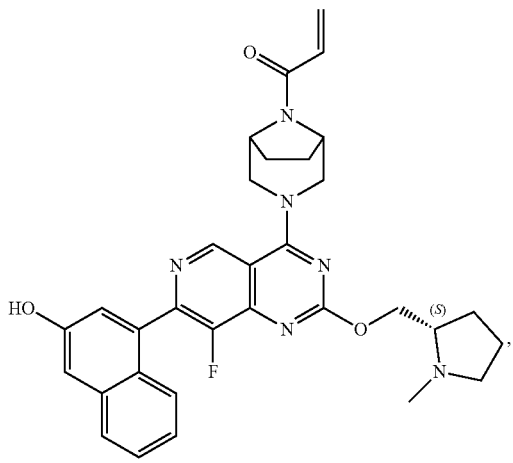

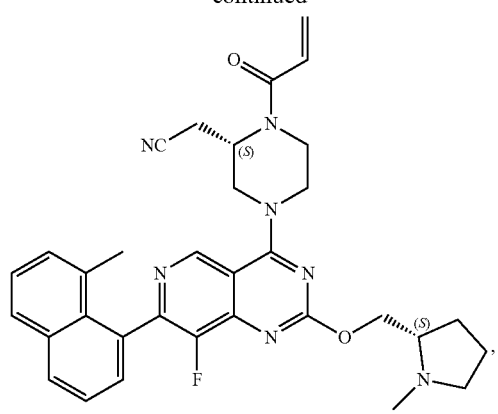
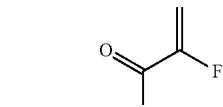
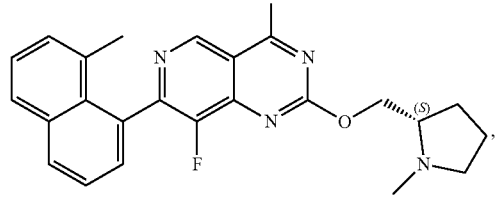
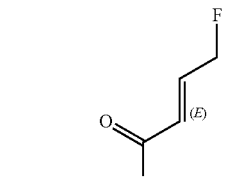
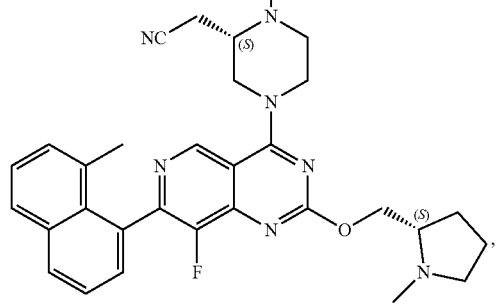
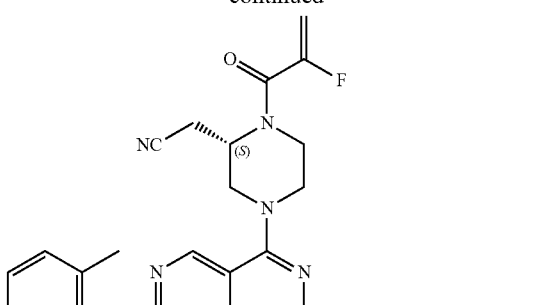
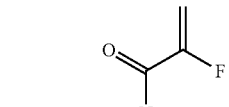
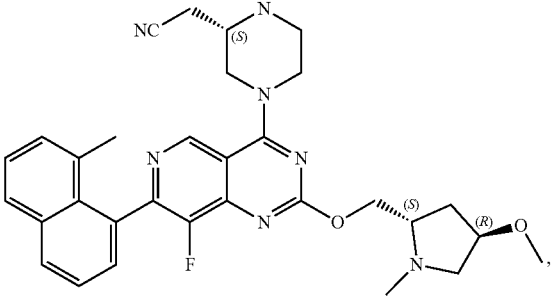
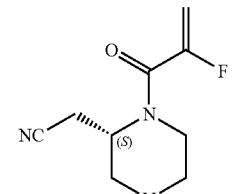
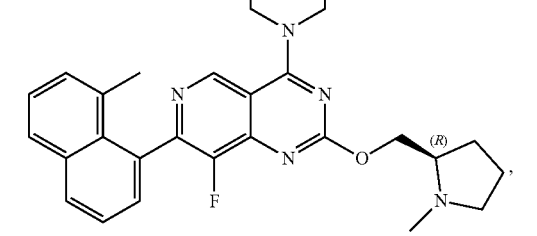
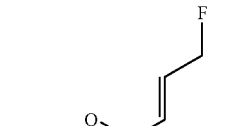
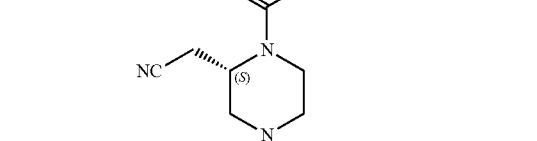
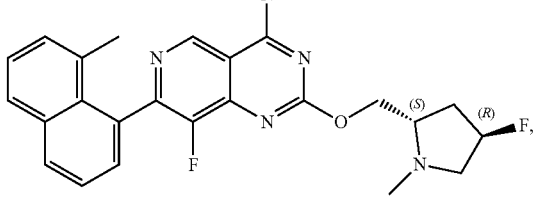

27
-continued
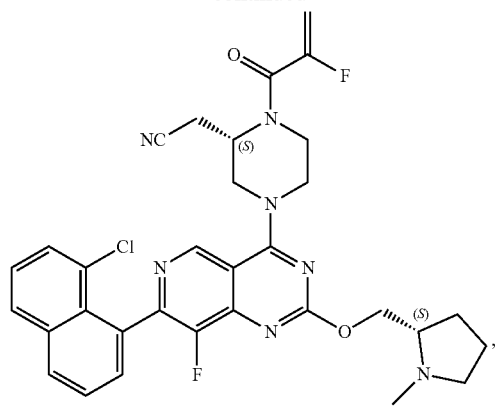
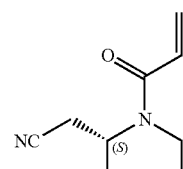
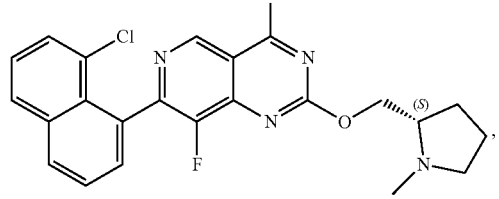
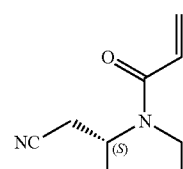
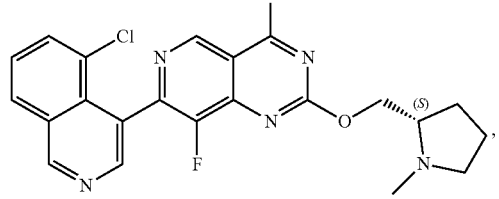
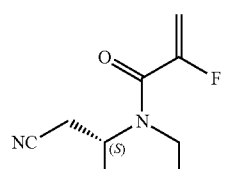
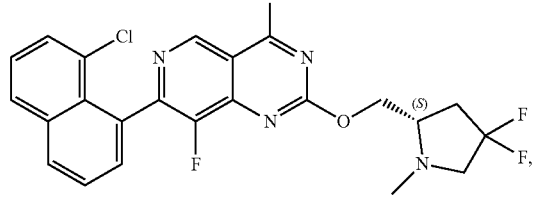
28
-continued
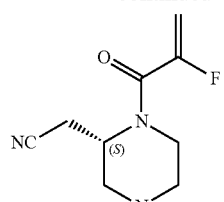
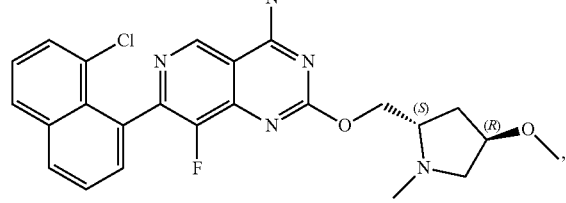
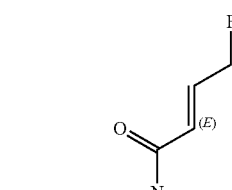
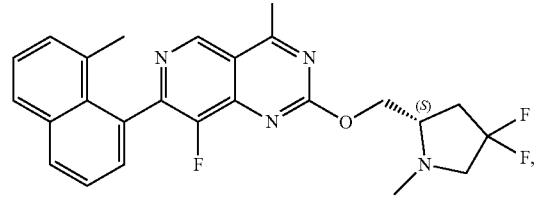
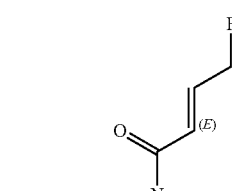
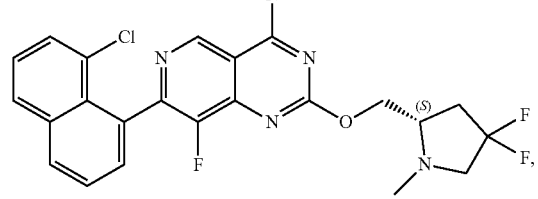

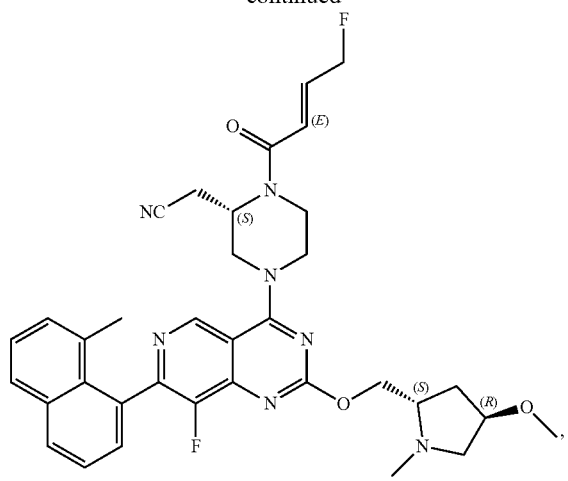
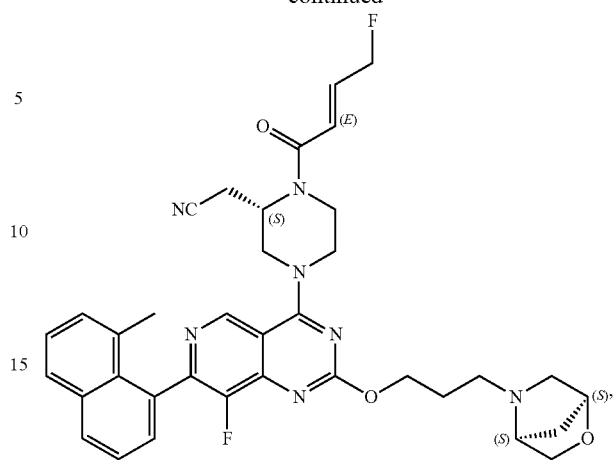
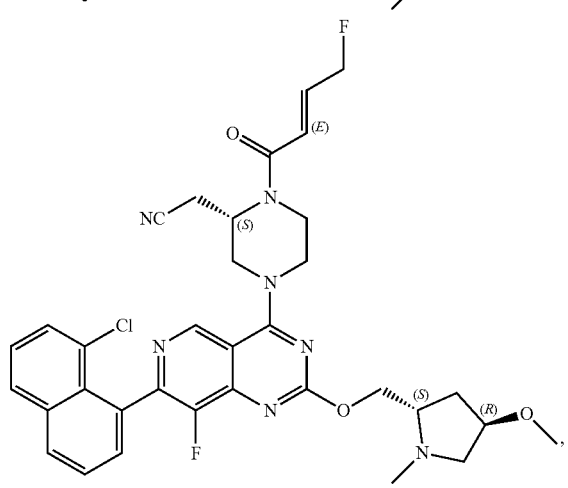
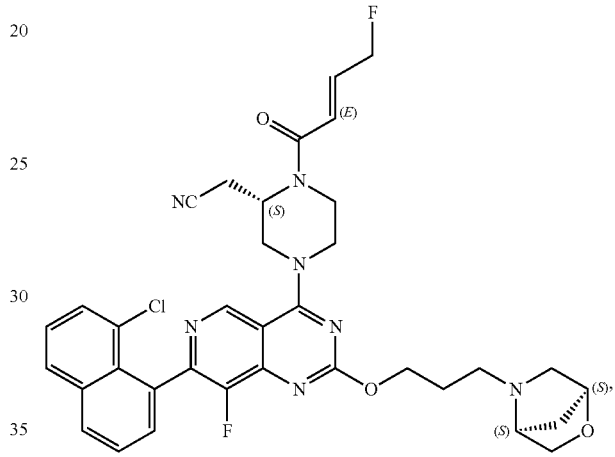
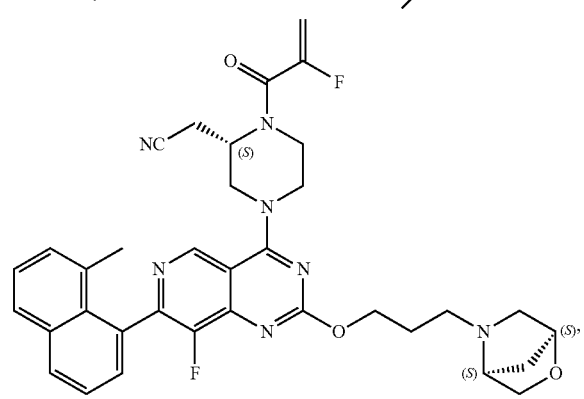
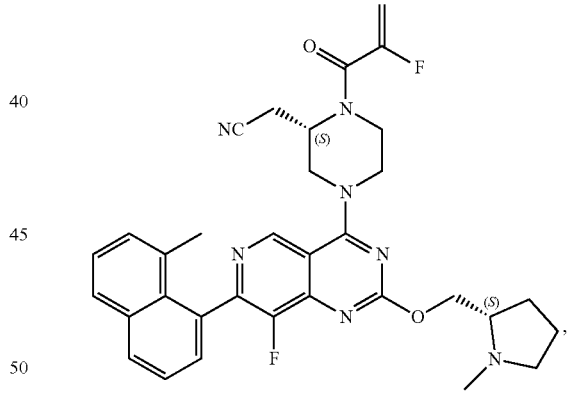
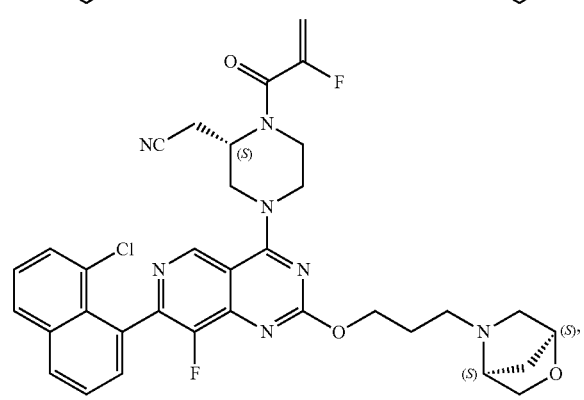
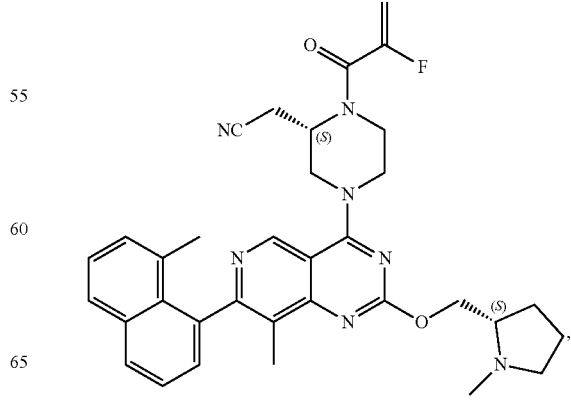

31
-continued
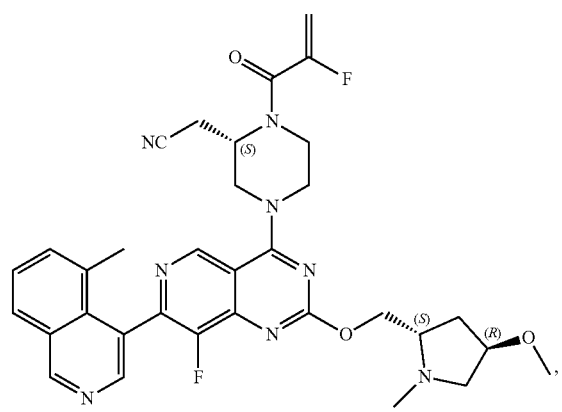
32
-continued
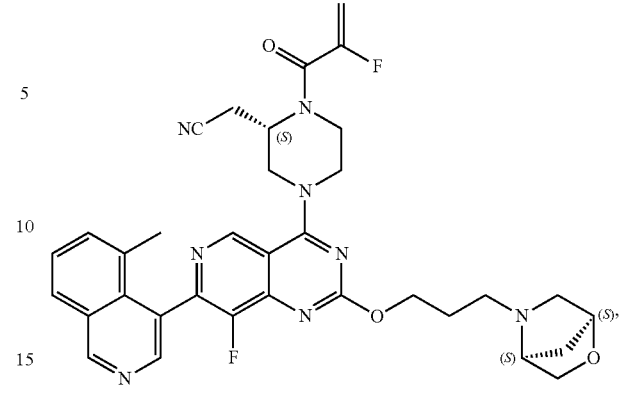
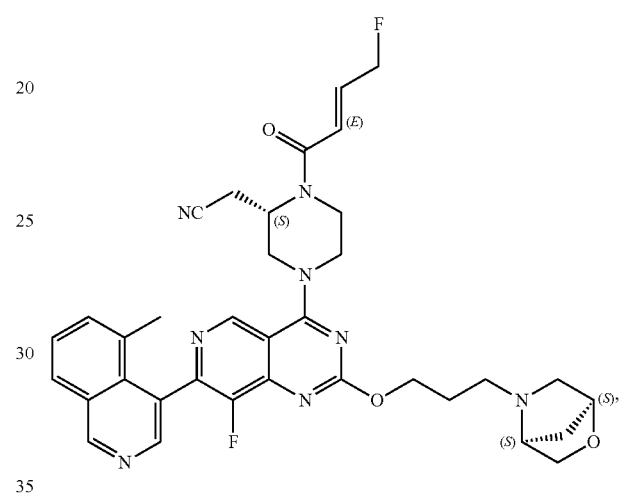
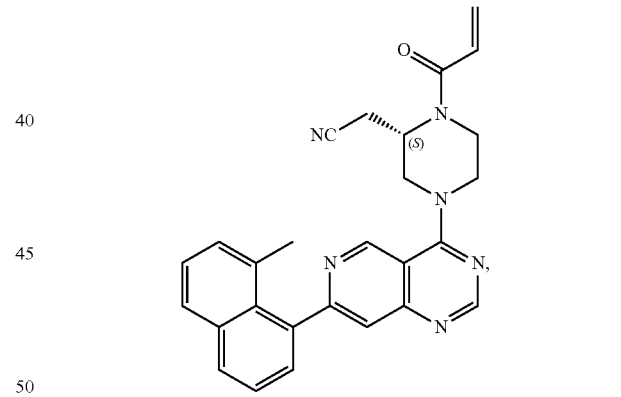
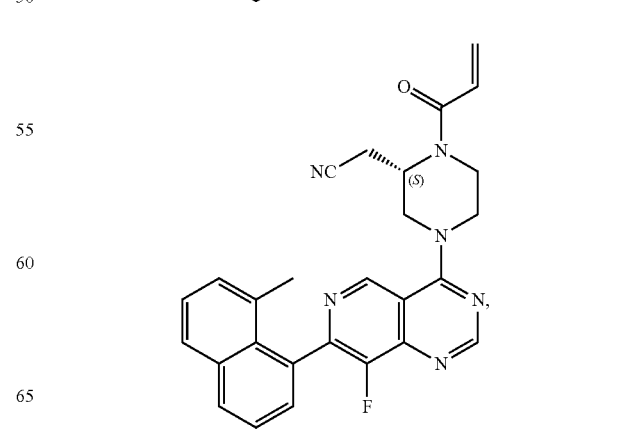

33
-continued
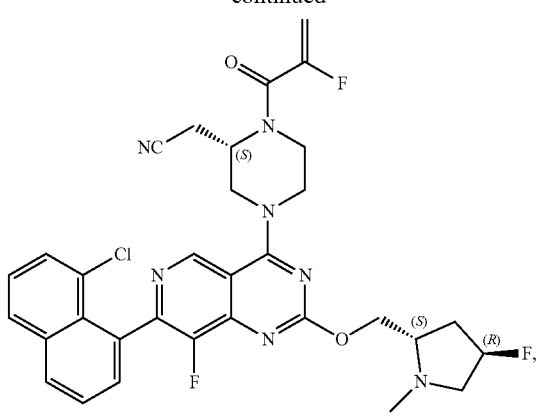
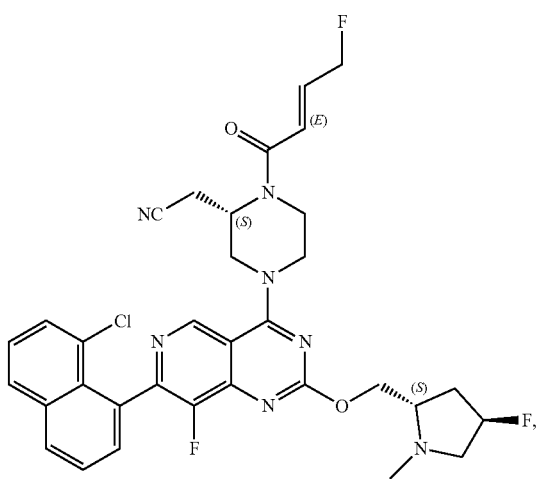
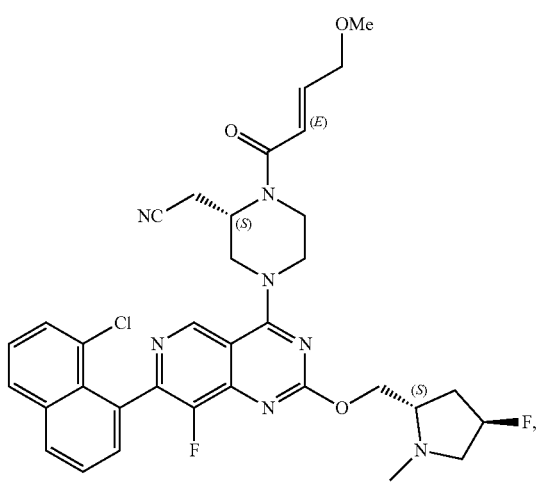
34
-continued
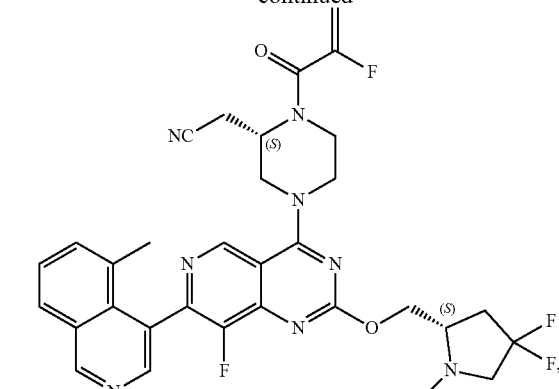
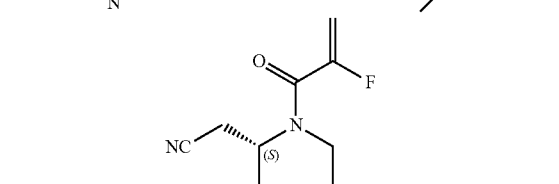
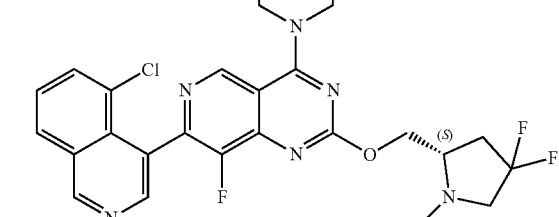
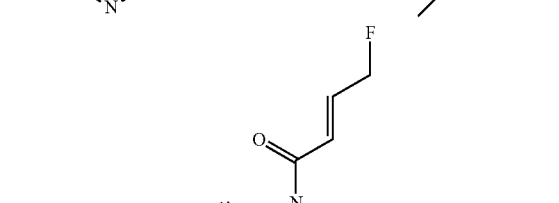
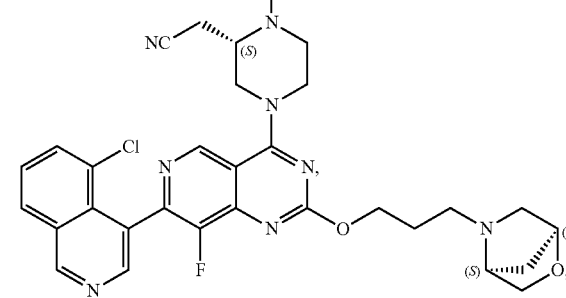

35
-continued
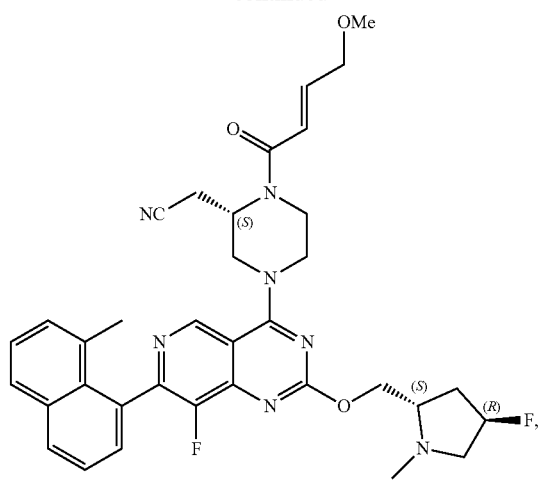
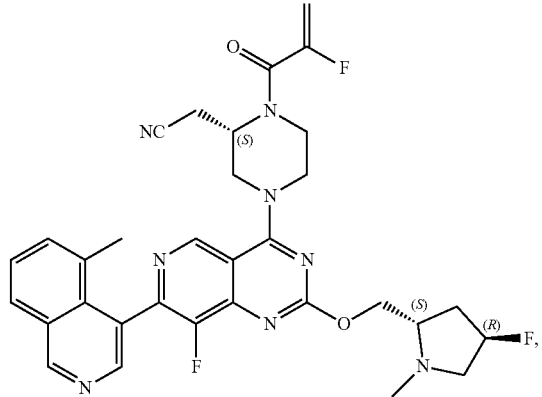
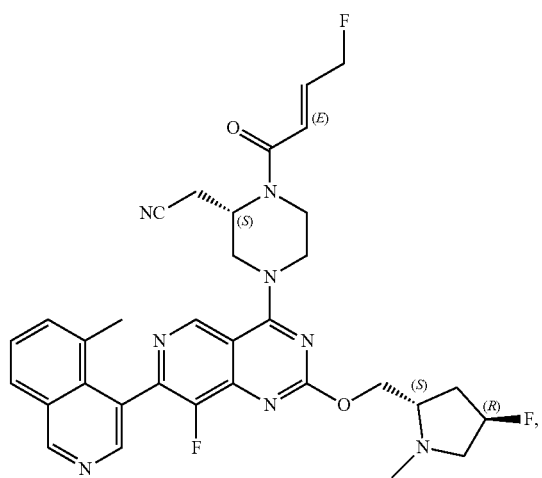
36
-continued
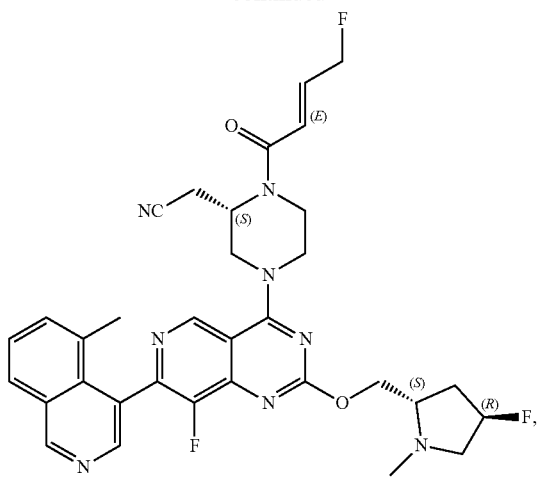
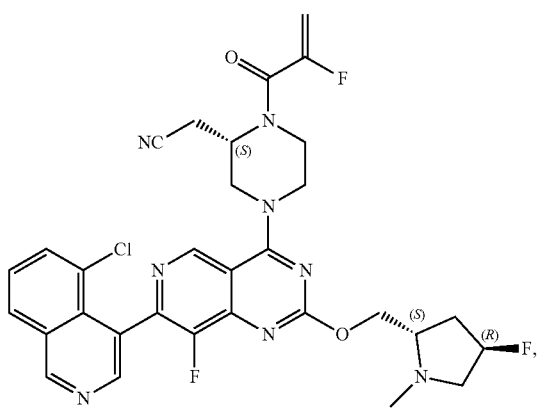
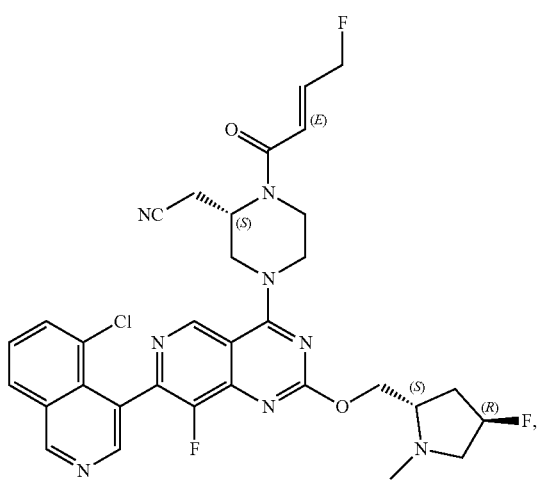

-continued
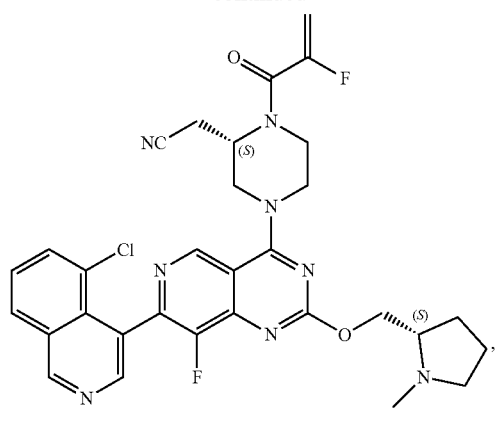
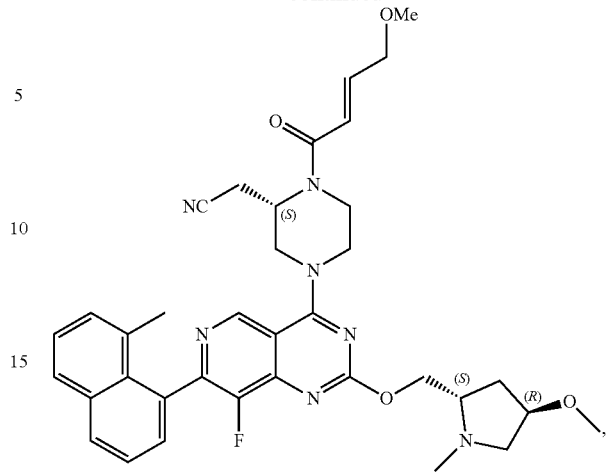
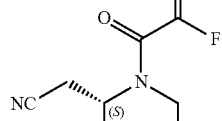
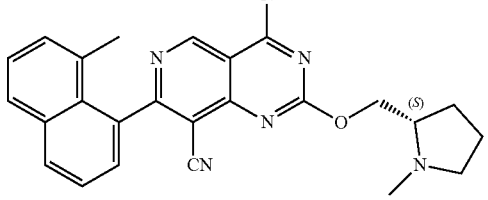
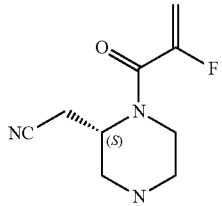
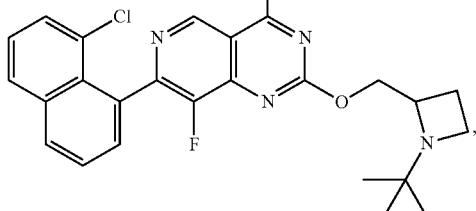
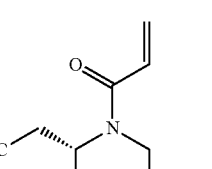
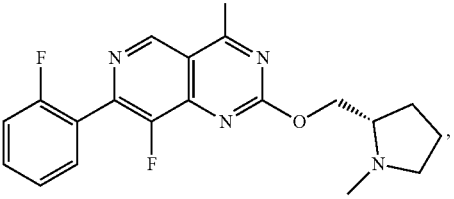

-continued
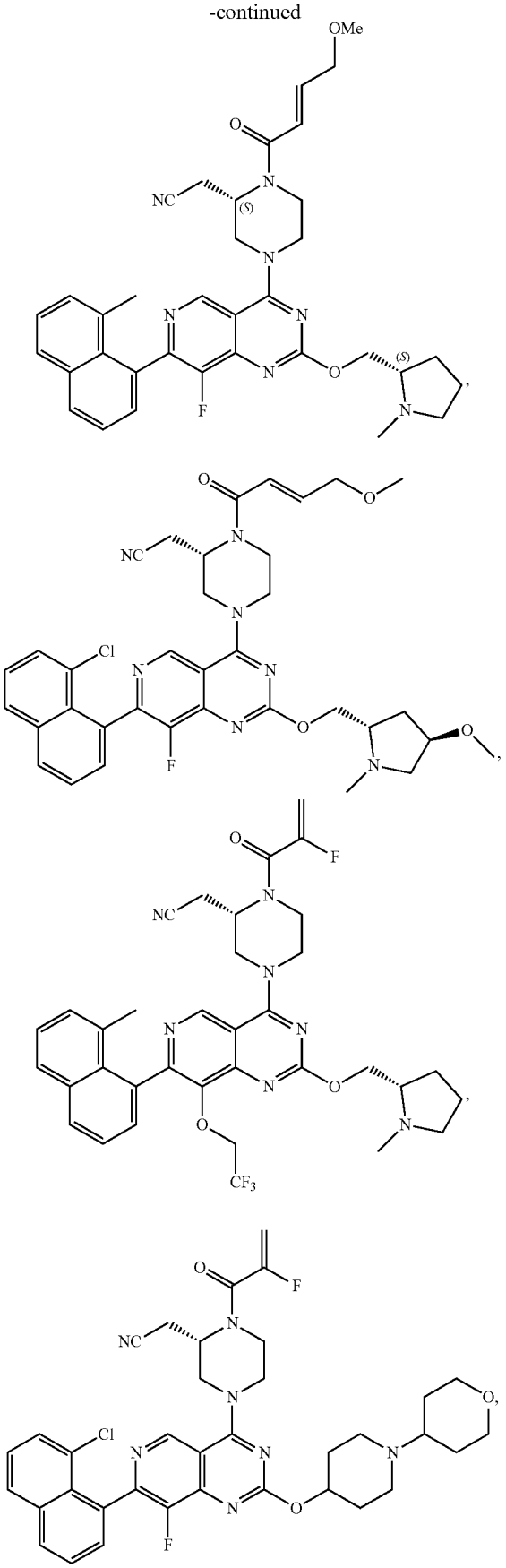
-continued
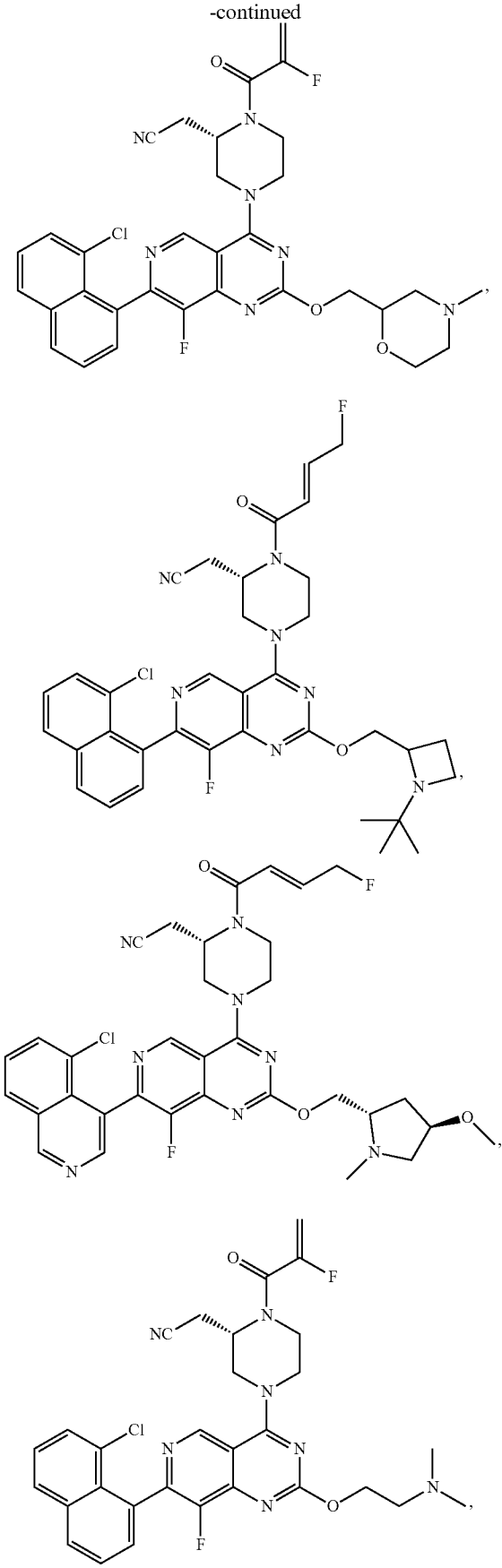

41
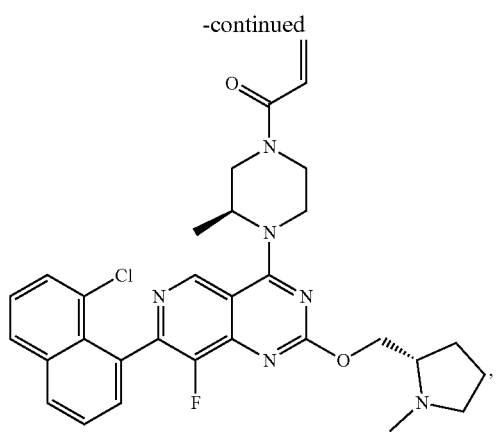
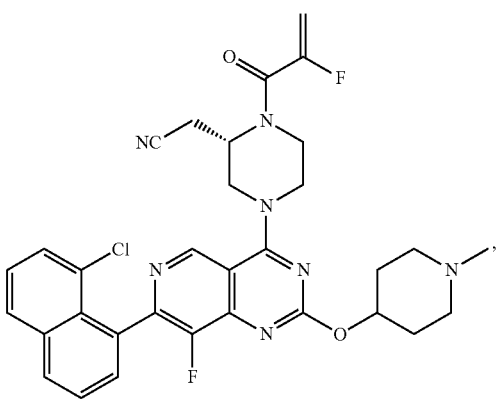
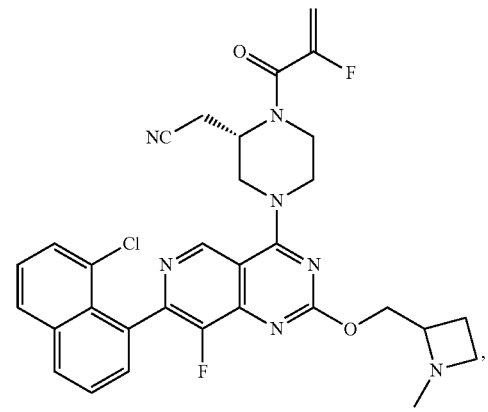
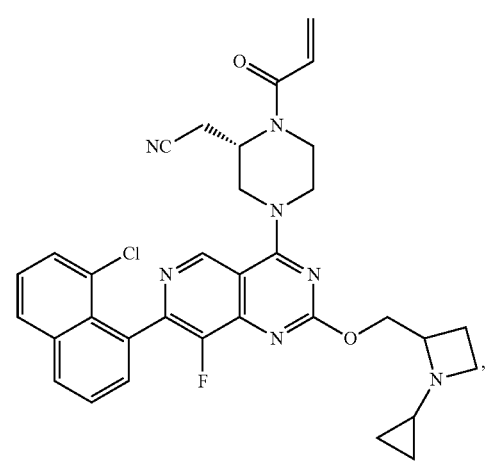
42
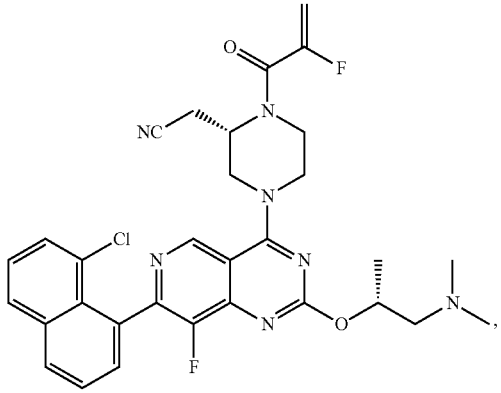
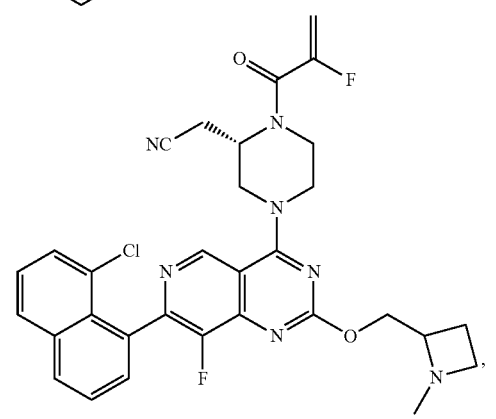
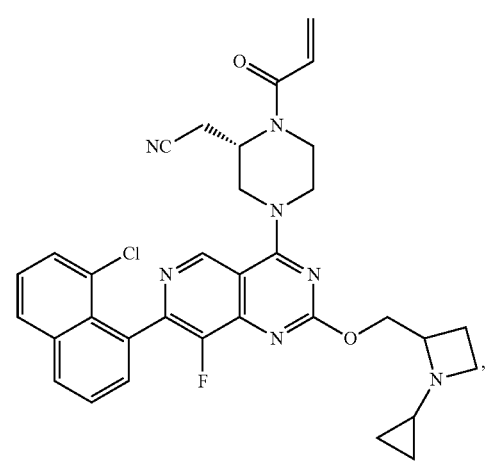
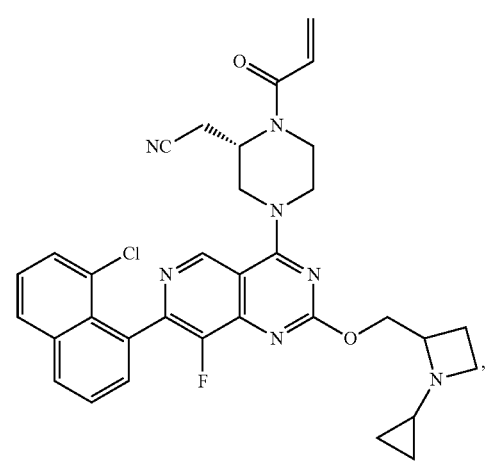

-continued
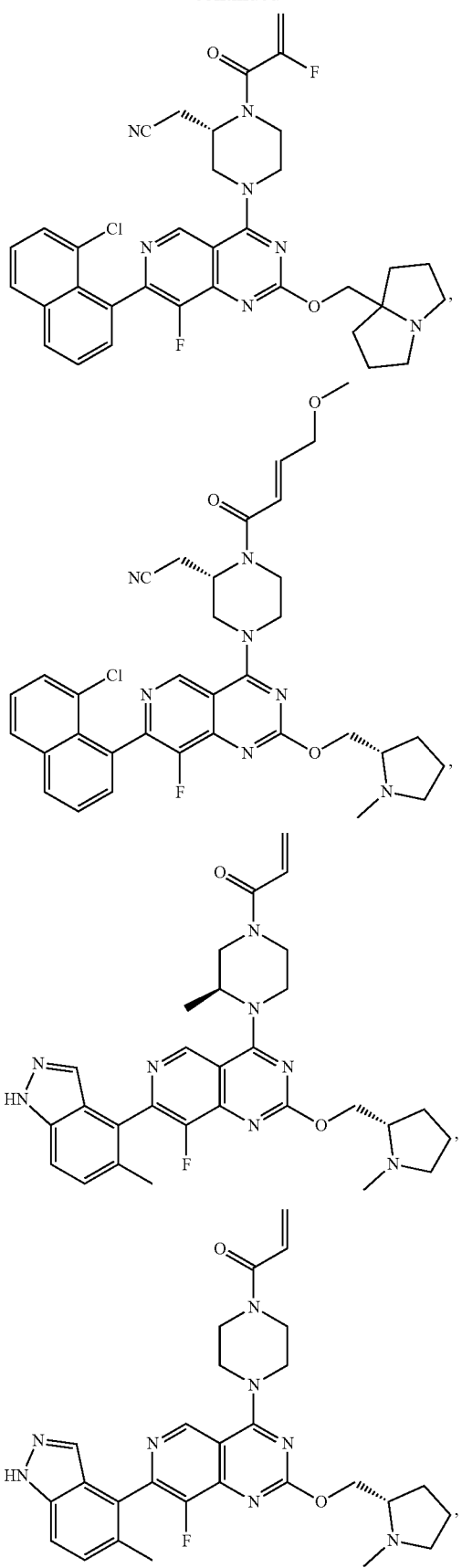
-continued
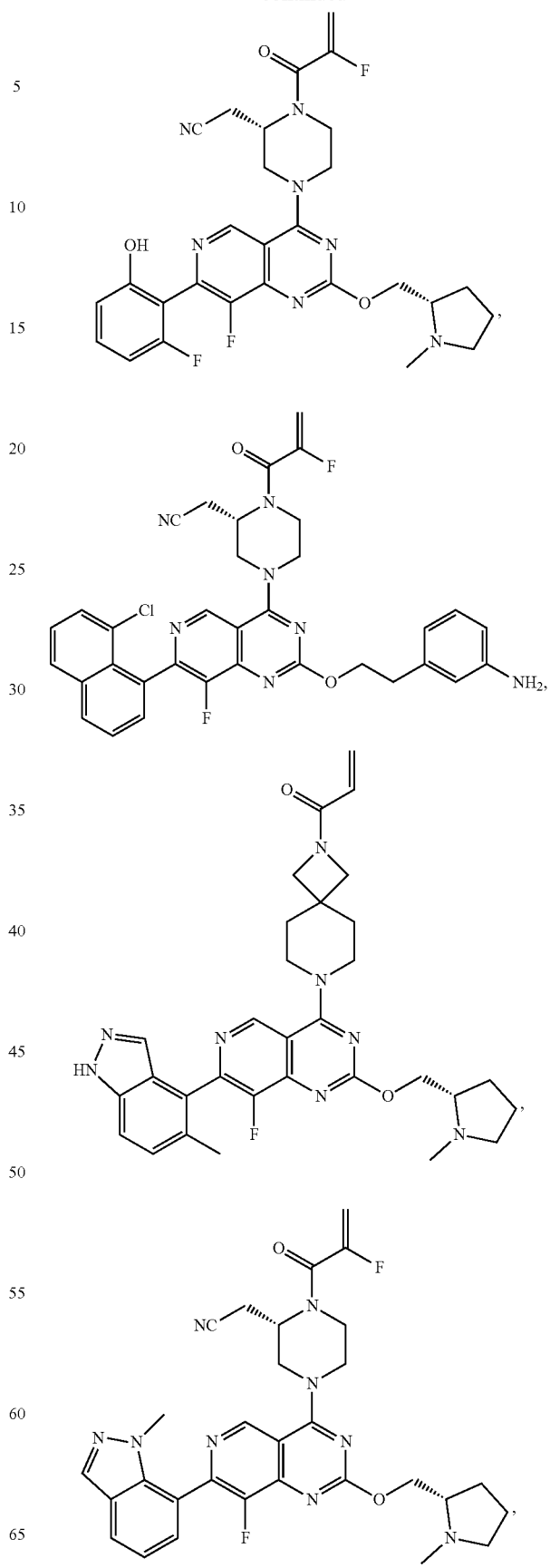

45
-continued
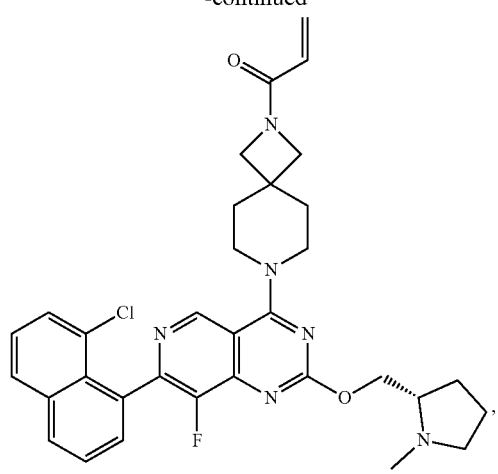
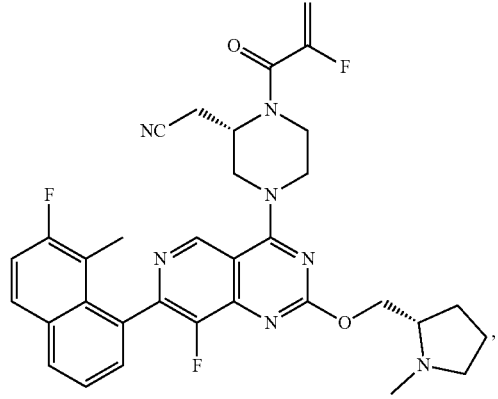
46
-continued
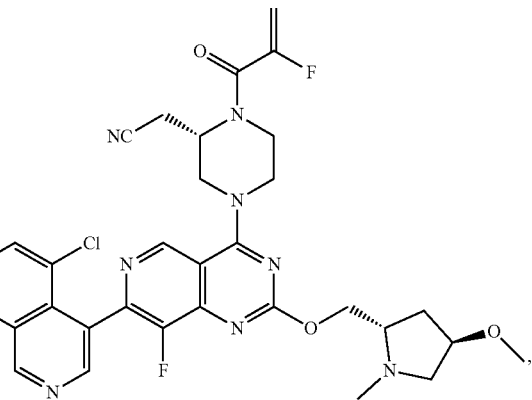
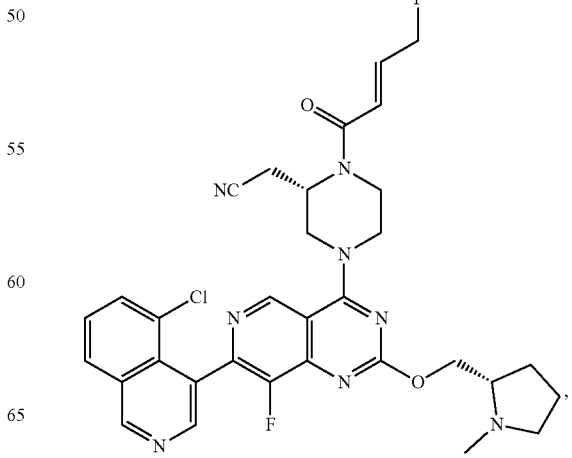

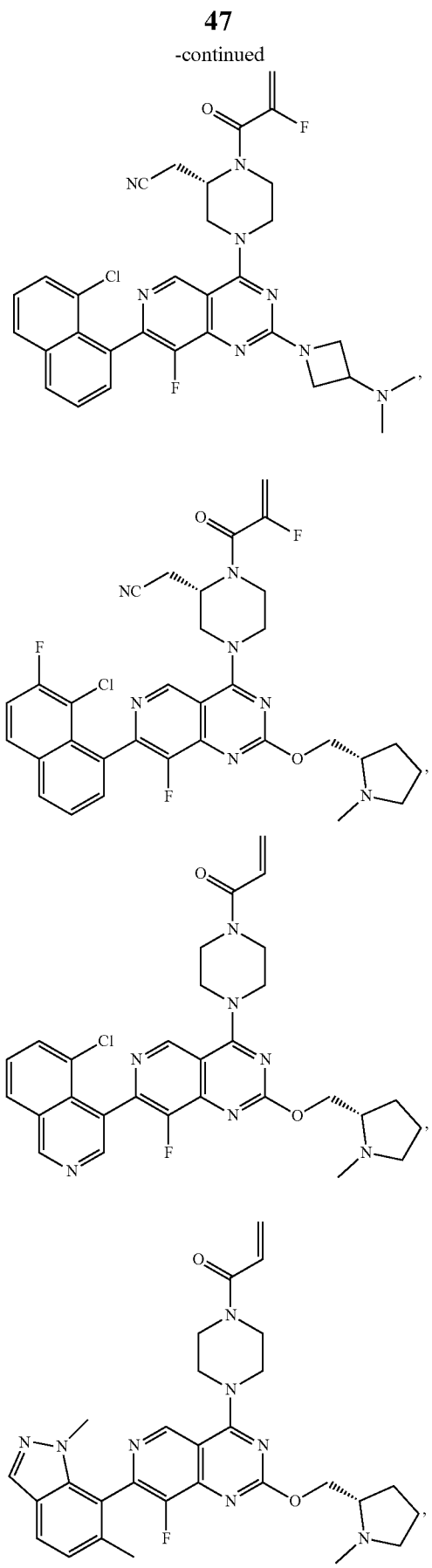
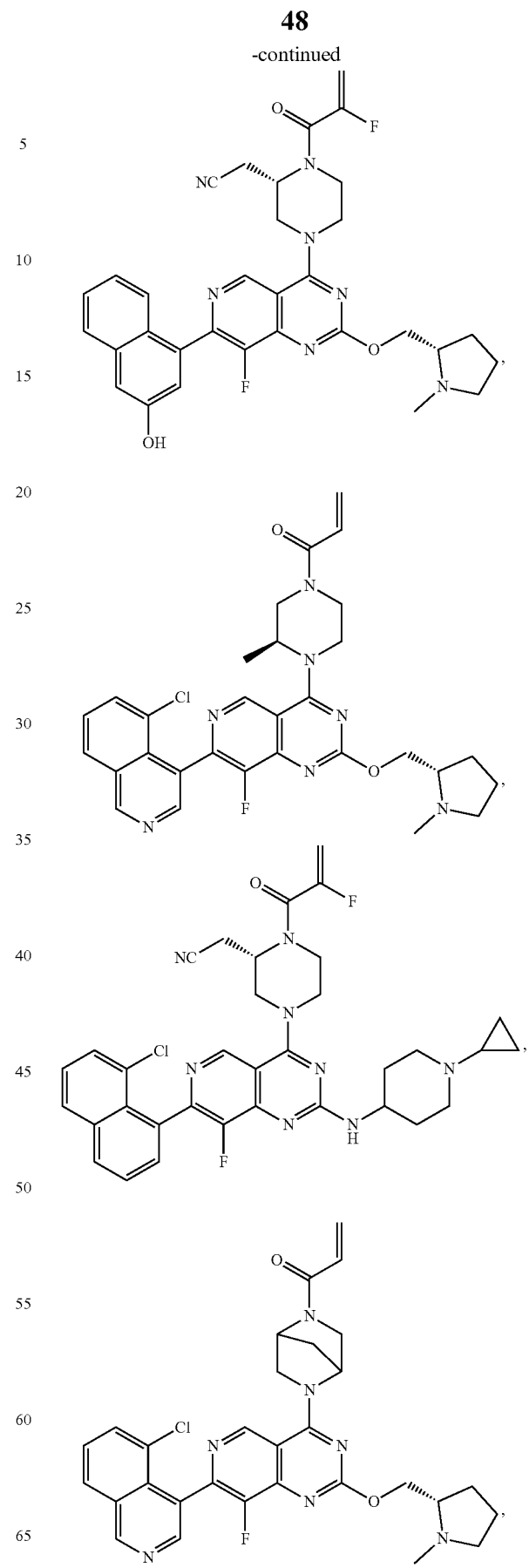

-continued
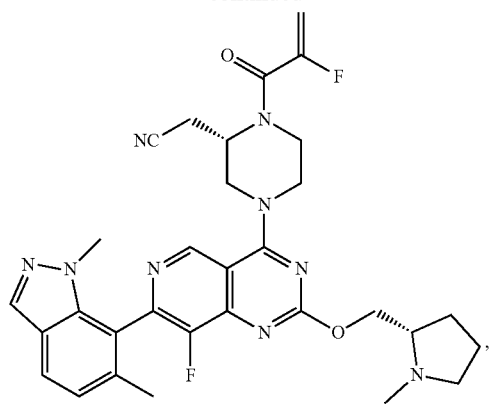
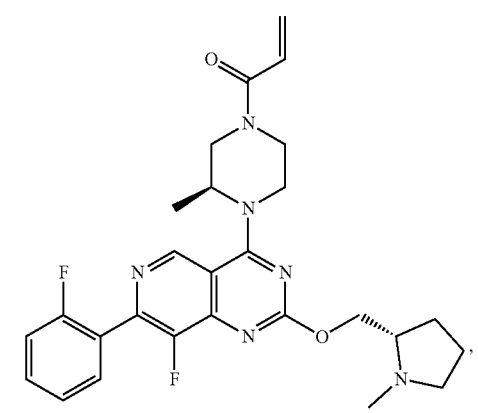
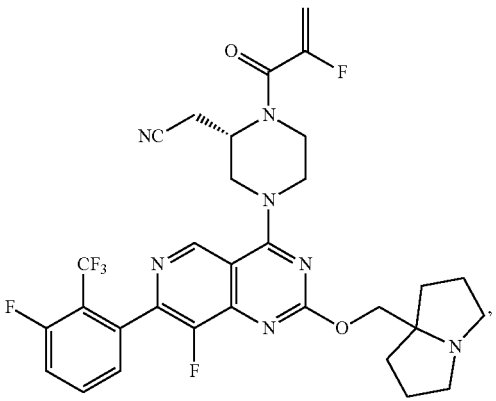
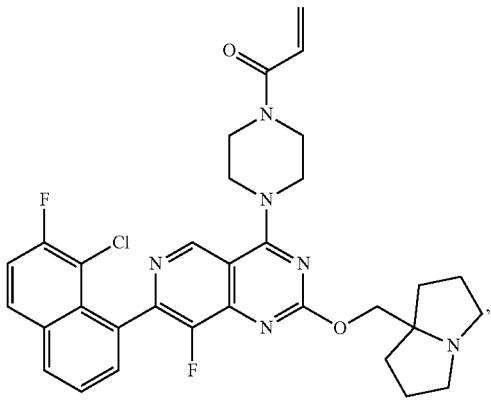
-continued
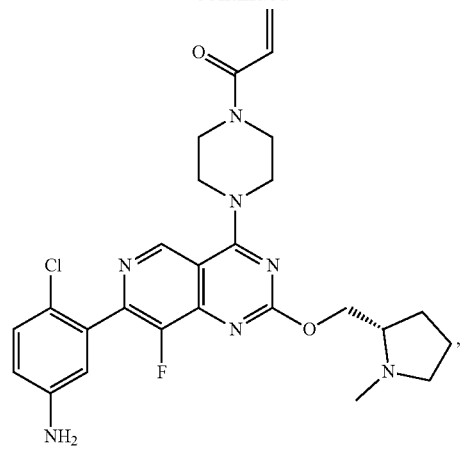
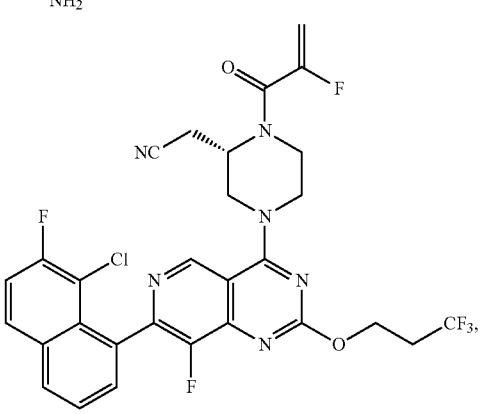
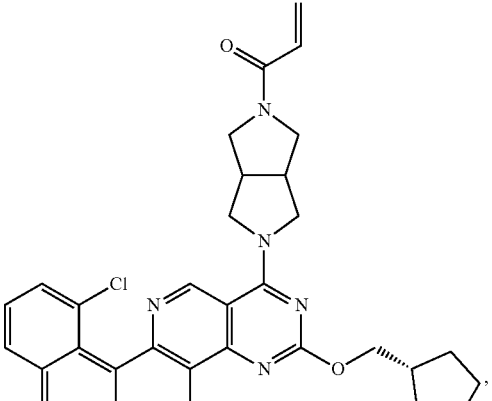
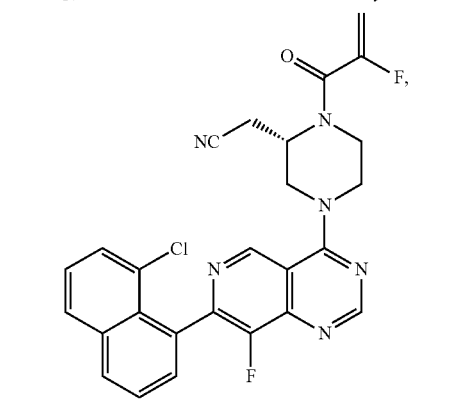

51
-continued
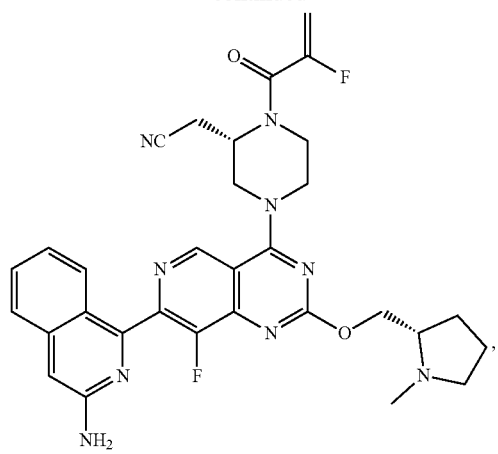
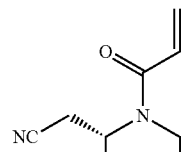
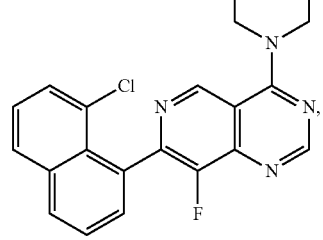
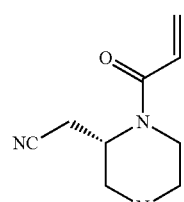
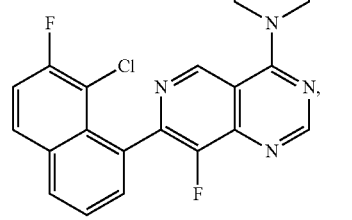
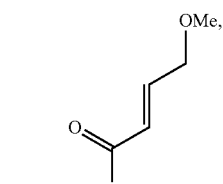
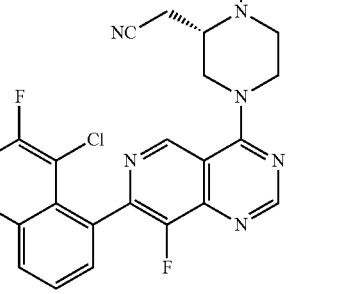
52
-continued
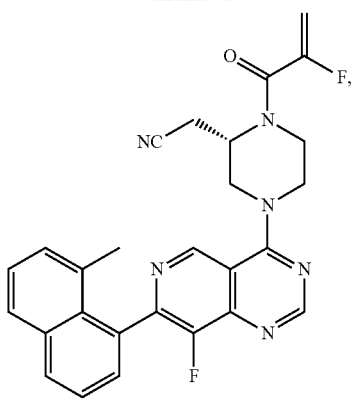
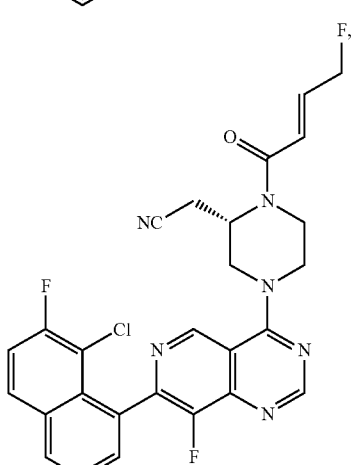
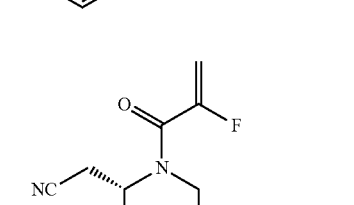
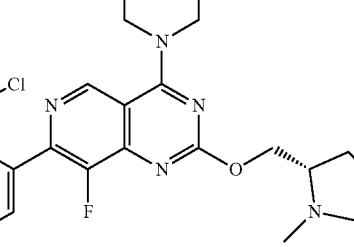
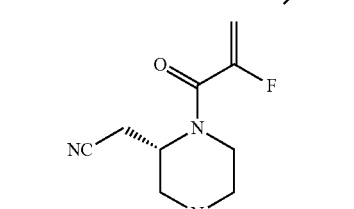
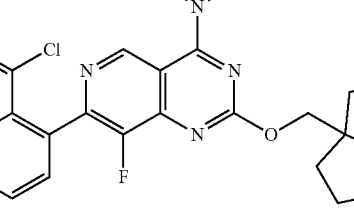

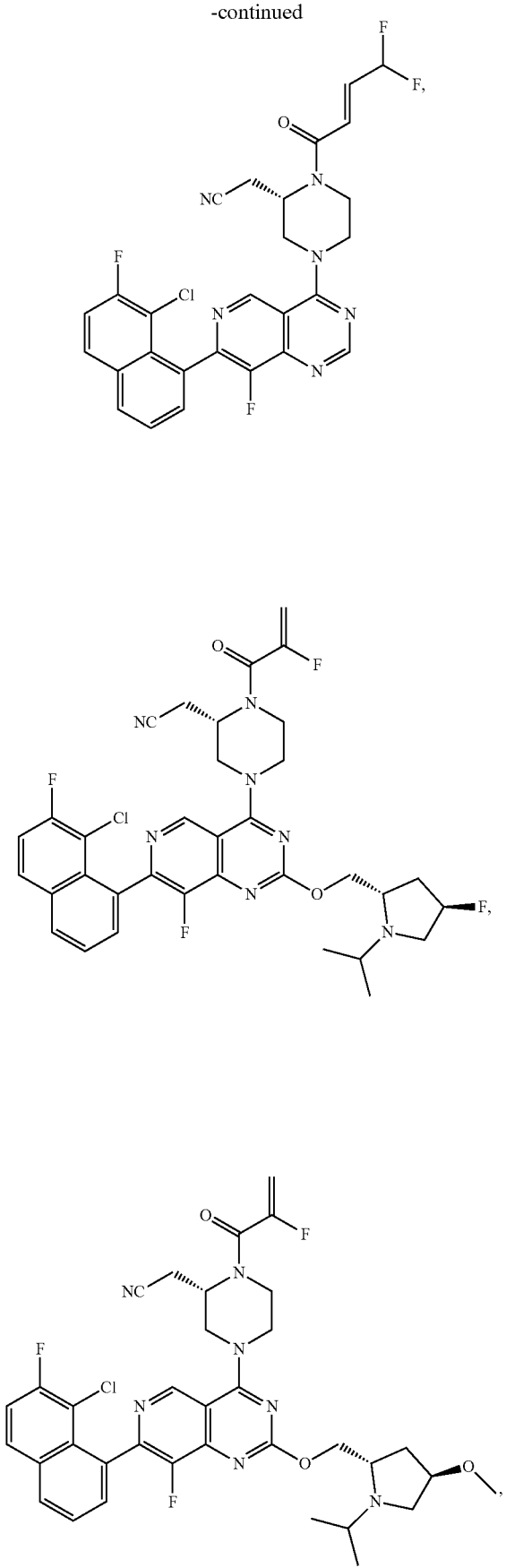
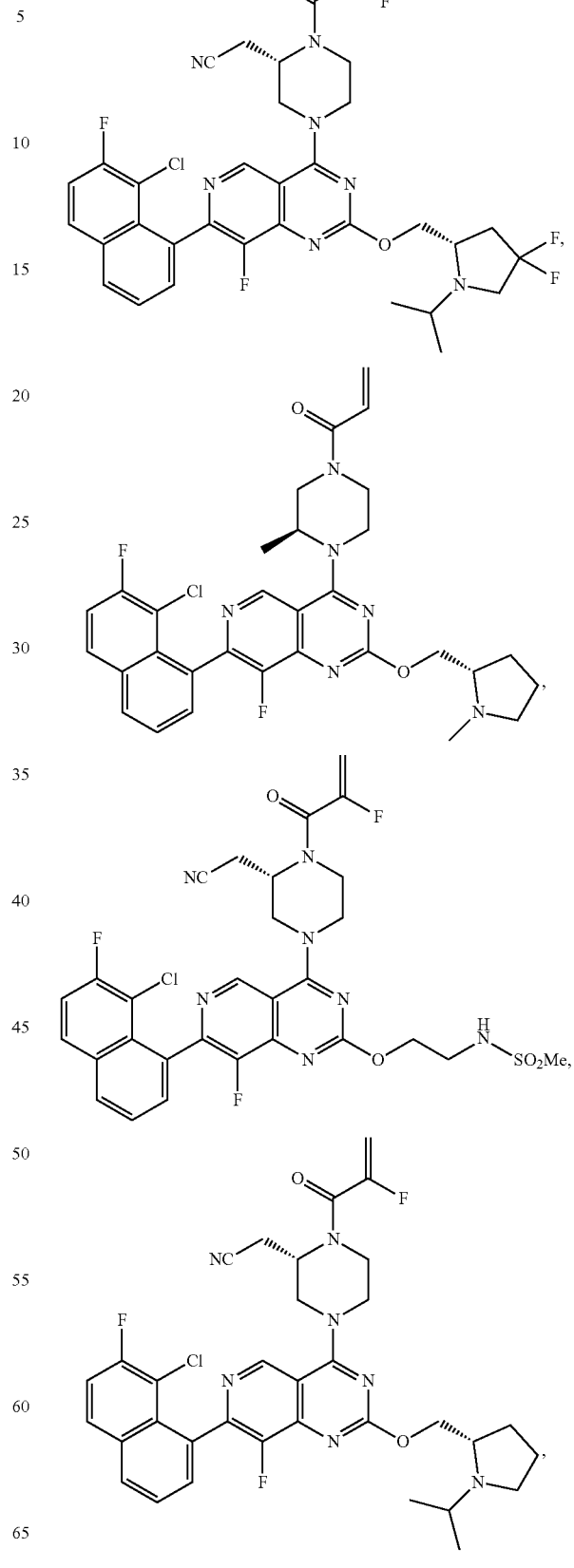

55
-continued
56
-continued
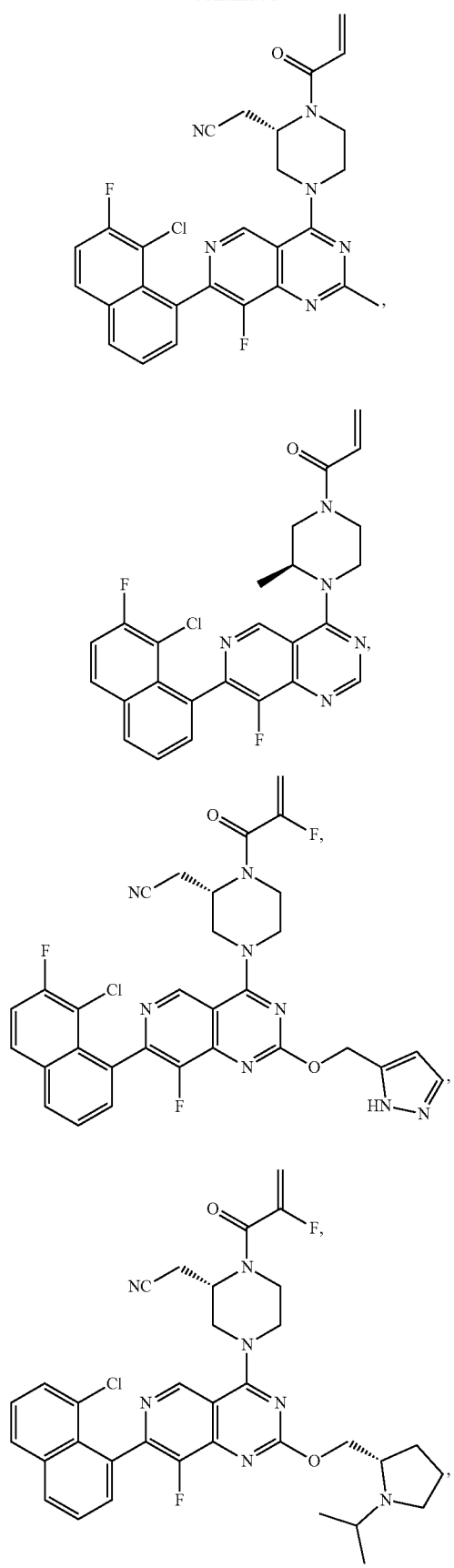
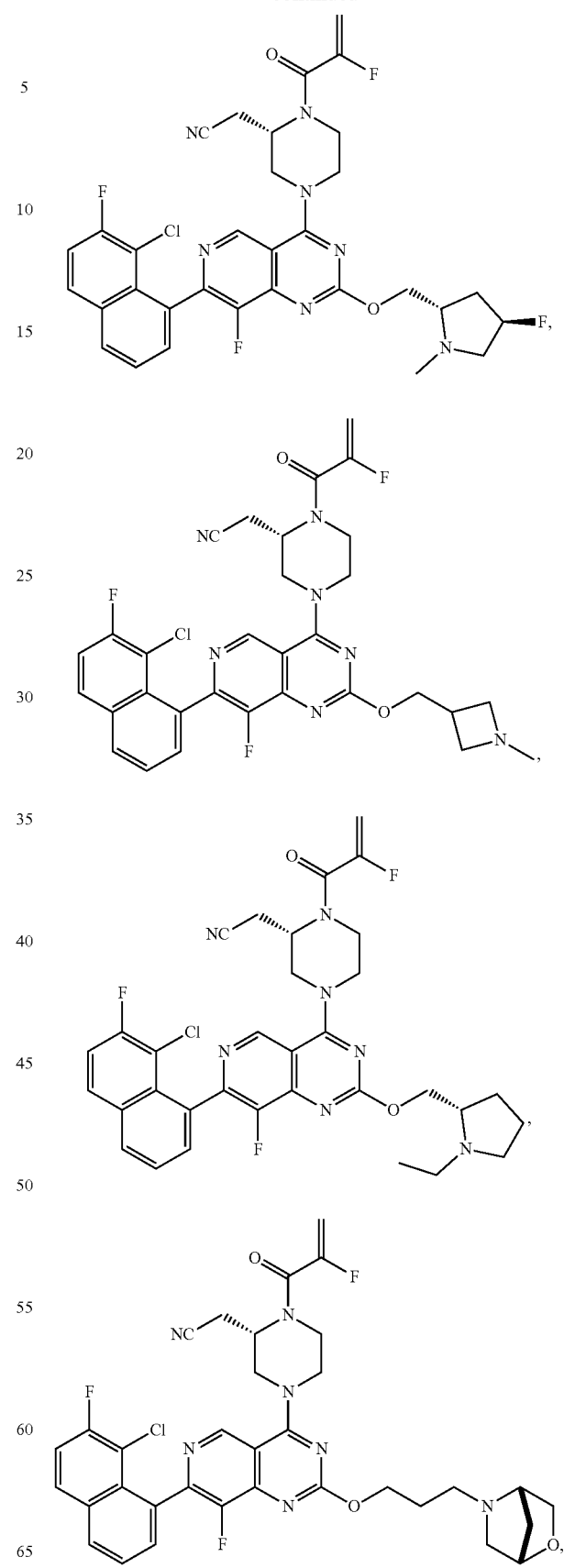

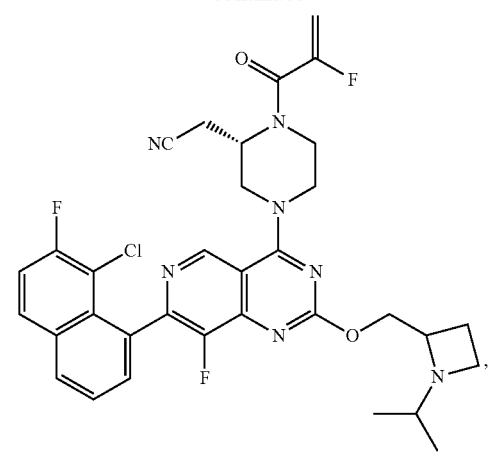
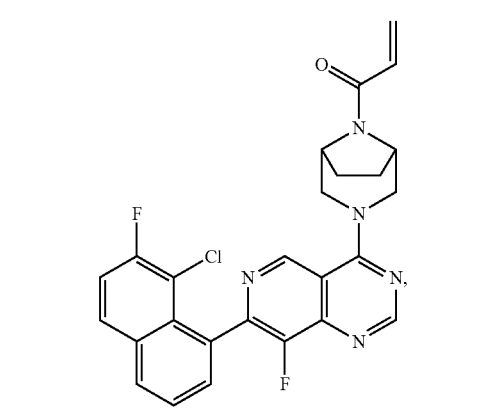
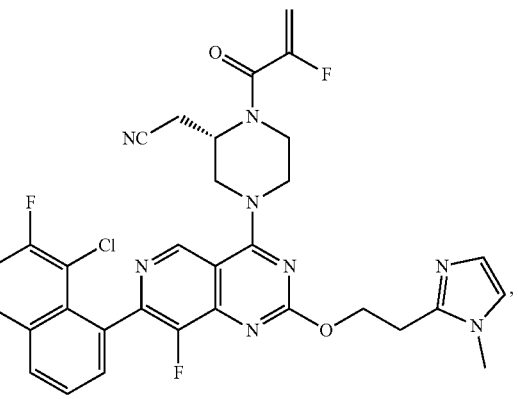
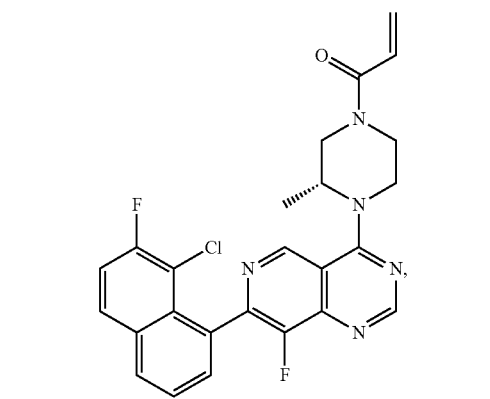
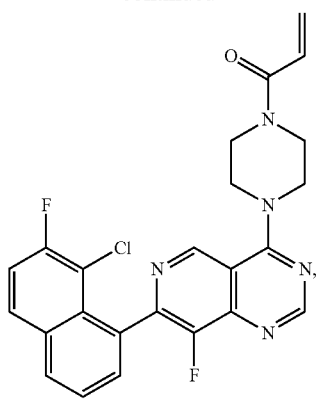
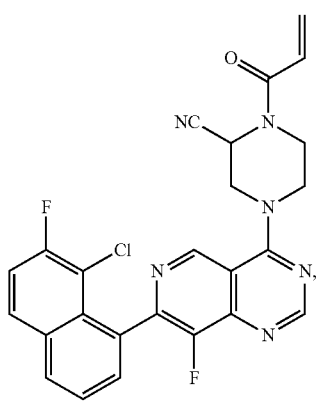
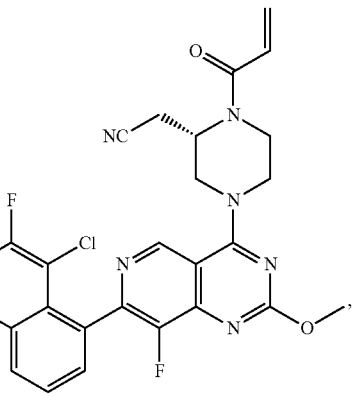
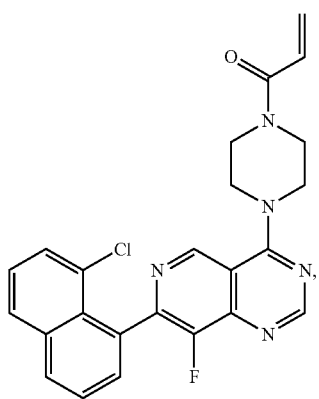

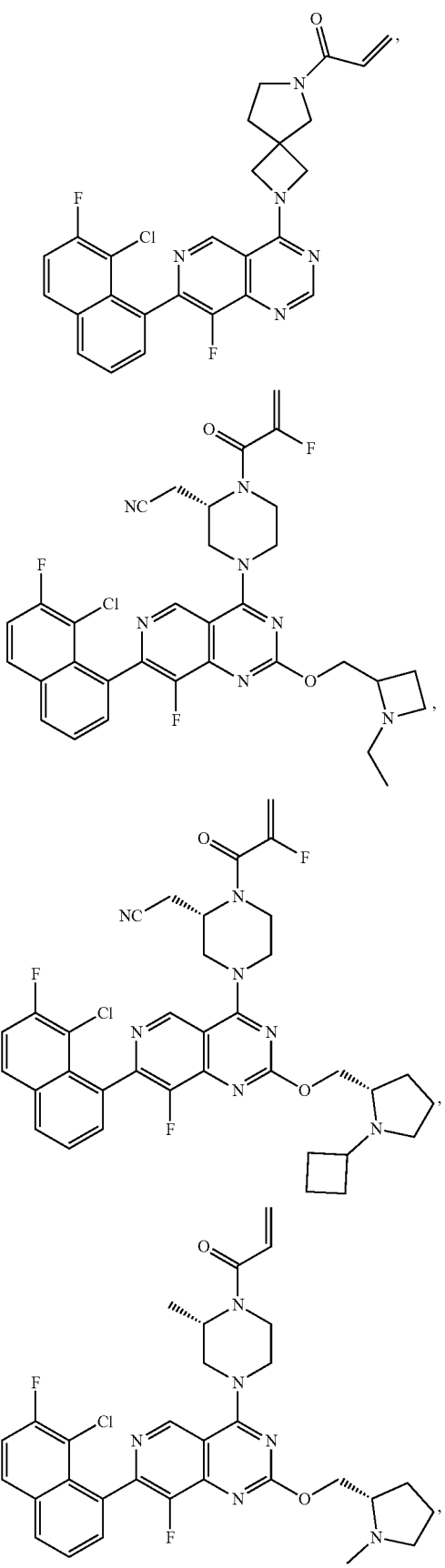
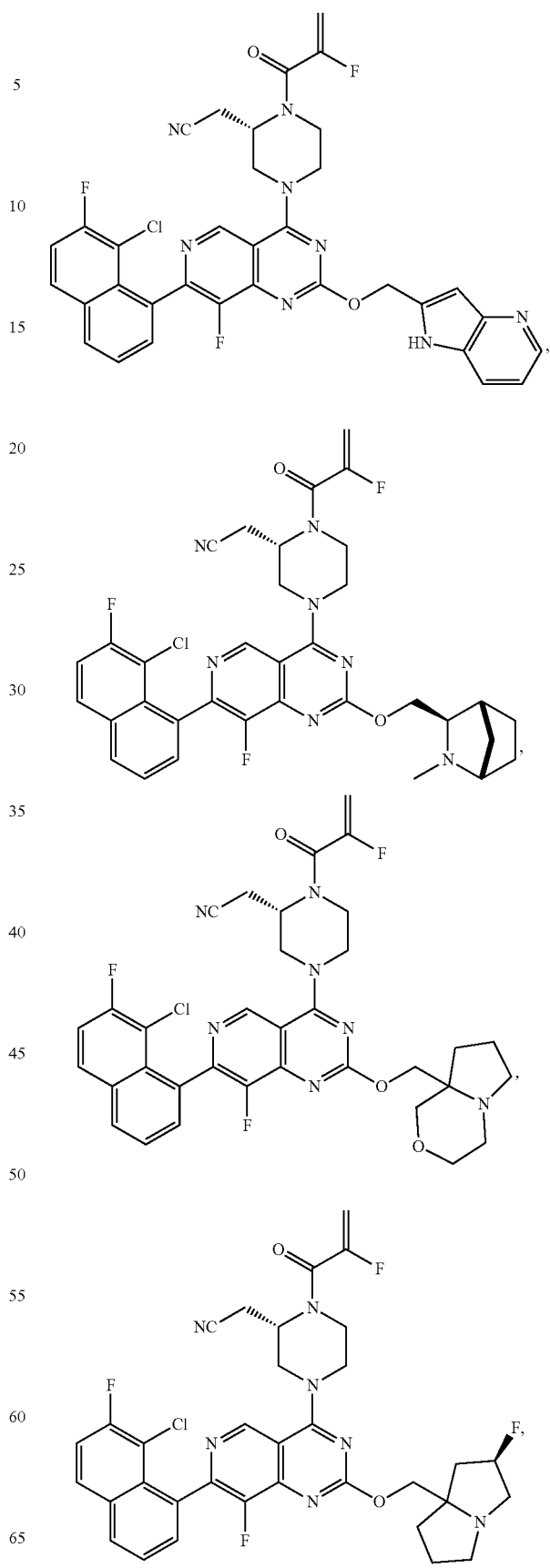

-continued
61
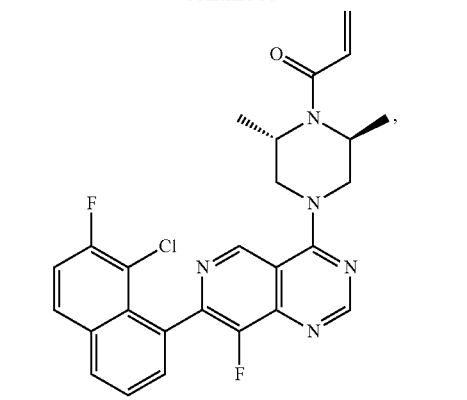
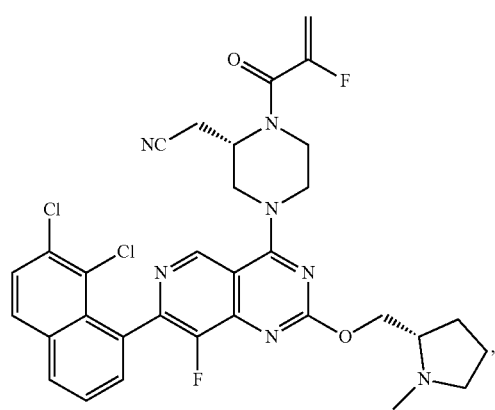
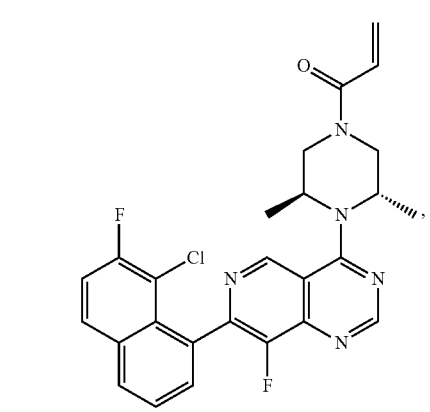
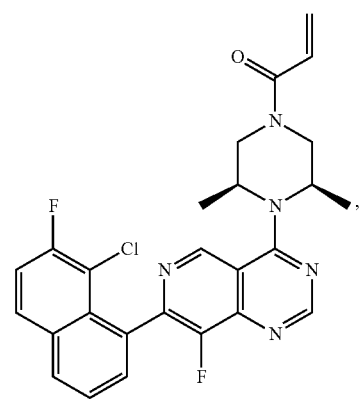
62
-continued
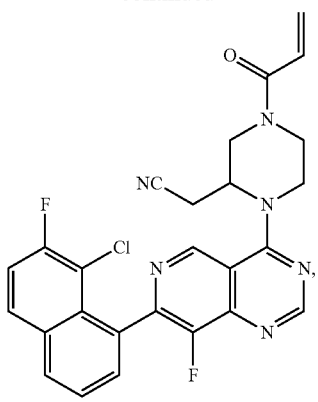
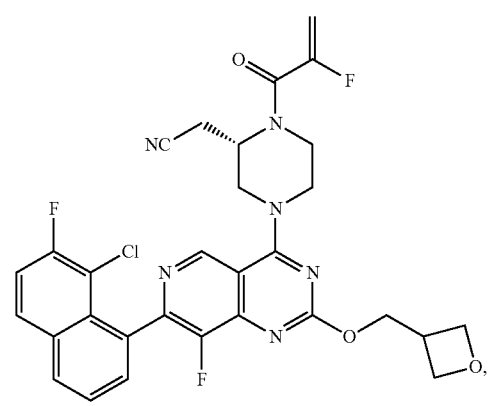
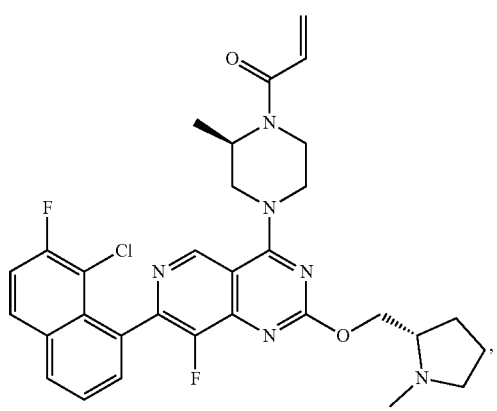
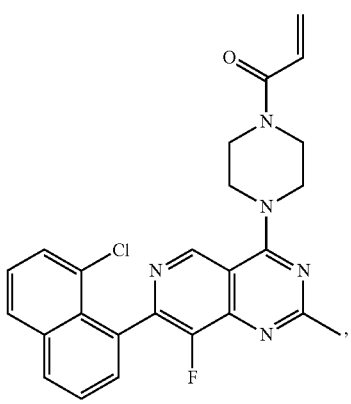

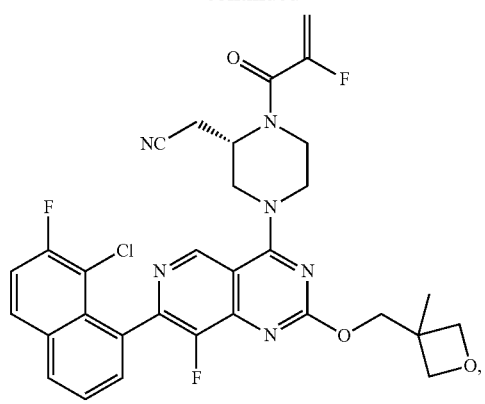 [SMILES: C=C(F)C(=O)N1CCN(c2nc(OCCC(F)(F)F)nc3c(F)c(-c4cccc5ccc(F)c(Cl)c45)ncc23)C[C@@H]1CC#N]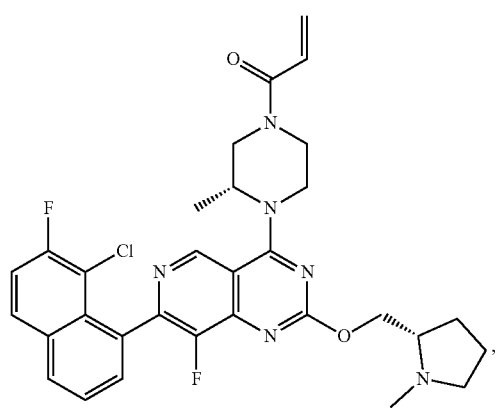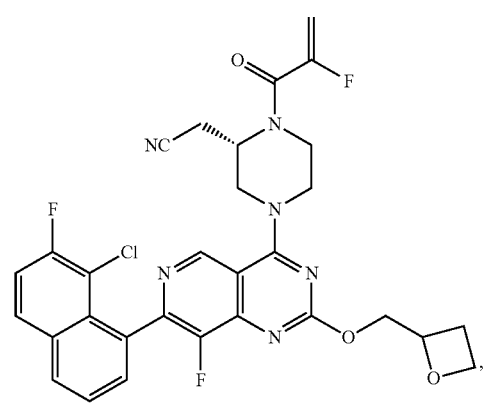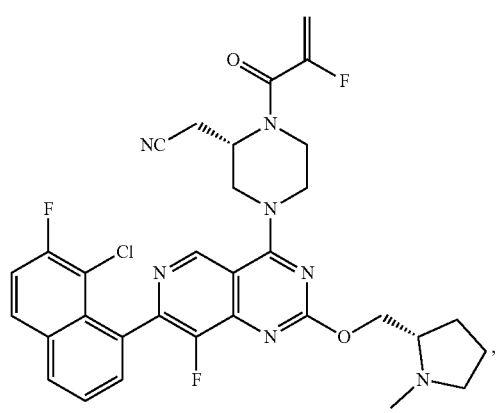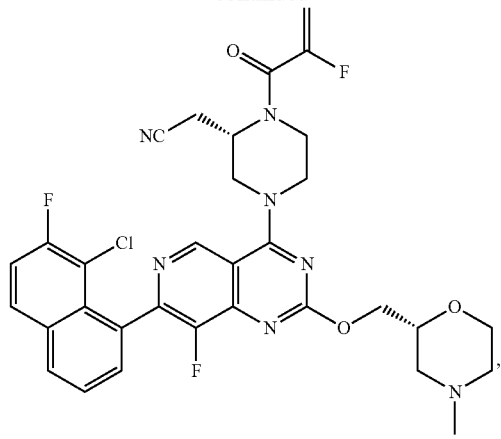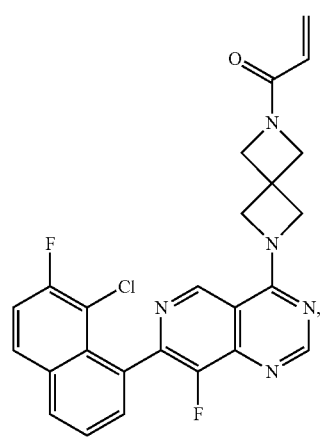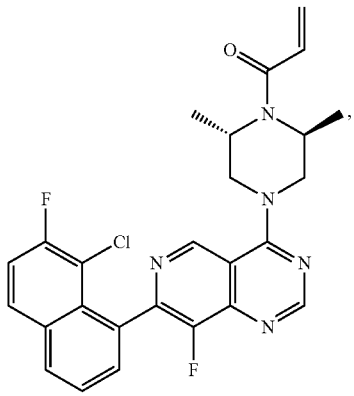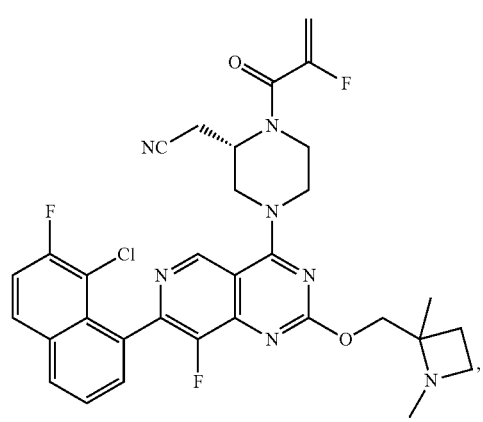

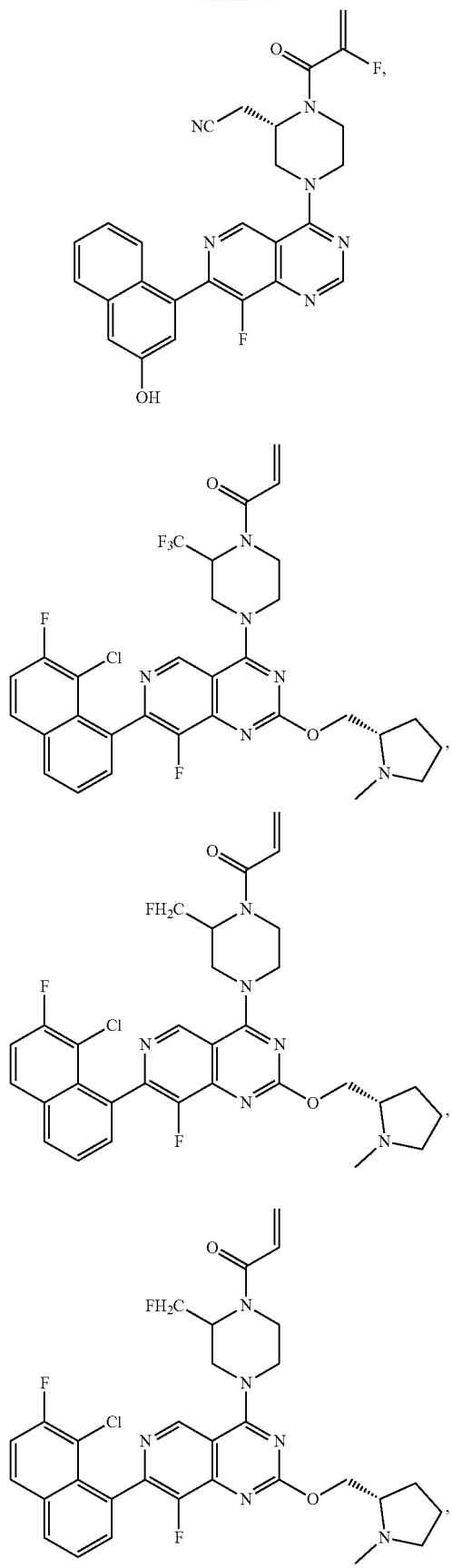

-continued
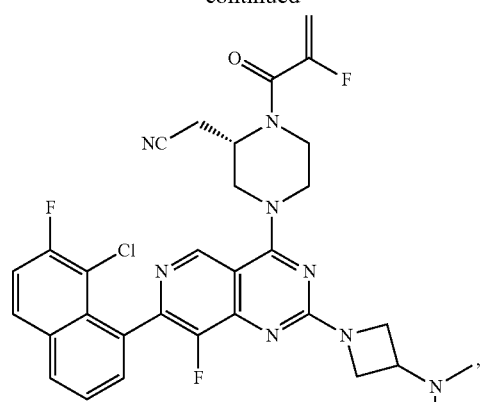
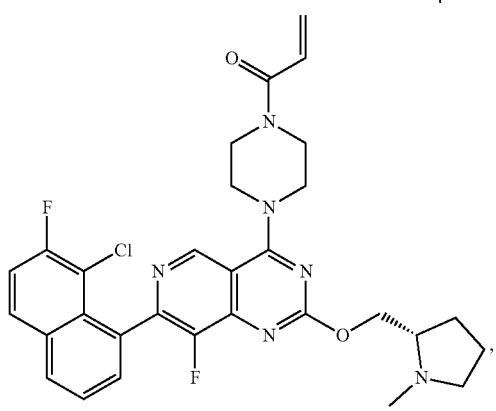
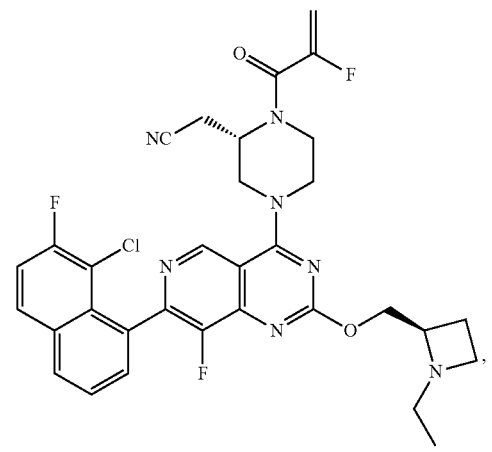
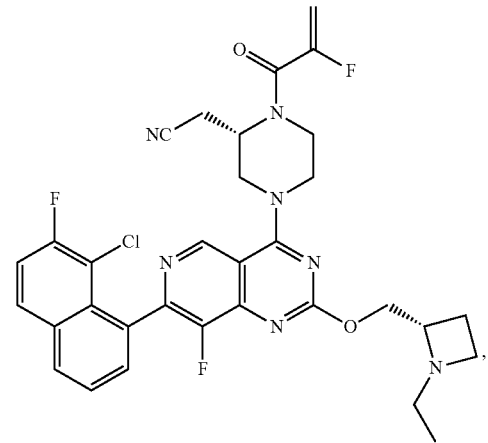
-continued
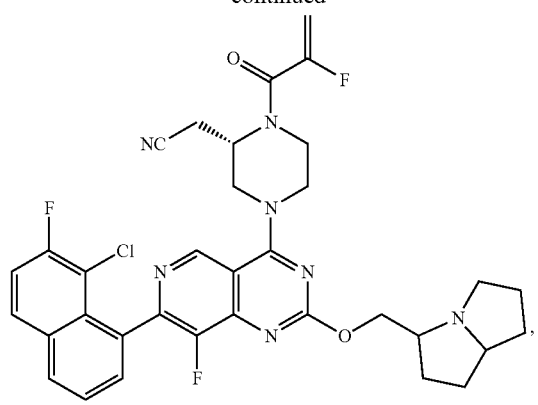
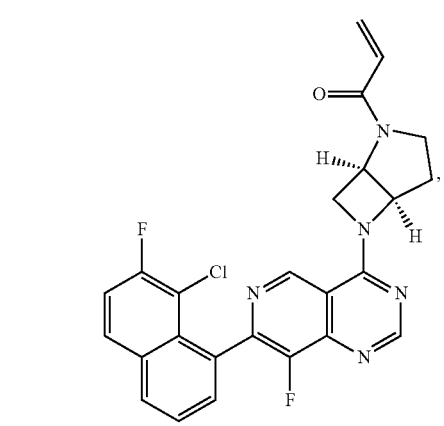
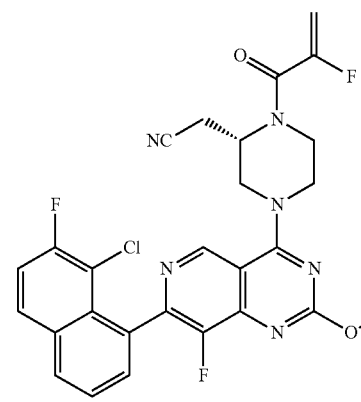
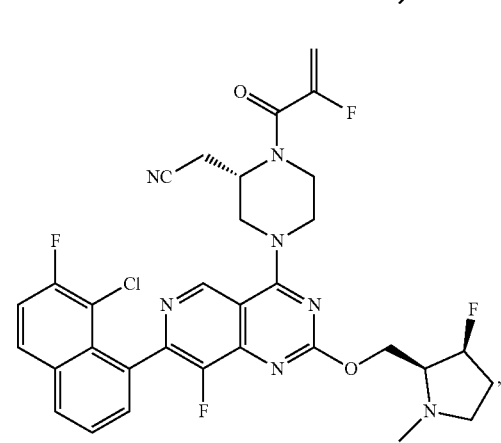

69
-continued
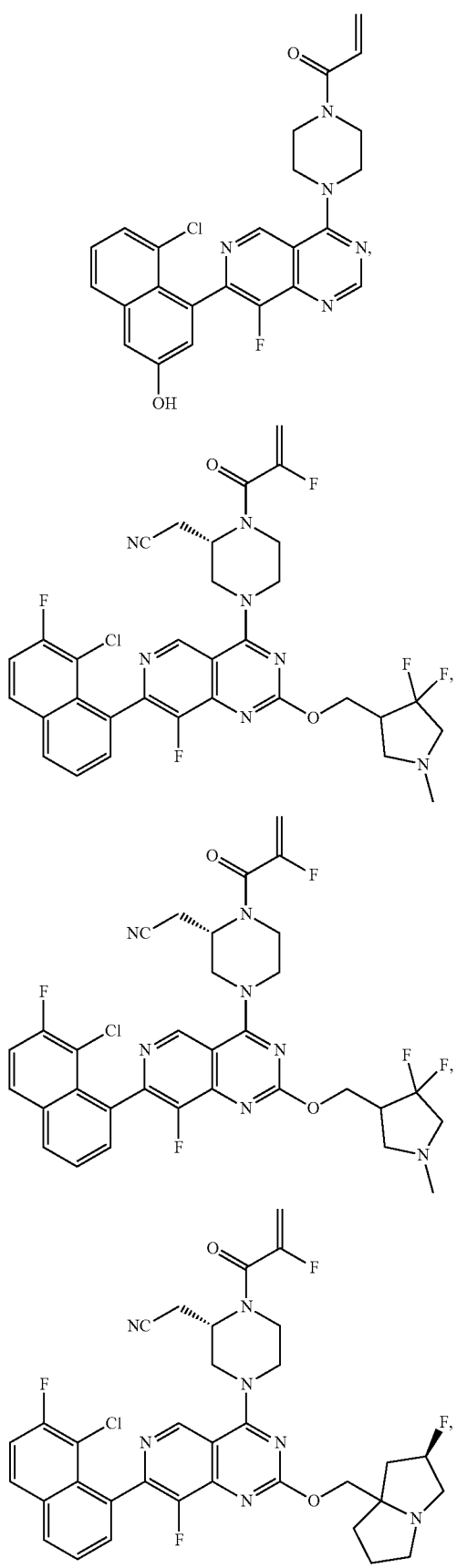 [SMILES: C=CC(=O)N1CCN(c2ncnc3c(F)c(-c4cc(O)cc5cccc(Cl)c45)ncc23)CC1 ; C=C(F)C(=O)N1CCN(c2nc(OCC3CN(C)CC3(F)F)nc3c(F)c(-c4cccc5ccc(F)c(Cl)c45)ncc23)C[C@@H]1CC#N ; C=C(F)C(=O)N1CCN(c2nc(OCC3CN(C)CC3(F)F)nc3c(F)c(-c4cccc5ccc(F)c(Cl)c45)ncc23)C[C@@H]1CC#N ; C=C(F)C(=O)N1CCN(c2nc(OCC34CCCN3C[C@H](F)C4)nc3c(F)c(-c4cccc5ccc(F)c(Cl)c45)ncc23)C[C@@H]1CC#N]
70
-continued
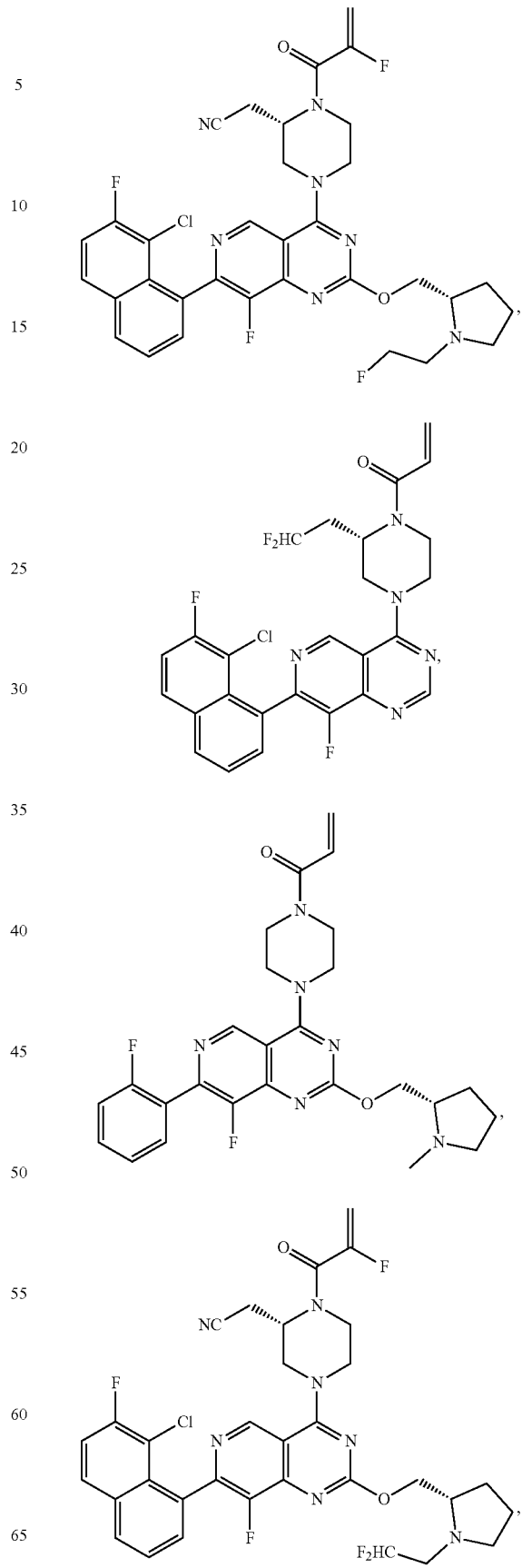

71
-continued
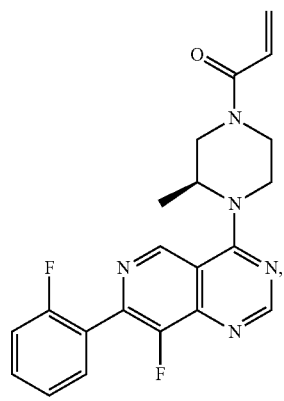
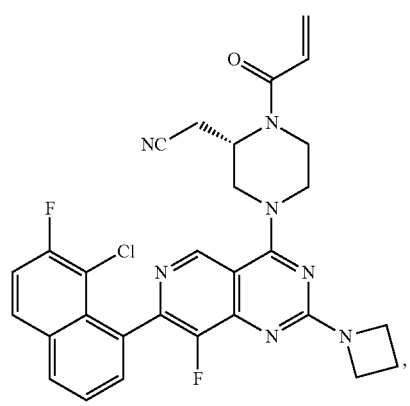
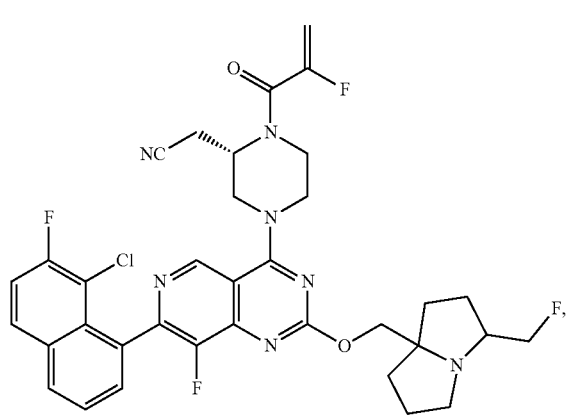
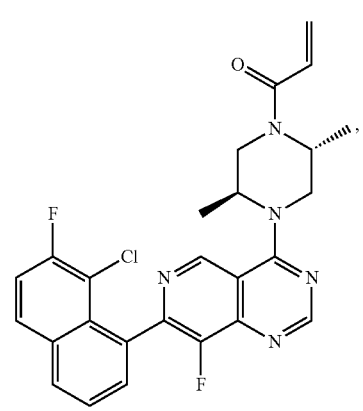
72
-continued
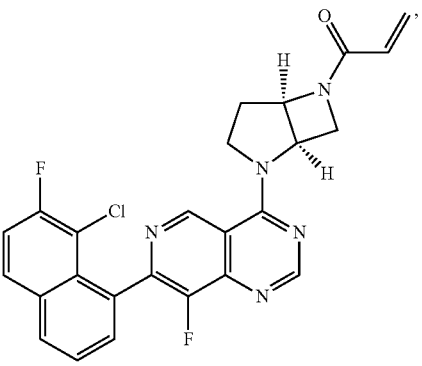 [SMILES: C=CC(=O)N1C[C@@H]2[C@H]1CCN2c1ncnc2c(F)c(-c3cccc4ccc(F)c(Cl)c34)ncc12]
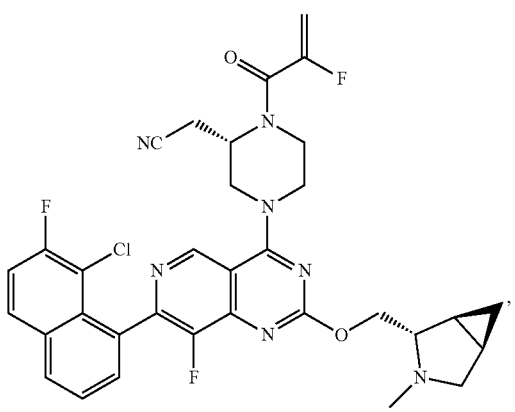
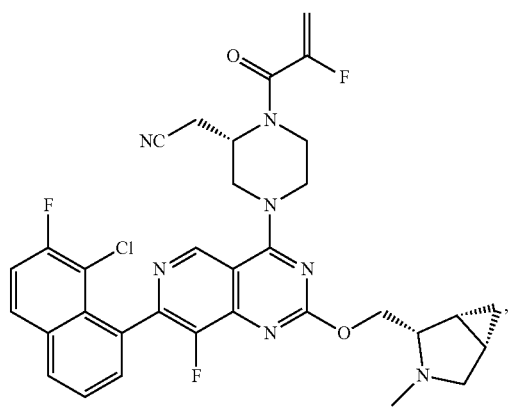
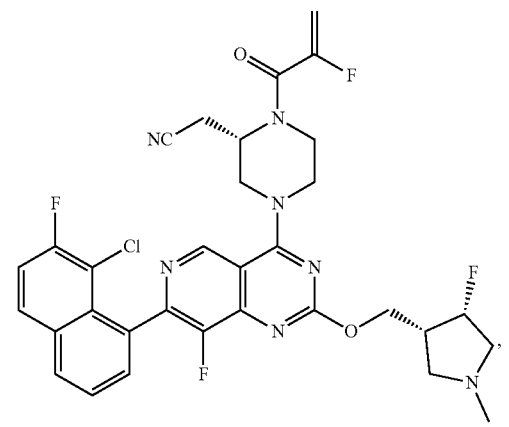

73
-continued
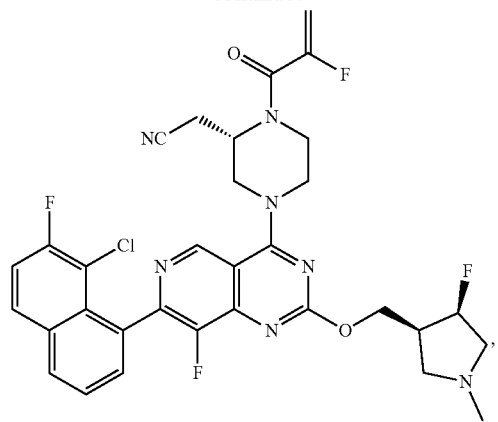
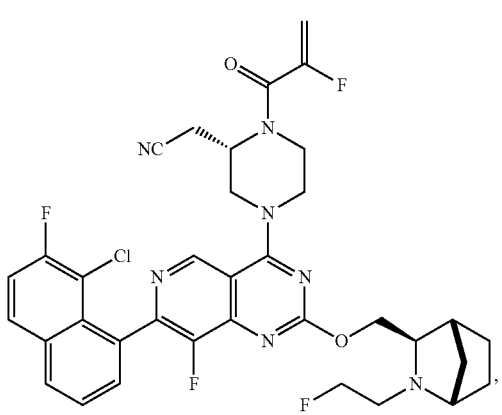
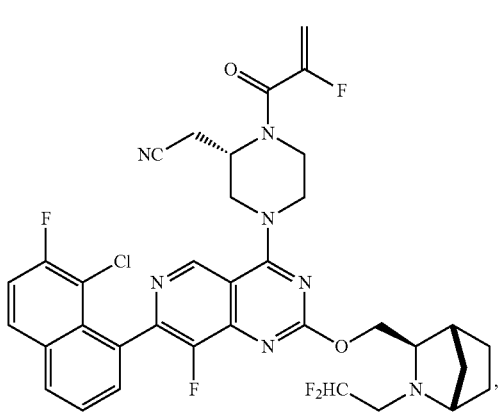
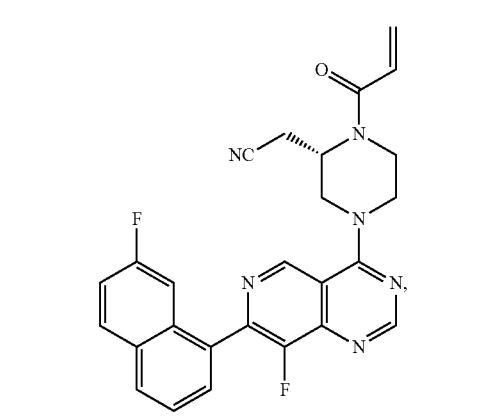
74
-continued
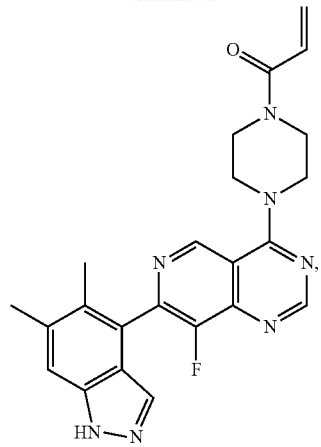
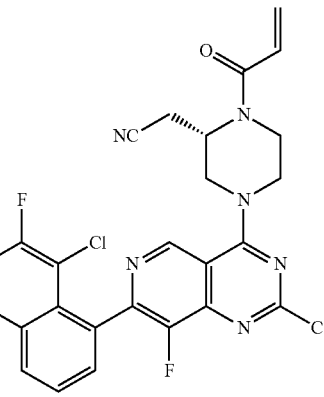
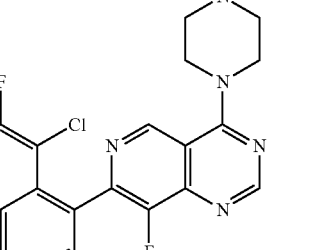
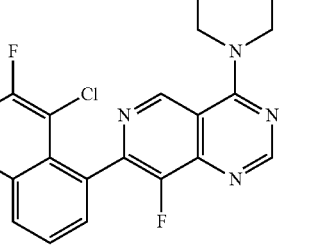

75
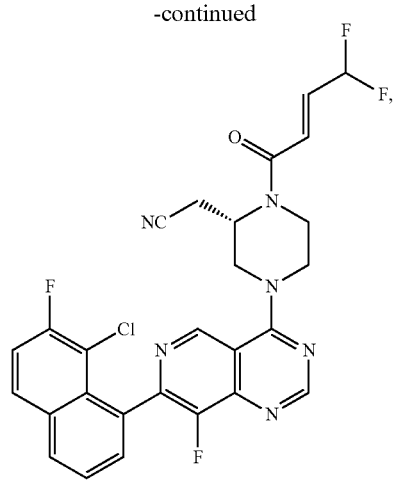
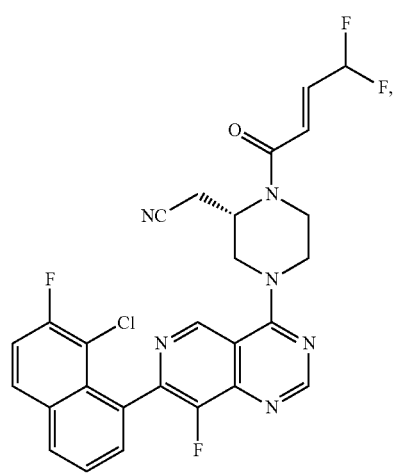
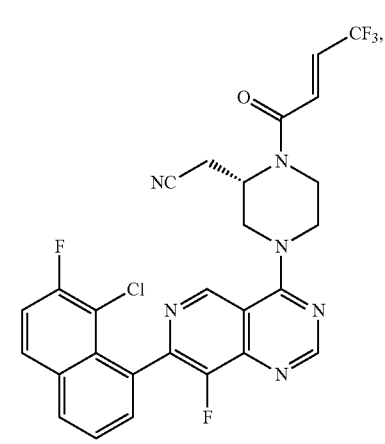
76
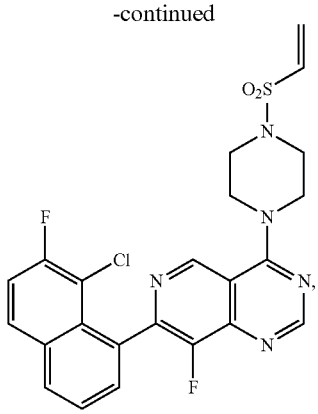
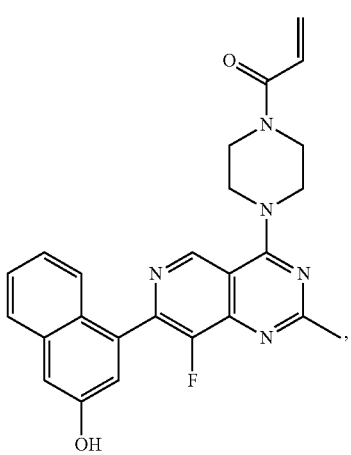
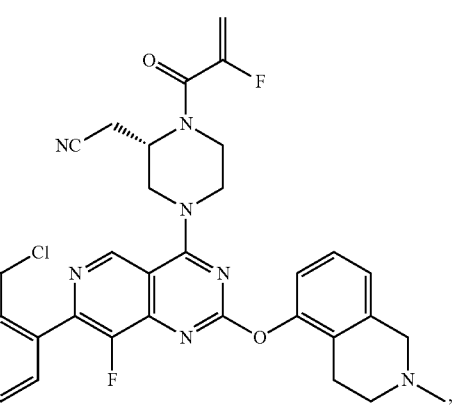
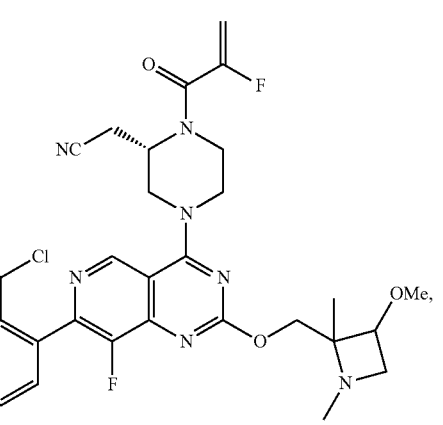

77
-continued
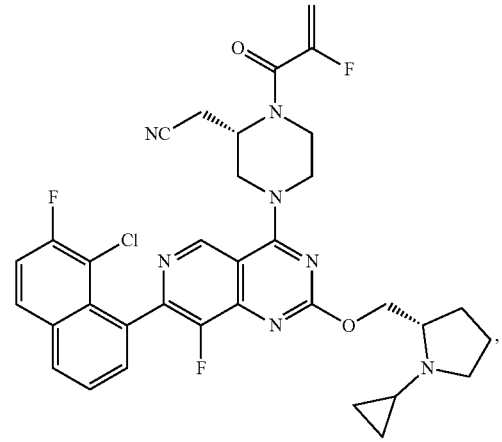
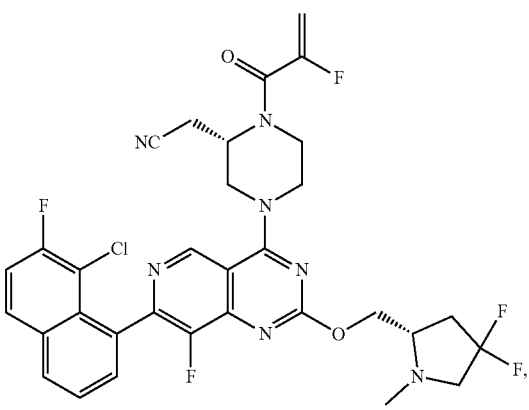
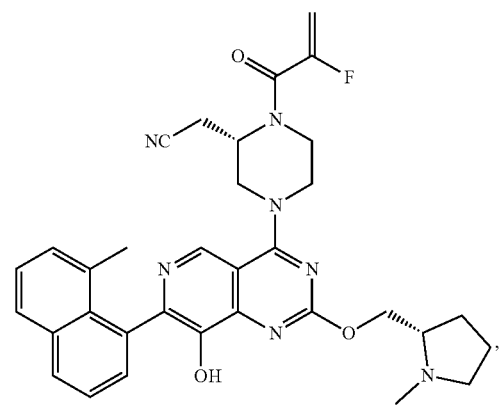
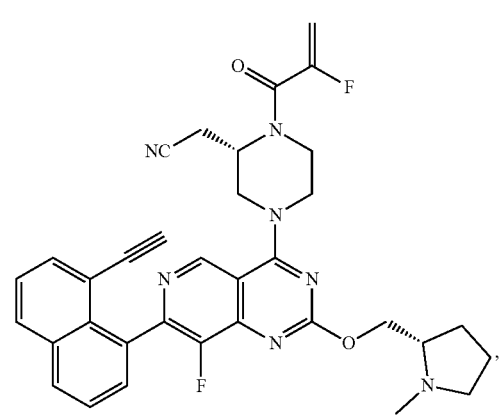
78
-continued
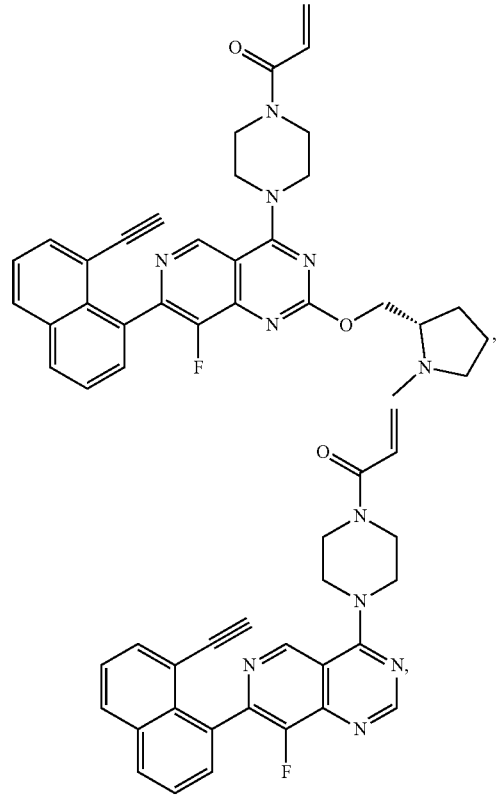
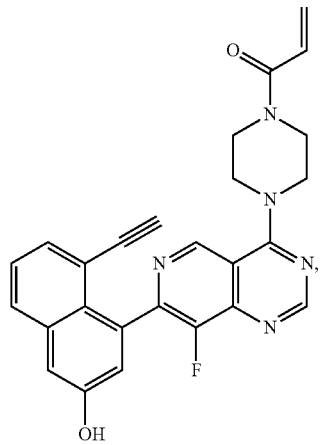
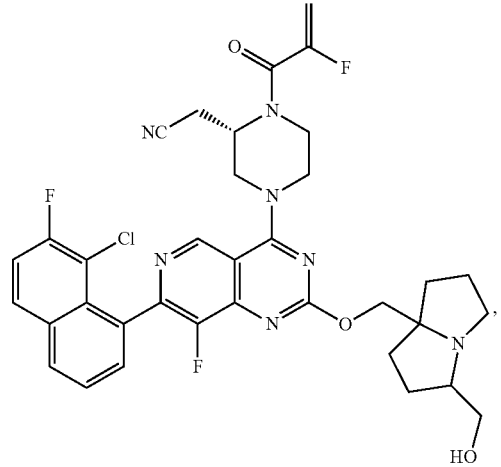

-continued
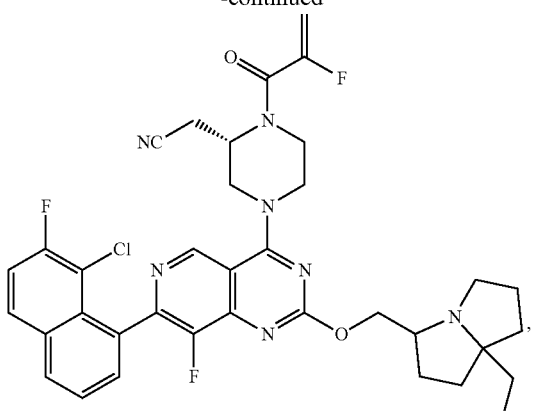
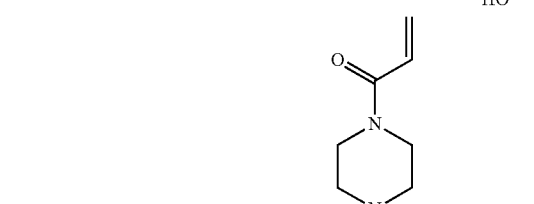
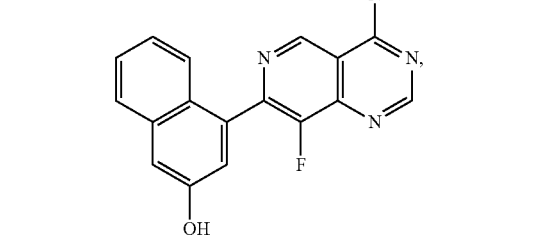
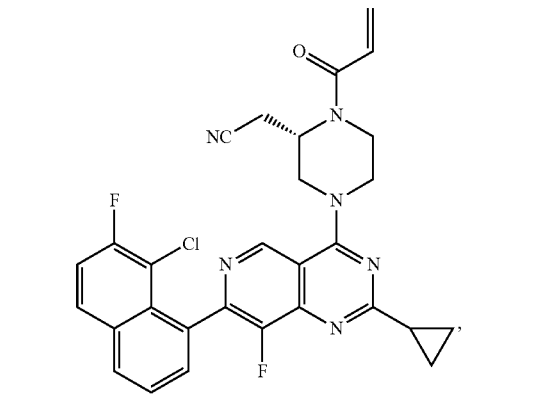
-continued
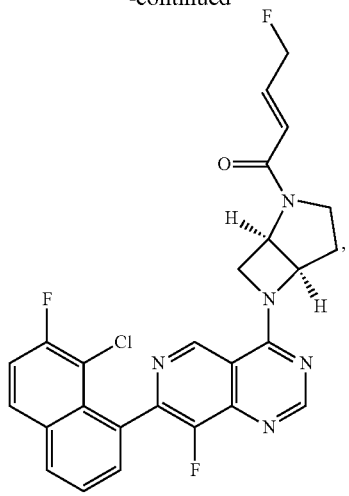
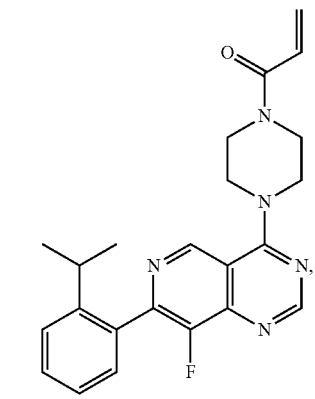
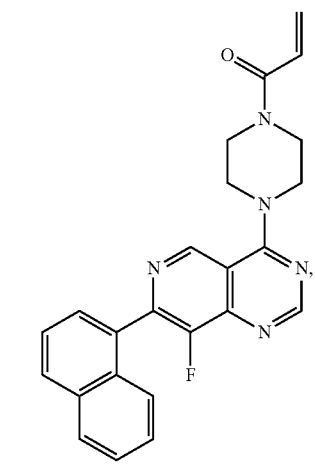

-continued
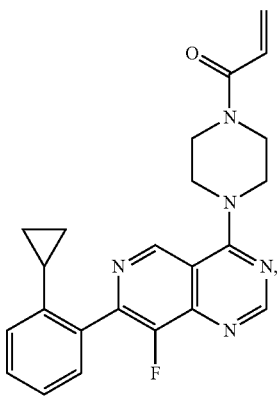
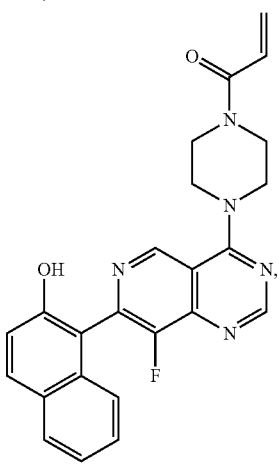
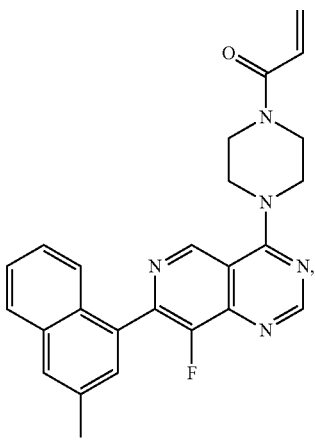
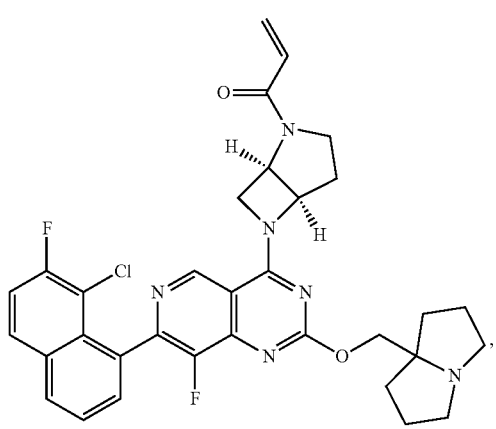
-continued
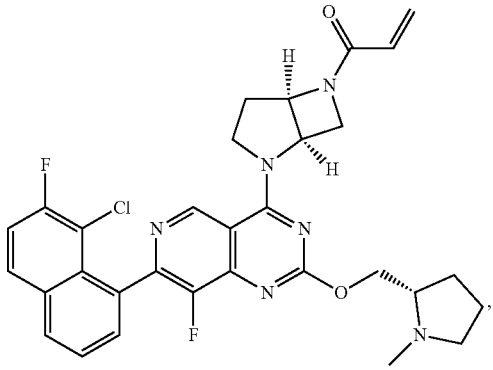
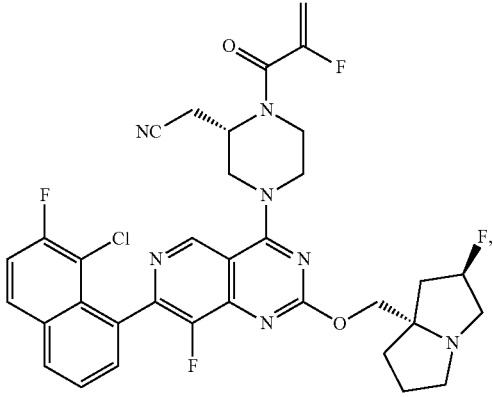
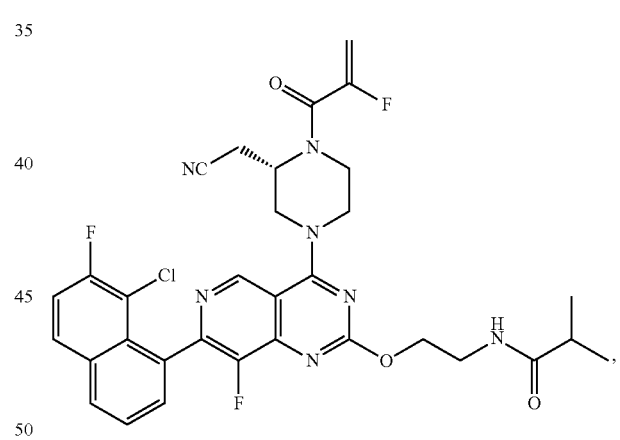
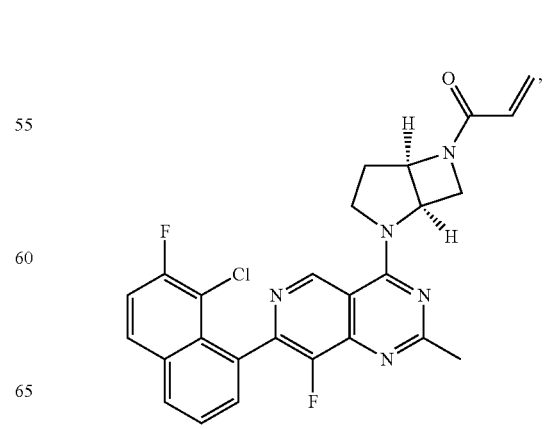

-continued
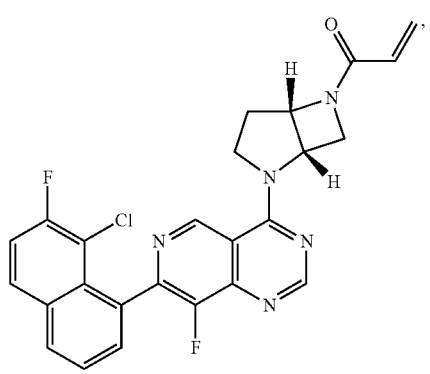
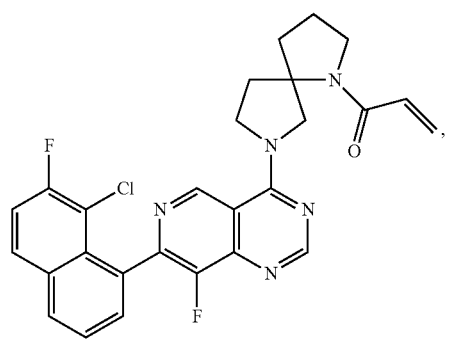
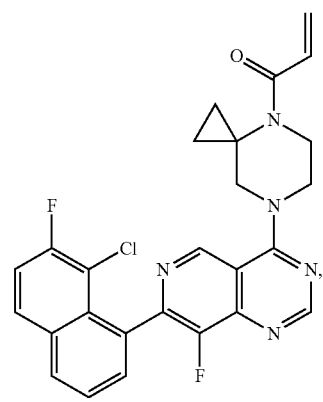
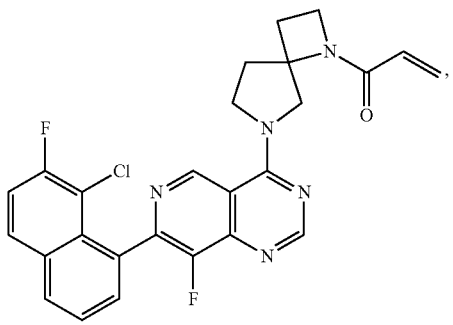
-continued
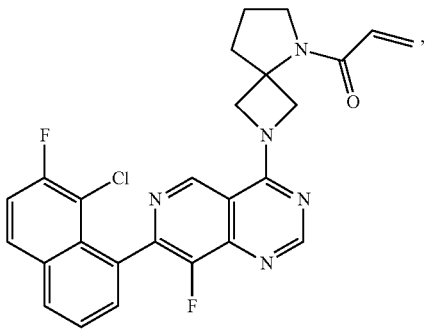
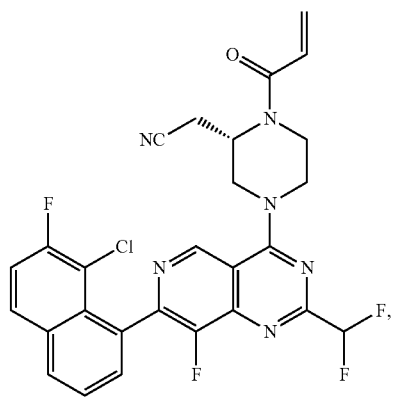
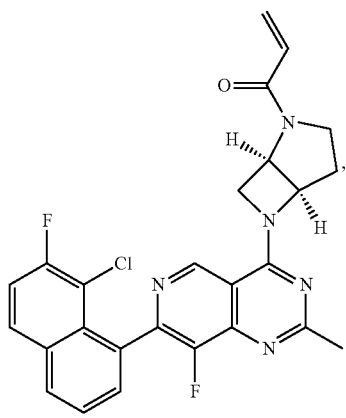 [SMILES: C#Cc1cccc2cccc(-c3ncc4c(N5C[C@@H]6[C@H]5CCN6C(=O)C=C)ncnc4c3F)c12]
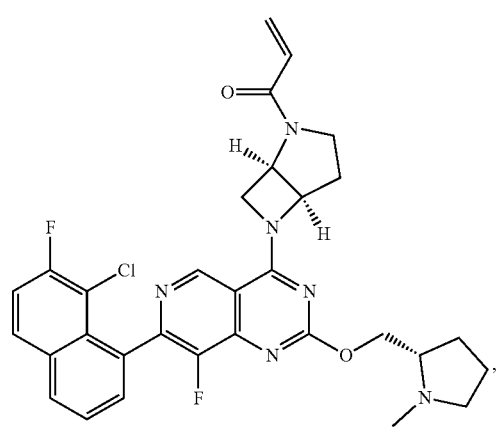

85
-continued
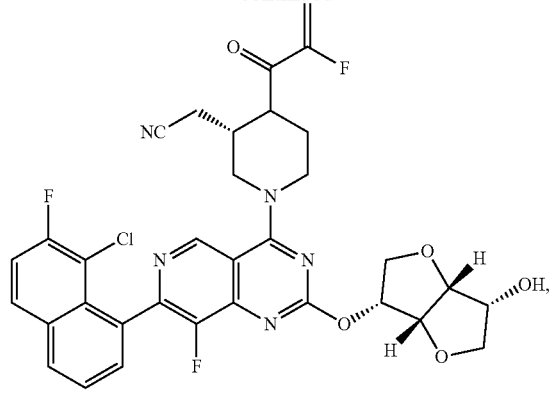
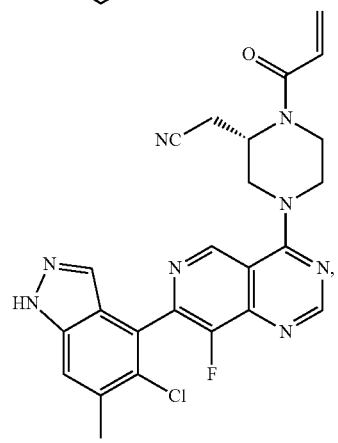
86
-continued
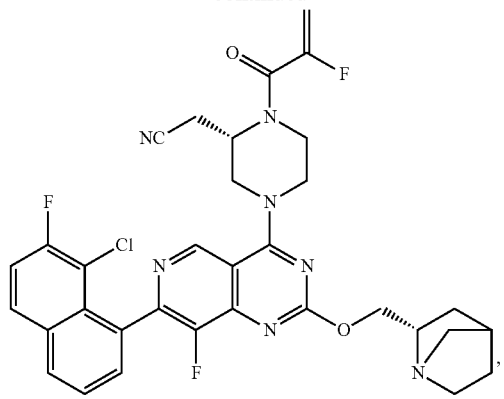
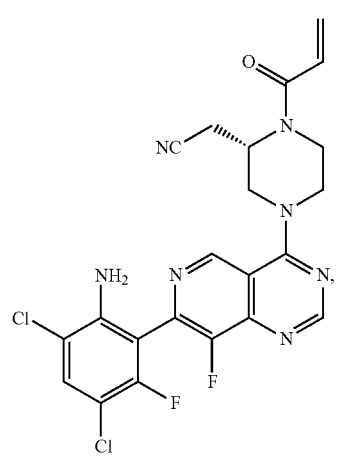
and pharmaceutically acceptable salts thereof.
Additional nonlimiting examples of compounds of Formula I and Formula I-A are selected from the group consisting of:

87
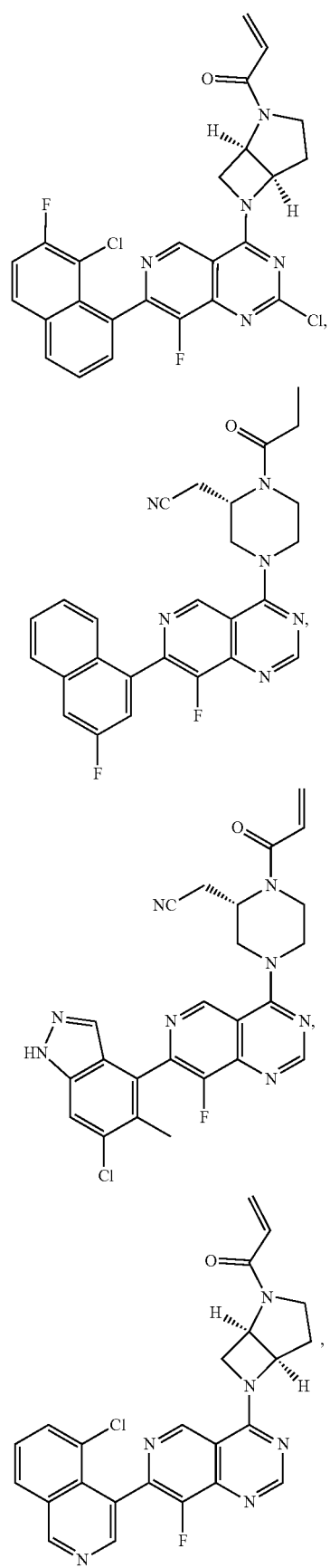
88
-continued
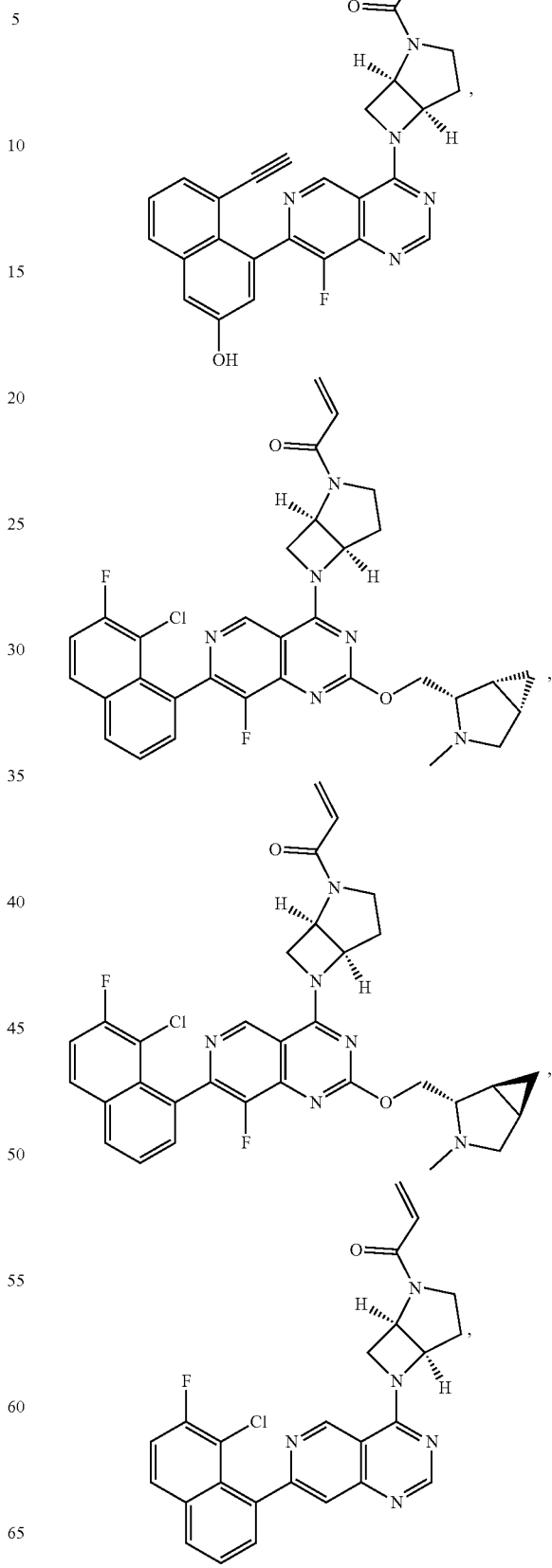

-continued
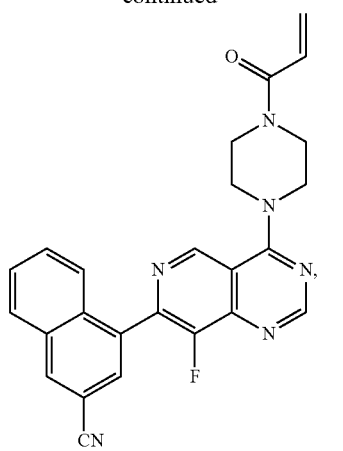
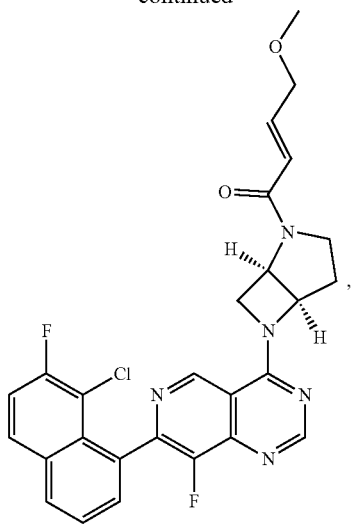
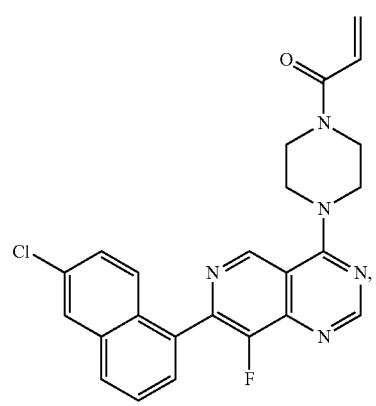
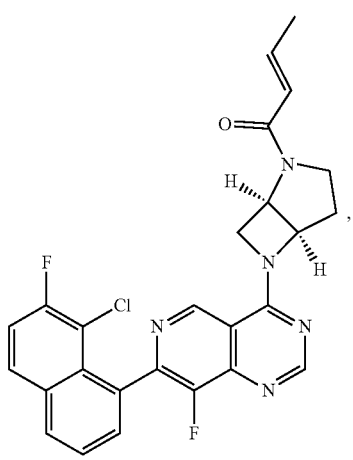
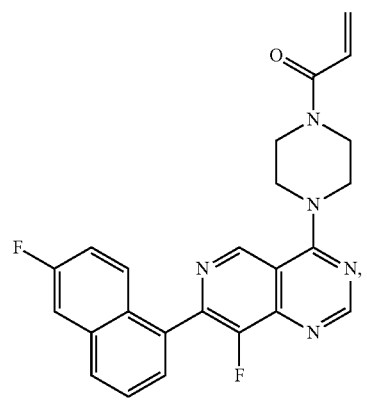
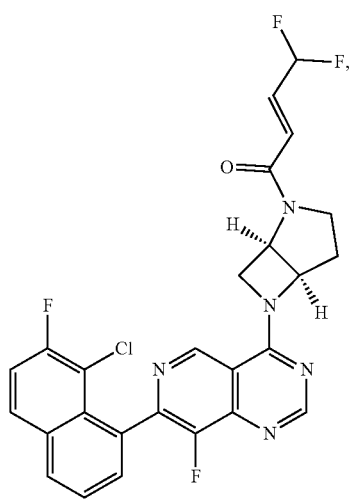

-continued
91
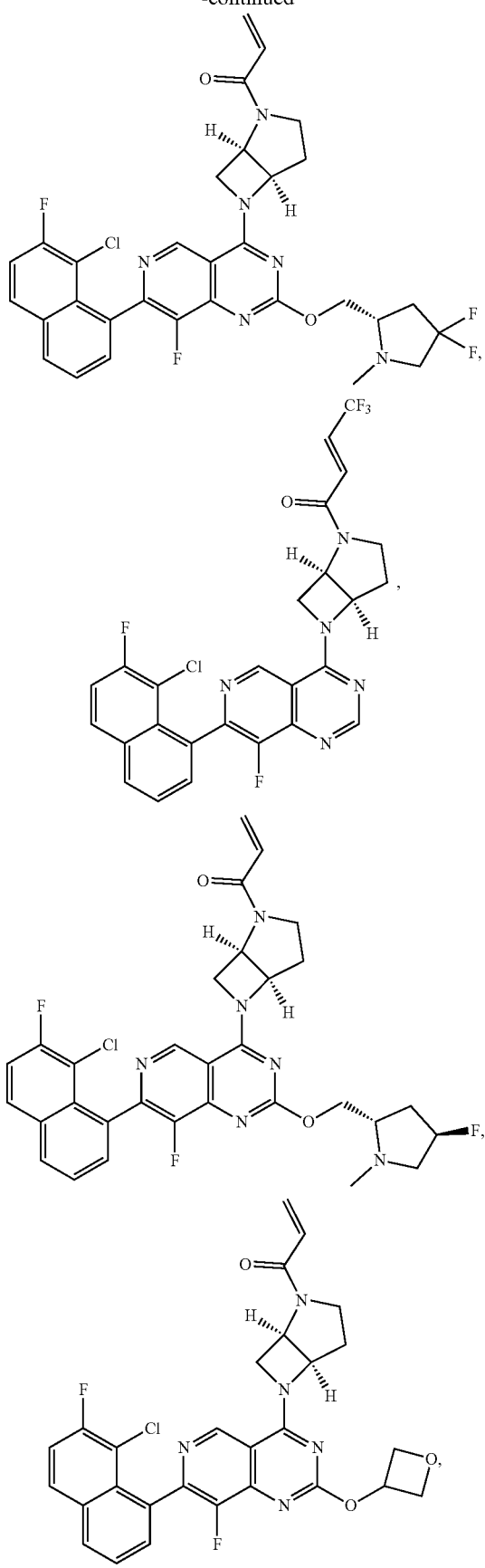
92
-continued
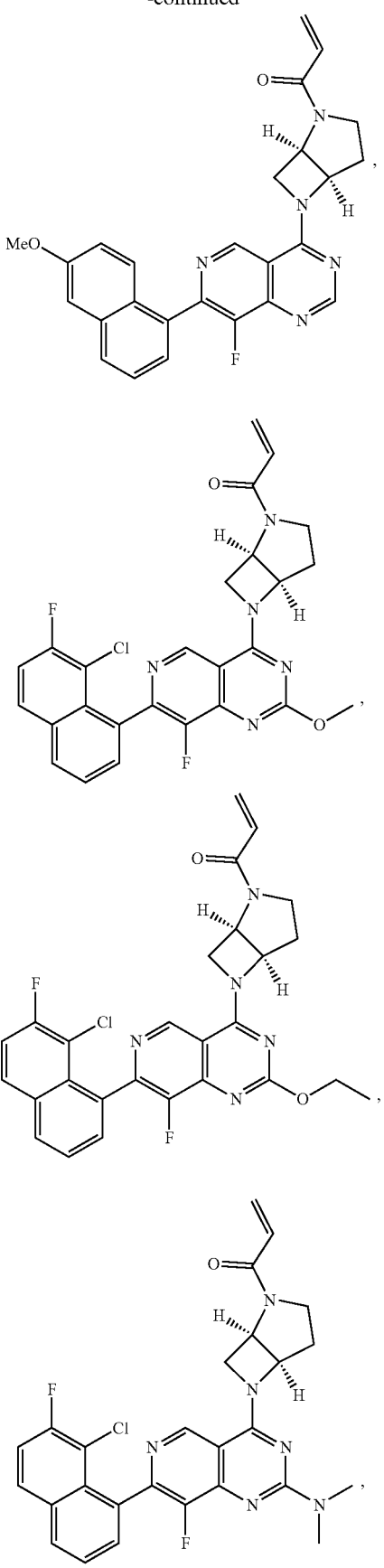

93
-continued
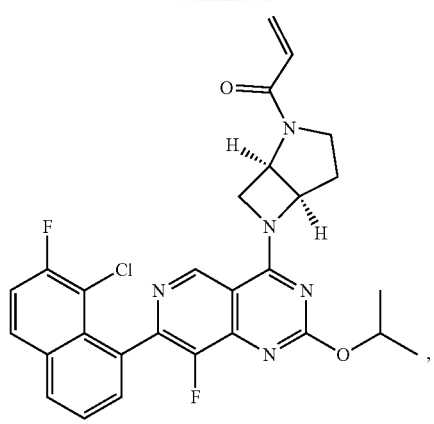
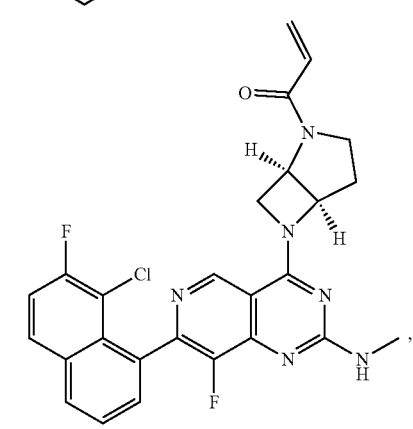
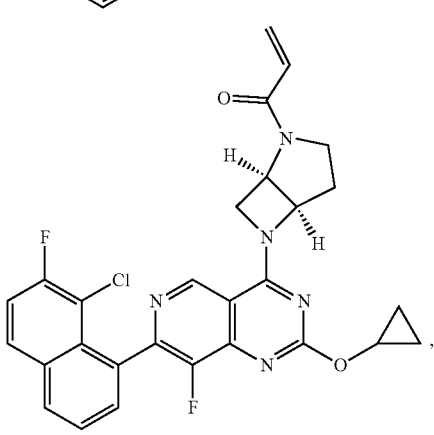
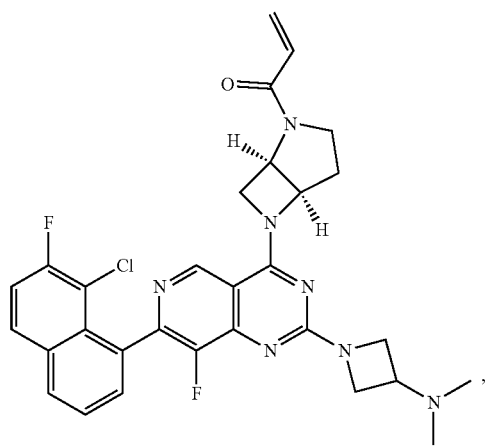
94
-continued
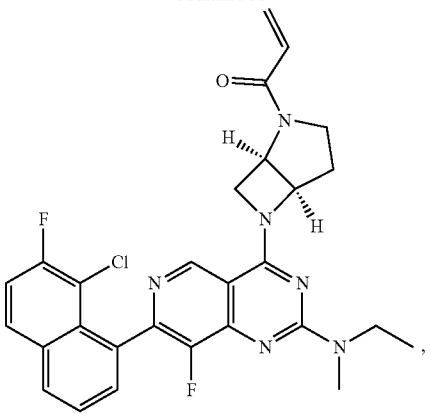
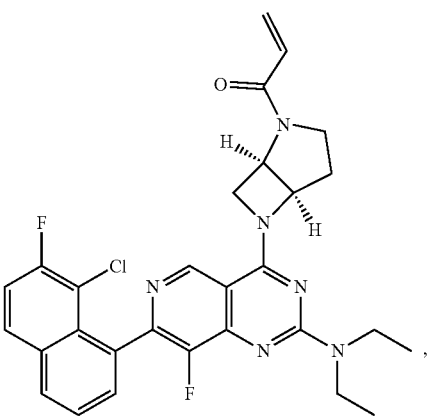
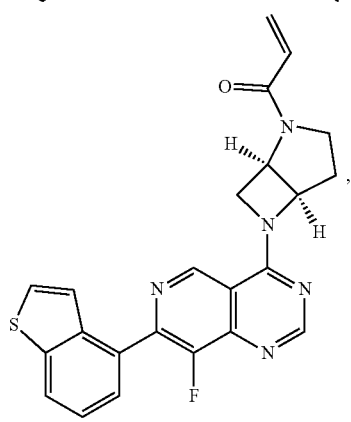
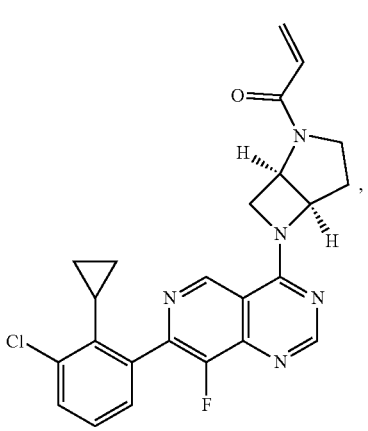

95
-continued
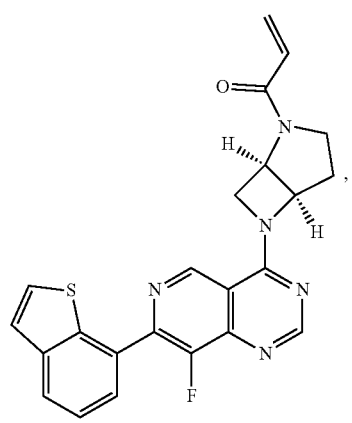
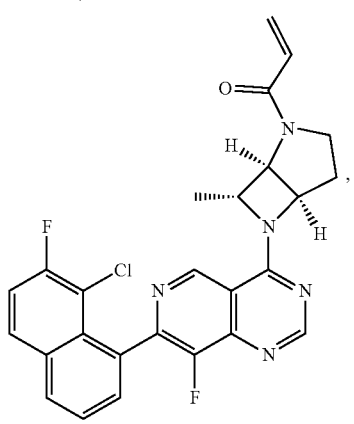
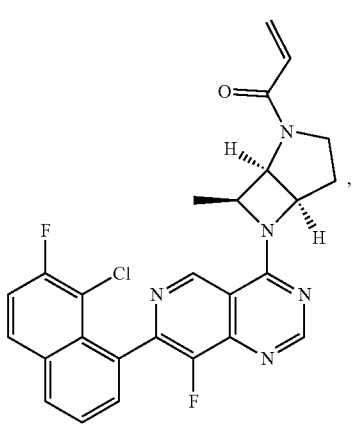
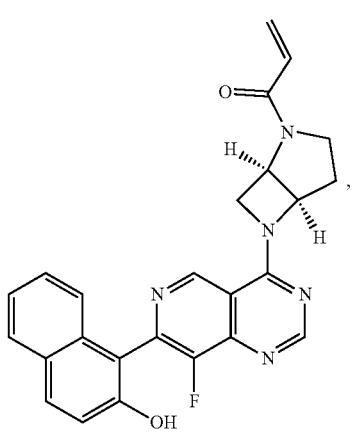
96
-continued
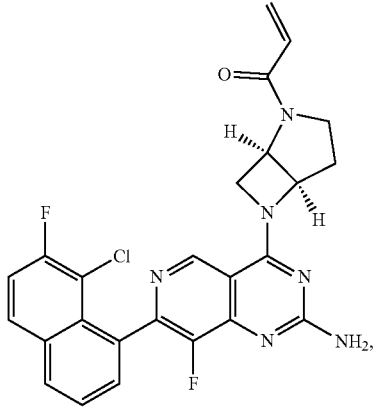
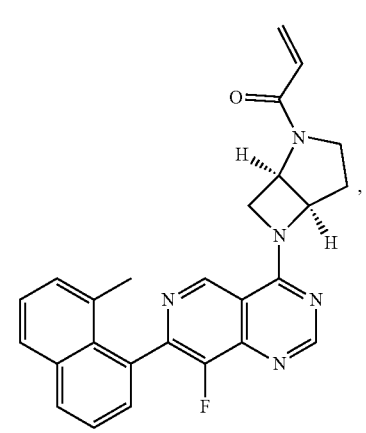
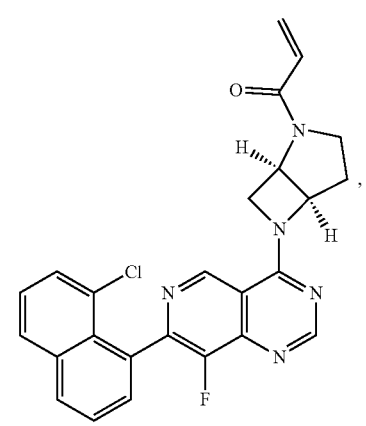
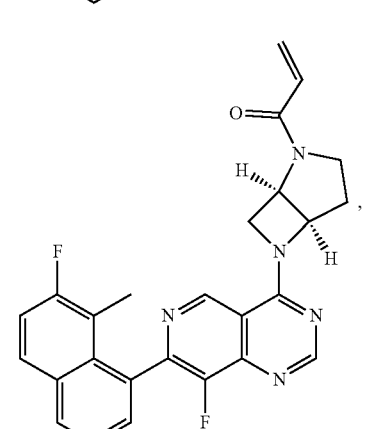

97
-continued
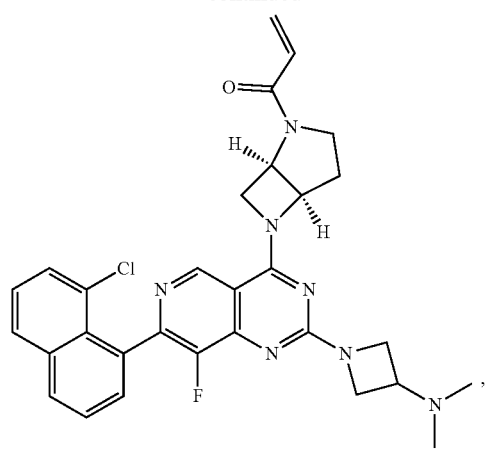
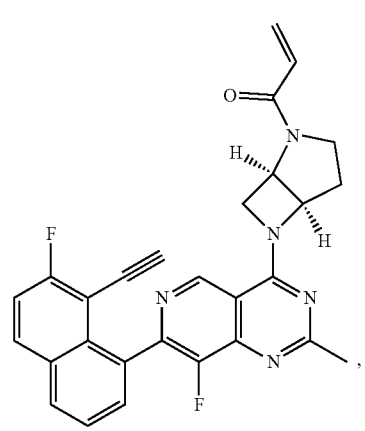
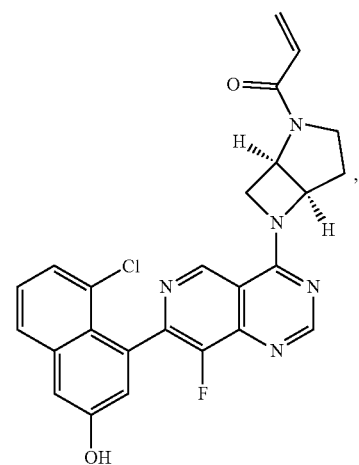
98
-continued
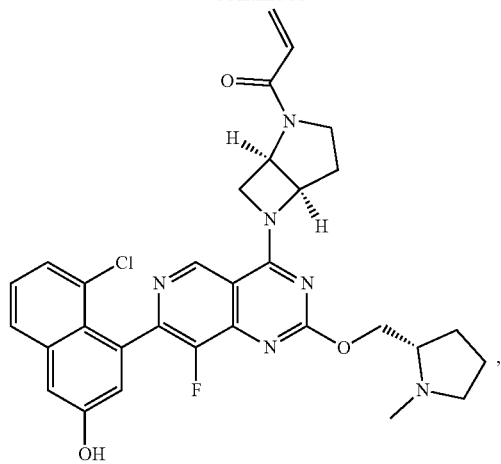
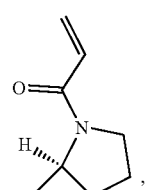
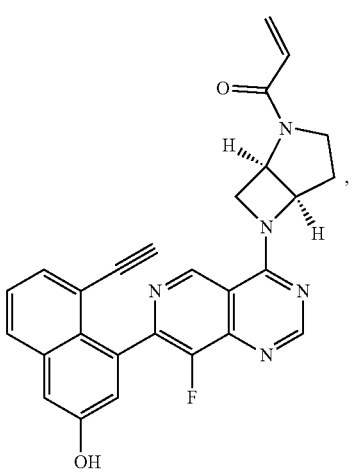

99
-continued
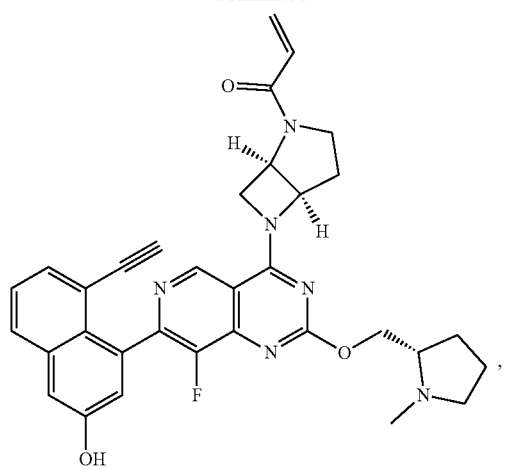
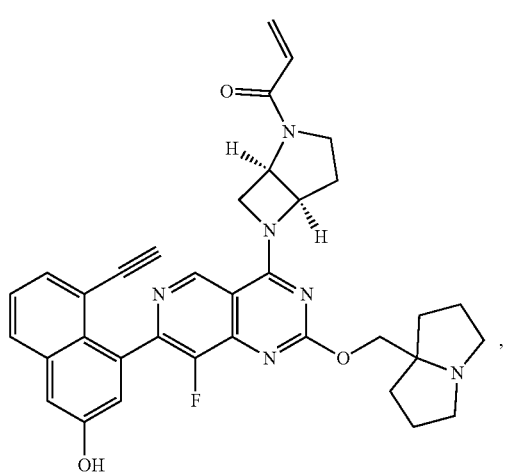
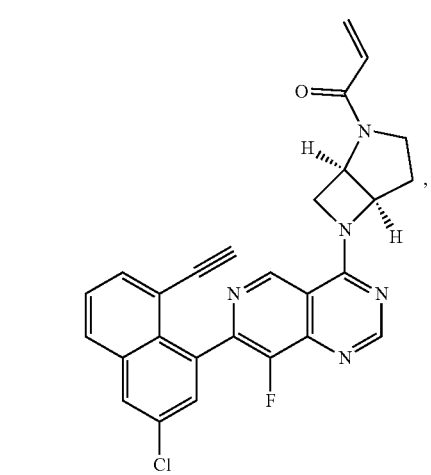
100
-continued
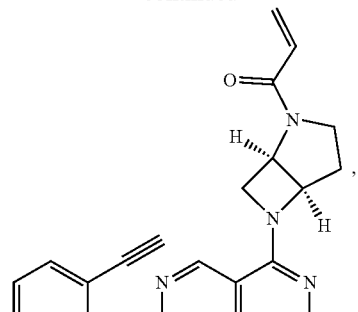
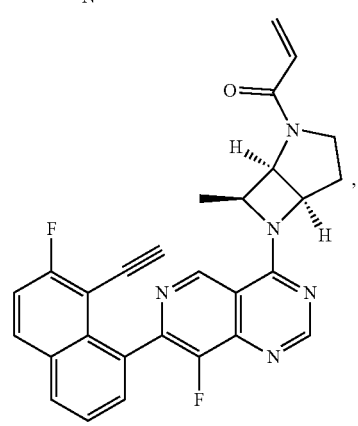
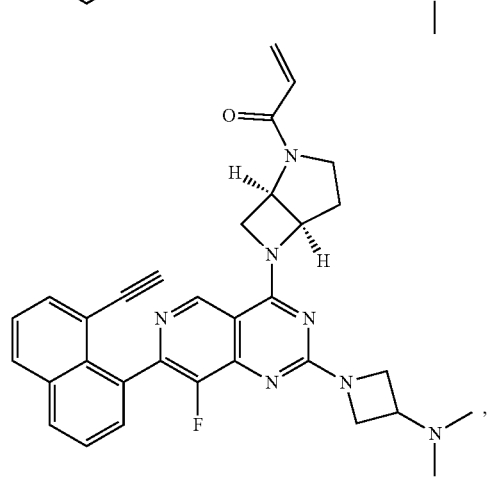

-continued

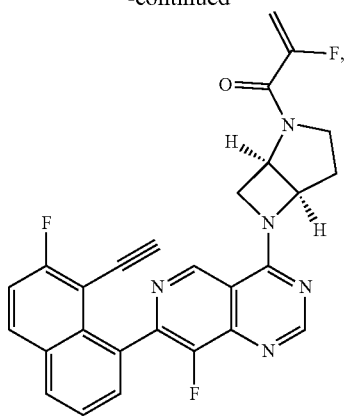

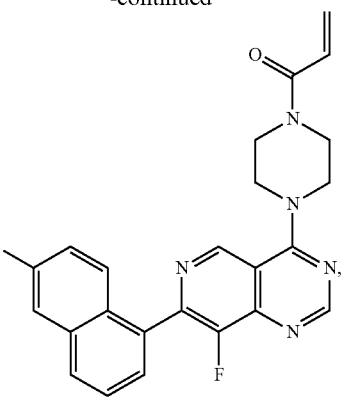

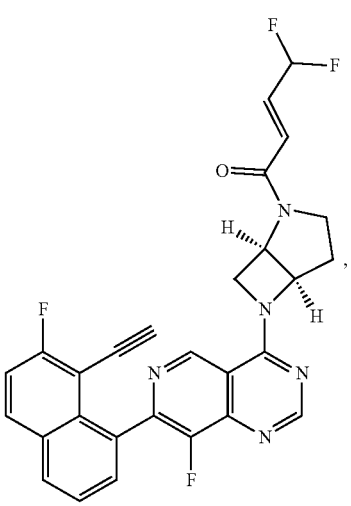

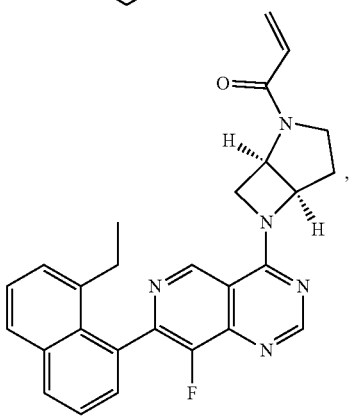

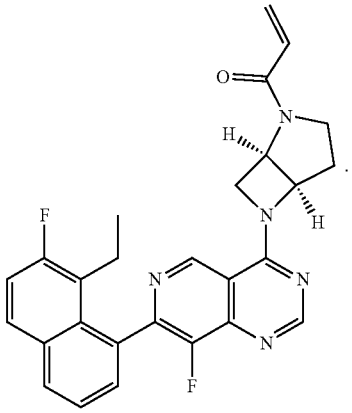

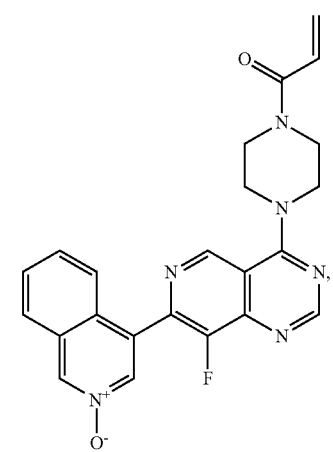

The compounds of Formula (I) and Formula I-A may be formulated into pharmaceutical compositions.

Pharmaceutical Compositions

In another aspect, the invention provides pharmaceutical compositions comprising a KRas G12C inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain embodiments, compounds of the invention are administered intravenously in a hospital setting. In one embodiment, administration may be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salt refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalene-disulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to 300 mg/kg, for example 0.1 to 100 mg/kg per day, and as a further example 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods of use described herein.

Methods of Use

In yet another aspect, the invention provides for methods for inhibiting KRas G12C activity in a cell, comprising contacting the cell in which inhibition of KRas G12C activity is desired with an effective amount of a compound of Formula I and Formula I-A, pharmaceutically acceptable salts thereof or pharmaceutical compositions containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" a KRas G12C with a compound provided herein includes the administration of a compound provided herein to an individual or patient, such as a human, having KRas G12C, as well as, for example, introducing a compound provided herein into a sample containing a cellular or purified preparation containing the KRas G12C.

In one embodiment, a cell in which inhibition of KRas G12C activity is desired is contacted with an effective amount of a compound of Formula I and Formula I-A to negatively modulate the activity of KRas G12C. In other embodiments, a therapeutically effective amount of pharmaceutically acceptable salt or pharmaceutical compositions containing the compound of Formula I and Formula I-A, may be used.

By negatively modulating the activity of KRas G12C, the methods described herein are designed to inhibit undesired cellular proliferation resulting from enhanced KRas G12C activity within the cell. The cells may be contacted in a single dose or multiple doses in accordance with a particular treatment regimen to effect the desired negative modulation of KRas G12C. The degree of covalent modification of KRas G12C may be monitored in vitro using well known methods, including those described in Example A below. In addition, the inhibitory activity of exemplary compounds in cells may be monitored, for example, by measuring the inhibition of KRas G12C activity of the amount of phosphorylated ERK, including those described in Example B below, to assess the effectiveness of treatment and dosages may be adjusted accordingly by the attending medical practitioner.

In another aspect, methods of treating cancer in a patient in need thereof, comprising administering to said patient a therapeutically effective amount of a compound of Formula I and Formula I-A, pharmaceutically acceptable salts thereof or pharmaceutical compositions comprising the compound or pharmaceutically acceptable salts thereof are provided.

The compositions and methods provided herein may be used for the treatment of a KRas G12C-associated cancer in a patient in need thereof, comprising administering to said patient a therapeutically effective amount of a compound of Formula I and Formula I-A, pharmaceutically acceptable salts thereof or pharmaceutical compositions comprising the compound or pharmaceutically acceptable salts thereof are provided. In one embodiment, the KRas G12C-associated cancer is lung cancer.

The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited, to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma);

Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer.

The concentration and route of administration to the patient will vary depending on the cancer to be treated. The compounds, pharmaceutically acceptable salts thereof and pharmaceutical compositions comprising such compounds and salts also may be co-administered with other anti-neoplastic compounds, e.g., chemotherapy, or used in combination with other treatments, such as radiation or surgical intervention, either as an adjuvant prior to surgery or post-operatively.

Also provided herein is a compound of Formula I and Formula I-A, or a pharmaceutically acceptable salt or solvate thereof, or a pharmaceutical composition thereof as defined herein for use in therapy.

Also provided herein is a compound of Formula I and Formula I-A, or a pharmaceutically acceptable salt or solvate thereof or a pharmaceutical composition thereof as defined herein for use in the treatment of cancer.

Also provided herein is a compound of Formula I and Formula I-A, or a pharmaceutically acceptable salt or solvate thereof for use in the inhibition of KRas G12C.

Also provided herein is a compound of Formula I and Formula I-A, or a pharmaceutically acceptable salt or solvate thereof or a pharmaceutical composition thereof as defined herein, for use in the treatment of a KRas G12C-associated disease or disorder.

Also provided herein is the use of a compound of Formula I and Formula I-A, or a pharmaceutically acceptable salt or solvate thereof, as defined herein in the manufacture of a medicament for the treatment of cancer.

Also provided herein is a use of a compound of Formula I and Formula I-A, or a pharmaceutically acceptable salt or solvate thereof, as defined herein in the manufacture of a medicament for the inhibition of activity of KRas G12C.

Also provided herein is the use of a compound of Formula I and Formula I-A, or a pharmaceutically acceptable salt or solvate thereof, as defined herein, in the manufacture of a medicament for the treatment of a KRas G12C-associated disease or disorder.

Also provided herein is a method for treating cancer in a patient in need thereof, the method comprising (a) determining that cancer is associated with a KRas G12C mutation (e.g., a KRas G12C-associated cancer) (e.g., as determined using a regulatory agency-approved, e.g., FDA-approved, assay or kit); and (b) administering to the patient a therapeutically effective amount of a compound of Formula I and Formula I-A, or a pharmaceutically acceptable salt thereof, or a pharmaceutical composition thereof.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

Reaction Schemes and Examples

The compounds of the present invention may be prepared from commercially available reagents using the synthetic methods and reaction schemes described herein, or using other reagents and conventional methods well known to those skilled in the art.

For instance, compounds of the present invention may be prepared according to the General Reaction Schemes I and II.

General Reaction Schemes

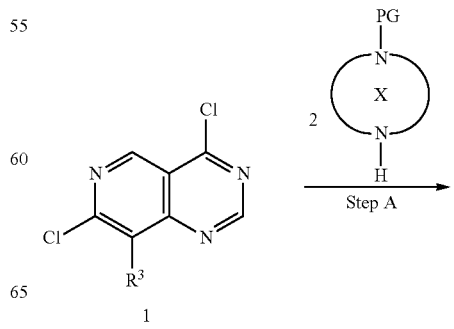

SCHEME I

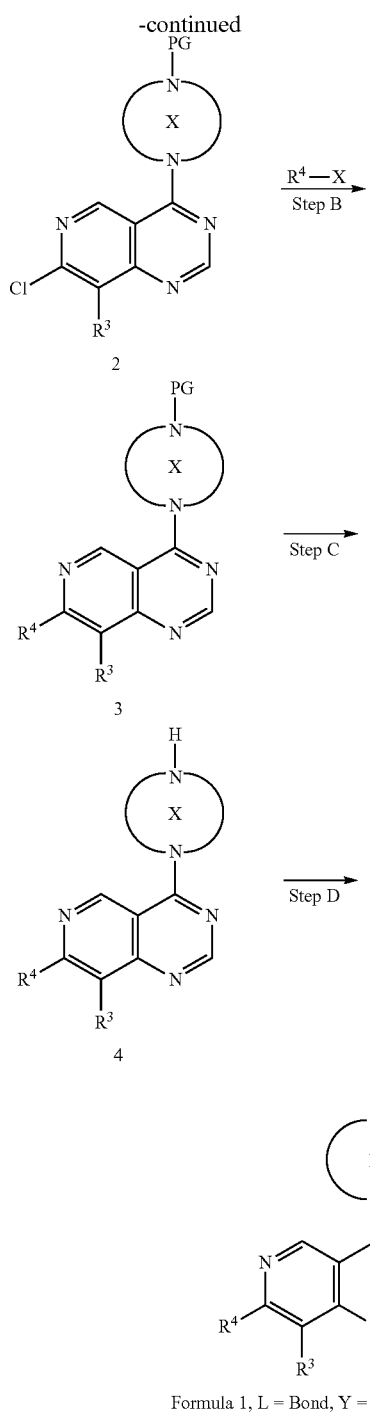

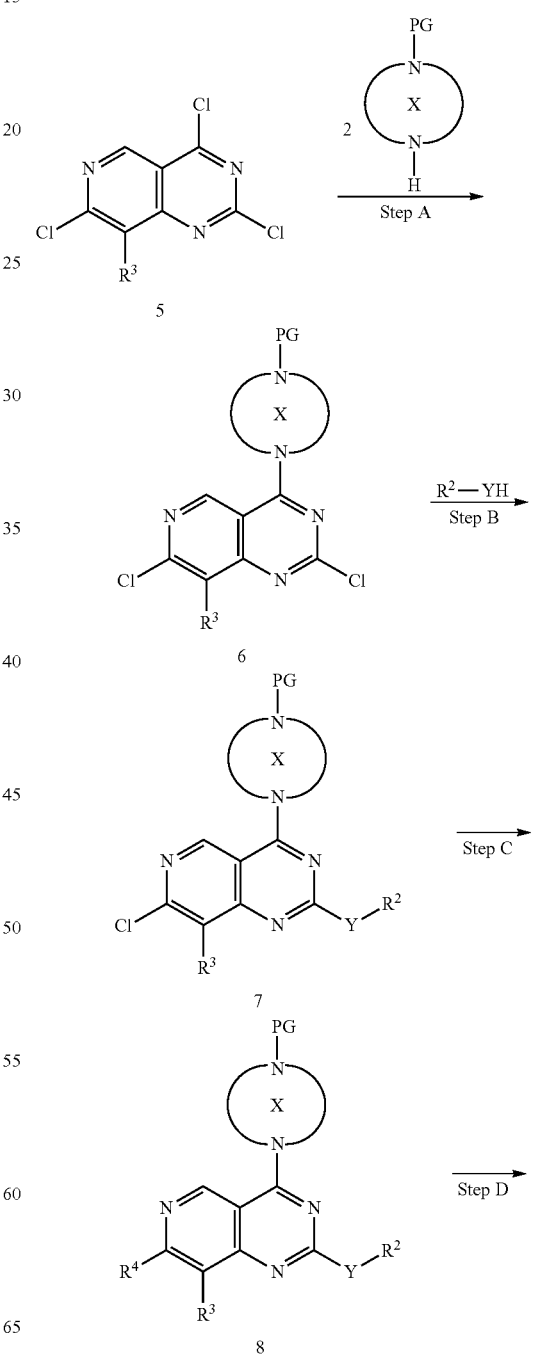

protecting group is removed under standard conditions. For example, if the protecting group is a carboxybenzyl group, it can be removed upon treatment with hydrogen in the presence of a palladium catalyst and ammonia, in a solvent such as methanol. The $R^1$ group is introduced, for example by treatment of intermediate 4 with an acid chloride in the presence of a base such as diisopropylethylaine in a solvent such as dichloromethane.

Compounds (1), (2), (3), and (4) (5) as shown and described above for Scheme 1 are useful as intermediates for preparing compounds of Formula I and are provided as further aspects of the invention.

SCHEME II

Formula 1, L = Bond, Y = Bond, $R^2$ = H

Compounds of Formula 1 where L and Y are bonds and $R^2$ is hydrogen can be prepared according to general Scheme 1. A suitably substituted compound 1 is reacted in Step A with a heterocycle, wherein one of the nitrogen atoms is protected with a suitable nitrogen protecting group PG, such as a carboxybenzyl group. This reaction proceeds in a solvent such as dichloromethane in the presence of a base such as diisopropylethylamine. In Step B, coupling of an $R^4$ group is accomplished by using a suitably functionalized $R^4$, for example a boronic acid or boronate ester, in the presence of a palladium catalyst and a base such as potassium phosphate in a solvent such as dioxane. In Step C, the

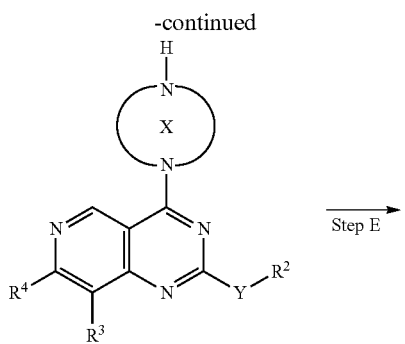

Step E →

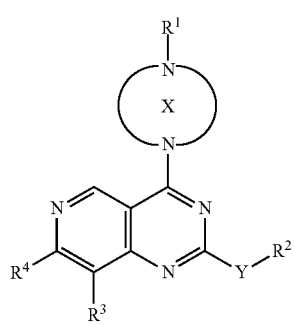

Formula 1, where L is a bond

Compounds of Formula 1 where L is a bond can be prepared according to general Scheme 2. A suitably substituted compound 5 is reacted in Step A with a heterocycle, wherein one of the nitrogen atoms is protected with a suitable nitrogen protecting group PG, such as a carboxybenzyl group. This reaction proceeds in a solvent such as dichloromethane in the presence of a base such as diisopropylethylamine. In Step B, addition of a Y—R$^2$ group is accomplished either by a transition metal-mediated coupling or an aromatic substitution. As an example, the aromatic substitution can be achieved by heating a mixture of HY—R$^2$ in a solvent such as dioxane in the presence of a base such as diisopropylethylamine. In Step C, coupling of an R$^4$ group is accomplished by using a suitably functionalized R$^4$, for example a boronic acid or boronate ester, in the presence of a palladium catalyst and a base such as potassium phosphate in a solvent such as dioxane. In Step D, the protecting group is removed under standard conditions. For example, if the protecting group is a carboxybenzyl group, it can be removed upon treatment with hydrogen in the presence of a palladium catalyst and ammonia, in a solvent such as methanol. Finally, in Step E, the R$^1$ group is introduced, for example by treatment of intermediate 9 with an acid chloride in the presence of a base such as diisopropylethylaine in a solvent such as dichloromethane.

Accordingly, also provide is a process for preparing a compound of Formula I, comprising:

(a) for a compound of Formula I where Y is a bond and R$^2$ is hydrogen, reacting a compound of formula 5

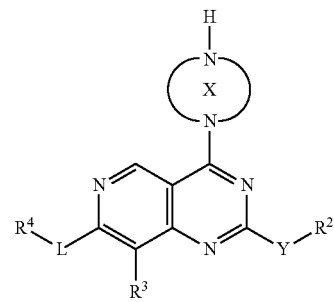

where X, R$^3$, R$^4$ and L are as defined for Formula I, wherein and —Y—R$^2$ is other than hydrogen, with an acid chloride having the formula Cl—C(O)C(R$^A$)═══ C(R$^A$)$_p$ or Cl—SO$_2$C(R$^A$)═══ C(R$^B$)$_p$ or an anhydride having the formula C(R$^B$)$_p$ C(R$^A$)C(O)OC(O)C(R$^A$)═══ C(R$^B$)$_p$, where R$^A$, R$^B$ and p are as defined for Formula I, in the presence of a base; and optionally forming a salt thereof.

Accordingly, also provide is a process for preparing a compound of Formula I, comprising:

(a) for a compound of Formula I where L is a bond, and —Y—R$^2$ is other than hydrogen, reacting a compound of formula 5

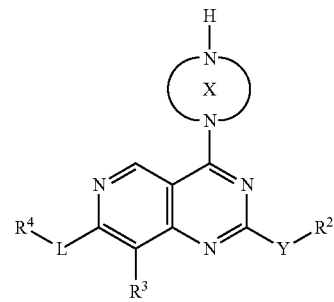

where X, R$^3$, R$^4$, as defined for Formula I, wherein L is a bond and —Y—R$^2$ is other than hydrogen, with an acid chloride having the formula Cl—C(O)C(R$^A$)═══ C(R$^B$)$_p$ or Cl—SO$_2$C(R$^A$)═══ C(R$^B$)$_p$ or an anhydride having the formula C(R$^B$)$_p$ C(R$^A$)C(O)OC(O)C(R$^A$)═══ C(R$^B$)$_p$, where R$^A$, R$^B$ and p are as defined for Formula I, in the presence of a base; and optionally forming a salt thereof.

The compounds of the present invention may have one or more chiral centers and may be synthesized as stereoisomeric mixtures or atropisomers, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

The following intermediates may be used to synthesize compounds of Formula I and Formula I-A.

Intermediate 1

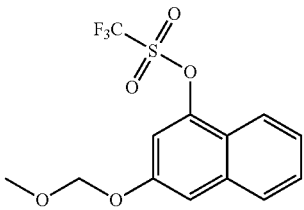 [SMILES: COCOc1cc(OS(=O)(=O)C(F)(F)F)c2ccccc2c1]

3-(methoxymethoxy)naphthalen-1-yl trifluoromethanesulfonate

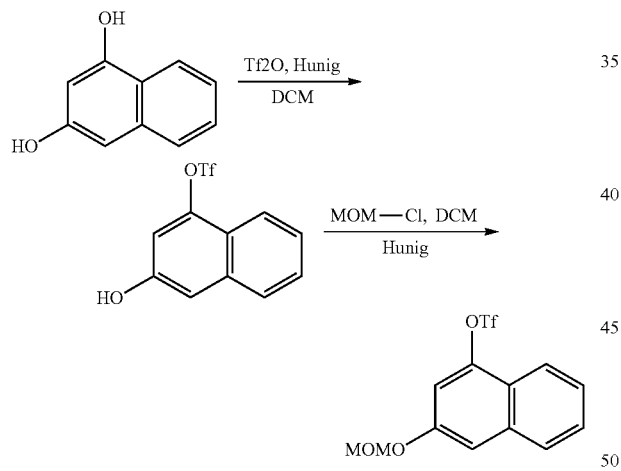

3-Hydroxynaphthalen-1-yl trifluoromethanesulfonate (13.101 g, 44.831 mmol) was dissolved in dichloromethane (100 mL) and stirred at 0° C. To this solution was added chloro(methoxy)methane (3.7456 ml, 49.315 mmol) and Hunig's base (11.745 mL, 67.247 mmol). The reaction was stirred at 0° C. for 4 hrs. The reaction was partitioned with 1M HCl and washed with saturated sodium bicarbonate. The combined organic layers were dried over magnesium sulfate and concentrated under vacuum. The concentrated material was loaded onto a 120 g RediSep® gold silica gel column with dichloromethane and purified by normal phase chromatography (CombiFlash®, 0%-20% ethyl acetate/hexanes as the eluent) to give 3-(methoxymethoxy)naphthalen-1-yl trifluoromethanesulfonate (11.785 g, 35.045 mmol, 78.171% yield).

Intermediate 2

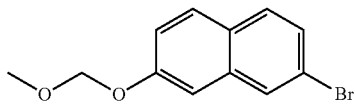

2-bromo-7-(methoxymethoxy)naphthalene

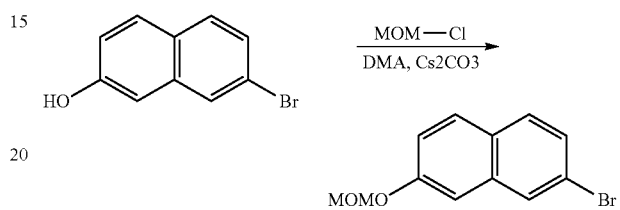

To a solution of 7-bromonaphthalen-2-ol (2.0 g, 9.0 mmol) in dimethyl acetamide (40 mL) was added chloro(methoxy)methane (1.4 g, 18 mmol) and cesium carbonate (5.8 g, 18 mmol) and the reaction mixture was stirred overnight at room temperature. The reaction was diluted with water and the aqueous layer washed with ethyl acetate. The combined organic layers were washed with water and brine, dried over magnesium sulfate and concentrated under vacuum. The crude material was purified by normal phase chromatography using 5-50% ethyl acetate/hexanes as the eluent to give 2-bromo-7-(methoxymethoxy)naphthalene (1.0 g, 3.7 mmol, 42% yield).

Intermediate 3

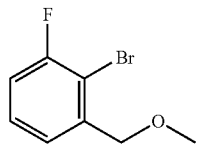

2-bromo-1-fluoro-3-(methoxymethyl)benzene

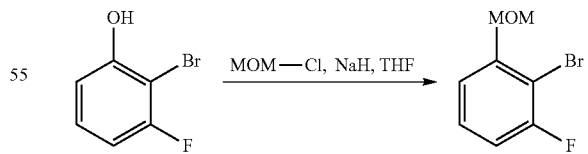

To a stirred solution of 2-bromo-3-fluorophenol (1422 mg, 7.445 mmol) in 22 mL tetrahydrofuran at room temperature under nitrogen was added NaH (327.6 mg, 8.190 mmol) neat as a solid portion wise. After 15 minutes, a solution had formed. Chloro(methoxy)methane (678.6 μL, 8.934 mmol) was added by syringe. After stirring for 2 hours, the reaction was quenched with saturated ammonium chloride solution and then partitioned between ethyl acetate (30 mL) and water (30 mL). The combined organic layers were isolated, washed with brine, dried over MgSO$_4$, filtered and concentrated. The crude product was loaded in a minimum of dichloromethane onto a 40 gram RediSep® column pre-wet with hexanes and eluted with an ethyl acetate/hexanes gradient (0% to 20% ethyl acetate). Fractions containing the product were combined and concentrated to provide the product as a clear oil (1.45 g, 83%).

Intermediate 4

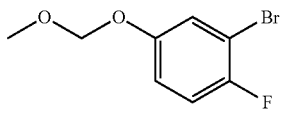

2-bromo-1-fluoro-4-(methoxymethoxy)benzene

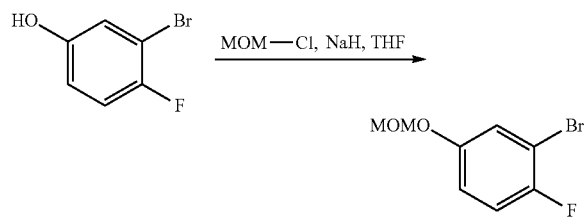

To a stirred solution of 3-bromo-4-fluorophenol (327 mg, 1.71 mmol) in 5.1 mL tetrahydrofuran at room temperature under nitrogen was added NaH (75.3 mg, 1.88 mmol) neat as a solid portion wise. After 15 minutes, a solution had formed. Chloro(methoxy)methane (156 µL, 2.05 mmol) was added by syringe. After stirring for 2 hours, the reaction was quenched with saturated ammonium chloride solution and partitioned between ethyl acetate and water. The combined organic layers were washed with brine, dried over MgSO$_4$, filtered and concentrated. The crude product was loaded in a minimum of dichloromethane onto a 24 gram RediSep® column pre-wet with hexanes and eluted with an ethyl acetate/hexanes gradient (0% to 20% ethyl acetate). Fractions containing the product were combined and concentrated to provide the product as a clear oil (120 mg, 29.8%)

Intermediate 5

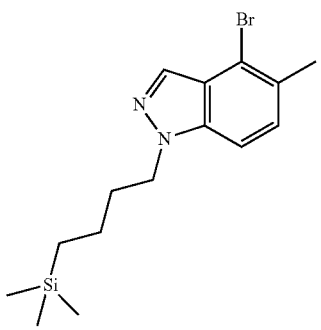

4-bromo-5-methyl-1-((2-(trimethylsilyl)ethoxy)methyl)-1H-indazole

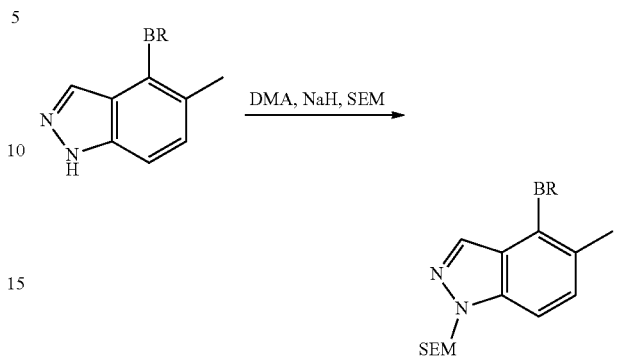

To a solution of 4-bromo-5-methyl-1H-indazole (0.7 g, 3.3 mmol) in dimethyl acetamide (30 mL) cooled to 0° C. was added NaH (0.19 g, 4.6 mmol) in portions and the reaction mixture was purged with nitrogen. The reaction was stirred for 20 minutes, and then (2-(chloromethoxy)ethyl)trimethylsilane (0.83 g, 5.0 mmol) was added and the reaction was stirred for 2 hours while warming to room temperature. The reaction was quenched by pouring into water and the aqueous layer was extracted into ethyl acetate. The combined organic layers were washed with water and brine, dried over MgSO$_4$ and concentrated under vacuum. The crude material was purified by chromatography using 10-50% ethyl acetate/hexanes as the eluent to give 4-bromo-5-methyl-1-((2-(trimethylsilyl)ethoxy)methyl)-1H-indazole (0.87 g, 79%).

Intermediate 6

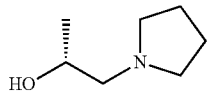

(R)-1-(pyrrolidin-1-yl)propan-2-ol

In a sealed tube, R-(+)-Propylene oxide (3.69 mL, 52.7 mmol) was cooled to −78° C. and then sparged with anhydrous dimethyl amine for a few minutes. The reaction mixture was heated to 70° C. for 16 hours. The reaction was cooled and concentrated in vacuo for 20 minutes to provide (R)-1-(pyrrolidin-1-yl)propan-2-ol (5.35 g, 41.4 mmol, 98.2% yield).

Intermediate 7

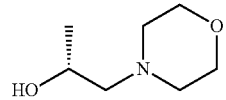

(R)-1-morpholinopropan-2-ol

In a sealed tube, R-(+)-Propylene oxide (2.111 mL, 30.13 mmol) and morpholine (1.490 mL, 17.22 mmol) were heated to 70° C. for 20 hours. The reaction was cooled and concentrated in vacuo to provide (R)-1-morpholinopropan-2-ol (2.47 g, 17.01 mmol, 98.80% yield).

Intermediate 8

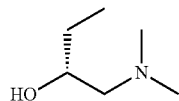

(R)-1-(dimethylamino)butan-2-ol

In a sealed tube, R-(+)-Propylene oxide (4.00 g, 55.5 mmol) and dimethylamine (1.00 g, 22.2 mmol), were heated to 65° C. for 18 hours. The reaction was cooled and concentrated in vacuo. The resulting residue was purified by silica gel (0-12% MeOH in DCM) to provide (R)-1-(dimethylamino)butan-2-ol (1.38 g, 11.8 mmol, 53.1% yield).

Intermediate 9

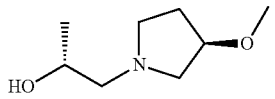

(R)-1-((R)-3-methoxypyrrolidin-1-yl)propan-2-ol

In a sealed tube, (R)-3-methoxypyrrolidine hydrochloride (1.00 g, 7.27 mmol), TEA (2.03 mL, 14.5 mmol) and R-(+)-Propylene oxide (1.27 mL, 18.2 mmol) were heated to 65° C. for 18 hours. The reaction was cooled and concentrated in vacuo. The resulting residue was purified by silica gel (0-12% MeOH in DCM) to provide (R)-1-((R)-3-methoxypyrrolidin-1-yl)propan-2-ol (775 mg, 4.87 mmol, 67.0% yield).

Intermediate 10

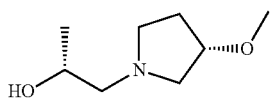

(R)-1-((S)-3-methoxypyrrolidin-1-yl)propan-2-ol

In a sealed tube, (S)-3-methoxypyrrolidine hydrochloride (1.00 g, 7.27 mmol), TEA (2.03 mL, 14.5 mmol) and R-(+)-Propylene oxide (1.27 mL, 18.2 mmol) were heated to 65° C. for 18 hours. The reaction was cooled and concentrated in vacuo. The resulting residue was purified by silica gel (0-12% MeOH in DCM) to provide (R)-1-((S)-3-methoxypyrrolidin-1-yl)propan-2-ol (781 mg, 4.90 mmol, 67.5% yield)

Intermediate 11

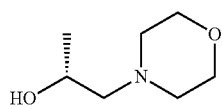

(R)-1-((S)-3-((tert-butyldimethylsilyl)oxy)pyrrolidin-1-yl)propan-2-ol

In a sealed tube, R-(+)-Propylene oxide (0.609 mL, 8.69 mmol) and (S)-3-((tert-butyldimethylsilyl)oxy)pyrrolidine (1.00 g, 4.97 mmol) were heated to 70° C. for 20 hours. The reaction was cooled and concentrated in vacuo to provide (R)-1-((S)-3-((tert-butyldimethylsilyl)oxy)pyrrolidin-1-yl)propan-2-ol (1.29 g, 4.20 mmol, 84.6% yield).

Intermediate 12

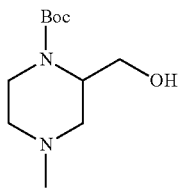 [SMILES: CN1CCN(C(=O)OC(C)(C)C)C(CO)C1]

tert-butyl 2-(hydroxymethyl)-4-methylpiperazine-1-carboxylate

To a suspension of lithium chloride (246 mg, 5.81 mmol) and Lithium Borohydride (126 mg, 5.81 mmol) in ethanol (9 mL), at 0° C. under nitrogen, a solution of 1-(tert-butyl) 2-methyl 4-methylpiperazine-1,2-dicarboxylate (750 mg, 2.90 mmol) in dry THF (6 mL) was added dropwise. The reaction was stirred overnight forming a white precipitate. The precipitate was filtered and washed with ethanol. The combined filtrate and organic extracts were concentrated to provide a white residue which was extracted with ethyl acetate. The combined organic layers were washed with saturated sodium chloride solution, dried over sodium sulfate and concentrated in vacuo. The residue was purified by chromatography with isocratic 10% MeOH in DCM with 0.2% NH$_4$OH to provide tert-butyl 2-(hydroxymethyl)-4-methylpiperazine-1-carboxylate (104 mg, 0.452 mmol, 15.6% yield).

Intermediate 13

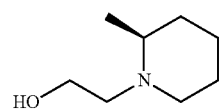

(S)-2-(2-methylpiperidin-1-yl)ethan-1-ol

A mixture of (S)-2-methylpiperidine (100 mg, 1.01 mmol), 2-bromoethanol (78 µL, 139 mg, 1.11 mmol, 1.1 eq.), sodium iodide (151 mg, 1 eq.), potassium carbonate (418 mg, 3 eq.) and acetonitrile (1 mL) in a 4-mL vial was purged with nitrogen, sealed and stirred at room temperature for 2 days. The reaction mixture was partitioned between diethyl ether (15 mL) and water (2 mL). The ether layer was washed with brine (2 mL), acidified with TFA and dried under high vacuum for 2 days. The residue was washed with ether (3 mL), diluted with water (0.5 mL) and basified with 10M NaOH (0.2 mL). The layers were separated and the upper layer was carefully dried over NaOH. The ether solution was evaporated under nitrogen to yield crude (S)-2-(2-methylpiperidin-1-yl)ethan-1-ol (100 mg, 0.698 mmol, 69.24% yield) as colorless oil.

Intermediate 14

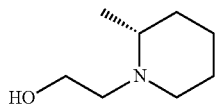

(R)-2-(2-methylpiperidin-1-yl)ethan-1-ol

Synthesized according to the method of Intermediate 13, using (R)-2-methylpiperidine (99 mg, 1 mmol) in place of (S)-2-methylpiperidine.

Intermediate 15

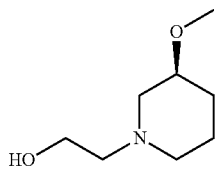

(S)-2-(3-methoxypiperidin-1-yl)ethan-1-ol

Synthesized according to the method of Intermediate 13, using (S)-3-methoxypiperidine (173 mg, 1.50 mmol) in place of (S)-2-methylpiperidine.

Intermediate 16

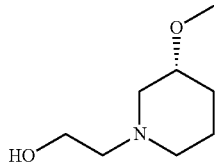

(R)-2-(3-methoxypiperidin-1-yl)ethan-1-ol

Synthesized according to the method of Intermediate 13, using R-3-methoxypiperidine (173 mg, 1.50 mmol) in place of (S)-2-methylpiperidine.

Intermediate 17

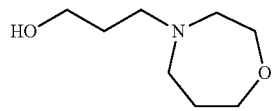

3-(1,4-oxazepan-4-yl)propan-1-ol

To a vial was added homomorpholine (0.250 g, 2.472 mmol), Acetonitrile (4.943 mL, 2.472 mmol) and 3-Bromo-1-propanol (0.2459 mL, 2.719 mmol). Potassium carbonate (0.6832 g, 4.943 mmol) was added and the mixture was warmed to 50° C. and stirred for 6 hours. The mixture was cooled to ambient temperature, diluted with DCM, filtered and the collected solids were washed with DCM. The filtrate was concentrated in vacuo and the crude oil was purified via column chromatography (Biotage Isolera, 12 g Isco RediSep Gold, 10-20% MeOH/DCM with 0.2% NH$_4$OH) to afford 3-(1,4-oxazepan-4-yl)propan-1-ol (0.272 g, 1.708 mmol) as a colorless oil.

Intermediate 18

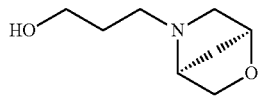

3-((1S,4S)-2-oxa-5-azabicyclo[2.2.1]heptan-5-yl)propan-1-ol

Synthesized according to the method of Intermediate 17, using (1S,4S)-2-Oxa-5-azabicyclo[2.2.1]heptane (0.250 g, 2.522 mmol) in place of homomorpholine.

Intermediate 19

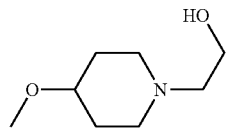

2-(4-methoxypiperidin-1-yl)ethan-1-ol

Synthesized according to the method of Intermediate 13, using 4-methoxypiperidine (173 mg, 1.50 mmol) in place of (S)-2-methylpiperidine.

Intermediate 20

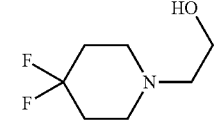

2-(4,4-difluoropiperidin-1-yl)ethan-1-ol

Synthesized according to the method of Intermediate 13, using 4,4-difluoropiperidine hydrochloride (173 mg, 1.50 mmol) in place of (S)-2-methylpiperidine.

Intermediate 21

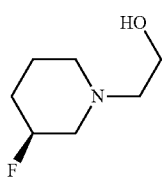

(S)-2-(3-fluoropiperidin-1-yl)ethan-1-ol

Synthesized according to the method of Intermediate 13, using S-3-fluoropiperidine hydrochloride (209 mg, 1.50 mmol) in place of (S)-2-methylpiperidine.

Intermediate 22

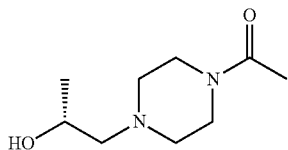

(R)-1-(4-(2-hydroxypropyl)piperazin-1-yl)ethan-1-one

Step A: 1-[4-[(2R)-2-hydroxypropyl]piperazin-1-yl]ethanone: (2R)-2-methyloxirane (1.00 g, 17.2 mmol, 1.20 mL, 1.00 eq) and 1-piperazin-1-ylethanone (8.00 g, 62.4 mmol, 3.62 eq) were taken up into a microwave tube. The sealed tube was heated at 150° C. for 1 hour under microwave. The mixture was dissolved in DCM (80.0 mL), added (Boc)$_2$O (3.62 eq, 13.6 g) and stirred at 20° C. for 1 hour. The residue was purified by column chromatography (DCM/MeOH 100/1 to 10/1) to give 1-[4-[(2R)-2-hydroxypropyl]piperazin-1-yl]ethanone (3.80 g, 13.5 mmol, 78.2% yield, 66.0% purity) as a yellow oil.

Intermediate 23

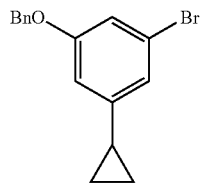

1-(benzyloxy)-3-bromo-5-cyclopropylbenzene

Step A: 1-benzyloxy-3,5-dibromo-benzene: To a mixture of 3,5-dibromophenol (1.50 g, 5.95 mmol, 1.00 eq) and K$_2$CO$_3$ (2.47 g, 17.9 mmol, 3.00 eq) in MeCN (30.0 mL) was added benzyl bromide (1.07 g, 6.25 mmol, 742 µL, 1.05 eq), the reaction mixture was stirred at 80° C. for 2 hours. The reaction mixture was filtered and concentrated. The residue was purified by column chromatography (SiO$_2$, Petroleum ether/Ethyl acetate=1:1 to give 1-benzyloxy-3,5-dibromobenzene (1.60 g, 4.68 mmol, 78.6% yield) as colorless oil.

Step B: 1-benzyloxy-3-bromo-5-cyclopropylbenzene: To a mixture of 1-benzyloxy-3,5-dibromobenzene (1.20 g, 3.51 mmol, 1.00 eq) and cyclopropylboronic acid (392 mg, 4.56 mmol, 1.30 eq) in H$_2$O (4.00 mL) and dioxane (20.0 mL) was added Pd(dppf)Cl$_2$ (513 mg, 702 µmol, 0.20 eq) and Cs$_2$CO$_3$ (2.29 g, 7.02 mmol, 2.00 eq). The reaction mixture was stirred at 90° C. for 12 hours under N$_2$. The reaction mixture was added to water (20 mL) and extracted with ethyl acetate (2×15 mL). The combined organic layers were dried over Na$_2$SO$_4$, filtered and concentrated. The residue was purified by column chromatography (SiO$_2$, Petroleum ether/Ethyl acetate=1:1 to give 1-benzyloxy-3-bromo-5-cyclopropyl-benzene (270 mg, 890 µmol, 25.4% yield) as colorless oil.

Intermediate 24

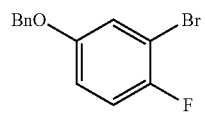

4-(benzyloxy)-2-bromo-1-fluorobenzene

To a solution of 3-bromo-4-fluorophenol (4.00 g, 20.9 mmol, 1.00 eq) and K$_2$CO$_3$ (8.68 g, 62.8 mmol, 3.00 eq) in ACN (80.0 mL) was added benzyl bromide (3.65 g, 21.4 mmol, 2.54 mL, 1.02 eq) and the reaction mixture was stirred at 60° C. for 2 hrs. The reaction mixture was filtered and concentrated in vacuum. The residue was purified by silica gel chromatography (petroleum ether:ethyl acetate; gradient from 1:0 to 10:1) to give 4-benzyloxy-2-bromo-1-fluoro-benzene (5.02 g, 17.0 mmol, 81.0% yield, 95% purity) was obtained as white solid.

Intermediate 25

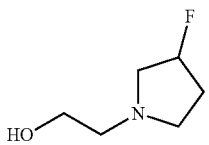

2-(3-fluoropyrrolidin-1-yl)ethan-1-ol

Step A: tert-butyl 3-fluoropyrrolidine-1-carboxylate: To a solution of tert-butyl 3-hydroxypyrrolidine-1-carboxylate (10.0 g, 53.4 mmol, 1.00 eq) in DCM (150.00 mL) was added diethylaminosulfur trifluoride (DAST) (12.9 g, 80.1 mmol, 10.6 mL, 1.50 eq) at −40° C. under a nitrogen atmosphere. After stirring at −40° C. for 2 hours, the mixture was warmed to 20° C. and stirred for 16 hours. The mixture was poured into 5% aqueous sodium bicarbonate (200 mL) and extracted with dichloromethane (2×100 mL). The organic layer was dried over sodium sulfate, filtered and concentrated under vacuum. The residue was purified by column chromatography over silica gel (petroleum ether/ ethyl acetate 100:1 to 5:1). The desired fractions were collected and concentrated under vacuum to give tert-butyl 3-fluoropyrrolidine-1-carboxylate (4.30 g, 22.7 mmol, 42.6% yield) as a colorless oil. $^1$H NMR (400 MHz, Chloroform-d) δ=5.27 (t, J=3.6 Hz, 0.5H), 5.13 (t, J=3.6 Hz, 0.5H), 3.77-3.38 (m, 4H), 2.26-2.15 (m, 1H), 2.08-1.85 (m, 1H), 1.46 (s, 9H).

Step B: 3-fluoropyrrolidine: To a solution of tert-butyl 3-fluoropyrrolidine-1-carboxylate (4.30 g, 22.7 mmol, 1.00 eq) in DCM (50.00 mL) was added HCl/dioxane (4 M, 35.0 mL, 6.16 eq) dropwise at 0° C. The mixture was warmed to 20° C. and stirred for 1 hour. The mixture was concentrated under vacuum. The residue was triturated with diisopropyl ether (20 mL) and the precipitate was filtered and dried under vacuum to provide 3-fluoropyrrolidine (2.70 g, 21.5 mmol, 94.6% yield, HCl) as a white solid. $^1$H NMR (400 MHz, Methanol-d4) δ=5.51 (t, J=3.6 Hz, 0.5H), 5.38 (t, J=3.6 Hz, 1H), 3.66-3.27 (m, 5H), 2.45-2.12 (m, 2H).

Step C: methyl 2-(3-fluoropyrrolidin-1-yl)acetate: A suspension of 3-fluoropyrrolidine (2.70 g, 21.5 mmol, 1.00 eq, HCl) in DCM (27.00 mL) was cooled to 0° C. Triethylamine (5.44 g, 53.8 mmol, 7.45 mL, 2.50 eq) and methyl 2-bromoacetate (3.62 g, 23.7 mmol, 2.23 mL, 1.10 eq) were added and the reaction mixture was stirred at 20° C. for 16 h. The reaction mixture was diluted with CH$_2$Cl$_2$ (100 mL) and water (50 mL). The organic layer was washed with 5% aqueous citric acid solution (1×50 mL). The water layer was basified by saturated aqueous sodium carbonate solution (20 mL) and extracted with ethyl acetate (3×100 mL). The combined organic layers were dried over sodium sulfate and concentrated in vacuo to give methyl 2-(3-fluoropyrrolidin-1-yl)acetate (2.20 g, 13.7 mmol, 63.5% yield). $^1$H NMR (400 MHz, Chloroform-d) δ=5.22-5.02 (m, 1H), 3.66 (s, 3H), 3.35 (s, 2H), 3.07-2.93 (m, 1H), 2.91-2.77 (m, 2H), 2.67 (dt, J=5.2, 8.4 Hz, 1H), 2.21-1.93 (m, 2H).

Step D: 2-(3-fluoropyrrolidin-1-yl)ethanol: To a solution of LiAlH$_4$ (706 mg, 18.6 mmol, 1.50 eq) in THF (20 mL) was added a solution of methyl 2-(3-fluoropyrrolidin-1-yl)acetate (2.00 g, 12.4 mmol, 1.00 eq) in THF (10 mL) dropwise at 0° C. The mixture was warmed up to 20° C. and stirred for 3 hours. The mixture was quenched with saturated aqueous sodium sulfate solution (1 mL). The mixture was filtered and the filtrate was concentrated under vacuum. The product was purified by silica gel chromatography using 5% MeOH in DMC. The desired fractions were collected and concentrated under vacuum to give 2-(3-fluoropyrrolidin-1-yl)ethanol (1.20 g, 9.01 mmol, 72.6% yield) as a colorless oil. $^1$H NMR (400 MHz, Chloroform-d) δ=5.28-5.05 (m, 1H), 3.68-3.61 (m, 2H), 2.99-2.73 (m, 4H), 2.72-2.67 (m, 2H), 2.58-2.45 (m, 1H), 2.28-1.97 (m, 2H).

Intermediate 26

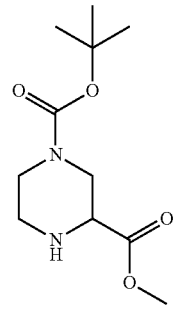

1-(tert-butyl) 3-methyl piperazine-1,3-dicarboxylate

Step A: methyl piperazine-2-carboxylate: To a mixture of 1-tert-butyl 2-methyl piperazine-1,2-dicarboxylate (5.0 g, 22.6 mmol, 1.00 eq) in MeOH (50.0 mL) was added HCl/dioxane (4.0 M, 134 mL). The reaction mixture was degassed and purged with nitrogen 3 times, and the mixture was stirred at 25° C. for 12 hours under a nitrogen atmosphere. The reaction mixture was concentrated under reduced pressure to dryness to give methyl piperazine-2-carboxylate (4.89 g, 2HCl, crude) as a white solid, which was used directly in the next step without further purification.

Step B: 1-(tert-butyl) 3-methyl piperazine-1,3-dicarboxylate: To a solution of methyl piperazine-2-carboxylate (4.30 g, crude) and TEA (8.02 g, 79.2 mmol, 11.0 mL) in MeOH (50.0 mL) was added di-tert-butyl dicarbonate (4.32 g, 19.8 mmol, 4.55 mL). After stirring at 25° C. for 12 hours, the reaction mixture was filtered and concentrated under reduced pressure to dryness. The residue was purified by column chromatography (SiO$_2$, DCM/MeOH=1:0 to 20:1) to give 1-(tert-butyl) 3-methyl piperazine-1,3-dicarboxylate (4.80 g, 19.7 mmol, two steps, 99.0% yield) as a colorless oil. $^1$H NMR (400 MHz, chloroform-d) δ=4.10-3.85 (m, 1H), 3.73 (s, 3H), 3.71-3.65 (m, 1H), 3.47-3.38 (m, 1H), 3.10-2.98 (m, 2H), 2.78-2.66 (m, 1H), 2.17 (s, 1H), 1.46 (s, 9H).

Intermediate 27

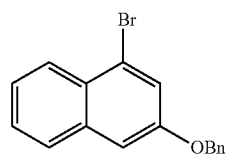 [SMILES: Brc1cc(OCc2ccccc2)cc2ccccc12]

4-bromonaphthalen-2-ol

Step A: 2,4-dibromonaphthalen-1-amine: To a solution of Br$_2$ (246 g, 1.54 mol, 79.3 mL, 2.18 eq) in AcOH (750 mL) was added a solution of naphthalen-1-amine (101 g, 705 mmol, 99.0 mL, 1.00 eq) in AcOH (500 mL) at ambient temperature, and the reaction was stirred at 70° C. for 1 hour. The reaction mixture was cooled at room temperature and filtered. The filter cake was washed with AcOH (300 mL), then added to 20% aqueous of NaOH (1.2 L). The mixture was stirred for 20 min and filtered. The isolated solid was washed with water (1 L) and dried under vacuum to provide 2,4-dibromonaphthalen-1-amine (200 g, 664 mmol, 94.2% yield) as gray solid. ESI MS m/z 301. 9 [M+H]⁺.

Step B: 4-bromo-1-diazonio-naphthalen-2-olate: To a solution of 2,4-dibromonaphthalen-1-amine (60.0 g, 199 mmol, 1.00 eq) in AcOH (900 mL) and propionic acid (150 mL) was added NaNO₂ (16.5 g, 239 mmol, 13.0 mL, 1.20 eq) portionwise at 5-8° C. over 30 min, and then the reaction mixture was stirred at 5-8° C. for 30 min. The reaction mixture was poured into ice-water (4000 mL), and the resulting solid was collected and washed with water (2×50 mL) to provide 4-bromo-1-diazonio-naphthalen-2-olate (150 g, wet crude) as gray solid which was used directly in the next step. ¹H NMR (400 MHz, CDCl₃) δ 8.12-8.10 (d, J=8.4 Hz, 1H), 7.62-7.58 (t, J=7.6 Hz, 1H), 7.41-7.37 (t, J=7.6 Hz, 1H), 7.31-7.29 (d, J=8.0 Hz, 1H), 7.20 (s, 1H).

Step C: 4-bromonaphthalen-2-ol: To a solution of 4-bromo-1-diazonio-naphthalen-2-olate (100 g, 402 mmol, 1.00 eq) in EtOH (2.00 L) was added portionwise NaBH₄ (30.4 g, 803 mmol, 2.00 eq) at 13-15° C. over 1 h, and the reaction mixture was stirred at 15-18° C. for 3 hrs. The reaction was filtered and concentrated to dryness. The residue was dissolved in DCM (1000 mL) and washed with water (500 mL×2). The organic phase was dried over Na₂SO₄ and concentrated to dryness. The residue was purified by silica gel column chromatograph, eluting with diethyl ether/ethyl acetate (60:1 to 10:1). The isolated product was further purified by reversed phase HPLC to provide 4-bromonaphthalen-2-ol (40.0 g, 139 mmol, 17.3% yield, 77.4% purity) as a gray solid. ¹H NMR (400 MHz, CDCl₃) δ 8.07-8.05 (d, J=8.0 Hz, 1H), 7.60-7.58 (d, J=7.6 Hz, 1H), 7.41-7.36 (m, 3H), 7.07 (s, 1H).

Step D: 3-benzyloxy-1-bromo-naphthalene: A mixture of 4-bromonaphthalen-2-ol (30.0 g, 134 mmol, 1.00 eq), benzyl bromide (25.3 g, 148 mmol, 17.6 mL, 1.10 eq) and K₂CO₃ (55.7 g, 403 mmol, 3.00 eq) in MeCN (500 mL) was heated at 80° C. for 1 hr. The reaction mixture was filtered and concentrated to dryness. The residue was purified by silica gel column chromatography, eluting with diethyl ether/ethyl acetate (100:1 to 60:1) to provide 3-benzyloxy-1-bromo-naphthalene (40.0 g, 128 mmol, 95% yield) as yellow oil. ¹H NMR (400 MHz, CDCl₃) δ 8.19-8.17 (d, J=8.0 Hz, 1H), 7.75-7.32 (d, J=8.8 Hz, 1H), 7.64-7.63 (d, J=2.4 Hz, 1H), 7.52-7.37 (m, 7H), 7.23-7.21 (d, J=2.0 Hz, 1H), 5.2 (s, 2H).

Intermediate 28

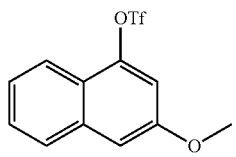 [SMILES: COc1cc(OS(=O)(=O)C(F)(F)F)c2ccccc2c1]

3-methoxynaphthalen-1-yl trifluoromethanesulfonate

Step A: 3-methoxynaphthalen-1-ol: To a solution of naphthalene-1,3-diol (3.00 g, 18.7 mmol, 1.00 eq) in MeOH (60.0 mL) was added HCl/MeOH (4 M, 60.0 mL, 12.8 eq) at 0° C. The mixture was stirred at 25° C. for 60 hours. The solvent was removed under vacuum. The residue was purified by silica gel chromatography (diethyl ether:ethyl acetate=10:1 to 5:1) to give 3-methoxynaphthalen-1-ol (2.10 g, 12.1 mmol, 64.4% yield) as a brown solid. ¹H NMR (400 MHz, CDCl₃-d₆) δ=8.10-8.08 (d, J=8.4 Hz, 1H).7.73-7.71 (d, J=8.4 Hz, 1H), 7.47-7.45 (m, 1H), 7.38-7.35 (m, 1H), 6.80-6.79 (d, J=2.0 Hz, 1H), 6.56-6.55 (d, J=2.4 Hz, 1H), 3.92 (s, 3H).

Step B: (3-methoxy-1-naphthyl) trifluoromethanesulfonate: To a solution of 3-methoxynaphthalen-1-ol (2.10 g, 12.0 mmol, 1.00 eq) in DCM (40.0 mL) was added DIEA (7.79 g, 60.3 mmol, 10.5 mL, 5.00 eq) and trifluoromethanesulfonic anhydride (5.10 g, 18.1 mmol, 2.98 mL, 1.50 eq) at 0° C. The mixture was stirred at 25° C. for 1 hour. The mixture was diluted with DCM (30 mL) and water (10 mL) and extracted with DCM (20 mL). The combined organic layers were washed with brine (5 mL), dried over Na₂SO₄ and concentrated under vacuum. The residue was purified by silica gel chromatography (diethyl ether:ethyl acetate=20:1 to 10:1) to give (3-methoxy-1-naphthyl) trifluoromethanesulfonate (3.00 g, 8.52 mmol, 70.7% yield, 87.0% purity) as a brown oil. ESI MS m/z 307.1 [M+H]⁺.

Intermediate 29

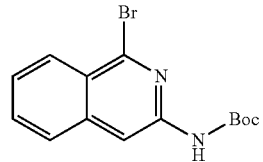 [SMILES: CC(C)(C)OC(=O)Nc1cc2ccccc2c(Br)n1]

tert-butyl (1-bromoisoquinolin-3-yl)carbamate

Step A: A mixture of 1-bromoisoquinolin-3-amine (400 mg, 1.79 mmol, 1.00 eq) and tert-butoxycarbonyl tert-butyl carbonate (3.91 g, 17.9 mmol, 4.12 mL, 10.0 eq) was stirred at 70° C. for 16 hours. The residue was purified by column chromatography (SiO₂, diethyl ether/ethyl acetate=5:1) to give tert-butyl N-(1-bromo-3-isoquinolyl) carbamate (400 mg, 1.24 mmol, 69.2% yield) as a yellow solid. ESI MS m/z 322.1, 324.1 [M+H]⁺.

Intermediate 30

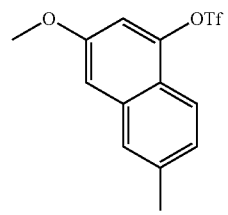 [SMILES: COc1cc(OS(=O)(=O)C(F)(F)F)c2ccc(C)cc2c1]

3-methoxy-6-methylnaphthalen-1-yl trifluoromethanesulfonate

Step A: 3-methoxynaphthalen-1-ol: To a solution of naphthalene-1,3-diol (40.0 g, 250 mmol, 1.00 eq) in MeOH (800 mL) was added HCl (4 M, 750 mL, 12.0 eq, 4 M in MeOH) at 0° C. The mixture was warmed up to 18° C. and stirred for 30 hours. The mixture was concentrated under vacuum. The residue was purified by column chromatography over silica gel (petroleum ether/ethyl acetate 100/1 to 1/1). The desired fractions were collected and concentrated under vacuum to give 3-methoxynaphthalen-1-ol (17.7 g, 96.5 mmol, 38.6% yield, 95% purity) as a red oil. $^1$H NMR (400 MHz, Chloroform-d) δ=8.17 (d, J=8.4 Hz, 1H), 7.74 (d, J=8.0 Hz, 1H), 7.50 (ddd, J=1.2, 6.8, 8.0 Hz, 1H), 7.38 (ddd, J=1.2, 6.8, 8.0 Hz, 1H), 6.81 (d, J=2.0 Hz, 1H), 6.76 (br s, 1H), 6.62 (d, J=2.4 Hz, 1H), 3.91 (s, 3H).

Step B: tert-butyl-[(3-methoxy-1-naphthyl)oxy]-dimethyl-silane: To a solution of 3-methoxynaphthalen-1-ol (20.0 g, 115 mmol, 1.00 eq) and imidazole (23.5 g, 344 mmol, 3.00 eq) in THF (400 mL) was added TBSCl (26.0 g, 172 mmol, 21.1 mL, 1.50 eq) dropwise at 0° C. The mixture was warmed up to 25° C. and stirred for 16 hours. The mixture was diluted with petroleum ether (600 mL) and ethyl acetate (200 mL), and then washed with water (1×200 mL) and brine (1×200 mL). The separated organic layer was dried over sodium sulfate, filtered and concentrated under vacuum. The residue was purified by column chromatography over silica gel (petroleum ether/ethyl acetate 100/1 to 10/1). tert-butyl-[(3-methoxy-1-naphthyl)oxy]-dimethyl-silane (28.0 g, 97.1 mmol, 84.6% yield) was obtained as a colorless oil. $^1$H NMR (400 MHz, Chloroform-d) δ=8.01 (d, J=8.4 Hz, 1H), 7.61 (d, J=8.0 Hz, 1H), 7.35 (dt, J=1.2, 7.6 Hz, 1H), 7.24 (dt, J=1.2, 7.6 Hz, 1H), 6.71 (d, J=2.0 Hz, 1H), 6.48 (d, J=2.4 Hz, 1H), 3.82 (s, 3H), 1.02 (s, 9H), 0.23 (s, 6H).

Step C: tert-butyl-[[3-methoxy-6-(4,4,5,5-tetramethyl-1,3,2-dioxaborolan-2-yl)-1-naphthyl]oxy]-dimethyl-silane and tert-butyl((3-methoxy-7-(4,4,5,5-tetramethyl-1,3,2-dioxaborolan-2-yl)naphthalen-1-yl)oxy)dimethylsilane: A mixture of tert-butyl-[(3-methoxy-1-naphthyl) oxy]-dimethyl-silane (26.0 g, 90.1 mmol, 1.00 eq), 4,4,5,5-tetramethyl-2-(4,4,5,5-tetramethyl-1,3,2-dioxaborolan-2-yl)-1,3,2-dioxaborolane (45.8 g, 180 mmol, 2.00 eq), (1Z,5Z)-cycloocta-1,5-diene; 2,4-dimethyl-BLAHbicyclo[1.1.0] butane (2.39 g, 3.61 mmol, 0.04 eq) and 4-tert-butyl-2-(4-tert-butyl-2-pyridyl)pyridine (1.45 g, 5.41 mmol, 0.06 eq) in hexane (500 mL) was stirred at 100° C. under nitrogen atmosphere for 16 hours. The mixture was diluted with water (500 mL) and ethyl acetate (1000 mL). The separated organic layer was washed with brine (1×500 mL), dried over sodium sulfate, filtered and concentrated under vacuum. The residue was purified by column chromatography over silica gel (petroleum ether/ethyl acetate 100/1 to 10/1). The desired fractions were collected and concentrated under vacuum to give a mixture of tert-butyl-[[3-methoxy-6-(4,4,5,5-tetramethyl-1,3,2-dioxaborolan-2-yl)-1-naphthyl]oxy]-dimethyl-silane and tert-butyl((3-methoxy-7-(4,4,5,5-tetramethyl-1,3,2-dioxaborolan-2-yl)naphthalen-1-yl)oxy) dimethylsilane (38.0 g, 85.3 mmol, 94.6% yield, 93% purity) as a light yellow oil. ESI MS m/z 415.5 [M+H]$^+$ Step D: 8-[tert-butyl(dimethyl)silyl]oxy-6-methoxy-naphthalen-2-ol: To a solution of mixture (36.0 g, 86.9 mmol, 1.00 eq) of tert-butyl-[[3-methoxy-6-(4,4,5,5-tetramethyl-1,3,2-dioxaborolan-2-yl)-1-naphthyl]oxy]-dimethyl-silane and tert-butyl((3-methoxy-7-(4,4,5,5-tetramethyl-1,3,2-dioxaborolan-2-yl)naphthalen-1-yl)oxy)dimethylsilanein in acetone (400 mL) was added a solution of Oxone (58.7 g, 95.6 mmol, 1.10 eq) in H$_2$O (400 mL) at 0° C. The mixture was stirred at 0° C. for 1 hour. The mixture was quenched with 5% aqueous sodium thiosulfate solution (50 mL) and extracted with ethyl acetate (2×300 mL). The extracts were combined and washed with water (1×200 mL), brine (1×200 mL), dried over magnesium sulfate, filtered and the filtrate was concentrated under vacuum. The residue was purified by column chromatography over silica gel (petroleum ether/ethyl acetate 200/1 to 20/1). The desired fractions were collected and concentrated under vacuum to give 8-[tert-butyl(dimethyl)silyl]oxy-6-methoxy-naphthalen-2-ol (9.00 g, 28.4 mmol, 32.7% yield, 96% purity) as a colorless oil and 5-[tert-butyl(dimethyl)silyl]oxy-7-methoxy-naphthalen-2-ol (9.00 g, 29.0 mmol, 33.4% yield, 98% purity) as a white solid. ESI MS m/z 305.2 [M+H]$^+$ Step E: [5[tert-butyl(dimethyl)silyl]oxy-7-methoxy-2-naphthyl] trifluoromethanesulfonate: To a solution of 5-[tert-butyl(dimethyl)silyl]oxy-7-methoxy-naphthalen-2-ol (11.0 g, 36.1 mmol, 1.00 eq) and DIEA (14.0 g, 108 mmol, 18.9 mL, 3.00 eq) in DCM (150 mL) was added Tf$_2$O (12.2 g, 43.4 mmol, 7.15 mL, 1.20 eq) dropwise at −40° C. The mixture was stirred for 1 hour. The mixture was diluted with dichloromethane (200 mL) and washed with water (1×200 mL) and brine (1×200 mL). The separated organic layer was dried over sodium sulfate, filtered and concentrated under vacuum. The residue was purified by column chromatography over silica gel (petroleum ether/ethyl acetate 100/1 to 10/1). The desired fractions were collected and concentrated under vacuum to give [5-[tert-butyl(dimethyl)silyl]oxy-7-methoxy-2-naphthyl] trifluoromethanesulfonate (13.0 g, 29.8 mmol, 82.4% yield, 100% purity) as a white solid. ESI MS m/z 436.9 [M+H]$^+$ Step F: tert-butyl-[(3-methoxy-6-methyl-1-naphthyl) oxy]-dimethyl-silane: To a solution of [5-[tert-butyl(dimethyl)silyl]oxy-7-methoxy-2-naphthyl]trifluoromethanesulfonate (12.5 g, 28.6 mmol, 1.00 eq) and K$_2$CO$_3$ (11.9 g, 85.9 mmol, 3.00 eq) in dioxane (160 mL) was added Pd(PPh$_3$)$_4$ (3.31 g, 2.86 mmol, 0.10 eq) and trimethylboroxine (14.4 g, 57.3 mmol, 16.0 mL, 2.00 eq) under nitrogen atmosphere. The reaction was heated to 100° C. for 16 hours. The mixture was diluted with ethyl acetate (200 mL) and then washed with water (1×200 mL) and brine (1×200 mL). The separated organic layer was dried over sodium sulfate, filtered and concentrated under vacuum. The residue was purified by column chromatography over silica gel (petroleum ether/ethyl acetate 100/1 to 5/1). The desired fractions were collected and concentrated under vacuum to give tert-butyl-[(3-methoxy-6-methyl-1-naphthyl)oxy]-dimethyl-silane (8.00 g, 24.6 mmol, 85.9% yield, 93% purity) as a colorless oil as red solid. ESI MS m/z 303.2 [M+H]$^+$ Step G: 3-methoxy-6-methyl-naphthalen-1-ol: To a solution of tert-butyl-[(3-methoxy-6-methyl-1-naphthyl) oxy]-dimethyl-silane (8.00 g, 26.5 mmol, 1.00 eq) in THF (100 mL) was added TBAF (10.4 g, 39.7 mmol, 1.50 eq) at 0° C. The mixture was stirred at 0° C. for 3 hours. The mixture was diluted with water (100 mL) and ethyl acetate (200 mL). The separated organic layer was washed with brine (1×100 mL), dried over sodium sulfate, filtered and concentrated under vacuum. The residue was purified by column chromatography over silica gel (petroleum ether/ethyl acetate 50/1 to 5/1). The desired fractions were collected and concentrated under vacuum to give 3-methoxy-6-methyl-naphthalen-1-ol (4.70 g, 25.0 mmol, 94.4% yield) as a red solid. ESI MS m/z 188.4 [M+H]$^+$ Step H: 3-methoxy-6-methyl-1-naphthyl trifluoromethanesulfonate: To a solution of 3-methoxy-6-methyl-naphthalen-1-ol (4.70 g, 25.0 mmol, 1.00 eq) and DIEA (9.68 g, 74.9 mmol, 13.1 mL, 3.00 eq) in DCM (3.00 mL) was added Tf$_2$O (8.45 g, 30.0 mmol, 4.94 mL, 1.20 eq) dropwise at −40° C. The mixture was stirred for 1 hour. The mixture was diluted with dichloromethane (200 mL) and washed with water (1×200 mL) and brine (1×200 mL). The separated organic layer was dried over sodium sulfate, filtered and concentrated under vacuum. The residue was purified by column chromatography over silica gel (petroleum ether/ ethyl acetate 100/1 to 10/1). 3-methoxy-6-methyl-1-naphthyl trifluoromethanesulfonate (7.70 g, 24.0 mmol, 96.2% yield, 99.9% purity) was obtained as a colorless oil. ESI MS m/z 320.7 [M+H]$^+$.

The following intermediates disclosed in Table 1 were prepared according to the preparation for Intermediate 3, substituting the appropriate phenol for 2-bromo-3-fluorophenol.

TABLE 1

| Intermediates 31-39 | | |
|---|---|---|
| Intermediate No. | Structure | Name |
| Intermediate 31 | | 2-bromo-4-(methoxymethoxy)-1-(trifluoromethoxy)benzene |
| Intermediate 32 | | 2-bromo-4-(methoxymethoxy)-1-(trifluoromethyl)benzene |
| Intermediate 33 | | 2-bromo-1-(methoxymethoxy)-4-(trifluoromethoxy)benzene |
| Intermediate 34 | | 2-bromo-4-fluoro-3-(methoxymethoxy)-1-methylbenzene |
| Intermediate 35 | | 1-bromo-3-(methoxymethoxy)-5-(trifluoromethoxy)benzene |
| Intermediate 36 | | 2-bromo-1-methoxy-4-(methoxymethoxy)benzene |
| Intermediate 37 | | 2-bromo-1-(methoxymethoxy)-3-methylbenzene |
| Intermediate 38 | | 2-bromo-4-(methoxymethoxy)-1-methylbenzene |

TABLE 1-continued

Intermediates 31-39

| Intermediate No. | Structure | Name |
|---|---|---|
| Intermediate 39 | ![structure] | 1-bromo-4-(methoxymethoxy)-2-(trifluoromethoxy)benzene |

Intermediate 40

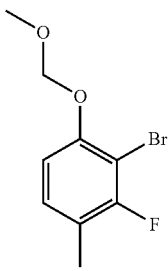

2-bromo-3-fluoro-1-(methoxymethoxy)-4-methylbenzene

Step 1: 3-fluoro-4-methylphenol (1.016 g, 8.055 mmol) was placed in Cs₂ (3.9 mL, 64.44 mmol) and was cooled to 0° C. Br₂ (0.4150 mL, 8.055 mmol) was added and the mixture was stirred at room temperature for 2 hrs. 10% Na₂S₂O₂ was added and the mixture was extracted with DCM. The organic layers were combined, dried and filtered to provide 2-bromo-3-fluoro-4-methylphenol (1.389 g, 6.775 mmol, 84.10% yield) which was used directly in the next step.

Step 2: 2-bromo-3-fluoro-1-(methoxymethoxy)-4-methylbenzene was prepared according to the procedure for Intermediate 8 using 2-bromo-3-fluoro-4-methylphenol in place of 2-bromo-3-fluorophenol.

Intermediate 41

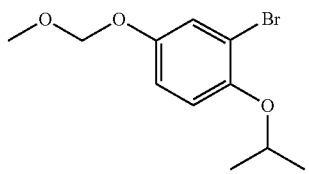

2-bromo-1-isopropoxy-4-(methoxymethoxy)benzene

Step 1: 4-isopropoxyphenol (1.00 g, 6.57 mmol) and TEA (1.83 mL, 13.1 mmol) were placed in DCM (25 mL). Acetyl chloride (7.56 mL, 7.56 mmol) was added dropwise and the reaction was stirred at room temperature for 2 hr. Water was added and the mixture was extracted with DCM. The organic layer was dried, filtered and concentrated to provide 4-isopropoxyphenyl acetate (1.24 g, 6.38 mmol, 97.2% yield) which was directly in the next step.

Step 2: 4-Isopropoxyphenyl acetate (1.24 g, 6.585 mmol) was placed in ACN (20 mL) and N-bromosuccinimide (1.173 g, 6.590 mmol) was added. The mixture was stirred for 18 hr. Water was added and the mixture was extracted with ether. The organic layers were combined, dried, and concentrated to provide 3-bromo-4-isopropoxyphenyl acetate (1.584 g, 5.800 mmol, 88.00% yield) which was directly in the next step.

Step 3: 3-Bromo-4-isopropoxyphenyl acetate (500 mg, 1.83 mmol) was placed in MeOH (7 mL). A solution of KOH (111 mg, 1.98 mmol) in water (2 mL) was added to mixture and was stirred for 1 hr at room temperature. The reaction mixture was adjusted to pH 3 by the addition of 1N HCl. The mixture was extracted with DCM. The extracts were combined, dried, filtered and concentrated to provide crude 3-bromo-4-isopropoxyphenol which was used directly the next reaction.

Step 4: 2-Bromo-1-isopropoxy-4-(methoxymethoxy)benzene was prepared according to the procedure for Intermediate 8 using 3-bromo-4-isopropoxyphenol in place of 2-bromo-3-fluorophenol Intermediate 42

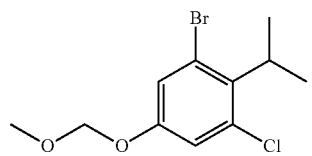

1-bromo-3-chloro-2-isopropyl-5-(methoxymethoxy)benzene

Step 1: 1-bromo-3-chloro-2-isopropyl-5-methoxybenzene (952 mg, 3.61 mmol) was placed in DCM (3 mL) and was cooled to 0° C. BBr3 (9030 µL, 9.03 mmol) was added and the reaction was stirred at 0° C. for 2 hr. Water was added and the mixture was extracted with DCM. The extracts were combined and concentrated. The resulting residue was purified by silica gel (0-20% EtOAc in hexane) to provide 3-bromo-5-chloro-4-isopropylphenol (575 mg, 2.30 mmol, 63.8% yield)

Step 2: 1-bromo-3-chloro-2-isopropyl-5-(methoxymethoxy)benzene was prepared according to the procedure for Intermediate 8 using 3-bromo-5-chloro-4-isopropylphenol in place of 2-

Intermediate 43

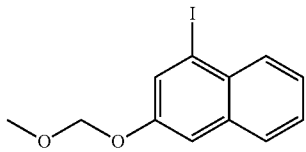

1-iodo-3-(methoxymethoxy)naphthalene

To a solution of 4-iodonaphthalen-2-ol (0.80 g, 3.0 mmol) in DCM (20 mL) was added N-ethyl-N-isopropylpropan-2-amine (1.1 mL, 5.9 mmol) and chloro(methoxy)methane (0.29 g, 3.6 mmol) and the reaction stirred at room temperature for 4 hours, with additional chloro(methoxy)methane (0.15 g) being added after 2 hours. The reaction was washed with brine and concentrated in vacuo. The material was purified by chromatography using a gradient of 0 to 10% EtOAc/hexanes as the eluent to give 1-iodo-3-(methoxymethoxy)naphthalene (0.80 g, 2.5 mmol, 86% yield).

Intermediate 44

3-benzyloxy-1-bromo-naphthalene

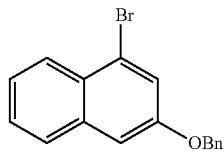 [SMILES: Brc1cc(OCc2ccccc2)cc2ccccc12]

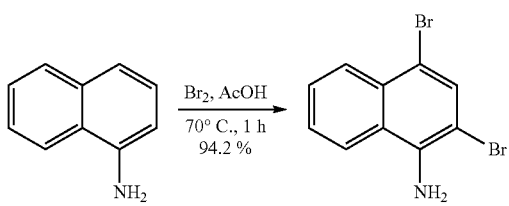 [SMILES: Nc1cccc2ccccc12 ; Nc1c(Br)cc(Br)c2ccccc12]

Step A: 2,4-dibromonaphthalen-1-amine: To a solution of Br₂ (246 g, 1.54 mol, 79.3 mL) in AcOH (750 mL) was added a solution of naphthalen-1-amine (101 g, 705 mmol, 99.0 mL) in AcOH (500 mL) at room temperature and the reaction stirred at 70° C. for 1 hour. The reaction mixture was cooled to room temperature and filtered. The filter cake was washed with AcOH (300 mL). The solid was next suspended in 20% aqueous of NaOH (1.2 L). The mixture was stirred for 20 minutes and filtered. The solid was washed with water (1 L) and dried under vacuum to give 2,4-dibromonaphthalen-1-amine (200 g, 664 mmol, 94.2% yield) as gray solid. ES+APCI MS m/z 301.9 [M+H]⁺.

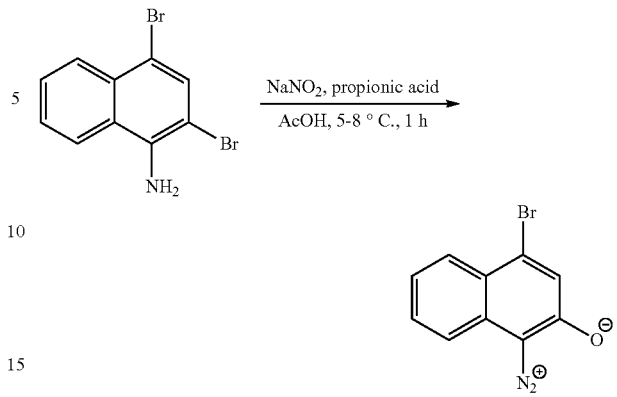

Step B: 4-bromo-1-diazonio-naphthalen-2-olate: To a solution of 2,4-dibromonaphthalen-1-amine (60.0 g, 199 mmol) in AcOH (900 mL) and propionic acid (150 mL) was added NaNO₂ (16.5 g, 239 mmol, 13.0 mL) portionwise at 5-8° C. over 30 minutes and the reaction mixture stirred at 5-8° C. for 30 minutes. The reaction mixture was poured into ice-water (4000 mL), the slurry filtered and the solid washed with water (2×50 mL) to give 4-bromo-1-diazonio-naphthalen-2-olate (150 g, wet crude) which was used crude in the next step immediately. ¹H NMR (400 MHz, CDCl₃) δ 8.12-8.10 (d, J=8.4 Hz, 1H), 7.62-7.58 (t, J=7.6 Hz, 1H), 7.41-7.37 (t, J=7.6 Hz, 1H), 7.31-7.29 (d, J=8.0 Hz, 1H), 7.20 (s, 1H).

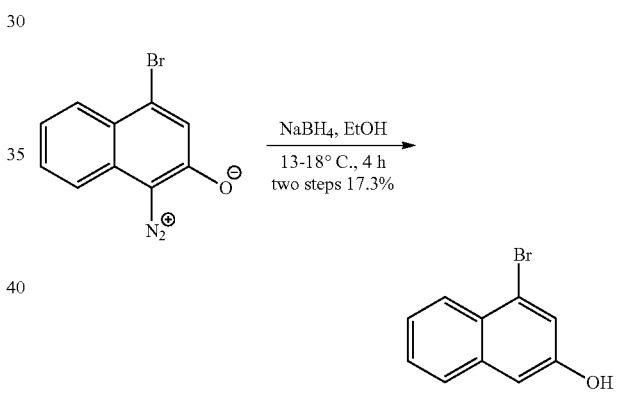

Step C: 4-bromonaphthalen-2-ol: To a solution of 4-bromo-1-diazonio-naphthalen-2-olate (100 g, 402 mmol) in EtOH (2.00 L) was added portion-wise NaBH₄ (30.4 g, 803 mmol) at 13-15° C. over 1 hour and the reaction stirred at 15-18° C. for 3 hours. The reaction was filtered and concentrated to dryness. The residue was dissolved in DCM (1000 mL) and washed with water (500 mL×2). The organics were dried over Na₂SO₄ and concentrated to dryness. The residue was purified by chromatography eluting with petroleum ether/EtOAc (60/1→10/1) and material re-purified by reversed phase HPLC to give 4-bromonaphthalen-2-ol (40.0 g, 139 mmol, 17.3% yield, 77.4% purity) as a gray solid. ¹H NMR (400 MHz, CDCl₃) δ 8.07-8.05 (d, J=8.0 Hz, 1H), 7.60-7.58 (d, J=7.6 Hz, 1H), 7.41-7.36 (m, 3H), 7.07 (s, 1H).

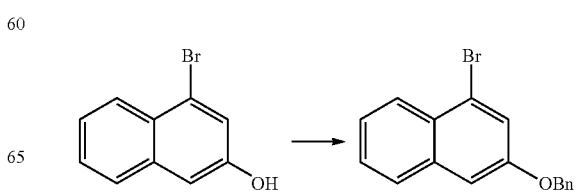

Step D: 3-benzyloxy-1-bromo-naphthalene: A mixture of 4-bromonaphthalen-2-ol (30.0 g, 134 mmol), BnBr (25.3 g, 148 mmol, 17.6 mL) and $K_2CO_3$ (55.7 g, 403 mmol) in MeCN (500 mL) was heated at 80° C. for 1 hr. The reaction mixture was filtered and concentrated to dryness. The residue was purified by silica gel column eluting with PE/EA (100/1 to 60/1) to give 3-benzyloxy-1-bromo-naphthalene (40.0 g, 128 mmol, 95% yield). $^1$H NMR (400 MHz, $CDCl_3$) δ 8.19-8.17 (d, J=8.0 Hz, 1H), 7.75-7.32 (d, J=8.8 Hz, 1H), 7.64-7.63 (d, J=2.4 Hz, 1H), 7.52-7.37 (m, 7H), 7.23-7.21 (d, J=2.0 Hz, 1H), 5.2 (s, 2H).

Intermediate 45

4-bromo-5-methyl-1-tetrahydropyran-2-yl-indazole

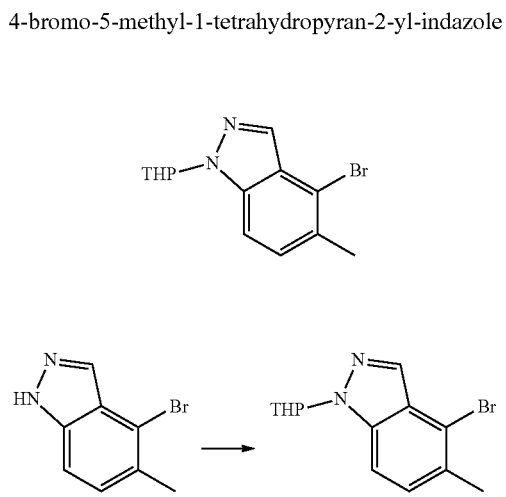

Step A: 4-bromo-5-methyl-1-tetrahydropyran-2-yl-indazole: To a mixture of 4-bromo-5-methyl-1H-indazole (3 g, 14.2 mmol) and 3,4-dihydro-2H-pyran (2.39 g, 28.4 mmol, 2.60 mL) in DCM (30 mL) was added TsOH*$H_2O$ (270 mg, 1.42 mmol) and the mixture stirred at 15° C. for 2 hours. After completion, the reaction mixture was concentrated under vacuum and the residue purified by column chromatography using 5→20& EtOAc/Petroleum Ether as eluent to give 4-bromo-5-methyl-1-tetrahydropyran-2-yl-indazole (4 g, 13.6 mmol, 95.3% yield) as white solid. $^1$H NMR (400 MHz, chloroform-d) δ 8.01 (s, 1H), 7.47 (d, J=8.4 Hz, 1H), 7.25 (d, J=8.4 Hz, 1H), 5.70 (dd, J=2.8, 9.2 Hz, 1H), 4.05-3.96 (m, 1H), 3.79-3.70 (m, 1H), 2.66-2.44 (m, 4H), 2.25-2.04 (m, 2H), 1.84-1.56 (m, 3H).

Intermediate 46

4-bromo-5-methoxy-1-(tetrahydro-2H-pyran-2-yl)-1H-indazole

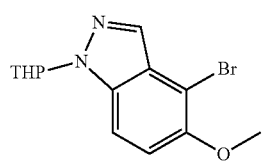

4-bromo-5-methoxy-1-(tetrahydro-2H-pyran-2-yl)-1H-indazole was prepared following Intermediate 51 substituting 4-bromo-5-methoxy-1H-indazole for 4-bromo-5-methyl-1H-indazole in Step A. $^1$H NMR (400 MHz, chloroform-d) δ 8.00 (s, 1H), 7.53 (d, J=9.2 Hz, 1H), 7.16 (d, J=9.2 Hz, 1H), 5.70 (dd, J=2.8, 9.2 Hz, 1H), 4.04-3.98 (m, 1H), 3.96 (s, 3H), 2.55-2.49 (m, 1H), 2.23-2.05 (m, 2H), 1.83-1.69 (m, 3H).

Intermediate 47

3-(benzyloxy)-1-bromo-2-methylnaphthalene

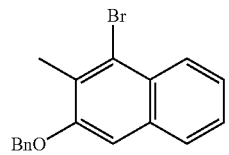

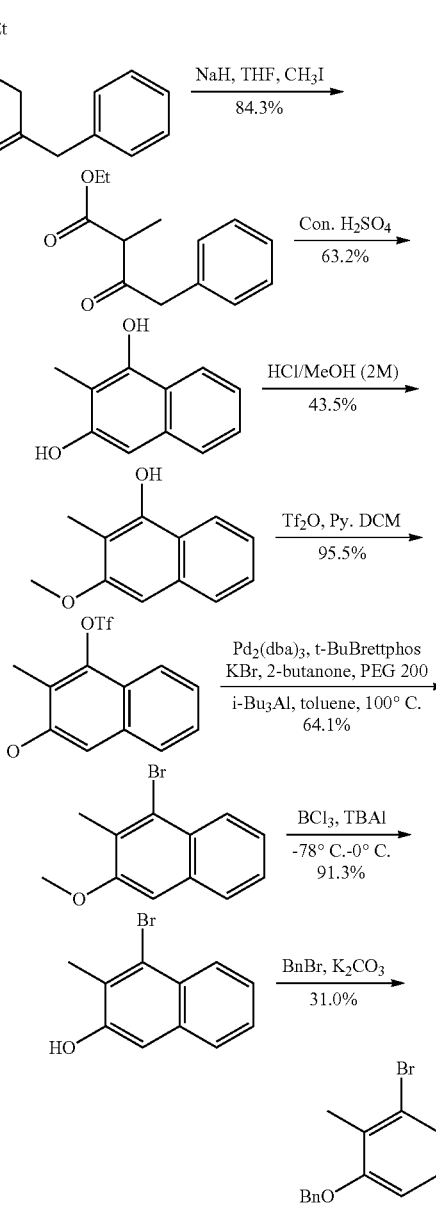

Step A: ethyl 2-methyl-3-oxo-4-phenyl-butanoate. To a dried 250 ml three-necked flask was added ethyl 3-oxo-4- phenyl-butanoate (4.00 g, 19.4 mmol.), THF (50.0 mL), sodium hydride (931 mg, 23.3 mmol) and the reaction stirred for 0.5 hours at 0° C. A solution of methyl iodide (3.03 g, 21.3) was next added drop-wise. After addition was completed, the reaction mixture was warmed to 20° C. and stirred for two hours at 20° C. The reaction mixture was quenched by addition of water (10.0 mL) at 20° C. and then diluted with ethyl acetate (20.0 mL) and the layers separated. The aqueous layer was next extracted with ethyl acetate (20.0 mL×3). The combined organic layers were washed with brine (30.0 mL), dried over anhydrous sodium sulfate, filtered and concentrated under reduced pressure to give a residue. The residue was purified by column chromatography ($SiO_2$, Petroleum ether:Ethyl acetate 20:1 to 10:1) to give ethyl 2-methyl-3-oxo-4-phenyl-butanoate (3.60 g, 16.3 mmol, 84.3% yield) as a colorless oil.

$^1$H NMR (400 MHz, $CDCl_3$) □=7.38-7.28 (m, 3H), 7.25-7.19 (m, 2H), 4.22-4.15 (m, 2H), 3.87 (d, J=2.0 Hz, 2H), 3.65 (q, J=7.2 Hz, 1H), 1.34 (d, J=7.2 Hz, 3H), 1.30-1.26 (m, 3H).

Step B: 2-methylnaphthalene-1,3-diol. A solution of ethyl 2-methyl-3-oxo-4-phenyl-butanoate (3.60 g, 16.3 mmol) in concentrated sulfuric acid (19.9 g, 203 mmol) was stirred at 15° C. for 12 hours. The reaction mixture was poured into ice-water (30.0 mL) and the resulting solid collected by filtration and dried under vacuum to afford 2-methylnaphthalene-1,3-diol (1.80 g, 10.3 mmol, 63.2% yield) as a red solid. $^1$H NMR (400 MHz, $CDCl_3$) □=8.02 (d, J=8.0 Hz, 1H), 7.65-7.54 (m, 1H), 7.41 (t, J=7.2 Hz, 1H), 7.36-7.31 (m, 1H), 6.80 (s, 1H), 4.29-4.20 (s, 2H), 2.41-2.24 (s, 3H).

Step C: 3-methoxy-2-methyl-naphthalen-1-ol. 2-methylnaphthalene-1,3-diol (1.70 g, 9.76 mmol) was added to HCl/MeOH (2 M, 35.0 mL) and the result mixture was stirred at 30° C. for 3 days. The reaction was concentrated in vacuo and the residue purified by Prep-TLC (Petroleum ether:Ethyl acetate 1:1) to give 3-methoxy-2-methyl-naphthalen-1-ol (800 mg, 4.25 mmol, 43.5% yield) as a white solid. $^1$H NMR (400 MHz, $CDCl_3$) □=8.02 (d, J=8.4 Hz, 1H), 7.69 (d, J=8.4 Hz, 1H), 7.44-7.38 (m, 1H), 7.37-7.31 (m, 1H), 6.79 (s, 1H), 5.14 (s, 1H), 3.94 (s, 3H), 2.29 (s, 3H).

Step D: (3-methoxy-2-methyl-1-naphthyl)trifluoromethanesulfonate. To a mixture of 3-methoxy-2-methyl-naphthalen-1-ol (800 mg, 4.25 mmol.) and pyridine (504 mg, 6.38 mmol) in DCM (10.0 mL) was added trifluoroacetic anhydride (1.44 g, 5.10 mmol) dropwise at 0° C. under $N_2$ atmosphere. The mixture was warmed to 20° C. and stirred for an additional 5 hours. The solvent was removed under vacuum and the residue purified by Prep-TLC (Petroleum ether: Ethyl acetate 1:1) to give (3-methoxy-2-methyl-1-naphthyl)trifluoromethanesulfonate (1.30 g, 4.06 mmol, 95.5% yield) as a white solid. $^1$H NMR (400 MHz, $CDCl_3$) □=7.97 (d, J=7.6 Hz, 1H), 7.79-7.74 (m, 1H), 7.52-7.43 (m, 2H), 7.14 (s, 1H), 3.99 (s, 3H), 2.42 (s, 3H)

Step E: 1-bromo-3-methoxy-2-methyl-naphthalene: In a sealed tube was added (3-methoxy-2-methyl-1-naphthyl) trifluoromethanesulfonate (466 mg, 1.45 mmol), t-Bu-Brettphos (154 mg, 290 μmol), potassium bromide (259 mg, 2.17 mmol), PEG-200 (175 mg), 2-butanone (157 mg, 2.17 mmol) and $Pd_2(dba)_3$ (133 mg, 145 μmol) in toluene (10.0 mL) and the mixture de-gassed with $N_2$ for 5 minutes. Next, triisobutylaluminum (431 mg, 2.17 mmol) was added dropwise at 20° C. The mixture was heated to 100° C. for 24 hrs. The reaction mixture was poured into water (30.0 mL) and the aqueous layer extracted with ethyl acetate (20.0 mL×3). The combined organics were washed with brine (30.0 mL), dried over anhydrous sodium sulfate and concentrated in vacuo to give a residue which was pre-purified by column chromatography (Petroleum ether:Ethyl acetate 10:1) and then by Prep-TLC (Petroleum ether:Ethyl acetate 10:1) to give 1-bromo-3-methoxy-2-methyl-naphthalene (700 mg, 2.79 mmol, 64.1% yield) as a white solid. $^1$H NMR (400 MHz, $CDCl_3$) □=8.26-8.17 (m, 1H), 7.73-7.69 (m, 1H), 7.47-7.40 (m, 2H), 7.09 (s, 1H), 3.98-3.95 (m, 3H), 2.56 (s, 3H).

Step F: 4-bromo-3-methyl-naphthalen-2-ol: To a solution of 1-bromo-3-methoxy-2-methyl-naphthalene (580 mg, 2.31 mmol) and tetrabutylammonium iodide (2.13 g, 5.78 mmol) in DCM (11.0 mL) cooled to −78° C. was added a solution of $BCl_3$ (1 M, 5.78 mL) dropwise over a period of 10 minutes while under $N_2$. The reaction mixture was warmed to 0° C. and stirred for 2 hours at room temperature. Next the solvent was removed under vacuum and the residue was purified by Prep-TLC (Petroleum ether:Ethyl acetate 5:1) to give 4-bromo-3-methyl-naphthalen-2-ol (500 mg, 2.11 mmol, 91.3% yield) as a white solid. $^1$H NMR (400 MHz, $CDCl_3$) □=8.26-8.15 (m, 1H), 7.63 (dd, J=3.6, 6.0 Hz, 1H), 7.45-7.38 (m, 2H), 7.11 (s, 1H), 5.09 (s, 1H), 2.60 (s, 3H), 1.56 (s, 3H).

Step G: 3-benzyloxy-1-bromo-2-methyl-naphthalene. To a mixture of 4-bromo-3-methyl-naphthalen-2-ol (265 mg, 1.12 mmol) and benzyl bromide (201 mg, 1.18 mmol) in acetonitrile (3.00 mL) was added potassium carbonate (310 mg, 2.24 mmol) in one portion at 20° C. under $N_2$. The mixture was next stirred at 60° C. for two hours. The solvent was removed under vacuum and the residue purified by Prep-TLC (Petroleum ether:Ethyl acetate 5:1) to give the 3-benzyloxy-1-bromo-2-methyl-naphthalene (250 mg, 695 μmol, 31.0% yield, 91.0% purity) as a white solid. ES+APCI MS m/z 327.0, 329.0 [M+H]$^+$.

Intermediate 48 tert-butyl-2-(cyanomethyl)-4-[2-[[(2S)-1-methylpyrrolidin-2-yl]methoxy]-5,6,7,8-tetrahydropyrido[3,4-d]pyrimidin-4-yl]piperazine-1-carboxylate

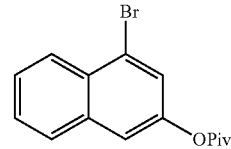

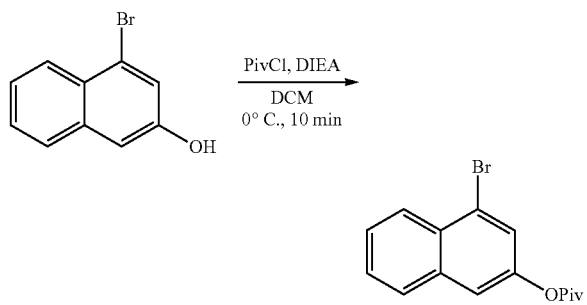

Step A: (4-bromo-2-naphthyl) 2,2-dimethylpropanoate. To a solution of 4-bromonaphthalen-2-ol (10 g, 44.8 mmol) and TEA (9.07 g, 89.7 mmol) in DCM (200 mL) was added 2,2-dimethylpropanoyl chloride (8.11 g, 67.2 mmol) at 0° C.

The reaction mixture was stirred at 0° C. for 10 min. T reaction mixture was quenched by addition of water (50 mL) and the layers separated. The organic layer was washed with brine (30 mL), dried over Na$_2$SO$_4$ filtered and concentrated under vacuum. The residue was purified by silica gel chromatography (PE: EA=1:0 to 100:1) to give (4-bromo-2-naphthyl) 2,2-dimethylpropanoate (9 g, 29.3 mmol, 65.4% yield) as a red oil. $^1$H NMR (400 MHz, CHLOROFORM-d) δ=8.22 (d, J=8.0 Hz, 1H), 7.83-7.77 (m, 1H), 7.63-7.49 (m, 4H), 1.41 (s, 9H).

Intermediate 49

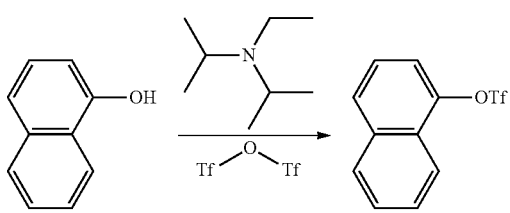

Naphthalen-1-yl trifluoromethanesulfonate. alpha-Naphthol (4 g, 27.74 mmol) was dissolved in DCM (200 mL) in a 3 neck flask. The reaction was cooled to 10° C. in a water bath. N-ethyl-N-isopropylpropan-2-amine (4.846 ml, 27.74 mmol) and trifluoromethanesulfonic anhydride (4.668 ml, 27.74 mmol) were added to the solution dropwise. The reaction was stirred at 10° C. for 2 hours. TLC (25% EtOAc, UV vis) showed reaction complete. The organics were with water (2×) and brine (2×). The organics were dried over MgSO$_4$ and concentrated in vacuo. The concentrate was purified using normal phase chromatography on the CombiFlash (0%-12% EtOAc:Hexanes). All fractions containing clean product were combined and concentrated in vacuo to give naphthalen-1-yl trifluoromethanesulfonate (6.77 g, 24.51 mmol, 88.34% yield).

Intermediate 50

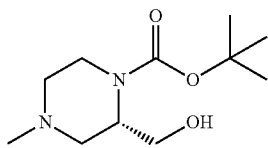 [SMILES: CN1CCN(C(=O)OC(C)(C)C)[C@H](CO)C1]

Tert-butyl (S)-2-(hydroxymethyl)-4-methylpiperazine-1-carboxylate

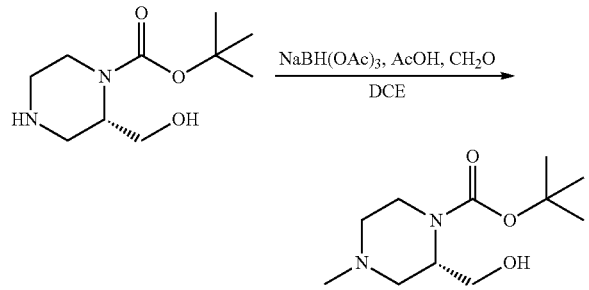

To a solution of (S)-1-Boc-2-hydroxymethylpiperazine (1.0 g, 4.62 mmol) in DCE (92.47 ml, 4.624 mmol) was added formaldehyde (3.474 ml, 46.24 mmol) (37% in water) followed by sodium triacetoxyborohydride (4.9 g, 23.12 mmol). The mixture was stirred vigorously at room temperature for 2.5 hours. The mixture was treated with saturated sodium bicarbonate (30 mL), stirred for 10 min then extracted with DCM (3×10 mL). The combined organic phases were dried over sodium sulfate, filtered and concentrated. ES+APCI MS m/z 231.1 [M+H]$^+$.

Intermediate 51

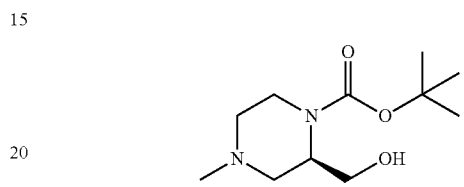

Tert-butyl (R)-2-(hydroxymethyl)-4-methylpiperazine-1-carboxylate

Title compound was prepared as in Intermediate 57, substituting tert-butyl (R)-2-(hydroxymethyl)piperazine-1-carboxylate for (S)-1-Boc-2-hydroxymethylpiperazine. ES+APCI MS m/z 231.1 [M+H]$^+$ Intermediate 52

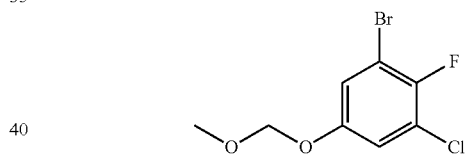

1-bromo-3-chloro-2-fluoro-5-(methoxymethoxy)benzene

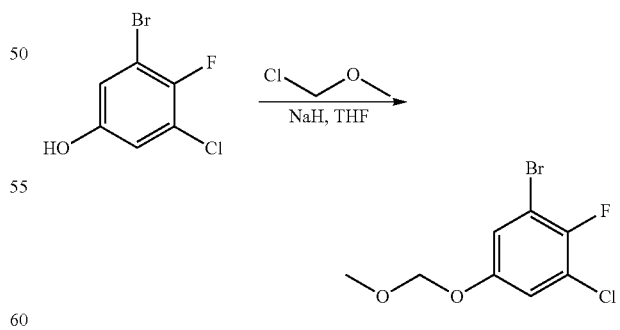

To a round bottom flask was added THF (8.87 ml, 4.44 mmol) followed by sodium hydride, 60% dispersion in mineral oil (0.213 g, 5.32 mmol). The mixture was cooled to 0° C. then 3-bromo-5-chloro-4-fluorophenol (1.0 g, 4.44 mmol) was added portionwise. Once the bubbling had ceased the resulting dark mixture was stirred at 0° C. for 30 min. Then chloromethyl methyl ether (0.421 ml, 5.54 mmol) was added and the mixture was warmed to ambient temperature where it was stirred for 2 hr. A saturated aqueous ammonium chloride solution was added and the mixture was extracted with DCM. The organic layer was dried over sodium sulfate, filtered and concentrated. Crude material was chromatographed (0-15% EtOAc in hexanes) to provide product as clear oil.

Intermediate 53

4-bromo-1-tetrahydropyran-2-yl-5-(trifluoromethyl) indazole

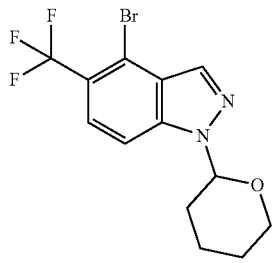 [SMILES: FC(F)(F)c1ccc2c(cnn2C2CCCCO2)c1Br]

Step A: 4-bromo-1-tetrahydropyran-2-yl-5-(trifluoromethyl)indazole: To a solution of 4-bromo-5-(trifluoromethyl)-1H-indazole (500 mg, 1.89 mmol, 1 eq) in DCM (10 mL) was added 3,4-dihydro-2H-pyran (476 mg, 5.66 mmol, 517 uL, 3 eq) and TsOH.H$_2$O (35.9 mg, 188 μmol, 0.1 eq). The mixture was stirred at 15° C. for 1 hour. The mixture was concentrated. The residue was purified by column chromatography (SiO$_2$, PE:EA=10:1 to 1:1) to give 4-bromo-1-tetrahydropyran-2-yl-5-(trifluoromethyl)indazole (480 mg, 1.37 mmol, 72.9% yield) as yellow oil. $^1$H NMR (400 MHz, chloroform-d) δ 8.20 (s, 1H), 7.69-7.63 (m, 2H), 5.70 (dd, J=2.8, 8.8 Hz, 1H), 4.05-3.96 (m, 1H), 3.79-3.70 (m, 1H), 2.56-2.50 (m, 1H), 2.27-2.04 (m, 2H), 1.80-1.74 (m, 2H), 1.60-1.54 (m, 1H).

Intermediate 54

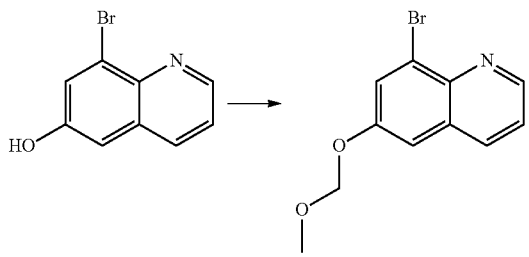

8-bromo-6-(methoxymethoxy)quinoline: A stirred suspension of 8-bromoquinolin-6-ol (1.00 g, 4.46 mmol) in DCM (20 mL) was cooled to 0° C. and diisopropylethylamine (1.2 mL, 6.7 mmol, 1.5 eq.) was added followed by chloro(methoxy)methane (0.41 mL, 5.4 mmol, 1.2 eq.) dropwise and the reaction mixture was warmed to room temperature overnight. Concentrated aqueous ammonia (0.5 mL, ~5 mmol) was next added and the resulted mixture was stirred for 1 hour at room temperature. The mixture was evaporated in vacuo and chromatographed on silica gel, Redisep 40 g, using 20% EtOAc/hexane as eluent to give a colorless powder (0.52 g, 44%). ES+APCI MS m/z 268.0, [M+H]$^+$.

Intermediate 55

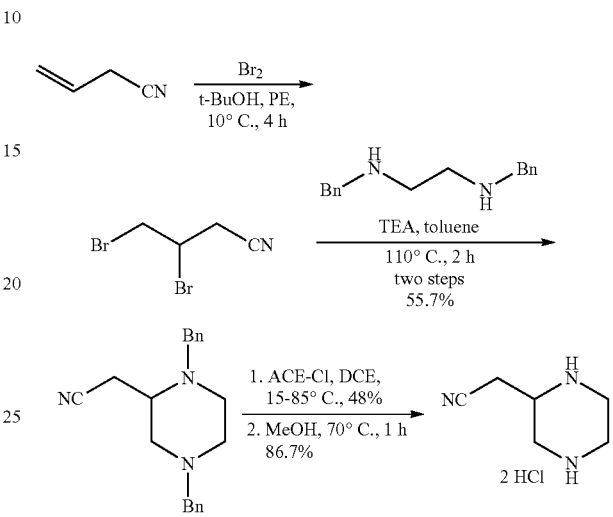

To a solution of but-3-enenitrile (80.0 g, 1.19 mol, 96.4 mL, 1.00 eq) in tert-butanol (130 mL) and petroleum ether (480 mL) was added a solution of Br$_2$ (191 g, 1.19 mol, 61.5 mL, 1.00 eq) in tert-butanol (130 mL). The mixture was stirred at 10° C. for 4 hours. The mixture was used into next step without any workup.

To the above mixture (274 mL) was added a solution of N,N-dibenzylethane-1,2-diamine (160 g, 445 mmol, 157 mL, 2 HOAc) and Et$_3$N (178 g, 1.76 mol, 245 mL) in toluene (300 mL). After was stirred at 110° C. for 2 hours, the mixture was filtered and the filtrate was concentrated under vacuum. The residue was purified by column chromatography (SiO$_2$, petroleum ether/ethyl acetate=3/1) to give 2-(1,4-dibenzylpiperazin-2-yl)acetonitrile (75.0 g, 246 mmol, two steps 55.7% yield) as a yellow solid. LCMS [ESI, M+1]: 306.

$^1$H NMR (400 MHz, chloroform-d) δ=7.37-7.23 (m, 10H), 3.80 (d, J=13.2 Hz, 1H), 3.60-3.42 (m, 3H), 3.06-2.96 (m, 1H), 2.95-2.83 (m, 1H), 2.69-2.53 (m, 4H), 2.52-2.35 (m, 3H).

To a solution of 2-(1,4-dibenzylpiperazin-2-yl)acetonitrile (160 g, 524 mmol, 1.00 eq) in dichloroethane (1.50 L) was added 1-chloroethyl carbonochloridate (300 g, 2.10 mol, 4.00 eq) at 15° C. After stirred at 85° C. for 48 h, the mixture was concentrated under vacuum. The residue was then taken up into methanol (1.50 L) and heated to reflux for 1 hour. The mixture was concentrated. The solid was treated with methyl tert-butyl ether (1.00 L), 2-piperazin-2-ylacetonitrile (Intermediate 62, 90.0 g, 454 mmol, 86.7% yield, 2HCl) was obtained as a white solid and used in the next step without further purification.

$^1$H NMR (400 MHz, DMSO-d6) δ=10.19 (br s, 2H), 4.01-3.73 (m, 1H), 3.69-3.41 (m, 4H), 3.32 (dt, J=2.8, 13.2 Hz, 1H), 3.27-3.10 (m, 3H).

Intermediate 56

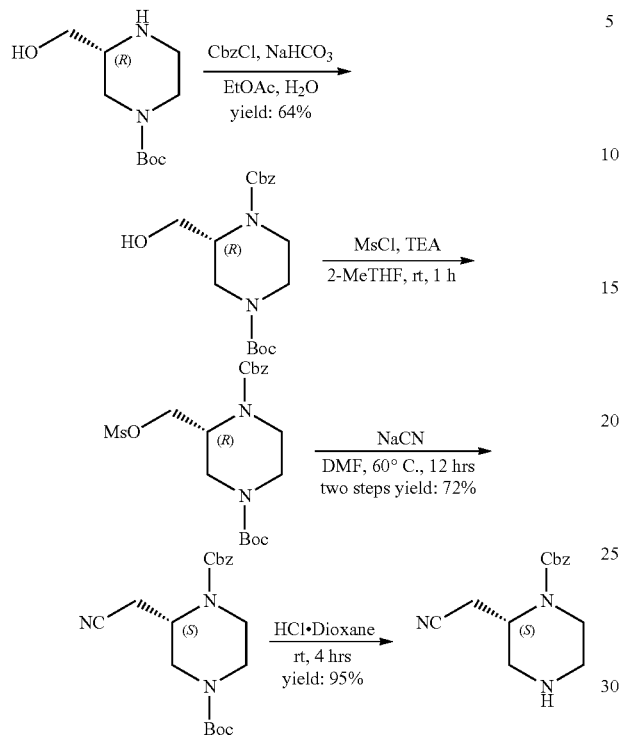

To a solution of tert-butyl (3R)-3-(hydroxymethyl)piperazine-1-carboxylate (80.0 g, 370 mmol, 1.0 eq) in Ethyl acetate (1400 mL) was added NaHCO₃ (93.2 g, 1.11 mol, 43.2 mL, 3.0 eq), H₂O (700 mL) and benzyl carbonochloridate (82.0 g, 481 mmol, 68.4 mL, 1.30 eq). The mixture was stirred at 25° C. for 12 hour. After completion, the organic phase was separated, washed with water (500 mL×2) dried over Na₂SO₄ and filtered. The solvent was removed under vacuum to give a residue. The residue was purified by column chromatography (SiO₂, Petroleum ether/Ethyl acetate=40/1 to 1/1). The product 1-benzyl 4-tert-butyl (2R)-2-(hydroxymethyl)piperazine-1,4-dicarboxylate (85.0 g, 235 mmol, 64% yield, 96% purity) was obtained as a yellow oil. LCMS [ESI, M−99]: 251.

To a solution of 1-benzyl 4-tert-butyl (2R)-2-(hydroxymethyl)piperazine-1,4-dicarboxylate (20.0 g, 57.1 mmol, 1.0 eq) in 2-Methyltetrahydrofuran (240 mL) was added TEA (17.3 g, 171.23 mmol, 23.8 mL, 3.0 eq) and methanesulfonyl chloride (7.74 g, 67.6 mmol, 5.23 mL, 1.18 eq). The mixture was stirred at 20° C. for 1 hour. The reaction mixture was quenched by addition H₂O 150 mL at 20° C. The reaction mixture was extracted with Ethyl acetate (300 mL×2). The organic layers were washed with H₂O (100 mL), dried over Na₂SO₄, and filtered. The solvent was removed under vacuum. 1-benzyl 4-tert-butyl (2R)-2-(methylsulfonyloxymethyl)piperazine-1,4-dicarboxylate (22.0 g, crude) was obtained as a yellow oil. The crude product was used directly to the next step without further purification.

To a solution of 1-benzyl 4-tert-butyl (2R)-2-(methylsulfonyloxymethyl)piperazine-1,4-dicarboxylate (22.0 g, 51.3 mmol) in DMA (150 mL) was added NaCN (10.4 g, 211 mmol). The mixture was stirred at 60° C. for 12 hour. The solvent was removed under vacuum to give a oil residue. The residue was diluted with H₂O (40.0 mL) and extracted with Ethyl acetate (50.0 mL×3). The combined organic layers were washed with saturated brine (80.0 mL), dried over Na₂SO₄, filtered and concentrated under reduced pressure to give a residue. The residue was purified by column chromatography (SiO₂, Petroleum ether/Ethyl acetate=40/1 to 5:1) The product 1-benzyl 4-tert-butyl (2S)-2-(cyanomethyl)piperazine-1,4-dicarboxylate (18.5 g, 46.4 mmol, two steps yield 72%) was obtained as a yellow oil. LCMS [ESI, M+1]: 360.

To a solution of 1-benzyl 4-tert-butyl (2S)-2-(cyanomethyl)piperazine-1,4-dicarboxylate (18.5 g, 43.3 mmol, 1.00 eq) in dioxane (40.0 mL) was added HCl•dioxane (4 M, 54.1 mL, 5.0 eq). The mixture was stirred at 20° C. for 1 hour. Then the reaction mixture was added NaHCO₃ to pH>7, and concentrated under reduced pressure to remove dioxane. The residue was diluted with H₂O (50.0 mL) and extracted with Ethyl acetate (50.0 mL×3). The combined organic layers were washed with H₂O (20.0 mL), dried over Na₂SO₄, filtered and concentrated under reduced pressure to give a residue. The product benzyl (2S)-2-(cyanomethyl)piperazine-1-carboxylate (Intermediate 63, 11.5 g, 91.8% purity, 95% yield) was obtained as a yellow oil. LCMS [ESI, M+1]: 260.

¹H NMR (400 MHz, CHLOROFORM-d) δ=7.37-7.31 (m, 5H), 5.14 (s, 2H), 4.49 (br, s, 1H), 3.93 (br, s, 1H), 3.07-2.81 (m, 5H), 2.78-2.54 (m, 2H).

Intermediate 57

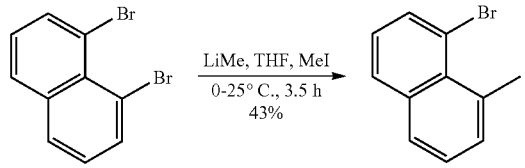

1-bromo-8-methylnaphthalene

Step A: 1-bromo-8-methyl-naphthalene. To a solution of 1,8-dibromonaphthalene (1 g, 3.50 mmol, 1 eq) in THF (20 mL) was added MeLi (1.6 M in diethyl ether, 2.62 mL, 1.2 eq) at 0° C. dropwise. After stirring for 30 minutes at 0° C., iodomethane (3.38 g, 23.8 mmol, 1.48 mL, 6.81 eq) was added dropwise. The mixture was warmed up to 25° C. and stirred for another 3 hours. The reaction mixture was quenched with water (20 mL) and extracted with ethyl acetate (20 mL×3). The combined organic layers were washed with brine (20 mL), dried over Na₂SO₄, filtered and concentrated under reduced pressure to give a residue. The residue was purified by prep-HPLC (column: Phenomenex Gemini C18 250*50 mm*10 um; mobile phase: [water (0.05% ammonia hydroxide v/v)—ACN]; B %: 45%-70%, 28 MIN; 40% min). Title compound 1-bromo-8-methyl-naphthalene (340 mg, 1.49 mmol, 43% yield, 97% purity) was obtained as a yellow solid after lyophilisation.

¹H NMR (400 MHz, chloroform-d) δ=7.75 (dd, J=0.8, 7.2 Hz, 1H), 7.69 (dd, J=0.8, 8.0 Hz, 1H), 7.66-7.59 (m, 1H), 7.30-7.22 (m, 2H), 7.13 (t, J=8.0 Hz, 1H), 3.05 (s, 3H).

Intermediate 58

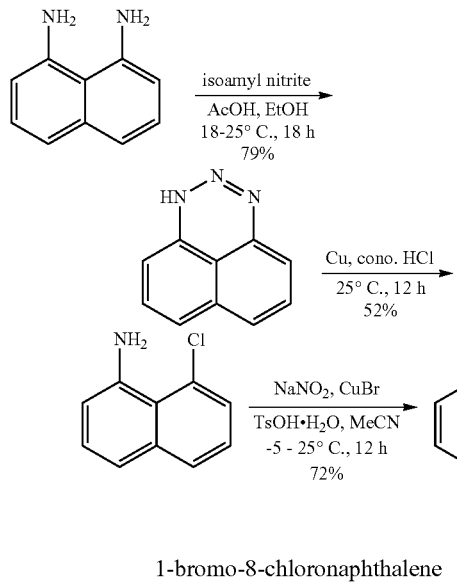

1-bromo-8-chloronaphthalene

Step A: 1H-naphtho[1,8-de][1,2,3]triazine. To a solution of naphthalene-1,8-diamine (100 g, 632 mmol, 1 eq) in AcOH (200 mL) and EtOH (1000 mL) was added isoamyl nitrite (72.6 g, 619 mmol, 83.4 mL, 0.98 eq) dropwise over a period of 2 h with temperature controlled between 18 and 21° C. under a cold-water bath. After the addition, the resulting red suspension was stirred at 25° C. for 16 hours. The solid was collected by filtration, washed with ethanol (2×500 mL) and dried under vacuum. Compound 1H-naphtho[1,8-de][1,2,3]triazine (84 g, 496 mmol, 79% yield) was obtained as a red crystalline solid and directly used next step without purification. LCMS [ESI, M+1]: 170.

Step B: 8-chloronaphthalen-1-amine. To a solution of 1H-naphtho[1,8-de][1,2,3]triazine (84 g, 496 mmol, 1 eq) in HCl (1.5 L) was added Cu (2.10 g, 33.1 mmol, 234 µL, 0.0665 eq). The stirred at 25° C. for 12 hours. The resulting mixture was diluted with water (500 mL) and heated at 85° C. for 30 mins. The resulting almost clear aqueous solution was filtered, cooled, basified with aqueous ammonia (until blue to litmus paper) and the solution was extracted with ether acetate (2×1000 mL). The combined extracts were dried over Na$_2$SO$_4$, filtered and concentrated under vacuum. The residue was purified by column chromatography (SiO$_2$, Petroleum ether/Ethyl acetate=200/1 to 5/1). Compound 8-chloronaphthalen-1-amine (57 g, 259 mmol, 52% yield, 81% purity) was obtained as a red solid. LCMS [ESI, M+1]: 178.

Step C: 1-bromo-8-chloro-naphthalene. To a solution of 8-chloronaphthalen-1-amine (57 g, 320 mmol, 1 eq) and TsOH.H$_2$O (219 g, 1.16 mol, 3.6 eq) in MeCN (1000 mL) was added a solution of NaNO$_2$ (39.8 g, 577 mmol, 1.8 eq) and CuBr (138 g, 963 mmol, 29.3 mL, 3 eq) in H$_2$O (120 mL) at −5° C., then the reaction mixture was stirred at 25° C. for 12 hours. The reaction mixture was added saturated Na$_2$SO$_3$ solution (100 mL) and stirred for 15 mins, then extracted with ethyl acetate (1000 mL×3). The combined organic layers were washed with brine (500 mL), dried over Na$_2$SO$_4$, filtered and concentrated under reduced pressure to give a residue. The residue was purified by column chromatography (SiO$_2$, Petroleum ether). Title compound 1-bromo-8-chloro-naphthalene (56 g, 229 mmol, 72% yield, 99% purity) was obtained as a white solid.
$^1$H NMR (400 MHz, chloroform-d) δ=7.93 (dd, J=1.2, 7.6 Hz, 1H), 7.82 (dd, J=1.2, 8.4, 1H), 7.79 (dd, J=1.2, 8.4, 1H), 7.67 (dd, J=1.2, 7.6 Hz, 1H), 7.37 (t, J=8.0 Hz, 1H), 7.28 (t, J=8.0 Hz, 1H).

Intermediate 59

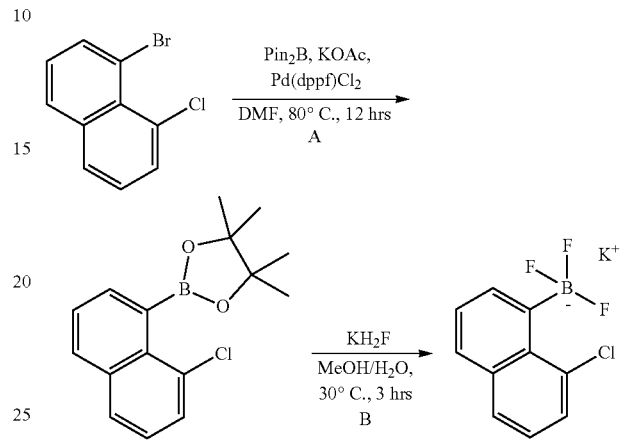

Intermediate 59

Potassium (8-chloronaphthalen-1-yl)trifluoroborate

Step A: A mixture of 1-bromo-8-chloro-naphthalene (20.0 g, 82.8 mmol, 1.00 eq), Pin$_2$B$_2$ (52.6 g, 207 mmol, 2.50 eq), KOAc (48.8 g, 497 mmol, 6.00 eq), Pd(dppf)Cl$_2$ (6.06 g, 8.28 mmol, 0.10 eq) in DMF (400 mL) was stirred at 80° C. for 12 hours under N$_2$. The mixture was diluted with ethyl acetate (60.0 mL) and water (60.0 mL), the mixture was separated. The water phase was extracted with ethyl acetate (50.0 mL). The combined organic layer was washed with brine (2×50.0 mL), dried over Na$_2$SO$_4$, filtered and concentrated under vacuum. The residue was purification by column chromatography (SiO$_2$, PE/EA=10/1) to give 2-(8-chloro-1-naphthyl)-4,4,5,5-tetramethyl-1,3,2-dioxaborolane (210 g, 72.8 mmol, 88% yield) as a yellow solid.
$^1$H NMR (400 MHz, chloroform-d) δ=7.87 (dd, J=1.2, 8.0 Hz, 1H), 7.76 (dd, J=1.2, 8.0 Hz, 1H), 7.68 (dd, J=1.0, 6.8 Hz, 1H), 7.59 (dd, J=1.2, 7.2 Hz, 1H), 7.51 (dd, J=6.8, 8.0 Hz, 1H), 7.40-7.35 (m, 1H), 1.46 (s, 12H).

Step B: To a mixture of 2-(8-chloro-1-naphthyl)-4,4,5,5-tetramethyl-1,3,2-dioxaborolane (2.00 g, 6.93 mmol, 1.00 eq) in methanol (20.0 mL) was added a solution of KHF$_2$ (4.87 g, 62.4 mmol, 2.06 mL, 9.00 eq) in H$_2$O (7 mL). After stirring at 30° C. for 3 hours, the mixture was concentrated under vacuum to removed methanol and filtered, the filtered cake was collected to give potassium [(8-chloro-1-naphthyl)-trifluoro-boranyl] (2.6 g, crude) as a yellow solid and used into next step without further purification.

Intermediate 60

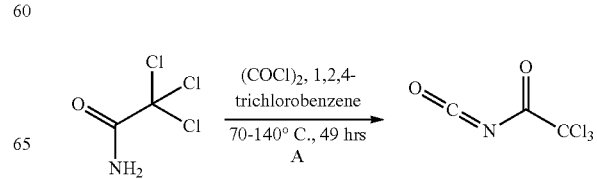

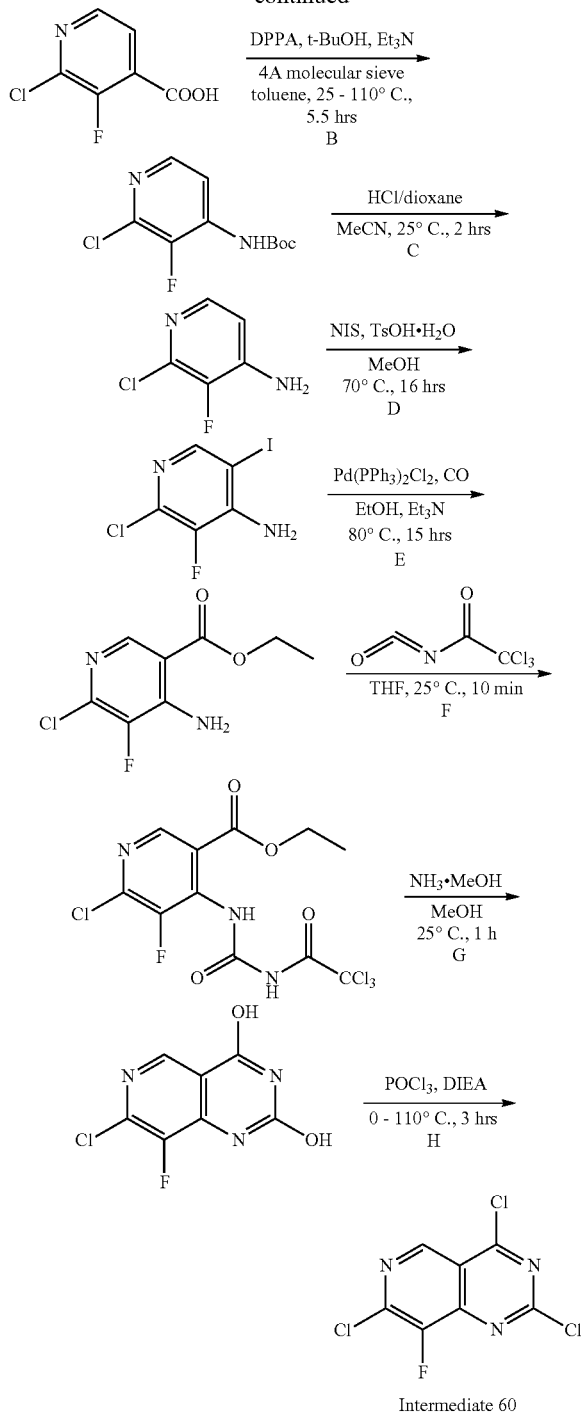

tert-butyl(2S)-2-(cyanomethyl)-4-(2,7-dichloro-8-fluoro-pyrido[4,3-d]pyrimidin-4-yl)piperazine-1-carboxylate Step A: A reaction mixture of 2,2,2-trichloroacetamide (100 g, 616 mmol, 1.0 eq) in (COCl)$_2$ (725 g, 5.71 mol, 500 mL, 9.28 eq) was heated to 70° C. for 24 hrs. The reaction mixture was concentrated under vacuum. To the mixture was added 1,2,4-trichlorobenzene (500 mL) and (COCl)$_2$ (116 g, 914 mmol, 80 mL, 1.48 eq). The reaction mixture was stirred at 100° C. for 5 hours. The warmed to 125° C. for 15 hours. Then the mixture was warmed to 140° C. for 5 hours. The reaction mixture was distilled under water pump (72° C.-76° C. fractions) to give 2,2,2-trichloroacetyl isocyanate (60 g, 319 mmol, 52% yield) as a colourless oil which was used in the next step without further purification.

Step B: A mixture of 2-chloro-3-fluoro-pyridine-4-carboxylic acid (180 g, 1.03 mol, 1.0 eq), 4A molecular sieve (300 g) and Et$_3$N (311 g, 3.08 mol, 428 mL, 3.0 eq) in toluene (1.3 L) and t-BuOH (1.01 kg, 13.6 mol, 1.3 L, 13.3 eq) was stirred at 110° C. for 0.5 hour under nitrogen, then the mixture was cooled to 25° C. and added diphenylphosphoryl azide (423 g, 1.54 mol, 333 mL, 1.5 eq). The mixture was stirred at 110° C. for 5 hours. Upon completion, the mixture was diluted with water (2000 mL) and extracted with ethyl acetate (2×2000 mL). The combined organic layers were washed with brine (1×2000 mL), dried over sodium sulfate, filtered and concentrated under vacuum. The residue was purified by column chromatography (SiO$_2$, Petroleum ether/Ethyl acetate=100/1 to 5/1). tert-butyl N-(2-chloro-3-fluoro-4-pyridyl)carbamate (197 g, 799 mmol, 78% yield, 100% purity) was obtained as a white solid. LCMS [ESI, M+1]: 247; LCMS [ESI, M−55]: 191.

$^1$H NMR (400 MHz, methanol-d$_4$) δ=8.11 (t, J=5.6 Hz, 1H), 7.99 (d, J=5.6 Hz, 1H), 1.52 (s, 9H).

Step C: To a solution of tert-butyl N-(2-chloro-3-fluoro-4-pyridyl)carbamate (199 g, 807 mmol, 1.0 eq) in MeCN (250 mL) was added HCl/dioxane (4 M, 796 mL, 3.95 eq). The mixture was stirred at 25° C. for 2 hours. Upon completion, the mixture was filtered and the filter cake was diluted with saturated NaHCO$_3$ solution (2000 mL) and extracted with ethyl acetate (2×2000 mL). The combined organic layers were dried over sodium sulfate, filtered and concentrated under vacuum. 2-chloro-3-fluoro-pyridin-4-amine (107 g, 731 mmol, 91% yield, 99.9% purity) was obtained as a yellow solid and used in the next step without further purification. LCMS [ESI, M+1]: 147.

$^1$H NMR (400 MHz, methanol-d$_4$) δ=7.61 (d, J=5.6 Hz, 1H), 6.67 (t, J=6.0 Hz, 1H).

Step D: To a solution of 2-chloro-3-fluoro-pyridin-4-amine (107 g, 730 mmol, 1.0 eq) and NIS (197 g, 876 mmol, 1.2 eq) in MeCN (550 mL) was added p-toluene sulfonic acid monohydrate (6.94 g, 36.5 mmol, 0.05 eq). The mixture was stirred at 70° C. for 16 hours. Upon completion, the mixture was diluted with water (300 mL) and ethyl acetate (2000 mL), The organic layer was washed with saturated Na$_2$CO$_3$ solution (2×1500 mL), saturated Na$_2$SO$_3$ (1×2000 mL) solution and brine (1×1500 mL), dried over Na$_2$SO$_4$, filtered and concentrated under vacuum. 2-chloro-3-fluoro-5-iodo-pyridin-4-amine (190 g, 676 mmol, 93% yield, 97.2% purity) was obtained as a yellow solid and used in the next step without further purification. LCMS [ESI, M+1]: 273.

Step E: To a solution of 2-chloro-3-fluoro-5-iodo-pyridin-4-amine (78.4 g, 288 mmol, 1.0 eq) in EtOH (1500 mL) was added Pd(PPh$_3$)$_2$Cl2 (20.2 g, 28.8 mmol, 0.1 eq) and Et$_3$N (105 g, 1.04 mol, 144 mL, 3.61 eq) under nitrogen. The suspension was degassed under vacuum and purged with nitrogen several times. The mixture was stirred under CO (15.0 psi) at 80° C. for 15 hours. Upon completion, the mixture was filtered and the filtrate was concentrated under vacuum to remove 70% of MeOH and the residue was filtered. The combined filter cakes were concentrated under vacuum. ethyl 4-amino-6-chloro-5-fluoro-pyridine-3-carboxylate (142 g, crude) was obtained as a yellow solid. LCMS [ESI, M+1]: 219.

¹H NMR (400 MHz, dmso-d6) δ=8.36 (s, 1H), 7.49-7.42 (m, 2H), 4.31 (q, J=7.2 Hz, 2H), 1.31 (t, J=7.2 Hz, 3H).

Step F: To a solution of ethyl 4-amino-6-chloro-5-fluoro-pyridine-3-carboxylate (20.3 g, 73.2 mmol, 1.0 eq) in THF (60 mL) was added 2,2,2-trichloroacetyl isocyanate (20.7 g, 110 mmol, 13.0 mL, 1.5 eq) at 25° C. The mixture was stirred at 25° C. for 10 min. Upon completion, the mixture was concentrated under vacuum. The crude product was triturated with MTBE (200 mL) at 25° C. for 5 min. ethyl 6-chloro-5-fluoro-4-[(2,2,2-trichloroacetyl) carbamoylamino]pyridine-3-carboxylate (29.3 g, 67.74 mmol, 92% yield, 94.1% purity) was obtained as a gray solid. LCMS [ESI, M+1]: 408.

Step G: To a solution of ethyl 6-chloro-5-fluoro-4-[(2,2,2-trichloroacetyl) carbamoylamino]pyridine-3-carboxylate (29.3 g, 63.1 mmol, 1.0 eq) in MeOH (290 mL) was added NH₃·MeOH (29 mL, 20% purity) at 25° C. The mixture was stirred at 25° C. for 1 h. Upon completion, the mixture was concentrated under vacuum. The crude product was triturated with MTBE (200 mL) at 25° C. for 10 min. 7-chloro-8-fluoro-pyrido[4,3-d] pyrimidine-2,4-diol (18 g, crude) was obtained as a brown solid. LCMS [ESI, M+1]: 216.

Step H: To a mixture of POCl₃ (165 g, 1.08 mol, 100 mL, 23.2 eq) and DIEA (30.0 g, 232 mmol, 40.4 mL, 5.0 eq) was added portionwise 7-chloro-8-fluoro-pyrido[4,3-d]pyrimidine-2,4-diol (10 g, 46.4 mmol, 1.0 eq) at 0° C. Then the mixture was warmed to 110° C. and stirred for 3 hours. Upon completion, the mixture was concentrated under vacuum and the oil was dried by azeotroping with CHCl₃. 2,4,7-trichloro-8-fluoro-pyrido [4,3-d]pyrimidine (11.7 g, crude) was obtained as a black oil and used in the next step without further purification.

Intermediate 61

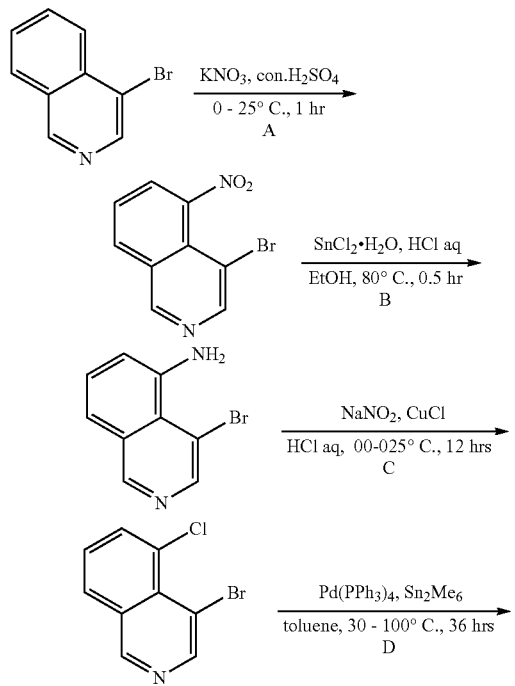

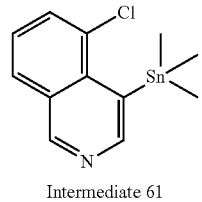

Intermediate 61

(5-chloro-4-isoquinolyl)-trimethyl-stannane

Step A: KNO₃ (26.3 g, 260 mmol, 1.08 eq) was added to H₂SO₄ (188 g, 1.88 mol, 102 mL, 98% purity, 7.81 eq) and slowly dissolved by careful heating. The resulting solution was added dropwise to a solution of 4-bromoisoquinoline (50 g, 240 mmol, 1.0 eq) in H₂SO₄ (375 g, 3.75 mol, 204 mL, 98% purity, 15.6 eq) at 0° C. After removal of the cooling bath, the solution was stirred for 1 hour at 25° C. The reaction mixture was then poured onto crushed ice (1000 g) and made basic (pH ~8) with NaOH solution (2 N). The mixture was extracted with ethyl acetate (3×2000 mL), dried over Na₂SO₄, filtered and concentrated under reduced pressure to give a residue. The residue was triturated with ethyl acetate (500 ml). 4-bromo-5-nitro-isoquinoline (50 g, 197 mmol, 82% yield, 100% purity) was obtained as a yellow solid. LCMS [ESI, M+2]: 255.

Step B: 4-bromo-5-nitro-isoquinoline (25 g, 98.7 mmol, 1.0 eq) and SnCl₂·2H₂O (111 g, 493 mmol, 5.0 eq) were suspended in EtOH (600 mL), added with HCl (12 M, 57.5 mL, 6.98 eq) and stirred at 80° C. for 30 minutes. The reaction mixture was poured onto crushed ice (1000 g) and adjusted to pH-12 with 2 N of aqueous sodium hydroxide. Then the mixture was extracted with ethyl acetate (3×2000 mL). The combined organic layers were washed with brine (1000 mL), dried over Na₂SO₄, filtered and concentrated under reduced pressure to give 4-bromoisoquinolin-5-amine (36 g, 150 mmol, 76% yield, 93% purity) as a brown solid and used to next step without further purification.

¹H NMR (400 MHz, chloroform-d) δ=8.99 (s, 1H), 8.51 (s, 1H), 7.47-7.32 (m, 2H), 6.93 (dd, J=1.2, 7.6 Hz, 1H), 5.24 (s, 2H).

Step C: To a solution of 4-bromoisoquinolin-5-amine (33 g, 147 mmol, 1.0 eq) in aqueous HCl (2 M, 1000 mL, 13.5 eq) cooled to 0° C. was added a solution of NaNO₂ (13.3 g, 192 mmol, 806 μL, 1.3 eq) in H₂O (400 mL). The reaction was stirred to 0° C. for 30 min and a solution of CuCl (19.0 g, 192 mmol, 4.60 mL, 1.3 eq) in con. HCl (400 mL) at 0° C., the reaction mixture was stirred at 25° C. for 12 hours. The reaction mixture was poured onto crushed ice (1000 g) and adjusted to pH ~8 with 2 N of aqueous sodium hydroxide. Then the mixture was extracted with ethyl acetate (3×1000 mL). The combined organic layers were washed with brine (500 mL), dried over Na₂SO₄, filtered and concentrated under reduced pressure to give a residue. The residue was purified by column chromatography (SiO₂, ethyl acetate/methanol=100/1 to 10/1). 4-bromo-5-chloro-isoquinoline (17 g, 69.4 mmol, 47% yield, 99% purity) was obtained as a yellow solid.

¹H NMR (400 MHz, chloroform-d) δ=9.11 (s, 1H), 8.79 (s, 1H), 7.91 (dd, J=1.2, 8.0 Hz, 1H), 7.84 (dd, J=1.2, 7.6 Hz, 1H), 7.53 (t, J=7.6 Hz, 1H).

Step D: To a solution of 4-bromo-5-chloro-isoquinoline (5 g, 20.6 mmol, 1.0 eq) in toluene (100 mL) was added Pd(PPh₃)₄ (2.38 g, 2.06 mmol, 0.1 eq) and trimethyl(trimethylstannyl)stannane (22.0 g, 67.2 mmol, 13.9 mL, 3.26 eq) at 30° C. The mixture was stirred at 100° C. for 36 hours. The reaction mixture was diluted with water (100 mL) and extracted with ethyl acetate (3×100 mL). The combined organic layers were washed with brine (100 mL), dried over $Na_2SO_4$, filtered and concentrated under reduced pressure to give a residue. The residue was triturated with ethyl acetate (50 mL) and further purified by reversed phase flash [water (0.1% formic acid)/acetonitrile]. The mixture was concentrated under reduced pressure to give (5-chloro-4-isoquinolyl)-trimethyl-stannane (1.7 g, 5.16 mmol, 25% yield, 99% purity) was obtained as a colourless oil. LCMS [ESI, M+1]: 328.

$^1$H NMR (400 MHz, chloroform-d) δ=9.21 (s, 1H), 8.72 (s, 1H), 7.98-7.87 (m, 1H), 7.82 (dd, J=1.2, 7.6 Hz, 1H), 7.53 (t, J=8.0 Hz, 1H), 0.55-0.40 (s, 9H).

In addition to the foregoing Intermediates 1-61 above, the following exemplary Intermediates A-1-A-10 may be used to couple —Y—$R^2$ to the azaquinazoline core of Formula (I).

Intermediate A-1

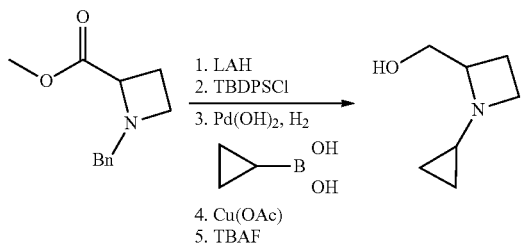

To a solution of $LiAlH_4$ (5.55 g, 146 mmol, 2.0 equiv) in THF (180 mL) was added methyl 1-benzylazetidine-2-carboxylate (15.0 g, 73.1 mmol, 1.0 equiv) at −20° C. under $N_2$. The reaction mixture was stirred at −20° C. for 1 h and was subsequently quenched with water (5.55 mL), 15% NaOH aqueous solution (5.55 mL) and water (16.6 mL). The mixture was filtered and the solid was washed with THF (20 mL). The filter cake was slurried in THF (50 mL) at 25° C. for 5 minutes and was filtered. The combined filtrate was dried over anh $Na_2SO_4$, filtered and concentrated under reduced pressure to afford (1-benzylazetidin-2-yl)methanol (12.1 g, 64.8 mmol, 89% yield) as a yellow oil. LCMS [M+1]: 178.

To a mixture of (1-benzylazetidin-2-yl)methanol (12.1 g, 68.3 mmol, 1.0 equiv) in THF (80.0 mL) was added DMAP (834 mg, 6.83 mmol, 0.1 equiv), imidazole (13.9 g, 205 mmol, 3.0 equiv) and TBDPSCl (20.6 g, 75.1 mmol, 19.3 mL, 1.1 equiv) at 0° C. The reaction mixture was stirred at 25° C. for 1 h and was subsequently concentrated under reduced pressure. The residue was diluted with water (50 mL) and extracted with ethyl acetate (2×200 mL). The combined organic layer was dried over anhydrous $Na_2SO_4$, filtered and concentrated under reduced pressure to provide the crude residue. The residue was purified by column chromatography ($SiO_2$, petroleum ether/ethyl acetate, 20:1 to 5:1). This material was further purified by reversed-phase flash chromatography [water (0.1% FA)/acetonitrile] to give (1-benzylazetidin-2-yl)methoxy-tert-butyl-diphenyl-silane (20.0 g, 47.6 mmol, 70% yield) as a yellow oil. LCMS [M+1]: 416. $^1$H NMR (400 MHz, chloroform-d) δ 7.73-7.65 (m, 4H), 7.48-7.35 (m, 6H), 7.34-7.22 (m, 5H), 3.98 (br d, J=12.4 Hz, 1H), 3.84-3.25 (m, 5H), 3.03-2.75 (m, 1H), 2.00 (br d, J=1.6 Hz, 2H), 1.07 (s, 9H).

To a solution of (1-benzylazetidin-2-yl)methoxy-tert-butyl-diphenyl-silane (19.0 g, 45.7 mmol, 1.0 equiv) in methanol (570 mL) was added HOAc (1.10 g, 18.3 mmol, 1.05 mL, 0.4 equiv) and $Pd(OH)_2$/C (13.0 g, 20 wt %) under $N_2$. The suspension was degassed under vacuum and purged with $H_2$ several times. The mixture was stirred under $H_2$ (50 psi) at 50° C. for 48 hours. The mixture was filtered and the solid was washed with methanol (100 mL). The filtrate was concentrated under reduced pressure to dryness. The crude product was purified by reversed-phase flash chromatography [water (0.1% FA)/acetonitrile] to afford azetidin-2-yl methoxy-tert-butyl-diphenyl-silane (5.7 g, 15.2 mmol, 33% yield) as a yellow oil. LCMS [M+1]: 326. $^1$H NMR (400 MHz, chloroform-d) δ 7.72-7.54 (m, 4H), 7.48-7.31 (m, 6H), 4.00-3.86 (m, 1H), 3.79-3.41 (m, 4H), 2.31 (ddd, J=2.8, 5.2, 10.8 Hz, 1H), 2.17-2.00 (m, 1H), 1.16-0.99 (m, 9H).

To a mixture of azetidin-2-ylmethoxy-tert-butyl-diphenyl-silane (2.8 g, 7.48 mmol, 1.0 equiv) and cyclopropylboronic acid (2.57 g, 29.9 mmol, 4.0 equiv) in 1,2-dichloroethane (30.0 mL) was added $Na_2CO_3$ (1.59 g, 15.0 mmol, 2.0 equiv), $Cu(OAc)_2$ (1.36 g, 7.48 mmol, 1.0 equiv) and 2,2'-bipyridine (1.17 g, 7.48 mmol, 1.0 equiv) at 25° C. The mixture was stirred at 70° C. under O2 (15 psi) for 2 hours. The mixture was cooled to room temperature and was filtered and washed with ethyl acetate (50 mL). The filtrate was diluted with water (40 mL) and then extracted with ethyl acetate (2×50 mL). The combined organic layer was washed with brine (80 mL), dried over anh $Na_2SO_4$, filtered and concentrated to provide the crude material.

The residue was purified by column chromatography ($SiO_2$, petroleum ether/ethyl acetate, 1:1 to 0:1) and then by reversed-phase flash chromatography [water (0.1% FA)/acetonitrile] to give tert-butyl-[(1-cyclopropylazetidin-2-yl)methoxy]-diphenyl-silane (1.48 g, 4.01 mmol, 54% yield) as a yellow oil. LCMS [M+1]: 366.

To a solution of tert-butyl-[(1-cyclopropylazetidin-2-yl)methoxy]-diphenyl-silane (880 mg, 2.41 mmol, 1.0 equiv) in THF (5.0 mL) was added TBAF (1.0 M, 2.89 mL, 1.2 equiv) at 0° C. The mixture was stirred at 0° C. for 12 hours. Subsequently, the mixture was diluted with water (10 mL) and extracted with ethyl acetate (8×20 mL). The combined organic layer was dried over anh $Na_2SO_4$, filtered and concentrated under reduced pressure to provide crude (1-cyclopropylazetidin-2-yl)methanol (910 mg) as a yellow oil.

Intermediate A-2

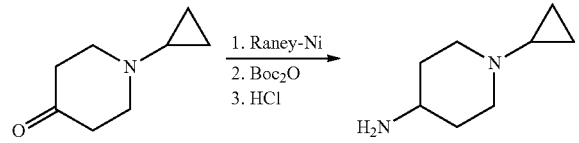

To a solution of 1-cyclopropylpiperidin-4-one (2.0 g, 14.4 mmol, 1.0 equiv) in MeOH (40 mL) was added Raney-Ni (167 mg) and 4 M $NH_3$.MeOH (14.4 mmol, 20 mL, 1.0 equiv) under $N_2$. The suspension was degassed under vacuum and purged with $H_2$ several times. The mixture was stirred under $H_2$ (15 psi) at 15° C. for 1 hour. The mixture was filtered and concentrated under reduced pressure to afford 1-cyclopropylpiperidin-4-amine (1.7 g, crude) as a green solid.

A mixture of 1-cyclopropylpiperidin-4-amine (1.3 g, 9.27 mmol, 1.0 equiv) in tert-butoxycarbonyl tert-butyl carbonate (2.85 g, 13.1 mmol, 3.0 mL, 1.4 equiv) was stirred at 40° C. for 3 hours. The residue was purified by column chromatography (SiO$_2$, petroleum ether/ethyl acetate, 10:1 to petroleum ether/ethyl acetate, 2:1) to afford tert-butyl N-(1-cyclopropyl-4-piperidyl) carbamate (1.7 g, 7.07 mmol, 76% yield) as a white solid. $^1$H NMR (400 MHz, chloroform-d) δ 4.40 (br s, 1H), 3.47 (br s, 1H), 2.95 (d, J=12.0 Hz, 2H), 2.35-2.21 (m, 2H), 1.90 (d, J=11.6 Hz, 2H), 1.63-1.52 (m, 1H), 1.44 (s, 9H), 1.35 (br dd, J=3.2, 12.0 Hz, 1H), 0.47-0.41 (m, 2H), 0.40-0.35 (m, 2H).

To a solution of tert-butyl N-(1-cyclopropyl-4-piperidyl) carbamate (500 mg, 2.08 mmol, 1.0 equiv) in methanol (2.0 mL) was added HCl (4 M in dioxane, 5.0 mL, 9.6 equiv) at 0° C. The mixture was stirred at 0° C. for 1 hour. The mixture was concentrated, diluted with saturated NaOH aqueous solution (25 mL) and extracted with dichloromethane (3×10 mL). The combined organic layer was washed with brine (20 mL), dried over anh Na$_2$SO$_4$, filtered and concentrated under reduced pressure to give 1-cyclopropylpiperidin-4-amine (120 mg, crude) as a yellow oil. $^1$H NMR (400 MHz, chloroform-d) δ 2.98 (d, J=12.0 Hz, 2H), 2.71 (br s, 1H), 2.22 (td, J=2.0, 11.6 Hz, 2H), 1.79 (br d, J=12.0 Hz, 2H), 1.59-1.51 (m, 1H), 1.38-1.25 (m, 2H), 0.48-0.34 (m, 4H).

Intermediate A-3

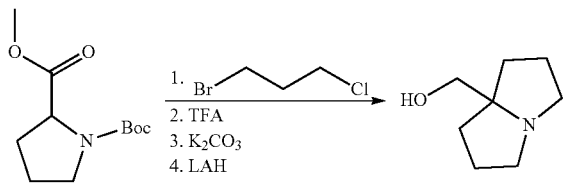 [SMILES: COC(=O)C1CCCN1C(=O)OC(C)(C)C ; ClCCCBr ; OCC12CCCN1CCC2]

To a solution of O1-tert-butyl O2-methyl pyrrolidine-1,2-dicarboxylate (58.0 g, 253 mmol, 1.0 equiv) in THF (1000 mL) was added LiHMDS (1 M, 379 mL, 1.5 equiv) at −65° C. The mixture was stirred at −65° C. for 1 hour prior to the addition of 1-bromo-3-chloro-propane (199 g, 1.26 mol, 124 mL, 5.0 equiv) at −65° C. The solution was warmed to room temperature while stirring over 2 h. The mixture was diluted with satd aq NH$_4$Cl (500 mL) and then extracted with ethyl acetate (1200 mL). The organic layer was dried over anh Na$_2$SO$_4$, filtered and concentrated under vacuum to provide the crude material. The residue was purified by column chromatography (SiO$_2$, petroleum ether/ethyl acetate, 50:1 to 5:1) to afford 1-(tert-butyl) 2-methyl 2-(3-chloropropyl) pyrrolidine-1,2-dicarboxylate (50.0 g, 60% yield) as a yellow oil.

To a solution of 1-(tert-butyl) 2-methyl 2-(3-chloropropyl)pyrrolidine-1,2-dicarboxylate (11.7 g, 38.3 mmol, 1.0 equiv) in dichloromethane (300 mL) was added TFA (117 g, 1.02 mol, 75.8 mL, 26.7 equiv) at 25° C. The mixture was stirred 25° C. for 0.5 hour. Subsequently, the mixture was concentrated under vacuum to provide methyl 2-(3-chloropropyl)pyrrolidine-2-carboxylate (12 g, crude, TFA salt) as a colorless oil.

To a solution of methyl methyl 2-(3-chloropropyl)pyrrolidine-2-carboxylate (12.0 g, 37.5 mmol, 1.0 equiv, TFA) in MeOH (250 mL) was added K$_2$CO$_3$ (15.6 g, 113 mmol, 3.0 equiv) and KI (623 mg, 3.75 mmol, 0.1 equiv) at 25° C. The mixture was stirred at 35° C. for 1.5 hours. The mixture was filtered and ~80% of the filtrate was removed under reduced pressure. The remaining filtrate was diluted with ethyl acetate (400 mL) and filtered. The filtrate was concentrated under vacuum to provide the crude material, which was purified by column chromatography (Al$_2$O$_3$, dichloromethane/methanol, 10:1) to afford methyl tetrahydro-1H-pyrrolizine-7a(5H)-carboxylate (5.40 g, 85% yield) as a yellow oil. $^1$H NMR (400 MHz, CDCl$_3$) δ 3.70 (br s, 3H), 3.22-3.08 (m, 2H), 2.71-2.56 (m, 2H), 2.36-2.22 (m, 2H), 1.87-1.73 (m, 4H), 1.72-1.59 (m, 2H); LCMS [ESI, M+1]: 170.

To a solution of methyl tetrahydro-1H-pyrrolizine-7a (5H)-carboxylate (11.8 g, 69.7 mmol, 1.0 equiv) in THF (250 mL) was added LiAlH$_4$ (7.94 g, 209 mmol, 3.0 equiv) at −10° C. The mixture was stirred at this temperature for 30 min prior to being quenched with water (7 mL) and 15% NaOH solution (8 mL). The mixture was filtered and the filtrate was concentrated under vacuum to provide (tetrahydro-1H-pyrrolizin-7a(5H)-yl)methanol (8.70 g, 88% yield) as a yellow oil. $^1$H NMR (400 MHz, CD$_3$OD) δ 3.31 (s, 2H), 3.00-2.91 (m, 2H), 2.67-2.57 (m, 2H), 1.96-1.80 (m, 4H), 1.78-1.68 (m, 2H), 1.62-1.52 (m, 2H).

Intermediate A-4

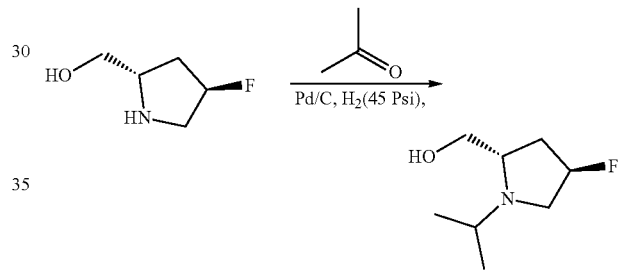

To a solution of ((2S,4R)-4-fluoropyrrolidin-2-yl)methanol (5.23 g, 33.6 mmol, 1.0 equiv, HCl salt) in MeOH (50 mL) was added acetone (25.5 g, 439 mmol, 32.3 mL, 13 equiv) and Pd/C (600 mg, 10% w/w) under N$_2$. The suspension was evacuated under vacuum and purged with H$_2$ several times. The mixture was stirred under H$_2$ (45 psi) at 25° C. for 12 hours. Subsequently, the mixture was filtered and the filtrate was concentrated to provide the crude material. The crude material was purified by flash chromatography (SiO$_2$, petroleum ether/ethyl acetate, 5:1 to DCM/MeOH, 5:1) to afford ((2S,4R)-4-fluoro-1-isopropylpyrrolidin-2-yl)methanol (2.7 g, 50% yield) as a colorless oil. Rf=0.30 (10:1, dichloromethane/methanol). $^1$H NMR (400 MHz, CDCl$_3$) δ 5.25-4.99 (m, 1H), 3.81-3.70 (m, 1H), 3.51-3.44 (m, 1H), 3.40-3.24 (m, 2H), 3.18 (s, 1H), 3.13-2.98 (m, 1H), 2.20-2.03 (m, 2H), 1.18 (d, J=6.8 Hz, 3H), 1.05 (d, J=6.4 Hz, 3H).

Intermediate A-5

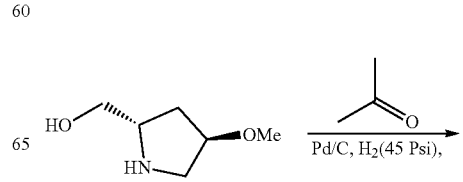

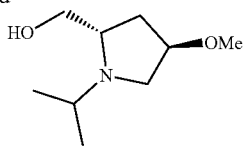

To a solution of ((2S,4R)-4-methoxypyrrolidin-2-yl)methanol (2.5 g, 14.9 mmol, 1 equiv, HCl salt) in MeOH (30 mL) was added acetone (19.1 g, 328 mmol, 24.1 mL, 22 equiv), Pd/C (500 mg, 10% w/w) under $N_2$. The suspension was evacuated under vacuum and purged with $H_2$ several times. The mixture was stirred under $H_2$ (30.1 mg, 14.9 mmol) (45 psi) at 25° C. for 12 hours. Subsequently, the reaction mixture was filtered and concentrated under reduced pressure. The residue was purified by column chromatography ($SiO_2$, petroleum ether/ethyl acetate, 5:1 to DCM/MeOH, 5:1) to afford ((2S,4R)-1-isopropyl-4-methoxypyrrolidin-2-yl)methanol (1.1 g, 43% yield) as a yellow oil. $^1H$ NMR (400 MHz, $CDCl_3$): δ 3.89-3.79 (m, 1H), 3.56 (d, J=4.0 Hz, 1H), 3.35-3.29 (m, 1H), 3.27 (s, 3H), 3.19-3.06 (m, 2H), 2.97 (s, 1H), 2.64-2.57 (m, 1H), 2.02-1.94 (m, 1H), 1.88-1.77 (m, 1H), 1.09 (d, J=6.8 Hz, 3H), 0.96 (d, J=6.4 Hz, 3H).

Intermediate A-6

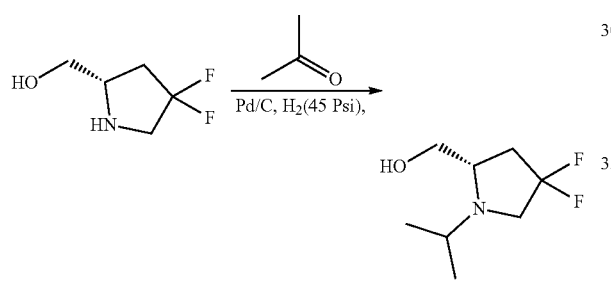

To a solution of (S)-(4,4-difluoropyrrolidin-2-yl)methanol (3.00 g, 17.3 mmol, 1.0 equiv, HCl salt) in methanol (50 mL) was added Pd/C (400 mg, 10% w/w) and acetone (39.5 g, 680 mmol, 50.0 mL, 39 equiv). The reaction mixture was stirred at 25° C. under $H_2$ (45 psi) for 24 hours. The reaction mixture was filtered and the filtrate was concentrated under reduced pressure. The residue was added to a solution of $NH_3$ in methanol (50 mL, $NH_3$ was bubbled through methanol at −40° C. for 10 min) and concentrated. The residue was purified by column chromatography ($Al_2O_3$, petroleum ether/ethyl acetate, 3:1 to 0:1) to afford (S)-(4,4-difluoro-1-isopropylpyrrolidin-2-yl)methanol (2.50 g, 81% yield) as a colorless oil. $^1H$ NMR (400 MHz, $CDCl_3$) δ 3.73-3.66 (m, 1H), 3.38 (br d, J=11.2 Hz, 1H), 3.29-3.15 (m, 2H), 3.11-2.95 (m, 2H), 2.65-2.48 (m, 1H), 2.46-2.20 (m, 2H), 1.12 (d, J=6.8 Hz, 3H), 0.97 (d, J=6.4 Hz, 3H). LCMS [ESI, M+1]: 180.

Intermediate A-7

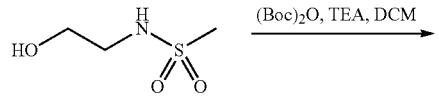

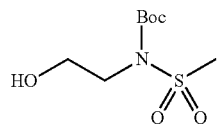

To a solution of N-(2-hydroxyethyl)methanesulfonamide (3.00 g, 21.6 mmol, 1.0 equiv) in dichloromethane (40.0 mL) was added $(Boc)_2O$ (5.17 g, 23.7 mmol, 5.45 mL, 1.1 equiv), TEA (3.27 g, 32.3 mmol, 4.50 mL, 1.5 equiv), and then DMAP (527 mg, 4.31 mmol, 0.2 equiv) at 0° C. The mixture and stirred at 0° C. for 1 hour. The mixture was filtered and concentrated under reduced pressure to provide the crude residue. The residue was purified by column chromatography ($SiO_2$, petroleum ether/ethyl acetate, 1:0 to 4:1) to afford tert-butyl (2-hydroxyethyl)(methylsulfonyl)carbamate (1.01 g, 20% yield) as a colorless oil. $R_f$=0.25 (dichloromethane/methanol, 1:1). $^1H$ NMR (400 MHz, $CDCl_3$): δ 4.27-4.16 (m, 2H), 3.48-3.38 (m, 2H), 3.00 (s, 3H), 1.50 (s, 9H).

Intermediate A-8

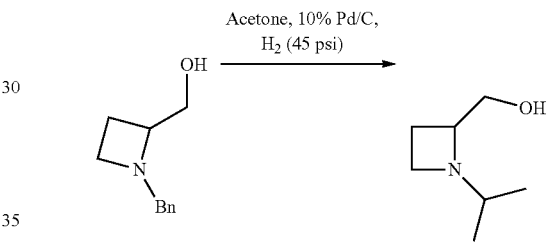

To a solution of (1-benzylazetidin-2-yl)methanol (1.50 g, 8.46 mmol, 1.0 equiv) and acetone (11.8 g, 204 mmol, 15.0 mL, 24 equiv) in MeOH (15 mL) was added Pd/C (1.60 g, 10% w/w) under $N_2$ atmosphere. The suspension was evacuated and purged with $H_2$ three times. The mixture was stirred under $H_2$ (45 psi) at 25° C. for 36 hours. The mixture was filtered and the filtered cake was washed with EtOH (10 mL) and THF (10 ml). The combined filtrate was concentrated under vacuum to dryness. The residue was purified by column chromatography ($Al_2O_3$, dichloromethane/methanol, 1:0 to 10:1) to afford (1-isopropylazetidin-2-yl)methanol (800 mg, 73% yield) as a white solid. $^1H$ NMR (400 MHz, $CDCl_3$): δ 3.67-3.57 (m, 1H), 3.50-3.33 (m, 3H), 2.92 (dt, J=7.6, 9.2 Hz, 1H), 2.54 (td, J=6.4, 12.8 Hz, 1H), 2.25-2.11 (m, 2H), 1.93 (dtd, J=3.2, 8.4, 10.8 Hz, 1H), 0.98 (d, J=6.4 Hz, 3H), 0.94 (d, J=6.4 Hz, 3H).

Intermediate A-9

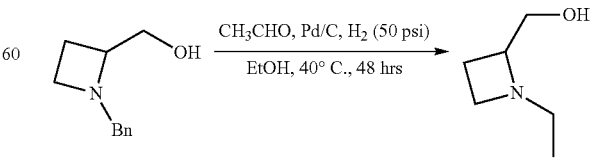

To a solution of (1-benzylazetidin-2-yl)methanol (2.00 g, 11.3 mmol, 1.0 equiv) and acetaldehyde (5 M, 9.03 mL, 4.0 equiv) in EtOH (20.0 mL) was added Pd/C (1.00 g, 10% wt/wt) under N₂ atmosphere. The suspension was evacuated and purged with H₂ several times. The mixture was stirred under H₂ at 40° C. for 48 hours. The mixture was filtered and the filtrate was concentrated under vacuum. The residue was purified by column chromatography (Al₂O₃, petroleum ether/ethyl acetate, 3:1 to 0:1) to afford (1-ethylazetidin-2-yl)methanol (330 mg, 25% yield) as a yellow oil. ¹H NMR (400 MHz, CDCl₃): δ 3.60 (dd, J=3.2, 11.6 Hz, 1H), 3.46-3.34 (m, 2H), 3.34-3.26 (m, 1H), 2.87-2.77 (m, 1H), 2.70-2.58 (m, 1H), 2.46-2.35 (m, 1H), 2.26-2.11 (m, 1H), 1.99-1.86 (m, 1H), 0.97 (t, J=7.2 Hz, 3H).

Intermediate A-10

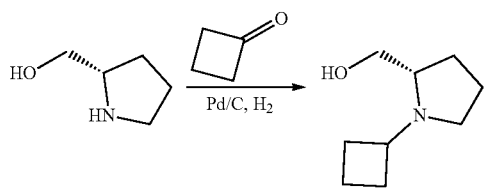

To a solution of (S)-pyrrolidin-2-ylmethanol (1.50 g, 14.8 mmol, 1.44 mL, 1.0 equiv) in methanol (50.0 mL) was added cyclobutanone (3.12 g, 44.5 mmol, 3.32 mL, 3.0 equiv) and Pd/C (150 mg, 10% wt/wt) under a nitrogen atmosphere. The suspension was evacuated under vacuum and purged with H₂ (15 psi) several times. The mixture was stirred under H₂ (15 psi) at 25° C. for 12 hours. The mixture was filtered and the filter cake was washed with methanol (40.0 mL). The filtrate was concentrated under reduced pressure to provide the crude residue. The residue was purified by column chromatography [SiO₂, petroleum ether/ethyl acetate, 0:1 to 5:1 to petroleum ether/ethyl acetate/ethanol (2% NH₄OH), 4:3:1] to afford (S)-(1-cyclobutylpyrrolidin-2-yl)methanol (890 mg, 38.7% yield) as a yellow oil. ¹H NMR (400 MHz, CDCl₃): δ 3.52 (dd, J=4.4, 10.4 Hz, 1H), 3.34 (dd, J=3.2, 10.4 Hz, 1H), 3.16-3.06 (m, 1H), 3.01-2.95 (m, 1H), 2.67 (dt, J=4.4, 8.8 Hz, 1H), 2.41-2.33 (m, 1H), 2.11-2.03 (m, 1H), 2.03-1.91 (m, 4H), 1.90-1.81 (m, 1H), 1.76-1.60 (m, 5H).

Intermediate A-11

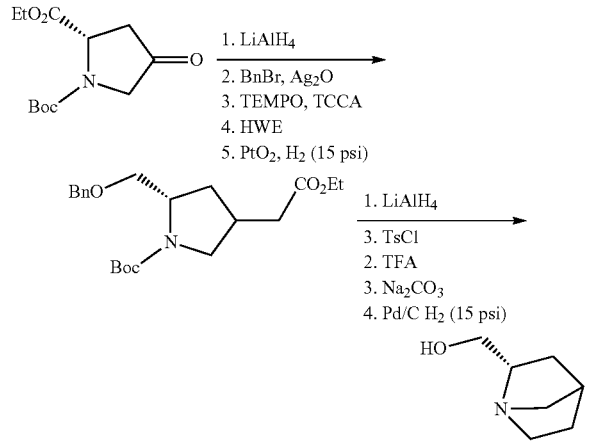

To a mixture of 1-(tert-butyl) 2-ethyl (S)-4-oxopyrrolidine-1,2-dicarboxylate (25.0 g, 103 mmol, 1.0 equiv) in THF (300 mL) at −40° C. was added LiAlH₄ (7.80 g, 205 mmol, 2.0 equiv). The mixture was stirred at this temperature for 30 min prior to the slow dropwise addition of water (7.8 mL), 15% aq NaOH (7.8 mL) and water (23.4 mL). The mixture was dried over anh sodium sulfate and filtered. The filtrate was concentrated under reduced pressure to afford tert-butyl (2S)-4-hydroxy-2-(hydroxymethyl)pyrrolidine-1-carboxylate (21.0 g, crude) as a yellow oil.

To a mixture of tert-butyl (2S)-4-hydroxy-2-(hydroxymethyl)pyrrolidine-1-carboxylate (30.0 g, 138 mmol, 1.0 equiv) and BnBr (26.0 g, 152 mmol, 18.0 mL, 1.1 equiv) in MeCN (500 mL) was added Ag₂O (96.0 g, 414 mmol, 3.0 equiv). The mixture was stirred at 85° C. for 12 h. Subsequently, the reaction mixture was filtered and concentrated under reduced pressure. The resultant residue was purified by column chromatography (SiO₂, petroleum ether/ethyl acetate, 30:1 to 1:1) to provide tert-butyl (2S)-2-((benzyloxy)methyl)-4-hydroxypyrrolidine-1-carboxylate (18.0 g, 42% yield) as a yellow oil.

To a mixture of tert-butyl (2S)-2-((benzyloxy)methyl)-4-hydroxypyrrolidine-1-carboxylate (17.0 g, 55.3 mmol, 1.0 equiv) in ethyl acetate (160 mL) at −5° C. was added trichloroisocyanuric acid (19.3 g, 83.0 mmol, 1.5 equiv) and TEMPO (13.0 g, 83.0 mmol, 1.5 equiv) in ethyl acetate (50 mL). The mixture was stirred at that temperature for 30 min and was then warmed to room temperature and stirred for 1 h. Subsequently, the mixture was diluted with satd aq NaS₂O₃ (100 mL) and extracted with ethyl acetate (100 mL×3). The combined organic layer was washed with brine (50 mL×1), dried over anh sodium sulfate and filtered. The filtrated was concentrated under reduced pressure to provide the crude residue. The residue was purified by reversed phase flash chromatography [water (0.1% FA)/acetonitrile] to afford tert-butyl (S)-2-((benzyloxy)methyl)-4-oxopyrrolidine-1-carboxylate (7.08 g, 37% yield) as a yellow oil. LCMS [ESI, M−99]: 206.

To a solution of ethyl 2-diethoxyphosphorylacetate (11.0 g, 49.1 mmol, 9.75 mL, 2.0 equiv) in THF (120 mL) at 0° C. was added NaH (1.18 g, 29.5 mmol, 60% purity, 1.2 equiv). The mixture was stirred at this temperature for 0.5 hour prior to the addition of tert-butyl (S)-2-((benzyloxy)methyl)-4-oxopyrrolidine-1-carboxylate (7.50 g, 24.6 mmol, 1.0 equiv) in THF (50 mL). The resulting mixture was allowed to warm to room temperature and was stirred for 30 min. The mixture was diluted with ice-cold water (50 mL) and then extracted with ethyl acetate (50 mL×3). The combined organic layer was washed with brine (30 mL), dried over anh sodium sulfate and filtered. The filtrate was concentrated under reduced pressure to provide the crude residue. The residue was purified by column chromatography (SiO₂, petroleum ether/ethyl acetate, 20:1 to 1:1) to afford tert-butyl (S)-2-((benzyloxy)methyl)-4-(2-ethoxy-2-oxoethylidene)pyrrolidine-1-carboxylate (7.50 g, 80% yield) as a yellow oil. LCMS [ESI, M−99]: 276.

A mixture of tert-butyl (S)-2-((benzyloxy)methyl)-4-(2-ethoxy-2-oxoethylidene)pyrrolidine-1-carboxylate (1.50 g, 4.00 mmol, 1.0 equiv), PtO₂ (907 mg, 4.00 mmol, 1.0 equiv) and Na₂CO₃ (423 mg, 4.00 mmol, 1.0 equiv) in THF (2.00 mL) and ethyl alcohol (2.00 mL) was purged with hydrogen gas and then was stirred at 25° C. for 3 h under H₂ (15 psi). The system was flushed with nitrogen and was filtered through a plug of Celite. The filtrate was concentrated under reduced pressure to provide the crude residue. The residue was purified by column chromatography (SiO₂, petroleum ether/ethyl acetate, 20:1 to 5:1) to afford tert-butyl (2S)-2-

((benzyloxy)methyl)-4-(2-ethoxy-2-oxoethyl)pyrrolidine-1-carboxylate (1.00 g, 60% yield) as a colorless oil. LCMS [ESI, M+1]: 378.

To a solution of tert-butyl (2S)-2-((benzyloxy)methyl)-4-(2-ethoxy-2-oxoethyl)pyrrolidine-1-carboxylate (1.50 g, 3.97 mmol, 1.0 equiv) in THF (20.0 mL) at −40° C. was added LiAlH$_4$ (452 mg, 11.9 mmol, 3.0 equiv) and the mixture was stirred at this temperature for 1 h. The mixture was cautiously diluted with H$_2$O (0.45 mL), 15% aq NaOH (0.45 mL), and H$_2$O (1.35 mL). The reaction mixture was filtered and concentrated under reduced pressure to dryness. The residue was purified by column chromatography (SiO$_2$, petroleum ether/ethyl acetate, 20:1 to 0:1) to afford tert-butyl (2S)-2-((benzyloxy)methyl)-4-(2-hydroxyethyl)pyrrolidine-1-carboxylate (1.00 g, 75% yield) as a colorless oil.

To a solution of tert-butyl (2S)-2-((benzyloxy)methyl)-4-(2-hydroxyethyl)pyrrolidine-1-carboxylate (1.00 g, 2.98 mmol, 1.0 equiv) in THF (10.0 mL) at 0° C. was added NaH (238 mg, 5.96 mmol, 60% purity, 2.0 equiv) and TsCl (1.14 g, 5.96 mmol, 2.0 equiv). The mixture was stirred at room temperature for 12 h prior to being diluted with H$_2$O (10 mL). The mixture was concentrated to give residue. The residue was diluted with H$_2$O (20 mL) and extracted with ethyl acetate (30 mL×3). The combined organic layer was washed with brine (30 mL), dried over anhydrous sodium sulfate and filtered. The filtrate was concentrated under reduced pressure to dryness. The residue was purified by column chromatography (SiO$_2$, petroleum ether/ethyl acetate, 50:1 to 0:1) to afford tert-butyl (2S)-2-((benzyloxy)methyl)-4-(2-(tosyloxy)ethyl)pyrrolidine-1-carboxylate (600 mg, 41% yield) as a colorless oil. LCMS [ESI, M−99]: 390.

A mixture of tert-butyl (2S)-2-((benzyloxy)methyl)-4-(2-(tosyloxy)ethyl)pyrrolidine-1-carboxylate (590 mg, 1.21 mmol, 1.0 equiv), TFA (1.65 g, 14.5 mmol, 1.07 mL, 12 equiv) in dichloromethane (5.0 mL) was stirred at 25° C. for 0.5 hour under a nitrogen atmosphere. Subsequently, the mixture was concentrated, diluted with saturated aq NaHCO$_3$ and extracted with ethyl acetate (5 mL×3). The combined organic layer was dried over anh Na$_2$SO$_4$ and filtered. The filtrate was concentrated under reduced pressure to afford 2-((5S)-5-((benzyloxy)methyl)pyrrolidin-3-yl)ethyl 4-methylbenzenesulfonate (600 mg, crude) as a colorless oil. LCMS [ESI, M+1]: 390.

To a solution of 2-((5S)-5-((benzyloxy)methyl)pyrrolidin-3-yl)ethyl 4-methylbenzenesulfonate (600 mg, 1.54 mmol, 1.0 equiv) in MeCN (30.0 mL) was added Na$_2$CO$_3$ (816 mg, 7.70 mmol, 5.0 equiv). The mixture was stirred at 25° C. for 1.0 h prior to being concentrated. The residue was diluted with saturated aq NaHCO$_3$ then extracted with ethyl acetate (50 mL×3). The combined organic layer was dried over anh Na$_2$SO$_4$ and filtered. The filtrate was concentrated under reduced pressure to provide the crude residue. The residue was purified by column chromatography [Al$_2$O$_3$, petroleum ether/ethyl acetate, 10:1 to ethyl acetate/ethanol (0.1% NH$_4$OH), 3:1] to provide (2S)-2-((benzyloxy)methyl)-1-azabicyclo[2.2.1]heptane (250 mg, 93% yield) as a yellow oil.

A mixture of (2S)-2-((benzyloxy)methyl)-1-azabicyclo[2.2.1]heptane (100 mg, 460 μmol, 1.0 equiv) and Pd/C (100 mg, 10 wt. %) in methyl alcohol (4.0 mL)/NH$_3$ (1.0 mL, 20% in MeOH) was purged with hydrogen (3×) and then was stirred at 25° C. for 8 h (15 psi H$_2$). The mixture was filtered and concentrated under reduced pressure to dryness. The residue was purified by column chromatography (Al$_2$O$_3$, petroleum ether/ethyl acetate, 10:1 to ethyl acetate/ethanol (0.1% NH$_4$.OH), 3:1) to afford ((2S)-1-azabicyclo[2.2.1]heptan-2-yl)methanol (50.0 mg, 85% yield) as a yellow oil.

Intermediate A-12

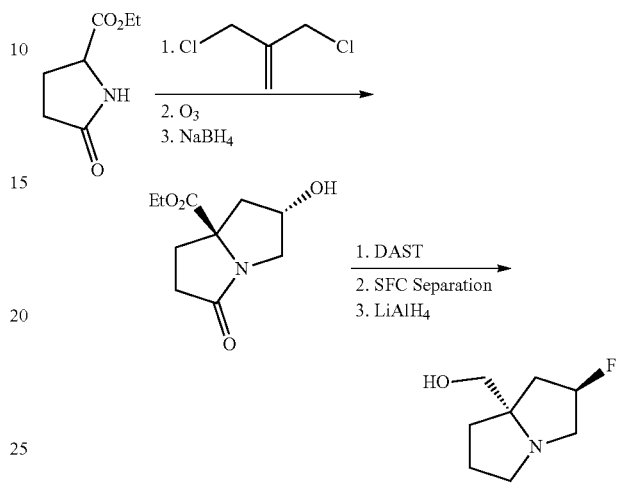

To a mixture of compound ethyl 5-oxopyrrolidine-2-carboxylate (1.50 kg, 9.54 mol, 1.00 equiv) and 3-chloro-2-(chloromethyl)prop-1-ene (1.91 kg, 15.3 mol, 1.77 L, 1.60 equiv) in THF (7.50 L) at −40° C. under nitrogen was added dropwise LiHMDS (1 M, 19.1 L, 2.00 equiv). The mixture was stirred at room temperature for 20 h. TLC (petroleum ether/ethyl acetate, 0:1) indicated compound 5-oxopyrrolidine-2-carboxylate was consumed (Rf=0.05) and three new major spots had formed (R$_f$=0.40, 0.35, 0.27). The reaction mixture was poured into aq HCl (1 M, 2.50 L) at 0° C. and the pH was adjusted to 7 with aq HCl (2 M). The resultant mixture was extracted with EtOAc (4.50 L×3). The combined organic layer was washed with brine (4.50 L), dried over anh Na$_2$SO$_4$, filtered and concentrated under reduced pressure to afford a residue. The residue was purified by column chromatography (SiO$_2$, petroleum ether/ethyl acetate, 10:1 to 1:1) to afford ethyl 2-methylene-5-oxotetrahydro-1H-pyrrolizine-7a(5H)-carboxylate (898 g, 4.29 mol, 45% yield, 82% purity) as a yellow oil. LCMS [ESI, M+1]: 210.1. $^1$H NMR (400 MHz, CDCl$_3$): δ 5.02-5.07 (m, 2H), 4.28 (d, J=15.6 Hz, 1H), 4.16-4.22 (m, 2H), 3.71 (dd, J=15.6, 1.6 Hz, 1H), 3.04 (d, J=15.6 Hz, 1H), 2.73-2.80 (m, 1H), 2.57-2.64 (m, 1H), 2.41-2.49 (m, 2H), 2.03-2.17 (m, 2H), 1.24-1.30 (m, 3H).

Ozone was bubbled through a mixture of ethyl 2-methylene-5-oxotetrahydro-1H-pyrrolizine-7a(5H)-carboxylate (165 g, 788 mmol, 1.00 equiv) in DCM (1650 mL) and MeOH (165 mL) at −70° C. After the solution became pale blue, excess O3 was purged with nitrogen for 30 min. The mixture was treated with Me$_2$S (80.4 g, 1.29 mol, 95.0 mL, 1.6 equiv) at −70° C. and was allowed to warm to room temperature and stir for 16 h. TLC (petroleum ether/ethyl acetate, 0:1) indicated the consumption of 2-methylene-5-oxotetrahydro-1H-pyrrolizine-7a(5H)-carboxylate (R$_f$=0.55) and the formation of one major spot (R$_f$=0.50). The reaction mixture was concentrated under reduced pressure to give a residue. From six identical reactions the combined residue was purified by column chromatography (SiO$_2$, petroleum ether/ethyl acetate, 10:1 to 1:1) to afford ethyl 2,5-dioxotetrahydro-1H-pyrrolizine-7a(5H)-carboxylate (821 g, 3.89 mol, 82% yield, 93% purity) as a yellow oil. LCMS [ESI, M+1]: 212.1. $^1$H NMR (400 MHz, CDCl$_3$): δ 4.23 (q, J=7.2 Hz, 2H), 4.12 (d, J=18.8 Hz, 1H), 3.56 (d, J=18.4 Hz, 1H), 2.96-3.01 (m, 2H), 2.77-2.86 (m, 1H), 2.43-2.50 (m, 2H), 2.14-2.22 (m, 1H), 1.28 (t, J=7.2 Hz, 1H).

To a solution of ethyl 2,5-dioxotetrahydro-1H-pyrrolizine-7a(5H)-carboxylate (257 g, 1.22 mol, 1.00 equiv) in EtOH (1300 mL) at 0° C. was added slowly NaBH$_4$ (13.8 g, 365 mmol, 0.30 equiv) under nitrogen. The mixture was stirred at 0° C. for 10 min. TLC (ethyl acetate) indicated the consumption of ethyl 2,5-dioxotetrahydro-1H-pyrrolizine-7a(5H)-carboxylate (R$_f$=0.55) and the formation of two major spots (R$_f$=0.30, 0.20). The reaction was diluted with satd aq NH$_4$Cl (65.0 mL) at 5° C. and stirred at that temperature for 30 min. The mixture was concentrated under reduced pressure to give a residue. The crude product from three identical reactions were combined. The combined crude material was purified by column chromatography (SiO$_2$, petroleum ether/ethyl acetate, 10:1 to 1:1) to afford rac-ethyl (2S,7aR)-2-hydroxy-5-oxotetrahydro-1H-pyrrolizine-7a(5H)-carboxylate (450 g, 2.11 mol, 57% yield) as a yellow oil. $^1$H NMR (400 MHz, CDCl$_3$): δ 4.65 (s, 1H), 4.14 (q, J=7.2 Hz, 2H), 3.95 (dd, J=12.8, 6.0 Hz, 1H), 3.10 (d, J=12.8 Hz, 1H), 2.75-2.84 (m, 2H), 2.49-2.49 (m, 2H), 2.39-2.45 (m, 1H), 2.02-2.10 (m, 1H), 1.84 (dd, J=13.6, 6.0 Hz, 1H), 1.30 (t, J=7.2 Hz, 1H).

To a solution of rac-ethyl (2S,7aR)-2-hydroxy-5-oxotetrahydro-1H-pyrrolizine-7a(5H)-carboxylate (100 g, 469 mmol, 1.00 equiv) in DCM (500 mL) −70° C. was added dropwise a solution of DAST (113 g, 703 mmol, 82.9 mL, 1.50 equiv) under nitrogen. The reaction mixture was warmed to 25° C. and stirred for 16 h. TLC (petroleum ether/ethyl acetate, 1:1) indicated the consumption of the starting material and the formation of one spot (R$_f$=0.30). The reaction mixture was cooled to 10° C. and was diluted with MeOH (25.0 mL), water (1000 mL) and extracted with DCM (500 mL×3). The combined organic layer was washed with brine (500 mL), dried over anh Na$_2$SO$_4$, filtered and concentrated under reduced pressure to give a residue. The residue was purified by column chromatography (SiO$_2$, petroleum ether/ethyl acetate, 1:0 to 0:1) to afford rac-ethyl (2S,7aR)-2-fluoro-5-oxotetrahydro-1H-pyrrolizine-7a(5H)-carboxylate (55.0 g, 251 mmol, 49% yield) as a yellow oil. LCMS [ESI, M+1]: 216.0. $^1$H NMR (400 MHz, CDCl$_3$): δ 5.30 (dt, J=52.4, 4.0 Hz, 1H), 4.17-4.25 (m, 3H), 3.11-3.24 (m, 1H), 2.59-2.83 (m, 3H), 2.41-2.47 (m, 1H), 2.09-2.30 (m, 2H), 1.29 (t, J=7.2 Hz, 1H).

The rac-ethyl (2S,7aR)-2-fluoro-5-oxotetrahydro-1H-pyrrolizine-7a(5H)-carboxylate (30.0 g, 139 mmol) was first purified by prep-HPLC [Welch Ultimate XB-NH$_2$ 250 mm×50 mm×10 μm; heptane-EtOH (0.1% NH$_4$OH); B %: 10%, 10 min). The mixture was concentrated under reduced pressure to give a residue (28.0 g, 130 mmol). The residue was purified by prep-SFC (DAICEL CHIRALPAK IC 250 mm×50 mm×10 μm; 0.1% NH$_4$OH in IPA; CO$_2$%: 40%, 4.7 min; desired product: peak 2, Rt=1.959 min). The fractions were concentrated under reduced pressure to afford ethyl (2S,7aR)-2-fluoro-5-oxotetrahydro-1H-pyrrolizine-7a(5H)-carboxylate (12.0 g, 55.4 mmol, 40% yield, 99% purity, ee>99%) as a yellow oil.

To a suspension of LiAlH$_4$ (4.81 g, 127 mmol, 1.50 equiv) in THF (90.0 mL) at 0° C. under nitrogen was added dropwise a solution of ethyl (2S,7aR)-2-fluoro-5-oxotetrahydro-1H-pyrrolizine-7a(5H)-carboxylate (18.2 g, 85.6 mmol, 1.00 equiv) in THF (55.0 mL). The reaction mixture was heated at 70° C. for 3 h at which time TLC analysis (petroleum ether/ether, 1:1) indicated the consumption of starting material (R$_f$=0.30) and the formation of one new spot (R$_f$=0.01). The mixture was cooled to 0° C. and was slowly diluted with water (5.00 mL), 15% aq NaOH (15.0 mL) and water (15.0 mL). The mixture was stirred at 0° C. for 5 min and was filtered. The filter cake was washed with EtOAc (80.0 mL×4) and the filtrate was dried over anh MgSO$_4$, filtered and concentrated under reduced pressure to give a residue. The residue was purified by column chromatography (SiO$_2$, dichloromethane/methanol, 100:1 to 10:1) to afford ((2R,7aS)-2-fluorotetrahydro-1H-pyrrolizin-7a(5H)-yl)methanol (10.8 g, 67.3 mmol, 99%, purity, 80.0% yield) as a yellow oil. $^1$H NMR (400 MHz, CDCl$_3$): δ 5.13-5.28 (m, 1H), 3.26 (s, 2H), 3.13-3.19 (m, 2H), 2.91-3.10 (m, 2H), 2.02-2.12 (m, 2H), 1.76-1.94 (m, 4H).

In addition to the foregoing Intermediates 1-61 and A-12 above, the following exemplary Intermediates B-1-B33 may be used to couple —Y—R$^2$ to the azaquinazoline core of Formula (I).

Intermediate B-1

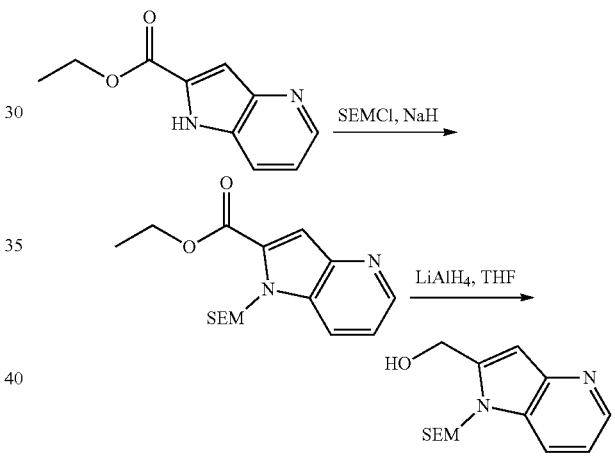

To a mixture of ethyl 1H-pyrrolo[3,2-b]pyridine-2-carboxylate (1.9 g, 9.99 mmol, 1.0 equiv) in DMF (20 mL) was added NaH (599 mg, 15.0 mmol, 60% purity, 1.5 equiv) at 0° C. The mixture was stirred at 15° C. for 30 min prior to the addition of SEMCl (2.50 g, 15.0 mmol, 2.65 mL, 1.5 eq). The mixture was stirred at 15° C. for an additional 30 min and was diluted with saturated aq NH$_4$Cl (30 mL) and extracted with ethyl acetate (3×30 mL). The combined organic layer was washed with brine (80 mL), dried over anh Na$_2$SO$_4$, filtered and concentrated under reduced pressure to give a residue. The residue was purified by column chromatography (SiO$_2$, petroleum ether/ethyl acetate, 20:1 to 5:1) to afford ethyl 1-((2-(trimethylsilyl)ethoxy)methyl)-1H-pyrrolo[3,2-b]pyridine-2-carboxylate (2 g, 6.05 mmol, 60% yield) as a colorless oil. $^1$H NMR (400 MHz, CDCl$_3$): δ 8.58 (dd, J=1.6, 4.4 Hz, 1H), 7.90-7.85 (m, 1H), 7.47 (d, J=0.8 Hz, 1H), 7.25 (dd, J=4.8, 8.4 Hz, 1H), 6.01 (s, 2H), 4.40 (q, J=7.2 Hz, 2H), 3.54-3.48 (m, 2H), 1.42 (t, J=7.2 Hz, 3H), 0.88-0.81 (m, 2H), −0.093 (s, 9H).

To a solution of 1-((2-(trimethylsilyl)ethoxy)methyl)-1H-pyrrolo[3,2-b]pyridine-2-carboxylate (1.9 g, 5.93 mmol, 1.0 equiv) in THF (20 mL) was added LiAlH$_4$ (450 mg, 11.9 mmol, 2.0 equiv) at −10° C. The mixture was stirred at −10°

C. for 30 min prior to the addition of satd aq Na₂SO₄ (6 mL) at 0° C. The suspension was filtered and the filtrate was concentrated to afford (1-((2-(trimethylsilyl)ethoxy)methyl)-1H-pyrrolo[3,2-b]pyridin-2-yl)methanol (1.5 g, 91% yield) as a colorless oil. LCMS [ESI, M+1]: 279.

Intermediate B-2

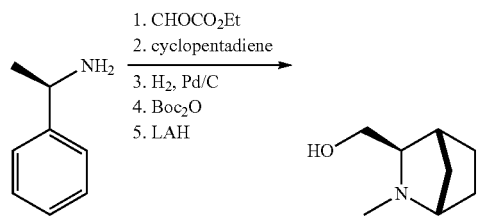

To a solution of (R)-1-phenylethan-1-amine (10 g, 82.5 mmol, 1 equiv) in toluene (120 mL) was added ethyl 2-oxoacetate (13.5 g, 66.0 mmol, 0.8 equiv). The mixture was stirred at 25° C. for 1 hour and was concentrated under reduced pressure to provide ethyl (R,E)-2-((1-phenylethyl)imino)acetate (20 g, crude) as a yellow oil.

To a solution of ethyl (R,E)-2-((1-phenylethyl)imino)acetate (20 g, 97.4 mmol, 1.0 equiv) in DMF (200 mL) was added freshly cracked cyclopenta-1,3-diene (13.5 g, 205 mmol, 2.1 equiv) and TFA (14.4 g, 127 mmol, 9.38 mL, 1.3 equiv). The mixture was stirred at 25° C. for 12 h and was diluted with satd aq NaHCO₃ (200 mL). The aqueous layer was extracted with ethyl acetate (50 mL×3). The combined organic layer was washed with brine (50 mL×3), dried over anh sodium sulfate and filtered. The filtrate was concentrated under reduced pressure to provide the crude residue. The residue was purified by column chromatography (SiO₂, petroleum ether/ethyl acetate, 100:1 to 3:1) to afford ethyl (1R,3R,4S)-2-((R)-1-phenylethyl)-2-azabicyclo[2.2.1]hept-5-ene-3-carboxylate (8.5 g, 32% yield) as a colorless oil. ¹H NMR (400 MHz, CDCl₃): δ 7.39-7.23 (m, 5H), 6.49-6.38 (m, 1H), 6.35-6.16 (m, 1H), 4.34-4.28 (m, 1H), 3.92-3.71 (m, 2H), 3.12-3.00 (m, 1H), 2.96-2.84 (m, 1H), 2.22 (s, 1H), 2.18-2.10 (m, 1H), 1.47-1.39 (m, 4H), 0.97 (t, J=6.8 Hz, 3H).

To a solution of ethyl (1R,3R,4S)-2-((R)-1-phenylethyl)-2-azabicyclo[2.2.1]hept-5-ene-3-carboxylate (1.80 g, 6.63 mmol, 1 eq) in EtOH (50 mL) was added Pd/C (300 mg, 10% wt/wt) under N₂. The suspension was evacuated under vacuum and purged with H₂ several times. The mixture was stirred under H₂ (15 psi) at 25° C. for 1 hour. The reaction mixture was filtered and concentrated under reduced pressure to afford ethyl (1S,3R,4R)-2-azabicyclo[2.2.1]heptane-3-carboxylate (1.1 g, crude) as a yellow oil which was used in next step without any purification.

To a solution of ethyl (1S,3R,4R)-2-azabicyclo[2.2.1]heptane-3-carboxylate (1.10 g, 6.50 mmol, 1.0 equiv) in DCM (15 mL) was added (Boc)₂O (2.84 g, 13.0 mmol, 2 equiv) and TEA (3.29 g, 32.5 mmol, 5 equiv). The mixture was stirred at 25° C. for 1 hour. Subsequently, the reaction mixture was diluted with water (30 mL) and extracted with ethyl acetate (30 mL×3). The combined organic layers were washed with brine (30 mL), dried over anh sodium sulfate, filtered and concentrated under reduced pressure. The resultant residue was purified by column chromatography (SiO₂, petroleum ether/ethyl acetate, 100:1 to 3:1) to afford 2-(tert-butyl) 3-ethyl (1S,3R,4R)-2-azabicyclo[2.2.1]heptane-2,3-dicarboxylate (960 mg, 50% yield) as a yellow oil. ¹H NMR (400 MHz, CDCl₃): δ 4.22 (s, 1H), 4.21-4.09 (m, 2H), 3.85-3.64 (m, 1H), 2.71-2.62 (m, 1H), 1.97-1.88 (m, 1H), 1.79-1.72 (m, 1H), 1.69-1.58 (m, 2H), 1.49-1.38 (m, 10H), 1.28-1.26 (m, 4H).

To a solution of 2-(tert-butyl) 3-ethyl (1S,3R,4R)-2-azabicyclo[2.2.1]heptane-2,3-dicarboxylate (2 g, 7.43 mmol, 1 equiv) in THF (5 mL) was added LiAlH₄ (845 mg, 22.3 mmol, 3 equiv) at −20° C. and the mixture was stirred at this temperature for 1 h. Subsequently, the reaction mixture was diluted with H₂O (0.85 mL), 15% NaOH (2.55 mL), and H₂O (2 mL). The suspension was filtered and the filtrate was concentrated in vacuum to afford ((1S,3R,4R)-2-methyl-2-azabicyclo[2.2.1]heptan-3-yl)methanol (1.1 g, crude) as a light yellow oil. ¹H NMR (400 MHz, CDCl₃): δ 4.15-4.08 (m, 1H), 3.59-3.46 (m, 2H), 2.37-2.27 (m, 1H), 1.76-1.70 (m, 2H), 1.63-1.57 (m, 3H), 1.48 (s, 9H), 1.29-1.24 (m, 2H).

Intermediate B-3

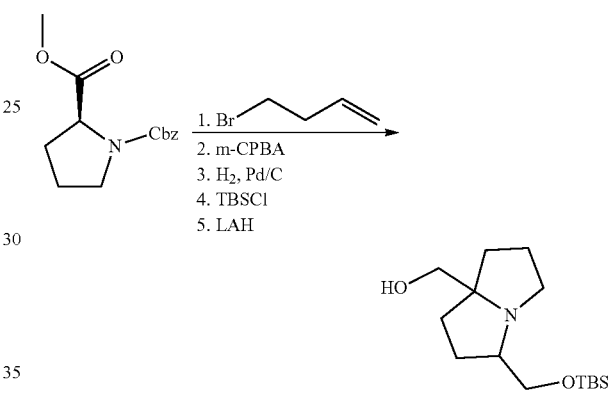

To a solution of 1-benzyl 2-methyl (S)-pyrrolidine-1,2-dicarboxylate (5.00 g, 19.0 mmol, 1.0 equiv) in THF (10.0 mL) was added dropwise a solution of LiHMDS (1 M, 22.8 mL, 1.2 equiv) at −78° C. The mixture was allowed to stir at this temperature for 1 h prior to the addition of 4-bromobut-1-ene (5.13 g, 38.0 mmol, 3.86 mL, 2.0 equiv). The mixture was stirred at 25° C. for 12 hours. The mixture was quenched by addition of saturated aq NH₄Cl (25.0 mL and was extracted with ethyl acetate (3×50 mL). The combined organic layer was washed with saturated brine (2×25 mL), dried over anhydrous sodium sulfate and filtered. The filtrate was concentrated under reduced pressure to provide the crude material. The residue was purified by column chromatography (SiO₂, petroleum ether/ethyl acetate, 10:1 to ethyl acetate/methanol, 5:1) to afford 1-benzyl 2-methyl 2-(but-3-en-1-yl)pyrrolidine-1,2-dicarboxylate (3.75 g, 62% yield) as a colorless oil.

To a solution of 1-benzyl 2-methyl 2-(but-3-en-1-yl) pyrrolidine-1,2-dicarboxylate (3.75 g, 11.8 mmol, 1.0 equiv) in dichloromethane (50.0 mL) was added m-CPBA (6.37 g, 29.5 mmol, 80% purity, 2.5 equiv). The mixture was stirred at 25° C. for 5 hours. Subsequently, the mixture was quenched by the addition of saturated aq NaS₂O₃ (35.0 mL). The aqueous layer was extracted with dichloromethane (3×65 mL). The combined organic layer was washed with brine (2×30 mL), dried over anhydrous sodium sulfate and filtered. The filtrate was concentrated under reduced pressure to provide the crude residue. The residue was purified by column chromatography (SiO₂, petroleum ether/ethyl acetate, 10:1 to ethyl acetate/methanol, 3:1) to afford 1-benzyl 2-methyl 2-(2-(oxiran-2-yl)ethyl)pyrrolidine-1,2-dicarboxylate (3.15 g, 80% yield) as a colorless oil. ¹H NMR (400 MHz, CDCl₃): δ 7.40-7.29 (m, 5H), 5.17-5.04 (m, 2H), 3.70 (d, J=4.0 Hz, 3H), 3.52-3.46 (m, 2H), 2.97-2.66 (m, 2H), 2.50-2.21 (m, 2H), 2.18-1.78 (m, 5H), 1.71-1.40 (m, 2H).

To a solution of 1-benzyl 2-methyl 2-(2-(oxiran-2-yl)ethyl)pyrrolidine-1,2-dicarboxylate (3.10 g, 9.30 mmol, 1.0 equiv) in methanol (1.0 mL) was added Pd/C (0.31 g, 9.30 mmol, 10% wt/wt) under a nitrogen atmosphere. The suspension was evacuated under vacuum and purged with H₂ several times. The mixture was stirred at 25° C. under H₂ (15 psi) for 4 hours. After completion, the mixture was filtered. The filtrate was concentrated under reduced pressure to afford methyl 3-(hydroxymethyl)tetrahydro-1H-pyrrolizine-7a(5H)-carboxylate (1.90 g, crude) as a colorless oil.

To a solution of methyl 3-(hydroxymethyl)tetrahydro-1H-pyrrolizine-7a(5H)-carboxylate (1.85 g, 9.28 mmol, 1.0 equiv) in dichloromethane (20.0 mL) was added TBSCl (2.10 g, 13.9 mmol, 1.71 mL, 1.5 equiv) and imidazole (1.90 g, 27.9 mmol, 3.0 equiv). The mixture was stirred at 25° C. for 1 hour and was poured into ice-water (20.0 mL) and stirred for 5 min. The dichloromethane layer was separated and the aqueous phase was extracted with ethyl acetate (3×35 mL). The combined organic phase was washed with saturated brine (2×20 mL), dried over anhydrous sodium sulfate and filtered. The filtrate was concentrated under reduced pressure to provide the crude residue. The residue was purified by silica gel chromatography (petroleum ether/ethyl acetate, 100:1 to 8:1) to afford methyl 3-(((tert-butyldimethylsilyl)oxy)methyl)tetrahydro-1H-pyrrolizine-7a(5H)-carboxylate (750 mg, 26% yield) as a colorless oil. ¹H NMR (400 MHz, CDCl₃): δ 3.89 (dd, J=4.4, 10.4 Hz, 1H), 3.78 (dd, J=6.0, 10.4 Hz, 1H), 3.74-3.67 (m, 3H), 3.36-3.25 (m, 1H), 2.95 (td, J=4.4, 9.2 Hz, 1H), 2.83 (q, J=8.4 Hz, 1H), 2.51-2.40 (m, 1H), 2.25-2.13 (m, 1H), 1.94-1.86 (m, 1H), 1.84-1.78 (m, 3H), 1.75-1.67 (m, 1H), 1.65-1.56 (m, 1H), 0.90 (s, 9H), 0.13-0.01 (s, 6H).

To a mixture of LiAlH₄ (484 mg, 12.8 mmol, 2.0 equiv) in THF (20.0 mL) was added 3-(((tert-butyldimethylsilyl)oxy)methyl)tetrahydro-1H-pyrrolizine-7a(5H)-carboxylate (2.00 g, 6.38 mmol, 1.0 equiv) at −20° C. The mixture was stirred at this temperature for 1 h. Subsequently, the reaction mixture was quenched with water (0.5 mL), 15% NaOH (0.5 mL) and water (1.5 mL) at 0° C. The resultant suspension was filtered and the filter cake was washed with THF (50 mL). The filter cake was dispersed in THF (30 mL) and stirred at 25° C. for 5 minutes prior to filtration. The combined filtrate was concentrated under reduced pressure to provide the crude material. The residue was diluted with ethyl acetate and dried over anhydrous sodium sulfate and filtered. The filtrate was concentrated under reduced pressure to afford (3-(((tert-butyldimethylsilyl)oxy)methyl)tetrahydro-1H-pyrrolizin-7a(5H)-yl)methanol (1.70 g, 93% yield) as a yellow oil. ¹H NMR (400 MHz, CDCl₃): δ 3.85 (dd, J=6.0, 10.4 Hz, 1H), 3.72 (dd, J=6.0, 10.4 Hz, 1H), 3.38-3.21 (m, 2H), 3.18-3.05 (m, 1H), 2.85 (ddd, J=2.4, 6.0, 8.8 Hz, 1H), 2.72 (dt, J=6.4, 9.6 Hz, 1H), 1.97 (ddd, J=2.8, 7.2, 12.4 Hz, 1H), 1.83-1.46 (m, 7H), 0.90 (s, 9H), 0.07 (s, 6H). LCMS [ELSD, M+1]: 286.

Intermediate B-4

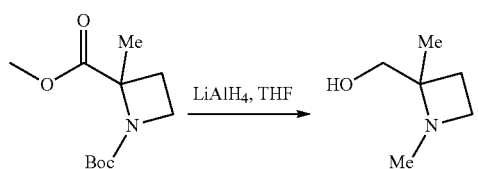 [SMILES: COC(=O)C1(C)CCN1C(=O)OC(C)(C)C ; CN1CCC1(C)CO]

To a solution of 1-(tert-butyl)-2-methyl 2-methylazetidine-1,2-dicarboxylate (300 mg, 1.31 mmol, 1.0 equiv) in THF (4 mL) was added LiAlH₄ (124 mg, 3.27 mmol, 2.50 equiv) at −40° C. The mixture was stirred at this temperature for 1 h and was then heated to 70° C. and stirred for an additional hour. The mixture was cooled to room temperature and quenched with saturated aq Na₂SO₄ (0.1 mL). The suspension was filtered and the filter cake was washed with dichloromethane (3×5 mL). The mixture was adjusted to pH ~3 with 4 M HCl•dioxane and concentrated to afford (1,2-dimethylazetidin-2-yl)methanol (200 mg, crude HCl salt) as a yellow oil. ¹H NMR (400 MHz, CD₃OD): δ 3.88-3.80 (m, 2H), 3.69-3.64 (m, 1H), 3.62-3.56 (m, 1H), 2.72 (s, 3H), 2.71-2.60 (m, 1H), 2.19-2.10 (m, 1H), 1.57 (s, 3H).

Intermediate B-5

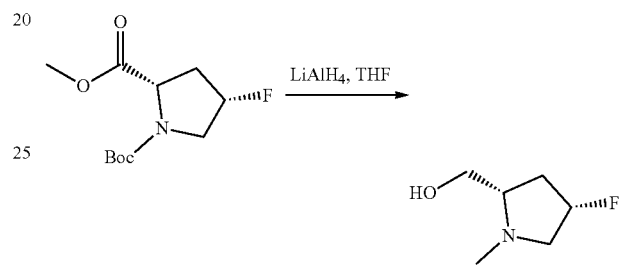

To a solution of 1-(tert-butyl)-2-methyl-(2S,4S)-4-fluoropyrrolidine-1,2-dicarboxylate (5.00 g, 20.2 mmol, 1.0 equiv) in THF (10.0 mL) was added LiAlH₄ (2.30 g, 60.7 mmol, 3.0 equiv) portionwise at 0° C. The mixture was stirred at this temperature for 1 h and then at 65° C. for 30 min. The mixture was cooled to room temperature and quenched with H₂O (2.30 mL), 15% of aq. NaOH (2.30 mL) and H₂O (5.00 mL). The suspension was filtered and the filtrate was concentrated under reduced pressure to afford ((2S,4S)-4-fluoro-1-methylpyrrolidin-2-yl)methanol (2.30 g, crude) as a light yellow oil. ¹H NMR (400 MHz, CDCl₃): δ 5.22-4.93 (m, 1H) 3.73 (dd, J=11.2, 3.2 Hz, 1H) 3.47 (br d, J=11.2 Hz, 1H) 3.33 (br dd, J=18.0, 11.2 Hz, 1H) 2.52-2.06 (m, 8H).

Intermediate B-6

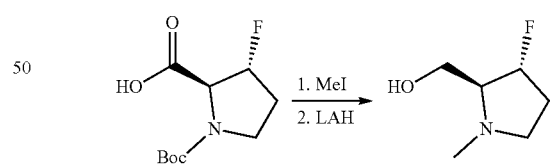

To a solution of (2S,3R)-1-(tert-butoxycarbonyl)-3-fluoropyrrolidine-2-carboxylic acid (400 mg, 1.72 mmol, 1.0 equiv) in DMF (4.0 mL) was added K₂CO₃ (355 mg, 2.57 mmol, 1.5 equiv) and MeI (1.46 g, 10.3 mmol, 641 μL, 6.0 equiv). The mixture was stirred at 25° C. for 1 hour and was then diluted with saturated aq NH₄Cl (10.0 mL) at 0° C. The aqueous layer was extracted with ethyl acetate (15 mL). The organic layer was washed with brine (3×15 mL), dried over anhydrous sodium sulfate and filtered. The filtrate was concentrated under reduced pressure to afford 1-(tert-butyl) 2-methyl (2S,3R)-3-fluoropyrrolidine-1,2-dicarboxylate (420 mg, crude) as a yellow oil. R_f=0.80 (petroleum ether/ethyl acetate, 1:1). ¹H NMR (400 MHz, CDCl₃): δ 5.28-5.07

(m, 1H), 4.66-4.40 (m, 1H), 3.77 (s, 3H), 3.75-3.65 (m, 1H), 3.62-3.50 (m, 1H), 2.29-2.00 (m, 2H), 1.49-1.42 (m, 9H).

To a mixture of LiAlH₄ (193 mg, 5.10 mmol, 3.0 eq) in THF (4.0 mL) was added 1-(tert-butyl) 2-methyl (2S,3R)-3-fluoropyrrolidine-1,2-dicarboxylate (420 mg, 1.70 mmol, 1.0 equiv) in THF (4.0 mL) at −20° C. The mixture was stirred at this temperature for 30 min and was then stirred at 66° C. for an additional hour. The mixture was cooled to 0° C. and was quenched with water (0.1 mL), 15% aq NaOH (0.1 mL) and water (0.3 mL). The suspension was filtered and the filter cake was dispersed in THF (15 mL) and stirred at 25° C. for 5 minutes prior to filtration. The combined filtrate was dried over anhydrous sodium sulfate and filtered. The filtrate was concentrated under reduced pressure to afford ((2S,3R)-3-fluoro-1-methylpyrrolidin-2-yl)methanol (200 mg, crude) as a yellow oil. R$_f$=0.50 (dichloromethane/methanol, 5:1). ¹H NMR (400 MHz, CDCl₃): δ 5.15-5.06 (m, 1H), 3.91-3.75 (m, 2H), 3.10-3.06 (m, 1H), 3.03-2.79 (m, 2H), 2.42 (s, 3H), 1.70 (td, J=2.8, 6.0 Hz, 2H).

Intermediate B-7

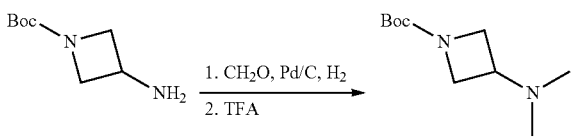

To a solution of tert-butyl 3-aminoazetidine-1-carboxylate (5.00 g, 29.0 mmol, 1.0 equiv) in MeOH (100 mL) was added Pd/C (5.00 g, 10% wt/wt) and formaline (109 g, 1.34 mol, 100 mL, 37% in water, 46.2 equiv). The mixture was stirred at 20° C. for 18 h under H₂ (15 psi). The mixture was filtered and the filter cake was washed with MeOH (3×50.0 mL). The filtrate was concentrated under vacuum to provide the crude material. The crude product was purified by column chouromatography (SiO₂, petroleum ether/ethyl acetate, 10:1 to 0:1) to afford tert-butyl 3-(dimethylamino)azetidine-1-carboxylate (6.00 g, 83% yield) as a colorless oil. ¹H NMR (400 MHz, DMSO-d₆): δ 3.83-3.78 (m, 2H), 3.62-3.59 (m, 2H), 3.00-2.87 (m, 1H), 2.04 (s, 6H), 1.37 (s, 9H). To a solution of tert-butyl 3-(dimethylamino)azetidine-1-carboxylate (2.00 g, 9.99 mmol, 1.0 equiv) in DCM (18.0 mL) at 0° C. was added TFA (6.00 mL). The mixture was stirred at room temperature for 2 h and was concentrated under reduced pressure and lyophilized to afford N,N-dimethylazetidin-3-amine (3.50 g, 96% yield, bis-TFA salt) as a yellow solid. ¹H NMR (400 MHz, D₂O): δ 4.50-4.41 (m, 5H), 2.84 (s, 6H).

Intermediate B-8

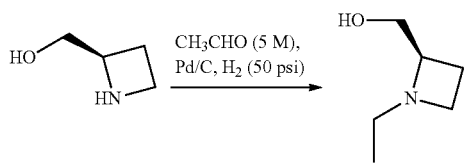

To a solution of (R)-azetidin-2-ylmethanol (1.32 g, 10.7 mmol, 1.0 equiv, HCl salt) and acetaldehyde (5 M in THF, 8.55 mL, 4.0 equiv) in EtOH (20.0 mL) was added Pd/C (0.500 g, 10% wt/wt) under a N₂ atmosphere. The suspension was evacuated and purged with H₂ several times. The mixture was stirred under H₂ at 50° C. for 36 h. Subsequently, the mixture was filtered and the filtrated was concentrated under vacuum to afford (R)-(1-ethylazetidin-2-yl)methanol (1.00 g, crude, HCl salt) as a brown oil. The same procedure was used for (S)-(1-ethylazetidin-2-yl)methanol.

Intermediate B-9

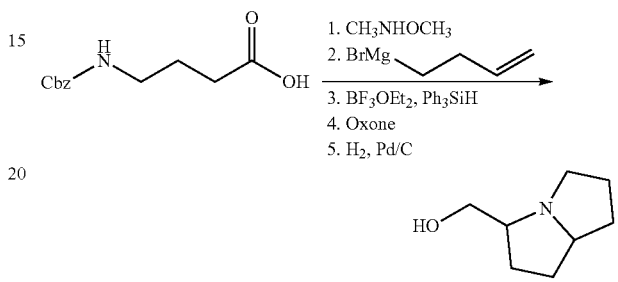

An oven-dried three-necked flask equipped with a reflux condenser was charged with Mg (584 mg, 24.0 mmol, 1.20 equiv) and I2 (507 mg, 2.00 mmol, 0.1 equiv) was heated with a heat gun until the iodine vapors were evenly distributed inside the flask. A solution of homoallyl bromide (2.70 g, 20.0 mmol, 2.03 mL, 1 equiv) in THF (20 mL) was added portionwise until gentle refluxing had initiated. The solution was then added dropwise over the course of 30 minutes maintaining a constant reflux. The dark reaction mixture was subsequently cooled to room temperature was used without filtration.

To a solution of 4-(((benzyloxy)carbonyl)amino)butanoic acid (5.00 g, 21.1 mmol, 1 equiv) in DCM (150 mL) at 0° C. was added TEA (6.40 g, 63.2 mmol, 8.80 mL, 3.0 equiv) followed by T3P (16.1 g, 25.3 mmol, 15.0 mL, 50% in EtOAc, 1.2 equiv) and N-methoxymethanamine (3.08 g, 31.6 mmol, 1.5 equiv, HCl salt), the mixture was stirred at 25° C. for 16 hours. The mixture was extracted with DCM (3×100 mL) and concentrated in vacuo. The residue was purified by column chromatography (SiO₂, petroleum ether/ethyl acetate, 1:0 to 1:1) to afford benzyl (4-(methoxy(methyl)amino)-4-oxobutyl)carbamate (5.50 g, 19.6 mmol, 93% yield) as a yellow oil. ¹H NMR (400 MHz, CDCl₃): δ 7.33-7.23 (m, 5H), 5.04-4.98 (m, 3H), 3.58 (s, 3H), 3.18 (q, J=6.4 Hz, 2H), 3.09 (s, 3H), 2.41 (br t, J=6.8 Hz, 2H), 1.82-1.73 (m, 2H). LCMS [ESI, M+1]: 281.2.

To a solution of benzyl (4-(methoxy(methyl)amino)-4-oxobutyl)carbamate (2.00 g, 7.13 mmol, 1.0 equiv) in THF (10 mL) at 0° C. was added the Grignard reagent (0.500 M in THF, 42.8 mL, 3.0 equiv) under N₂. The mixture was stirred at 25° C. for 1 h and then the pH was adjusted to 3-4 with 1M aq HCl. The mixture was extracted with ethyl acetate (5×50 mL). The combined organic layer was washed with satd aq NaHCO₃, brine (50 mL), dried over anh Na₂SO₄, filtered and concentrated under the reduced pressure to give the crude residue. The residue was purified by column chromatography (SiO₂, petroleum ether/ethyl acetate, 10:1 to 5:1) to afford benzyl (4-oxooct-7-en-1-yl)carbamate (1.50 g, 5.45 mmol, 38% yield) as a yellow oil. ¹H NMR (400 MHz, CDCl₃): δ 7.36-7.22 (m, 5H), 5.75-5.65

(m, 1H), 5.12-4.69 (m, 5H), 3.10 (q, J=6.4 Hz, 2H), 2.43-2.32 (m, 4H), 2.22 (q, J=6.80 Hz, 2H), 1.75-1.62 (m, 2H). LCMS [ESI, M+1]: 276.1.

To a solution of triphenylsilane (2.38 g, 9.15 mmol, 1.8 equiv) in DCM (10 mL) at 20° C. was added $BF_3.Et_2O$ (2.64 g, 18.6 mmol, 2.30 mL, 3.66 equiv). The mixture was stirred for 10 min prior to cooling to −78° C. followed by the addition of a solution of benzyl (4-oxooct-7-en-1-yl)carbamate (1.40 g, 5.08 mmol, 1 equiv) in DCM (10 mL). The mixture was stirred for 30 min at this temperature and then allowed to warm to 20° C. with continued stirring for 2 h. The mixture was diluted with satd aq $NaHCO_3$ and extracted with ethyl acetate (3×50 mL). The combined organic layer was washed with brine (50 mL), dried over anh $Na_2SO_4$, filtered and concentrated under the reduced pressure to give a residue. The residue was purified by column chromatography ($SiO_2$, petroleum ether/ethyl acetate, 30:1 to 3:1) to afford benzyl 2-(but-3-en-1-yl)pyrrolidine-1-carboxylate (1.10 g, 4.24 mmol, 83% yield) as a colorless oil. $^1H$ NMR (400 MHz, $CDCl_3$): δ 7.41-7.22 (m, 5H), 5.85-5.59 (m, 1H), 5.12-4.82 (m, 4H), 3.79 (br s, 1H), 3.46-3.27 (m, 2H), 2.03-1.95 (m, 1H), 1.89-1.71 (m, 4H), 1.62-1.57 (m, 1H), 1.39-1.28 (m, 1H), 1.25-1.15 (m, 1H).

To a mixture of benzyl 2-(but-3-en-1-yl)pyrrolidine-1-carboxylate (1.00 g, 3.86 mmol, 1 equiv), $NaHCO_3$ (2.59 g, 30.9 mmol, 8.0 equiv) in acetone (25 mL) and $H_2O$ (25 mL) at 0° C. was added dropwise a solution of Oxone (11.9 g, 19.3 mmol, 5.0 equiv) in $H_2O$ (25 mL). The mixture was stirred at 0° C. for an additional 2 h prior to being diluted with $H_2O$ (50 mL). The mixture was extracted with ethyl acetate (3×30 mL). The combined organic layer was washed with brine (50 mL), dried over anh $Na_2SO_4$, filtered and concentrated under the reduced pressure to give a residue. The residue was purified by column chromatography ($SiO_2$, petroleum ether/ethyl acetate, 10:1 to 1:1) to afford benzyl 2-(2-(oxiran-2-yl)ethyl)pyrrolidine-1-carboxylate (800 mg, 2.91 mmol, 75% yield) as a yellow oil.

Intermediate B-10

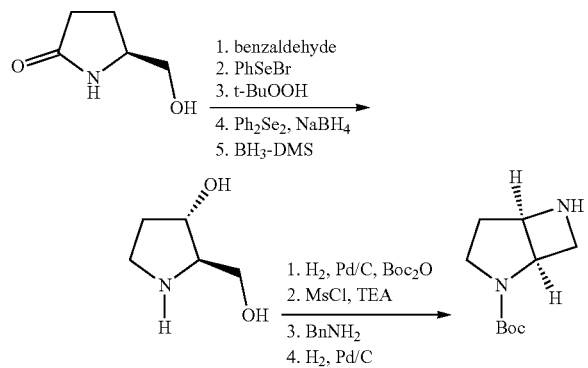

To a mixture of (S)-5-(hydroxymethyl)pyrrolidin-2-one (7.26 g, 63.1 mmol, 1.0 equiv) in toluene (150 mL) was added benzaldehyde (7.36 g, 69.4 mmol, 7.01 mL, 1.1 equiv), $TsOH.H_2O$ (163 mg, 946 μmol, 0.015 equiv) under $N_2$. The mixture was stirred at 125° C. for 48 h and was then diluted with water (100 mL) and extracted with ethyl acetate (300 mL). The combined organic layer was washed with saturated aq $NaHCO_3$ (300 mL), dried over anh sodium sulfate, filtered and concentrated under vacuum to provide the crude residue. The residue was purified by column chromatography ($SiO_2$, petroleum ether/ethyl acetate, 20:1 to 1:1) to afford (7aS)-3-phenyltetrahydro-3H,5H-pyrrolo[1,2-c]oxazol-5-one (5.70 g, 33% yield) as a brown oil. LCMS [ESI, M+1]: 204.

To a solution of (7aS)-3-phenyltetrahydro-3H,5H-pyrrolo[1,2-c]oxazol-5-one (5.00 g, 24.6 mmol, 1.0 eq) in THF (50.0 mL) at −65° C. was added LiHMDS (1 M, 49.2 mL, 2.0 eq). The mixture was stirred at this temperature for 30 min prior to the dropwise addition of PhSeBr (6.39 g, 27.1 mmol, 1.1 equiv) in THF (15.0 mL). The mixture was stirred at −65° C. for 1 h and was diluted with satd aq $NH_4Cl$ (100 mL) and extracted with ethyl acetate (200 mL). The combined organic layer was dried over anh sodium sulfate, filtered and concentrated under vacuum. The resultant residue was dissolved in DCM (120 mL) at 0° C. and to this solution was added $H_2O_2$ (16.7 g, 148 mmol, 14.2 mL, 30% in water, 6.0 equiv). The mixture was stirred at 25° C. for 3 h and was then diluted with DCM (50 mL) and washed with HCl (150 mL, 1 M), satd aq $NaHCO_3$ (150 mL), satd and aq $Na_2S_2O_3$ (150 mL). The organic layer was dried over anh sodium sulfate, filtered and concentrated under vacuum. The resultant residue was purified by column chromatography ($SiO_2$, petroleum ether/ethyl acetate, 20:1 to 1:1) to afford (7aS)-3-phenyl-1,7a-dihydro-3H,5H-pyrrolo[1,2-c]oxazol-5-one (3.30 g, 63% yield) as a yellow solid. $^1H$ NMR (400 MHz, $CDCl_3$): δ=7.45 (d, J=7.2 Hz, 2H), 7.35-7.24 (m, 3H), 7.19 (dd, J=1.6, 5.6 Hz, 1H), 6.17-6.04 (m, 2H), 4.61-4.49 (m, 1H), 4.19 (t, J=7.6 Hz, 1H), 3.35 (t, J=8.0 Hz, 1H). LCMS [ESI, M+1]: 202.

To a solution of (7aS)-3-phenyl-1,7a-dihydro-3H,5H-pyrrolo[1,2-c]oxazol-5-one (2.80 g, 13.9 mmol, 1.0 equiv) in DMF (50.0 mL) was added $K_2CO_3$ (1.92 g, 13.9 mmol, 1.0 equiv) and 70% t-butyl hydroperoxide (5.52 g, 61.2 mmol, 5.87 mL, 4.4 equiv) in portions under $N_2$. The mixture was stirred at 25° C. for 30 min prior to the addition of $Bu_4NF.3H_2O$ (13.2 g, 41.7 mmol, 3.0 equiv). The mixture was stir at room temperature for 1 h prior to being diluted with satd aq $NH_4Cl$ (50 mL) and extracted with MTBE (2×100 mL). The organic layer was washed with water (3×100 mL), dried over anh $Na_2SO_4$, filtered and concentrated under vacuum. The resultant residue was purified by column chromatography ($SiO_2$, petroleum ether/ethyl acetate, 20:1 to 1:1) to afford (1aR,1bR,6aR)-4-phenyltetrahydro-4H,6H-oxireno[2',3':3,4]pyrrolo[1,2-c]oxazol-6-one (1.20 g, 38% yield, 94.8% purity) as a brown solid. $^1H$ NMR (400 MHz, $CDCl_3$): δ=7.42-7.31 (m, 5H), 6.34 (s, 1H), 4.29-4.17 (m, 2H), 4.06 (d, J=2.4 Hz, 1H), 3.81 (d, J=2.0 Hz, 1H), 3.56 (dd, J=7.6, 8.4 Hz, 1H). LCMS [ESI, M+1]: 218.

To a solution of PhSeSePh (2.09 g, 6.70 mmol, 1.5 equiv) in EtOH (20.0 mL) at 0° C. was added $NaBH_4$ (506 mg, 13.4 mmol, 3.0 equiv) and the mixture was stirred for 15 min prior to the addition of HOAc (1.21 g, 20.1 mmol, 1.15 mL, 4.5 equiv). The resultant solution was added to (1aR,1bR,6aR)-4-phenyltetrahydro-4H,6H-oxireno[2',3':3,4]pyrrolo[1,2-c]oxazol-6-one (1.20 g, 4.46 mmol, 1.0 equiv) in EtOH (12.0 mL) and stirred at 25° C. for 30 min. The reaction mixture was diluted with EtOAc (150 mL) and oxygen gas was bubble through for 5 min. The residue was concentrated under vacuum and the resultant residue was purified by column chromatography ($SiO_2$, petroleum ether/ethyl acetate, 3:1 to 0:1) to afford (7S,7aR)-7-hydroxy-3-phenyltetrahydro-3H,5H-pyrrolo[1,2-c]oxazol-5-one (1.06 g, crude) as a brown solid. LCMS [ESI, M+1]: 220.

To a solution of (7S,7aR)-7-hydroxy-3-phenyltetrahydro-3H,5H-pyrrolo[1,2-c]oxazol-5-one (1.39 g, 6.34 mmol, 1.0 equiv) in THF (25.0 mL) was added BH$_3$-Me$_2$S (10 M, 6.34 mL, 10 equiv). The reaction mixture was stirred at 70° C. for 2 h and then cooled to room temperature. The reaction mixture was quenched with HCl (4 M, 12 mL) and stirred at 70° C. for 1 h. The mixture was diluted with saturated aq Na$_2$CO$_3$ and was extracted with ethyl acetate (3×100 mL). The combined organic layer was dried over anh Na$_2$SO$_4$, filtered and concentrated under vacuum to afford (2R,3S)-1-benzyl-2-(hydroxymethyl)pyrrolidin-3-ol (1.55 g, 70% yield) as a colorless oil. LCMS [ESI, M+1]: 208.

To a solution of (2R,3S)-1-benzyl-2-(hydroxymethyl)pyrrolidin-3-ol (500 mg, 1.43 mmol, 1.0 equiv) and tert-butoxycarbonyl tert-butyl carbonate (933 mg, 4.28 mmol, 982 uL, 3.0 equiv) in MeOH (50.0 mL) was added Pd/C (500 mg, 334 umol, 10% wt/wt). The mixture was stirred at 40° C. for 16 h under H$_2$ (50 psi). The system was flushed with nitrogen, the mixture was filtered and the filtrate was concentrated under vacuum. The resultant residue was purified by column chromatography (SiO$_2$, petroleum ether/ethyl acetate, 5:1 to dichloromethane/methanol, 10:1) to afford tert-butyl (2R,3S)-3-hydroxy-2-(hydroxymethyl)pyrrolidine-1-carboxylate (380 mg, crude) as a yellow oil. $^1$H NMR (400 MHz, CDCl$_3$): δ 4.56 (br s, 1H), 4.20 (br s, 1H), 3.85-3.62 (m, 2H), 3.44-3.03 (m, 2H), 2.12-1.94 (m, 1H), 1.92-1.79 (m, 1H), 1.46 (s, 9H).

To a solution of tert-butyl (2R,3S)-3-hydroxy-2-(hydroxymethyl)pyrrolidine-1-carboxylate (380 mg, 1.75 mmol, 1.0 equiv) in DCM (10.0 mL) at 0° C. was added TEA (708 mg, 7.00 mmol, 974 μL, 4.0 equiv) and MSCl (501 mg, 4.37 mmol, 338 uL, 2.5 equiv). The mixture was stirred at 0° C. for 4 h and was then concentrated under vacuum. The resultant residue was diluted with ethyl acetate (20 mL) and washed with satd aq NaHCO$_3$ (10 mL). The organic layer was dried over anh Na$_2$SO$_4$, filtered and concentrated under vacuum. The residue was purified by column chromatography (SiO$_2$, petroleum ether/ethyl acetate, 20:1 to 1:1) to afford tert-butyl (2R,3S)-3-((methylsulfonyl)oxy)-2-(((methylsulfonyl)oxy)methyl)pyrrolidine-1-carboxylate (680 mg, crude) as a colorless oil. $^1$H NMR (400 MHz, CD$_3$OD): δ=5.24 (br s, 1H), 4.46-4.27 (m, 2H), 4.19 (br s, 1H), 3.59-3.45 (m, 2H), 3.19-3.09 (m, 6H), 2.44-2.30 (m, 1H), 2.29-2.18 (m, 1H), 1.49 (br s, 9H). LCMS [ESI, M–99]: 274.

To a solution of tert-butyl (2R,3S)-3-((methylsulfonyl)oxy)-2-(((methylsulfonyl)oxy)methyl)pyrrolidine-1-carboxylate (680 mg, 1.82 mmol, 1.0 equiv) in toluene (10.0 mL) was added benzyl amine (611 mg, 5.70 mmol, 621 μL, 3.13 equiv). The mixture was stirred at 110° C. for 16 h and then cooled to room temperature. The mixture was concentrated under vacuum and the residue was diluted with DCM (20 mL). The organic layer was washed with 1 N NaOH, was dried over anh Na$_2$SO$_4$, filtered and concentrated under vacuum. The resultant residue was purified by column chromatography (SiO$_2$, petroleum ether/ethyl acetate, 20:1 to 3:1) to afford tert-butyl (1R,5R)-6-benzyl-2,6-diazabicyclo[3.2.0]heptane-2-carboxylate (320 mg, 58% yield) as a colorless oil. $^1$H NMR (400 MHz, CDCl$_3$): δ 7.25-7.14 (m, 5H), 4.27-4.07 (m, 1H), 3.81 (t, J=4.8 Hz, 1H), 3.73-3.51 (m, 4H), 3.29-3.11 (m, 1H), 3.10-2.95 (m, 1H), 1.60-1.44 (m, 2H), 1.37 (br d, J=16.8 Hz, 9H). LCMS [ESI, M+1]: 289.

To a solution of tert-butyl (1R,5R)-6-benzyl-2,6-diazabicyclo[3.2.0]heptane-2-carboxylate (320 mg, 1.11 mmol, 1.0 equiv) in EtOH (10.0 mL) was added Pd/C (150 mg, 10% wt/wt). The mixture was stirred at 60° C. for 36 h under a hydrogen atmosphere (50 psi). The system was flushed with nitrogen and the mixture was filtered. The filtrate was concentrated under vacuum to provide the crude residue. The residue was purified by column chromatography (Al$_2$O$_3$, petroleum ether/ethyl acetate, 5:1 to 1:1 to ethyl acetate/methanol, 100:1 to 10:1) to afford tert-butyl (1R,5R)-2,6-diazabicyclo[3.2.0]heptane-2-carboxylate (80.0 mg, 36% yield) as a colorless oil. $^1$H NMR (400 MHz, CDCl$_3$): δ 4.63 (br t, J=5.2 Hz, 1H), 4.57-4.34 (m, 1H), 3.95-3.59 (m, 3H), 3.32-3.05 (m, 2H), 1.95-1.71 (m, 2H), 1.48-1.43 (m, 9H).

Intermediate B-11

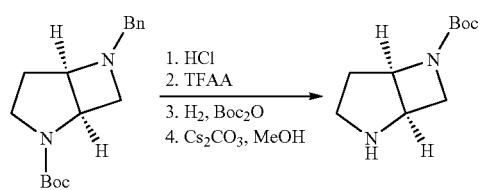 [SMILES: CC(C)(C)OC(=O)N1CC[C@@H]2[C@H]1CN2Cc1ccccc1 ; CC(C)(C)OC(=O)N1C[C@H]2NCC[C@H]21]

To a solution of tert-butyl (1R,5R)-6-benzyl-2,6-diazabicyclo[3.2.0]heptane-2-carboxylate (500 mg, 1.73 mmol, 1.0 equiv) in MeCN (8.00 mL) was added HCl in dioxane (4 M, 16.0 mL, 36.9 equiv). The mixture was stirred at 25° C. for 30 min and then was concentrated under vacuum to afford (1R,5R)-6-benzyl-2,6-diazabicyclo[3.2.0]heptane (1.00 g, crude, bis-HCl salt) as a yellow solid. LCMS [ESI, M–99]: 189.

To a solution of (1R,5R)-6-benzyl-2,6-diazabicyclo[3.2.0]heptane (900 mg, 4.00 mmol, 1.0 equiv, bis-HCl) in DCM (15.0 mL) at 0° C. was added TEA (1.01 g, 10.0 mmol, 1.39 mL, 2.5 equiv) followed by TFAA (1.01 g, 4.81 mmol, 668 μL, 1.2 equiv). The mixture was warmed to 25° C. and stirred for 1 h prior to the addition of satd aq NH$_4$Cl (15 mL) and water (20 mL). The organic layer was separated and the aqueous phase was extracted with ethyl acetate (30 mL). The combined organic layer was dried over anh Na$_2$SO$_4$, filtered and concentrated under vacuum. The residue was purified by column chromatography (SiO$_2$, petroleum ether/ethyl acetate, 10:1 to 3:1) to afford (1R,5R)-6-benzyl-2,6-diazabicyclo[3.2.0]heptane (180 mg, 36% over two steps) as a yellow oil. LCMS [ESI, M+1]: 285.

To a solution of (1R,5R)-6-benzyl-2,6-diazabicyclo[3.2.0]heptane (180 mg, 633 umol, 1.0 equiv) and (Boc)$_2$O (414 mg, 1.90 mmol, 436 μL, 3.0 equiv) in MeOH (10.0 mL) was added Pd/C (200 mg, 10% wt/wt). The mixture was stirred at 40° C. for 16 h under an atmosphere of hydrogen (50 psi). The mixture was filtered and the filtrate was concentrated under vacuum to afford 1-((1R,5R)-6-benzyl-2,6-diazabicyclo[3.2.0]heptan-2-yl)-2,2,2-trifluoroethan-1-one (412 mg, crude) as a colorless oil.

To a solution of 1-((1R,5R)-6-benzyl-2,6-diazabicyclo[3.2.0]heptan-2-yl)-2,2,2-trifluoroethan-1-one (412 mg, 1.40 mmol, 1.0 equiv) in MeOH (20.0 mL) was added Cs$_2$CO$_3$ (456 mg, 1.40 mmol, 1.0 equiv) and H$_2$O (0.5 mL). The reaction mixture was stirred at 40° C. for 30 min and was then concentrated under reduced pressure to remove the methanol. The residue was diluted with ethyl acetate (20 mL) and was dried over anh sodium sulfate, filtered and concentrated under vacuum to afford tert-butyl (1R,5R)-2-(2,2,2-trifluoroacetyl)-2,6-diazabicyclo[3.2.0]heptane-6-carboxylate (210 mg, crude) as a colorless oil.

Intermediate B-12

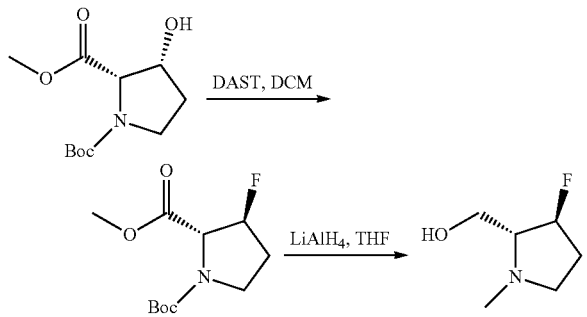

To a solution of 1-(tert-butyl) 2-methyl (2S,3R)-3-hydroxypyrrolidine-1,2-dicarboxylate (3.0 g, 12.2 mmol, 1.0 equiv) in dichloromethane (30 mL) was added DAST (5.91 g, 36.7 mmol, 4.85 mL, 3.0 equiv). The mixture was stirred at 0° C. for 1 h prior to being diluted with 0° C. water (20 mL). The aqueous phase was extracted with ethyl acetate (3×10 mL). The combined organic layer was dried over anh Na$_2$SO$_4$, filtered and concentrated. The residue was purified by column chromatography (SiO$_2$, petroleum ether/ethyl acetate, 30:1-5:1) to afford 1-(tert-butyl) 2-methyl (2R,3S)-3-fluoropyrrolidine-1,2-dicarboxylate (1.60 g, 53% yield) as a colorless oil. $^1$H NMR (400 MHz, chloroform-d): δ 5.25-5.06 (m, 1H), 4.64-4.46 (m, 1H), 3.76 (s, 3H), 3.71-3.62 (m, 1H), 3.60-3.49 (m, 1H), 2.28-1.97 (m, 2H), 1.47-1.41 (m, 9H).

To a solution of 1-(tert-butyl) 2-methyl (2R,3S)-3-fluoropyrrolidine-1,2-dicarboxylate (1.50 g, 6.07 mmol, 1.0 equiv) in THF (20 mL) at −40° C. was added LiAlH$_4$ (576 mg, 15.2 mmol, 2.50 equiv). The mixture was stirred at this temperature for 1 h and was then heated to 70° C. and stirred for 1 h. The mixture was cooled to room temperature and was quenched with saturated aq Na$_2$SO$_4$ (1.5 mL), filtered and concentrated to afford ((2R,3S)-3-fluoro-1-methylpyrrolidin-2-yl)methanol (800 mg, crude) as a colorless oil.

Intermediate B-13

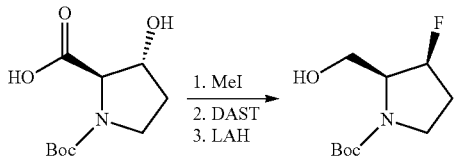 [SMILES: CC(C)(C)OC(=O)N1CC[C@@H](O)[C@@H]1C(=O)O ; CC(C)(C)OC(=O)N1CC[C@H](F)[C@@H]1CO]

To a mixture of (2R,3R)-1-(tert-butoxycarbonyl)-3-hydroxypyrrolidine-2-carboxylic acid (3.00 g, 13.0 mmol, 1.0 equiv) in DMF (75.0 mL) at 0° C. was added K$_2$CO$_3$ (5.38 g, 38.9 mmol, 3.0 equiv) in one portion under nitrogen. The mixture was stirred at 0° C. for 5 min prior to the addition of methyl iodide (9.21 g, 64.9 mmol, 4.04 mL, 5.0 equiv). The mixture was stirred at 25° C. for 4 h and then was concentrated under reduced pressure. The resultant residue was adjusted to pH=4 using hydrochloric acid (0.5 M) and then was extracted with ethyl acetate (3×50 mL). The combined organic layer was washed with brine (3×50 mL), dried over anh Na$_2$SO$_4$ and filtered. The filtrate was concentrated under reduced pressure to afford 1-(tert-butyl) 2-methyl (2R,3R)-3-hydroxypyrrolidine-1,2-dicarboxylate (3.8 g, crude) as a brown oil. $^1$H NMR (400 MHz, CDCl$_3$): δ 4.44 (br s, 1H), 4.32-4.16 (m, 1H), 3.75 (s, 3H), 3.70-3.56 (m, 2H), 2.48 (br d, J=7.6 Hz, 1H), 2.17-2.07 (m, 1H), 1.97-1.85 (m, 1H), 1.50-1.39 (m, 9H).

To a solution of 1-(tert-butyl) 2-methyl (2R,3R)-3-hydroxypyrrolidine-1,2-dicarboxylate (1.17 g, 4.77 mmol, 1.0 equiv) in dichloromethane (50.0 mL) at 0° C. was added DAST (769 mg, 4.77 mmol, 630 μL, 1.0 equiv). The mixture was stirred at 0° C. for 30 min and was subsequently concentrated under reduced pressure. Then the residue was diluted with satd aq NaHCO$_3$ and was extracted with ethyl acetate (3×10 mL). The combined organic layer was washed with brine (10 mL), dried over anh Na$_2$SO$_4$ and filtered. The filtrate was concentrated under reduced. The residue was purified by column chromatography (SiO$_2$, petroleum ether/ethyl acetate, 1:0 to 7:1) to afford 41712-C (204 mg, crude); Black brown oil; $^1$H NMR (400 MHz, CDCl$_3$) δ 5.45-5.27 (m, 1H), 4.62-4.45 (m, 1H), 3.78 (s, 3H), 3.76-3.58 (m, 2H), 2.31-1.96 (m, 2H), 1.49-1.42 (m, 9H).

To a solution of 41712-C (320 mg, 1.29 mmol, 1.0 eq) in THF (10.0 mL) was added LiAlH$_4$ (98.2 mg, 2.59 mmol, 2.0 eq) at −40° C. under N$_2$, the mixture was stirred at −40° C. for 30 minutes, then warm to 50° C. and the mixture was stirred at 50° C. for 30 minutes. After completion, the mixture was quenched by water (100 uL) at 0° C., and then added NaOH aqueous solution (15%, 100 uL) and water (300 uL). The mixture was stirred at 0° C. for 5 minutes, then the mixture was filtered and washed with THF (20 mL), the filtrate was concentrated under reduced pressure at 40° C. to dryness affording 41711-D (170 mg, crude); Black brown oil.

Intermediate B-14

To a solution of (1S,2S,5R)-3-(tert-butoxycarbonyl)-3-azabicyclo[3.1.0]hexane-2-carboxylic acid (1.20 g, 5.28 mmol, 1 equiv) in THF (20.0 mL) at −20° C. was added LiAlH$_4$ (601 mg, 15.8 mmol, 3 equiv). The mixture was allowed to stir at this temperature for 2 h and then heated at 55° C. for 2 h. The mixture was quenched at 0° C. with H$_2$O (0.60 mL), 15% of NaOH aqueous (0.6 mL), and water (1.8 mL). The suspension was filtered and concentrated under reduced pressure to afford ((1S,2S,5R)-3-methyl-3-azabicyclo[3.1.0]hexan-2-yl)methanol (420 mg, 3.14 mmol, 59% yield) as a colorless oil. $^1$H NMR (400 MHz, CDCl$_3$): δ 3.66-3.56 (m, 1H), 3.55-3.44 (m, 1H), 3.36-3.25 (m, 1H), 2.75-2.60 (m, 2H), 2.54-2.44 (m, 1H), 2.37 (s, 3H), 1.55-1.34 (m, 2H), 0.82-0.69 (m, 1H), 0.30-0.20 (m, 1H).

Intermediate B-15

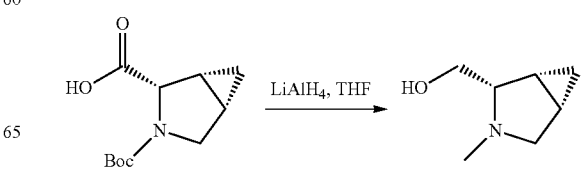

Using the method depicted for Intermediate B-13, ((1R,2S,5S)-3-methyl-3-azabicyclo[3.1.0]hexan-2-yl)methanol was prepared: Yellow oil; ¹H NMR (400 MHz, CDCl₃) δ 3.81-3.74 (m, 1H), 3.70-3.63 (m, 1H), 3.11 (d, J=8.8 Hz, 1H), 2.62-2.55 (m, 1H), 2.52 (dd, J=4.0, 8.8 Hz, 1H), 2.29 (s, 3H), 1.51-1.42 (m, 1H), 1.37-1.27 (m, 1H), 0.82-0.79 (m, 1H), 0.39-0.34 (m, 1H).

Intermediate B-16

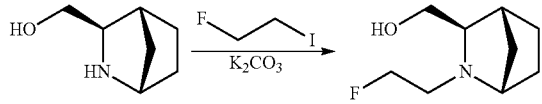

To a solution of ((1S,3R,4R)-2-azabicyclo[2.2.1]heptan-3-yl)methanol (0.4 g, 2.44 mmol, 1 equiv, HCl salt) in MeCN (2 mL) was added K₂CO₃ (1.01 g, 7.33 mmol, 3 equiv) and 1-fluoro-2-iodo-ethane (850 mg, 4.89 mmol, 2 equiv). The mixture was stirred at 50° C. for 12 h and then was filtered and concentrated in vacuum. The residue was purified by prep-TLC (PE/EA, 0:1) to afford ((1S,3R,4R)-2-(2-fluoroethyl)-2-azabicyclo[2.2.1]heptan-3-yl)methanol (0.2 g, 1.15 mmol, 47% yield) as a light yellow oil. ¹H NMR (400 MHz, CDCl₃): δ 4.66-4.35 (m, 2H), 3.53-3.29 (m, 3H), 3.04-2.50 (m, 4H), 2.17 (br d, J=4.0 Hz, 1H), 2.14 (t, J=5.6 Hz, 1H), 1.93-1.83 (m, 1H), 1.80-1.74 (m, 1H), 1.64-1.55 (m, 1H), 1.43-1.32 (m, 1H), 1.31-1.26 (m, 1H).

Intermediate B-17

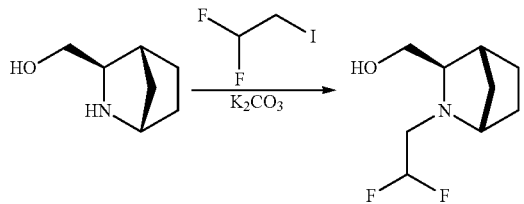

Using the method depicted for Intermediate B-16, ((1S,3R,4R)-2-(2,2-difluoroethyl)-2-azabicyclo[2.2.1]heptan-3-yl)methanol was prepared: Light yellow oil; ¹H NMR (400 MHz, CDCl₃) δ 6.01-5.59 (m, 1H), 3.52-3.27 (m, 3H), 3.10-2.74 (m, 2H), 2.23-2.18 (m, 1H), 2.15 (br t, J=5.20 Hz, 2H), 1.88-1.75 (m, 2H), 1.69-1.57 (m, 1H), 1.46-1.35 (m, 1H), 1.33-1.27 (m, 1H).

Intermediates B-18 & B-19

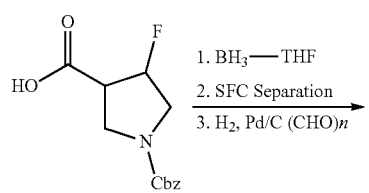

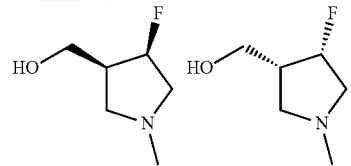

To a solution of cis-racemic 1-((benzyloxy)carbonyl)-4-fluoropyrrolidine-3-carboxylic acid (3.70 g, 13.8 mmol, 1 equiv) in THF (40 mL) at 0° C. was added BH₃.THF (1 M, 41.5 mL, 3 equiv). The mixture was stirred at 25° C. for 16 h and was subsequently quenched with MeOH (20 mL) and concentrated in vacuum. The residue was purified by column chromatography (SiO₂, PE:EA, 2:1 to 1:1) to afford cis-racemic benzyl 3-fluoro-4-(hydroxymethyl)pyrrolidine-1-carboxylate (2.6 g, 10.3 mmol, 74% yield) as a colorless oil. ¹H NMR (400 MHz, CDCl₃): δ 7.40-7.28 (m, 5H), 5.31-5.09 (m, 3H), 3.95-3.69 (m, 4H), 3.68-3.50 (m, 1H), 3.27 (td, J=2.8, 10.8 Hz, 1H), 2.57-2.37 (m, 1H). LCMS [ESI, M−1]: 252.0.

cis-racemic benzyl 3-fluoro-4-(hydroxymethyl)pyrrolidine-1-carboxylate (2.6 g, 10.3 mmol) was separated by SFC chromatography [column: DAICEL CHIRALPAK AD (250 mm*50 mm, 10 μm)]; mobile phase— A: CO₂, B: [0.1% NH₄OH in MeOH], B %: 35%, 4 min; to afford benzyl (3R,4S)-3-fluoro-4-(hydroxymethyl)pyrrolidine-1-carboxylate (1.00 g, 3.95 mmol, 77% yield, 99.8% e.e.) as light yellow oil and benzyl (3S,4R)-3-fluoro-4-(hydroxymethyl)pyrrolidine-1-carboxylate (1.00 g, 3.95 mmol, 77% yield, 99.1% e.e.) as light yellow oil. The absolute stereochemical configuration of these two compounds was arbitrarily depicted.

To a solution of (3R,4S)-3-fluoro-4-(hydroxymethyl)pyrrolidine-1-carboxylate (1 g, 3.95 mmol, 1 equiv) in MeOH (6 mL) was added Pd/C (70 mg, 10% wt/wt) and formalin (2.56 g, 31.59 mmol, 2.35 mL, 37% in water, 8 equiv). The mixture was stirred at 25° C. for 16 h under H₂ (15 psi). The system was purged with nitrogen and the mixture was filtered and concentrated in vacuum. The residue was purified by column chromatography (Al₂O₃, EA:PE, 1:1 to EA:EtOH, 6:1) to afford ((3S,4R)-4-fluoro-1-methylpyrrolidin-3-yl)methanol (110 mg, 826 umol, 21% yield). Yellow oil; ¹H NMR (400 MHz, CDCl₃) δ 5.36-5.04 (m, 1H), 3.94-3.57 (m, 2H), 2.92-2.82 (m, 1H), 2.67-2.49 (m, 3H), 2.47-2.26 (m, 4H).

The same reductive amination procedure was used to obtain ((3R,4S)-4-fluoro-1-methylpyrrolidin-3-yl)methanol: Yellow oil; ¹H NMR (400 MHz, CDCl₃): δ 5.36-5.04 (m, 1H), 3.94-3.57 (m, 2H), 3.11-2.71 (m, 2H), 2.67-2.49 (m, 2H), 2.47-2.20 (m, 4H).

Intermediate B-20

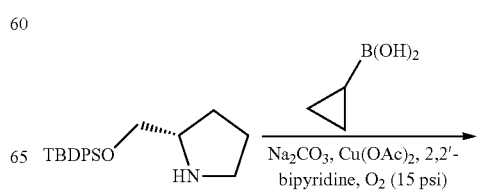

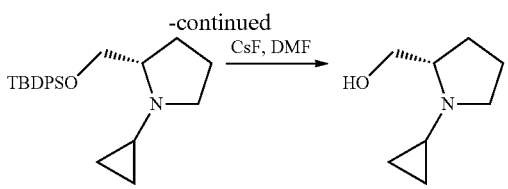

To a mixture of (S)-2-(((tert-butyldiphenylsilyl)oxy) methyl)pyrrolidine (3 g, 8.84 mmol, 1.0 equiv) and cyclopropylboronic acid (3.17 g, 36.9 mmol, 4.18 equiv) in DCE (40 mL) was added $Na_2CO_3$ (1.95 g, 18.4 mmol, 2.08 equiv), $Cu(OAc)_2$ (1.67 g, 9.19 mmol, 1.04 equiv) and 2-(2-pyridyl)pyridine (1.44 g, 9.22 mmol, 1.04 equiv). The mixture was stirred at 70° C. under $O_2$ (15 psi) for 2 h prior to being filtered. The filtrate was diluted with water (40 mL) and extracted with ethyl acetate (2×50 mL). The combined organic layer was washed with brine (80 mL), dried over anh $Na_2SO_4$ and filtered. The filtrate was concentrated under reduced pressure. The residue was purified by column chromatography ($SiO_2$, petroleum ether/ethyl acetate, 10:1 to 4:1) to afford (S)-2-(((tert-butyldiphenylsilyl)oxy) methyl)-1-cyclopropylpyrrolidine (1.5 g, 44% yield) as a colorless oil. $^1H$ NMR (400 MHz, $CDCl_3$): δ 7.75-7.70 (m, 4H), 7.47-7.38 (m, 6H), 3.95 (dd, J=4.0, 9.6 Hz, 1H), 3.47 (dd, J=8.8, 10.0 Hz, 1H), 3.10-3.02 (m, 1H), 2.88-2.80 (m, 1H), 2.57-2.49 (m, 1H), 2.12-2.03 (m, 1H), 1.84-1.64 (m, 4H), 1.11 (s, 9H), 0.39-0.25 (m, 4H).

To a solution of (S)-2-(((tert-butyldiphenylsilyl)oxy) methyl)-1-cyclopropylpyrrolidine (1.5 g, 3.95 mmol, 1.0 equiv) in DMF (15 mL) was added CsF (1.75 g, 11.5 mmol, 2.9 equiv). The reaction mixture was stirred at 50° C. for 20 h. The reaction mixture was cooled to room temperature and diluted with $H_2O$ (20 mL) and extracted with ethyl acetate (3×30 mL). The combined organic layer was washed with brine (80 mL), dried over anh $Na_2SO_4$, filtered and concentrated under reduced pressure to give a residue. The residue was purified by column chromatography ($SiO_2$, petroleum ether/ethyl acetate, 10:1 to 1:1) to afford (S)-(1-cyclopropylpyrrolidin-2-yl)methanol (380 mg, 68% yield) as a yellow oil. $^1H$ NMR (400 MHz, $CDCl_3$): δ 3.74 (dd, J=3.6, 10.4 Hz, 1H), 3.42 (dd, J=2.4, 10.8 Hz, 1H), 3.13-3.04 (m, 1H), 2.82-2.75 (m, 1H), 2.60-2.52 (m, 1H), 2.48-2.30 (m, 1H), 1.98-1.88 (m, 1H), 1.80-1.60 (m, 4H), 0.53-0.39 (m, 3H), 0.38-0.30 (m, 1H).

Intermediate B-21

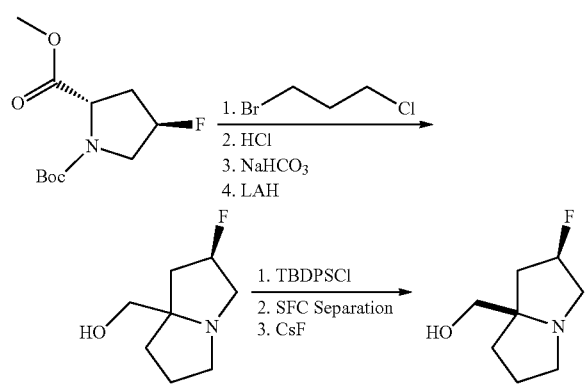

To a solution of (2S,4R)-1-tert-butyl 2-methyl 4-fluoropyrrolidine-1,2-dicarboxylate (5.0 g, 20.2 mmol, 1.0 equiv) and HMPA (4.71 g, 26.3 mmol, 4.62 mL, 1.30 equiv) in THF (20 mL) at −70° C. was added LiHMDS (1.0 M, 26.3 mL, 1.3 equiv). The mixture was stirred at this temperature for 1 h prior to the addition of 1-bromo-3-chloro-propane (15.9 g, 101 mmol, 9.95 mL, 5.0 equiv). The mixture was allowed to warm to room temperature over 1 h and was quenched with satd aq $NH_4Cl$ (50 mL) and then diluted with $H_2O$ (30 mL). The mixture was extracted with ethyl acetate (3×50 mL). The combined organic layer was dried over anh $Na_2SO_4$, filtered and concentrated under vacuum. The residue was purified by column chromatography ($SiO_2$, petroleum ether/ethyl acetate, 20:1 to 5:1) to afford 1-(tert-butyl) 2-methyl (4R)-2-(3-chloropropyl)-4-fluoropyrrolidine-1,2-dicarboxylate (2.7 g, 37% yield) as a yellow oil. LCMS [ESI, M−99]: 224.

To a solution of 1-(tert-butyl) 2-methyl (4R)-2-(3-chloropropyl)-4-fluoropyrrolidine-1,2-dicarboxylate (2.70 g, 8.34 mmol, 1.0 equiv) in $CH_3CN$ (6 mL) was added HCl in dioxane (4 M, 20 mL). The mixture was stirred at 20° C. for 2 h and then was concentrated under reduced pressure to afford methyl (4R)-2-(3-chloropropyl)-4-fluoropyrrolidine-2-carboxylate (2.2 g, crude, HCl salt) as a yellow oil.

To a solution of methyl (4R)-2-(3-chloropropyl)-4-fluoropyrrolidine-2-carboxylate (2.0 g, 7.69 mmol, 1.0 equiv, HCl salt) in $CH_3CN$ (20 mL) was added $NaHCO_3$ (3.23 g, 38.4 mmol, 5.0 equiv) and KI (128 mg, 769 μmol, 0.10 equiv). The mixture was stirred at 50° C. for 12 h prior to being filtered and concentrated under reduced pressure. The residue was purified by column chromatography ($SiO_2$, petroleum ether/ethyl acetate, 10/1 to 1/1) to afford methyl (2R)-2-fluorotetrahydro-1H-pyrrolizine-7a(5H)-carboxylate (1.10 g, 76% over two steps) as a yellow oil. $^1H$ NMR (400 MHz, $CDCl_3$): δ 5.37-5.08 (m, 1H), 3.74 (s, 3H), 3.60-3.45 (m, 1H), 3.29-3.17 (m, 1H), 2.95-2.74 (m, 2H), 2.73-2.63 (m, 1H), 2.20-2.09 (m, 1H), 2.03-1.72 (m, 5H). LCMS [ESI, M+1]: 188.

To a solution methyl (2R)-2-fluorotetrahydro-1H-pyrrolizine-7a(5H)-carboxylate (1.10 g, 5.88 mmol, 1.0 equiv) in THF (15 mL) at −40° C. was added $LiAlH_4$ (669 mg, 17.6 mmol, 3.0 equiv). The mixture was stirred at this temperature for 1 h prior to being quenched with saturated $Na_2SO_4$ (1.7 mL) at 0° C. The mixture was diluted with THF (15 mL) and was filtered and concentrated under reduced pressure to afford ((2R)-2-fluorotetrahydro-1H-pyrrolizin-7a(5H)-yl)methanol (950 mg, 90% purity, 91% yield) as a yellow oil. $^1H$ NMR (400 MHz, $CDCl_3$): δ 5.36-5.08 (m, 1H), 3.51-3.29 (m, 3H), 3.25-3.10 (m, 1H), 3.04-2.93 (m, 1H), 2.90-2.73 (m, 1H), 2.71-2.59 (m, 1H), 2.28-2.12 (m, 1H), 1.95-1.73 (m, 4H), 1.65-1.53 (m, 1H).

To a mixture of ((2R)-2-fluorotetrahydro-1H-pyrrolizin-7a(5H)-yl)methanol (600 mg, 3.77 mmol, 1.0 equiv) and TBDPSCl (2.07 g, 7.54 mmol, 1.94 mL, 2 equiv) in DMF (10 mL) was added imidazole (1.03 g, 15.1 mmol, 4.0 equiv). The mixture was stirred at 20° C. for 2 hours. The mixture was poured into water (20 mL) and the aqueous phase was extracted with ethyl acetate (3×20 mL). The combined organic phase was washed with brine (2×20 mL), dried with anhydrous $Na_2SO_4$, filtered and concentrated in vacuum. The residue was purified by prep-HPLC (column: Phenomenex luna C18 150*40 mm*15 μm; mobile phase: A: [water (0.1% TFA)]; B % (ACN): 30%-60%, 10 min) and then by SFC—column: DAICEL CHIRALPAK IC (250 mm*30 mm, 10 μm); mobile phase: B: [0.1% $NH_4OH$ in MeOH]; B %: 30%-30%, 2.4 min; 60 min; to afford (2R, 7aR)-7a-(((tert-butyldiphenylsilyl)oxy)methyl)-2-fluorohexahydro-1H-pyrrolizine (660 mg, 1.58 mmol, 42% yield) as a colorless oil. $^1H$ NMR (400 MHz, DMSO-$d_6$): δ

7.64-7.59 (m, 4H), 7.49-7.37 (m, 6H), 5.40-5.20 (m, 1H), 3.46 (d, J=9.2 Hz, 1H), 3.31-3.27 (m, 1H), 3.23-3.15 (m, 1H), 2.85-2.82 (m, 1H), 2.81-2.65 (m, 1H), 2.54-2.51 (m, 1H), 2.28-2.23 (m 1H), 1.97-1.92 (m, 1H), 1.87-1.52 (m, 4H), 1.00 (s, 9H).

To a solution of (2R,7aR)-7a-(((tert-butyldiphenylsilyl)oxy)methyl)-2-fluorohexahydro-1H-pyrrolizine (580 mg, 1.46 mmol, 1.0 equiv) in DMF (3 mL) was added CsF (665 mg, 4.38 mmol, 161 μL, 3.0 equiv). The mixture was stirred at 50° C. for 20 h prior to being cooled to room temperature and being directly purified by column chromatography (SiO$_2$, petroleum ether/ethyl acetate, 2:1 to ethyl acetate/methanol, 5:1) to afford ((2R,7aR)-2-fluorotetrahydro-1H-pyrrolizin-7a(5H)-yl)methanol (210 mg, 90% yield) as a colorless oil. $^1$H NMR (400 MHz, CDCl$_3$): δ 5.32-5.14 (m, 1H), 3.55-3.49 (m, 1H), 3.45-3.31 (m, 2H), 3.06-2.84 (m, 2H), 2.81-2.63 (m, 2H), 2.27-2.16 (m, 1H), 1.98-1.76 (m, 4H), 1.67-1.57 (m, 1H).

Intermediate B-22

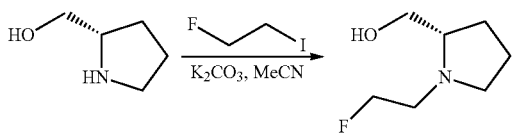

To a solution of (S)-pyrrolidin-2-ylmethanol (5 g, 49.4 mmol, 4.81 mL, 1 equiv) in MeCN (50 mL) was added K$_2$CO$_3$ (7.52 g, 54.38 mmol, 1.1 equiv). The mixture was cooled to 0° C. and 1-fluoro-2-iodo-ethane (8.94 g, 51.41 mmol, 1.04 equiv) was added dropwise and the resultant mixture was warmed to room temperature and stirred for 16 h. The mixture was filtered and concentrated under vacuum. The residue was purified by column chromatography (SiO$_2$, DCM:MeOH, 20:1) to afford (S)-(1-(2-fluoroethyl)pyrrolidin-2-yl)methanol (4 g, 27.2 mmol, 55% yield) as a yellow oil. $^1$H NMR (400 MHz, CDCl$_3$): δ 4.65-4.53 (m, 1H), 4.52-4.41 (m, 1H), 3.61 (dd, J=3.6, 10.8 Hz, 1H), 3.41 (dd, J=2.8, 10.8 Hz, 1H), 3.33-3.18 (m, 1H), 3.14-2.97 (m, 1H), 2.76-2.58 (m, 2H), 2.44-2.32 (m, 1H), 1.95-1.69 (m, 4H).

Intermediate B-23

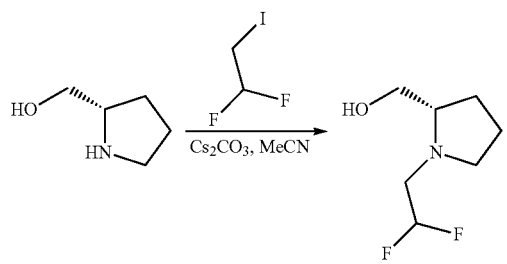

The procedure used to prepare Intermediate B-22 was used to prepare (S)-(1-(2,2-difluoroethyl)pyrrolidin-2-yl)methanol. Yellow oil; $^1$H NMR (400 MHz, CDCl$_3$): δ 6.17-5.83 (m, 1H), 3.38-3.31 (m, 1H), 3.29-3.12 (m, 2H), 3.08-3.00 (m, 1H), 2.77-2.52 (m, 2H), 2.32 (td, J=7.2, 9.2 Hz, 1H), 1.83-1.56 (m, 3H), 1.49-1.37 (m, 1H).

Intermediate B-24

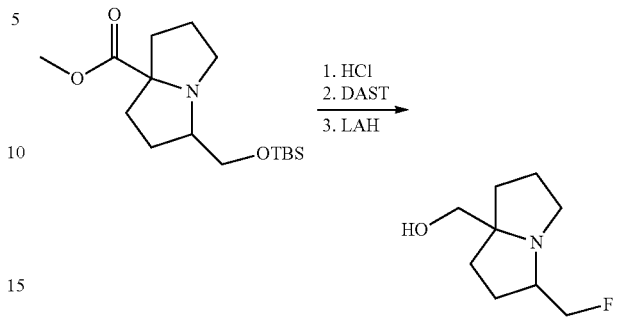

To a solution of methyl 3-(((tert-butyldimethylsilyl)oxy)methyl)tetrahydro-1H-pyrrolizine-7a(5H)-carboxylate (1.00 g, 3.19 mmol, 1.0 equiv) in CH$_3$CN (10.0 mL) was added HCl in dioxane (4.0 M, 10.0 mL, 12.5 equiv). The mixture was stirred at 0° C. for 0.5 hour. Subsequently, the reaction mixture was concentrated under reduced pressure. The residue was diluted with methanol (30.0 mL) and adjusted to pH 8 using solid Na$_2$CO$_3$. The mixture was concentrated under reduced pressure to provide a residue. The residue was diluted with dichloromethane (30.0 mL) and filtered. The filtrate was concentrated under reduced pressure to afford methyl 3-(hydroxymethyl)tetrahydro-1H-pyrrolizine-7a(5H)-carboxylate (700 mg, crude) as a yellow oil. R$_f$=0.20 [petroleum ether/ethyl acetate/ethanol (2% NH$_4$OH), 4:3:1]. $^1$H NMR (400 MHz, CDCl$_3$): δ 3.90-3.84 (m, 1H), 3.75 (dd, J=5.2, 11.2 Hz, 1H), 3.71 (s, 3H), 3.37 (tdd, J=5.2, 8.0, 10.8 Hz, 1H), 3.11-2.95 (m, 1H), 2.79-2.60 (m, 2H), 2.54-2.45 (m, 1H), 2.20 (ddd, J=8.0, 10.4, 13.2 Hz, 1H), 1.88-1.73 (m, 4H), 1.67-1.49 (m, 2H).

To a solution of methyl 3-(hydroxymethyl)tetrahydro-1H-pyrrolizine-7a(5H)-carboxylate (700 mg, 3.51 mmol, 1.0 equiv) in dichloromethane (7.0 mL) at 0° C. was added DAST (1.70 g, 10.5 mmol, 1.39 mL, 3.0 equiv). The mixture was stirred at 0° C. for 0.5 hour. Subsequently, the reaction mixture was diluted with satd aq Na$_2$CO$_3$ (5.0 mL) and water (5.0 mL). The mixture was extracted with ethyl acetate (3×10 mL). The combined organic layer was dried over anhydrous sodium sulfate and filtered. The filtrate was concentrated under reduced pressure to afford methyl 3-(fluoromethyl)tetrahydro-1H-pyrrolizine-7a(5H)-carboxylate (700 mg, 99% yield) as a yellow oil. R$_f$=0.50 (petroleum ether/ethyl acetate, 1:1). $^1$H NMR (400 MHz, CDCl$_3$): δ 4.82-4.61 (m, 1H), 3.71 (s, 3H), 3.28-3.05 (m, 4H), 2.18-2.00 (m, 4H), 1.92-1.75 (m, 4H).

To a mixture of LiAlH$_4$ (264 mg, 6.96 mmol, 2.0 equiv) in THF (10.0 mL) at −20° C. was added methyl 3-(fluoromethyl)tetrahydro-1H-pyrrolizine-7a(5H)-carboxylate (700 mg, 3.48 mmol, 1.0 equiv) and the mixture was stirred at this temperature for 1 h. Subsequently, the reaction mixture was quenched with water (0.3 mL), 15% NaOH (0.3 mL) and water (0.9 mL). The suspension was filtered and the THF was collected. The filter cake was dispersed in THF (30.0 mL) and stirred at 25° C. for 5 minutes and filtered. The combined filtrate was concentrated under reduced pressure to provide a residue. The residue was diluted with ethyl acetate and dried over anhydrous sodium sulfate and filtered. The filtrate was concentrated under reduced pressure to afford (3-(fluoromethyl)tetrahydro-1H-pyrrolizin-7a(5H)-yl)methanol (400 mg, 66% yield) as a yellow oil. $^1$H NMR (400 MHz, CDCl$_3$): δ 4.76-4.66 (m, 1H), 4.63-4.54 (m, 1H), 3.80-3.69 (m, 1H), 3.40-3.26 (m, 2H), 3.22-3.17 (m, 1H), 3.15-3.09 (m, 1H), 2.07-1.85 (m, 8H).

Intermediate B-25

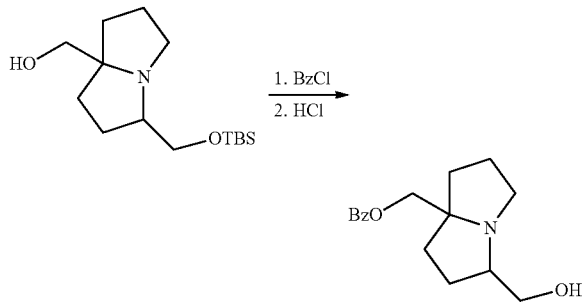

To a solution of (3-(((tert-butyldimethylsilyl)oxy)methyl) tetrahydro-1H-pyrrolizin-7a(5H)-yl)methanol (1.30 g, 4.55 mmol, 1.0 equiv) in dichloromethane (10.0 mL) at 0° C. was added TEA (921 mg, 9.11 mmol, 1.27 mL, 2.0 equiv) and benzoyl chloride (960 mg, 6.83 mmol, 793 μL, 1.5 equiv). The mixture was stirred at 25° C. for 0.5 hour. Subsequently, the reaction mixture was diluted with water (40.0 mL) and extracted with ethyl acetate (3×50 mL). The combined organic layer was dried over anhydrous sodium sulfate and filtered. The filtrate was concentrated under reduced pressure to dryness. The crude product was purified by reversed-phase flash chromatography to afford (3-(((tert-butyldimethylsilyl)oxy)methyl)tetrahydro-1H-pyrrolizin-7a(5H)-yl) methyl benzoate (1.10 g, 62% yield) as a yellow oil. R$_f$=0.50 (petroleum ether/ethyl acetate, 3:1). $^1$H NMR (400 MHz, CDCl$_3$): δ 8.10-8.04 (m, 2H), 7.54-7.52 (m, 1H), 7.46-7.40 (m, 2H), 4.42-4.26 (m, 2H), 3.94 (d, J=4.8 Hz, 2H), 3.57-3.42 (m, 1H), 3.22 (br s, 1H), 3.09-2.93 (m, 1H), 2.15 (ddd, J=2.4, 6.8, 12.4 Hz, 1H), 2.02-1.79 (m, 6H), 1.66 (ddd, J=7.2, 11.2, 12.4 Hz, 1H), 0.90 (s, 9H), 0.08 (s, 6H); LCMS [ESI, M+1]: 390.

To a solution of (3-(((tert-butyldimethylsilyl)oxy)methyl) tetrahydro-1H-pyrrolizin-7a(5H)-yl)methyl benzoate (1.10 g, 2.82 mmol, 1.0 equiv) in CH$_3$CN (10.0 mL) at 0° C. was added HCl in dioxane (4 M, 10.0 mL, 14.2 equiv). The mixture was stirred at 0° C. for 0.5 hour. Subsequently, the reaction mixture was diluted with water (20 mL) and adjusted to pH 8 using solid NaHCO$_3$. The mixture was extracted with ethyl acetate (3×30 mL). The combined organic layer was dried over anhydrous sodium sulfate and filtered. The filtrate was concentrated under reduced pressure to afford (3-(hydroxymethyl)tetrahydro-1H-pyrrolizin-7a(5H)-yl)methyl benzoate (800 mg, 95% yield) as a yellow oil. $^1$H NMR (400 MHz, CDCl$_3$): δ 8.10-8.01 (m, 2H), 7.61-7.53 (m, 1H), 7.49-7.41 (m, 2H), 3.92-3.75 (m, 2H), 3.46-3.33 (m, 1H), 3.13-3.04 (m, 1H), 2.83-2.55 (m, 3H), 2.19-2.11 (m, 1H), 1.93-1.72 (m, 5H), 1.70-1.53 (m, 2H). LCMS [ESI, M+1]: 276.

Intermediate B-26

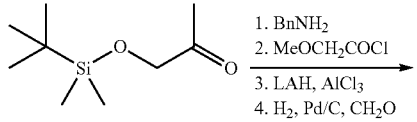
1. BnNH$_2$
2. MeOCH$_2$COCl
3. LAH, AlCl$_3$
4. H$_2$, Pd/C, CH$_2$O

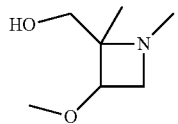

A mixture of 1-((tert-butyldimethylsilyl)oxy)propan-2-one (25.0 g, 133 mmol, 1.0 equiv), phenylmethanamine (14.2 g, 133 mmol, 14.5 mL, 1.0 equiv), and 4 Å MS (25.0 g) in dichloromethane (100 mL) was stirred at 45° C. for 12 h. To this suspension at −78° C. was added dropwise a mixture of 2-methoxyacetyl chloride (18.3 g, 168 mmol, 15.4 mL, 1.3 equiv) and TEA (30.6 g, 302 mmol, 42.1 mL, 2.3 equiv) in dichloromethane (20.0 mL). The mixture was allowed to warm to room temperature and stirred for 12 h and then filtered. The filtrate was diluted with saturated aq NH$_4$Cl (100 mL) and concentrated under reduced pressure to remove the volatiles. The remaining aqueous phase was extracted with ethyl acetate (100 mL×2). The combined organic layer was washed with brine (100 mL×1), dried over anh Na$_2$SO$_4$ and filtered. The filtrate was concentrated under reduced pressure to provide the crude residue. The crude product was purified by reversed-phase flash chromatography to afford 1-benzyl-4-(((tert-butyldimethylsilyl)oxy) methyl)-3-methoxy-4-methylazetidin-2-one (7.00 g, 13.4% yield) as a brown oil. $^1$H NMR (400 MHz, CDCl$_3$): δ 7.35-7.28 (m, 5H), 4.46-4.33 (m, 2H), 4.11 (s, 1H), 3.68-3.59 (m, 2H), 3.51 (s, 3H), 1.25-1.22 (m, 1H), 1.24 (s, 2H), 0.89-0.87 (m, 9H), 0.00 (d, J=8.0 Hz, 6H).

To a mixture of AlCl$_3$ (916 mg, 6.87 mmol, 1.2 equiv) in THF (20.0 mL) at −10° C. was added LiAlH$_4$ (434 mg, 11.4 mmol, 2.0 equiv) and the mixture was warmed to 25° C. and stirred for 3 hours. To this mixture at −10° C. was added dropwise a solution of 1-benzyl-4-(((tert-butyldimethylsilyl) oxy)methyl)-3-methoxy-4-methylazetidin-2-one (2.00 g, 5.72 mmol, 1.0 equiv) in THF (10 mL) and the mixture was stirred at 25° C. for 30 minutes. Subsequently, the mixture was diluted with water (434 μL) at 0° C., 15% aq NaOH (434 μL) and water (1.30 mL). The suspension was filtered, washed with THF (20.0 mL) and the filtrate was concentrated under reduced pressure to provide the crude residue. The crude product was purified by reversed-phase flash chromatography to afford 1-benzyl-2-(((tert-butyldimethylsilyl)oxy)methyl)-3-methoxy-2-methylazetidine (700 mg, 35.7% yield) as a yellow oil. $^1$H NMR (400 MHz, CDCl$_3$): δ 7.34-7.27 (m, 4H), 7.25-7.20 (m, 1H), 3.84-3.69 (m, 4H), 3.62 (br d, J=12.8 Hz, 1H), 3.41-3.31 (m, 1H), 3.30 (s, 3H), 3.06 (br s, 1H), 1.30 (s, 3H), 0.91 (s, 9H), 0.07 (d, J=2.8 Hz, 6H).

To a solution of 1-benzyl-2-(((tert-butyldimethylsilyl) oxy)methyl)-3-methoxy-2-methylazetidine (700 mg, 2.09 mmol, 1.0 equiv) in MeOH (20.0 mL) was added formalin (2.18 g, 2.00 mL, 37% in water) and Pd/C (300 mg, 10% wt/wt) under N$_2$. The suspension was evacuated under vacuum and purged with H$_2$ several times. The mixture was stirred under H$_2$ (15 psi) at 25° C. for 12 hours. Subsequently, the mixture was adjusted to pH 4 with HCl in dioxane (4 M) and recharged with hydrogen (45 psi). The mixture was continued to stir at 25° C. for 16 hours. The mixture was flushed with nitrogen, filtered and the filtrate was concentrated. The residue was purified by column chromatography [SiO$_2$, petroleum ether/ethyl acetate, 1:0 to 0:1 to ethyl acetate/ethyl alcohol (1% NH$_4$OH), 3:1] to afford (3-methoxy-1,2-dimethylazetidin-2-yl)methanol (454 mg, crude) as a light yellow solid. $^1$H NMR (400 MHz, CDCl$_3$): δ 4.18 (d, J=12.8 Hz, 1H), 3.91 (dd, J=4.4, 6.8 Hz, 1H), 3.62-3.57 (m, 2H), 3.56 (d, J=6.8 Hz, 1H), 3.32 (s, 3H), 2.53 (s, 3H), 1.41 (s, 3H).

Intermediate B-27

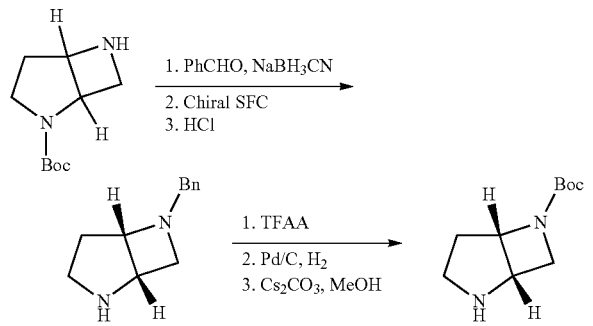

To a mixture of tert-butyl 2,6-diazabicyclo[3.2.0]heptane-2-carboxylate (412 mg, 2.08 mmol, 1.0 equiv) and benzaldehyde (661 mg, 6.23 mmol, 630 μL, 3.0 equiv) in MeOH (10.0 mL) was added AcOH (249 mg, 4.16 mmol, 238 μL, 2.0 equiv). The mixture was stirred at 25° C. for 10 min and then cooled to 0° C. To this solution was added NaBH$_3$CN (392 mg, 6.23 mmol, 3.0 equiv) and the mixture was stirred at 0° C. for 1 h and then was concentrated under reduced pressure. The residue was taken up in ethyl acetate (20 mL) and washed with satd aq NaHCO$_3$. The organic layer was separated, dried over anh sodium sulfate, filtered and concentrated at reduced pressure. The residue was purified by prep-HPLC [Phenomenex luna C18 150×40 mm×15 μm; A: water (0.225% FA), B: ACN, B %: 2-32%, 11 min]. The enantiomers were separated by chiral SFC [daicel chiralpak AD-H (250 mm×30 mm×5 μm); A: 0.1% NH$_4$OH in MeOH, B: CO$_2$, B %: 20%] to provide tert-butyl (1S,5S)-6-benzyl-2,6-diazabicyclo[3.2.0]heptane-2-carboxylate (239 mg, 25% yield) as a white solid. Analytical SFC conditions: [Chiralpak AD-3 50×4.6 mm I.D., 3 μm, A: CO$_2$, B: MeOH (0.05% DEA), B: 5% to 40%, 3 mL/min, column temp: 35° C., back pressure: 100 Bar, t$_R$=0.724 min, isomer=0.607 min]. LCMS [ESI, M+1]: 289.

To a solution of tert-butyl (1S,5S)-6-benzyl-2,6-diazabicyclo[3.2.0]heptane-2-carboxylate (239 mg, 829 μmol, 1.0 equiv) in MeCN (5.00 mL) was added HCl (4 M in dioxane, 10.0 mL, 48.3 equiv). The mixture was stirred at 25° C. for 0.5 hour and was subsequently concentrated at reduced pressure to afford (1S,5S)-6-benzyl-2,6-diazabicyclo[3.2.0]heptane (186 mg, bis-HCl salt).

To a solution of (1S,5S)-6-benzyl-2,6-diazabicyclo[3.2.0]heptane (186 mg, 828 μmol, 1.0 equiv, bis-HCl) in DCM (5.00 mL) at 0° C. was added TEA (335 mg, 3.31 mmol, 461 μL, 4.0 equiv) and TFAA (209 mg, 993 μmol, 138 μL, 1.2 equiv). The reaction was stirred at this temperature for 1 h prior to being diluted with water (5 mL). The aqueous layer was extracted with ethyl acetate (10 mL×3). The combined organic layer was dried over anh sodium sulfate, filtered and concentrated at reduced pressure. The resultant residue was purified by column chromatography (SiO$_2$, petroleum ether/ethyl acetate, 20:1 to 3:1) to afford 1-((1S,5S)-6-benzyl-2,6-diazabicyclo[3.2.0]heptan-2-yl)-2,2,2-trifluoroethan-1-one (80.0 mg, 34% over two steps) as a yellow oil. LCMS [ESI, M+1]: 285.

To a solution of 1-((1S,5S)-6-benzyl-2,6-diazabicyclo[3.2.0]heptan-2-yl)-2,2,2-trifluoroethan-1-one (80.0 mg, 281 μmol, 1.0 equiv) and Boc$_2$O (184 mg, 844 μmol, 194 μL, 3.0 equiv) in MeOH (10.0 mL) under nitrogen was added Pd/C (40.0 mg, 10 wt. %). The mixture was stirred at 50° C. for 16 h under H$_2$ (50 psi). The system was flushed with nitrogen and the suspension was filtered through a plug of Celite and concentrated at reduced pressure. The residue was purified by column chromatography (SiO$_2$, petroleum ether/ethyl acetate, 20:1 to 3:1) to afford tert-butyl (1S,5S)-2-(2,2,2-trifluoroacetyl)-2,6-diazabicyclo[3.2.0]heptane-6-carboxylate (60.0 mg. 71% yield) as a yellow oil. LCMS [ESI, M−55]: 239.

To a solution of tert-butyl (1S,5S)-2-(2,2,2-trifluoroacetyl)-2,6-diazabicyclo[3.2.0]heptane-6-carboxylate (60.0 mg, 204 μma 1.0 equiv) in MeOH (5.00 mL) at room temperature was added Cs$_2$CO$_3$ (66.4 mg, 204 μma 1.0 equiv) and H$_2$O (0.200 mL). The reaction mixture was stirred at 40° C. for 30 min and was subsequently concentrated under reduced pressure. The residue was diluted with ethyl acetate (10 mL), dried over anh sodium sulfate, filtered and concentrated at reduced pressure to afford tert-butyl (1S,5S)-2,6-diazabicyclo[3.2.0]heptane-6-carboxylate (41.0 mg, crude) as a colorless oil.

Intermediate B-28

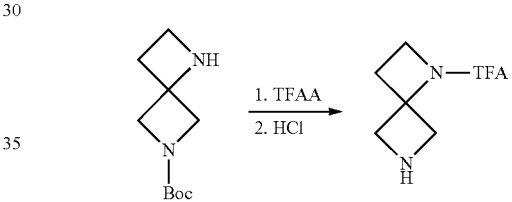

To a solution of tert-butyl 1,6-diazaspiro[3.3]heptane-6-carboxylate (500 mg, 2.06 mmol, 1.0 equiv, 0.5 oxalic acid) in DCM (10 mL) at 0° C. was added TEA (520 mg, 5.14 mmol, 715 μL, 2.5 equiv) followed by TFAA (518 mg, 2.47 mmol, 343 μL, 1.2 equiv). The reaction was warmed to 25° C. and stirred for 1 h. An additional portion of TEA (312 mg, 3.08 mmol, 429 μL, 1.5 equiv) and TFAA (647 mg, 3.08 mmol, 429 μL, 1.5 equiv) was added and the reaction was stirred at 25° C. for an additional hour. The mixture was diluted with water (10 mL) and the aqueous phase was extracted with ethyl acetate (3×10 mL). The combined organic layer was dried over anhydrous Na$_2$SO$_4$, filtered and concentrated at reduced pressure. The resultant residue was purified by silica gel chromatography (petroleum ether/ethyl acetate, 5:1 to 1:1) to afford tert-butyl 1-(2,2,2-trifluoroacetyl)-1,6-diazaspiro[3.3]heptane-6-carboxylate (390 mg, 64%) as a yellow solid. R$_f$=0.98 (10:1, dichloromethane/methanol); $^1$H NMR (400 MHz, CDCl$_3$): δ 4.69-4.67 (d, J=10.0 Hz, 2H), 4.31-4.24 (m, 2H), 3.98-3.95 (d, J=9.6 Hz, 2H), 2.63-2.59 (t, J=7.6 Hz, 2H), 1.44 (s, 9H).

To a solution of tert-butyl 1-(2,2,2-trifluoroacetyl)-1,6-diazaspiro[3.3]heptane-6-carboxylate (390 mg, 1.33 mmol, 1.0 equiv) at 0° C. in ACN (3.0 mL) was added HCl (4 M in dioxane, 4.97 mL, 15 equiv). The mixture was stirred at this temperature for 1 h and was concentrated at reduced pressure to afford 2,2,2-trifluoro-1-(1,6-diazaspiro[3.3]heptan-1-yl)ethan-1-one (400 mg, crude, HCl salt) as a yellow solid.

Intermediate B-29

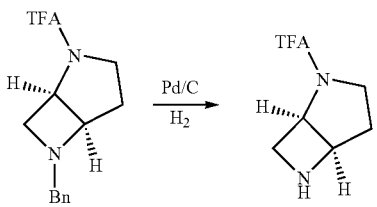

To a solution of 1-((1R,5R)-6-benzyl-2,6-diazabicyclo[3.2.0]heptan-2-yl)-2,2,2-trifluoroethan-1-one (1.50 g, 5.28 mmol, 1.0 equiv) in MeOH (100 mL) was added Pd/C (1.00 g, 10 wt. %). The mixture was stirred at 40° C. for 16 h under hydrogen (50 psi). The system was purged with nitrogen and the mixture was filtered through a plug of Celite. The filtrate was concentrated at reduced pressure to afford 1-(((1R,5R)-2,6-diazabicyclo[3.2.0]heptan-2-yl)-2,2,2-trifluoroethan-1-one (1.00 g, crude) as a colorless oil.

Intermediates B-30 and B-31

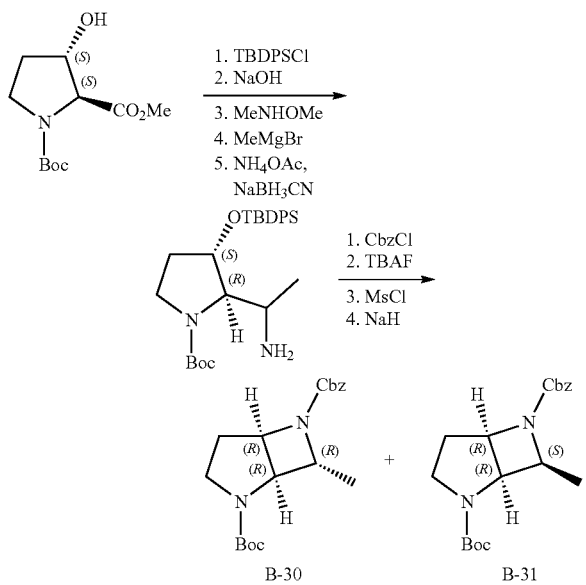

To a mixture of compound 1-(tert-butyl) 2-methyl (2S,3S)-3-hydroxypyrrolidine-1,2-dicarboxylate (100 g, 407.7 mmol, 1.00 equiv) in DMF (1.3 L) at 0° C. was added DMAP (4.98 g, 40.7 mmol, 0.100 equiv), TBDPSCl (126 mL, 489.3 mmol, 1.2 equiv) and imidazole (138.8 g, 2.04 mol, 5.0 equiv). The mixture was stirred at 20° C. for 2 h prior to being poured into water (2500 mL) and extracted with EtOAc (1000 mL×3). The combined organic layer was washed with brine (1500 mL×3), dried with anhydrous $Na_2SO_4$, filtered and concentrated in vacuum. The crude product was purified by silica gel column chromatography (petroleum ether/ethyl acetate, 50:1 to 10:1) to give 1-(tert-butyl) 2-methyl (2S,3S)-3-((tert-butyldiphenylsilyl)oxy)pyrrolidine-1,2-dicarboxylate (90 g, 186.1 mmol, 45.6% yield) as a yellow oil. LCMS [ESI, M+1]: 384.2; $^1$H NMR (400 MHz, $CDCl_3$): δ 7.66-7.64 (m, 4H), 7.41-7.39 (m, 6H), 4.39-4.38 (m, 1H), 4.33-4.18 (m, 1H), 3.64-3.58 (m, 5H), 1.84-1.80 (m, 2H), 1.65-1.41 (m, 9H), 1.03 (s, 9H).

The mixture of compound 1-(tert-butyl) 2-methyl (2S,3S)-3-((tert-butyldiphenylsilyl)oxy)pyrrolidine-1,2-dicarboxylate (90.0 g, 186.1 mmol, 1.00 equiv) in EtOH (200 mL) was added the solution of NaOH (14.9 g, 372.2 mmol, 2.00 equiv) in water (20 mL). The mixture was stirred at room temperature for 1 h prior to being poured into water (500 mL) and adjusted to pH 6 with 0.1 M HCl. The mixture partially concentrated to remove the EtOH and then was extracted with EtOAc (150 mL×3). The organic layer was dried over anh $Na_2SO_4$, filtered and concentrated to dryness to afford (2S,3S)-1-(tert-butoxycarbonyl)-3-((tert-butyldiphenylsilyl)oxy)pyrrolidine-2-carboxylic acid (88 g) as a colorless oil. $^1$H NMR (400 MHz, $CDCl_3$): δ 7.73-7.43 (m, 4H), 7.40-7.37 (m, 6H), 4.75-4.47 (m, 1H), 4.25-4.12 (m, 1H), 3.68-3.43 (m, 2H), 1.84-1.82 (m, 2H), 1.52-1.40 (m, 8H), 1.23 (s, 9H).

To a mixture of (2S,3S)-1-(tert-butoxycarbonyl)-3-((tert-butyldiphenylsilyl)oxy)pyrrolidine-2-carboxylic acid (82.0 g, 174.6 mmol, 1.00 equiv) and N-methoxymethanamine (16.5 g, 168.6 mmol, 1.20 equiv, HCl salt) in ACN (600 mL) was added $Et_3N$ (59 mL, 421.6 mmol, 3.00 equiv) and T3P (125 mL, 211 mmol, 50.0% in EtOAc, 1.50 equiv). The reaction mixture was stirred at 20° C. for 10 h prior to being concentrated, poured into water (3 L) and extracted with EtOAc (1000 mL×3). The combined organic layer was washed with water (2000 mL×3), dried over anh $Na_2SO_4$, filtered and concentrated to dryness. The residue was purified by silica gel chromatography (petroleum ether/ethyl acetate, 10:1 to 1:1) to provide compound tert-butyl (2S,3S)-3-((tert-butyldiphenylsilyl)oxy)-2-(methoxy(methyl)carbamoyl)pyrrolidine-1-carboxylate (63.0 g, 122.9 mmol, 87.4% yield) as a yellow oil. LCMS [ESI, M−100]: 413.2; $^1$H NMR (400 MHz, $CDCl_3$): δ 7.69-7.66 (m, 4H), 7.44-7.39 (m, 6H), 4.85-4.82 (m, 1H), 4.36-4.33 (m, 1H), 3.72-3.69 (m, 2H), 3.63-3.53 (m, 3H), 3.38-3.06 (m, 3H), 1.89-1.83 (m, 2H), 1.74-1.50 (d, 9H) 1.03 (s, 9H).

To a solution of compound tert-butyl (2S,3S)-3-((tert-butyldiphenylsilyl)oxy)-2-(methoxy(methyl)carbamoyl)pyrrolidine-1-carboxylate (60 g, 117.0 mmol) in THF (200 mL) at −70° C. was added MeMgBr (3.00 M, 78.02 mL, 2.00 equiv) under an atmosphere of nitrogen.

The mixture allowed to warm to room temperature and stirred for 10 h. The reaction mixture was diluted with $NH_4Cl$ (1.50 L) and extracted with EtOAc (500 mL×3). The combined organic layer was dried over anh $Na_2SO_4$, filtered and concentrated to dryness. The residue was purified by silica gel chromatography (petroleum ether/ethyl acetate, 20:1 to 3:1) to provide tert-butyl (2S,3S)-2-acetyl-3-((tert-butyldiphenylsilyl)oxy)pyrrolidine-1-carboxylate (54 g, 115.5 mmol, 98.7% yield) as a yellow oil.

To a mixture of tert-butyl (2S,3S)-2-acetyl-3-((tert-butyldiphenylsilyl)oxy)pyrrolidine-1-carboxylate (46 g, 98.36 mmol, 1.00 equiv) in MeOH (500 mL) was added $NH_4OAc$ (303 g, 3.93 mol, 40 equiv) and $NaBH_3CN$ (7.42 g, 118.0 mmol, 1.2 equiv). The mixture was stirred at 85° C. for 1 h prior to being concentrated. To the residue was added water (1.00 L) and the mixture was extracted with EtOAc (500 mL×3). The combined organic layer was dried over anh sodium sulfate, filtered and concentrated to dryness to provide tert-butyl (2R,3S)-2-(1-aminoethyl)-3-((tert-butyldiphenylsilyl)oxy)pyrrolidine-1-carboxylate (51 g) as a light-yellow oil. LCMS [ESI, M+1]: 469.2.

To a mixture of tert-butyl (2R,3S)-2-(1-aminoethyl)-3-((tert-butyldiphenylsilyl)oxy)pyrrolidine-1-carboxylate (57 g, 121.61 mmol, 1.00 equiv) and $Et_3N$ (51 mL, 364.8 mmol, 3.00 equiv) in DCM (500 mL) was added CbzCl (18 mL, 123 mmol, 1.0 equiv). The mixture was stirred at 20° C. for 1 h prior to being diluted with water (1000 mL) and extracted with EtOAc (500 mL×3). The organic layer was dried over anhydrous $Na_2SO_4$, filtered and concentrated. The residue was purified by silica gel chromatography (petroleum ether/ethyl acetate, 10:1 to 3:1) to afford tert-butyl (2R,3S)-2-(1-(((benzyloxy)carbonyl)amino)ethyl)-3-((tert-butyldiphenylsilyl)oxy)pyrrolidine-1-carboxylate (25 g, 41.47 mmol, 34% yield) as a yellow oil. LCMS [ESI, M+1]: 603.4.

To a mixture of tert-butyl (2R,3S)-2-(1-(((benzyloxy)carbonyl)amino)ethyl)-3-((tert-butyldiphenylsilyl)oxy)pyrrolidine-1-carboxylate (25.00 g, 41.5 mmol, 1.00 equiv) in DMF (200 mL) was added TBAF (1.00 M in THF, 50 mL, 1.2 equiv). The mixture was stirred at 20° C. for 2 h prior to being diluted with water (500 mL) and extracted with EtOAc (200 mL×3). The combined organic layer was washed with brine (300 mL), dried over anhydrous $Na_2SO_4$, filtered and concentrated. The residue was purified by silica gel chromatography (petroleum ether/ethyl acetate, 10:1 to 2:1) to afford tert-butyl (2R,3S)-2-(1-(((benzyloxy)carbonyl)amino)ethyl)-3-hydroxypyrrolidine-1-carboxylate (7.00 g, 19.2 mmol, 46.3% yield) as a yellow oil. LCMS [ESI, M+1]: 364.2.

To a mixture of tert-butyl (2R,3S)-2-(1-(((benzyloxy)carbonyl)amino)ethyl)-3-hydroxypyrrolidine-1-carboxylate (7.00 g, 19.2 mmol, 1.00 equiv) and TEA (5.4 mL, 38 mmol, 2.0 equiv) in DCM (100 mL) was added MSCl (3.0 mL, 38 mmol, 2.0 equiv). The mixture was stirred at room temperature for 60 h prior to being diluted with water (150 mL). The mixture was extracted with DCM (50 mL×3). The combined organic layer was washed with water (50 mL×3), dried over anh sod sulfate, filtered and concentrated. The residue was purified by silica gel chromatography (petroleum ether/ethyl acetate, 10:1 to 1:1) and then by reverse phase chromatography [Phenomenex luna C18 250×50 mm×10 µm; A: water (0.225% FA), B: ACN; B %: 30%-60%, 15 min] to give tert-butyl (2R,3S)-2-(1-(((benzyloxy)carbonyl)amino)ethyl)-3-((methylsulfonyl)oxy)pyrrolidine-1-carboxylate (8.2 g) as a yellow oil. LCMS [ESI, M+1]: 343.0.

To the mixture of NaH (1.30 g, 32.5 mmol, 60.0% purity, 2.0 equiv) in DMF (70.0 mL) at room temperature was added dropwise a solution of tert-butyl (2R,3S)-2-(1-(((benzyloxy)carbonyl)amino)ethyl)-3-((methylsulfonyl)oxy)pyrrolidine-1-carboxylate (7.20 g, 16.3 mmol, 1.00 equiv) in DMF (20 mL). The mixture was stirred at room temperature for 1 h prior to being diluted with satd aq $NaHCO_3$ (200 mL) and extracted with EtOAc (200 mL×3). The organic layer was dried over anhydrous $Na_2SO_4$, filtered and concentrated. The residue was purified by prep-HPLC [Phenomenex luna C18 (250×70 mm, 10 µm); A: [water (0.1% TFA)], B: ACN; B %: 40%-70%, 20 min] and then 4 g of the mixture by chiral SFC [DAICEL CHIRALPAK IG (250 mm×30 mm, 10 µm); A: MeOH (0.1% $NH_4OH$), B: $CO_2$; B %: 40%, 4.5 min] to provide 6-benzyl 2-(tert-butyl) (1R,5R,7R)-7-methyl-2,6-diazabicyclo[3.2.0]heptane-2,6-dicarboxylate (B-30) (Pt eluting) (1.5 g) as a yellow oil. $^1H$ NMR (400 MHz, $CDCl_3$): δ 7.37-7.27 (m, 5H), 5.10 (m, 2H), 4.80-4.77 (m, 1H), 4.48-4.43 (m, 2H), 4.15-3.96 (m, 1H), 3.46-3.41 (m, 1H), 3.19-3.16 (m, 1H), 2.14-2.05 (m, 1H), 1.76-1.72 (m, 1H) 1.47-1.45 (m, 9H), 1.26-1.19 (m, 3H). The second eluting peak, 6-benzyl 2-(tert-butyl) (1R,5R,7S)-7-methyl-2,6-diazabicyclo[3.2.0]heptane-2,6-dicarboxylate (B-31) was obtained as a yellow oil. $^1H$ NMR (400 MHz, $CDCl_3$): δ 7.38-7.27 (m, 5H), 5.17-5.13 (m, 2H), 4.87-4.86 (m, 1H), 4.03-3.79 (m, 3H), 3.47 (s, 1H), 2.41-2.36 (m, 1H), 1.84-1.81 (m, 1H), 1.78-1.26 (m, 12H).

Intermediate B-32

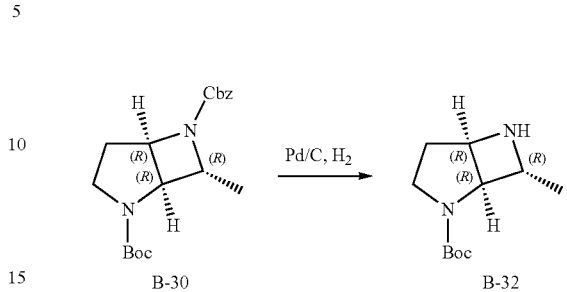

A mixture of 6-benzyl 2-(tert-butyl) (1R,5R,7R)-7-methyl-2,6-diazabicyclo[3.2.0]heptane-2,6-dicarboxylate (B-30) (600 mg, 1.73 mmol, 1.00 equiv) and Pd/C (200 mg, 10.0 wt. %) in MeOH (10.0 mL) was stirred under $H_2$ (15.0 psi) at 15° C. for 1 h. The vessel was flushed with nitrogen and reaction mixture was filtered and the filtrate was concentrated to afford tert-butyl (1R,5R,7R)-7-methyl-2,6-diazabicyclo[3.2.0]heptane-2-carboxylate (B-32) (278.9 mg, 1.24 mmol, 71.6% yield, 94% purity) as a white solid. $^1H$ NMR (400 MHz, $CDCl_3$): δ 4.37 (s, 1H), 3.86-3.78 (m, 1H), 3.59-3.49 (m, 2H), 3.19-3.16 (m, 1H), 1.68-1.64 (m, 2H), 1.39-1.36 (m, 9H), 1.23-1.21 (m, 3H).

Intermediate B-33

Procedure as with B-32: tert-butyl (1R,5R,7S)-7-methyl-2,6-diazabicyclo[3.2.0]heptane-2-carboxylate (B-33) as a white solid; LCMS [ESI, M+1]: 213.3; $^1H$ NMR (400 MHz, $CDCl_3$): δ 4.30-4.16 (m, 2H), 3.87-3.68 (m, 1H), 3.40-3.38 (m, 1H), 3.36-3.22 (m, 1H), 1.55-1.52 (m, 2H), 1.47-1.36 (d, 9H), 0.84-0.79 (m, 3H)

In addition to the foregoing Intermediates above, the following exemplary Intermediates C-1-C-25 may be used to couple -L-$R^4$ to the azaquinazoline core of Formula (I).

Intermediate C-1

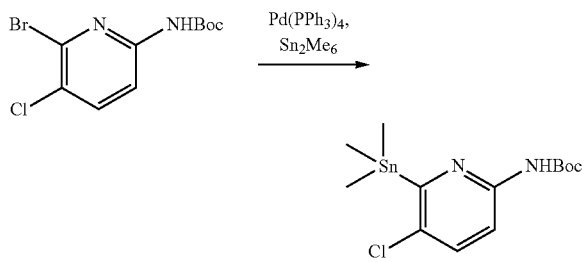

A mixture of trimethyl(trimethylstannyl)stannane (12.6 g, 38.4 mmol, 7.97 mL, 3.7 equiv), tert-butyl N-(6-bromo-5-chloro-2-pyridyl)carbamate (3.2 g, 10.4 mmol, 1.0 equiv), $Pd(PPh_3)_4$ (1.20 g, 1.04 mmol, 0.1 equiv) in toluene (60 mL) was purged with $N_2$ and then the mixture was stirred at 100° C. for 12 h. The reaction mixture was filtered and concentrated. The residue was purified by reversed phase flash chromatography [water (0.1% formic acid)/acetonitrile]. The mixture was concentrated under reduced pressure to give tert-butyl N-(5-chloro-6-trimethylstannyl-2-pyridyl) carbamate (2.5 g, 6.39 mmol, 61% yield) as a brown solid. LCMS [ESI, M+1]: 393.

Intermediate C-2

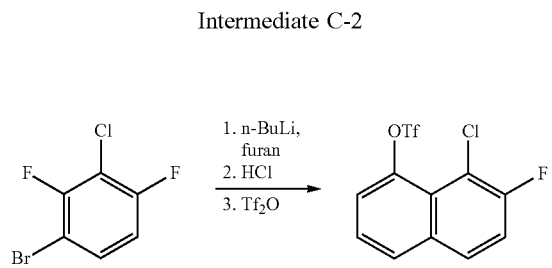

To a mixture of 1-bromo-3-chloro-2,4-difluorobenzene (250 g, 1.10 mol, 1.00 equiv) and furan (150 g, 2.20 mol, 160 mL, 2.00 equiv) in toluene (2.50 L) at −15° C. was added n-BuLi (2.50 M, 528 mL, 1.2 equiv) dropwise over 0.5 hour. The mixture was allowed to warm to room temperature and stirring continued for 12 h. Subsequently, the mixture was quenched with water (2 L) and was filtered. The organic layer was collected and the aqueous layer was extracted with ethyl acetate (2 L×2). The combined organic layer was dried over anh $Na_2SO_4$ and filtered. The filtrate was concentrated under vacuum. The residue was purified by reversed phase flash [C18, 0.1% FA in water, 0-80% MeCN] to afford 5-chloro-6-fluoro-1,4-dihydro-1,4-epoxynaphthalene (81.0 g, 37% yield) as a yellow oil. $^1$H NMR (400 MHz, $CDCl_3$): δ 7.11-7.06 (m, 2H), 7.06-7.01 (m, 1H), 6.73 (dd, J=7.6, 9.6 Hz, 1H), 5.88 (s, 1H), 5.74 (s, 1H).

A mixture of 5-chloro-6-fluoro-1,4-dihydro-1,4-epoxynaphthalene (162 g, 824 mmol, 1.00 equiv) in concentrated hydrochloric acid (1.02 kg, 10.1 mol, 1.00 L, 12.2 equiv) and ethyl alcohol (1.20 L) was heated at 80° C. with stirring for 6 h. Subsequently, the reaction mixture was concentrated under vacuum. The residue was adjusted to pH ~7 with saturated aq $NaHCO_3$ and then extracted with ethyl acetate (2 L×2). The combined organic layer was dried over anh $Na_2SO_4$, and filtered. The filtrate was concentrated under vacuum. The residue was triturated with petroleum ether (100 mL), and then filtered; the filter cake was dried under vacuum to afford 8-chloro-7-fluoronaphthalen-1-ol (124 g, 76% yield) a white solid. $^1$H NMR (400 MHz, $CDCl_3$): δ 7.92 (s, 1H), 7.75 (dd, J=5.2, 8.8 Hz, 1H), 7.44-7.36 (m, 2H), 7.33-7.26 (m, 1H), 7.12-7.06 (m, 1H).

A mixture of 8-chloro-7-fluoronaphthalen-1-ol (124 g, 631 mmol, 1.00 equiv), DIEA (489 g, 3.78 mol, 659 mL, 6.00 equiv), 4 Å MS (120 g) in dichloromethane (1.5 L) was stirred for 10 minutes at 20° C. To this suspension cooled to −40° C. was added dropwise trifluoromethylsulfonyl trifluoromethanesulfonate (231 g, 820 mmol, 135 mL, 1.30 equiv). After 20 min the reaction mixture was diluted with water (1 L) and the organic layer was collected. The aqueous layer was then extracted with ethyl acetate (1 L×2). The combined organic layer was dried over anh $Na_2SO_4$ and filtered. The filtrate was concentrated under vacuum. The residue was purified by silica gel chromatography (petroleum ether:ethyl acetate, 1:0 to 20:1) to afford 8-chloro-7-fluoronaphthalen-1-yl trifluoromethanesulfonate (196 g, 92% yield). Yellow solid; $^1$H NMR (400 MHz, $CDCl_3$) δ 7.86 (d, J=8.0 Hz, 1H), 7.83-7.76 (m, 1H), 7.57 (d, J=8.0 Hz, 1H), 7.53-7.44 (m, 1H), 7.43-7.35 (m, 1H).

Intermediate C-3

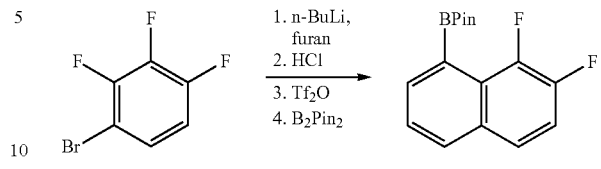

To a mixture of 1-bromo-2,3,4-trifluorobenzene (10.0 g, 47.4 mmol, 5.62 mL, 1.0 equiv) and furan (6.45 g, 94.8 mmol, 6.89 mL, 2.0 equiv) in toluene (130 mL)−15° C. was added n-BuLi (2.50 M, 22.7 mL, 1.2 equiv) in one portion under $N_2$. The mixture was stirred at −15° C. for 30 minutes and was then warmed to room temperature and stirred for 12 hours. Subsequently, the reaction mixture was diluted with water (100 mL) and filtered. The aqueous layer was extracted with ethyl acetate (3×100 mL). The combined organic layer was dried over anh $Na_2SO_4$, filtered and concentrated under reduced pressure. The residue was purified by reversed-phase flash [C18, 0.1% FA in water, 0-65% MeCN]. The fractions were concentrated under vacuum and extracted with ethyl acetate (3×100 mL). The combined organic layer was dried over anh $Na_2SO_4$, filtered and concentrated under vacuum to afford 5,6-difluoro-1,4-dihydro-1,4-epoxynaphthalene (1.6 g, 19% yield) as a yellow oil. $^1$H NMR (400 MHz, $CDCl_3$): δ 7.11-7.06 (m, 2H), 6.93 (dd, J=3.2, 7.6 Hz, 1H), 6.77-6.74 (m, 1H), 5.98 (s, 1H), 5.72 (s, 1H).

To a solution of 5,6-difluoro-1,4-dihydro-1,4-epoxynaphthalene (4.30 g, 23.9 mmol, 1.0 equiv) in EtOH (90.0 mL) was added conc HCl (40.6 g, 334 mmol, 39.8 mL, 14.0 equiv) at 25° C. The mixture was stirred at 80° C. for 2 hours. The mixture was cooled to room temperature and was concentrated under vacuum. The residue was purified by reversed phase flash chromatography [C18, 0.1% FA in water, 0-80% MeCN]. The fractions were adjusted to pH 8 with $Na_2CO_3$ extracted with ethyl acetate (2×100 mL). The combined organic layer was dried over anh $Na_2SO_4$, filtered and concentrated under vacuum to give 7,8-difluoronaphthalen-1-ol (3.8 g, 88% yield) as a black solid. $^1$H NMR (400 MHz, $CDCl_3$): δ 7.51-7.49 (m, 1H), 7.31-7.29 (m, 2H), 7.20-7.17 (m, 1H), 6.95-6.93 (m, 1H), 6.59-6.53 (m, 1H).

A mixture of 7,8-difluoronaphthalen-1-ol (3.30 g, 18.3 mmol, 1.0 equiv), DIEA (11.8 g, 91.5 mmol, 16.0 mL, 5.0 equiv) and 4 Å MS (3.00 g, 18.3 mmol, 1.0 equiv) in dichloromethane (10.0 mL) was stirred for 10 minutes at 20° C. The mixture was cooled to −40° C. followed by the addition of $Tf_2O$ (6.72 g, 23.8 mmol, 3.93 mL, 1.3 equiv) and continued stirring at this temperature for 30 min. The reaction mixture was diluted with $H_2O$ (10 mL) and extracted with ethyl acetate (3×15 mL). The combined organic layer was washed with brine (40 mL), dried over anh $Na_2SO_4$, filtered and concentrated under reduced pressure to give a residue. The residue was purified by column chromatography ($SiO_2$, petroleum ether/ethyl acetate, 1:0 to 50:1) to afford 7,8-difluoronaphthalen-1-yl trifluoromethanesulfonate (5.58 g, 98% yield) as a red oil. $^1$H NMR (400 MHz, $CDCl_3$): δ 7.89-7.87 (m, 1H), 7.73-7.67 (m, 1H), 7.52-7.46 (m, 3H).

To a mixture of 7,8-difluoronaphthalen-1-yl trifluoromethanesulfonate (1.50 g, 4.80 mmol, 1.0 equiv) and 4,4,5,5-tetramethyl-2-(4,4,5,5-tetramethyl-1,3,2-dioxaborolan-2-yl)-1,3,2-dioxaborolane (3.05 g, 12.0 mmol, 2.5 equiv) in dioxane (15.0 mL) was added Pd(dppf)Cl₂ (352 mg, 480 μmol, 0.1 equiv) and KOAc (1.41 g, 14.4 mmol, 3.0 equiv) under N₂. The mixture was stirred at 25° C. for 5 minutes and then heated to 100° C. and stirred for 16 h. Subsequently, the reaction mixture was diluted with H₂O (40 mL) and extracted with ethyl acetate (3×30 mL). The combined organic layer was washed with brine (80 mL), dried over anh Na₂SO₄, filtered and concentrated under reduced pressure to give a residue. The residue was purified by column chromatography (SiO₂, petroleum ether/ethyl acetate, 1:0 to 100:1) to afford 2-(7,8-difluoronaphthalen-1-yl)-4,4,5,5-tetramethyl-1,3,2-dioxaborolane (1.28 g, 92% yield) as a white solid. ¹H NMR (400 MHz, CDCl₃): δ 7.86-7.84 (m, 1H), 7.73-7.71 (m, 1H), 7.61-7.58 (m, 1H), 7.49-7.45 (m, 1H), 7.37-7.32 (m, 1H), 1.46 (s, 12H).

Intermediate C-4

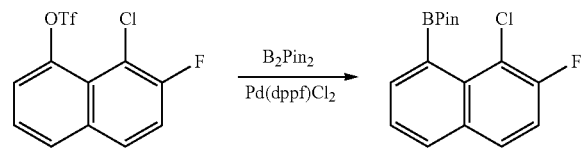

A mixture of 8-chloro-7-fluoronaphthalen-1-yl trifluoromethanesulfonate (27.0 g, 82.1 mmol, 1.00 equiv), (PinB)₂ (41.7 g, 164 mmol, 2.00 equiv), KOAc (40.3 g, 411 mmol, 5.00 equiv) and Pd(dppf)Cl₂ (6.01 g, 8.22 mmol, 0.10 equiv) in DMF (300 mL) was purged with nitrogen and then the mixture was stirred at 80° C. for 12 h. The mixture was cooled to room temperature and was diluted with ethyl acetate (500 mL) and water (400 mL). The organic layer was separated and the aqueous layer was extracted with ethyl acetate (400 mL×2). The combined organic layer was washed with brine (800 mL), dried over anh Na₂SO₄ and filtered. The filtrate was concentrated under vacuum. The residue was purified by column chromatography (SiO₂, petroleum ether/ethyl acetate, 1:0 to 50:1) to afford 2-(8-chloro-7-fluoronaphthalen-1-yl)-4,4,5,5-tetramethyl-1,3,2-dioxaborolane (19 g, 74% yield) as a white solid. ¹H NMR (400 MHz, CDCl₃): δ 7.86 (dd, J=1.2, 8.4 Hz, 1H), 7.76 (dd, J=5.6, 9.2 Hz, 1H), 7.71 (d, J=6.8 Hz, 1H), 7.49 (dd, J=7.2, 8.0 Hz, 1H), 7.33 (t, J=8.8 Hz, 1H), 1.46 (s, 12H).

Intermediate C-5

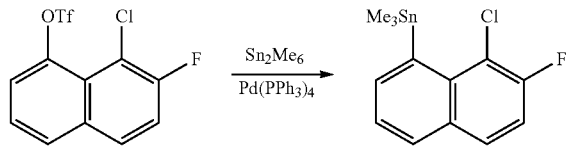

A mixture of (8-chloro-7-fluoro-1-naphthyl) trifluoromethanesulfonate (80.0 mg, 243 μmol, 1.0 equiv), trimethyl(trimethylstannyl)stannane (360 mg, 1.10 mmol, 228 μL, 4.5 equiv), Pd(PPh₃)₄ (28.1 mg, 24.3 μmol, 0.1 equiv), LiCl (61.9 mg, 1.46 mmol, 6.0 equiv) in toluene (1 mL) was purged with N₂ and then the mixture was stirred at 100° C. for 16 h. The reaction mixture was cooled to room temperature and filtered. The filtrate was diluted with water (5 mL) and extracted with ethyl acetate (2×10 mL). The combined organic layer was dried over anh Na₂SO₄ and concentrated under vacuum. The residue was purified by column chromatography (SiO₂, petroleum ether/ethyl acetate, 1:0 to 10:1) to afford (8-chloro-7-fluoro-1-naphthyl)-trimethylstannane (50.0 mg, 96.1 μmol, 39% yield) as a colorless oil. ¹H NMR (400 MHz, chloroform-d) δ 7.88 (d, J=6.8 Hz, 1H), 7.83 (dd, J=1.2, 8.0 Hz, 1H), 7.78 (dd, J=6.0, 9.2 Hz, 1H), 7.45 (dd, J=6.8, 8.0 Hz, 1H), 7.35 (t, J=8.8 Hz, 1H), 0.44 (s, 9H).

Intermediate C-6

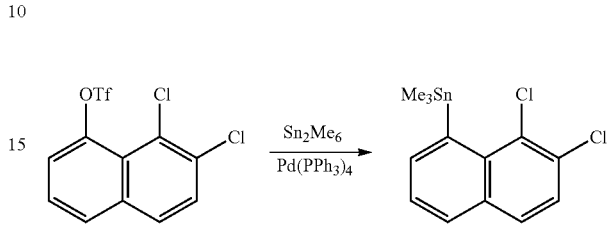

A mixture of 7,8-dichloronaphthalen-1-yl trifluoromethanesulfonate (200 mg, 579 μmol, 1.0 equiv), trimethyl(trimethylstannyl)stannane (522 mg, 1.59 mmol, 330 μL, 2.7 equiv), Pd(PPh₃)₄ (67.0 mg, 57.9 μmol, 0.1 equiv), LiCl (98.3 mg, 2.32 mmol, 4.0 equiv) in toluene (5 mL) was purged with N₂ and then stirred at 100° C. for 16 h. The reaction mixture was filtered and concentrated under vacuum. The residue was purified by column chromatography (SiO₂, petroleum ether/ethyl acetate, 1:0) followed by reversed phase flash to afford (7,8-dichloronaphthalen-1-yl) trimethylstannane (80.0 mg, 36% yield) as a colorless oil. ¹H NMR (400 MHz, CDCl₃): δ 7.89 (dd, J=1.2, 6.8 Hz, 1H), 7.82 (d, J=8.0 Hz, 1H), 7.72 (d, J=8.8 Hz, 1H), 7.53 (d, J=8.8 Hz, 1H), 7.48 (dd, J=7.2, 8.0 Hz, 1H), 0.44 (s, 9H).

Intermediate C-7

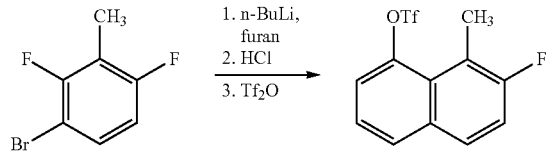

To a mixture of 1-bromo-2,4-difluoro-3-methyl-benzene (20.0 g, 96.6 mmol, 1.0 equiv) and furan (13.1 g, 193 mmol, 14.0 mL, 2.0 equiv) in toluene (300 mL) at −20° C. was added dropwise n-BuLi (2.5 M, 46.4 mL, 1.2 equiv). The mixture was allowed to warm to room temperature and stirred at for 16 hours. Subsequently, the mixture was diluted with satd aq NH₄Cl (200 mL) and then extracted with ethyl acetate (150 mL×3). The combined organic layer was concentrated under reduced pressure to provide a crude residue. The residue was purified by reversed-phase flash chromatography [C18, 0.1% FA in water, 0-65% MeCN] to afford 7-fluoro-5-methyl-11-oxatricycloundeca-1,3,5(7),6(8)-tetraene (5.0 g, 27.8 mmol, 28.8% yield) as a yellow oil. LCMS [ESI, M+1]: 177.

To a solution of 7-fluoro-5-methyl-11-oxatricycloundeca-1,3,5(7),6(8)-tetraene (5.0 g, 28.4 mmol, 1.0 equiv) in ethanol (80.0 mL) was added conc hydrochloric acid (30.7 mL, 13.0 equiv). The mixture was stirred at 80° C. for 3 h and was cooled to room temperature. The mixture was concentrated under reduced pressure to provide the crude residue. The residue was purified by reversed-phase flash chromatography [C18, 0.1% FA in water, 0-65% MeCN] to afford 7-fluoro-8-methyl-naphthalen-1-ol (5.0 g, 28.4 mmol, 100% yield) as a brown oil. $^1$H NMR (400 MHz, chloroform): δ 7.60 (dd, J=5.6, 8.8 Hz, 1H), 7.38 (d, J=7.6 Hz, 1H), 7.25-7.18 (m, 2H), 6.75 (d, J=7.6 Hz, 1H), 5.26 (s, 1H), 2.84 (d, J=2.8 Hz, 3H).

A mixture of 7-fluoro-8-methyl-naphthalen-1-ol (5.0 g, 28.4 mmol, 1.0 equiv), DIEA (11.0 g, 85.1 mmol, 14.8 mL, 3.0 equiv) and molecular sieve 4 Å (500 mg) in dichloromethane (100 mL) was stirred at −40° C. under nitrogen for 20 minutes prior to the addition of Tf$_2$O (8.81 g, 31.2 mmol, 5.15 mL, 1.1 equiv). The mixture was stirred at −40° C. for 40 min and was then concentrated under reduced pressure to provide the crude residue. The residue was purified by column chromatography (SiO$_2$, petroleum ether/ethyl acetate, 1:0 to 100:1) to afford (7-fluoro-8-methyl-1-naphthyl) trifluoromethanesulfonate (7.4 g, 24.0 mmol, 84.6% yield) as a white solid. $^1$H NMR (400 MHz, chloroform-d): δ=7.84 (dd, J=1.2, 8.4 Hz, 1H), 7.74 (dd, J=5.6, 8.8 Hz, 1H), 7.54 (d, J=7.6 Hz, 1H), 7.45-7.40 (m, 1H), 7.34 (t, J=9.2 Hz, 1H), 2.78 (d, J=2.8 Hz, 3H).

Intermediate C-8

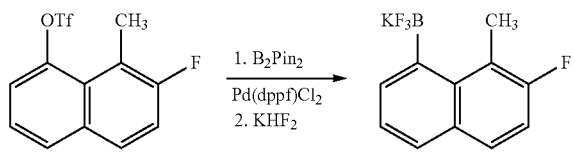

A mixture of (7-fluoro-8-methyl-1-naphthyl) trifluoromethanesulfonate (2.0 g, 6.49 mmol, 1.0 equiv), Pin$_2$B$_2$ (3.30 g, 13.0 mmol, 2.0 equiv), KOAc (1.91 g, 19.5 mmol, 3.0 equiv) and Pd(dppf)Cl$_2$ (949 mg, 1.30 mmol, 0.2 equiv) in dioxane (30.0 mL) was heated at 90° C. for 10 h. Subsequently, the mixture was concentrated under reduced pressure to provide the crude residue. The residue was purified by column chromatography (SiO$_2$, petroleum ether/ethyl acetate, 1:0 to 30:1) to afford 2-(7-fluoro-8-methyl-1-naphthyl)-4,4,5,5-tetramethyl-1,3,2-dioxaborolane (1.4 g, 4.89 mmol, 75.4% yield) as a yellow oil. $^1$H NMR (400 MHz, chloroform-d) δ=7.85 (dd, J=1.2, 8.0 Hz, 1H), 7.74-7.66 (m, 2H), 7.41 (dd, J=6.8, 8.0 Hz, 1H), 7.27-7.20 (m, 1H), 2.66 (d, J=2.4 Hz, 3H), 1.45 (s, 12H).

To a solution of 2-(7-fluoro-8-methyl-1-naphthyl)-4,4,5,5-tetramethyl-1,3,2-dioxaborolane (1.4 g, 4.89 mmol, 1.0 equiv) in methanol (21.0 mL) and H$_2$O (7.0 mL) was added KHF$_2$ (3.82 g, 48.9 mmol, 10.0 equiv) at 10° C. The mixture was stirred at this temperature for 30 min prior to being concentrated under reduced pressure to give a white solid. The solid was slurried in acetone (100 mL) for 30 min and was filtered. The filtrate was concentrated under reduced pressure at 40° C. to afford potassium (8-chloro-7-fluoronaphthalen-1-yl)trifluoroborate (1.7 g, 2.62 mmol, 53.5% yield) as a yellow oil.

Intermediate C-9

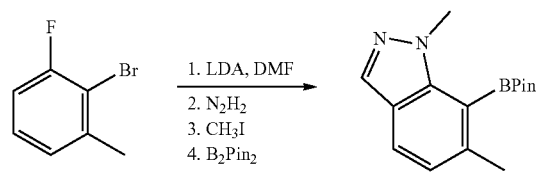

To a mixture of 2-bromo-1-fluoro-3-methyl-benzene (30 g, 158 mmol, 1.0 equiv) in THF (300 mL) at −70° C. under nitrogen was added dropwise LDA (2 M in THF, 119 mL, 1.5 equiv). The mixture was stirred at −70° C. for 0.5 hour prior to the dropwise addition of DMF (34.8 g, 476 mmol, 36.6 mL, 3.0 equiv). The reaction mixture was stirred at −70° C. for an additional 2 h and was then poured into satd aq NH$_4$Cl solution (400 mL). The mixture was extracted with ethyl acetate (3×200 mL). The combined organic layer was washed with brine (200 mL), dried over anhydrous sodium sulfate and concentrated in vacuo. The residue was purified by column chromatography (SiO$_2$, petroleum ether/ethyl acetate, 10:1). The material was then triturated with petroleum ether (50 mL) and the solid was collected and dried in vacuum to afford 3-bromo-2-fluoro-4-methyl-benzaldehyde (9.2 g, 42.4 mmol, 27% yield) as a white solid. $^1$H NMR (400 MHz, chloroform-d): δ=10.31 (s, 1H), 7.72 (t, J=7.2 Hz, 1H), 7.18 (d, J=8.0 Hz, 1H), 2.51 (s, 3H), A solution of 3-bromo-2-fluoro-4-methyl-benzaldehyde (9.2 g, 42.4 mmol, 1.0 equiv) and NH$_2$NH$_2$H$_2$O (42.4 g, 848 mmol, 41.2 mL, 20 equiv) in DMSO (150 mL) was stirred at 60° C. for 2 h and then at 130° C. for 16 h. Subsequently, the solution was cooled to 20° C. and poured into brine (600 mL) and filtered. The white solid was collected, washed with water (100 mL) and dried under reduced pressure to afford 7-bromo-6-methyl-1H-indazole (6.2 g, 29.4 mmol, 69% yield) as a light yellow solid. $^1$H NMR (400 MHz, chloroform-d): δ 10.69 (br s, 1H), 8.15 (s, 1H), 7.59 (d, J=8.0 Hz, 1H), 7.06 (d, J=8.4 Hz, 1H), 2.55 (s, 3H).

A mixture of 7-bromo-6-methyl-1H-indazole (7.9 g, 37.4 mmol, 1.0 equiv) in CH$_3$CN (250 mL), Cs$_2$CO$_3$ (15.9 g, 48.7 mmol, 1.3 equiv) and CH$_3$I (15.9 g, 112 mmol, 6.99 mL, 3.0 equiv) was heated at 80° C. for 1.5 hour. Subsequently, the mixture was cooled to room temperature and filtered. The filtrate was concentrated to provide the crude residue. The residue was diluted with water (200 mL) and extracted with ethyl acetate (60 mL×3). The combined organic layer was washed with brine 200 mL, dried over anh Na$_2$SO$_4$, filtered and concentrated under reduced. The residue was purified by column chromatography (SiO$_2$, petroleum ether/ethyl acetate, 10:1 to 2:1) to afford 7-bromo-1,6-dimethyl-indazole (4.9 g, 21.8 mmol, 58% yield) as a yellow solid.

To a mixture of 7-bromo-1,6-dimethyl-indazole (2.00 g, 8.89 mmol, 1.0 equiv), 4,4,5,5-tetramethyl-2-(4,4,5,5-tetramethyl-1,3,2-dioxaborolan-2-yl)-1,3,2-dioxaborolane (6.77 g, 26.7 mmol, 3.0 equiv) and KOAc (2.62 g, 26.7 mmol, 3.0 equiv) in DMF (40 mL) was added Pd(dppf)Cl$_2$ (325 mg, 444 umol, 0.05 equiv) under N$_2$. The mixture was heated at 80° C. for 15 hours under N$_2$. Subsequently, the mixture was cooled to room temperature and diluted with ethyl acetate (50 mL) and water (200 mL). The aqueous phase was extracted with ethyl acetate (40 mL). The combined organic layer was washed with brine (3×40 mL), dried over anh Na$_2$SO$_4$, filtered and concentrated to provide a residue. The residue was purified by column chromatography (SiO$_2$, petroleum ether/ethyl acetate, 30:1) to afford 1,6-dimethyl-7-(4,4,5,5-tetramethyl-1,3,2-dioxaborolan-2-yl)indazole (1.46 g, 4.98 mmol, 56% yield, 92.9% purity) as a white solid. LCMS [ESI, M+1]: 273. $^1$H NMR (400 MHz, chloroform-d) δ=7.89 (s, 1H), 7.61 (d, J=8.0 Hz, 1H), 6.97 (d, J=8.4 Hz, 1H), 4.15 (s, 3H), 2.60 (s, 3H), 1.46 (s, 12H).

Intermediate C-10

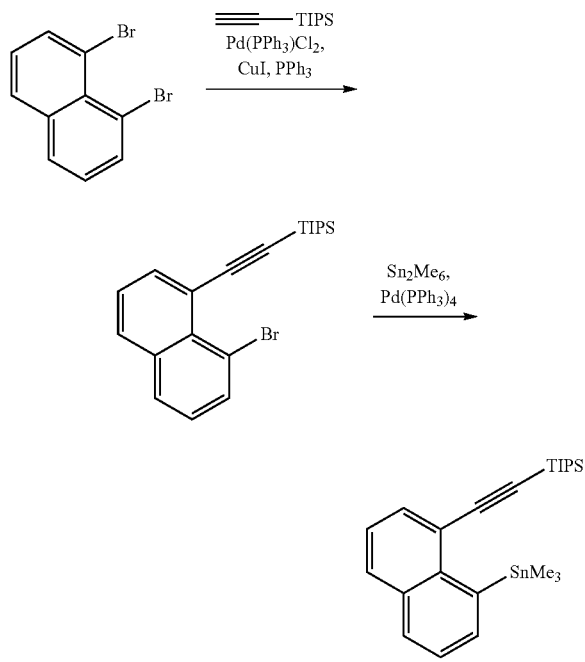

A mixture of 1,8-dibromonaphthalene (7 g, 24.5 mmol, 1.0 equiv), ethynyl(triisopropyl)silane (4.91 g, 26.9 mmol, 6.04 mL, 1.1 equiv), CuI (466 mg, 2.45 mmol, 0.1 equiv), PPh$_3$ (642 mg, 2.45 mmol, 0.1 equiv) and Pd(PPh$_3$)$_2$C12 (859 mg, 1.22 mmol, 0.05 equiv) in TEA (100 mL) was stirred at 80° C. for 3 h under N$_2$. The mixture was cooled to room temperature and was diluted with water (50 mL) and extracted with ethyl acetate (2×50 mL). The combined organic layer was washed with brine (50 mL), dried over anh Na$_2$SO$_4$, filtered and concentrated under vacuum. The residue was purified by column chromatography (SiO$_2$, petroleum ether) to afford ((8-bromonaphthalen-1-yl)ethynyl)triisopropylsilane (7 g, 18.1 mmol, 74% yield) as a yellow solid. $^1$H NMR (400 MHz, chloroform-d): δ=7.87 (dd, J=1.2, 7.2 Hz, 1H), 7.82-7.73 (m, 3H), 7.41-7.34 (m, 1H), 7.24 (t, J=7.6 Hz, 1H), 1.19-1.16 (m, 21H).

A mixture of ((8-bromonaphthalen-1-yl)ethynyl)triisopropylsilane (6.5 g, 16.8 mmol, 1.0 equiv), trimethyl(trimethylstannyl)stannane (27.5 g, 83.9 mmol, 17.4 mL, 5.0 equiv) and Pd(PPh$_3$)$_4$ (1.94 g, 1.68 mmol, 0.1 equiv) in toluene (100 mL) was stirred at 110° C. for 48 h under N$_2$. Subsequently, the mixture was diluted with water (100 mL) and the mixture was extracted with ethyl acetate (2×100 mL). The combined organic layer was washed with brine (100 mL), dried over anh Na$_2$SO$_4$, filtered and concentrated under vacuum. The residue was purified by column chromatography (SiO$_2$, petroleum ether) and then reversed phase flash chromatography [water (FA, 0.1%)/acetonitrile] to afford triisopropyl((8-(trimethylstannyl)naphthalen-1-yl)ethynyl)silane (0.65 g, 1.37 mmol, 8.1% yield, 99% purity) as a colourless oil. $^1$H NMR (400 MHz, chloroform-d) δ=7.90 (dd, J=1.2, 7.2 Hz, 1H), 7.86-7.79 (m, 3H), 7.47-7.39 (m, 2H), 1.25-1.18 (m, 21H), 0.54-0.44 (m, 9H).

Intermediate C-11

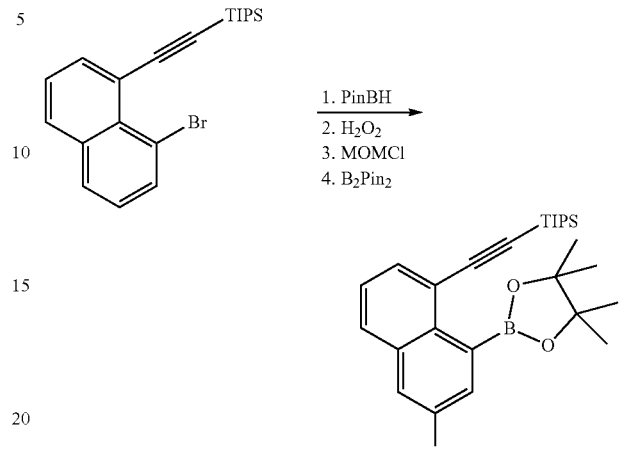

To a solution of ((8-bromonaphthalen-1-yl)ethynyl)triisopropylsilane (1.50 g, 3.87 mmol, 1.00 equiv) in THF (15.0 mL) was added dtbbpy (125 mg, 465 µmol, 0.12 equiv), (1,5-cyclooctadiene)(methoxy)iridium(I) dimer (257 mg, 387 µmol, 0.10 equiv) and 4,4,5,5-tetramethyl-1,3,2-dioxaborolane (1.24 g, 9.68 mmol, 1.40 mL, 2.50 equiv) under an atmosphere of argon. The mixture was stirred at 60° C. for 10 h and was concentrated under reduced pressure to afford a mixture of two borylation isomers (15.0 g, crude).

To a solution of the crude mixture of borylation isomers (15.0 g, 29.2 mmol, 1.00 equiv) in H$_2$O (20.0 mL) and THF (60.0 mL) was added H$_2$O$_2$ (29.8 g, 263 mmol, 25.3 mL, 9.00 equiv) and acetic acid (121 g, 2.02 mol, 115 mL, 69.0 equiv), the mixture was stirred at 10° C. for 1 h prior to being diluted with satd aq NaHSO$_3$ (300 mL). The mixture was extracted with ethyl acetate (3×200 mL). The combined organic layer was washed with brine (200 mL), dried over anhydrous Na$_2$SO$_4$, filtered and concentrated under reduced pressure. The mixture was purified by column chromatography (SiO$_2$, petroleum ether/ethyl acetate, 1:0 to 20:1), then by prep-HPLC [column: Phenomenex luna C18 (250*70 mm, 10 µm); mobile phase: water (0.225% FA)—ACN]; ACN: 70%-99%, 40 min], and then by SFC separation [column: DAICEL CHIRALPAK AD (250 mm*30 mm, 10 µm); mobile phase: (0.1% NH$_4$OH in IPA)] to afford 4-bromo-5-((triisopropylsilyl)ethynyl)naphthalen-2-ol (3.00 g, 7.44 mmol, 13% yield) as a light yellow solid. $^1$H NMR (400 MHz, CDCl$_3$): δ 7.73-7.72 (m, 1H), 7.64-7.51 (m, 1H), 7.49 (d, J=2.8 Hz, 1H), 7.35-7.32 (m, 1H), 7.12 (d, J=2.8 Hz, 1H), 1.20-1.16 (m, 21H).

To a solution of 4-bromo-5-((triisopropylsilyl)ethynyl)naphthalen-2-ol (2.90 g, 7.19 mmol, 1.00 equiv) and DIEA (2.79 g, 21.6 mmol, 3.76 mL, 3.00 equiv) in DCM (3.00 mL) at 0° C. was added dropwise MOMCl (1.10 g, 13.7 mmol, 1.04 mL, 1.90 equiv). The mixture was stirred at 0° C. for 0.5 h prior to being diluted with H$_2$O (40 mL). The mixture was extracted with DCM (90 mL). The organic layer was washed with brine (20 mL), dried over anh Na$_2$SO$_4$, filtered and concentrated under reduced pressure to give a residue. The residue was purified by column chromatography (SiO$_2$, petroleum ether/ethyl acetate, 1:0 to 50:1) to afford ((8-bromo-6-(methoxymethoxy)naphthalen-1-yl)ethynyl)triisopropylsilane (2.00 g, 4.47 mmol, 62% yield) as a light yellow solid. $^1$H NMR (400 MHz, CDCl$_3$) δ 7.75 (dd, J=1.2, 7.2 Hz, 1H), 7.72-7.65 (m, 1H), 7.60 (d, J=2.4 Hz, 1H), 7.39-7.30 (m, 2H), 5.27 (s, 2H), 3.52 (s, 3H), 1.21-1.15 (m, 21H).

To a mixture of ((8-bromo-6-(methoxymethoxy)naphthalen-1-yl)ethynyl)triisopropylsilane (400 mg, 893 umol, 1.00 equiv), 4,4,5,5-tetramethyl-2-(4,4,5,5-tetramethyl-1,3,2-dioxaborolan-2-yl)-1,3,2-dioxaborolane (454 mg, 1.79 mmol, 2.00 equiv) and KOAc (263 mg, 2.68 mmol, 3.00 equiv) in toluene (8.00 mL) was added Pd(dppf)Cl₂ (196 mg, 268 umol, 0.30 equiv) under an atmosphere of nitrogen. The mixture was stirred at 80° C. for 12 h and then cooled to room temperature. The mixture was filtered and the filtrate was concentrated in vacuo. The residue was purified by prep-TLC (petroleum ether/ethyl acetate, 5:1, R$_f$=0.5) to afford triisopropyl((8-(4,4,5,5-tetramethyl-1,3,2-dioxaborolan-2-yl)naphthalen-1-yl)ethynyl)silane (390 mg, 787 μmol, 88% yield) as a light yellow solid. ¹H NMR (400 MHz, CDCl₃): δ 7.69 (dd, J=3.2, 7.6 Hz, 2H), 7.47 (d, J=2.8 Hz, 1H), 7.40-7.31 (m, 2H), 5.29 (s, 2H), 3.51 (s, 3H), 1.44 (s, 12H), 1.20-1.12 (m, 21H).

Intermediate C-12

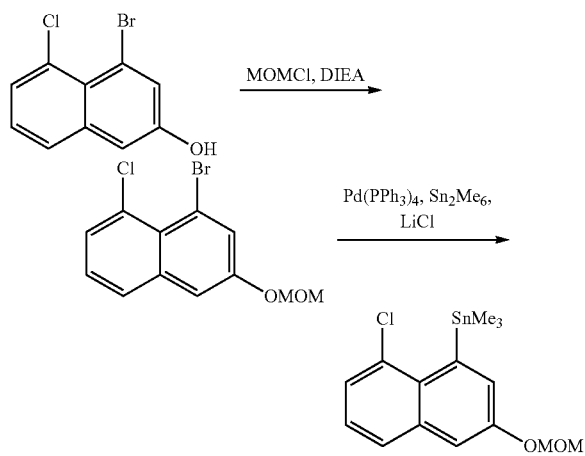

To a solution of 4-bromo-5-chloronaphthalen-2-ol (0.90 g, 3.49 mmol, 1.0 equiv) and DIEA (1.36 g, 10.5 mmol, 1.83 mL, 3.0 equiv) in DCM (20.0 mL) at 0° C. was added dropwise MOMCl (422 mg, 5.24 mmol, 398 μL, 1.5 equiv). The mixture was stirred at 0° C. for 0.5 h and was then diluted with H₂O (40.0 mL) and extracted with DCM (60.0 mL). The organic layer was washed with brine (20.0 mL), dried over anh Na₂SO₄, filtered and concentrated under reduced pressure to give a residue. The residue was purified by column chromatography (SiO₂, petroleum ether/ethyl acetate, 1:0 to 20:1) to afford 1-bromo-8-chloro-3-(methoxymethoxy)naphthalene (2.00 g, 5.97 mmol, 85% yield) as a light yellow solid. ¹H NMR (400 MHz, CDCl₃): δ 7.73-7.62 (m, 2H), 7.50 (dd, J=1.2, 7.6 Hz, 1H), 7.38 (d, J=2.50 Hz, 1H), 7.33-7.26 (m, 1H), 5.27 (s, 2H), 3.52 (s, 3H).

To a solution of 1-bromo-8-chloro-3-(methoxymethoxy) naphthalene (1.60 g, 5.31 mmol, 1.0 equiv) in toluene (30.0 mL) was added trimethyl(trimethylstannyl)stannane (7.82 g, 23.9 mmol, 4.5 equiv), Pd(PPh₃)₄ (613 mg, 530 μmol, 0.1 equiv), and LiCl (1.35 g, 31.8 mmol, 6.0 equiv). The mixture was stirred at 110° C. for 12 hours under N₂. Subsequently, the mixture was filtered and concentrated to give the crude residue. The residue was purified by column chromatography (SiO₂, petroleum ether/ethyl acetate, 1:10 to 20:1) to afford (8-chloro-3-(methoxymethoxy)naphthalen-1-yl)trimethylstannane (1.50 g, 3.89 mmol, 73% yield) as a colorless oil. ¹H NMR (400 MHz, CDCl₃): δ 7.71-7.66 (m, 1H), 7.57 (d, J=2.4 Hz, 1H), 7.49-7.43 (m, 1H), 7.39-7.37 (m, 1H), 7.35-7.30 (m, 1H), 5.31 (s, 2H), 3.54 (s, 3H), 0.42 (s, 9H).

Intermediate C-13

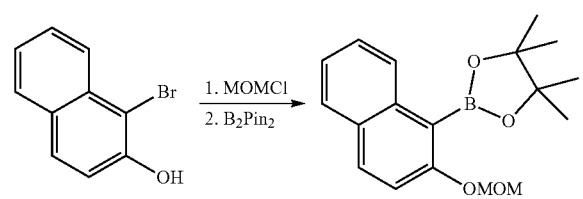

To a mixture of 1-bromonaphthalen-2-ol (1.5 g, 6.72 mmol, 1.0 equiv) in DCM (15 mL) at −40° C. was added DIEA (2.61 g, 20.2 mmol, 3.51 mL, 3.0 equiv) followed by MOMCl (704 mg, 8.74 mmol, 664 μL, 1.3 equiv) in DCM (0.5 mL). The solution was stirred at 0° C. for 30 minutes and was subsequently diluted with water (5.0 mL). The aqueous phase was extracted with ethyl acetate (3×10 mL) and the combined organic phase was washed with brine (15 mL), dried over anhydrous Na₂SO₄, filtered and concentrated at reduced pressure. The resultant residue was purified by column chromatography (SiO₂, petroleum ether/ethyl acetate, 1:0 to 10:1) to afford 1-bromo-2-(methoxymethoxy) naphthalene (1.55 g, 86% yield) as a yellow solid.

To a mixture of 1-bromo-2-(methoxymethoxy)naphthalene (1.55 g, 5.80 mmol, 1.0 equiv), KOAc (1.71 g, 17.4 mmol, 3.0 equiv) and 4,4,5,5-tetramethyl-2-(4,4,5,5-tetramethyl-1,3,2-dioxaborolan-2-yl)-1,3,2-dioxaborolane (2.95 g, 11.6 mmol, 2.0 equiv) in dioxane (16 mL) was added Pd(dppf)Cl₂ (424 mg, 580 μmol, 0.1 equiv) under nitrogen. The mixture was stirred at 110° C. for 1.5 h. The reaction mixture was cooled to room temperature and diluted with water (10 mL). The aqueous phase was extracted with ethyl acetate (3×15 mL) and the combined organic phase was washed with brine (15 mL), dried over anhydrous Na₂SO₄, filtered and concentrated at reduced pressure. The resultant residue was purified by column chromatography (SiO₂, petroleum ether/ethyl acetate, 1:0 to 20:1) to afford 2-(2-(methoxymethoxy)naphthalen-1-yl)-4,4,5,5-tetramethyl-1,3,2-dioxaborolane (1.7 g, 93% yield) as a white solid. ¹H NMR (400 MHz, CDCl₃): δ=7.94 (d, J=8.4 Hz, 1H), 7.82 (d, J=8.8 Hz, 1H), 7.8-7.74 (m, 1H), 7.47-7.41 (m, 1H), 7.37-7.3 (m, 2H), 5.26 (s, 2H), 3.54 (s, 3H), 1.52-1.46 (m, 12H).

Intermediate C-14

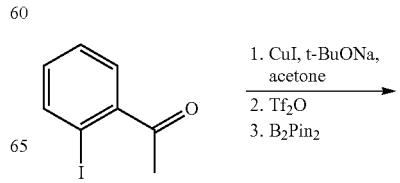

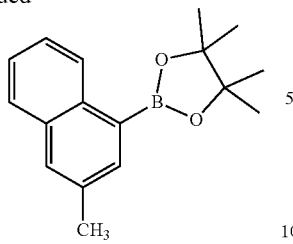

A sealed tube was charged with a mixture of CuI (387 mg, 2.03 mmol, 0.1 equiv), 1,10-phenanthroline (732 mg, 4.06 mmol, 0.2 equiv) and t-BuONa (11.7 g, 122 mmol, 6.0 equiv). The system was evacuated and recharged with nitrogen three times followed by the addition of a solution of 1-(2-iodophenyl)ethan-1-one (5 g, 20.3 mmol, 1.0 equiv) and acetone (3.54 g, 61.0 mmol, 4.48 mL, 3.0 equiv) in toluene (50 mL) at −20° C. The mixture was allowed to warm to room temperature and stirred for 2 h. The mixture was diluted with water (50 mL) and layers were separated. The aqueous phase was extracted with ethyl acetate (50 mL) and the combined organic layer was dried over anh $Na_2SO_4$, filtered and concentrated under reduced pressure. The resultant residue was purified by reversed phase flash chromatography [water (0.1% FA)/acetonitrile]. The desired fractions were collected and concentrated at reduced pressure to remove MeCN and then extracted with ethyl acetate (2×20 mL). The combined organic layer was dried over anh $Na_2SO_4$ and concentrated at reduced pressure. The crude residue was purified by silica gel chromatography (petroleum ether/ethyl acetate, 20:1 to 5:1) to afford 3-methylnaphthalen-1-ol (1.12 g, 33%) as a brown solid; $R_f$=0.60 (5:1, petroleum ether/ethyl acetate); $^1H$ NMR (400 MHz, $CDCl_3$): δ 8.15-8.09 (m, 1H), 7.73 (d, J=7.6 Hz, 1H), 7.50-7.39 (m, 2H), 7.26-7.21 (m, 1H), 6.70-6.66 (m, 1H), 5.38 (s, 1H), 2.46 (s, 3H); LCMS [ESI, M−1]: 157.

To a solution of 3-methylnaphthalen-1-ol (0.1 g, 632 μmol, 1.0 equiv) in DCM (2.0 mL) at −40° C. was added TEA (160 mg, 1.58 mmol, 220 μL, 2.5 equiv) and $Tf_2O$ (232 mg, 822 μmol, 135 μL, 1.3 equiv). The mixture was stirred at this temperature for 15 min prior to being diluted with water (2.0 mL). The aqueous phase was extracted with ethyl acetate (3×2.0 mL) and the combined organic layer was dried over anh $Na_2SO_4$, filtered and concentrated at reduced pressure. The residue was purified by silica gel chromatography (petroleum ether/ethyl acetate, 100:1 to 20:1) to give 3-methylnaphthalen-1-yl trifluoromethanesulfonate (120 mg, 64%) as a yellow oil; $R_f$=0.70 (10:1, petroleum ether/ethyl acetate); LCMS [ESI, M−1]: 289.

A mixture of 3-methylnaphthalen-1-yl trifluoromethanesulfonate (120 mg, 413 μmol, 1.0 equiv), Pd(dppf)Cl$_2$ (30.2 mg, 41.3 μmol, 0.1 equiv), 4,4,5,5-tetramethyl-2-(4,4,5,5-tetramethyl-1,3,2-dioxaborolan-2-yl)-1,3,2-dioxaborolane (315 mg, 1.24 mmol, 3.0 equiv) and KOAc (122 mg, 1.24 mmol, 3.0 equiv) in dioxane (2.5 mL) was purged with nitrogen and then heated at 80° C. for 6 h. The mixture was cooled to room temperature and was diluted with water (4.0 mL). The aqueous layer was extracted with ethyl acetate (2×5.0 mL). The combined organic layer was dried over anh $Na_2SO_4$ and concentrated at reduced pressure. The resultant residue was purified by silica gel chromatography (petroleum ether/ethyl acetate, 1:0 to 50:1) to afford 4,4,5,5-tetramethyl-2-(3-methylnaphthalen-1-yl)-1,3,2-dioxaborolane (100 mg, 81%) as a yellow solid; $R_f$=0.43 (3:1, petroleum ether/ethyl acetate); $^1H$ NMR (400 MHz, $CDCl_3$): δ 8.74-8.69 (m, 1H), 7.94-7.91 (m, 1H), 7.78-7.74 (m, 1H), 7.72-7.69 (m, 1H), 7.49-7.41 (m, 2H), 2.52 (s, 3H), 1.44 (s, 12H).

Intermediate C-15

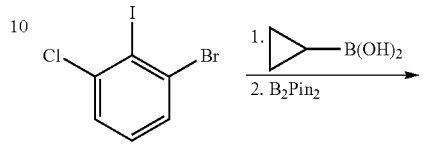

To a solution of 1-bromo-3-chloro-2-iodobenzene (2.50 g, 7.88 mmol, 1.00 equiv) in 1,4-dioxane (18.0 mL) and $H_2O$ (6.0 mL) was added $K_3PO_4$ (6.02 g, 28.4 mmol, 3.60 equiv), Pd(dppf)Cl$_2$ (288 mg, 394 μmol, 0.05 equiv) and cyclopropylboronic acid (880 mg, 10.2 mmol, 1.30 equiv). The mixture was stirred at 100° C. for 18 h and was then cooled to room temperature and diluted with water (30 mL). The mixture was extracted with ethyl acetate (30 mL×3). The combined organic layer was dried over anhydrous sodium sulfate and filtered. The filtrate was concentrated under reduced pressure to dryness. The residue was purified by column chromatography (SiO$_2$, petroleum ether/ethyl acetate, 1:0) and then reversed phase flash chromatography [water (0.1% FA)/acetonitrile] to afford 1-bromo-3-chloro-2-cyclopropylbenzene (1.18 g, 40% yield) as a yellow solid. $^1H$ NMR (400 MHz, $CDCl_3$): δ 7.46 (dd, J=1.2, 8.0 Hz, 1H), 7.30 (dd, J=1.2, 8.0 Hz, 1H), 6.99 (t, J=8.0 Hz, 1H), 1.88-1.73 (m, 1H), 1.23-1.14 (m, 2H), 0.80-0.74 (m, 2H).

To a solution of 1-bromo-3-chloro-2-cyclopropylbenzene (0.980 g, 4.23 mmol, 1.00 equiv) in 1,4-dioxane (30.0 mL) was added KOAc (1.25 g, 12.7 mmol, 3.00 equiv), Pin$_2$B$_2$ (2.15 g, 8.47 mmol, 2.00 equiv) and Pd(dppf)Cl$_2$ (310 mg, 423 μmol, 0.100 equiv). The mixture was stirred at 110° C. for 6 h. The mixture was cooled to room temperature and was diluted with water (30 mL). The mixture was extracted with ethyl acetate (30 mL×3). The combined organic layer was dried over anhydrous sodium sulfate and filtered. The filtrate was concentrated under reduced pressure to dryness. The residue was purified by column chromatography (SiO$_2$, petroleum ether/ethyl acetate, I/O), reversed-phase flash chromatography [water (0.1% FA)/acetonitrile] and finally prep-HPLC (Phenomenex luna C18 150×40 mm×15 μm; A: water (0.225% FA), B: ACN; B %: 68%-98%, 11 min) to afford 2-(3-chloro-2-cyclopropylphenyl)-4,4,5,5-tetramethyl-1,3,2-dioxaborolane (320 mg, 27% yield) as a yellow solid. $^1H$ NMR (400 MHz, $CDCl_3$): δ 7.45 (dd, J=1.2, 7.2 Hz, 1H), 7.37 (dd, J=1.2, 8.0 Hz, 1H), 7.17-7.06 (m, 1H), 2.07 (tt, J=5.6, 8.4 Hz, 1H), 1.39 (s, 12H), 1.08-0.97 (m, 2H), 0.62-0.53 (m, 2H).

Intermediate C-16

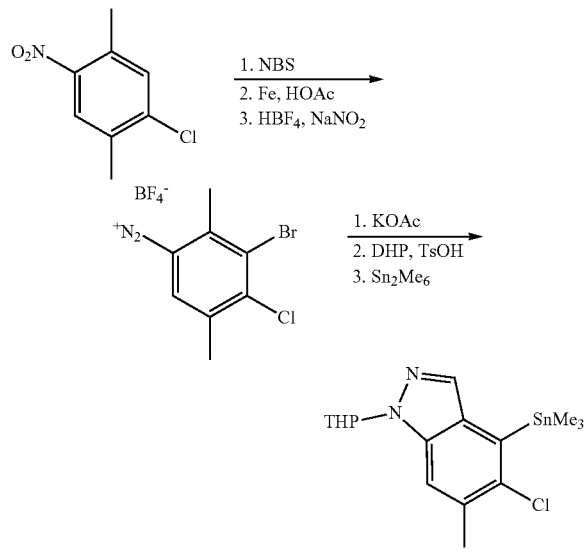

To a solution of 1-chloro-2,5-dimethyl-4-nitrobenzene (6.50 g, 35.0 mmol, 1.0 equiv) in TFA (50 mL) and $H_2SO_4$ (12.0 g, 122 mmol, 6.50 mL, 3.5 equiv) 40° C. was added portionwise NBS (6.86 g, 38.5 mmol, 1.1 equiv). The mixture was stirred at 40° C. for 8 h and was cooled to room temperature. The mixture was diluted with water (300 mL) at 0° C. and then filtered. The filter cake was washed with water (50 mL) and dried under reduced pressure to give a solid. The crude product was purified by reversed-phase flash chromatography [water (0.1% TFA)/acetonitrile] to afford 3-bromo-2-chloro-1,4-dimethyl-5-nitrobenzene (6.25 g, 19.8 mmol, 57% yield) as a white solid. $^1$H NMR (400 MHz, $CDCl_3$): δ=7.65 (s, 1H), 2.60 (s, 3H), 2.49 (s, 3H).

To a flask containing 3-bromo-4-chloro-2,5-dimethylaniline (500 mg, 2.13 mmol, 1.0 equiv) was added $HBF_4$ (3.86 g, 17.6 mmol, 2.74 mL, 40 wt % in water, 8.2 equiv) followed by the dropwise addition of a satd aq solution of $NaNO_2$ (221 mg, 3.20 mmol, 1.5 equiv) at 0° C. The mixture was stirred at 0° C. for 1 h and then room temperature for 30 min. The mixture was cooled to 0° C. and an additional satd aq $NaNO_2$ (147 mg, 2.13 mmol, 1.0 equiv) solution was added. The mixture was stirred at 0° C. for 0.5 h prior to filtration. The filter cake was washed with i-$Pr_2O$ (30 mL) to afford 3-bromo-4-chloro-2,5-dimethylbenzenediazonium tetrafluoroborate (700 mg, crude) as a white solid.

To a stirred mixture of KOAc (412 mg, 4.20 mmol, 2.0 equiv) and 18-Crown-6 (27.8 mg, 105 μmol, 0.05 equiv) in $CHCl_3$ (15 mL) was added 3-bromo-4-chloro-2,5-dimethylbenzenediazonium tetrafluoroborate (700 mg, 2.10 mmol, 1.0 equiv) in one portion at 25° C. under nitrogen. The mixture was stirred at room temperature for 30 min prior to being filtered. The filtrate was concentrated under reduced pressure. The resultant residue was purified by silica gel chromatography (petroleum ether/ethyl acetate, 1:0 to 3:1) to afford 4-bromo-5-chloro-6-methyl-1H-indazole (270 mg, 52% yield) as a yellow solid. $^1$H NMR (400 MHz, $CDCl_3$): δ 8.02 (s, 1H), 7.35 (d, J=0.8 Hz, 1H), 2.57 (d, J=0.8 Hz, 3H). LCMS [ESI, M+1]: 247.

To a solution of 4-bromo-5-chloro-6-methyl-1H-indazole (1.00 g, 4.07 mmol, 1.0 equiv) in DCM (40 mL) was added TsOH.$H_2O$ (77.5 mg, 407 μmol, 0.1 equiv) followed by DHP (685 mg, 8.15 mmol, 2.0 equiv). The reaction mixture was stirred at 25° C. for 15 h prior to being concentrated under vacuum. The resultant residue was purified by silica gel chromatography (petroleum ether/ethyl acetate, 1:0 to 4:1) to afford 4-bromo-5-chloro-6-methyl-1-(tetrahydro-2H-pyran-2-yl)-1H-indazole (1.30 g, 93% yield) as a yellow solid. LCMS [ESI, M+1]: 329.

A mixture of trimethyl(trimethylstannyl)stannane (656 mg, 2.00 mmol, 2.7 equiv), 4-bromo-5-chloro-6-methyl-1-(tetrahydro-2H-pyran-2-yl)-1H-indazole (240 mg, 728 μmol, 1.0 equiv), Pd(PPh$_3$)$_4$ (84.1 mg, 72.8 μmol, 0.1 equiv) and LiCl (123 mg, 2.91 mmol, 4.0 equiv) in toluene (5 mL) was purged with nitrogen and then was stirred at 100° C. for 16 h. The mixture was cooled to room temperature the and was filtered. The filtrate was concentrated under reduced pressure to dryness. The residue was purified by column chromatography ($SiO_2$, petroleum ether) followed by reversed-phase flash chromatography [water (0.1% FA)/acetonitrile] to afford 5-chloro-6-methyl-1-(tetrahydro-2H-pyran-2-yl)-4-(trimethylstannyl)-1H-indazole (190 mg, 444 μmol, 61% yield) as a colorless oil. LCMS [ESI, M+1]: 415. $^1$H NMR (400 MHz, $CDCl_3$): δ 8.00 (s, 1H), 7.43 (s, 1H), 5.67 (dd, J=2.8, 9.2 Hz, 1H), 4.07-3.95 (m, 1H), 3.81-3.68 (m, 1H), 2.63-2.53 (m, 1H), 2.50 (s, 3H), 2.22-2.01 (m, 2H), 1.80-1.64 (m, 3H), 0.59-0.41 (m, 9H).

Intermediate C-17

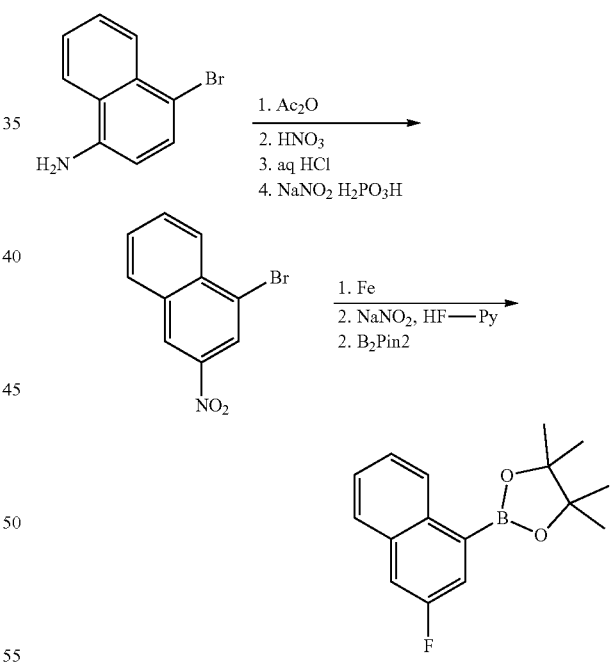

To a solution of 4-bromonaphthalen-1-amine (20 g, 90.0 mmol, 1 equiv) in MeOH (160 mL) was added acetic anhydride (10.1 mL, 108 mmol, 1.2 equiv). The reaction mixture was stirred at 60° C. for 1 h and was subsequently concentrated under vacuum. The mixture was triturated with MTBE (80 mL). The solid was collected, washed with MTBE (20 mL) and dried under vacuum to give N-(4-bromonaphthalen-1-yl)acetamide (23.5 g, 99% yield) as a yellow solid. LCMS [ESI, M+1]: 264, 266.

To a solution of N-(4-bromonaphthalen-1-yl)acetamide (24.4 g, 92.4 mmol, 1 equiv) in HOAc (200 mL) was added fuming nitric acid (4.19 mL, 102 mmol, 1.1 equiv) dropwise at 45° C. The mixture was stirred at 75° C. for 30 min and was then cooled to room temperature. The suspension was filtered, the solid was washed with cold MeOH (50 mL), MTBE (150 mL) and dried under vacuum to give N-(4-bromo-2-nitronaphthalen-1-yl)acetamide (21 g, 74% yield) as a yellow solid. LCMS [ESI, M−41]: 267, 269.

A mixture of N-(4-bromo-2-nitronaphthalen-1-yl)acetamide (18 g, 58.2 mmol, 1 equiv) in aqueous HCl (2 M, 108 mL, 3.71 equiv), EtOH (100 mL) and THF (200 mL) was heated to 80° C. for 50 h. Subsequently, the reaction mixture was concentrated under vacuum and was filtered. The solid was washed with ethyl acetate (50 mL) and dried under vacuum to give 4-bromo-2-nitronaphthalen-1-amine (12 g, 76% yield) as a red solid. LCMS [ESI, M+1]: 267, 269.

To a solution of 4-bromo-2-nitronaphthalen-1-amine (10 g, 37.4 mmol, 1 equiv) in HOAc (100 mL) and conc H$_2$SO$_4$ (100 mL, 1.84 mol, 49 eq) was added NaNO$_2$ (4.65 g, 67.4 mmol, 1.8 equiv) at 5° C. The reaction mixture was stirred at 5-20° C. for 2 h. To the mixture was added EtOH (100 mL) followed by CuSO$_4$ (7.17 g, 44.9 mmol, 1.2 equiv) in aq H$_3$PO$_2$ (30.00 g, 148 mmol, in 100 mL water, 3.95 equiv). The mixture was stirred at 65° C. for 1 h and then cooled to room temperature. The mixture was extracted by ethyl acetate (3×200 mL). The combined organic layer was washed with brine (80 mL), dried over anh Na$_2$SO$_4$, filtered and concentrated under reduced pressure. The resultant residue was purified by silica gel chromatography (petroleum ether/ethyl acetate, 1:0 to 20:1) to afford 1-bromo-3-nitronaphthalene (8.6 g, 91% yield) as a yellow solid. $^1$H NMR (400 MHz, CDCl$_3$): δ 8.80 (d, J=2.0 Hz, 1H), 8.59 (d, J=2.0 Hz, 1H), 8.35 (d, J=8.8 Hz, 1H), 8.07 (d, J=8.0 Hz, 1H), 7.84 (dt, J=0.8, 7.6 Hz, 1H), 7.77-7.68 (m, 1H).

To a solution of 1-bromo-3-nitronaphthalene (2.00 g, 7.93 mmol, 1.0 equiv) in EtOH (20 mL) was added H$_2$O (10 mL) and HCl (12 M, 661 µL, 1.0 equiv) at 25° C. The reaction mixture was heated at 80° C. prior to the addition of Fe (2.22 g, 39.7 mmol, 5.0 equiv) in one portion. The mixture was stirred at 80° C. for 1 h prior to being cooled to room temperature, filtered and concentrated under vacuum. The residue was purified by column chromatography (SiO$_2$, petroleum ether/ethyl acetate, 10:1 to 3:1) to give 4-bromonaphthalen-2-amine (1.58 g, 88% yield) as a brown solid. $^1$H NMR (400 MHz, CDCl$_3$): δ 8.06 (d, J=8.4 Hz, 1H), 7.58 (d, J=8.4 Hz, 1H), 7.44-7.38 (m, 1H), 7.36-7.29 (m, 2H), 6.96 (d, J=2.0 Hz, 1H), 3.85 (br s, 2H). LCMS [ESI, M+1]: 222, 224.

To a solution of 4-bromonaphthalen-2-amine (1.10 g, 4.95 mmol, 1.0 equiv) in pyridine hydrofluoride (11.0 mL, 122 mmol, 25 equiv) at 0° C. was added NaNO$_2$ (444 mg, 6.44 mmol, 1.3 equiv) in one portion. The reaction mixture was stirred at 25° C. for 10 min and then the mixture was heated at 80° C. for 2 h. Subsequently, the mixture was cooled to 0° C. and adjusted to pH 8 with saturated NaHCO$_3$ (50 mL). The mixture was extracted with ethyl acetate (50 mL). The organic layer was dried over anh Na$_2$SO$_4$, filtered and concentrated under vacuum. The residue was purified by column chromatography (SiO$_2$, petroleum ether) to give 1-bromo-3-fluoronaphthalene (620 mg, 55% yield) as a white solid.

A mixture of Pin$_2$B$_2$ (429 mg, 1.69 mmol, 2.0 equiv), 1-bromo-3-fluoronaphthalene (190 mg, 844 µmol, 1.0 equiv), Pd(dppf)Cl$_2$ (61.8 mg, 84.4 µmol, 0.1 equiv) and KOAc (248 mg, 2.53 mmol, 3.0 equiv) in dioxane (10 mL) was purged with N$_2$ and then stirred at 110° C. for 1.5 h. Subsequently, the reaction mixture was concentrated under reduced pressure to dryness. The residue was purified by column chromatography (SiO$_2$, petroleum ether/ethyl acetate, 1:0 to 10:1) to give 2-(3-fluoronaphthalen-1-yl)-4,4,5,5-tetramethyl-1,3,2-dioxaborolane (60.0 mg, 184 µmol, 22% yield) as a yellow oil. $^1$H NMR (400 MHz, CDCl$_3$): δ 8.78-8.70 (m, 1H), 7.84 (dd, J=2.8, 8.8 Hz, 1H), 7.80-7.75 (m, 1H), 7.56-7.46 (m, 3H), 1.43 (s, 12H).

Intermediate C-18

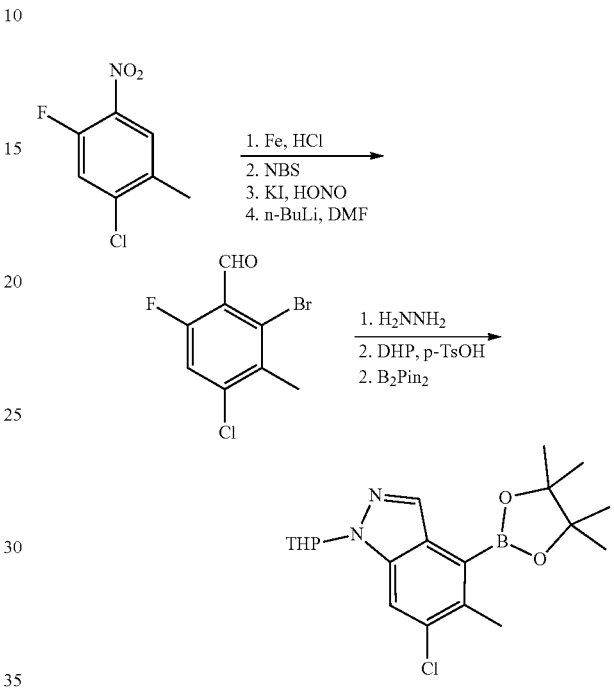

To a solution of 1-chloro-5-fluoro-2-methyl-4-nitrobenzene (20 g, 105 mmol, 1 equiv) in EtOH (100 mL) and H$_2$O (100 mL) was added HCl (12 M, 8.79 mL, 1 equiv). The mixture was heated at 80° C. and Fe (20.6 g, 369 mmol, 3.5 equiv) was added slowly over a period of 30 min. The mixture was stirred at this temperature for an additional hour. The mixture was cooled to room temperature, diluted with ethyl acetate (300 mL), and adjusted to pH 8-9 with saturated aqueous NaHCO$_3$. The mixture was filtered and the layers separated. The aqueous layer was extracted with ethyl acetate (2×300 mL). The combined organic layer was washed with brine, dried over anh Na$_2$SO$_4$, filtered and concentrated under reduced pressure to afford 4-chloro-2-fluoro-5-methylaniline (13.8 g, 81% yield) as a black solid. LCMS [ESI, M+1]: 160.

To a mixture of 4-chloro-2-fluoro-5-methylaniline (16.8 g, 105 mmol, 1 equiv) in DMF (150 mL) was added NBS (16.9 g, 94.7 mmol, 0.9 equiv) at 0° C. The mixture was stirred at 25° C. for 1 h and was diluted with saturated aqueous NaHCO$_3$. The mixture was extracted with ethyl acetate (2×250 mL). The combined organic layer was washed with water, brine, dried over anh Na$_2$SO$_4$, filtered and concentrated under reduced pressure. The resultant residue was purified by column chromatography (SiO$_2$, petroleum ether/ethyl acetate, 100:1 to 5:1) to afford 2-bromo-4-chloro-6-fluoro-3-methylaniline (20 g, 79% yield) as a red solid. LCMS [ESI, M+1]: 238, 240.

To a solution of TsOH (18.2 g, 106 mmol, 3.6 equiv) in MeCN (175 mL) was added 2-bromo-4-chloro-6-fluoro-3-methylaniline (7 g, 29.3 mmol, 1 equiv). The mixture was stirred at 0° C. for 10 min. To this mixture was added dropwise a binary solution of KI (17.5 g, 106 mmol, 3.6 equiv) and NaNO$_2$ (3.65 g, 52.8 mmol, 1.8 eq) in H$_2$O (25 mL). The resulting mixture was stirred at 25° C. for 18 h. The reaction mixture was diluted with water (50 mL) and extracted with ethyl acetate (100 mL×3). The combined organic layer was washed with satd aq Na$_2$SO$_3$ solution (100 mL), dried over anh sodium sulfate, filtered and concentrated under reduced pressure. The residue was purified by column chromatography (SiO$_2$, petroleum ether/ethyl acetate, 1:0 to 5:1) to afford 3-bromo-1-chloro-5-fluoro-4-iodo-2-methylbenzene (8 g, 76% yield) as a yellow solid. $^1$H NMR (400 MHz, DMSO-d$_6$): δ 7.64-7.40 (m, 1H), 2.55 (d, J=0.8 Hz, 3H).

To a solution of 3-bromo-1-chloro-5-fluoro-4-iodo-2-methylbenzene (2 g, 5.72 mmol, 1 equiv) in THF (20 mL) was added dropwise n-BuLi (2.5 M, 2.29 mL, 1 equiv) at −60° C. The mixture was stirred at this temperature for 30 min. To this solution was added DMF (460 mg, 6.30 mmol, 484 μL, 1.1 equiv) and the mixture was stirred at −60° C. for 30 min. The mixture was warmed to room temperature and was diluted with HCl (1N, 30 mL). The aqueous layer was extracted with ethyl acetate (3×50 mL). The combined organic layer was washed with H$_2$O, dried over anh Na$_2$SO$_4$, filtered and concentrated under reduced pressure. The residue was purified by column chromatography (SiO$_2$, petroleum ether/ethyl acetate, 1:0 to 20:1) to afford 2-bromo-4-chloro-6-fluoro-3-methylbenzaldehyde (1.2 g, 77% yield) as a yellow solid. $^1$H NMR (400 MHz, DMSO-d$_6$): δ 10.17 (s, 1H), 7.73 (d, J=10.4 Hz, 1H), 2.48 (d, J=0.8 Hz, 3H).

To a mixture of 2-bromo-4-chloro-6-fluoro-3-methylbenzaldehyde (1.2 g, 4.77 mmol, 1 equiv) in DMSO (30 mL) was added NH$_2$NH$_2$—H$_2$O (3.42 mL, 68.9 mmol, 14.4 equiv). The mixture was stirred at 130° C. for 15 h. The mixture was cooled to room temperature, was poured into ice water (150 mL) and extracted with DCM (2×30 mL). The combined organics were dried over anhydrous Na$_2$SO$_4$, filtered and concentrated. The residue was purified by column chromatography (SiO$_2$, petroleum ether/ethyl acetate, 100:1 to 1:1) to afford 4-bromo-6-chloro-5-methyl-1H-indazole (800 mg, 66% yield) as a brown oil. LCMS [ESI, M+1]: 247. $^1$H NMR (400 MHz, DMSO-d$_6$): δ 13.58-13.31 (m, 1H), 8.07-7.66 (m, 2H), 2.52 (s, 3H).

To a stirred solution of 4-bromo-6-chloro-5-methyl-1H-indazole (750 mg, 3.05 mmol, 1 equiv) in THF (10 mL) was added PPTS (76.8 mg, 305 μmol, 0.1 equiv) followed by DHP (838 μL, 9.16 mmol, 3 equiv). The mixture was stirred at 80° C. for 12 h. The mixture was cooled to room temperature and was diluted with H$_2$O (20 mL). The aqueous layer was extracted with DCM (50 mL). The combined organic layer was washed with H$_2$O (10 mL), brine (10 mL), dried over anh Na$_2$SO$_4$, filtered and concentrated. The residue was purified by column chromatography (SiO$_2$, petroleum ether/ethyl acetate, 100:1 to 1:1) to afford 4-bromo-6-chloro-5-methyl-1-(tetrahydro-2H-pyran-2-yl)-1H-indazole (550 mg, 55%) as a white solid. $^1$H NMR (400 MHz, DMSO-d$_6$): δ 8.06-8.03 (m, 1H), 8.02-7.99 (m, 1H), 5.91-5.83 (m, 1H), 3.91-3.82 (m, 1H), 3.80-3.71 (m, 1H), 2.56-2.52 (m, 3H), 2.42-2.28 (m, 1H), 2.08-1.91 (m, 2H), 1.80-1.64 (m, 1H), 1.62-1.53 (m, 2H).

A mixture of 4-bromo-6-chloro-5-methyl-1-(tetrahydro-2H-pyran-2-yl)-1H-indazole (350 mg, 1.06 mmol, 1 equiv), Pin$_2$B$_2$ (323 mg, 1.27 mmol, 1.2 equiv), KOAc (313 mg, 3.19 mmol, 3 equiv) and Pd(dppf)Cl$_2$ (77.7 mg, 106 μmol, 0.1 equiv) in dioxane (6 mL) was heated to 85° C. under N$_2$ for 12 h. The mixture was cooled to room temperature, diluted with water (20 mL) and extracted with ethyl acetate (30 mL×3). The combined organic layer was washed with brine (30 mL), dried over anh sodium sulfate, filtered and concentrated under reduced pressure. The residue was purified by column chromatography (SiO$_2$, petroleum ether/ethyl acetate, 1:0 to 1:1) to afford 6-chloro-5-methyl-1-(tetrahydro-2H-pyran-2-yl)-4-(4,4,5,5-tetramethyl-1,3,2-dioxaborolan-2-yl)-1H-indazole (343 mg, 83% yield) as a yellow solid. LCMS [ESI, M+1]: 377.

Intermediate C-19

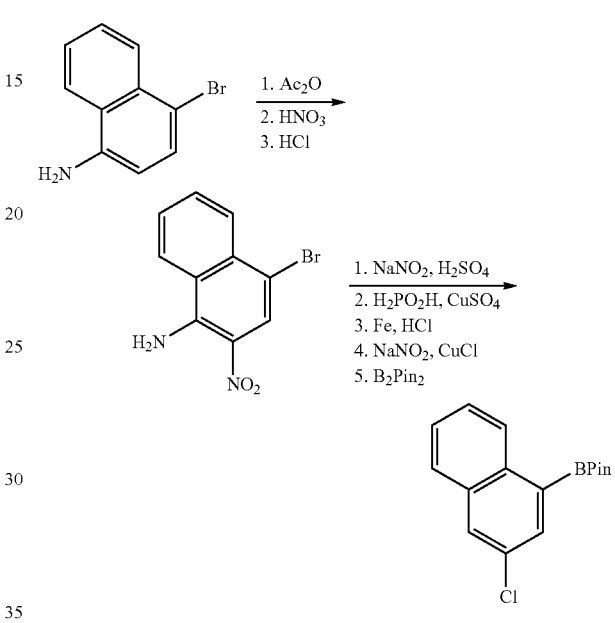

To a solution of 4-bromonaphthalen-1-amine (20 g, 90.0 mmol, 1 equiv) in MeOH (160 mL) was added acetic anhydride (10.1 mL, 108 mmol, 1.2 equiv). The reaction mixture was stirred at 60° C. for 1 h. The mixture was concentrated under reduced pressure and the resultant residue was triturated with MTBE (80 mL). The solid was filtered, washed with MTBE (20 mL) and dried under reduced pressure to give N-(4-bromonaphthalen-1-yl)acetamide (23.5 g, 99% yield) as a yellow solid. LCMS [ESI, M+1]: 264, 266.

To a solution of N-(4-bromonaphthalen-1-yl)acetamide (24.4 g, 92.4 mmol, 1 equiv) in HOAc at 45° C. (200 mL) was added dropwise fuming nitric acid (6.40 g, 102 mmol, 4.19 mL, 1.1 equiv). The mixture was stirred at 75° C. for 30 min. The mixture was cooled to room temperature and the suspension was filtered. The solid was washed with cold MeOH (50 mL), MTBE (150 mL) and dried at reduced pressure to give N-(4-bromo-2-nitronaphthalen-1-yl)acetamide (21 g, 74% yield) as a yellow solid. LCMS [ESI, M−41]: 267, 269.

A reaction mixture of N-(4-bromo-2-nitronaphthalen-1-yl)acetamide (18 g, 58.2 mmol, 1 eq) in aqueous HCl (2 M, 108 mL, 3.71 equiv), EtOH (100 mL) and THF (200 mL) was heated at 80° C. for 50 h. Subsequently, the reaction mixture was concentrated under vacuum. The concentrated mixture was filtered and the solid washed with ethyl acetate (50 mL) to give 4-bromo-2-nitronaphthalen-1-amine (12 g, 76% yield) as a red solid. LCMS [ESI, M+1]: 267, 269.

To a solution of 4-bromo-2-nitronaphthalen-1-amine (10 g, 37.4 mmol, 1 equiv) in HOAc (100 mL) and conc. H$_2$SO$_4$ (100 mL, 1.84 mol, 49 equiv) was added NaNO$_2$ (4.65 g, 67.4 mmol, 1.8 equiv) at 5° C. The reaction mixture was allowed to warm to room temperature over 2 h. To the mixture was added EtOH (100 mL) followed by CuSO$_4$ (7.17 g, 44.9 mmol, 1.2 equiv) in aqueous H$_3$PO$_2$ (100 mL, 32% in water, 147 mmol, 3.95 equiv). The mixture was heated at 65° C. for 1 h, cooled to room temperature and then extracted with ethyl acetate (3×200 mL). The combined organic layer was washed with brine (80 mL), dried over anh Na$_2$SO$_4$, filtered and concentrated under reduced pressure. The residue was purified by silica gel chromatography (petroleum ether/ethyl acetate, 1:0 to 20:1) to afford 1-bromo-3-nitronaphthalene (8.6 g, 91% yield) as a yellow solid. $^1$H NMR (400 MHz, CDCl$_3$): δ 8.80 (d, J=2.0 Hz, 1H), 8.59 (d, J=2.0 Hz, 1H), 8.35 (d, J=8.8 Hz, 1H), 8.07 (d, J=8.0 Hz, 1H), 7.84 (dt, J=0.8, 7.6 Hz, 1H), 7.77-7.68 (m, 1H).

To a solution of 1-bromo-3-nitronaphthalene (2.00 g, 7.93 mmol, 1.0 equiv) in EtOH (20 mL) was added H$_2$O (10 mL) and conc. HCl (661 μL, 1.0 equiv) at 25° C. The reaction mixture was heated to 80° C. prior to the addition of Fe (2.22 g, 39.7 mmol, 5.0 equiv) in portions at 80° C. The mixture was stirred at 80° C. for an additional hour. The mixture was cooled to room temperature, filtered and concentrated under reduced pressure. The residue was purified by column chromatography (SiO$_2$, petroleum ether/ethyl acetate, 10/1 to 3/1) to give 4-bromonaphthalen-2-amine (1.58 g, 88% yield) as a brown solid. $^1$H NMR (400 MHz, CDCl$_3$): δ 8.06 (d, J=8.4 Hz, 1H), 7.58 (d, J=8.4 Hz, 1H), 7.44-7.38 (m, 1H), 7.36-7.29 (m, 2H), 6.96 (d, J=2.0 Hz, 1H), 3.85 (br s, 2H). LCMS [ESI, M+1]: 222, 224.

A solution of 4-bromonaphthalen-2-amine (830 mg, 3.74 mmol, 1.0 equiv) and TsOH.H$_2$O (2.56 g, 13.4 mmol, 3.6 equiv) in MeCN (30 mL) was dropwise added a solution of NaNO$_2$ (572 mg, 8.29 mmol, 2.2 equiv) in H$_2$O (3 mL) followed by CuCl (1.11 g, 11.2 mmol, 3.0 equiv) at 0° C. The reaction mixture was stirred at 0° C. for 10 minutes then warmed to 25° C. The mixture was stirred at 25° C. for 2 hours. The reaction mixture was concentrated under vacuum. The residue was purified by column chromatography (SiO$_2$, petroleum ether/ethyl acetate=I/O to 10/1) to give 1-bromo-3-chloronaphthalene (420 mg, 1.45 mmol, 39% yield). White solid. $^1$H NMR (400 MHz, CDCl$_3$) δ=8.21 (d, J=8.4 Hz, 1H), 7.82 (d, J=1.6 Hz, 1H), 7.80-7.74 (m, 2H), 7.64-7.53 (m, 2H).

A mixture of Pin$_2$B$_2$ (94.6 mg, 373 umol, 2.0 equiv), 1-bromo-3-chloronaphthalene (45.0 mg, 186 umol, 1.0 equiv), Pd(dppf)Cl$_2$ (13.6 mg, 18.6 umol, 0.1 equiv) and KOAc (54.9 mg, 559 umol, 3.0 equiv) in dioxane (3 mL) was degassed and purged with N$_2$ for 3 times, and then the mixture was stirred at 110° C. for 1.5 hours under N$_2$ atmosphere. The reaction mixture was concentrated under reduced pressure to dryness. The residue was purified by column chromatography (SiO$_2$, petroleum ether/ethyl acetate=1/0 to 10/1) to give 2-(3-chloronaphthalen-1-yl)-4,4,5,5-tetramethyl-1,3,2-dioxaborolane (32.0 mg, 48% yield). Yellow solid.

Intermediate C-20

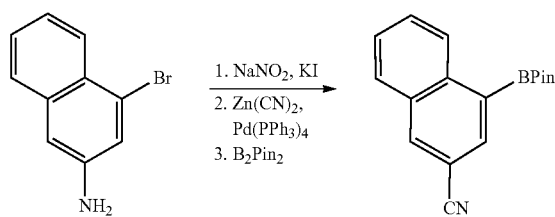

To a solution of 4-bromonaphthalen-2-amine (600 mg, 2.70 mmol, 1.0 equiv) and TsOH.H$_2$O (1.85 g, 9.73 mmol, 3.6 equiv) in MeCN (20 mL) at 0° C. was added a solution of KI (1.35 g, 8.11 mmol, 3.0 equiv) in H$_2$O (2 mL) followed by NaNO$_2$ (367 mg, 5.33 mmol, 2.0 equiv). The reaction mixture was stirred at 0° C. for 10 min and then room temperature for 2 h. The reaction mixture was concentrated under reduced pressure. The residue was purified by column chromatography (SiO$_2$, petroleum ether/ethyl acetate, 1:0 to 10:1) to give 1-bromo-3-iodonaphthalene (580 mg, 1.72 mmol, 64% yield) as a yellow solid.

A mixture of 1-bromo-3-iodonaphthalene (450 mg, 1.35 mmol, 1.0 equiv), Zn(CN)$_2$ (159 mg, 1.35 mmol, 1.0 equiv), Pd(PPh$_3$)$_4$ (156 mg, 135 μmol, 0.1 equiv) in DMF (2 mL) was purged with N$_2$ and then stirred at 90° C. for 1 h. The reaction mixture was diluted with water (5 mL) and extracted with ethyl acetate (20 mL×2). The combined organic layer was washed with H$_2$O (20 mL×2), dried over anh Na$_2$SO$_4$ and concentrated under reduced pressure to give a residue. The residue was purified by column chromatography (SiO$_2$, petroleum ether/ethyl acetate, 1:0 to 10:1) to give 4-bromo-2-naphthonitrile (130 mg, 560 μmol, 41% yield) as a yellow solid. $^1$H NMR (400 MHz, CDCl$_3$): δ 8.31 (d, J=8.4 Hz, 1H), 8.22 (s, 1H), 7.96-7.89 (m, 2H), 7.79 (ddd, J=1.2, 7.2, 8.4 Hz, 1H), 7.72-7.66 (m, 1H).

A mixture of 4-bromo-2-naphthonitrile (100 mg, 431 μmol, 1.0 equiv), B$_2$Pin$_2$ (219 mg, 862 μmol, 2.0 equiv), Pd(dppf)Cl$_2$ (31.5 mg, 43.1 μmol, 0.1 equiv) and KOAc (127 mg, 1.29 mmol, 3.0 equiv) in dioxane (5 mL) was purged with N$_2$ and then stirred at 100° C. for 2 h. The reaction mixture was cooled to room temperature and concentrated under reduced pressure. The residue was purified by column chromatography (SiO$_2$, petroleum ether/ethyl acetate, 1:0 to 10:1) to give 4-(4,4,5,5-tetramethyl-1,3,2-dioxaborolan-2-yl)-2-naphthonitrile (110 mg, 327 μmol, 76% yield) as a white solid. $^1$H NMR (400 MHz, CDCl$_3$): δ 8.81 (d, J=8.4 Hz, 1H), 8.30 (s, 1H), 8.21 (d, J=2.0 Hz, 1H), 7.89 (d, J=8.4 Hz, 1H), 7.69 (ddd, J=1.6, 6.8, 8.4 Hz, 1H), 7.63-7.57 (m, 1H), 1.44 (s, 12H). LCMS [ESI, M+1]: 280.

Intermediate C-21

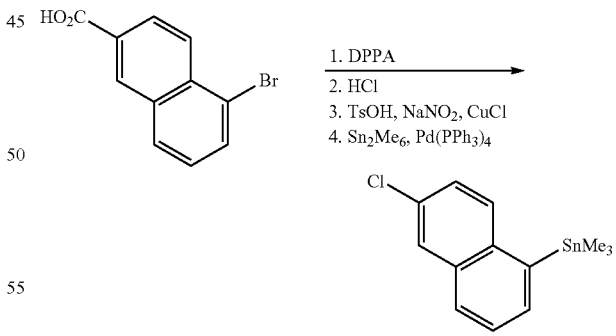

A mixture of 5-bromo-2-naphthoic acid (10.0 g, 39.8 mmol, 1.0 equiv), t-BuOH (40.0 mL, 418 mmol, 11 equiv), 4 Å MS (10.0 g) and TEA (11.1 mL, 79.7 mmol, 2.0 equiv) in toluene (100 mL) was purged with N$_2$ and was stirred at 80° C. for 12 h. To this mixture was added DPPA (16.4 g, 59.7 mmol, 12.9 mL, 1.5 equiv) and the mixture was stirred at 80° C. for 12 h under an atmosphere of nitrogen. The reaction mixture was cooled to room temperature and the pH was adjusted to around 7 using satd aq NH$_4$Cl. The mixture was filtered and the filtrate was extracted with dichloromethane (3×50 mL). The combined organic layer was washed with brine (50 mL), dried over anh Na$_2$SO$_4$, filtered and concentrated. The residue was purified by column chromatography (SiO$_2$, petroleum ether/ethyl acetate, 1:0 to 20:1) to afford tert-butyl (5-bromonaphthalen-2-yl)carbamate (12.6 g, 93% yield) as a white solid. $^1$H NMR (400 MHz, CDCl$_3$): δ 9.74 (s, 1H), 8.17 (d, J=1.2 Hz, 1H), 8.01 (d, J=9.2 Hz, 1H), 7.82 (d, J=8.4 Hz, 1H), 7.71-7.64 (m, 2H), 7.37-7.34 (m, 1H), 1.51 (s, 9H); LCMS [ESI, M+1]: 266.0.

To a solution of tert-butyl (5-bromonaphthalen-2-yl)carbamate (12.0 g, 37.2 mmol, 1.0 equiv) in MeOH (100 mL) was added HCl (4 M in MeOH, 100 mL, 11 equiv). The mixture was stirred at 40° C. for 1 h. The reaction mixture was concentrated under reduced pressure, filtered and concentrated to dryness to afford 5-bromonaphthalen-2-amine (8.10 g, HCl salt, 84% yield) as a white solid. $^1$H NMR (400 MHz, CDCl$_3$): δ 8.16 (d, J=8.8 Hz, 1H), 7.96 (d, J=8.4 Hz, 1H), 7.83 (d, J=7.6 Hz, 1H), 7.78 (d, J=2.0 Hz, 1H), 7.56 (dd, J=2.0, 8.8 Hz, 1H), 7.48-7.42 (m, 1H).

To a solution of 5-bromonaphthalen-2-amine (2.00 g, 9.01 mmol, 1.0 equiv) and TsOH.H$_2$O (6.17 g, 32.4 mmol, 3.6 equiv) in MeCN (40 mL) at −5° C. was added a solution of NaNO$_2$ (1.12 g, 16.2 mmol, 1.8 equiv) and CuCl (2.67 g, 27.0 mmol, 3.0 equiv) in H$_2$O (5 mL). The resultant reaction mixture was stirred at 25° C. for 2 h prior to being concentrated under reduced pressure. The residue was diluted with satd aq NaHCO$_3$ and extracted with ethyl acetate (3×50 mL). The combined organic layer was washed with brine (50 mL), dried over anh Na$_2$SO$_4$, filtered and concentrated to dryness. The residue was purified by column chromatography (SiO$_2$, petroleum ether/ethyl acetate, 1:0) to provide 1-bromo-6-chloronaphthalene (1.00 g, 46% yield) as a white solid. $^1$H NMR (400 MHz, CDCl$_3$): δ 8.18 (d, J=9.2 Hz, 1H), 7.83 (d, J=2.0 Hz, 1H), 7.77 (dd, J=1.2, 7.6 Hz, 1H), 7.72 (d, J=8.4 Hz, 1H), 7.53 (dd, J=2.0, 9.2 Hz, 1H), 7.34 (dd, J=7.6, 8.0 Hz, 1H).

To a solution of 1-bromo-6-chloronaphthalene (470 mg, 1.95 mmol, 1.0 equiv) in toluene (5 mL) was added trimethyl(trimethylstannyl)stannane (1.91 g, 5.84 mmol, 1.21 mL, 3.0 equiv), LiCl (330 mg, 7.78 mmol, 4.0 equiv), Pd(PPh$_3$)$_4$ (225 mg, 195 μmol, 0.1 equiv). The vessel was stirred at 110° C. for 4 h. The mixture was cooled to room temperature and diluted with water (20 mL). The aqueous layer was extracted with ethyl acetate (30 mL×3). The combined organic layer was dried over anhydrous sodium sulfate and filtered. The filtrate was concentrated under reduced pressure to dryness. The residue was purified by column chromatography (SiO$_2$, petroleum ether/ethyl acetate, 1:0 to 1:0) to afford (6-chloronaphthalen-1-yl)trimethylstannane (590 mg, 1.81 mmol, 93% yield) as a yellow solid. $^1$H NMR (400 MHz, CDCl$_3$): δ 7.85 (d, J=2.2 Hz, 1H), 7.74 (br d, J=9.0 Hz, 2H), 7.65 (dd, J=1.0, 6.6 Hz, 1H), 7.51-7.42 (m, 2H), 0.53-0.37 (m, 9H).

Intermediate C-22

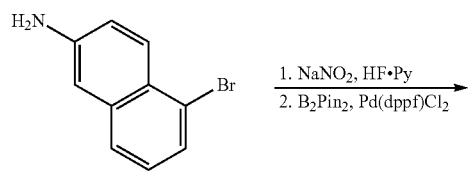

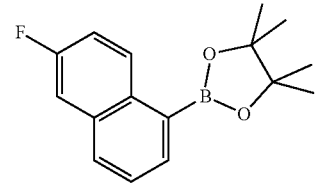

Pyridine (2.50 mL) was slowly added to pyridine-hydrofluoride (5.50 g, 55.5 mmol, 5.00 mL, 25 equiv) at −60° C. To this solution was added 5-bromonaphthalen-2-amine (500 mg, 2.25 mmol, 1.0 equiv) and NaNO$_2$ (311 mg, 4.50 mmol, 2.0 equiv)—the temperature was maintained below 0° C. The reaction mixture was warmed to 20° C., stirred for 0.5 h, and then at 60° C. for 2 h. The was diluted with NaOH (1M) and NaHCO$_3$ saturated aqueous solution (100 mL) and extracted with ethyl acetate (3×5 mL). The combined organic layer was washed with brine (5 mL), dried over anh Na$_2$SO$_4$, filtered and concentrated to dryness. The residue was purified by column chromatography (SiO$_2$, petroleum ether) to provide 1-bromo-6-fluoronaphthalene (164 mg, 32.4%) as a white solid. $^1$H NMR (400 MHz, CDCl$_3$): δ 8.27 (dd, J=5.6, 9.2 Hz, 1H), 7.75 (dd, J=3.2, 7.6 Hz, 2H), 7.48 (dd, J=2.4, 9.6 Hz, 1H), 7.41-7.30 (m, 2H).

To a solution of 1-bromo-6-fluoronaphthalene (400 mg, 1.78 mmol, 1.0 equiv) in dioxane (15 mL) was added Pd(dppf)Cl$_2$ (130 mg, 178 μmol, 0.1 equiv), Pin$_2$B$_2$ (1.13 g, 4.44 mmol, 2.5 equiv) and KOAc (523 mg, 5.33 mmol, 3.0 equiv). The mixture was stirred at 110° C. for 12 h under nitrogen. The mixture was diluted with water (5 mL) and extracted with ethyl acetate (3×5 mL). The combined organic layer was washed with brine (5 mL), dried over anh Na$_2$SO$_4$, filtered and concentrated under reduced pressure. The residue was purified by column chromatography (SiO$_2$, petroleum ether/ethyl acetate, 1:0 to 50:1) to afford 2-(6-fluoronaphthalen-1-yl)-4,4,5,5-tetramethyl-1,3,2-dioxaborolane (426 mg, crude) as a white solid.

Intermediate C-23

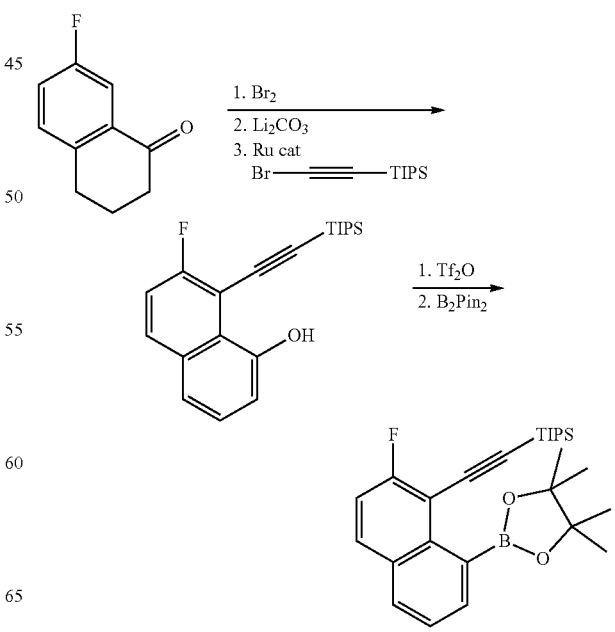

To a solution of 7-fluoro-3,4-dihydronaphthalen-1(2H)-one (75.0 g, 457 mmol, 1.00 equiv) in acetic acid (1.50 L) and hydrogen bromide (33% in acetic acid, 7.50 mL) at 0° C. was added bromine (25.9 mL, 503 mmol, 1.1 equiv) in acetic acid (50 mL). The mixture was stirred at 25° C. for 3 hours. The mixture was diluted with DCM (1.5 L) and washed with water (3×500 mL). The organic layer was dried over anhydrous sodium sulfate, filtered and concentrated to afford a brown oil. The oil was dissolved in DMF (750 mL) and to this mixture was added lithium bromide (67.4 g, 777 mmol, 1.70 equiv) and lithium carbonate (57.4 g, 777 mmol, 1.70 equiv). The reaction mixture was stirred at 160° C. for 3.5 h and then cooled to room temperature. The mixture was extracted with ethyl acetate (1.00 L). The organic layer was washed with brine (2×500 mL), dried over anhydrous sodium sulfate, filtered and concentrated in vacuum to give a residue. The residue was purified by silica gel chromatography (petroleum ether/ethyl acetate, 1:0 to 5:1) to afford 7-fluoronaphthalen-1-ol (61.0 g, 82% yield) as a brown solid. $^1$H NMR (400 MHz, CDCl$_3$) δ 7.84-7.77 (m, 2H), 7.44 (d, J=8.0 Hz, 1H), 7.31-7.24 (m, 2H), 6.84 (d, J=7.6 Hz, 1H), 5.39 (s, 1H).

To a solution of 7-fluoro-3,4-dihydronaphthalen-1(2H)-one (72.0 g, 275 mmol, 1.20 equiv) and 7-fluoronaphthalen-1-ol (37.2 g, 230 mmol, 1.0 equiv) in DCE (500 mL) was added (p-cymene)ruthenium(II) chloride dimer (21.1 g, 34.4 mmol, 0.15 equiv), K$_2$CO$_3$ (31.7 g, 230 mmol, 1.0 equiv) and NaOAc (3.77 g, 45.9 mmol, 0.20 equiv). The mixture was stirred at 40° C. for 12 hours. The reaction mixture was filtered and concentrated under reduced pressure to give a residue. The residue was purified by column chromatography (SiO$_2$, petroleum ether/ethyl acetate, 1:0 to 50:1) to afford 7-fluoro-8-((triisopropylsilyl)ethynyl)naphthalen-1-ol (73.0 g, 93% yield) as a yellow oil. $^1$H NMR (400 MHz, CDCl$_3$): δ 9.10 (s, 1H), 7.79 (dd, J=5.6, 8.8 Hz, 1H), 7.41-7.33 (m, 2H), 7.23 (t, J=8.8 Hz, 1H), 7.08-7.00 (m, 1H), 1.24-1.14 (m, 21H). LCMS [ESI, M+1, 2M+1]: 343.1.

To a solution of 7-fluoro-8-((triisopropylsilyl)ethynyl)naphthalen-1-ol (73.0 g, 213 mmol, 1.00 equiv) in DCM (600 mL) at −40° C. was added DIEA (55.1 g, 426 mmol, 74.2 mL, 2.00 equiv) and Tf$_2$O (90.2 g, 320 mmol, 52.7 mL, 1.50 equiv). The mixture was stirred at this temperature for 30 min prior to being filtered and concentrated under reduced pressure to give a residue. The residue was purified by column chromatography (SiO$_2$, petroleum ether/ethyl acetate, 1:0 to 50:1) to provide 7-fluoro-8-((triisopropylsilyl)ethynyl)naphthalen-1-yl trifluoromethanesulfonate (78.0 g, 77% yield) as a yellow solid. $^1$H NMR (400 MHz, CDCl$_3$): δ 7.88-7.79 (m, 2H), 7.59-7.52 (m, 1H), 7.46 (t, J=8.0 Hz, 1H), 7.37 (t, J=8.8 Hz, 1H), 1.32-1.16 (m, 21H).

To a solution of 7-fluoro-8-((triisopropylsilyl)ethynyl)naphthalen-1-yl trifluoromethanesulfonate (20.0 g, 42.1 mmol, 1.00 equiv) and Pin$_2$B$_2$ (16.0 g, 63.2 mmol, 1.50 equiv) in dioxane (6.00 mL) was added KOAc (8.27 g, 84.3 mmol, 2.0 equiv) and Pd(dppf)Cl$_2$ (3.08 g, 4.21 mmol, 0.10 equiv). The mixture was stirred at 110° C. for 12 h under an atmosphere of nitrogen prior to being filtered and concentrated under reduced pressure. The resultant residue was purified by column chromatography (SiO$_2$, petroleum ether/ethyl acetate, 1:0 to 10:1) to afford ((2-fluoro-8-(4,4,5,5-tetramethyl-1,3,2-dioxaborolan-2-yl)naphthalen-1-yl)ethynyl)triisopropylsilane (9.0 g, 47% yield) as a yellow solid. LCMS [ESI, M+1]: 453.2; $^1$H NMR (400 MHz, CDCl$_3$) δ 7.85-7.75 (m, 3H), 7.43 (dd, J=7.2, 8.0 Hz, 1H), 7.30-7.24 (m, 1H), 1.45 (s, 12H), 1.21-1.14 (m, 21H).

Intermediate C-24

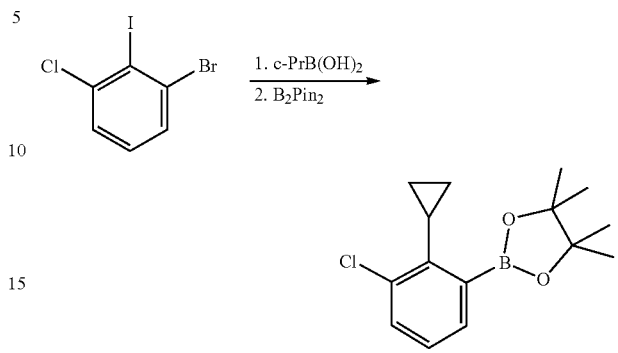

To a solution of 7-fluoro-8-((triisopropylsilyl)ethynyl)naphthalen-1-yl trifluoromethanesulfonate (20.0 g, 42.1 mmol, 1.00 equiv) and Pin$_2$B$_2$ (16.0 g, 63.2 mmol, 1.50 equiv) in dioxane (6.00 mL) was added KOAc (8.27 g, 84.3 mmol, 2.0 equiv) and Pd(dppf)Cl$_2$ (3.08 g, 4.21 mmol, 0.10 equiv). The mixture was stirred at 110° C. for 12 h under an atmosphere of nitrogen prior to being filtered and concentrated under reduced pressure. The resultant residue was purified by column chromatography (SiO$_2$, petroleum ether/ethyl acetate, 1:0 to 10:1) to afford ((2-fluoro-8-(4,4,5,5-tetramethyl-1,3,2-dioxaborolan-2-yl)naphthalen-1-yl)ethynyl)triisopropylsilane (9.0 g, 47% yield) as a yellow solid. LCMS [ESI, M+1]: 453.2; $^1$H NMR (400 MHz, CDCl$_3$) δ 7.85-7.75 (m, 3H), 7.43 (dd, J=7.2, 8.0 Hz, 1H), 7.30-7.24 (m, 1H), 1.45 (s, 12H), 1.21-1.14 (m, 21H).

To a solution of 1-bromo-3-chloro-2-cyclopropylbenzene (1.22 g, 5.27 mmol, 1.0 equiv) in 1,4-dioxane (30 mL) was added KOAc (1.55 g, 15.8 mmol, 3.0 equiv), Pin$_2$B$_2$ (2.68 g, 10.5 mmol, 2.0 equiv) and Pd(dppf)Cl$_2$ (385 mg, 527 μmol, 0.1 equiv). The mixture was stirred at 110° C. for 6 h prior to being diluted with water (30 mL). The mixture was extracted with ethyl acetate (30 mL×3). The combined organic layer was dried over anhydrous sodium sulfate, filtered and concentrated to dryness. The residue was purified by column chromatography (SiO$_2$, petroleum ether/ethyl acetate, 1:0 to 5:1) and then by prep-HPLC [Phenomenex luna C18 250×50 mm×10 μm; A: water (0.225% FA), B: ACN; 52%-82%, 17 min] to provide 2-(3-chloro-2-cyclopropylphenyl)-4,4,5,5-tetramethyl-1,3,2-dioxaborolane (580 mg, 39% yield) as a white solid. $^1$H NMR (400 MHz, CDCl$_3$): δ 7.44 (dd, J=1.2, 7.2 Hz, 1H), 7.36 (dd, J=1.2, 8.0 Hz, 1H), 7.15-7.09 (m, 1H), 2.11-1.98 (m, 1H), 1.38 (s, 12H), 1.05-0.99 (m, 2H), 0.60-0.53 (m, 2H).

Intermediate C-25

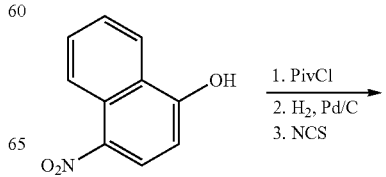

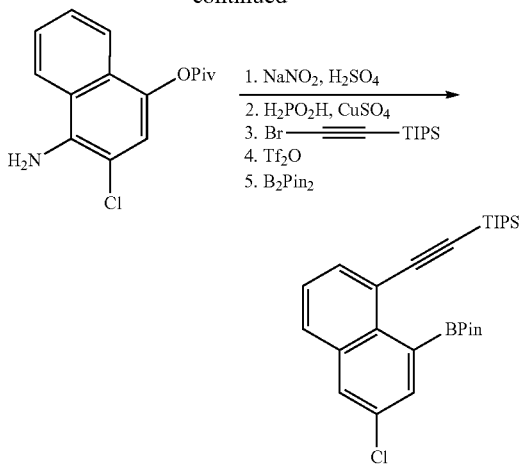

To a solution of 4-nitronaphthalen-1-ol (18 g, 95.1 mmol, 1 equiv) in THF (360 mL) containing TEA (19.9 mL, 143 mmol, 1.5 equiv) at 5° C. was added dropwise pivaloyl chloride (14.1 mL, 114 mmol, 1.2 equiv). After stirring at 5° C. for 1 h, the mixture was diluted with water (200 mL) and extracted with ethyl acetate (2×200 mL). The combined organic layer was dried over anh Na$_2$SO$_4$, filtered and concentrated to dryness. The residue was purified by silica gel chromatography (petroleum ether/ethyl acetate, 10:1 to 1:1) to give 4-nitronaphthalen-1-yl pivalate (24.6 g, 85%) as a yellow solid. R$_f$=0.70 (petroleum ether/ethyl acetate, 5:1); $^1$H NMR (400 MHz, CDCl$_3$): δ 8.67 (d, J=8.8 Hz, 1H), 8.31 (d, J=8.4 Hz, 1H), 8.04 (d, J=8.4 Hz, 1H), 7.77 (ddd, J=1.2, 7.2, 8.8 Hz, 1H), 7.70-7.64 (m, 1H), 7.36-7.32 (m, 1H), 1.52 (s, 9H).

To a solution of 4-nitronaphthalen-1-yl pivalate (24.6 g, 90.0 mmol, 1 equiv) in MeOH (500 mL) was added Pd/C (2.5 g, 10 wt. %) under N$_2$. The suspension was evacuated and purged with H$_2$ several times. The mixture was stirred under H$_2$ (15 psi) at 20° C. for 12 h. The vessel was flushed with nitrogen and the mixture was filtered through a plug of Celite. The filtrate was concentrated to afford 4-aminonaphthalen-1-yl pivalate (21 g, 86%) as a brown solid. $^1$H NMR (400 MHz, CDCl$_3$): δ 7.87-7.76 (m, 2H), 7.53-7.46 (m, 2H), 7.02 (d, J=8.0 Hz, 1H), 6.74 (d, J=8.0 Hz, 1H), 1.51-1.48 (m, 9H).

To a solution of 4-nitronaphthalen-1-yl pivalate (24.6 g, 90.0 mmol, 1 equiv) in MeOH (500 mL) was added Pd/C (2.5 g, 10 wt. %) under N$_2$. The suspension was evacuated and purged with H$_2$ several times. The mixture was stirred under H$_2$ (15 psi) at 20° C. for 12 h. The vessel was flushed with nitrogen and the mixture was filtered through a plug of Celite. The filtrate was concentrated to afford 4-aminonaphthalen-1-yl pivalate (21 g, 86%) as a brown solid. $^1$H NMR (400 MHz, CDCl$_3$): δ 7.87-7.76 (m, 2H), 7.53-7.46 (m, 2H), 7.02 (d, J=8.0 Hz, 1H), 6.74 (d, J=8.0 Hz, 1H), 1.51-1.48 (m, 9H).

To a solution of 4-amino-3-chloronaphthalen-1-yl pivalate (18.8 g, 67.7 mmol, 1 equiv) in AcOH (188 mL) and conc H$_2$SO$_4$ (188 mL, 3.46 mol) at 5° C. was added NaNO$_2$ (8.41 g, 122 mmol, 1.8 equiv). The reaction mixture was allowed to warm to room temperature over 2 h. To the mixture was added EtOH (188 mL) followed by CuSO$_4$ (13.0 g, 81.2 mmol, 1.2 eq) in aqueous H$_3$PO$_2$ (56.4 g, 278 mmol, 32% in water, 4.10 equiv). The mixture was stirred at 65° C. for 1 h and was cooled to room temperature, neutralized with aqueous NaOH (20%) solution and extracted with ethyl acetate (2×300 mL). The combined organic layer was washed with brine (200 mL), dried over anh Na$_2$SO$_4$, filtered and concentrated under vacuum. The residue was purified by silica gel chromatography (petroleum ether/ethyl acetate, 50:1 to 10:1) to afford 3-chloronaphthalen-1-ol (1.1 g, 8.2%) as a brown solid. R$_f$=0.70 (petroleum ether/ethyl acetate, 3:1); $^1$H NMR (400 MHz, DMSO-d$_6$): δ 10.70 (s, 1H), 8.13-8.07 (m, 1H), 7.83-7.76 (m, 1H), 7.57-7.41 (m, 3H), 6.85-6.81 (m, 1H).

A mixture of 3-chloronaphthalen-1-ol (900 mg, 5.04 mmol, 1 equiv), 2-bromoethynyl(triisopropyl)silane (1.58 g, 6.05 mmol, 1.2 equiv), dichloro(p-cymene)ruthenium(II) dimer (309 mg, 504 μmol, 0.1 equiv), KOAc (989 mg, 10.1 mmol, 2 equiv) in dioxane (15 mL) was stirred at 110° C. for 2 h under N$_2$. The mixture was diluted with water (20 mL) and extracted with ethyl acetate (2×20 mL). The organic layer was dried over anh Na$_2$SO$_4$, filtered and concentrated under vacuum. The residue was purified by silica gel chromatography (petroleum ether/ethyl acetate, 40:1 to 20:1) to provide 3-chloro-8-((triisopropylsilyl)ethynyl)naphthalen-1-ol (1.8 g, 89%) as a greenish oil. R$_f$=0.70 (petroleum ether/ethyl acetate, 10:1); $^1$H NMR (400 MHz, CDCl$_3$): δ 9.36 (s, 1H), 7.74-7.67 (m, 1H), 7.65-7.58 (m, 1H), 7.42-7.35 (m, 2H), 7.01-6.96 (m, 1H), 1.21-1.16 (m, 21H).

To a mixture of 3-chloro-8-((triisopropylsilyl)ethynyl) naphthalen-1-ol (2 g, 5.57 mmol, 1 equiv) and DIEA (2.91 mL, 16.7 mmol, 3.0 equiv) in DCM (40 mL) at −40° C. was added Tf$_2$O (1.38 mL, 8.36 mmol, 1.5 equiv). After stirring at −40° C. for 30 min the mixture was diluted with water (30 mL) and layers were separated. The aqueous phase was extracted with ethyl acetate (20 mL). Combined organic layer was dried over anh Na$_2$SO$_4$, filtered and concentrated under vacuum. The residue was purified by silica gel chromatography (petroleum ether to petroleum ether/ethyl acetate, 100:1) to give 3-chloro-8-((triisopropylsilyl)ethynyl)naphthalen-1-yl trifluoromethanesulfonate (2 g, 66%) as a greenish oil. R$_f$=0.43 (petroleum ether); $^1$H NMR (400 MHz, CDCl$_3$): δ 7.90-7.85 (m, 2H), 7.77 (dd, J=1.2, 8.4 Hz, 1H), 7.57-7.50 (m, 2H), 1.22-1.15 (m, 21H).

4,4,5,5-tetramethyl-2-(4,4,5,5-tetramethyl-1,3,2-dioxaborolan-2-yl)-1,3,2-dioxaborolane (1.97 g, 7.74 mmol, 2 equiv), 3-chloro-8-((triisopropylsilyl)ethynyl)naphthalen-1-yl trifluoromethanesulfonate (1.9 g, 3.87 mmol, 1 equiv), KOAc (1.33 g, 13.5 mmol, 3.5 equiv) and Pd(dppf)Cl$_2$ (283 mg, 387 μmol, 0.1 equiv) in dioxane (40 mL) was heated at 110° C. for 3 h under N$_2$. The mixture was filtered and the filtrate was diluted with water (20 mL). The aqueous layer was extracted with ethyl acetate (2×20 mL). The combined organic layer was dried over anh Na$_2$SO$_4$, filtered and concentrated under vacuum. The residue was purified by silica gel chromatography (petroleum ether/ethyl acetate, 1:0 to 50:1) to afford ((6-chloro-8-(4,4,5,5-tetramethyl-1,3, 2-dioxaborolan-2-yl)naphthalen-1-yl)ethynyl)triisopropylsilane (0.42 g, 21%) as an orange oil. R$_f$=0.10 (petroleum ether); $^1$H NMR (400 MHz, CDCl$_3$): δ 7.84-7.78 (m, 2H), 7.72-7.69 (m, 1H), 7.68-7.65 (m, 1H), 7.42 (dd, J=7.3, 8.1 Hz, 1H), 1.44 (s, 12H), 1.17-1.15 (m, 21H).

In addition to the foregoing Intermediates above, the following exemplary Intermediates D-1 to D-11 may be used to prepare substituted azaquinazoline core intermediates suitable for synthesizing compounds of Formula (I).

Intermediate D-1

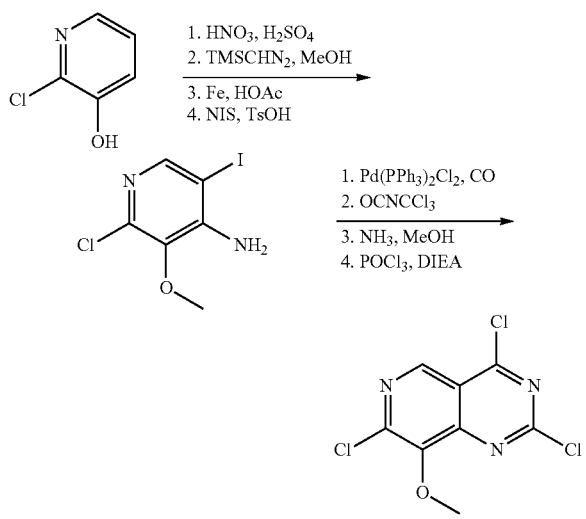

A solution of 2-chloropyridin-3-ol (20 g, 154 mmol, 1.0 equiv) in $H_2SO_4$ (40 mL) was cooled to 0° C. and a mixture of conc $H_2SO_4$ (36.8 g, 368 mmol, 20 mL, 2.4 equiv) and conc $HNO_3$ (28 g, 311 mmol, 20 mL, 70% purity, 2.0 equiv) was added slowly. After the addition was complete, the mixture was stirred at 0° C. for 1 h and then at room temperature for an additional hour. The reaction mixture was poured onto crushed ice (800 g) and extracted with ethyl acetate (2×300 mL). The combined organic layer was washed with brine (300 mL), dried over anh $Na_2SO_4$, filtered and concentrated under reduced pressure. The residue was purified by column chromatography ($SiO_2$, petroleum ether/ethyl acetate, 10:1) to afford 2-chloro-4-nitro-pyridin-3-ol (10.4 g, 59.6 mmol, 39% yield) as a yellow solid. LCMS [ESI, M+1]: 175.

A mixture of 2-chloro-4-nitro-pyridin-3-ol (12 g, 68.8 mmol, 1.0 equiv) in acetonitrile (200 mL) and methanol (30 mL) was added $TMSCHN_2$ (2.0 M in hexane, 85.9 mL, 2.5 equiv) over 1 h. After stirring at room temperature for 12 h the mixture was quenched with AcOH (20 mL). The mixture was extracted with ethyl acetate (2×200 mL), the combined organic layer was washed with brine (100 mL), dried over $Na_2SO_4$, filtered and concentrated under vacuum. The residue was purified by column chromatography ($SiO_2$, petroleum ether/ethyl acetate, 1:1) and reversed phase flash chromatography [water (FA, 0.1%)/acetonitrile] to afford 2-chloro-3-methoxy-4-nitro-pyridine (6.46 g, 34.3 mmol, 50% yield) as a yellow solid. LCMS [ESI, M+1]: 189.

A mixture of 2-chloro-3-methoxy-4-nitro-pyridine (6.0 g, 31.8 mmol, 1.0 equiv) and Fe (10.7 g, 191 mmol, 6.0 equiv) in AcOH (60 mL) was stirred at 40° C. for 1 h. Subsequently, the mixture was diluted with water (10 mL) and ethyl acetate (20 mL). The biphasic mixture was filtered and the organic and aqueous layers were separated. The aqueous phase was extracted with ethyl acetate (2×20 mL). The combined organic layer was washed with brine (20 mL), dried over anh $Na_2SO_4$, filtered and concentrated under reduced pressure to afford the crude residue. The residue was purified by column chromatography ($SiO_2$, petroleum ether/ethyl acetate, 1:1) to afford 2-chloro-3-methoxy-pyridin-4-amine (4.9 g, 30.6 mmol, 96% yield) as a yellow solid. LCMS [ESI, M+1]: 159. $^1$H NMR (400 MHz, $CDCl_3$) δ 7.81-7.73 (m, 1H), 6.60-6.52 (m, 1H), 4.66 (br s, 2H), 3.89-3.80 (m, 3H).

A mixture of 2-chloro-3-methoxy-pyridin-4-amine (5.2 g, 32.8 mmol, 1.0 equiv), NIS (11.1 g, 49.2 mmol, 1.5 equiv) and $TsOH.H_2O$ (624 mg, 3.28 mmol, 0.1 equiv) in acetonitrile (50 mL) was allowed to stir at 70° C. for 12 h. The mixture was cooled to room temperature and was concentrated under vacuum. The residue was dissolved in water (50 mL) and the mixture was extracted with ethyl acetate (2×50 mL). The combined organic layer was washed with brine (50 mL), dried over anh $Na_2SO_4$, filtered and concentrated at reduced pressure to afford the crude residue. The residue was purified by column chromatography ($SiO_2$, petroleum ether/ethyl acetate, 1:1) to afford 2-chloro-5-iodo-3-methoxy-pyridin-4-amine (7.9 g, 26.9 mmol, 82% yield) as a yellow solid. LCMS [ESI, M+1]: 285.

A mixture of 2-chloro-5-iodo-3-methoxy-pyridin-4-amine (8.0 g, 28.1 mmol, 1.0 equiv), $Pd(PPh_3)_2Cl_2$ (1.97 g, 2.81 mmol, 0.1 equiv) and TEA (10.2 g, 101 mmol, 14.1 mL, 3.6 equiv) in ethanol (100 mL) was stirred at 80° C. for 12 h under CO (50 psi). The mixture was concentrated under vacuum. The residue was diluted with water (50 mL) and extracted with ethyl acetate (2×50 mL). The combined organic layer was washed with brine (50 mL), dried over anh $Na_2SO_4$, filtered and concentrated under vacuum to provide the crude residue. The residue was purified by reversed phase flash chromatography [water (FA, 0.1%)/acetonitrile] to afford ethyl 4-amino-6-chloro-5-methoxy-pyridine-3-carboxylate (6.0 g, 16.7 mmol, 59% yield) as a yellow solid. LCMS [ESI, M+1]: 231.

A mixture of ethyl 4-amino-6-chloro-5-methoxy-pyridine-3-carboxylate (1.0 g, 4.34 mmol, 1.0 equiv) and trichloro(isocyanato)methane (1.39 g, 8.67 mmol, 2.0 equiv) in THF (10 mL) was stirred at room temperature for 30 min. The mixture was concentrated under vacuum and the resultant residue was triturated with petroleum ether (10 mL) to afford ethyl 6-chloro-5-methoxy-4[(2,2,2-trichloroacetyl)carbamoylamino]pyridine-3-carboxylate (2 g, crude) as a yellow oil and used in next step without purification. LCMS [ESI, M+1]: 420.

A mixture of ethyl 6-chloro-5-methoxy-4-[(2,2,2-trichloroacetyl)carbamoylamino]pyridine-3-carboxylate (2.0 g, crude) in $NH_3.MeOH$ (4 mL, 10% purity) was stirred at 15° C. for 10 minutes. After completion, the mixture was concentrated under vacuum. The residue was triturated with MTBE (10 mL) and concentrated under vacuum to give 7-chloro-8-methoxy-pyrido[4,3-d]pyrimidine-2,4-diol (0.6 g, 2.64 mmol, two steps 61% yield) as a white solid and used into next batch without further purification. LCMS [ESI, M+1]: 228.

A mixture of 7-chloro-8-methoxy-pyrido[4,3-d]pyrimidine-2,4-diol (0.6 g, 2.64 mmol, 1.0 eq) and DIEA (1.70 g, 13.2 mmol, 2.30 mL, 5.0 eq) in $POCl_3$ (14.1 g, 92.2 mmol, 8.57 mL, 35 eq) was stirred at 110° C. for 2 hours. After completion, the mixture was concentrated under vacuum to give 2,4,7-trichloro-8-methoxy-pyrido[4,3-d]pyrimidine (0.7 g, crude) as a yellow oil and used into next batch without further purification LCMS [ESI, M−7]: 256.

Intermediate D-2

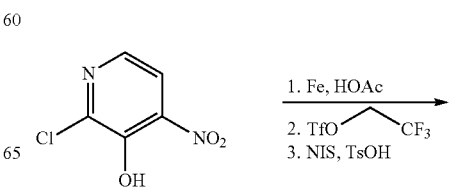

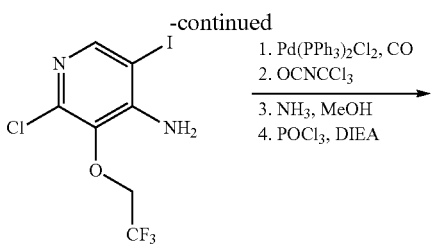

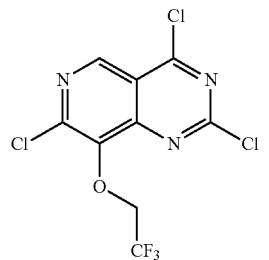

A mixture of 2-chloro-4-nitro-pyridin-3-ol (9.0 g, 51.6 mmol, 1.0 equiv) and Fe (17.3 g, 309 mmol, 6.0 equiv) in AcOH (90 mL) was stirred at 40° C. for 2 h. The mixture was cooled to room temperature and was diluted with $H_2O$ (100 mL) and ethyl acetate (150 mL). The aqueous phase was extracted with ethyl acetate (2×100 mL) and the combined organic layer was washed with brine (150 mL), dried over anh $Na_2SO_4$, filtered and concentrated under reduced pressure to provide the crude residue. The residue was purified by column chromatography ($SiO_2$, petroleum ether/ethyl acetate, 1:1) to afford 4-amino-2-chloro-pyridin-3-ol (4.5 g, 31.1 mmol, 60% yield) as a yellow solid. LCMS [ESI, M+1]: 145.

A mixture of 4-amino-2-chloro-pyridin-3-ol (1.5 g, 10.4 mmol, 1.0 equiv), 2,2,2-trifluoroethyl trifluoromethanesulfonate (2.89 g, 12.5 mmol, 1.2 equiv) and $K_2CO_3$ (2.87 g, 20.8 mmol, 2.0 equiv) in DMF (30 mL) and acetonitrile (3.0 mL) was stirred at 60° C. for 30 min. The mixture was cooled to room temperature and was diluted with $H_2O$ (100 mL). The aqueous layer was extracted with ethyl acetate (2×100 mL). The combined organic layer was washed with brine (2×150 mL), dried over anh $Na_2SO_4$, filtered and concentrated under reduced pressure to provide the crude residue. The residue was purified by column chromatography ($SiO_2$, petroleum ether/ethyl acetate, 1:1) to afford 2-chloro-3-(2,2,2-trifluoroethoxy)pyridin-4-amine (1.75 g, 7.65 mmol, 74% yield, 99% purity) as a yellow solid. LCMS [ESI, M+1]: 227. $^1$H NMR (400 MHz, DMSO-$d_6$) δ 7.66 (d, J=5.6 Hz, 1H), 6.66 (d, J=5.6 Hz, 1H), 6.26 (br s, 2H), 4.52 (q, J=8.8 Hz, 2H).

A mixture of 2-chloro-3-(2,2,2-trifluoroethoxy)pyridin-4-amine (5.3 g, 23.4 mmol, 1.0 equiv), NIS (6.32 g, 28.1 mmol, 1.2 equiv) and TsOH.$H_2O$ (445 mg, 2.34 mmol, 0.1 equiv) in acetonitrile (50 mL) was stirred at 70° C. for 2 h. The mixture cooled to room temperature and was concentrated at reduced pressure. The resultant residue was diluted with water (20 mL) and the mixture was extracted with ethyl acetate (2×30 mL). The combined organic layer was washed with brine (30 mL), dried over anh $Na_2SO_4$, filtered and concentrated under reduced pressure to afford the crude residue. The residue was purified by column chromatography ($SiO_2$, petroleum ether/ethyl acetate, 3:1) to afford 2-chloro-5-iodo-3-(2,2,2-trifluoroethoxy)pyridin-4-amine (6.2 g, 17.4 mmol, 74% yield, 99% purity) as a yellow solid. LCMS [ESI, M+1]: 353.

A mixture of 2-chloro-5-iodo-3-(2,2,2-trifluoroethoxy)pyridin-4-amine (1.0 g, 2.84 mmol, 1.0 equiv), Pd(PPh$_3$)$_2$C12 (199 mg, 284 μmol, 0.1 equiv) and TEA (1.03 g, 10.2 mmol, 1.42 mL, 3.6 equiv) in ethanol (20 mL) was heated at 80° C. for 12 h under CO (50 psi). The mixture was cooled to room temperature and concentrated at reduced pressure. The residue was diluted with water (10 mL) and the mixture was extracted with ethyl acetate (2×10 mL). The combined organic layer was washed with brine (20 mL), dried over anh $Na_2SO_4$, filtered and concentrated at reduced pressure to provide the crude residue. The residue was purified by column chromatography ($SiO_2$, petroleum ether/ethyl acetate, 3:1) to afford ethyl 4-amino-6-chloro-5-(2,2,2-trifluoroethoxy)pyridine-3-carboxylate (700 mg, 2.32 mmol, 82% yield) as a yellow solid. LCMS [ESI, M+1]: 299.

A mixture of ethyl 4-amino-6-chloro-5-(2,2,2-trifluoroethoxy)pyridine-3-carboxylate (0.2 g, 669 μmol, 1.0 equiv) and 2,2,2-trichloroacetyl isocyanate (189 mg, 1.00 mmol, 119 μL, 1.5 equiv) in THF (2 mL) was allowed to stir at room temperature for 30 min. The mixture was concentrated at reduced pressure and the resultant residue was triturated with MTBE (10 mL). The residue was dried at reduced pressure to afford ethyl 6-chloro-4-[(2,2,2-trichloroacetyl)carbamoylamino]-5-(2,2,2-trifluoroethoxy)pyridine-3-carboxylate (350 mg, crude) was obtained as a yellow solid. LCMS [ESI, M+1]: 488.

A mixture of ethyl 6-chloro-4-[(2,2,2-trichloroacetyl)carbamoylamino]-5-(2,2,2-trifluoroethoxy)pyridine-3-carboxylate (0.35 g, crude) in 10% NH$_3$.MeOH (5 mL) was allowed to stir at room temperature for 10 min. Subsequently, the mixture was concentrated at reduced pressure and the residue was triturated with MBTE (5 mL). The residue was dried at reduced pressure to afford 7-chloro-8-(2,2,2-trifluoroethoxy)pyrido[4,3-d]pyrimidine-2,4-diol (0.2 g, crude) as a white solid. LCMS [ESI, M+1]: 296.

A mixture of 7-chloro-8-(2,2,2-trifluoroethoxy)pyrido[4,3-d]pyrimidine-2,4-diol (700 mg, crude) and DIEA (1.53 g, 11.8 mmol, 2.06 mL) in POCl$_3$ (11.6 g, 75.3 mmol, 7 mL) was allowed to stir at 110° C. for 2 h. The mixture was cooled to room temperature and was concentrated at reduced pressure to afford 2,4,7-trichloro-8-(2,2,2-trifluoroethoxy)pyrido[4,3-d]pyrimidine (2.0 g, crude) as a yellow oil.

Intermediate D-3

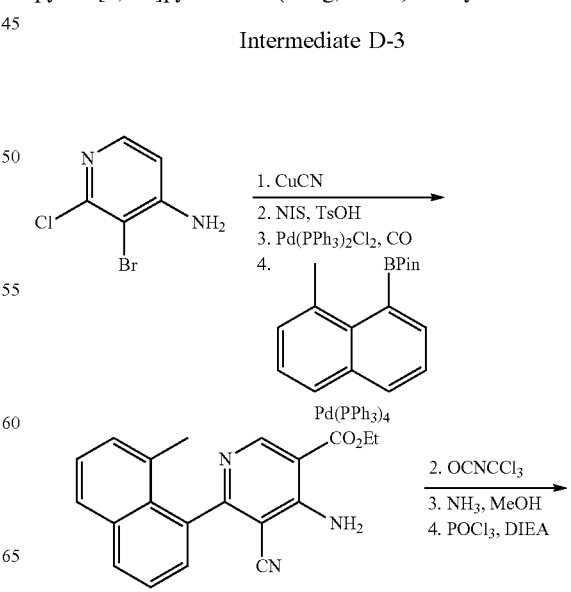

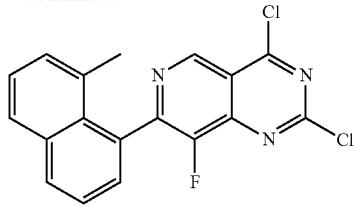

A mixture of 3-bromo-2-chloro-pyridin-4-amine (3.0 g, 14.5 mmol, 1.0 equiv), CuCN (3.89 g, 43.4 mmol, 3.0 equiv) in DMSO (30 mL) was stirred at 130° C. for 12 h. The mixture was concentrated under vacuum. To the residue was added NH₄OH (100 mL) and the mixture was stirred at 15° C. for 10 min prior to being extracted with ethyl acetate (2×200 mL). The combined organic layer was washed with brine (200 mL), dried over anh Na₂SO₄, filtered and concentrated under vacuum to afford 4-amino-2-chloro-pyridine-3-carbonitrile (1.0 g, 5.93 mmol, 41% yield) as a yellow solid. LCMS [ESI, M+1]: 154. ¹H NMR (400 MHz, DMSO-d₆): δ 7.92 (d, J=6.0 Hz, 1H), 7.43 (br s, 2H), 6.67 (d, J=6.0 Hz, 1H).

A mixture of 4-amino-2-chloro-pyridine-3-carbonitrile (3.2 g, 20.8 mmol, 1.0 equiv), TsOH.H₂O (198 mg, 1.04 mmol, 0.05 equiv) and NIS (7.03 g, 31.3 mmol, 1.5 equiv) in acetonitrile (30 mL) was stirred at 70° C. for 12 h prior to being concentrated under vacuum. The resultant residue was diluted with H₂O (50 mL), extracted with ethyl acetate (2×50 mL), and the combined organic layer was washed with brine (50 mL), dried over anh Na₂SO₄, filtered and concentrated under vacuum to provide the crude residue. The residue was purified by column chromatography (SiO₂, PE/EA, 3/1). The solid was triturated with acetonitrile (20 mL) and dried under vacuum to afford 4-amino-2-chloro-5-iodo-pyridine-3-carbonitrile (3.0 g, 10.7 mmol, 52% yield) as a yellow solid. LCMS [ESI, M+1]: 280. ¹H NMR (400 MHz, chloroform-d): δ 8.45 (s, 1H), 5.56 (br s, 2H).

A mixture of 4-amino-2-chloro-5-iodo-pyridine-3-carbonitrile (2.8 g, 10 mmol, 1.0 equiv), TEA (3.65 g, 36.1 mmol, 5.02 mL, 3.6 equiv) and Pd(PPh₃)₂Cl2 (703 mg, 1.0 mmol, 0.1 equiv) in ethanol (30 mL) was stirred at 80° C. for 12 h under CO (50 psi). The mixture was concentrated under reduced pressure. The resultant residue was triturated with methanol (20 mL) and the solid was collected and dried under vacuum to afford ethyl 4-amino-6-chloro-5-cyano-pyridine-3-carboxylate (2.0 g, 8.78 mmol, 88% yield) as a yellow solid. LCMS [ESI, M+1]: 226. ¹H NMR (400 MHz, DMSO-d₆): δ 8.63 (s, 1H), 8.11 (br s, 2H), 4.32 (q, J=7.2 Hz, 2H), 1.32 (t, J=7.2 Hz, 3H).

A mixture of ethyl 4-amino-6-chloro-5-cyano-pyridine-3-carboxylate (1.7 g, 7.53 mmol, 1.0 equiv), (8-methyl-1-naphthyl)boronic acid (1.82 g, 9.79 mmol, 1.3 equiv), Pd(PPh₃)₄ (871 mg, 753 μmol, 0.1 equiv) and Cs₂CO₃ (7.36 g, 22.6 mmol, 3.0 equiv) in dioxane (30 mL) and H₂O (10 mL) was stirred at 100° C. for 6 h under N₂. The mixture was cooled to room temperature and diluted with water (10.0 mL). The mixture was extracted with ethyl acetate (2×10 mL). The combined organic layer was washed with brine (10 mL), dried over anh Na₂SO₄, filtered and concentrated under vacuum. The residue was purified by column chromatography (SiO₂, PE/EA, 3/1) and then by reversed phase flash chromatography [water (FA, 0.1%)/acetonitrile] to afford ethyl 4-amino-5-cyano-6-(8-methyl-1-naphthyl)pyridine-3-carboxylate (450 mg, 1.29 mmol, 17% yield) as a yellow oil. LCMS [ESI, M+1]: 332.

A mixture of ethyl 4-amino-5-cyano-6-(8-methyl-1-naphthyl)pyridine-3-carboxylate (0.45 g, 1.36 mmol, 1.0 equiv) and trichloro(isocyanato)methane (436 mg, 2.72 mmol, 2.0 equiv) in THF (4 mL) was stirred at 15° C. for 10 min. The mixture was concentrated under vacuum to provide a residue. The residue was triturated with MBTE (10 mL) and dried under vacuum to afford ethyl 5-cyano-6-(8-methyl-1-naphthyl)-4-[(2,2,2-trichloroacetyl)carbamoylamino]pyridine-3-carboxylate (0.7 g, crude) as a white solid. LCMS [ESI, M+2]: 521.

A mixture of ethyl 5-cyano-6-(8-methyl-1-naphthyl)-4-[(2,2,2-trichloroacetyl)carbamoylamino]pyridine-3-carboxylate (0.7 g, crude) in NH₃ (1 mL, 30% in MeOH) was stirred at 15° C. for 10 min and was then concentrated under vacuum. The residue was washed with MTBE (10 mL) and dried under vacuum to afford 2,4-dihydroxy-7-(8-methyl-1-naphthyl)pyrido[4,3-d]pyrimidine-8-carbonitrile (0.41 g, 1.25 mmol, 91% over two steps) as a white solid. LCMS [ESI, M+1]: 329.

To a mixture of 2,4-dihydroxy-7-(8-methyl-1-naphthyl)pyrido[4,3-d]pyrimidine-8-carbonitrile (200 mg, 609 μmol, 1.0 equiv) in POCl₃ (6.60 g, 43 mmol, 4.0 mL, 70.7 equiv) at 0° C. was added DIEA (236 mg, 1.83 mmol, 318 μL, 3.0 equiv). The mixture was heated for 2 h at 110° C. at which time an additional portion of DIEA (157 mg, 1.22 mmol, 212 μL, 2.0 equiv) was added and heating was continued for 3 h. The mixture was cooled to room temperature and was concentrated under reduced pressure to provide 2,4-dichloro-7-(8-methyl-1-naphthyl)pyrido[4,3-d]pyrimidine-8-carbonitrile (0.4 g, crude) as a yellow oil. LCMS [ESI, M−8]: 357.

Intermediate D-4

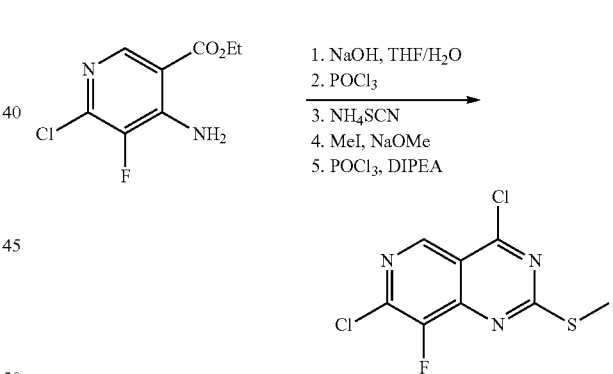

To a solution of ethyl 4-amino-6-chloro-5-fluoro-pyridine-3-carboxylate (100 g, 457 mmol, 1 equiv) in THF (900 mL) was added a solution of NaOH (73.2 g, 1.83 mol, 4 equiv) in H₂O (450 mL). The mixture was stirred at 25° C. for 16 h and then was concentrated under vacuum to remove THF. The residue was acidified to pH 2 with 2M HCl and was filtered. The filter cake was dried under vacuum, triturated with DCM and dried under vacuum to provide 4-amino-6-chloro-5-fluoro-pyridine-3-carboxylic acid (67 g, 352 mmol, 77% yield) as a gray solid. LCMS [ESI, M+1]: 191.

To a flask containing 4-amino-6-chloro-5-fluoro-pyridine-3-carboxylic acid (15 g, 78.7 mmol, 1.0 equiv) was added slowly POCl₃ (248 g, 1.61 mol, 150 mL, 20.5 equiv). The mixture was gradually warmed to 90° C. and stirred for 2 h. Then the mixture was cooled to 25° C. and concentrated under reduced pressure. The residue was dissolved in anhydrous THF (100 mL) and added dropwise to a solution of NH₄SCN (11.9 g, 157 mmol, 12.0 mL, 2.0 equiv) in THF (200 mL) and stirred at 25° C. for 16 h. The reaction mixture was diluted with water (500 mL) at 20° C. and was extracted with ethyl acetate (300 mL×3). The combined organic layer was washed with brine (200 mL), dried over anh Na₂SO₄, filtered and concentrated under reduced pressure to give a residue. The residue was triturated with ethyl acetate (50.0 mL) and dried under vacuum to afford 7-chloro-8-fluoro-2-thioxo-1H-pyrido[4,3-d]pyrimidin-4-one (12 g, 50.2 mmol, 64% yield) as a yellow solid. LCMS [ESI, M+1]: 232.

To a solution of 7-chloro-8-fluoro-2-thioxo-1H-pyrido[4,3-d]pyrimidin-4-one (55 g, 237 mmol, 1.0 equiv) in DMF (500 mL) was added NaOMe (12.8 g, 237 mmol, 1.0 equiv). The mixture was allowed to stir for 10 min prior to the dropwise addition of CH₃I (33.7 g, 237 mmol, 14.8 mL, 1.0 equiv). The resultant suspension was stirred at 25° C. for 2 h prior to being poured into ice water (500 mL). The yellow precipitate was filtered, washed with ice water (100 mL×3) and dried under reduced pressure to afford 7-chloro-8-fluoro-2-methylsulfanyl-pyrido[4,3-d]pyrimidin-4-ol (42.2 g, 172 mmol, 72% yield) as a yellow solid. LCMS [ESI, M+1]: 246. ¹H NMR (400 MHz, DMSO-d₆) δ=13.23 (s, 1H), 8.78 (s, 1H), 2.60 (s, 3H).

To a suspension of 7-chloro-8-fluoro-2-methylsulfanyl-pyrido[4,3-d]pyrimidin-4-ol (20 g, 81.4 mmol, 1 equiv) in POCl₃ (275 g, 1.79 mol, 167 mL, 22.0 equiv) was added DIPEA (21.0 g, 163 mmol, 28.4 mL, 2.0 equiv) and the reaction was heated to 90° C. and stirred for 6 h. The POCl₃ was removed under reduced pressure. The residue was diluted with ethyl acetate (500 mL), poured into ice (1000 g) and was extracted with ethyl acetate (300 mL×3). The combined organic layer was washed with brine (500 mL×2), dried over anh Na₂SO₄ and concentrated to afford 4,7-dichloro-8-fluoro-2-methylsulfanyl-pyrido[4,3-d]pyrimidine (22 g, crude) as a brown solid. LCMS [ESI, M+1]: 264.

Intermediate D-5

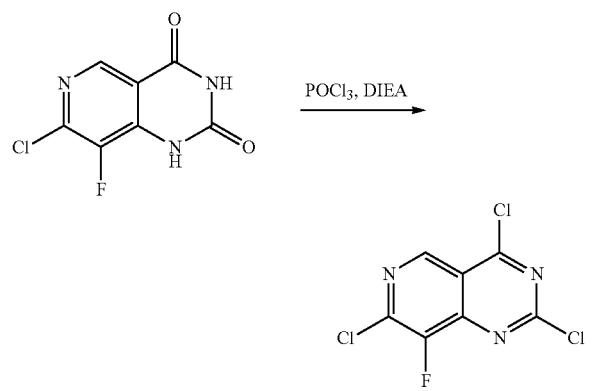

To a mixture of POCl₃ (165 g, 1.08 mol, 100 mL, 23.2 equiv) and DIEA (30.0 g, 232 mmol, 40.4 mL, 5.0 equiv) at 0° C. was added portionwise 7-chloro-8-fluoro-pyrido[4,3-d] pyrimidine-2,4-diol (10 g, 46.4 mmol, 1.0 equiv). The mixture was stirred at 110° C. for 3 hours. Subsequently, the mixture was cooled to room temperature and concentrated under vacuum. The resultant oil was azeotroped with CHCl₃ to afford 2,4,7-trichloro-8-fluoro-pyrido [4,3-d]pyrimidine (11.7 g, crude) as a black oil.

Intermediate D-6

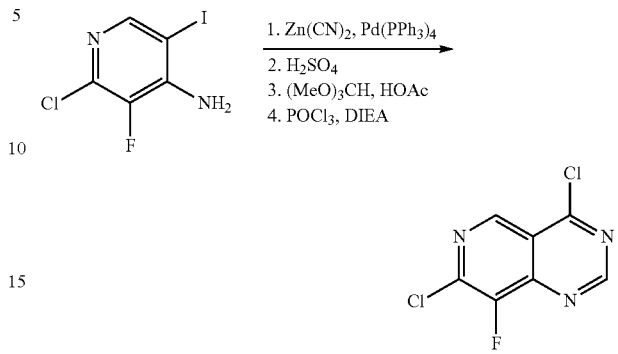

To a mixture of 2-chloro-3-fluoro-5-iodopyridin-4-amine (10.0 g, 36.7 mmol, 1.0 equiv), 4 Å molecular sieve (3.00 g) and Zn(CN)₂ (5.60 g, 47.7 mmol, 3.03 mL, 1.3 equiv) in DMF (200 mL) was added Pd(PPh₃)₄ (2.12 g, 1.84 mmol, 0.05 equiv). The mixture was stirred at 100° C. for 3 h prior to being diluted with H₂O (30 mL) and extracted with ethyl acetate (3×30 mL). The combined organic layer was dried over anh Na₂SO₄, filtered and the filtrated was concentrated under reduced pressure to afford 4-amino-6-chloro-5-fluoronicotinonitrile (6.00 g, 32.5 mmol, 88.6% yield) as a yellow solid. LCMS [ESI, M+1]: 172.

A mixture of 4-amino-6-chloro-5-fluoronicotinonitrile (6.00 g, 35.0 mmol, 1.0 equiv) in conc H₂SO₄ (20 mL) was stirred at 60° C. for 1 hour. The reaction mixture was cooled to room temperature and was diluted with H₂O (50 mL) at 25° C. The pH was adjusted to 8 using solid Na₂CO₃ and the mixture was extracted with ethyl acetate (100 mL×5). The combined organic layer was washed brine (200 mL×2) and concentrated under reduced pressure to afford 4-amino-6-chloro-5-fluoronicotinamide (6.50 g, 33.1 mmol, 95% yield, 96.4% purity) as white solid. LCMS [ESI, M+1]: 190.

To a mixture of 4-amino-6-chloro-5-fluoronicotinamide (6.00 g, 31.7 mmol, 1.0 equiv) in acetic acid (60.0 mL) was added trimethoxymethane (67.2 g, 633 mmol, 69.4 mL, 20 equiv). The mixture was stirred at 135° C. for 4 h and was cooled to room temperature. The mixture was diluted with H₂O (50 mL) and then extracted with ethyl acetate (100 mL×3). The combined organic layer was washed brine (300 mL×1), filtered and the filtrate was concentrated under reduced pressure to give a residue. The crude product was triturated with acetonitrile to afford 7-chloro-8-fluoropyrido[4,3-d]pyrimidin-4(3H)-one (2.80 g, 14.0 mmol, 44% yield) as yellow solid. LCMS [ESI, M+1]: 200. ¹H NMR (400 MHz, chloroform-d): δ 8.94 (s, 1H), 8.41 (s, 1H).

A mixture of 7-chloro-8-fluoropyrido[4,3-d]pyrimidin-4(3H)-one (2.80 g, 14.0 mmol, 1.0 equiv) in DIEA (3.63 g, 28.1 mmol, 4.89 mL, 2.0 equiv) and POCl₃ (99.0 g, 646 mmol, 60.0 mL, 46 equiv) was stirred at 110° C. for 3 h. The mixture was cooled to room temperature and was concentrated under reduced pressure to give 4,7-dichloro-8-fluoropyrido[4,3-d]pyrimidine (5.00 g, crude) as a black oil.

Intermediate D-7

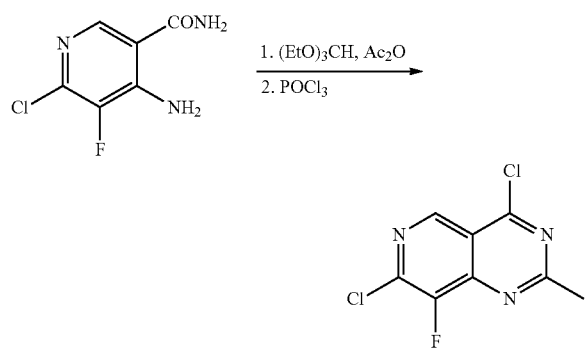

To a mixture of 4-amino-6-chloro-5-fluoronicotinamide (3.50 g, 18.5 mmol, 1.0 equiv) in acetic anhydride (70.0 mL) was added 1,1,1-triethoxyethane (65.9 g, 406 mmol, 74.5 mL, 22.0 equiv). The mixture was stirred at 185° C. for 36 h. The reaction mixture was cooled to room temperature, diluted with H$_2$O (50.0 mL) and extracted with ethyl acetate (100 mL×3). The combined organic layer was washed with saturated brine (300 mL×1), dried over anhydrous sodium sulfate and filtered. The filtrate was concentrated under reduced pressure. The resultant residue was adjusted to pH 3 with aq 1 M HCl and the mixture was extracted with ethyl acetate (100 mL×3). The combined organic layer was washed with brine (300 mL×1), dried over anhydrous sodium sulfate and filtered. The filtrate was concentrated under reduced pressure to afford 7-chloro-8-fluoro-2-methylpyrido[4,3-d]pyrimidin-4-ol (800 mg, 20% yield) as a white solid. $^1$H NMR (400 MHz, DMSO-d$_6$): δ 13.27-12.47 (m, 1H), 8.89 (s, 1H), 2.43 (s, 3H). LCMS [ESI, M+1]: 214.

A mixture of 7-chloro-8-fluoro-2-methylpyrido[4,3-d]pyrimidin-4-ol (0.40 g, 1.87 mmol, 1.0 equiv), DIEA (726 mg, 5.62 mmol, 979 μL, 3.0 equiv) and POCl$_3$ (861 mg, 5.62 mmol, 522 μL, 3.0 equiv) in toluene (30.0 mL) was stirred at 110° C. for 3 h. Subsequently, the POCl$_3$ was removed under vacuum to afford 4,7-dichloro-8-fluoro-2-methylpyrido[4,3-d]pyrimidine (800 mg, crude) as a black oil.

Intermediate D-8

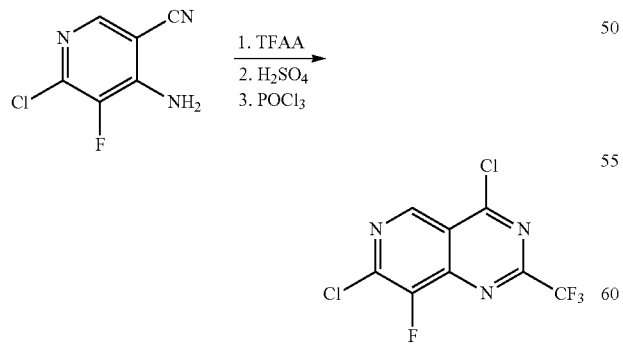

To a solution of 4-amino-6-chloro-5-fluoronicotinonitrile (100 mg, 583 umol, 1.0 equiv) in DCM (3 mL) at 0° C. was added TFAA (184 mg, 874 μmol, 122 μL, 1.5 equiv) and TEA (118 mg, 1.17 mmol, 162 μL, 2 equiv). The mixture was stirred at 20° C. for 20 h, diluted with satd aq NaHCO$_3$ and extracted with ethyl acetate (3×10 mL). The combined organic layer was washed with brine (10 mL), dried over anh Na$_2$SO$_4$, filtered and concentrated in vacuo to afford N-(2-chloro-5-cyano-3-fluoropyridin-4-yl)-2,2,2-trifluoroacetamide (100 mg, crude) as a brown oil. LCMS [ESI, M−1]: 265.8.

Concentrated H$_2$SO$_4$ (1 mL) was added to N-(2-chloro-5-cyano-3-fluoropyridin-4-yl)-2,2,2-trifluoroacetamide (100 mg, 374 μmol, 1.0 equiv) and the mixture was stirred at 60° C. for 8 h. The mixture was cooled to room temperature and poured into ice water. The pH was adjusted to 7-8 with satd aq NaHCO$_3$ and then the mixture was extracted with ethyl acetate (3×10 mL). The combined organic layer was washed with brine (10 mL), dried over anh Na$_2$SO$_4$, filtered and concentrated under the reduced pressure to give the residue. The residue was purified by prep-TLC (SiO$_2$, DCM:MeOH, 5:1) to afford 7-chloro-8-fluoro-2-(trifluoromethyl)pyrido[4,3-d]pyrimidin-4-ol (30.0 mg, 30% yield) as a brown solid. $^1$H NMR (400 MHz, DMSO-d$_6$): δ 8.75 (s, 1H). LCMS [ESI, M−1]: 265.8.

To a solution of 7-chloro-8-fluoro-2-(trifluoromethyl)pyrido[4,3-d]pyrimidin-4-ol (30.0 mg, 112 μmol, 1.0 equiv) in toluene (1 mL) at 0° C. was added POCl$_3$ (51.6 mg, 336 μmol, 31.2 uL, 3.0 equiv) and DIEA (43.5 mg, 336 μmol, 58.6 μL, 3.0 equiv). The mixture was stirred at 110° C. for 3 h and was concentrated under reduced pressure to afford 4,7-dichloro-8-fluoro-2-(trifluoromethyl)pyrido[4,3-d]pyrimidine (30.0 mg, crude) as a brown oil.

Intermediate D-9

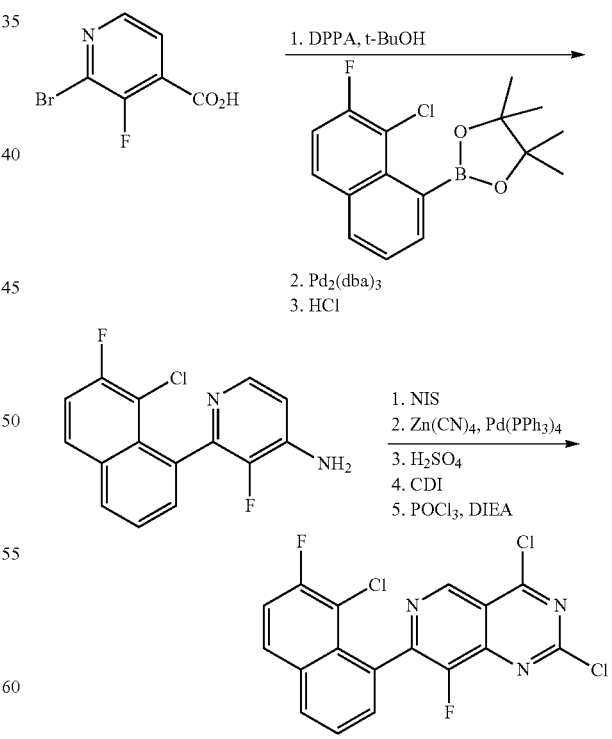

A mixture of 2-bromo-3-fluoroisonicotinic acid (90.0 g, 409 mmol, 1.00 equiv), 4 Å MS (50.0 g, 1.00 equiv) and TEA (124 g, 1.23 mol, 171 mL, 3.00 equiv) in toluene (50.0 mL) and t-BuOH (182 g, 2.45 mol, 235 mL, 6.00 equiv) was stirred at 110° C. for 0.5 hour under nitrogen. The mixture was cooled to 15° C. and DPPA (135 g, 491 mmol, 106 mL, 1.2 equiv) was added thereto. The mixture was stirred at 110° C. for 5 h prior to being diluted with water (300 mL) and extracted with ethyl acetate (300 mL×3). The combined organic layer was washed with brine (300 mL), dried over anhydrous sodium sulfate and filtered. The filtrate was concentrated under reduced pressure. The residue was purified by column chromatography (SiO$_2$, petroleum ether/ethyl acetate, 50:1 to 5:1) to afford tert-butyl (2-bromo-3-fluoropyridin-4-yl)carbamate (53.0 g, 39.4% yield) as a yellow solid. LCMS [ESI, M+1]: 291.

To a mixture of tert-butyl (2-bromo-3-fluoropyridin-4-yl)carbamate (40.0 g, 137 mmol, 1.00 equiv), 2-(8-chloro-7-fluoronaphthalen-1-yl)-4,4,5,5-tetramethyl-1,3,2-dioxaborolane (63.2 g, 206 mmol, 1.50 equiv), K$_3$PO$_4$ (87.5 g, 412 mmol, 3.0 equiv) in 1,4-dioxane (800 mL) and H$_2$O (160 mL) was added Pd$_2$(dba)$_3$ (12.6 g, 13.7 mmol, 0.10 equiv) and Ataphos (7.29 g, 27.5 mmol, 0.20 equiv). The mixture was purged with N$_2$ and then stirred at 70° C. for 2 h. Subsequently, the reaction mixture was diluted with water (200 mL) and extracted with ethyl acetate (200 mL×3). The combined organic layer was washed with brine (300 mL), dried over anhydrous sodium sulfate and filtered. The filtrate was concentrated under reduced pressure. The residue was purified by column chromatography (SiO$_2$, petroleum ether/ethyl acetate, 50:1 to 5:1) to afford tert-butyl (2-(8-chloro-7-fluoronaphthalen-1-yl)-3-fluoropyridin-4-yl)carbamate (55.0 g, 81.9% yield) as a yellow solid. LCMS [ESI, M+1]: 391.

To a mixture of tert-butyl (2-(8-chloro-7-fluoronaphthalen-1-yl)-3-fluoropyridin-4-yl)carbamate (72.0 g, 147 mmol, 1.00 equiv) in MeCN (500 mL) was added dropwise HCl in dioxane (4 M, 368 mL, 10.0 equiv). The mixture was stirred at room temperature for 5 h was concentrated. The residue was diluted with satd aq NaHCO$_3$ and was extracted with ethyl acetate (400 mL×3). The combined organic layer was dried over anhydrous sodium sulfate and filtered. The filtrate was concentrated under reduced pressure to afford 2-(8-chloro-7-fluoronaphthalen-1-yl)-3-fluoropyridin-4-amine (45.0 g, 99.8% yield) as a yellow solid. LCMS [ESI, M+1]: 291.

To a mixture of 2-(8-chloro-7-fluoronaphthalen-1-yl)-3-fluoropyridin-4-amine in glacial acetic acid (270 mL) was added NIS (27.9 g, 124 mmol, 2.00 equiv). The reaction mixture was stirred at 80° C. for 5 hours. The mixture was cooled to room temperature and was concentrated under reduced pressure to remove most of acetic acid. The mixture was poured into ice water (200 mL) and this mixture was extracted with ethyl acetate (400 mL×3). The combined organic layer was washed with saturated aq sodium carbonate (300 mL×3), brine (300 mL×3), dried over anhydrous sodium sulfate and filtered. The filtrate was concentrated under reduced pressure to afford 2-(8-chloro-7-fluoronaphthalen-1-yl)-3-fluoro-5-iodopyridin-4-amine (21.0 g, 77.3% yield) as a yellow solid. LCMS [ESI, M+1]: 417.

To a mixture of 2-(8-chloro-7-fluoronaphthalen-1-yl)-3-fluoro-5-iodopyridin-4-amine (30.0 g, 72.01 mmol, 1.00 equiv), Zn(CN)$_2$ (25.4 g, 216 mmol, 13.7 mL, 3.00 equiv) and 4 Å MS (9.00 g) in DMF (400 mL) was added Pd(PPh$_3$)$_4$ (8.32 g, 7.20 mmol, 0.10 equiv). The mixture was purged with N$_2$ and stirred at 120° C. for 12 h. Subsequently, the reaction mixture was quenched by the addition of water (200 mL) and was extracted with ethyl acetate (200 mL×3). The combined organic layer was washed with brine (300 mL), dried over anhydrous sodium sulfate and filtered. The filtrate was concentrated under reduced pressure. The residue was purified by column chromatography (SiO$_2$, petroleum ether/ethyl acetate, 50:1 to 5:1) to afford 4-amino-6-(8-chloro-7-fluoronaphthalen-1-yl)-5-fluoronicotinonitrile (19.6 g, 83% yield) as a yellow solid. LCMS [ESI, M+1]: 316.

A mixture of 4-amino-6-(8-chloro-7-fluoronaphthalen-1-yl)-5-fluoronicotinonitrile (32.6 g, 103 mmol, 1.00 equiv) in H$_2$SO$_4$ (50.6 g, 516 mmol, 27.5 mL, 5.0 equiv) was stirred at 45° C. for 1 h. Subsequently, the reaction mixture was diluted with H$_2$O (500 mL) and the pH was adjusted to 8 with solid Na$_2$CO$_3$. The mixture was extracted with ethyl acetate (500 mL×5). The combined organic layer was dried over anhydrous Na$_2$SO$_4$ and filtered. The filtrate was concentrated under vacuum to afford 4-amino-6-(8-chloro-7-fluoronaphthalen-1-yl)-5-fluoronicotinamide (34.0 g, 96.7% yield) as a white solid. LCMS [ESI, M+1]: 334.

To a solution of 4-amino-6-(8-chloro-7-fluoronaphthalen-1-yl)-5-fluoronicotinamide (23.0 g, 68.9 mmol, 1.00 equiv) in DMF (500 mL) at 0° C. was added NaH (5.51 g, 138 mmol, 60% purity, 2.00 equiv) in portions. The mixture was stirred at 0° C. for 1 hour. To this mixture was added CDI (16.8 g, 103 mmol, 1.50 equiv) and the mixture was stirred at 75° C. for 12 h. Subsequently, the reaction mixture was poured into ice water (200 mL) and the pH was adjusted to 7 with aq hydrochloric acid (2 M). The mixture was extracted with ethyl acetate (500 mL×3). The combined organic layer was washed with brine (500 mL), dried over anh Na$_2$SO$_4$ and filtered. The filtrate was concentrated under reduced pressure to afford 7-(8-chloro-7-fluoronaphthalen-1-yl)-8-fluoropyrido[4,3-d]pyrimidine-2,4(1H,3H)-dione (20.9 g, 76.7% yield) as a yellow solid. LCMS [ESI, M+1]: 360.

To a mixture of 7-(8-chloro-7-fluoronaphthalen-1-yl)-8-fluoropyrido[4,3-d]pyrimidine-2,4(1H,3H)-dione (24.0 g, 66.7 mmol, 1.00 equiv) and DIEA (25.9 g, 200 mmol, 34.9 mL, 3.00 equiv) in toluene (200 mL) at 0° C. was added POCl$_3$ (61.4 g, 400 mmol, 37.2 mL, 6.0 equiv). The mixture was stirred at 110° C. for 2 h. The reaction mixture was concentrated under reduced pressure to afford 2,4-dichloro-7-(8-chloro-7-fluoronaphthalen-1-yl)-8-fluoropyrido[4,3-d]pyrimidine (40.0 g, crude) as a brown oil.

Intermediate D-10

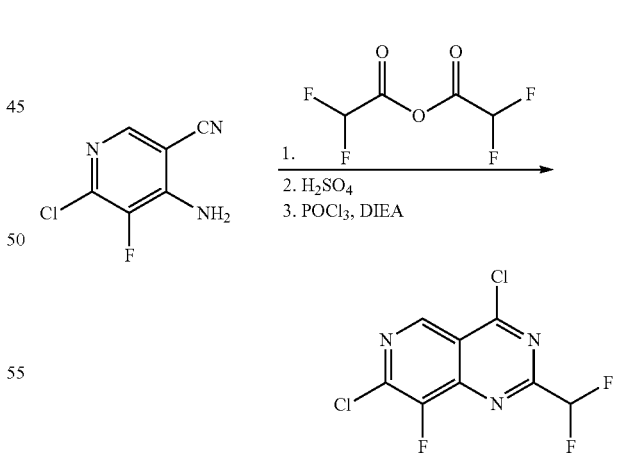

To a solution of 4-amino-6-chloro-5-fluoronicotinonitrile (150 mg, 874 μmol, 1 equiv) in DCM (5.00 mL) at 0° C. was added (2,2-difluoroacetyl)2,2-difluoroacetate (228 mg, 1.31 mmol, 1.5 equiv) and TEA (177 mg, 1.75 mmol, 243 μL, 2 equiv). The mixture was warmed to room temperature and stirred for 16 h. The mixture was diluted with satd aq NaHCO$_3$ (20 mL) and extracted with DCM (3×10 mL). The combined organic layer was washed with brine (10 mL), dried over anh Na$_2$SO$_4$, filtered and concentrated at reduced pressure to afford N-(2-chloro-5-cyano-3-fluoropyridin-4-yl)-2,2-difluoroacetamide (155 mg, crude) as a brown oil.

A flask containing N-(2-chloro-5-cyano-3-fluoropyridin-4-yl)-2,2-difluoroacetamide (155 mg, 621 μmol, 1 equiv) in $H_2SO_4$ (1.84 g, 18.3 mmol, 1 mL, 29.6 equiv) was stirred at 60° C. for 1 h prior to being cooled to room temperature. The mixture was poured into ice water (10 mL) and neutralized with satd aq $NaHCO_3$. The mixture was extracted with EtOAc (3×10 mL) and the combined organic layer was washed with brine (10 mL), dried over anh $Na_2SO_4$, filtered and concentrated under reduced pressure to afford 7-chloro-2-(difluoromethyl)-8-fluoropyrido[4,3-d]pyrimidin-4-ol (100 mg, crude) as a yellow solid. LCMS [ESI, M+1]: 250.0.

To a solution of 7-chloro-2-(difluoromethyl)-8-fluoropyrido[4,3-d]pyrimidin-4-ol (100 mg, 401 umol, 1 equiv) in toluene (1 mL) at 0° C. was added $POCl_3$ (184 mg, 1.20 mmol, 112 μL, 3 equiv) and DIEA (155 mg, 1.20 mmol, 209 μL, 3 equiv). The mixture was stirred at 110° C. for 3 h prior to being cooled to room temperature. The mixture was concentrated under reduced pressure to afford 4,7-dichloro-2-(difluoromethyl)-8-fluoropyrido[4,3-d]pyrimidine (107 mg, crude) as a brown oil.

Intermediate D-11

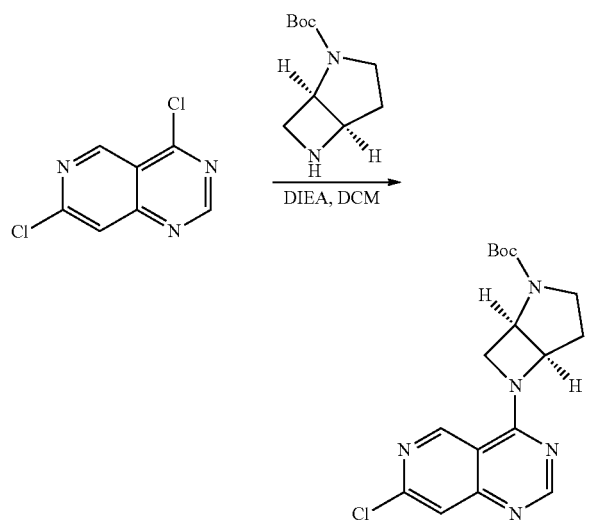

To a solution of 4,7-dichloropyrido[4,3-d]pyrimidine (150 mg, 750 μmol, 1.0 equiv) in DCM (3.0 mL) was added DIEA (392 μL, 2.25 mmol, 3.0 equiv) and tert-butyl (1R,5R)-2,6-diazabicyclo[3.2.0]heptane-2-carboxylate (134 mg, 675 μmol, 0.9 equiv). The mixture was stirred at −40° C. for 1 h and then at 0° C. for 30 min. The mixture was diluted with water (2.0 mL) and was extracted with ethyl acetate (3×2.0 mL). The combined organic layer was dried over anh $Na_2SO_4$, filtered and concentrated under reduced pressure. The resultant residue was purified by reversed phase flash chromatography [water (0.1% FA) in acetonitrile]. The desired fractions were collected, neutralized with solid $NaHCO_3$, and concentrated under reduced pressure to remove the ACN. The aqueous phase was extracted with ethyl acetate (2×5.0 mL). The combined organic phase was dried with anhydrous $Na_2SO_4$, filtered and concentrated under reduced pressure to give tert-butyl (1R,5R)-6-(7-chloropyrido[4,3-d]pyrimidin-4-yl)-2,6-diazabicyclo[3.2.0]heptane-2-carboxylate (150 mg, 52%) as a yellow solid. $^1$H NMR (400 MHz, $CDCl_3$): δ 8.97 (s, 1H), 8.67 (s, 1H), 7.67 (s, 1H), 5.48-5.42 (m, 1H), 4.91-4.68 (m, 2H), 4.33 (br s, 1H), 4.08-3.93 (m, 1H), 3.68-3.54 (m, 1H), 2.51 (br dd, J=6.4, 14.0 Hz, 1H), 2.19-2.08 (m, 1H), 1.51 (s, 9H); LCMS [ESI, M+1]: 362

In addition to the foregoing Intermediates above, the following exemplary Intermediates E-1-E-29 may be used to couple —Y—$R^2$, -L-$R^4$ and/or $R^1$ to the azaquinazoline core of Formula (I).

Intermediate E-1

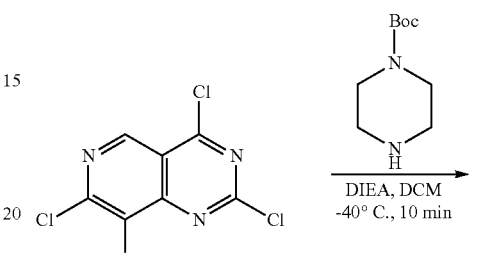

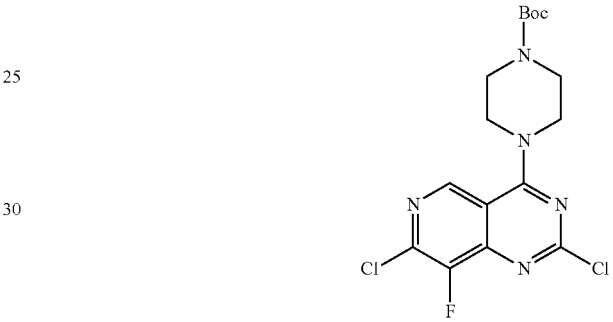

To a solution of 2,4,7-trichloro-8-fluoro-pyrido[4,3-d]pyrimidine (5.8 g, 23.0 mmol, 1.0 equiv) and tert-butyl piperazine-1-carboxylate (5.56 g, 29.9 mmol, 1.3 equiv) in DCM (50 mL) was added DIEA (8.91 g, 68.9 mmol, 12 mL, 3.0 equiv). The mixture was stirred at −40° C. for 10 min. The reaction mixture was diluted with saturated aq $NaHCO_3$ (200 mL) and extracted with ethyl acetate (200 mL×3). The combined organic layer was dried over anh $Na_2SO_4$, filtered and concentrated under reduced pressure to give a residue. The residue was purified by column chromatography ($SiO_2$, petroleum ether/ethyl acetate, 10:1 to 1:10). The resultant solid was triturated with petroleum ether/ethyl acetate (1:5, 50 mL) to afford tert-butyl 4-(2,7-dichloro-8-fluoro-pyrido[4,3-d]pyrimidin-4-yl)piperazine-1-carboxylate (3.34 g, 8.30 mmol, 36% yield) as a red solid. LCMS [ESI, M+1]: 402. $^1$H NMR (400 MHz, chloroform-d): δ 8.88 (s, 1H), 4.09-4.04 (m, 4H), 3.73-3.66 (m, 4H), 1.51 (s, 9H).

Intermediate E-2

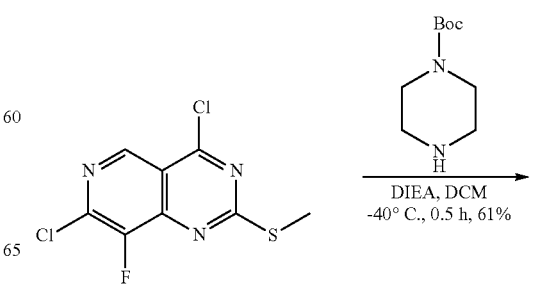

227

-continued

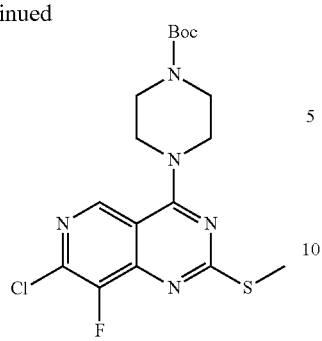

To a solution of 4,7-dichloro-8-fluoro-2-methylsulfanyl-pyrido[4,3-d]pyrimidine (900 mg, 3.41 mmol, 1.0 equiv) and tert-butyl piperazine-1-carboxylate (666 mg, 3.58 mmol, 1.05 equiv) in dichloromethane (18 mL) was added DIEA (1.10 g, 8.52 mmol, 1.48 mL, 2.5 equiv). The mixture was stirred at −40° C. for 0.5 hour. The mixture was diluted with water (10 mL) and extracted with dichloromethane (2×20 mL). The combined organic layer was dried over anh Na$_2$SO$_4$ and concentrated at reduced pressure to provide the crude residue. The residue was purified by silica gel chromatography (petroleum ether/ethyl acetate, 5:1 to 0:1) to afford tert-butyl 4-(7-chloro-8-fluoro-2-methylsulfanyl-pyrido[4,3-d]pyrimidin-4-yl)piperazine-1-carboxylate (950 mg, 2.08 mmol, 61% yield) as a yellow solid. LCMS [ESI, M+1]: 414.

Intermediate E-3

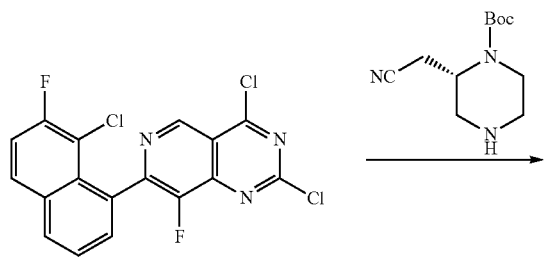

228

-continued

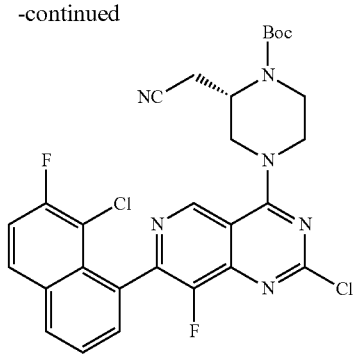

To a mixture of 2,4-dichloro-7-(8-chloro-7-fluoronaphthalen-1-yl)-8-fluoropyrido[4,3-d]pyrimidine (40.0 g, 101 mmol, 1.00 equiv) in dichloromethane (500 mL) was added DIEA (65.2 g, 504 mmol, 87.8 mL, 5.00 equiv) and tert-butyl (S)-2-(cyanomethyl)piperazine-1-carboxylate (27.3 g, 121 mmol, 1.20 equiv). The mixture was stirred at room temperature for 1 h prior to being diluted with NaHCO$_3$ (100 mL). The organic layer was separated and the aqueous layer was extracted with ethyl acetate (200 mL×3). The combined organic layer was dried over anhydrous sodium sulfate and filtered. The filtrate was concentrated under reduced pressure to dryness. The residue was purified by column chromatography (SiO$_2$, petroleum ether/ethyl acetate, 50:1 to 0:1) to afford tert-butyl (S)-4-(2-chloro-7-(8-chloro-7-fluoronaphthalen-1-yl)-8-fluoropyrido[4,3-d]pyrimidin-4-yl)-2-(cyanomethyl)piperazine-1-carboxylate (36 g, 79% yield) as a yellow solid. LCMS [ESI, M+1]: 585.

Following the teachings of the General Reaction Schemes and Intermediates E1-E3, Intermediates E-4 to E-29 were prepared as shown in Table 2A.

TABLE 2A

| Intermediates E-4 to E-55 | | |
|---|---|---|
| Int. # | Structure | Characterization Data |
| E-4 | ![structure] tert-butyl 7-(7-chloro-8-fluoro-2-(methylthio)pyrido[4,3-d]pyrimidin-4-yl)-2,7-diazaspiro[3.5]nonane-2-carboxylate | LCMS [ESI, M + 1]: 454 |

TABLE 2A-continued

Intermediates E-4 to E-55

| Int. # | Structure | Characterization Data |
|---|---|---|
| E-5 | 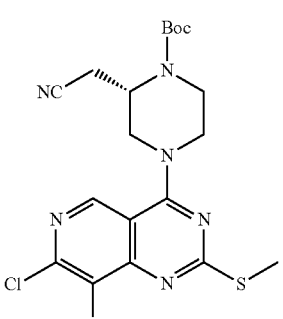<br>tert-butyl (S)-4-(7-chloro-8-fluoro-2-(methylthio)pyrido[4,3-d]pyrimidin-4-yl)-2-(cyanomethyl)piperazine-1-carboxylate | LCMS [ESI, M + 1]: 453 |
| E-6 | 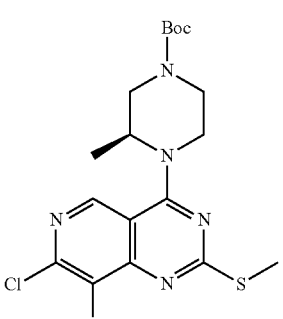<br>tert-butyl (S)-4-(7-chloro-8-fluoro-2-(methylthio)pyrido[4,3-d]pyrimidin-4-yl)-3-methylpiperazine-1-carboxylate | LCMS [ESI, M + 1]: 428 |
| E-7 | 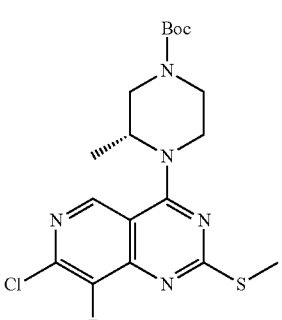<br>tert-butyl (R)-4-(7-chloro-8-fluoro-2-(methylthio)pyrido[4,3-d]pyrimidin-4-yl)-3-methylpiperazine-1-carboxylate | LCMS [ESI, M + 1]: 428 |

TABLE 2A-continued

Intermediates E-4 to E-55

| Int. # | Structure | Characterization Data |
|---|---|---|
| E-8 | 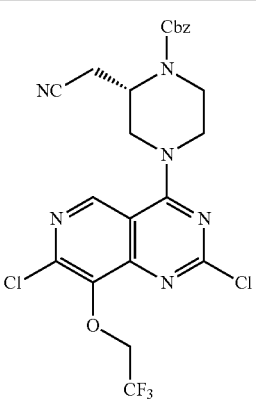 [SMILES: N#CC[C@H]1CN(c2nc(Cl)nc3c(OCC(F)(F)F)c(Cl)ncc23)CCN1C(=O)OCc1ccccc1]<br>benzyl (S)-2-(cyanomethyl)-4-(2,7-dichloro-8-(2,2,2-trifluoroethoxy)pyrido[4,3-d]pyrimidin-4-yl)piperazine-1-carboxylate | LCMS [ESI, M + 1]: 555 |
| E-9 | 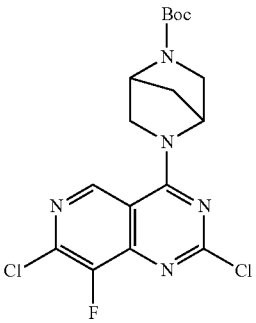 [SMILES: CC(C)(C)OC(=O)N1CC2CC1CN2c1nc(Cl)nc2c(F)c(Cl)ncc12]<br>tert-butyl 5-(2,7-dichloro-8-fluoropyrido[4,3-d]pyrimidin-4-yl)-2,5-diazabicyclo[2.2.1]heptane-2-carboxylate | LCMS [ESI, M + 1]: 414 |
| E-10 | 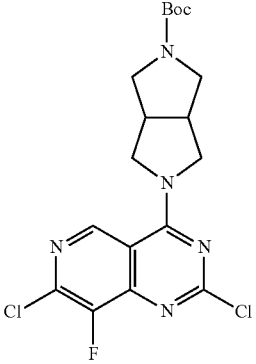 [SMILES: CC(C)(C)OC(=O)N1CC2CN(c3nc(Cl)nc4c(F)c(Cl)ncc34)CC2C1]<br>tert-butyl 5-(2,7-dichloro-8-fluoropyrido[4,3-d]pyrimidin-4-yl)hexahydropyrrolo[3,4-c]pyrrole-2(1H)-carboxylate | LCMS [ESI, M + 1]: 428 |

TABLE 2A-continued

Intermediates E-4 to E-55

| Int. # | Structure | Characterization Data |
|---|---|---|
| E-11 | 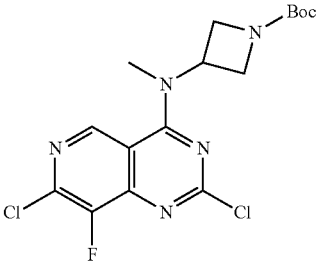 [SMILES: CN(c1nc(Cl)nc2c(F)c(Cl)ncc12)C1CN(C(=O)OC(C)(C)C)C1]<br>tert-butyl 3-((2,7-dichloro-8-fluoropyrido[4,3-d]pyrimidin-4-yl)(methyl)amino)azetidine-1-carboxylate | LCMS [ESI, M + 1]: 402 |
| E-12 | 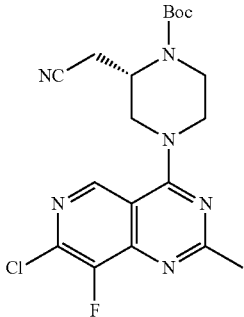 [SMILES: Cc1nc(N2CCN(C(=O)OC(C)(C)C)[C@@H](CC#N)C2)c2cnc(Cl)c(F)c2n1]<br>tert-butyl (S)-4-(7-chloro-8-fluoro-2-methylpyrido[4,3-d]pyrimidin-4-yl)-2-(cyanomethyl)piperazine-1-carboxylate | LCMS [ESI, M + 1]: 421 |
| E-13 | 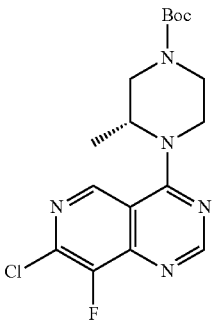 [SMILES: C[C@@H]1CN(C(=O)OC(C)(C)C)CCN1c1ncnc2c(F)c(Cl)ncc12]<br>tert-butyl (R)-4-(7-chloro-8-fluoropyrido[4,3-d]pyrimidin-4-yl)-3-methylpiperazine-1-carboxylate | LCMS [ESI, M + 1]: 382 |

TABLE 2A-continued
Intermediates E-4 to E-55
| Int. # | Structure | Characterization Data |
|---|---|---|
| E-14 | 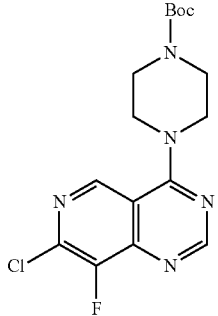 [SMILES: CC(C)(C)OC(=O)N1CCN(c2ncnc3c(F)c(Cl)ncc23)CC1]<br>tert-butyl 4-(7-chloro-8-fluoropyrido[4,3-d]pyrimidin-4-yl)piperazine-1-carboxylate | LCMS [ESI, M + 1]: 368 |
| E-15 | 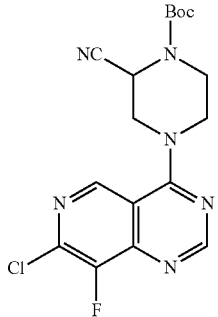 [SMILES: CC(C)(C)OC(=O)N1CCN(c2ncnc3c(F)c(Cl)ncc23)CC1C#N]<br>tert-butyl 4-(7-chloro-8-fluoropyrido[4,3-d]pyrimidin-4-yl)-2-cyanopiperazine-1-carboxylate | LCMS [ESI, M + 1]: 393 |
| E-16 | 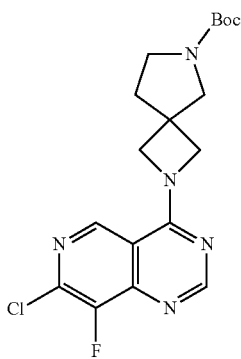 [SMILES: CC(C)(C)OC(=O)N1CCC2(C1)CN(c1ncnc3c(F)c(Cl)ncc13)C2]<br>tert-butyl 2-(7-chloro-8-fluoropyrido[4,3-d]pyrimidin-4-yl)-2,6-diazaspiro[3.4]octane-6-carboxylate | LCMS [ESI, M + 1]: 394 |

TABLE 2A-continued

Intermediates E-4 to E-55

| Int. # | Structure | Characterization Data |
| --- | --- | --- |
| E-17 | 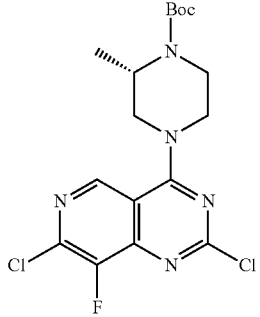 [SMILES: C[C@H]1CN(c2nc(Cl)nc3c(F)c(Cl)ncc23)CCN1C(=O)OC(C)(C)C]<br>tert-butyl (S)-4-(2,7-dichloro-8-fluoropyrido[4,3-d]pyrimidin-4-yl)-2-methylpiperazine-1-carboxylate | LCMS [ESI, M + 1]: 416 |
| E-18 | 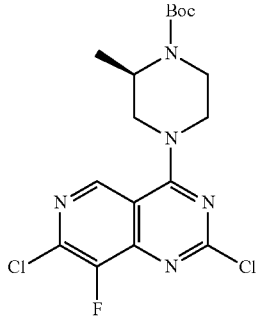 [SMILES: C[C@@H]1CN(c2nc(Cl)nc3c(F)c(Cl)ncc23)CCN1C(=O)OC(C)(C)C]<br>tert-butyl (R)-4-(2,7-dichloro-8-fluoropyrido[4,3-d]pyrimidin-4-yl)-2-methylpiperazine-1-carboxylate | LCMS [ESI, M + 1]: 416 |
| E-19 | 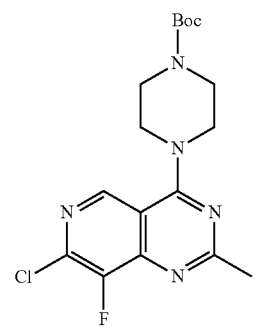<br>tert-butyl 4-(7-chloro-8-fluoro-2-methylpyrido[4,3-d]pyrimidin-4-yl)piperazine-1-carboxylate | LCMS [ESI, M + 1]: 421 |

TABLE 2A-continued

Intermediates E-4 to E-55

| Int. # | Structure | Characterization Data |
|---|---|---|
| E-20 | 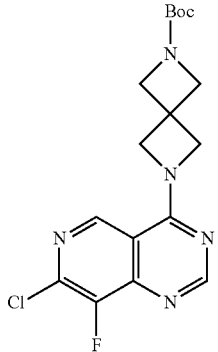 [SMILES: CC(C)(C)OC(=O)N1CC2(C1)CN(c1ncnc3c(F)c(Cl)ncc13)C2]<br>tert-butyl 6-(7-chloro-8-fluoropyrido[4,3-d]pyrimidin-4-yl)-2,6-diazaspiro[3.3]heptane-2-carboxylate | $^1$H NMR (400 MHz, CDCl$_3$) δ 8.76 (s, 1H), 8.72 (s, 1H), 4.71 (br s, 4H), 4.22 (s, 4H), 1.46 (s, 9H) |
| E-21 | 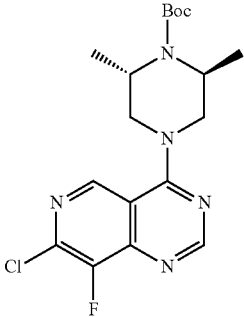 [SMILES: C[C@H]1CN(c2ncnc3c(F)c(Cl)ncc23)C[C@H](C)N1C(=O)OC(C)(C)C]<br>tert-butyl (2S,6S)-4-(7-chloro-8-fluoropyrido[4,3-d]pyrimidin-4-yl)-2,6-dimethylpiperazine-1-carboxylate | LCMS [ESI, M + 1]: 396<br>$^1$H NMR (400 MHz, CDCl$_3$-d) δ 8.99 (s, 1H), 8.80 (s, 1H), 4.39-4.19 (m, 4H), 3.98 (br d, J = 12.0 Hz, 2H), 1.52 (s, 9H), 1.31 (d, J = 6.4 Hz, 6H) |
| E-22 | 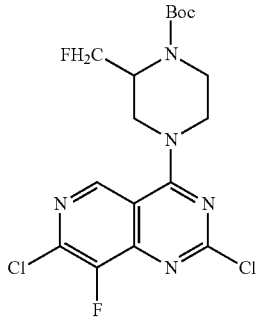<br>tert-butyl 4-(2,7-dichloro-8-fluoropyrido[4,3-d]pyrimidin-4-yl)-(fluoromethyl)piperazine-1-carboxylate | LCMS [ESI, M + 1]: 434 |

TABLE 2A-continued

Intermediates E-4 to E-55

| Int. # | Structure | Characterization Data |
|---|---|---|
| E-23 | 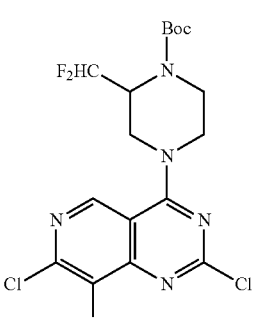<br>tert-butyl 4-(2,7-dichloro-8-fluoropyrido[4,3-d]pyrimidin-4-yl)-2-(difluoromethyl)piperazine-1-carboxylate | LCMS [ESI, M + 1]: 452 |
| E-24 | 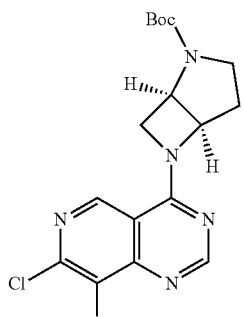<br>tert-butyl (1R,5R)-6-(7-chloro-8-fluoropyrido[4,3-d]pyrimidin-4-yl)-2,6-diazabicyclo[3.2.0]heptane-2-carboxylate | LCMS [ESI, M + 1]: 380 |
| E-25 | 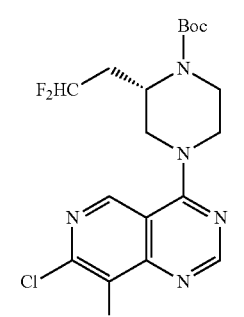<br>tert-butyl (S)-4-(7-chloro-8-fluoropyrido[4,3-d]pyrimidin-4-yl)-2-(2,2-difluoroethyl)piperazine-1-carboxylate | LCMS [ESI, M + 1]: 432 |

TABLE 2A-continued

Intermediates E-4 to E-55

| Int. # | Structure | Characterization Data |
|---|---|---|
| E-26 | 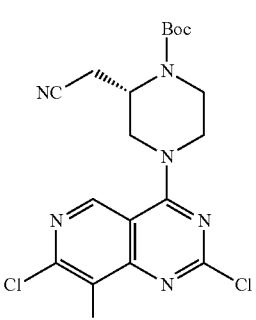<br>tert-butyl (S)-2-(cyanomethyl)-4-(2,7-dichloro-8-fluoropyrido[4,3-d]pyrimidin-4-yl)piperazine-1-carboxylate | LCMS [ESI, M + 1]: 441 |
| E-27 | 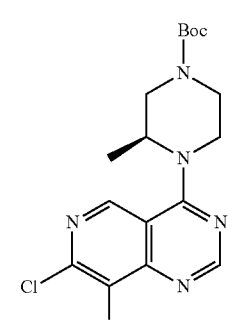<br>tert-butyl (S)-4-(7-chloro-8-fluoropyrido[4,3-d]pyrimidin-4-yl)-3-methylpiperazine-1-carboxylate | $^1$H NMR (400 MHz, CDCl$_3$) δ 8.86 (s, 1H), 8.78 (s, 1H), 4.88-4.82 (m, 1H), 4.41 (br d, J = 13.2 Hz, 1H), 4.31-4.15 (m, 1H), 4.04-3.85 (m, 1H), 3.71-3.62 (m, 1H), 3.26-3.01 (m, 2H), 1.52-1.48 (m, 12H) |
| E-28 | 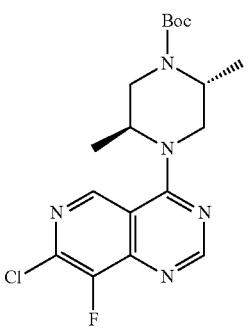 [SMILES: C[C@@H]1CN(c2ncnc3c(F)c(Cl)ncc23)[C@@H](C)CN1C(=O)OC(C)(C)C]<br>tert-butyl (2R,5S)-4-(7-chloro-8-fluoropyrido[4,3-d]pyrimidin-4-yl)-2,5-dimethylpiperazine-1-carboxylate | LCMS [ESI, M + 1]: 396 |

TABLE 2A-continued

Intermediates E-4 to E-55

| Int. # | Structure | Characterization Data |
|---|---|---|
| E-29 | 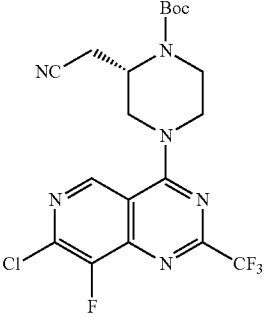 [SMILES: CC(C)(C)OC(=O)N1CCN(c2nc(C(F)(F)F)nc3c(F)c(Cl)ncc23)C[C@@H]1CC#N]<br>tert-butyl (S)-4-(7-chloro-8-fluoro-2-(trifluoromethyl)pyrido[4,3-d]pyrimidin-4-yl)-2-(cyanomethyl)piperazine-1-carboxylate | LCMS [ESI, M + 1]: 475 |
| E-30 | 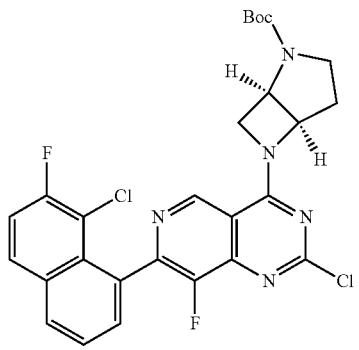 [SMILES: CC(C)(C)OC(=O)N1CC[C@@H]2[C@H]1CN2c1nc(Cl)nc2c(F)c(-c3cccc4ccc(F)c(Cl)c34)ncc12]<br>tert-butyl (1R,5R)-6-(2-chloro-7-(8-chloro-7-fluoronaphthalen-1-yl)-8-fluoropyrido[4,3-d]pyrimidin-4-yl)-2,6-diazabicyclo[3.2.0]heptane-2-carboxylate | Prepared from intermediate D-9 430 mg, 44% yield |
| E-31 | 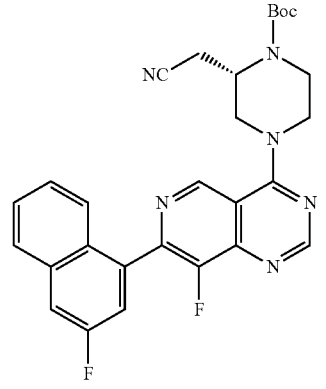 [SMILES: CC(C)(C)OC(=O)N1CCN(c2ncnc3c(F)c(-c4cc(F)cc5ccccc45)ncc23)C[C@@H]1CC#N]<br>tert-butyl (S)-2-(cyanomethyl)-4-(8-fluoro-7-(3-fluoronaphthalen-1-yl)pyrido[4,3-d]pyrimidin-4-yl)piperazine-1-carboxylate | LCMS [ESI, M + 1]: 517 |

TABLE 2A-continued

| Intermediates E-4 to E-55 | | |
|---|---|---|
| Int. # | Structure | Characterization Data |
| E-32 | tert-butyl (2S)-4-(7-(6-chloro-5-methyl-1-(tetrahydro-2H-pyran-2-yl)-1H-indazol-4-yl)-8-fluoropyrido[4,3-d]pyrimidin-4-yl)-2-(cyanomethyl)piperazine-1-carboxylate | LCMS [ESI, M + 1]: 621 |
| E-33 | tert-butyl (1R,5R)-6-(7-(5-chloroisoquinolin-4-yl)-8-fluoropyrido[4,3-d]pyrimidin-4-yl)-2,6-diazabicyclo[3.2.0]heptane-2-carboxylate | LCMS [ESI, M + 1]: 507 |
| E-34 | tert-butyl (1R,5R)-6-(8-fluoro-7-(3-(methoxymethoxy)-8-((triisopropylsilyl)ethynyl)naphthalen-1-yl)pyrido[4,3-d]pyrimidin-4-yl)-2,6-diazabicyclo[3.2.0]heptane-2-carboxylate | LCMS [ESI, M + 1]: 713 |

TABLE 2A-continued

Intermediates E-4 to E-55

| Int. # | Structure | Characterization Data |
|---|---|---|
| E-35 | 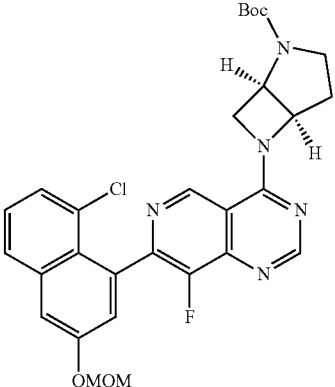<br>tert-butyl (1R,5R)-6-(7-(8-chloro-3-(methoxymethoxy)naphthalen-1-yl)-8-fluoropyrido[4,3-d]pyrimidin-4-yl)-2,6-diazabicyclo[3.2.0]heptane-2-carboxylate | LCMS [ESI, M + 1]: 566 |
| E-36 | 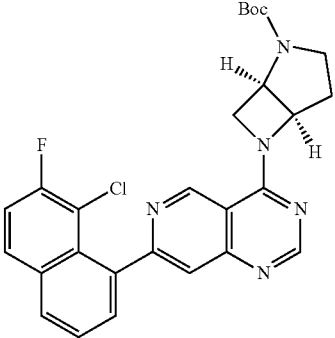 [SMILES: CC(C)(C)OC(=O)N1CC[C@@H]2[C@H]1CN2c1ncnc2cc(-c3cccc4ccc(F)c(Cl)c34)ncc12]<br>tert-butyl (1R,5R)-6-(7-(8-chloro-7-fluoronaphthalen-1-yl)pyrido[4,3-d]pyrimidin-4-yl)-2,6-diazabicyclo[3.2.0]heptane-2-carboxylate | LCMS [ESI, M + 1]: 506<br>$^1$H NMR (400 MHz, CDCl$_3$): δ 9.27 (s, 1H), 8.76 (br s, 1H), 7.98-7.96 (d, J = 7.6 Hz, 1H), 7.91-7.82 (m, 2H), 7.61-7.53 (m, 2H), 7.42-7.38 (t, J = 8.4 Hz, 1H), 5.56-5.47 (m, 1H), 4.94-4.68 (m, 2H), 4.49-4.31 (m, 1H), 4.09-3.97 (m, 1H), 3.71-3.57 (m, 1H), 2.64-2.50 (m, 1H), 2.26-2.08 (m, 1H), 1.51 (s, 9H) |
| E-37 | 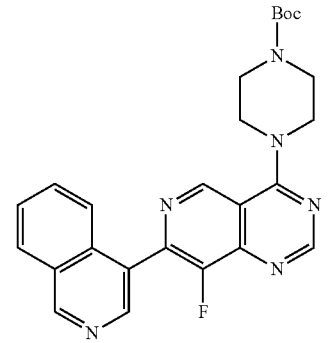 [SMILES: CC(C)(C)OC(=O)N1CCN(c2ncnc3c(F)c(-c4cncc5ccccc45)ncc23)CC1]<br>tert-butyl 4-(8-fluoro-7-(isoquinolin-4-yl)pyrido[4,3-d]pyrimidin-4-yl)piperazine-1-carboxylate | LCMS [ESI, M + 1]: 461<br>$^1$H NMR (400 MHz, CDCl$_3$): δ 9.32 (s, 1H), 9.21 (s, 1H), 8.82 (s, 1H), 8.70 (s, 1H), 8.03 (d, J = 7.6 Hz, 1H), 7.81 (br d, J = 8.2 Hz, 1H), 7.69-7.56 (m, 2H), 4.04-3.98 (m, 4H), 3.68-3.60 (m, 4H), 1.44 (s, 9H) |

TABLE 2A-continued

Intermediates E-4 to E-55

| Int. # | Structure | Characterization Data |
|---|---|---|
| E-38 | 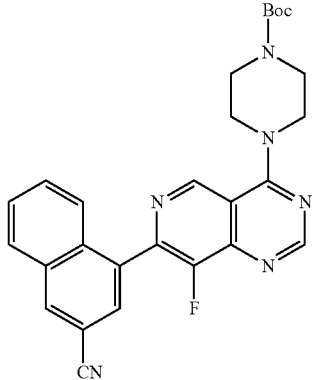 [SMILES: CC(C)(C)OC(=O)N1CCN(c2ncnc3c(F)c(-c4cc(C#N)cc5ccccc45)ncc23)CC1]<br>tert-butyl 4-(7-(3-cyanonaphthalen-1-yl)-8-fluoropyrido[4,3-d]pyrimidin-4-yl)piperazine-1-carboxylate | LCMS [ESI, M + 1]: 485 |
| E-39 | 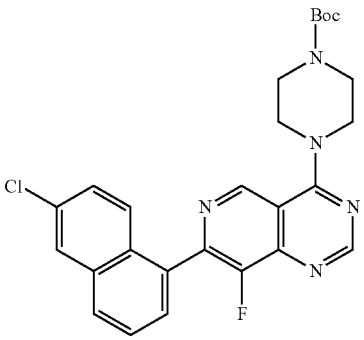 [SMILES: CC(C)(C)OC(=O)N1CCN(c2ncnc3c(F)c(-c4cccc5cc(Cl)ccc45)ncc23)CC1]<br>tert-butyl 4-(7-(6-chloronaphthalen-1-yl)-8-fluoropyrido[4,3-d]pyrimidin-4-yl)piperazine-1-carboxylate | LCMS [ESI, M + 1]: 494<br>$^1$H NMR (400 MHz, CDCl$_3$): δ 9.27 (s, 1H), 8.89 (s, 1H), 7.97-7.90 (m, 2H), 7.79-7.76 (m, 1H), 7.74-7.71 (m, 1H), 7.68-7.64 (m, 1H), 7.42 (dd, J = 2.0, 9.2 Hz, 1H), 4.11-4.05 (m, 4H), 3.75-3.69 (m, 4H), 1.52 (s, 9H) |
| E-40 | 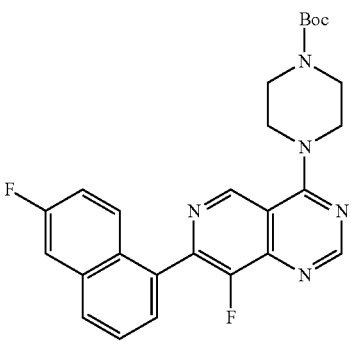 [SMILES: CC(C)(C)OC(=O)N1CCN(c2ncnc3c(F)c(-c4cccc5cc(F)ccc45)ncc23)CC1]<br>tert-butyl 4-(8-fluoro-7-(6-fluoronaphthalen-1-yl)pyrido[4,3-d]pyrimidin-4-yl)piperazine-1-carboxylate | LCMS [ESI, M + 1]: 478<br>$^1$H NMR (400 MHz, CDCl$_3$): δ 9.37 (s, 1H), 8.78 (s, 1H), 8.11 (d, J = 8.0 Hz, 1H), 7.91-7.65 (m, 4H), 7.43 (dt, J = 2.8, 8.8 Hz, 1H), 4.16-4.01 (m, 4H), 3.62 (br d, J = 4.4 Hz, 4H), 1.45 (s, 9H) |

TABLE 2A-continued

Intermediates E-4 to E-55

| Int. # | Structure | Characterization Data |
|---|---|---|
| E-41 | 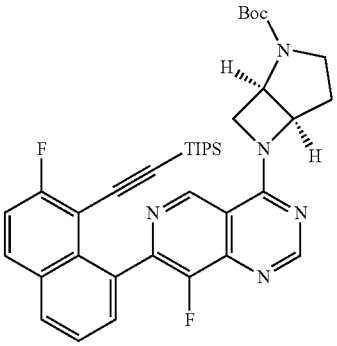<br>tert-butyl (1R,5R)-6-(8-fluoro-7-(7-fluoro-8-((triisopropylsilyl)ethynyl)naphthalen-1-yl)pyrido[4,3-d]pyrimidin-4-yl)-2,6-diazabicyclo[3.2.0]heptane-2-carboxylate | LCMS [ESI, M + 1]: 670<br>$^1$H NMR (400 MHz, CDCl$_3$): δ 9.10-9.03 (m, 1H), 8.81-8.76 (m, 1H), 8.00-7.89 (m, 2H), 7.61-7.53 (m, 2H), 7.39-7.31 (m, 1H), 5.56-5.40 (m, 1H), 4.98-4.64 (m, 2H), 4.45-4.23 (m, 1H), 4.09-3.95 (m, 1H), 3.70-3.53 (m, 1H), 2.70-2.48 (m, 1H), 2.23-2.08 (m, 1H), 1.52 (s, 9H), 0.92-0.85 (m, 18H), 0.63-0.49 (m, 3H) |
| E-42 | 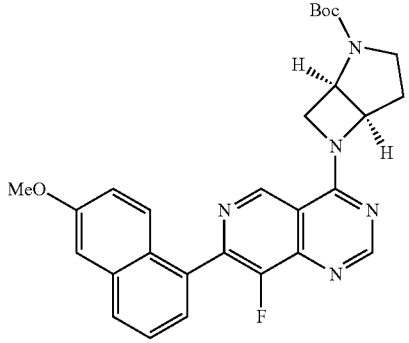 [SMILES: COc1ccc2c(-c3ncc4c(N5C[C@@H]6[C@H]5CCN6C(=O)OC(C)(C)C)ncnc4c3F)cccc2c1]<br>tert-butyl (1R,5R)-6-(8-fluoro-7-(6-methoxynaphthalen-1-yl)pyrido[4,3-d]pyrimidin-4-yl)-2,6-diazabicyclo[3.2.0]heptane-2-carboxylate | LCMS [ESI, M + 1]: 502 |
| E-43 | 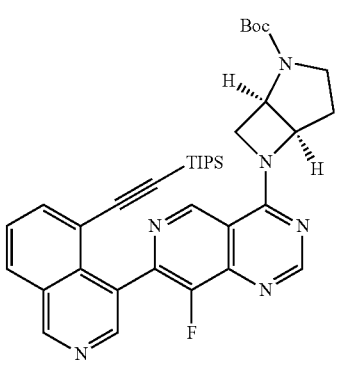<br>tert-butyl (1R,5R)-6-(8-fluoro-7-(5-((triisopropylsilyl)ethynyl)isoquinolin-4-yl)pyrido[4,3-d]pyrimidin-4-yl)-2,6-diazabicyclo[3.2.0]heptane-2-carboxylate | Prepd from E-33: TIPS—CCH PdCl$_2$(ACN)$_2$, XPhos, Cs$_2$CO$_3$ ACN, 80° C.<br>[ESI, M + 1]: 653 |

TABLE 2A-continued

Intermediates E-4 to E-55

| Int. # | Structure | Characterization Data |
|---|---|---|
| E-44 | tert-butyl (1R,5R)-6-(7-(benzo[b]thiophen-4-yl)-8-fluoropyrido[4,3-d]pyrimidin-4-yl)-2,6-diazabicyclo[3.2.0]heptane-2-carboxylate | LCMS [ESI, M + 1]: 478 |
| E-45 | tert-butyl (1R,5R)-6-(7-(3-chloro-2-cyclopropylphenyl)-8-fluoropyrido[4,3-d]pyrimidin-4-yl)-2,6-diazabicyclo[3.2.0]heptane-2-carboxylate | LCMS [ESI, M + 1]: 496 |
| E-46 | tert-butyl (1R,5R)-6-(7-(benzo[b]thiophen-7-yl)-8-fluoropyrido[4,3-d]pyrimidin-4-yl)-2,6-diazabicyclo[3.2.0]heptane-2-carboxylate | LCMS [ESI, M + 1]: 478<br>$^1$H NMR (400 MHz, CDCl$_3$): δ 9.17 (s, 1H), 8.79 (s, 1H), 8.13 (d, J = 7.6 Hz, 1H), 7.97 (d, J = 7.6 Hz, 1H), 7.59-7.53 (m, 2H), 7.44 (d, J = 5.6 Hz, 1H), 5.49 (br s, 1H), 4.94-4.67 (m, 2H), 4.42 (br s, 1H), 4.02 (br s, 1H), 3.64 (br d, J = 6.4 Hz, 1H), 2.57 (br dd, J = 6.4, 14.0 Hz, 1H), 2.22-2.09 (m, 1H), 1.53 (s, 9H) |

TABLE 2A-continued

Intermediates E-4 to E-55

| Int. # | Structure | Characterization Data |
|---|---|---|
| E-47 | 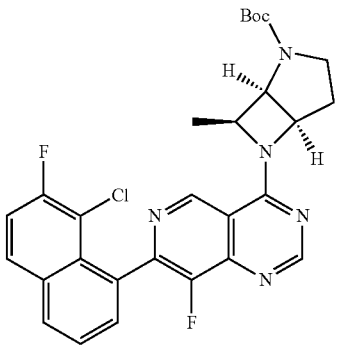 [SMILES: C[C@H]1[C@@H]2[C@@H](CCN2C(=O)OC(C)(C)C)N1c1ncnc2c(F)c(-c3cccc4ccc(F)c(Cl)c34)ncc12]<br>tert-butyl (1R,5R,7S)-6-(7-(8-chloro-7-fluoronaphthalen-1-yl)-8-fluoropyrido[4,3-d]pyrimidin-4-yl)-7-methyl-2,6-diazabicyclo[3.2.0]heptane-2-carboxylate | LCMS [ESI, M + 1]: 538.2<br>$^1$H NMR (400 MHz, CDCl$_3$): δ 9.16-9.07 (m, 1H), 8.81 (s, 1H), 8.03-7.98 (m, 1H), 7.89 (dd, J = 5.6, 9.2 Hz, 1H), 7.64-7.56 (m, 2H), 7.40 (t, J = 8.8 Hz, 1H), 5.49-5.41 (m, 1H), 5.10-4.74 (m, 2H), 4.11-3.97 (m, 1H), 3.71-3.54 (m, 1H), 2.67-2.51 (m, 1H), 2.34-2.17 (m, 1H), 1.56-1.48 (m, 12H) |
| E-48 | 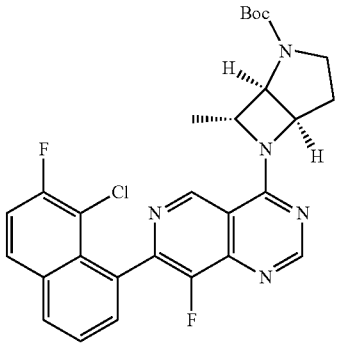 [SMILES: C[C@@H]1[C@@H]2[C@@H](CCN2C(=O)OC(C)(C)C)N1c1ncnc2c(F)c(-c3cccc4ccc(F)c(Cl)c34)ncc12]<br>tert-butyl (1R,5R,7R)-6-(7-(8-chloro-7-fluoronaphthalen-1-yl)-8-fluoropyrido[4,3-d]pyrimidin-4-yl)-7-methyl-2,6-diazabicyclo[3.2.0]heptane-2-carboxylate | LCMS [ESI, M + 1]: 538.2<br>$^1$H NMR (400 MHz, CDCl$_3$): δ 9.09-8.90 (m, 1H), 8.82 (s, 1H), 8.01 (d, J = 7.2 Hz, 1H), 7.90 (dd, J = 5.6, 9.2 Hz, 1H), 7.69-7.57 (m, 2H), 7.41 (td, J = 1.6, 8.8 Hz, 1H), 5.81-5.30 (m, 1H), 4.78-4.53 (m, 1H), 4.42-4.16 (m, 1H), 4.05-3.81 (m, 1H), 3.78-3.37 (m, 1H), 2.65-2.30 (m, 1H), 2.28-2.07 (m, 1H), 1.67-1.63 (m, 3H), 1.51 (s, 9H) |
| E-49 | 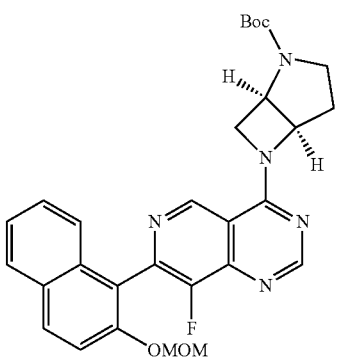<br>tert-butyl (1R,5R)-6-(8-fluoro-7-(2-(methoxymethoxy)naphthalen-1-yl)pyrido[4,3-d]pyrimidin-4-yl)-2,6-diazabicyclo[3.2.0]heptane-2-carboxylate | LCMS [ESI, M + 1]: 532.2 |

TABLE 2A-continued

Intermediates E-4 to E-55

| Int. # | Structure | Characterization Data |
|---|---|---|
| E-50 | tert-butyl (1R,5R,7S)-6-(8-fluoro-7-(7-fluoro-8-((triisopropylsilyl)ethynyl)naphthalen-1-yl)pyrido[4,3-d]pyrimidin-4-yl)-7-methyl-2,6-diazabicyclo[3.2.0]heptane-2-carboxylate | LCMS [ESI, M + 1]: 684.3 |
| E-51 | tert-butyl (1R,5R)-6-(8-fluoro-7-(8-((triisopropylsilyl)ethynyl)naphthalen-1-yl)pyrido[4,3-d]pyrimidin-4-yl)-2,6-diazabicyclo[3.2.0]heptane-2-carboxylate | [ESI, M + 1]: 652 |
| E-52 | tert-butyl (1R,5R)-6-(8-fluoro-7-(8-methylnaphthalen-1-yl)pyrido[4,3-d]pyrimidin-4-yl)-2,6-diazabicyclo[3.2.0]heptane-2-carboxylate | [ESI, M + 1]: 486 |

TABLE 2A-continued

Intermediates E-4 to E-55

| Int. # | Structure | Characterization Data |
|---|---|---|
| E-53 | 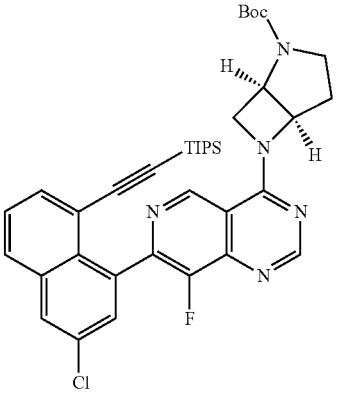<br>tert-butyl (1R,5R)-6-(7-(3-chloro-8-((triisopropylsilyl)ethynyl)naphthalen-1-yl)-8-fluoropyrido[4,3-d]pyrimidin-4-yl)-2,6-diazabicyclo[3.2.0]heptane-2-carboxylate | $^1$H NMR (400 MHz, CDCl$_3$): δ 9.10-9.04 (m, 1H), 8.82-8.76 (m, 1H), 7.97 (d, J = 2.0 Hz, 1H), 7.88-7.82 (m, 1H), 7.82-7.77 (m, 1H), 7.54-7.47 (m, 2H), 5.54-5.41 (m, 1H), 4.94-4.67 (m, 2H), 4.43-4.25 (m, 1H), 4.10-3.95 (m, 1H), 3.70-3.55 (m, 1H), 2.68-2.46 (m, 1H), 2.24-2.08 (m, 1H), 1.52 (s, 9H), 0.92-0.81 (m, 21H) |
| E-54 | 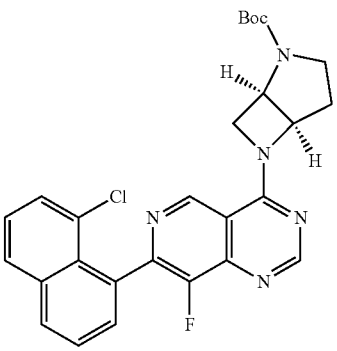 [SMILES: CC(C)(C)OC(=O)N1CC[C@@H]2[C@H]1CN2c1ncnc2c(F)c(-c3cccc4cccc(Cl)c34)ncc12]<br>tert-butyl (1R,5R)-6-(7-(8-chloronaphthalen-1-yl)-8-fluoropyrido[4,3-d]pyrimidin-4-yl)-2,6-diazabicyclo[3.2.0]heptane-2-carboxylate | [ESI, M + 1]: 506 |
| E-55 | 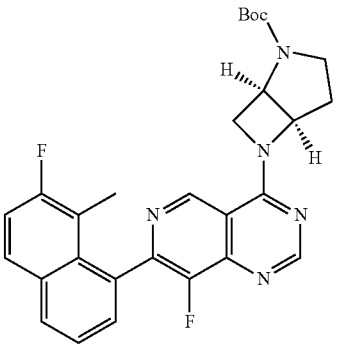 [SMILES: Cc1c(F)ccc2cccc(-c3ncc4c(N5C[C@@H]6[C@H]5CCN6C(=O)OC(C)(C)C)ncnc4c3F)c12]<br>tert-butyl (1R,5R)-6-(8-fluoro-7-(7-fluoro-8-methylnaphthalen-1-yl)pyrido[4,3-d]pyrimidin-4-yl)-2,6-diazabicyclo[3.2.0]heptane-2-carboxylate | Prepd from F-138: MeB(OH)$_2$, Ad$_2$nBuP—Pd G3, K$_3$PO$_4$, toluene, 80° C., 10 h.<br>LCMS [ESI, M + 1]: 504.2 |

In addition to the foregoing Intermediates above, the following exemplary Intermediates F-1-F-183 may be used to couple R¹ to the azaquinazoline core of Formula (I).

Intermediate F-1

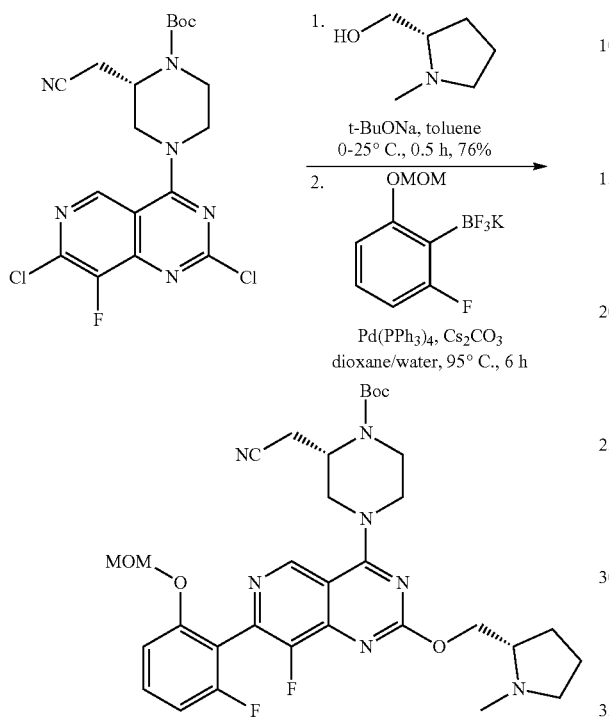

To a mixture of tert-butyl (S)-2-(cyanomethyl)-4-(2,7-dichloro-8-fluoropyrido[4,3-d]pyrimidin-4-yl)piperazine-1-carboxylate (700 mg, 1.59 mmol, 1.0 equiv) in dioxane (10.0 mL) was added DIEA (615 mg, 4.76 mmol, 829 μL, 3.0 equiv) and [(2S)-1-methylpyrrolidin-2-yl]methanol (365 mg, 3.17 mmol, 377 μL, 2.0 equiv) at 25° C. The mixture was stirred at 80° C. for 8 h and was then concentrated under reduced pressure to provide the crude residue. The crude product was purified by reverse phase flash chromatography [water (0.1% FA)/acetonitrile] to afford tert-butyl (S)-4-(7-chloro-8-fluoro-2-(((S)-1-methylpyrrolidin-2-yl)methoxy)pyrido[4,3-d]pyrimidin-4-yl)-2-(cyanomethyl)piperazine-1-carboxylate (550 mg, 1.04 mmol, 66% yield) as a yellow solid. LCMS [ESI, M+1]: 520.

To a mixture of tert-butyl (S)-4-(7-chloro-8-fluoro-2-(((S)-1-methylpyrrolidin-2-yl)methoxy)pyrido[4,3-d]pyrimidin-4-yl)-2-(cyanomethyl)piperazine-1-carboxylate (500 mg, 961 μmol, 1.0 equiv) and potassium trifluoro(2-fluoro-6-(methoxymethoxy)phenyl)borate (378 mg, 1.44 mmol, 1.5 equiv) in dioxane (12.0 mL) and H₂O (4.0 mL) was added Cs₂CO₃ (940 mg, 2.88 mmol, 3.0 equiv) and Pd(PPh₃)₄ (222 mg, 192 μmol, 0.2 equiv) at 10° C. The mixture was stirred at 100° C. for 14 h and then was concentrated under reduced pressure at 40° C. to provide a crude residue. The residue was purified by column chromatography (SiO₂, petroleum ether/ethyl acetate, 3:1 to petroleum ether/ethyl acetate/ethanol (2% NH₄OH v/v), 4:3:1). The product was further purified by reverse phase flash chromatography [water (0.1% FA)/acetonitrile] to afford tert-butyl (2S)-2-(cyanomethyl)-4-(8-fluoro-7-(2-fluoro-6-(methoxymethoxy)phenyl)-2-(((S)-1-methylpyrrolidin-2-yl)methoxy)pyrido[4,3-d]pyrimidin-4-yl)piperazine-1-carboxylate (210 mg, 294 μmol, 31% yield, 90% purity) as a yellow solid. LCMS [ESI, M+1]: 640. ¹H NMR (400 MHz, CDCl₃) δ 9.11 (s, 1H), 7.40 (dt, J=6.8, 8.4 Hz, 1H), 7.09 (d, J=8.4 Hz, 1H), 6.90 (t, J=8.8 Hz, 1H), 5.25-5.16 (m, 1H), 5.15-5.05 (m, 1H), 4.70-4.55 (m, 2H), 4.50-4.33 (m, 3H), 4.19-4.13 (m, 1H), 3.93-3.77 (m, 1H), 3.74-3.62 (m, 1H), 3.57-3.44 (m, 1H), 3.40 (d, J=2.4 Hz, 3H), 3.11 (br t, J=7.2 Hz, 1H), 2.90-2.68 (m, 3H), 2.51 (s, 3H), 2.30 (dt, J=7.2, 9.2 Hz, 1H), 2.11-2.05 (m, 1H), 1.93-1.69 (m, 3H), 1.53 (s, 9H).

Intermediate F-2

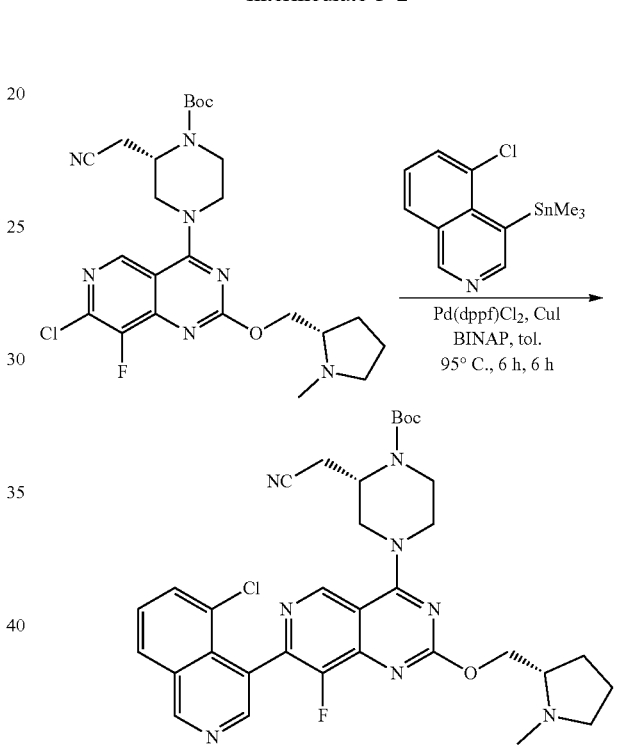

To a mixture of tert-butyl (S)-4-(7-chloro-8-fluoro-2-(((S)-1-methylpyrrolidin-2-yl)methoxy)pyrido[4,3-d]pyrimidin-4-yl)-2-(cyanomethyl)piperazine-1-carboxylate (500 mg, 962 μmol, 1.0 equiv), (5-chloro-4-isoquinolyl)-trimethyl-stannane (628 mg, 1.92 mmol, 2.0 equiv), CuI (54.9 mg, 288 μmol, 0.3 equiv) and BINAP (120 mg, 192 umol, 0.2 eq) in toluene (10 mL) was added Pd(dppf)Cl₂ (70.4 mg, 96.2 μmol, 0.1 equiv) under nitrogen. The mixture was heated at 90° C. for 6 h under nitrogen, filtered and diluted with ethyl acetate (13 mL) and water (13 mL). The aqueous phase was extracted with ethyl acetate (2×10 mL). The combined organic layer was washed with saturated brine (12 mL), dried over anh Na₂SO₄, filtered and concentrated under reduced pressure to provide the crude residue. The residue was purified by reverse phase flash chromatography [water (FA, 0.1%)/acetonitrile] to afford tert-butyl (S)-4-(7-(5-chloroisoquinolin-4-yl)-8-fluoro-2-(((S)-1-methylpyrrolidin-2-yl)methoxy)pyrido[4,3-d]pyrimidin-4-yl)-2-(cyanomethyl)piperazine-1-carboxylate (377 mg, 574 μmol, 60% yield) as a yellow solid. LCMS [ESI, M+1]: 647.

Intermediate F-3

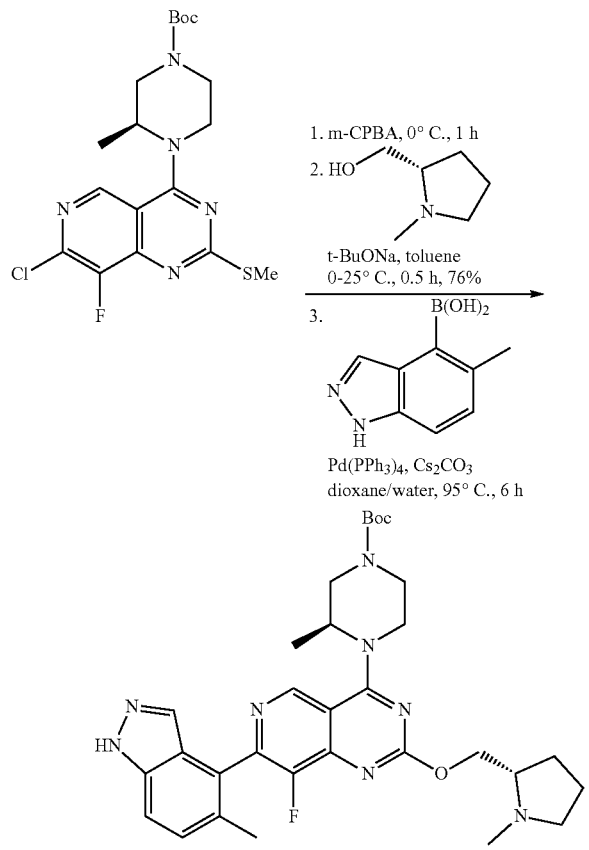

To a solution of tert-butyl (S)-4-(7-chloro-8-fluoro-2-(methylthio)pyrido[4,3-d]pyrimidin-4-yl)-3-methylpiperazine-1-carboxylate (1.0 g, 2.34 mmol, 1.0 equiv) in ethyl acetate (20 mL) was added m-CPBA (854 mg, 4.21 mmol, 85%, 1.8 equiv) at 0° C. The mixture was stirred at 0° C. for 30 min prior to the addition of another portion of m-CPBA (237 mg, 1.17 mmol, 85% purity, 0.5 equiv). The mixture was stirred at 0° C. for an additional 30 min and then was diluted with satd aq NaHCO₃ (30 mL) and extracted with ethyl acetate (2×20 mL). The combined organic layer was dried over anh Na₂SO₄, filtered and concentrated under reduced pressure to provide the crude residue. The residue was purified by reversed phase flash chromatography [water (0.1% FA)/acetonitrile] to afford tert-butyl (S)-4-(7-chloro-8-fluoro-2-(methylsulfonyl)pyrido[4,3-d]pyrimidin-4-yl)-3-methylpiperazine-1-carboxylate (0.62 g, 1.17 mmol, 50% yield, 87% purity) as a yellow solid. LCMS [ESI, M+1]: 460.

To a solution of tert-butyl (S)-4-(7-chloro-8-fluoro-2-(methylsulfonyl)pyrido[4,3-d]pyrimidin-4-yl)-3-methylpiperazine-1-carboxylate (570 mg, 1.24 mmol, 1.0 equiv) and [(2S)-1-methylpyrrolidin-2-yl]methanol (285 mg, 2.48 mmol, 294 µL, 2.0 equiv) in toluene (12 mL) was added 4 Å molecular sieve (200 mg). The suspension was stirred at 10° C. for 30 min followed by the addition of t-BuONa (238 mg, 2.48 mmol, 2.0 equiv). The mixture was stirred at 0° C. for 10 minutes, diluted with water (10 mL) and extracted with ethyl acetate (2×40 mL). The combined organic layer was dried over anh Na₂SO₄, filtered and concentrated at reduced pressure to provide the crude residue. The residue was purified by reversed phase flash chromatography [water (0.1% FA)/acetonitrile] to afford tert-butyl (S)-4-(7-chloro-8-fluoro-2-(((S)-1-methylpyrrolidin-2-yl)methoxy)pyrido[4,3-d]pyrimidin-4-yl)-3-methylpiperazine-1-carboxylate (320 mg, 646 µmol, 52% yield) as a yellow solid. ¹H NMR (400 MHz, CDCl₃): δ 8.72 (s, 1H), 4.85-4.74 (m, 1H), 4.53 (dd, J=4.4, 10.4 Hz, 1H), 4.40-4.27 (m, 2H), 4.18-3.80 (m, 2H), 3.69-3.57 (m, 1H), 3.30-3.18 (m, 1H), 3.16-2.99 (m, 2H), 2.76-2.68 (m, 1H), 2.53-2.48 (m, 3H), 2.35-2.25 (m, 1H), 2.12-2.04 (m, 1H), 1.91-1.74 (m, 3H), 1.50 (s, 9H), 1.47 (d, J=6.8 Hz, 3H).

To a solution of tert-butyl (S)-4-(7-chloro-8-fluoro-2-(((S)-1-methylpyrrolidin-2-yl)methoxy)pyrido[4,3-d]pyrimidin-4-yl)-3-methylpiperazine-1-carboxylate (300 mg, 606 µmol, 1.0 equiv) and (5-methyl-1H-indazol-4-yl)boronic acid (213 mg, 1.21 mmol, 2.0 equiv) in dioxane (6 mL) and H₂O (1.2 mL) was added Pd(PPh₃)₄ (70.0 mg, 60.6 µmol, 0.1 equiv) and Cs₂CO₃ (395 mg, 1.21 mmol, 2.0 equiv). The mixture was heated at 95° C. for 6 h under nitrogen. The mixture was diluted with water (5 mL) and extracted with ethyl acetate (3×10 mL). The combined organic layer was dried over anh Na₂SO₄, filtered and concentrated under reduced pressure to provide the crude residue. The residue was purified by reverse phase flash chromatography [water (0.1% FA)/acetonitrile] to afford tert-butyl (3S)-4-(8-fluoro-7-(5-methyl-1H-indazol-4-yl)-2-(((S)-1-methylpyrrolidin-2-yl)methoxy)pyrido[4,3-d]pyrimidin-4-yl)-3-methylpiperazine-1-carboxylate (280 mg, 474 µmol, 78% yield) as a yellow solid. ¹H NMR (400 MHz, CDCl₃) δ 10.23 (br s, 1H), 9.09 (s, 1H), 7.82 (s, 1H), 7.54-7.47 (m, 1H), 7.38 (d, J=8.4 Hz, 1H), 4.99-4.81 (m, 1H), 4.58 (dd, J=4.4, 10.8 Hz, 1H), 4.50-4.32 (m, 2H), 4.30-4.14 (m, 1H), 4.05-3.91 (m, 1H), 3.75-3.62 (m, 1H), 3.33-3.07 (m, 3H), 2.79-2.68 (m, 1H), 2.51 (s, 3H), 2.39 (d, J=0.8 Hz, 3H), 2.34-2.27 (m, 1H), 2.13-2.06 (m, 1H), 1.92-1.76 (m, 3H), 1.51 (s, 12H).

Intermediate F-4

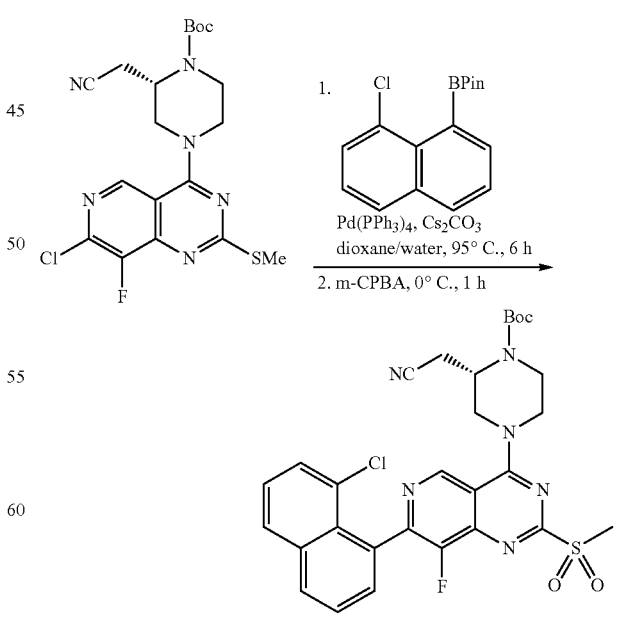

To a solution of tert-butyl (2S)-4-(7-chloro-8-fluoro-2-methylsulfanyl-pyrido[4,3-d]pyrimidin-4-yl)-2-(cyanomethyl)piperazine-1-carboxylate (2.1 g, 4.64 mmol, 1.0 equiv) and 2-(8-chloronaphthalen-1-yl)-4,4,5,5-tetramethyl-1,3,2-dioxaborolane (1.87 g, 6.95 mmol, 1.5 equiv) in dioxane (50.0 mL) and H$_2$O (10 mL) was added Cs$_2$CO$_3$ (4.53 g, 13.9 mmol, 3 equiv) and Pd(PPh$_3$)$_4$ (2.68 g, 2.32 mmol, 0.5 equiv). The system was flushed with nitrogen and then heated to 100° C. for 5 h. The reaction mixture was diluted with water 50.0 mL and extracted with ethyl acetate (30.0 mL×3). The combined organic layer was washed with brine (30.0 mL×2), dried over anh Na$_2$SO$_4$, filtered and concentrated under reduced pressure. The residue was purified by column chromatography (SiO$_2$, petroleum ether/ethyl acetate, 5:1 to 3:1) to afford tert-butyl (2S)-4-[7-(8-chloro-1-naphthyl)-8-fluoro-2-methylsulfanyl-pyrido[4,3-d]pyrimidin-4-yl]-2-(cyanomethyl)piperazine-1-carboxylate (1.00 g, 1.62 mmol, 35% yield) as a light yellow solid. LCMS [ESI, M+1]: 579.

To a solution of tert-butyl (2S)-4-[7-(8-chloro-1-naphthyl)-8-fluoro-2-methylsulfanyl-pyrido[4,3-d]pyrimidin-4-yl]-2-(cyanomethyl)piperazine-1-carboxylate (2.4 g, 4.14 mmol, 1.0 equiv) in ethyl acetate (40.0 mL) at 0° C. was added portionwise m-CPBA (2.68 g, 12.4 mmol, 80% purity, 3.0 equiv). The mixture was stirred at 0° C. for 2 h and was diluted with satd aq NaHSO$_3$ (30.0 mL) at and ethyl acetate (60.0 mL). The combined organic layer was washed with satd aq NaHCO$_3$ (30.0 mL×2), dried over anh Na$_2$SO$_4$, filtered and concentrated under reduced pressure to give a residue. The crude product was purified by reversed-phase HPLC (0.1% FA in ACN) to afford tert-butyl (2S)-4-[7-(8-chloro-1-naphthyl)-8-fluoro-2-methylsulfonyl-pyrido[4,3-d]pyrimidin-4-yl]-2-(cyanomethyl)piperazine-1-carboxylate (2.1 g, 3.41 mmol, 82% yield) as a yellow solid. LCMS [ESI, M+1]: 611.

Intermediate F-5

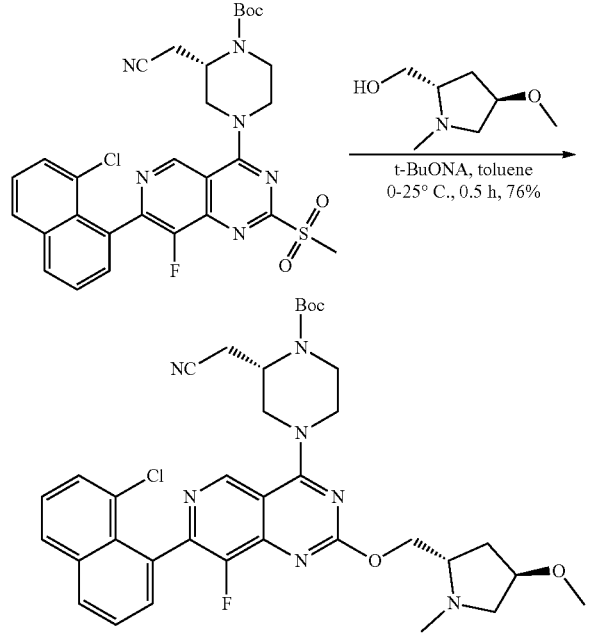

To a mixture of tert-butyl (S)-4-(7-(8-chloronaphthalen-1-yl)-8-fluoro-2-(methylsulfonyl)pyrido[4,3-d]pyrimidin-4-yl)-2-(cyanomethyl)piperazine-1-carboxylate (270 mg, 442 μmol, 1.00 equiv) and ((2S,4R)-4-methoxy-1-methylpyrrolidin-2-yl)methanol (192 mg, 1.33 mmol, 3.00 equiv) in toluene (6.00 mL) was added t-BuONa (127 mg, 1.33 mmol, 3.00 equiv) in one portion at 0° C. under an atmosphere of nitrogen. The mixture was stirred at room temperature for 30 min and was subsequently diluted with ethyl acetate (30.0 mL). The pH was neutralized to ~8 with 2 M HCl at 0° C. and the mixture was extracted with ethyl acetate (10.0 mL×2). The combined organic layer was washed with water (10.0 mL), dried over anh sodium sulfate, filtered and concentrated under reduced pressure to afford a crude residue. The residue was purified by reversed phase flash chromatography [water (0.1% FA)/acetonitrile]. The desired fractions were collected, neutralized with saturated NaHCO$_3$ solution (5.00 mL) and extracted with ethyl acetate (50.0 mL×2). The separated organic layer was dried over anh sodium sulfate, filtered and concentrated under reduced pressure to afford tert-butyl (S)-4-(7-(8-chloronaphthalen-1-yl)-8-fluoro-2-(((2S,4R)-4-methoxy-1-methylpyrrolidin-2-yl)methoxy)pyrido[4,3-d]pyrimidin-4-yl)-2-(cyanomethyl)piperazine-1-carboxylate (227 mg, 336 μmol, 76% yield) was obtained as a yellow solid. LCMS [ESI, M+1]: 676.

Intermediate F-6

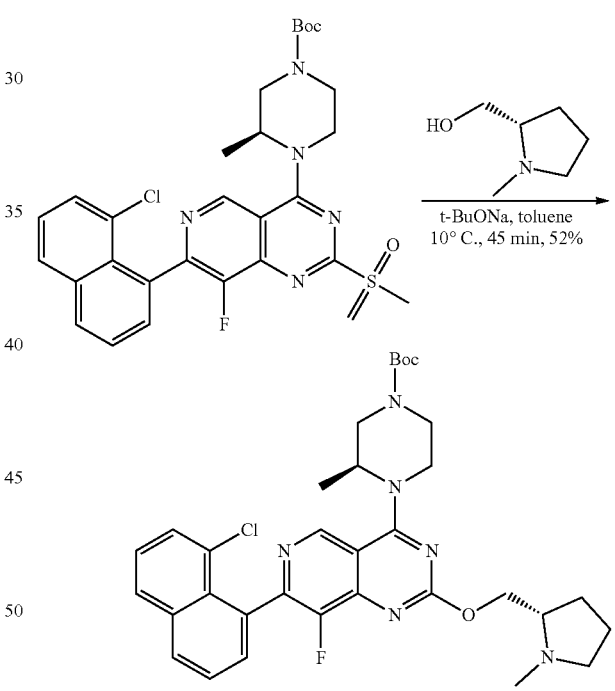

To a solution of tert-butyl (S)-4-(7-(8-chloronaphthalen-1-yl)-8-fluoro-2-(methylsulfonyl)pyrido[4,3-d]pyrimidin-4-yl)-3-methylpiperazine-1-carboxylate (570 mg, 1.24 mmol, 1.0 equiv) and (S)-(1-methylpyrrolidin-2-yl)methanol (285 mg, 2.48 mmol, 294 μL, 2.0 equiv) in toluene (12 mL) was added 4 Å molecular sieve (200 mg). The suspension was stirred at 10° C. for 0.5 hour. Subsequently, t-BuONa (238 mg, 2.48 mmol, 2.0 equiv) was added to the mixture at 0° C. and stirring was continued for 10 min. The mixture diluted with water (10 mL) and extracted with ethyl acetate (2×40 mL). The combined organic layer was dried over anh Na$_2$SO$_4$, filtered and concentrated under reduced pressure to provide the crude residue. The residue was purified by reversed phase flash chromatography [water (0.1% FA)/ acetonitrile] to afford tert-butyl (S)-4-(7-(8-chloronaphthalen-1-yl)-8-fluoro-2-(((S)-1-methylpyrrolidin-2-yl)methoxy)pyrido[4,3-d]pyrimidin-4-yl)-3-methylpiperazine-1-carboxylate (320 mg, 646 μmol, 52% yield) as a yellow solid.

$^1$H NMR (400 MHz, CDCl$_3$) δ=8.72 (s, 1H), 4.85-4.74 (m, 1H), 4.53 (dd, J=4.4, 10.4 Hz, 1H), 4.40-4.27 (m, 2H), 4.18-3.80 (m, 2H), 3.69-3.57 (m, 1H), 3.30-3.18 (m, 1H), 3.16-2.99 (m, 2H), 2.76-2.68 (m, 1H), 2.53-2.48 (m, 3H), 2.35-2.25 (m, 1H), 2.12-2.04 (m, 1H), 1.91-1.74 (m, 3H), 1.50 (s, 9H), 1.47 (d, J=6.8 Hz, 3H).

Following the teachings of the General Reaction Schemes and Intermediates F1-F3, Intermediates F-7 to F-167 were prepared as shown in Table 2B.

TABLE 2B

Intermediates F-7 to F-167

| Int. # | Structure | Characterization Data |
|---|---|---|
| F-7 | 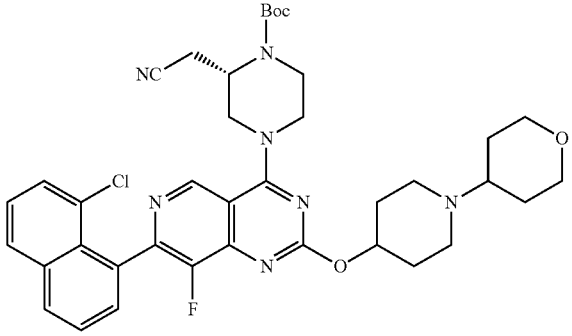 [SMILES: CC(C)(C)OC(=O)N1CCN(c2nc(OC3CCN(C4CCOCC4)CC3)nc3c(F)c(-c4cccc5cccc(Cl)c45)ncc23)C[C@@H]1CC#N]<br>tert-butyl (S)-4-(7-(8-chloronaphthalen-1-yl)-8-fluoro-2-((1-(tetrahydro-2H-pyran-4-yl)piperidin-4-yl)oxy)pyrido[4,3-d]pyrimidin-4-yl)-2-(cyanomethyl)piperazine-1-carboxylate | LCMS [ESI, M + 1]: 716 |
| F-8 | 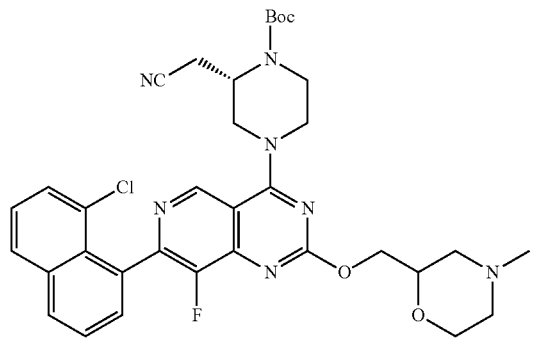 [SMILES: CN1CCOC(COc2nc(N3CCN(C(=O)OC(C)(C)C)[C@@H](CC#N)C3)c3cnc(-c4cccc5cccc(Cl)c45)c(F)c3n2)C1]<br>tert-butyl (2S)-4-(7-(8-chloronaphthalen-1-yl)-8-fluoro-2-((4-methylmorpholin-2-yl)methoxy)pyrido[4,3-d]pyrimidin-4-yl)-2-(cyanomethyl)piperazine-1-carboxylate | LCMS [ESI, M + 1]: 662 |
| F-9 | 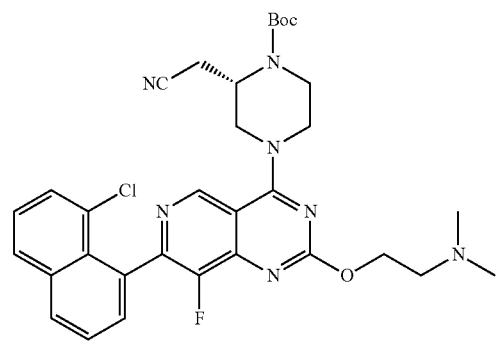 [SMILES: CN(C)CCOc1nc(N2CCN(C(=O)OC(C)(C)C)[C@@H](CC#N)C2)c2cnc(-c3cccc4cccc(Cl)c34)c(F)c2n1]<br>tert-butyl (S)-4-(7-(8-chloronaphthalen-1-yl)-2-(2-(dimethylamino)ethoxy)-8-fluoropyrido[4,3-d]pyrimidin-4-yl)-2-(cyanomethyl)piperazine-1-carboxylate | LCMS [ESI, M + 1]: 620 |

TABLE 2B-continued

Intermediates F-7 to F-167

| Int. # | Structure | Characterization Data |
|---|---|---|
| F-10 | 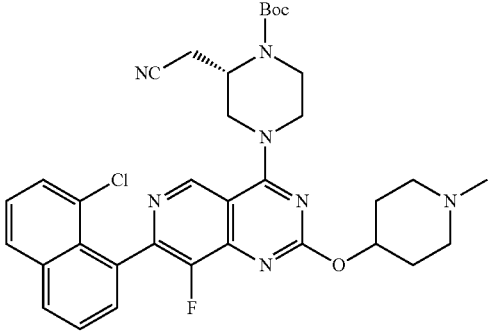 [SMILES: CN1CCC(Oc2nc(N3CCN(C(=O)OC(C)(C)C)[C@@H](CC#N)C3)c3cnc(-c4cccc5cccc(Cl)c45)c(F)c3n2)CC1]<br>tert-butyl (S)-4-(7-(8-chloronaphthalen-1-yl)-8-fluoro-2-((1-methylpiperidin-4-yl)oxy)pyrido[4,3-d]pyrimidin-4-yl)-2-(cyanomethyl)piperazine-1-carboxylate | LCMS [ESI, M + 1]: 646 |
| F-11 | 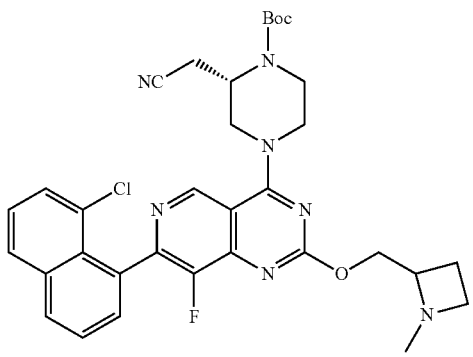 [SMILES: CN1CCC1COc1nc(N2CCN(C(=O)OC(C)(C)C)[C@@H](CC#N)C2)c2cnc(-c3cccc4cccc(Cl)c34)c(F)c2n1]<br>tert-butyl (2S)-4-(7-(8-chloronaphthalen-1-yl)-8-fluoro-2-((1-methylazetidin-2-yl)methoxy)pyrido[4,3-d]pyrimidin-4-yl)-2-(cyanomethyl)piperazine-1-carboxylate | LCMS [ESI, M + 1]: 632 |
| F-12 | 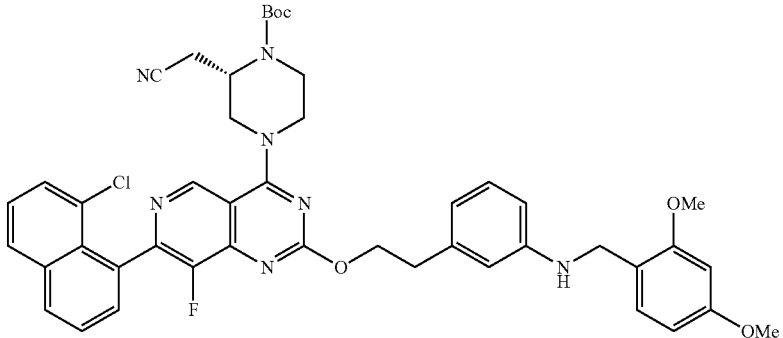 [SMILES: COc1ccc(CNc2cccc(CCOc3nc(N4CCN(C(=O)OC(C)(C)C)[C@@H](CC#N)C4)c4cnc(-c5cccc6cccc(Cl)c56)c(F)c4n3)c2)c(OC)c1]<br>tert-butyl (S)-4-(7-(8-chloronaphthalen-1-yl)-2-(3-((2,4-dimethoxybenzyl)amino)phenethoxy)-8-fluoropyrido[4,3-d]pyrimidin-4-yl)-2-(cyanomethyl)piperazine-1-carboxylate | LCMS [ESI, M + 1]: 818 |

TABLE 2B-continued

Intermediates F-7 to F-167

| Int. # | Structure | Characterization Data |
|---|---|---|
| F-13 | 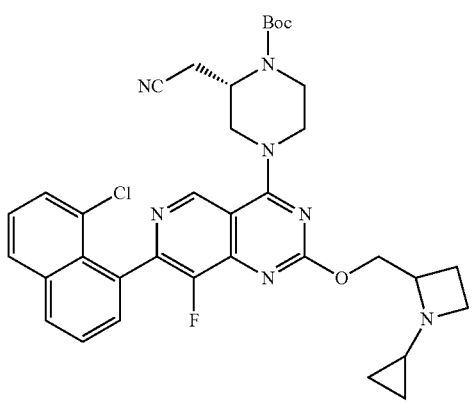 [SMILES: CC(C)(C)OC(=O)N1CCN(c2nc(OCC3CCN3C3CC3)nc3c(F)c(-c4cccc5cccc(Cl)c45)ncc23)C[C@@H]1CC#N] tert-butyl (2S)-4-(7-(8-chloronaphthalen-1-yl)-2-((1-cyclopropylazetidin-2-yl)methoxy)-8-fluoropyrido[4,3-d]pyrimidin-4-yl)-2-(cyanomethyl)piperazine-1-carboxylate | LCMS [ESI, M + 1]: 658 |
| F-14 | 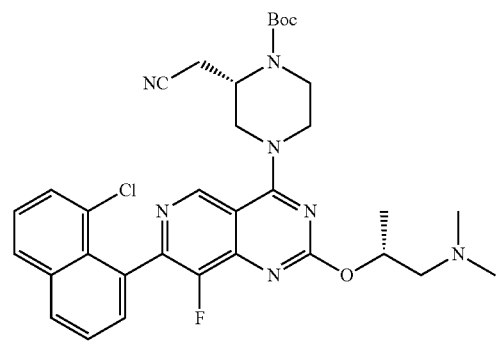 tert-butyl (S)-4-(7-(8-chloronaphthalen-1-yl)-2-(((R)-1-(dimethylamino)propan-2-yl)oxy)-8-fluoropyrido[4,3-d]pyrimidin-4-yl)-2-(cyanomethyl)piperazine-1-carboxylate | LCMS [ESI, M + 1]: 620 |
| F-15 | 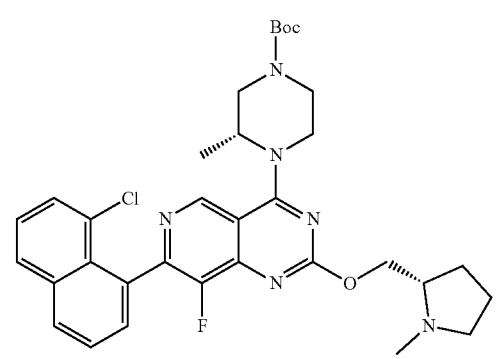 [SMILES: C[C@@H]1CN(C(=O)OC(C)(C)C)CCN1c1nc(OC[C@@H]2CCCN2C)nc2c(F)c(-c3cccc4cccc(Cl)c34)ncc12] tert-butyl (R)-4-(7-(8-chloronaphthalen-1-yl)-8-fluoro-2-(((S)-1-methylpyrrolidin-2-yl)methoxy)pyrido[4,3-d]pyrimidin-4-yl)-3-methylpiperazine-1-carboxylate | LCMS [ESI, M + 1]: 621 |

TABLE 2B-continued

Intermediates F-7 to F-167

| Int. # | Structure | Characterization Data |
|---|---|---|
| F-16 | tert-butyl 7-(7-(8-chloronaphthalen-1-yl)-8-fluoro-2-((1-(tetrahydro-2H-pyran-4-yl)piperidin-4-yl)oxy)pyrido[4,3-d]pyrimidin-4-yl)-2,7-diazaspiro[3.5]nonane-2-carboxylate | LCMS [ESI, M + 1]: 717 |
| F-17 | tert-butyl (S)-7-(7-(8-chloronaphthalen-1-yl)-8-fluoro-2-((1-methylpyrrolidin-2-yl)methoxy)pyrido[4,3-d]pyrimidin-4-yl)-2,7-diazaspiro[3.5]nonane-2-carboxylate | LCMS [ESI, M + 1]: 647 |
| F-18 | tert-butyl (S)-4-(7-(8-chloronaphthalen-1-yl)-8-fluoro-2-((tetrahydro-1H-pyrrolizin-7a(5H)-yl)methoxy)pyrido[4,3-d]pyrimidin-4-yl)-2-(cyanomethyl)piperazine-1-carboxylate | LCMS [ESI, M + 1]: 672 |

TABLE 2B-continued

Intermediates F-7 to F-167

| Int. # | Structure | Characterization Data |
|---|---|---|
| F-19 | tert-butyl (3S)-4-(8-fluoro-7-(5-methyl-1H-indazol-4-yl)-2-(((S)-1-methylpyrrolidin-2-yl)methoxy)pyrido[4,3-d]pyrimidin-4-yl)-3-methylpiperazine-1-carboxylate | $^1$H NMR (400 MHz, CDCl$_3$) δ = 10.23 (br s, 1H), 9.09 (s, 1H), 7.82 (s, 1H), 7.54-7.47 (m, 1H), 7.38 (d, J = 8.4 Hz, 1H), 4.99-4.81 (m, 1H), 4.58 (dd, J = 4.4, 10.8 Hz, 1H), 4.50-4.32 (m, 2H), 4.30-4.14 (m, 1H), 4.05-3.91 (m, 1H), 3.75-3.62 (m, 1H), 3.33-3.07 (m, 3H), 2.7-2.68 (m, 1H), 2.51 (s, 3H), 2.39 (d, J = 0.8 Hz, 3H), 2.34-2.27 (m, 1H), 2.13-2.06 (m, 1H), 1.92-1.76 (m, 3H), 1.51 (s, 12H) |
| F-20 | tert-butyl (2S)-2-(cyanomethyl)-4-(8-fluoro-7-(2-fluoro-6-(methoxymethoxy)phenyl)-2-(((S)-1-methylpyrrolidin-2-yl)methoxy)pyrido[4,3-d]pyrimidin-4-yl)piperazine-1-carboxylate | LCMS [ESI, M + 1]: 672 |
| F-21 | tert-butyl (S)-4-(7-(5-chloroisoquinolin-4-yl)-8-fluoro-2-((((2S,4R)-4-methoxy-1-methylpyrrolidin-2-yl)methoxy)pyrido[4,3-d]pyrimidin-4-yl)-2-(cyanomethyl)piperazine-1-carboxylate | LCMS [ESI, M + 1]: 677 |

TABLE 2B-continued

Intermediates F-7 to F-167

| Int. # | Structure | Characterization Data |
|---|---|---|
| F-22 | 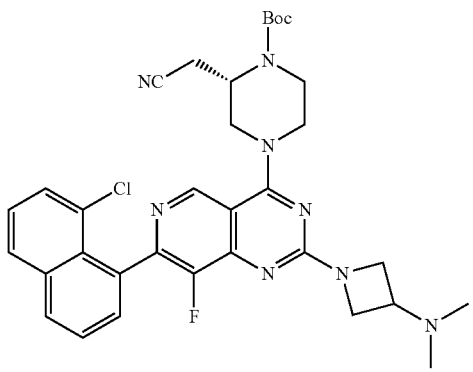 [SMILES: CN(C)C1CN(c2nc(N3CCN(C(=O)OC(C)(C)C)[C@@H](CC#N)C3)c3cnc(-c4cccc5cccc(Cl)c45)c(F)c3n2)C1]<br>tert-butyl (S)-4-(7-(8-chloronaphthalen-1-yl)-2-(3-(dimethylamino)azetidin-1-yl)-8-fluoropyrido[4,3-d]pyrimidin-4-yl)-2-(cyanomethyl)piperazine-1-carboxylate | LCMS [ESI, M + 1]: 631 |
| F-23 | 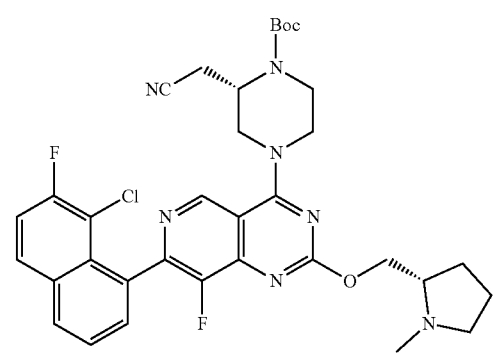 [SMILES: CN1CCC[C@H]1COc1nc(N2CCN(C(=O)OC(C)(C)C)[C@@H](CC#N)C2)c2cnc(-c3cccc4ccc(F)c(Cl)c34)c(F)c2n1]<br>tert-butyl (S)-4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-2-(cyanomethyl)piperazine-1-carboxylate | LCMS [ESI, M + 1]: 664 |
| F-24 | 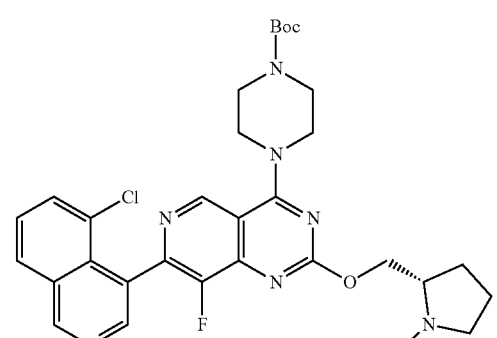<br>tert-butyl (S)-4-(7-(5-chloroisoquinolin-4-yl)-8-fluoro-2-((1-methylpyrrolidin-2-yl)methoxy)pyrido[4,3-d]pyrimidin-4-yl)piperazine-1-carboxylate | LCMS [ESI, M + 1]: 608 |

TABLE 2B-continued

Intermediates F-7 to F-167

| Int. # | Structure | Characterization Data |
|---|---|---|
| F-25 | 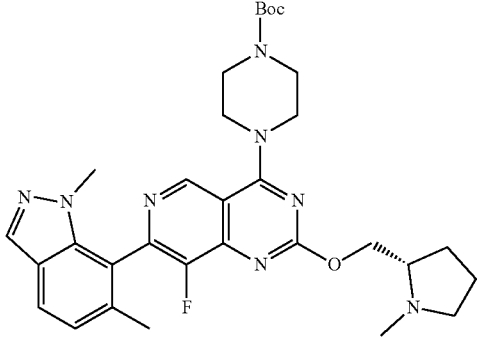 [SMILES: Cc1ccc2cnn(C)c2c1-c1ncc2c(N3CCN(C(=O)OC(C)(C)C)CC3)nc(OC[C@@H]3CCCN3C)nc2c1F]<br>tert-butyl 4-(7-(1,6-dimethyl-1H-indazol-7-yl)-8-fluoro-2-(((S)-1-methylpyrrolidin-2-yl)methoxy)pyrido[4,3-d]pyrimidin-4-yl)piperazine-1-carboxylate | LCMS [ESI, M + 1]: 591 |
| F-26 | 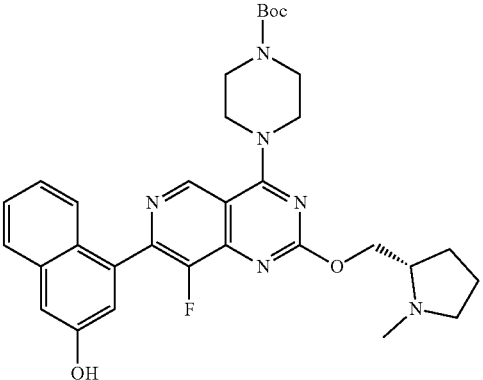<br>tert-butyl (S)-4-(8-fluoro-7-(3-hydroxynaphthalen-1-yl)-2-((1-methylpyrrolidin-2-yl)methoxy)pyrido[4,3-d]pyrimidin-4-yl)piperazine-1-carboxylate | LCMS [ESI, M + 1]: 608 |
| F-27 | 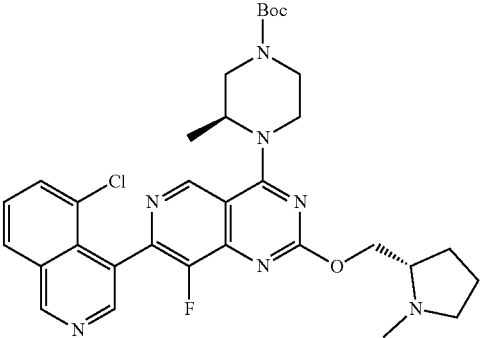 [SMILES: C[C@H]1CN(C(=O)OC(C)(C)C)CCN1c1nc(OC[C@@H]2CCCN2C)nc2c(F)c(-c3cncc4cccc(Cl)c34)ncc12]<br>tert-butyl (S)-4-(7-(5-chloroisoquinolin-4-yl)-8-fluoro-2-(((S)-1-methylpyrrolidin-2-yl)methoxy)pyrido[4,3-d]pyrimidin-4-yl)-3-methylpiperazine-1-carboxylate | LCMS [ESI, M + 1]: 622 |

TABLE 2B-continued

Intermediates F-7 to F-167

| Int. # | Structure | Characterization Data |
|---|---|---|
| F-28 | 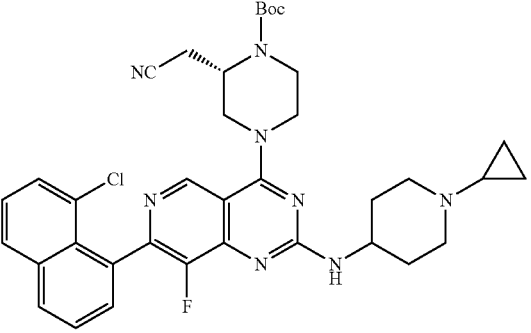 [SMILES: CC(C)(C)OC(=O)N1CCN(c2nc(NC3CCN(C4CC4)CC3)nc3c(F)c(-c4cccc5cccc(Cl)c45)ncc23)C[C@@H]1CC#N]

tert-butyl (S)-4-(7-(8-chloronaphthalen-1-yl)-2-((1-cyclopropylpiperidin-4-yl)amino)-8-fluoropyrido[4,3-d]pyrimidin-4-yl)-2-(cyanomethyl)piperazine-1-carboxylate | LCMS [ESI, M + 1]: 671 |
| F-29 | 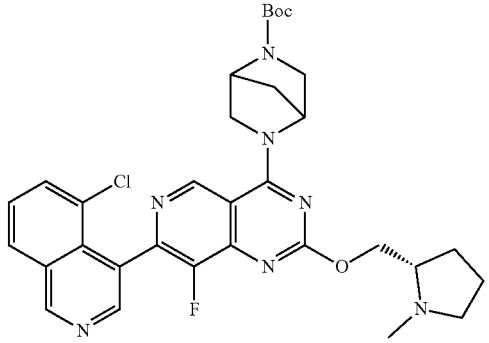 [SMILES: CN1CCC[C@H]1COc1nc(N2CC3CC2CN3C(=O)OC(C)(C)C)c2cnc(-c3cncc4cccc(Cl)c34)c(F)c2n1]

tert-butyl 5-(7-(5-chloroisoquinolin-4-yl)-8-fluoro-2-(((S)-1-methylpyrrolidin-2-yl)methoxy)pyrido[4,3-d]pyrimidin-4-yl)-2,5-diazabicyclo[2.2.1]heptane-2-carboxylate | LCMS [ESI, M + 1]: 620 |
| F-30 | 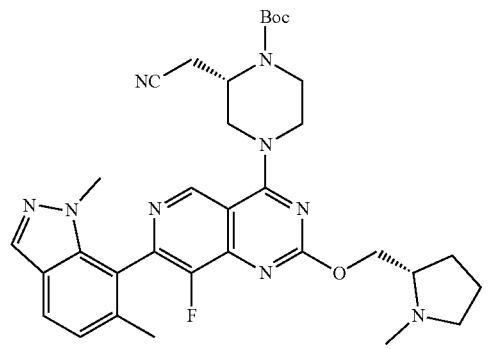 [SMILES: Cc1ccc2cnn(C)c2c1-c1ncc2c(N3CCN(C(=O)OC(C)(C)C)[C@@H](CC#N)C3)nc(OC[C@@H]3CCCN3C)nc2c1F]

tert-butyl (2S)-2-(cyanomethyl)-4-(7-(1,6-dimethyl-1H-indazol-7-yl)-8-fluoro-2-(((S)-1-methylpyrrolidin-2-yl)methoxy)pyrido[4,3-d]pyrimidin-4-yl)piperazine-1-carboxylate | LCMS [ESI, M + 1]: 630 |

US 11,548,888 B2

285                                                                                              286

TABLE 2B-continued

Intermediates F-7 to F-167

| Int. # | Structure | Characterization Data |
|---|---|---|
| F-31 | 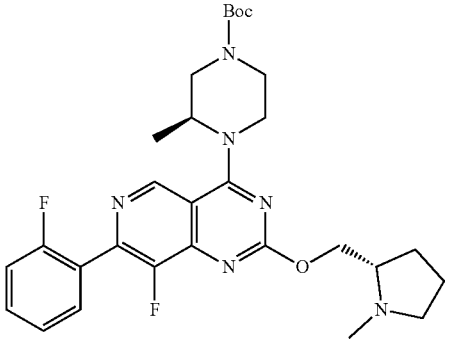 [SMILES: C[C@H]1CN(C(=O)OC(C)(C)C)CCN1c1nc(OC[C@@H]2CCCN2C)nc2c(F)c(-c3ccccc3F)ncc12]<br>tert-butyl (S)-4-(8-fluoro-7-(2-fluorophenyl)-2-(((S)-1-methylpyrrolidin-2-yl)methoxy)pyrido[4,3-d]pyrimidin-4-yl)-3-methylpiperazine-1-carboxylate | LCMS [ESI, M + 1]: 555 |
| F-32 | 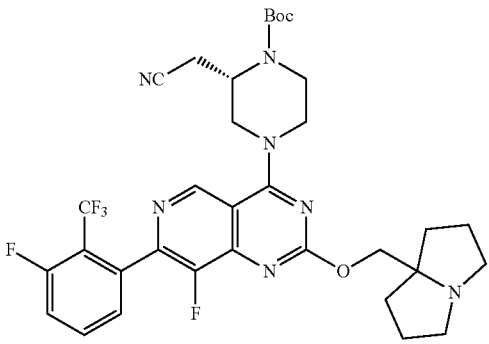 [SMILES: CC(C)(C)OC(=O)N1CCN(c2nc(OCC34CCCN3CCC4)nc3c(F)c(-c4cccc(F)c4C(F)(F)F)ncc23)C[C@@H]1CC#N]<br>tert-butyl (S)-2-(cyanomethyl)-4-(8-fluoro-7-(3-fluoro-2-(trifluoromethyl)phenyl)-2-((tetrahydro-1H-pyrrolizin-7a(5H)-yl)methoxy)pyrido[4,3-d]pyrimidin-4-yl)piperazine-1-carboxylate | LCMS [ESI, M + 1]: 674 |
| F-33 | 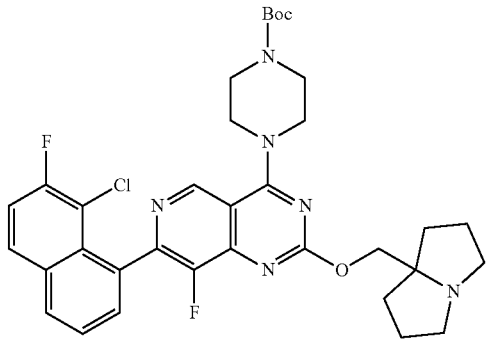 [SMILES: CC(C)(C)OC(=O)N1CCN(c2nc(OCC34CCCN3CCC4)nc3c(F)c(-c4cccc5ccc(F)c(Cl)c45)ncc23)CC1]<br>tert-butyl 4-(7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)piperazine-1-carboxylate | LCMS [ESI, M + 1]: 551 |

TABLE 2B-continued

Intermediates F-7 to F-167

| Int. # | Structure | Characterization Data |
|---|---|---|
| F-34 | 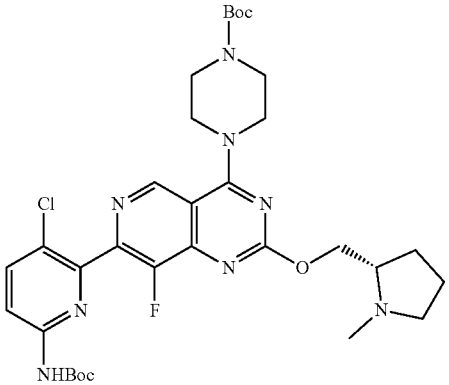<br>tert-butyl (S)-4-(7-(6-((tert-butoxycarbonyl)amino)-3-chloropyridin-2-yl)-8-fluoro-2-((1-methylpyrrolidin-2-yl)methoxy)pyrido[4,3-d]pyrimidin-4-yl)piperazine-1-carboxylate | LCMS [ESI, M + 1]: 608 |
| F-35 | 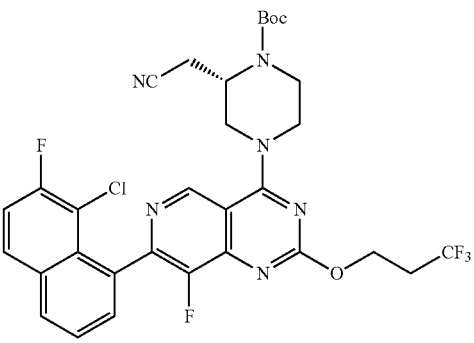 [SMILES: CC(C)(C)OC(=O)N1CCN(c2nc(OCCC(F)(F)F)nc3c(F)c(-c4cccc5ccc(F)c(Cl)c45)ncc23)C[C@@H]1CC#N]<br>tert-butyl (S)-4-(7-(8-chloro-7-fluoronaphthalen-1-yl)-8-fluoro-2-(3,3,3-trifluoropropoxy)pyrido[4,3-d]pyrimidin-4-yl)-2-(cyanomethyl)piperazine-1-carboxylate | LCMS [ESI, M + 1]: 663 |
| F-36 | 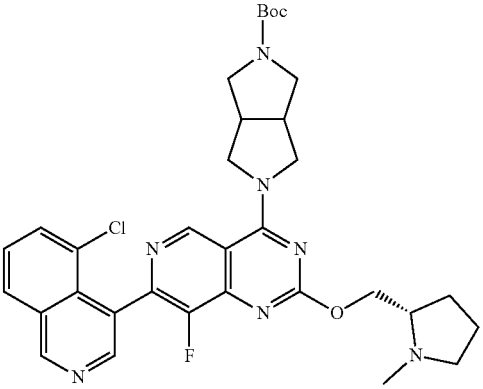 [SMILES: CN1CCC[C@H]1COc1nc(N2CC3CN(C(=O)OC(C)(C)C)CC3C2)c2cnc(-c3cncc4cccc(Cl)c34)c(F)c2n1]<br>tert-butyl 5-(7-(5-chloroisoquinolin-4-yl)-8-fluoro-2-(((S)-1-methylpyrrolidin-2-yl)methoxy)pyrido[4,3-d]pyrimidin-4-yl)hexahydropyrrolo[3,4-c]pyrrole-2(H)-carboxylate | LCMS [ESI, M + 1]: 634 |

TABLE 2B-continued

Intermediates F-7 to F-167

| Int. # | Structure | Characterization Data |
| --- | --- | --- |
| F-37 | 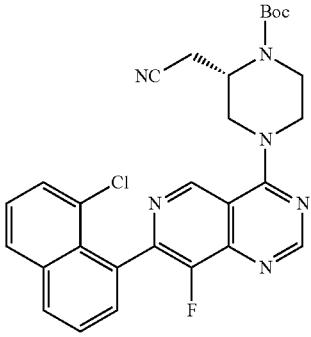 [SMILES: CC(C)(C)OC(=O)N1CCN(c2ncnc3c(F)c(-c4cccc5cccc(Cl)c45)ncc23)C[C@@H]1CC#N]<br>tert-butyl (S)-4-(7-(8-chloronaphthalen-1-yl)-8-fluoropyrido[4,3-d]pyrimidin-4-yl)-2-(cyanomethyl)piperazine-1-carboxylate | LCMS [ESI, M + 1]: 533 |
| F-38 | 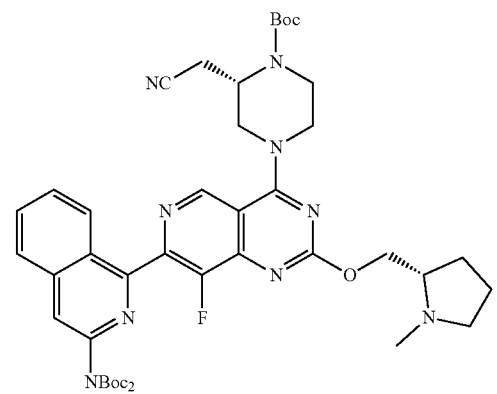<br>tert-butyl (S)-4-(7-(3-(bis(tert-butoxycarbonyl)amino)isoquinolin-1-yl)-8-fluoro-2-(((S)-1-methylpyrrolidin-2-yl)methoxy)pyrido[4,3-d]pyrimidin-4-yl)-2-(cyanomethyl)piperazine-1-carboxylate | LCMS [ESI, M + 1]: 828<br>$^1$H NMR (400 MHz, CDCl$_3$): δ 9.16 (s, 1H), 7.98-7.73 (m, 2H), 7.77-7.69 (m, 2H), 7.60-7.53 (m, 1H), 4.71-4.57 (m, 2H), 4.52-4.33 (m, 3H), 4.12-4.04 (m, 1H), 3.96-3.84 (m, 1H), 3.77-3.64 (m, 1H), 3.60-3.42 (m, 1H), 3.18-3.07 (m, 1H), 2.91-2.67 (m, 3H), 2.52 (s, 3H), 2.35-2.24 (m, 1H), 2.12-2.05 (m, 1H), 1.84-1.76 (m, 3H), 1.53 (s, 9H), 1.41 (s, 18H) |
| F-39 | 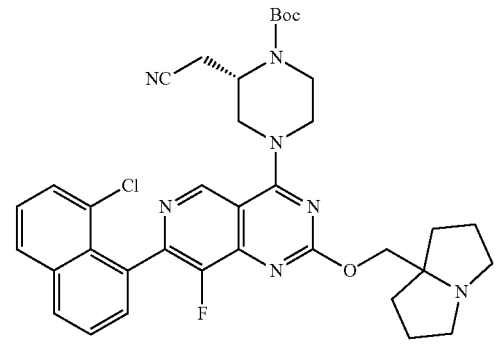<br>tert-butyl (S)-4-(7-(8-chloronaphthalen-1-yl)-8-fluoro-2-((tetrahydro-1H-pyrrolizin-7a(5H)-yl)methoxy)pyrido[4,3-d]pyrimidin-4-yl)-2-(cyanomethyl)piperazine-1-carboxylate | LCMS [ESI, M + 1]: 672 |

TABLE 2B-continued

Intermediates F-7 to F-167

| Int. # | Structure | Characterization Data |
|---|---|---|
| F-40 | 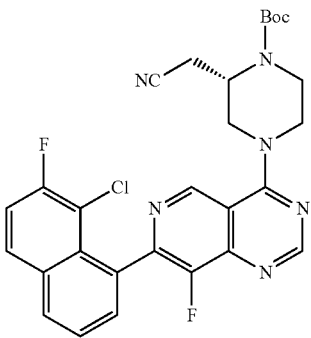 [SMILES: CC(C)(C)OC(=O)N1CCN(c2ncnc3c(F)c(-c4cccc5ccc(F)c(Cl)c45)ncc23)C[C@@H]1CC#N]<br>tert-butyl (S)-4-(7-(8-chloro-7-fluoronaphthalen-1-yl)-8-fluoropyrido[4,3-d]pyrimidin-4-yl)-2-(cyanomethyl)piperazine-1-carboxylate | LCMS [ESI, M + 1]: 551 |
| F-41 | 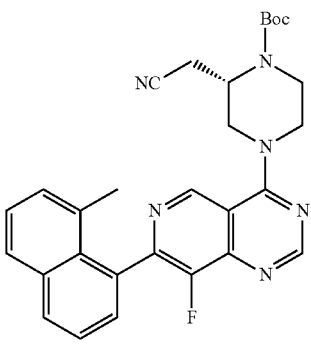 [SMILES: Cc1cccc2cccc(-c3ncc4c(N5CCN(C(=O)OC(C)(C)C)[C@@H](CC#N)C5)ncnc4c3F)c12]<br>tert-butyl (S)-2-(cyanomethyl)-4-(8-fluoro-7-(8-methylnaphthalen-1-yl)pyrido[4,3-d]pyrimidin-4-yl)piperazine-1-carboxylate | LCMS [ESI, M + 1]: 513 |
| F-42 | 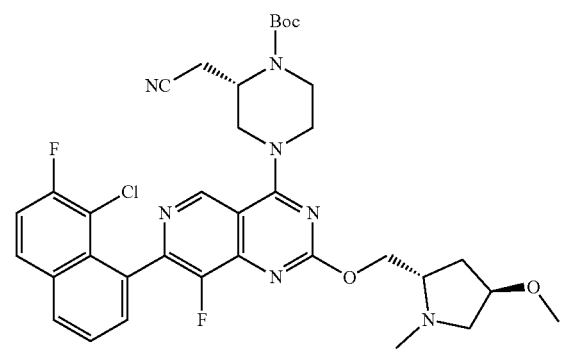 [SMILES: CO[C@@H]1C[C@@H](COc2nc(N3CCN(C(=O)OC(C)(C)C)[C@@H](CC#N)C3)c3cnc(-c4cccc5ccc(F)c(Cl)c45)c(F)c3n2)N(C)C1]<br>tert-butyl (S)-4-(7-(8-chloro-7-fluoronaphthalen-1-yl)-8-fluoro-2-(((2S,4R)-4-methoxy-1-methylpyrrolidin-2-yl)methoxy)pyrido[4,3-d]pyrimidin-4-yl)-2-(cyanomethyl)piperazine-1-carboxylate | LCMS [ESI, M + 1]: 694 |

TABLE 2B-continued

Intermediates F-7 to F-167

| Int. # | Structure | Characterization Data |
|---|---|---|
| F-43 | 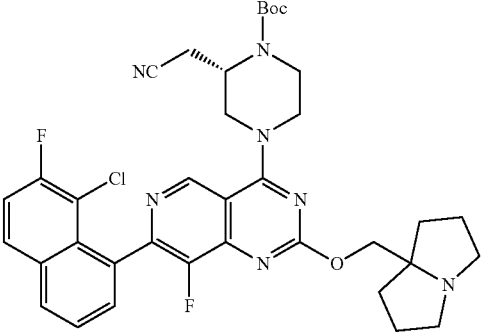 [SMILES: CC(C)(C)OC(=O)N1CCN(c2nc(OCC34CCCN3CCC4)nc3c(F)c(-c4cccc5ccc(F)c(Cl)c45)ncc23)C[C@@H]1CC#N]<br>tert-butyl (S)-4-(7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)-2-(cyanomethyl)piperazine-1-carboxylate | LCMS [ESI, M + 1]: 690 |
| F-44 | 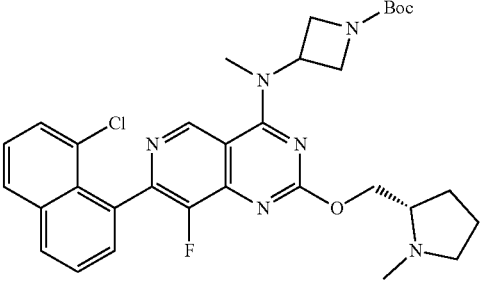 [SMILES: CN(c1nc(OC[C@@H]2CCCN2C)nc2c(F)c(-c3cccc4cccc(Cl)c34)ncc12)C1CN(C(=O)OC(C)(C)C)C1]<br>tert-butyl (S)-3-((7-(8-chloronaphthalen-1-yl)-8-fluoro-2-((1-methylpyrrolidin-2-yl)methoxy)pyrido[4,3-d]pyrimidin-4-yl)(methyl)amino)azetidine-1-carboxylate | LCMS [ESI, M + 1]: 507 |
| F-45 | 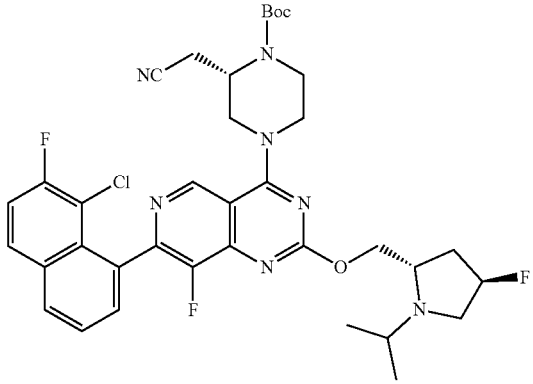 [SMILES: CC(C)N1C[C@H](F)C[C@H]1COc1nc(N2CCN(C(=O)OC(C)(C)C)[C@@H](CC#N)C2)c2cnc(-c3cccc4ccc(F)c(Cl)c34)c(F)c2n1]<br>tert-butyl (S)-4-(7-(8-chloro-7-fluoronaphthalen-1-yl)-8-fluoro-2-(((2S,4R)-4-fluoro-1-isopropylpyrrolidin-2-yl)methoxy)pyrido[4,3-d]pyrimidin-4-yl)-2-(cyanomethyl)piperazine-1-carboxylate | LCMS [ESI, M + 1]: 710 |

TABLE 2B-continued

Intermediates F-7 to F-167

| Int. # | Structure | Characterization Data |
|---|---|---|
| F-46 | 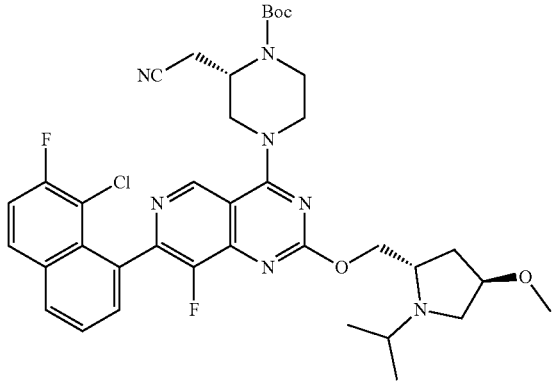 [SMILES: CO[C@@H]1C[C@@H](COc2nc(N3CCN(C(=O)OC(C)(C)C)[C@@H](CC#N)C3)c3cnc(-c4cccc5ccc(F)c(Cl)c45)c(F)c3n2)N(C(C)C)C1]<br>tert-butyl (S)-4-(7-(8-chloro-7-fluoronaphthalen-1-yl)-8-fluoro-2-(((2S,4R)-1-isopropyl-4-methoxypyrrolidin-2-yl)methoxy)pyrido[4,3-d]pyrimidin-4-yl)-2-(cyanomethyl)piperazine-1-carboxylate | LCMS [ESI, M + 1]: 722 |
| F-47 | 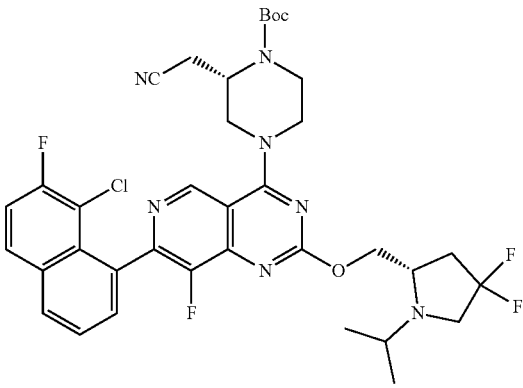 [SMILES: CC(C)N1CC(F)(F)C[C@H]1COc1nc(N2CCN(C(=O)OC(C)(C)C)[C@@H](CC#N)C2)c2cnc(-c3cccc4ccc(F)c(Cl)c34)c(F)c2n1]<br>tert-butyl (S)-4-(7-(8-chloro-7-fluoronaphthalen-1-yl)-2-(((S)-4,4-difluoro-1-isopropylpyrrolidin-2-yl)methoxy)-8-fluoropyrido[4,3-d]pyrimidin-4-yl)-2-(cyanomethyl)piperazine-1-carboxylate | LCMS [ESI, M + 1]: 728 |
| F-48 | 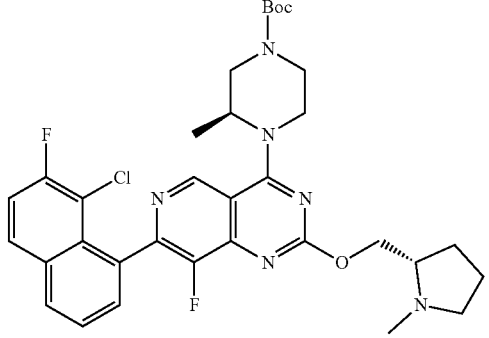 [SMILES: C[C@H]1CN(C(=O)OC(C)(C)C)CCN1c1nc(OC[C@@H]2CCCN2C)nc2c(F)c(-c3cccc4ccc(F)c(Cl)c34)ncc12]<br>tert-butyl (S)-4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-3-methylpiperazine-1-carboxylate | LCMS [ESI, M + 1]: 639 |

TABLE 2B-continued

Intermediates F-7 to F-167

| Int. # | Structure | Characterization Data |
|---|---|---|
| F-49 | tert-butyl (S)-4-(2-(2-(N-(tert-butoxycarbonyl)methylsulfonamido)ethoxy)-7-(8-chloro-7-fluoronaphthalen-1-yl)-8-fluoropyrido[4,3-d]pyrimidin-4-yl)-2-(cyanomethyl)piperazine-1-carboxylate | LCMS [ESI, M + 1]: 788 |
| F-50 | tert-butyl (S)-4-(7-(8-chloro-7-fluoronaphthalen-1-yl)-8-fluoro-2-(((S)-1-isopropylpyrrolidin-2-yl)methoxy)pyrido[4,3-d]pyrimidin-4-yl)-2-(cyanomethyl)piperazine-1-carboxylate | LCMS [ESI, M + 1]: 692 |
| F-51 | tert-butyl (S)-4-(7-(8-chloro-7-fluoronaphthalen-1-yl)-8-fluoro-2-methylpyrido[4,3-d]pyrimidin-4-yl)-2-(cyanomethyl)piperazine-1-carboxylate | LCMS [ESI, M + 1]: 565 |

TABLE 2B-continued

Intermediates F-7 to F-167

| Int. # | Structure | Characterization Data |
|---|---|---|
| F-52 | 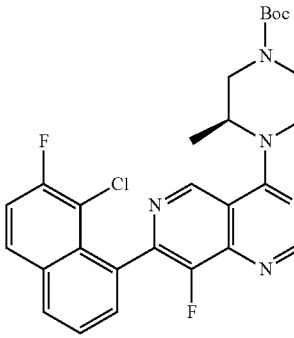<br>tert-butyl (S)-4-(7-(8-chloro-7-fluoronaphthalen-1-yl)-8-fluoropyrido[4,3-d]pyrimidin-4-yl)-3-methylpiperazine-1-carboxylate | LCMS [ESI, M + 1]: 426 |
| F-53 | 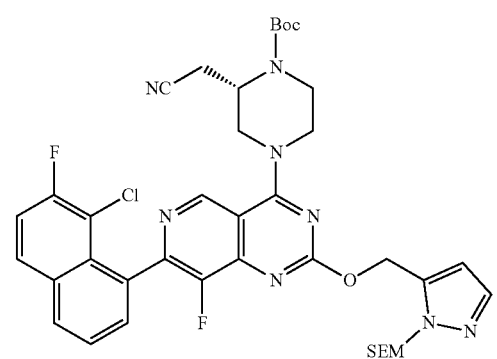 [SMILES: CC(C)(C)OC(=O)N1CCN(c2nc(OCc3ccnn3COCC[Si](C)(C)C)nc3c(F)c(-c4cccc5ccc(F)c(Cl)c45)ncc23)C[C@@H]1CC#N]<br>tert-butyl (S)-4-(7-(8-chloro-7-fluoronaphthalen-1-yl)-8-fluoro-2-((1-((2-(trimethylsilyl)ethoxy)methyl)-1H-pyrazol-5-yl)methoxy)pyrido[4,3-d]pyrimidin-4-yl)-2-(cyanomethyl)piperazine-1-carboxylate | LCMS [ESI, M + 1]: 777 |
| F-54 | 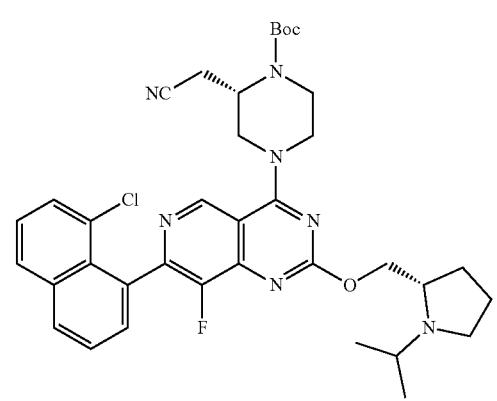<br>tert-butyl (S)-4-(7-(8-chloronaphthalen-1-yl)-8-fluoro-2-(((S)-1-isopropylpyrrolidin-2-yl)methoxy)pyrido[4,3-d]pyrimidin-4-yl)-2-(cyanomethyl)piperazine-1-carboxylate | LCMS [ESI, M + 1]: 774 |

TABLE 2B-continued

Intermediates F-7 to F-167

| Int. # | Structure | Characterization Data |
|---|---|---|
| F-55 | 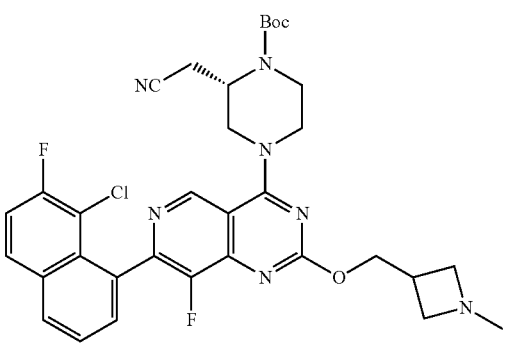 [SMILES: CN1CC(COc2nc(N3CCN(C(=O)OC(C)(C)C)[C@@H](CC#N)C3)c3cnc(-c4cccc5ccc(F)c(Cl)c45)c(F)c3n2)C1] tert-butyl (S)-4-(7-(8-chloro-7-fluoronaphthalen-1-yl)-8-fluoro-2-((1-methylazetidin-3-yl)methoxy)pyrido[4,3-d]pyrimidin-4-yl)-2-(cyanomethyl)piperazine-1-carboxylate | LCMS [ESI, M + 1]: 650 |
| F-56 | 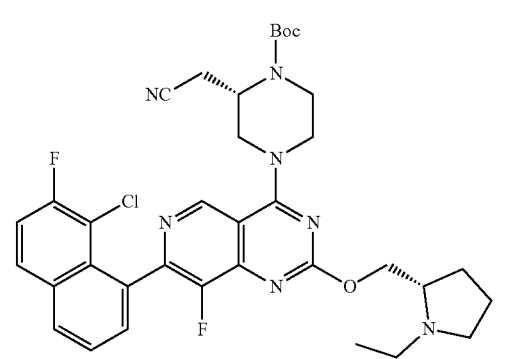 [SMILES: CCN1CCC[C@H]1COc1nc(N2CCN(C(=O)OC(C)(C)C)[C@@H](CC#N)C2)c2cnc(-c3cccc4ccc(F)c(Cl)c34)c(F)c2n1] tert-butyl (S)-4-(7-(8-chloro-7-fluoronaphthalen-1-yl)-2-(((S)-1-ethylpyrrolidin-2-yl)methoxy)-8-fluoropyrido[4,3-d]pyrimidin-4-yl)-2-(cyanomethyl)piperazine-1-carboxylate | LCMS [ESI, M + 1]: 678 |
| F-57 | 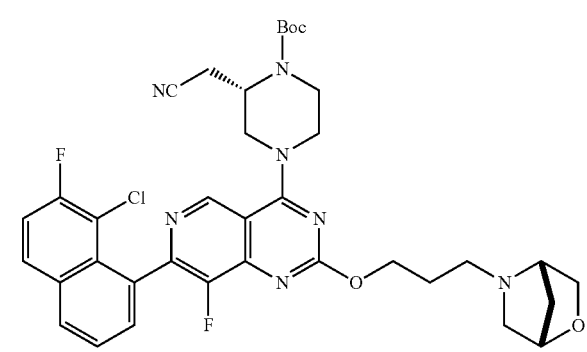 [SMILES: CC(C)(C)OC(=O)N1CCN(c2nc(OCCCN3C[C@@H]4C[C@H]3CO4)nc3c(F)c(-c4cccc5ccc(F)c(Cl)c45)ncc23)C[C@@H]1CC#N] tert-butyl (S)-4-(2-(3-((1S,4S)-2-oxa-5-azabicyclo[2.2.1]heptan-5-yl)propoxy)-7-(8-chloro-7-fluoronaphthalen-1-yl)-8-fluoropyrido[4,3-d]pyrimidin-4-yl)-2-(cyanomethyl)piperazine-1-carboxylate | LCMS [ESI, M + 1]: 706 |

TABLE 2B-continued

Intermediates F-7 to F-167

| Int. # | Structure | Characterization Data |
|---|---|---|
| F-58 | 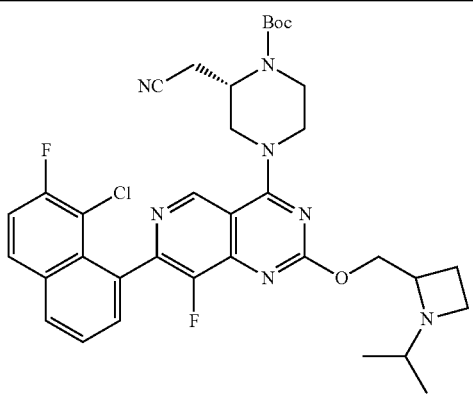

tert-butyl (2S)-4-(7-(8-chloro-7-fluoronaphthalen-1-yl)-8-fluoro-2-((1-isopropylazetidin-2-yl)methoxy)pyrido[4,3-d]pyrimidin-4-yl)-2-(cyanomethyl)piperazine-1-carboxylate | LCMS [ESI, M + 1]: 578 |
| F-59 | 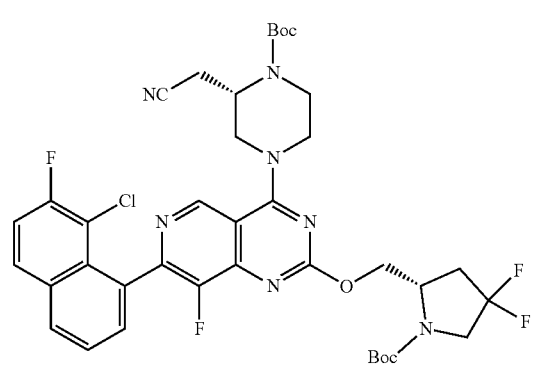 [SMILES: CC(C)(C)OC(=O)N1CCN(c2nc(OC[C@@H]3CC(F)(F)CN3C(=O)OC(C)(C)C)nc3c(F)c(-c4cccc5ccc(F)c(Cl)c45)ncc23)C[C@@H]1CC#N]

tert-butyl (S)-4-(2-(((S)-1-(tert-butoxycarbonyl)-4,4-difluoropyrrolidin-2-yl)methoxy)-7-(8-chloro-7-fluoronaphthalen-1-yl)-8-fluoropyrido[4,3-d]pyrimidin-4-yl)-2-(cyanomethyl)piperazine-1-carboxylate | LCMS [ESI, M + 1]: 586 |
| F-60 | 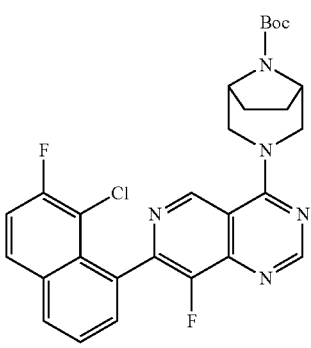 [SMILES: CC(C)(C)OC(=O)N1C2CCC1CN(c1ncnc3c(F)c(-c4cccc5ccc(F)c(Cl)c45)ncc13)C2]

tert-butyl (1R,5S)-3-(7-(8-chloro-7-fluoronaphthalen-1-yl)-8-fluoropyrido[4,3-d]pyrimidin-4-yl)-3,8-diazabicyclo[3.2.1]octane-8-carboxylate | LCMS [ESI, M + 1]: 438 |

TABLE 2B-continued

Intermediates F-7 to F-167

| Int. # | Structure | Characterization Data |
|---|---|---|
| F-61 | tert-butyl (S)-4-(7-(8-chloro-7-fluoronaphthalen-1-yl)-8-fluoro-2-(2-(1-methyl-1H-imidazol-2-yl)ethoxy)pyrido[4,3-d]pyrimidin-4-yl)-2-(cyanomethyl)piperazine-1-carboxylate | LCMS [ESI, M + 1]: 675 |
| F-62 | tert-butyl (R)-4-(7-(8-chloro-7-fluoronaphthalen-1-yl)-8-fluoropyrido[4,3-d]pyrimidin-4-yl)-3-methylpiperazine-1-carboxylate | LCMS [ESI, M + 1]: 526<br>$^1$H NMR (400 MHz, CDCl$_3$) δ 9.12 (d, J = 3.2 Hz, 1H), 8.85 (d, J = 1.6 Hz, 1H), 8.30-7.98 (m, 2H), 7.65-7.60 (m, 2H), 7.40 (t, J = 8.8 Hz, 1H), 4.93 (br d, J = 7.2 Hz, 1H), 4.56-4.43 (m, 1H), 4.40-4.16 (m, 1H), 4.00 (br s, 1H), 3.78-3.64 (m, 1H), 3.32-3.13 (m, 2H), 1.51 (s, 9H), 1.46 (s, 3H) |
| F-63 | tert-butyl 4-(7-(8-chloro-7-fluoronaphthalen-1-yl)-8-fluoropyrido[4,3-d]pyrimidin-4-yl)piperazine-1-carboxylate | LCMS [ESI, M + 1]: 512 |

TABLE 2B-continued

Intermediates F-7 to F-167

| Int. # | Structure | Characterization Data |
|---|---|---|
| F-64 | 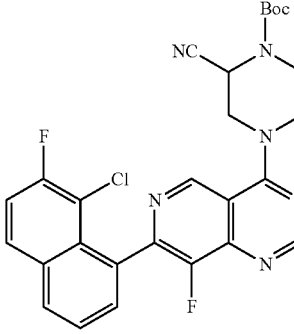<br>tert-butyl 4-(7-(8-chloro-7-fluoronaphthalen-1-yl)-8-fluoropyrido[4,3-d]pyrimidin-4-yl)-2-cyanopiperazine-1-carboxylate | LCMS [ESI, M + 1]: 536 |
| F-65 | 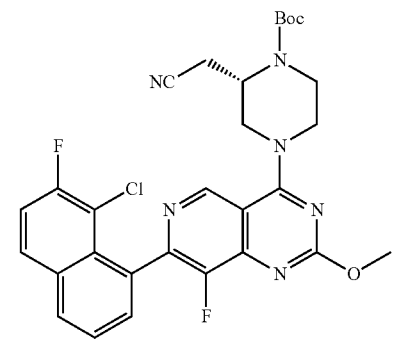 [SMILES: COc1nc(N2CCN(C(=O)OC(C)(C)C)[C@@H](CC#N)C2)c2cnc(-c3cccc4ccc(F)c(Cl)c34)c(F)c2n1]<br>tert-butyl (S)-4-(7-(8-chloro-7-fluoronaphthalen-1-yl)-8-fluoro-2-methoxypyrido[4,3-d]pyrimidin-4-yl)-2-(cyanomethyl)piperazine-1-carboxylate | LCMS [ESI, M + 1]: 581 |
| F-66 | 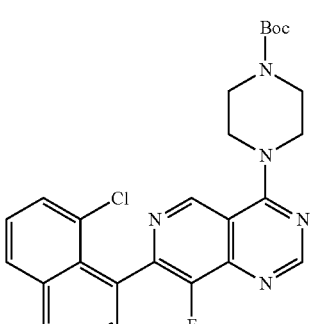<br>tert-butyl 4-(7-(8-chloronaphthalen-1-yl)-8-fluoropyrido[4,3-d]pyrimidin-4-yl)piperazine-1-carboxylate | LCMS [ESI, M + 1]: 494 |

TABLE 2B-continued

Intermediates F-7 to F-167

| Int. # | Structure | Characterization Data |
|---|---|---|
| F-67 | tert-butyl (2S)-4-(7-(8-chloro-7-fluoronaphthalen-1-yl)-2-((1-ethylazetidin-2-yl)methoxy)-8-fluoropyrido[4,3-d]pyrimidin-4-yl)-2-(cyanomethyl)piperazine-1-carboxylate | LCMS [ESI, M + 1]: 664 |
| F-68 | tert-butyl (S)-4-(7-(8-chloro-7-fluoronaphthalen-1-yl)-2-(((S)-1-cyclobutylpyrrolidin-2-yl)methoxy)-8-fluoropyrido[4,3-d]pyrimidin-4-yl)-2-(cyanomethyl)piperazine-1-carboxylate | LCMS [ESI, M + 1]: 704 |
| F-69 | tert-butyl (S)-4-(7-(8-chloro-7-fluoronaphthalen-1-yl)-8-fluoro-2-((1-((2-(trimethylsilyl)ethoxy)methyl)-1H-pyrrolo[3,2-b]pyridin-2-yl)methoxy)pyrido[4,3-d]pyrimidin-4-yl)-2-(cyanomethyl)piperazine-1-carboxylate | LCMS [ESI, M + 1]: 827 |

TABLE 2B-continued

Intermediates F-7 to F-167

| Int. # | Structure | Characterization Data |
| --- | --- | --- |
| F-70 | tert-butyl (S)-4-(7-(8-chloro-7-fluoronaphthalen-1-yl)-8-fluoro-2-((((1S,3R,4R)-2-methyl-2-azabicyclo[2.2.1]heptan-3-yl)methoxy)pyrido[4,3-d]pyrimidin-4-yl)-2-(cyanomethyl)piperazine-1-carboxylate | LCMS [ESI, M + 1]: 690 |
| F-71 | tert-butyl (2S)-4-(7-(8-chloro-7-fluoronaphthalen-1-yl)-8-fluoro-2-((tetrahydro-1H-pyrrolo[2,1-c][1,4]oxazin-8a(6H)-yl)methoxy)pyrido[4,3-d]pyrimidin-4-yl)-2-(cyanomethyl)piperazine-1-carboxylate | LCMS [ESI, M + 1]: 706 |
| F-72 | tert-butyl (S)-4-(2-(((2S,4R)-1-(tert-butoxycarbonyl)-4-fluoropyrrolidin-2-yl)methoxy)-7-(8-chloro-7-fluoronaphthalen-1-yl)-8-fluoropyrido[4,3-d]pyrimidin-4-yl)-2-(cyanomethyl)piperazine-1-carboxylate | LCMS [ESI, M + 1]: 768 |

TABLE 2B-continued

Intermediates F-7 to F-167

| Int. # | Structure | Characterization Data |
| --- | --- | --- |
| F-73 | 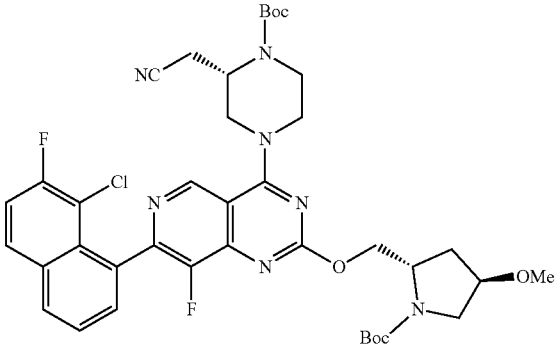 [SMILES: CO[C@@H]1C[C@@H](COc2nc(N3CCN(C(=O)OC(C)(C)C)[C@@H](CC#N)C3)c3cnc(-c4cccc5ccc(F)c(Cl)c45)c(F)c3n2)N(C(=O)OC(C)(C)C)C1]
tert-butyl (S)-4-(2-(((2S,4R)-1-(tert-butoxycarbonyl)-4-methoxypyrrolidin-2-yl)methoxy)-7-(8-chloro-7-fluoronaphthalen-1-yl)-8-fluoropyrido[4,3-d]pyrimidin-4-yl)-2-(cyanomethyl)piperazine-1-carboxylate | LCMS [ESI, M + 1]: 780 |
| F-74 | 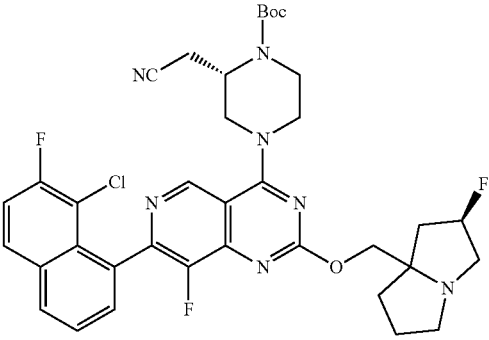 [SMILES: CC(C)(C)OC(=O)N1CCN(c2nc(OCC34CCCN3C[C@H](F)C4)nc3c(F)c(-c4cccc5ccc(F)c(Cl)c45)ncc23)C[C@@H]1CC#N]
tert-butyl (2S)-4-(7-(8-chloro-7-fluoronaphthalen-1-yl)-8-fluoro-2-(((2R)-2-fluorotetrahydro-1H-pyrrolizin-7a(5H)-yl)methoxy)pyrido[4,3-d]pyrimidin-4-yl)-2-(cyanomethyl)piperazine-1-carboxylate | LCMS [ESI, M + 1]: 708 |
| F-75 | 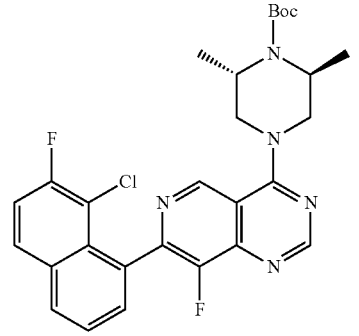 [SMILES: C[C@H]1CN(c2ncnc3c(F)c(-c4cccc5ccc(F)c(Cl)c45)ncc23)C[C@H](C)N1C(=O)OC(C)(C)C]
tert-butyl (2S,6S)-4-(7-(8-chloro-7-fluoronaphthalen-1-yl)-8-fluoropyrido[4,3-d]pyrimidin-4-yl)-2,6-dimethylpiperazine-1-carboxylate | LCMS [ESI, M + 1]: 540 |

TABLE 2B-continued

Intermediates F-7 to F-167

| Int. # | Structure | Characterization Data |
| --- | --- | --- |
| F-76 | 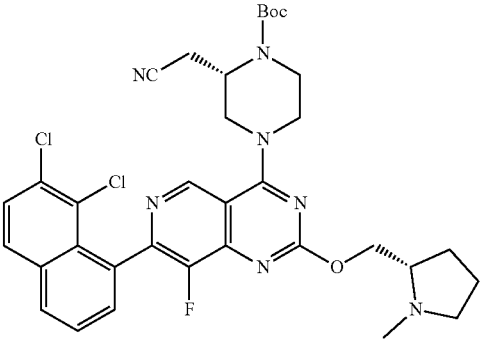 [SMILES: CN1CCC[C@H]1COc1nc(N2CCN(C(=O)OC(C)(C)C)[C@@H](CC#N)C2)c2cnc(-c3cccc4ccc(Cl)c(Cl)c34)c(F)c2n1]<br>tert-butyl (S)-2-(cyanomethyl)-4-(7-(7,8-dichloronaphthalen-1-yl)-8-fluoro-2-(((S)-1-methylpyrrolidin-2-yl)methoxy)pyrido[4,3-d]pyrimidin-4-yl)piperazine-1-carboxylate | LCMS [ESI, M + 1]: 680 |
| F-77 | 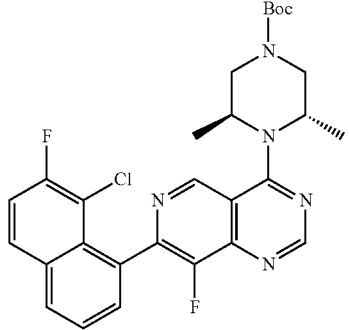 [SMILES: C[C@H]1CN(C(=O)OC(C)(C)C)C[C@H](C)N1c1ncnc2c(F)c(-c3cccc4ccc(F)c(Cl)c34)ncc12]<br>tert-butyl (3S,5S)-4-(7-(8-chloro-7-fluoronaphthalen-1-yl)-8-fluoropyrido[4,3-d]pyrimidin-4-yl)-3,5-dimethylpiperazine-1-carboxylate | LCMS [ESI, M + 1]: 540 |
| F-78 | 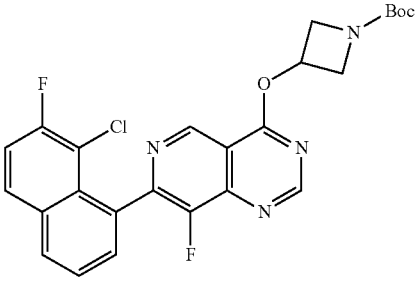 [SMILES: CC(C)(C)OC(=O)N1CC(Oc2ncnc3c(F)c(-c4cccc5ccc(F)c(Cl)c45)ncc23)C1]<br>tert-butyl 3-((7-(8-chloro-7-fluoronaphthalen-1-yl)-8-fluoropyrido[4,3-d]pyrimidin-4-yl)oxy)azetidine-1-carboxylate | LCMS [ESI, M + 1]: 499 |

TABLE 2B-continued

Intermediates F-7 to F-167

| Int. # | Structure | Characterization Data |
| --- | --- | --- |
| F-79 | tert-butyl 4-(7-(8-chloro-7-fluoronaphthalen-1-yl)-8-fluoropyrido[4,3-d]pyrimidin-4-yl)-3-(cyanomethyl)piperazine-1-carboxylate | LCMS [ESI, M + 1]: 551 |
| F-80 | tert-butyl 3-((7-(8-chloro-7-fluoronaphthalen-1-yl)-8-fluoropyrido[4,3-d]pyrimidin-4-yl)oxy)pyrrolidine-1-carboxylate | LCMS [ESI, M + 1]: 513 |
| F-81 | tert-butyl (S)-4-(7-(8-chloro-7-fluoronaphthalen-1-yl)-8-fluoro-2-(oxetan-3-ylmethoxy)pyrido[4,3-d]pyrimidin-4-yl)-2-(cyanomethyl)piperazine-1-carboxylate | LCMS [ESI, M + 1]: 637 |

TABLE 2B-continued

Intermediates F-7 to F-167

| Int. # | Structure | Characterization Data |
| --- | --- | --- |
| F-82 | tert-butyl (R)-4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-2-methylpiperazine-1-carboxylate | LCMS [ESI, M + 1]: 639 |
| F-83 | tert-butyl 4-(7-(8-chloronaphthalen-1-yl)-8-fluoro-2-methylpyrido[4,3-d]pyrimidin-4-yl)piperazine-1-carboxylate | LCMS [ESI, M + 1]: 408 |
| F-84 | tert-butyl (S)-4-(7-(8-chloro-7-fluoronaphthalen-1-yl)-8-fluoro-2-((3-methyloxetan-3-yl)methoxy)pyrido[4,3-d]pyrimidin-4-yl)-2-(cyanomethyl)piperazine-1-carboxylate | LCMS [ESI, M + 1]: 651 |

TABLE 2B-continued

Intermediates F-7 to F-167

| Int. # | Structure | Characterization Data |
| --- | --- | --- |
| F-85 | tert-butyl (R)-4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-3-methylpiperazine-1-carboxylate | LCMS [ESI, M + 1]: 639 |
| F-86 | tert-butyl (2S)-4-(7-(8-chloro-7-fluoronaphthalen-1-yl)-8-fluoro-2-(oxetan-2-ylmethoxy)pyrido[4,3-d]pyrimidin-4-yl)-2-(cyanomethyl)piperazine-1-carboxylate | LCMS [ESI, M + 1]: 637 |
| F-87 | tert-butyl (S)-2-(cyanomethyl)-4-(7-(7,8-difluoronaphthalen-1-yl)-8-fluoro-2-(((S)-1-methylpyrrolidin-2-yl)methoxy)pyrido[4,3-d]pyrimidin-4-yl)piperazine-1-carboxylate | LCMS [ESI, M + 1]: 648<br>$^1$H NMR (400 MHz, CDCl$_3$-d) δ 9.09 (s, 1H), 8.02-7.95 (m, 1H), 7.73 (m, 1H), 7.68-7.58 (m, 2H), 7.46-7.36 (m, 1H), 4.74-4.55 (m, 2H), 4.54-4.35 (m, 3H), 3.94-3.80 (m, 1H), 3.71 (s, 2H), 3.17-3.09 (m, 1H), 2.88-2.68 (m, 3H), 2.51 (s, 3H), 2.35-2.24 (m, 1H), 1.90-1.74 (m, 5H), 1.55-1.51 (m, 9H) |

TABLE 2B-continued

Intermediates F-7 to F-167

| Int. # | Structure | Characterization Data |
|---|---|---|
| F-88 | 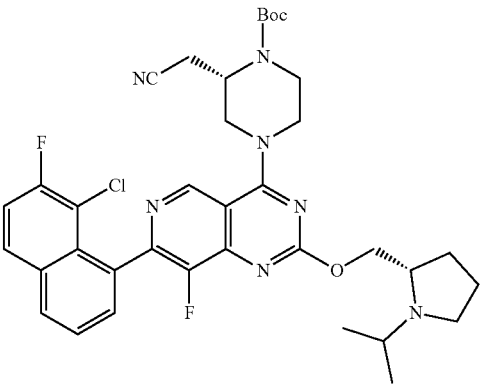 [SMILES: CC(C)N1CCC[C@H]1COc1nc(N2CCN(C(=O)OC(C)(C)C)[C@@H](CC#N)C2)c2cnc(-c3cccc4ccc(F)c(Cl)c34)c(F)c2n1]<br>tert-butyl (S)-4-(7-(8-chloro-7-fluoronaphthalen-1-yl)-8-fluoro-2-(((S)-1-isopropylpyrrolidin-2-yl)methoxy)pyrido[4,3-d]pyrimidin-4-yl)-2-(cyanomethyl)piperazine-1-carboxylate | LCMS [ESI, M + 1]: 692<br>$^1$H NMR (400 MHz, CDCl$_3$-d) δ 9.06 (s, 1H), 8.05-7.97 (m, 1H), 7.90 (dd, J = 5.6, 8.8 Hz, 1H), 7.67-7.56 (m, 2H), 7.41 (dt, J = 2.8, 8.8 Hz, 1H), 4.72-4.62 (m, 1H), 4.58-4.34 (m, 3H), 4.20-4.12 (m, 2H), 3.94-3.80 (m, 1H), 3.75-3.63 (m, 1H), 3.60-3.42 (m, 1H), 3.31 (br s, 1H), 3.06-2.71 (m, 4H), 2.60-2.48 (m, 1H), 1.95-1.74 (m, 4H), 1.53 (s, 9H), 1.20-1.14 (m, 3H), 1.09 (br d, J = 6.4 Hz, 3H) |
| F-89 | 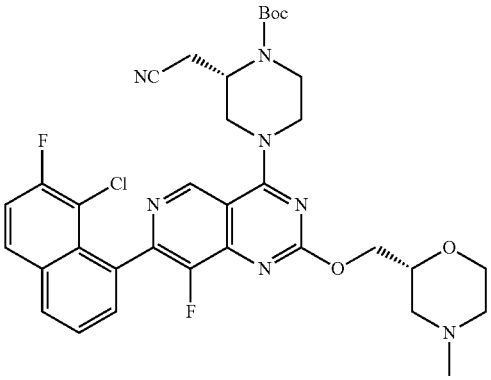 [SMILES: CN1CCO[C@@H](COc2nc(N3CCN(C(=O)OC(C)(C)C)[C@@H](CC#N)C3)c3cnc(-c4cccc5ccc(F)c(Cl)c45)c(F)c3n2)C1]<br>tert-butyl (S)-4-(7-(8-chloro-7-fluoronaphthalen-1-yl)-8-fluoro-2-(((R)-4-methylmorpholin-2-yl)methoxy)pyrido[4,3-d]pyrimidin-4-yl)-2-(cyanomethyl)piperazine-1-carboxylate | LCMS [ESI, M + 1]: 680<br>$^1$H NMR (400 MHz, CDCl$_3$-d) δ 9.08 (s, 1H), 8.01 (br d, J = 9.6 Hz, 1H), 7.90 (dd, J = 5.6, 9.2 Hz, 1H), 7.67-7.55 (m, 2H), 7.42 (dd, J = 2.4, 8.8 Hz, 1H), 4.71-4.36 (m, 6H), 4.08-3.99 (m, 1H), 3.99-3.84 (m, 2H), 3.81-3.66 (m, 2H), 3.60-3.44 (m, 1H), 2.99-2.60 (m, 5H), 2.37-2.29 (m, 3H), 2.26-2.15 (m, 1H), 1.53 (s, 9H) |
| F-90 | 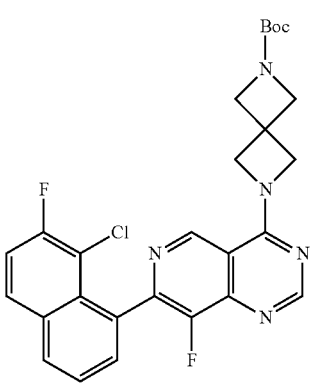 [SMILES: CC(C)(C)OC(=O)N1CC2(C1)CN(c1ncnc3c(F)c(-c4cccc5ccc(F)c(Cl)c45)ncc13)C2]<br>tert-butyl 6-(7-(8-chloro-7-fluoronaphthalen-1-yl)-8-fluoropyrido[4,3-d]pyrimidin-4-yl)-2,6-diazaspiro[3.3]heptane-2-carboxylate | LCMS [ESI, M + 1]: 524 |

TABLE 2B-continued

Intermediates F-7 to F-167

| Int. # | Structure | Characterization Data |
| --- | --- | --- |
| F-91 | 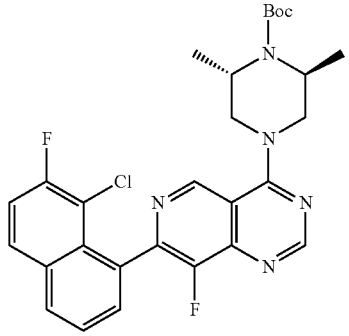 [SMILES: C[C@H]1CN(c2ncnc3c(F)c(-c4cccc5ccc(F)c(Cl)c45)ncc23)C[C@H](C)N1C(=O)OC(C)(C)C]<br>tert-butyl (2S,6S)-4-(7-(8-chloro-7-fluoronaphthalen-1-yl)-8-fluoropyrido[4,3-d]pyrimidin-4-yl)-2,6-dimethylpiperazine-1-carboxylate | LCMS [ESI, M + 1]: 540 |
| F-92 | 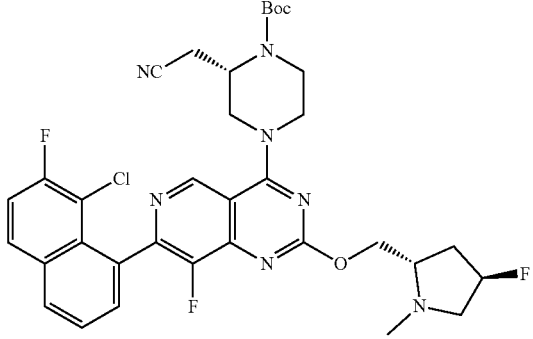 [SMILES: CN1C[C@H](F)C[C@H]1COc1nc(N2CCN(C(=O)OC(C)(C)C)[C@@H](CC#N)C2)c2cnc(-c3cccc4ccc(F)c(Cl)c34)c(F)c2n1]<br>tert-butyl (S)-4-(7-(8-chloro-7-fluoronaphthalen-1-yl)-8-fluoro-2-(((2S,4R)-4-fluoro-1-methylpyrrolidin-2-yl)methoxy)pyrido[4,3-d]pyrimidin-4-yl)-2-(cyanomethyl)piperazine-1-carboxylate | LCMS [ESI, M + 1]: 682 |
| F-93 | 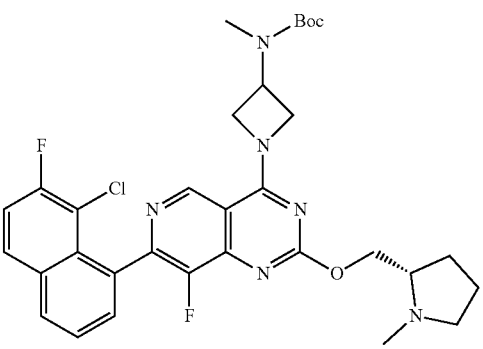 [SMILES: CN(C(=O)OC(C)(C)C)C1CN(c2nc(OC[C@@H]3CCCN3C)nc3c(F)c(-c4cccc5ccc(F)c(Cl)c45)ncc23)C1]<br>tert-butyl (S)-(1-(7-(8-chloro-7-fluoronaphthalen-1-yl)-8-fluoro-2-((1-methylpyrrolidin-2-yl)methoxy)pyrido[4,3-d]pyrimidin-4-yl)azetidin-3-yl)(methyl)carbamate | LCMS [ESI, M + 1]: 625 |

TABLE 2B-continued

Intermediates F-7 to F-167

| Int. # | Structure | Characterization Data |
|---|---|---|
| F-94 | 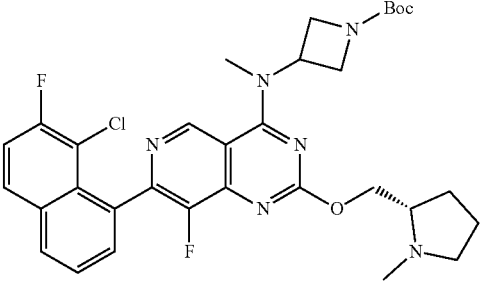 [SMILES: CN(c1nc(OC[C@@H]2CCCN2C)nc2c(F)c(-c3cccc4ccc(F)c(Cl)c34)ncc12)C1CN(C(=O)OC(C)(C)C)C1]<br>tert-butyl (S)-3-((7-(8-chloro-7-fluoronaphthalen-1-yl)-8-fluoro-2-((1-methylpyrrolidin-2-yl)methoxy)pyrido[4,3-d]pyrimidin-4-yl)(methyl)amino)azetidine-1-carboxylate | LCMS [ESI, M + 1]: 625 |
| F-95 | 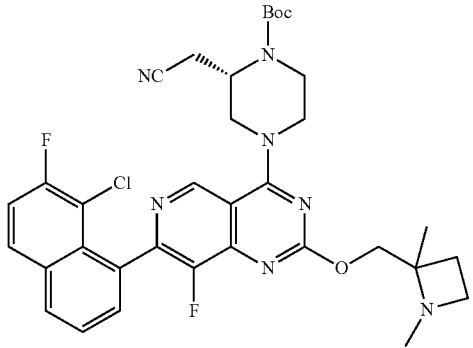 [SMILES: CN1CCC1(C)COc1nc(N2CCN(C(=O)OC(C)(C)C)[C@@H](CC#N)C2)c2cnc(-c3cccc4ccc(F)c(Cl)c34)c(F)c2n1]<br>tert-butyl (2S)-4-(7-(8-chloro-7-fluoronaphthalen-1-yl)-2-((1,2-dimethylazetidin-2-yl)methoxy)-8-fluoropyrido[4,3-d]pyrimidin-4-yl)-2-(cyanomethyl)piperazine-1-carboxylate | LCMS [ESI, M + 1]: 664 |
| F-96 | 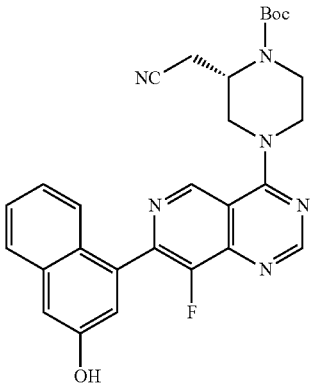 [SMILES: CC(C)(C)OC(=O)N1CCN(c2ncnc3c(F)c(-c4cc(O)cc5ccccc45)ncc23)C[C@@H]1CC#N]<br>tert-butyl (S)-2-(cyanomethyl)-4-(8-fluoro-7-(3-hydroxynaphthalen-1-yl)pyrido[4,3-d]pyrimidin-4-yl)piperazine-1-carboxylate | LCMS [ESI, M + 1]: 515 |

US 11,548,888 B2

TABLE 2B-continued

Intermediates F-7 to F-167

| Int. # | Structure | Characterization Data |
|---|---|---|
| F-97 | 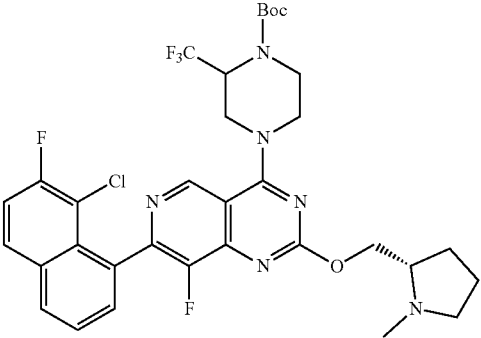 [SMILES: CN1CCC[C@H]1COc1nc(N2CCN(C(=O)OC(C)(C)C)C(C(F)(F)F)C2)c2cnc(-c3cccc4ccc(F)c(Cl)c34)c(F)c2n1]<br>tert-butyl 4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-2-(trifluoromethyl)piperazine-1-carboxylate | LCMS [ESI, M + 1]: 693 |
| F-98 | 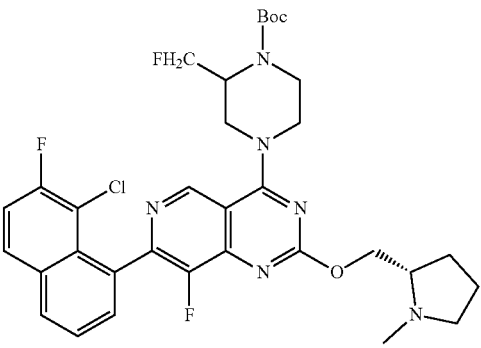<br>tert-butyl 4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-2-(fluoromethyl)piperazine-1-carboxylate | LCMS [ESI, M + 1]: 657 |
| F-99 | 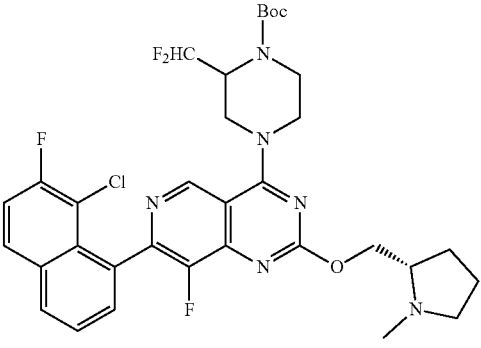<br>tert-butyl 4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-2-(difluoromethyl)piperazine-1-carboxylate | LCMS [ESI, M + 1]: 675 |

TABLE 2B-continued

Intermediates F-7 to F-167

| Int. # | Structure | Characterization Data |
|---|---|---|
| F-100 | 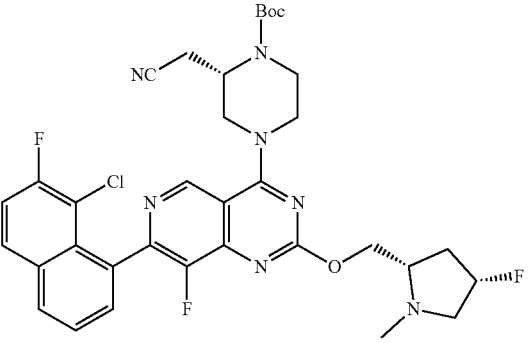 [SMILES: CN1C[C@@H](F)C[C@H]1COc1nc(N2CCN(C(=O)OC(C)(C)C)[C@@H](CC#N)C2)c2cnc(-c3cccc4ccc(F)c(Cl)c34)c(F)c2n1]<br>tert-butyl (S)-4-(7-(8-chloro-7-fluoronaphthalen-1-yl)-8-fluoro-2-(((2S,4S)-4-fluoro-1-methylpyrrolidin-2-yl)methoxy)pyrido[4,3-d]pyrimidin-4-yl)-2-(cyanomethyl)piperazine-1-carboxylate | LCMS [ESI, M + 1]: 682 |
| F-101 | 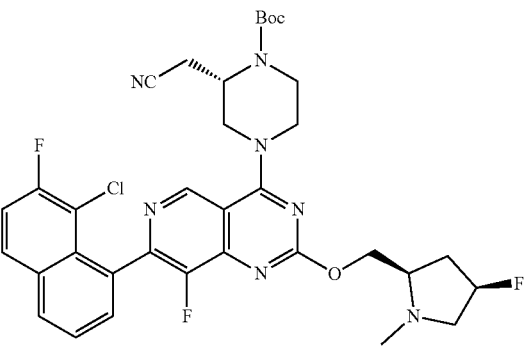 [SMILES: CN1C[C@H](F)C[C@@H]1COc1nc(N2CCN(C(=O)OC(C)(C)C)[C@@H](CC#N)C2)c2cnc(-c3cccc4ccc(F)c(Cl)c34)c(F)c2n1]<br>tert-butyl (S)-4-(7-(8-chloro-7-fluoronaphthalen-1-yl)-8-fluoro-2-(((2R,4R)-4-fluoro-1-methylpyrrolidin-2-yl)methoxy)pyrido[4,3-d]pyrimidin-4-yl)-2-(cyanomethyl)piperazine-1-carboxylate | LCMS [ESI, M + 1]: 682 |
| F-102 | 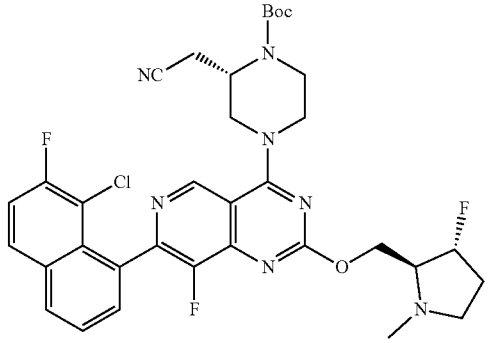 [SMILES: CN1CC[C@@H](F)[C@@H]1COc1nc(N2CCN(C(=O)OC(C)(C)C)[C@@H](CC#N)C2)c2cnc(-c3cccc4ccc(F)c(Cl)c34)c(F)c2n1]<br>tert-butyl (S)-4-(7-(8-chloro-7-fluoronaphthalen-1-yl)-8-fluoro-2-(((2S,3R)-3-fluoro-1-methylpyrrolidin-2-yl)methoxy)pyrido[4,3-d]pyrimidin-4-yl)-2-(cyanomethyl)piperazine-1-carboxylate | LCMS [ESI, M + 1]: 682 |

TABLE 2B-continued

Intermediates F-7 to F-167

| Int. # | Structure | Characterization Data |
|---|---|---|
| F-103 | 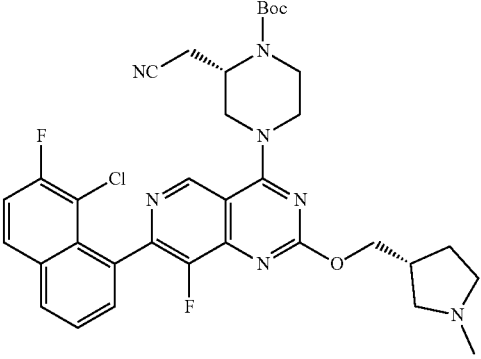 [SMILES: CN1CC[C@@H](COc2nc(N3CCN(C(=O)OC(C)(C)C)[C@@H](CC#N)C3)c3cnc(-c4cccc5ccc(F)c(Cl)c45)c(F)c3n2)C1]<br>tert-butyl (S)-4-(7-(8-chloro-7-fluoronaphthalen-1-yl)-8-fluoro-2-(((R)-1-methylpyrrolidin-3-yl)methoxy)pyrido[4,3-d]pyrimidin-4-yl)-2-(cyanomethyl)piperazine-1-carboxylate | LCMS [ESI, M + 1]: 664 |
| F-104 | 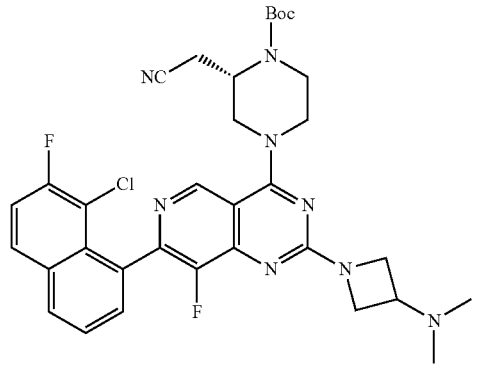 [SMILES: CN(C)C1CN(c2nc(N3CCN(C(=O)OC(C)(C)C)[C@@H](CC#N)C3)c3cnc(-c4cccc5ccc(F)c(Cl)c45)c(F)c3n2)C1]<br>tert-butyl (S)-4-(7-(8-chloro-7-fluoronaphthalen-1-yl)-2-(3-(dimethylamino)azetidin-1-yl)-8-fluoropyrido[4,3-d]pyrimidin-4-yl)-2-(cyanomethyl)piperazine-1-carboxylate | $^1$H NMR (400 MHz, CDCl$_3$) δ 8.83 (d, J = 1.2 Hz, 1H), 7.97 (br d, J = 7.6 Hz, 1H), 7.87 (dd, J = 5.6, 8.8 Hz, 1H), 7.69-7.50 (m, 2H), 7.38 (td, J = 8.4, 1.6 Hz, 1H), 4.78-4.72 (m, 1H), 4.56-4.41 (m, 1H), 4.39-3.95 (m, 6H), 3.70-3.44 (m, 2H), 3.42-3.10 (m, 2H), 2.93-2.61 (m, 2H), 2.24 (s, 6H), 1.52 (s, 9H) |
| F-105 | 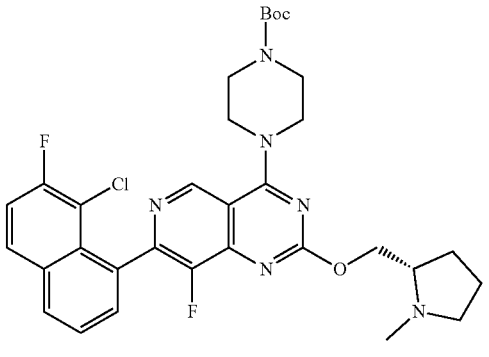 [SMILES: CN1CCC[C@H]1COc1nc(N2CCN(C(=O)OC(C)(C)C)CC2)c2cnc(-c3cccc4ccc(F)c(Cl)c34)c(F)c2n1]<br>tert-butyl (S)-4-(7-(8-chloro-7-fluoronaphthalen-1-yl)-8-fluoro-2-((1-methylpyrrolidin-2-yl)methoxy)pyrido[4,3-d]pyrimidin-4-yl)piperazine-1-carboxylate | LCMS [ESI, M + 1]: 625 |

TABLE 2B-continued

Intermediates F-7 to F-167

| Int. # | Structure | Characterization Data |
|---|---|---|
| F-106 | 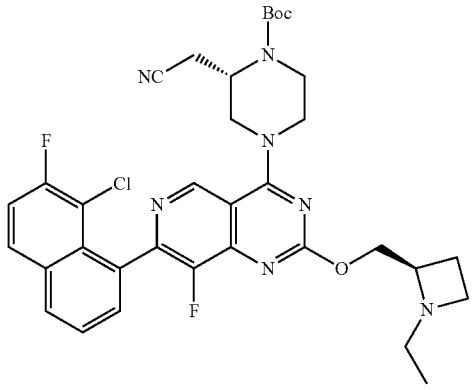 [SMILES: CCN1CC[C@@H]1COc1nc(N2CCN(C(=O)OC(C)(C)C)[C@@H](CC#N)C2)c2cnc(-c3cccc4ccc(F)c(Cl)c34)c(F)c2n1] tert-butyl (S)-4-(7-(8-chloro-7-fluoronaphthalen-1-yl)-2-(((R)-1-ethylazetidin-2-yl)methoxy)-8-fluoropyrido[4,3-d]pyrimidin-4-yl)-2-(cyanomethyl)piperazine-1-carboxylate | LCMS [ESI, M + 1]: 664 |
| F-107 | 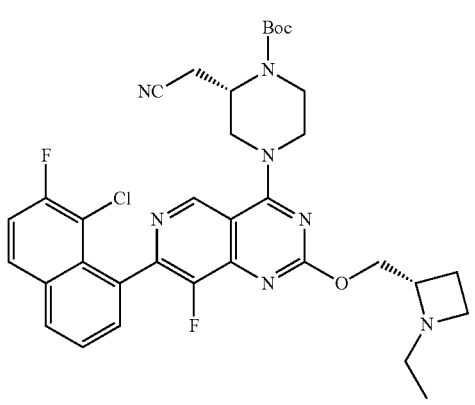 [SMILES: CCN1CC[C@H]1COc1nc(N2CCN(C(=O)OC(C)(C)C)[C@@H](CC#N)C2)c2cnc(-c3cccc4ccc(F)c(Cl)c34)c(F)c2n1] tert-butyl (S)-4-(7-(8-chloro-7-fluoronaphthalen-1-yl)-2-(((S)-1-ethylazetidin-2-yl)methoxy)-8-fluoropyrido[4,3-d]pyrimidin-4-yl)-2-(cyanomethyl)piperazine-1-carboxylate | LCMS [ESI, M + 1]: 664 |
| F-108 | 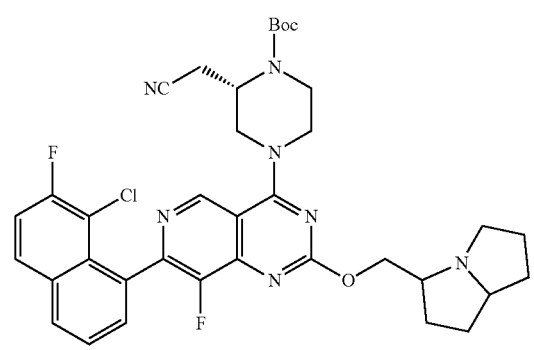 [SMILES: CC(C)(C)OC(=O)N1CCN(c2nc(OCC3CCC4CCCN43)nc3c(F)c(-c4cccc5ccc(F)c(Cl)c45)ncc23)C[C@@H]1CC#N] tert-butyl (2S)-4-(7-(8-chloro-7-fluoronaphthalen-1-yl)-8-fluoro-2-((hexahydro-1H-pyrrolizin-3-yl)methoxy)pyrido[4,3-d]pyrimidin-4-yl)-2-(cyanomethyl)piperazine-1-carboxylate | LCMS [ESI, M + 1]: 690 |

TABLE 2B-continued

Intermediates F-7 to F-167

| Int. # | Structure | Characterization Data |
|---|---|---|
| F-109 | 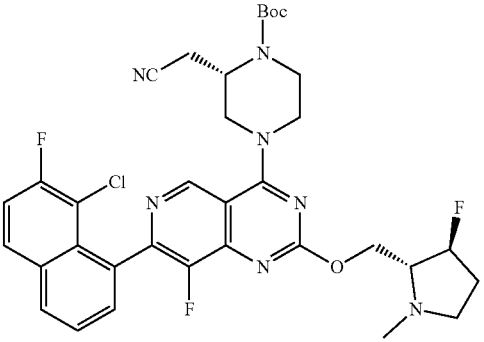 [SMILES: CN1CC[C@H](F)[C@H]1COc1nc(N2CCN(C(=O)OC(C)(C)C)[C@@H](CC#N)C2)c2cnc(-c3cccc4ccc(F)c(Cl)c34)c(F)c2n1]<br>tert-butyl (S)-4-(7-(8-chloro-7-fluoronaphthalen-1-yl)-8-fluoro-2-(((2R,3S)-3-fluoro-1-methylpyrrolidin-2-yl)methoxy)pyrido[4,3-d]pyrimidin-4-yl)-2-(cyanomethyl)piperazine-1-carboxylate | $^1$H NMR (400 MHz, CDCl$_3$) δ 9.08 (d, J = 0.8 Hz, 1H), 8.05-7.97 (m, 1H), 7.90 (dd, J = 5.6, 9.2 Hz, 1H), 7.65-7.56 (m, 2H), 7.41 (td, J = 2.4, 8.8 Hz, 1H), 5.30-5.05 (m, 1H), 4.76-4.57 (m, 2H), 4.54-4.33 (m, 3H), 4.21-4.13 (m, 1H), 3.97-3.82 (m, 1H), 3.78-3.64 (m, 1H), 3.63-3.36 (m, 1H), 3.14-2.91 (m, 2H), 2.90-2.70 (m, 2H), 2.69-2.58 (m, 1H), 2.56 (d, J = 1.2 Hz, 3H), 2.18-2.06 (m, 1H), 2.05-2.00 (m, 1H), 1.53 (s, 9H) |
| F-110 | 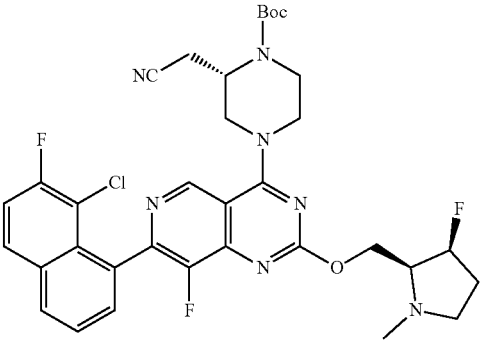 [SMILES: CN1CC[C@H](F)[C@@H]1COc1nc(N2CCN(C(=O)OC(C)(C)C)[C@@H](CC#N)C2)c2cnc(-c3cccc4ccc(F)c(Cl)c34)c(F)c2n1]<br>tert-butyl (S)-4-(7-(8-chloro-7-fluoronaphthalen-1-yl)-8-fluoro-2-(((2S,3S)-3-fluoro-1-methylpyrrolidin-2-yl)methoxy)pyrido[4,3-d]pyrimidin-4-yl)-2-(cyanomethyl)piperazine-1-carboxylate | LCMS [ESI, M + 1]: 682 |
| F-111 | 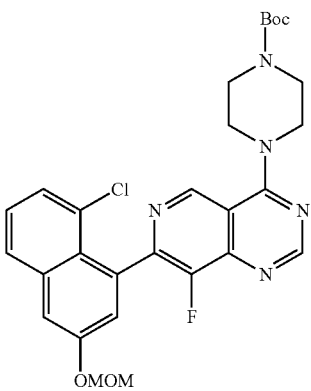<br>tert-butyl 4-(7-(8-chloro-3-(methoxymethoxy)naphthalen-1-yl)-8-fluoropyrido[4,3-d]pyrimidin-4-yl)piperazine-1-carboxylate | LCMS [ESI, M + 1]: 554 |

TABLE 2B-continued

Intermediates F-7 to F-167

| Int. # | Structure | Characterization Data |
| --- | --- | --- |
| F-112 | tert-butyl (2S)-4-(7-(8-chloro-7-fluoronaphthalen-1-yl)-2-((4,4-difluoro-1-methylpyrrolidin-3-yl)methoxy)-8-fluoropyrido[4,3-d]pyrimidin-4-yl)-2-(cyanomethyl)piperazine-1-carboxylate | LCMS [ESI, M + 1]: 700 |
| F-113 | tert-butyl (2S)-4-(7-(8-chloro-7-fluoronaphthalen-1-yl)-8-fluoro-2-(((2R)-2-fluorotetrahydro-1H-pyrrolizin-7a(5H)-yl)methoxy)pyrido[4,3-d]pyrimidin-4-yl)-2-(cyanomethyl)piperazine-1-carboxylate | LCMS [ESI, M + 1]: 708 |
| F-114 | tert-butyl (S)-4-(7-(8-chloro-7-fluoronaphthalen-1-yl)-8-fluoro-2-(((S)-1-(2-fluoroethyl)pyrrolidin-2-yl)methoxy)pyrido[4,3-d]pyrimidin-4-yl)-2-(cyanomethyl)piperazine-1-carboxylate | LCMS [ESI, M + 1]: 697 |

TABLE 2B-continued

Intermediates F-7 to F-167

| Int. # | Structure | Characterization Data |
|---|---|---|
| F-115 | 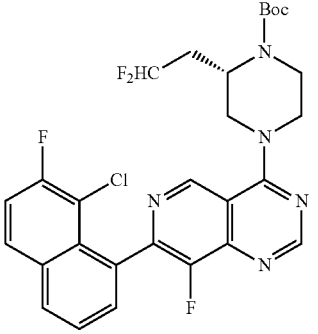 [SMILES: CC(C)(C)OC(=O)N1CCN(c2ncnc3c(F)c(-c4cccc5ccc(F)c(Cl)c45)ncc23)C[C@@H]1CC(F)F]<br>tert-butyl (S)-4-(7-(8-chloro-7-fluoronaphthalen-1-yl)-8-fluoropyrido[4,3-d]pyrimidin-4-yl)-2-(2,2-difluoroethyl)piperazine-1-carboxylate | LCMS [ESI, M + 1]: 576 |
| F-116 | 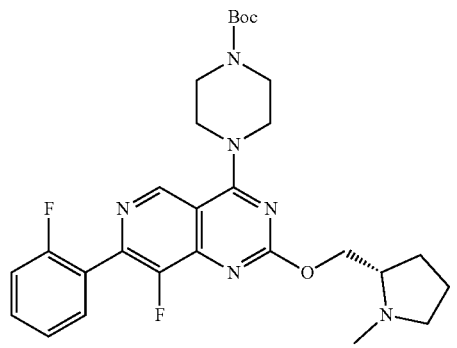 [SMILES: CN1CCC[C@H]1COc1nc(N2CCN(C(=O)OC(C)(C)C)CC2)c2cnc(-c3ccccc3F)c(F)c2n1]<br>tert-butyl (S)-4-(8-fluoro-7-(2-fluorophenyl)-2-((1-methylpyrrolidin-2-yl)methoxy)pyrido[4,3-d]pyrimidin-4-yl)piperazine-1-carboxylate | LCMS [ESI, M + 1]: 541 |
| F-117 | 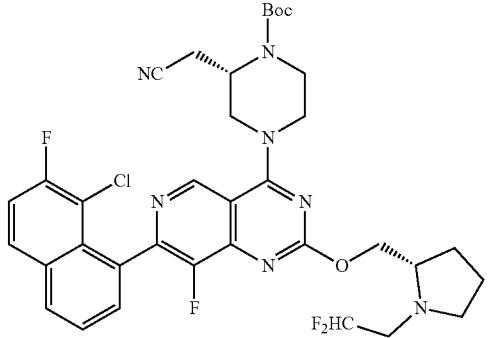 [SMILES: CC(C)(C)OC(=O)N1CCN(c2nc(OC[C@@H]3CCCN3CC(F)F)nc3c(F)c(-c4cccc5ccc(F)c(Cl)c45)ncc23)C[C@@H]1CC#N]<br>tert-butyl (S)-4-(7-(8-chloro-7-fluoronaphthalen-1-yl)-2-(((S)-1-(2,2-difluoroethyl)pyrrolidin-2-yl)methoxy)-8-fluoropyrido[4,3-d]pyrimidin-4-yl)-2-(cyanomethyl)piperazine-1-carboxylate | LCMS [ESI, M + 1]: 714 |

TABLE 2B-continued

Intermediates F-7 to F-167

| Int. # | Structure | Characterization Data |
|---|---|---|
| F-118 | 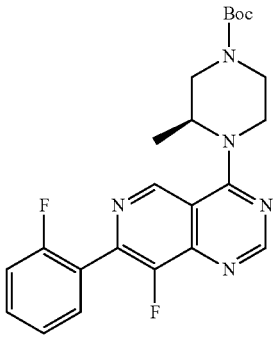 [SMILES: C[C@H]1CN(C(=O)OC(C)(C)C)CCN1c1ncnc2c(F)c(-c3ccccc3F)ncc12]<br>tert-butyl (S)-4-(8-fluoro-7-(2-fluorophenyl)pyrido[4,3-d]pyrimidin-4-yl)-3-methylpiperazine-1-carboxylate | LCMS [ESI, M + 1]: 442 |
| F-119 | 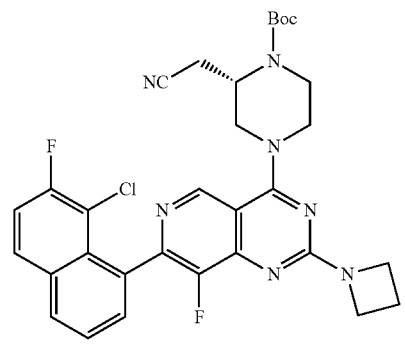 [SMILES: CC(C)(C)OC(=O)N1CCN(c2nc(N3CCC3)nc3c(F)c(-c4cccc5ccc(F)c(Cl)c45)ncc23)C[C@@H]1CC#N]<br>tert-butyl (S)-4-(2-(azetidin-1-yl)-7-(8-chloro-7-fluoronaphthalen-1-yl)-8-fluoropyrido[4,3-d]pyrimidin-4-yl)-2-(cyanomethyl)piperazine-1-carboxylate | LCMS [ESI, M + 1]: 606 |
| F-120 | 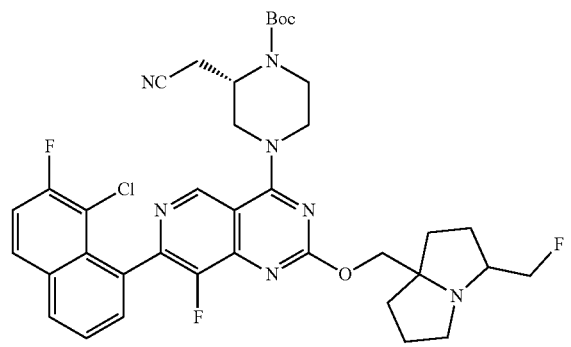 [SMILES: CC(C)(C)OC(=O)N1CCN(c2nc(OCC34CCCN3C(CF)CC4)nc3c(F)c(-c4cccc5ccc(F)c(Cl)c45)ncc23)C[C@@H]1CC#N]<br>tert-butyl (2S)-4-(7-(8-chloro-7-fluoronaphthalen-1-yl)-8-fluoro-2-((3-(fluoromethyl)tetrahydro-1H-pyrrolizin-7a(5H)-yl)methoxy)pyrido[4,3-d]pyrimidin-4-yl)-2-(cyanomethyl)piperazine-1-carboxylate | LCMS [ESI, M + 1]: 722 |

TABLE 2B-continued

Intermediates F-7 to F-167

| Int. # | Structure | Characterization Data |
|---|---|---|
| F-121 | 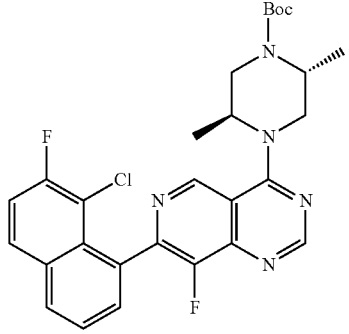 [SMILES: C[C@@H]1CN(c2ncnc3c(F)c(-c4cccc5ccc(F)c(Cl)c45)ncc23)[C@@H](C)CN1C(=O)OC(C)(C)C]<br>tert-butyl (2R,5S)-4-(7-(8-chloro-7-fluoronaphthalen-1-yl)-8-fluoropyrido[4,3-d]pyrimidin-4-yl)-2,5-dimethylpiperazine-1-carboxylate | LCMS [ESI, M + 1]: 540 |
| F-122 | 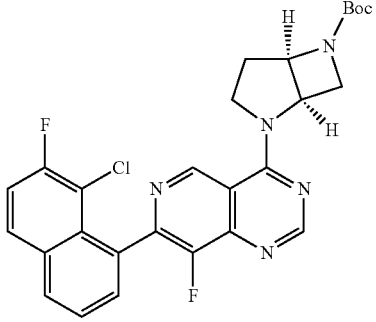 [SMILES: CC(C)(C)OC(=O)N1C[C@@H]2[C@H]1CCN2c1ncnc2c(F)c(-c3cccc4ccc(F)c(Cl)c34)ncc12]<br>tert-butyl (1R,5R)-2-(7-(8-chloro-7-fluoronaphthalen-1-yl)-8-fluoropyrido[4,3-d]pyrimidin-4-yl)-2,6-diazabicyclo[3.2.0]heptane-6-carboxylate | LCMS [ESI, M + 1]: 524 |
| F-123 | 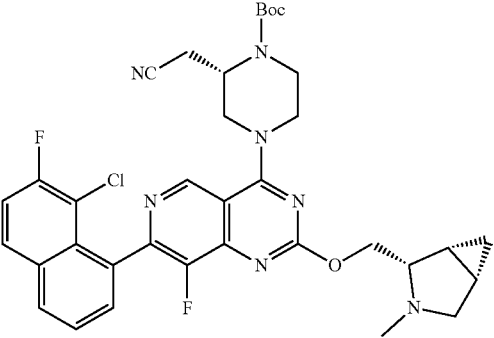 [SMILES: CN1C[C@H]2C[C@H]2[C@H]1COc1nc(N2CCN(C(=O)OC(C)(C)C)[C@@H](CC#N)C2)c2cnc(-c3cccc4ccc(F)c(Cl)c34)c(F)c2n1]<br>tert-butyl (S)-4-(7-(8-chloro-7-fluoronaphthalen-1-yl)-8-fluoro-2-(((1R,2S,5S)-3-methyl-3-azabicyclo[3.1.0]hexan-2-yl)methoxy)pyrido[4,3-d]pyrimidin-4-yl)-2-(cyanomethyl)piperazine-1-carboxylate | LCMS [ESI, M + 1]: 676 |

TABLE 2B-continued

Intermediates F-7 to F-167

| Int. # | Structure | Characterization Data |
|---|---|---|
| F-124 | 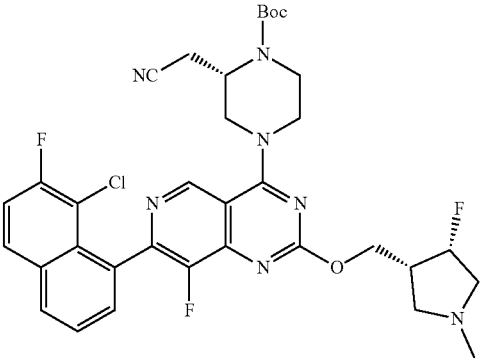 [SMILES: CN1C[C@H](COc2nc(N3CCN(C(=O)OC(C)(C)C)[C@@H](CC#N)C3)c3cnc(-c4cccc5ccc(F)c(Cl)c45)c(F)c3n2)[C@H](F)C1]<br>tert-butyl (S)-4-(7-(8-chloro-7-fluoronaphthalen-1-yl)-8-fluoro-2-(((3R,4S)-4-fluoro-1-methylpyrrolidin-3-yl)methoxy)pyrido[4,3-d]pyrimidin-4-yl)-2-(cyanomethyl)piperazine-1-carboxylate | LCMS [ESI, M + 1]: 682 |
| F-125 | 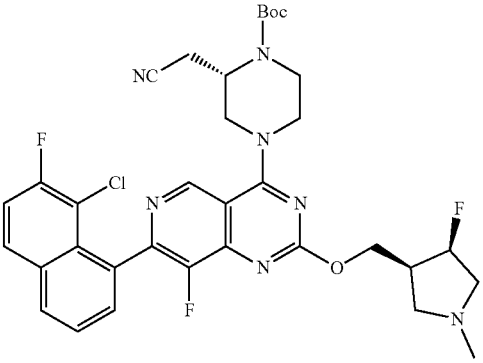 [SMILES: CN1C[C@@H](COc2nc(N3CCN(C(=O)OC(C)(C)C)[C@@H](CC#N)C3)c3cnc(-c4cccc5ccc(F)c(Cl)c45)c(F)c3n2)[C@@H](F)C1]<br>tert-butyl (S)-4-(7-(8-chloro-7-fluoronaphthalen-1-yl)-8-fluoro-2-(((3S,4R)-4-fluoro-1-methylpyrrolidin-3-yl)methoxy)pyrido[4,3-d]pyrimidin-4-yl)-2-(cyanomethyl)piperazine-1-carboxylate | LCMS [ESI, M + 1]: 682 |
| F-126 | 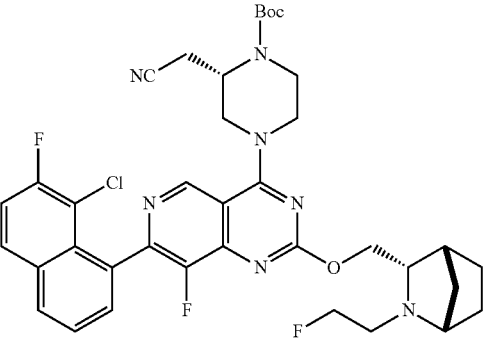 [SMILES: CC(C)(C)OC(=O)N1CCN(c2nc(OC[C@@H]3[C@@H]4CC[C@@H](C4)N3CCF)nc3c(F)c(-c4cccc5ccc(F)c(Cl)c45)ncc23)C[C@@H]1CC#N]<br>tert-butyl (S)-4-(7-(8-chloro-7-fluoronaphthalen-1-yl)-8-fluoro-2-(((1S,3S,4R)-2-(2-fluoroethyl)-2-azabicyclo[2.2.1]heptan-3-yl)methoxy)pyrido[4,3-d]pyrimidin-4-yl)-2-(cyanomethyl)piperazine-1-carboxylate | LCMS [ESI, M + 1]: 722 |

TABLE 2B-continued

Intermediates F-7 to F-167

| Int. # | Structure | Characterization Data |
|---|---|---|
| F-127 | 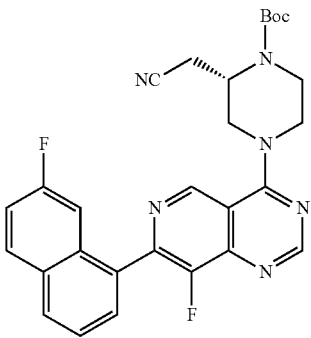 [SMILES: CC(C)(C)OC(=O)N1CCN(c2ncnc3c(F)c(-c4cccc5ccc(F)cc45)ncc23)C[C@@H]1CC#N]<br>tert-butyl (S)-2-(cyanomethyl)-4-(8-fluoro-7-(7-fluoronaphthalen-1-yl)pyrido[4,3-d]pyrimidin-4-yl)piperazine-1-carboxylate | LCMS [ESI, M + 1]: 517 |
| F-128 | 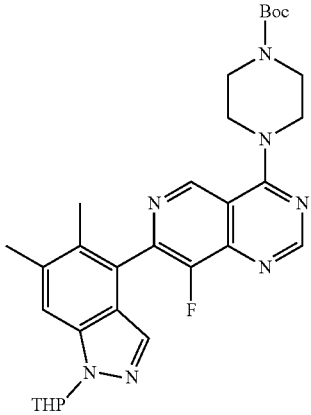<br>tert-butyl 4-(7-(5,6-dimethyl-1-(tetrahydro-2H-pyran-2-yl)-1H-indazol-4-yl)-8-fluoropyrido[4,3-d]pyrimidin-4-yl)piperazine-1-carboxylate | LCMS [ESI, M + 1]: 562 |
| F-129 | 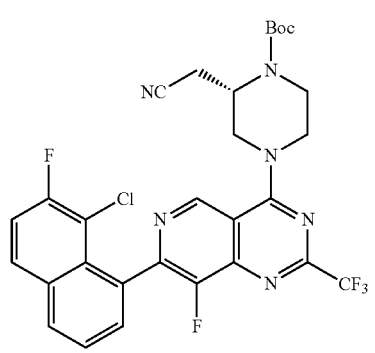 [SMILES: CC(C)(C)OC(=O)N1CCN(c2nc(C(F)(F)F)nc3c(F)c(-c4cccc5ccc(F)c(Cl)c45)ncc23)C[C@@H]1CC#N]<br>tert-butyl (S)-4-(7-(8-chloro-7-fluoronaphthalen-1-yl)-8-fluoro-2-(trifluoromethyl)pyrido[4,3-d]pyrimidin-4-yl)-2-(cyanomethyl)piperazine-1-carboxylate | LCMS [ESI, M + 1]: 619 |

TABLE 2B-continued

Intermediates F-7 to F-167

| Int. # | Structure | Characterization Data |
|---|---|---|
| F-130 | 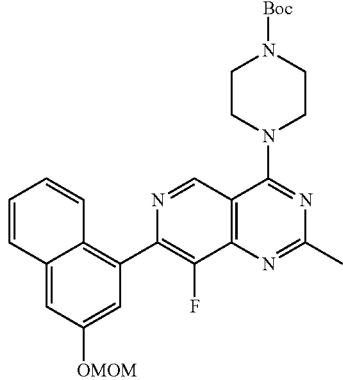tert-butyl 4-(8-fluoro-7-(3-(methoxymethoxy)naphthalen-1-yl)-2-methylpyrido[4,3-d]pyrimidin-4-yl)piperazine-1-carboxylate | LCMS [ESI, M + 1]: 534 |
| F-131 | 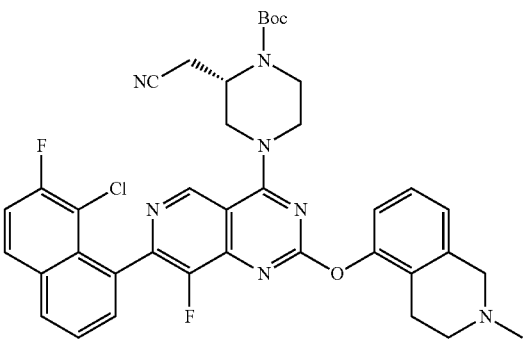 [SMILES: CN1CCc2c(cccc2Oc2nc(N3CCN(C(=O)OC(C)(C)C)[C@@H](CC#N)C3)c3cnc(-c4cccc5ccc(F)c(Cl)c45)c(F)c3n2)C1]tert-butyl (S)-4-(7-(8-chloro-7-fluoronaphthalen-1-yl)-8-fluoro-2-((2-methyl-1,2,3,4-tetrahydroisoquinolin-5-yl)oxy)pyrido[4,3-d]pyrimidin-4-yl)-2-(cyanomethyl)piperazine-1-carboxylate | LCMS [ESI, M + 1]: 712 |
| F-132 | 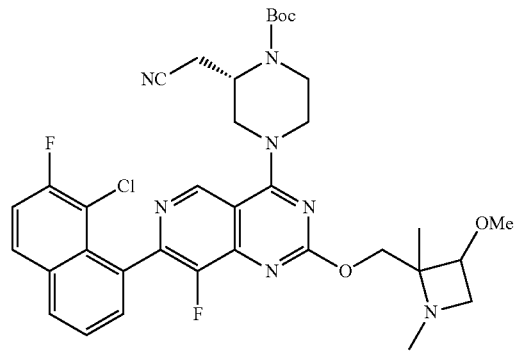 [SMILES: COC1CN(C)C1(C)COc1nc(N2CCN(C(=O)OC(C)(C)C)[C@@H](CC#N)C2)c2cnc(-c3cccc4ccc(F)c(Cl)c34)c(F)c2n1]tert-butyl (2S)-4-(7-(8-chloro-7-fluoronaphthalen-1-yl)-8-fluoro-2-((3-methoxy-1,2-dimethylazetidin-2-yl)methoxy)pyrido[4,3-d]pyrimidin-4-yl)-2-(cyanomethyl)piperazine-1-carboxylate | LCMS [ESI, M + 1]: 694 |

US 11,548,888 B2

TABLE 2B-continued

Intermediates F-7 to F-167

| Int. # | Structure | Characterization Data |
| --- | --- | --- |
| F-133 | 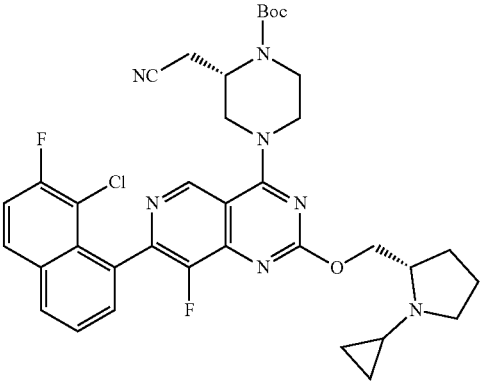 [SMILES: CC(C)(C)OC(=O)N1CCN(c2nc(OC[C@@H]3CCCN3C3CC3)nc3c(F)c(-c4cccc5ccc(F)c(Cl)c45)ncc23)C[C@@H]1CC#N]<br>tert-butyl (S)-4-(7-(8-chloro-7-fluoronaphthalen-1-yl)-2-(((S)-1-cyclopropylpyrrolidin-2-yl)methoxy)-8-fluoropyrido[4,3-d]pyrimidin-4-yl)-2-(cyanomethyl)piperazine-1-carboxylate | LCMS [ESI, M + 1]: 690 |
| F-134 | 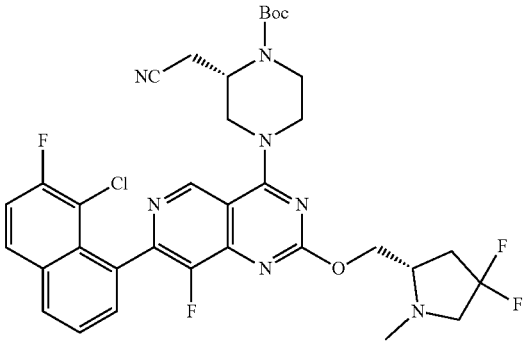 [SMILES: CN1CC(F)(F)C[C@H]1COc1nc(N2CCN(C(=O)OC(C)(C)C)[C@@H](CC#N)C2)c2cnc(-c3cccc4ccc(F)c(Cl)c34)c(F)c2n1]<br>tert-butyl (S)-4-(7-(8-chloro-7-fluoronaphthalen-1-yl)-2-(((S)-4,4-difluoro-1-methylpyrrolidin-2-yl)methoxy)-8-fluoropyrido[4,3-d]pyrimidin-4-yl)-2-(cyanomethyl)piperazine-1-carboxylate | $^1$H NMR (400 MHz, CD$_3$OD): δ 9.15 (s, 1H), 8.20-8.12 (m, 1H), 8.08 (dd, J = 5.6, 9.2 Hz, 1H), 7.72-7.62 (m, 2H), 7.53 (t, J = 8.8 Hz, 1H), 4.70 (br dd, J = 4.0, 6.8 Hz, 1H), 4.64-4.56 (m, 3H), 4.51 (br d, J = 12.4 Hz, 1H), 4.08-4.02 (m, 1H), 3.98-3.78 (m, 2H), 3.54 (br s, 1H), 3.39 (dt, J = 4.8, 12.0 Hz, 1H), 3.12-3.03 (m, 1H), 3.01-2.90 (m, 2H), 2.74 (ddd, J = 11.2, 15.6, 18.0 Hz, 1H), 2.62-2.54 (m, 1H), 2.50 (s, 3H), 2.27-2.22 (m, 1H), 1.52 (s, 9H) |
| F-135 | 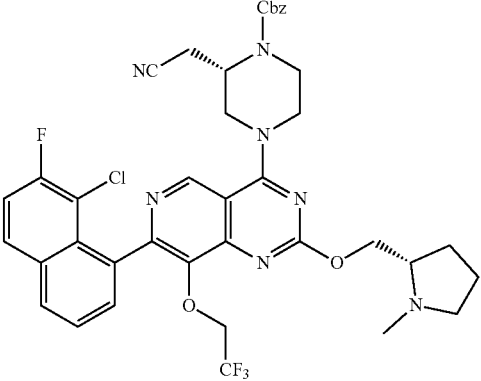<br>benzyl (S)-4-(7-(8-chloro-7-fluoronaphthalen-1-yl)-2-(((S)-1-methylpyrrolidin-2-yl)methoxy)-8-(2,2,2-trifluoroethoxy)pyrido[4,3-d]pyrimidin-4-yl)-2-(cyanomethyl)piperazine-1-carboxylate | LCMS [ESI, M + 1]: 740 |

TABLE 2B-continued

Intermediates F-7 to F-167

| Int. # | Structure | Characterization Data |
|---|---|---|
| F-136 | 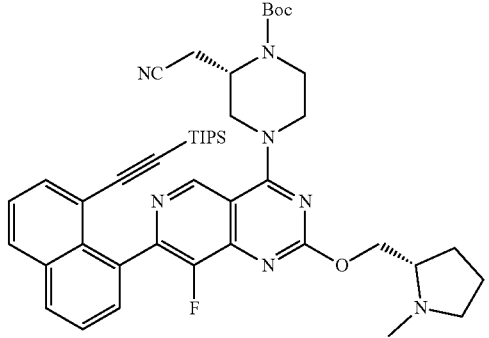<br>tert-butyl (S)-2-(cyanomethyl)-4-(8-fluoro-2-(((S)-1-methylpyrrolidin-2-yl)methoxy)-7-(8-((triisopropylsilyl)ethynyl)naphthalen-1-yl)pyrido[4,3-d]pyrimidin-4-yl)piperazine-1-carboxylate | LCMS [ESI, M + 1]: 792 |
| F-137 | 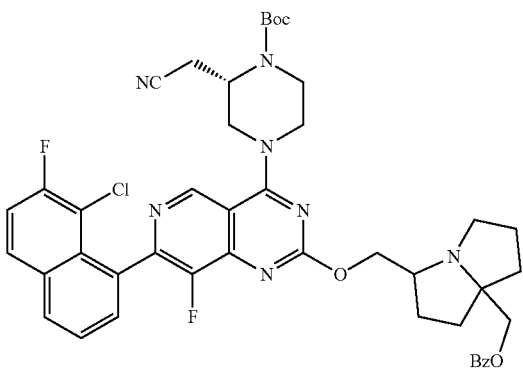<br>tert-butyl (2S)-4-(2-((7a-((benzoyloxy)methyl)hexahydro-1H-pyrrolizin-3-yl)methoxy)-7-(8-chloro-7-fluoronaphthalen-1-yl)-8-fluoropyrido[4,3-d]pyrimidin-4-yl)-2-(cyanomethyl)piperazine-1-carboxylate | LCMS [ESI, M + 1]: 824 |
| F-138 | 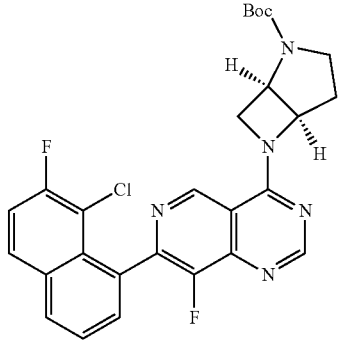<br>tert-butyl (1R,5R)-6-(7-(8-chloro-7-fluoronaphthalen-1-yl)-8-fluoropyrido[4,3-d]pyrimidin-4-yl)-2,6-diazabicyclo[3.2.0]heptane-2-carboxylate | LCMS [ESI, M + 1]: 524 |

TABLE 2B-continued

Intermediates F-7 to F-167

| Int. # | Structure | Characterization Data |
|---|---|---|
| F-139 | tert-butyl 4-(8-fluoro-7-(2-isopropylphenyl)pyrido[4,3-d]pyrimidin-4-yl)piperazine-1-carboxylate | LCMS [ESI, M + 1]: 452 |
| F-140 | tert-butyl 4-(8-fluoro-7-(naphthalen-1-yl)pyrido[4,3-d]pyrimidin-4-yl)piperazine-1-carboxylate | LCMS [ESI, M + 1]: 460 |
| F-141 | tert-butyl 4-(7-(2-cyclopropylphenyl)-8-fluoropyrido[4,3-d]pyrimidin-4-yl)piperazine-1-carboxylate | LCMS [ESI, M + 1]: 450 |

TABLE 2B-continued

Intermediates F-7 to F-167

| Int. # | Structure | Characterization Data |
|---|---|---|
| F-142 | 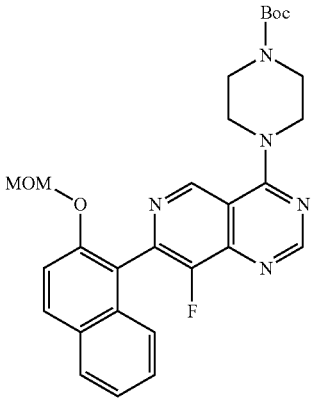<br>tert-butyl 4-(8-fluoro-7-(2-(methoxymethoxy)naphthalen-1-yl)pyrido[4,3-d]pyrimidin-4-yl)piperazine-1-carboxylate | LCMS [ESI, M + 1]: 520 |
| F-143 | 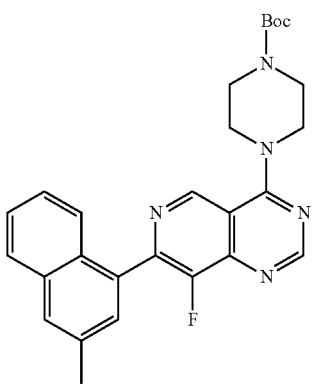 [SMILES: Cc1cc(-c2ncc3c(N4CCN(C(=O)OC(C)(C)C)CC4)ncnc3c2F)c2ccccc2c1]<br>tert-butyl 4-(8-fluoro-7-(3-methylnaphthalen-1-yl)pyrido[4,3-d]pyrimidin-4-yl)piperazine-1-carboxylate | LCMS [ESI, M + 1]: 474 |
| F-144 | 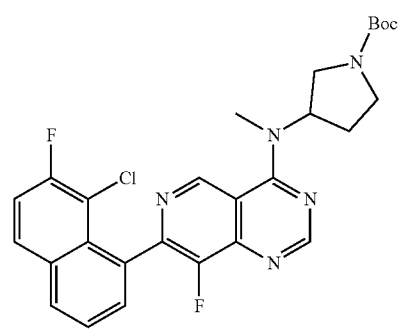 [SMILES: CN(c1ncnc2c(F)c(-c3cccc4ccc(F)c(Cl)c34)ncc12)C1CCN(C(=O)OC(C)(C)C)C1]<br>tert-butyl 3-((7-(8-chloro-7-fluoronaphthalen-1-yl)-8-fluoropyrido[4,3-d]pyrimidin-4-yl)(methyl)amino)pyrrolidine-1-carboxylate | LCMS [ESI, M + 1]: 526 |

TABLE 2B-continued

Intermediates F-7 to F-167

| Int. # | Structure | Characterization Data |
|---|---|---|
| F-145 | tert-butyl (1R,5R)-6-(7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)-2,6-diazabicyclo[3.2.0]heptane-2-carboxylate | LCMS [ESI, M + 1]: 663 |
| F-146 | tert-butyl (1R,5R)-2-(7-(8-chloro-7-fluoronaphthalen-1-yl)-8-fluoro-2-(((S)-1-methylpyrrolidin-2-yl)methoxy)pyrido[4,3-d]pyrimidin-4-yl)-2,6-diazabicyclo[3.2.0]heptane-6-carboxylate | LCMS [ESI, M + 1]: 637 |
| F-147 | tert-butyl (S)-4-(7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2-(cyanomethyl)piperazine-1-carboxylate | LCMS [ESI, M + 1]: 708<br>¹H NMR (400 MHz, CDCl₃): δ 9.08-9.04 (m, 1H), 8.04-7.97 (m, 1H), 7.94-7.86 (m, 1H), 7.65-7.56 (m, 2H), 7.44-7.36 (m, 1H), 5.40-5.17 (m, 1H), 4.74-4.61 (m, 1H), 4.58-4.49 (m, 1H), 4.47-4.36 (m, 1H), 4.36-4.28 (m, 1H), 4.27-4.20 (m, 1H), 4.12-4.06 (m, 1H), 3.90-3.78 (m, 1H), 3.75-3.66 (m, 1H), 3.61-3.34 (m, 1H), 3.33-3.22 (m, 2H), 3.21-3.15 (m, 1H), 3.03-2.94 (m, 1H), 2.91-2.70 (m, 2H), 2.29-2.23 (m, 1H), 2.23-2.09 (m, 2H), 2.00-1.85 (m, 3H), 1.53 (s, 9H) |

TABLE 2B-continued

Intermediates F-7 to F-167

| Int. # | Structure | Characterization Data |
|---|---|---|
| F-148 | 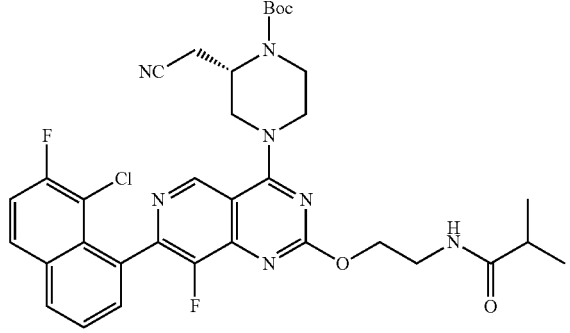 [SMILES: CC(C)C(=O)NCCOc1nc(N2CCN(C(=O)OC(C)(C)C)[C@@H](CC#N)C2)c2cnc(-c3cccc4ccc(F)c(Cl)c34)c(F)c2n1] tert-butyl (S)-4-(7-(8-chloro-7-fluoronaphthalen-1-yl)-8-fluoro-2-(2-isobutyramidoethoxy)pyrido[4,3-d]pyrimidin-4-yl)-2-(cyanomethyl)piperazine-1-carboxylate | LCMS [ESI, M + 1]: 680 |
| F-149 | 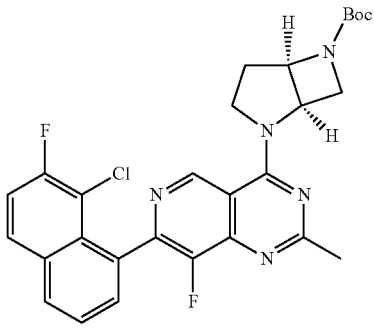 [SMILES: Cc1nc(N2CC[C@@H]3[C@H]2CN3C(=O)OC(C)(C)C)c2cnc(-c3cccc4ccc(F)c(Cl)c34)c(F)c2n1] tert-butyl (1R,5R)-2-(7-(8-chloro-7-fluoronaphthalen-1-yl)-8-fluoro-2-methylpyrido[4,3-d]pyrimidin-4-yl)-2,6-diazabicyclo[3.2.0]heptane-6-carboxylate | LCMS [ESI, M + 1]: 538 |
| F-150 | 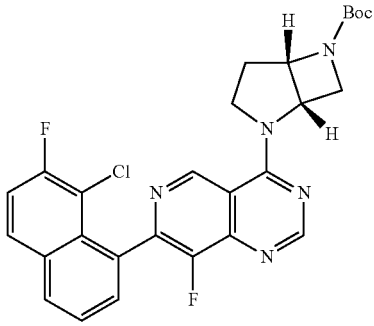 [SMILES: CC(C)(C)OC(=O)N1C[C@H]2[C@@H]1CCN2c1ncnc2c(F)c(-c3cccc4ccc(F)c(Cl)c34)ncc12] tert-butyl (1S,5S)-2-(7-(8-chloro-7-fluoronaphthalen-1-yl)-8-fluoropyrido[4,3-d]pyrimidin-4-yl)-2,6-diazabicyclo[3.2.0]heptane-6-carboxylate | LCMS [ESI, M + 1]: 524 |

TABLE 2B-continued

Intermediates F-7 to F-167

| Int. # | Structure | Characterization Data |
|---|---|---|
| F-151 | 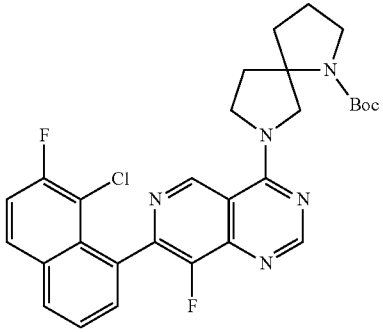 [SMILES: CC(C)(C)OC(=O)N1CCCC12CCN(c1ncnc3c(F)c(-c4cccc5ccc(F)c(Cl)c45)ncc13)C2]<br>tert-butyl 7-(7-(8-chloro-7-fluoronaphthalen-1-yl)-8-fluoropyrido[4,3-d]pyrimidin-4-yl)-1,7-diazaspiro[4.4]nonane-1-carboxylate | LCMS [ESI, M + 1]: 552 |
| F-152 | 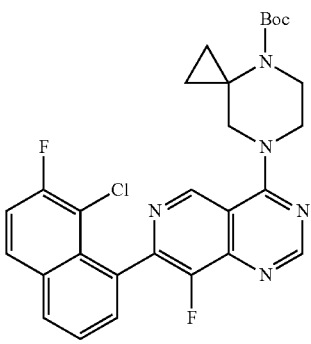 [SMILES: CC(C)(C)OC(=O)N1CCN(c2ncnc3c(F)c(-c4cccc5ccc(F)c(Cl)c45)ncc23)CC12CC2]<br>tert-butyl 7-(7-(8-chloro-7-fluoronaphthalen-1-yl)-8-fluoropyrido[4,3-d]pyrimidin-4-yl)-4,7-diazaspiro[2.5]octane-4-carboxylate | LCMS [ESI, M + 1]: 552 |
| F-153 | 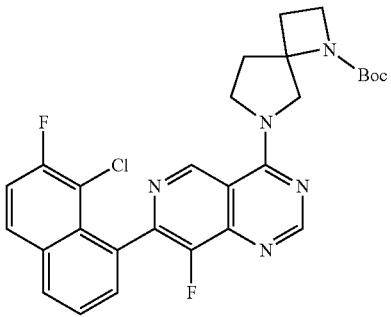 [SMILES: CC(C)(C)OC(=O)N1CCC12CCN(c1ncnc3c(F)c(-c4cccc5ccc(F)c(Cl)c45)ncc13)C2]<br>tert-butyl 6-(7-(8-chloro-7-fluoronaphthalen-1-yl)-8-fluoropyrido[4,3-d]pyrimidin-4-yl)-1,6-diazaspiro[3.4]octane-1-carboxylate | LCMS [ESI, M + 1]: 538<br><sup>1</sup>H NMR (400 MHz, CDCl<sub>3</sub>): δ 9.36 (s, 1H), 8.81 (s, 1H), 8.05-7.98 (m, 1H), 7.91-7.88 (dd, J = 5.2, 8.8 Hz, 1H), 7.68-7.56 (m, 2H), 7.41-7.43 (t, J = 8.8 Hz, 1H), 4.77-4.19 (m, 2H), 4.12-4.03 (m, 2H), 3.96-3.88 (m, 2H), 2.97-2.67 (m, 1H), 2.48-2.18 (m, 3H), 1.40 (br s, 9H) |

TABLE 2B-continued

Intermediates F-7 to F-167

| Int. # | Structure | Characterization Data |
|---|---|---|
| F-154 | 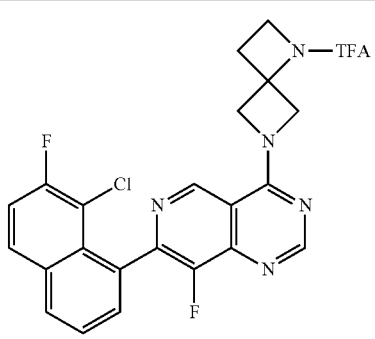<br>1-(6-(7-(8-chloro-7-fluoronaphthalen-1-yl)-8-fluoropyrido[4,3-d]pyrimidin-4-yl)-1,6-diazaspiro[3.3]heptan-1-yl)-2,2,2-trifluoroethan-1-one | LCMS [ESI, M + 1]: 520 |
| F-155 | 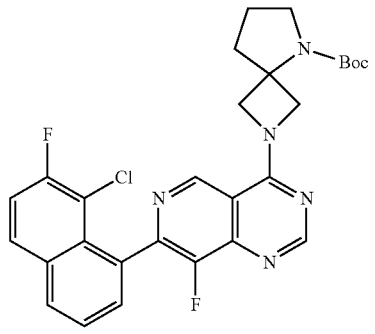 [SMILES: CC(C)(C)OC(=O)N1CCCC12CN(c1ncnc3c(F)c(-c4cccc5ccc(F)c(Cl)c45)ncc13)C2]<br>tert-butyl 2-(7-(8-chloro-7-fluoronaphthalen-1-yl)-8-fluoropyrido[4,3-d]pyrimidin-4-yl)-2,5-diazaspiro[3.4]octane-5-carboxylate | LCMS [ESI, M + 1]: 538 |
| F-156 | 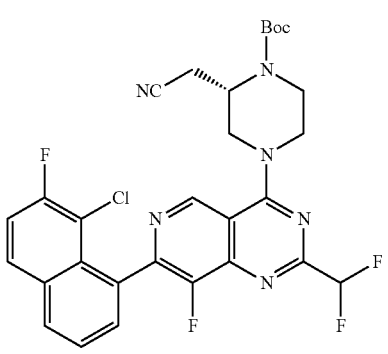 [SMILES: CC(C)(C)OC(=O)N1CCN(c2nc(C(F)F)nc3c(F)c(-c4cccc5ccc(F)c(Cl)c45)ncc23)C[C@@H]1CC#N]<br>tert-butyl (S)-4-(7-(8-chloro-7-fluoronaphthalen-1-yl)-2-(difluoromethy)-8-fluoropyrido[4,3-d]pyrimidin-4-yl)-2-(cyanomethyl)piperazine-1-carboxylate | LCMS [ESI, M + 1]: 601 |

TABLE 2B-continued

Intermediates F-7 to F-167

| Int. # | Structure | Characterization Data |
|---|---|---|
| F-157 | tert-butyl (1R,5R)-6-(7-(8-chloro-7-fluoronaphthalen-1-yl)-8-fluoro-2-methylpyrido[4,3-d]pyrimidin-4-yl)-2,6-diazabicyclo[3.2.0]heptane-2-carboxylate | LCMS [ESI, M + 1]: 538 |
| F-158 | tert-butyl (S)-4-(7-(8-chloro-7-fluoronaphthalen-1-yl)-8-fluoro-2-(((3R,3aR,6R,6aR)-6-hydroxyhexahydrofuro[3,2-b]furan-3-yl)oxy)pyrido[4,3-d]pyrimidin-4-yl)-2-(cyanomethyl)piperazine-1-carboxylate | LCMS [ESI, M + 1]: 695<br>$^1$H NMR (400 MHz, CDCl$_3$): δ 9.09 (s, 1H), 8.05-7.97 (m, 1H), 7.90 (dd, J = 5.6, 8.8 Hz, 1H), 7.66-7.57 (m, 2H), 7.41 (dt, J = 2.0, 8.8 Hz, 1H), 5.69-5.56 (m, 1H), 5.03 (q, J = 5.2 Hz, 1H), 4.72-4.56 (m, 2H), 4.52-4.26 (m, 4H), 4.10-3.87 (m, 3H), 3.79-3.65 (m, 2H), 3.63-3.35 (m, 1H), 2.97-2.59 (m, 3H), 1.53 (s, 9H) |
| F-159 | tert-butyl (S)-4-(7-(3-chloro-2-cyclopropylphenyl)-8-fluoropyrido[4,3-d]pyrimidin-4-yl)-2-(cyanomethyl)piperazine-1-carboxylate | LCMS [ESI, M + 1]: 523 |

TABLE 2B-continued

Intermediates F-7 to F-167

| Int. # | Structure | Characterization Data |
|---|---|---|
| F-160 | tert-butyl (2S)-4-(7-(5-chloro-6-methyl-1-(tetrahydro-2H-pyran-2-yl)-1H-indazol-4-yl)-8-fluoropyrido[4,3-d]pyrimidin-4-yl)-2-(cyanomethyl)piperazine-1-carboxylate | LCMS [ESI, M + 1]: 621 |
| F-161 | tert-butyl (2S)-4-(7-(2-amino-6-fluorophenyl)-8-fluoropyrido[4,3-d]pyrimidin-4-yl)-2-(cyanomethyl)piperazine-1-carboxylate | LCMS [ESI, M + 1]: 482<br>$^1$H NMR (400 MHz, CDCl$_3$): δ 9.22 (s, 1H), 8.88 (s, 1H), 7.22 (dt, J = 6.4, 8.4 Hz, 1H), 6.66-6.56 (m, 2H), 4.66 (br s, 1H), 4.62-4.47 (m, 3H), 4.46-4.34 (m, 1H), 3.99-3.82 (m, 1H), 3.74 (dt, J = 4.0, 11.6 Hz, 1H), 3.59-3.31 (m, 1H), 2.92-2.76 (m, 1H), 2.75-2.63 (m, 1H), 1.52 (s, 9H) |
| F-162 | tert-butyl (2S)-4-(2-(((2S)-1-azabicyclo[2.2.1]heptan-2-yl)methoxy)-7-(8-chloro-7-fluoronaphthalen-1-yl)-8-fluoropyrido[4,3-d]pyrimidin-4-yl)-2-(cyanomethyl)piperazine-1-carboxylate | LCMS [ESI, M + 1]: 676 |

TABLE 2B-continued

Intermediates F-7 to F-167

| Int. # | Structure | Characterization Data |
|---|---|---|
| F-163 | 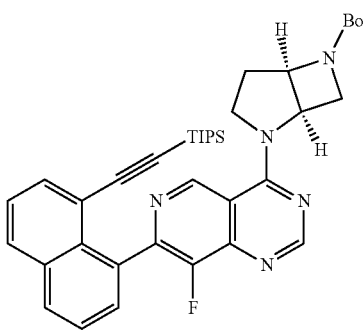<br><br>tert-butyl (1R,5R)-2-(8-fluoro-7-(8-((triisopropylsilyl)ethynyl)naphthalen-1-yl)pyrido[4,3-d]pyrimidin-4-yl)-2,6-diazabicyclo[3.2.0]heptane-6-carboxylate | LCMS [ESI, M + 1]: 652<br>$^1$H NMR (400 MHz, CDCl$_3$): δ 9.37-9.15 (m, 1H), 8.83-8.73 (m, 1H), 8.06-7.90 (m, 2H), 7.87-7.77 (m, 1H), 7.64-7.53 (m, 2H), 7.53-7.44 (m, 1H), 5.25-5.07 (m, 1H), 5.02 (br s, 1H), 4.92-4.52(m,1H), 4.43-4.14 (m, 2H), 3.80-3.54 (m, 1H), 2.73-2.51 (m, 1H), 2.19-2.05 (m, 1H), 1.51-1.44 (m, 9H), 0.89-0.82 (m, 18H), 0.61-0.48 (m, 3H) |
| F-164 | 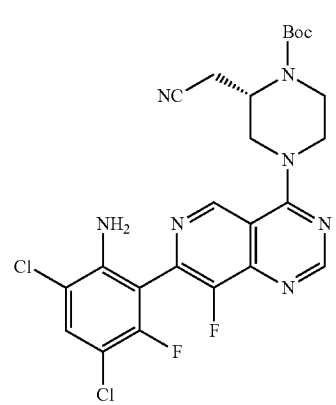 [SMILES: CC(C)(C)OC(=O)N1CCN(c2ncnc3c(F)c(-c4c(N)c(Cl)cc(Cl)c4F)ncc23)C[C@@H]1CC#N]<br><br>tert-butyl (2S)-4-(7-(2-amino-3,5-dichloro-6-fluorophenyl)-8-fluoropyrido[4,3-d]pyrimidin-4-yl)-2-(cyanomethyl)piperazine-1-carboxylate | Prepd from F-161 (NCS, ACN, 80° C., 3 h, 49% Yield)<br>LCMS [ESI, M + 1]: 550<br>$^1$H NMR (400 MHz, CDCl$_3$): δ 9.24 (s, 1H), 8.90 (s, 1H), 7.45 (d, J = 7.2 Hz, 1H), 4.95 (s, 2H), 4.75-4.53 (m, 2H), 4.50-4.38 (m, 1H), 4.20-4.14 (m, 1H), 3.96 (br dd, J = 3.6, 13.6 Hz, 1H), 3.84-3.70 (m, 1H), 3.62-3.30 (m, 1H), 2.92-2.60 (m, 2H), 1.52 (s, 9H) |
| F-165 | 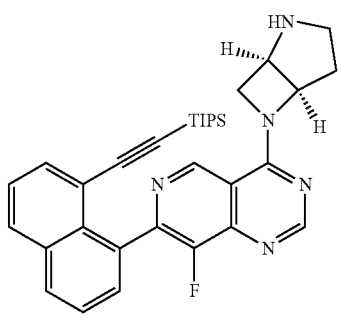<br><br>4-((1R,5R)-2,6-diazabicyclo[3.2.0]heptan-6-yl)-8-fluoro-7-(8-((triisopropylsilyl)ethynyl)naphthalen-1-yl)pyrido[4,3-d]pyrimidine | Prepared from Intermediate B-29 (TFA hydrolysis during Suzuki coupling)<br>LCMS [ESI, M + 1]: 552 |

TABLE 2B-continued

Intermediates F-7 to F-167

| Int. # | Structure | Characterization Data |
| --- | --- | --- |
| F-166 | 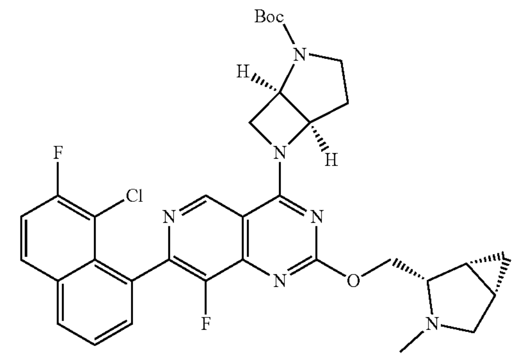 [SMILES: CN1C[C@H]2C[C@H]2[C@H]1COc1nc(N2C[C@@H]3[C@H]2CCN3C(=O)OC(C)(C)C)c2cnc(-c3cccc4ccc(F)c(Cl)c34)c(F)c2n1] | LCMS [ESI, M + 1]: 649 |
| F-167 | 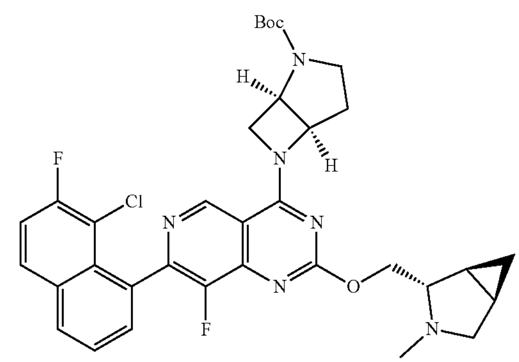 [SMILES: CN1C[C@@H]2C[C@@H]2[C@H]1COc1nc(N2C[C@@H]3[C@H]2CCN3C(=O)OC(C)(C)C)c2cnc(-c3cccc4ccc(F)c(Cl)c34)c(F)c2n1] | LCMS [ESI, M + 1]: 649<br>$^1$H NMR (400 MHz, CDCl$_3$): δ 8.92 (d, J = 2.4 Hz, 1H), 8.04-7.95 (m, 1H), 7.89 (dd, J = 5.6, 9.2 Hz, 1H), 7.64-7.55 (m, 2H), 7.40 (t, J = 8.8 Hz, 1H), 5.59-5.47 (m, 1H), 4.93-4.62 (m, 3H), 4.45-4.28 (m, 2H), 4.09-3.95 (m, 1H), 3.76-3.57 (m, 1H), 3.38-3.23 (m, 1H), 3.17-3.02 (m, 1H), 2.81-2.68 (m, 1H), 2.64-2.47 (m, 4H), 2.23-2.08 (m, 1H), 1.58-1.45 (m, 11H), 0.69-0.46 (m, 2H) |
| F-168 | tert-butyl (1R,5R)-6-(7-(8-chloro-7-fluoronaphthalen-1-yl)-2-(((S)-4,4-difluoro-1-methylpyrrolidin-2-yl)methoxy)-8-fluoropyrido[4,3-d]pyrimidin-4-yl)-2,6-diazabicyclo[3.2.0]heptane-2-carboxylate | LCMS [ESI, M + 1]: 673 |

TABLE 2B-continued

Intermediates F-7 to F-167

| Int. # | Structure | Characterization Data |
|---|---|---|
| F-169 | 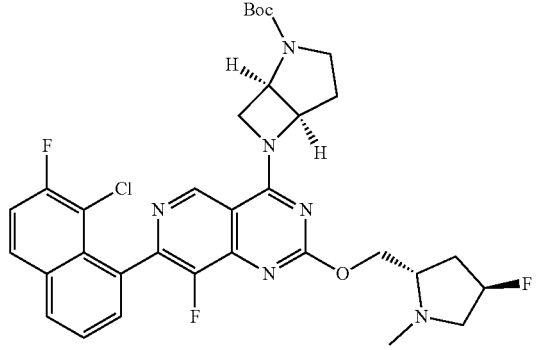 [SMILES: CN1C[C@H](F)C[C@H]1COc1nc(N2C[C@@H]3[C@H]2CCN3C(=O)OC(C)(C)C)c2cnc(-c3cccc4ccc(F)c(Cl)c34)c(F)c2n1]<br>tert-butyl (1R,5R)-6-(7-(8-chloro-7-fluoronaphthalen-1-yl)-8-fluoro-2-(((2S,4R)-4-fluoro-1-methylpyrrolidin-2-yl)methoxy)pyrido[4,3-d]pyrimidin-4-yl)-2,6-diazabicyclo[3.2.0]heptane-2-carboxylate | LCMS [ESI, M + 1]: 655 |
| F-170 | 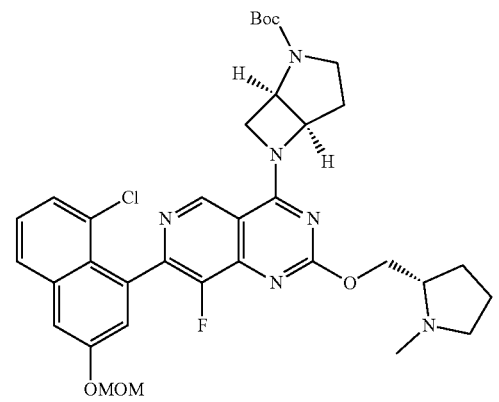<br>tert-butyl (1R,5R)-6-(7-(8-chloro-3-(methoxymethoxy)naphthalen-1-yl)-8-fluoro-2-(((S)-1-methylpyrrolidin-2-yl)methoxy)pyrido[4,3-d]pyrimidin-4-yl)-2,6-diazabicyclo[3.2.0]heptane-2-carboxylate | LCMS [ESI, M + 1]: 679 |
| F-171 | 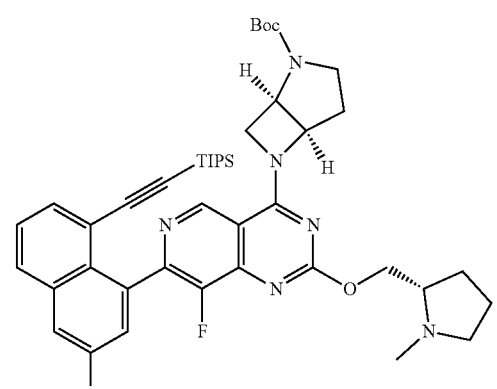<br>tert-butyl (1R,5R)-6-(8-fluoro-7-(3-(methoxymethoxy)-8-((triisopropylsilyl)ethynyl)naphthalen-1-yl)-2-(((S)-1-methylpyrrolidin-2-yl)methoxy)pyrido[4,3-d]pyrimidin-4-yl)-2,6-diazabicyclo[3.2.0]heptane-2-carboxylate | LCMS [ESI, M + 1]: 825 |

TABLE 2B-continued

Intermediates F-7 to F-167

| Int. # | Structure | Characterization Data |
|---|---|---|
| F-172 | 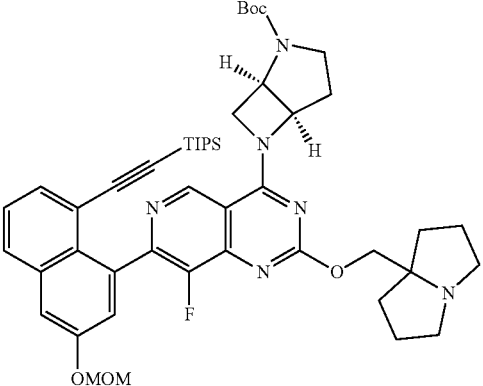<br>tert-butyl (1R,5R)-6-(8-fluoro-7-(3-(methoxymethoxy)-8-((triisopropylsilyl)ethynyl)naphthalen-1-yl)-2-((tetrahydro-1H-pyrrolizin-7a(5H)-yl)methoxy)pyrido[4,3-d]pyrimidin-4-yl)-2,6-diazabicyclo[3.2.0]heptane-2-carboxylate | LCMS [ESI, M + 1]: 851 |
| F-173 | 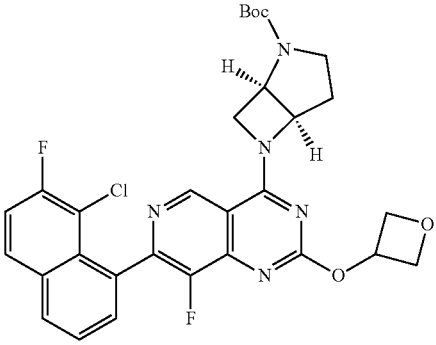 [SMILES: CC(C)(C)OC(=O)N1CC[C@@H]2[C@H]1CN2c1nc(OC2COC2)nc2c(F)c(-c3cccc4ccc(F)c(Cl)c34)ncc12]<br>tert-butyl (1R,5R)-6-(7-(8-chloro-7-fluoronaphthalen-1-yl)-8-fluoro-2-(oxetan-3-yloxy)pyrido[4,3-d]pyrimidin-4-yl)-2,6-diazabicyclo[3.2.0]heptane-2-carboxylate | LCMS [ESI, M + 1]: 596 |
| F-174 | 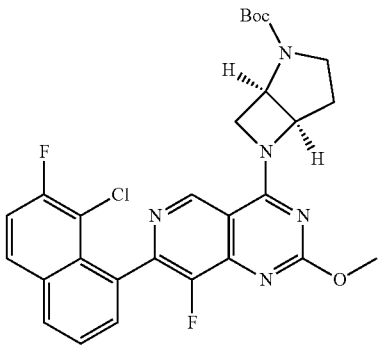<br>tert-butyl (1R,5R)-6-(7-(8-chloro-7-fluoronaphthalen-1-yl)-8-fluoro-2-methoxypyrido[4,3-d]pyrimidin-4-yl)-2,6-diazabicyclo[3.2.0]heptane-2-carboxylate | LCMS [ESI, M + 1]: 554 |

TABLE 2B-continued

Intermediates F-7 to F-167

| Int. # | Structure | Characterization Data |
| --- | --- | --- |
| F-175 | tert-butyl (1R,5R)-6-(7-(8-chloro-7-fluoronaphthalen-1-yl)-2-(dimethylamino)-8-fluoropyrido[4,3-d]pyrimidin-4-yl)-2,6-diazabicyclo[3.2.0]heptane-2-carboxylate | LCMS [ESI, M + 1]: 567 |
| F-176 | tert-butyl (1R,5R)-6-(7-(8-chloro-7-fluoronaphthalen-1-yl)-8-fluoro-2-isopropoxypyrido[4,3-d]pyrimidin-4-yl)-2,6-diazabicyclo[3.2.0]heptane-2-carboxylate | LCMS [ESI, M + 1]: 582 |
| F-177 | tert-butyl (1R,5R)-6-(7-(8-chloro-7-fluoronaphthalen-1-yl)-8-fluoro-2-(methylamino)pyrido[4,3-d]pyrimidin-4-yl)-2,6-diazabicyclo[3.2.0]heptane-2-carboxylate | LCMS [ESI, M + 1]: 553 |

TABLE 2B-continued

Intermediates F-7 to F-167

| Int. # | Structure | Characterization Data |
| --- | --- | --- |
| F-178 | tert-butyl (1R,5R)-6-(7-(8-chloro-7-fluoronaphthalen-1-yl)-2-cyclopropoxy-8-fluoropyrido[4,3-d]pyrimidin-4-yl)-2,6-diazabicyclo[3.2.0]heptane-2-carboxylate | LCMS [ESI, M + 1]: 580 |
| F-179 | tert-butyl (1R,5R)-6-(7-(8-chloro-7-fluoronaphthalen-1-yl)-2-(3-(dimethylamino)azetidin-1-yl)-8-fluoropyrido[4,3-d]pyrimidin-4-yl)-2,6-diazabicyclo[3.2.0]heptane-2-carboxylate | LCMS [ESI, M + 1]: 580 |
| F-180 | tert-butyl (1R,5R)-6-(7-(8-chloro-7-fluoronaphthalen-1-yl)-2-(ethyl(methyl)amino)-8-fluoropyrido[4,3-d]pyrimidin-4-yl)-2,6-diazabicyclo[3.2.0]heptane-2-carboxylate | LCMS [ESI, M + 1]: 581<br>$^1$H NMR (400 MHz, CDCl$_3$): δ 8.70 (d, J = 4.0 Hz, 1H), 7.96-7.94 (m, 1H), 7.86-7.85 (m, 1H), 7.65-7.52 (m, 2H), 7.37 (t, J = 8.8 Hz, 1H), 5.40 (br s, 1H), 4.89-4.58 (m, 2H), 4.26 (br d, J = 3.2 Hz, 1H), 4.07-3.74 (m, 3H), 3.70-3.48 (m, 2H), 3.35-3.16 (m, 3H), 2.61-2.42 (m, 1H), 1.50 (s, 9H), 1.24-1.19 (m, 3H) |

TABLE 2B-continued

Intermediates F-7 to F-167

| Int. # | Structure | Characterization Data |
|---|---|---|
| F-181 | 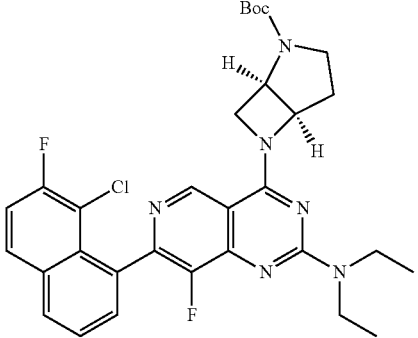 [SMILES: CCN(CC)c1nc(N2C[C@@H]3[C@H]2CCN3C(=O)OC(C)(C)C)c2cnc(-c3cccc4ccc(F)c(Cl)c34)c(F)c2n1]<br>tert-butyl (1R,5R)-6-(7-(8-chloro-7-fluoronaphthalen-1-yl)-2-(diethylamino)-8-fluoropyrido[4,3-d]pyrimidin-4-yl)-2,6-diazabicyclo[3.2.0]heptane-2-carboxylate | LCMS [ESI, M + 1]: 595 |
| F-182 | 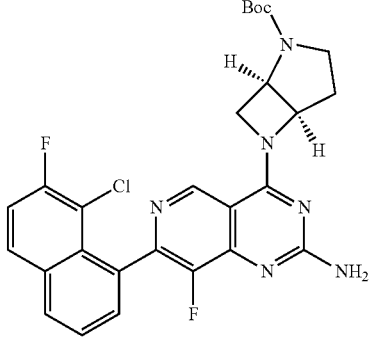 [SMILES: CC(C)(C)OC(=O)N1CC[C@@H]2[C@H]1CN2c1nc(N)nc2c(F)c(-c3cccc4ccc(F)c(Cl)c34)ncc12]<br>tert-butyl (1R,5R)-6-(2-amino-7-(8-chloro-7-fluoronaphthalen-1-yl)-8-fluoropyrido[4,3-d]pyrimidin-4-yl)-2,6-diazabicyclo[3.2.0]heptane-2-carboxylate | LCMS [ESI, M + 1]: 539<br>$^1$H NMR (400 MHz, CDCl$_3$): δ 8.49 (s, 1H), 7.24-7.09 (m, 2H), 5.42-5.24 (m, 1H), 4.70-4.43 (m, 2H), 3.88-3.67 (m, 1H), 3.60-3.45 (m, 1H), 3.38 (br d, J = 3.6 Hz, 1H), 2.28 (br dd, J = 6.2, 13.6 Hz, 1H), 2.03-1.94 (m, 1H), 1.43 (s, 9H) |
| F-183 | 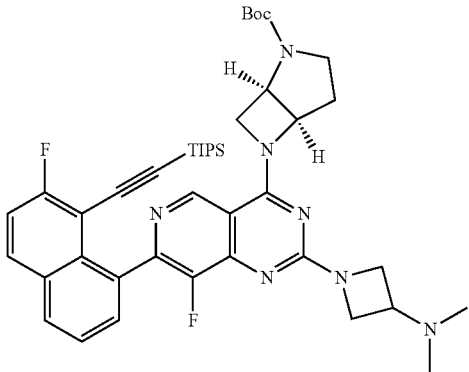<br>tert-butyl (1R,5R)-6-(2-(3-(dimethylamino)azetidin-1-yl)-8-fluoro-7-(7-fluoro-8-((triisopropylsilyl)ethynyl)naphthalen-1-yl)pyrido[4,3-d]pyrimidin-4-yl)-2,6-diazabicyclo[3.2.0]heptane-2-carboxylate | LCMS [ESI, M + 1]: 768 |

The following Examples are intended to illustrate further certain embodiments of the invention and are not intended to limit the scope of the invention.

Example 1

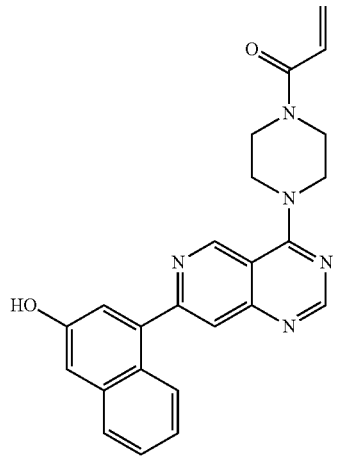

1-(4-(7-(3-hydroxynaphthalen-1-yl)pyrido[4,3-d]pyrimidin-4-yl)piperazin-1-yl)prop-2-en-1-one

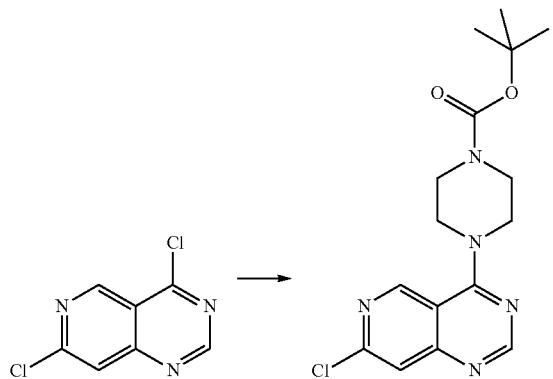

Step A: tert-butyl 4-(7-chloropyrido[4,3-d]pyrimidin-4-yl)piperazine-1-carboxylate: To a solution of 4,7-dichloropyrido[4,3-d]pyrimidine (0.36 g, 1.8 mmol) in DCM was added N-ethyl-N-isopropylpropan-2-amine (0.23 g, 1.8 mmol) and tert-butyl piperazine-1-carboxylate (0.37 g, 2.0 mmol) and the reaction stirred at room temperature for 2 hrs. The reaction was next concentrated in vacuo and the material chromatographed using 0→100% EtOAc/DCM as eluent to give tert-butyl 4-(7-chloropyrido[4,3-d]pyrimidin-4-yl)piperazine-1-carboxylate (0.60 g, 1.7 mmol, 95% yield).

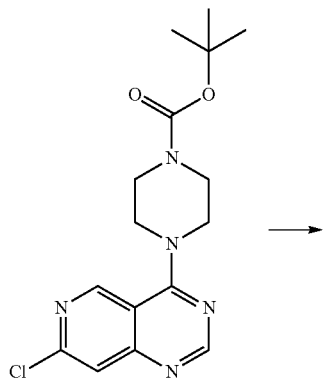

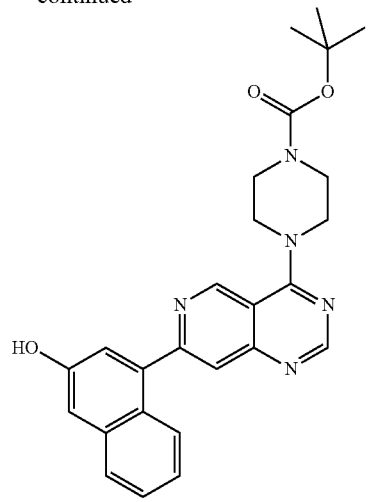

Step B: tert-butyl 4-(7-(3-hydroxynaphthalen-1-yl)pyrido[4,3-d]pyrimidin-4-yl)piperazine-1-carboxylate: To a solution of tert-butyl 4-(7-chloropyrido[4,3-d]pyrimidin-4-yl)piperazine-1-carboxylate (0.3 g, 0.86 mmol) in dioxanes was added potassium carbonate (2.1 ml, 4.3 mmol) and (3-hydroxynaphthalen-1-yl)boronic acid (0.24 g, 1.3 mmol) and the reaction sparged with $N_2$ for 15 minutes followed by addition of 150 mg each of X-phos and $Pd_2DBA_3$ and the reaction heated to 80° C. for overnight. The reaction was next diluted with EtOAc and the organics washed with water, brine, dried over $MgSO_4$ and concentrated in vacuo. The material was next chromatographed using 0→20% MeOH/DCM as eluent to give tert-butyl 4-(7-(3-hydroxynaphthalen-1-yl)pyrido[4,3-d]pyrimidin-4-yl)piperazine-1-carboxylate (0.23 g, 0.50 mmol, 59% yield). ES+APCI MS m/z 458.2 [M+H]+

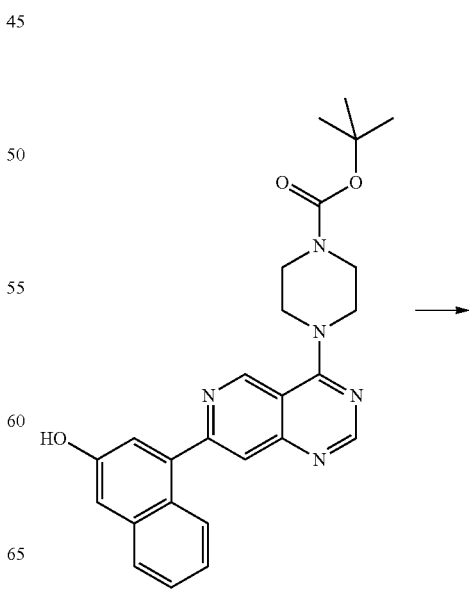

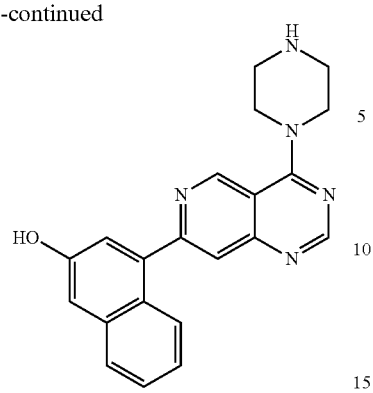

Step C: 4-(4-(piperazin-1-yl)pyrido[4,3-d]pyrimidin-7-yl)naphthalen-2-ol bis(2,2,2-trifluoroacetate): To a solution of tert-butyl 4-(7-(3-hydroxynaphthalen-1-yl)pyrido[4,3-d]pyrimidin-4-yl)piperazine-1-carboxylate (0.22 g, 0.48 mmol) in DCM was added 2,2,2-trifluoroacetic acid (0.55 g, 4.8 mmol) and the reaction stirred at room temperature for 1 hr. The reaction was next concentrated in vacuo and the material used crude in the next reaction.

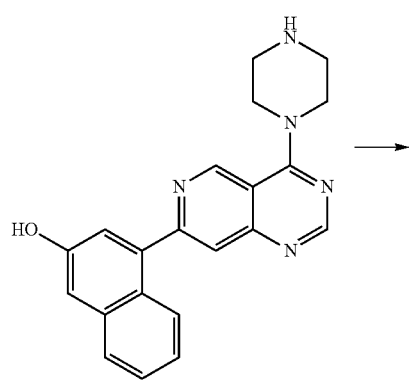

→

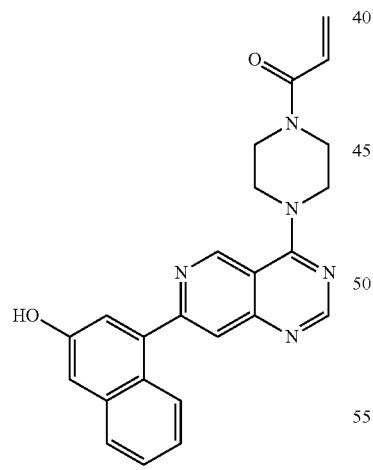

Step D: 1-(4-(7-(3-hydroxynaphthalen-1-yl)pyrido[4,3-d]pyrimidin-4-yl)piperazin-1-yl)prop-2-en-1-one: To a solution of 4-(4-(piperazin-1-yl)pyrido[4,3-d]pyrimidin-7-yl)naphthalen-2-ol bis(2,2,2-trifluoroacetate) (0.288 g, 0.492 mmol) in DCM/ACN was added N-ethyl-N-isopropylpropan-2-amine (0.318 g, 2.46 mmol) followed by acryloyl chloride (0.0445 g, 0.492 mmol) and the reaction stirred at room temperature for 20 minutes. The reaction was next concentrated in vacuo an the material purified by Gilson reverse prep HPLC (0→95% ACN/water with 0.1% TFA modifier as eluent) to give 1-(4-(7-(3-hydroxynaphthalen-1-yl)pyrido[4,3-d]pyrimidin-4-yl)piperazin-1-yl)prop-2-en-1-one (0.050 g, 0.122 mmol, 24.7% yield). ES+APCI MS m/z 412.2 [M+H]$^+$.

Example 2

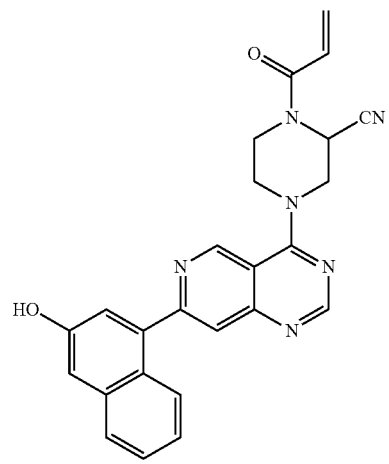

1-acryloyl-4-(7-(3-hydroxynaphthalen-1-yl)pyrido[4,3-d]pyrimidin-4-yl)piperazine-2-carbonitrile 1-acryloyl-4-(7-(3-hydroxynaphthalen-1-yl)pyrido[4,3-d]pyrimidin-4-yl)piperazine-2-carbonitrile was prepared following Example 1 substituting tert-butyl 2-cyanopiperazine-1-carboxylate for tert-butyl piperazine-1-carboxylate in Step A. ES+APCI MS m/z 437.1[M+H]$^+$.

Example 3

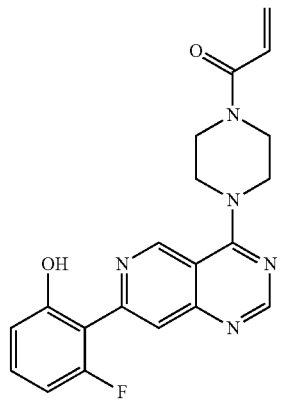

1-(4-(7-(2-fluoro-6-hydroxyphenyl)pyrido[4,3-d]pyrimidin-4-yl)piperazin-1-yl)prop-2-en-1-one 1-(4-(7-(2-fluoro-6-hydroxyphenyl)pyrido[4,3-d]pyrimidin-4-yl)piperazin-1-yl)prop-2-en-1-one was prepared following Example 1 substituting (2-hydroxy-6-fluorophenyl)boronic acid for (3-hydroxynaphthalen-1-yl)boronic acid in Step B. ES+APCI MS m/z 380.1[M+H]$^+$.

Example 4

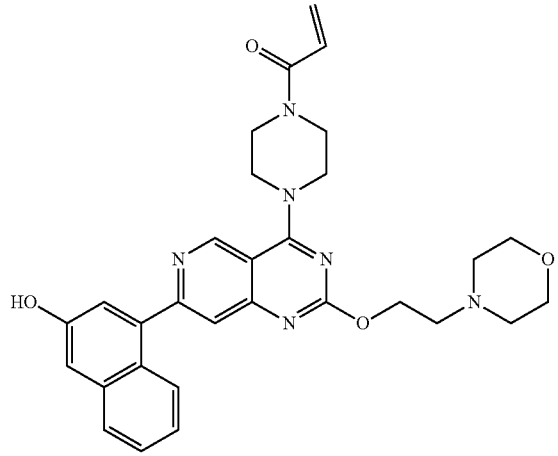 [SMILES: C=CC(=O)N1CCN(c2nc(OCCN3CCOCC3)nc3cc(-c4cc(O)cc5ccccc45)ncc23)CC1]

1-(4-(7-(3-hydroxynaphthalen-1-yl)-2-(2-morpholinoethoxy)pyrido[4,3-d]pyrimidin-4-yl)piperazin-1-yl)prop-2-en-1-one

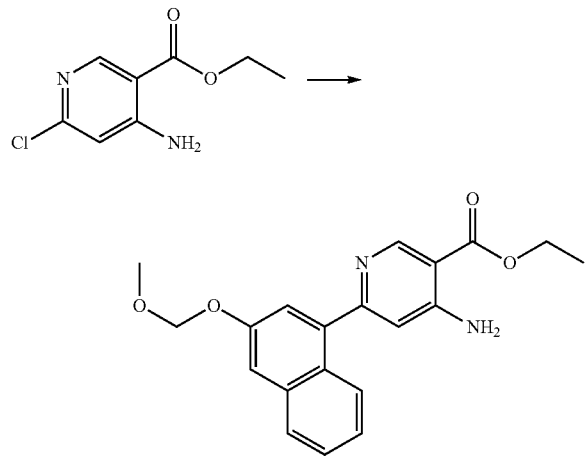

Step A: ethyl 4-amino-6-(3-(methoxymethoxy)naphthalen-1-yl)nicotinate: To a solution of ethyl 4-amino-6-chloronicotinate (0.85 g, 4.2 mmol) in dioxanes was added potassium carbonate (11 ml, 21 mmol), 2-(3-(methoxymethoxy)naphthalen-1-yl)-4,4,5,5-tetramethyl-1,3,2-dioxaborolane (2.0 g, 6.4 mmol) and the reaction degassed with $N_2$ for 15 minutes followed by addition 0.15 g each of Xphos and $Pd_2DBA_3$ and the reaction heated over night at 80° C. The reaction was diluted with EtOAc and the organics washed with water, brine, dried over $MgSO_4$ and concentrated in vacuo. The material was next chromatographed using 0→100% EtOAc/DCM as eluent to give ethyl 4-amino-6-(3-(methoxymethoxy)naphthalen-1-yl)nicotinate (0.70 g, 2.0 mmol, 47% yield). ES+APCI MS m/z 353.1 [M+H]+.

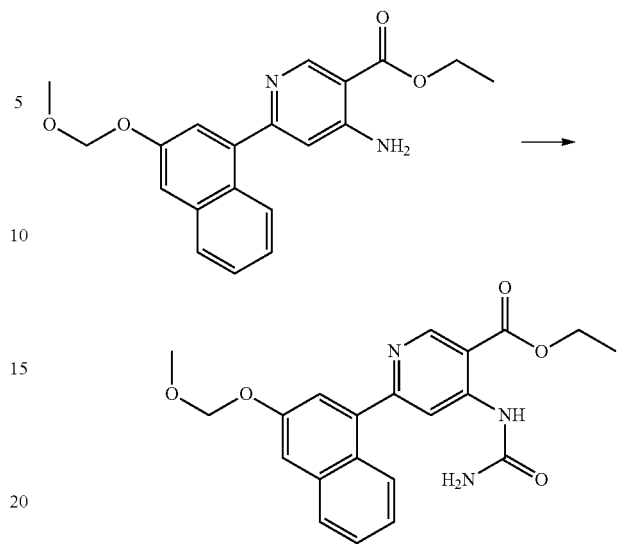

Step B: ethyl 6-(3-(methoxymethoxy)naphthalen-1-yl)-4-ureidonicotinate: To a solution of phosgene (1.2 g, 2.4 mmol) diluted in DCM and cooled to 0° C. was added a solution of ethyl 4-amino-6-(3-(methoxymethoxy)naphthalen-1-yl)nicotinate (0.70 g, 2.0 mmol) and N-ethyl-N-isopropylpropan-2-amine (0.71 ml, 4.0 mmol) in DCM. The reaction was stirred for 1 hr while warming to room temperature. LCMS (dilution with MeOH to see methyl carbamate) confirms isocyante formation. To the reaction was next added ammonia (7.9 ml, 4.0 mmol) (in dioxanes) and the reaction stirred an additional 1 hour. The reaction was next concentrated in vacuo and the residue partitioned between EtOAc and water. The organics were separated and washed with brine, dried over $MgSO_4$ and concentrated in vacuo to give ethyl 6-(3-(methoxymethoxy)naphthalen-1-yl)-4-ureidonicotinate (0.69 g, 1.7 mmol, 88% yield). ES+APCI MS m/z 396.1[M+H]+

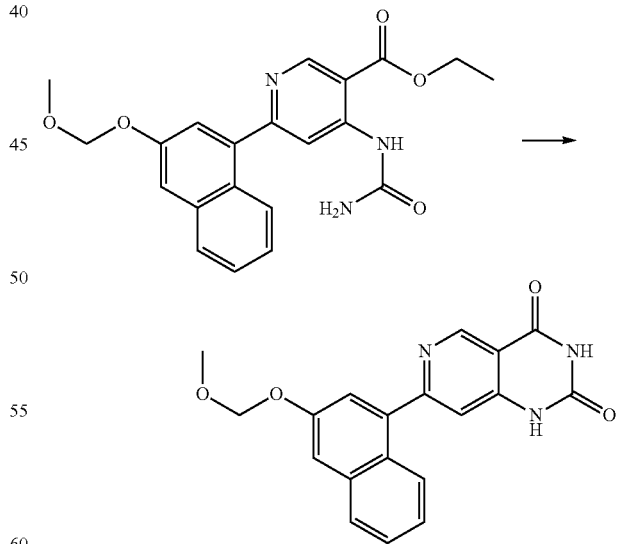

Step C: 7-(3-(methoxymethoxy)naphthalen-1-yl)pyrido[4,3-d]pyrimidine-2,4(1H,3H)-dione: To the solid ethyl 6-(3-(methoxymethoxy)naphthalen-1-yl)-4-ureidonicotinate (0.68 g, 1.7 mmol) in MeOH was added sodium 2-methylpropan-2-olate (0.17 g, 1.7 mmol) and the reaction stirred at 60° C. for 1 hour. The reaction was next concentrated in vacuo and the residue taken up in water the aqueous layer was acidified to pH 3. The resulting solid was filtered and washed with ether. The solid was next dried in vacuo to give 7-(3-(methoxymethoxy)naphthalen-1-yl)pyrido[4,3-d]pyrimidine-2,4(1H,3H)-dione (0.60 g, 1.7 mmol, 100% yield). ES+APCI MS m/z 350.0[M+H]⁺.

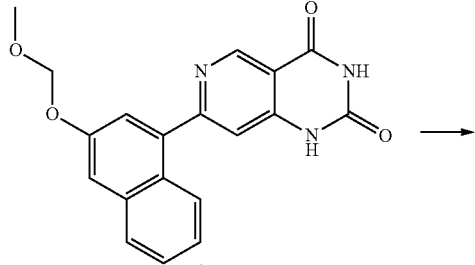

Step D: 2,4-dichloro-7-(3-(methoxymethoxy)naphthalen-1-yl)pyrido[4,3-d]pyrimidine: To the solid 7-(3-(methoxymethoxy)naphthalen-1-yl)pyrido[4,3-d]pyrimidine-2,4(1H,3H)-dione (0.60 g, 1.7 mmol) was added phosphoryl trichloride (7.9 g, 52 mmol) and N-ethyl-N-isopropylpropan-2-amine (0.62 ml, 3.4 mmol) and the reaction degassed with Ar twice and the reaction heated to 100° C. for 1 hour. LCMS (dilute only with ACN otherwise the product hydrolyzes) shows product. The reaction was concentrated in vacuo and the oil chased with toluene 3×. The thick oil was next concentrated under high vac until the oil solidified. The solid was chromatographed using 10% EtOAc/DCM as eluent to give 2,4-dichloro-7-(3-(methoxymethoxy)naphthalen-1-yl)pyrido[4,3-d]pyrimidine (0.30 g, 0.78 mmol, 45% yield).

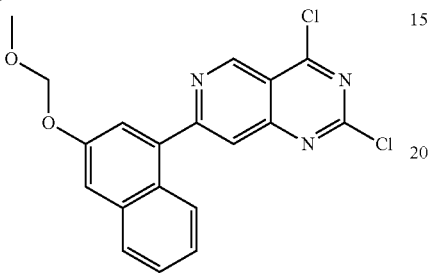

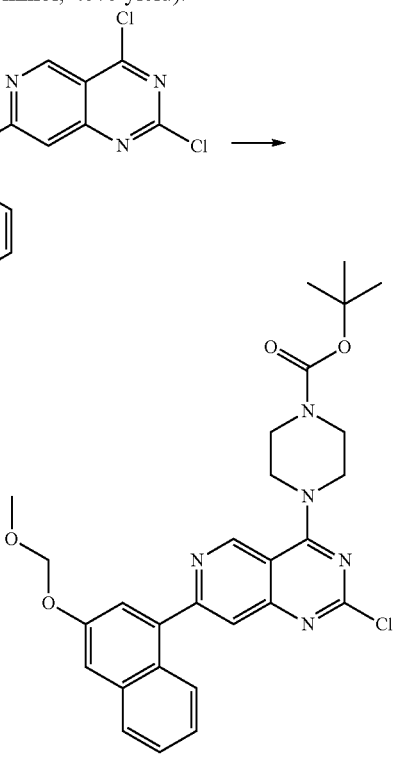

Step E: tert-butyl 4-(2-chloro-7-(3-(methoxymethoxy)naphthalen-1-yl)pyrido[4,3-d]pyrimidin-4-yl)piperazine-1-carboxylate: To a solution of 2,4-dichloro-7-(3-(methoxymethoxy)naphthalen-1-yl)pyrido[4,3-d]pyrimidine (0.30 g, 0.78 mmol) in DCM was added tert-butyl piperazine-1-carboxylate (0.14 g, 0.78 mmol) and N-ethyl-N-isopropylpropan-2-amine (0.15 ml, 0.85 mmol) and the reaction stirred at room temperature for 1 hour. The organics were next washed with brine, dried over MgSO₄ and concentrated in vacuo and the material used crude in the next reaction. tert-butyl 4-(2-chloro-7-(3-(methoxymethoxy)naphthalen-1-yl)pyrido[4,3-d]pyrimidin-4-yl)piperazine-1-carboxylate (0.37 g, 0.69 mmol, 89% yield). ES+APCI MS m/z 536.2[M+H]⁺

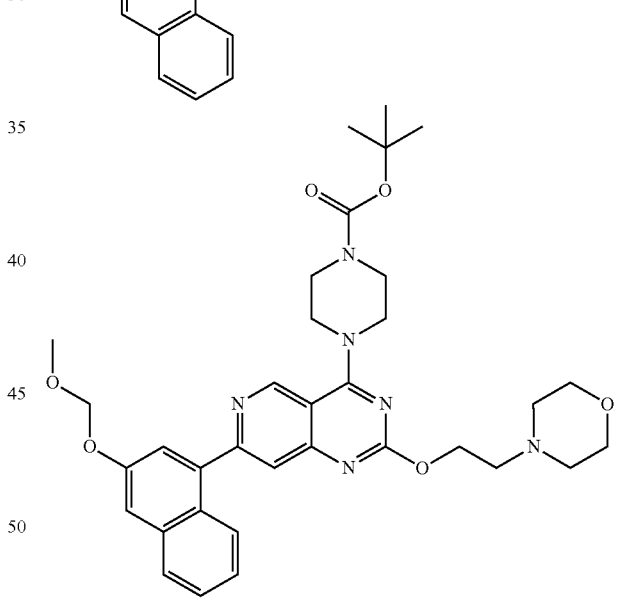

Step E: tert-butyl 4-(7-(3-(methoxymethoxy)naphthalen-1-yl)-2-(2-morpholinoethoxy)pyrido[4,3-d]pyrimidin-4-yl)piperazine-1-carboxylate: To a solution of tert-butyl 4-(2-chloro-7-(3-(methoxymethoxy)naphthalen-1-yl)pyrido[4,3-d]pyrimidin-4-yl)piperazine-1-carboxylate (0.40 g, 0.75 mmol) in dioxanes (10 mL) was added N-ethyl-N-isopropylpropan-2-amine (0.96 g, 7.5 mmol), 2-morpholinoethan-1-ol (0.69 g, 5.2 mmol), and Cs₂CO₃ (0.73 g, 2.2 mmol) and the reaction heated to 150° C. in a sealed tube in the microwave.

The material was next diluted with EtOAc and filtered through gff paper. The organics were next concentrated in vauco and the material chromatographed using 0→15% MeOH/DCM as eluent to give tert-butyl 4-(7-(3-(methoxymethoxy)naphthalen-1-yl)-2-(2-morpholinoethoxy)pyrido[4,3-d]pyrimidin-4-yl)piperazine-1-carboxylate (0.37 g, 0.59 mmol, 79% yield). ES+APCI MS m/z 631.30 [M+H]⁺

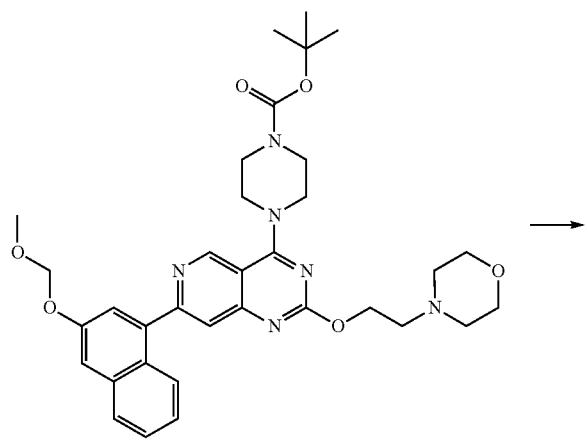

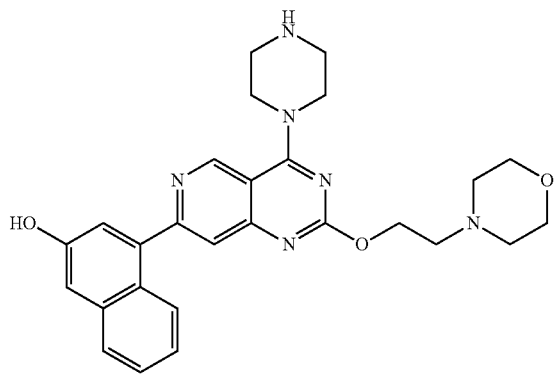

Step F: 4-(2-(2-morpholinoethoxy)-4-(piperazin-1-yl)pyrido[4,3-d]pyrimidin-7-yl)naphthalen-2-ol: To a solution of tert-butyl 4-(7-(3-(methoxymethoxy)naphthalen-1-yl)-2-(2-morpholinoethoxy)pyrido[4,3-d]pyrimidin-4-yl)piperazine-1-carboxylate (0.18 g, 0.285 mmol) in DCM (10 mL) was added 2,2,2-trifluoroacetic acid (6.51 g, 57.1 mmol) and the reaction stirred at room temperature for 1 hr. The reaction was next concentrated in vacuo and the material used crude in the next reaction. 4-(2-(2-morpholinoethoxy)-4-(piperazin-1-yl)pyrido[4,3-d]pyrimidin-7-yl)naphthalen-2-ol (0.14 g, 0.288 mmol, 101% yield). ES+APCI MS m/z 487.20[M+H]⁺.

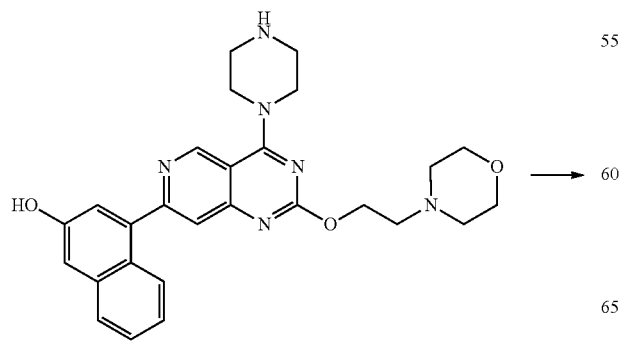

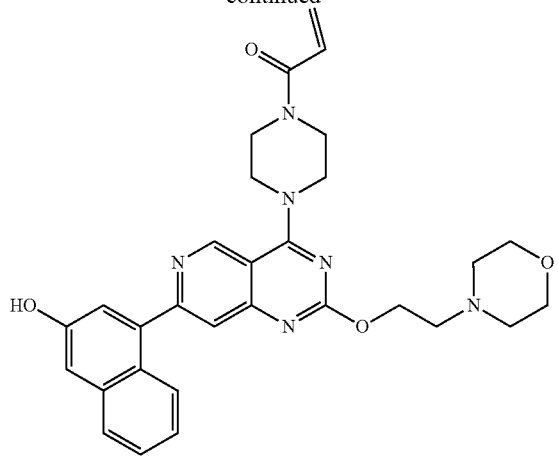

Step G: 1-(4-(7-(3-hydroxynaphthalen-1-yl)-2-(2-morpholinoethoxy)pyrido[4,3-d]pyrimidin-4-yl)piperazin-1-yl)prop-2-en-1-one: To a solution of 4-(2-(2-morpholinoethoxy)-4-(piperazin-1-yl)pyrido[4,3-d]pyrimidin-7-yl)naphthalen-2-ol (0.14 g, 0.29 mmol) in DCM (10 mL) and ACN (2 mL) cooled to 0° C. was added Hunig's Base (0.30 ml, 1.7 mmol) and acryloyl chloride (0.026 g, 0.29 mmol) and the reaction stirred at room temperature for 1 hr. The organics were concentrated in vacuo and the material purified by Gilson reverse prep HCPL (5→95% ACN/water with 0.1% TFA as modifier) to give 1-(4-(7-(3-hydroxynaphthalen-1-yl)-2-(2-morpholinoethoxy)pyrido[4,3-d]pyrimidin-4-yl)piperazin-1-yl)prop-2-en-1-one (0.031 g, 0.052 mmol, 18% yield). ES+APCI MS m/z 541.20[M+H]⁺.

Example 5

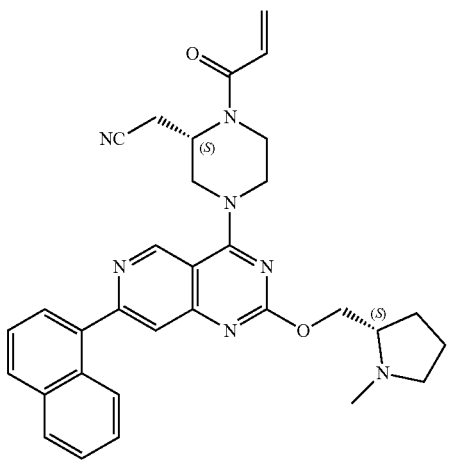

397
2-[(2S)-4-[2-[[(2S)-1-methylpyrrolidin-2-yl]methoxy]-7-(1-naphthyl)pyrido[4,3-d]pyrimidin-4-yl]-1-prop-2-enoyl-piperazin-2-yl]acetonitrile
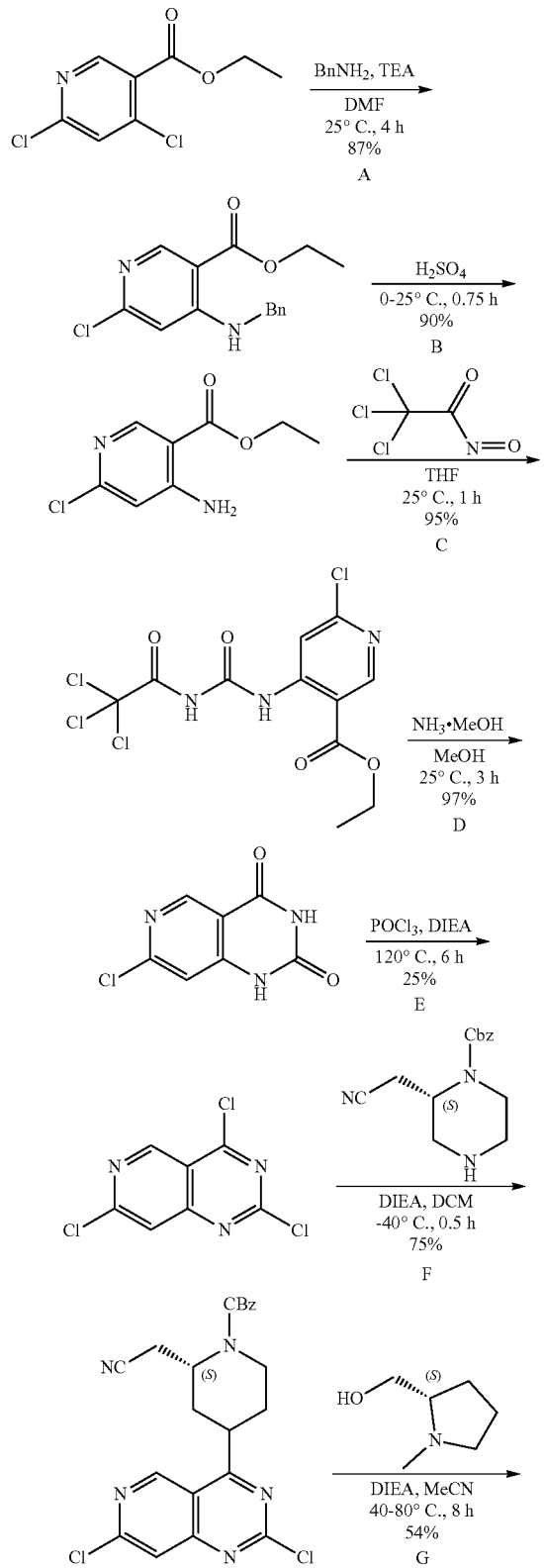
398
-continued
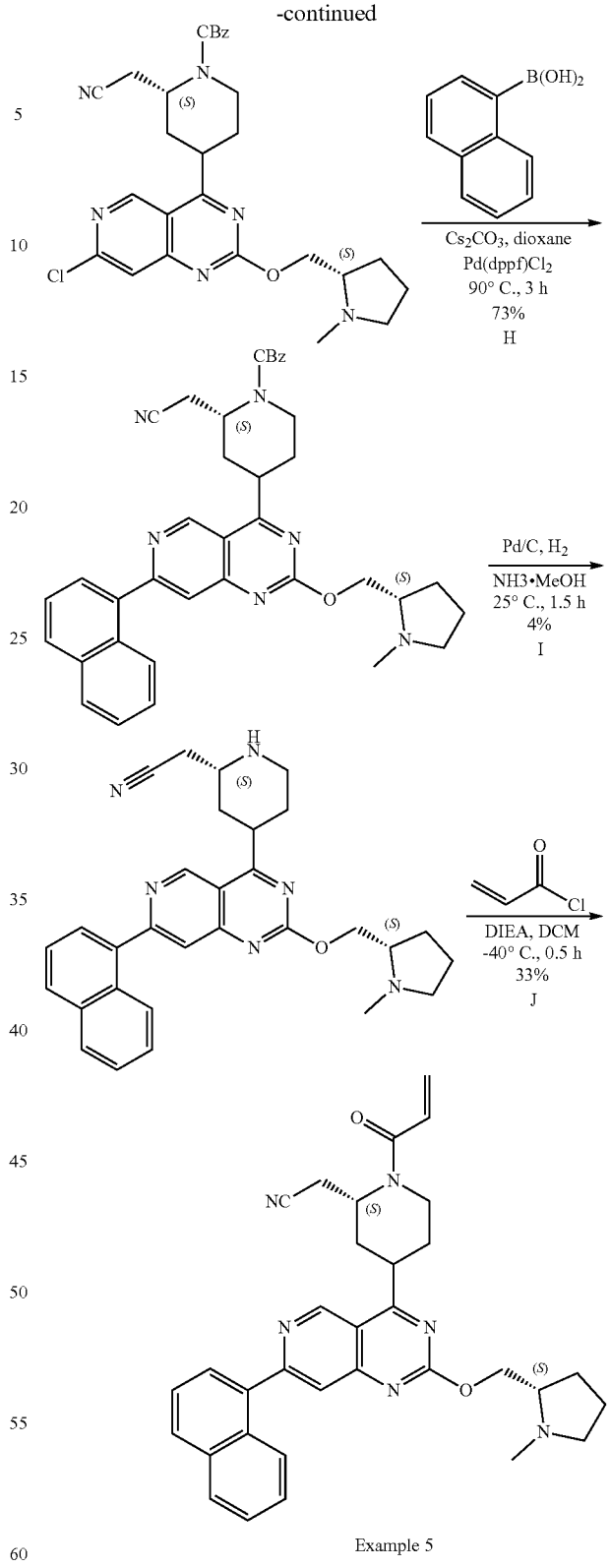
Example 5
Step A: The mixture of ethyl 4,6-dichloropyridine-3-carboxylate (19.5 g, 88.6 mmol, 1.0 eq), BnNH$_2$ (10.4 g, 97.5 mmol, 10.6 mL, 1.1 eq) and TEA (26.9 g, 266 mmol, 37.0 mL, 3.0 eq) in DMF (200 mL) was stirred at 25° C. for 4 hours. To the reaction mixture was added water (600 mL) and EtOAc (100 mL). To the mixture was added NaCl solid (20 g), the mixture was stirred for 0.5 hour. The mixture was extracted with EtOAc (2×100 mL). The combined organic layers were washed with brine (80 mL). The combined organic layers were dried over anhydrous $Na_2SO_4$, filtered and concentrated under vacuum to give ethyl 4-(benzylamino)-6-chloro-pyridine-3-carboxylate (28 g, 77.0 mmol, 87% yield, 80% purity) as a white solid which was used in the next step without further purification. LCMS [ESI, M+1]: 291.

Step B: The mixture of ethyl 4-(benzylamino)-6-chloro-pyridine-3-carboxylate (27 g, 74.3 mmol, 1.0 eq) and $H_2SO_4$ (146 g, 1.49 mol, 79.2 mL, 20.0 eq) was stirred at 0-5° C. for 15 mins. Then the mixture was stirred at 25° C. for 0.5 hour. The mixture was poured into ice-water (600 mL) while stirring. Then solution was adjusted with solid $K_2CO_3$ to pH=8. The precipitate was filtered off and the residue was extracted with ethyl acetate (2×500 mL). The combined organic layers were dried over anhydrous $Na_2SO_4$, filtered and concentrated under vacuum to give ethyl 4-amino-6-chloro-pyridine-3-carboxylate (15 g, 67.3 mmol, 90% yield, 90% purity) as a brown solid which was used in the next step without further purification. LCMS [ESI, M+1]: 201.

Step C: To the solution of ethyl 4-amino-6-chloro-pyridine-3-carboxylate (14 g, 69.8 mmol, 1.0 eq) in THF (280 mL) was added 2,2,2-trichloroacetylisocyanate (26.3 g, 140 mmol, 16.5 mL, 2.0 eq) at 25° C., the mixture was stirred at 25° C. for 1 hour. The reaction mixture was concentrated under vacuum. The crude product was triturated with MBTE (50 mL). The mixture was filtered and the filter cake was collected to give ethyl 6-chloro-4-[(2,2,2-trichloroacetyl) carbamoylamino]pyridine-3-carboxylate (25.7 g, 66.1 mmol, 95% yield, 100% purity) as a white solid. LCMS [ESI, M+1]: 390.

Step D: To the solution of ethyl 6-chloro-4-[(2,2,2-trichloroacetyl) carbamoylamino]pyridine-3-carboxylate (23.7 g, 60.9 mmol, 1.0 eq) in MeOH (400 mL) was added $NH_3$.MeOH (18 mL, 40% purity), the mixture was stirred at 25° C. for 3 hours. The reaction mixture was concentrated under vacuum. The crude product was triturated with MeOH (50 mL). Then the mixture was filtered and the filter cake was collected to give 7-chloro-1H-pyrido[4,3-d]pyrimidine-2,4-dione (13 g, 59.2 mmol, 97% yield, 90% purity) as a white solid. LCMS [ESI, M+1]: 198.

Step E: The mixture of 7-chloro-1H-pyrido[4,3-d]pyrimidine-2,4-dione (3 g, 15.2 mmol, 1.0 eq), DIEA (5.89 g, 45.6 mmol, 7.93 mL, 3.0 eq) and $POCl_3$ (82.5 g, 538 mmol, 50 mL, 35.4 eq) was heated to 120° C. and stirred for 6 hours. The reaction mixture was concentrated under vacuum. The residue was purified by silica gel chromatography (PE: EtOAc=40:1) to give 2,4,7-trichloropyrido[4,3-d]pyrimidine (1 g, 3.84 mmol, 25% yield, 90% purity) as a yellow solid.

Step F: To the solution of 2,4,7-trichloropyrido[4,3-d] pyrimidine (995 mg, 4.24 mmol, 1.1 eq) in DCM (20 mL) was added DIEA (1.50 g, 11.6 mmol, 2.02 mL, 3.0 eq) at −40° C., the mixture was stirred at −40° C. for 15 mins. Then to the mixture was added benzyl (2S)-2-(cyanomethyl) piperazine-1-carboxylate (1 g, 3.86 mmol, 1.0 eq), the mixture was stirred at −40° C. for 15 mins. Water (30 mL) was added into the mixture. The mixture was extracted with DCM (2×20 mL). The combined organic layers were washed with brine (30 mL). The combined organic layers were dried over anhydrous $Na_2SO_4$, filtered and concentrated under vacuum. The residue was purified by silica gel chromatography (PE:EtOAc=10:1-1:1) to give benzyl (2S)-2-(cyanomethyl)-4-(2,7-dichloropyrido[4,3-d]pyrimidin-4-yl)pipera zine-1-carboxylate (1.4 g, 2.91 mmol, 75% yield, 95% purity) as a yellow solid. LCMS [ESI, M+1]: 457.

Step G: The mixture of benzyl (2S)-2-(cyanomethyl)-4-(2,7-dichloropyrido[4,3-d]pyrimidin-4-yl)piperazine-1-carboxylate (800 mg, 1.75 mmol, 1.0 eq), [(2S)-1-methylpyrrolidin-2-yl]methanol (242 mg, 2.10 mmol, 249 µL, 1.2 eq) and DIEA (678 mg, 5.25 mmol, 914 µL, 3.0 eq) in MeCN (16 mL) was heated to 40° C. and stirred for 5 hours. The mixture was heated to 80° C. and stirred for 3 hours. The reaction mixture was concentrated under vacuum. The residue was purified by reversed-phase flash [water (0.1% formic acid/acetonitrile] to give benzyl (2S)-4-[7-chloro-2-[[(2S)-1-methylpyrrolidin-2-yl]methoxy]pyrido[4,3-d]pyrimidin-4-yl]-2-(cyanomethyl)piperazine-1-carboxylate (510 mg, 951 µmol, 54% yield, 100% purity) as a yellow solid. LCMS [ESI, M+1]: 536.

Step H: To the mixture of benzyl (2S)-4-[7-chloro-2-[[(2S)-1-methylpyrrolidin-2-yl]methoxy]pyrido[4,3-d]pyrimidin-4-yl]-2-(cyanomethyl)piperazine-1-carboxylate (200 mg, 373 umol, 1.0 eq), 1-naphthylboronic acid (128 mg, 746 umol, 2.0 eq) and $Cs_2CO_3$ (365 mg, 1.12 mmol, 3.0 eq) in dioxane (5 mL) was added Pd(dppf)$Cl_2$ (54.6 mg, 74.6 µmol, 0.2 eq) under $N_2$. The suspension was degassed under vacuum and purged with $N_2$ several times. The mixture was stirred under $N_2$ at 90° C. for 3 hours. Water (15 mL) was added into the mixture. The mixture was diluted with EtOAc (10 mL) and filtered, the filtrate was extracted with EtOAc (2×15 mL). The combined organic layers were washed with brine (20 mL). The combined organic layers were dried over anhydrous $Na_2SO_4$, filtered and concentrated under vacuum. The residue was purified by reversed-phase flash [water (0.1% formic acid)/acetonitrile]. Then the residue was purified by $Al_2O_3$ chromatography (EtOAc:MeOH=1:0~30:1) to give benzyl (2S)-2-(cyanomethyl)-4-[2-[[(2S)-1-methylpyrrolidin-2-yl]methoxy]-7-(1-naphthyl)pyrido[4,3-d]pyrimidin-4-yl]piperazine-1-carboxylate (180 mg, 272 µmol, 73% yield, 95% purity) as a yellow solid. LCMS [ESI, M+1]: 628.

$^1$H NMR (400 MHz, chloroform-d) δ=9.34 (s, 1H), 8.17 (br d, J=8.0 Hz, 1H), 7.95 (br t, J=8.4 Hz, 2H), 7.80 (s, 1H), 7.70 (d, J=6.4 Hz, 1H), 7.62-7.56 (m, 1H), 7.55-7.47 (m, 2H), 7.42-7.35 (m, 5H), 5.22 (s, 2H), 4.74 (br s, 1H), 4.56 (dd, J=4.8, 10.8 Hz, 1H), 4.44 (br t, J=12.4 Hz, 2H), 4.36 (dd, J=6.0, 10.8 Hz, 1H), 4.21 (br s, 1H), 3.87 (br s, 1H), 3.75-3.47 (m, 2H), 3.12 (br t, J=7.6 Hz, 1H), 2.87 (br s, 1H), 2.82-2.70 (m, 2H), 2.51 (s, 3H), 2.36-2.24 (m, 1H), 2.13-2.06 (m, 1H), 1.92-1.79 (m, 3H).

Step I: To the solution of benzyl (2S)-2-(cyanomethyl)-4-[2-[[(2S)-1-methylpyrrolidin-2-yl]methoxy]-7-(1-naphthyl)pyrido[4,3-d]pyrimidin-4-yl]piperazine-1-carboxylate (160 mg, 255 µmol, 1.0 eq) and $NH_3$.MeOH (2 mL, 20% purity) in MeOH (2 mL) was added Pd/C (80 mg, 10% purity) under $N_2$. The suspension was degassed under vacuum and purged with $H_2$ several times. The mixture was stirred under $H_2$ (15 psi) at 25° C. for 1.5 hour. The reaction mixture was concentrated under vacuum. The residue was purified by prep-HPLC (column: Waters Xbridge 150*25 5u; mobile phase: [water (0.05% ammonia hydroxide v/v)—ACN]; B %: 35%-59%,10 min). The desired fractions were collected and lyophilized to give 2-[(2S)-4-[2-[[(2S)-1-methylpyrrolidin-2-yl]methoxy]-7-(1-naphthyl)pyrido[4,3-d]pyrimidin-4-yl]piperazin-2-yl]acetonitrile (5.10 mg, 10.3 µmol, 4% yield, 100% purity) as a white solid. LCMS [ESI, M+1]: 494.

$^1$H NMR (400 MHz, CHLOROFORM-d) δ=9.31 (s, 1H), 8.21-8.16 (m, 1H), 7.95 (t, J=8.0 Hz, 2H), 7.78 (s, 1H), 7.70 (dd, J=1.2, 7.2 Hz, 1H), 7.59 (dd, J=7.2, 8.0 Hz, 1H), 7.56-7.47 (m, 2H), 4.59-4.49 (m, 2H), 4.43 (br dd, J=1.6, 13.2 Hz, 1H), 4.36 (dd, J=6.4, 10.8 Hz, 1H), 3.56 (ddd, J=3.2, 10.4, 13.2 Hz, 1H), 3.41-3.33 (m, 1H), 3.26-3.18 (m, 2H), 3.17-3.09 (m, 2H), 2.77-2.69 (m, 1H), 2.68-2.54 (m, 2H), 2.51 (s, 3H), 2.30 (dt, J=7.2, 9.6 Hz, 1H), 2.13-2.02 (m, 1H), 1.91-1.79 (m, 3H).

Example 5: To the solution of 2-[(2S)-4-[2-[[(2S)-1-methylpyrrolidin-2-yl]methoxy]-7-(1-naphthyl)pyrido[4,3-d]pyrimidin-4-yl]piperazin-2-yl]acetonitrile (80 mg, 162 µmol, 1.0 eq) and DIEA (62.8 mg, 486 µmol, 84.7 µL, 3.0 eq) in DCM (2 mL) was added prop-2-enoyl chloride (22.0 mg, 243 μmol, 19.8 μL, 1.5 eq) at −40° C., the mixture was stirred at −40° C. for 0.5 hour. The reaction mixture was quenched by water (5 mL) and extracted with DCM (2×5 mL). The combined organic layers were dried over anhydrous Na$_2$SO$_4$, filtered and concentrated under vacuum. The residue was purified by silica gel chromatography (EtOAC: MeOH=1:0~30:1). The residue was purified by prep-HPLC (column: Xtimate C18 150*25 mm*5 μm; mobile phase: [water (0.05% ammonia hydroxide v/v)—ACN]; B %: 48%-78%, 1 min). The desired fractions were collected and lyophilized to give 2-[(2S)-4-[2-[[(2S)-1-methylpyrrolidin-2-yl]methoxy]-7-(1-naphthyl)pyrido[4,3-d]pyrimidin-4-yl]-1-prop-2-enoyl-piperazin-2-yl]acetonitrile (29.3 mg, 53.4 μmol, 33% yield, 99.8% purity) as a white solid. LCMS [ESI, M+1]: 548.

$^1$H NMR (400 MHz, chloroform-d) δ=9.35 (s, 1H), 8.16 (d, J=8.0 Hz, 1H), 7.95 (t, J=8.8 Hz, 2H), 7.80 (s, 1H), 7.69 (dd, J=1.2, 7.2 Hz, 1H), 7.58 (dd, J=7.2, 8.0 Hz, 1H), 7.55-7.46 (m, 2H), 6.68-6.53 (m, 1H), 6.47-6.37 (m, 1H), 5.89-5.80 (m, 1H), 5.03 (br s, 1H), 4.61 (dd, J=5.2, 10.8 Hz, 1H), 4.53-4.43 (m, 2H), 4.39 (dd, J=6.0, 10.9 Hz, 1H), 4.17-3.57 (m, 4H), 3.17 (br t, J=7.2 Hz, 1H), 2.98 (br dd, J=6.8, 16.4 Hz, 1H), 2.89-2.73 (m, 2H), 2.54 (s, 3H), 2.40-2.29 (m, 1H), 2.15-2.08 (m, 1H), 1.92-1.75 (m, 3H).

Example 6

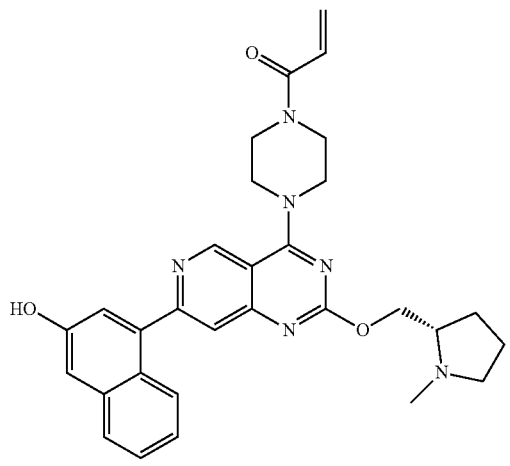 [SMILES: C=CC(=O)N1CCN(c2nc(OC[C@@H]3CCCN3C)nc3cc(-c4cc(O)cc5ccccc45)ncc23)CC1]

1-[4-[7-(3-hydroxy-1-naphthyl)-2-[[(2S)-1-methylpyrrolidin-2-yl]methoxy]pyrido[4,3-d]pyrimidin-4-yl]piperazin-1-yl]prop-2-en-1-one

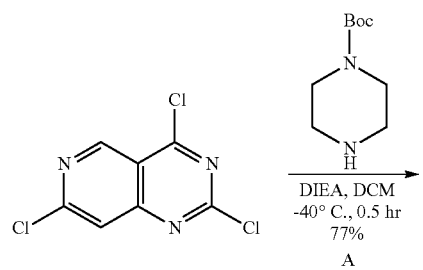

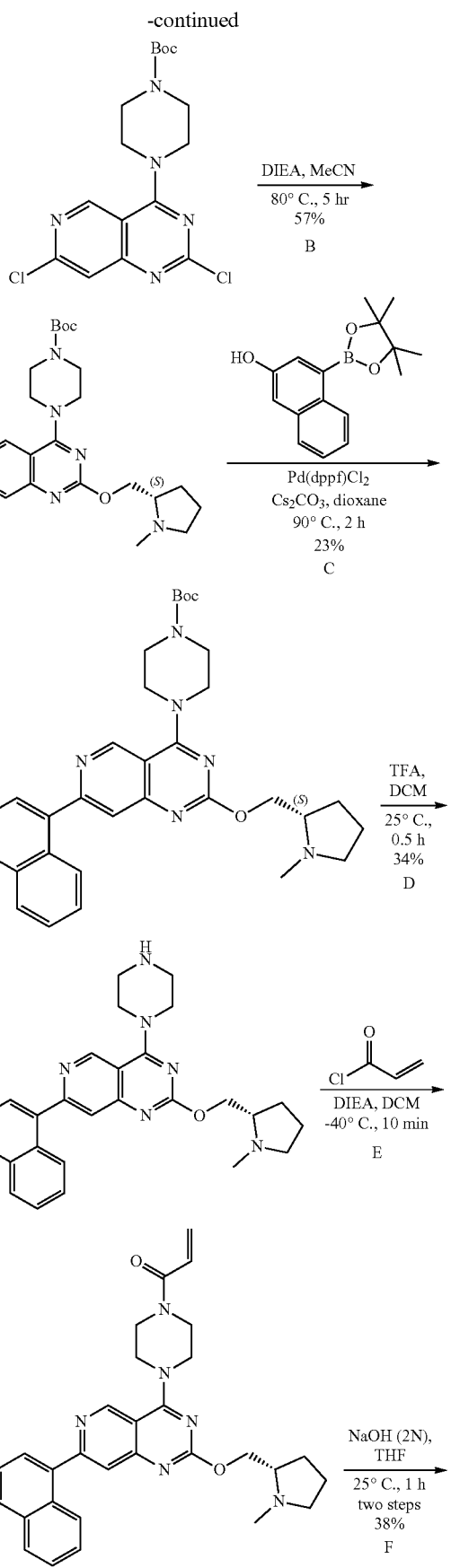

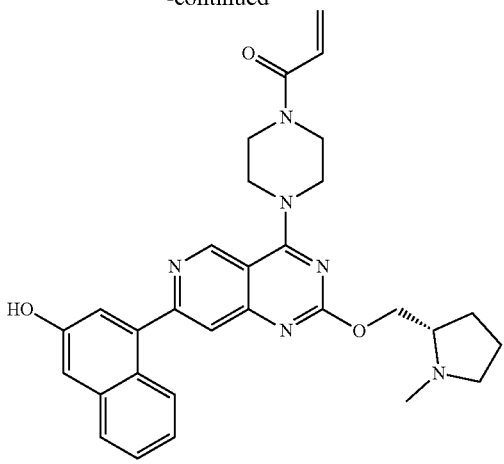

Example 6

Step A: To the solution of 2,4,7-trichloropyrido[4,3-d]pyrimidine (1.8 g, 7.68 mmol, 1.0 eq) in DCM (40 mL) was added DIEA (2.98 g, 23.0 mmol, 4.01 mL, 3.0 eq) at −40° C., the mixture was stirred at −40° C. for 15 min. Then to the mixture was added tert-butyl piperazine-1-carboxylate (1.43 g, 7.68 mmol, 1.0 eq), the mixture was stirred at −40° C. for 15 min. Water (50 mL) was added into the mixture. The mixture was extracted with DCM (2×30 mL). The combined organic layers were washed with brine (40 mL). The combined organic layers were dried over anhydrous Na$_2$SO$_4$, filtered and concentrated under vacuum. The residue was purified by reversed-phase flash [water (0.1% formic acid)/acetonitrile]. The desired fractions were collected and basified with solid NaHCO$_3$, concentrated under vacuum to remove MeCN and extracted with ethyl acetate (2×30 mL). The organic layers were dried over Na$_2$SO$_4$ and concentrated under vacuum to give tert-butyl 4-(2,7-dichloropyrido[4,3-d]pyrimidin-4-yl)piperazine-1-carboxylate (2.4 g, 5.93 mmol, 77% yield, 95% purity) as a brown solid. LCMS [ESI, M+1]: 384.

Step B: The mixture of tert-butyl 4-(2,7-dichloropyrido[4,3-d]pyrimidin-4-yl)piperazine-1-carboxylate (500 mg, 1.30 mmol, 1.0 eq), [(2S)-1-methylpyrrolidin-2-yl]methanol (180 mg, 1.56 mmol, 185 μL, 1.2 eq) and DIEA (504 mg, 3.90 mmol, 680 μL, 3.0 eq) in MeCN (10 mL) was heated to 80° C. and stirred for 6 hours. The reaction mixture was concentrated under vacuum. The residue was purified by reversed-phase flash [water (0.1% formic acid)/acetonitrile]. The desired fractions were collected and basified with solid NaHCO$_3$, concentrated under vacuum to remove MeCN and extracted with ethyl acetate (2×40 mL). The organic layers were dried over Na$_2$SO$_4$ and concentrated under vacuum to give tert-butyl 4-[7-chloro-2-[[(2S)-1-methylpyrrolidin-2-yl]methoxy]pyrido[4,3-d]pyrimidin-4-yl]piperazine-1-carboxylate (360 mg, 739 μmol, 57% yield, 95% purity) as a yellow solid. LCMS [ESI, M+1]: 463.

$^1$H NMR (400 MHz, chloroform-d) δ=8.92 (s, 1H), 7.48 (s, 1H), 4.48 (dd, J=4.8, 10.8 Hz, 1H), 4.29 (dd, J=6.8, 10.8 Hz, 1H), 3.97-3.88 (m, 4H), 3.64 (dd, J=4.0, 6.0 Hz, 1H), 3.10 (br t, J=7.6 Hz, 1H), 2.73-2.64 (m, 1H), 2.48 (s, 3H), 2.34-2.23 (m, 1H), 2.10-2.00 (m, 1H), 1.85-1.69 (m, 3H), 1.49 (s, 9H).

Step C: To the mixture of tert-butyl 4-[7-chloro-2-[[(2S)-1-methylpyrrolidin-2-yl]methoxy]pyrido[4,3-d]pyrimidin-4-yl]piperazine-1-carboxylate (200 mg, 432 μmol, 1.0 eq), 4-(4,4,5,5-tetramethyl-1,3,2-dioxaborolan-2-yl) naphthalene-2-ol (233 mg, 864 μmol, 2 eq) and Cs$_2$CO$_3$ (422 mg, 1.30 mmol, 3.0 eq) in dioxane (4 mL) was added Pd(dppf)Cl$_2$ (63.2 mg, 86.4 μmol, 0.2 eq) under N$_2$. The suspension was degassed under vacuum and purged with N$_2$ several times. The mixture was stirred under N$_2$ at 90° C. for 3 hours. Water (15 mL) was added into the mixture. The mixture was diluted with ethyl acetate (10 mL) and filtered, and the filtrate was extracted with ethyl acetate (2×15 mL). The combined organic layers were washed with brine (20 mL). The combined organic layers were dried over anhydrous Na$_2$SO$_4$, filtered and concentrated under vacuum. The residue was purified by reversed-phase flash [water (0.1% formic acid)/acetonitrile]. Then the residue was purified by prep-HPLC (column: Phenomenex Synergi C18 150*25*10 μm; mobile phase: [water (0.1% TFA)—ACN]; B %: 17%-44%,10 min). The desired fractions were collected and basified with solid NaHCO$_3$, concentrated under vacuum to remove MeCN and extracted with ethyl acetate (3×15 mL). The organic layers were dried over Na$_2$SO$_4$ and concentrated under vacuum to give tert-butyl 4-[7-(3-hydroxy-1-naphthyl)-2-[[(2S)-1-methylpyrrolidin-2-yl]methoxy]pyrido[4,3-d]pyrimidin-4-yl]piperazine-1-carboxylate (60 mg, 100 μmol, 23% yield, 95% purity) as a yellow solid. LCMS [ESI, M+1]: 571.

Step D: To the solution of tert-butyl 4-[7-(3-hydroxy-1-naphthyl)-2-[[(2S)-1-methylpyrrolidin-2-yl]methoxy]pyrido[4,3-d]pyrimidin-4-yl]piperazine-1-carboxylate (60 mg, 105 μmol, 1.0 eq) in DCM (0.05 mL) was added TFA (180 mg, 1.58 mmol, 117 μL, 15 eq), the mixture was stirred at 25° C. for 0.5 hour. The reaction mixture was concentrated under vacuum. The reaction mixture was diluted with DMF and adjusted with saturated NaHCO$_3$ to pH=7~8. The mixture was purified by prep-HPLC (column: Xtimate C18 150*25 mm*5 μm; mobile phase: [water (0.05% ammonia hydroxide v/v)—ACN]; B %: 25%-55%, 1 min). The desired fractions were collected and lyophilized to give 4-[2-[[(2S)-1-methylpyrrolidin-2-yl]methoxy]-4-piperazin-1-yl-pyrido[4,3-d]pyrimidin-7-yl]naphthalen-2-ol (17 mg, 36.0 μmol, 34% yield, 99.7% purity) as a yellow solid. LCMS [ESI, M+1]: 471.

$^1$H NMR (400 MHz, methanol-d$_4$) δ=9.26 (s, 1H), 7.76 (d, J=8.4 Hz, 1H), 7.66 (d, J=8.4 Hz, 1H), 7.60 (s, 1H), 7.34 (t, J=7.6 Hz, 1H), 7.22 (d, J=2.4 Hz, 1H), 7.18-7.12 (m, 2H), 4.47 (dq, J=6.0, 11.2 Hz, 2H), 4.11-4.03 (m, 4H), 3.12-3.08 (m, 1H), 3.07-3.03 (m, 4H), 2.83-2.74 (m, 1H), 2.52 (s, 3H), 2.36 (q, J=9.2 Hz, 1H), 2.17-2.06 (m, 1H), 1.89-1.68 (m, 3H).

Step E: To the solution of 4-[2-[[(2S)-1-methylpyrrolidin-2-yl]methoxy]-4-piperazin-1-yl-pyrido[4,3-d]pyrimidin-7-yl]naphthalen-2-ol (45 mg, 95.6 μmol, 1.0 eq) and DIEA (74.2 mg, 574 μmol, 99.9 μL, 6.0 eq) in DCM (1 mL) was added prop-2-enoyl chloride (8.66 mg, 95.6 μmol, 7.80 μL, 1.0 eq) at −40° C., the mixture was stirred at −40° C. for 10 min. Water (3 mL) was added into the mixture. The mixture was diluted with DCM (2 mL) and extracted with DCM (2×3 mL). The combined organic layers were dried over anhydrous Na$_2$SO$_4$, filtered and concentrated under vacuum to give [4-[2-[[(2S)-1-methylpyrrolidin-2-yl]methoxy]-4-(4-prop-2-enoylpiperazin-1-yl)pyrido[4,3-d]pyrimidin-7-yl]-2-naphthyl] prop-2-enoate (60 mg, crude) as a yellow solid which was used in the next step without further purification.

Example 6: To the mixture of [4-[2-[[(2S)-1-methylpyrrolidin-2-yl] methoxy]-4-(4-prop-2-enoylpiperazin-1-yl)pyrido[4,3-d]pyrimidin-7-yl]-2-naphthyl] prop-2-enoate (50 mg, crude) in THF (0.5 mL) was added NaOH (2 M, 173 μL), the mixture was stirred at 25° C. for 1 hour. Water (3 mL) was added into the mixture. The mixture was diluted with ethyl acetate (2 mL) and extracted with ethyl acetate (3×5 mL). The combined organic layers were dried over anhydrous Na$_2$SO$_4$, filtered and concentrated under vacuum. The residue was purified by prep-HPLC (column: Waters Xbridge 150*25 5μ; mobile phase: [water (0.05% ammonia hydroxide v/v)—ACN]; B %: 32%-53%,10 min). The desired fractions were collected and lyophilized to give 1-[4-[7-(3-hydroxy-1-naphthyl)-2-[[(2S)-1-methylpyrrolidin-2-yl]methoxy]pyrido[4,3-d]pyrimidin-4-yl]piperazin-1-yl]prop-2-en-1-one (17.5 mg, 32.7 μmol, two steps 38% yield, 97.9% purity) as a yellow solid. LCMS [ESI, M+1]: 525.

¹H NMR (400 MHz, chloroform-d) δ=9.08 (s, 1H), 8.00 (d, J=8.4 Hz, 1H), 7.63-7.58 (m, 2H), 7.35 (t, J=7.2 Hz, 1H), 7.26-7.20 (m, 2H), 7.15 (d, J=2.4 Hz, 1H), 6.59-6.50 (m, 1H), 6.42-6.34 (m, 1H), 5.82-5.75 (m, 1H), 4.60 (dd, J=6.4, 11.2 Hz, 1H), 4.35 (dd, J=5.2, 11.2 Hz, 1H), 3.92 (br s, 4H), 3.86-3.64. (m, 4H), 3.21 (br t, J=7.6 Hz, 1H), 2.86-2.82 (m, 1H), 2.65 (s, 3H), 2.39 (dt, J=7.2, 9.6 Hz, 1H), 2.16-2.06 (m, 1H), 2.00-1.93 (m, 3H).

Example 7

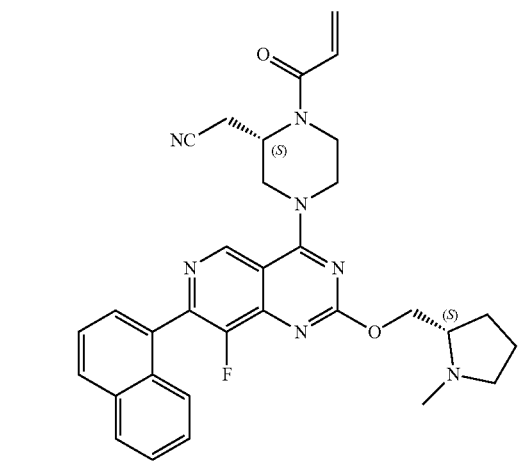

2-[(2S)-4-[8-fluoro-2-[[(2S)-1-methylpyrrolidin-2-yl]methoxy]-7-(1-naphthyl)pyrido[4,3-d]pyrimidin-4-yl]-1-prop-2-enoyl-piperazin-2-yl]acetonitrile

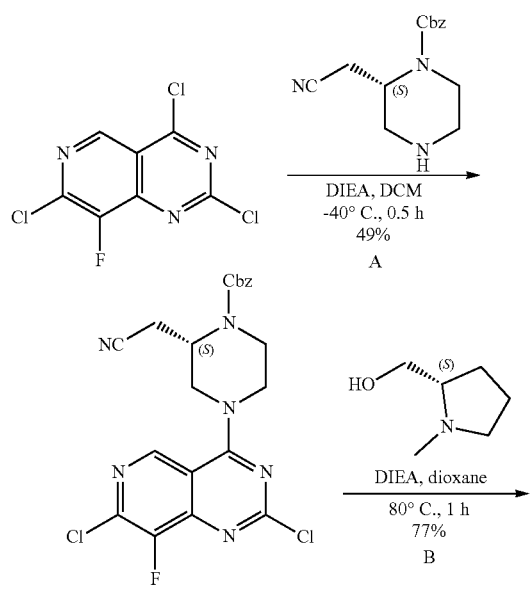

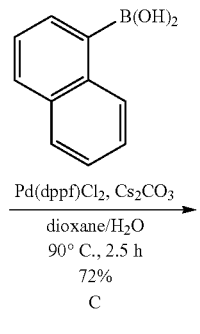

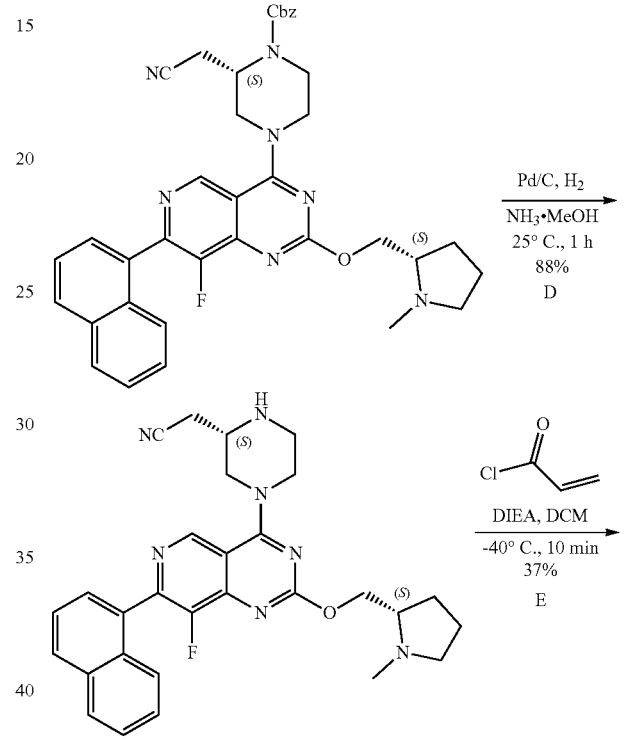

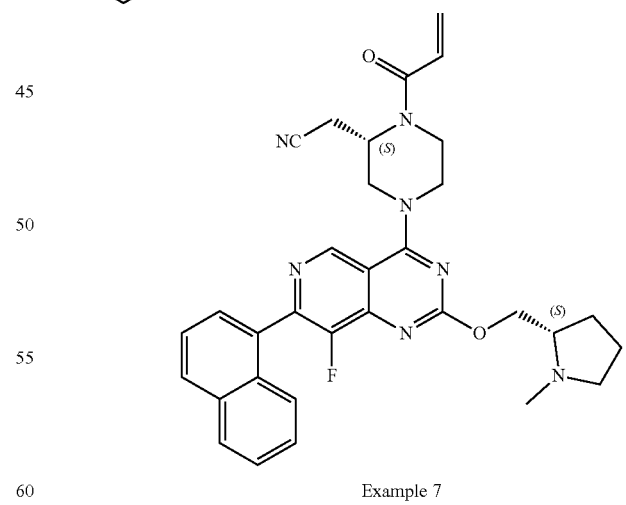

Example 7

Step A: To a solution of 2,4,7-trichloro-8-fluoro-pyrido[4,3-d]pyrimidine (500 mg, 1.98 mmol, 1 eq) in DCM (10 mL) was added DIEA (640 mg, 4.95 mmol, 862 μL, 2.5 eq), benzyl (2S)-2-(cyanomethyl)piperazine-1-carboxylate (359 mg, 1.39 mmol, 0.7 eq) at −40° C. The reaction mixture was stirred at –40° C. for 0.5 hour. Upon completion, the mixture was added water (10 mL) and layers were separated. The aqueous phase was extracted with EtOAc (20 mL). Combined organic layers were dried over Na$_2$SO$_4$, filtered and concentrated under vacuum. The residue was purified by reversed phase flash [water (0.1% formic acid/acetonitrile]. The desired fractions were collected and neutralized with solid NaHCO$_3$, concentrated under vacuum to remove MeCN and extracted with EtOAc (2×30 mL). The organic layers were dried over Na$_2$SO$_4$ and concentrated under vacuum to give benzyl (2S)-2-(cyanomethyl)-4-(2,7-dichloro-8-fluoro-pyrido[4,3-d]pyrimidin-4-yl)piperazine-1-carboxylate (460 mg, 968 µmol, 49% yield, 100% purity) as a yellow solid. LCMS [ESI, M+1]: 475.

Step B: To a solution of benzyl (2S)-2-(cyanomethyl)-4-(2,7-dichloro-8-fluoro-pyrido[4,3-d]pyrimidin-4-yl)piperazine-1-carboxylate (420 mg, 884 µmol, 1 eq) and DIEA (343 mg, 2.65 mmol, 462 µL, 3 eq) in dioxane (8 mL) was added [(2S)-1-methylpyrrolidin-2-yl]methanol (509 mg, 4.42 mmol, 525 µL, 5 eq). The reaction mixture was stirred at 80° C. for 1 hour. Upon completion, the mixture was diluted with water (10 mL) and extracted with EtOAc (2×40 mL). The organic layers were dried over Na$_2$SO$_4$ and concentrated under vacuum. The residue was purified by reversed phase flash [water (0.1% formic acid/acetonitrile]. The desired fractions were collected and neutralized with solid NaHCO$_3$, concentrated under vacuum to remove MeCN and extracted with EtOAc (2×40 mL). The organic layers were dried over Na$_2$SO$_4$ and concentrated under vacuum to give benzyl (2S)-4-[7-chloro-8-fluoro-2-[[(2S)-1-methylpyrrolidin-2-yl]methoxy]pyrido[4,3-d]pyrimidin-4-yl]-2-(cyanomethyl)piperazine-1-carboxylate (420 mg, 682 µmol, 77% yield, 90% purity) as a yellow solid.

$^1$H NMR (400 MHz, chloroform-d) δ=8.79 (s, 1H), 7.48-7.32 (m, 5H), 5.20 (s, 2H), 4.72-4.62 (m, 1H), 4.55 (dd, J=4.8, 10.8 Hz, 1H), 4.38 (dd, J=5.6, 10.8 Hz, 2H), 4.30 (br d, J=12.0 Hz, 1H), 4.25-4.11 (m, 1H), 3.97 (br s, 1H), 3.75-3.51 (m, 2H), 3.11 (br t, J=7.6 Hz, 1H), 2.86 (br s, 1H), 2.75-2.64 (m, 2H), 2.49 (s, 3H), 2.35-2.24 (m, 1H), 2.10-1.97 (m, 1H), 1.92-1.78 (m, 3H).

Step C: To a solution of benzyl (2S)-4-[7-chloro-8-fluoro-2-[[(2S)-1-methyl pyrrolidin-2-yl]methoxy]pyrido[4,3-d]pyrimidin-4-yl]-2-(cyanomethyl)piperazine-1-carboxylate (230 mg, 415 µmol, 1 eq) and 1-naphthylboronic acid (143 mg, 830 µmol, 2 eq) in dioxane (4 mL) and H$_2$O (0.8 mL) was added Cs$_2$CO$_3$ (271 mg, 830 µmol, 2 eq), Pd(dppf)Cl$_2$ (30.4 mg, 41.5 µmol, 0.1 eq). The mixture was de-gassed and then heated to 90° C. for 2.5 hours under N$_2$. Upon completion, the mixture was concentrated under vacuum. The residue was purified by reversed phase flash [water (0.1% formic acid/acetonitrile]. The desired fractions were collected and neutralized with solid NaHCO$_3$, concentrated under vacuum to remove MeCN and extracted with EtOAc (2×20 mL). The organic layers were dried over Na$_2$SO$_4$ and concentrated under vacuum to give benzyl (2S)-2-(cyanomethyl)-4-[8-fluoro-2-[[(2S)-1-methylpyrrolidin-2-yl]methoxy]-7-(1-naphthyl)pyrido[4,3-d]pyrimidin-4-yl]piperazine-1-carboxylate (210 mg, 299 µmol, 72% yield, 92% purity) as a yellow solid.

$^1$H NMR (400 MHz, chloroform-d) δ=9.15 (s, 1H), 8.00 (d, J=8.0 Hz, 1H), 7.95 (d, J=7.6 Hz, 1H), 7.80 (br d, J=8.4 Hz, 1H), 7.71-7.67 (m, 1H), 7.64-7.58 (m, 1H), 7.55-7.47 (m, 2H), 7.43-7.37 (m, 5H), 5.22 (s, 2H), 4.71 (br s, 1H), 4.61 (dd, J=4.8, 10.8 Hz, 1H), 4.50-4.35 (m, 3H), 4.33-4.09 (m, 1H), 3.94 (br s, 1H), 3.72 (dt, J=3.7, 11.7 Hz, 1H), 3.59 (br s, 1H), 3.18-3.07 (m, 1H), 2.87 (br s, 1H), 2.75 (br dd, J=6.0, 17.2 Hz, 2H), 2.51 (s, 3H), 2.35-2.26 (m, 1H), 2.11-2.01 (m, 1H), 1.94-1.79 (m, 3H).

Step D: To a solution of benzyl (2S)-2-(cyanomethyl)-4-[8-fluoro-2-[[(2S)-1-methylpyrrolidin-2-yl]methoxy]-7-(1-naphthyl)pyrido[4,3-d]pyrimidin-4-yl]piperazine-1-carboxylate (90 mg, 139 µmol, 1 eq) in MeOH (1 mL) was added NH$_3$.MeOH (1 mL, 20% purity), Pd/C (45 mg, 10% purity) under N$_2$. The suspension was degassed under vacuum and purged with H$_2$ several times. The mixture was stirred under H$_2$ (15 psi) at 25° C. for 1 hour. Upon completion, the catalyst was removed by filtering through a plug of celite. The solvent was removed under reduced pressure to give 2-[(2S)-4-[8-fluoro-2-[[(2S)-1-methylpyrrolidin-2-yl]methoxy]-7-(1-naphthyl)pyrido[4,3-d]pyrimidin-4-yl]piperazin-2-yl]acetonitrile (80 mg, 78.2 µmol, 50% purity) as a yellow solid. Taking 40 mg of impure product was purified by prep-HPLC (column: Xtimate C18 150*25 mm*5 µm; mobile phase: [water (0.05% ammonia hydroxide v/v)—ACN]; B %: 36%-66%, 1 min). The desired fractions were collected and lyophilized to give 2-[(2S)-4-[8-fluoro-2-[[(2S)-1-methylpyrrolidin-2-yl]methoxy]-7-(1-naphthyl)pyrido[4,3-d]pyrimidin-4-yl]piperazin-2-yl]acetonitrile (17.8 mg, 34.6 µmol, 88% yield, 99.5% purity) as a white solid.

$^1$H NMR (400 MHz, chloroform-d) δ=9.12 (s, 1H), 7.99 (d, J=8.4 Hz, 1H), 7.95 (d, J=8.0 Hz, 1H), 7.81 (br d, J=8.0 Hz, 1H), 7.71-7.67 (m, 1H), 7.64-7.58 (m, 1H), 7.56-7.50 (m, 1H), 7.50-7.45 (m, 1H), 4.60 (dd, J=4.4, 10.8 Hz, 1H), 4.56 (br d, J=12.8 Hz, 1H), 4.47-4.37 (m, 2H), 3.57 (ddd, J=3.2, 10.8, 13.2 Hz, 1H), 3.40-3.31 (m, 1H), 3.27-3.18 (m, 2H), 3.16-3.06 (m, 2H), 2.77-2.68 (m, 1H), 2.68-2.53 (m, 2H), 2.50 (s, 3H), 2.29 (dt, J=7.2, 9.2 Hz, 1H), 2.10-2.04 (m, 1H), 1.93-1.81 (m, 3H). LCMS [ESI, M+1]: 512.

Example 7: To a solution of 2-[(2S)-4-[8-fluoro-2-[[(2S)-1-methylpyrrolidin-2-yl]methoxy]-7-(1-naphthyl)pyrido[4,3-d]pyrimidin-4-yl]piperazin-2-yl]acetonitrile (50 mg, 97.7 µmol, 1 eq) and DIEA (37.9 mg, 293 µmol, 51.1 µL, 3 eq) in DCM (1 mL) was added prop-2-enoyl chloride (13.3 mg, 147 µmol, 12.0 µL, 1.5 eq) dropwise at –40° C. The mixture was stirred at –40° C. for 10 minutes. Upon completion, the mixture was quenched with saturated aqueous sodium bicarbonate (0.5 mL) and layers were separated. The aqueous phase was extracted with DCM (3 mL). Combined organic layers were dried over Na$_2$SO$_4$, filtered and concentrated under vacuum. The residue was purified by prep-HPLC (column: Xtimate C18 150*25 mm*5 um; mobile phase: [water (0.05% ammonia hydroxide v/v)—ACN]; B %: 40%-70%, 1 min). The desired fractions were collected and lyophilized to give 2-[(2S)-4-[8-fluoro-2-[[(2S)-1-methylpyrrolidin-2-yl]methoxy]-7-(1-naphthyl)pyrido[4,3-d]pyrimidin-4-yl]-1-prop-2-enoyl-piperazin-2-yl]acetonitrile (21.5 mg, 36.2 µmol, 37% yield, 95.2% purity) as a white solid.

$^1$H NMR (400 MHz, chloroform-d) δ=9.17 (s, 1H), 8.00 (d, J=8.0 Hz, 1H), 7.95 (d, J=7.6 Hz, 1H), 7.80 (br d, J=8.4 Hz, 1H), 7.72-7.66 (m, 1H), 7.65-7.58 (m, 1H), 7.56-7.44 (m, 2H), 6.67-6.49 (m, 1H), 6.48-6.36 (m, 1H), 5.92-5.80 (m, 1H), 5.00 (br s, 1H), 4.61 (dd, J=4.8, 10.8 Hz, 1H), 4.54-4.38 (m, 3H), 4.04 (br s, 2H), 3.91-3.54 (m, 2H), 3.19-3.07 (m, 1H), 3.02-2.89 (m, 1H), 2.87-2.66 (m, 2H), 2.51 (s, 3H), 2.30 (dt, J=7.2, 9.2 Hz, 1H), 2.16-2.02 (m, 1H), 1.95-1.76 (m, 3H). LCMS [ESI, M+1]: 566.

Example 8

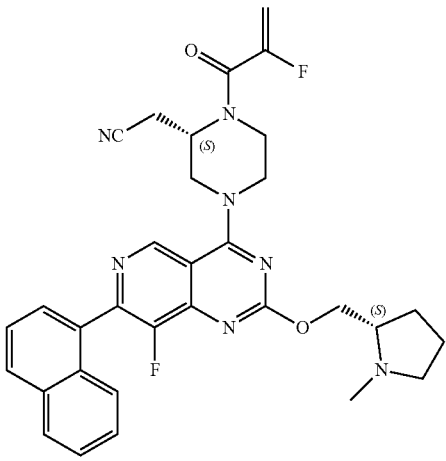

2-[(2S)-4-[8-fluoro-2-[[(2S)-1-methylpyrrolidin-2-yl]methoxy]-7-(1-naphthyl)pyrido[4,3-d]pyrimidin-4-yl]-1-(2-fluoroprop-2-enoyl)piperazin-2-yl]acetonitrile

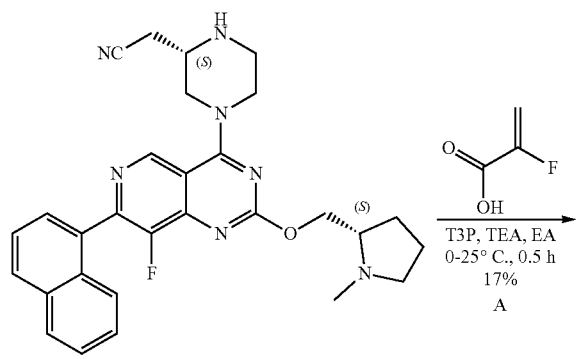

Example 8: To a solution of 2-[(2S)-4-[8-fluoro-2-[[(2S)-1-methylpyrrolidin-2-yl] methoxy]-7-(1-naphthyl)pyrido[4,3-d]pyrimidin-4-yl]piperazin-2-yl]acetonitrile (50 mg, 97.7 1 eq), T3P (187 mg, 293 μmol, 174 μL, 50% purity in EtOAc, 3 eq) and TEA (79.1 mg, 782 μmol, 109 μL, 8 eq) in EtOAc (1 mL) was added 2-fluoroprop-2-enoic acid (17.6 mg, 195 μmol, 2 eq) at 0° C. The mixture was stirred at 25° C. for 0.5 hour. Upon completion, the mixture was diluted with water (2 mL) and extracted with EtOAc (3×5 mL). The organic layers were dried over $Na_2SO_4$ and concentrated under vacuum. The residue was purified by prep-HPLC (column: Waters Xbridge 150*25 5μ; mobile phase: [water (0.05% ammonia hydroxide v/v)—ACN]; B %: 35%-65%, 10 min). The desired fractions were collected and lyophilized to give 2-[(2S)-4-[8-fluoro-2-[[(2S)-1-methylpyrrolidin-2-yl]methoxy]-7-(1-naphthyl)pyrido[4,3-d]pyrimidin-4-yl]-1-(2-fluoroprop-2-enoyl)piperazin-2-yl]acetonitrile (10.0 mg, 16.8 μmol, 17% yield, 97.7% purity) as a off-white solid.

$^1$H NMR (400 MHz, chloroform-d) δ=9.17 (s, 1H), 8.00 (d, J=8.0 Hz, 1H), 7.95 (d, J=7.6 Hz, 1H), 7.80 (br d, J=8.0 Hz, 1H), 7.72-7.66 (m, 1H), 7.64-7.58 (m, 1H), 7.56-7.51 (m, 1H), 7.50-7.44 (m, 1H), 5.57-5.39 (m, 1H), 5.29 (dd, J=4.4, 16.8 Hz, 1H), 4.87 (br s, 1H), 4.61 (dd, J=4.8, 10.8 Hz, 1H), 4.54-4.40 (m, 3H), 4.34-4.13 (m, 1H), 4.04 (br s, 1H), 3.78 (br s, 2H), 3.17-3.08 (m, 1H), 3.07-2.97 (m, 1H), 2.92-2.79 (m, 1H), 2.79-2.65 (m, 1H), 2.51 (s, 3H), 2.36-2.24 (m, 1H), 2.14-1.99 (m, 1H), 1.96-1.76 (m, 3H). LCMS [ESI, M+1]: 584.

Example 9

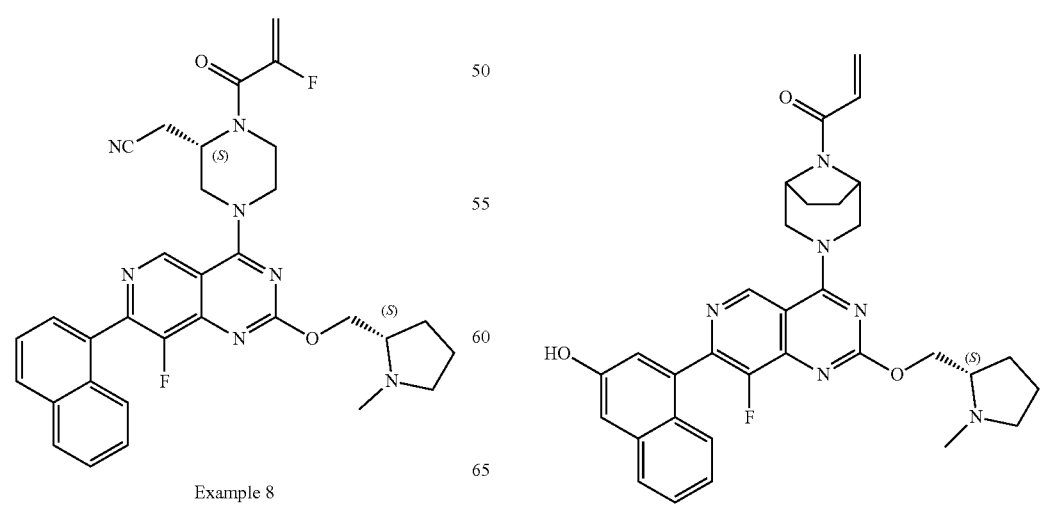

1-[3-[8-fluoro-7-(3-hydroxy-1-naphthyl)-2-[[(2S)-1-methylpyrrolidin-2-yl]methoxy]pyrido[4,3-d]pyrimidin-4-yl]-3,8-diazabicyclo[3.2.1]octan-8-yl]prop-2-en-1-one
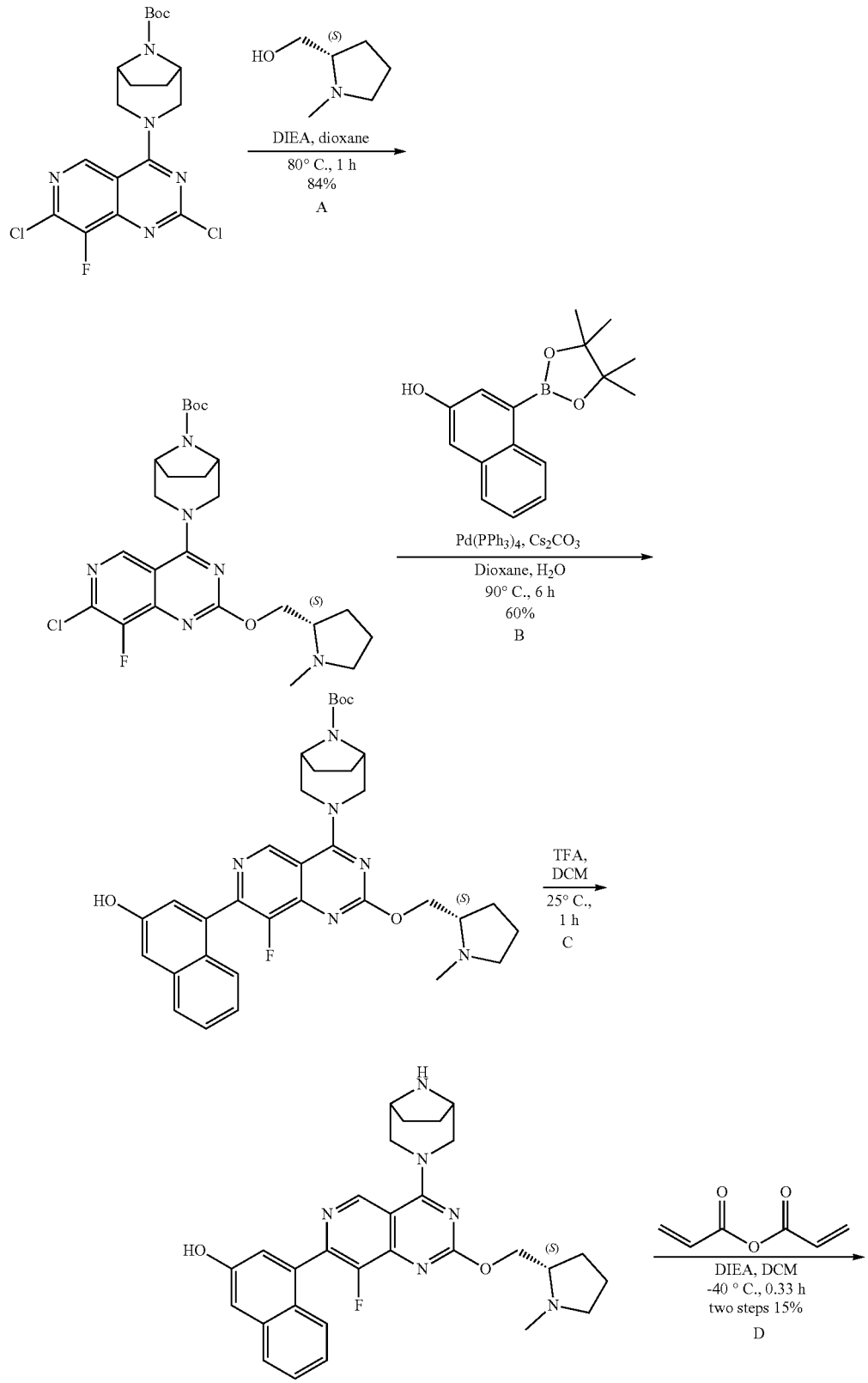

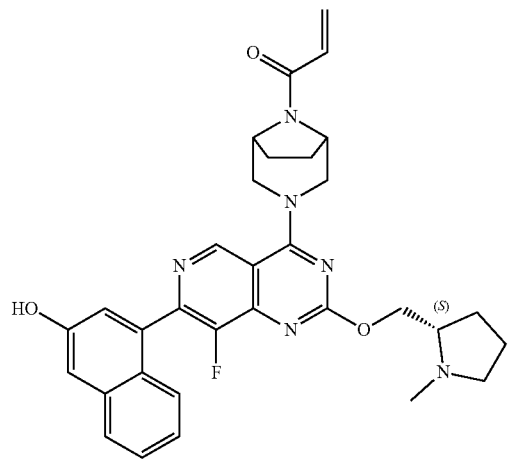

Example 9

Step A: To a solution of tert-butyl 3-(2,7-dichloro-8-fluoro-pyrido[4,3-d]pyrimidin-4-yl)-3,8-diazabicyclo[3.2.1]octane-8-carboxylate (400 mg, 934 µmol, 1 eq) and DIEA (362 mg, 2.80 mmol, 488 µL, 3 eq) in dioxane (8 mL) was added [(2S)-1-methyl pyrrolidin-2-yl]methanol (538 mg, 4.67 mmol, 554 µL eq). The reaction mixture was stirred at 80° C. for 1 hour. Upon completion, the mixture was diluted with water (10 mL) and extracted with EtOAc (2×40 mL). The organic layers were dried over $Na_2SO_4$ and concentrated under vacuum. The residue was purified by silica gel chromatography (Petroleum ether/Ethyl acetate 3/1 to Ethyl acetate/Methanol 5/1) to give tert-butyl 3-[7-chloro-8-fluoro-2-[[(2S)-1-methylpyrrolidin-2-yl]methoxy]pyrido[4,3-d]pyrimidin-4-yl]-3,8-diazabicyclo[3.2.1]octane-8-carboxylate (440 mg, 781 µmol, 84% yield, 90% purity) as a yellow solid.

$^1$H NMR (400 MHz, chloroform-d) δ=8.73 (s, 1H), 4.55 (dd, J=4.8, 10.8 Hz, 1H), 4.48 (br dd, J=7.2, 11.6 Hz, 2H), 4.35 (br dd, J=6.4, 10.8 Hz, 3H), 3.77-3.56 (m, 2H), 3.16 (br t, J=7.2 Hz, 1H), 2.77 (td, J=6.4, 13.2 Hz, 1H), 2.52 (s, 3H), 2.39-2.29 (m, 1H), 1.95-1.74 (m, 6H), 1.73-1.65 (m, 2H), 1.52 (s, 9H).

Step B: To a solution of tert-butyl 3-[7-chloro-8-fluoro-2-[[(2S)-1-methyl pyrrolidin-2-yl]methoxy]pyrido[4,3-d]pyrimidin-4-yl]-3,8-diazabicyclo[3.2.1]octane-8-carboxylate (420 mg, 828 µmol, 1 eq) and 4-(4,4,5,5-tetramethyl-1,3,2-dioxaborolan-2-yl) naphthalene-2-ol (403 mg, 1.49 mmol, 1.8 eq) in dioxane (12 mL) and $H_2O$ (3 mL) was added $Cs_2CO_3$ (540 mg, 1.66 mmol, 2 eq), $Pd(PPh_3)_4$ (95.7 mg, 82.8 µmol, 0.1 eq). The mixture was de-gassed and then heated to 90° C. for 6 hours under $N_2$. Upon completion, the mixture was diluted with water (10 mL) and extracted with EtOAc (2×40 mL). The organic layers were dried over $Na_2SO_4$ and concentrated under vacuum. The residue was purified by reversed phase flash [water (0.1% formic acid/acetonitrile]. The desired fractions were collected and neutralized with solid $NaHCO_3$, concentrated under vacuum to remove MeCN and extracted with EtOAc (2×40 mL). The organic layers were dried over $Na_2SO_4$ and concentrated under vacuum to give tert-butyl 3-[8-fluoro-7-(3-hydroxy-1-naphthyl)-2-[[(2S)-1-methylpyrrolidin-2-yl]methoxy]pyrido[4,3-d]pyrimidin-4-yl]-3,8-diazabicyclo[3.2.1]octane-8-carboxylate (340 mg, 498 µmol, 60% yield, 90% purity) as a yellow solid.

$^1$H NMR (400 MHz, chloroform-d) δ=8.95 (s, 1H), 7.67-7.58 (m, 2H), 7.36 (t, J=7.6 Hz, 1H), 7.27-7.17 (m, 3H), 4.57 (dd, J=5.2, 10.8 Hz, 1H), 4.51-4.41 (m, 2H), 4.41-4.20 (m, 3H), 3.59 (br s, 2H), 3.17 (br t, J=7.6 Hz, 1H), 2.86-2.74 (m, 1H), 2.56 (s, 3H), 2.40-2.34 (m, 1H), 1.97-1.74 (m, 6H), 1.62 (br d, J=7.6 Hz, 2H), 1.52 (s, 9H).

Step C: To a solution of tert-butyl 3-[8-fluoro-7-(3-hydroxy-1-naphthyl)-2-[[(2S)-1-methylpyrrolidin-2-yl]methoxy]pyrido[4,3-d]pyrimidin-4-yl]-3,8-diazabicyclo[3.2.1]octane-8-carboxylate (100 mg, 163 µmol, 1 eq) in DCM (0.1 mL) was added TFA (278 mg, 2.44 mmol, 181 µL, 15 eq). The mixture was stirred at 25° C. for 1 hour. Upon completion, the mixture was concentrated under vacuum to give 4-[4-(3,8-diazabicyclo[3.2.1]octan-3-yl)-8-fluoro-2-[[(2S)-1-methylpyrrolidin-2-yl]methoxy]pyrido[4,3-d]pyrimidin-7-yl]naphthalen-2-ol (100 mg, 90% purity, TFA) as a yellow oil. 4-[4-(3,8-diazabicyclo[3.2.1]octan-3-yl)-8-fluoro-2-[[(2S)-1-methylpyrrolidin-2-yl]methoxy]pyrido[4,3-d]pyrimidin-7-yl]naphthalen-2-ol (60 mg, TFA) was used directly in the next step without further purification. The rest of the TFA salt was diluted with DCM (1 mL) and neutralized with saturated $NaHCO_3$ solution. The separated aqueous layer was extracted with DCM (6×2 mL). Combined organic layers were dried over $Na_2SO_4$ and concentrated under vacuum to give 20 mg of impure product. The impure product was purified by prep-HPLC (column: Xtimate C18 150*25 mm*5 µm; mobile phase: [water (0.05% ammonia hydroxide v/v)—ACN]; B %: 22%-52%, 1 min). The desired fractions were collected and lyophilized to give 4-[4-(3,8-diazabicyclo[3.2.1]octan-3-yl)-8-fluoro-2-[[(2S)-1-methylpyrrolidin-2-yl]methoxy]pyrido[4,3-d]pyrimidin-7-yl]naphthalen-2-ol (7.92 mg, 99.4% purity) as a yellow solid.

$^1$H NMR (400 MHz, chloroform-d) δ=9.00 (s, 1H), 7.65 (t, J=8.0 Hz, 2H), 7.38 (t, J=7.6 Hz, 1H), 7.30 (d, J=2.4 Hz, 1H), 7.26-7.20 (m, 2H), 4.56 (dd, J=5.2, 10.8 Hz, 1H), 4.48 (br d, J=12.0 Hz, 2H), 4.35 (dd, J=6.0, 10.8 Hz, 1H), 3.62-3.48 (m, 4H), 3.14 (br t, J=8.0 Hz, 1H), 2.82-2.72 (m, 1H), 2.53 (s, 3H), 2.39-2.27 (m, 1H), 2.12-1.82 (m, 8H). LCMS [ESI, M+1]: 515.

Example 9: To a solution of 4-[4-(3,8-diazabicyclo[3.2.1]octan-3-yl)-8-fluoro-2-[[(2S)-1-methylpyrrolidin-2-yl]methoxy]pyrido[4,3-d]pyrimidin-7-yl]naphthalen-2-ol (60 mg, 95.5 µmol, 1 eq, TFA) and DIEA (493 mg, 3.82 mmol, 665 µL, 40 eq) in DCM (1.5 mL) was added prop-2-enoyl prop-2-enoate (9.63 mg, 76.4 µmol, 0.8 eq) dropwise at −40° C. The mixture was stirred at −40° C. for 10 minutes. Then prop-2-enoyl prop-2-enoate (5 mg) was added. The mixture was stirred at −40° C. for another 10 minutes. Upon completion, the mixture was quenched with MeOH (0.1 mL), added water (2 mL) and layers were separated. The aqueous phase was extracted with EtOAc (5 mL). Combined organic layers were dried over Na$_2$SO$_4$, filtered and concentrated under vacuum. The residue was purified by chromatography (Al$_2$O$_3$, Ethyl acetate/Methanol 15/1 to 5/1) followed by prep-HPLC (column: Xtimate C18 150*25 mm*5 µm; mobile phase: [water (0.05% ammonia hydroxide v/v)—ACN]; B %: 22%-52%, 1 min). The desired fractions were collected and lyophilized to give 1-[3-[8-fluoro-7-(3-hydroxy-1-naphthyl)-2-[[(2S)-1-methylpyrrolidin-2-yl]methoxy]pyrido[4,3-d]pyrimidin-4-yl]-3,8-diazabicyclo[3.2.1]octan-8-yl]prop-2-en-1-one (10.4 mg, 17.8 µmol, two steps 15% yield, 97.0% purity) as a white solid.

$^1$H NMR (400 MHz, chloroform-d) δ=8.92 (br s, 1H), 7.68 (d, J=8.4 Hz, 1H), 7.61 (br d, J=8.4 Hz, 1H), 7.38 (t, J=7.6 Hz, 1H), 7.29 (s, 1H), 7.26-7.20 (m, 2H), 6.46 (br d, J=4.8 Hz, 2H), 5.79 (t, J=6.0 Hz, 1H), 4.84 (br s, 1H), 4.57 (br dd, J=5.2, 10.8 Hz, 2H), 4.47 (br s, 1H), 4.39 (dd, J=5.6, 10.8 Hz, 1H), 4.28 (br s, 1H), 3.69 (br s, 1H), 3.50-3.35 (m, 1H), 3.18 (br t, J=7.6 Hz, 1H), 2.87-2.75 (m, 1H), 2.56 (s, 3H), 2.42-2.32 (m, 1H), 2.17-1.91 (m, 8H). LCMS [ESI, M+1]: 569.

Example 10

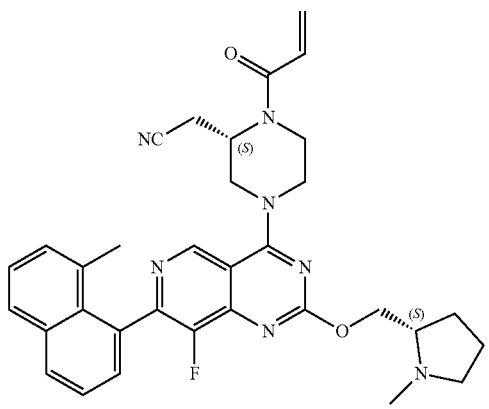

2-[(2S)-4-[8-fluoro-7-(8-methyl-1-naphthyl)-2-[[(2S)-1-methylpyrrolidin-2-yl]methoxy]pyrido[4,3-d]pyrimidin-4-yl]-1-prop-2-enoyl-piperazin-2-yl]acetonitrile

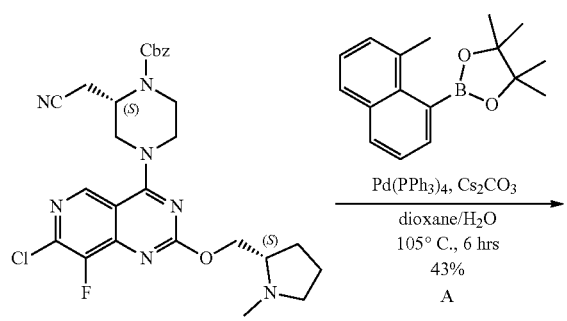

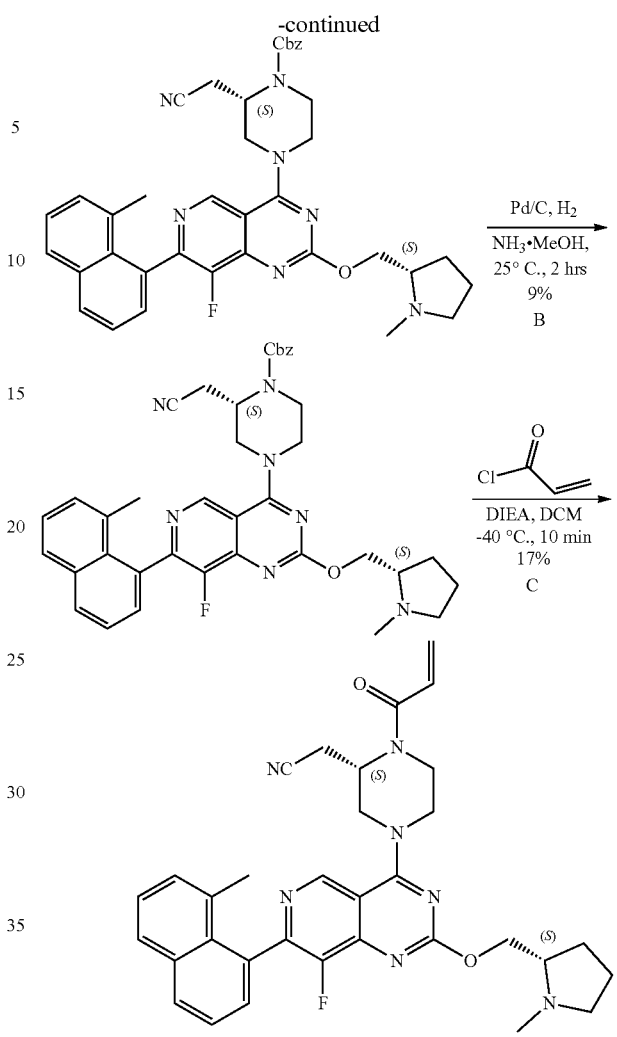

Step A: To a solution of benzyl (2S)-4-[7-chloro-8-fluoro-2-[[(2S)-1-methyl pyrrolidin-2-yl]methoxy]pyrido[4,3-d]pyrimidin-4-yl]-2-(cyanomethyl)piperazine-1-carboxylate (70 mg, 126 µmol, 1.0 eq) and 4,4,5,5-tetramethyl-2-(8-methyl-1-naphthyl)-1,3,2-di oxaborolane (50.8 mg, 190 µmol, 1.5 eq) in dioxane (1.5 mL) and H$_2$O (0.3 mL) was added Cs$_2$CO$_3$ (82.3 mg, 253 µmol, 2.0 eq), Pd(PPh$_3$)$_4$ (14.6 mg, 12.6 µmol, 0.1 eq). The mixture was de-gassed and then heated to 105° C. for 6 hours under N$_2$. Upon completion, the mixture was concentrated under vacuum, diluted with water (4 mL) and extracted with EtOAc (2×10 mL). The organic layers were dried over Na$_2$SO$_4$ and concentrated under vacuum. The residue was purified by reversed phase flash [water (0.1% formic acid/acetonitrile]. The desired fractions were collected and neutralized with solid NaHCO$_3$, concentrated under vacuum to remove MeCN and extracted with EtOAc (2×10 mL). The organic layers were dried over Na$_2$SO$_4$ and concentrated under vacuum to give benzyl (2S)-2-(cyanomethyl)-4-[8-fluoro-7-(8-methyl-1-naphthyl)-2-[[(2S)-1-methylpyrrolidin-2-yl]methoxy]pyrido[4,3-d]pyrimidin-4-yl]piperazine-1-carboxylate (40 mg, 54.6 µmol, 43% yield, 90% purity) as a yellow solid. LCMS [ESI, M+1]: 660.

Step B: To a solution of benzyl (2S)-2-(cyanomethyl)-4-[8-fluoro-7-(8-methyl-1-naphthyl)-2-[[(2S)-1-methylpyrrolidin-2-yl]methoxy]pyrido[4,3-d]pyrimidin-4-yl]piperazine-1-carboxylate (90 mg, 136 μmol, 1 eq) in MeOH (1.0 mL) was added NH₃.MeOH (1.5 mL, 20% purity), Pd/C (45 mg, 10% purity) under N₂. The suspension was degassed under vacuum and purged with H₂ several times. The mixture was stirred under H₂ (15 psi) at 25° C. for 2 hours. Upon completion, the catalyst was removed by filtering through a plug of Celite®. The solvent was removed under reduced pressure to give 60 mg of impure product. Taking 20 mg of the residue was purified by prep-HPLC (column: Xtimate C18 150*25 mm*5 μm; mobile phase: [water (0.05% ammonia hydroxide v/v)—ACN]; B %: 46%-76%, 10 min). The desired fractions were collected, concentrated under vacuum to remove MeCN and extracted with DCM (2×5 mL). The organic layers were dried over Na₂SO₄ and concentrated under vacuum. The crude product was purified by prep-HPLC (column: Phenomenex luna C18 150*25 10μ; mobile phase: [water (0.225% formic acid)—ACN]; B %: 10%-40%, 7.8 min). The desired fractions were collected and neutralized with solid NaHCO₃, concentrated under vacuum to remove MeCN and extracted with DCM (2×10 mL). The organic layers were dried over Na₂SO₄ and concentrated under vacuum to give 2-[(2S)-4-[8-fluoro-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (2.07 mg, 3.92 μmol, 9% yield, 99.5% purity) as a white solid.

¹H NMR (400 MHz, chloroform-d) δ=9.02 (s, 1H), 7.98 (dd, J=1.2, 8.4 Hz, 1H), 7.82 (d, J=8.0 Hz, 1H), 7.57-7.51 (m, 1H), 7.45 (d, J=6.8 Hz, 1H), 7.41 (t, J=7.6 Hz, 1H), 7.29 (br d, J=7.2 Hz, 1H), 4.64-4.49 (m, 2H), 4.47-4.33 (m, 2H), 3.64-3.48 (m, 1H), 3.40-3.30 (m, 1H), 3.28-3.18 (m, 2H), 3.17-3.05 (m, 2H), 2.79-2.68 (m, 1H), 2.68-2.53 (m, 2H), 2.50 (d, J=1.6 Hz, 3H), 2.35-2.26 (m, 1H), 2.12-2.05 (m, 4H), 1.86-1.76 (m, 3H). LCMS [ESI, M+1]: 526.

Example 10: To a solution of 2-[(2S)-4-[8-fluoro-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (40 mg, 76.1 μmol, 1.0 eq) and DIEA (29.5 mg, 228 μmol, 39.8 μL, 3.0 eq) in DCM (1.0 mL) was added prop-2-enoyl chloride (10.3 mg, 114 μmol, 9.31 μL, 1.5 eq) dropwise at −40° C. The mixture was stirred at −40° C. for 10 minutes. Upon completion, the mixture was quenched with saturated aqueous sodium bicarbonate (0.5 mL) and layers were separated. The aqueous phase was extracted with DCM (5×3 mL). Combined organic layers were dried over Na₂SO₄, filtered and concentrated under vacuum. The residue was purified by prep-HPLC (column: Waters Xbridge 150*25 5μ; mobile phase: [water (10 mM NH₄HCO₃)—ACN]; B %: 35%-65%, 10 min). The desired fractions were collected and lyophilized to give 2-[(2S)-4-[8-fluoro-7-(8-methyl-1-naphthyl)-2-[[(2S)-1-methylpyrrolidin-2-yl]methoxy]pyrido[4,3-d]pyrimidin-4-yl]-1-prop-2-enoyl-piperazin-2-yl]acetonitrile (7.41 mg, 12.6 μmol, 17% yield, 98.6% purity) as a white solid.

¹H NMR (400 MHz, chloroform-d) δ=9.09 (d, J=2.4 Hz, 1H), 7.99 (dd, J=1.2, 8.4 Hz, 1H), 7.82 (d, J=8.0 Hz, 1H), 7.54 (dt, J=3.6, 7.6 Hz, 1H), 7.48-7.39 (m, 2H), 7.30 (br d, J=4.4 Hz, 1H), 6.66-6.50 (m, 1H), 6.48-6.36 (m, 1H), 5.86 (br d, J=10.4 Hz, 1H), 5.02 (br s, 1H), 4.65-4.57 (m, 1H), 4.55-4.38 (m, 3H), 4.29-3.56 (m, 4H), 3.19-3.08 (m, 1H), 3.06-2.91 (m, 1H), 2.87-2.66 (m, 2H), 2.52 (d, J=1.6 Hz, 3H), 2.38-2.25 (m, 1H), 2.10-2.02 (m, 4H), 1.94-1.78 (m, 3H). LCMS [ESI, M+1]: 580.

Example 11

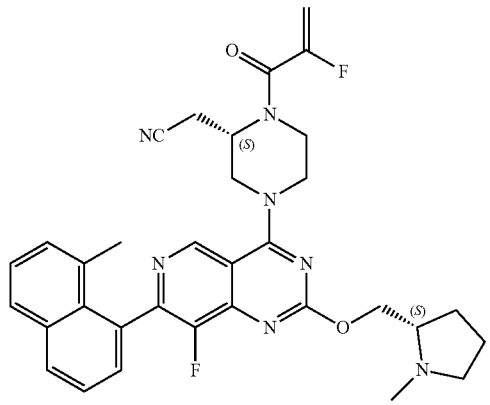

2-[(2S)-4-[8-fluoro-7-(8-methyl-1-naphthyl)-2-[[(2S)-1-methylpyrrolidin-2-yl]methoxy]pyrido[4,3-d]pyrimidin-4-yl]-1-(2-fluoroprop-2-enoyl)piperazin-2-yl]acetonitrile

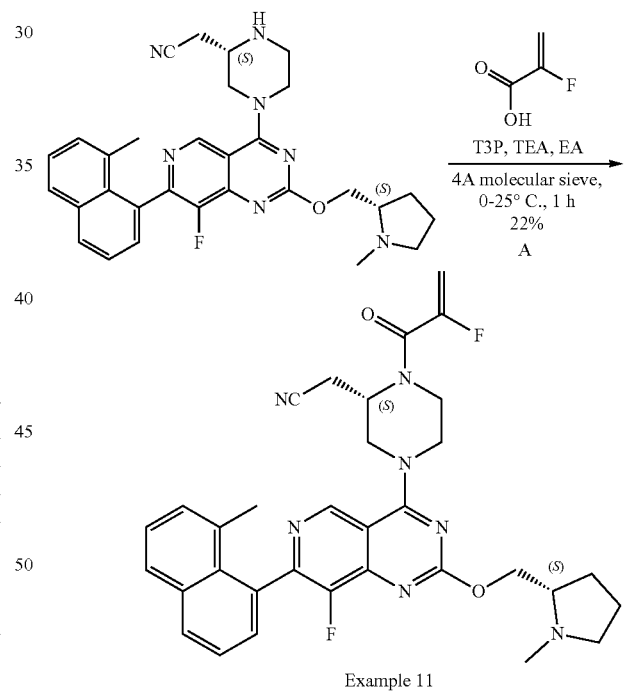

Example 11

Example 11: To a solution of 2-[(2S)-4-[8-fluoro-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (80 mg, 152 μmol, 1.0 eq), 2-fluoroprop-2-enoic acid (27.4 mg, 304 μmol, 2.0 eq) in ethyl acetate (1.6 mL) was added 4A molecular sieve (40 mg). After stirring at 25° C. for 0.5 hour, T3P (291 mg, 457 μmol, 272 μL, 50% purity in ethyl acetate, 3.0 eq) and TEA (123 mg, 1.22 mmol, 169 μL, 8.0 eq) was added at 0° C. The mixture was stirred at 25° C. for 0.5 hour. Upon completion, the mixture was diluted with water (2 mL) and extracted with ethyl acetate (4×5 mL). The organic layers were dried over Na₂SO₄ and concentrated under vacuum. The residue was purified by chromatography (Al₂O₃, petroleum ether/ethyl acetate 10/1 to ethyl acetate/methanol 10/1) followed by prep-HPLC (column: Waters Xbridge 150*25 5μ; mobile phase: [water (0.05% ammonia hydroxide v/v)—ACN]; B %: 42%-72%, 10 min). The desired fractions were collected and lyophilized to give 2-[(2S)-4-[8-fluoro-7-(8-methyl-1-naphthyl)-2-[[(2S)-1-methylpyrrolidin-2-yl]methoxy]pyrido[4,3-d]pyrimidin-4-yl]-1-(2-fluoroprop-2-enoyl)piperazin-2-yl]acetonitrile (20.1 mg, 33.2 μmol, 22% yield, 98.5% purity) as a white solid.

¹H NMR (400 MHz, chloroform-d) δ=9.08 (d, J=2.0 Hz, 1H), 8.02-7.96 (m, 1H), 7.82 (d, J=8.0 Hz, 1H), 7.58-7.50 (m, 1H), 7.49-7.38 (m, 2H), 7.32-7.28 (m, 1H), 5.58-5.37 (m, 1H), 5.34-5.23 (m, 1H), 4.98-4.71 (m, 1H), 4.65-4.56 (m, 1H), 4.55-4.35 (m, 3H), 4.34-3.91 (m, 2H), 3.90-3.56 (m, 2H), 3.16-3.08 (m, 1H), 3.07-2.95 (m, 1H), 2.91-2.79 (m, 1H), 2.78-2.67 (m, 1H), 2.54-2.47 (m, 3H), 2.36-2.26 (m, 1H), 2.13-2.00 (m, 4H), 1.93-1.73 (m, 3H). LCMS [ESI, M+1]: 598.

Example 12

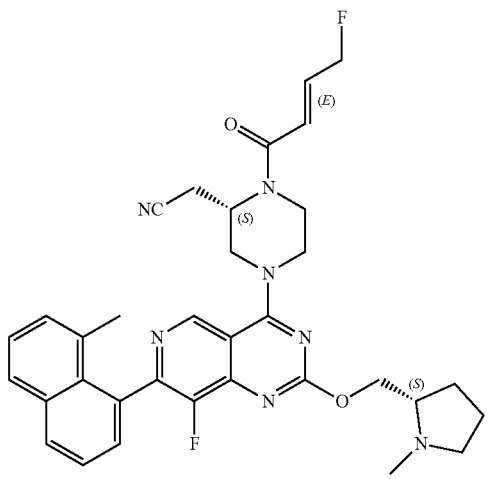

2-[(2S)-1-[(E)-4-fluorobut-2-enoyl]-4-[8-fluoro-7-(8-methyl-1-naphthyl)-2-[[(2S)-1-methylpyrrolidin-2-yl]methoxy]pyrido[4,3-d]pyrimidin-4-yl]piperazin-2-yl]acetonitrile

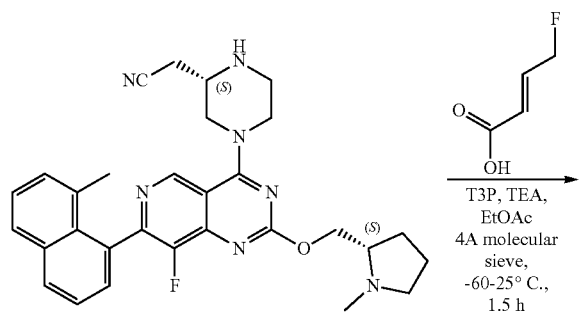

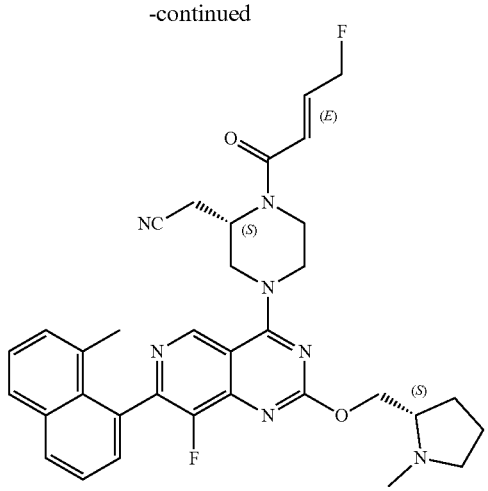

Example 12

Example 12: To a solution of 2-[(2S)-4-[8-fluoro-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (80 mg, 152 μmol, 1.0 eq), (E)-4-fluorobut-2-enoic acid (31.7 mg, 304 μmol, 2.0 eq) in ethyl acetate (1.6 mL) was added 4A molecular sieve (40 mg). After stirring at 25° C. for 0.5 hour, TEA (123 mg, 1.22 mmol, 169 μL, 8.0 eq) and T3P (291 mg, 457 μmol, 272 μL, 50% purity in ethyl acetate, 3.0 eq) were added at −60° C. The mixture was stirred at −60° C. for 0.5 hour. Then (E)-4-fluorobut-2-enoic acid (31.7 mg, 304 μmol, 2.0 eq), T3P (291 mg, 457 μmol, 272 uL, 50% purity in ethyl acetate, 3.0 eq), TEA (123 mg, 1.22 mmol, 169 uL, 8.0 eq) were added at −60° C. The mixture was stirred at −60° C. for 0.5 hour. Upon completion, the mixture was diluted with water (3 mL) and extracted with ethyl acetate (4×5 mL). The organic layers were dried over Na₂SO₄ and concentrated under vacuum. The residue was purified by chromatography (Al₂O₃, petroleum ether/ethyl acetate 10/1 to ethyl acetate/methanol 10/1) followed by prep-HPLC (column: Xtimate C18 150*25 mm*5 um; mobile phase: [water (0.05% ammonia hydroxide v/v)—ACN]; B %: 43%-73%, 10 min). The desired fractions were collected and lyophilized to give 2-[(2S)-1-[(E)-4-fluorobut-2-enoyl]-4-[8-fluoro-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (32.5 mg, 53.0 μmol, 35% yield, 99.8% purity) as a white solid.

¹H NMR (400 MHz, chloroform-d) δ=9.09 (d, J=2.8 Hz, 1H), 7.99 (dd, J=1.2, 8.4 Hz, 1H), 7.82 (d, J=8.0 Hz, 1H), 7.54 (dt, J=3.6, 7.6 Hz, 1H), 7.49-7.38 (m, 2H), 7.33-7.27 (m, 1H), 7.11-6.95 (m, 1H), 6.65-6.52 (m, 1H), 5.30-4.85 (m, 3H), 4.65-4.56 (m, 1H), 4.55-4.36 (m, 3H), 4.26-3.25 (m, 4H), 3.18-3.07 (m, 1H), 3.05-2.91 (m, 1H), 2.89-2.65 (m, 2H), 2.55-2.45 (m, 3H), 2.36-2.25 (m, 1H), 2.12-2.00 (m, 4H), 1.94-1.77 (m, 3H). LCMS [ESI, M+1]: 612.

Example 13

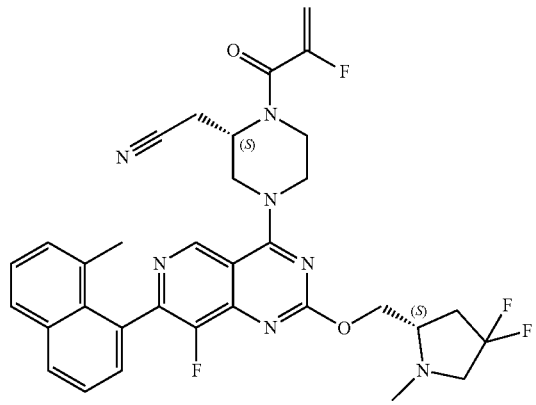

2-((S)-4-(2-(((S)-4,4-difluoro-1-methylpyrrolidin-2-yl)methoxy)-8-fluoro-7-(8-methylnaphthalen-1-yl)pyrido[4,3-d]pyrimidin-4-yl)-1-(2-fluoroacryloyl)piperazin-2-yl)acetonitrile

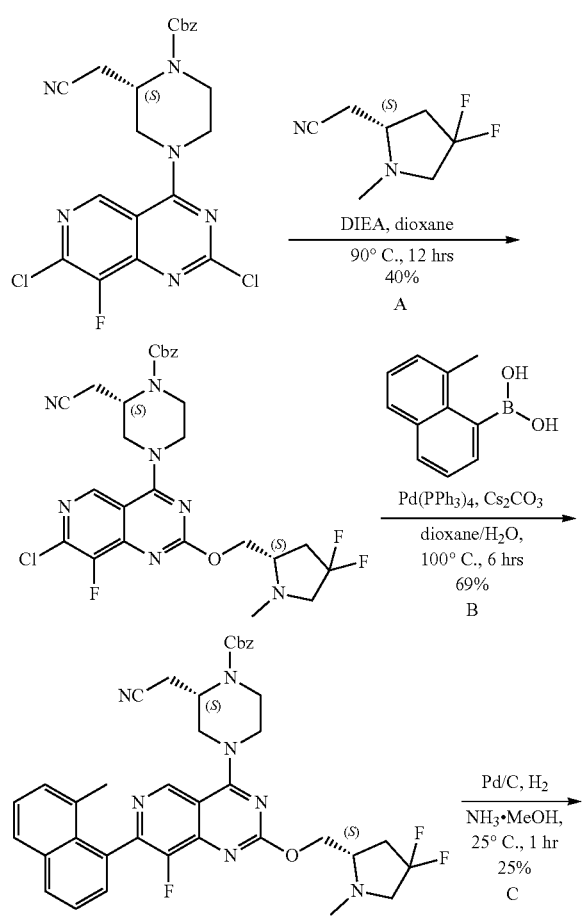

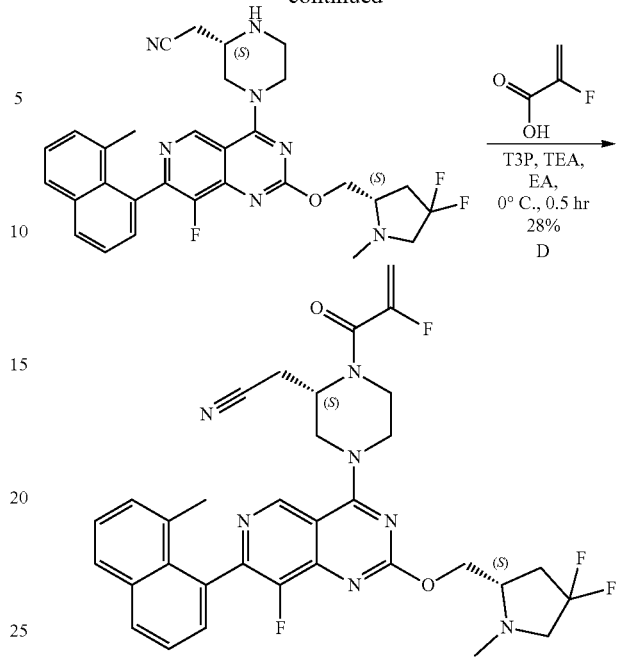

Step A: To a solution of [(2S)-4,4-difluoro-1-methyl-pyrrolidin-2-yl] methanol (954 mg, 6.31 mmol, 3.0 eq) in dioxane (10 mL) was added DIEA (816 mg, 6.31 mmol, 1.1 mL, 3.0 eq) and benzyl (2S)-2-(cyanomethyl)-4-(2,7-dichloro-8-fluoro-pyrido[4,3-d]pyrimidin-4-yl)piperazine-1-carboxylate (1 g, 2.10 mmol, 1.0 eq). The mixture was stirred at 90° C. for 12 hours. The reaction mixture was diluted with water (30 mL) and extracted with ethyl acetate (3×50 mL). The combined organic layers were washed with brine (20 mL), dried over $Na_2SO_4$, filtered and concentrated under reduced pressure. The residue was purified by reversed phase flash [water (0.1% formic acid)/acetonitrile]. The mixture was adjusted pH ~7 with saturated $NaHCO_3$ aqueous solution and extracted with ethyl acetate (3×20 mL). The combined organic layers were washed with brine (20 mL), dried over $Na_2SO_4$, filtered and concentrated under reduced pressure to give the product. benzyl (2S)-4-[7-chloro-2-[[(2S)-4,4-difluoro-1-methyl-pyrrolidin-2-yl]methoxy]-8-fluoro-pyrido[4,3-d]pyrimidin-4-yl]-2-(cyanomethyl)piperazine-1-carboxylate (550 mg, 848 μmol, 40% yield, 91% purity) was obtained as a yellow solid. LCMS [ESI, M+1]: 590.

$^1$H NMR (400 MHz, chloroform-d) δ=8.82 (s, 1H), 7.45-7.32 (m, 5H), 5.20 (s, 2H), 4.73-4.58 (m, 2H), 4.56-4.48 (m, 1H), 4.45-4.27 (m, 2H), 4.25-4.11 (m, 1H), 4.00 (br s, 1H), 3.78-3.52 (m, 2H), 3.44 (dt, J=5.6, 11.6 Hz, 1H), 3.07-2.97 (m, 1H), 2.96-2.62 (m, 3H), 2.59-2.44 (m, 4H), 2.39-2.24 (m, 1H).

Step B: A mixture of benzyl (2S)-4-[7-chloro-2-[[(2S)-4,4-difluoro-1-methyl-pyrrolidin-2-yl]methoxy]-8-fluoro-pyrido[4,3-d]pyrimidin-4-yl]-2-(cyanomethyl)piperazine-1-carboxylate (500 mg, 847 μmol, 1.0 eq), (8-methyl-1-naphthyl) boronic acid (236 mg, 1.27 mmol, 1.5 eq), $Cs_2CO_3$ (552 mg, 1.69 mmol, 2.0 eq), $Pd(PPh_3)_4$ (97.9 mg, 84.7 μmol, 0.1 eq) in dioxane (10 mL) and $H_2O$ (2 mL) was degassed and purged with $N_2$ for 3 times, and then the mixture was stirred at 100° C. for 6 hours under $N_2$ atmosphere. The reaction mixture was diluted with water (20 mL) and extracted with ethyl acetate (3×50 mL). The combined organic layers were washed with brine (20 mL), dried over Na₂SO₄, filtered and concentrated under reduced pressure to give a residue. The residue was purified by column chromatography (SiO₂, Petroleum ether/Ethyl acetate=20/1 to 1/1). benzyl (2S)-2-(cyanomethyl)-4-[2-[[(2S)-4,4-difluoro-1-methyl-pyrrolidin-2-yl]methoxy]-8-fluoro-7-(8-methyl-1-naphthyl)pyrido[4,3-d]pyrimidin-4-yl]piperazine-1-carboxylate (450 mg, 588 μmol, 69% yield, 91% purity) was obtained as a yellow solid. LCMS [ESI, M+1]: 696.

Step C: To a solution of benzyl (2S)-2-(cyanomethyl)-4-[2-[[(2S)-4,4-difluoro-1-methyl-pyrrolidin-2-yl]methoxy]-8-fluoro-7-(8-methyl-1-naphthyl)pyrido[4,3-d]pyrimidin-4-yl]piperazine-1-carboxylate (30 mg, 43.1 μmol, 1.0 eq) in methanol (2 mL) was added dry Pd/C (10 mg, 10% purity) and NH₃.MeOH (1 mL, 20% purity) under N₂. The suspension was degassed under vacuum and purged with H₂ several times. The mixture was stirred under H₂ (15 psi) at 25° C. for 1 hour. The reaction mixture was concentrated under vacuum. The residue was purified by prep-HPLC (column: Waters Xbridge 150*25 5μ; mobile phase: [water (0.05% ammonia hydroxide v/v)—ACN]; B %: 35%-65%, 10 min). The desired fraction was collected and lyophilized. 2-[(2S)-4-[2-[[(2S)-4,4-difluoro-1-methyl-pyrrolidin-2-yl]methoxy]-8-fluoro-7-(8-methyl-1-naphthyl)pyrido[4,3-d]pyrimidin-4-yl]piperazin-2-yl]acetonitrile (6.23 mg, 11.0 μmol, 25% yield, 99.2% purity) was obtained as white solid. LCMS [ESI, M+1]: 562.

¹H NMR (400 MHz, chloroform-d) δ=9.04 (s, 1H), 7.99 (dd, J=1.2, 8.0 Hz, 1H), 7.82 (d, J=8.0 Hz, 1H), 7.62-7.51 (m, 1H), 7.49-7.38 (m, 2H), 7.29 (br d, J=7.2 Hz, 1H), 4.69-4.61 (m, 1H), 4.60-4.48 (m, 2H), 4.43 (br d, J=14.0 Hz, 1H), 3.66-3.53 (m, 1H), 3.44 (dt, 11.6 Hz, 1H), 3.39-3.30 (m, 1H), 3.28-3.19 (m, 2H), 3.18-3.00 (m, 2H), 2.79-2.65 (m, 1H), 2.64-2.46 (m, 6H), 2.44-2.26 (m, 1H), 2.07 (s, 3H).

Example 13: To a solution of 2-[(2S)-4-[2-[[(2S)-4,4-difluoro-1-methyl-pyrrolidin-2-yl]methoxy]-8-fluoro-7-(8-methyl-1-naphthyl)pyrido[4,3-d]pyrimidin-4-yl]piperazin-2-yl]acetonitrile (80 mg, 142 μmol, 1.0 eq) and 2-fluoroprop-2-enoic acid (38.5 mg, 427 μmol, 3.0 eq) in ethyl acetate (2 mL) was added T3P (272 mg, 427 μmol, 254 μL, 50% purity in ethyl acetate, 3.0 eq) and TEA (115 mg, 1.14 mmol, 158 μL, 8.0 eq). The mixture was stirred at 0° C. for 30 min. The reaction mixture was diluted with water (20 mL) and extracted with ethyl acetate (3×30 mL). The combined organic layers were washed with brine (20 mL), dried over Na₂SO₄, filtered and concentrated under reduced pressure to give a residue. The residue was purified by column chromatography (SiO₂, Ethyl acetate/Methanol=100/1 to 10/1) and further purification by prep-HPLC (column: Waters Xbridge 150*25 5μ; mobile phase: [water (0.05% ammonia hydroxide v/v)—ACN]; B %: 38%-68%, 10 min). The desired fraction was collected and lyophilized. 2-[(2S)-4-[2-[[(2S)-4,4-difluoro-1-methyl-pyrrolidin-2-yl]methoxy]-8-fluoro-7-(8-methyl-1-naphthyl)pyrido[4,3-d]pyrimidin-4-yl]-1-(2-fluoroprop-2-enoyl)piperazin-2-yl]acetonitrile (25 mg, 39.4 μmol, 28% yield, 100% purity, 100% ee) was obtained as a white solid. LCMS [ESI, M+1]: 634.

¹H NMR (400 MHz, chloroform-d) δ=9.10 (d, J=2.4 Hz, 1H), 8.00 (dd, J=1.2, 8.0 Hz, 1H), 7.83 (d, J=8.0 Hz, 1H), 7.55 (dt, J=2.4, 7.6 Hz, 1H), 7.49-7.39 (m, 2H), 7.32-7.27 (m, 1H), 5.49 (dd, J=2.8, 47.2 Hz, 1H), 5.36-5.23 (m, 1H), 4.86 (s, 1H), 4.71-4.61 (m, 1H), 4.59-4.38 (m, 3H), 4.35-3.55 (m, 4H), 3.45 (dt, J=5.6, 11.6 Hz, 1H), 3.11-2.95 (m, 2H), 2.92-2.79 (m, 1H), 2.71 (dt, J=11.2, 16.4 Hz, 1H), 2.63-2.45 (m, 4H), 2.43-2.26 (m, 1H), 2.06 (d, J=8.0 Hz, 3H).

Example 14

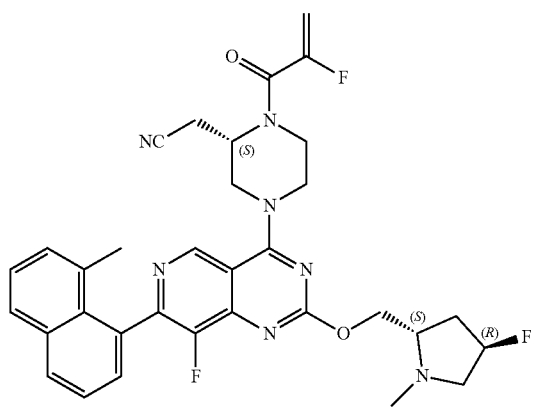

2-[(2S)-4-[8-fluoro-2-[[(2S,4R)-4-fluoro-1-methyl-pyrrolidin-2-yl]methoxy]-7-(8-methyl-1-naphthyl)pyrido[4,3-d]pyrimidin-4-yl]-1-(2-fluoroprop-2-enoyl)piperazin-2-yl]acetonitrile

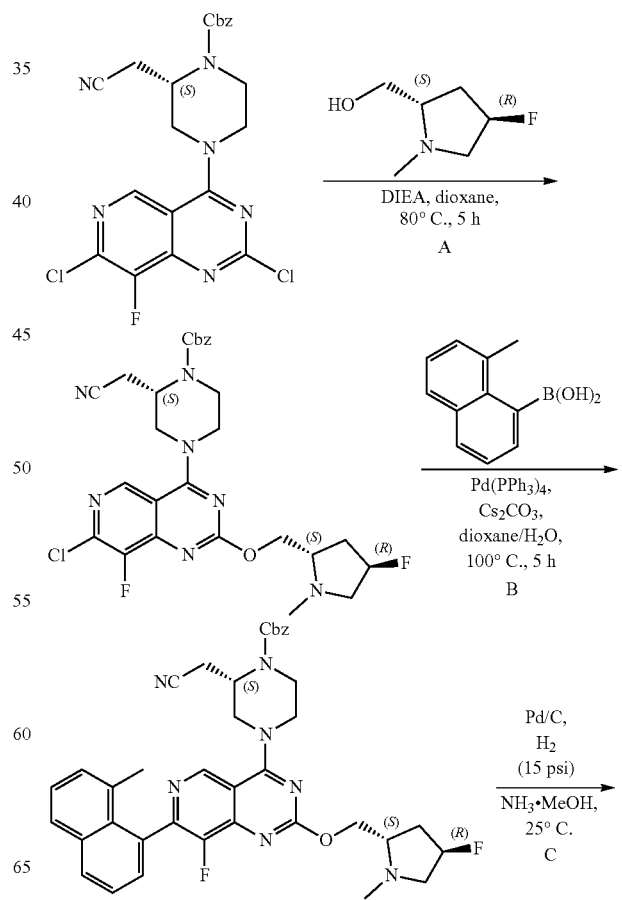

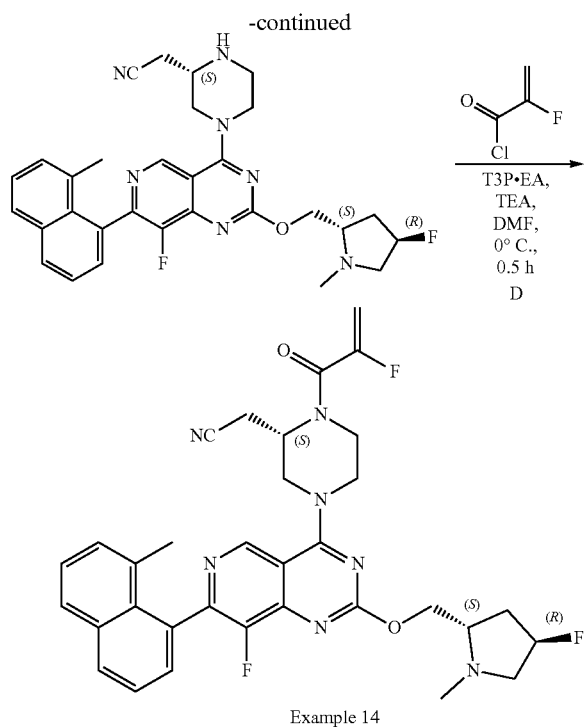

Example 14

Step A: To a mixture of benzyl (2S)-2-(cyanomethyl)-4-(2,7-dichloro-8-fluoro-pyrido[4,3-d]pyrimidin-4-yl)piperazine-1-carboxylate (700 mg, 1.5 mmol, 1.0 eq) in dioxane (7.0 mL) was added DIEA (571 mg, 4.4 mmol, 769 μL, 3.0 eq) and [(2S,4R)-4-fluoro-1-methyl-pyrrolidin-2-yl]methanol (392 mg, 2.9 mmol, 2.0 eq) at 25° C. The mixture was stirred at 80° C. for 5 hrs. The mixture was diluted with saturated NH$_4$Cl aqueous solution (100 mL), and then extracted with ethyl acetate (100 mL×2), the combined organic layers were concentrated under reduced pressure at 45° C. The crude product was purified by reversed-phase HPLC (0.1% formic acid conditions). The desired fractions were collected, concentrated to remove acetonitrile and adjusted to pH 9~10 using Na$_2$CO$_3$ solid. Then the mixture was extracted with ethyl acetate (60 mL×3), the organic layers were dried over anhydrous Na$_2$SO$_4$, filtered and the filtrate was concentrated under reduced pressure at 45° C. to give compound benzyl(2S)-4-[7-chloro-8-fluoro-2-[[(2S,4R)-4-fluoro-1-methyl-pyrrolidin-2-yl]methoxy]pyrido[4,3-d]pyrimidin-4-yl]-2-(cyanomethyl)piperazine-1-carboxylate (400 mg, 699 μmol, 47.5% yield, 100% purity) as a yellow solid. LCMS [M+1]: 572.

Step B: To a mixture of benzyl (2S)-4-[7-chloro-8-fluoro-2-[[(2S,4R)-4-fluoro-1-methyl-pyrrolidin-2-yl]methoxy]pyrido[4,3-d]pyrimidin-4-yl]-2-(cyanomethyl)piperazine-1-carboxylate (250 mg, 437 μmol, 1.0 eq), (8-methyl-1-naphthyl) boronic acid (122 mg, 655 μmol, 1.5 eq), Pd(PPh$_3$)$_4$ (101 mg, 87.4 μmol, 0.2 eq) in dioxane (5.0 mL) and H$_2$O (1.0 mL) was added Cs$_2$CO$_3$ (427 mg, 1.3 mmol, 3.0 eq) at 25° C. The mixture was stirred at 100° C. for 5 hrs. The mixture was diluted with water (100 mL), and then extracted with ethyl acetate (80 mL×2), the combined organic layers were concentrated under reduced pressure at 40° C. The residue was purified by column chromatography (MgO, Petroleum ether/Ethyl acetate=5/1 to 1:1). The obtained product was further purified by reversed-phase HPLC (0.1% FA condition), then the mixture was concentrated to remove acetonitrile and extracted with ethyl acetate (100 mL×3), the organic layers were dried over anhydrous Na$_2$SO$_4$, filtered and the filtrate was concentrated under reduced pressure at 45° C. to give compound benzyl (2S)-2-(cyanomethyl)-4-[8-fluoro-2-[[(2S,4R)-4-fluoro-1-methyl-pyrrolidin-2-yl]methoxy]-7-(8-methyl-1-naphthyl)pyrido[4,3-d]pyrimidin-4-yl]piperazine-1-carboxylate (173 mg, 245 μmol, 56.1% yield, 96% purity) as a yellow solid. LCMS [M+1]: 678.

Step C: To a solution of benzyl (2S)-2-(cyanomethyl)-4-[8-fluoro-2-[[(2S,4R)-4-fluoro-1-methyl-pyrrolidin-2-yl]methoxy]-7-(8-methyl-1-naphthyl)pyrido[4,3-d]pyrimidin-4-yl]piperazine-1-carboxylate (30 mg, 44 μmol, 1.0 eq) in methyl alcohol (3.0 mL) and NH$_3$.MeOH (0.5 mL, 10% purity) was added Pd/C (100 mg, 10% purity) under N$_2$. The suspension was degassed under vacuum and purged with H$_2$ several times. The mixture was stirred under H$_2$ (15 psi) at 25° C. for 2 hours. The mixture was filtered, washed with methyl alcohol (20 mL), the filtrate was concentrated under reduced pressure at 40° C. The residue was purified by prep-HPLC (FA condition; column: Phenomenex Synergi C18 150*30 mm*4 μm; mobile phase: [water (0.225% formic acid)—ACN]; B %: 5%-35%, 10 min.). The desired fraction was collected and concentrated under reduced pressure at 40° C. to removed acetonitrile, and the residual aqueous solution was adjusted to pH 9~10 using Na$_2$CO$_3$ solid, then extracted with dichloromethane (20 mL×3), the combined organic layers was dried over anhydrous Na$_2$SO$_4$, filtered and the filtrated was concentrated under reduced pressure at 40° C. The residue was lyophilized to give compound 2-[(2S)-4-[8-fluoro-2-[[(2S,4R)-4-fluoro-1-methyl-pyrrolidin-2-yl]methoxy]-7-(8-methyl-1-naphthyl)pyrido[4,3-d]pyrimidin-4-yl]piperazin-2-yl]acetonitrile (9 mg, 16.3 μmol, 36.8% yield, 98.4% purity) as a white solid. LCMS [M+1]: 544.

$^1$H NMR (400 MHz, chloroform-d) δ=2.01-2.14 (m, 4H), 2.25-2.41 (m, 1H), 2.54 (d, J=0.8 Hz, 3H), 2.55-2.69 (m, 3H), 3.05-3.17 (m, 2H), 3.18-3.28 (m, 2H), 3.35 (ddd, J=7.2, 5.2, 2.4 Hz, 1H), 3.50-3.66 (m, 2H), 4.37-4.45 (m, 1H), 4.48 (ddd, J=11.2, 5.6, 2.4 Hz, 1H), 4.51-4.58 (m, 1H), 4.59-4.66 (m, 1H), 5.05-5.32 (m, 1H), 7.29 (d, J=6.8 Hz, 1H), 7.39-7.47 (m, 2H), 7.51-7.57 (m, 1H), 7.82 (d, J=8.0 Hz, 1H), 7.98 (dd, J=8.0, 1.2 Hz, 1H), 9.03 (s, 1H).

Example 14: To a mixture of 2-[(2S)-4-[8-fluoro-2-[[(2S,4R)-4-fluoro-1-methyl-pyrrolidin-2-yl]methoxy]-7-(8-methyl-1-naphthyl)pyrido[4,3-d]pyrimidin-4-yl]piperazin-2-yl]acetonitrile (100 mg, 184 μmol, 1.0 eq), 2-fluoroprop-2-enoic acid (166 mg, 1.8 mmol, 10 eq) in DMF (2 mL) was added T3P (585 mg, 920 μmol, 547 μL, 50% purity, 5.0 eq) and TEA (186 mg, 1.8 mmol, 256 μL, 10 eq) at 0° C. The mixture was stirred at 0° C. for 1 hour. The mixture was diluted with saturated NH$_4$Cl aqueous solution (30 mL), then extracted with ethyl acetate (20 mL×2), the combined organic layers were washed with brine (30 mL×3) and concentrated under reduced pressure at 40° C. The crude product was first purified by reversed-phase HPLC (0.1% FA condition). The desired fraction was collected and concentrated under reduced pressure at 40° C. to removed acetonitrile, and the residual aqueous solution was adjusted to pH 9-10 using Na$_2$CO$_3$ solid, then extracted ethyl acetate (20 mL×3), the combined organic layers were dried over anhydrous Na$_2$SO$_4$, filtered and the filtrated was concentrated under reduced pressure at 40° C. The residue was then purified by prep-HPLC (basic condition, column: Xtimate C18 150*25 mm*5 μm; mobile phase: [water (0.05% ammonia hydroxide v/v)—ACN]; B %: 40%-70%, 10 min) and lyophilized to give compound 2-[(2S)-4-[8-fluoro-2-[[(2S,4R)-4-fluoro-1-methyl-pyrrolidin-2-yl]methoxy]-7-

(8-methyl-1-naphthyl)pyrido[4,3-d]pyrimidin-4-yl]-1-(2-fluoroprop-2-enoyl)piperazin-2-yl]acetonitrile (19 mg, 30.2 μmol, 16.4% yield, 97.8% purity) as a white solid. LCMS [M+1]: 616.

¹H NMR (400 MHz, chloroform-d) δ=2.06 (d, J=7.2 Hz, 3H), 2.25-2.39 (m, 1H), 2.54 (d, J=0.8 Hz, 3H), 2.56-2.70 (m, 1H), 2.79-2.91 (m, 1H), 2.97-3.05 (m, 1H), 3.06-3.14 (m, 1H), 3.51-3.64 (m, 1H), 3.80 (br s, 2H), 3.96-4.35 (m, 2H), 4.41-4.55 (m, 3H), 4.59-4.67 (m, 1H), 4.86 (br d, J=1.6 Hz, 1H), 5.07-5.36 (m, 2H), 5.38-5.64 (m, 1H), 7.30 (br dd, J=6.8, 3.6 Hz, 1H), 7.39-7.49 (m, 2H), 7.55 (td, J=7.6, 2.8 Hz, 1H), 7.83 (d, J=8.0 Hz, 1H), 7.99 (dd, J=8.0, 1.2 Hz, 1H), 9.09 (d, J=2.0 Hz, 1H).

Example 15

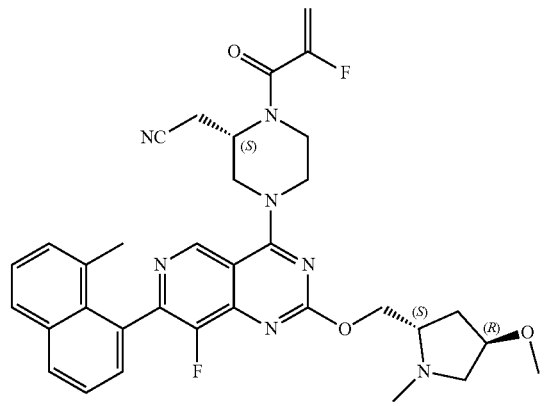

2-[(2S)-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]-1-(2-fluoro-prop-2-enoyl)piperazin-2-yl]acetonitrile

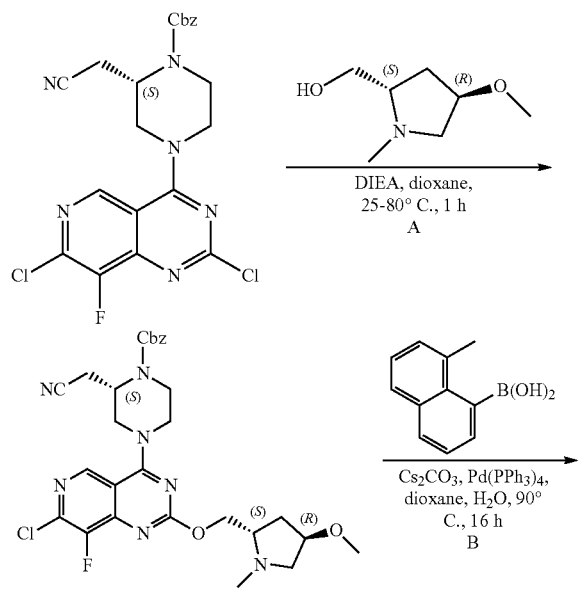

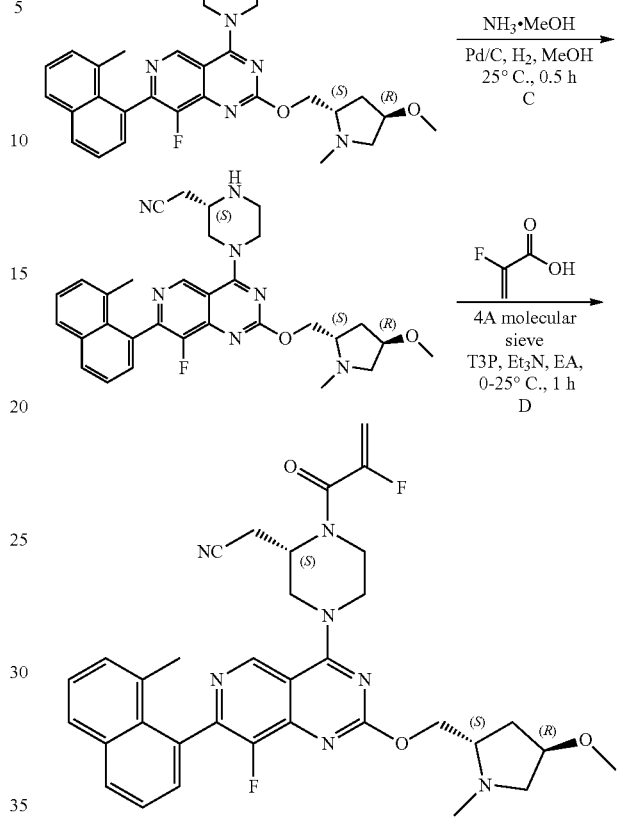

Example 15

Step A: To a mixture of benzyl (2S)-2-(cyanomethyl)-4-(2,7-dichloro-8-fluoro-pyrido[4,3-d]pyrimidin-4-yl)piperazine-1-carboxylate (1.00 g, 2.10 mmol, 1 eq) and [(2S,4R)-4-methoxy-1-methyl-pyrrolidin-2-yl]methanol (916 mg, 6.31 mmol, 3 eq) in dioxane (25 mL) was added DIEA (816 mg, 6.31 mmol, 1.10 mL, 3 eq) at 25° C. The mixture was stirred at 80° C. for 1 hour. After that, 400 mg of [(2S,4R)-4-methoxy-1-methyl-pyrrolidin-2-yl]methanol was added to the mixture and the mixture was stirred at 80° C. for 0.5 h. Upon completion, the residue was diluted with water (10 mL) and extracted with ethyl acetate (1×40 mL). The organic layer was washed with brine (1×30 mL), dried over sodium sulfate, filtered and concentrated under vacuum. The residue was purified by reversed phase flash [water (0.1% formic acid/acetonitrile]. The desired fractions were collected and neutralized with saturated NaHCO₃ solution and extracted with ethyl acetate (1×40 mL). The separated organic layer was dried over sodium sulfate, filtered and concentrated under vacuum. benzyl (2S)-4-[7-chloro-8-fluoro-2-[[(2S,4R)-4-methoxy-1-methyl-pyrrolidin-2-yl]methoxy]pyrido[4,3-d]pyrimidin-4-yl]-2-(cyanomethyl)piperazine-1-carboxylate (760 mg, 1.28 mmol, 61% yield, 98.6% purity) was obtained as a yellow solid. LCMS [ESI, M+1]: 584.

Step B: To a solution of benzyl (2S)-4-[7-chloro-8-fluoro-2-[[(2S,4R)-4-methoxy-1-methyl-pyrrolidin-2-yl]methoxy]pyrido[4,3-d]pyrimidin-4-yl]-2-(cyanomethyl)piperazine-1-carboxylate (630 mg, 1.08 mmol, 1 eq) and (8-methyl-1- naphthyl)boronic acid (401 mg, 2.16 mmol, 2 eq) in dioxane (20 mL) and H$_2$O (4 mL) was added Pd(PPh$_3$)$_4$ (125 mg, 108 μmol, 0.1 eq), Cs$_2$CO$_3$ (703 mg, 2.16 mmol, 2 eq). The mixture was degassed and then heated to 90° C. for 16 hours under N$_2$. Upon completion, the residue was diluted with water (15 mL) and extracted with ethyl acetate (1×50 mL). The organic layer was washed with brine (1×40 mL), dried over sodium sulfate, filtered and concentrated under vacuum. The residue was purified by reversed phase flash [water (0.1% formic acid)/acetonitrile]. The desired fractions were collected and neutralized with saturated NaHCO$_3$ solution and extracted with ethyl acetate (1×100 mL). The separated organic layer was dried over sodium sulfate, filtered and concentrated under vacuum. benzyl (2S)-2-(cyanomethyl)-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]piperazine-1-carboxylate (314 mg, 317 μmol, 29% yield, 69.6% purity) was obtained as a yellow solid. LCMS [ESI, M+1]: 691.

Step C: To a solution of benzyl (2S)-2-(cyanomethyl)-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]piperazine-1-carboxylate (50.0 mg, 72.5 μmol, 1 eq) in MeOH (2 mL) was added NH$_3$.MeOH (1 mL, 20% purity) and Pd/C (30.0 mg, 10% purity) under N$_2$. The suspension was degassed under vacuum and purged with H$_2$ several times. The mixture was stirred under H$_2$ (15 psi) at 25° C. for 0.5 hour. Upon completion, the mixture was filtered and the filtrate was concentrated under vacuum. The residue was purified by prep-HPLC (column: Waters Xbridge 150*25 5μ; mobile phase: [water (0.05% ammonia hydroxide v/v)—ACN]; B %: 30%-60%, 10 min). The residue was concentrated under reduced pressure to remove ACN, and then lyophilized. 2-[(2S)-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]piperazin-2-yl]acetonitrile (13.9 mg, 24.5 μmol, 34% yield, 98.2% purity) was obtained as a white solid. LCMS [ESI, M+1]: 556.

$^1$H NMR (400 MHz, chloroform-d) δ=9.03 (s, 1H), 7.98 (dd, J=1.2, 8.4 Hz, 1H), 7.82 (d, J=8.4 Hz, 1H), 7.57-7.50 (m, 1H), 7.48-7.38 (m, 2H), 7.29 (d, J=6.8 Hz, 1H), 4.67-4.50 (m, 2H), 4.48-4.35 (m, 2H), 4.04-3.92 (m, 1H), 3.65-3.50 (m, 1H), 3.46 (dd, J=6.0, 10.0 Hz, 1H), 3.40-3.28 (m, 4H), 3.27-3.18 (m, 2H), 3.17-3.04 (m, 1H), 3.00-2.90 (m, 1H), 2.69-2.53 (m, 2H), 2.50 (d, J=1.2 Hz, 3H), 2.39-2.30 (m, 1H), 2.12-1.98 (m, 5H).

Example 15: To a solution of 2-[(2S)-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]piperazin-2-yl]acetonitrile (80.0 mg, 144 μmol, 1 eq), 2-fluoroprop-2-enoic acid (104 mg, 1.15 mmol, 8 eq) in EA (16 mL) was added 4A molecular sieve (400 mg). The mixture was stirred at 25° C. for 0.5 hour. After that, the mixture was cooled to 0° C. and added Et$_3$N (131 mg, 1.30 mmol, 180 μL, 9 eq) and T3P (366 mg, 576 μmol, 342 μL, 50% purity, 4 eq) at 0° C. The mixture was stirred at 0° C. for 0.5 hour. Upon completion, the residue was diluted with water (10 mL). The organic layer was separated, washed with brine (20 mL), dried over sodium sulfate, filtered and concentrated under vacuum. The residue was purified by prep-HPLC (column: Waters Xbridge 150*25 5μ; mobile phase: [water (0.05% ammonia hydroxide v/v)—ACN]; B %: 35%-65%, 10 min). The residue was concentrated under reduced pressure to remove ACN, and then lyophilized. 2-[(2S)-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]-1-(2-fluoroprop-2-enoyl)piperazin-2-yl]acetonitrile (37.4 mg, 58.6 μmol, 41% yield, 98.4% purity) was obtained as a white solid. LCMS [ESI, M+1]: 628.

$^1$H NMR (400 MHz, chloroform-d) δ=9.08 (d, J=2.4 Hz, 1H), 7.99 (dd, J=1.2, 8.4 Hz, 1H), 7.82 (d, J=8.4 Hz, 1H), 7.54 (dt, J=2.8, 6.8 Hz, 1H), 7.49-7.38 (m, 2H), 7.32-7.28 (m, 1H), 5.64-5.39 (m, 1H), 5.36-5.23 (m, 1H), 5.02-4.75 (m, 1H), 4.70-4.56 (m, 1H), 4.55-4.36 (m, 3H), 4.32-3.92 (m, 3H), 3.89-3.65 (m, 2H), 3.53-3.42 (m, 1H), 3.31 (s, 3H), 3.08-2.78 (m, 3H), 2.50 (s, 3H), 2.40-2.29 (m, 1H), 2.13-2.00 (m, 5H).

Example 16

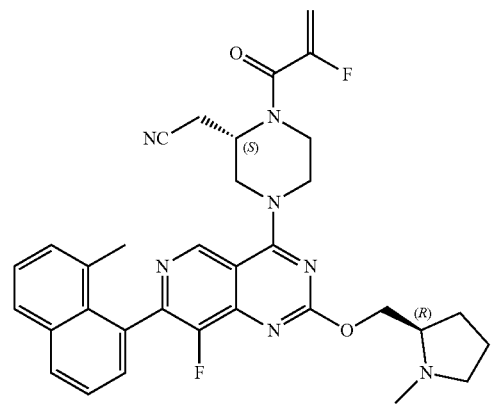

2-((S)-4-(8-fluoro-7-(8-methylnaphthalen-1-yl)-2-(((R)-1-methylpyrrolidin-2-yl)methoxy)pyrido[4,3-d]pyrimidin-4-yl)-1-(2-fluoroacryloyl)piperazin-2-yl)acetonitrile

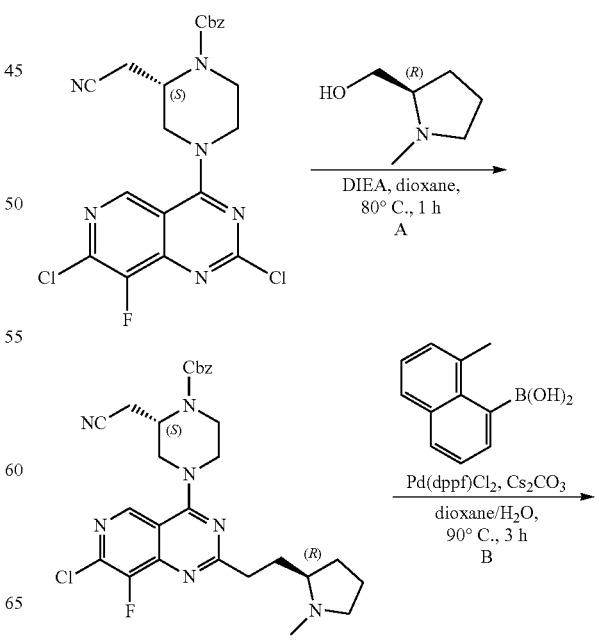

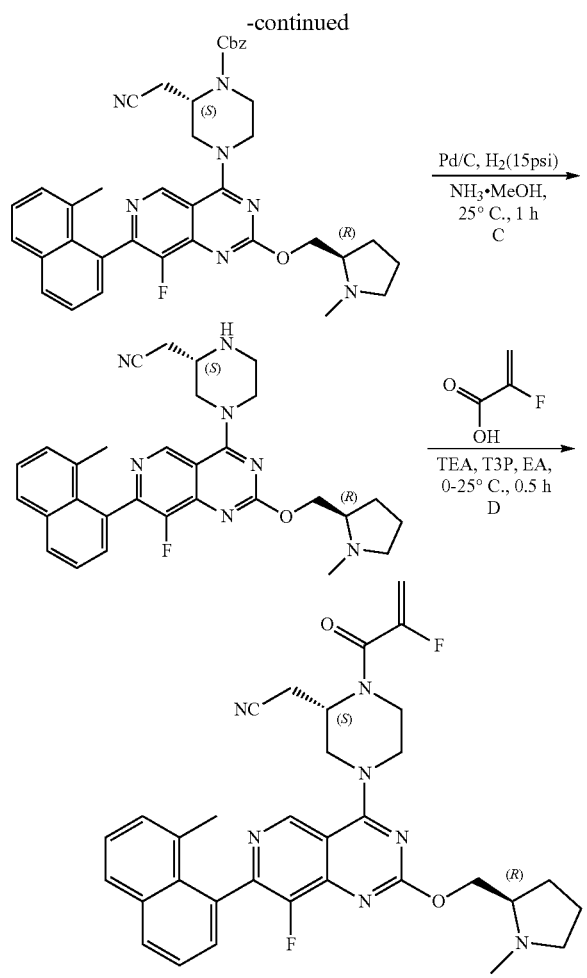

Example 16

Step A: To a mixture of benzyl (2S)-2-(cyanomethyl)-4-(2,7-dichloro-8-fluoro-pyrido[4,3-d]pyrimidin-4-yl)piperazine-1-carboxylate (1.00 g, 2.10 mmol, 1.00 eq) in dioxane (25.0 mL) was added DIEA (816 mg, 6.31 mmol, 1.10 mL, 3.00 eq) and [(2S)-1-methylpyrrolidin-2-yl]methanol (1.21 g, 10.5 mmol, 1.25 mL, 5.00 eq) in portion under $N_2$. The mixture was heated to 80° C. and stirred for 1 hour. The reaction mixture was diluted with water (15 mL) and extracted with ethyl acetate (20.0 mL×3). The combined organic layers were washed with brine (20.0 mL×1), dried over sodium sulfate, filtered and concentrated under reduced pressure to give a residue. The residue was purified by column chromatography ($Al_2O_3$, Petroleum ether/Ethyl acetate=3:1 to 0:1). Compound benzyl (2S)-4-[7-chloro-8-fluoro-2-[[(2R)-1-methylpyrrolidin-2-yl]methoxy]pyrido[4,3-d]pyrimidin-4-yl]-2-(cyanomethyl)piperazine-1-carboxylate (1.00 g, 1.79 mmol, 85% yield, 99.3% purity) was obtained as a yellow solid. LCMS [ESI, M+1]: 554.

Step B: To a mixture of benzyl (2S)-4-[7-chloro-8-fluoro-2-[[(2R)-1-methylpyrrolidin-2-yl]methoxy]pyrido[4,3-d]pyrimidin-4-yl]-2-(cyanomethyl)piperazine-1-carboxylate (450 mg, 812 µmol, 1.00 eq) and (8-methyl-1-naphthyl)boronic acid (302 mg, 1.62 mmol, 2.00 eq) in dioxane (8.00 mL) was added $H_2O$ (1.60 mL), $Cs_2CO_3$ (529 mg, 1.62 mmol, 2.00 eq), $Pd(dppf)Cl_2$ (59.4 mg, 81.2 µmol, 0.10 eq) under $N_2$. The mixture was stirred at 90° C. for 3 hours. The reaction mixture was diluted with water (10.0 mL) and extracted with ethyl acetate (10.0 mL×3). The combined organic layers were washed with brine (10.0 mL×1), dried over sodium sulfate, filtered and concentrated under reduced pressure to give a residue. The residue was purified by reversed phase flash [water (0.1% formic acid)/acetonitrile]. The desired fractions were collected and neutralized with solid $NaHCO_3$, concentrated under vacuum to remove acetonitrile and extracted with ethyl acetate (20.0 mL×2). The organic layers were dried over $Na_2SO_4$ and concentrated under vacuum to give residue. Compound benzyl (2S)-2-(cyanomethyl)-4-[8-fluoro-7-(8-methyl-1-naphthyl)-2-[[(2R)-1-methylpyrrolidin-2-yl]methoxy]pyrido[4,3-d]pyrimidin-4-yl]piperazine-1-carboxylate (270 mg, 409 µmol, 50% yield) was obtained as a yellow solid.

Step C: To a solution of benzyl (2S)-2-(cyanomethyl)-4-[8-fluoro-7-(8-methyl-1-naphthyl)-2-[[(2R)-1-methylpyrrolidin-2-yl]methoxy]pyrido[4,3-d]pyrimidin-4-yl]piperazine-1-carboxylate (100 mg, 152 µmol, 1.00 eq) in MeOH (5.00 mL) was added Pd/C (30.0 mg, 10% purity), $NH_3$·MeOH (2.00 mL, 20% purity) under $N_2$. The suspension was degassed under vacuum and purged with $H_2$ several times. The mixture was stirred under $H_2$ (15 psi) at 25° C. for 1 hours. The reaction mixture was filtered and concentrated under reduced pressure to give a residue. The residue was purified by prep-HPLC (column: Waters Xbridge 150×25 5µ; mobile phase: [water (0.05% ammonia hydroxide v/v)—ACN]; B %: 32%-62%, 10 min). Compound 2-[(2S)-4-[8-fluoro-7-(8-methyl-1-naphthyl)-2-[[(2R)-1-methylpyrrolidin-2-yl]methoxy]pyrido[4,3-d]pyrimidin-4-yl]piperazin-2-yl]acetonitrile (36.0 mg, 67.8 µmol, 45% yield, 99% purity) was obtained as a yellow solid. LCMS [ESI, M+1]: 526.

$^1$H NMR (400 MHz, chloroform-d) δ ppm 1.83-1.96 (m, 3H) 2.01-2.12 (m, 4H) 2.27-2.36 (m, 1H) 2.48-2.53 (m, 3H) 2.54-2.67 (m, 2H) 2.71-2.81 (m, 1H) 3.05-3.16 (m, 2H) 3.17-3.27 (m, 2H) 3.29-3.41 (m, 1H) 3.49-3.61 (m, 1H) 4.36-4.45 (m, 2H) 4.49-4.66 (m, 2H) 7.29 (d, J=7.2 Hz, 1H) 7.38-7.47 (m, 2H) 7.50-7.58 (m, 1H) 7.82 (d, J=8.0 Hz, 1H) 7.98 (dd, J=8.0, 1.2 Hz, 1H) 9.02 (s, 1H)

Example 16: To a mixture of 2-[(2S)-4-[8-fluoro-7-(8-methyl-1-naphthyl)-2-[[(2R)-1-methylpyrrolidin-2-yl]methoxy]pyrido[4,3-d]pyrimidin-4-yl]piperazin-2-yl]acetonitrile (60.0 mg, 114 µmol, 1.00 eq) and 2-fluoroprop-2-enoic acid (82.2 mg, 913 µmol, 8.00 eq) in ethyl acetate (3.00 mL) was added TEA (185 mg, 1.83 mmol, 254 µL, 16.0 eq), T3P (726 mg, 1.14 mmol, 679 µL, 50% purity, 10.0 eq) in portion at 0° C. under $N_2$. The mixture was stirred at 25° C. for 30 min. The reaction mixture was quenched by addition water (3.00 mL) at 0° C. and then extracted with ethyl acetate (10.0 mL×3). The combined organic layers were washed with brine (3.00 mL), dried over sodium sulfate, filtered and concentrated under reduced pressure to give a residue. The residue was purified by prep-HPLC (column: Waters Xbridge 150×25 5µ; mobile phase: [water (0.05% ammonia hydroxide v/v)—ACN]; B %: 40%-70%, 10 min). Compound 2-[(2S)-4-[8-fluoro-7-(8-methyl-1-naphthyl)-2-[[(2R)-1-methylpyrrolidin-2-yl]methoxy]pyrido[4,3-d]pyrimidin-4-yl]-1-(2-fluoroprop-2-enoyl)piperazin-2-yl]acetonitrile (13.4 mg, 22.2 µmol, 19% yield, 99.3% purity) was obtained as a white solid. LCMS [ESI, M+1]: 598.

$^1$H NMR (400 MHz, chloroform-d) δ ppm 1.78-1.91 (m, 3H) 2.00-2.12 (m, 4H) 2.26-2.35 (m, 2H) 2.47-2.53 (m, 3H) 2.69-2.79 (m, 1H) 2.80-2.90 (m, 1H) 2.96-3.07 (m, 1H) 3.09-3.17 (m, 1H) 3.47-3.88 (m, 2H) 3.91-4.34 (m, 2H) 4.37-4.54 (m, 3H) 4.55-4.64 (m, 1H) 4.73-4.99 (m, 1H) 5.23-5.35 (m, 1H) 5.38-5.58 (m, 1H) 7.27-7.31 (m, 1H) 7.38-7.48 (m, 2H) 7.54 (td, J=6.8, 2.0 Hz, 1H) 7.82 (d, J=8.4 Hz, 1H) 7.99 (dd, J=8.0, 1.2 Hz, 1H) 9.06-9.09 (m, 1H).

Example 17

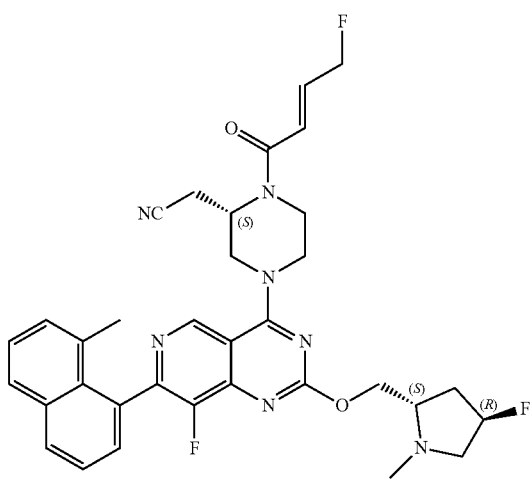

2-[(2S)-1-[(E)-4-fluorobut-2-enoyl]-4-[8-fluoro-2-[[(2S,4R)-4-fluoro-1-methyl-pyrrolidin-2-yl]methoxy]-7-(8-methyl-1-naphthyl)pyrido[4,3-d]pyrimidin-4-yl]piperazin-2-yl]acetonitrile

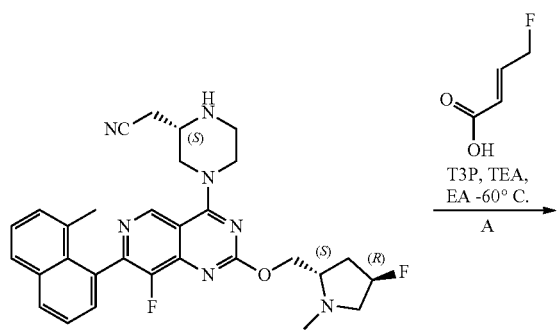

Example 17: To a mixture of 2-[(2S)-4-[8-fluoro-2-[[(2S,4R)-4-fluoro-1-methyl-pyrrolidin-2-yl]methoxy]-7-(8-methyl-1-naphthyl)pyrido[4,3-d]pyrimidin-4-yl]piperazin-2-yl]acetonitrile (60 mg, 110 µmol, 1.0 eq), (E)-4-fluorobut-2-enoic acid (172 mg, 1.66 mmol, 15.0 eq) in ethyl acetate (2 mL) was added T3P (1.05 g, 1.66 mmol, 985 µL, 50% purity, 15.0 eq) and TEA (167 mg, 1.66 mmol, 230 µL, 15.0 eq) at −60° C. The mixture was stirred at −60° C. for 2 hours. The mixture was diluted with saturated NH$_4$Cl aqueous solution (50 mL), and then extracted with ethyl acetate (50 mL×3), the combined organic layers were concentrated under reduced pressure at 40° C. The residue was purified by prep-HPLC (basic condition, column: Xtimate C18 150*25 mm*5 µm; mobile phase: [water (0.05% ammonia hydroxide v/v)—ACN]; B %: 40%-70%, 10 min) to give compound 2-[(2S)-1-[(E)-4-fluorobut-2-enoyl]-4-[8-fluoro-2-[[(2S,4R)-4-fluoro-1-methyl-pyrrolidin-2-yl]methoxy]-7-(8-methyl-1-naphthyl)pyrido[4,3-d]pyrimidin-4-yl]piperazin-2-yl]acetonitrile (20 mg, 30.6 µmol, 27% yield, 89.5% purity) as a white solid. LCMS [M+1]: 630.

$^1$H NMR (400 MHz, chloroform-d) δ=2.06 (d, J=6.00 Hz, 3H), 2.22-2.41 (m, 1H), 2.54 (d, J=1.32 Hz, 3H), 2.73-2.89 (m, 1H), 2.90-3.04 (m, 1H), 3.10 (br dd, J=2.00, 5.36 Hz, 1H), 3.50-3.65 (m, 1H), 3.67-3.99 (m, 2H), 4.00-4.25 (m, 1H), 4.41-4.57 (m, 3H), 4.63 (ddd, J=11.08, 6.48, 4.34 Hz, 1H), 4.94-5.31 (m, 4H), 6.59 (br d, J=15.20 Hz, 1H), 6.97-7.10 (m, 1H), 7.30 (br dd, J=6.80, 3.79 Hz, 1H), 7.39-7.50 (m, 2H), 7.54 (td, J=7.60, 3.85 Hz, 1H), 7.82 (d, J=8.32 Hz, 1H), 7.99 (dd, J=8.12, 1.16 Hz, 1H), 9.10 (d, J=2.44 Hz, 1H).

Example 18

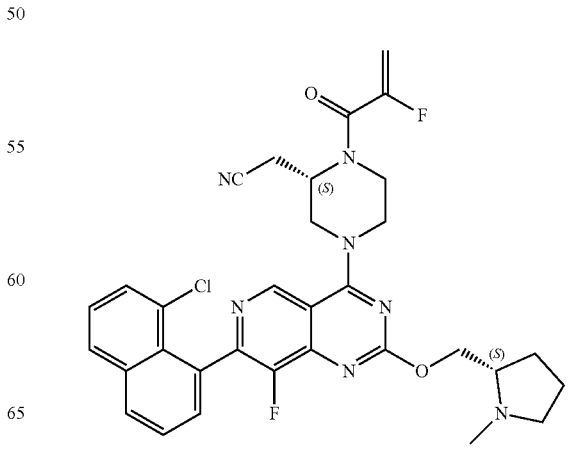

2-((S)-4-(7-(8-chloronaphthalen-1-yl)-8-fluoro-2-(((S)-1-methylpyrrolidin-2-yl)methoxy)pyrido[4,3-d]pyrimidin-4-yl)-1-(2-fluoroacryloyl)piperazin-2-yl)acetonitrile

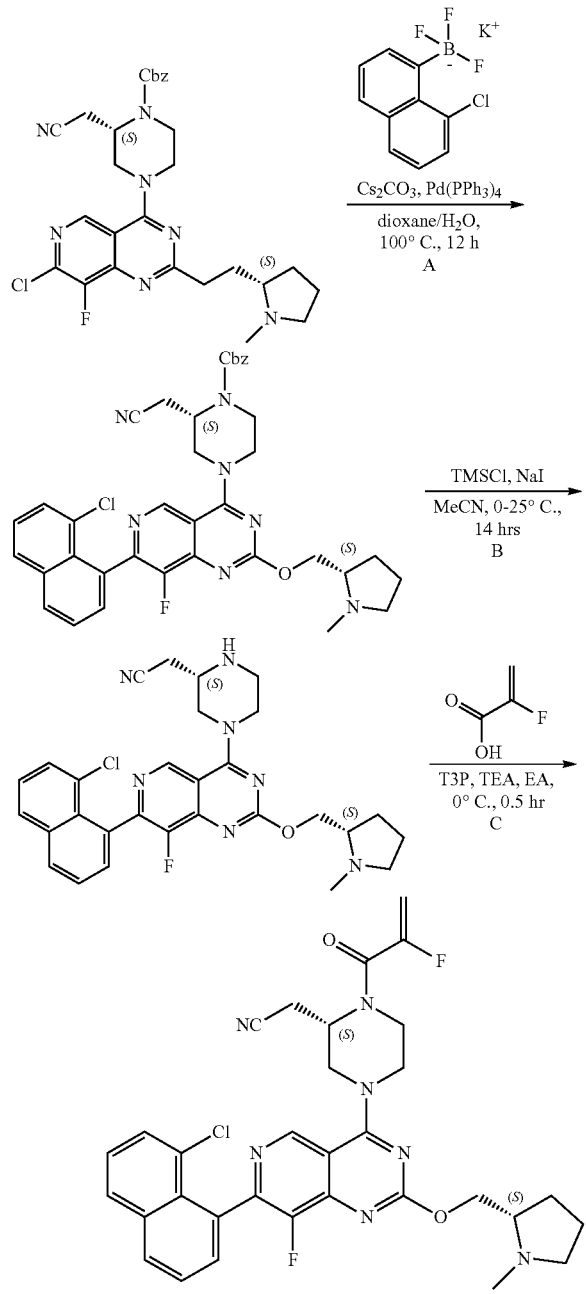

Example 18

Step A: A mixture of (8-chloro-1-naphthyl)-trifluoro-boranuide; potassium hydride (1.65 g, 6.14 mmol, 2.0 eq), benzyl (2S)-4-[7-chloro-8-fluoro-2-[[(2S)-1-methylpyrrolidin-2-yl]methoxy]pyrido[4,3-d]pyrimidin-4-yl]-2-(cyanomethyl)piperazine-1-carboxylate (1.7 g, 3.07 mmol, 1.0 eq), Pd(PPh₃)₄ (354 mg, 306 μmol, 0.1 eq), Cs₂CO₃ (2.00 g, 6.14 mmol, 2.0 eq) in dioxane (30 mL) and H₂O (6 mL) was degassed and purged with N₂ for 3 times, and then the mixture was stirred at 100° C. for 12 hours under N₂ atmosphere. The reaction mixture was diluted with water (20 mL) and extracted with ethyl acetate (3×50 mL). The combined organic layers were washed with brine (20 mL), dried over Na₂SO₄, filtered and concentrated under reduced pressure to give a residue. The residue was purified by column chromatography (SiO₂, Ethyl acetate/Methanol=100/1 to 10/1) and further purified by reversed phase flash [water (0.1% formic acid)/acetonitrile)]. The mixture was adjusted pH ~7 with saturated NaHCO₃ aqueous solution and extracted with ethyl acetate (3×200 mL). The combined organic layers were washed with brine (50 mL), dried over Na₂SO₄, filtered and concentrated under reduced pressure to give the product. benzyl (2S)-4-[7-(8-chloro-1-naphthyl)-8-fluoro-2-[[(2S)-1-methylpyrrolidin-2-yl]methoxy]pyrido[4,3-d]pyrimidin-4-yl]-2-(cyanomethyl)piperazine-1-carboxylate (600 mg, 820 μmol, 27% yield, 93% purity) was obtained as a yellow solid. LCMS [ESI, M+1]: 680.

Step B: To a solution of TMSCl (119 mg, 1.10 mmol, 139 μL, 15.0 eq) and 4A MOLECULAR SIEVE (50 mg) in MeCN (500 μL) was added NaI (176 mg, 1.18 mmol, 16.0 eq) in portions at 0° C. Stirring was continued for a period of 2 hours at 0° C. Then a solution of benzyl (2S)-4-[7-(8-chloro-1-naphthyl)-8-fluoro-2-[[(2S)-1-methylpyrrolidin-2-yl]methoxy]pyrido[4,3-d]pyrimidin-4-yl]-2-(cyanomethyl)piperazine-1-carboxylate (50 mg, 73.5 μmol, 1.0 eq) in MeCN (500 μL) was added to the above mixture. After addition, the mixture was stirred at 25° C. for 12 hours. The mixture was added 1 M HCl aqueous (5 mL) and concentrated under vacuum. Then the mixture was added MTBE (10 mL) and filtered. The mother liquor was separated and the aqueous layer was washed with MTBE (3×10 mL), the organic layer was discarded. The aqueous layer was adjusted with saturated Na₂CO₃ aqueous to pH ~8 and extracted with dichloromethane (3×20 mL). The combined organic layers were washed with brine (20 mL), dried over Na₂SO₄, filtered and concentrated under reduced pressure to give the residue. The residue was purified by prep-HPLC (column: Waters Xbridge 150*25 5μ; mobile phase: [water (0.05% ammonia hydroxide v/v)—ACN]; B %: 35%-65%, 10 min). The desired fraction was collected and lyophilized. 2-[(2S)-4-[7-(8-chloro-1-naphthyl)-8-fluoro-2-[[(2S)-1 methylpyrrolidin-2-yl]methoxy]pyrido[4,3-d]pyrimidin-4-yl]piperazin-2-yl]acetonitrile (5.08 mg, 9.27 μmol, 13% yield, 99.6% purity) was obtained as a white solid. LCMS [ESI, M+1]: 546.

¹H NMR (400 MHz, chloroform-d) δ=9.01 (s, 1H), 8.01 (dd, J=1.6, 7.6 Hz, 1H), 7.89 (dd, J=0.8, 8.0 Hz, 1H), 7.66-7.53 (m, 3H), 7.43 (t, J=8.0 Hz, 1H), 4.65-4.33 (m, 4H), 3.64-3.47 (m, 1H), 3.42-3.28 (m, 1H), 3.27-3.04 (m, 4H), 2.79-2.53 (m, 3H), 2.51 (s, 3H), 2.36-2.23 (m, 1H), 2.13-2.02 (m, 1H), 1.91-1.80 (m, 3H).

Example 18: To a solution of 2-[(2S)-4-[7-(8-chloro-1-naphthyl)-8-fluoro-2-[[(2S)-1-methylpyrrolidin-2-yl]methoxy]pyrido[4,3-d]pyrimidin-4-yl]piperazin-2-yl]acetonitrile (20 mg, 36.6 μmol, 1.0 eq), 2-fluoroprop-2-enoic acid (9.90 mg, 109 μmol, 4.48 μL, 3.0 eq) and TEA (29.6 mg, 293 μmol, 40.8 μL, 8.0 eq) in ethyl acetate (1 mL) was added T3P (69.9 mg, 109 μmol, 65.3 μL, 50% purity in ethyl acetate, 3.0 eq) at 0° C. The mixture was stirred at 0° C. for 30 min. The reaction mixture was diluted with water (20 mL) and extracted with ethyl acetate (3×30 mL). The combined organic layers were washed with brine (20 mL), dried over Na₂SO₄, filtered and concentrated under reduced pressure to give a residue. The residue was purified by prep-HPLC (column: Waters Xbridge 150*25 5μ; mobile phase: [water (0.05% ammonia hydroxide v/v)—ACN]; B %: 35%-65%, 10 min). The desired fraction was collected and lyophilized. 2-[(2S)-4-[7-(8-chloro-1-naphthyl)-8-fluoro-2-[[(2S)-1-methylpyrrolidin-2-yl]methoxy]pyrido[4,3-d]pyrimidin-4-yl]-1-(2-fluoroprop-2-enoyl)piperazin-2-yl]acetonitrile (7.5 mg, 12.0 μmol, 33% yield, 99.3% purity) was obtained as a white solid. LCMS [ESI, M+1]: 618.

$^1$H NMR (400 MHz, chloroform-d) δ=9.07 (s, 1H), 8.02 (dd, J=1.6, 7.6 Hz, 1H), 7.90 (d, J=8.4 Hz, 1H), 7.67-7.51 (m, 3H), 7.44 (dt, J=2.4, 8.0 Hz, 1H), 5.48 (dd, J=3.2, 47.6 Hz, 1H), 5.29 (dd, J=3.6, 16.8 Hz, 1H), 4.86 (s, 1H), 4.68-4.56 (m, 1H), 4.55-4.37 (m, 3H), 4.35-3.53 (m, 4H), 3.15 (t, J=7.2 Hz, 1H), 3.08-2.95 (m, 1H), 2.94-2.69 (m, 2H), 2.53 (s, 3H), 2.38-2.25 (m, 1H), 2.15-2.00 (m, 1H), 1.95-1.79 (m, 3H).

Example 19

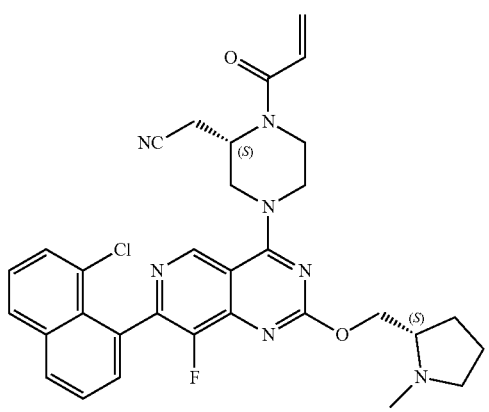

2-((S)-1-acryloyl-4-(7-(8-chloronaphthalen-1-yl)-8-fluoro-2-(((S)-1-methylpyrrolidin-2-yl)methoxy)pyrido[4,3-d]pyrimidin-4-yl)piperazin-2-yl)acetonitrile

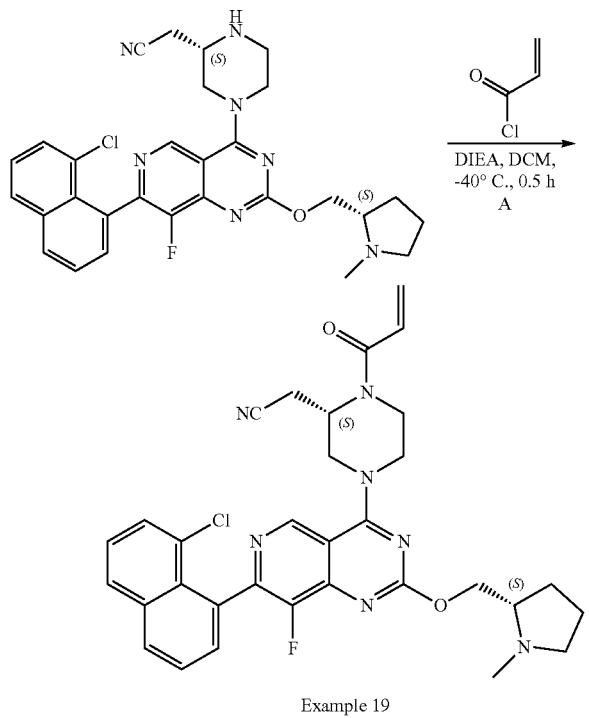

Example 19

Example 19: To a solution of 2-[(2S)-4-[7-(8-chloro-1-naphthyl)-8-fluoro-2-[[(2S)-1-methylpyrrolidin-2-yl]methoxy]pyrido[4,3-d]pyrimidin-4-yl]piperazin-2-yl]acetonitrile (20 mg, 36.6 μmol, 1.0 eq) and DIEA (14.2 mg, 110 μmol, 19.1 μL, 3.0 eq) in dichloromethane (1 mL) was added prop-2-enoyl chloride (4.97 mg, 54.9 μmol, 4.48 μL, 1.5 eq) at −40° C. The mixture was stirred at −40° C. for 30 min. The reaction mixture was diluted with water (20 mL) and extracted with dichloromethane (3×30 mL). The combined organic layers were washed with brine (20 mL), dried over Na$_2$SO$_4$, filtered and concentrated under reduced pressure. The residue was purified by column chromatography (SiO$_2$, Ethyl acetate/Methanol=100/1 to 10/1) and further purification by prep-HPLC (column: Waters Xbridge 150*25 5μ; mobile phase: [water (0.05% ammonia hydroxide v/v)—ACN]; B %: 35%-65%, 10 min). The desired fraction was collected and lyophilized. 2-[(2S)-4-[7-(8-chloro-1-naphthyl)-8-fluoro-2-[[(2S)-1-methylpyrrolidin-2-yl]methoxy]pyrido[4,3-d]pyrimidin-4-yl]-1-prop-2-enoyl-piperazin-2-yl]acetonitrile (7.63 mg, 12.4 μmol, 34% yield, 97.3% purity) was obtained as a white solid. LCMS [ESI, M+1]: 600.

$^1$H NMR (400 MHz, chloroform-d) δ=9.07 (s, 1H), 8.07-7.97 (m, 1H), 7.89 (d, J=8.4 Hz, 1H), 7.67-7.52 (m, 3H), 7.44 (dt, J=2.4, 7.6 Hz, 1H), 6.70-6.53 (m, 1H), 6.43 (d, J=12.8 Hz, 1H), 5.86 (d, J=10.4 Hz, 1H), 5.03 (br s, 1H), 4.67-4.55 (m, 1H), 4.53-4.28 (m, 3H), 4.24-3.43 (m, 4H), 3.11 (t, J=7.6 Hz, 1H), 3.05-2.91 (m, 1H), 2.89-2.65 (m, 2H), 2.50 (d, J=1.2 Hz, 3H), 2.36-2.23 (m, 1H), 2.12-1.98 (m, 1H), 1.94-1.70 (m, 3H).

Example 20

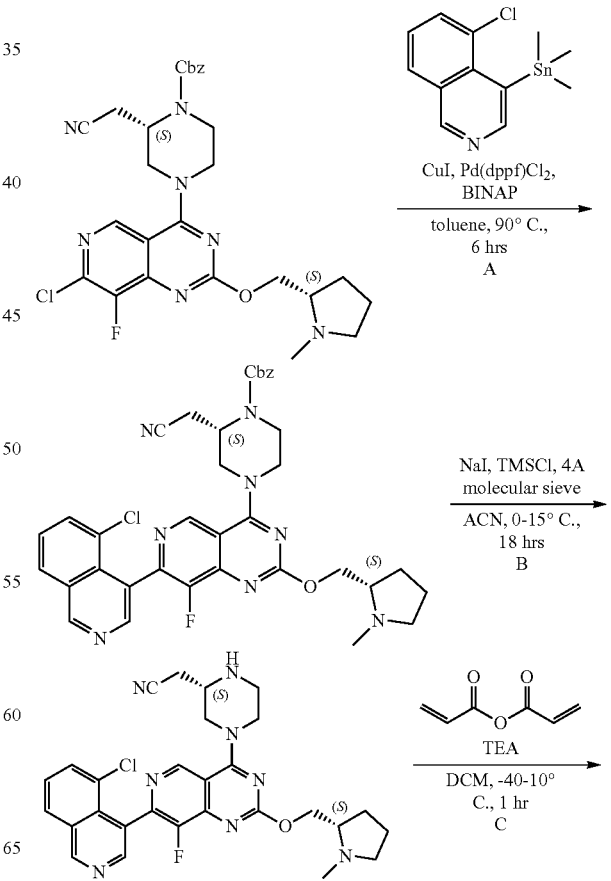

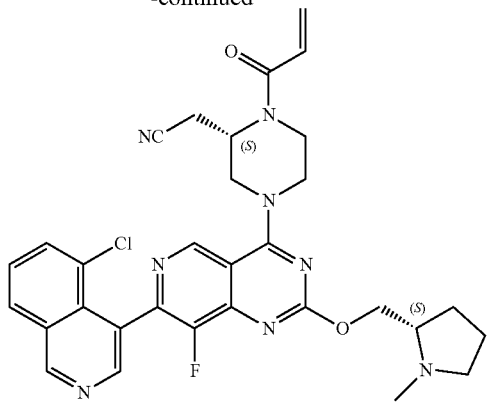

Example 20

2-[(2S)-4-[7-(5-chloro-4-isoquinolyl)-8-fluoro-2-
[[(2S)-1-methylpyrrolidin-2-yl]methoxy]pyrido[4,3-
d]pyrimidin-4-yl]-1-prop-2-enoyl-piperazin-2-yl]
acetonitrile Step A: To a solution of benzyl (2S)-4-[7-chloro-8-fluoro-2-[[(2S)-1-methyl pyrrolidin-2-yl]methoxy]pyrido[4,3-d]pyrimidin-4-yl]-2-(cyanomethyl)piperazine-1-carboxylate (100 mg, 181 μmol, 1.0 eq) and (5-chloro-4-isoquinolyl)-trimethyl-stannane (118 mg, 361 μmol, 2.0 eq) in toluene (3.0 mL) was added CuI (10.3 mg, 54.2 μmol, 0.3 eq), Pd(dppf)Cl₂ (13.2 mg, 18.1 μmol, 0.1 eq) and BINAP (22.5 mg, 36.1 μmol, 0.2 eq), the reaction mixture was stirred at 90° C. for 6 hours under N₂. The mixture was diluted with ethyl acetate (8.0 mL) and water (7.0 mL) then separated. The aqueous phase was extracted with ethyl acetate (3×9.0 mL) and the organic layer was washed with saturated brine (10.0 mL), dried over Na₂SO₄, filtered and concentrated under vacuum. The residue was purified by prep-TLC (SiO₂, dichloromethane:methanol=10:1) to give benzyl (2S)-4-[7-(5-chloro-4-isoquinolyl)-8-fluoro-2-[[(2S)-1-methylpyrrolidin-2-yl]methoxy]pyrido[4,3-d]pyrimidin-4-yl]-2-(cyanomethyl)piperazine-1-carboxylate (50 mg, 66.8 μmol, 37% yield, 91% purity) as a yellow solid. LCMS [ESI, M+1]: 681.

¹H NMR (400 MHz, chloroform-d) δ=9.39 (br s, 1H), 9.09 (s, 1H), 8.59 (br d, J=11.6 Hz, 1H), 8.05 (d, J=8.0 Hz, 1H), 7.77 (br d, J=7.2 Hz, 1H), 7.64-7.56 (m, 1H), 7.44-7.33 (m, 5H), 5.22 (s, 2H), 4.78-4.67 (m, 1H), 4.60 (td, J=5.6, 10.8 Hz, 1H), 4.51-4.36 (m, 3H), 4.28-4.17 (m, 1H), 3.97 (br d, J=12.4 Hz, 1H), 3.79-3.52 (m, 2H), 3.12 (br t, J=7.2 Hz, 1H), 2.95-2.69 (m, 3H), 2.51 (s, 3H), 2.36-2.25 (m, 1H), 2.08-2.01 (m, 1H), 1.94-1.82 (m, 3H).

Step B: To a solution of benzyl (2S)-4-[7-(5-chloro-4-isoquinolyl)-8-fluoro-2-[[(2S)-1-methylpyrrolidin-2-yl]methoxy]pyrido[4,3-d]pyrimidin-4-yl]-2-(cyanomethyl)piperazine-1-carboxylate (75.0 mg, 110 μmol, 1.0 eq) and 4A MOLECULAR SIEVE (35.0 mg, 110 μmol, 1.0 eq) in ACN (2.0 mL) was added TMSCl (179 mg, 1.65 mmol, 210 μL, 15 eq), the mixture was stirred at 0° C. for 0.5 hour. Then NaI (264 mg, 1.76 mmol, 16 eq) was added to the above mixture at 0° C. After addition, the mixture was stirred at 15° C. for 17.5 hours. The mixture was purified by column chromatography (Al₂O₃, ethyl acetate:methanol=0:1). The desired fraction was collected and concentrated under vacuum. The residue was purified by reversed phase flash [water (FA, 0.1%)/acetiontrile]. The desired fractions were collected and neutralized with NaHCO₃ solid and extracted with ethyl acetate (3×8.0 mL). The combined organic phase was washed with saturated brine (5.0 mL), dried over anhydrous Na₂SO₄, filtered and concentrated under vacuum to give 2-[(2S)-4-[7-(5-chloro-4-isoquinolyl)-8-fluoro-2-[[(2S)-1-methylpyrrolidin-2-yl]methoxy]pyrido[4,3-d]pyrimidin-4-yl]piperazin-2-yl]acetonitrile (22.0 mg, 36.6 μmol, 33% yield, 91% purity) as a yellow solid. LCMS [ESI, M+1]: 547.

Example 20: To a solution of 2-[(2S)-4-[7-(5-chloro-4-isoquinolyl)-8-fluoro-2-[[(2S)-1-methylpyrrolidin-2-yl]methoxy]pyrido[4,3-d]pyrimidin-4-yl]piperazin-2-yl]acetonitrile (22.0 mg, 40.2 μmol, 1.0 eq) and TEA (20.4 mg, 201 μmol, 28.0 μL, 5.0 eq) in dichloromethane (1.0 mL) was added prop-2-enoyl prop-2-enoate (7.61 mg, 60.3 μmol, 4.92 μL, 1.5 eq) in dichloromethane (1.0 mL) at −40° C. After stirring at 0-10° C. for 1 hour, the mixture was diluted with dichloromethane (4.0 mL) and H₂O (4.0 mL) then separated. The aqueous phase was extracted with dichloromethane (2×4.0 mL) and the organic layer was washed with saturated brine (5.0 mL), dried over Na₂SO₄, filtered and concentrated under vacuum. The residue was purified by prep-HPLC (column: Waters Xbridge 150*25 5μ; mobile phase: [water (0.05% ammonia hydroxide v/v)—ACN]; B %: 25%-55%, 10 min). The desired fraction was collected and concentrated under vacuum to remove acetonitrile. The residue was lyophilized to give 2-[(2S)-4-[7-(5-chloro-4-isoquinolyl)-8-fluoro-2-[[(2S)-1-methylpyrrolidin-2-yl]methoxy]pyrido[4,3-d]pyrimidin-4-yl]-1-prop-2-enoyl-piperazin-2-yl]acetonitrile (5.85 mg, 9.54 μmol, 24% yield, 98% purity) as a yellow solid. LCMS [ESI, M+1]: 601.

¹H NMR (400 MHz, chloroform-d) δ=9.39 (s, 1H), 9.10 (s, 1H), 8.59 (d, J=11.6 Hz, 1H), 8.06 (d, J=8.4 Hz, 1H), 7.81-7.76 (m, 1H), 7.61 (dt, J=2.4, 7.8 Hz, 1H), 6.66-6.55 (m, 1H), 6.47-6.39 (m, 1H), 5.87 (br d, J=10.4 Hz, 1H), 5.13-4.76 (m, 1H), 4.60 (ddd, J=4.8, 6.2, 10.8 Hz, 1H), 4.54-4.38 (m, 3H), 4.32-3.43 (m, 4H), 3.15-3.09 (m, 1H), 3.07-2.91 (m, 1H), 2.88-2.68 (m, 2H), 2.50 (s, 3H), 2.35-2.24 (m, 1H), 2.12-2.00 (m, 1H), 1.93-1.73 (m, 3H).

Example 21

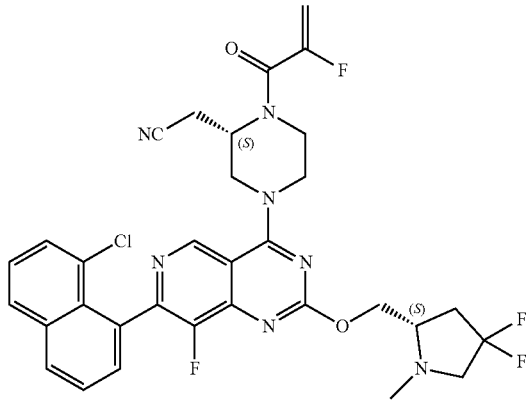

2-((S)-4-(7-(8-chloronaphthalen-1-yl)-2-(((S)-4,4-difluoro-1-methylpyrrolidin-2-yl)methoxy)-8-fluoro-pyrido[4,3-d]pyrimidin-4-yl)-1-(2-fluoroacryloyl)piperazin-2-yl)acetonitrile

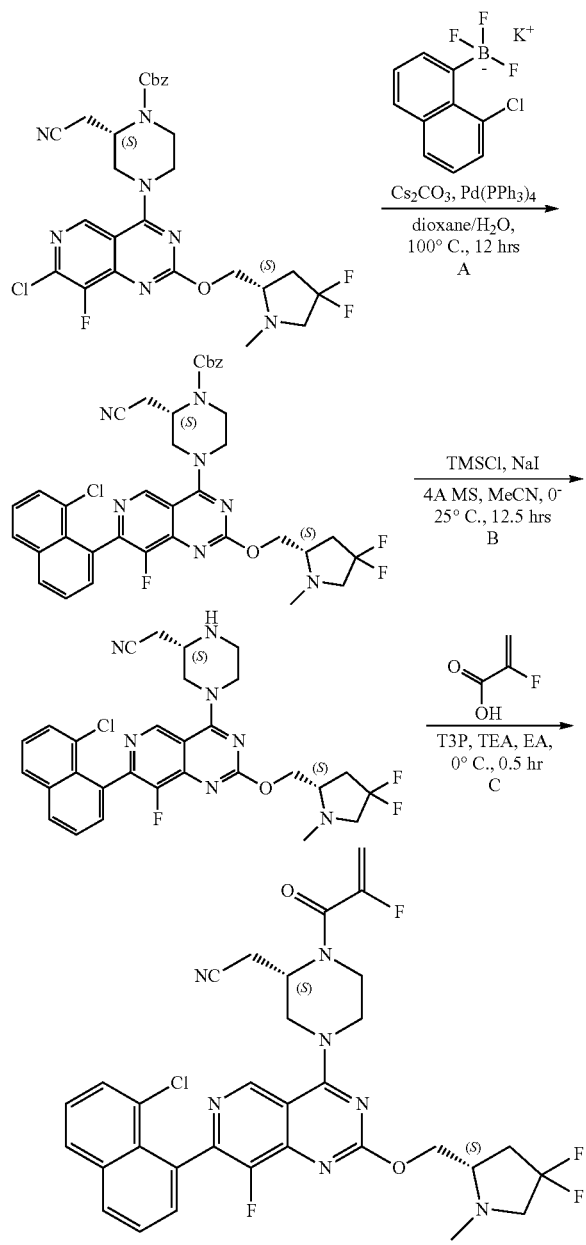

Example 21

Step A: A mixture of [(8-chloro-1-naphthyl)-trifluoroboranyl] potassium(1+) (319 mg, 1.19 mmol, 1.0 eq), benzyl (2S)-4-[7-chloro-2-[[(2S)-4,4-difluoro-1-methyl-pyrrolidin-2-yl]methoxy]-8-fluoro-pyrido[4,3-d]pyrimidin-4-yl]-2-(cyanomethyl)piperazine-1-carboxylate (700 mg, 1.19 mmol, 1.0 eq), Pd(PPh$_3$)$_4$ (137 mg, 119 μmol, 0.1 eq), Cs$_2$CO$_3$ (775 mg, 2.38 mmol, 2.0 eq) in dioxane (15 mL) and H$_2$O (3 mL) was degassed and purged with N$_2$ for 3 times, and then the mixture was stirred at 100° C. for 12 hours under N$_2$ atmosphere. The reaction mixture was diluted with water (20 mL) and extracted with ethyl acetate (3×50 mL). The combined organic layers were washed with brine (20 mL), dried over Na$_2$SO$_4$, filtered and concentrated under reduced pressure to give a residue. The residue was purified by column chromatography (SiO$_2$, Ethyl acetate/Methanol=100/1 to 10/1) and further purified by reversed phase flash [water (0.1% formic acid)/acetonitrile)]. The mixture was adjusted pH ~7 with saturated NaHCO$_3$ aqueous solution and extracted with ethyl acetate (3×200 mL). The combined organic layers were washed with brine (50 mL), dried over Na$_2$SO$_4$, filtered and concentrated under reduced pressure to give benzyl (2S)-4-[7-(8-chloro-1-naphthyl)-2-[[(2S)-4,4-difluoro-1-methyl-pyrrolidin-2-yl]methoxy]-8-fluoro-pyrido[4,3-d]pyrimidin-4-yl]-2-(cyanomethyl)piperazine-1-carboxylate (390 mg, 522 μmol, 44% yield, 96% purity) as a yellow solid. LCMS [ESI, M+1]: 716.

Step B: To a solution of benzyl (2S)-4-[7-(8-chloro-1-naphthyl)-2-[[(2S)-4,4-difluoro-1-methyl-pyrrolidin-2-yl]methoxy]-8-fluoro-pyrido[4,3-d]pyrimidin-4-yl]-2-(cyanomethyl)piperazine-1-carboxylate (40 mg, 55.8 μmol, 1.0 eq) and 4A molecular sieve (100 mg) in MeCN (1 mL) was added NaI (134 mg, 894 μmol, 16.0 eq). Stirring was continued for a period of 0.5 hour at 0° C. Then TMSCl (91 mg, 838 μmol, 106 μL, 15.0 eq) was added to the above mixture. After addition, the mixture was stirred at 25° C. for 12 hours. The reaction mixture was filtered and the filter was purified by reversed phase flash [water (0.1% formic acid)/acetonitrile)] directly. The mixture was adjusted pH ~7 with saturated NaHCO$_3$ aqueous solution and extracted with ethyl acetate (3×100 mL). The combined organic layers were washed with brine (50 mL), dried over Na$_2$SO$_4$, filtered and concentrated under reduced pressure to give the residue. The residue was further purified by prep-HPLC (column: Waters Xbridge 150*25 5μ; mobile phase: [water (0.05% ammonia hydroxide v/v)—ACN]; B %: 32%-62%, 10 min). The desired fraction was collected and lyophilized. 2-[(2S)-4-[7-(8-chloro-1-naphthyl)-2-[[(2S)-4,4-difluoro-1-methyl-pyrrolidin-2-yl]methoxy]-8-fluoro-pyrido[4,3-d]pyrimidin-4-yl]piperazin-2-yl]acetonitrile (7.51 mg, 12.8 μmol, 23% yield, 99.3% purity) was obtained as a yellow solid. LCMS [ESI, M+1]: 582.

$^1$H NMR (400 MHz, chloroform-d) δ=9.03 (s, 1H), 8.02 (dd, J=1.6, 7.6 Hz, 1H), 7.90 (dd, J=1.2, 8.0 Hz, 1H), 7.66-7.52 (m, 3H), 7.44 (t, J=8.0 Hz, 1H), 4.71-4.60 (m, 1H), 4.59-4.37 (m, 3H), 3.64-3.49 (m, 1H), 3.44 (dt, J=5.2, 11.6 Hz, 1H), 3.38-3.31 (m, 1H), 3.28-2.98 (m, 4H), 2.79-2.46 (m, 7H), 2.43-2.25 (m, 1H).

Example 21: To a solution of 2-[(2S)-4-[7-(8-chloro-1-naphthyl)-2-[[(2S)-4,4-difluoro-1-methyl-pyrrolidin-2-yl]methoxy]-8-fluoro-pyrido[4,3-d]pyrimidin-4-yl]piperazin-2-yl]acetonitrile (70 mg, 120 μmol, 1.0 eq), 2-fluoroprop-2-enoic acid (32.5 mg, 361 μmol, 4.48 μL, 3.0 eq) and TEA (974 mg, 962 μmol, 134 μL, 8.0 eq) in ethyl acetate (1 mL) was added T3P (229 mg, 361 μmol, 214 uL, 50% purity in ethyl acetate, 3.0 eq) at 0° C. The mixture was stirred at 0° C. for 30 minutes. The reaction mixture was diluted with water (20 mL) and extracted with ethyl acetate (3×30 mL). The combined organic layers were washed with brine (20 mL), dried over Na$_2$SO$_4$, filtered and concentrated under reduced pressure to give a residue. The residue was purified by prep-HPLC (column: Waters Xbridge 150*25 5μ; mobile phase: [water (0.05% ammonia hydroxide v/v)—ACN]; B %: 38%-68%, 10 min). The desired fraction was collected and lyophilized. 2-[(2S)-4-[7-(8-chloro-1-naphthyl)-2-[[(2S)-4,4-difluoro-1-methyl-pyrrolidin-2-yl]methoxy]-8-fluoro-pyrido[4,3-d]pyrimidin-4-yl]-1-(2-fluoroprop-2- enoyl)piperazin-2-yl]acetonitrile (14.3 mg, 21.8 μmol, 18% yield, 99.7% purity, 100% ee) was obtained as a white solid. LCMS [ESI, M+1]: 654.

$^1$H NMR (400 MHz, chloroform-d) δ=9.09 (s, 1H), 8.03 (dd, J=1.6, 7.6 Hz, 1H), 7.90 (d, J=8.0 Hz, 1H), 7.67-7.53 (m, 3H), 7.44 (dt, J=2.0, 7.6 Hz, 1H), 5.60-5.38 (m, 1H), 5.29 (dd, J=3.6, 16.8 Hz, 1H), 4.86 (br s, 1H), 4.71-4.61 (m, 1H), 4.59-4.40 (m, 3H), 4.37-3.53 (m, 4H), 3.44 (dt, J=5.6, 11.6 Hz, 1H), 3.12-2.95 (m, 2H), 2.93-2.79 (m, 1H), 2.71 (td, J=11.2, 16.4 Hz, 1H), 2.62-2.45 (m, 4H), 2.44-2.25 (m, 1H).

Example 22

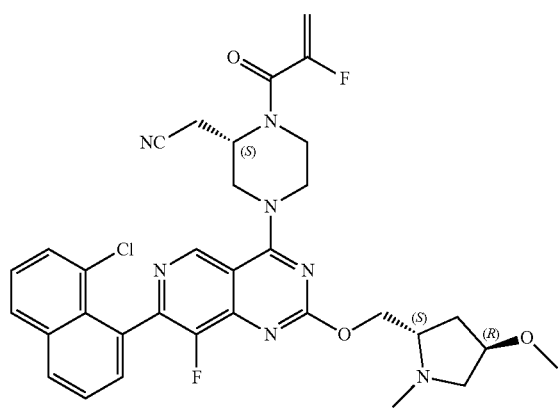

2-[(2S)-4-[7-(8-chloro-1-naphthyl)-8-fluoro-2-[[(2S,4R)-4-methoxy-1-methyl-pyrrolidin-2-yl]methoxy]pyrido[4,3-d]pyrimidin-4-yl]-1-(2-fluoroprop-2-enoyl)piperazin-2-yl]acetonitrile

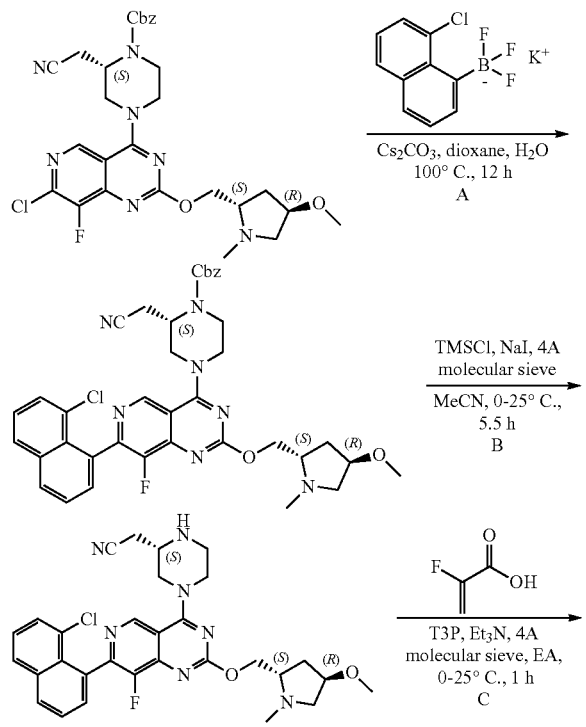

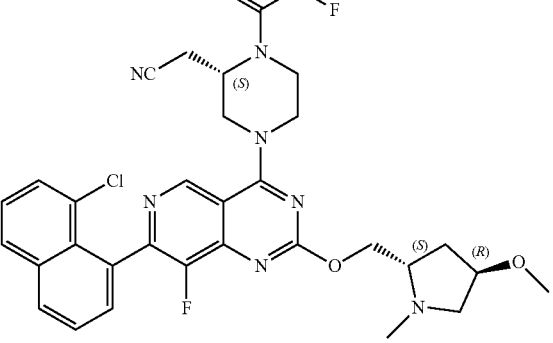

Example 22

Step A: A mixture of benzyl (2S)-4-[7-chloro-8-fluoro-2-[[(2S,4R)-4-methoxy-1-methyl-pyrrolidin-2-yl]methoxy]pyrido[4,3-d]pyrimidin-4-yl]-2-(cyanomethyl)piperazine-1-carboxylate (1 g, 1.71 mmol, 1.0 eq), [(8-chloro-1-naphthyl)-trifluoro-boranyl]potassium(1+) (2.76 g, 10.3 mmol, 6.0 eq), Pd(PPh$_3$)$_4$ (198 mg, 171 μmol, 0.1 eq), Cs$_2$CO$_3$ (1.12 g, 3.42 mmol, 2.0 eq) in dioxane (20 mL) and H$_2$O (4 mL) was degassed and purged with N$_2$ for 3 times, and then the mixture was stirred at 100° C. for 12 hours under N$_2$ atmosphere. Upon completion, the residue was diluted with water (15 mL) and extracted with ethyl acetate (1×60 mL). The organic layer was washed with brine (1×40 mL), dried over sodium sulfate, filtered and concentrated under vacuum. The residue was purified by reversed phase flash [water (0.1% formic acid)/acetonitrile]. The desired fractions were collected and neutralized with saturated NaHCO$_3$ solution and extracted with ethyl acetate (1×100 mL). The separated organic layer was dried over sodium sulfate, filtered and concentrated under vacuum. benzyl (2S)-4-[7-(8-chloro-1-naphthyl)-8-fluoro-2-[[(2S,4R)-4-methoxy-1-methyl-pyrrolidin-2-yl]methoxy]pyrido[4,3-d]pyrimidin-4-yl]-2-(cyanomethyl)piperazine-1-carboxylate (770 mg, 774 μmol, 45% yield, 71.4% purity) was obtained as a yellow solid. LCMS [ESI, M+1]: 710.

$^1$H NMR (400 MHz, chloroform-d) δ=9.02 (s, 1H), 8.00 (dd, J=1.2, 8.0 Hz, 1H), 7.88 (d, J=8.0 Hz, 1H), 7.81-7.72 (m, 1H), 7.64-7.57 (m, 2H), 7.57-7.51 (m, 2H), 7.49-7.40 (m, 2H), 7.38-7.32 (m, 2H), 5.20 (s, 2H), 4.78-4.62 (m, 1H), 4.60-4.50 (m, 1H), 4.45-4.29 (m, 3H), 4.02-3.86 (m, 1H), 3.86-3.77 (m, 1H), 3.72-3.62 (m, 1H), 3.61-3.43 (m, 1H), 3.37-3.26 (m, 1H), 3.24 (d, J=2.0 Hz, 3H), 2.94-2.66 (m, 4H), 2.40 (s, 3H), 2.27-2.20 (m, 1H), 2.02-1.98 (m, 1H), 1.97-1.88 (m, 1H).

Step B: A mixture of benzyl (2S)-4-[7-(8-chloro-1-naphthyl)-8-fluoro-2-[[(2S,4R)-4-methoxy-1-methyl-pyrrolidin-2-yl]methoxy]pyrido[4,3-d]pyrimidin-4-yl]-2-(cyanomethyl)piperazine-1-carboxylate (60 mg, 84.5 μmol, 1.0 eq), NaI (203 mg, 1.35 mmol, 16.0 eq) and 4A molecular sieve (60 mg, 70.4 μmol) in MeCN (1.5 mL) was stirred at 0° C. for 30 min. Then to the mixture was added TMSCl (138 mg, 1.27 mmol, 161 μL, 15.0 eq) at 0° C. The mixture was stirred at 25° C. for 5 hours. Upon completion, the mixture was filtered and the filtrate was purified directly. The residue was purified by column chromatography (Al$_2$O$_3$, petroleum ether/ethyl acetate=10/1 to 0/1 and dichloromethane/methanol=10/1 to 3/1). The residue was purified by prep-HPLC (column: Xtimate C18 150*25 mm*5 μm; mobile phase: [water (0.05% ammonia hydroxide v/v)—ACN]; B %: 28%-58%, 10 min). The residue was concentrated under reduced pressure to remove MeCN, and then lyophilized. 2-[(2S)-4-[7-(8-chloro-1-naphthyl)-8-fluoro-2-[[(2S,4R)-4-methoxy- 1-methyl-pyrrolidin-2-yl]methoxy]pyrido[4,3-d]pyrimidin-4-yl]piperazin-2-yl]acetonitrile (4.06 mg, 7.02 μmol, 8% yield, 99.6% purity) was obtained as a white solid. LCMS [ESI, M+1]: 576.

$^1$H NMR (400 MHz, chloroform-d) δ=9.02 (br s, 1H), 8.01 (br d, J=6.8 Hz, 1H), 7.89 (br d, J=6.8 Hz, 1H), 7.67-7.50 (m, 3H), 7.48-7.38 (m, 1H), 4.67-4.48 (m, 2H), 4.48-4.34 (m, 2H), 3.97 (br s, 1H), 3.63-3.50 (m, 1H), 3.49-3.41 (m, 1H), 3.40-3.03 (m, 8H), 2.94 (br s, 1H), 2.69-2.56 (m, 2H), 2.50 (s, 3H), 2.33 (br s, 1H), 2.14-2.00 (m, 2H).

Example 22: A mixture of 2-[(2S)-4-[7-(8-chloro-1-naphthyl)-8-fluoro-2-[[(2S,4R)-4-methoxy-1-methyl-pyrrolidin-2-yl]methoxy]pyrido[4,3-d]pyrimidin-4-yl]piperazin-2-yl]acetonitrile (40 mg, 69.4 μmol, 1.0 eq), 2-fluoroprop-2-enoic acid (50.0 mg, 555 μmol, 8.0 eq) in Ethyl acetate (1 mL) was added 4A molecular sieve (25 mg). The mixture was stirred at 25° C. for 0.5 hour. After that, the mixture was cooled to 0° C. and added Et$_3$N (63.2 mg, 625 μmol, 87.0 μL, 9.0 eq) and T3P (177 mg, 278 μmol, 165 μL, 50% purity, 4.0 eq) at 0° C. The mixture was stirred at 0° C. for 0.5 hour. Upon completion, the residue was diluted with water (2 mL) and ethyl acetate (3 mL). The organic layer was separated, washed with brine (1×5 mL), dried over sodium sulfate, filtered and concentrated under vacuum. The residue was purified by prep-HPLC (column: Waters Xbridge 150*25 5μ; mobile phase: [water (0.05% ammonia hydroxide v/v)—ACN]; B %: 32%-62%, 10 min). The residue was concentrated under reduced pressure to remove MeCN, and then lyophilized. 2-[(2S)-4-[7-(8-chloro-1-naphthyl)-8-fluoro-2-[[(2S,4R)-4-methoxy-1-methyl-pyrrolidin-2-yl]methoxy]pyrido[4,3-d]pyrimidin-4-yl]-1-(2-fluoroprop-2-enoyl)piperazin-2-yl]acetonitrile (11.1 mg, 17.1 μmol, 25% yield, 100% purity) was obtained as a white solid. LCMS [ESI, M+1]: 648.

$^1$H NMR (400 MHz, chloroform-d) δ=9.07 (s, 1H), 8.02 (d, J=7.6 Hz, 1H), 7.90 (d, J=8.4 Hz, 1H), 7.67-7.51 (m, 3H), 7.44 (dt, J=2.4, 8.0 Hz, 1H), 5.60-5.38 (m, 1H), 5.29 (dd, J=3.6, 16.8 Hz, 1H), 4.99-4.76 (m, 1H), 4.68-4.56 (m, 1H), 4.55-4.39 (m, 3H), 4.35-4.14 (m, 1H), 4.11-3.91 (m, 2H), 3.89-3.65 (m, 2H), 3.55-3.40 (m, 1H), 3.31 (br s, 3H), 3.11-2.79 (m, 3H), 2.50 (br s, 3H), 2.40-2.27 (m, 1H), 2.18-1.95 (m, 2H).

Example 23

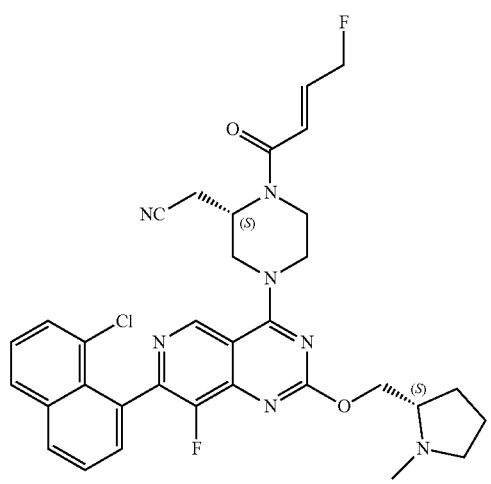

2-((S)-4-(7-(8-chloronaphthalen-1-yl)-8-fluoro-2-(((S)-1-methylpyrrolidin-2-yl)methoxy)pyrido[4,3-d]pyrimidin-4-yl)-1-((E)-4-fluorobut-2-enoyl)piperazin-2-yl)acetonitrile

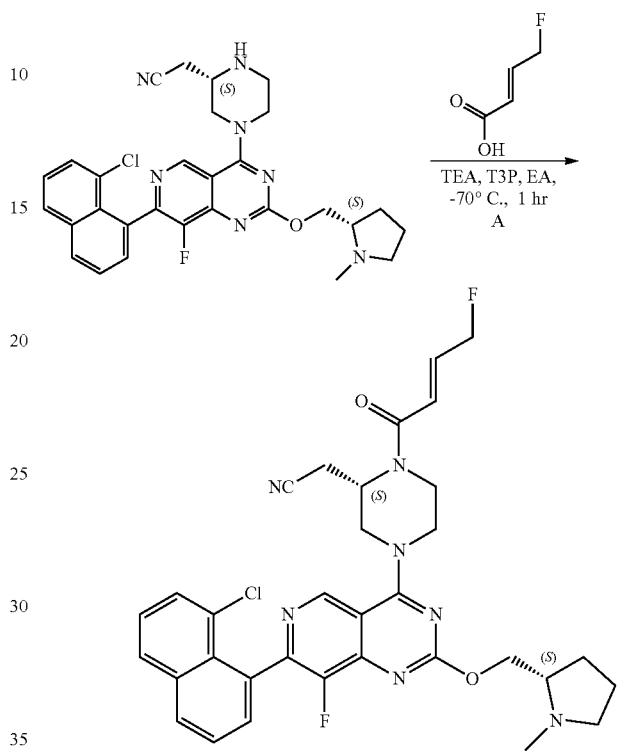

Example 23

Example 23: To a solution of 2-[(2S)-4-[7-(8-chloro-1-naphthyl)-8-fluoro-2-[[(2S)-1-methylpyrrolidin-2-yl]methoxy]pyrido[4,3-d]pyrimidin-4-yl]piperazin-2-yl]acetonitrile (20 mg, 36.6 μmol, 1.0 eq), (E)-4-fluorobut-2-enoic acid (11.4 mg, 109 μmol, 4.48 μL, 3.0 eq) and TEA (29.6 mg, 293 μmol, 40.8 μL, 8.0 eq) in ethyl acetate (1 mL) was added T3P (69.9 mg, 10 μmol, 65.3 μL, 50% purity in ethyl acetate, 3.0 eq) at −70° C. The mixture was stirred at −70° C. for 1 hour. The reaction mixture was quenched with HCl (1 M, 1 mL). Then the mixture was adjusted pH ~7 with saturated NaHCO$_3$ aqueous solution and extracted with ethyl acetate (3×20 mL). The combined organic layers were washed with brine (10 mL), dried over Na$_2$SO$_4$, filtered and concentrated under reduced pressure to give the residue. The residue was purified by prep-HPLC (column: Waters Xbridge 150*25 5μ; mobile phase: [water (0.05% ammonia hydroxide v/v)—ACN]; B %: 35%-65%, 10 min). The desired fraction was collected and lyophilized. 2-[(2S)-4-[7-(8-chloro-1-naphthyl)-8-fluoro-2-[[(2S)-1-methylpyrrolidin-2-yl]methoxy]pyrido[4,3-d]pyrimidin-4-yl]-1-[(E)-4-fluorobut-2-enoyl]piperazin-2-yl]acetonitrile (6.62 mg, 9.95 μmol, 27% yield, 95% purity) was obtained as a white solid. LCMS [ESI, M+1]: 632.

$^1$H NMR (400 MHz, chloroform-d) δ=9.08 (s, 1H), 8.02 (d, J=7.6 Hz, 1H), 7.90 (d, J=8.0 Hz, 1H), 7.67-7.52 (m, 3H), 7.44 (dt, J=2.0, 7.6 Hz, 1H), 7.13-6.94 (m, 1H), 6.60 (br d, J=15.6 Hz, 1H), 5.25-4.59 (m, 4H), 4.56-4.37 (m, 3H), 4.27-3.52 (m, 4H), 3.43-3.11 (m, 1H), 3.08-2.72 (m, 3H), 2.58 (s, 3H), 2.38 (s, 1H), 2.19-2.01 (m, 1H), 1.97-1.80 (m, 3H).

Example 24

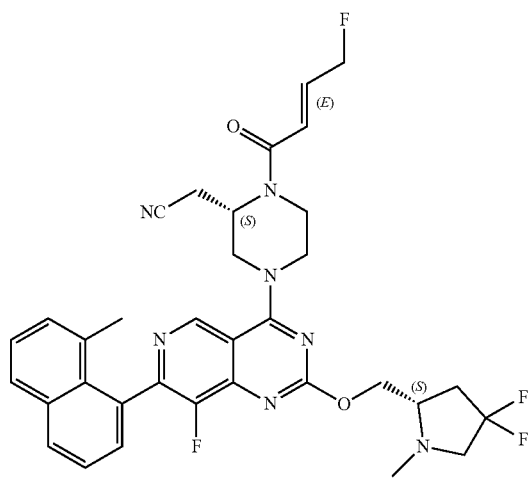

2-((S)-4-(2-(((S)-4,4-difluoro-1-methylpyrrolidin-2-yl)methoxy)-8-fluoro-7-(8-methylnaphthalen-1-yl)pyrido[4,3-d]pyrimidin-4-yl)-1-((E)-4-fluorobut-2-enoyl)piperazin-2-yl)acetonitrile

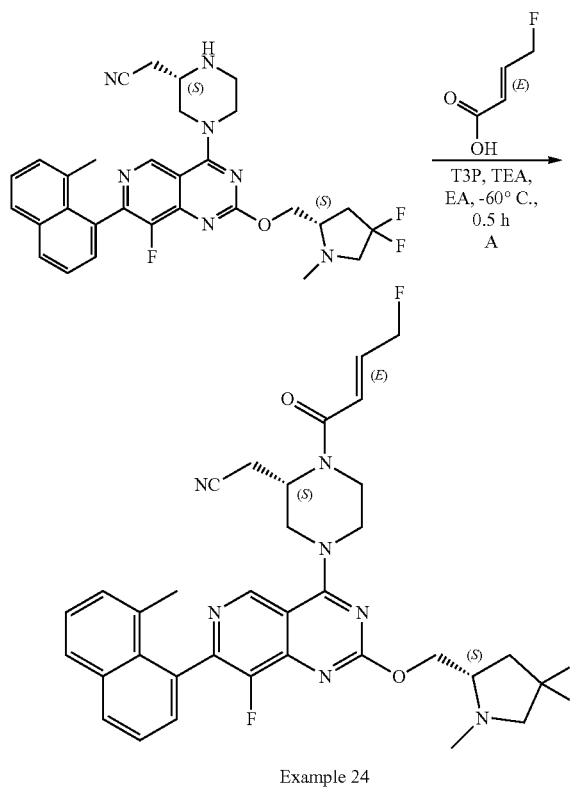

Example 24

Example 24: To a solution of 2-[(2S)-4-[2-[[(2S)-4,4-difluoro-1-methyl-pyrrolidin-2-yl]methoxy]-8-fluoro-7-(8-methyl-1-naphthyl)pyrido[4,3-d]pyrimidin-4-yl]piperazin-2-yl]acetonitrile (90 mg, 160 μmol, 1.0 eq) and (E)-4-fluorobut-2-enoic acid (50 mg, 481 μmol, 3.0 eq) in ethyl acetate (2 mL) was added T3P (305 mg, 481 μmol, 286 μL, 50% purity in ethyl acetate, 3.0 eq) and TEA (129 mg, 1.28 mmol, 178.45 μL, 8.0 eq). The mixture was stirred at −60° C. for 30 minutes. The reaction mixture was quenched with HCl (1 M, 1 mL). The mixture was separated and the aqueous layer was adjusted pH ~8 with saturated NaHCO$_3$ aqueous solution. Then the mixture was extracted with ethyl acetate (3×10 mL). The combined organic layers were washed with brine (10 mL), dried over Na$_2$SO$_4$, filtered and concentrated under reduced pressure to give the product. The residue was purified by column chromatography (SiO$_2$, ethyl acetate/methanol 100/1 to 10/1) and further purification by prep-HPLC (column: Waters Xbridge 150*25 5μ; mobile phase: [water (0.05% ammonia hydroxide v/v)—ACN]; B %: 40%-70%, 10 min). The desired fraction was collected and lyophilized. 2-[(2S)-4-[2-[[(2S)-4,4-difluoro-1-methyl-pyrrolidin-2-yl] methoxy]-8-fluoro-7-(8-methyl-1-naphthyl)pyrido[4,3-d]pyrimidin-4-yl]-1-[(E)-4-fluorobut-2-enoyl]piperazin-2-yl]acetonitrile (54 mg, 83.1 μmol, 52% yield, 89.6% purity) was obtained as a white solid. LCMS [ESI, M+1]: 648.

$^1$H NMR (400 MHz, chloroform-d) δ=9.11 (d, J=2.8 Hz, 1H), 7.99 (dd, J=1.2, 8.0 Hz, 1H), 7.83 (d, J=8.0 Hz, 1H), 7.54 (dt, J=3.86, 7.6 Hz, 1H), 7.50-7.38 (m, 2H), 7.34-7.28 (m, 1H), 7.11-6.93 (m, 1H), 6.59 (br d, J=14.8 Hz, 1H), 5.27-4.75 (m, 3H), 4.70-4.60 (m, 1H), 4.59-4.38 (m, 3H), 4.35-3.58 (m, 4H), 3.44 (dt, J=5.78, 11.6 Hz, 1H), 3.10-2.90 (m, 2H), 2.88-2.64 (m, 2H), 2.61-2.45 (m, 4H), 2.44-2.26 (m, 1H), 2.06 (d, J=7.2 Hz, 3H).

Example 25

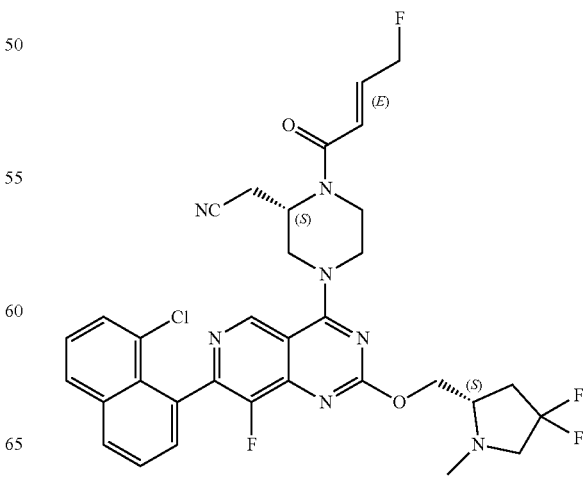

449

2-((S)-4-(7-(8-chloronaphthalen-1-yl)-2-(((S)-4,4-difluoro-1-methylpyrrolidin-2-yl)methoxy)-8-fluoro-pyrido[4,3-d]pyrimidin-4-yl)-1-((E)-4-fluorobut-2-enoyl)piperazin-2-yl)acetonitrile

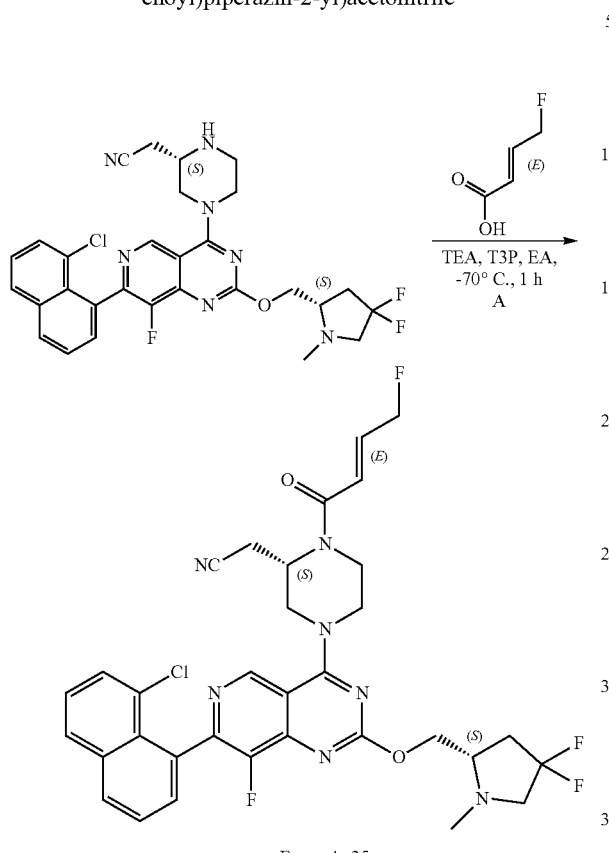

Example 25

Example 25: To a solution of 2-[(2S)-4-[7-(8-chloro-1-naphthyl)-2-[[(2S)-4,4-difluoro-1-methyl-pyrrolidin-2-yl]methoxy]-8-fluoro-pyrido[4,3-d]pyrimidin-4-yl]piperazin-2-yl]acetonitrile (100 mg, 172 μmol, 1.0 eq), (E)-4-fluorobut-2-enoic acid (53.6 mg, 515 μmol, 4.48 μL, 3.0 eq) and TEA (139 mg, 1.37 mmol, 191 μL, 8.0 eq) in ethyl acetate (1 mL) was added T3P (328 mg, 515 μmol, 306 μL, 50% purity in ethyl acetate, 3.0 eq) at −70° C. The mixture was stirred at −70° C. for 1 hour. The reaction mixture was quenched with HCl (1 M, 1.5 mL). Then the mixture was adjusted pH ~7 with saturated NaHCO$_3$ aqueous solution and extracted with ethyl acetate (3×20 mL). The combined organic layers were washed with brine (10 mL), dried over Na$_2$SO$_4$, filtered and concentrated under reduced pressure to give the residue. The residue was purified by prep-HPLC (column: Waters Xbridge 150*25 5μ; mobile phase: [water (0.05% ammonia hydroxide v/v)—ACN]; B %: 38%-68%, 8 min). The desired fraction was collected and lyophilized. 2-[(2S)-4-[7-(8-chloro-1-naphthyl)-2-[[(2S)-4,4-difluoro-1-methyl-pyrrolidin-2-yl]methoxy]-8-fluoro-pyrido[4,3-d]pyrimidin-4-yl]-1-[(E)-4-fluorobut-2-enoyl]piperazin-2-yl]acetonitrile (33 mg, 48.8 μmol, 28% yield, 98.9% purity) was obtained as a white solid. LCMS [ESI, M+1]: 668.

$^1$H NMR (400 MHz, chloroform-d) δ=9.10 (s, 1H), 8.09-7.96 (m, 1H), 7.90 (d, J=8.4 Hz, 1H), 7.69-7.50 (m, 3H), 7.44 (dt, J=2.0, 7.6 Hz, 1H), 7.13-6.95 (m, 1H), 6.60 (d, J=15.2 Hz, 1H), 5.26-4.85 (m, 3H), 4.72-4.60 (m, 1H), 4.58-4.39 (m, 3H), 4.38-3.57 (m, 4H), 3.56-3.36 (m, 1H), 3.15-2.64 (m, 4H), 2.62-2.45 (m, 4H), 2.44-2.24 (m, 1H).

450

Example 26

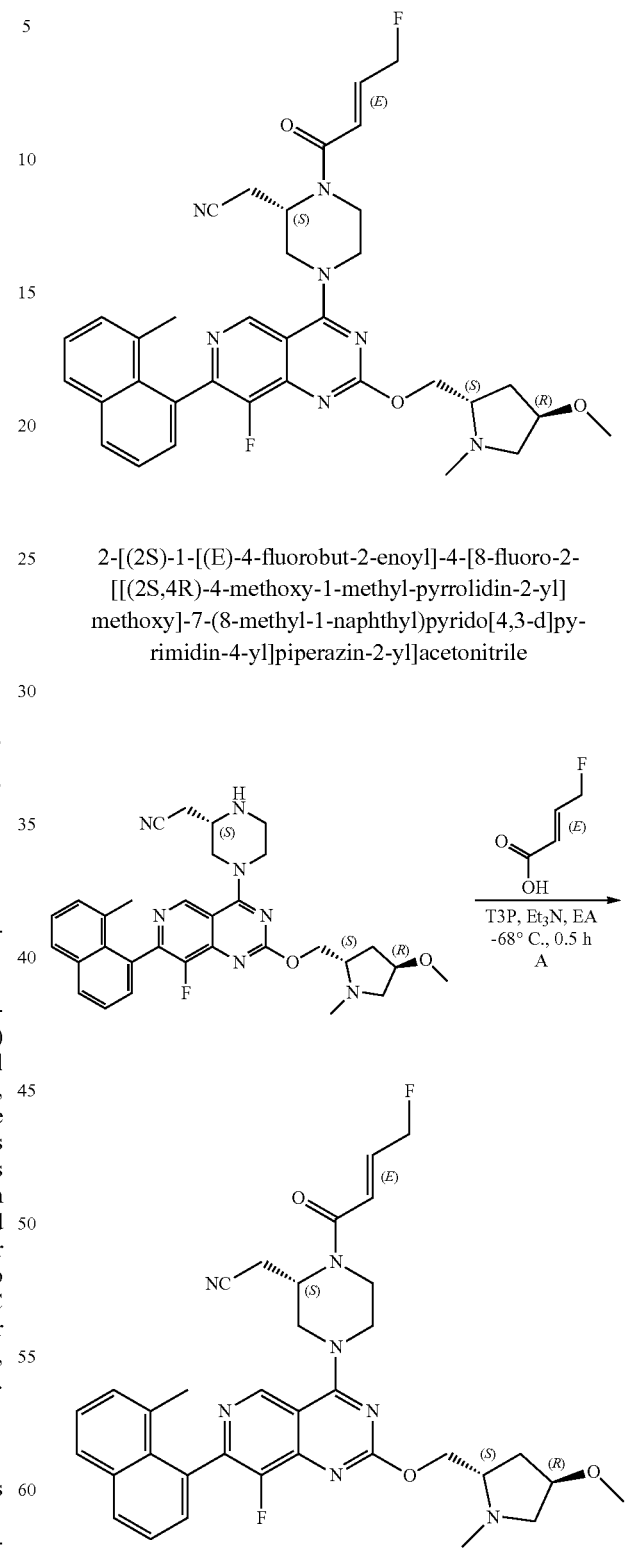

2-[(2S)-1-[(E)-4-fluorobut-2-enoyl]-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]piperazin-2-yl]acetonitrile Example 26

Example 26: To a solution of 2-[(2S)-4-[8-fluoro-2-[[(2S,4R)-4-methoxy-1-methyl-pyrrolidin-2-yl]methoxy]-7-(8- methyl-1-naphthyl)pyrido[4,3-d]pyrimidin-4-yl]piperazin-2-yl]acetonitrile (85.0 mg, 153 μmol, 1.0 eq), (E)-4-fluorobut-2-enoic acid (95.5 mg, 918 μmol, 6.0 eq) and Et₃N (92.9 mg, 918 μmol, 128 μL, 6.0 eq) in Ethyl acetate (9 mL) was added T3P (389 mg, 612 μmol, 364 μL, 50% purity, 4.0 eq) at −68° C. The mixture was stirred at −68° C. for 0.5 hour. Upon completion, the mixture was acidified with aqueous HCl solution (1 mol/L) to pH=3~4. To the separated water layer was added ethyl acetate (60 mL) and basified with saturated aqueous NaHCO₃ solution to pH=7~8. The organic phase was separated, dried over sodium sulfate, filtered and concentrated under vacuum. The residue was purified by prep-HPLC (column: Xtimate C18 150*25 mm*5 μm; mobile phase: [water (0.05% ammonia hydroxide v/v)—ACN]; B %: 35%-65%, 10 min). The residue was concentrated under reduced pressure to remove ACN, and then lyophilized. 2-[(2S)-1-[(E)-4-fluorobut-2-enoyl]-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]piperazin-2-yl]acetonitrile (24.1 mg, 36.5 μmol, 24% yield, 97.2% purity) was obtained as a white solid. LCMS [ESI, M+1]: 642.

¹H NMR (400 MHz, chloroform-d) δ=9.09 (d, J=2.8 Hz, 1H), 7.99 (d, J=8.0 Hz, 1H), 7.82 (d, J=8.0 Hz, 1H), 7.57-7.37 (m, 3H), 7.34-7.27 (m, 1H), 7.17-6.92 (m, 1H), 6.59 (br d, J=14.4 Hz, 1H), 5.19 (br s, 1H), 5.07 (br s, 2H), 4.76-4.55 (m, 1H), 4.55-4.35 (m, 3H), 4.23-3.61 (m, 5H), 3.49-3.37 (m, 1H), 3.31 (s, 3H), 3.04-2.88 (m, 2H), 2.87-2.67 (m, 1H), 2.49 (s, 3H), 2.34 (dd, J=5.6, 9.6 Hz, 1H), 2.10-1.98 (m, 5H).

Example 27

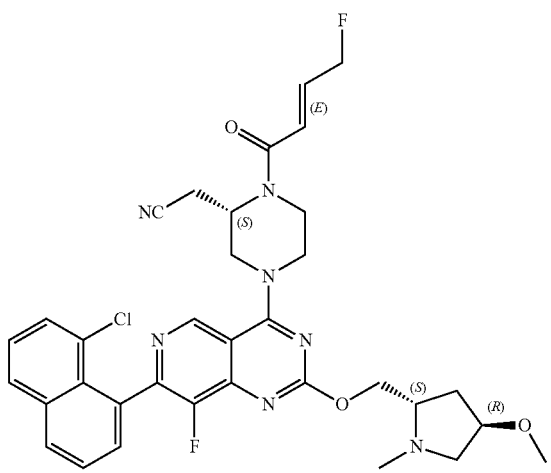

2-[(2S)-4-[7-(8-chloro-1-naphthyl)-8-fluoro-2-[[(2S,4R)-4-methoxy-1-methyl-pyrrolidin-2-yl]methoxy]pyrido[4,3-d]pyrimidin-4-yl]-1-[(E)-4-fluorobut-2-enoyl]piperazin-2-yl]acetonitrile

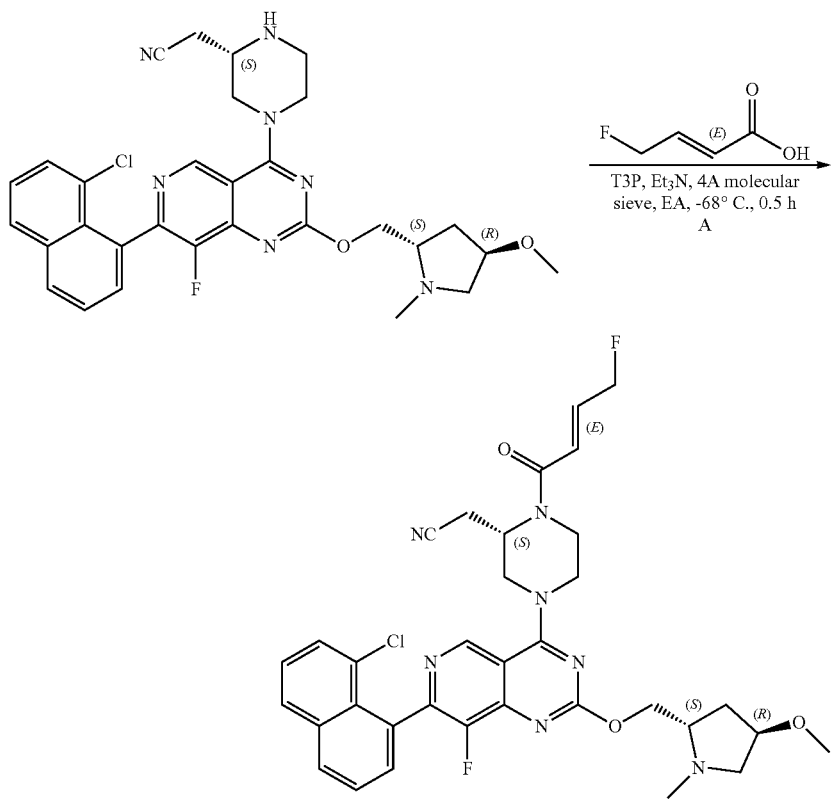

Example 27

Example 27: To a solution of 2-[(2S)-4-[7-(8-chloro-1-naphthyl)-8-fluoro-2-[[(2S,4R)-4-methoxy-1-methyl-pyrrolidin-2-yl]methoxy]pyrido[4,3-d]pyrimidin-4-yl]piperazin-2-yl]acetonitrile (40.0 mg, 69.4 μmol, 1.0 eq), (E)-4-fluorobut-2-enoic acid (43.4 mg, 417 μmol, 6.0 eq), 4A molecular sieve (100 mg) and Et$_3$N (42.2 mg, 417 μmol, 58.0 μL, 6.0 eq) in Ethyl acetate (1 mL) was added T3P (177 mg, 278 μmol, 165 μL, 50% purity, 4.0 eq) at −68° C. The reaction mixture was stirred at −68° C. for 0.5 hour. Upon completion, the mixture was acidified with aqueous HCl solution (1 mol/L) to pH=3~4. To the mixture was added ethyl acetate (20 mL) and basified with saturated aqueous NaHCO$_3$ solution to pH=7~8. The organic phase was separated, dried over sodium sulfate, filtered and concentrated under vacuum. The residue was purified by prep-HPLC (column: Waters Xbridge 150*25 5μ; mobile phase: [water (0.05% ammonia hydroxide v/v)—ACN]; B %: 32%-62%, 10 min). The residue was concentrated under reduced pressure to remove ACN, and then lyophilized. 2-[(2S)-4-[7-(8-chloro-1-naphthyl)-8-fluoro-2-[[(2S,4R)-4-methoxy-1-methyl-pyrrolidin-2-yl]methoxy]pyrido[4,3-d]pyrimidin-4-yl]-1-[(E)-4-fluorobut-2-enoyl]piperazin-2-yl]acetonitrile (8.78 mg, 12.0 μmol, 17% yield, 90.8% purity) was obtained as a white solid. LCMS [ESI, M+1]: 662.

$^1$H NMR (400 MHz, chloroform-d) δ=9.08 (s, 1H), 8.02 (br d, J=8.0 Hz, 1H), 7.90 (d, J=8.4 Hz, 1H), 7.67-7.50 (m, 3H), 7.44 (td, J=2.0, 8.0 Hz, 1H), 7.11-6.93 (m, 1H), 6.60 (br d, J=15.2 Hz, 1H), 5.28-4.91 (m, 3H), 4.68-4.56 (m, 1H), 4.54-4.34 (m, 3H), 4.20-3.60 (m, 5H), 3.53-3.39 (m, 1H), 3.31 (s, 3H), 3.06-2.69 (m, 3H), 2.51 (s, 3H), 2.39-2.29 (m, 1H), 2.16-1.93 (m, 2H).

Example 28

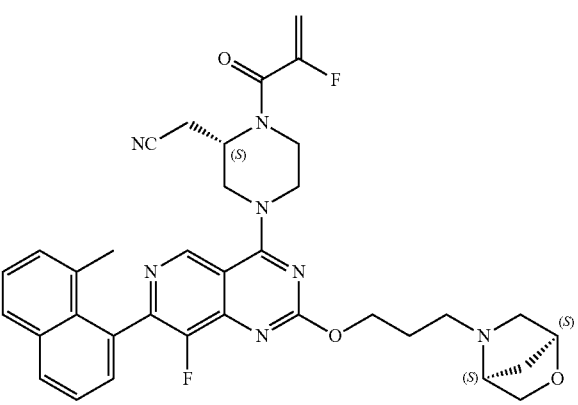

2-[(2S)-4-[8-fluoro-7-(8-methyl-1-naphthyl)-2-[3-[(1S,4S)-2-oxa-5-azabicyclo[2.2.1]heptan-5-yl]propoxy]pyrido[4,3-d]pyrimidin-4-yl]-1-(2-fluoro-prop-2-enoyl)piperazin-2-yl]acetonitrile

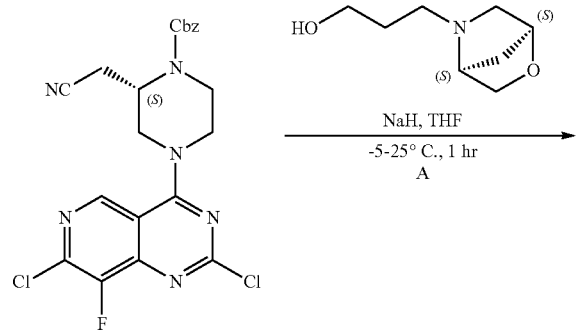

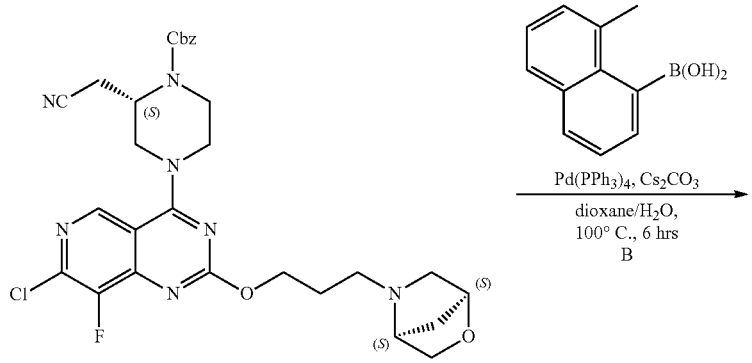

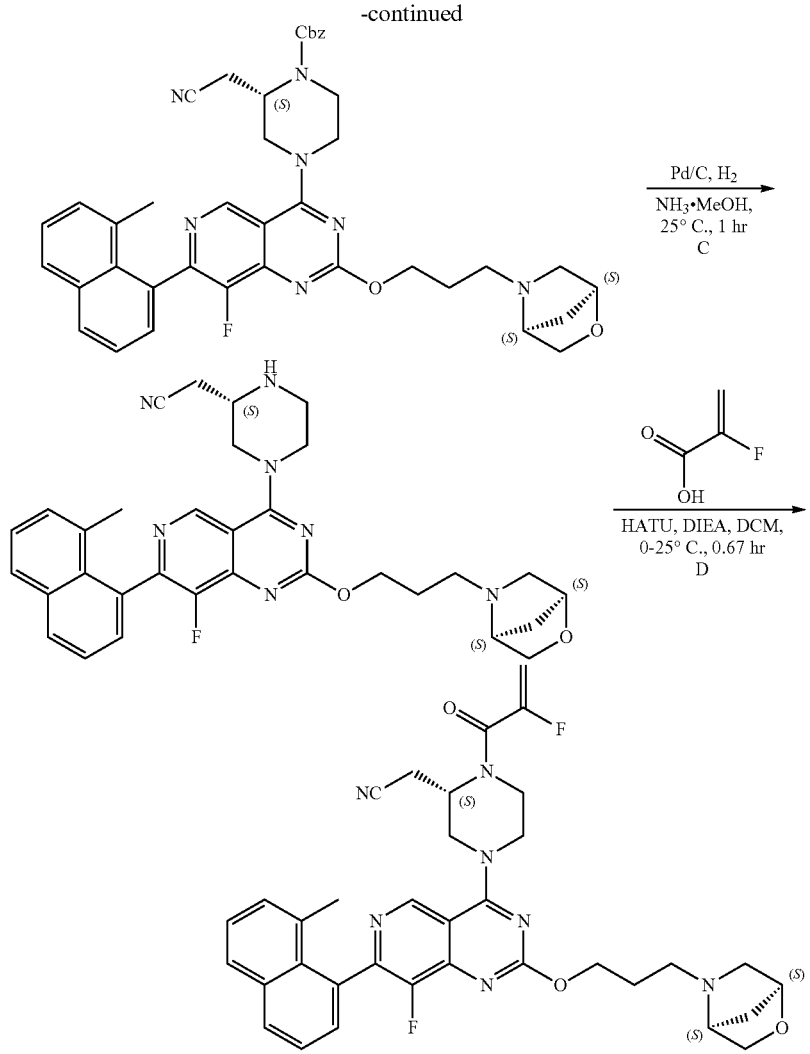

Example 28

Step A: To a solution of 3-[(1S,4S)-2-oxa-5-azabicyclo[2.2.1]heptan-5-yl] propan-1-ol (1.98 g, 12.6 mmol, 2.0 eq) in THF (60 mL) was added NaH (757 mg, 18.9 mmol, 60% purity, 3.0 eq). After stirring at 25° C. for 0.5 hour, benzyl (2S)-2-(cyanomethyl)-4-(2,7-dichloro-8-fluoro-pyrido[4,3-d]pyrimidin-4-yl)piperazine-1-carboxylate (3 g, 6.31 mmol, 1 eq) was added to the mixture at −5° C., then the mixture was stirred at −5° C. for 0.5 hour. Upon completion, the mixture was diluted with water (50 mL) and extracted with ethyl acetate (2×50 mL). The organic layers were dried over $Na_2SO_4$ and concentrated under vacuum. The residue was purified by reversed phase flash [water (0.1% formic acid)/acetonitrile]. The desired fractions were collected and neutralized with solid $NaHCO_3$, concentrated under vacuum to remove acetonitrile and extracted with ethyl acetate (2×100 mL). The organic layers were dried over $Na_2SO_4$ and concentrated under vacuum to give benzyl (2S)-4-[7-chloro-8-fluoro-2-[3-[(1S,4S)-2-oxa-5-azabicyclo[2.2.1]heptan-5-yl]propoxy]pyrido[4,3-d]pyrimidin-4-yl]-2-(cyanomethyl)piperazine-1-carboxylate (2.2 g, 3.32 mmol, 53% yield, 90% purity) as a yellow solid.

$^1$H NMR (400 MHz, chloroform-d) δ=8.80 (s, 1H), 7.44-7.33 (m, 5H), 5.24-5.14 (m, 2H), 4.72-4.62 (m, 1H), 4.61-4.52 (m, 2H), 4.47-4.07 (m, 5H), 4.04 (d, J=7.6 Hz, 1H), 4.01-3.82 (m, 1H), 3.74-3.52 (m, 3H), 3.50 (s, 1H), 2.97-2.92 (m, 1H), 2.91-2.65 (m, 4H), 2.53 (d, J=10.0 Hz, 1H), 1.99 (quin, J=6.8 Hz, 2H), 1.85 (dd, J=2.0, 10.0 Hz, 1H).

Step B: To a solution of benzyl(2S)-4-[7-chloro-8-fluoro-2-[3-[(1S,4S)-2-oxa-5-azabicyclo[2.2.1]heptan-5-yl]propoxy]pyrido[4,3-d]pyrimidin-4-yl]-2-(cyanomethyl)piperazine-1-carboxylate (450 mg, 755 μmol, 1.0 eq) and (8-methyl-1-naphthyl)boronic acid (211 mg, 1.13 mmol, 1.5 eq) in dioxane (9 mL) and $H_2O$ (1.8 mL) was added $Cs_2CO_3$ (738 mg, 2.26 mmol, 3.0 eq), $Pd(PPh_3)_4$ (87.2 mg, 75.5 μmol, 0.1 eq). The mixture was de-gassed and then heated to 100° C. for 6 hours under $N_2$. Upon completion, the mixture was diluted with water (10 mL) and extracted with ethyl acetate (2×20 mL). The organic layers were washed with brine (20 mL), dried over $Na_2SO_4$ and concentrated under vacuum. The residue was purified by chromatography ($Al_2O_3$, petroleum ether/ethyl acetate=2/1 to ethyl acetate/methanol=10/1) to give benzyl(2S)-2-(cyanomethyl)-4-[8-fluoro-7-(8-methyl-1-naphthyl)-2-[3-[(1S,4S)-2-oxa-5-azabicyclo[2.2.1]heptan-5-yl]propoxy]pyrido[4,3-d]pyrimidin-4-yl]piperazine-1-carboxylate (460 mg, 524 μmol, 69% yield, 80% purity) as a yellow solid.

Step C: To a solution of benzyl(2S)-2-(cyanomethyl)-4-[8-fluoro-7-(8-methyl-1-naphthyl)-2-[3-[(1S,4S)-2-oxa-5-azabicyclo[2.2.1]heptan-5-yl]propoxy]pyrido[4,3-d]pyrimidin-4-yl]piperazine-1-carboxylate (460 mg, 655 μmol, 1.0 eq) in MeOH (10 mL) and NH₃.MeOH (5 mL, 20% purity) was added Pd/C (230 mg, 10% purity) under N₂. The suspension was degassed under vacuum and purged with H₂ several times. The mixture was stirred under H₂ (15 psi) at 25° C. for 1 hour. Upon completion, the catalyst was removed by filtering through a plug of Celite®. The solvent was removed under reduced pressure. The residue was purified by reversed phase flash [water (0.1% formic acid/acetonitrile]. The desired fractions were collected and neutralized with solid NaHCO₃, concentrated under vacuum to remove MeCN and extracted with ethyl acetate (2×20 mL). The organic layers were dried over Na₂SO₄ and concentrated under vacuum to give desired product (175 mg) as a yellow solid. Taking 20 mg of it was purified by prep-HPLC (column: Xtimate C18 150*25 mm*5 μm; mobile phase: [water (0.05% ammonia hydroxide v/v)—ACN]; B %: 27%-57%, 10 min). The desired fractions were collected and lyophilized to give 2-[(2S)-4-[8-fluoro-7-(8-methyl-1-naphthyl)-2-[3-[(1S,4S)-2-oxa-5-azabicyclo[2.2.1]heptan-5-yl]propoxy]pyrido[4,3-d]pyrimidin-4-yl]piperazin-2-yl]acetonitrile (4.36 mg, 7.64 μmol, 22% yield, 99.5% purity) as a white solid. LCMS [ESI, M+1]: 568.

¹H NMR (400 MHz, chloroform-d) δ=9.03 (s, 1H), 8.01-7.96 (m, 1H), 7.85-7.79 (m, 1H), 7.57-7.51 (m, 1H), 7.48-7.44 (m, 1H), 7.44-7.39 (m, 1H), 7.31-7.28 (m, 1H), 4.64-4.57 (m, 2H), 4.57-4.50 (m, 1H), 4.45-4.36 (m, 2H), 4.05 (d, J=7.6 Hz, 1H), 3.64-3.60 (m, 1H), 3.60-3.49 (m, 2H), 3.43-3.30 (m, 1H), 3.28-3.08 (m, 3H), 2.98-2.92 (m, 1H), 2.88-2.70 (m, 2H), 2.68-2.50 (m, 3H), 2.10-2.06 (m, 3H), 2.05-1.98 (m, 2H), 1.88-1.83 (m, 1H), 1.75-1.71 (m, 1H).

Example 28: To a solution of 2-fluoroprop-2-enoic acid (19.0 mg, 211 μmol, 2.0 eq) in dichloromethane (2 mL) was added DIEA (54.6 mg, 423 μmol, 73.6 μL, 4.0 eq) and HATU (60.3 mg, 159 μmol, 1.5 eq) at 0° C. After stirring at 0° C. for 20 minutes, 2-[(2S)-4-[8-fluoro-7-(8-methyl-1-naphthyl)-2-[3-[(1S,4S)-2-oxa-5-azabicyclo[2.2.1]heptan-5-yl]propoxy]pyrido[4,3-d]pyrimidin-4-yl]piperazin-2-yl]acetonitrile (60 mg, 105.70 μmol, 1.0 eq) was added into the mixture. The mixture was stirred at 25° C. for 20 minutes. Upon completion, the mixture was diluted with water (2 mL) and extracted with dichloromethane (3×5 mL). The organic layers were dried over Na₂SO₄ and concentrated under vacuum. The residue was purified by chromatography (Al₂O₃, ethyl acetate/methanol 1/0 to 10/1) followed by prep-HPLC (column: Xtimate C18 150*25 mm*5 μm; mobile phase: [water (0.05% ammonia hydroxide v/v)—ACN]; B %: 38%-68%, 10 min). The desired fractions were collected and lyophilized to give 2-[(2S)-4-[8-fluoro-7-(8-methyl-1-naphthyl)-2-[3-[(1S,4S)-2-oxa-5-azabicyclo[2.2.1]heptan-5-yl]propoxy]pyrido[4,3-d]pyrimidin-4-yl]-1-(2-fluoroprop-2-enoyl)piperazin-2-yl]acetonitrile (30.4 mg, 47.1 μmol, 45% yield, 99.1% purity, 100% ee) as a white solid. LCMS [ESI, M+1]: 640.

¹H NMR (400 MHz, chloroform-d) δ=9.08 (d, J=1.6 Hz, 1H), 8.02-7.96 (m, 1H), 7.85-7.79 (m, 1H), 7.57-7.51 (m, 1H), 7.49-7.39 (m, 2H), 7.32-7.28 (m, 1H), 5.60-5.38 (m, 1H), 5.37-5.23 (m, 1H), 4.98-4.73 (m, 1H), 4.67-4.57 (m, 2H), 4.56-4.42 (m, 2H), 4.40 (s, 1H), 4.35-4.13 (m, 1H), 4.12-3.94 (m, 2H), 3.93-3.67 (m, 2H), 3.62 (dd, J=1.6, 7.6 Hz, 1H), 3.52 (s, 1H), 3.07-2.93 (m, 2H), 2.91-2.71 (m, 3H), 2.54 (d, J=10.0 Hz, 1H), 2.09-2.05 (m, 3H), 2.04-1.98 (m, 2H), 1.89-1.83 (m, 1H), 1.76-1.70 (m, 1H).

Example 29

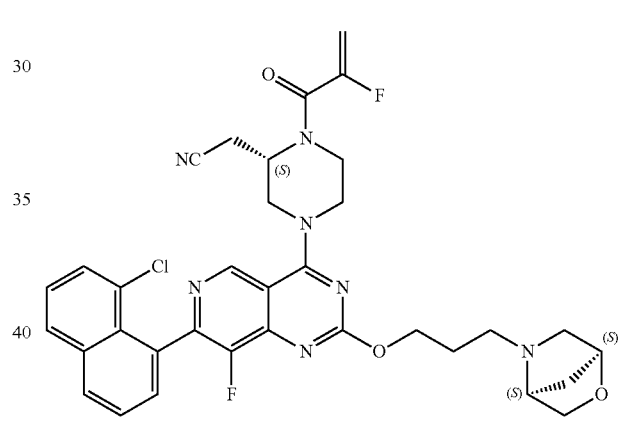

2-[(2S)-4-[7-(8-chloro-1-naphthyl)-8-fluoro-2-[3-[(1S,4S)-2-oxa-5-azabicyclo[2.2.1]heptan-5-yl]propoxy]pyrido[4,3-d]pyrimidin-4-yl]-1-(2-fluoroprop-2-enoyl)piperazin-2-yl]acetonitrile

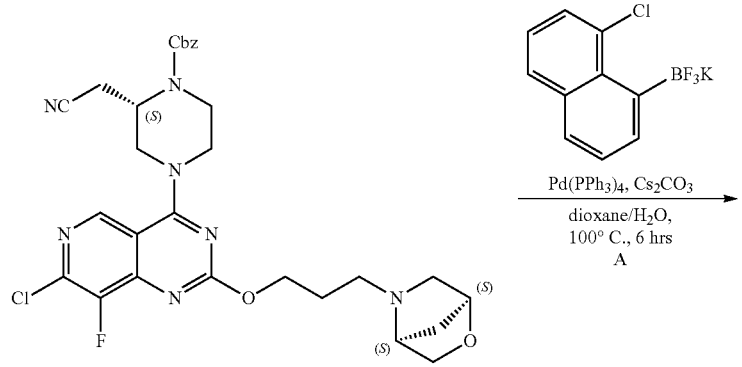

-continued

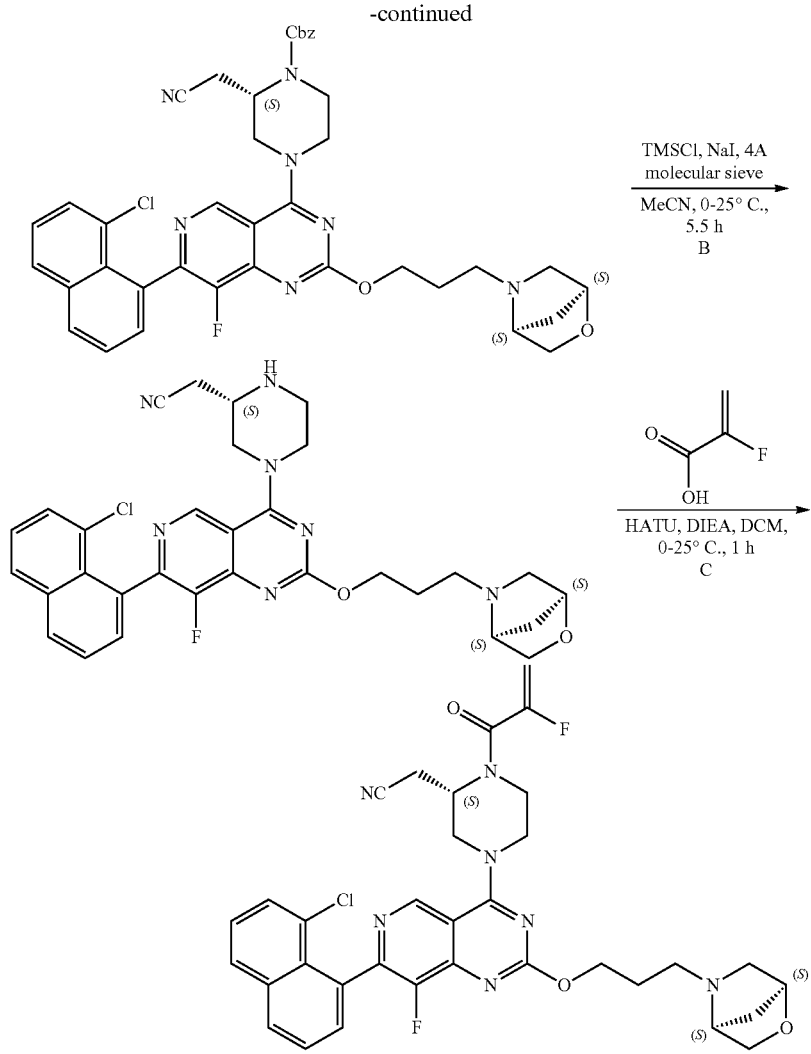

Example 29

Step A: To a solution of benzyl (2S)-4-[7-chloro-8-fluoro-2-[3-[(1S,4S)-2-oxa-5-azabicyclo[2.2.1]heptan-5-yl]propoxy]pyrido[4,3-d]pyrimidin-4-yl]-2-(cyanomethyl)piperazine-1-carboxylate (900 mg, 1.51 mmol, 1.0 eq) and potassium; (8-chloro-1-naphthyl)-trifluoro-boranuide (1.62 g, 6.04 mmol, 4.0 eq) in dioxane (18 mL) and H₂O (3 mL) was added Cs₂CO₃ (1.48 g, 4.53 mmol, 3.0 eq), Pd(PPh₃)₄ (174 mg, 151 µmol, 0.1 eq). The mixture was de-gassed and then heated to 100° C. for 6 hours under N₂. Upon completion, the mixture was diluted with water (10 mL) and extracted with ethyl acetate (2×40 mL). The organic layers were dried over Na₂SO₄ and concentrated under vacuum. The residue was purified by reversed phase flash [water (0.1% formic acid)/acetonitrile]. The desired fractions were collected and neutralized with solid NaHCO₃, concentrated under vacuum to remove MeCN and extracted with ethyl acetate (2×30 mL). The organic layers were dried over Na₂SO₄ and concentrated under vacuum to give benzyl (2S)-4-[7-(8-chloro-1-naphthyl)-8-fluoro-2-[3-[(1S,4S)-2-oxa-5-azabicyclo[2.2.1]heptan-5-yl]propoxy]pyrido[4,3-d]pyrimidin-4-yl]-2-(cyanomethyl)piperazine-1-carboxylate (440 mg, 445 µmol, 29% yield, 73% purity) as a yellow solid.

Step B: A mixture of benzyl (2S)-4-[7-(8-chloro-1-naphthyl)-8-fluoro-2-[3-[(1S,4S)-2-oxa-5-azabicyclo[2.2.1]heptan-5-yl]propoxy]pyrido[4,3-d]pyrimidin-4-yl]-2-(cyanomethyl)piperazine-1-carboxylate (360 mg, 498 µmol, 1 eq), NaI (1.20 g, 7.98 mmol, 16 eq) and 4A molecular sieve (300 mg) in MeCN (11 mL) was stirred at 0° C. for 30 minutes. Then to the mixture was added TMSCl (812 mg, 7.48 mmol, 949 µL, 15 eq) at 0° C. After stirring at 25° C. for 5 hours, the mixture was filtered and the filtrate was purified by reversed phase flash [water (0.1% formic acid)/acetonitrile]. The desired fractions were collected and neutralized with solid NaHCO₃, concentrated under vacuum to remove MeCN and extracted with ethyl acetate (3×30 mL). The organic layers were dried over Na₂SO₄ and concentrated under vacuum to give 110 mg of impure desired product, 30 mg of which was further purified by prep-HPLC (column: Waters Xbridge 150*25 5µ; mobile phase: [water (0.05% ammonia hydroxide v/v)—ACN]; B %: 25%-55%, 10 min). The desired fractions were collected and lyophilized to give 2-[(2S)-4-[7-(8-chloro-1-naphthyl)-8-fluoro-2-[3-[(1S,4S)-2-oxa-5-azabicyclo[2.2.1]heptan-5-yl]propoxy]pyrido[4,3-d]pyrimidin-4-yl]piperazin-2-yl]acetonitrile (4.16 mg, 7.06 µmol, 5.2% yield, 99.8% purity) as a white solid. LCMS [ESI, M+1]: 588.

¹H NMR (400 MHz, chloroform-d) δ=9.02 (s, 1H), 8.02 (dd, J=1.6, 7.6 Hz, 1H), 7.89 (dd, J=1.2, 8.4 Hz, 1H), 7.64-7.54 (m, 3H), 7.46-7.40 (m, 1H), 4.63-4.56 (m, 2H), 4.56-4.47 (m, 1H), 4.45-4.36 (m, 2H), 4.07-4.02 (m, 1H), 3.64-3.60 (m, 1H), 3.59-3.49 (m, 2H), 3.41-3.32 (m, 1H), 3.28-3.09 (m, 3H), 2.98-2.92 (m, 1H), 2.88-2.70 (m, 2H), 2.68-2.51 (m, 3H), 2.06-1.98 (m, 2H), 1.88-1.84 (m, 1H), 1.74-1.71 (m, 1H).

Example 29: To a solution of 2-fluoroprop-2-enoic acid (12.3 mg, 136 μmol, 2.0 eq) in DCM (1.0 mL) was added DIEA (35.2 mg, 272 μmol, 47.4 μL, 4.0 eq) and HATU (38.8 mg, 102 μmol, 1.5 eq) at 0° C. After stirring at 0° C. for 0.5 hour, 2-[(2S)-4-[7-(8-chloro-1-naphthyl)-8-fluoro-2-[3-[(1S,4S)-2-oxa-5-azabicyclo[2.2.1]heptan-5-yl]propoxy]pyrido[4,3-d]pyrimidin-4-yl]piperazin-2-yl]acetonitrile (40 mg, 68.0 μmol, 1.0 eq) was added into the mixture. After stirring at 25° C. for 0.5 hour, the mixture was diluted with water (2 mL) and extracted with dichloromethane (3×5 mL). The organic layers were dried over Na₂SO₄ and concentrated under vacuum. The residue was purified by chromatography (Al₂O₃, ethyl acetate/methanol 1/0 to 10/1) followed by prep-HPLC (column: Waters Xbridge 150*25 5μ; mobile phase: [water (0.05% ammonia hydroxide v/v)—ACN]; B %: 32%-62%, 10 min). The desired fractions were collected and lyophilized to give 2-[(2S)-4-[7-(8-chloro-1-naphthyl)-8-fluoro-2-[3-[(1S,4S)-2-oxa-5-azabicyclo[2.2.1]heptan-5-yl]propoxy]pyrido[4,3-d]pyrimidin-4-yl]-1-(2-fluoroprop-2-enoyl)piperazin-2-yl]acetonitrile (13.5 mg, 19.9 μmol, 29% yield, 97.3% purity) as a white solid. LCMS [ESI, M+1]: 660.

¹H NMR (400 MHz, chloroform-d) δ=9.06 (s, 1H), 8.02 (dd, J=1.6, 8.0 Hz, 1H), 7.89 (d, J=8.4 Hz, 1H), 7.65-7.51 (m, 3H), 7.43 (dt, J=2.0, 7.8 Hz, 1H), 5.57-5.37 (m, 1H), 5.28 (dd, J=3.6, 16.4 Hz, 1H), 4.98-4.73 (m, 1H), 4.67-4.55 (m, 2H), 4.45 (br t, J=12.4 Hz, 2H), 4.39 (s, 1H), 4.33-4.10 (m, 1H), 4.08-3.88 (m, 2H), 3.88-3.65 (m, 2H), 3.64-3.58 (m, 1H), 3.53-3.47 (m, 1H), 3.07-2.70 (m, 5H), 2.57-2.49 (m, 1H), 2.06-1.97 (m, 2H), 1.85 (dd, J=1.6, 9.6 Hz, 1H), 1.73-1.71 (m, 1H).

Example 30

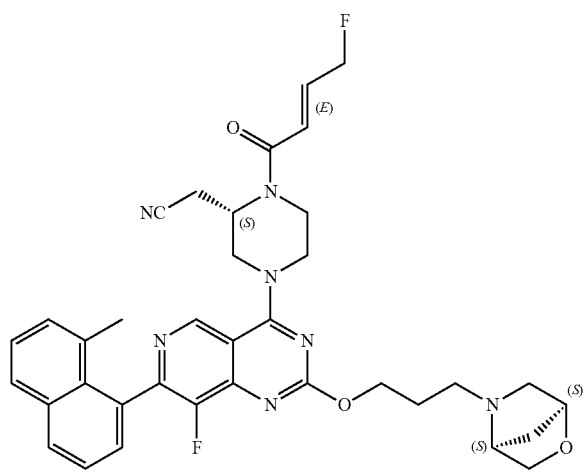

2-[(2S)-1-[(E)-4-fluorobut-2-enoyl]-4-[8-fluoro-7-(8-methyl-1-naphthyl)-2-[3-[(1S,4S)-2-oxa-5-azabicyclo[2.2.1]heptan-5-yl]propoxy]pyrido[4,3-d]pyrimidin-4-yl]piperazin-2-yl]acetonitrile

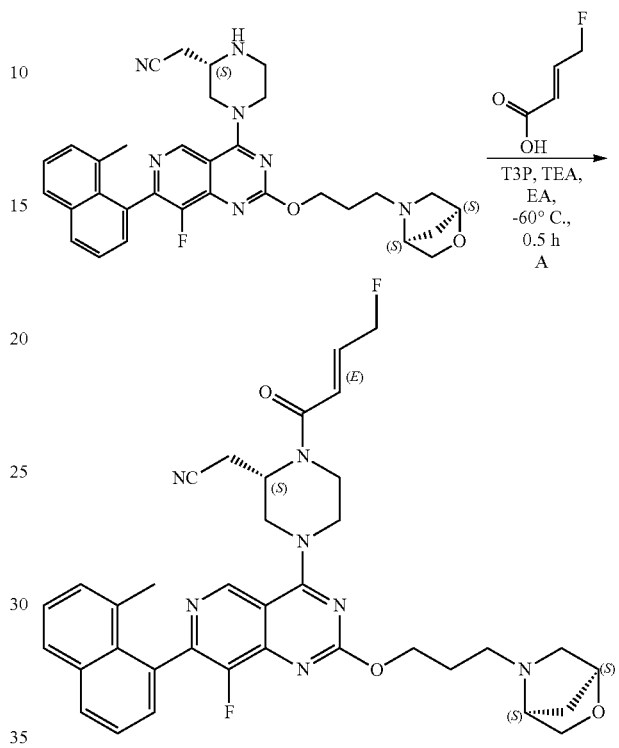

Example 30

Example 30: To a solution of 2-[(2S)-4-[8-fluoro-7-(8-methyl-1-naphthyl)-2-[3-[(1S,4S)-2-oxa-5-azabicyclo[2.2.1]heptan-5-yl]propoxy]pyrido[4,3-d]pyrimidin-4-yl]piperazin-2-yl]acetonitrile (60 mg, 106 μmol, 1.0 eq), (E)-4-fluorobut-2-enoic acid (22.0 mg, 211 μmol, 2.0 eq) and TEA (85.6 mg, 846 μmol, 118 μL, 8.0 eq) in EtOAc (2 mL) was added T3P (202 mg, 317 μmol, 189 μL, 50% purity in ethyl acetate, 3.0 eq) at −60° C. The mixture was stirred at −60° C. for 0.5 hour. Upon completion, the mixture was quenched by 1M HCl (0.2 mL), diluted with water (2 mL) and extracted with ethyl acetate (3×5 mL). The organic layers were dried over Na₂SO₄ and concentrated under vacuum. The residue was purified by chromatography (Al₂O₃, ethyl acetate/methanol 1/0 to 10/1) followed by prep-HPLC (column: Xtimate C18 150*25 mm*5 μm; mobile phase: [water (0.05% ammonia hydroxide v/v)—ACN]; B %: 35%-65%, 10 min). The desired fractions were collected and lyophilized to give 2-[(2S)-1-[(E)-4-fluorobut-2-enoyl]-4-[8-fluoro-7-(8-methyl-1-naphthyl)-2-[3-[(1S,4S)-2-oxa-5-azabicyclo[2.2.1]heptan-5-yl]propoxy]pyrido[4,3-d]pyrimidin-4-yl]piperazin-2-yl]acetonitrile (23.0 mg, 33.9 μmol, 32% yield, 96.5% purity) as a white solid. LCMS [ESI, M+1]: 654.

¹H NMR (400 MHz, chloroform-d) δ=9.09 (d, J=2.0 Hz, 1H), 7.99 (dd, J=0.8, 8.0 Hz, 1H), 7.82 (d, J=8.0 Hz, 1H), 7.58-7.51 (m, 1H), 7.49-7.38 (m, 2H), 7.34-7.28 (m, 1H), 7.12-6.96 (m, 1H), 6.66-6.54 (m, 1H), 5.26-5.16 (m, 1H), 5.14-4.83 (m, 2H), 4.64-4.57 (m, 2H), 4.55-4.42 (m, 2H), 4.41-4.37 (m, 1H), 4.33-3.96 (m, 3H), 3.97-3.68 (m, 2H), 3.65-3.59 (m, 1H), 3.54-3.48 (m, 1H), 3.06-2.90 (m, 2H), 2.88-2.70 (m, 3H), 2.54 (d, J=10.0 Hz, 1H), 2.07 (d, J=5.6 Hz, 3H), 2.04-1.98 (m, 2H), 1.89-1.82 (m, 1H), 1.73 (br d, J=10.8 Hz, 1H).

Example 31

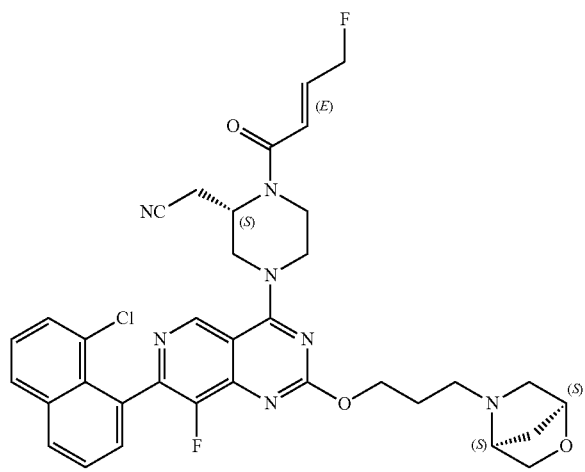

2-[(2S)-4-[7-(8-chloro-1-naphthyl)-8-fluoro-2-[3-[(1S,4S)-2-oxa-5-azabicyclo[2.2.1]heptan-5-yl]propoxy]pyrido[4,3-d]pyrimidin-4-yl]-1-[(E)-4-fluorobut-2-enoyl]piperazin-2-yl]acetonitrile (40 mg, 68.0 μmol, 1 eq), (E)-4-fluorobut-2-enoic acid (14.16 mg, 136.04 μmol, 2 eq) and TEA (55.1 mg, 544 μmol, 75.7 μL, 8 eq) in ethyl acetate (1 mL) was added T3P (130 mg, 204 μmol, 121 μL, 50% purity in ethyl acetate, 3 eq) at −60° C. After stirring at −60° C. for 0.5 hour, the mixture was quenched by 1M HCl (0.2 mL), diluted with water (2 mL) and extracted with ethyl acetate (3×5 mL). The organic layers were dried over Na₂SO₄ and concentrated under vacuum. The residue was purified by chromatography (Al₂O₃, ethyl acetate/methanol 1/0 to 10/1) followed by prep-HPLC (column: Waters Xbridge 150*25 5μ; mobile phase: [water (0.05% ammonia hydroxide v/v)—ACN]; B %: 30%-60%, 10 min). The desired fractions were collected and lyophilized to give 2-[(2S)-4-[7-(8-chloro-1-naphthyl)-8-fluoro-2-[3-[(1S,4S)-2-oxa-5-azabicyclo[2.2.1]heptan-5-yl]propoxy]pyrido[4,3-d]pyrimidin-4-yl]-1-[(E)-4-fluorobut-2-enoyl]piperazin-2-yl]acetonitrile (6.53 mg, 9.34 μmol, 14% yield, 96.4% purity) was obtained as a white solid. LCMS [ESI, M+1]: 674.

¹H NMR (400 MHz, chloroform-d) δ=9.07 (s, 1H), 8.02 (dd, J=1.6, 8.0 Hz, 1H), 7.90 (d, J=8.0 Hz, 1H), 7.66-7.54 (m, 3H), 7.47-7.40 (m, 1H), 7.10-6.95 (m, 1H), 6.59 (br d, J=14.8 Hz, 1H), 5.22-5.15 (m, 1H), 5.15-4.94 (m, 2H), 4.66-4.55 (m, 2H), 4.48 (br d, J=12.2 Hz, 2H), 4.39 (s, 1H), 4.24-3.65 (m, 5H), 3.62 (dd, J=1.6, 8.0 Hz, 1H), 3.55-3.48 (m, 1H), 3.05-2.92 (m, 2H), 2.89-2.71 (m, 3H), 2.54 (d, J=10.0 Hz, 1H), 2.06-1.98 (m, 2H), 1.86 (br d, J=9.6 Hz, 1H), 1.74-1.71 (m, 1H).

Example 32

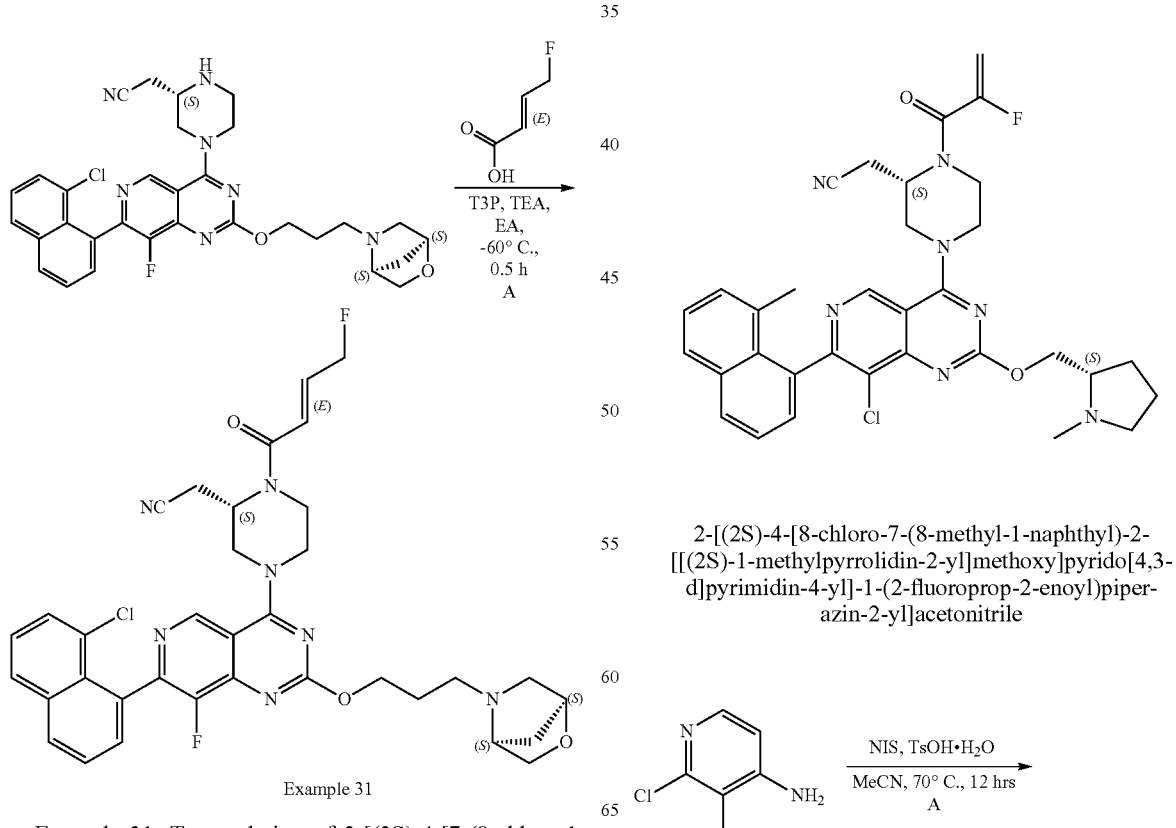

2-[(2S)-4-[8-chloro-7-(8-methyl-1-naphthyl)-2-[[(2S)-1-methylpyrrolidin-2-yl]methoxy]pyrido[4,3-d]pyrimidin-4-yl]-1-(2-fluoroprop-2-enoyl)piperazin-2-yl]acetonitrile Example 31: To a solution of 2-[(2S)-4-[7-(8-chloro-1-naphthyl)-8-fluoro-2-[3-[(1S,4S)-2-oxa-5-azabicyclo[2.2.1]

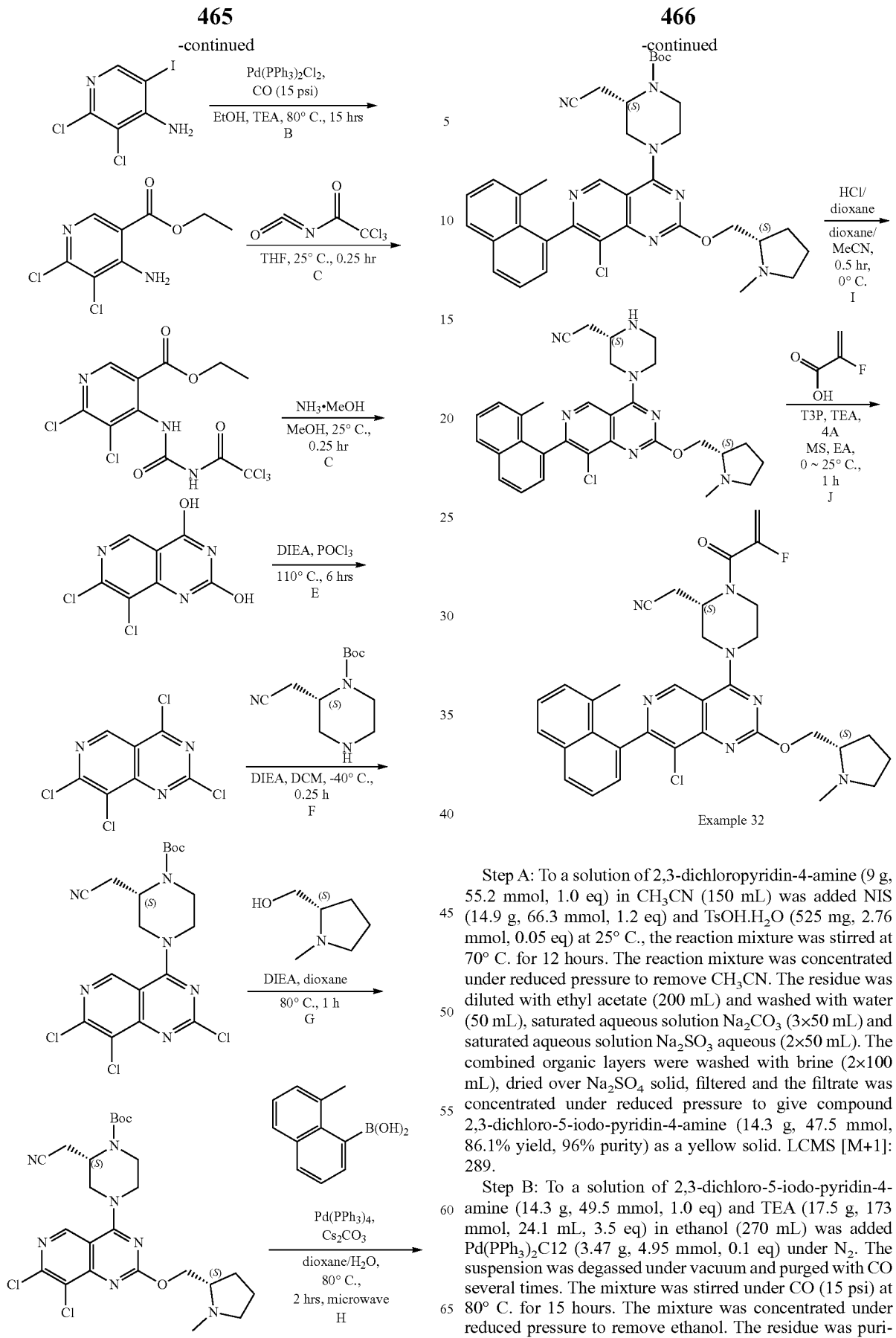

Example 32

Step A: To a solution of 2,3-dichloropyridin-4-amine (9 g, 55.2 mmol, 1.0 eq) in $CH_3CN$ (150 mL) was added NIS (14.9 g, 66.3 mmol, 1.2 eq) and $TsOH \cdot H_2O$ (525 mg, 2.76 mmol, 0.05 eq) at 25° C., the reaction mixture was stirred at 70° C. for 12 hours. The reaction mixture was concentrated under reduced pressure to remove $CH_3CN$. The residue was diluted with ethyl acetate (200 mL) and washed with water (50 mL), saturated aqueous solution $Na_2CO_3$ (3×50 mL) and saturated aqueous solution $Na_2SO_3$ aqueous (2×50 mL). The combined organic layers were washed with brine (2×100 mL), dried over $Na_2SO_4$ solid, filtered and the filtrate was concentrated under reduced pressure to give compound 2,3-dichloro-5-iodo-pyridin-4-amine (14.3 g, 47.5 mmol, 86.1% yield, 96% purity) as a yellow solid. LCMS [M+1]: 289.

Step B: To a solution of 2,3-dichloro-5-iodo-pyridin-4-amine (14.3 g, 49.5 mmol, 1.0 eq) and TEA (17.5 g, 173 mmol, 24.1 mL, 3.5 eq) in ethanol (270 mL) was added $Pd(PPh_3)_2Cl2$ (3.47 g, 4.95 mmol, 0.1 eq) under $N_2$. The suspension was degassed under vacuum and purged with CO several times. The mixture was stirred under CO (15 psi) at 80° C. for 15 hours. The mixture was concentrated under reduced pressure to remove ethanol. The residue was purified by column chromatography ($SiO_2$, Petroleum ether/

Ethyl acetate=20/1 to 10/1). The desired fractions were collected and concentrated to give compound ethyl 4-amino-5,6-dichloro-pyridine-3-carboxylate (13 g, 48.1 mmol, 97.2% yield, 87% purity) as a yellow solid. LCMS [M+1]: 235.

Step C: To a solution of ethyl 4-amino-5,6-dichloro-pyridine-3-carboxylate (12.5 g, 46.3 mmol, 1.0 eq) in THF (100 mL) was added 2,2,2-trichloroacetyl isocyanate (10.5 g, 55.5 mmol, 6.58 mL, 1.2 eq) at 25° C., the reaction mixture was stirred at 25° C. for 0.25 hour. The reaction mixture was concentrated under reduced pressure to remove THF. The crude product was triturated with methyl tert-butyl ether (100 mL) at 25° C. for 20 minutes. The mixture was filtered with methyl tert-butyl ether (10 mL) and washed with methyl tert-butyl ether (2×30 mL). The filter cake was dried under reduced pressure to give compound ethyl 5,6-dichloro-4-[(2,2,2-trichloroacetyl)carbamoylamino]pyridine-3-carboxylate (17.3 g, 40.4 mmol, 86.5% yield, 98% purity) as a red solid. LCMS [M+1]: 422.

Step D: To a solution of ethyl 5,6-dichloro-4-[(2,2,2-trichloroacetyl) carbamoylamino]pyridine-3-carboxylate (0.55 g, 1.30 mmol, 1.0 eq) in methanol (5.0 mL) was added $NH_3$.methanol (0.5 mL, 15% purity) at 0° C., the reaction mixture was stirred at 25° C. for 0.25 hour. The mixture was filtered with methanol (5 mL) and washed with methyl tert-butyl ether (2×10 mL). The filter cake was dried under reduced pressure to give compound 7,8-dichloropyrido[4,3-d]pyrimidine-2,4-diol (320 mg, crude) as a white solid. LCMS [M+1]: 232.

Step E: To a solution of DIEA (1.67 g, 12.9 mmol, 2.25 mL, 5.0 eq) in $POCl_3$ (7.89 g, 51.5 mmol, 4.78 mL, 19.9 eq) was added 7,8-dichloropyrido[4,3-d]pyrimidine-2,4-diol (600 mg, 2.59 mmol, 1.0 eq) at 0° C., the reaction mixture was stirred at 110° C. for 6 hours. The reaction mixture was concentrated under reduced pressure to remove $POCl_3$. Compound 2,4,7,8-tetrachloropyrido[4,3-d]pyrimidine (695 mg, crude) was obtained as a yellow oil. LCMS [M+1]: 267.

Step F: To a solution of 2,4,7,8-tetrachloropyrido[4,3-d]pyrimidine (370 mg, 1.38 mmol, 1.0 eq) in dichloromethane (4.0 mL) was added DIEA (444 mg, 3.44 mmol, 599 µL, 2.5 eq) at −40° C., then a solution of tert-butyl (2S)-2-(cyanomethyl) piperazine-1-carboxylate (310 mg, 1.38 mmol, 1.0 eq) in dichloromethane (0.5 mL) was added at −40° C., the reaction mixture was stirred at −40° C. for 0.25 hour. The reaction mixture was quenched by addition water (10 mL) at 0° C., and then extracted with dichloromethane (3×10 mL). The combined organic layers were washed with brine (2×10 mL), dried over $Na_2SO_4$ solid, filtered and the filtrate was concentrated under reduced pressure to give a residue. The residue was purified by column chromatography ($SiO_2$, Petroleum ether/Ethyl acetate=5/1 to 2/1). The desired fractions were collected and concentrated to give compound tert-butyl (2S)-2-(cyanomethyl)-4-(2,7,8-trichloropyrido[4,3-d]pyrimidin-4-yl)piperazine-1-carboxylate (450 mg, 983 µmol, 71.4% yield, 100% purity) as a yellow solid. LCMS [M+1]: 457.

$^1$H NMR (400 MHz, chloroform-d) δ=9.01 (s, 1H), 4.64-4.58 (m, 1H), 4.50 (dd, J=4.4, 14.0 Hz, 1H), 4.37 (td, J=3.6, 12.4 Hz, 1H), 4.05 (br d, J=12.4 Hz, 1H), 3.88-3.78 (m, 1H), 3.70-3.40 (m, 1H), 3.01-2.77 (m, 1H), 2.68 (dd, J=5.6, 17.2 Hz, 1H), 1.52 (s, 8H).

Step G: To a solution of tert-butyl (2S)-2-(cyanomethyl)-4-(2,7,8-trichloropyrido[4,3-d]pyrimidin-4-yl)piperazine-1-carboxylate (450 mg, 983 µmol, 1.0 eq) in dioxane (10 mL) was added DIEA (381 mg, 2.95 mmol, 514 µL, 3.0 eq) and [(2S)-1-methylpyrrolidin-2-yl]methanol (340 mg, 2.95 mmol, 350 µL, 3.0 eq) at 25° C., the reaction mixture was stirred at 80° C. for 1 hour. The reaction mixture was quenched by addition water (10 mL) at 25° C., and then extracted with ethyl acetate (3×20 mL). The combined organic layers were washed with brine (2×10 mL), dried over $Na_2SO_4$ solid, filtered and the filtrate was concentrated under reduced pressure to give a residue. The crude product was purified by reversed-phase HPLC (0.1% FA condition). The desired fractions were collected and the mixture was added $Na_2CO_3$ solid to pH=7~8. Then the mixture was extracted with ethyl acetate (3×50 mL), The combined organic layers were washed with brine (2×40 mL), dried over $Na_2SO_4$ solid, filtered and the filtrate was concentrated under reduced pressure to give tert-butyl(2S)-2-(cyanomethyl)-4-[7,8-dichloro-2-[[(2S)-1-methylpyrrolidin-2-yl]methoxy]pyrido[4,3-d]pyrimidin-4-yl]piperazine-1-carboxylate (350 mg, 646 µmol, 65.7% yield, 99% purity) as a yellow solid. LCMS [M+1]: 536.

$^1$H NMR (400 MHz, chloroform-d) δ=8.87 (s, 1H), 4.65-4.58 (m, 2H), 4.44-4.36 (m, 2H), 4.33-4.26 (m, 1H), 4.11-4.02 (m, 1H), 3.92-3.84 (m, 1H), 3.70-3.61 (m, 1H), 3.56-3.39 (m, 1H), 3.12 (br t, J=7.2 Hz, 1H), 2.87-2.65 (m, 3H), 2.51 (s, 3H), 2.35-2.25 (m, 1H), 2.10-2.06 (m, 1H), 1.89-1.74 (m, 3H), 1.52 (s, 9H).

Step H: To a solution of tert-butyl (2S)-2-(cyanomethyl)-4-[7,8-dichloro-2-[[(2S)-1-methylpyrrolidin-2-yl]methoxy] pyrido[4,3-d]pyrimidin-4-yl]piperazine-1-carboxylate (930 mg, 1.73 mmol, 1.0 eq) in dioxane (40 mL) and $H_2O$ (10 mL) was added $Cs_2CO_3$ (1.69 g, 5.20 mmol, 3.0 eq), $Pd(PPh_3)_4$ (401 mg, 347 µmol, 0.2 eq) and (8-methyl-1-naphthyl)boronic acid (484 mg, 2.60 mmol, 1.5 eq) at 25° C., the reaction mixture was added to a microwave tube and stirred at 80° C. under microwave (12 bar) for 2 hours. The reaction mixture was diluted with water (20 mL), and then extracted with dichloromethane (3×60 mL). The combined organic layers were washed with brine (2×60 mL), dried over $Na_2SO_4$ solid, filtered and the filtrate was concentrated under reduced pressure to give a residue. The residue was purified by column chromatography [$SiO_2$, Petroleum ether/ Ethyl acetate=1/1 to Ethyl acetate/ethanol (0.5% $NH_3H_2O$) =3/1]. The desired fractions were collected and concentrated to give a residue. The residue was purified by prep-HPLC (basic condition, column: Phenomenex Gemini C18 250*50 mm*10 µm; mobile phase: [water (0.05% ammonia hydroxide v/v)—ACN]; B %: 64%-89%, 31 min/60% min). The desired fractions were collected and concentrated to remove $CH_3CN$. The mixture was extracted with ethyl acetate (3×60 mL). The combined organic layers were washed with brine (2×60 mL), dried over $Na_2SO_4$ solid, filtered and the filtrate was concentrated under reduced pressure to give compound tert-butyl (2S)-4-[8-chloro-7-(8-methyl-1-naphthyl)-2-[[(2S)-1-methylpyrrolidin-2-yl]methoxy]pyrido[4,3-d]pyrimidin-4-yl]-2-(cyanomethyl)piperazine-1-carboxylate (270 mg, 416 µmol, 24.0% yield, 99% purity) as a yellow solid. LCMS [M+1]: 642.

¹H NMR (400 MHz, methanol-d₄) δ=9.19 (s, 1H), 8.02 (d, J=8.0 Hz, 1H), 7.85 (d, J=8.0 Hz, 1H), 7.56 (dt, J=2.0, 7.6 Hz, 1H), 7.45-7.38 (m, 1H), 7.37-7.32 (m, 1H), 7.29 (br d, J=7.2 Hz, 1H), 4.75-4.66 (m, 1H), 4.63-4.44 (m, 4H), 4.07-4.01 (m, 1H), 3.94-3.71 (m, 2H), 3.63-3.43 (m, 1H), 3.20-3.07 (m, 1H), 2.94 (br d, J=6.4 Hz, 2H), 2.89-2.79 (m, 1H), 2.54 (s, 3H), 2.39 (q, J=8.8 Hz, 1H), 2.19-2.07 (m, 1H), 1.99 (d, J=7.2 Hz, 3H), 1.92-1.72 (m, 3H), 1.52 (s, 9H).

Step I: To a solution of tert-butyl (2S)-4-[8-chloro-7-(8-methyl-1-naphthyl)-2-[[(2S)-1-methylpyrrolidin-2-yl]methoxy]pyrido[4,3-d]pyrimidin-4-yl]-2-(cyanomethyl)piperazine-1-carboxylate (70 mg, 98.1 µmol, 1.0 eq) in dioxane (3 mL) and MeCN (1 mL) was added HCl•dioxane (4.0 M, 4.0 mL) at 0° C., the reaction mixture was stirred at 0° C. for 0.5 hour. The reaction mixture was quenched by addition Na₂CO₃ solid to pH=8~9 at 0° C., and then diluted with water (10 mL) and extracted with ethyl acetate (3×20 mL). The combined organic layers were washed with brine (2×20 mL), dried over Na₂SO₄ solid, filtered and the filtrate was concentrated under reduced pressure to give a residue. The residue was purified by prep-HPLC (basic condition, column: Xtimate C18 150*25 mm*5 µm; mobile phase: [water (0.05% ammonia hydroxide v/v)—ACN]; B %: 48%-78%, 10 min). The desired fractions were collected and concentrated to remove CH₃CN, the water layers were lyophilized to give compound 2-[(2S)-4-[8-chloro-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (12.8 mg, 23.5 µmol, 24.0% yield, 99.7% purity) as a white solid. LCMS [M+1]: 542.

¹H NMR (400 MHz, methanol-d₄) δ=9.13 (s, 1H), 8.01 (d, J=7.6 Hz, 1H), 7.85 (d, J=8.0 Hz, 1H), 7.56 (t, J=7.6 Hz, 1H), 7.41 (t, J=7.6 Hz, 1H), 7.34 (d, J=7.2 Hz, 1H), 7.29 (d, J=7.2 Hz, 1H), 4.72-4.39 (m, 5H), 3.69-3.56 (m, 1H), 3.30-3.26 (m, 1H), 3.19-2.97 (m, 3H), 2.87-2.67 (m, 3H), 2.53 (s, 3H), 2.45-2.30 (m, 1H), 2.19-2.05 (m, 1H), 1.99 (s, 3H), 1.92-1.73 (m, 3H).

Example 32: To a mixture of 2-[(2S)-4-[8-chloro-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (230 mg, 424 µmol, 1.0 eq) and 2-fluoroacrylic acid (76.4 mg, 848 µmol, 2.0 eq) was added 4A MOLECULAR SIEVE (10.0 mg) at 25° C., the reaction mixture was stirred at 25° C. for 0.5 hour. Then the mixture was added TEA (644 mg, 6.36 mmol, 886 µL, 15.0 eq) and T3P (1.08 g, 1.70 mmol, 1.01 mL, 50% purity, 4.0 eq) at 0° C., the reaction mixture was stirred at 0° C. for 0.5 hour. The reaction mixture was quenched by addition NH₄Cl aqueous (10 mL) at 0° C., and then diluted with water (10 mL) and extracted with ethyl acetate (3×40 mL). The combined organic layers were washed with brine (2×40 mL), dried over Na₂SO₄ solid, filtered and the filtrate was concentrated under reduced pressure to give a residue. The residue was purified by column chromatography (Al₂O₃, Petroleum ether/Ethyl acetate=1/1 to ethyl acetate/Methanol=3/1). The desired fractions were collected and concentrated to give a residue. The residue was purified by prep-HPLC (basic condition, column: Xtimate C18 150*25 mm*5 µm; mobile phase: [water (0.05% ammonia hydroxide v/v)—ACN]; B %: 53%-83%, 10 min). The desired fractions were collected and concentrated to remove CH₃CN, the water layers were lyophilized to give compound 2-[(2S)-4-[8-chloro-7-(8-methyl-1-naphthyl)-2-[[(2S)-1-methylpyrrolidin-2-yl]methoxy]pyrido[4,3-d]pyrimidin-4-yl]-1-(2-fluoroprop-2-enoyl)piperazin-2-yl]acetonitrile (62 mg, 100 µmol, 23.6% yield, 99.1% purity) as a white solid. LCMS [M+1]: 614.

¹H NMR (400 MHz, methanol-d₄) δ=9.20 (s, 1H), 8.01 (dd, J=1.2, 8.4 Hz, 1H), 7.85 (d, J=8.4 Hz, 1H), 7.56 (t, J=7.6 Hz, 1H), 7.41 (t, J=7.6 Hz, 1H), 7.37-7.32 (m, 1H), 7.28 (br d, J=7.2 Hz, 1H), 5.45-5.33 (m, 1H), 5.31 (s, 1H), 4.73-4.46 (m, 5H), 4.31-3.68 (m, 4H), 3.08 (br dd, J=2.8, 6.8 Hz, 3H), 2.92-2.73 (m, 1H), 2.53 (s, 3H), 2.42-2.30 (m, 1H), 2.18-2.05 (m, 1H), 1.99 (d, J=8.0 Hz, 3H), 1.83 (br dd, J=4.0, 8.8 Hz, 3H).

Example 33

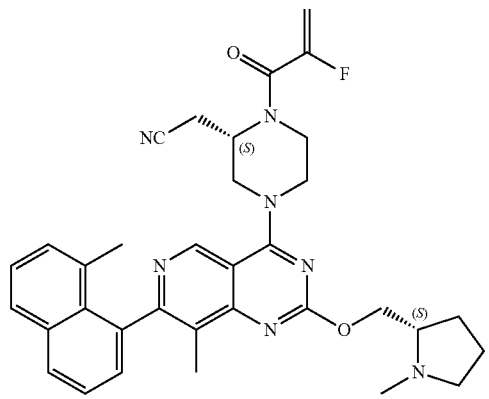

2-[(2S)-1-(2-fluoroprop-2-enoyl)-4-[8-methyl-7-(8-methyl-1-naphthyl)-2-[[(2S)-1-methylpyrrolidin-2-yl]methoxy]pyrido[4,3-d]pyrimidin-4-yl]piperazin-2-yl]acetonitrile

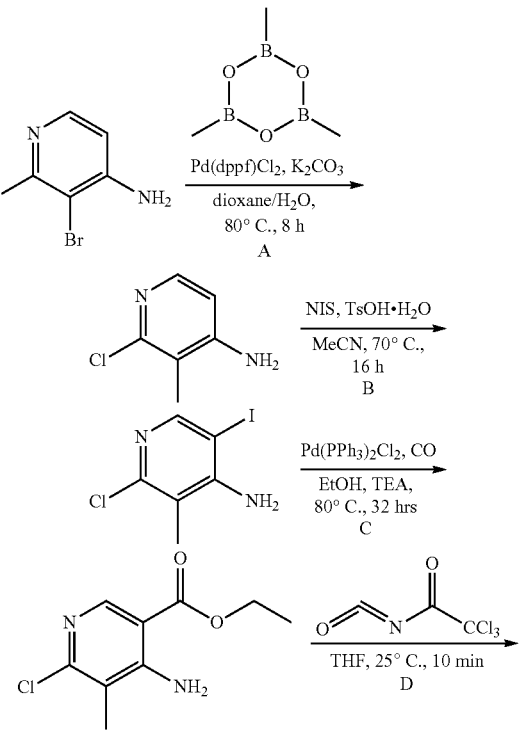

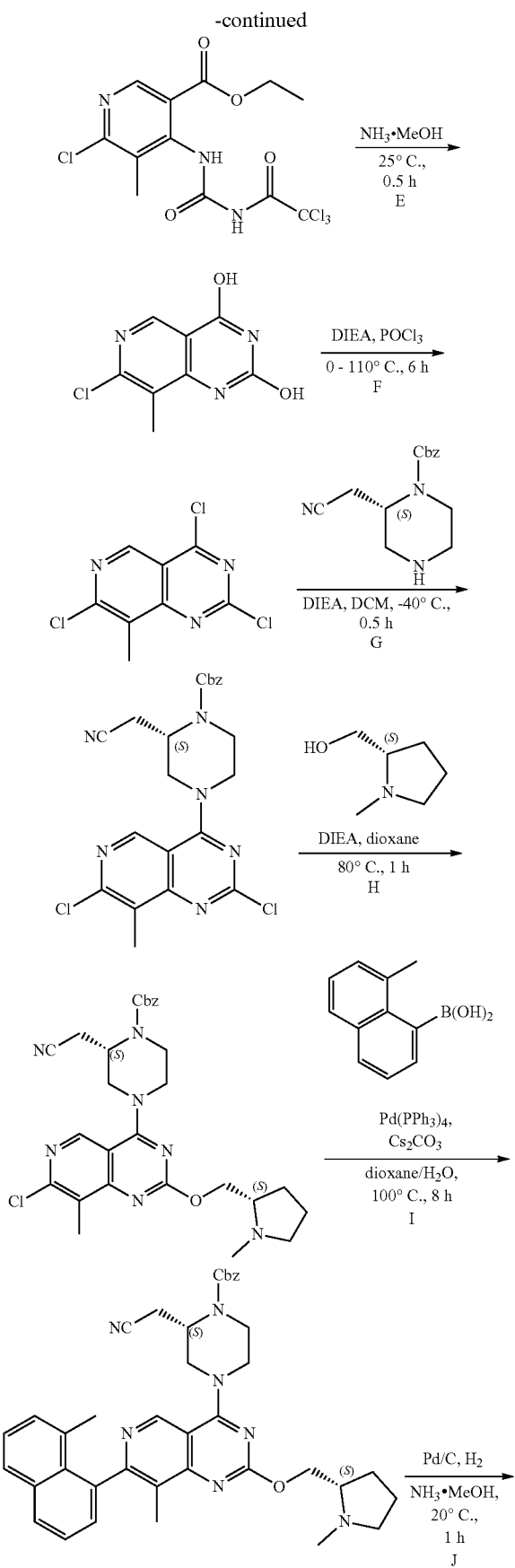

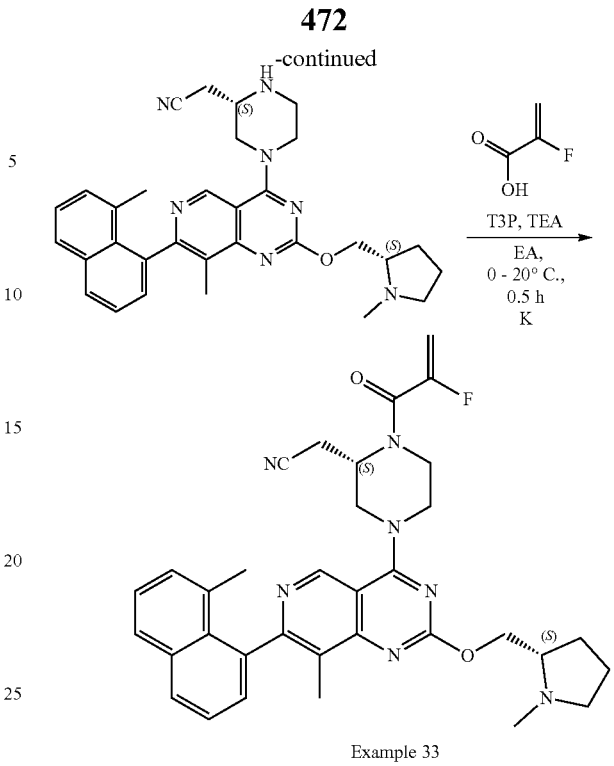

Example 33

Step A: A mixture of 3-bromo-2-chloro-pyridin-4-amine (10 g, 48.2 mmol, 1.0 eq), 2,4,6-trimethyl-1,3,5,2,4,6-trioxatriborinane (12.1 g, 96.4 mmol, 13.5 mL, 2.0 eq), Pd(dppf)Cl$_2$ (3.53 g, 4.82 mmol, 0.1 eq) and K$_2$CO$_3$ (20.0 g, 145 mmol, 3.0 eq) in dioxane (200 mL) and H$_2$O (40.0 mL) was stirred at 80° C. for 8 hours under N$_2$. Upon completion, the mixture was filtered and concentrated in vacuum. The residue was diluted with water (40.0 mL) and extracted with ethyl acetate (3×50.0 mL). The organic layers were dried over Na$_2$SO$_4$ and concentrated under vacuum. The residue was purified by reversed phase flash [water (0.1% NH$_3$H$_2$O)/acetonitrile]. The desired fractions were collected and concentrated under vacuum to give 2-chloro-3-methyl-pyridin-4-amine (3.49 g, 22.0 mmol, 46% yield, 90% purity) as a yellow solid.

Step B: To a solution of 2-chloro-3-methyl-pyridin-4-amine (3.26 g, 22.9 mmol, 1.0 eq) and NIS (6.17 g, 27.4 mmol, 1.2 eq) in MeCN (16.0 mL) was added TsOH.H$_2$O (217 mg, 1.14 mmol, 0.05 eq). The mixture was stirred at 70° C. for 16 hours. The mixture was diluted with water (10.0 mL) and ethyl acetate (70.0 mL), washed with saturated Na$_2$CO$_3$ solution (2×50.0 mL) and saturated Na$_2$SO$_3$ solution (70.0 mL). The organic layer was dried over Na$_2$SO$_4$, filtered and concentrated under vacuum. The residue was purified by reversed phase flash [water (0.1% formic acid)/acetonitrile]. The desired fractions were collected and neutralized with solid NaHCO$_3$, concentrated under vacuum to remove MeCN and extracted with ethyl acetate (2×100 mL). The organic layers were dried over Na$_2$SO$_4$ and concentrated under vacuum to give 2-chloro-5-iodo-3-methyl-pyridin-4-amine (4.80 g, 17.9 mmol, 78% yield, 100% purity) as a yellow solid. LCMS [ESI, M+1]: 269.

$^1$H NMR (400 MHz, DMSO-d$_6$) δ=8.11 (s, 1H), 6.21 (s, 2H), 2.19 (s, 3H).

Step C: To a solution of 2-chloro-5-iodo-3-methyl-pyridin-4-amine (4.8 g, 17.9 mmol, 1.0 eq) in EtOH (120 mL) was added Pd(PPh$_3$)$_2$C12 (1.25 g, 1.79 mmol, 0.1 eq) and TEA (6.53 g, 64.5 mmol, 8.98 mL, 3.6 eq) under argon. The suspension was degassed under vacuum and purged with argon several times. The mixture was stirred under CO (15 psi) at 80° C. for 16 hours. The mixture was added Pd(PPh$_3$)$_2$Cl2 (1.25 g, 1.79 mmol, 0.1 eq) and TEA (6.53 g, 64.5 mmol, 8.98 mL, 3.6 eq). The suspension was degassed under vacuum and purged with argon several times. The mixture was stirred under CO (50 psi) at 80° C. for 16 hours. Upon completion, the mixture was concentrated under vacuum, diluted with ethyl acetate (100 mL) and extracted with water (3×40.0 mL). The organic layers were dried over Na$_2$SO$_4$ and concentrated under vacuum to give ethyl 4-amino-6-chloro-5-methyl-pyridine-3-carboxylate (3.78 g, 17.6 mmol, 98% yield) as a yellow solid which was used directly in the next step without further purification.

$^1$H NMR (400 MHz, chloroform-d) δ=8.63 (s, 1H), 4.37 (q, J=7.2 Hz, 2H), 2.23 (s, 3H), 1.43-1.38 (m, 3H).

Step D: To a solution of ethyl 4-amino-6-chloro-5-methyl-pyridine-3-carboxylate (4.08 g, 19.0 mmol, 1.0 eq) in THF (10.0 mL) was added 2,2,2-trichloroacetyl isocyanate (3.22 g, 17.1 mmol, 2.03 mL, 0.9 eq) at 25° C. for 10 minutes. Upon completion, the mixture was concentrated under vacuum. The residue was triturated with MTBE (10.0 mL) at 25° C. for 5 minutes. Ethyl 6-chloro-5-methyl-4-[(2,2,2-trichloroacetyl)carbamoylamino] pyridine-3-carboxylate (6.7 g, 15.8 mmol, 83% yield, 95% purity) was obtained as a yellow solid. LCMS [ESI, M+1]: 404.

Step E: A solution of ethyl 6-chloro-5-methyl-4-[(2,2,2-trichloroacetyl) carbamoylamino]pyridine-3-carboxylate (6.7 g, 16.6 mmol, 1.0 eq) in NH$_3$.MeOH (14 mL, 20% purity) was stirred at 25° C. for 0.5 hour. Upon completion, the mixture was concentrated under vacuum. The residue was triturated with MTBE (20.0 mL) at 25° C. for 10 minutes. 7-chloro-8-methyl-pyrido[4,3-d]pyrimidine-2,4-diol (4.52 g, crude) was obtained as a yellow solid. LCMS [ESI, M+1]: 212.

$^1$H NMR (400 MHz, DMSO-d$_6$) δ=8.47 (s, 1H), 7.08-6.65 (m, 2H), 2.28 (s, 3H).

Step F: A solution of POCl$_3$ (8.6 g, 56.1 mmol, 5.21 mL, 23.7 eq) and DIEA (916 mg, 7.09 mmol, 1.23 mL, 3.0 eq) was stirred at 0° C., followed by 7-chloro-8-methyl-pyrido[4,3-d]pyrimidine-2,4-diol (0.5 g, 2.36 mmol, 1.0 eq). The suspension was stirred at 110° C. Then DIEA (611 mg, 4.73 mmol, 823 µL, 2.0 eq) was added until the suspension clarified. The mixture was stirred at 110° C. for 6 hours. Upon completion, the mixture was concentrated under vacuum to give 2,4,7-trichloro-8-methyl-pyrido[4,3-d]pyrimidine (1.5 g, crude) as a black oil which was used directly in the next step without further purification.

Step G: To a solution of 2,4,7-trichloro-8-methyl-pyrido[4,3-d]pyrimidine (587 mg, 2.36 mmol, 1.0 eq) in DCM (12 mL) was added DIEA (1.51 g, 11.7 mmol, 2.04 mL, 4.9 eq) at −40° C. until the pH of the resulting mixture was adjusted to 8 followed by benzyl (2S)-2-(cyanomethyl)piperazine-1-carboxylate (368 mg, 1.42 mmol, 0.6 eq) in DCM (1.00 mL). Then mixture was stirred at −40° C. for 0.5 hour. Upon completion, the mixture was added water (10.0 mL) and layers were separated. The aqueous phase was extracted with ethyl acetate (2×20.0 mL). Combined organic layers were dried over Na$_2$SO$_4$, filtered and concentrated under vacuum. The residue was purified by silica gel chromatography (petroleum ether/ethyl acetate 10/1 to 1/1). The desired fractions were collected and concentrated under vacuum to give benzyl (2S)-2-(cyanomethyl)-4-(2,7-dichloro-8-methyl-pyrido[4,3-d]pyrimidin-4-yl) piperazine-1-carboxylate (470 mg, 878 µmol, three steps 48% yield, 88% purity) as a yellow solid. LCMS [ESI, M+1]: 471.

Step H: To a solution of benzyl (2S)-2-(cyanomethyl)-4-(2,7-dichloro-8-methyl-pyrido[4,3-d]pyrimidin-4-yl)piperazine-1-carboxylate (420 mg, 891 µmol, 1.0 eq) and DIEA (345 mg, 2.67 mmol, 466 µL, 3.0 eq) in dioxane (9.00 mL) was added [(2S)-1-methylpyrrolidin-2-yl]methanol (513 mg, 4.46 mmol, 529 µL, 5.0 eq). The reaction mixture was stirred at 80° C. for 1 hour. Upon completion, the solvent was removed under reduced pressure. The residue was diluted with water (10 mL) and extracted with ethyl acetate (2×20 mL). The organic layers were dried over Na$_2$SO$_4$ and concentrated under vacuum. The residue was purified by reversed phase flash [water (0.1% formic acid/acetonitrile]. The desired fractions were collected and neutralized with solid NaHCO$_3$, concentrated under vacuum to remove MeCN and extracted with ethyl acetate (2×30 mL). The organic layers were dried over Na$_2$SO$_4$ and concentrated under vacuum to give benzyl (2S)-4-[7-chloro-8-methyl-2-[[(2S)-1-methylpyrrolidin-2-yl] methoxy]pyrido[4,3-d]pyrimidin-4-yl]-2-(cyanomethyl)piperazine-1-carboxylate (304 mg, 531 µmol, 60% yield, 96% purity) as a yellow solid. LCMS [ESI, M+1]: 550.

$^1$H NMR (400 MHz, chloroform-d) δ=8.84 (s, 1H), 7.44-7.33 (m, 5H), 5.25-5.15 (m, 2H), 4.73-4.65 (m, 1H), 4.57 (dd, J=4.8, 10.8 Hz, 1H), 4.40-4.25 (m, 3H), 4.22-4.06 (m, 1H), 3.92-3.72 (m, 1H), 3.65-3.41 (m, 2H), 3.17-3.07 (m, 1H), 2.96-2.77 (m, 1H), 2.76-2.68 (m, 2H), 2.62 (s, 3H), 2.51 (s, 3H), 2.35-2.25 (m, 1H), 2.13-2.00 (m, 1H), 1.92-1.75 (m, 3H).

Step I: To a solution of benzyl (2S)-4-[7-chloro-8-methyl-2-[[(2S)-1-methylpyrrolidin-2-yl]methoxy]pyrido[4,3-d]pyrimidin-4-yl]-2-(cyanomethyl)piperazine-1-carboxylate (310 mg, 564 µmol, 1.0 eq) and (8-methyl-1-naphthyl) boronic acid (157 mg, 845 µmol, 1.5 eq) in dioxane (7.00 mL) and H$_2$O (1.40 mL) was added Pd(PPh$_3$)$_4$ (65.1 mg, 56.4 µmol, 0.1 eq), Cs$_2$CO$_3$ (367 mg, 1.13 mmol, 2.0 eq). The mixture was de-gassed and then heated to 100° C. for 8 hours under N$_2$. Upon completion, the mixture was concentrated under vacuum, diluted with water (5.00 mL) and extracted with ethyl acetate (2×10.0 mL). The organic layers were dried over Na$_2$SO$_4$ and concentrated under vacuum. The residue was purified by reversed phase flash [water (0.1% formic acid/acetonitrile]. The desired fractions were collected and neutralized with solid NaHCO$_3$, concentrated under vacuum to remove MeCN and extracted with ethyl acetate (2×20.0 mL). The organic layers were dried over Na$_2$SO$_4$ and concentrated under vacuum to give benzyl (2S)-2-(cyanomethyl)-4-[8-methyl-7-(8-methyl-1-naphthyl)-2-[[(2S)-1-methylpyrrolidin-2-yl]methoxy]pyrido[4,3-d]pyrimidin-4-yl]piperazine-1-carboxylate (227 mg, 277 µmol, 49% yield, 80% purity) as a yellow solid. LCMS [ESI, M+1]: 656.

Step J: To a solution of benzyl (2S)-2-(cyanomethyl)-4-[8-methyl-7-(8-methyl-1-naphthyl)-2-[[(2S)-1-methylpyrrolidin-2-yl]methoxy]pyrido[4,3-d]pyrimidin-4-yl]piperazine-1-carboxylate (50 mg, 61.0 µmol, 1.0 eq) in MeOH (1.00 mL) was added NH$_3$.MeOH (1.00 mL, 20% purity), Pd/C (25 mg, 10% purity) under N$_2$. The suspension was degassed under vacuum and purged with H$_2$ several times. The mixture was stirred under H$_2$ (15 psi) at 20° C. for 1 hour. Upon completion, the catalyst was removed by filtering through a plug of Celite®. The solvent was removed under reduced pressure. The residue was purified by prep-HPLC (column: Xtimate C18 150*25 mm*5 µm; mobile phase: [water (0.05% ammonia hydroxide v/v)—ACN]; B %: 46%-76%, 10 min). The desired fractions were collected and lyophilized to give 2-[(2S)-4-[8-methyl-7-(8-methyl-1-naphthyl)-2-[[[(2S)-1-methylpyrrolidin-2-yl]methoxy]

pyrido[4,3-d]pyrimidin-4-yl]piperazin-2-yl]acetonitrile (11.5 mg, 21.7 µmol, 36% yield, 98.5% purity) as a off-white solid. LCMS [ESI, M+1]: 522.

¹H NMR (400 MHz, chloroform-d) δ=9.10-9.05 (m, 1H), 7.94 (dd, J=1.2, 8.0 Hz, 1H), 7.81 (d, J=8.0 Hz, 1H), 7.51 (t, J=7.6 Hz, 1H), 7.42-7.36 (m, 1H), 7.31-7.28 (m, 1H), 7.24 (d, J=6.8 Hz, 1H), 4.61 (td, J=5.2, 10.4 Hz, 1H), 4.50-4.42 (m, 1H), 4.41-4.31 (m, 2H), 3.57-3.45 (m, 1H), 3.43-3.30 (m, 1H), 3.25-3.09 (m, 4H), 2.78 (br d, J=1.2 Hz, 1H), 2.68-2.56 (m, 2H), 2.52 (s, 3H), 2.36-2.27 (m, 4H), 2.14-2.03 (m, 1H), 1.96-1.91 (m, 3H), 1.87-1.77 (m, 3H).

Example 33 To a solution of 2-[(2S)-4-[8-methyl-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (100 mg, 192 µmol, 1.0 eq), T3P (488 mg, 767 µmol, 456 µL, 50% purity in ethyl acetate, 4.0 eq) and TEA (233 mg, 2.30 mmol, 320 µL, 12.0 eq) in ethyl acetate (3 mL) was added 2-fluoroprop-2-enoic acid (51.8 mg, 575 µmol, 3.0 eq) at 0° C. The mixture was stirred at 20° C. for 0.5 hour. Upon completion, the mixture was added water (3.00 mL) and extracted with ethyl acetate (2×5.00 mL). The organic layers were dried over Na₂SO₄ and concentrated under vacuum. The residue was purified by reversed phase flash [water (0.1% formic acid/acetonitrile]. The desired fractions were collected and neutralized with solid NaHCO₃, concentrated under vacuum to remove MeCN and extracted with ethyl acetate (2×10 mL). The organic layers were dried over Na₂SO₄ and concentrated under vacuum. The residue was further purified by prep-HPLC (column: Xtimate C18 150*25 mm*5 µm; mobile phase: [water (0.05% ammonia hydroxide v/v)—ACN]; B %: 52%-82%, 10 min). The desired fractions were collected and lyophilized to give 2-[(2S)-1-(2-fluoroprop-2-enoyl)-4-[8-methyl-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (29.2 mg, 48.9 µmol, 25% yield, 99.3% purity) as a white solid.

¹H NMR (400 MHz, chloroform-d) δ=9.12 (d, J=1.2 Hz, 1H), 7.97-7.91 (m, 1H), 7.81 (d, J=8.0 Hz, 1H), 7.52 (ddd, J=4.4, 7.2, 8.0 Hz, 1H), 7.40 (dt, J=3.2, 7.6 Hz, 1H), 7.33-7.27 (m, 1H), 7.26-7.22 (m, 1H), 5.59-5.36 (m, 1H), 5.28 (dd, J=3.2, 16.8 Hz, 1H), 5.04-4.71 (m, 1H), 4.65-4.56 (m, 1H), 4.53-4.34 (m, 3H), 4.32-4.03 (m, 1H), 4.01-3.81 (m, 1H), 3.80-3.44 (m, 2H), 3.13 (br t, J=7.6 Hz, 1H), 3.06-2.95 (m, 1H), 2.94-2.82 (m, 1H), 2.82-2.71 (m, 1H), 2.52 (s, 3H), 2.36-2.27 (m, 4H), 2.14-2.03 (m, 1H), 1.93 (d, J=14.8 Hz, 3H), 1.89-1.74 (m, 3H).

Example 34

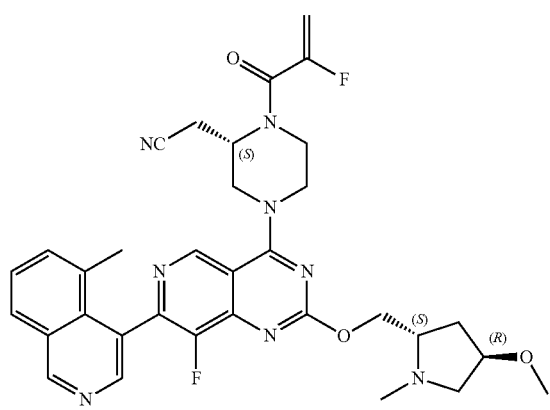

2-[(2S)-4-[8-fluoro-2-[[(2S,4R)-4-methoxy-1-methyl-pyrrolidin-2-yl]methoxy]-7-(5-methyl-4-isoquinolyl)pyrido[4,3-d]pyrimidin-4-yl]-1-(2-fluoroprop-2-enoyl)piperazin-2-yl]acetonitrile

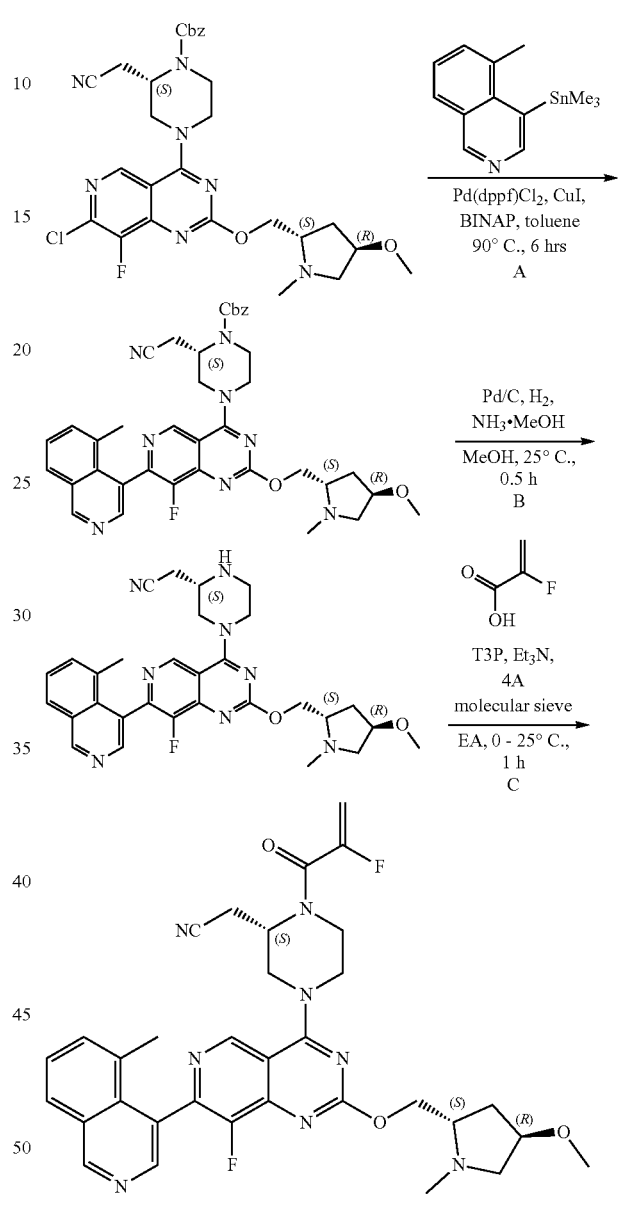

Example 34

Step A: To a solution of benzyl (2S)-4-[7-chloro-8-fluoro-2-[[(2S,4R)-4-methoxy-1-methyl-pyrrolidin-2-yl]methoxy]pyrido[4,3-d]pyrimidin-4-yl]-2-(cyanomethyl)piperazine-1-carboxylate (230 mg, 394 µmol, 1.0 eq) and trimethyl-(5-methyl-4-isoquinolyl)stannane (241 mg, 788 µmol, 2.0 eq) in toluene (10 mL) was added Pd(dppf)Cl₂ (28.8 mg, 39.4 µmol, 0.1 eq), CuI (22.5 mg, 118 µmol, 0.3 eq), and BINAP (49.0 mg, 78.8 µmol, 0.2 eq). The reaction mixture was stirred at 90° C. for 6 hours. Upon completion, the mixture was diluted with water (15 mL) and extracted with ethyl acetate (2×20 mL). The combined organic layers were washed with brine (25 mL), dried over Na₂SO₄, filtered and concentrated under vacuum. The residue was purified by reversed phase flash [water (0.1% formic acid)/acetonitrile]. The desired fractions were collected and neutralized with saturated NaHCO₃ solution and extracted with ethyl acetate (50 mL). The separated organic layer was dried over sodium sulfate, filtered and concentrated under vacuum. benzyl (2S)-2-(cyanomethyl)-4-[8-fluoro-2-[[(2S,4R)-4-methoxy-1-methyl-pyrrolidin-2-yl]methoxy]-7-(5-methyl-4-isoquinolyl)pyrido[4,3-d]pyrimidin-4-yl]piperazine-1-carboxylate (157 mg, 227 μmol, 58% yield, 100% purity) was obtained as a yellow solid. LCMS [ESI, M+1]: 691.

Step B: To a solution of benzyl (2S)-2-(cyanomethyl)-4-[8-fluoro-2-[[(2S,4R)-4-methoxy-1-methyl-pyrrolidin-2-yl]methoxy]-7-(5-methyl-4-isoquinolyl)pyrido[4,3-d]pyrimidin-4-yl]piperazine-1-carboxylate (30 mg, 43.4 μmol, 1.0 eq) in MeOH (1 mL) was added NH₃.MeOH (0.5 mL, 50% purity) and Pd/C (10 mg, 10% purity) under N₂. The suspension was degassed under vacuum and purged with Hz several times. The mixture was stirred under Hz (15 psi) at 25° C. for 0.5 hour. Upon completion, the mixture was filtered and the filtrate was concentrated under vacuum. The residue was purified by prep-HPLC (column: Waters Xbridge 150*25 5μ; mobile phase: [water (0.05% ammonia hydroxide v/v)—ACN]; B %: 15%-45%, 10 min). The residue was concentrated under reduced pressure to remove ACN, and then lyophilized. 2-[(2S)-4-[8-fluoro-2-[[(2S,4R)-4-methoxy-1-methyl-pyrrolidin-2-yl]methoxy]-7-(5-methyl-4-isoquinolyl)pyrido[4,3-d]pyrimidin-4-yl]piperazin-2-yl]acetonitrile (10.0 mg, 17.9 μmol, 41% yield, 99.5% purity) was obtained as a white solid. LCMS [ESI, M+1]: 557.

¹H NMR (400 MHz, chloroform-d) δ=9.33 (s, 1H), 9.05 (s, 1H), 8.46 (s, 1H), 7.95 (d, J=8.0 Hz, 1H), 7.59-7.48 (m, 2H), 4.64-4.50 (m, 2H), 4.48-4.37 (m, 2H), 4.02-3.92 (m, 1H), 3.66-3.51 (m, 1H), 3.49-3.41 (m, 1H), 3.40-3.28 (m, 4H), 3.28-3.05 (m, 3H), 2.99-2.89 (m, 1H), 2.69-2.53 (m, 2H), 2.49 (s, 3H), 2.33 (dd, J=5.6, 9.6 Hz, 1H), 2.09 (s, 3H), 2.07-1.98 (m, 2H).

Example 34: To a solution of 2-[(2S)-4-[8-fluoro-2-[[(2S,4R)-4-methoxy-1-methyl-pyrrolidin-2-yl]methoxy]-7-(5-methyl-4-isoquinolyl)pyrido[4,3-d]pyrimidin-4-yl]piperazin-2-yl]acetonitrile (45 mg, 80.8 μmol, 1.0 eq), 2-fluoroprop-2-enoic acid (58.2 mg, 647 μmol, 8.0 eq) in ethyl acetate (5 mL) was added 4A molecular sieve (200 mg). The mixture was stirred at 25° C. for 0.5 hour. After that, the mixture was cooled to 0° C. and added Et₃N (73.6 mg, 727 μmol, 101 μL, 9.0 eq) and T3P (206 mg, 323 μmol, 192 μL, 50% purity, 4.0 eq) at 0° C. The mixture was stirred at 0° C. for 0.5 hour. Upon completion, the residue was diluted with water (4 mL) and ethyl acetate (3 mL). The organic layer was separated, washed with brine (5 mL), dried over sodium sulfate, filtered and concentrated under vacuum. The residue was purified by prep-HPLC (column: Waters Xbridge 150*25 5μ; mobile phase: [water (0.05% ammonia hydroxide v/v)—ACN]; B %: 22%-52%, 10 min). The residue was concentrated under reduced pressure to remove ACN, and then lyophilized. 2-[(2S)-4-[8-fluoro-2-[[(2S,4R)-4-methoxy-1-methyl-pyrrolidin-2-yl]methoxy]-7-(5-methyl-4-isoquinolyl)pyrido[4,3-d]pyrimidin-4-yl]-1-(2-fluoroprop-2-enoyl)piperazin-2-yl]acetonitrile (16.8 mg, 26.2 μmol, 32% yield, 98.3% purity) was obtained as a white solid. LCMS [ESI, M+1]: 629.

¹H NMR (400 MHz, chloroform-d) δ=9.34 (s, 1H), 9.11 (br s, 1H), 8.47 (br d, J=7.6 Hz, 1H), 7.96 (br d, J=7.2 Hz, 1H), 7.63-7.45 (m, 2H), 5.60-5.38 (m, 1H), 5.29 (br d, J=16.0 Hz, 1H), 4.94-4.76 (m, 1H), 4.68-4.56 (m, 1H), 4.55-4.38 (m, 3H), 4.32-4.17 (m, 1H), 4.15-4.04 (m, 1H), 4.03-3.71 (m, 3H), 3.53-3.39 (m, 1H), 3.31 (br s, 3H), 3.11-2.79 (m, 3H), 2.50 (br s, 3H), 2.39-2.26 (m, 1H), 2.17-1.95 (m, 5H).

Example 35

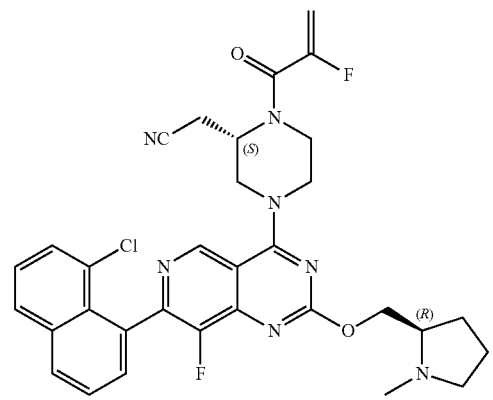

2-[(2S)-4-[7-(8-chloro-1-naphthyl)-8-fluoro-2-[[(2R)-1-methylpyrrolidin-2-yl]methoxy]pyrido[4,3-d]pyrimidin-4-yl]-1-(2-fluoroprop-2-enoyl)piperazin-2-yl]acetonitrile

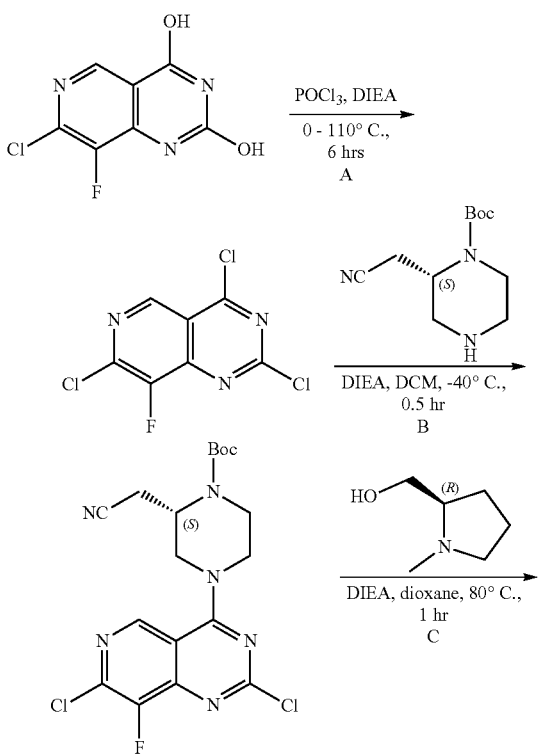

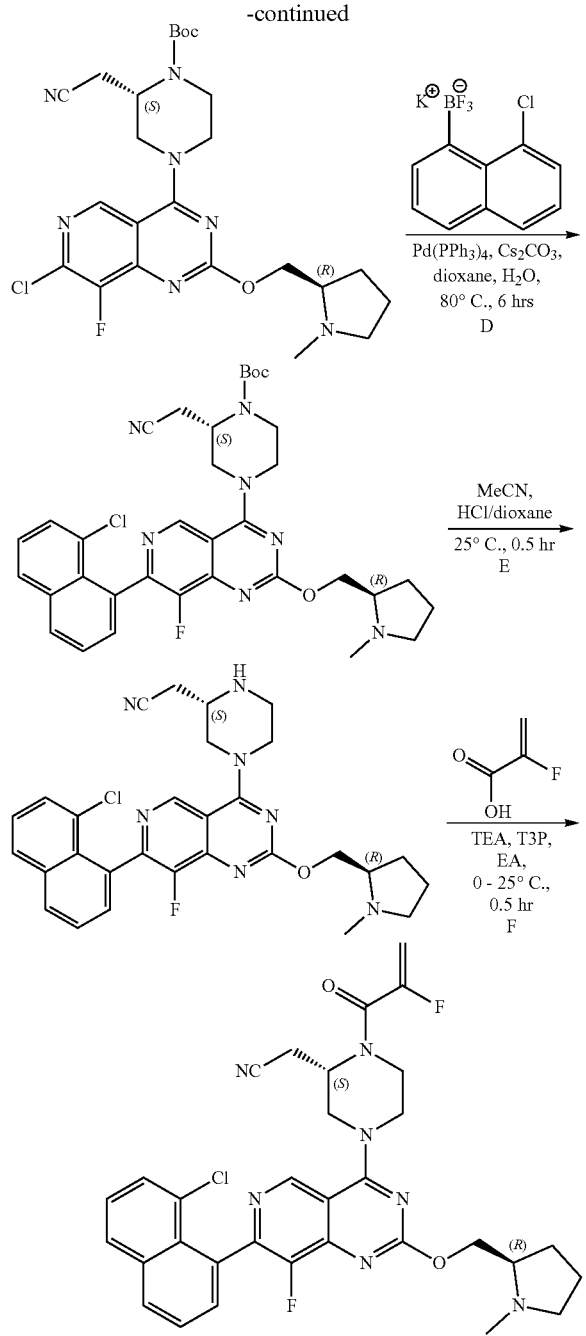

Example 35

Step A: A mixture of DIEA (8.99 g, 69.6 mmol, 12.1 mL, 5.00 eq) in POCl$_3$ (100 g, 654 mmol, 60.8 mL, 47.0 eq) was added 7-chloro-8-fluoro-pyrido[4,3-d]pyrimidine-2,4-diol (3.00 g, 13.9 mmol, 1.00 eq) in portion at 0° C. under N$_2$. The mixture was stirred at 110° C. for 6 hours. The reaction mixture was concentrated under reduced pressure to give a crude product. Compound 2,4,7-trichloro-8-fluoro-pyrido[4,3-d]pyrimidine (3.51 g, crude) was obtained as a brown oil which was used in the next step directly without further purification.

Step B: To a mixture of 2,4,7-trichloro-8-fluoro-pyrido [4,3-d]pyrimidine (3.51 g, 13.9 mmol, 1.00 eq) in DCM (50.0 mL) was added DIEA (18.0 g, 139 mmol, 24.2 mL, 10.0 eq) and tert-butyl (2S)-2-(cyanomethyl)piperazine-1-carboxylate (2.19 g, 9.73 mmol, 0.70 eq) in portion at −40° C. under N$_2$. The mixture was stirred at −40° C. for 30 min. The reaction mixture was diluted with saturated NaHCO$_3$ solution (150 mL) and extracted with DCM (100 mL×2). The separated organic layer was dried over sodium sulfate, filtered and concentrated under vacuum. The residue was purified by column chromatography (SiO$_2$, Petroleum ether/Ethyl acetate=20:1 to 1:1). Compound tert-butyl (2S)-2-(cyanomethyl)-4-(2,7-dichloro-8-fluoro-pyrido[4,3-d]pyrimidin-4-yl)piperazine-1-carboxylate (2.57 g, 5.82 mmol, 42% yield) was obtained as a yellow solid. LCMS [ESI, M+1]: 441.

Step C: To a mixture of tert-butyl (2S)-2-(cyanomethyl)-4-(2,7-dichloro-8-fluoro-pyrido[4,3-d]pyrimidin-4-yl)piperazine-1-carboxylate (500 mg, 1.13 mmol, 1.00 eq) and [(2R)-1-methylpyrrolidin-2-yl]methanol (652 mg, 5.67 mmol, 5.00 eq) in dioxane (10.0 mL) was added DIEA (439 mg, 3.40 mmol, 592 µL, 3.00 eq) in portion under N$_2$. The mixture was stirred at 80° C. for 1 hour. The reaction mixture was diluted with water (5.00 mL) and extracted with ethyl acetate (10.0 mL×3). The combined organic layers were washed with brine (10.0 mL×1), dried over sodium sulfate, filtered and concentrated under reduced pressure. The residue was purified by column chromatography (SiO$_2$, Petroleum ether:Ethyl acetate=5:1 to Ethyl acetate:methanol=5:1). Compound tert-butyl (2S)-4-[7-chloro-8-fluoro-2-[[(2R)-1-methylpyrrolidin-2-yl]methoxy]pyrido[4,3-d]pyrimidin-4-yl]-2-(cyanomethyl)piperazine-1-carboxylate (400 mg, 769 µmol, 68% yield) was obtained as a yellow solid.

Step D: To a mixture of tert-butyl (2S)-4-[7-chloro-8-fluoro-2-[[(2R)-1-methylpyrrolidin-2-yl]methoxy]pyrido[4,3-d]pyrimidin-4-yl]-2-(cyanomethyl)piperazine-1-carboxylate (200 mg, 385 µmol, 1.00 eq) and [(8-chloro-1-naphthyl)-trifluoro-boranyl]potassium(1+) (413 mg, 1.54 mmol, 4.00 eq) in dioxane (6.00 mL) and H$_2$O (1.50 mL) was added Cs$_2$CO$_3$ (376 mg, 1.15 mmol, 3.00 eq) and Pd(PPh$_3$)$_4$ (133 mg, 115 µmol, 0.30 eq) under N$_2$. The mixture was stirred at 80° C. for 6 hours. The reaction mixture was diluted with diluted with water (5.00 mL) and extracted with ethyl acetate (10.0 mL×3). The combined organic layers were washed with brine (10.0 mL), dried over sodium sulfate, filtered and concentrated under reduced pressure. The residue was purified by prep-HPLC (column: Waters Xbridge 150×25 5µ; mobile phase: [water (0.05% ammonia hydroxide v/v)—ACN]; B %: 50%-80%, 10 min). Compound tert-butyl (2S)-4-[7-(8-chloro-1-naphthyl)-8-fluoro-2-[[(2R)-1-methylpyrrolidin-2-yl]methoxy]pyrido[4,3-d]pyrimidin-4-yl]-2-(cyanomethyl)piperazine-1-carboxylate (32.0 mg, 49.5 µmol, 13% yield, 100% purity) was obtained as a yellow solid. LCMS [ESI, M+1]: 646.

Step E: To a mixture of tert-butyl (2S)-4-[7-(8-chloro-1-naphthyl)-8-fluoro-2-[[(2R)-1-methylpyrrolidin-2-yl]methoxy]pyrido[4,3-d]pyrimidin-4-yl]-2-(cyanomethyl)piperazine-1-carboxylate (20.0 mg, 31.0 µmol, 1.00 eq) in MeCN (1.00 mL) was added HCl/dioxane (4 M, 667 µL, 86.2 eq) under N$_2$. The mixture was stirred at 25° C. for 30 min. The reaction mixture was concentrated under reduced pressure. Then the residue was dissolved with ethyl acetate and adjusted pH to 8 with saturated NaHCO$_3$ solution and extracted with ethyl acetate (10.0 mL×3). The combined organic layers were washed with brine (5.00 mL), dried over sodium sulfate, filtered and concentrated under reduced pressure. The residue was purified by prep-HPLC (column: Waters Xbridge 150×25 5µ; mobile phase: [water (0.05% ammonia hydroxide v/v)—ACN]; B %: 38%-68%, 10 min). Compound 2-[(2S)-4-[7-(8-chloro-1-naphthyl)-8-fluoro-2-[[(2R)-1-methylpyrrolidin-2-yl]methoxy]pyrido[4,3-d]pyrimidin-4-yl]piperazin-2-yl]acetonitrile (10.0 mg, 18.1 µmol, 59% yield, 99% purity) was obtained as a yellow solid. LCMS [ESI, M+1]: 546.

$^1$H NMR (400 MHz, chloroform-d) δ=9.01 (s, 1H), 8.04-7.98 (m, 1H), 7.91-7.87 (m, 1H), 7.64-7.53 (m, 3H), 7.46-7.40 (m, 1H), 4.61-4.54 (m, 1H), 4.54-4.47 (m, 1H), 4.46-4.35 (m, 2H), 3.61-3.47 (m, 1H), 3.40-3.30 (m, 1H), 3.27-3.18 (m, 2H), 3.17-3.06 (m, 2H), 2.77-2.70 (m, 1H), 2.68-2.61 (m, 1H), 2.61-2.53 (m, 1H), 2.51-2.48 (m, 3H), 2.34-2.25 (m, 1H), 2.11-2.03 (m, 1H), 1.93-1.80 (m, 3H)

Example 35: To a mixture of 2-[(2S)-4-[7-(8-chloro-1-naphthyl)-8-fluoro-2-[[(2R)-1-methylpyrrolidin-2-yl]methoxy]pyrido[4,3-d]pyrimidin-4-yl]piperazin-2-yl]acetonitrile (40.0 mg, 73.3 μmol, 1.00 eq) and 2-fluoroprop-2-enoic acid (19.8 mg, 220 μmol, 3.00 eq) in ethyl acetate (1.00 mL) was added TEA (59.3 mg, 586 μmol, 81.6 μL, 8.00 eq) and T3P (140 mg, 220 μmol, 131 μL, 50% purity, 3.00 eq) in portion at 0° C. under N$_2$. The mixture was stirred at 25° C. for 30 min. The reaction mixture was diluted with water (2.00 mL) and extracted with ethyl acetate (5.00 mL×3). The combined organic layers were washed with brine (3.00 mL), dried over sodium sulfate, filtered and concentrated under reduced pressure. The residue was purified by prep-HPLC (column: Waters Xbridge 150×25 5μ; mobile phase: [water (0.05% ammonia hydroxide v/v)—ACN]; B %: 38%-68%, 10 min). Compound 2-[(2S)-4-[7-(8-chloro-1-naphthyl)-8-fluoro-2-[[(2R)-1-methylpyrrolidin-2-yl]methoxy]pyrido[4,3-d]pyrimidin-4-yl]-1-(2-fluoroprop-2-enoyl)piperazin-2-yl]acetonitrile (5.20 mg, 8.33 μmol, 11% yield, 99% purity) was obtained as a yellow solid. LCMS [ESI, M+1]: 618.

$^1$H NMR (400 MHz, chloroform-d) δ=9.09-9.03 (m, 1H), 8.05-7.98 (m, 1H), 7.93-7.86 (m, 1H), 7.65-7.54 (m, 3H), 7.47-7.40 (m, 1H), 5.42 (br s, 1H), 5.34-5.24 (m, 1H), 4.96-4.77 (m, 1H), 4.62-4.55 (m, 1H), 4.51-4.39 (m, 3H), 4.31-3.94 (m, 2H), 3.86-3.65 (m, 2H), 3.17-3.08 (m, 1H), 3.07-2.94 (m, 1H), 2.92-2.80 (m, 1H), 2.78-2.65 (m, 1H), 2.54-2.47 (m, 3H), 2.36-2.25 (m, 1H), 2.12-2.01 (m, 1H), 1.92-1.78 (m, 3H).

Example 36

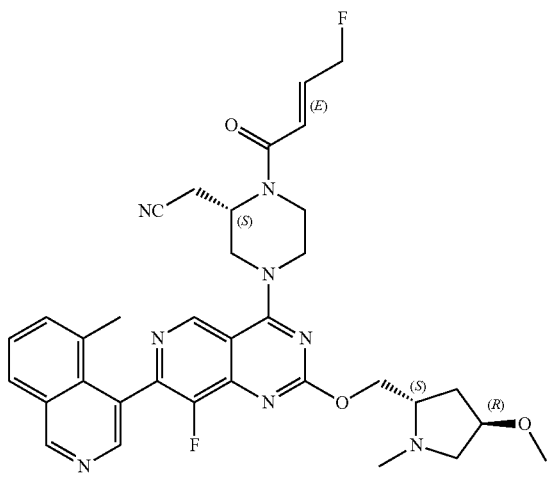

2-[(2S)-1-[(E)-4-fluorobut-2-enoyl]-4-[8-fluoro-2-[[(2S,4R)-4-methoxy-1-methyl-pyrrolidin-2-yl]methoxy]-7-(5-methyl-4-isoquinolyl)pyrido[4,3-d]pyrimidin-4-yl]piperazin-2-yl]acetonitrile

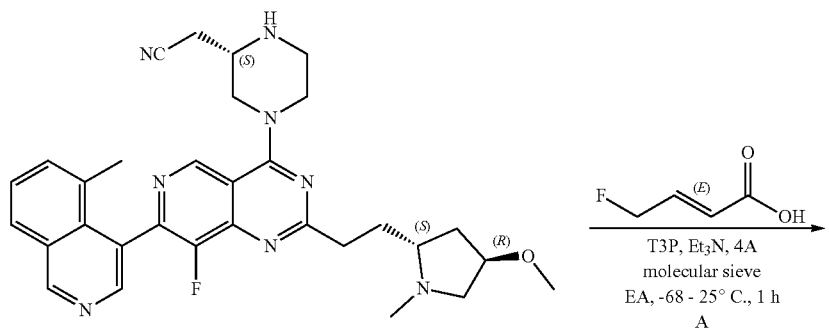

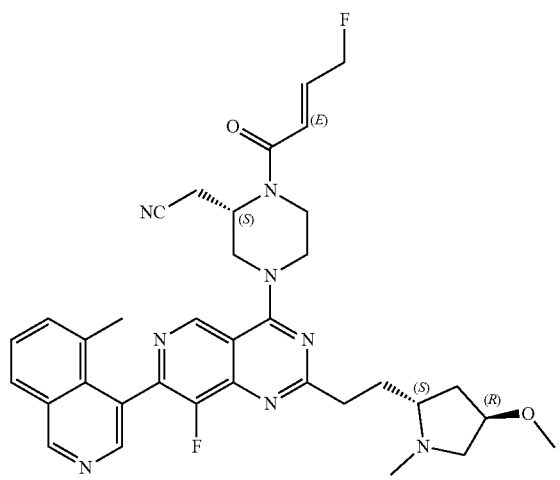

Example 36

Example 36: To a solution of 2-[(2S)-4-[8-fluoro-2-[[(2S,4R)-4-methoxy-1-methyl-pyrrolidin-2-yl]methoxy]-7-(5-methyl-4-isoquinolyl)pyrido[4,3-d]pyrimidin-4-yl]piperazin-2-yl]acetonitrile (45 mg, 80.8 μmol, 1.0 eq), (E)-4-fluorobut-2-enoic acid (50.5 mg, 485 μmol, 6.0 eq) in ethyl acetate (5 mL) was added 4A molecular sieve (200 mg). The mixture was stirred at 25° C. for 0.5 hour. After that, the mixture was cooled to −68° C. and added Et₃N (49.1 mg, 485 μmol, 67.5 μL, 6.0 eq) and T3P (206 mg, 323 μmol, 192 μL, 50% purity, 4.0 eq) at −68° C. The mixture was stirred at −68° C. for 0.5 hour. Upon completion, the mixture was acidified with aqueous HCl solution (1 mol/L) to pH=3~4. To the mixture was added ethyl acetate (20 mL) and basified with saturated aqueous NaHCO₃ solution to pH=7~8. The organic phase was separated, dried over sodium sulfate, filtered and concentrated under vacuum. The residue was purified by prep-HPLC (column: Waters Xbridge 150*25 5μ; mobile phase: [water (0.05% ammonia hydroxide v/v)—ACN]; B %: 22%-52%, 10 min). The fractions were concentrated under reduced pressure to remove ACN, and then lyophilized. 2-[(2S)-1-[(E)-4-fluorobut-2-enoyl]-4-[8-fluoro-2-[[(2S,4R)-4-methoxy-1-methyl-pyrrolidin-2-yl]methoxy]-7-(5-methyl-4-isoquinolyl)pyrido[4,3-d]pyrimidin-4-yl]piperazin-2-yl]acetonitrile (4.12 mg, 6.01 μmol, 7% yield, 93.7% purity) was obtained as a white solid. LCMS [ESI, M+1]: 643.

¹H NMR (400 MHz, chloroform-d) δ=9.34 (s, 1H), 9.12 (s, 1H), 8.47 (br d, J=10.0 Hz, 1H), 7.96 (br d, J=8.0 Hz, 1H), 7.62-7.47 (m, 2H), 7.13-6.95 (m, 1H), 6.60 (br d, J=15.6 Hz, 1H), 5.24-4.97 (m, 3H), 4.66-4.39 (m, 4H), 4.23-3.71 (m, 5H), 3.51-3.41 (m, 1H), 3.32 (s, 3H), 3.09-2.73 (m, 3H), 2.50 (s, 3H), 2.39-2.30 (m, 1H), 2.13-1.98 (m, 5H).

Example 37

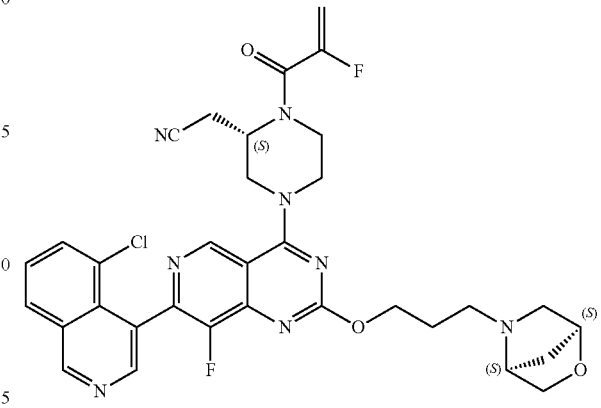

2-[(2S)-4-[7-(5-chloro-4-isoquinolyl)-8-fluoro-2-[3-[(1S,4S)-2-oxa-5-azabicyclo[2.2.1]heptan-5-yl]propoxy]pyrido[4,3-d]pyrimidin-4-yl]-1-(2-fluoro-prop-2-enoyl)piperazin-2-yl]acetonitrile

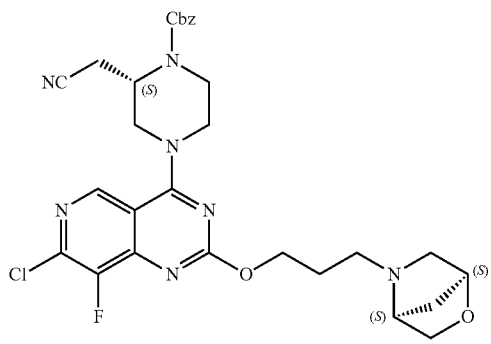 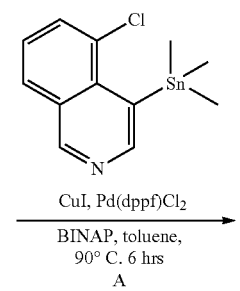

CuI, Pd(dppf)Cl₂
BINAP, toluene,
90° C. 6 hrs
A

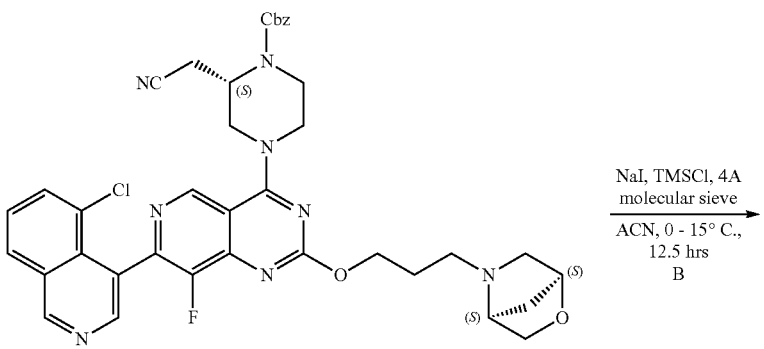

NaI, TMSCl, 4A molecular sieve
ACN, 0 - 15° C., 12.5 hrs
B

-continued

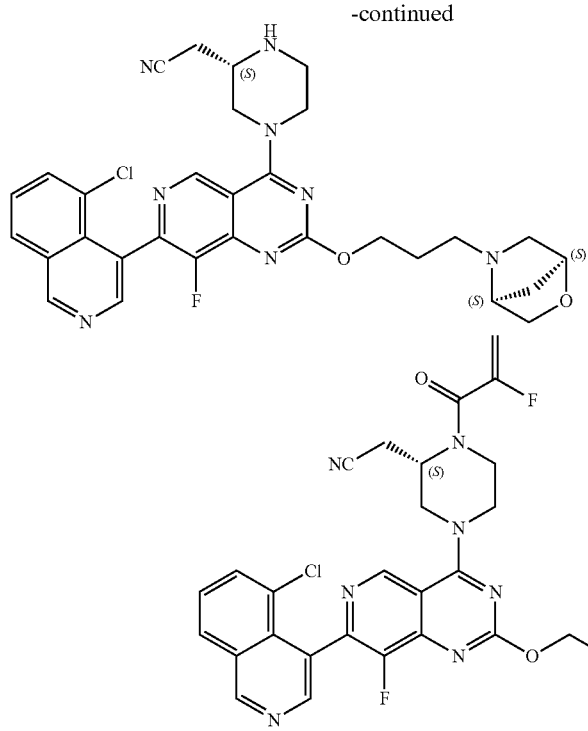

Example 37

Step A: To a solution of benzyl (2S)-4-[7-chloro-8-fluoro-2-[3-[(1S,4S)-2-oxa-5-azabicyclo[2.2.1]heptan-5-yl]propoxy]pyrido[4,3-d]pyrimidin-4-yl]-2-(cyanomethyl)piperazine-1-carboxylate (300 mg, 503 μmol, 1.0 eq), (5-chloro-4-isoquinolyl)-trimethyl-stannane (493 mg, 1.51 mmol, 3.0 eq), CuI (28.8 mg, 151 μmol, 0.3 eq), BINAP (62.7 mg, 101 μmol, 0.2 eq) in toluene (10.0 mL) was added Pd(dppf)Cl$_2$ (36.8 mg, 50.3 μmol, 0.1 eq) under N$_2$. The mixture was de-gassed and then heated to 90° C. for 6 hours under N$_2$. Upon completion, the mixture was filtered and the filtrate was concentrated under vacuum. The residue was diluted with water (10.0 mL) and extracted with ethyl acetate (2×20.0 mL). The organic layers were dried over Na$_2$SO$_4$ and concentrated under vacuum. The residue was purified by reversed phase flash [water (0.1% formic acid/acetonitrile]. The desired fractions were collected and neutralized with solid NaHCO$_3$, concentrated under vacuum to remove MeCN and extracted with ethyl acetate (2×20.0 mL). The organic layers were dried over Na$_2$SO$_4$ and concentrated under vacuum to give benzyl (2S)-4-[7-(5-chloro-4-isoquinolyl)-8-fluoro-2-[3-[(1S,4S)-2-oxa-5-azabicyclo[2.2.1]heptan-5-yl]propoxy]pyrido[4,3-d]pyrimidin-4-yl]-2-(cyanomethyl)piperazine-1-carboxylate (240 mg, 297 μmol, 59% yield, 90% purity) as a yellow oil. LCMS [ESI, M+1]: 723.

Step B: A mixture of benzyl (2S)-4-[7-(5-chloro-4-isoquinolyl)-8-fluoro-2-[3-[(1S,4S)-2-oxa-5-azabicyclo[2.2.1]heptan-5-yl]propoxy]pyrido[4,3-d]pyrimidin-4-yl]-2-(cyanomethyl)piperazine-1-carboxylate (140 mg, 194 μmol, 1.0 eq), NaI (464 mg, 3.10 mmol, 16 eq) and 4A molecular sieve (90 mg) in MeCN (5.0 mL) was stirred at 0° C. for 30 minutes. Then to the mixture was added TMSCl (315 mg, 2.90 mmol, 369 μL, 15 eq) at 0° C. The mixture was stirred at 15° C. for 12 hours. Upon completion, the mixture was filtered and the filtrate was purified by reversed phase flash [water (0.1% formic acid)/acetonitrile]. The desired fractions were collected and neutralized with solid NaHCO$_3$, concentrated under vacuum to remove MeCN and extracted with ethyl acetate (3×20.0 mL). The organic layers were dried over Na$_2$SO$_4$ and concentrated under vacuum to give 45 mg of crude product. Taking 10 mg of it was purified by prep-HPLC (column: Waters Xbridge 150*25 5μ; mobile phase: [water (0.05% ammonia hydroxide v/v)—ACN]; B %: 15%-45%, 10 min). The desired fractions were collected and lyophilized to give 2-[(2S)-4-[7-(5-chloro-4-isoquinolyl)-8-fluoro-2-[3-[(1S, 4S)-2-oxa-5-azabicyclo[2.2.1]heptan-5-yl]propoxy]pyrido[4,3-d]pyrimidin-4-yl]piperazin-2-yl]acetonitrile (1.01 mg, 1.63 μmol, 9.6% yield, 95.2% purity) as a white solid. LCMS [ESI, M+1]: 589.

$^1$H NMR (400 MHz, chloroform-d) δ=9.39 (s, 1H), 9.05 (s, 1H), 8.59 (s, 1H), 8.08-8.03 (m, 1H), 7.78 (d, J=7.2 Hz, 1H), 7.64-7.58 (m, 1H), 4.63-4.58 (m, 2H), 4.57-4.52 (m, 1H), 4.46-4.38 (m, 2H), 4.07-4.02 (m, 1H), 3.64-3.55 (m, 2H), 3.51 (br s, 1H), 3.42-3.33 (m, 1H), 3.28-3.19 (m, 2H), 3.18-3.10 (m, 1H), 2.97-2.92 (m, 1H), 2.86-2.71 (m, 2H), 2.69-2.58 (m, 2H), 2.53 (d, J=10.0 Hz, 1H), 2.01 (t, J=6.8 Hz, 2H), 1.87-1.84 (m, 1H), 1.72 (br d, J=10.0 Hz, 1H).

Example 37: To a solution of 2-[(2S)-4-[7-(5-chloro-4-isoquinolyl)-8-fluoro-2-[3-[(1S,4S)-2-oxa-5-azabicyclo[2.2.1]heptan-5-yl]propoxy]pyrido[4,3-d]pyrimidin-4-yl]piperazin-2-yl]acetonitrile (27.0 mg, 45.8 μmol, 1.0 eq), 2-fluoroprop-2-enoic acid (12.4 mg, 138 μmol, 3.0 eq) in ethyl acetate (1.0 mL) was added TEA (55.7 mg, 550 μmol, 76.6 μL, 12 eq) and T3P (117 mg, 183 μmol, 109 μL, 50% purity in ethyl acetate, 4.0 eq) at 0° C. The mixture was stirred at 25° C. for 0.5 hour. Upon completion, the mixture was diluted with water (3.0 mL) and extracted with ethyl acetate (4×5.0 mL). The organic layers were dried over $Na_2SO_4$ and concentrated under vacuum. The residue was purified by chromatography ($Al_2O_3$, petroleum ether/ethyl acetate 1/1 to ethyl acetate/methanol 10/1) followed by prep-HPLC (column: Waters Xbridge 150*25 5µ; mobile phase: [water (0.05% ammonia hydroxide v/v)—ACN]; B %: 20%-50%, 10 min). The desired fractions were collected and lyophilized to give 2-[(2S)-4-[7-(5-chloro-4-isoquinolyl)-8-fluoro-2-[3-[(1S,4S)-2-oxa-5-azabicyclo[2.2.1]heptan-5-yl]propoxy]pyrido[4,3-d]pyrimidin-4-yl]-1-(2-fluoroprop-2-enoyl)piperazin-2-yl]acetonitrile (5.74 mg, 7.95 µmol, 17% yield, 91.6% purity) as a white solid.

$^1$H NMR (400 MHz, chloroform-d) δ=9.40 (s, 1H), 9.13-9.07 (m, 1H), 8.59 (d, J=9.2 Hz, 1H), 8.06 (d, J=8.4 Hz, 1H), 7.78 (br d, J=7.6 Hz, 1H), 7.66-7.57 (m, 1H), 5.59-5.38 (m, 1H), 5.35-5.23 (m, 1H), 4.98-4.75 (m, 1H), 4.65-4.58 (m, 2H), 4.54-4.43 (m, 2H), 4.42-4.38 (m, 1H), 4.34-4.06 (m, 2H), 4.05 (d, J=8.0 Hz, 1H), 3.92-3.68 (m, 2H), 3.65-3.60 (m, 1H), 3.52-3.47 (m, 1H), 3.09-2.93 (m, 2H), 2.91-2.72 (m, 3H), 2.57-2.50 (m, 1H), 2.02 (quin, J=6.8 Hz, 2H), 1.86 (br d, J=8.4 Hz, 1H), 1.73 (br d, J=10.0 Hz, 1H).

Example 38

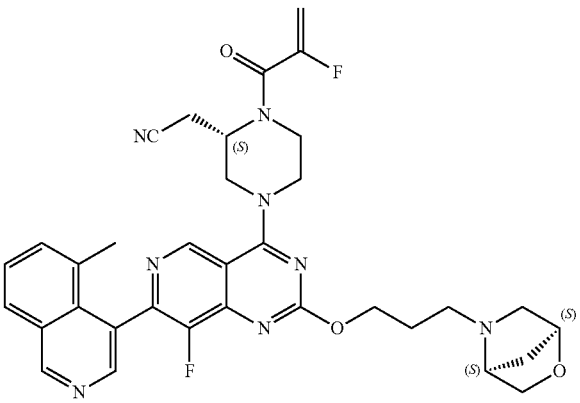

2-[(2S)-4-[8-fluoro-7-(5-methyl-4-isoquinolyl)-2-[3-[(1S,4S)-2-oxa-5-azabicyclo[2.2.1]heptan-5-yl]propoxy]pyrido[4,3-d]pyrimidin-4-yl]-1-(2-fluoroprop-2-enoyl)piperazin-2-yl]acetonitrile

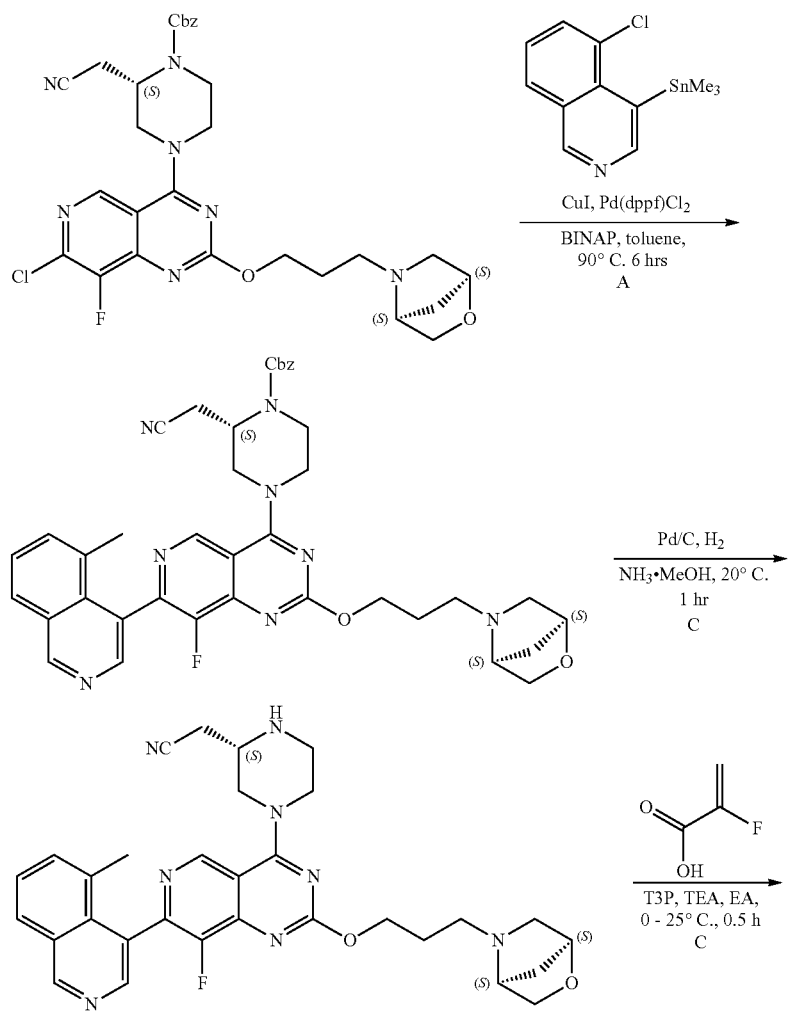

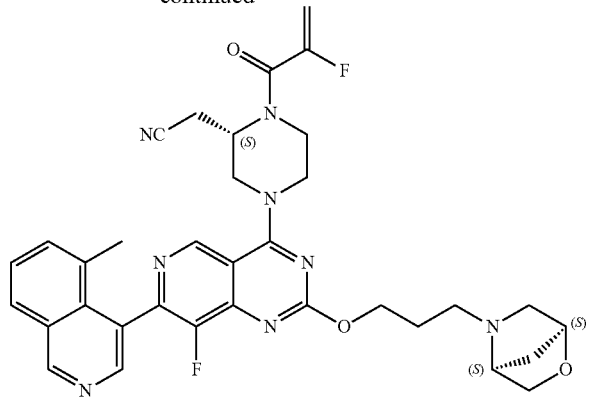

Example 38

Step A: To a solution of benzyl (2S)-4-[7-chloro-8-fluoro-2-[3-[(1S,4S)-2-oxa-5-azabicyclo[2.2.1]heptan-5-yl]propoxy]pyrido[4,3-d]pyrimidin-4-yl]-2-(cyanomethyl)piperazine-1-carboxylate (300 mg, 503 μmol, 1.0 eq), trimethyl-(5-methyl-4-isoquinolyl)stannane (462 mg, 1.51 mmol, 3.0 eq), CuI (28.8 mg, 151 μmol, 0.3 eq), BINAP (62.7 mg, 101 μmol, 0.2 eq) in toluene (10.0 mL) was added Pd(dppf)Cl$_2$ (36.8 mg, 50.3 μmol, 0.1 eq) under N$_2$. The mixture was de-gassed and then heated to 90° C. for 6 hours under N$_2$. Upon completion, the mixture was filtered and the filtrate was concentrated under vacuum. The residue was diluted with water (10.0 mL) and extracted with ethyl acetate (2×20.0 mL). The organic layers were dried over Na$_2$SO$_4$ and concentrated under vacuum. The residue was purified by reversed phase flash [water (0.1% formic acid/acetonitrile]. The desired fractions were collected and neutralized with solid NaHCO$_3$, concentrated under vacuum to remove MeCN and extracted with ethyl acetate (2×20.0 mL). The organic layers were dried over Na$_2$SO$_4$ and concentrated under vacuum to give benzyl (2S)-2-(cyanomethyl)-4-[8-fluoro-7-(5-methyl-4-isoquinolyl)-2-[3-[(1S,4S)-2-oxa-5-azabicyclo[2.2.1]heptan-5-yl]propoxy]pyrido[4,3-d]pyrimidin-4-yl]piperazine-1-carboxylate (260 mg, 360 μmol, 71% yield, 97.2% purity) as a yellow oil. LCMS [ESI, M+1]: 703.

Step B: To a solution of benzyl (2S)-2-(cyanomethyl)-4-[8-fluoro-7-(5-methyl-4-isoquinolyl)-2-[3-[(1S,4S)-2-oxa-5-azabicyclo[2.2.1]heptan-5-yl]propoxy]pyrido[4,3-d]pyrimidin-4-yl]piperazine-1-carboxylate (60.0 mg, 85.4 μmol, 1.0 eq) in MeOH (1.0 mL) and NH$_3$.MeOH (1.0 mL, 25% purity) was added Pd/C (30.0 mg, 10% purity) under N$_2$. The suspension was degassed under vacuum and purged with H$_2$ several times. The mixture was stirred under H$_2$ (15 psi) at 20° C. for 1 hour. Upon completion, the catalyst was removed by filtering through a plug of Celite®. The solvent was removed under reduced pressure. The residue was purified by prep-HPLC (column: Waters Xbridge 150*25 5μ; mobile phase: [water (0.05% ammonia hydroxide v/v)—ACN]; B %: 18%-48%, 10 min). The desired fractions were collected and lyophilized to give 2-[(2S)-4-[8-fluoro-7-(5-methyl-4-isoquinolyl)-2-[3-[(1S,4S)-2-oxa-5-azabicyclo[2.2.1]heptan-5-yl]propoxy]pyrido[4,3-d]pyrimidin-4-yl]piperazin-2-yl]acetonitrile (6.44 mg, 11.3 μmol, 13% yield, 99.6% purity) as a white solid. LCMS [ESI, M+1]: 569.

$^1$H NMR (400 MHz, chloroform-d) δ=9.34 (s, 1H), 9.06 (s, 1H), 8.47 (s, 1H), 7.96 (d, J=7.6 Hz, 1H), 7.60-7.54 (m, 1H), 7.53-7.48 (m, 1H), 4.65-4.58 (m, 2H), 4.58-4.49 (m, 1H), 4.47-4.37 (m, 2H), 4.04 (d, J=7.6 Hz, 1H), 3.66-3.53 (m, 2H), 3.52-3.48 (m, 1H), 3.44-3.31 (m, 1H), 3.30-3.20 (m, 2H), 3.19-3.06 (m, 1H), 2.95 (dd, J=1.6, 10.0 Hz, 1H), 2.88-2.69 (m, 2H), 2.68-2.56 (m, 2H), 2.56-2.51 (m, 1H), 2.12-2.08 (m, 3H), 2.06-1.97 (m, 2H), 1.87-1.83 (m, 1H), 1.74-1.71 (m, 1H).

SFC condition: Column: Chiralpak IC-3 50×4.6 mm I.D., 3 μm, Mobile phase: Phase A for CO$_2$, and Phase B for MeOH+ACN (0.05% DEA); Gradient elution: 60% MeOH+ACN (0.05% DEA) in CO$_2$, Flow rate: 3 mL/min; Wavelength: 220 nm, Column Temp: 35C; Back Pressure: 100 Bar.

Example 38: To a solution of 2-[(2S)-4-[8-fluoro-7-(5-methyl-4-isoquinolyl)-2-[3-[(1S,4S)-2-oxa-5-azabicyclo[2.2.1]heptan-5-yl]propoxy]pyrido[4,3-d]pyrimidin-4-yl]piperazin-2-yl]acetonitrile (60.0 mg, 106 μmol, 1.0 eq), 2-fluoroprop-2-enoic acid (28.5 mg, 317 μmol, 3.0 eq) in ethyl acetate (2.0 mL) was added TEA (128 mg, 1.27 mmol, 176 μL, 12 eq) and T3P (269 mg, 422 μmol, 251 μL, 50% purity in ethyl acetate, 4.0 eq) at 0° C. The mixture was stirred at 25° C. for 0.5 hour. Upon completion, the mixture was diluted with water (3.0 mL) and extracted with ethyl acetate (4×5.0 mL). The organic layers were dried over Na$_2$SO$_4$ and concentrated under vacuum. The residue was purified by chromatography (Al$_2$O$_3$, petroleum ether/ethyl acetate 1/1 to ethyl acetate/methanol 10/1) followed by prep-HPLC (column: Waters Xbridge 150*25 5μ; mobile phase: [water (0.05% ammonia hydroxide v/v)—ACN]; B %: 20%-50%, 10 min). The desired fractions were collected and lyophilized to give 2-[(2S)-4-[8-fluoro-7-(5-methyl-4-isoquinolyl)-2-[3-[(1S,4S)-2-oxa-5-azabicyclo[2.2.1]heptan-5-yl]propoxy]pyrido[4,3-d]pyrimidin-4-yl]-1-(2-fluoroprop-2-enoyl)piperazin-2-yl]acetonitrile (22.2 mg, 34.5 μmol, 33% yield, 99.7% purity) as a white solid. LCMS [ESI, M+1]: 641.

$^1$H NMR (400 MHz, chloroform-d) δ=9.34 (s, 1H), 9.11 (d, J=1.6 Hz, 1H), 8.46 (d, J=8.0 Hz, 1H), 8.00-7.92 (m, 1H), 7.62-7.54 (m, 1H), 7.53-7.47 (m, 1H), 5.63-5.39 (m, 1H), 5.30 (br dd, J=2.8, 17.2 Hz, 1H), 4.98-4.79 (m, 1H), 4.66-4.58 (m, 2H), 4.55-4.42 (m, 2H), 4.39 (s, 1H), 4.35-4.06 (m, 2H), 4.04 (d, J=7.6 Hz, 1H), 3.95-3.70 (m, 2H), 3.62 (dd, J=1.2, 7.6 Hz, 1H), 3.54-3.48 (m, 1H), 3.09-2.92 (m, 2H), 2.90-2.71 (m, 3H), 2.53 (d, J=10.0 Hz, 1H), 2.09 (d, J=5.2 Hz, 3H), 2.02 (quin, J=6.8 Hz, 2H), 1.88-1.82 (m, 1H), 1.74 (br d, J=0.8 Hz, 1H).

Example 39

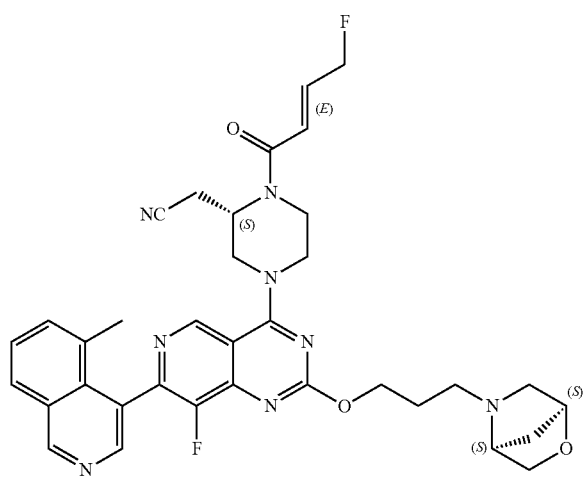

2-[(2S)-1-[(E)-4-fluorobut-2-enoyl]-4-[8-fluoro-7-(5-methyl-4-isoquinolyl)-2-[3-[(1S,4S)-2-oxa-5-azabicyclo[2.2.1]heptan-5-yl]propoxy]pyrido[4,3-d]pyrimidin-4-yl]piperazin-2-yl]acetonitrile

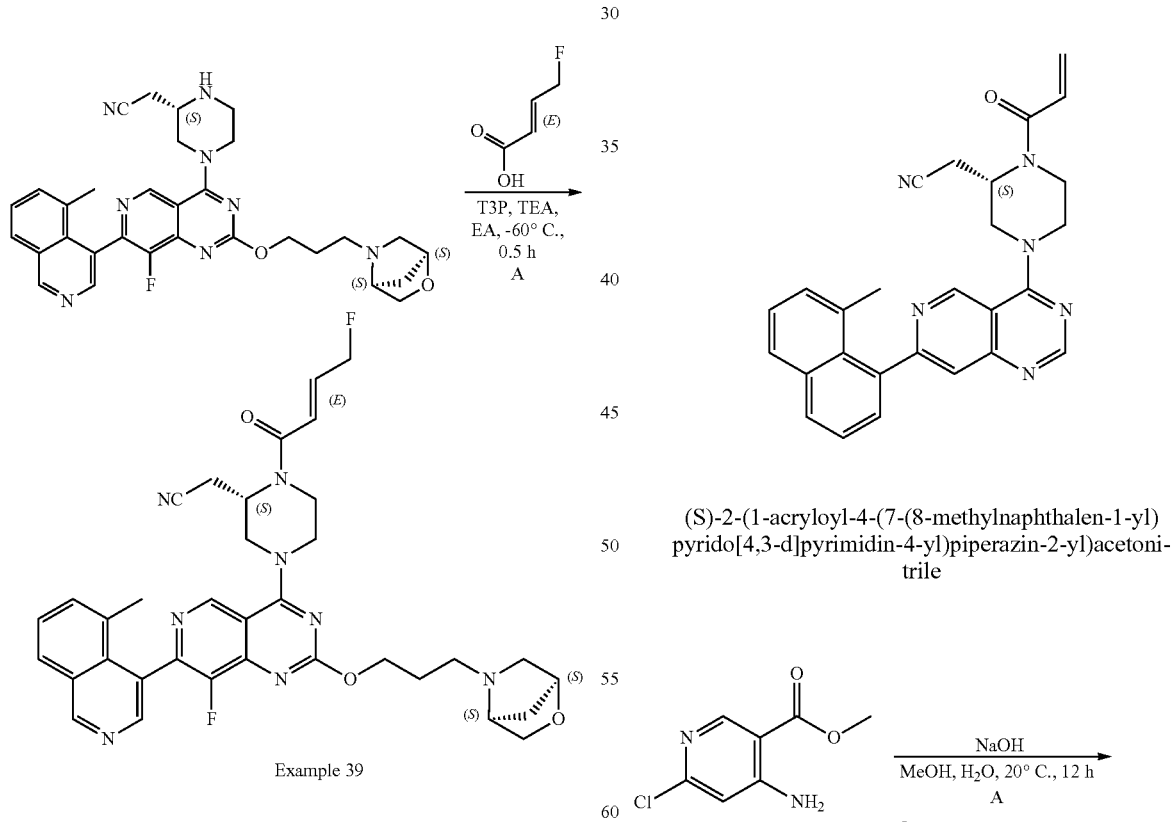

Example 39

Example 39: To a solution of 2-[(2S)-4-[8-fluoro-7-(5-methyl-4-isoquinolyl)-2-[3-[(1S,4S)-2-oxa-5-azabicyclo[2.2.1]heptan-5-yl]propoxy]pyrido[4,3-d]pyrimidin-4-yl]piperazin-2-yl]acetonitrile (60.0 mg, 106 µmol, 1.0 eq), (E)-4-fluorobut-2-enoic acid (33.0 mg, 317 µmol, 3.0 eq) in ethyl acetate (2.0 mL) was added TEA (128 mg, 1.27 mmol, 176 µL, 12 eq) and T3P (269 mg, 422 µmol, 251 µL, 50% purity in ethyl acetate, 4.0 eq) at −60° C. The mixture was stirred at −60° C. for 0.5 hour. Upon completion, the mixture was diluted with water (3.0 mL) and extracted with ethyl acetate (4×5.0 mL). The organic layers were dried over $Na_2SO_4$ and concentrated under vacuum. The residue was purified by chromatography ($Al_2O_3$, petroleum ether/ethyl acetate 1/1 to ethyl acetate/methanol 10/1) followed by prep-HPLC (column: Waters Xbridge 150*25 5µ; mobile phase: [water (0.05% ammonia hydroxide v/v)—ACN]; B %: 20%-50%, 10 min). The desired fractions were collected and lyophilized to give 2-[(2S)-1-[(E)-4-fluorobut-2-enoyl]-4-[8-fluoro-7-(5-methyl-4-isoquinolyl)-2-[3-[(1S,4S)-2-oxa-5-azabicyclo[2.2.1]heptan-5-yl]propoxy]pyrido[4,3-d]pyrimidin-4-yl]piperazin-2-yl]acetonitrile (22.3 mg, 31.9 µmol, 30% yield, 93.6% purity) as a white solid. LCMS [ESI, M+1]: 655.

$^1$H NMR (400 MHz, chloroform-d)$_{6=9.38}$-9.31 (m, 1H), 9.12 (s, 1H), 8.47 (d, J=10.4 Hz, 1H), 7.96 (d, J=8.0 Hz, 1H), 7.62-7.54 (m, 1H), 7.53-7.47 (m, 1H), 7.12-6.96 (m, 1H), 6.65-6.54 (m, 1H), 5.26-5.17 (m, 1H), 5.16-4.92 (m, 2H), 4.65-4.58 (m, 2H), 4.56-4.43 (m, 2H), 4.40 (s, 1H), 4.26-4.01 (m, 3H), 4.00-3.75 (m, 2H), 3.62 (dd, J=1.2, 7.6 Hz, 1H), 3.54-3.48 (m, 1H), 3.10-2.92 (m, 2H), 2.89-2.71 (m, 3H), 2.58-2.51 (m, 1H), 2.10 (d, J=3.2 Hz, 3H), 2.02 (quin, J=6.8 Hz, 2H), 1.86 (br d, J=8.4 Hz, 1H), 1.74 (br s, 1H).

Example 40

(S)-2-(1-acryloyl-4-(7-(8-methylnaphthalen-1-yl)pyrido[4,3-d]pyrimidin-4-yl)piperazin-2-yl)acetonitrile

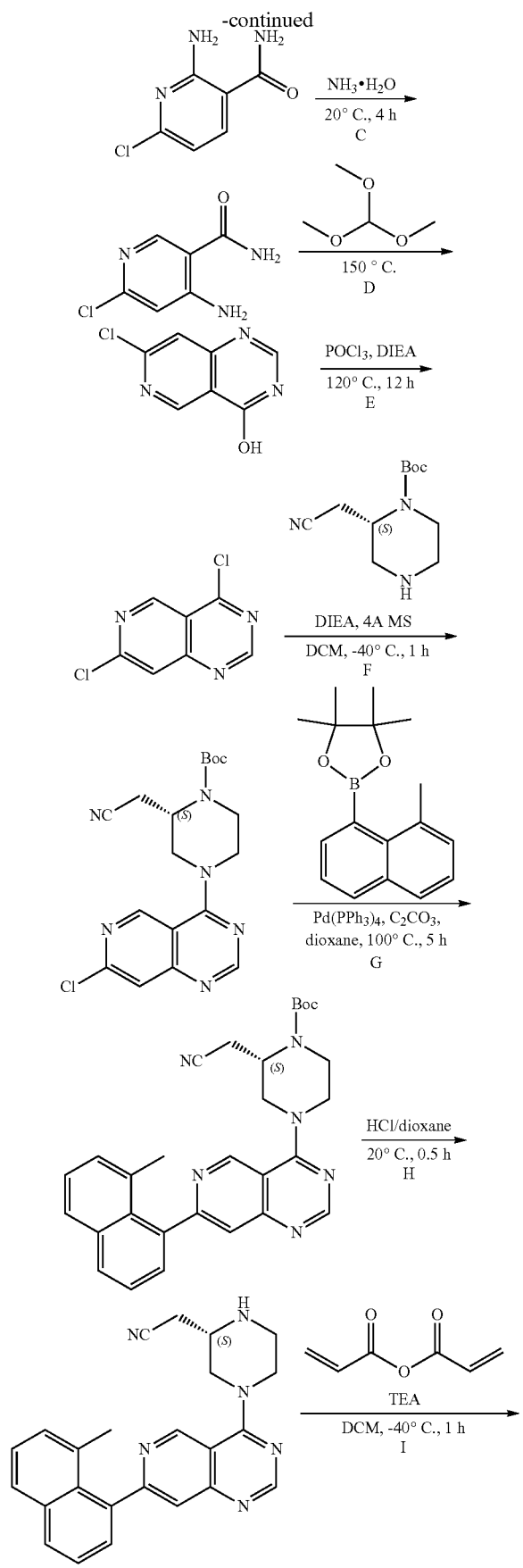

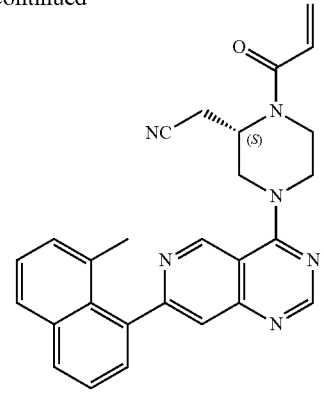

Example 40

Step A: To a solution of methyl 4-amino-6-chloro-pyridine-3-carboxylate (1.00 g, 5.36 mmol, 1.00 eq) in methyl alcohol (12.0 mL) and water (6.00 mL) was added sodium hydroxide (643 mg, 16.1 mmol, 3.00 eq). The mixture was stirred at 20° C. for 12 hrs. The reaction mixture was concentrated under reduced pressure. The residue was dissolved in water (0.50 mL) and acidified with hydrochloric acid (1.00 M) to pH=6. The solid was filtered and concentrated under reduced pressure to give 4-amino-6-chloro-pyridine-3-carboxylic acid (630 mg, 3.65 mmol, 68.1% yield) as a white solid which used for the next step without further purification.

Step B: A mixture of 4-amino-6-chloro-pyridine-3-carboxylic acid (630 mg, 3.65 mmol, 1.00 eq) and thionyl chloride (16.4 g, 138 mmol, 10.0 mL, 37.8 eq) was stirred at 80° C. for 12 hrs. The reaction mixture was concentrated under reduced pressure to give a residue. Compound 4-amino-6-chloro-pyridine-3-carbonyl chloride (697 mg, crude) was obtained as a yellow solid, which was used into next step directly without further purification.

Step C: A mixture of 4-amino-6-chloro-pyridine-3-carbonyl chloride (697 mg, 3.65 mmol, 1.00 eq) and ammonium hydroxide (9.10 g, 72.7 mmol, 10.0 mL, 19.9 eq) was stirred at 20° C. for 4 hr. The reaction mixture was extracted with ethyl acetate (12.0 mL×3). Combined organic phase was washed with brine (12.0 mL), dried, filtered and concentrated to give a residue. The residue was purified by prep-TLC (dichloromethane:methyl alcohol=10:1) to give 4-amino-6-chloro-pyridine-3-carboxamide (490 mg, crude) as a yellow solid. LCMS [M+1]: 172.1.

Step D: A mixture of 4-amino-6-chloro-pyridine-3-carboxamide (0.44 g, 2.56 mmol, 1.00 eq) in was added triethyl orthoformate (8.00 g, 54.0 mmol, 8.98 mL, 21.1 eq) was stirred at 150° C. for 5 hours. The reaction mixture was concentrated under reduced pressure to give a residue. Compound 7-chloropyrido[4,3-d]pyrimidin-4-ol (465 mg, crude) was obtained as a brown solid, which was used into next step directly without further purification.

Step E: To a solution of 7-chloropyrido[4,3-d]pyrimidin-4-ol (465 mg, 2.56 mmol, 1.00 eq) in phosphorus oxychloride (15.4 g, 100 mmol, 9.30 mL, 39.1 eq) was added diisopropylethylamine (993 mg, 7.68 mmol, 1.34 mL, 3.00 eq). The mixture was stirred at 120° C. for 12 hrs. The reaction mixture was concentrated under reduced pressure to give a residue. Compound 4,7-dichloropyrido[4,3-d]pyrimidine (512 mg, crude) was obtained as a brown oil, which was used into next step directly without further purification.

Step F: To a solution of 4,7-dichloropyrido[4,3-d]pyrimidine (512 mg, 2.56 mmol, 1.00 eq) in dichloromethane (10.0 mL) was added diisopropylethylamine (992 mg, 7.68 mmol, 1.34 mL, 3.00 eq), 4A MS (100 mg, 2.56 mmol, 1.00 eq) and tert-butyl (2S)-2-(cyanomethyl)piperazine-1-carboxylate (577 mg, 2.56 mmol, 1.00 eq). The mixture was stirred at −40° C. for 1 hr. The reaction mixture was filtered and quenched with water (20.0 mL). The mixture was extracted with dichloromethane (20.0 mL×3). Combined organic phase was washed with brine (10.0 mL), dried, filtered and concentrated to give a residue. The residue was purified by reversed-phase HPLC (0.1% formic acid condition) to give tert-butyl (2S)-4-(7-chloropyrido[4,3-d]pyrimidin-4-yl)-2-(cyanomethyl)piperazine-1-carboxylate (0.40 g, 1.03 mmol, 40.2% yield) as a brown solid.

$^1$H NMR (400 MHz, CDCl$_3$) δ=9.13 (s, 1H), 8.76 (s, 1H), 7.75 (s, 1H), 4.69 (s, 1H), 4.51 (dd, J=3.6, 13.6 Hz, 1H), 4.33 (br d, J=12.8 Hz, 1H), 4.19-4.05 (m, 1H), 3.95-3.83 (m, 1H), 3.78-3.68 (m, 1H), 3.52-3.37 (m, 1H), 2.89-2.76 (m, 1H), 2.72-2.63 (m, 1H), 1.52 (s, 9H)

Step G: A mixture of tert-butyl (2S)-4-(7-chloropyrido[4,3-d]pyrimidin-4-yl)-2-(cyanomethyl)piperazine-1-carboxylate (270 mg, 694 μmol, 1.00 eq), 4,4,5,5-tetramethyl-2-(8-methyl-1-naphthyl)-1,3,2-dioxaborolane (279 mg, 1.04 mmol, 1.50 eq), Pd(PPh$_3$)$_4$ (80.2 mg, 69.4 μmol, 0.10 eq) and cesium carbonate (452 mg, 1.39 mmol, 2.00 eq) in dioxane (4.50 mL) and water (1.50 mL) was degassed and purged with nitrogen atmosphere for 3 times, and then the mixture was stirred at 100° C. for 5 hrs under nitrogen atmosphere. The reaction mixture was concentrated under reduced pressure to give a residue. The residue was diluted with water (5.00 mL) and extracted with ethyl acetate (5.00 mL×3). Combined organic phase was washed with brine (5.00 mL), dried, filtered and concentrated to give a residue. The residue was purified by column chromatography (SiO$_2$, petroleum ether/ethyl acetate=10/1 to 1:2) to give tert-butyl (2S)-2-(cyanomethyl)-4-[7-(8-methyl-1-naphthyl)pyrido[4,3-d]pyrimidin-4-yl]piperazine-1-carboxylate (134 mg, 262 μmol, 37.7% yield, 96.6% purity) as a brown oil. LCMS [M+1]: 495.1.

Step H: To a solution of tert-butyl (2S)-2-(cyanomethyl)-4-[7-(8-methyl-1-naphthyl)pyrido[4,3-d]pyrimidin-4-yl] piperazine-1-carboxylate (30.0 mg, 60.7 μmol, 1.00 eq) in acetonitrile (0.60 mL) was added hydrochloric acid/dioxane (4.00 M, 0.60 mL, 39.6 eq). The mixture was stirred at 20° C. for 0.5 hrs. The reaction mixture was neutralized with triethylamine (1.00 mL) to pH=8 and concentrated under reduced pressure to give a residue. The residue was purified by prep-HPLC (neutral condition) to give 2-[(2S)-4-[7-(8-methyl-1-naphthyl)pyrido[4,3-d]pyrimidin-4-yl]piperazin-2-yl]acetonitrile (7.70 mg, 19.3 μmol, 31.8% yield, 98.7% purity) as a white solid. LCMS [M+1]: 395.4.

$^1$H NMR (400 MHz, MeOD) δ=9.35 (s, 1H), 8.72 (s, 1H), 8.01 (dd, J=1.2, 8.0 Hz, 1H), 7.85 (d, J=8.0 Hz, 1H), 7.75-7.71 (m, 1H), 7.56-7.51 (m, 1H), 7.47-7.40 (m, 2H), 7.34-7.29 (m, 1H), 4.71 (br d, J=12.4 Hz, 1H), 4.53 (br d, J=13.2 Hz, 1H), 3.69-3.57 (m, 1H), 3.39-3.32 (m, 1H), 3.29-3.22 (m, 1H), 3.20-3.13 (m, 1H), 3.02 (dt, J=3.2, 11.6 Hz, 1H), 2.80-2.65 (m, 2H), 2.00 (s, 3H).

Example 40: To a solution of 2-[(2S)-4-[7-(8-methyl-1-naphthyl)pyrido[4,3-d]pyrimidin-4-yl]piperazin-2-yl]acetonitrile (103 mg, 261 μmol, 1.00 eq) in dichloromethane (10.0 mL) was added triethylamine (79.3 mg, 783 μmol, 109 μL, 3.00 eq) and prop-2-enoyl prop-2-enoate (65.9 mg, 522 μmol, 2.00 eq). The mixture was stirred at −40° C. for 1 hr. The reaction mixture was concentrated under reduced pressure to give a residue. The residue was purified by prep-HPLC (neutral condition) to give 2-[(2S)-4-[7-(8-methyl-1-naphthyl)pyrido[4,3-d]pyrimidin-4-yl]-1-prop-2-enoyl-piperazin-2-yl]acetonitrile (25.6 mg, 57.2 μmol, 21.9% yield, 100% purity) as a white solid. LCMS [M+1]: 449.4

$^1$H NMR (400 MHz, MeOD) δ=9.44 (s, 1H), 8.76 (s, 1H), 8.02 (d, J=8.4 Hz, 1H), 7.86 (d, J=8.4 Hz, 1H), 7.77 (s, 1H), 7.59-7.51 (m, 1H), 7.48-7.41 (m, 2H), 7.32 (br d, J=7.6 Hz, 1H), 6.96-6.75 (m, 1H), 6.31 (br d, J=17.2 Hz, 1H), 5.84 (br d, J=9.6 Hz, 1H), 5.12-4.93 (m, 1H), 4.79-4.67 (m, 1H), 4.66-4.46 (m, 2H), 4.25-4.00 (m, 1H), 3.97-3.70 (m, 2H), 3.09-2.93 (m, 2H), 2.01 (br s, 3H).

Example 41

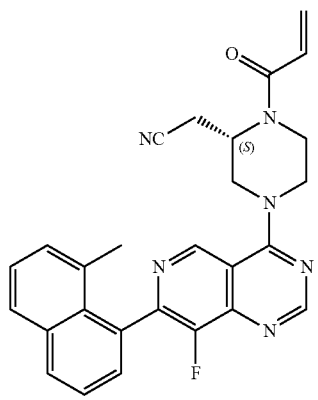

(S)-2-(1-acryloyl-4-(8-fluoro-7-(8-methylnaphthalen-1-yl)pyrido[4,3-d]pyrimidin-4-yl)piperazin-2-yl)acetonitrile

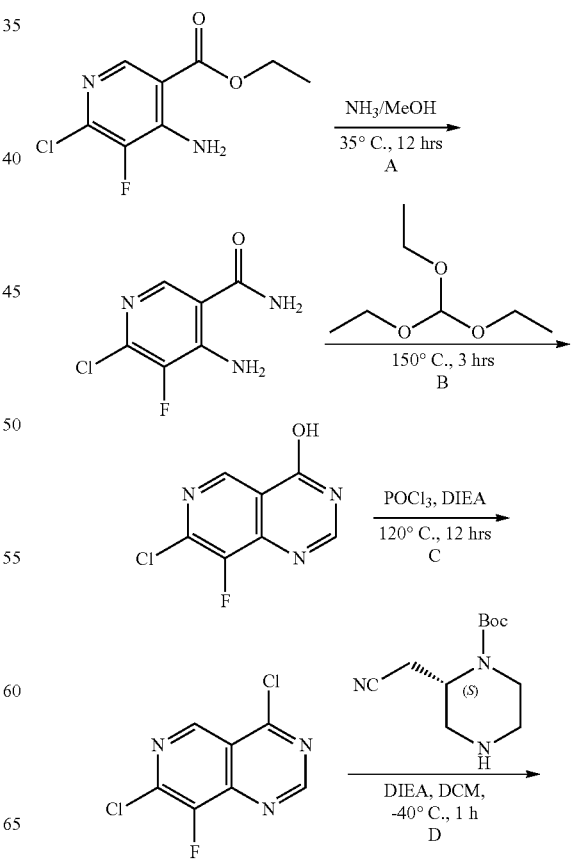

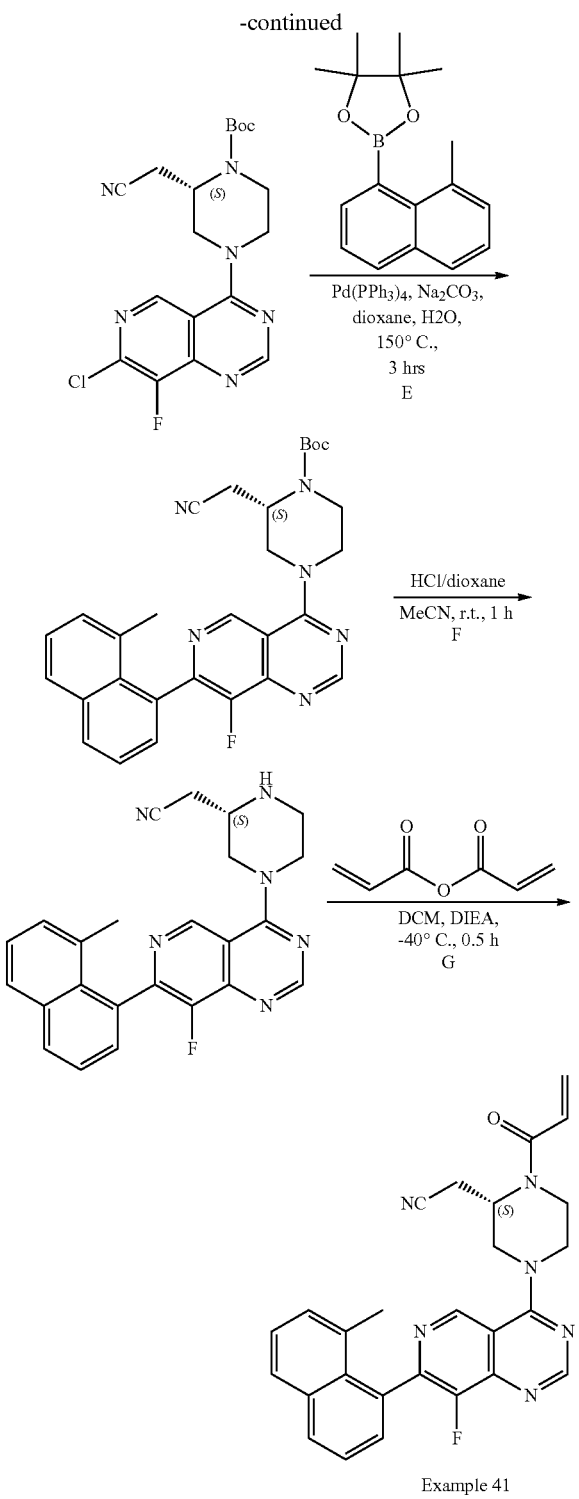

Example 41

Step A: ammonia was bubbled into a solution of methyl alcohol (10 mL) was added ethyl 4-amino-6-chloro-5-fluoro-pyridine-3-carboxylate (500 mg, 2.29 mmol, 1.00 eq) and the mixture was stirred at 35° C. for 12 hours. The reaction mixture was concentrated under reduced pressure to give crude product 4-amino-6-chloro-5-fluoro-pyridine-3-carboxamide (391 mg, crude) as a yellow solid and used into the next step without further purification.

$^1$H NMR (400 MHz, DMSO-d$_6$) δ=8.32 (s, 1H), 8.10 (br s, 1H), 7.56 (br d, J=5.6 Hz, 2H), 7.48 (br s, 1H).

Step B: To a solution of 4-amino-6-chloro-5-fluoro-pyridine-3-carboxamide (270 mg, 1.11 mmol, 1.00 eq.) in triethyl orthoformate (1.00 mL) was stirred at 150° C. for 3 hours. The reaction mixture was filtered and the filter cake concentrated under reduced pressure to give crude product 7-chloro-8-fluoro-pyrido[4,3-d]pyrimidin-4-ol (505 mg, crude) as a gray solid and used into the next step without further purification.

$^1$H NMR (400 MHz, DMSO-d$_6$) δ=13.0 (br s, 1H), 8.94 (br s, 1H), 8.40 (br s, 1H).

Step C: To a solution of 7-chloro-8-fluoro-pyrido[4,3-d]pyrimidin-4-ol (500 mg, 2.51 mmol, 1.00 eq.) in phosphorus oxychloride (8.25 g, 53.8 mmol, 5.00 mL, 21.5 eq.) was added diisopropylethylamine (971 mg, 7.52 mmol, 1.31 mL, 3.00 eq.). The mixture was stirred at 120° C. for 12 hours. The reaction mixture was concentrated under reduced pressure to give a residue. The crude product 4,7-dichloro-8-fluoro-pyrido[4,3-d]pyrimidine (550 mg, crude) as a brown gum and used into the next step without further purification.

Step D: To a solution of 4,7-dichloro-8-fluoro-pyrido[4,3-d]pyrimidine (540 mg, 2.48 mmol, 1.00 eq) in dichloromethane (10.0 mL) was added diisopropylethylamine to adjust PH to 10. After added, the mixture was stirred at −40° C. for 0.5 hour and tert-butyl (2S)-2-(cyanomethyl)piperazine-1-carboxylate (558 mg, 2.48 mmol, 1.00 eq) was added and the resulting mixture was stirred at −40° C. for 0.5 hour. The reaction mixture was concentrated under reduced pressure to give a residue. The residue was purified by column chromatography (SiO$_2$, Petroleum ether:Ethyl acetate=10:1 to 0:1) to give tert-butyl (2S)-4-(7-chloro-8-fluoro-pyrido[4,3-d]pyrimidin-4-yl)-2-(cyanomethyl)piperazine-1-carboxylate (603 mg, 1.48 mmol, 59.8% yield) as a yellow solid.

$^1$H NMR (400 MHz, CDCl$_3$) δ=8.96 (s, 1H), 8.81 (s, 1H), 4.67-4.59 (m, 1H), 4.53 (dd, J=4.0, 13.6 Hz, 1H), 4.34 (td, J=3.2, 12.8 Hz, 1H), 4.12 (q, J=7.2 Hz, 1H), 3.97 (br d, J=10.8 Hz, 1H), 3.76 (ddd, J=4.0, 10.8, 12.8 Hz, 1H), 3.56-3.37 (m, 1H), 2.89-2.76 (m, 1H), 2.71-2.64 (m, 1H), 1.50 (s, 9H).

Step E: A mixture of tert-butyl (2S)-4-(7-chloro-8-fluoro-pyrido[4,3-d]pyrimidin-4-yl)-2-(cyanomethyl)piperazine-1-carboxylate (105 mg, 258 µmol, 1.00 eq.), 4,4,5,5-tetramethyl-2-(8-methyl-1-naphthyl)-1,3,2-dioxaborolane (104 mg, 387 µmol, 1.50 eq.), Pd(PPh$_3$)$_4$ (29.8 mg, 25.8 µmol, 0.100 eq.) and sodium carbonate (54.7 mg, 516 µmol, 2.00 eq.) in dioxane (1.00 mL) and water (0.20 mL) was degassed and purged with nitrogen for 3 times, and then the mixture was stirred at 105° C. for 5 hours under nitrogen atmosphere. The reaction mixture was concentrated under reduced pressure to give a residue. The residue was purified by prep-TLC (SiO$_2$, Petroleum ether:Ethyl acetate=1:1) to give tert-butyl (2S)-2-(cyanomethyl)-4-[8-fluoro-7-(8-methyl-1-naphthyl)pyrido[4,3-d]pyrimidin-4-yl]piperazine-1-carboxylate (71.0 mg, 95.4 µmol, 37.0% yield, 68.9% purity) as a yellow oil. LCMS [M+1]=513.4.

Step F: To a solution of tert-butyl (2S)-2-(cyanomethyl)-4-[8-fluoro-7-(8-methyl-1-naphthyl)pyrido[4,3-d]pyrimidin-4-yl]piperazine-1-carboxylate (70.0 mg, 94.1 µmol, 1.00 eq.) in acetonitrile (0.50 mL) was added dioxane hydrochloride (4.00 M, 0.50 mL). The mixture was stirred at 20° C. for 1 hour. The reaction mixture was adjust pH to 8 with triethylamine and concentrated under reduced pressure to give crude product 2-[(2S)-4-[8-fluoro-7-(8-methyl-1-naphthyl)pyrido[4,3-d]pyrimidin-4-yl]piperazin-2-yl]acetonitrile (41 mg, crude) as a yellow solid and used into the next step without further purification. LCMS [M+1]=413.3.

$^1$H NMR (400 MHz, MeOD) δ=9.23 (s, 1H), 8.75 (s, 1H), 8.05 (d, J=8.0 Hz, 1H), 7.87 (d, J=8.0 Hz, 1H), 7.58 (t, J=7.6 Hz, 1H), 7.49-7.41 (m, 2H), 7.32 (br d, J=7.2 Hz, 1H), 4.76 (br d, J=12.8 Hz, 1H), 4.57 (br d, J=12.8 Hz, 1H), 3.69-3.59

(m, 1H), 3.43-3.33 (m, 1H), 3.28 (br s, 1H), 3.17 (br d, J=12.4 Hz, 1H), 3.07-2.97 (m, 1H), 2.81-2.68 (m, 2H), 2.01 (s, 3H).

Example 41: To a solution of 2-[(2S)-4-[8-fluoro-7-(8-methyl-1-naphthyl)pyrido[4,3-d]pyrimidin-4-yl]piperazin-2-yl]acetonitrile (40.0 mg, 97.0 µmol, 1.00 eq.) and prop-2-enoyl prop-2-enoate (24.5 mg, 194 µmol, 2.00 eq.) in dichloromethane (1.00 mL) was added diisopropylethylamine (25.1 mg, 194 µmol, 33.9 µL, 2.00 eq.). The mixture was stirred at −40° C. for 0.5 hour. The reaction mixture was concentrated under reduced pressure to give a residue. The residue was purified by prep-HPLC (neutral condition) to give 2-[(2S)-4-[8-fluoro-7-(8-methyl-1-naphthyl)pyrido[4,3-d]pyrimidin-4-yl]-1-prop-2-enoyl-piperazin-2-yl]acetonitrile (17.3 mg, 35.9 µmol, 37.0% yield, 96.6% purity) as a yellow solid. LCMS [M+1]=467.3.

$^1$H NMR (400 MHz, MeOD) δ=9.32 (s, 1H), 8.79 (s, 1H), 8.06 (d, J=8.0 Hz, 1H), 7.88 (br d, J=8.0 Hz, 1H), 7.59 (br t, J=7.2 Hz, 1H), 7.50-7.40 (m, 2H), 7.33 (br d, J=6.4 Hz, 1H), 6.82 (br s, 1H), 6.31 (br dd, J=17.2 Hz, 1H), 5.85 (br d, J=9.6 Hz, 1H), 5.06 (br s, 1H), 4.80-4.68 (m, 2H), 4.61 (br s, 1H), 4.24-3.78 (m, 3H), 3.01 (br s, 2H), 2.01 (br d, J=5.6 Hz, 3H).

Example 42

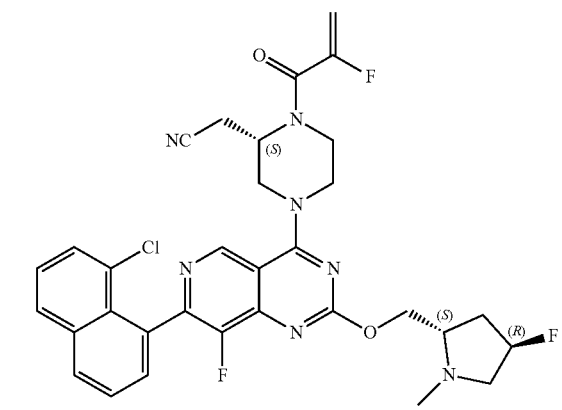

2-[(2S)-4-[7-(8-chloro-1-naphthyl)-8-fluoro-2-[[(2S,4R)-4-fluoro-1-methyl-pyrrolidin-2-yl]methoxy]pyrido[4,3-d]pyrimidin-4-yl]-1-(2-fluoroprop-2-enoyl)piperazin-2-yl]acetonitrile

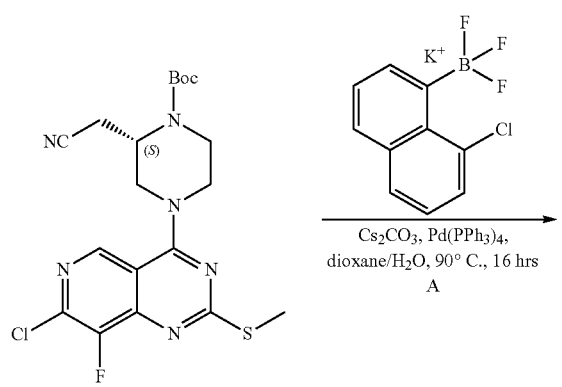

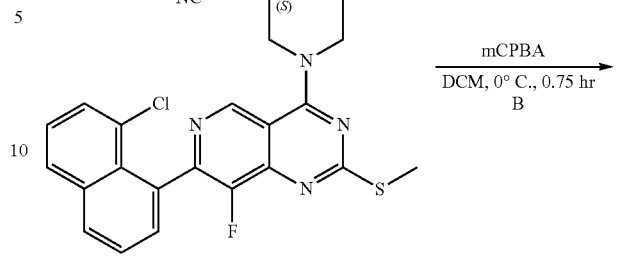

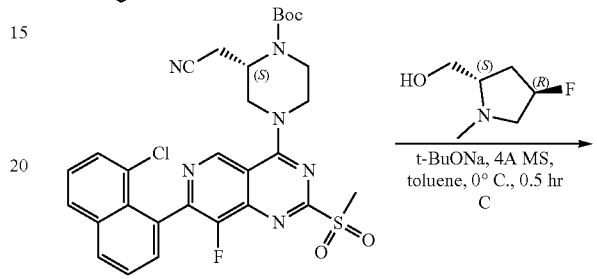

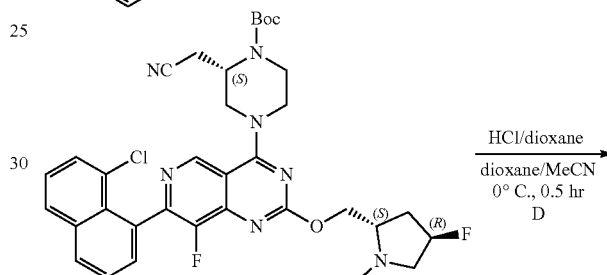

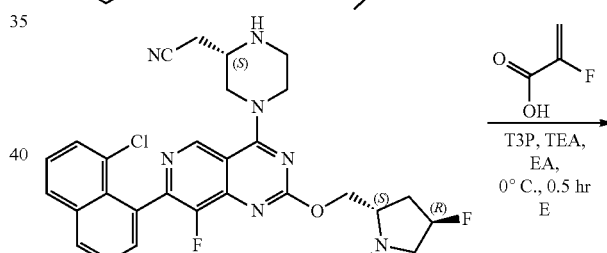

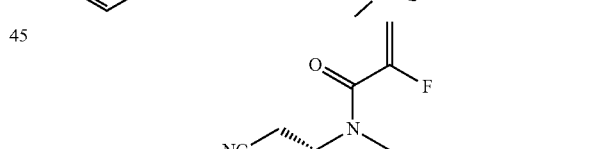

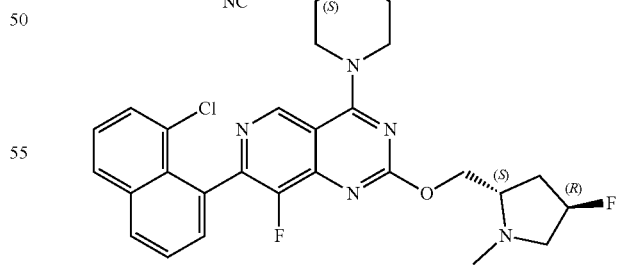

Example 42

Step A: To a mixture of tert-butyl (2S)-4-(7-chloro-8-fluoro-2-methylsulfanyl-pyrido[4,3-d]pyrimidin-4-yl)-2-(cyanomethyl)piperazine-1-carboxylate (4.5 g, 9.93 mmol, 1.0 eq) and [(8-chloro-1-naphthyl)-trifluoro-boranyl]potassium ($^{1+}$) (4.0 g, 14.9 mmol, 1.5 eq) in dioxane (75.0 mL)

and H$_2$O (15.0 mL) was added Cs$_2$CO$_3$ (9.71 g, 29.8 mmol, 3.0 eq) and Pd(PPh$_3$)$_4$ (5.74 g, 4.97 mmol, 0.5 eq) at 25° C., the reaction mixture was stirred at 90° C. for 16 hours. The reaction mixture was concentrated under reduced pressure to remove dioxane. The residue was diluted with water (5 mL) and extracted with methyl-tert-butyl ether (60 mL). The combined organic layers were filtered and the filtrate was dried over Na$_2$SO$_4$ solid, filtered and the filtrate was concentrated under reduced pressure to give a residue. The residue was purified by column chromatography (SiO$_2$, Petroleum ether/Ethyl acetate=5/1 to 2/1). The desired fractions were collected and concentrated under reduced pressure to give a residue. The crude product was purified by reversed-phase flash (0.1% FA condition). The desired fractions were collected and concentrated to remove CH$_3$CN. The combined water layers were added Na$_2$CO$_3$ solid to pH=9~10, the mixture was extracted with ethyl acetate (2×100 mL). The combined organic layers were washed with brine (80 mL), dried over Na$_2$SO$_4$ solid, filtered and the filtrate was concentrated under reduced pressure to give compound tert-butyl (2S)-4-[7-(8-chloro-1-naphthyl)-8-fluoro-2-methylsulfanyl-pyrido[4,3-d]pyrimidin-4-yl]-2-(cyanomethyl)piperazine-1-carboxylate (1.6 g, 2.76 mmol, 27.8% yield, 100% purity) as a yellow solid. LCMS [M+1]: 579.

$^1$H NMR (400 MHz, chloroform-d) δ=9.06 (s, 1H), 8.02 (dd, J=1.2, 8.0 Hz, 1H), 7.89 (d, J=8.0 Hz, 1H), 7.66-7.53 (m, 3H), 7.43 (dt, J=2.4, 8.0 Hz, 1H), 4.76-4.62 (m, 1H), 4.57-4.47 (m, 1H), 4.46-4.34 (m, 1H), 3.89-3.62 (m, 2H), 3.41 (dt, J=1.6, 4.8 Hz, 1H), 2.90-2.70 (m, 2H), 2.65 (s, 3H), 1.53 (s, 9H).

Step B: To a solution of tert-butyl (2S)-4-[7-(8-chloro-1-naphthyl)-8-fluoro-2-methylsulfanyl-pyrido[4,3-d]pyrimidin-4-yl]-2-(cyanomethyl)piperazine-1-carboxylate (1.18 g, 2.04 mmol, 1.0 eq) in dichloromethane (10.0 mL) was added mCPBA (396 mg, 1.83 mmol, 80% purity, 0.9 eq) at 0° C., the mixture was stirred at 0° C. under N$_2$ for 0.25 hour. Then mCPBA (220 mg, 1.02 mmol, 80% purity, 0.5 eq) was added, the mixture was stirred at 0° C. for 0.25 hour. Then mCPBA (176 mg, 815 μmol, 80% purity, 0.4 eq) was added, the mixture was stirred at 0° C. for 0.25 hour. The reaction mixture was quenched by addition Na$_2$SO$_3$ saturate aqueous solution (20 mL) at 0° C., and then diluted with water (20 mL) and extracted with ethyl acetate (2×80 mL). The combined organic layers were dried over Na$_2$SO$_4$ solid, filtered and the filtrate was concentrated under reduced pressure to give a residue. The crude product was purified by reversed-phase HPLC (0.1% FA condition). The desired fractions were collected and concentrated to remove CH$_3$CN. The water layers were added NaHCO$_3$ solid to pH=7~8 and extracted with ethyl acetate (2×300 mL). The combined organic layers were dried over Na$_2$SO$_4$ solid, filtered and the filtrate was concentrated under reduce pressure to give compound tert-butyl (2S)-4-[7-(8-chloro-1-naphthyl)-8-fluoro-2-methylsulfonyl-pyrido[4,3-d]pyrimidin-4-yl]-2-(cyanomethyl)piperazine-1-carboxylate (820 mg, 1.33 mmol, 65.3% yield, 99% purity) as a yellow solid. LCMS [M+1]: 611.

Step C: To a mixture of tert-butyl (2S)-4-[7-(8-chloro-1-naphthyl)-8-fluoro-2-methylsulfonyl-pyrido[4,3-d]pyrimidin-4-yl]-2-(cyanomethyl)piperazine-1-carboxylate (890 mg, 1.46 mmol, 1.0 eq) and [(2S,4R)-4-fluoro-1-methyl-pyrrolidin-2-yl]methanol (291 mg, 2.18 mmol, 1.5 eq) in toluene (10.0 mL) was added 4A molecular sieve (900 mg) at 0° C., the mixture was stirred at 0° C. for 0.25 hour, then NaOtBu (280 mg, 2.91 mmol, 2.0 eq) was added, the reaction mixture was stirred at 0° C. for 0.25 hour. The reaction mixture was filtered with ethyl acetate (40 mL), and the filtrate was diluted with water (30 mL) and extracted with ethyl acetate (2×40 mL). The combined organic layers were washed with brine (40 mL), dried over Na$_2$SO$_4$ solid, filtered and the filtrate was concentrated under reduced pressure to give a residue. The crude product was purified by reversed-phase flash (0.1% FA condition). The desired fractions were collected and concentrated to remove CH$_3$CN, the water layers were added Na$_2$CO$_3$ solid to pH=9~10 and extracted with ethyl acetate (3×100 mL). The combined organic layers were washed with brine (80 mL), dried over Na$_2$SO$_4$ solid, filtered and the filtrate was concentrated under reduced pressure to give compound tert-butyl(2S)-4-[7-(8-chloro-1-naphthyl)-8-fluoro-2-[[(2S,4R)-4-fluoro-1-methyl-pyrrolidin-2-yl]methoxy]pyrido[4,3-d]pyrimidin-4-yl]-2-(cyanomethyl)piperazine-1-carboxylate (590 mg, 886 μmol, 60.8% yield, 99.7% purity) as a yellow solid. LCMS [M+1]: 664.

$^1$H NMR (400 MHz, chloroform-d) δ=9.08 (s, 1H), 8.06-7.99 (m, 1H), 7.90 (d, J=8.0 Hz, 1H), 7.66-7.53 (m, 3H), 7.44 (dt, J=2.4, 8.0 Hz, 1H), 5.34-5.04 (m, 1H), 4.80-4.56 (m, 2H), 4.55-4.36 (m, 3H), 3.97-3.79 (m, 1H), 3.78-3.64 (m, 1H), 3.63-3.41 (m, 2H), 3.17-3.02 (m, 1H), 2.94-2.59 (m, 3H), 2.54 (s, 3H), 2.41-2.25 (m, 1H), 2.09 (br dd, J=5.2, 9.6 Hz, 1H), 2.04-1.95 (m, 1H), 1.53 (s, 9H).

Step D: To a solution of tert-butyl (2S)-4-[7-(8-chloro-1-naphthyl)-8-fluoro-2-[[(2S,4R)-4-fluoro-1-methyl-pyrrolidin-2-yl]methoxy]pyrido[4,3-d]pyrimidin-4-yl]-2-(cyanomethyl)piperazine-1-carboxylate (580 mg, 873 μmol, 1.0 eq) in dioxane (15.0 mL) and CH$_3$CN (5.0 mL) was added HCl•dioxane (4.0 M, 20.0 mL) at 0° C., the reaction mixture was stirred at 0° C. for 0.5 hour. The reaction mixture was quenched by addition Na$_2$CO$_3$ solid at 0° C. to pH=9~10, and then diluted with water (20 mL) and extracted with ethyl acetate (3×50 mL). The combined organic layers were dried over Na$_2$SO$_4$ solid, filtered and the filtrate was concentrated under reduced pressure to give a residue. The residue was purified by prep-HPLC (basic condition, column: Waters Xbridge 150*50 10μ; mobile phase: [water (0.05% ammonia hydroxide v/v)—ACN]; B %: 32%-62%, 11.5 min). The desired fractions were collected and concentrated to remove CH$_3$CN, the water layers were lyophilized to give compound 2-[(2S)-4-[7-(8-chloro-1-naphthyl)-8-fluoro-2-[[(2S,4R)-4-fluoro-1-methyl-pyrrolidin-2-yl]methoxy]pyrido[4,3-d]pyrimidin-4-yl]piperazin-2-yl]acetonitrile (28.7 mg, 50.6 μmol, 5.79% yield, 99.3% purity) as a white solid. LCMS [M+1]: 564.

$^1$H NMR (400 MHz, chloroform-d) δ=9.03 (s, 1H), 8.02 (dd, J=1.6, 7.6 Hz, 1H), 7.90 (d, J=7.6 Hz, 1H), 7.67-7.52 (m, 3H), 7.48-7.39 (m, 1H), 5.35-5.05 (m, 1H), 4.71-4.35 (m, 4H), 3.67-3.48 (m, 2H), 3.43-3.31 (m, 1H), 3.29-3.05 (m, 4H), 2.70-2.56 (m, 3H), 2.54 (s, 3H), 2.41-2.26 (m, 1H), 2.13-1.96 (m, 1H).

Example 42: To a mixture of 2-[(2S)-4-[7-(8-chloro-1-naphthyl)-8-fluoro-2-[[(2S,4R)-4-fluoro-1-methyl-pyrrolidin-2-yl]methoxy]pyrido[4,3-d]pyrimidin-4-yl]piperazin-2-yl]acetonitrile (100 mg, 177 μmol, 1.0 eq) and 2-fluoroprop-2-enoic acid (31.9 mg, 354 μmol, 2.0 eq) in ethyl acetate (5.0 mL) was added 4A molecular sieve (100 mg) at 0° C., the mixture was stirred at 0° C. for 0.25 hour. Then TEA (269 mg, 2.66 mmol, 370 μL, 15.0 eq) and T3P (451 mg, 709 μmol, 422 μL, 50% purity, 4.0 eq) was added at 0° C., the reaction mixture was stirred at 0° C. for 0.25 hour. The reaction mixture was quenched by addition saturate NH$_4$Cl aqueous solution (5 mL) at 0° C., and then diluted with water (5 mL) and extracted with ethyl acetate (2×15 mL). The combined organic layers were dried over Na$_2$SO$_4$ solid, filtered and the filtrate was concentrated under reduced pressure to give a residue. The residue was purified by prep-HPLC (basic condition, column: Waters Xbridge 150*50 10μ; mobile phase: [water (0.05% ammonia hydroxide v/v)—ACN]; B %: 42%-72%, 11.5 min). The desired fractions were collected and concentrated to remove CH$_3$CN, the water layers were lyophilized to give compound 2-[(2S)-4-[7-(8-chloro-1-naphthyl)-8-fluoro-2-[[(2S,4R)-4-fluoro-1-methyl-pyrrolidin-2-yl]methoxy]pyrido[4,3-d]pyrimidin-4-yl]-1-(2-fluoroprop-2-enoyl)piperazin-2-yl]acetonitrile (36.2 mg, 56.9 μmol, 32.1% yield) as a white solid. LCMS [M+1]: 636.

$^1$H NMR (400 MHz, chloroform-d) δ=9.07 (s, 1H), 8.06-8.00 (m, 1H), 7.90 (d, J=8.0 Hz, 1H), 7.66-7.53 (m, 3H), 7.44 (dt, J=2.4, 8.0 Hz, 1H), 5.59-5.38 (m, 1H), 5.36-5.07 (m, 2H), 4.97-4.76 (m, 1H), 4.63 (dt, J=4.4, 10.8 Hz, 1H), 4.56-4.41 (m, 3H), 4.37-4.14 (m, 1H), 4.13-3.93 (m, 1H), 3.92-3.65 (m, 2H), 3.64-3.49 (m, 1H), 3.14-2.96 (m, 2H), 2.93-2.78 (m, 1H), 2.70-2.57 (m, 1H), 2.54 (s, 3H), 2.43-2.23 (m, 1H), 2.17-1.91 (m, 1H).

Example 43

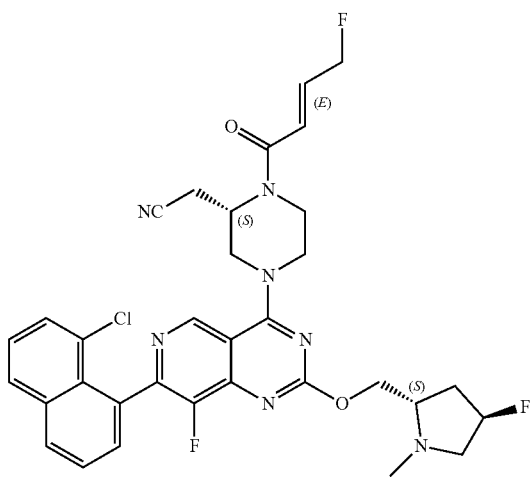

2-[(2S)-4-[7-(8-chloro-1-naphthyl)-8-fluoro-2-[[(2S,4R)-4-fluoro-1-methyl-pyrrolidin-2-yl]methoxy]pyrido[4,3-d]pyrimidin-4-yl]-1-[(E)-4-fluorobut-2-enoyl]piperazin-2-yl]acetonitrile

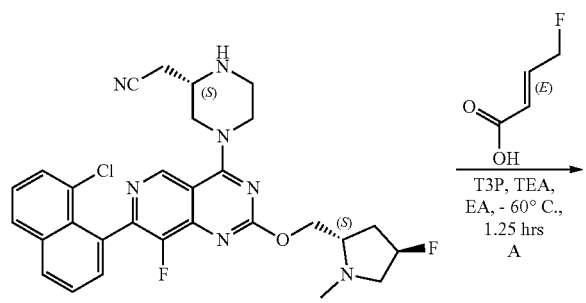

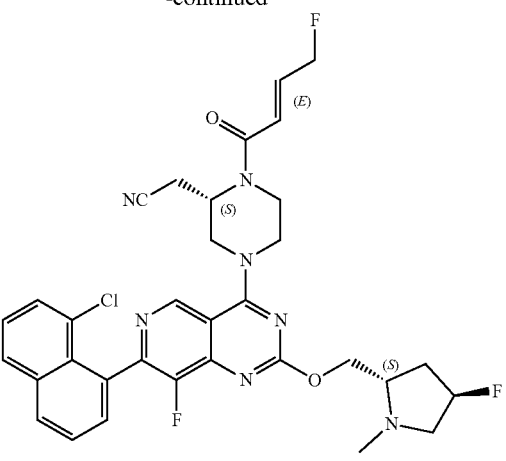

Example 43

Example 43: To a mixture of 2-[(2S)-4-[7-(8-chloro-1-naphthyl)-8-fluoro-2-[[(2S,4R)-4-fluoro-1-methyl-pyrrolidin-2-yl]methoxy]pyrido[4,3-d]pyrimidin-4-yl]piperazin-2-yl]acetonitrile (100 mg, 177 μmol, 1.0 eq) and (E)-4-fluorobut-2-enoic acid (184 mg, 1.77 mmol, 10.0 eq) was added 4A molecular sieve (150 mg) at −60° C., the mixture was stirred at −60° C. for 0.25 hour. Then TEA (269 mg, 2.66 mmol, 370 μL, 15.0 eq) and T3P (903 mg, 1.42 mmol, 843 μL, 50% purity, 8.0 eq) was added, the reaction mixture was stirred at −60° C. for 1 hour. The reaction mixture was quenched by addition saturate NH$_4$Cl aqueous solution (5 mL) at −60° C., and then diluted with water (5 mL) and extracted with ethyl acetate (2×15 mL). The combined organic layers were dried over Na$_2$SO$_4$ solid, filtered and the filtrate was concentrated under reduced pressure to give a residue. The residue was purified by prep-HPLC (basic condition, column: Waters Xbridge 150*50 10μ; mobile phase: [water (0.05% ammonia hydroxide v/v)—ACN]; B %: 40%-70%, 11.5 min). The desired fractions were collected and concentrated to remove CH$_3$CN, the water layers were lyophilized to give compound 2-[(2S)-4-[7-(8-chloro-1-naphthyl)-8-fluoro-2-[[(2S,4R)-4-fluoro-1-methyl-pyrrolidin-2-yl]methoxy]pyrido[4,3-d]pyrimidin-4-yl]-1-[(E)-4-fluorobut-2-enoyl]piperazin-2-yl]acetonitrile (13.3 mg, 20.4 μmol, 11.5% yield, 99.7% purity) as a white solid. LCMS [M+1]: 650.

$^1$H NMR (400 MHz, chloroform-d) δ=9.09 (s, 1H), 8.07-7.99 (m, 1H), 7.90 (d, J=8.0 Hz, 1H), 7.67-7.53 (m, 3H), 7.44 (dt, J=2.0, 8.0 Hz, 1H), 7.11-6.95 (m, 1H), 6.60 (br d, J=15.2 Hz, 1H), 5.34-4.91 (m, 4H), 4.73-4.61 (m, 1H), 4.58-4.43 (m, 3H), 4.24-3.25 (m, 5H), 3.22-3.07 (m, 1H), 3.05-2.91 (m, 1H), 2.90-2.77 (m, 1H), 2.64 (br s, 1H), 2.58 (br s, 3H), 2.42-2.27 (m, 1H), 2.19-1.92 (m, 1H).

Example 44

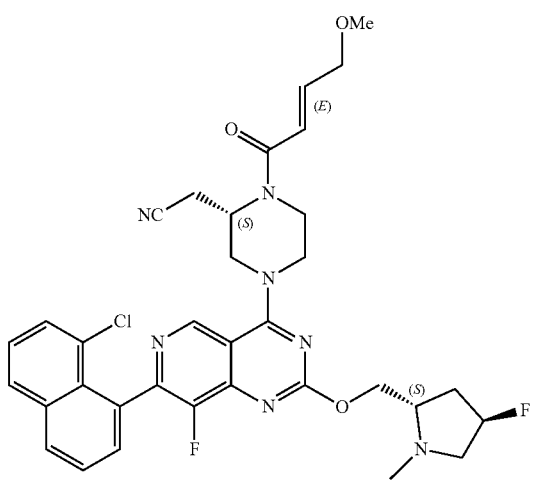

2-[(2S)-4-[7-(8-chloro-1-naphthyl)-8-fluoro-2-[[(2S,4R)-4-fluoro-1-methyl-pyrrolidin-2-yl]methoxy]pyrido[4,3-d]pyrimidin-4-yl]-1-[(E)-4-methoxybut-2-enoyl]piperazin-2-yl]acetonitrile

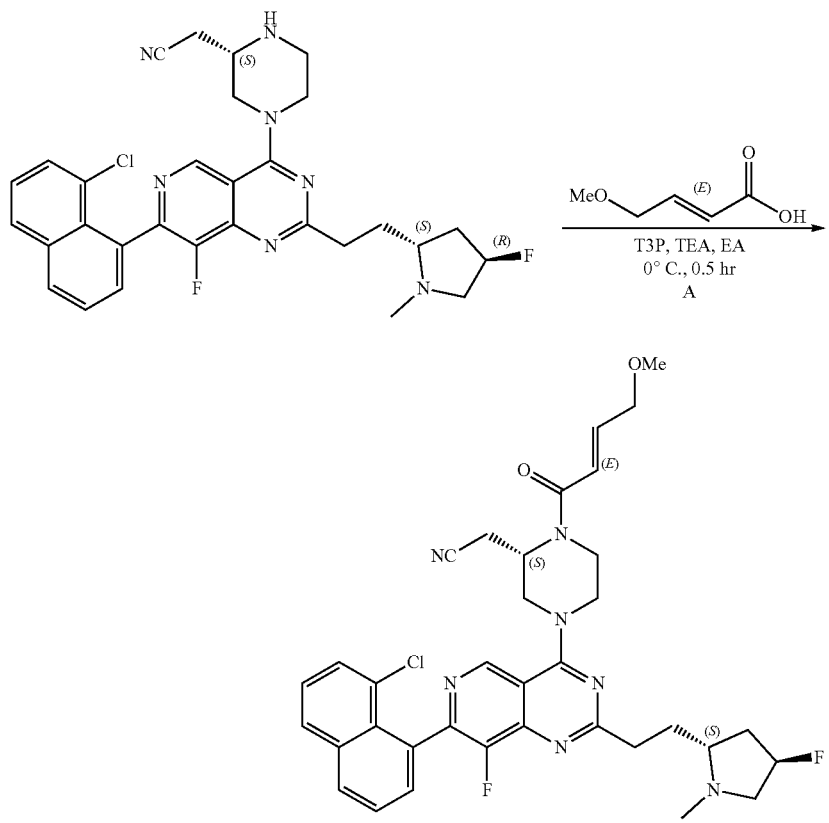

Example 44

Example 44: To a mixture of 2-[(2S)-4-[7-(8-chloro-1-naphthyl)-8-fluoro-2-[[(2S,4R)-4-fluoro-1-methyl-pyrrolidin-2-yl]methoxy]pyrido[4,3-d]pyrimidin-4-yl]piperazin-2-yl]acetonitrile (100 mg, 177 μmol, 1.0 eq) and (E)-4-methoxybut-2-enoic acid (41.2 mg, 354 μmol, 2.0 eq) in ethyl acetate (5 mL) was added 4A molecular sieve (100 mg) at 0° C., the mixture was stirred at 0° C. for 0.25 hour. Then TEA (269 mg, 2.66 mmol, 370 μL, 15.0 eq) and T3P (451 mg, 709 μmol, 422 μL, 50% purity, 4.0 eq) was added, the reaction mixture was stirred at 0° C. for 0.25 hour. The reaction mixture was quenched by addition saturate NH$_4$Cl aqueous solution (5 mL) at 0° C., and then diluted with water (5 mL) and extracted with ethyl acetate (2×15 mL). The combined organic layers were dried over Na$_2$SO$_4$ solid, filtered and the filtrate was concentrated under reduced pressure to give a residue. The residue was purified by prep-HPLC (basic condition, column: Waters Xbridge 150*50 10u; mobile phase: [water (0.05% ammonia hydroxide v/v)—ACN]; B %: 36%-66%, 11.5 min). The desired fractions were collected and concentrated to remove CH$_3$CN, the water layers were lyophilized to give compound 2-[(2S)-4-[7-(8-chloro-1-naphthyl)-8-fluoro-2-[[(2S,4R)-4-fluoro-1-methyl-pyrrolidin-2-yl]methoxy]pyrido[4,3-d]pyrimidin-4-yl]-1-[(E)-4-methoxybut-2-enoyl]piperazin-2-yl]acetonitrile (41.2 mg, 62.2 μmol, 35.1% yield) as a white solid. LCMS [M+1]: 662.

$^1$H NMR (400 MHz, chloroform-d) δ=9.08 (s, 1H), 8.09-7.98 (m, 1H), 7.90 (d, J=8.0 Hz, 1H), 7.68-7.53 (m, 3H), 7.44 (dt, J=2.4, 8.0 Hz, 1H), 7.02 (br d, J=14.4 Hz, 1H), 6.55 (br d, J=14.8 Hz, 1H), 5.34-4.93 (m, 2H), 4.63 (dt, J=4.4, 10.4 Hz, 1H), 4.55-4.41 (m, 3H), 4.26-3.65 (m, 6H), 3.63-

3.51 (m, 1H), 3.44 (s, 3H), 3.16-2.73 (m, 3H), 2.71-2.56 (m, 1H), 2.54 (s, 3H), 2.43-2.22 (m, 1H), 2.17-1.90 (m, 1H).

Example 45

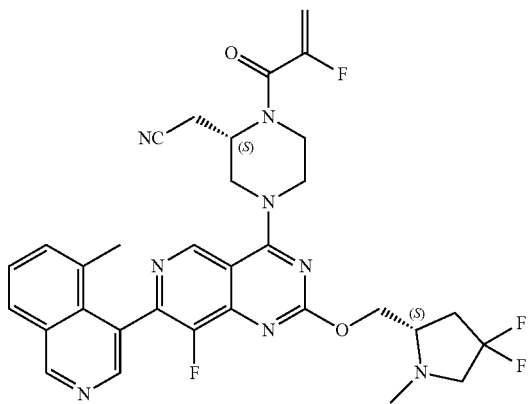

2-((S)-4-(2-(((S)-4,4-difluoro-1-methylpyrrolidin-2-yl)methoxy)-8-fluoro-7-(5-methylisoquinolin-4-yl)pyrido[4,3-d]pyrimidin-4-yl)-1-(2-fluoroacryloyl)piperazin-2-yl)acetonitrile

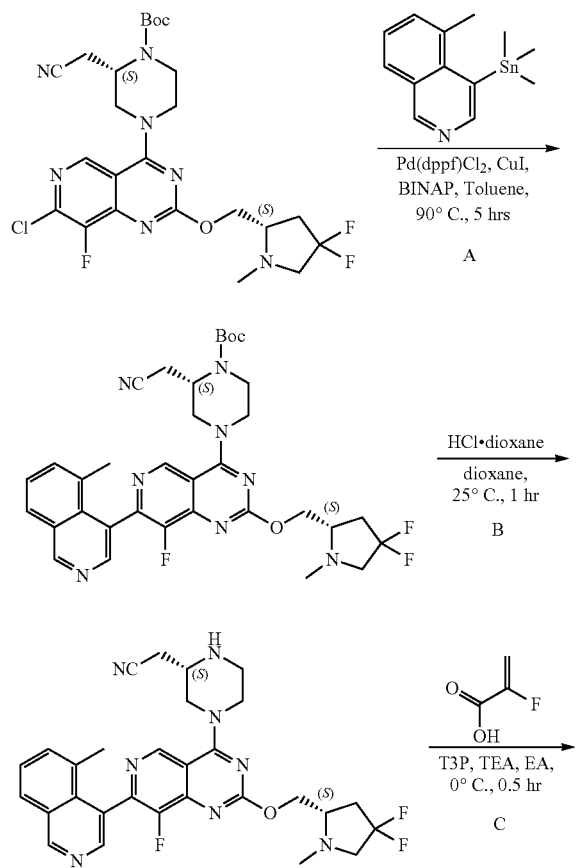

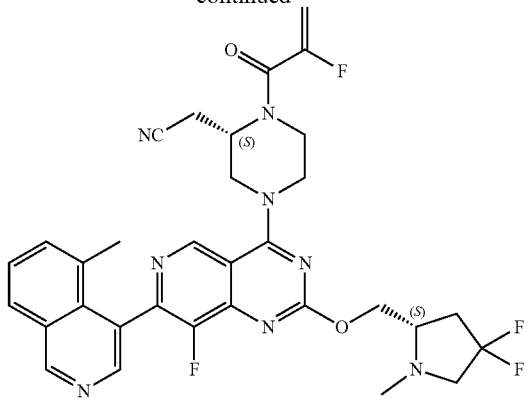

Example 45

Step A: A mixture of trimethyl-(5-methyl-4-isoquinolyl)stannane (275 mg, 899 μmol, 2.0 eq), tert-butyl (2S)-4-[7-chloro-2-[[(2S)-4,4-difluoro-1-methyl-pyrrolidin-2-yl]methoxy]-8-fluoro-pyrido[4,3-d]pyrimidin-4-yl]-2-(cyanomethyl)piperazine-1-carboxylate (250 mg, 449 μmol, 1.0 eq), CuI (25.6 mg, 134 μmol, 0.3 eq), Pd(dppf)Cl₂ (32.9 mg, 44.9 μmol, 0.1 eq) and BINAP (56.0 mg, 89.9 μmol, 0.2 eq) in toluene (5.00 mL) was degassed and purged with N₂ for 3 times, then the mixture was stirred at 90° C. for 5 hours under N₂ atmosphere. The reaction mixture was diluted with water (20.0 mL) and extracted with ethyl acetate (3×30.0 mL). The combined organic layers were washed with brine (20.0 mL), dried over Na₂SO₄, filtered and concentrated under reduced pressure to give a residue. The residue was purified by reversed phase flash [water (0.1% formic acid)/acetonitrile)]. The mixture was adjusted pH ~7 with saturated NaHCO₃ aqueous solution and extracted with ethyl acetate (3×50.0 mL). The combined organic layers were washed with brine (50.0 mL), dried over Na₂SO₄, filtered and concentrated under reduced pressure to give tert-butyl (2S)-2-(cyanomethyl)-4-[2-[[(2S)-4,4-difluoro-1-methyl-pyrrolidin-2-yl]methoxy]-8-fluoro-7-(5-methyl-4-isoquinolyl)pyrido[4,3-d]pyrimidin-4-yl]piperazine-1-carboxylate (230 mg, 340 μmol, 76% yield, 98% purity) was obtained as a white solid. LCMS [ESI, M+1]: 663.

Step B: To a solution of tert-butyl (2S)-2-(cyanomethyl)-4-[2-[[(2S)-4,4-difluoro-1-methyl-pyrrolidin-2-yl]methoxy]-8-fluoro-7-(5-methyl-4-isoquinolyl)pyrido[4,3-d]pyrimidin-4-yl]piperazine-1-carboxylate (30 mg, 45.2 μmol, 1.0 eq) in dioxane (200 μL) was added HCl·dioxane (4 M, 169 μL). The mixture was stirred at 25° C. for 1 hour. The mixture was concentrated under vacuum. The reaction mixture was diluted with water (20.0 mL). Then the mixture was adjusted pH ~8 with saturated NaHCO₃ aqueous solution and extracted with ethyl acetate (3×20.0 mL). The combined organic layers were washed with brine (20.0 mL), dried over Na₂SO₄, filtered and concentrated under reduced pressure to give the residue. The residue was purified by prep-HPLC (column: Waters Xbridge 150*25 5μ; mobile phase: [water (0.05% ammonia hydroxide v/v)—ACN]; B %: 25%-55%, 10 min). The desired fraction was collected and lyophilized. 2-[(2S)-4-[2-[[(2S)-4,4-difluoro-1-methyl-pyrrolidin-2-yl]methoxy]-8-fluoro-7-(5-methyl-4-isoquinolyl)pyrido[4,3-d]pyrimidin-4-yl]piperazin-2-yl]acetonitrile (10.1 mg, 17.4 μmol, 39% yield, 97% purity) was obtained as a off-white solid. LCMS [ESI, M+1]: 563.

¹H NMR (400 MHz, chloroform-d) δ=9.34 (s, 1H), 9.07 (s, 1H), 8.46 (s, 1H), 7.96 (d, J=7.6 Hz, 1H), 7.61-7.47 (m, 2H), 4.78-4.36 (m, 4H), 3.65-3.51 (m, 1H), 3.50-3.31 (m, 2H), 3.30-2.97 (m, 4H), 2.79-2.46 (m, 7H), 2.43-2.22 (m, 1H), 2.19-1.90 (m, 4H).

Example 45: To a solution of 2-[(2S)-4-[2-[[(2S)-4,4-difluoro-1-methyl-pyrrolidin-2-yl]methoxy]-8-fluoro-7-(5-methyl-4-isoquinolyl)pyrido[4,3-d]pyrimidin-4-yl]piperazin-2-yl]acetonitrile (50 mg, 88.8 μmol, 1.0 eq), 2-fluoroprop-2-enoic acid (24.0 mg, 266 μmol, 4.48 uL, 3.0 eq) and TEA (71.9 mg, 711 μmol, 98.9 μL, 8.0 eq) in ethyl acetate (1.00 mL) was added T3P (169 mg, 266 μmol, 158 uL, 50% purity in ethyl acetate, 3.0 eq) at 0° C. The mixture was stirred at 0° C. for 30 minutes. The reaction mixture was diluted with water (20.0 mL) and extracted with ethyl acetate (3×30.0 mL). The combined organic layers were washed with brine (20.0 mL), dried over $Na_2SO_4$, filtered and concentrated under reduced pressure to give a residue. The residue was purified by prep-HPLC (column: Xtimate C18 150*25 mm*5 um; mobile phase: [water (0.05% ammonia hydroxide v/v)—ACN]; B %: 34%-64%, 10 min). The desired fraction was collected and lyophilized. 2-[(2S)-4-[2-[[(2S)-4,4-difluoro-1-methyl-pyrrolidin-2-yl]methoxy]-8-fluoro-7-(5-methyl-4-isoquinolyl)pyrido[4,3-d]pyrimidin-4-yl]-1-(2-fluoroprop-2-enoyl)piperazin-2-yl]acetonitrile (21.6 mg, 34.0 μmol, 38% yield, 99.8% purity) was obtained as a white solid. LCMS [ESI, M+1]: 635.

$^1$H NMR (400 MHz, chloroform-d) δ=9.35 (s, 1H), 9.13 (d, J=1.2 Hz, 1H), 8.47 (d, J=47.6 Hz, 1H), 7.97 (d, J=8.0 Hz, 1H), 7.62-7.48 (m, 2H), 5.50 (dd, J=3.6, 17.1 Hz, 1H), 5.30 (dd, J=3.6, 17.2 Hz, 1H), 4.86 (br s, 1H), 4.71-4.61 (m, 1H), 4.59-4.39 (m, 3H), 4.38-3.94 (m, 2H), 3.83 (br s, 2H), 3.54-3.34 (m, 1H), 3.15-2.93 (m, 2H), 2.92-2.63 (m, 2H), 2.61-2.46 (m, 4H), 2.44-2.24 (m, 1H), 2.10 (d, J=5.6 Hz, 3H).

Example 46

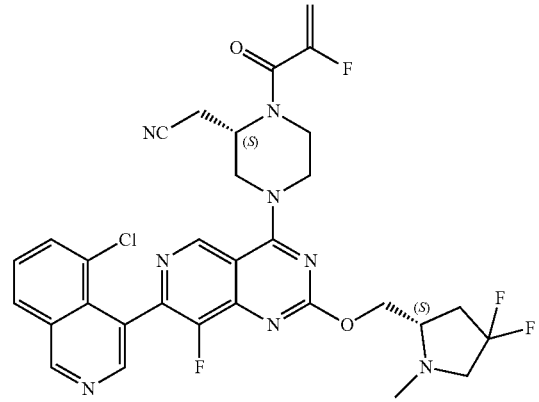

2-((S)-4-(7-(5-chloroisoquinolin-4-yl)-2-(((S)-4,4-difluoro-1-methylpyrrolidin-2-yl)methoxy)-8-fluoro-pyrido[4,3-d]pyrimidin-4-yl)-1-(2-fluoroacryloyl)piperazin-2-yl)acetonitrile

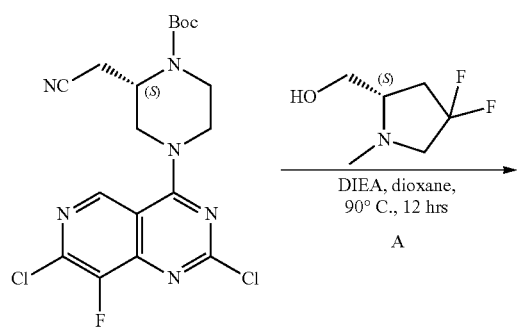

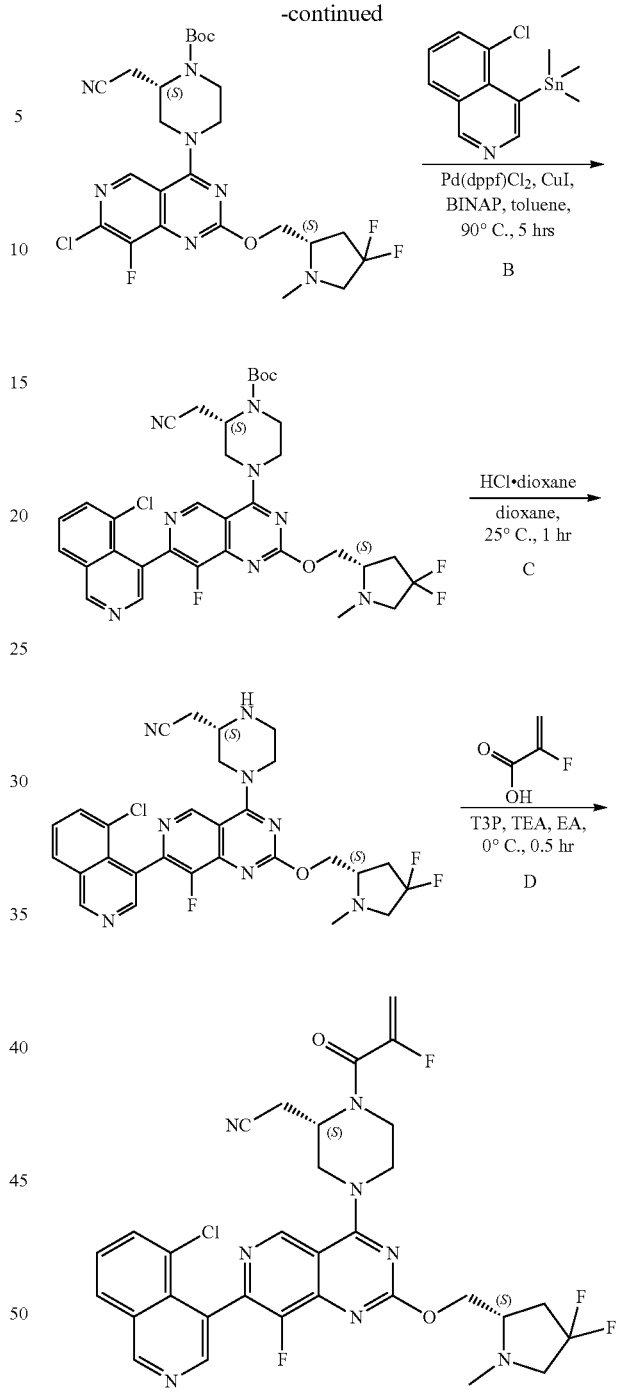

Example 46

Step A: To a solution of [(2S)-4,4-difluoro-1-methyl-pyrrolidin-2-yl] methanol (1.34 g, 8.84 mmol, 3.0 eq) in dioxane (20.0 mL) was added DIEA (1.14 g, 8.84 mmol, 1.54 mL, 3.0 eq) and tert-butyl (2S)-2-(cyanomethyl)-4-(2,7-dichloro-8-fluoro-pyrido[4,3-d]pyrimidin-4-yl)piperazine-1-carboxylate (1.3 g, 2.95 mmol, 1.0 eq). The mixture was stirred at 90° C. for 12 hours. The reaction mixture was diluted with water (30.0 mL) and extracted with ethyl acetate (3×50.0 mL). The combined organic layers were washed with brine (20.0 mL), dried over $Na_2SO_4$, filtered and concentrated under reduced pressure to give a residue. The residue was purified by reversed phase flash [water (0.1% formic acid)/acetonitrile)]. The mixture was adjusted pH ~7 with saturated NaHCO₃ aqueous solution and extracted with ethyl acetate (3×200 mL). The combined organic layers were washed with brine (100 mL), dried over Na₂SO₄, filtered and concentrated under reduced pressure to give tert-butyl (2S)-4-[7-chloro-2-[[(2S)-4,4-difluoro-1-methyl-pyrrolidin-2-yl]methoxy]-8-fluoro-pyrido[4,3-d]pyrimidin-4-yl]-2-(cyanomethyl)piperazine-1-carboxylate (600 mg, 1.07 mmol, 36% yield, 99% purity) as a yellow solid. LCMS [ESI, M+1]: 556.

Step B: A mixture of (5-chloro-4-isoquinolyl)-trimethyl-stannane (293 mg, 899 µmol, 2.0 eq), tert-butyl (2S)-4-[7-chloro-2-[[(2S)-4,4-difluoro-1-methyl-pyrrolidin-2-yl]methoxy]-8-fluoro-pyrido[4,3-d]pyrimidin-4-yl]-2-(cyanomethyl)piperazine-1-carboxylate (250 mg, 449 µmol, 1.0 eq), CuI (25.7 mg, 134 µmol, 0.3 eq), Pd(dppf)Cl₂ (32.9 mg, 44.9 µmol, 0.1 eq) and BINAP (56.0 mg, 89.9 µmol, 0.2 eq) in toluene (5.00 mL) was degassed and purged with N₂ for 3 times, then the mixture was stirred at 90° C. for 5 hours under N₂ atmosphere. The reaction mixture was diluted with water (20.0 mL) and extracted with ethyl acetate (3×30.0 mL). The combined organic layers were washed with brine (20.0 mL), dried over Na₂SO₄, filtered and concentrated under reduced pressure to give a residue. The residue was purified by column chromatography (SiO₂, ethyl acetate/methanol=100/1 to 10/1) and further purified by reversed phase flash [water (0.1% formic acid)/acetonitrile)]. The mixture was adjusted pH ~7 with saturated NaHCO₃ aqueous solution and extracted with ethyl acetate (3×20.0 mL). The combined organic layers were washed with brine (20.0 mL), dried over Na₂SO₄, filtered and concentrated under reduced pressure to give tert-butyl (2S)-4-[7-(5-chloro-4-isoquinolyl)-2-[[(2S)-4,4-difluoro-1-methyl-pyrrolidin-2-yl]methoxy]-8-fluoro-pyrido[4,3-d]pyrimidin-4-yl]-2-(cyanomethyl)piperazine-1-carboxylate (230 mg, 319 µmol, 71% yield, 95% purity) was obtained as a yellow solid. LCMS [ESI, M+1]: 683.

Step C: To a solution of tert-butyl (2S)-4-[7-(5-chloro-4-isoquinolyl)-2-[[(2S)-4,4-difluoro-1-methyl-pyrrolidin-2-yl]methoxy]-8-fluoro-pyrido[4,3-d]pyrimidin-4-yl]-2-(cyanomethyl)piperazine-1-carboxylate (30 mg, 43.9 µmol, 1.0 eq) in dioxane (200 µL) was added HCl•dioxane (4 M, 164 The mixture was stirred at 25° C. for 1 hour. The mixture was concentrated under vacuum and diluted with water (20.0 mL). Then the mixture was adjusted pH ~8 with saturated NaHCO₃ aqueous solution and extracted with ethyl acetate (3×20.0 mL). The combined organic layers were washed with brine (20.0 mL), dried over Na₂SO₄, filtered and concentrated under reduced pressure to give the residue. The residue was purified by prep-HPLC (column: Xtimate C18 150*25 mm*5 µm; mobile phase: [water (0.05% ammonia hydroxide v/v)—ACN]; B %: 27%-57%, 10 min). The desired fraction was collected and lyophilized. 2-[(2S)-4-[7-(5-chloro-4-isoquinolyl)-2-[[(2S)-4,4-difluoro-1-methyl-pyrrolidin-2-yl]methoxy]-8-fluoro-pyrido[4,3-d]pyrimidin-4-yl]piperazin-2-yl]acetonitrile (12.1 mg, 19.8 µmol, 45% yield, 95.4% purity) was obtained as a white solid. LCMS [ESI, M+1]: 583.

¹H NMR (400 MHz, chloroform-d) δ=9.39 (s, 1H), 9.06 (s, 1H), 8.59 (d, J=0.8 Hz, 1H), 8.06 (dd, J=1.2, 8.0 Hz, 1H), 7.78 (dd, J=1.2, 7.6 Hz, 1H), 7.61 (t, J=8.0 Hz, 1H), 4.74-4.38 (m, 4H), 3.65-3.53 (m, 1H), 3.51-3.31 (m, 2H), 3.29-2.98 (m, 4H), 2.79-2.48 (m, 7H), 2.43-2.24 (m, 1H), 2.04 (br s, 1H).

Example 46: To a solution of 2-[(2S)-4-[7-(5-chloro-4-isoquinolyl)-2-[[(2S)-4,4-difluoro-1-methyl-pyrrolidin-2-yl]methoxy]-8-fluoro-pyrido[4,3-d]pyrimidin-4-yl]piperazin-2-yl]acetonitrile (50 mg, 85.7 µmol, 1.0 eq), 2-fluoroprop-2-enoic acid (23.2 mg, 257 µmol, 4.48 3.0 eq) and TEA (69.4 mg, 686 µmol, 95.5 µL, 8.0 eq) in ethyl acetate (1.00 mL) was added T3P (163 mg, 257 µmol, 153 µL, 50% purity in ethyl acetate, 3.0 eq) at 0° C. The mixture was stirred at 0° C. for 30 minutes. The reaction mixture was diluted with water (20.0 mL) and extracted with ethyl acetate (3×30.0 mL). The combined organic layers were washed with brine (20.0 mL), dried over Na₂SO₄, filtered and concentrated under reduced pressure to give a residue. The residue was purified by prep-HPLC (column: Xtimate C18 150*25 mm*5 µm; mobile phase: [water (0.05% ammonia hydroxide v/v)—ACN]; B %: 27%-57%, 10 min). The desired fraction was collected and lyophilized. 2-[(2S)-4-[7-(5-chloro-4-isoquinolyl)-2-[[(2S)-4,4-difluoro-1-methyl-pyrrolidin-2-yl]methoxy]-8-fluoro-pyrido[4,3-d]pyrimidin-4-yl]-1-(2-fluoroprop-2-enoyl)piperazin-2-yl]acetonitrile (11.5 mg, 16.3 µmol, 19% yield, 92.8% purity) was obtained as a white solid. LCMS [ESI, M+1]: 655.

¹H NMR (400 MHz, chloroform-d) δ=9.40 (s, 1H), 9.11 (s, 1H), 8.60 (d, J=9.2 Hz, 1H), 8.06 (d, J=8.4 Hz, 1H), 7.79 (td, J=1.2, 6.2 Hz, 1H), 7.62 (dt, J=2.4, 7.6 Hz, 1H), 5.49 (d, J=47.6 Hz, 1H), 5.30 (dd, J=3.6, 16.8 Hz, 1H), 4.87 (br s, 1H), 4.65 (ddd, J=4.4, 7.2, 11.2 Hz, 1H), 4.60-4.40 (m, 3H), 4.38-3.93 (m, 2H), 3.82 (br s, 2H), 3.51-3.41 (m, 1H), 3.13-2.96 (m, 2H), 2.93-2.65 (m, 2H), 2.63-2.44 (m, 4H), 2.43-2.25 (m, 1H).

Example 47

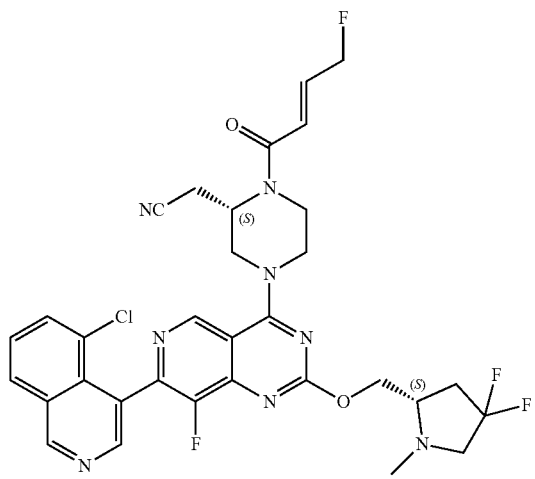

2-((S)-4-(7-(5-chloroisoquinolin-4-yl)-2-(((S)-4,4-difluoro-1-methylpyrrolidin-2-yl)methoxy)-8-fluoropyrido[4,3-d]pyrimidin-4-yl)-1-((E)-4-fluorobut-2-enoyl)piperazin-2-yl)acetonitrile

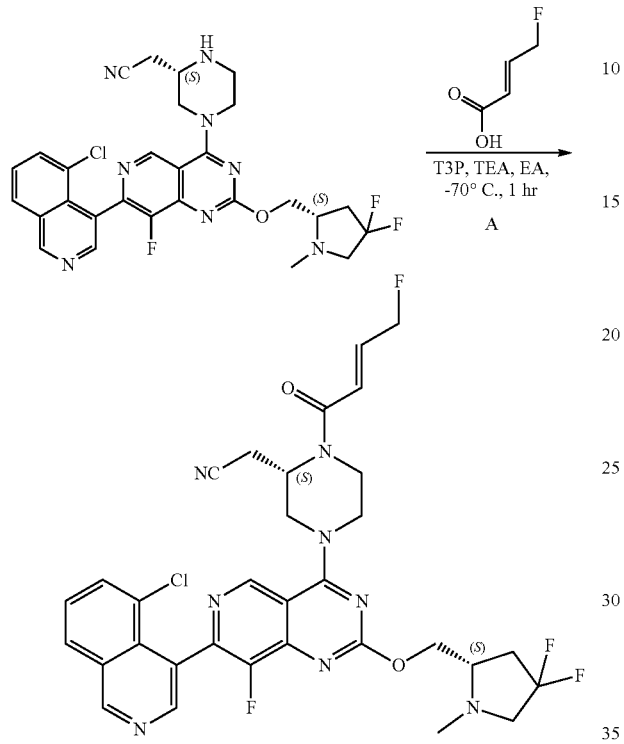

Example 47

Example 47: To a solution of 2-[(2S)-4-[7-(5-chloro-4-isoquinolyl)-2-[[(2S)-4,4-difluoro-1-methyl-pyrrolidin-2-yl]methoxy]-8-fluoro-pyrido[4,3-d]pyrimidin-4-yl]piperazin-2-yl]acetonitrile (80 mg, 137 μmol, 1.0 eq), (E)-4-fluorobut-2-enoic acid (142 mg, 1.37 mmol, 4.48 μL, 10.0 eq) and TEA (111 mg, 1.10 mmol, 152 μL, 8.0 eq) in ethyl acetate (1.0 mL) was added T3P (261 mg, 411 μmol, 244 μL, 50% purity in ethyl acetate, 3.0 eq) at −70° C. The mixture was stirred at −70° C. for 1 hour. After completion, the reaction mixture was quenched with HCl aqueous (1 M, 1.5 mL). Then the mixture was adjusted pH ~7 with saturated NaHCO₃ aqueous solution and extracted with ethyl acetate (3×20 mL). The combined organic layers were washed with saturated brine (10 mL), dried over Na₂SO₄, filtered and concentrated under reduced pressure to give the residue. The residue was purified by prep-HPLC (column: Waters Xbridge 150*50 10μ; mobile phase: [water (0.05% ammonia hydroxide v/v)—ACN]; B %: 33%-63%, 11.5 min). The desired fraction was collected and lyophilized to give the compound 2-[(2S)-4-[7-(5-chloro-4-isoquinolyl)-2-[[(2S)-4,4-difluoro-1-methyl-pyrrolidin-2-yl]methoxy]-8-fluoro-pyrido[4,3-d]pyrimidin-4-yl]-1-[(E)-4-fluorobut-2-enoyl]piperazin-2-yl]acetonitrile (26.8 mg, 40.0 μmol, 29% yield, 99.7% purity, 100% ee) as a white solid. LCMS [ESI, M+1]: 669.

¹H NMR (400 MHz, chloroform-d) δ=9.40 (s, 1H), 9.12 (s, 1H), 8.60 (d, J=12.0 Hz, 1H), 8.06 (d, J=8.4 Hz, 1H), 7.82-7.75 (m, 1H), 7.61 (dt, J=2.4, 7.6 Hz, 1H), 7.13-6.92 (m, 1H), 6.60 (br d, J=14.8 Hz, 1H), 5.30-4.88 (m, 3H), 4.74-4.60 (m, 1H), 4.59-4.40 (m, 3H), 4.34-3.57 (m, 4H), 3.44 (dt, J=5.6, 11.6 Hz, 1H), 3.12-2.89 (m, 2H), 2.88-2.63 (m, 2H), 2.61-2.45 (m, 4H), 2.43-2.24 (m, 1H).

Example 48

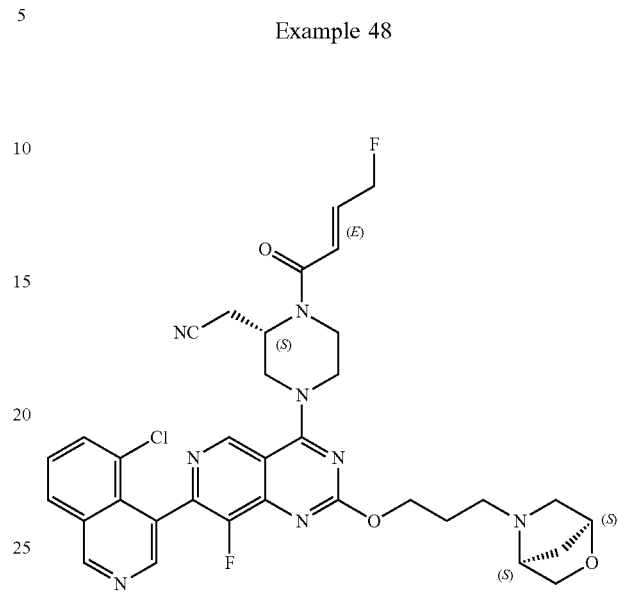

2-[(2S)-4-[7-(5-chloro-4-isoquinolyl)-8-fluoro-2-[3-[(1S,4S)-2-oxa-5-azabicyclo[2.2.1]heptan-5-yl]propoxy]pyrido[4,3-d]pyrimidin-4-yl]-1-[(E)-4-fluorobut-2-enoyl]piperazin-2-yl]acetonitrile

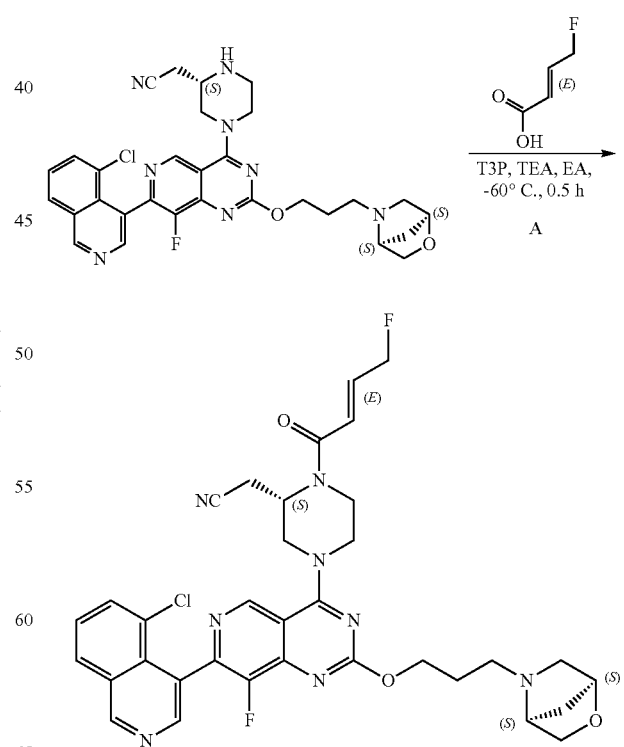

Example 48

Example 48: To a solution of 2-[(2S)-4-[7-(5-chloro-4-isoquinolyl)-8-fluoro-2-[3-[(1S,4S)-2-oxa-5-azabicyclo[2.2.1]heptan-5-yl]propoxy]pyrido[4,3-d]pyrimidin-4-yl]piperazin-2-yl]acetonitrile (30 mg, 50.9 μmol, 1.0 eq), (E)-4-fluorobut-2-enoic acid (15.9 mg, 153 μmol, 3.0 eq) in ethyl acetate (1.0 mL) was added TEA (61.8 mg, 611 μmol, 85.1 μL, 12.0 eq) and T3P (130 mg, 204 μmol, 121 μL, 50% purity in ethyl acetate, 4.0 eq) at −60° C. The mixture was stirred at −60° C. for 0.5 hour. Upon completion, the mixture was diluted with water (3 mL) and extracted with ethyl acetate (4×5 mL). The organic layers were dried over Na₂SO₄ and concentrated under vacuum. The residue was purified by chromatography (Al₂O₃, ethyl acetate to ethyl acetate/methanol 10/1) followed by prep-HPLC (column: Waters Xbridge 150*25 5μ; mobile phase: [water (0.05% ammonia hydroxide v/v)—ACN]; B %: 18%-48%, 10 min). The desired fractions were collected and lyophilized to give 2-[(2S)-4-[7-(5-chloro-4-isoquinolyl)-8-fluoro-2-[3-[(1S,4S)-2-oxa-5-azabicyclo[2.2.1]heptan-5-yl]propoxy]pyrido[4,3-d]pyrimidin-4-yl]-1-[(E)-4-fluorobut-2-enoyl]piperazin-2-yl]acetonitrile (7.31 mg, 10.6 μmol, 21% yield, 98.1% purity) as a white solid. LCMS [ESI, M+1]: 675.

Example 49

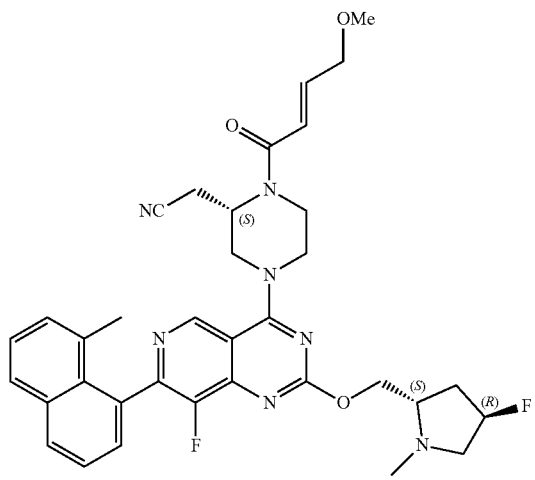

2-[(2S)-4-[8-fluoro-2-[[(2S,4R)-4-fluoro-1-methyl-pyrrolidin-2-yl]methoxy]-7-(8-methyl-1-naphthyl)pyrido[4,3-d]pyrimidin-4-yl]-1-[(E)-4-methoxybut-2-enoyl]piperazin-2-yl]acetonitrile

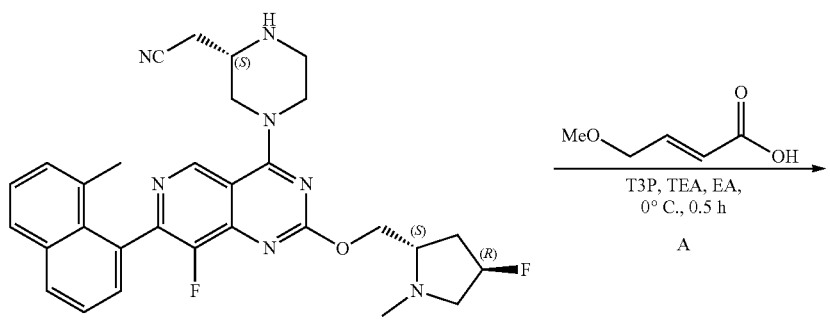

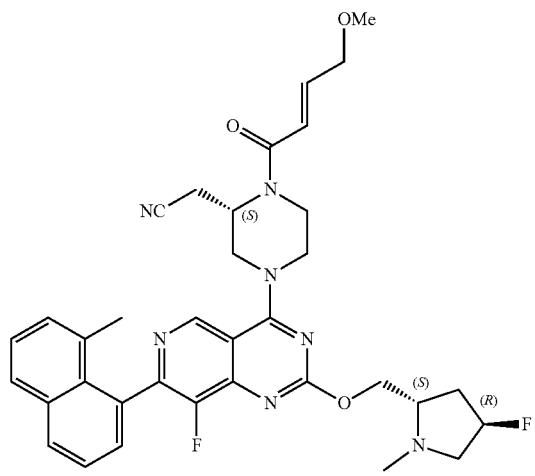

Example 49

Example 49: To a solution of 2-[(2S)-4-[8-fluoro-2-[[(2S, 4R)-4-fluoro-1-methyl-pyrrolidin-2-yl]methoxy]-7-(8-methyl-1-naphthyl)pyrido[4,3-d]pyrimidin-4-yl]piperazin-2-yl]acetonitrile (53 mg, 97.5 μmol, 1.0 eq) and (E)-4-methoxybut-2-enoic acid (33.9 mg, 292 μmol, 3.0 eq) in ethyl acetate (3 mL) was added T3P (186 mg, 292 μmol, 173 μL, 50% purity in ethyl acetate, 3.0 eq) and TEA (78.9 mg, 779 μmol, 108 μL, 8.0 eq). The mixture was stirred at 0° C. for 30 minutes. The reaction mixture was diluted with water (20 mL) and extracted with ethyl acetate (3×30 mL). The combined organic layers were washed with brine (20 mL), dried over $Na_2SO_4$, filtered and concentrated under reduced pressure to give a residue. The residue was purified by column chromatography ($Al_2O_3$, ethyl acetate/methanol=100/1 to 10/1) and then further purified by prep-HPLC (column: Xtimate C18 150*25 mm*5 um; mobile phase: [water (0.05% ammonia hydroxide v/v)—ACN]; B %: 43%-62%, 10 min). The desired fraction was collected and lyophilized overnight. 2-[(2S)-4-[8-fluoro-2-[[(2S,4R)-4-fluoro-1-methyl-pyrrolidin-2-yl]methoxy]-7-(8-methyl-1-naphthyl)pyrido[4,3-d]pyrimidin-4-yl]-1-[(E)-4-methoxy-but-2-enoyl]piperazin-2-yl]acetonitrile (8 mg, 12.3 μmol, 13% yield, 99% purity, 100% ee) was obtained as a white solid. LCMS [ESI, M+1]: 642.

$^1$H NMR (400 MHz, chloroform-d) δ=9.09 (d, J=2.2 Hz, 1H), 7.99 (d, J=8.0 Hz, 1H), 7.82 (d, J=8.0 Hz, 1H), 7.54 (dt, J=4.0, 7.6 Hz, 1H), 7.49-7.33 (m, 2H), 7.33-7.27 (m, 1H), 7.14-6.90 (m, 1H), 6.56-6.52 (m, 1H), 5.44-4.84 (m, 2H), 4.63 (td, J=5.4, 11.0 Hz, 1H), 4.57-4.36 (m, 3H), 4.36-3.66 (m, 6H), 3.65-3.50 (m, 1H), 3.48-3.34 (m, 3H), 3.10 (dd, J=5.2, 9.6 Hz, 1H), 3.04-2.88 (m, 1H), 2.88-2.71 (m, 1H), 2.71-2.57 (m, 1H), 2.57-2.40 (m, 3H), 2.40-2.21 (m, 1H), 2.16-1.91 (m, 4H).

Example 50

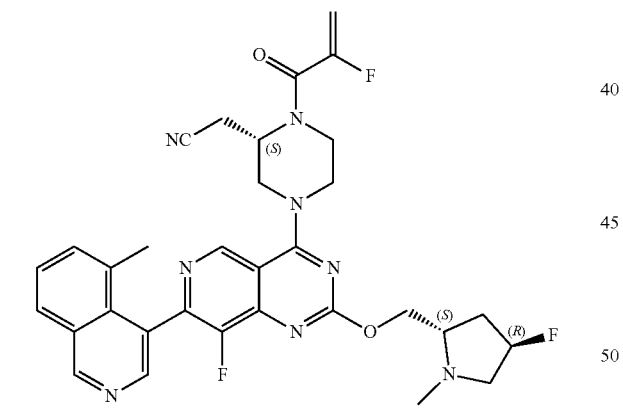

2-[(2S)-4-[8-fluoro-2-[[(2S,4R)-4-fluoro-1-methyl-pyrrolidin-2-yl]methoxy]-7-(5-methyl-4-isoquinolyl)pyrido[4,3-d]pyrimidin-4-yl]-1-(2-fluoroprop-2-enoyl)piperazin-2-yl]acetonitrile

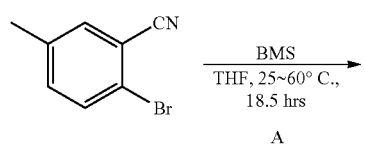

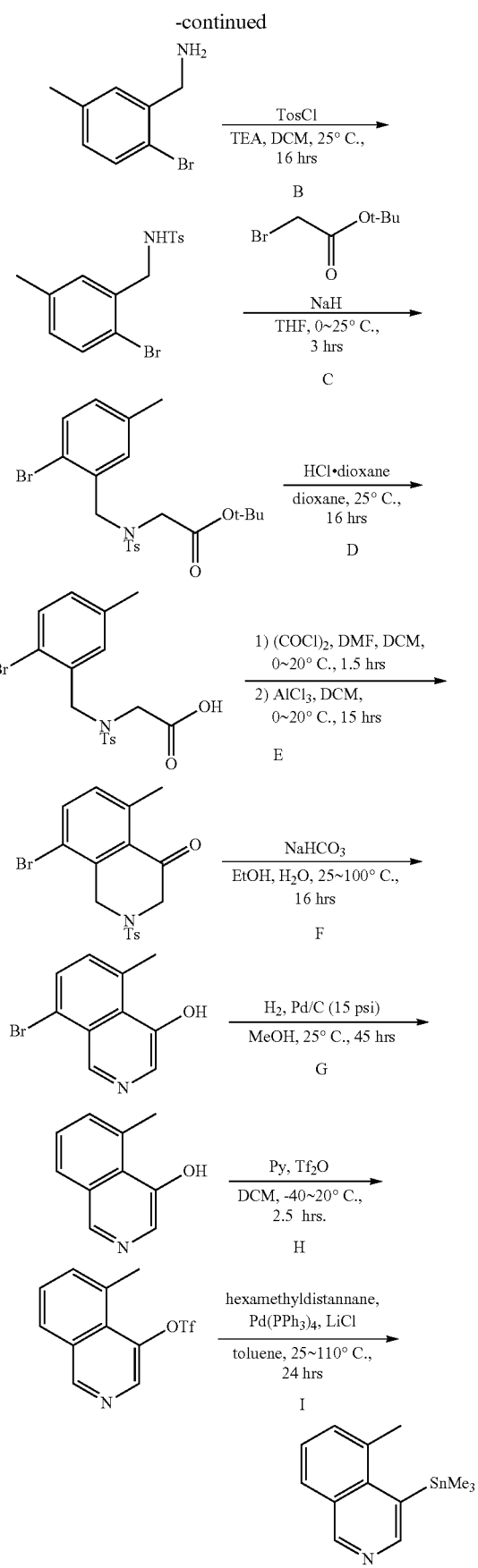

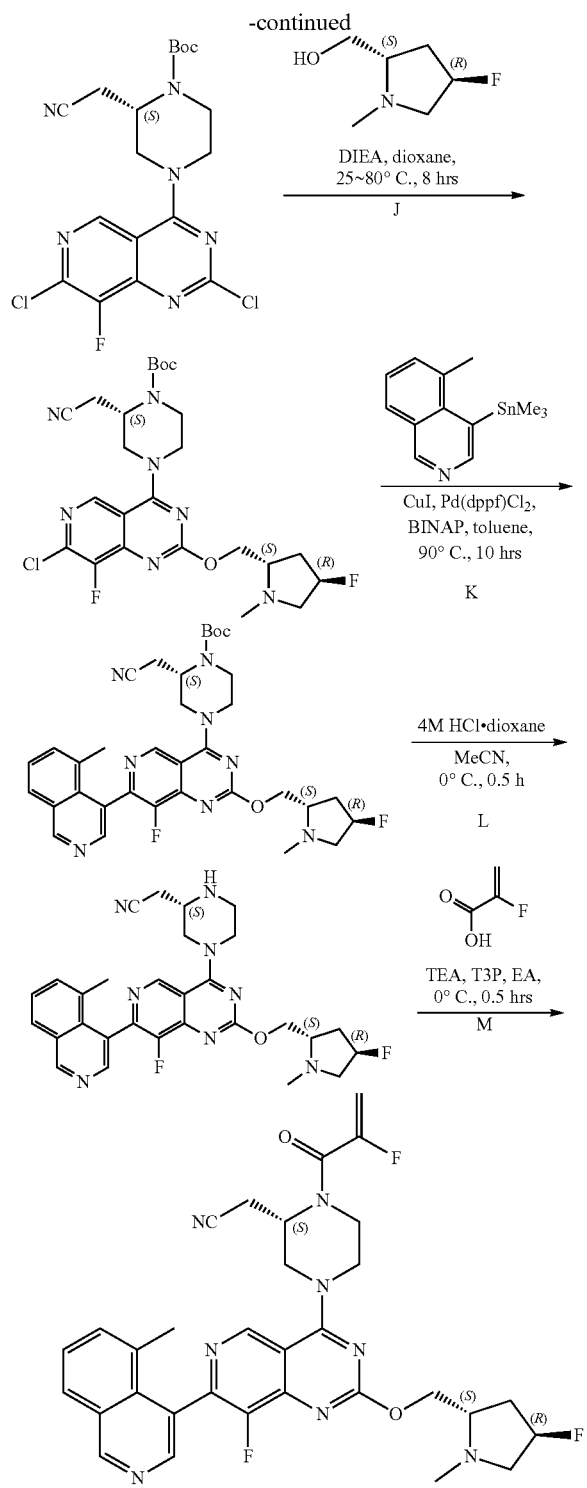

Example 50

Step A: To a solution of 2-bromo-5-methyl-benzonitrile (34.7 g, 177 mmol, 1.0 eq) in THF (250 mL) was added BMS (10 M, 70.7 mL, 4.0 eq) at 25° C. and stirred for 0.5 hour, then the reaction mixture was warmed to 60° C. and stirred for an additional 18 hours, then the mixture was cooled to 25° C. and stirred for 0.5 hour. The reaction mixture was quenched by addition methanol (400 mL) and HCl (4 M, 90 mL) at 0° C. and stirred for 0.5 hour; the mixture was warmed to 50° C. and stirred for 3 hours. After that, the reaction mixture was concentrated under reduced pressure to remove methanol. The residue was adjusted to pH about 8 using $Na_2CO_3$ solid, then the mixture was diluted with water (120 mL) and extracted with dichloromethane (40 mL×3). The combined organic layers were washed with brine (40 mL×3), dried over anhydrous $Na_2SO_4$, filtered and the filtrated was concentrated under reduced pressure to give (2-bromo-5-methyl-phenyl)methanamine (36 g, crude) as a white solid which was used in the next step without further purification.

Step B: To a solution of (2-bromo-5-methyl-phenyl)methanamine (36 g, 180 mmol, 1.0 eq) in dichloromethane (150 mL) was added TosCl (41.2 g, 216 mmol, 1.2 eq) and TEA (27.3 g, 270 mmol, 37.6 mL, 1.5 eq) at 25° C., the mixture was stirred at 25° C. for 16 hours. After completion, the reaction mixture was concentrated under reduced pressure to give a residue. The residue was added to a saturated $NH_4Cl$ aqueous solution (120 mL), then extracted with ethyl acetate (30 mL×3). The combined organic layers were washed with brine (40 mL×3), dried over $Na_2SO_4$, filtered and the filtrate was concentrated under reduced pressure to give a residue. The residue was purified by column chromatography ($SiO_2$, Petroleum ether/Ethyl acetate=1:0 to 5:1) to give N-[(2-bromo-5-methyl-phenyl)methyl]-4-methyl-benzene sulfonamide (33.0 g, 86.8 mmol, 48.2% yield, 93.2% purity) as a white solid. LCMS [ESI, M+1]: 354, 356.

$^1$HNMR (400 MHz, chloroform-d) δ=7.71 (d, J=8.0 Hz, 2H), 7.32 (d, J=8.0 Hz, 1H), 7.25 (d, J=8.0 Hz, 2H), 7.04 (d, J=1.6 Hz, 1H), 6.91 (dd, J=1.6, 8.0 Hz, 1H), 4.91 (br t, J=6.4 Hz, 1H), 4.20 (d, J=6.4 Hz, 2H), 2.41 (s, 3H), 2.22 (s, 3H).

Step C: To a solution of N-[(2-bromo-5-methyl-phenyl)methyl]-4-methyl-benzenesulfonamide (33.0 g, 93.1 mmol, 1.0 eq) in THF (150 mL) was added NaH (4.47 g, 112 mmol, 60% purity, 1.2 eq) at 0° C. with $N_2$. After addition, the mixture was stirred at 0° C. for 0.5 hour, and then tert-butyl 2-bromoacetate (21.8 g, 112 mmol, 16.5 mL, 1.2 eq) was added at 0° C. The resulting mixture was stirred at 25° C. for 2.5 hours. The reaction mixture was quenched by addition saturated $NH_4Cl$ aqueous solution (60 mL) at 25° C., and extracted with ethyl acetate (40 mL×3). The combined organic layers were washed with brine (30 mL), dried over anhydrous $Na_2SO_4$, filtered and the filtrate was concentrated under reduced pressure to give a residue. The residue was purified by triturated with petroleum ether (60 mL) to give tert-butyl 2-[(2-bromo-5-methyl-phenyl)methyl-(p-tolylsulfonyl)amino]acetate (37.7 g, 78.7 mmol, 84.6% yield, 99.7% purity) as a white solid. LCMS [ESI, M+23]: 490, 492.

$^1$HNMR (400 MHz, chloroform-d) δ=7.77 (d, J=8.4 Hz, 2H), 7.38 (d, J=8.0 Hz, 1H), 7.32 (d, J=8.0 Hz, 2H), 7.26 (d, J=1.6 Hz, 1H), 6.96 (dd, J=1.6, 8.0 Hz, 1H), 4.63 (s, 2H), 3.89 (s, 2H), 2.44 (s, 3H), 2.28 (s, 3H), 1.34 (s, 9H).

Step D: To a solution of tert-butyl 2-[(2-bromo-5-methyl-phenyl) methyl-(p-tolylsulfonyl)amino]acetate (37.7 g, 80.5 mmol, 1.0 eq) in dioxane (100 mL) was added HCl•dioxane (4 M, 200 mL, 9.9 eq) at 25° C. and the mixture was stirred at 25° C. for 16 hours. The reaction mixture was concentrated under reduced pressure to give 2-[(2-bromo-5-methyl-phenyl)methyl-(p-tolylsulfonyl)amino]acetic acid (35 g, crude) as a yellow solid which was used in the next step without further purification. LCMS [ESI, M+1]: 412, 414.

$^1$HNMR (400 MHz, chloroform-d) δ=7.75 (d, J=8.4 Hz, 2H), 7.38 (d, J=8.0 Hz, 1H), 7.31 (d, J=8.0 Hz, 2H), 7.17 (s, 1H), 6.96 (dd, J=1.6, 8.0 Hz, 1H), 4.58 (s, 2H), 4.01 (s, 2H), 2.44 (s, 3H), 2.26 (s, 3H).

Step E: To a solution of 2-[(2-bromo-5-methyl-phenyl)methyl-(p-tolylsulfonyl)amino]acetic acid (35 g, 84.9 mmol, 1.0 eq) in dichloromethane (90.0 mL) was added (COCl)$_2$ (16.2 g, 127 mmol, 11.1 mL, 1.5 eq) and DMF (620 mg, 8.49 mmol, 653 μL, 0.1 eq) at 0° C. The mixture was stirred at 20° C. for 1.5 hours. Then the mixture was concentrated under reduced pressure at 40° C. The residue was dissolved in dichloromethane (120 mL), then AlCl$_3$ (45.3 g, 340 mmol, 18.6 mL, 4.0 eq) was added thereto at 0° C. The mixture stirred at 20° C. for 15 hours under N$_2$. The reaction mixture was quenched by addition H$_2$O (300 mL) at 0° C., and then concentrated under reduced pressure at 40° C., the mixture was diluted extracted with ethyl acetate (300 mL×2). The combined organic layers were washed with brine (180 mL), dried over anhydrous Na$_2$SO$_4$, filtered and the filtrate was concentrated under reduced pressure to give 8-bromo-5-methyl-2-(p-tolylsulfonyl)-1,3-dihydroiso quinolin-4-one (26.8 g, 59.5 mmol, 70.1% yield, 87.6% purity) as a yellow solid which was used in the next step without further purification. LCMS [ESI, M+1]: 394, 396.

$^1$HNMR (400 MHz, chloroform-d) δ=7.58 (dd, J=8.0, 13.2 Hz, 3H), 7.19 (d, J=8.0 Hz, 2H), 6.97 (d, J=8.0 Hz, 1H), 4.61 (s, 2H), 4.05 (s, 2H), 2.44 (s, 3H), 2.36 (s, 3H).

Step F: To a solution of 8-bromo-5-methyl-2-(p-tolylsulfonyl)-1,3-dihydroisoquinolin-4-one (26.8 g, 59.5 mmol, 1.0 eq) in ethanol (180 mL) was added saturated NaHCO$_3$ aqueous solution (100 mL) at 25° C. The mixture was stirred at 100° C. for 16 hours. The reaction mixture was concentrated under reduced pressure to give a residue. The residue was diluted with H$_2$O (120 mL) and extracted with ethyl acetate (30 mL×4). The combined organic layers were washed with brine (40 mL×3), dried over anhydrous Na$_2$SO$_4$, filtered and the filtrate was concentrated under reduced pressure to give a residue. The residue was purified by triturated with ethyl acetate (30 mL) to give 12.1 gram of 8-bromo-5-methyl-isoquinolin-4-ol as a yellow solid and the mother liquid was purified by column chromatography (SiO$_2$, Petroleum ether/Ethanol/Ethyl acetate=5/0/1 to 4/1/3) give 4.5 gram of 8-bromo-5-methyl-isoquinolin-4-ol as a yellow solid.

$^1$HNMR (400 MHz, DMSO-d$_6$) δ=8.83 (s, 1H), 8.11 (s, 1H), 7.75 (d, J=7.6 Hz, 1H), 7.26 (d, J=7.6 Hz, 1H), 2.85 (s, 3H).

Step G: To a solution of 8-bromo-5-methyl-isoquinolin-4-ol (16.6 g, 69.7 mmol, 1.0 eq) in methanol (300 mL) was added Pd/C (1.0 g, 10% purity) under N$_2$. The suspension was degassed under vacuum and purged with H$_2$ several times. The mixture was stirred under H$_2$ (15 psi) at 25° C. for 45 hours. The mixture was filtered and the filtrate was concentrated in vacuum to give 5-methylisoquinolin-4-ol (15.6 g, crude, HBr) as a yellow solid. LCMS [ESI, M+1]: 160.

$^1$HNMR (400 MHz, DMSO-d$_6$) δ=9.24 (s, 1H), 8.21 (dd, J=2.4, 7.2 Hz, 1H), 8.00 (s, 1H), 7.84-7.77 (m, 2H), 2.92 (s, 3H).

Step H: To a mixture of 5-methylisoquinolin-4-ol (13.6 g, crude, HBr) in ethyl acetate (180 mL) and H$_2$O (180 mL) was added Na$_2$CO$_3$ solid to adjust pH about 7~8. The organic phase was separated, washed with brine (40 mL×3), dried over Na$_2$SO$_4$, filtered and the filtrate was concentrated under reduced pressure to give 5-methylisoquinolin-4-ol (9.67 g, crude, 94.5% purity) as a white solid. To a solution of 5-methylisoquinolin-4-ol (7.17 g, 45.0 mmol, 1.0 eq) in dichloromethane (20.0 mL) was added pyridine (17.8 g, 225 mmol, 18.2 mL, 5.0 eq) and Tf$_2$O (25.4 g, 90.1 mmol, 14.9 mL, 2.0 eq) at −40° C. The mixture was stirred at −40° C. for 1.5 hours under N$_2$, the mixture was warmed to 20° C. and stirred at 20° C. for 1 hour under N$_2$. The mixture was concentrated under reduced pressure at 40° C. to give a residue. The residue was purified by column chromatography (SiO$_2$, Petroleum ether/Ethyl acetate=1:0 to 50:1) to give (5-methyl-4-isoquinolyl) trifluoromethanesulfonate (6.86 g, 23.3 mmol, 51.7% yield, 98.9% purity) as a yellow solid. LCMS [ESI, M+1]: 292.

$^1$HNMR (400 MHz, chloroform-d) δ=9.22 (s, 1H), 8.56 (s, 1H), 7.97-7.89 (m, 1H), 7.72-7.54 (m, 2H), 2.92 (s, 3H).

Step I: To a solution of (5-methyl-4-isoquinolyl) trifluoromethane sulfonate (3.6 g, 12.4 mmol, 1.0 eq) in toluene (140 mL) was added trimethyl (trimethylstannyl)stannane (12.1 g, 37.1 mmol, 7.7 mL, 3.0 eq) and Pd(PPh$_3$)$_4$ (714 mg, 618 μmol, 0.05 eq) and LiCl (3.14 g, 74.2 mmol, 1.52 mL, 6.0 eq) under N$_2$ atmosphere at 25° C. The suspension was degassed and purged with N$_2$ for 3 times. The mixture was stirred at 110° C. for 24 hours. The mixture was diluted with water (200 mL), and then filtered, the filtrate was extracted with ethyl acetate (150 mL×2), the combined organic layers were dried over anhydrous Na$_2$SO$_4$, filtered and the filtrate was concentrated under reduced pressure at 45° C. The residue was purified by column chromatography (SiO$_2$, Petroleum ether/Ethyl acetate=100:1 to 40:1) to give trimethyl-(5-methyl-4-isoquinolyl)stannane (1.2 g, 3.92 mmol, 31.7% yield, 100% purity) as a yellow oil. LCMS [ESI, M+1]: 308.

$^1$HNMR (400 MHz, chloroform-d) δ=9.16 (s, 1H), 8.61 (s, 1H), 7.82 (br d, J=7.8 Hz, 1H), 7.59-7.54 (m, 1H), 7.53-7.45 (m, 1H), 2.81 (s, 3H), 0.56-0.41 (m, 9H).

Step J: To a mixture of tert-butyl (2S)-2-(cyanomethyl)-4-(2,7-dichloro-8-fluoro-pyrido[4,3-d]pyrimidin-4-yl)piperazine-1-carboxylate (1.5 g, 3.4 mmol, 1.0 eq) in dioxane (15.0 mL) was added DIEA (1.32 g, 10.2 mmol, 1.8 mL, 3.0 eq) and [(2S,4R)-4-fluoro-1-methyl-pyrrolidin-2-yl]methanol (905 mg, 6.8 mmol, 2.0 eq) at 25° C. The mixture was stirred at 80° C. for 8 hours. The mixture was concentrated under reduced pressure at 40° C. The crude product was purified by reversed-phase HPLC (0.1% formic acid condition) to give tert-butyl (2S)-4-[7-chloro-8-fluoro-2-[[(2S,4R)-4-fluoro-1-methyl-pyrrolidin-2-yl]methoxy]pyrido[4,3-d]pyrimidin-4-yl]-2-(cyanomethyl)piperazine-1-carboxylate (820 mg, 1.51 mmol, 44.5% yield, 99.2% purity) as a yellow solid. LCMS [ESI, M+1]: 538.

$^1$HNMR (400 MHz, chloroform-d) δ=8.82 (s, 1H), 5.33-5.06 (m, 1H), 4.59 (br dd, J=4.4, 11.2 Hz, 2H), 4.52-4.46 (m, 1H), 4.42 (br dd, J=3.6, 14.0 Hz, 1H), 4.31 (br d, J=12.4 Hz, 1H), 4.14-4.01 (m, 1H), 3.97-3.86 (m, 1H), 3.76-3.65 (m, 1H), 3.63-3.42 (m, 2H), 3.08 (qd, J=5.2, 10.4 Hz, 1H), 2.91-2.78 (m, 1H), 2.75-2.57 (m, 2H), 2.54 (s, 3H), 2.39-2.23 (m, 1H), 2.13-1.97 (m, 1H), 1.52 (s, 9H).

Step K: To a mixture solution of tert-butyl (2S)-4-[7-chloro-8-fluoro-2-[[(2S,4R)-4-fluoro-1-methyl-pyrrolidin-2-yl]methoxy]pyrido[4,3-d]pyrimidin-4-yl]-2-(cyanomethyl)piperazine-1-carboxylate (350 mg, 651 μmol, 1.0 eq) and trimethyl-(5-methyl-4-isoquinolyl)stannane (398 mg, 1.3 mmol, 2.0 eq) in toluene (20.0 mL) was added CuI (37.2 mg, 195 μmol, 0.3 eq), Pd(dppf)Cl$_2$ (47.6 mg, 65.1 μmol, 0.1 eq), and BINAP (81.0 mg, 130 μmol, 0.2 eq), the reaction mixture was stirred at 90° C. for 10 hours. The mixture was quenched by water (100 mL), and then the mixture was extracted with ethyl acetate (100 mL×3), the combined organic layers were concentrated under reduced pressure 40° C. The residue was purified by column chromatography (SiO$_2$, Petroleum ether/Ethyl acetate=3:1 to Petroleum ether/Ethyl acetate/EtOH=4:3:1 added 2% NH$_3$.H$_2$O), then the desired fraction was collected and concentrated under reduced pressure at 40° C. The obtained product was further purified by reversed-phase HPLC (0.1% formic acid condition). The desired fractions were collected and concentrated to remove acetonitrile and then adjusted to pH about 9~10 using Na₂CO₃ solid. Then the mixture was extracted with ethyl acetate (100 mL×3), the organic layers were dried over anhydrous Na₂SO₄, filtered and the filtrate was concentrated under reduced pressure at 45° C. to give tert-butyl (2S)-2-(cyano methyl)-4-[8-fluoro-2-[[(2S,4R)-4-fluoro-1-methyl-pyrrolidin-2-yl]methoxy]-7-(5-methyl-4-isoquinolyl)pyrido[4,3-d]pyrimidin-4-yl]piperazine-1-carboxylate (318 mg, 494 μmol, 75.9% yield, 100% purity) as a yellow solid. LCMS [ESI, M+1]: 645.

¹HNMR (400 MHz, chloroform-d) δ=9.34 (s, 1H), 9.12 (s, 1H), 8.47 (d, J=9.2 Hz, 1H), 7.96 (d, J=8.4 Hz, 1H), 7.61-7.49 (m, 2H), 5.37-5.05 (m, 1H), 4.73-4.36 (m, 6H), 4.02-3.90 (m, 1H), 3.79-3.71 (m, 1H), 3.65-3.48 (m, 2H), 3.21-3.07 (m, 1H), 2.95-2.57 (m, 4H), 2.55 (s, 3H), 2.39-2.27 (m, 1H), 2.10 (br d, J=5.6 Hz, 3H), 1.53 (s, 9H).

Step L: To a solution of tert-butyl (2S)-2-(cyanomethyl)-4-[8-fluoro-2-[[(2S,4R)-4-fluoro-1-methyl-pyrrolidin-2-yl]methoxy]-7-(5-methyl-4-isoquinolyl)pyrido[4,3-d]pyrimidin-4-yl]piperazine-1-carboxylate (50 mg, 77.5 μmol, 1.0 eq) in acetonitrile (1.0 mL) was added HCl•dioxane (4 M, 1 mL, 51.6 eq) at 0° C. The mixture was stirred at 0° C. for 0.5 hour. The mixture was concentrated under reduced pressure at 40° C. to give was residue, after that, 20 mL of water was added thereto, the mixture was adjusted to pH about 10 using Na₂CO₃ solid, then the mixture was extracted with ethyl acetate (15 mL×3), the combined organic layers were dried over anhydrous Na₂SO₄, filtered and the filtrate was concentrated under reduced pressure at 40° C. The residue was purified by prep-HPLC (formic acid condition; column: Xtimate C18 150*25 mm*5 μm; mobile phase: [water (0.05% ammonia hydroxide v/v)—ACN]; B %: 22%-52%, 10 min) and lyophilized to give 2-[(2S)-4-[8-fluoro-2-[[(2S,4R)-4-fluoro-1-methyl-pyrrolidin-2-yl]methoxy]-7-(5-methyl-4-isoquinolyl)pyrido[4,3-d]pyrimidin-4-yl]piperazin-2-yl]acetonitrile (14 mg, 25.0 μmol, 32.3% yield, 97.4% purity) as a white solid. LCMS [ESI, M+1]: 545.6.

¹HNMR (400 MHz, chloroform-d) δ=9.34 (s, 1H), 9.06 (s, 1H), 8.46 (s, 1H), 7.96 (d, J=7.6 Hz, 1H), 7.64-7.47 (m, 2H), 5.34-5.03 (m, 1H), 4.69-4.37 (m, 4H), 3.68-3.49 (m, 2H), 3.42-3.31 (m, 1H), 3.30-3.04 (m, 4H), 2.72-2.56 (m, 3H), 2.54 (s, 3H), 2.45-2.23 (m, 1H), 2.13-1.95 (m, 5H).

Example 50: A mixture of 2-[(2S)-4-[8-fluoro-2-[[(2S,4R)-4-fluoro-1-methyl-pyrrolidin-2-yl]methoxy]-7-(5-methyl-4-isoquinolyl)pyrido[4,3-d]pyrimidin-4-yl]piperazin-2-yl]acetonitrile (100 mg, 184 μmol, 1.0 eq), molecular sieve 4A (200 mg) and 2-fluoroprop-2-enoic acid (49.6 mg, 551 μmol, 3.0 eq) in ethyl acetate (10.0 mL) was stirred at 0° C. for 10 min, then T3P (467 mg, 734 μmol, 437 μL, 50% purity, 4.0 eq) and TEA (74.3 mg, 734 μmol, 102 μL, 4.0 eq) were added thereto at 0° C. The mixture was stirred for 20 min. After completion, the mixture was quenched by saturated NH₄Cl aqueous solution (80 mL), and then extracted with ethyl acetate (50 mL×3), the combined organic layers were dried over anhydrous Na₂SO₄, filtered and the filtrate was concentrated under reduced pressure at 40° C. The residue was purified by prep-HPLC (formic acid condition; column: Xtimate C18 150*25 mm*5 μm; mobile phase: [water (0.05% ammonia hydroxide v/v)—ACN]; B %: 31%-61%, 10 min) and lyophilized to give 2-[(2S)-4-[8-fluoro-2-[[(2S,4R)-4-fluoro-1-methyl-pyrrolidin-2-yl]methoxy]-7-(5-methyl-4-isoquinolyl)pyrido[4,3-d]pyrimidin-4-yl]-1-(2-fluoroprop-2-enoyl)piperazin-2-yl]acetonitrile (42.0 mg, 67.8 μmol, 36.9% yield, 99.5% purity) as a white solid. LCMS [ESI, M+1]: 617.6.

¹HNMR (400 MHz, chloroform-d) δ=9.34 (s, 1H), 9.12 (s, 1H), 8.47 (d, J=7.6 Hz, 1H), 7.96 (br d, J=7.6 Hz, 1H), 7.63-7.47 (m, 2H), 5.62-5.41 (m, 1H), 5.35-5.10 (m, 2H), 4.98-4.74 (m, 1H), 4.69-4.59 (m, 1H), 4.57-4.40 (m, 3H), 4.36-3.95 (m, 2H), 3.94-3.67 (m, 2H), 3.65-3.50 (m, 1H), 3.17-2.96 (m, 2H), 2.91-2.78 (m, 1H), 2.71-2.57 (m, 1H), 2.55 (s, 3H), 2.40-2.25 (m, 1H), 2.09 (br d, J=5.2 Hz, 3H), 2.08-1.94 (m, 1H).

Example 51

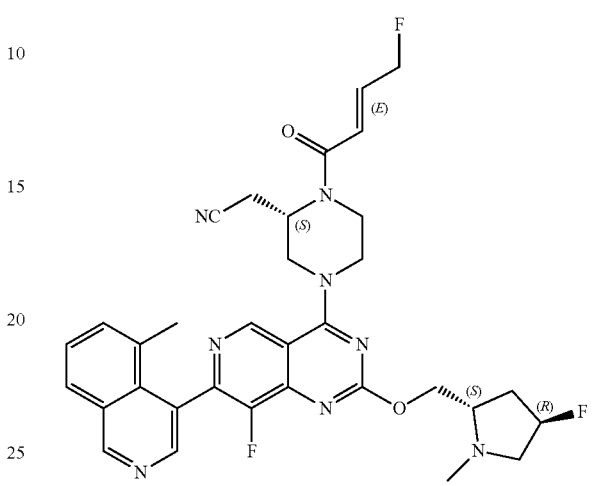

2-[(2S)-1-[(E)-4-fluorobut-2-enoyl]-4-[8-fluoro-2-[[(2S,4R)-4-fluoro-1-methyl-pyrrolidin-2-yl]methoxy]-7-(5-methyl-4-isoquinolyl)pyrido[4,3-d]pyrimidin-4-yl]piperazin-2-yl]acetonitrile

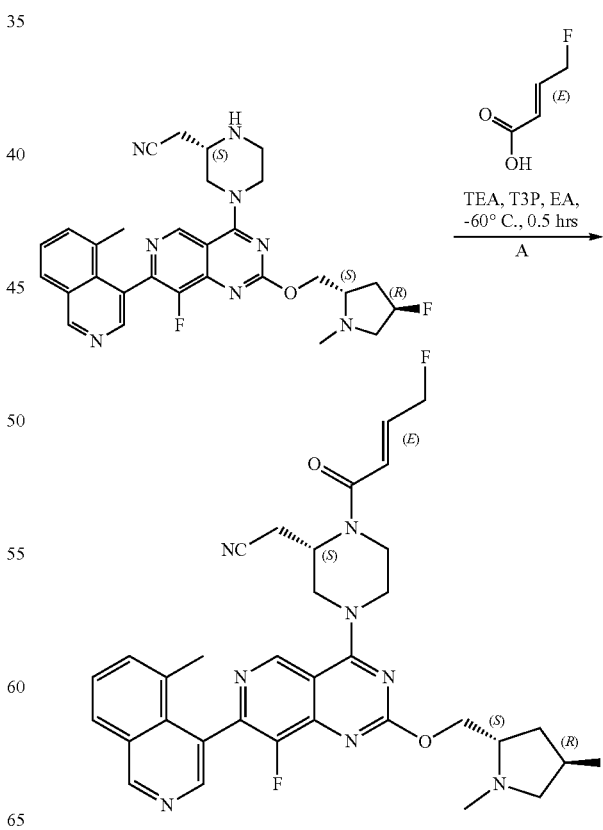

Example 51

Example 51: A mixture of 2-[(2S)-4-[8-fluoro-2-[[(2S,4R)-4-fluoro-1-methyl-pyrrolidin-2-yl]methoxy]-7-(5-methyl-4-isoquinolyl)pyrido[4,3-d]pyrimidin-4-yl]piperazin-2-yl]acetonitrile (90 mg, 165 μmol, 1.0 eq), molecular sieve 4A (200 mg) and (E)-4-fluorobut-2-enoic acid (51.6 mg, 496 μmol, 3.0 eq) in ethyl acetate (10.0 mL) was stirred at −60° C. for 10 min, then T3P (421 mg, 661 μmol, 393 μL, 50% purity, 4.0 eq) and TEA (66.9 mg, 661 μmol, 92.0 μL, 4.0 eq) was added thereto at −60° C. The mixture was stirred at −60° C. for 20 min. After completion, the mixture was quenched by saturated NH₄Cl aqueous solution (90 mL), and then extracted with ethyl acetate (60 mL×3), the combined organic layers were dried over anhydrous Na₂SO₄, filtered and the filtrate was concentrated under reduced pressure at 40° C. The residue was purified by prep-HPLC (formic acid condition; column: Xtimate C18 150*25 mm*5 μm; mobile phase: [water (0.05% ammonia hydroxide v/v)—ACN]; B %: 32%-62%, 10 min) and lyophilized to give 2-[(2S)-1-[(E)-4-fluorobut-2-enoyl]-4-[8-fluoro-2-[[(2S,4R)-4-fluoro-1-methyl-pyrrolidin-2-yl]methoxy]-7-(5-methyl-4-isoquinolyl)pyrido[4,3-d]pyrimidin-4-yl]piperazin-2-yl]acetonitrile (19 mg, 30.0 μmol, 17.5% yield, 95.9% purity) as a white solid. LCMS [ESI, M+1]: 631.

¹H NMR (400 MHz, chloroform-d) δ=9.34 (s, 1H), 9.13 (s, 1H), 8.47 (d, J=10.8 Hz, 1H), 7.97 (d, J=7.6 Hz, 1H), 7.67-7.45 (m, 2H), 7.14-6.96 (m, 1H), 6.60 (br d, J=15.2 Hz, 1H), 5.34-4.94 (m, 4H), 4.73-4.39 (m, 4H), 4.37-3.61 (m, 4H), 3.60-3.35 (m, 1H), 3.17-2.90 (m, 2H), 2.90-2.74 (m, 1H), 2.73-2.43 (m, 4H), 2.41-2.26 (m, 1H), 2.17-1.93 (m, 4H).

Example 52

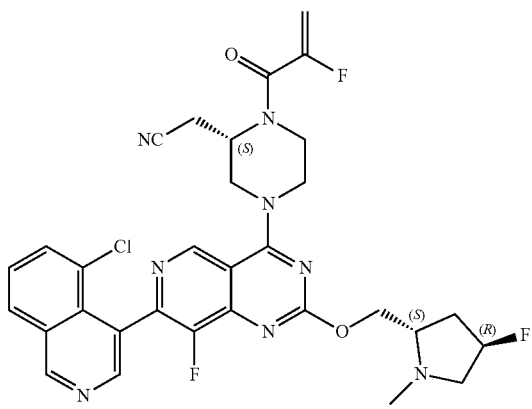

2-[(2S)-4-[7-(5-chloro-4-isoquinolyl)-8-fluoro-2-[[(2S,4R)-4-fluoro-1-methyl-pyrrolidin-2-yl]methoxy]pyrido[4,3-d]pyrimidin-4-yl]-1-(2-fluoroprop-2-enoyl)piperazin-2-yl]acetonitrile

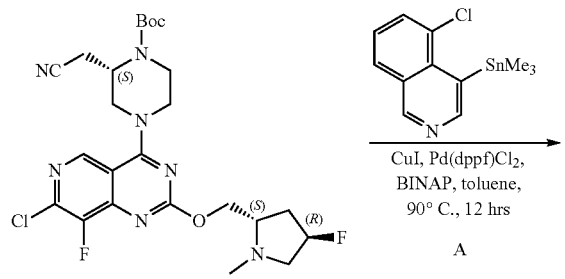

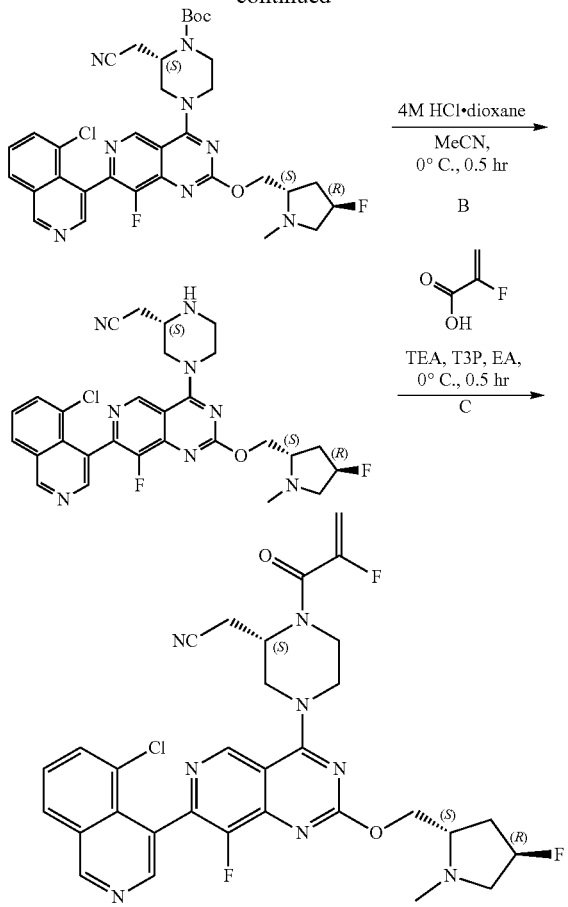

Example 52

Step A: To a mixture solution of tert-butyl (2S)-4-[7-chloro-8-fluoro-2-[[(2S,4R)-4-fluoro-1-methyl-pyrrolidin-2-yl]methoxy]pyrido[4,3-d]pyrimidin-4-yl]-2-(cyanomethyl)piperazine-1-carboxylate (370 mg, 688 μmol, 1.0 eq) and (5-chloro-4-isoquinolyl)-trimethyl-stannane (449 mg, 1.38 mmol, 2.0 eq) in toluene (20.0 mL) was added CuI (39.3 mg, 206 μmol, 0.3 eq), Pd(dppf)Cl₂ (50.3 mg, 68.8 μmol, 0.1 eq), and BINAP (85.6 mg, 137 μmol, 0.2 eq), the reaction mixture was stirred at 90° C. for 6 hours, then 5-chloro-4-isoquinolyl)-trimethyl-stannane (150 mg) was added, the reaction mixture was stirred at 90° C. for 6 hours. The mixture was quenched by water (100 mL), and then the mixture was extracted with ethyl acetate (100 mL×3), the combined organic layers were concentrated under reduced pressure at 40° C. The residue was purified by column chromatography (SiO₂, Petroleum ether/Ethyl acetate=3:1 to Petroleum ether/Ethyl acetate/Ethanol=4:3:1 added 2% NH₃₄₁₂ₒ), the desired fraction was collected and concentrated under reduced pressure at 40° C. The obtained product was further purified by reversed-phase HPLC (0.1% formic acid condition). The desired fractions were collected and concentrated to remove acetonitrile and then adjusted to pH about 9~10 using Na₂CO₃ solid. Then the mixture was extracted with ethyl acetate (100 mL×3), the organic layers were dried over anhydrous Na₂SO₄, filtered and the filtrate was concentrated under reduced pressure at 45° C. to give tert-butyl (2S)-4-[7-(5-chloro-4-isoquinolyl)-8-fluoro-2-[[(2S,4R)-4-fluoro-1-methyl-pyrrolidin-2-yl]methoxy]pyrido[4,3-d]pyrimidin-4-yl]-2-(cyanomethyl)piperazine-1- carboxylate (190 mg, 271 μmol, 39.5% yield, 95% purity) as a yellow solid. LCMS [ESI, M+1]: 665.

Step B: To a solution of tert-butyl (2S)-4-[7-(5-chloro-4-isoquinolyl)-8-fluoro-2-[[(2S,4R)-4-fluoro-1-methyl-pyrrolidin-2-yl]methoxy]pyrido[4,3-d]pyrimidin-4-yl]-2-(cyanomethyl)piperazine-1-carboxylate (40.0 mg, 60.1 μmol, 1.0 eq) in acetonitrile (1.0 mL) was added HCl·dioxane (4 M, 1.0 mL, 66.5 eq) at 0° C. The mixture was stirred at 0° C. for 0.5 hour. The mixture was concentrated under reduced pressure at 40° C. to give was residue, after that, 30 mL of water was added thereto, the mixture was adjusted to pH about 10 using Na₂CO₃ solid. Then the mixture was extracted with ethyl acetate (20 mL×3), the combined organic layers were dried over anhydrous Na₂SO₄, filtered and the filtrate was concentrated under reduced pressure at 40° C. The residue was purified by prep-HPLC (FA condition; column: Xtimate C18 150*25 mm*5 μm; mobile phase: [water (0.05% ammonia hydroxide v/v)—ACN]; B %: 22%-52%, 10 min) and lyophilized to give 2-[(2S)-4-[7-(5-chloro-4-iso quinolyl)-8-fluoro-2-[[(2S,4R)-4-fluoro-1-methyl-pyrrolidin-2-yl]methoxy]pyrido[4,3-d]pyrimidin-4-yl]piperazin-2-yl]acetonitrile (13.0 mg, 22.2 μmol, 36.9% yield, 96.4% purity) as a white solid. LCMS [ESI, M+1]: 565.

¹HNMR (400 MHz, chloroform-d) δ=9.39 (s, 1H), 9.05 (s, 1H), 8.59 (s, 1H), 8.05 (d, J=8.0 Hz, 1H), 7.78 (dd, J=0.8, 7.6 Hz, 1H), 7.61 (t, J=7.6 Hz, 1H), 5.34-5.08 (m, 1H), 4.71-4.35 (m, 4H), 3.72-3.48 (m, 2H), 3.42-3.31 (m, 1H), 3.30-3.19 (m, 2H), 3.18-3.02 (m, 2H), 2.70-2.56 (m, 3H), 2.54 (s, 3H), 2.40-2.26 (m, 1H), 2.14-1.95 (m, 2H).

Example 52: A mixture of 2-[(2S)-4-[7-(5-chloro-4-isoquinolyl)-8-fluoro-2-[[(2S,4R)-4-fluoro-1-methyl-pyrrolidin-2-yl]methoxy]pyrido[4,3-d]pyrimidin-4-yl]piperazin-2-yl]acetonitrile (60.0 mg, 106 μmol, 1.0 eq), molecular sieve 4A (100 mg) and 2-fluoroprop-2-enoic acid (28.7 mg, 319 μmol, 3.0 eq) in ethyl acetate (6.0 mL) was stirred at 0° C. for 10 min, then T3P (270 mg, 425 μmol, 252.6 μL, 50% purity, 4.0 eq) and TEA (43.0 mg, 425 μmol, 59.1 μL, 4.0 eq) was added thereto at 0° C. The mixture was stirred at 0° C. for 20 min. After completion, the mixture was quenched by saturated NH₄Cl aqueous solution (80 mL), and then extracted with ethyl acetate (50 mL×3), the combined organic layers were dried over anhydrous Na₂SO₄, filtered and the filtrate was concentrated under reduced pressure at 40° C. The residue was purified by prep-HPLC (formic acid condition; column: Waters Xbridge 150*50 10u; mobile phase: [water (0.05% ammonia hydroxide v/v)—ACN]; B %: 25%-55%, 11.5 min) to give 2-[(2S)-4-[7-(5-chloro-4-isoquinolyl)-8-fluoro-2-[[(2S,4R)-4-fluoro-1-methyl-pyrrolidin-2-yl]methoxy]pyrido[4,3-d]pyrimidin-4-yl]-1-(2-fluoroprop-2-enoyl)piperazin-2-yl]acetonitrile (16.0 mg, 24.5 μmol, 23.1% yield, 97.6% purity) as a white solid. LCMS [ESI, M+1]: 637.

¹HNMR (400 MHz, chloroform-d) δ=9.40 (s, 1H), 9.10 (s, 1H), 8.59 (d, J=9.2 Hz, 1H), 8.06 (d, J=8.0 Hz, 1H), 7.85-7.73 (m, 1H), 7.61 (dt, J=2.4, 7.6 Hz, 1H), 5.61-5.38 (m, 1H), 5.34-5.09 (m, 2H), 4.98-4.79 (m, 1H), 4.63 (ddd, J=4.4, 7.6, 11.2 Hz, 1H), 4.57-4.41 (m, 3H), 4.35-3.95 (m, 2H), 3.93-3.68 (m, 2H), 3.64-3.49 (m, 1H), 3.16-2.94 (m, 2H), 2.93-2.78 (m, 1H), 2.72-2.56 (m, 1H), 2.54 (s, 3H), 2.41-2.25 (m, 1H), 2.17-1.94 (m, 1H).

Example 53

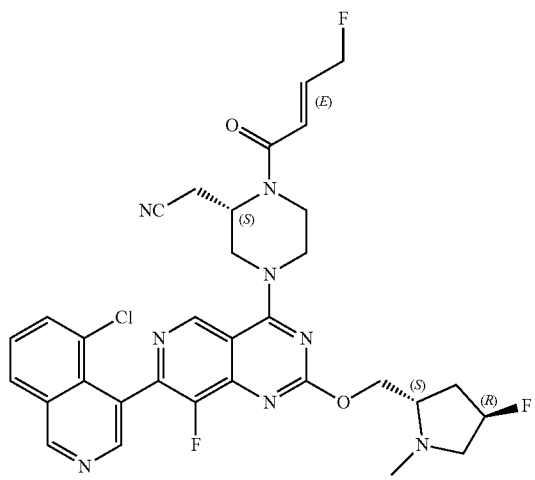

2-[(2S)-4-[7-(5-chloro-4-isoquinolyl)-8-fluoro-2-[[(2S,4R)-4-fluoro-1-methyl-pyrrolidin-2-yl]methoxy]pyrido[4,3-d]pyrimidin-4-yl]-1-[(E)-4-fluorobut-2-enoyl]piperazin-2-yl]acetonitrile

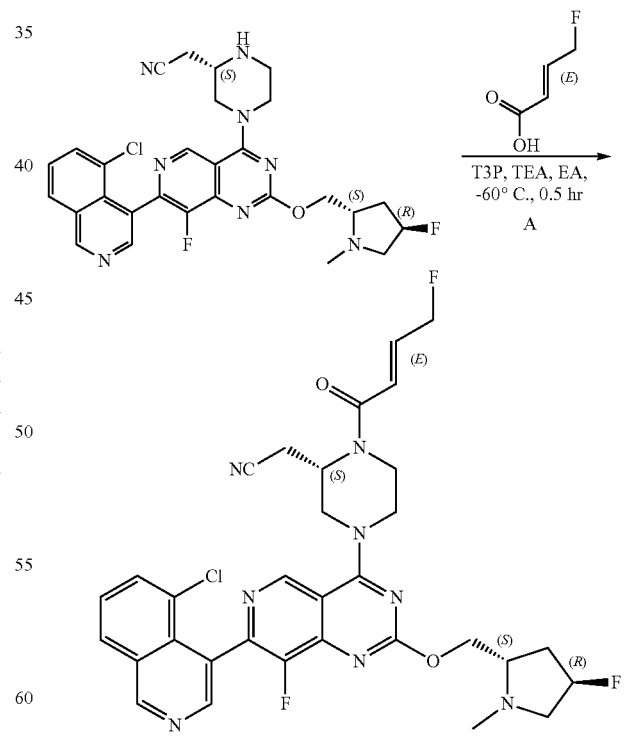

Example 53

Example 53: A mixture of 2-[(2S)-4-[7-(5-chloro-4-isoquinolyl)-8-fluoro-2-[[(2S,4R)-4-fluoro-1-methyl-pyrrolidin-2-yl]methoxy]pyrido[4,3-d]pyrimidin-4-yl]piperazin-2- yl]acetonitrile (70.0 mg, 124 μmol, 1.0 eq), molecular sieve 4A (200 mg) and (E)-4-fluorobut-2-enoic acid (38.7 mg, 372 μmol, 3.0 eq) in ethyl acetate (10.0 mL) was stirred at −60° C. for 10 min, then T3P (394 mg, 619 μmol, 368 μL, 50% purity, 5.0 eq) and TEA (62.7 mg, 619 μmol, 86.2 μL, 5.0 eq) was added thereto at −60° C. The mixture was stirred at −60° C. for 20 min. After completion, the mixture was quenched by saturated NH₄Cl aqueous solution (100 mL), and then extracted with ethyl acetate (70 mL×3), the combined organic layers were dried over anhydrous Na₂SO₄, filtered and the filtrate was concentrated under reduced pressure at 40° C. The residue was purified by prep-HPLC (formic acid condition; column: Xtimate C18 150*25 mm*5 μm; mobile phase: [water (0.05% ammonia hydroxide v/v)—ACN]; B %: 29%-59%,10 min) and lyophilized to give 2-[(2S)-4-[7-(5-chloro-4-isoquinolyl)-8-fluoro-2-[[(2S,4R)-4-fluoro-1-methyl-pyrrolidin-2-yl]methoxy]pyrido[4,3-d]pyrimidin-4-yl]-1-[(E)-4-fluorobut-2-enoyl]piperazin-2-yl]acetonitrile (15 mg, 22.0 μmol, 17.8% yield, 95.5% purity) as a white solid. LCMS [ESI, M+1]: 651.

¹HNMR (400 MHz, chloroform-d) δ=9.40 (s, 1H), 9.11 (s, 1H), 8.59 (d, J=12.0 Hz, 1H), 8.06 (d, J=8.0 Hz, 1H), 7.87-7.74 (m, 1H), 7.61 (dt, J=2.4, 7.6 Hz, 1H), 7.14-6.96 (m, 1H), 6.60 (br d, J=14.4 Hz, 1H), 5.61-4.75 (m, 4H), 4.63 (ddd, J=4.4, 6.8, 11.2 Hz, 1H), 4.57-4.39 (m, 3H), 3.61 (br d, J=5.6 Hz, 4H), 3.59-3.42 (m, 1H), 3.20-2.73 (m, 3H), 2.72-2.44 (m, 4H), 2.41-2.25 (m, 1H), 2.15-1.95 (m, 1H).

Example 54

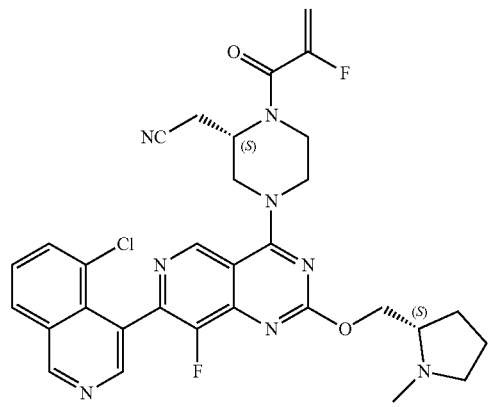

2-((S)-4-(7-(5-chloroisoquinolin-4-yl)-8-fluoro-2-(((S)-1-methylpyrrolidin-2-yl)methoxy)pyrido[4,3-d]pyrimidin-4-yl)-1-(2-fluoroacryloyl)piperazin-2-yl)acetonitrile

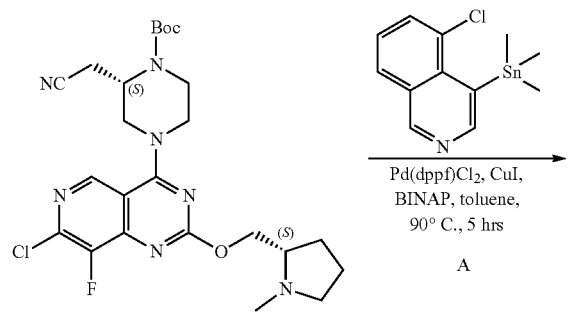

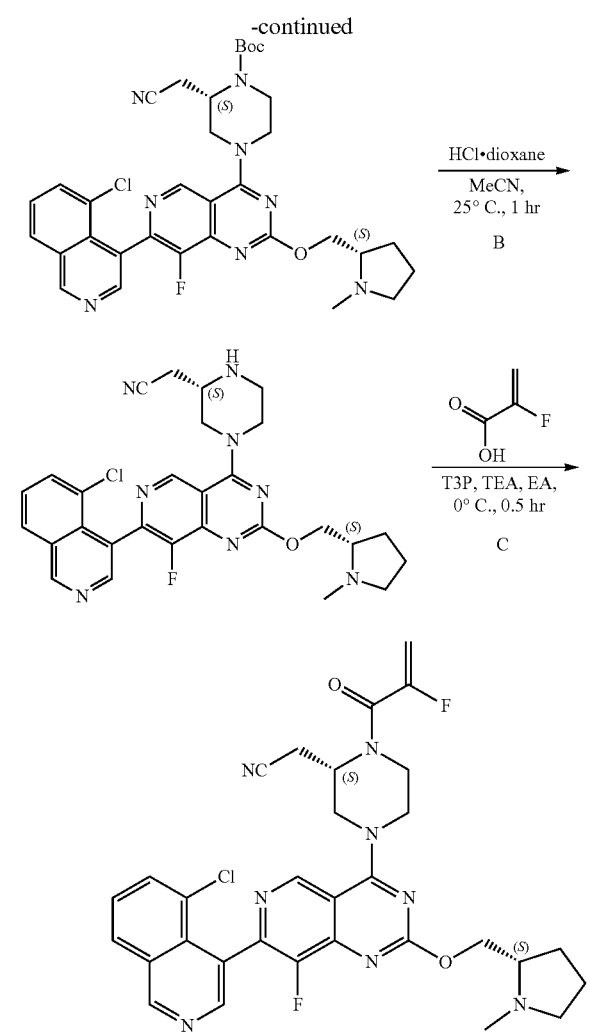

Example 54

Step A: A mixture of (5-chloro-4-isoquinolyl)-trimethylstannane (470 mg, 1.44 mmol, 3.0 eq), tert-butyl (2S)-4-[7-chloro-8-fluoro-2-[[(2S)-1-methylpyrrolidin-2-yl]methoxy]pyrido[4,3-d]pyrimidin-4-yl]-2-(cyanomethyl)piperazine-1-carboxylate (250 mg, 480 μmol, 1.0 eq), CuI (27.4 mg, 144 μmol, 0.3 eq), Pd(dppf)Cl₂ (35.1 mg, 48.1 μmol, 0.1 eq) and BINAP (59.8 mg, 96.1 μmol, 0.2 eq) in toluene (5 mL) was degassed and purged with N₂ for 3 times, and then the mixture was stirred at 90° C. for 5 hours under N₂ atmosphere. The reaction mixture was diluted with water (20 mL) and extracted with ethyl acetate (3×30 mL). The combined organic layers were washed with brine (30 mL), dried over Na₂SO₄, filtered and concentrated under reduced pressure. The residue was purified by reversed phase flash [water (0.1% formic acid)/acetonitrile)]. The mixture was adjusted pH ~7 with saturated NaHCO₃ aqueous solution and extracted with ethyl acetate (3×30 mL). The combined organic layers were washed with brine (30 mL), dried over Na₂SO₄, filtered and concentrated under reduced pressure to give tert-butyl (2S)-4-[7-(5-chloro-4-isoquinolyl)-8-fluoro-2-[[(2S)-1-methylpyrrolidin-2-yl]methoxy]pyrido[4,3-d]pyrimidin-4-yl]-2-(cyanomethyl)piperazine-1-carboxylate (170 mg, 233 μmol, 49% yield, 89% purity) as a yellow solid. LCMS [ESI, M+1]: 647.

Step B: To a solution of tert-butyl (2S)-4-[7-(5-chloro-4-isoquinolyl)-8-fluoro-2-[[(2S)-1-methylpyrrolidin-2-yl]methoxy]pyrido[4,3-d]pyrimidin-4-yl]-2-(cyanomethyl)piperazine-1-carboxylate (40 mg, 61.8 μmol, 1.0 eq) in MeCN (100 uL) was added HCl•dioxane (4 M, 231 μL, 15.0 eq). The mixture was stirred at 25° C. for 1 hour. The mixture was concentrated under vacuum. The reaction mixture was diluted with water (20 mL). Then the mixture was adjusted pH ~8 with saturated NaHCO₃ aqueous solution and extracted with ethyl acetate (3×20 mL). The combined organic layers were washed with brine (20 mL), dried over Na₂SO₄, filtered and concentrated under reduced pressure to give the residue. The residue was purified by prep-HPLC (column: Waters Xbridge 150*50 10μ; mobile phase: [water (0.05% ammonia hydroxide v/v)—ACN]; B %: 28%-58%, 10 min). The desired fraction was collected and lyophilized. 2-[(2S)-4-[7-(5-chloro-4-isoquinolyl)-8-fluoro-2-[[(2S)-1-methylpyrrolidin-2-yl]methoxy]pyrido[4,3-d]pyrimidin-4-yl]piperazin-2-yl]acetonitrile (7.88 mg, 14.3 μmol, 23% yield, 99.5% purity) was obtained as a white solid. LCMS [ESI, M+1]: 547.

¹H NMR (400 MHz, chloroform-d) δ=9.39 (s, 1H), 9.04 (s, 1H), 8.59 (d, J=0.8 Hz, 1H), 8.05 (dd, J=0.8, 7.2 Hz, 1H), 7.78 (dd, J=0.8, 6.8 Hz, 1H), 7.6 ((t, J=8.0 Hz, 1H), 4.67-4.50 (m, 2H), 4.48-4.34 (m, 2H), 3.66-3.51 (m, 1H), 3.43-3.31 (m, 1H), 3.29-3.19 (m, 2H), 3.18-3.05 (m, 2H), 2.81-2.54 (m, 3H), 2.51 (s, 3H), 2.35-2.23 (m, 1H), 2.15-1.98 (m, 1H), 1.92-1.79 (m, 3H).

Example 54: To a solution of 2-[(2S)-4-[7-(5-chloro-4-isoquinolyl)-8-fluoro-2-[[(2S)-1-methylpyrrolidin-2-yl]methoxy]pyrido[4,3-d]pyrimidin-4-yl]piperazin-2-yl]acetonitrile (50 mg, 91.4 μmol, 1.0 eq), 2-fluoroprop-2-enoic acid (24.6 mg, 274 μmol, 4.48 μL, 3.0 eq) and TEA (73.9 mg, 731 μmol, 101 μL, 8.0 eq) in ethyl acetate (1 mL) was added T3P (174 mg, 274 μmol, 163 μL, 50% purity in ethyl acetate, 3.0 eq) at 0° C. The mixture was stirred at 0° C. for 30 minutes. The reaction mixture was diluted with water (20 mL) and extracted with ethyl acetate (3×30 mL). The combined organic layers were washed with brine (20 mL), dried over Na₂SO₄, filtered and concentrated under reduced pressure to give a residue. The residue was purified by prep-HPLC (column: Waters Xbridge 150*50 10μ; mobile phase: [water (0.05% ammonia hydroxide v/v)—ACN]; B %: 28%-58%, 10 min). The desired fraction was collected and lyophilized. 2-[(2S)-4-[7-(5-chloro-4-isoquinolyl)-8-fluoro-2-[[(2S)-1-methylpyrrolidin-2-yl]methoxy]pyrido[4,3-d]pyrimidin-4-yl]-1-(2-fluoroprop-2-enoyl)piperazin-2-yl]acetonitrile (17.4 mg, 27 μmol, 31% yield, 99.0% purity) was obtained as a white solid. LCMS [ESI, M+1]: 619.

¹H NMR (400 MHz, chloroform-d) δ=9.39 (s, 1H), 9.09 (s, 1H), 8.59 (d, J=9.2 Hz, 1H), 8.06 (d, J=8.2 Hz, 1H), 7.81-7.75 (m, 1H), 7.61 (dt, J=2.4, 8.0 Hz, 1H), 5.62-5.38 (m, 1H), 5.29 (dd, J=3.6, 16.8 Hz, 1H), 4.87 (br s, 1H), 4.65-4.55 (m, 1H), 4.55-4.37 (m, 3H), 4.35-3.52 (m, 4H), 3.18-2.95 (m, 2H), 2.92-2.80 (m, 1H), 2.77-2.67 (m, 1H), 2.51 (s, 3H), 2.38-2.22 (m, 1H), 2.14-2.03 (m, 1H), 1.93-1.73 (m, 3H).

Example 55

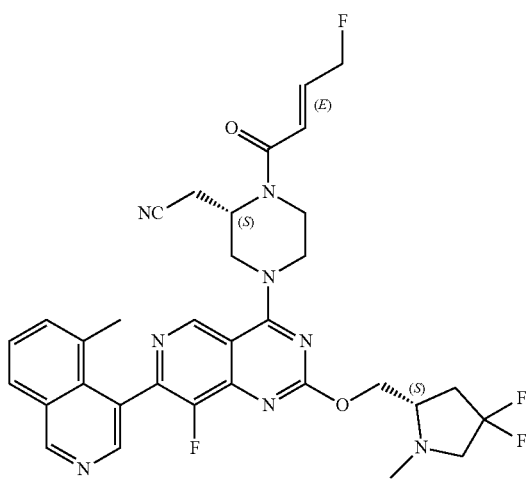

2-((S)-4-(2-(((S)-4,4-difluoro-1-methylpyrrolidin-2-yl)methoxy)-8-fluoro-7-(5-methylisoquinolin-4-yl)pyrido[4,3-d]pyrimidin-4-yl)-1-((E)-4-fluorobut-2-enoyl)piperazin-2-yl)acetonitrile

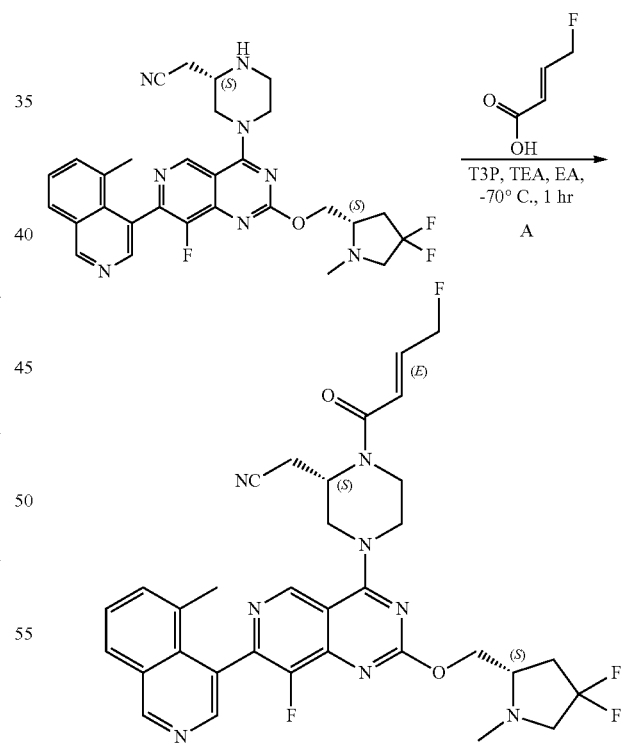

Example 55

Example 55: To a solution of 2-[(2S)-4-[2-[[(2S)-4,4-difluoro-1-methyl-pyrrolidin-2-yl]methoxy]-8-fluoro-7-(5-methyl-4-isoquinolyl)pyrido[4,3-d]pyrimidin-4-yl]piperazin-2-yl]acetonitrile (80 mg, 142 μmol, 1.0 eq), (E)-4-fluorobut-2-enoic acid (148 mg, 1.42 mmol, 4.48 μL, 10.0 eq) and TEA (115 mg, 1.14 mmol, 158. μL, 8.0 eq) in ethyl acetate (1 mL) was added T3P (271 mg, 426 μmol, 253 μL, 50% purity in ethyl acetate, 3.0 eq) at −70° C. The mixture was stirred at −70° C. for 1 hour. The reaction mixture was quenched with HCl (1 M, 1.5 mL). Then the mixture was adjusted pH ~7 with saturated NaHCO₃ aqueous solution and extracted with ethyl acetate (3×20 mL). The combined organic layers were washed with brine (10 mL), dried over Na₂SO₄, filtered and concentrated under reduced pressure to give the residue. The residue was purified by prep-HPLC (column: Waters Xbridge 150*50 10μ; mobile phase: [water (0.05% ammonia hydroxide v/v)—ACN]; B %: 33%-63%, 11.5 min). The desired fraction was collected and lyophilized. 2-[(2S)-4-[2-[[(2S)-4,4-difluoro-1-methyl-pyrrolidin-2-yl] methoxy]-8-fluoro-7-(5-methyl-4-isoquinolyl) pyrido[4,3-d]pyrimidin-4-yl]-1-[(E)-4-fluorobut-2-enoyl] piperazin-2-yl]acetonitrile (13.2 mg, 20.2 μmol, 14% yield, 99.7% purity) was obtained as a white solid. LCMS [ESI, M+1]: 649.

¹H NMR (400 MHz, chloroform-d) δ=9.35 (s, 1H), 9.14 (s, 1H), 8.47 (d, J=10.8 Hz, 1H), 7.97 (d, J=7.6 Hz, 1H), 7.64-7.48 (m, 2H), 7.15-6.93 (m, 1H), 6.60 (br d, J=15.2 Hz, 1H), 5.28-4.93 (m, 3H), 4.73-4.61 (m, 1H), 4.60-4.41 (m, 3H), 4.37-3.60 (m, 4H), 3.45 (dt, J=6.0, 11.8 Hz, 1H), 3.11-2.90 (m, 2H), 2.88-2.65 (m, 2H), 2.61-2.45 (m, 4H), 2.44-2.27 (m, 1H), 2.10 (d, J=4.0 Hz, 3H).

Example 56

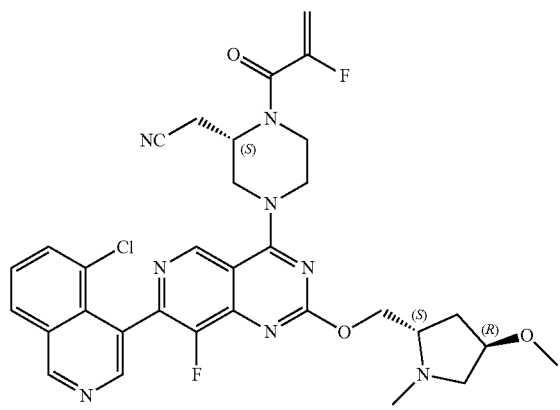

2-[(2S)-4-[7-(5-chloro-4-isoquinolyl)-8-fluoro-2-[[(2S,4R)-4-methoxy-1-methyl-pyrrolidin-2-yl] methoxy]pyrido[4,3-d]pyrimidin-4-yl]-1-(2-fluoroprop-2-enoyl)piperazin-2-yl]acetonitrile

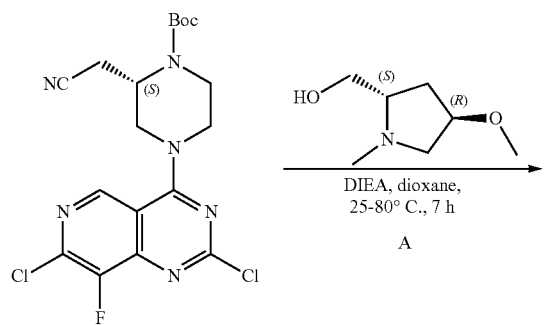

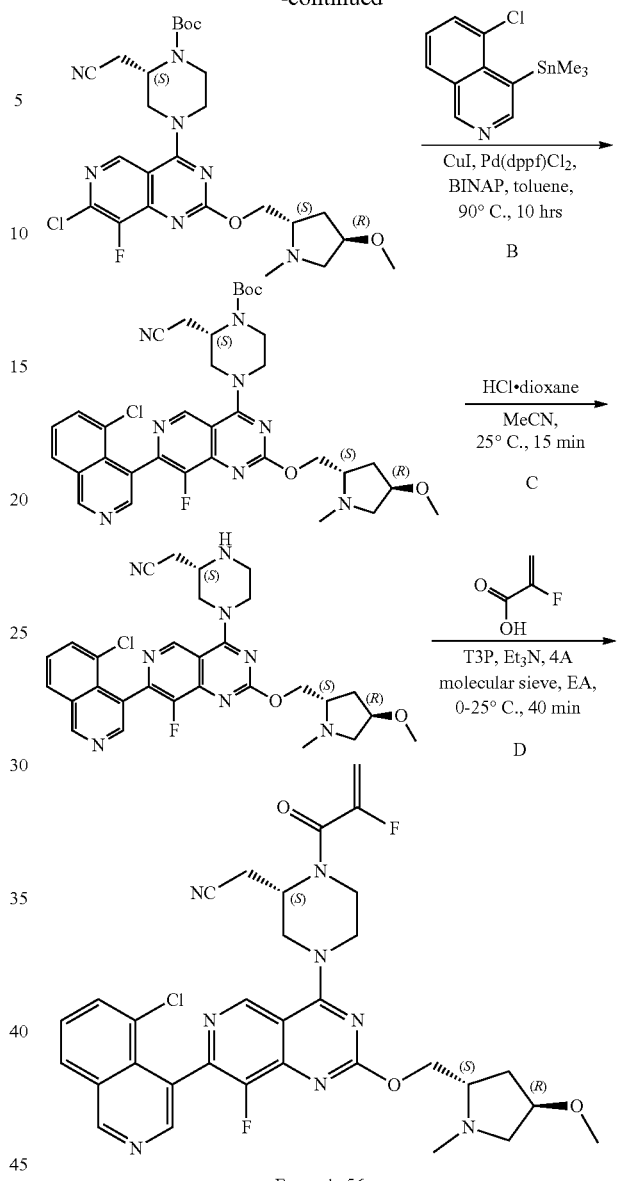

Example 56

Step A: To a mixture of tert-butyl (2S)-2-(cyanomethyl)-4-(2,7-dichloro-8-fluoro-pyrido[4,3-d]pyrimidin-4-yl)piperazine-1-carboxylate (1.50 g, 3.40 mmol, 1.0 eq) and [(2S,4R)-4-methoxy-1-methyl-pyrrolidin-2-yl]methanol (1.48 g, 10.2 mmol, 3.0 eq) in dioxane (40 mL) was added DIEA (1.32 g, 10.2 mmol, 1.78 mL, 3.0 eq) at 25° C. The mixture was stirred at 80° C. for 7 hours. Upon completion, the mixture was diluted with water (50 mL) and extracted with ethyl acetate (100 mL). The combined organic layers were washed with brine (50 mL), dried over sodium sulfate, filtered and concentrated under vacuum. The residue was purified by reversed phase flash [water (0.1% formic acid)/acetonitrile]. The desired fractions were collected and neutralized with saturated NaHCO₃ solution and extracted with ethyl acetate (100 mL). The separated organic layer was dried over sodium sulfate, filtered and concentrated under vacuum. tert-butyl (2S)-4-[7-chloro-8-fluoro-2-[[(2S,4R)-4-methoxy-1-methyl-pyrrolidin-2-yl]methoxy]pyrido[4,3-d] pyrimidin-4-yl]-2-(cyanomethyl)piperazine-1-carboxylate (1.21 g, 2.18 mmol, 64% yield, 99.0% purity) was obtained as a yellow solid. LCMS [ESI, M+1]: 550.

¹H NMR (400 MHz, chloroform-d) δ=8.80 (s, 1H), 4.67-4.50 (m, 2H), 4.48-4.36 (m, 2H), 4.35-4.24 (m, 1H), 4.18-4.02 (m, 1H), 4.01-3.84 (m, 2H), 3.74-3.62 (m, 1H), 3.59-3.39 (m, 2H), 3.35-3.26 (m, 3H), 2.97-2.77 (m, 2H), 2.75-2.63 (m, 1H), 2.54-2.45 (m, 3H), 2.37-2.28 (m, 1H), 2.10-2.01 (m, 2H), 1.51 (s, 9H).

Step B: To a solution of tert-butyl (2S)-4-[7-chloro-8-fluoro-2-[[(2S,4R)-4-methoxy-1-methyl-pyrrolidin-2-yl]methoxy]pyrido[4,3-d]pyrimidin-4-yl]-2-(cyanomethyl)piperazine-1-carboxylate (400 mg, 727 μmol, 1.0 eq) and (5-chloro-4-isoquinolyl)-trimethyl-stannane (712 mg, 2.18 mmol, 3.0 eq) in toluene (35 mL) was added CuI (41.5 mg, 218 μmol, 0.3 eq), Pd(dppf)Cl₂ (53.2 mg, 72.7 μmol, 0.1 eq) and BINAP (90.6 mg, 145 μmol, 0.2 eq). The reaction mixture was stirred at 90° C. for 6 hours. After that, 237 mg of (5-chloro-4-isoquinolyl)-trimethyl-stannane, 10 mg of CuI, 15 mg of Pd(dppf)Cl₂ and 25 mg of BINAP were added to the mixture and the mixture was stirred at 90° C. for 4 hours. Upon completion, the mixture was diluted with water (20 mL) and extracted with ethyl acetate (2×40 mL). The combined organic layers were washed with brine (40 mL), dried over Na₂SO₄, filtered and concentrated under vacuum. The residue was purified by reversed phase flash [water (0.1% formic acid)/acetonitrile]. The desired fractions were collected and neutralized with saturated NaHCO₃ solution and extracted with ethyl acetate (100 mL). The separated organic layer was dried over sodium sulfate, filtered and concentrated under vacuum. tert-butyl (2S)-4-[7-(5-chloro-4-isoquinolyl)-8-fluoro-2-[[(2S,4R)-4-methoxy-1-methyl-pyrrolidin-2-yl]methoxy]pyrido[4,3-d]pyrimidin-4-yl]-2-(cyanomethyl)piperazine-1-carboxylate (340 mg, 496 μmol, 68% yield, 98.8% purity) was obtained as a yellow solid. LCMS [ESI, M+1]: 677.

¹H NMR (400 MHz, chloroform-d) δ=9.38 (br s, 1H), 9.09 (s, 1H), 8.58 (br d, J=10.4 Hz, 1H), 8.04 (d, J=8.0 Hz, 1H), 7.84-7.70 (m, 1H), 7.59 (dt, J=2.4, 8.0 Hz, 1H), 4.72-4.54 (m, 2H), 4.53-4.35 (m, 3H), 4.02-3.83 (m, 2H), 3.78-3.66 (m, 1H), 3.57-3.41 (m, 2H), 3.30 (s, 3H), 3.05-2.67 (m, 4H), 2.49 (s, 3H), 2.33 (br dd, J=5.6, 10.0 Hz, 1H), 2.19-2.04 (m, 2H), 1.52 (s, 9H).

Step C: To a solution of tert-butyl (2S)-4-[7-(5-chloro-4-isoquinolyl)-8-fluoro-2-[[(2S,4R)-4-methoxy-1-methyl-pyrrolidin-2-yl]methoxy]pyrido[4,3-d]pyrimidin-4-yl]-2-(cyanomethyl)piperazine-1-carboxylate (290 mg, 428 μmol, 1.0 eq) in MeCN (3 mL) was added HCl/dioxane (4 M, 9 mL, 84.1 eq) at 25° C. The mixture was stirred at 25° C. for 15 min. Upon completion, the mixture was concentrated under vacuum and the residue was basified with saturated NaHCO₃ solution to pH=8. The residue was extracted with ethyl acetate (2×30 mL). The combined organic layers were dried over sodium sulfate, filtered and concentrated under vacuum. The residue was purified by prep-HPLC (column: Waters Xbridge 150*50 10μ; mobile phase: [water (0.05% ammonia hydroxide v/v)—ACN]; B %: 22%-52%, 10 min). The residue was concentrated under reduced pressure to remove ACN, and then lyophilized. 2-[(2S)-4-[7-(5-chloro-4-isoquinolyl)-8-fluoro-2-[[(2S,4R)-4-methoxy-1-methyl-pyrrolidin-2-yl]methoxy]pyrido[4,3-d]pyrimidin-4-yl]piperazin-2-yl]acetonitrile (120 mg, 205 μmol, 48% yield, 99.1% purity) was obtained as a white solid. LCMS [ESI, M+1]: 577.

¹H NMR (400 MHz, chloroform-d) δ=9.38 (s, 1H), 9.04 (s, 1H), 8.58 (s, 1H), 8.04 (d, J=8.0 Hz, 1H), 7.77 (d, J=7.6 Hz, 1H), 7.65-7.55 (m, 1H), 4.64-4.48 (m, 2H), 4.47-4.35 (m, 2H), 4.01-3.92 (m, 1H), 3.64-3.52 (m, 1H), 3.44 (dd, J=6.0, 9.6 Hz, 1H), 3.40-3.28 (m, 4H), 3.27-3.18 (m, 2H), 3.17-3.05 (m, 1H), 3.00-2.87 (m, 1H), 2.70-2.53 (m, 2H), 2.48 (s, 3H), 2.33 (dd, J=5.6, 9.6 Hz, 1H), 2.14-1.97 (m, 3H).

Example 56: To a solution of 2-[(2S)-4-[7-(5-chloro-4-isoquinolyl)-8-fluoro-2-[[(2S,4R)-4-methoxy-1-methyl-pyrrolidin-2-yl]methoxy]pyrido[4,3-d]pyrimidin-4-yl]piperazin-2-yl]acetonitrile (50.0 mg, 86.6 μmol, 1.0 eq), 2-fluoroprop-2-enoic acid (23.4 mg, 260 μmol, 3.0 eq) in ethyl acetate (10 mL) was added 4A molecular sieve (50 mg). The mixture was stirred at 25° C. for 10 min. After that, the mixture was cooled to 0° C. and added Et₃N (78.9 mg, 780 μmol, 108 μL, 9.0 eq) and T3P (220 mg, 346 μmol, 206 μL, 50% purity, 4.0 eq) at 0° C. The mixture was stirred at 0° C. for 0.5 hour. Upon completion, the mixture was diluted with water (3 mL) and extracted with ethyl acetate (2×10 mL). The combined organic layers were washed with brine (30 mL), dried over Na₂SO₄, filtered and concentrated under vacuum. The residue was purified by column chromatography (SiO₂, dichloromethane/methanol=50/1 to 10/1). The residue was purified by prep-HPLC (column: Xtimate C18 150*25 mm*5 μm; mobile phase: [water (0.05% ammonia hydroxide v/v)—ACN]; B %: 25%-55%, 10 min). The residue was concentrated under reduced pressure to remove ACN, and then lyophilized. 2-[(2S)-4-[7-(5-chloro-4-isoquinolyl)-8-fluoro-2-[[(2S,4R)-4-methoxy-1-methyl-pyrrolidin-2-yl]methoxy]pyrido[4,3-d]pyrimidin-4-yl]-1-(2-fluoroprop-2-enoyl)piperazin-2-yl]acetonitrile (44.9 mg, 69.1 μmol, 80% yield, 99.9% purity) was obtained as a white solid. LCMS [ESI, M+1]: 649.

¹H NMR (400 MHz, chloroform-d) δ=9.40 (s, 1H), 9.10 (s, 1H), 8.59 (d, J=9.2 Hz, 1H), 8.06 (d, J=8.4 Hz, 1H), 7.81-7.74 (m, 1H), 7.61 (dt, J=2.4, 7.6 Hz, 1H), 5.59-5.39 (m, 1H), 5.29 (dd, J=3.6, 16.8 Hz, 1H), 4.99-4.79 (m, 1H), 4.66-4.55 (m, 1H), 4.53-4.39 (m, 3H), 4.37-3.63 (m, 5H), 3.52-3.38 (m, 1H), 3.31 (s, 3H), 3.13-2.78 (m, 3H), 2.50 (s, 3H), 2.34 (dd, J=5.6, 9.6 Hz, 1H), 2.15-1.96 (m, 2H).

Example 57

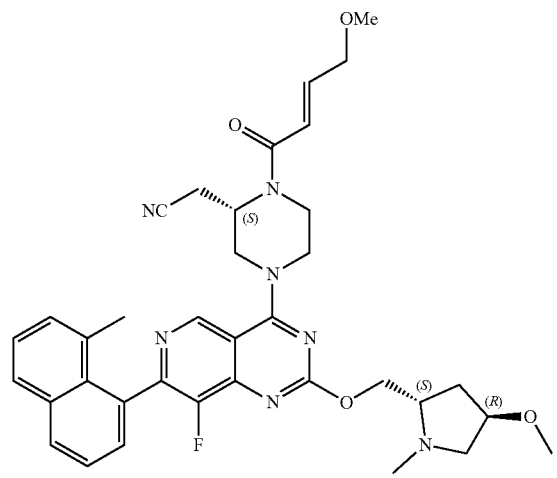

2-[(2S)-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]-1-[(E)-4-methoxybut-2-enoyl]piperazin-2-yl]acetonitrile
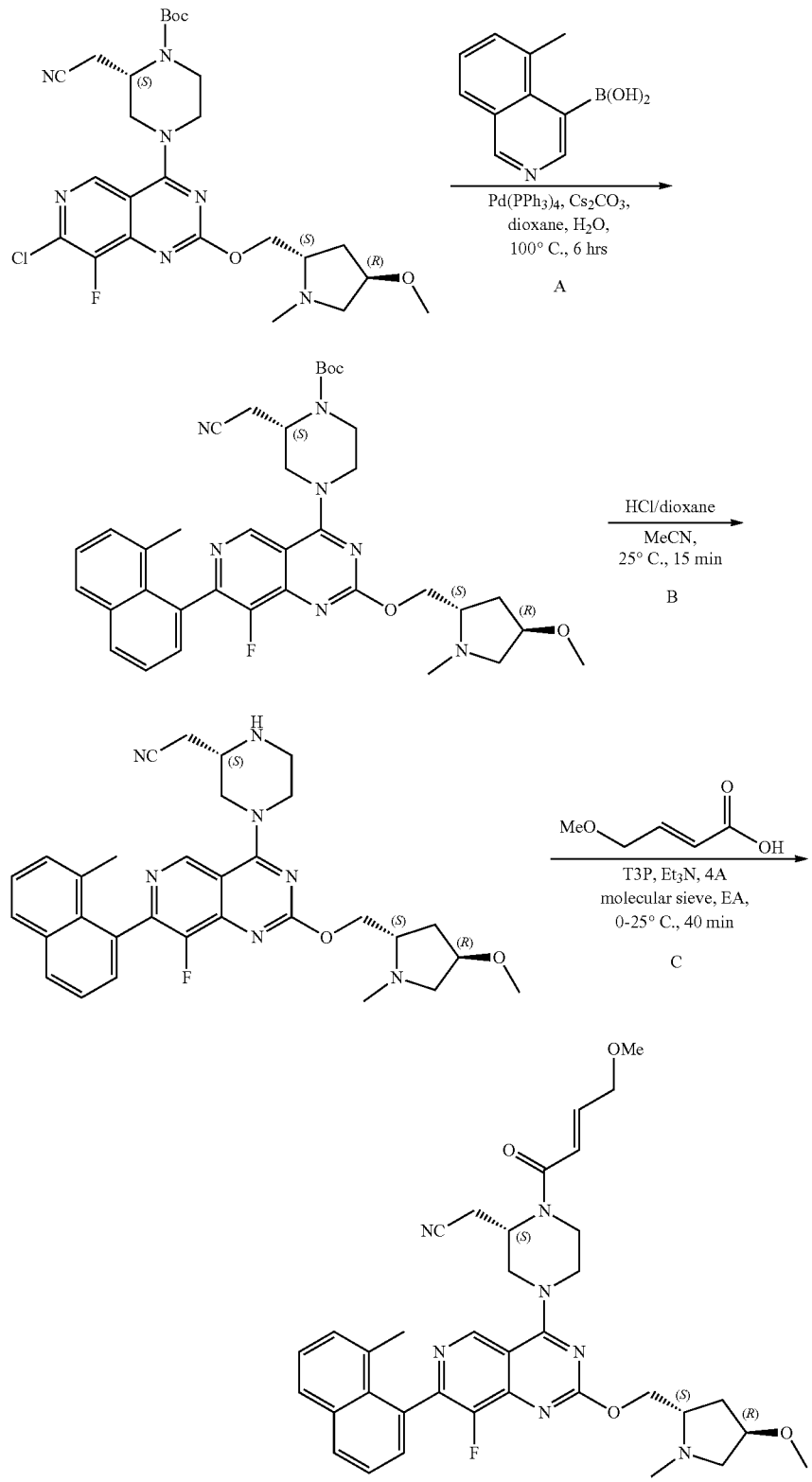
Example 57

Step A: A mixture of tert-butyl (2S)-4-[7-chloro-8-fluoro-2-[[(2S,4R)-4-methoxy-1-methyl-pyrrolidin-2-yl]methoxy]pyrido[4,3-d]pyrimidin-4-yl]-2-(cyanomethyl)piperazine-1-carboxylate (300 mg, 545 μmol, 1.0 eq), (8-methyl-1-naphthyl)boronic acid (203 mg, 1.09 mmol, 2.0 eq), Pd(PPh3)4 (63.0 mg, 54.5 μmol, 0.1 eq), Cs2CO3 (355 mg, 1.09 mmol, 2.0 eq) in dioxane (20 mL) and H2O (4 mL) was degassed and purged with N2 for 3 times, and then the mixture was stirred at 100° C. for 6 hours under N2 atmosphere. Upon completion, the residue was diluted with water (20 mL) and extracted with ethyl acetate (50 mL). The combined organic layers were washed with brine (30 mL), dried over sodium sulfate, filtered and concentrated under vacuum. The residue was purified by reversed phase flash [water (0.1% formic acid/acetonitrile]. The desired fractions were collected and neutralized with saturated NaHCO3 solution and extracted with ethyl acetate (80 mL). The separated organic layer was dried over sodium sulfate, filtered and concentrated under vacuum. tert-butyl (2S)-2-(cyanomethyl)-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]piperazine-1-carboxylate (335 mg, 319 μmol, 58% yield, 62.5% purity) was obtained as a yellow solid. LCMS [ESI, M+1]: 656.

Step B: To a solution of tert-butyl (2S)-2-(cyanomethyl)-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]piperazine-1-carboxylate (285 mg, 272 μmol, 1.0 eq) in MeCN (3 mL) was added HCl/dioxane (4 M, 9 mL, 132 eq) at 25° C. The mixture was stirred at 25° C. for 15 min. Upon completion, the mixture was concentrated under vacuum and the residue was basified with saturated NaHCO3 solution to pH=8. The residue was extracted with ethyl acetate (2×30 mL). The combined organic layers were dried over sodium sulfate, filtered and concentrated under vacuum. 2-[(2S)-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]piperazin-2-yl]acetonitrile (230 mg, crude) was obtained as a yellow solid and used in the next step without further purification. LCMS [ESI, M+1]: 556.

Example 57: To a solution of 2-[(2S)-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]piperazin-2-yl]acetonitrile (100 mg, 180 μmol, 1.0 eq), (E)-4-methoxybut-2-enoic acid (62.7 mg, 540 μmol, 3.0 eq) in ethyl acetate (15 mL) was added 4A molecular sieve (200 mg, 90.0 μmol). The mixture was stirred at 25° C. for 10 min. After that, the mixture was cooled to 0° C. and added T3P (458 mg, 720 μmol, 428 μL, 50% purity, 4.0 eq) and Et3N (164 mg, 1.62 mmol, 225 μL, 9.0 eq) at 0° C. The mixture was stirred at 0° C. for 0.5 hour. Upon completion, the residue was diluted with water (20 mL) and ethyl acetate (25 mL). The organic layer was separated, washed with brine (30 mL), dried over sodium sulfate, filtered and concentrated under vacuum. The residue was purified by column chromatography (SiO2, dichloromethane/methanol=50/1 to 10/1). The residue was purified by prep—HPLC (column: Waters Xbridge 150*50 10μ; mobile phase: [water (0.05% ammonia hydroxide v/v)—ACN]; B %: 37%-67%, 10 min). The residue was concentrated under reduced pressure to remove ACN, and then lyophilized. 2-[(2S)-4-[8-fluoro-2-[[(2S,4R)-4-methoxy-1-methyl-pyrrolidin-2-yl]methoxy]-7-(8-methyl-1-naphthyl)pyrido[4,3-d]pyrimidin-4-yl]-1-[(E)-4-methoxybut-2-enoyl]piperazin-2-yl]acetonitrile (16.7 mg, 25.5 μmol, 14% yield, 99.9% purity) was obtained as a white solid. LCMS [ESI, M+1]: 654.

$^1$H NMR (400 MHz, chloroform-d) δ=9.09 (d, J=2.4 Hz, 1H), 7.99 (d, J=8.0 Hz, 1H), 7.82 (d, J=8.4 Hz, 1H), 7.58-7.51 (m, 1H), 7.49-7.38 (m, 2H), 7.33-7.28 (m, 1H), 7.09-6.93 (m, 1H), 6.55 (br d, J=15.2 Hz, 1H), 5.16-4.92 (m, 1H), 4.67-4.57 (m, 1H), 4.55-4.37 (m, 3H), 4.24-3.69 (m, 7H), 3.51-3.40 (m, 4H), 3.31 (s, 3H), 3.06-2.88 (m, 2H), 2.85-2.72 (m, 1H), 2.50 (d, J=1.2 Hz, 3H), 2.34 (dd, J=5.6, 10.0 Hz, 1H), 2.16-1.97 (m, 5H).

Example 58

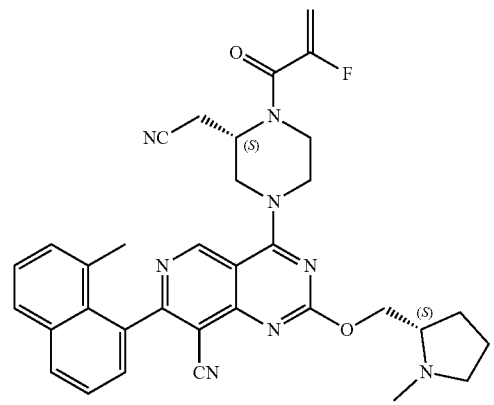

4-[(3S)-3-(cyanomethyl)-4-(2-fluoroprop-2-enoyl)piperazin-1-yl]-7-(8-methyl-1-naphthyl)-2-[[(2S)-1-methylpyrrolidin-2-yl]methoxy]pyrido[4,3-d]pyrimidine-8-carbonitrile

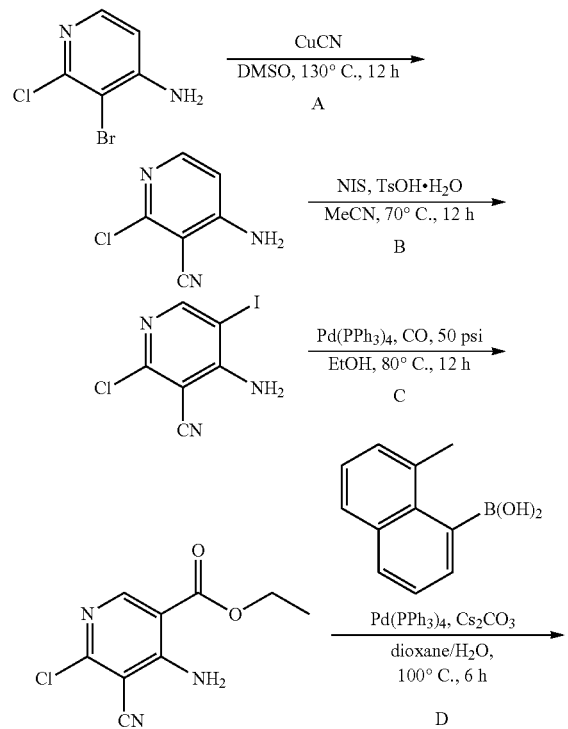

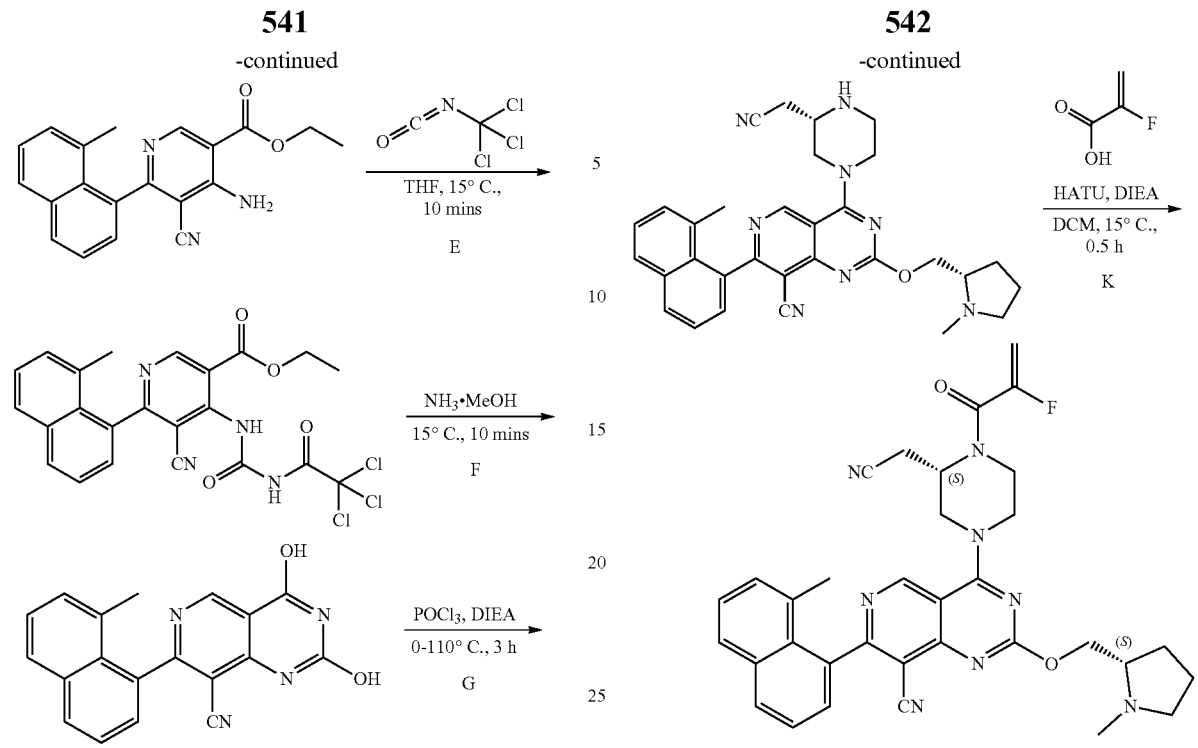

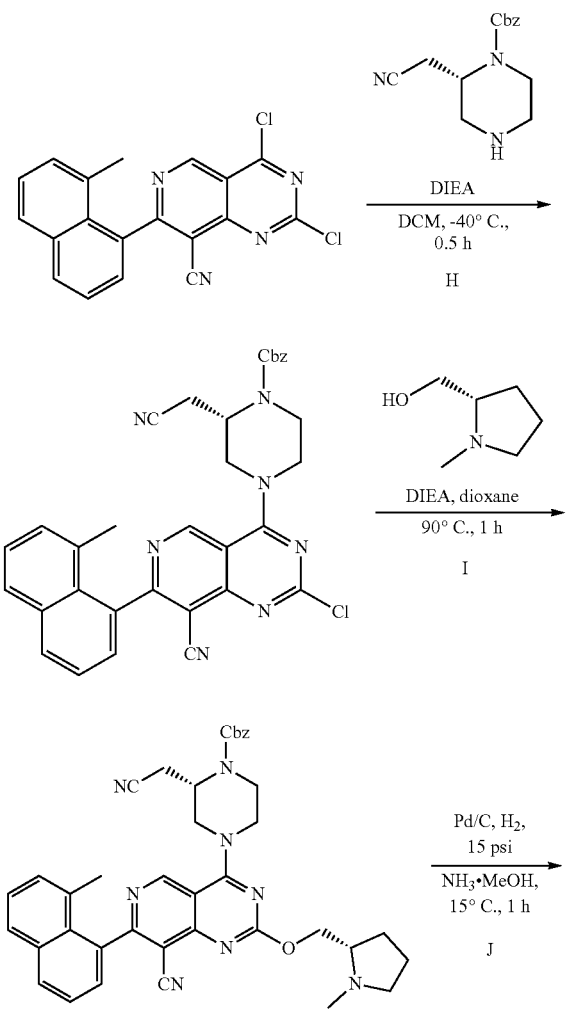

Example 58

Step A: A mixture of 3-bromo-2-chloro-pyridin-4-amine (3.0 g, 14.5 mmol, 1.0 eq), CuCN (3.89 g, 43.4 mmol, 9.48 mL, 3.0 eq) in DMSO (30 mL) was stirred at 130° C. for 12 hours. The mixture was concentrated under vacuum. The residue was added $NH_3H_2O$ (100 mL) and stirred at 15° C. for 10 mins, the mixture was extracted with ethyl acetate (2×200 mL) and the combined organic layer was washed with brine (200 mL), dried over $Na_2SO_4$, filtered and concentrated under vacuum to give 4-amino-2-chloro-pyridine-3-carbonitrile (1.0 g, 5.93 mmol, 41% yield, 91% purity) as a yellow solid and used into next step without further purification. LCMS [ESI, M+1]: 154.

$^1$H NMR (400 MHz, DMSO-$d_6$) δ=7.92 (d, J=6.0 Hz, 1H), 7.43 (br s, 2H), 6.67 (d, J=6.0 Hz, 1H).

Step B: A mixture of 4-amino-2-chloro-pyridine-3-carbonitrile (3.2 g, 20.8 mmol, 1.0 eq), TsOH.$H_2O$ (198 mg, 1.04 mmol, 0.05 eq) and NIS (7.03 g, 31.3 mmol, 1.5 eq) in acetonitrile (30 mL) was stirred at 70° C. for 12 hours. The mixture was concentrated under vacuum. The residue was diluted with $H_2O$ (50 mL), extracted with ethyl acetate (2×50 mL), the combined organic layer was washed with brine (50 mL), dried over $Na_2SO_4$, filtered and concentrated under vacuum. The residue was purified by column chromatography ($SiO_2$, PE/EA=3/1). The fraction was collected and concentrated under vacuum. The residue was triturated with acetonitrile (20 mL), the residue was dry under vacuum to give 4-amino-2-chloro-5-iodo-pyridine-3-carbonitrile (3.0 g, 10.7 mmol, 52% yield, 100% purity) as a yellow solid. LCMS [ESI, M+1]: 280.

$^1$H NMR (400 MHz, chloroform-d) δ=8.45 (s, 1H), 5.56 (br s, 2H).

Step C: A mixture of 4-amino-2-chloro-5-iodo-pyridine-3-carbonitrile (2.8 g, 10 mmol, 1.0 eq), TEA (3.65 g, 36.1 mmol, 5.02 mL, 3.6 eq) and Pd(PPh$_3$)$_2$Cl2 (703 mg, 1.0 mmol, 0.1 eq) in ethanol (30 mL) was stirred at 80° C. for 12 hours under CO under 50 psi. The mixture was concentrated under vacuum. The residue was triturated with methanol (20 mL), the solid was collected and dried under vacuum to give ethyl 4-amino-6-chloro-5-cyano-pyridine-3-carboxylate (2.0 g, 8.78 mmol, 88% yield, 99% purity) as a yellow solid which was used into next step without further purification. LCMS [ESI, M+1]: 226.

$^1$H NMR (400 MHz, DMSO-$d_6$) δ=8.63 (s, 1H), 8.11 (br s, 2H), 4.32 (q, J=7.2 Hz, 2H), 1.32 (t, J=7.2 Hz, 3H).

Step D: A mixture of ethyl 4-amino-6-chloro-5-cyano-pyridine-3-carboxylate (1.7 g, 7.53 mmol, 1.0 eq), (8-methyl-1-naphthyl)boronic acid (1.82 g, 9.79 mmol, 1.3 eq), Pd(PPh$_3$)$_4$ (871 mg, 753 μmol, 0.1 eq) and Cs$_2$CO$_3$ (7.36 g, 22.6 mmol, 3.0 eq) in dioxane (30 mL) and H$_2$O (10 mL) was stirred at 100° C. for 6 hours under N$_2$. The mixture was diluted with water (10.0 mL), extracted with ethyl acetate (2×10 mL), the combined organic layer was washed with brine (10 mL), dried over Na$_2$SO$_4$, filtered and concentrated under vacuum. The residue was purified by column chromatography (SiO$_2$, PE/EA=3/1), the desired fraction was collected and concentrated under vacuum. The residue was purified by reversed phase flash [water (FA, 0.1%)/acetonitrile]. The desired fraction was collected and basified by NaHCO$_3$ (1.0 g). The mixture was concentrated under vacuum to removed acetonitrile. The mixture was extracted with ethyl acetate (3×10 mL), the combined organic layers were washed brine (10 mL), dried over Na$_2$SO$_4$, filtered and concentrated under vacuum to give ethyl 4-amino-5-cyano-6-(8-methyl-1-naphthyl)pyridine-3-carboxylate (450 mg, 1.29 mmol, 17% yield, 95% purity) as a yellow oil. LCMS [ESI, M+1]: 332.

Step E: A mixture of ethyl 4-amino-5-cyano-6-(8-methyl-1-naphthyl)pyridine-3-carboxylate (0.45 g, 1.36 mmol, 1.0 eq) and trichloro(isocyanato)methane (436 mg, 2.72 mmol, 2.0 eq) in THF (4 mL) was stirred at 15° C. for 10 mins. The mixture was concentrated under vacuum. The residue was washed with MBTE (10 mL), the residue was dried under vacuum to give ethyl 5-cyano-6-(8-methyl-1-naphthyl)-4-[(2,2,2-trichloroacetyl)carbamoylamino]pyridine-3-carboxylate (0.7 g, crude) as a white solid which was used into next step without further purification. LCMS [ESI, M+2]: 521.

Step F: A mixture of ethyl 5-cyano-6-(8-methyl-1-naphthyl)-4-[(2,2,2-trichloroacetyl)carbamoylamino]pyridine-3-carboxylate (0.7 g, crude) in NH$_3$.MeOH (1 mL, 30% purity) was stirred at 15° C. for 10 mins. The mixture was concentrated under vacuum. The residue was washed with MTBE (10 mL), dried under vacuum to give 2,4-dihydroxy-7-(8-methyl-1-naphthyl)pyrido[4,3-d]pyrimidine-8-carbonitrile (0.41 g, 1.25 mmol, two steps 91% yield) as a white solid and used into next step without further purification. LCMS [ESI, M+1]: 329.

Step G: To a mixture of 2,4-dihydroxy-7-(8-methyl-1-naphthyl)pyrido[4,3-d]pyrimidine-8-carbonitrile (200 mg, 609 μmol, 1.0 eq) in POCl$_3$ (6.60 g, 43 mmol, 4.0 mL, 70.7 eq) was added DIEA (236 mg, 1.83 mmol, 318 μL, 3.0 eq) at 0° C., then the mixture was heating to 110° C., then DIEA (157 mg, 1.22 mmol, 212 μL, 2.0 eq) was added into the mixture. After stirring at 110° C. for 3 hours, the mixture was concentrated under vacuum. The residue was dissolved in dichloromethane (5.0 mL) and concentrated under vacuum to give 2,4-dichloro-7-(8-methyl-1-naphthyl)pyrido[4,3-d]pyrimidine-8-carbonitrile (0.4 g, crude) as a yellow oil and used into next step without further purification. LCMS [ESI, M-8]: 357.

Step H: To a mixture of 2,4-dichloro-7-(8-methyl-1-naphthyl)pyrido[4,3-d]pyrimidine-8-carbonitrile (0.4 g, crude) and 4A MOLECULAR SIEVE (0.1 g) in dichloromethane (4 mL) was added DIEA (566 mg, 4.38 mmol, 763 μL) at −40° C., then benzyl (2S)-2-(cyanomethyl)piperazine-1-carboxylate (284 mg, 1.10 mmol) was added into the mixture. After stirring at −40° C. for 0.5 h, the mixture was diluted with H$_2$O (4.0 mL), the water phase was extracted with dichloromethane (2×5.0 mL), the combined layer was dried over Na$_2$SO$_4$, filtered and concentrated under vacuum. The residue was purified by column chromatography (SiO$_2$, PE/EA=1/1) to give benzyl (2S)-4-[2-chloro-8-cyano-7-(8-methyl-1-naphthyl)pyrido[4,3-d]pyrimidin-4-yl]-2-(cyanomethyl)piperazine-1-carboxylate (0.2 g, 340 μmol, two steps 56% yield, 100% purity) as a yellow solid. LCMS [ESI, M+1]: 588.

Step I: A mixture of benzyl (2S)-4-[2-chloro-8-cyano-7-(8-methyl-1-naphthyl)pyrido[4,3-d]pyrimidin-4-yl]-2-(cyanomethyl)piperazine-1-carboxylate (0.2 g, 340 μmol, 1.0 eq), [(2S)-1-methylpyrrolidin-2-yl]methanol (58.8 mg, 510 μmol, 60.6 μL, 1.5 eq) and DIEA (132 mg, 1.02 mmol, 178 μL, 3.0 eq) in dioxane (2 mL) was stirred at 90° C. for 1 hours. The mixture was concentrated under vacuum. The residue was purified by reversed phase flash [water (FA, 0.1%)/acetonitrile]. The desired fraction was collected and basified by NaHCO$_3$ (2 g). The mixture was concentrated under vacuum to removed acetonitrile, the residue was extracted with ethyl acetate (3×10 mL), the organic layers were washed brine (10 mL), dried over Na$_2$SO$_4$, filtered and concentrated under vacuum to give benzyl (2S)-2-(cyanomethyl)-4-[8-cyano-7-(8-methyl-1-naphthyl)-2-[[(2S)-1-methylpyrrolidin-2-yl]methoxy]pyrido[4,3-d]pyrimidin-4-yl]piperazine-1-carboxylate (158 mg, 237 μmol, 70% yield, 100% purity) as a yellow solid. LCMS [ESI, M+1]: 667.

Step J: A mixture of benzyl (2S)-2-(cyanomethyl)-4-[8-cyano-7-(8-methyl-1-naphthyl)-2-[[(2S)-1-methylpyrrolidin-2-yl]methoxy]pyrido[4,3-d]pyrimidin-4-yl]piperazine-1-carboxylate (50 mg, 75 μmol, 1.0 eq), Pd/C (10% purity) in methanol (5 mL) and NH$_3$.MeOH (5 mL, 20% purity) was stirred at 15° C. for 1 hour under H$_2$ at 15 psi. The mixture was filtered and concentrated under vacuum to give 4-[(3S)-3-(cyanomethyl)piperazin-1-yl]-7-(8-methyl-1-naphthyl)-2-[[(2S)-1-methylpyrrolidin-2-yl]methoxy]pyrido[4,3-d]pyrimidine-8-carbonitrile (44 mg, crude) as a blue solid and used into next batch without further purification. LCMS [ESI, M+1]: 533.

Example 58: To a solution of 4-[(3S)-3-(cyanomethyl)piperazin-1-yl]-7-(8-methyl-1-naphthyl)-2-[[(2S)-1-methylpyrrolidin-2-yl]methoxy]pyrido[4,3-d]pyrimidine-8-carbonitrile (100 mg, 188 μmol, crude), 2-fluoroprop-2-enoic acid (33.8 mg, 375 μmol) and DIEA (97.1 mg, 751 μmol, 131 μL) in dichloromethane (2 mL) was added HATU (143 mg, 375 μmol) at 15° C. After stirring at 15° C. for 0.5 h, the mixture was washed with water (2.0 mL) and brine (2.0 mL), dried over Na$_2$SO$_4$, filtered and concentrated under vacuum. The residue was purified by prep-HPLC (column: Xtimate C18 150*25 mm*5 μm; mobile phase: [water (0.05% ammonia hydroxide v/v)—ACN]; B %: 40%-70%, 10 min). The desired fraction was collected and concentrated under vacuum to removed acetonitrile. The residue was lyophilized to give 4-[(3S)-3-(cyanomethyl)-4-(2-fluoroprop-2-enoyl)piperazin-1-yl]-7-(8-methyl-1-naphthyl)-2-[[(2S)-1-methylpyrrolidin-2-yl]methoxy]pyrido[4,3-d]pyrimidine-8-carbonitrile (15.9 mg, 23.9 μmol, two steps 13% yield, 91.2% purity) as a white solid. LCMS [ESI, M+1]: 605.

Example 59

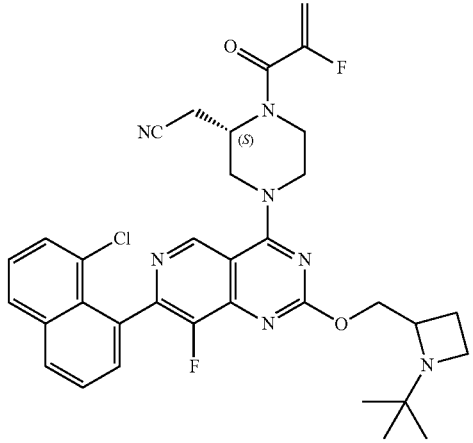

2-[(2S)-4-[2-[(1-tert-butylazetidin-2-yl)methoxy]-7-(8-chloro-1-naphthyl)-8-fluoro-pyrido[4,3-d]pyrimidin-4-yl]-1-(2-fluoroprop-2-enoyl)piperazin-2-yl]acetonitrile

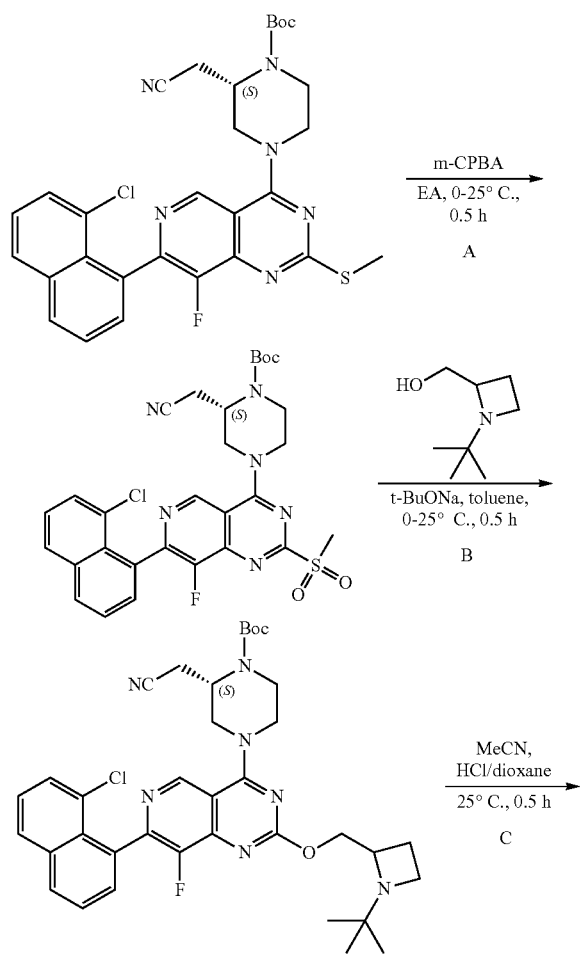

Example 59

Step A: To a mixture of tert-butyl (2S)-4-[7-(8-chloro-1-naphthyl)-8-fluoro-2-methyl sulfanyl-pyrido [4,3-d]pyrimidin-4-yl]-2-(cyanomethyl)piperazine-1-carboxylate (950 mg, 1.64 mmol, 1.00 eq) in ethyl acetate (15.0 mL) was added m-CPBA (999 mg, 4.92 mmol, 85% purity, 3.00 eq) in portion at 0° C. under $N_2$. The mixture was stirred at 25° C. for 30 min. The reaction mixture was diluted with ethyl acetate (100 mL) and washed with saturated $Na_2S_2O_3$ solution (30.0 mL) and saturated $NaHCO_3$ solution (20.0 mL), brine (20.0 mL), dried over sodium sulfate, filtered and concentrated under reduced pressure. The crude product was used in the next step directly without further purification. Compound tert-butyl (2S)-4-[7-(8-chloro-1-naphthyl)-8-fluoro-2-methylsulfonyl-pyrido[4,3-d]pyrimidin-4-yl]-2-(cyanomethyl)piperazine-1-carboxylate (1.00 g, crude) was obtained as a yellow solid.

Step B: To a mixture of tert-butyl (2S)-4-[7-(8-chloro-1-naphthyl)-8-fluoro-2-methylsulfonyl-pyrido[4,3-d]pyrimidin-4-yl]-2-(cyanomethyl)piperazine-1-carboxylate (500 mg, 818 µmol, 1.00 eq) and (1-tert-butylazetidin-2-yl)methanol (352 mg, 2.45 mmol, 3.00 eq) in toluene (25.0 mL) was added t-BuONa (236 mg, 2.45 mmol, 3.00 eq) in portion at 0° C. under $N_2$. The mixture was stirred at 25° C. for 30 min. The reaction mixture was diluted with ethyl acetate (30.0 mL) and adjusted pH to 8-9 with 2 M HCl at 0° C., then extracted with ethyl acetate (20.0 mL×2). The combined organic layers were washed with water (15.0 mL), dried over sodium sulfate, filtered and concentrated under reduced pressure. The residue was purified by reversed phase flash [water (0.1% formic acid/acetonitrile]. The desired fractions were collected and neutralized with saturated $NaHCO_3$ solution (10.0 mL) and extracted with ethyl acetate (30.0 mL×3). The separated organic layer was dried over sodium sulfate, filtered and concentrated under vacuum. Compound tert-butyl (2S)-4-[2-[(1-tert-butylazetidin-2-yl)methoxy]-7-(8-chloro-1-naphthyl)-8-fluoro-pyrido[4,3-d]pyrimidin-4-yl]-2-(cyanomethyl)piperazine-1-carboxylate (290 mg, 381 µmol, 47% yield, 88.6% purity) was obtained as a yellow solid. LCMS [ESI, M+1]: 674.

Step C: To a mixture of tert-butyl (2S)-4-[2-[(1-tert-butylazetidin-2-yl)methoxy]-7-(8-chloro-1-naphthyl)-8-fluoro-pyrido[4,3-d]pyrimidin-4-yl]-2-(cyanomethyl)piperazine-1-carboxylate (80.0 mg, 119 µmol, 1.00 eq) in MeCN (1.50 mL) was added HCl/dioxane (4 M, 3.00 mL, 101 eq) under N₂. The mixture was stirred at 25° C. for 30 min. The reaction mixture was concentrated under reduced pressure to give a residue. Then the residue was dissolved with ethyl acetate (5.00 mL) and adjusted pH to 8 with saturated NaHCO₃ solution and extracted with ethyl acetate (10.0 mL×3). The combined organic layers were washed with brine (5.00 mL), dried over sodium sulfate, filtered and concentrated under reduced pressure. The residue was purified by prep-HPLC (column: Waters Xbridge 150×50 10µ; mobile phase: [water (0.05% ammonia hydroxide v/v)—ACN]; B %: 47%-77%, 10 min). Compound 2-[(2S)-4-[2-[(1-tert-butylazetidin-2-yl)methoxy]-7-(8-chloro-1-naphthyl)-8-fluoro-pyrido[4,3-d]pyrimidin-4-yl]piperazin-2-yl]acetonitrile (36.0 mg, 62.5 µmol, 53% yield, 99.7% purity) was obtained as a white solid. LCMS [ESI, M+1]: 574.

¹H NMR (400 MHz, chloroform-d) δ=9.09-8.95 (m, 1H), 8.03-7.98 (m, 1H), 7.91-7.87 (m, 1H), 7.64-7.53 (m, 3H), 7.46-7.40 (m, 1H), 4.73-4.64 (m, 1H), 4.57-4.36 (m, 3H), 3.95-3.85 (m, 1H), 3.60-3.47 (m, 1H), 3.40-3.30 (m, 1H), 3.27-3.06 (m, 5H), 2.69-2.51 (m, 2H), 2.18-1.99 (m, 3H), 1.12-0.99 (m, 9H).

Example 59: To a mixture of 2-[(2S)-4-[2-[(1-tert-butylazetidin-2-yl)methoxy]-7-(8-chloro-1-naphthyl)-8-fluoro-pyrido[4,3-d]pyrimidin-4-yl]piperazin-2-yl]acetonitrile (60.0 mg, 105 µmol, 1.0 eq) and 2-fluoroprop-2-enoic acid (28.2 mg, 314 µmol, 3.00 eq) in ethyl acetate (3.00 mL) was added T3P (266 mg, 418 µmol, 249 µL, 50% purity, 4.0 eq) in portion at 0° C. under N₂. The mixture was stirred at 25° C. for 30 min. The reaction mixture was quenched by addition water (2.00 mL) at 0° C. and then extracted with ethyl acetate (5.00 mL×3). The combined organic layers were washed with brine (3.00 mL), dried over sodium sulfate, filtered and concentrated under reduced pressure. The residue was purified by prep-HPLC (column: Waters Xbridge 150×25 5µ; mobile phase: [Water—ACN]; B %: 33%-63%, 10 min). Compound 2-[(2S)-4-[2-[(1-tert-butylazetidin-2-yl)methoxy]-7-(8-chloro-1-naphthyl)-8-fluoro-pyrido[4,3-d]pyrimidin-4-yl]-1-(2-fluoroprop-2-enoyl)piperazin-2-yl]acetonitrile (6.15 mg, 9.52 µmol, 9% yield, 96% purity) was obtained as a white solid. LCMS [ESI, M+1]: 646.

¹H NMR (400 MHz, chloroform-d) δ=9.12-9.00 (m, 1H), 8.04-7.99 (m, 1H), 7.91-7.86 (m, 1H), 7.65-7.52 (m, 3H), 7.46-7.40 (m, 1H), 5.56-5.37 (m, 1H), 5.33-5.24 (m, 1H), 4.96-4.77 (m, 1H), 4.75-4.65 (m, 1H), 4.52-4.37 (m, 3H), 4.33-3.58 (m, 5H), 3.26-3.14 (m, 2H), 3.08-2.94 (m, 1H), 2.92-2.76 (m, 1H), 2.19-2.03 (m, 2H), 1.07-1.00 (m, 9H).

Example 60

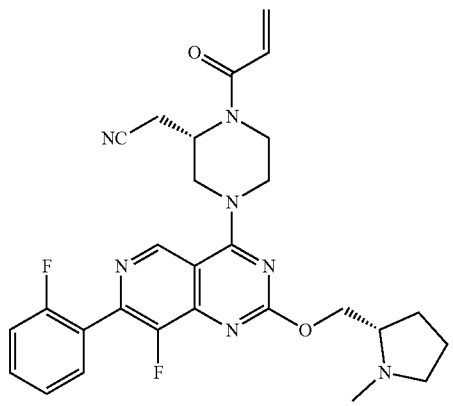 [SMILES: C=CC(=O)N1CCN(c2nc(OC[C@@H]3CCCN3C)nc3c(F)c(-c4ccccc4F)ncc23)C[C@@H]1CC#N]

2-[(2S)-4-[8-fluoro-7-(2-fluorophenyl)-2-[[(2S)-1-methylpyrrolidin-2-yl]methoxy]pyrido[4,3-d]pyrimidin-4-yl]-1-prop-2-enoyl-piperazin-2-yl]acetonitrile

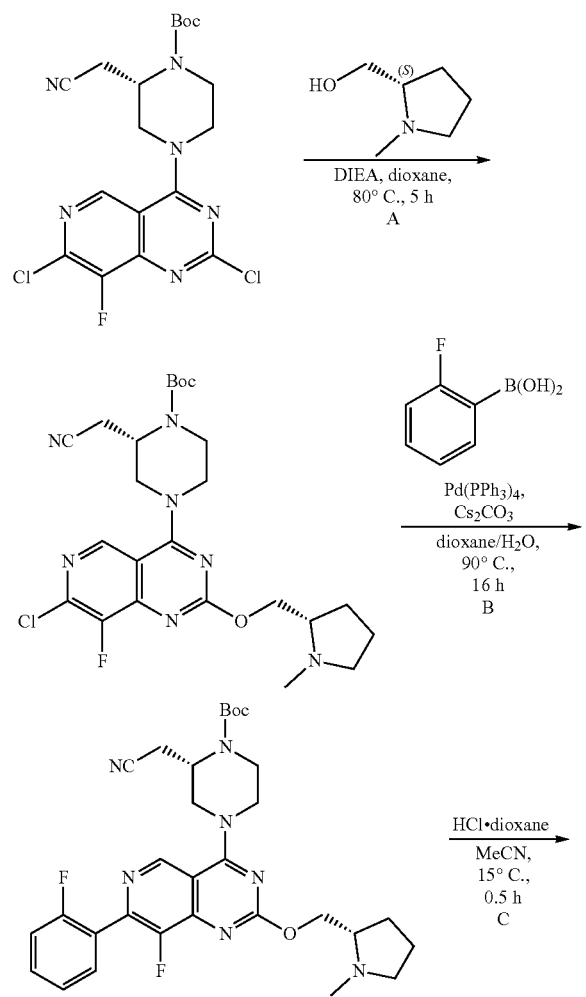

-continued

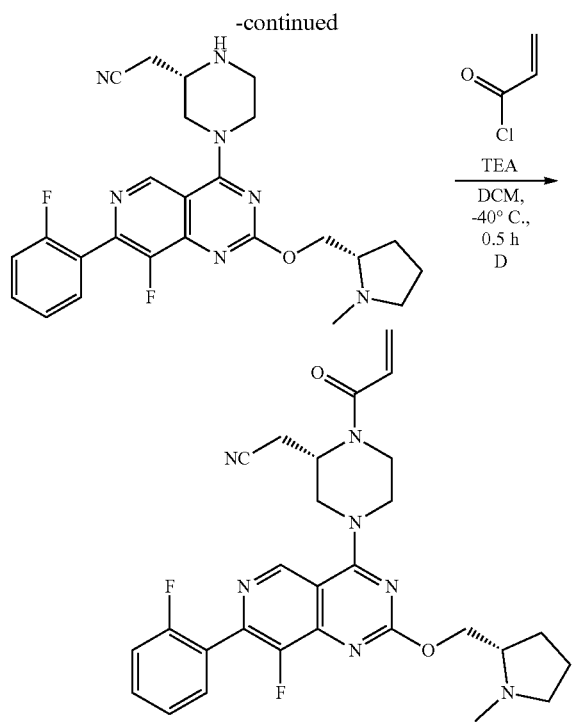

Example 60

Step A: A mixture of tert-butyl (2S)-2-(cyanomethyl)-4-(2,7-dichloro-8-fluoro-pyrido[4,3-d]pyrimidin-4-yl)piperazine-1-carboxylate (290 mg, 657 μmol, 1.0 eq), [(2S)-1-methylpyrrolidin-2-yl]methanol (151 mg, 1.31 mmol, 156 μL, 2.0 eq), DIEA (255 mg, 1.97 mmol, 343 μL, 3.0 eq) in dioxane (3.0 mL) was degassed and purged with $N_2$ for 3 times, and then the mixture was stirred at 80° C. for 5 hours under $N_2$ atmosphere. After completion, the mixture was added $H_2O$ (3 mL), the liquor was extracted with ethyl acetate (3×3 mL). The combined organic layers were dried over anhydrous $Na_2SO_4$, filtered and the filtrated was concentrated under reduced pressure to give tert-butyl (2S)-4-[7-chloro-8-fluoro-2-[[(2S)-1-methylpyrrolidin-2-yl]methoxy]pyrido[4,3-d]pyrimidin-4-yl]-2-(cyanomethyl)piperazine-1-carboxylate (330 mg, crude) as a yellow solid which was used in the next step without further purification. LCMS [ESI, M+1]: 520.

Step B: To a solution of tert-butyl (2S)-4-[7-chloro-8-fluoro-2-[[(2S)-1-methylpy rrolidin-2-yl]methoxy]pyrido[4,3-d]pyrimidin-4-yl]-2-(cyanomethyl)piperazine-1-carboxylate (300 mg, 577 μmol, 1.0 eq) and (2-fluorophenyl)boronic acid (161 mg, 1.15 mmol, 2.0 eq) in dioxane (2.5 mL) and $H_2O$ (0.5 mL) was added $Pd(PPh_3)_4$ (66.7 mg, 57.7 μmol, 0.1 eq), $Cs_2CO_3$ (376 mg, 1.15 mmol, 2.0 eq). The mixture was degassed and then heated to 90° C. for 16 hours under $N_2$. After completion, the mixture was added $H_2O$ (3 mL), the liquor was extracted with ethyl acetate (3×5 mL). The residue was purified by column chromatography ($Al_2O_3$, Petroleum ether/Ethyl acetate=1/1 to Ethyl acetate/ethanol (0.1% $NH_3H_2O$)=3:1). The desired fractions were collected and concentrated to give a residue. The crude product was purified by reversed-phase HPLC (C18, 0.1% FA in water, 0-100% MeCN) to give tert-butyl (2S)-2-(cyanomethyl)-4-[8-fluoro-7-(2-fluorophenyl)-2-[[(2S)-1-methylpyrrolidin-2-yl]methoxy]pyrido[4,3-d]pyrimidin-4-yl]piperazine-1-carboxylate (300 mg, 505 μmol, 87.6% yield, 97.7% purity) as a yellow solid. LCMS [ESI, M+1]: 580.

Step C: To a solution of tert-butyl (2S)-2-(cyanomethyl)-4-[8-fluoro-7-(2-fluorophenyl)-2-[[(2S)-1-methylpyrrolidin-2-yl]methoxy]pyrido[4,3-d]pyrimidin-4-yl]piperazine-1-carboxylate (290 mg, 500 μmol, 1.0 eq) in dichloromethane (3.0 mL) were added HCl•dioxane (4 M, 2.50 mL, 20.0 eq) at 15° C. After addition, the mixture was stirred at 15° C. for 0.5 hour. After completion, the mixture was concentrated, the residue was added to a saturated $NaHCO_3$ solution at 25° C. until pH ~8, and then extracted with ethyl acetate (3×3 mL). The combined organic layers were dried over $Na_2SO_4$, filtered and concentrated under reduced pressure to give residue. The residue was purified by prep-HPLC (column: Xtimate C18 150*25 mm*5 μm; mobile phase: [water (0.05% ammonia hydroxide v/v)—ACN]; B %: 30%-60%, 10 min). The fraction was lyophilized to give 2-[(2S)-4-[8-fluoro-7-(2-fluorophenyl)-2-[[(2S)-1-methylpyrrolidin-2-yl]methoxy]pyrido[4,3-d]pyrimidin-4-yl]piperazin-2-yl]acetonitrile (37.1 mg, 76.1 μmol, 15.2% yield, 98.3% purity) as a white solid. LCMS [ESI, M+1]: 480.

$^1$HNMR (400 MHz, chloroform-d) δ=9.03 (d, J=2.8 Hz, 1H), 7.72-7.64 (m, 1H), 7.52-7.43 (m, 1H), 7.34-7.27 (m, 1H), 7.21 (br t, J=9.2 Hz, 1H), 4.62-4.55 (m, 1H), 4.50 (br d, J=12.8 Hz, 1H), 4.42-4.32 (m, 2H), 3.57-3.46 (m, 1H), 3.31 (br s, 1H), 3.25-3.14 (m, 2H), 3.14-3.03 (m, 2H), 2.72 (br d, J=4.8 Hz, 1H), 2.66-2.51 (m, 2H), 2.50 (d, J=2.4 Hz, 3H), 2.34-2.23 (m, 1H), 2.11-1.96 (m, 2H), 1.91-1.70 (m, 3H).

Example 60: To a solution of 2-[(2S)-4-[8-fluoro-7-(2-fluorophenyl)-2-[[(2S)-1-methylpyrrolidin-2-yl]methoxy]pyrido[4,3-d]pyrimidin-4-yl]piperazin-2-yl]acetonitrile (120 mg, 250 μmol, 1.0 eq) and TEA (76.0 mg, 751 μmol, 104 μL, 3.0 eq) in dichloromethane (3.0 mL) were added prop-2-enoyl chloride (45.3 mg, 501 μmol, 40.8 μL, 2.0 eq) at −40° C. After addition, the mixture was stirred at −40° C. for 0.5 hour. After completion, the mixture was added $H_2O$ (3 mL), the liquor was extracted with ethyl acetate (3×3 mL). The combined organic layers were dried over anhydrous $Na_2SO_4$, filtered and the filtrate was concentrated under reduced pressure to give a residue. The residue was purified by prep-HPLC (column: Xtimate C18 150*25 mm*5 μm; mobile phase: [water (0.05% ammonia hydroxide v/v)—ACN]; B %: 30%-60%, 10 min). The fraction was lyophilized to give 2-[(2S)-4-[8-fluoro-7-(2-fluorophenyl)-2-[[(2S)-1-methylpyrrolidin-2-yl]methoxy]pyrido[4,3-d]pyrimidin-4-yl]-1-prop-2-enoyl-piperazin-2-yl]acetonitrile (49.1 mg, 91.5 μmol, 39.9% yield, 99.6% purity) as a off-white solid. LCMS [ESI, M+1]: 534.

$^1$H NMR (400 MHz, chloroform-d) δ=9.10 (s, 1H), 7.68 (br t, J=7.2 Hz, 1H), 7.54-7.44 (m, 1H), 7.35-7.28 (m, 1H), 7.23 (br t, J=9.2 Hz, 1H), 6.66-6.52 (m, 1H), 6.47-6.36 (m, 1H), 5.85 (br d, J=10.4 Hz, 1H), 5.14-4.87 (m, 1H), 4.60 (br dd, J=4.6, 10.8 Hz, 1H), 4.52-4.34 (m, 3H), 4.19-3.84 (m, 2H), 3.74 (br d, J=4.8 Hz, 1H), 3.11 (br t, J=7.6 Hz, 1H), 3.05-2.90 (m, 1H), 2.87-2.64 (m, 2H), 2.55-2.47 (m, 3H), 2.36-2.23 (m, 1H), 2.14-1.99 (m, 1H), 1.94-1.57 (m, 4H).

Example 61

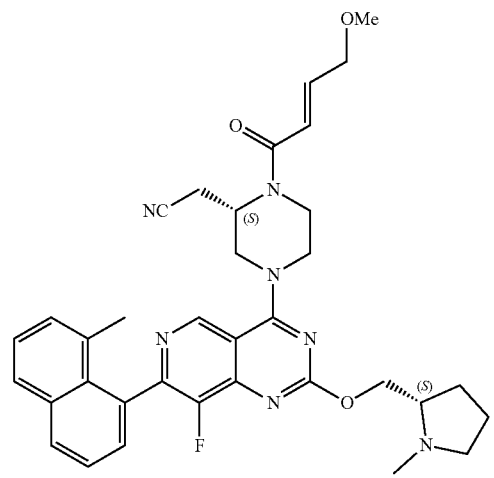

2-[(2S)-4-[8-fluoro-7-(8-methyl-1-naphthyl)-2-[[(2S)-1-methylpyrrolidin-2-yl]methoxy]pyrido[4,3-d]pyrimidin-4-yl]-1-[(E)-4-methoxybut-2-enoyl]piperazin-2-yl]acetonitrile

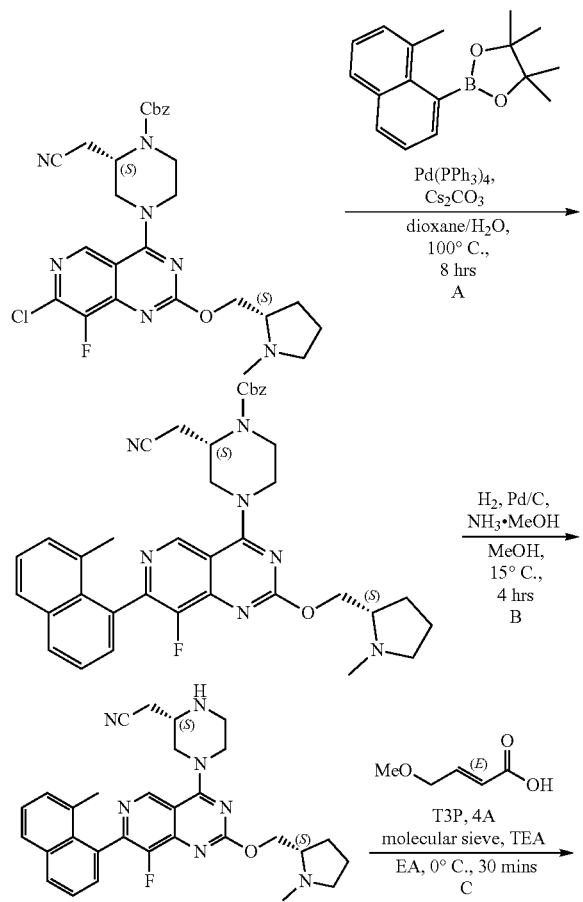

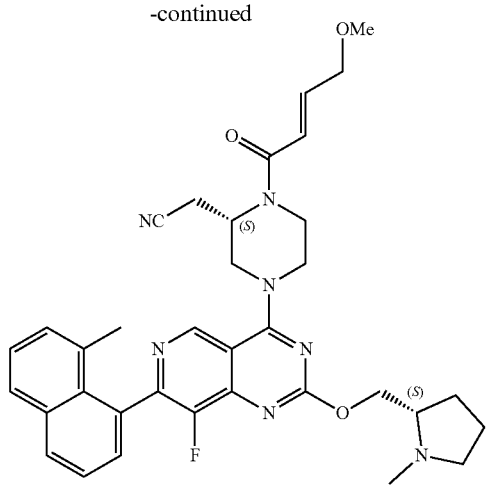

Example 61

Step A: To a solution of benzyl (2S)-4-[7-chloro-8-fluoro-2-[[(2S)-1-methylpyrrolidin-2-yl]methoxy]pyrido[4,3-d]pyrimidin-4-yl]-2-(cyanomethyl)piperazine-1-carboxylate (300 mg, 542 µmol, 1.0 eq), 4,4,5,5-tetramethyl-2-(8-methyl-1-naphthyl)-1,3,2-dioxaborolane (174 mg, 650 µmol, 1.2 eq) and $Cs_2CO_3$ (353 mg, 1.08 mmol, 2.0 eq) in dioxane (3.0 mL) and $H_2O$ (1.0 mL) was added Pd(PPh$_3$)$_4$ (62.6 mg, 54.2 µmol, 0.10 eq) under $N_2$, after stirring at 100° C. for 8 hours under $N_2$. The mixture was diluted with ethyl acetate (7.0 mL) and water (8.0 mL) then separated. The aqueous phase was extracted with ethyl acetate (2×8.0 mL) and the combined organic layers were washed with saturated brine (10.0 mL), dried over $Na_2SO_4$, filtered and concentrated under vacuum. The residue was purified by reversed phase flash [water (FA, 0.1%)/acetonitrile]. The desired fractions were collected and neutralized with $NaHCO_3$ solid and extracted with ethyl acetate (2×15.0 mL). The combined organic phase was washed with saturated brine (15.0 mL), dried over anhydrous $Na_2SO_4$, filtered and concentrated under vacuum to give benzyl(2S)-2-(cyanomethyl)-4-[8-fluoro-7-(8-methyl-1-naphthyl)-2-[[(2S)-1-methylpyrrolidin-2-yl]methoxy]pyrido[4,3-d]pyrimidin-4-yl]piperazine-1-carboxylate (82 mg, 104 µmol, 19% yield, 84% purity) as a yellow solid. LCMS [ESI, M+1]: 660.

Step B: To a solution of benzyl (2S)-2-(cyanomethyl)-4-[8-fluoro-7-(8-methyl-1-naphthyl)-2-[[(2S)-1-methylpyrrolidin-2-yl]methoxy]pyrido[4,3-d]pyrimidin-4-yl]piperazine-1-carboxylate (82.0 mg, 124 µmol, 1.0 eq) in methanol (6.0 mL) was added Pd/C (15.0 mg, 10% purity) and $NH_3$·MeOH (6.0 mL, 20% purity), after stirring at 15° C. under $H_2$ at 15 psi for 4 hours. The reaction mixture was filtered through a pad of Celite® and concentrated in vacuum to give 2-[(2S)-4-[8-fluoro-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (62.0 mg, crude) as a yellow solid which was used into next step without further purification. LCMS [ESI, M+1]: 526.

Example 61: To a solution of 2-[(2S)-4-[8-fluoro-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (62.0 mg, crude), (E)-4-methoxybut-2-enoic acid (41.5 mg, 354 μmol), TEA (95.5 mg, 944 μmol, 131 uL) and 4A MOLECULAR SIEVE (15 mg) in ethyl acetate (3.0 mL) was added T3P (225 mg, 354 μmol, 210 μL, 50% purity in EtOAc) at 0° C., after stirring at 0° C. for 30 mins. The mixture was filtered, diluted with ethyl acetate (8.0 mL) and water (7.0 mL), then separated. The aqueous phase was extracted with ethyl acetate (3×8.0 mL) and dried over Na₂SO₄, filtered and concentrated under vacuum. The residue was purified by column chromatography (Al₂O₃, ethyl acetate/methanol=10/1). The desired fraction was collected and concentrated under vacuum. The residue was purified by prep-HPLC (column: Xtimate C18 150*25 mm*5 μm; mobile phase: [water (0.05% ammonia hydroxide v/v)—ACN]; B %: 40%-70%, 10 min). The desired fraction was collected and concentrated under vacuum to remove acetonitrile. The residue was lyophilized to give 2-[(2S)-4-[8-fluoro-7-(8-methyl-1-naphthyl)-2-[[(2S)-1-methylpyrrolidin-2-yl]methoxy]pyrido[4,3-d]pyrimidin-4-yl]-1-[(E)-4-methoxybut-2-enoyl]piperazin-2-yl]acetonitrile (4.28 mg, 10.5 μmol, two steps 5.5% yield, 96% purity) as a white solid. LCMS [ESI, M+1]: 624.

¹H NMR (400 MHz, chloroform-d) δ=9.15-9.05 (m, 1H), 8.06-7.95 (m, 1H), 7.87-7.79 (m, 1H), 7.59-7.37 (m, 4H), 7.07-6.98 (m, 1H), 6.61-6.50 (m, 1H), 5.16-4.78 (m, 1H), 4.74-4.26 (m, 4H), 4.24-3.59 (m, 6H), 3.52-3.33 (m, 3H), 3.31-2.62 (m, 4H), 2.59-2.40 (m, 3H), 2.36-2.24 (m, 1H), 2.15-2.00 (m, 4H), 1.86-1.73 (m, 3H).

Example 62

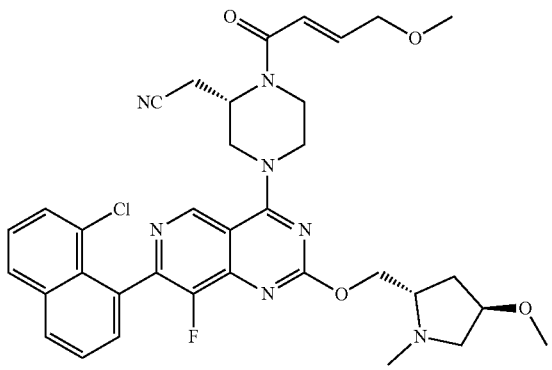 [SMILES: COC/C=C/C(=O)N1CCN(c2nc(OC[C@@H]3C[C@@H](OC)CN3C)nc3c(F)c(-c4cccc5cccc(Cl)c45)ncc23)C[C@@H]1CC#N]

2-((S)-4-(7-(8-chloronaphthalen-1-yl)-8-fluoro-2-(((2S,4R)-4-methoxy-1-methylpyrrolidin-2-yl)methoxy)pyrido[4,3-d]pyrimidin-4-yl)-1-((E)-4-methoxybut-2-enoyl)piperazin-2-yl)acetonitrile

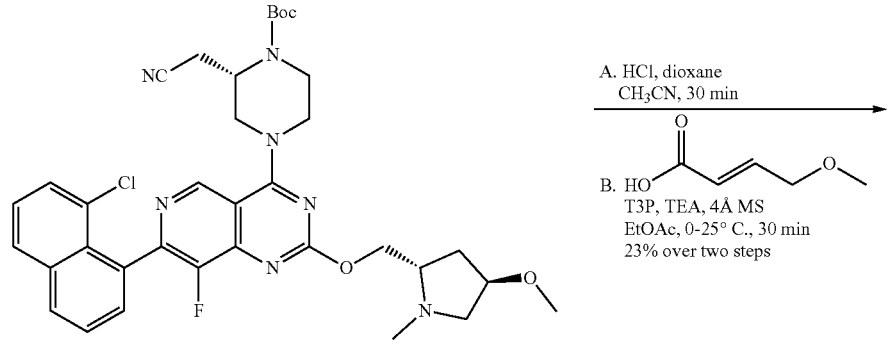

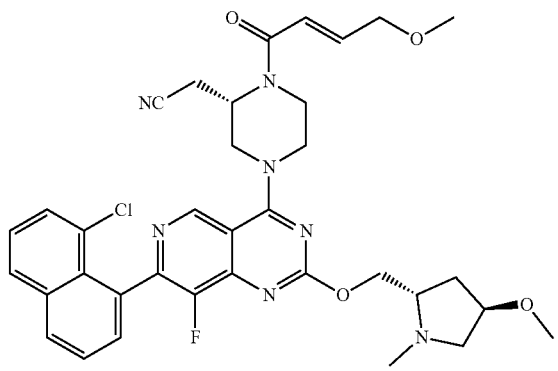

Example 62

Step A: To a solution of tert-butyl (S)-4-(7-(8-chloronaphthalen-1-yl)-8-fluoro-2-(((2S,4R)-4-methoxy-1-methylpyrrolidin-2-yl)methoxy)pyrido[4,3-d]pyrimidin-4-yl)-2-(cyanomethyl)piperazine-1-carboxylate (30 mg, 41.9 μmol, 1.0 equiv) in MeCN (1.5 mL) was added HCl (4 M in dioxane, 4.5 mL, 430 equiv) at 25° C. and the mixture was stirred for 30 min. Concentration under reduced pressure provided the crude residue. The residue was diluted with saturated NaHCO₃ solution and was extracted with ethyl acetate (2×10 mL). The combined organic layer was dried over sodium sulfate, filtered and concentrated under reduced pressure. The residue was purified by prep-HPLC; Xtimate C18 150*25 mm*5 um, A: [water (0.05% ammonia hydroxide v/v)], B: ACN, B %: 32%-62%. The desired fractions were combined and concentrated under reduced pressure to remove ACN and then lyophilized to afford 2-((S)-4-(7-(8-chloronaphthalen-1-yl)-8-fluoro-2-(((2S,4R)-4-methoxy-1-methylpyrrolidin-2-yl)methoxy)pyrido[4,3-d]pyrimidin-4-yl)piperazin-2-yl)acetonitrile (4.75 mg, 7.49 μmol, 18% yield, 97% purity) was obtained as a white solid. LCMS [ESI, M+1]: 616. ¹H NMR (400 MHz, CDCl₃) δ=9.01 (s, 1H), 8.04-7.99 (m, 1H), 7.89 (d, J=8.0 Hz, 1H), 7.65-7.53 (m, 3H), 7.47-7.40 (m, 1H), 5.29-5.16 (m, 1H), 4.61-4.34 (m, 2H), 4.10-3.97 (m, 2H), 3.65-3.47 (m, 1H), 3.45-3.31 (m, 3H), 3.29-3.06 (m, 3H), 3.02-2.86 (m, 2H), 2.68-2.57 (m, 2H), 2.57-2.42 (m, 3H), 2.23-2.12 (m, 2H), 2.06-1.85 (m, 3H), 1.85-1.73 (m, 3H).

Example 62: To a solution of 2-((S)-4-(7-(8-chloronaphthalen-1-yl)-8-fluoro-2-(((2S,4R)-4-methoxy-1-methylpyrrolidin-2-yl)methoxy)pyrido[4,3-d]pyrimidin-4-yl)piperazin-2-yl)acetonitrile (55 mg, 89.3 μmol, 1.0 equiv), 2-fluoroprop-2-enoic acid (24.1 mg, 268 μmol, 3.0 equiv) in ethyl acetate (10 mL) was added 4 Å molecular sieve (10 mg) and the mixture was stirred at 25° C. for 10 min. The mixture was cooled to 0° C. and was added Et₃N (81.3 mg, 803 μmol, 112 μL, 9.0 equiv) and T3P (227 mg, 357 μmol, 212 μL, 50% purity it EtOAc, 4.0 equiv) and the mixture was stirred at 0° C. for 30 min. The mixture was diluted with water (5 mL) and extracted with ethyl acetate (2×10 mL). The combined organic layer was washed with brine (30 mL), dried over anh Na₂SO₄, filtered and concentrated under reduced pressure. The residue was purified by prep-HPLC; Waters Xbridge 150*50 10 μm; A: [water (0.05% ammonia hydroxide v/v)], B: ACN, B %: 42%-72%, over 10 min. The desired fractions were concentrated under reduced pressure to remove ACN and then were lyophilized to afford 2-((S)-4-(7-(8-chloronaphthalen-1-yl)-8-fluoro-2-(((2S,4R)-4-methoxy-1-methylpyrrolidin-2-yl)methoxy)pyrido[4,3-d]pyrimidin-4-yl)-1-((E)-4-methoxybut-2-enoyl)piperazin-2-yl)acetonitrile (17.6 mg, 24.9 μmol, 28% yield, 98% purity) was obtained as a white solid. LCMS [ESI, M+1]: 689. ¹H NMR (400 MHz, CDCl₃) δ=9.06 (s, 1H), 8.09-7.98 (m, 1H), 7.90 (d, J=8.0 Hz, 1H), 7.67-7.52 (m, 3H), 7.48-7.38 (m, 1H), 5.59-5.38 (m, 1H), 5.34-5.17 (m, 2H), 4.98-4.74 (m, 1H), 4.55-4.35 (m, 2H), 4.35-4.14 (m, 1H), 4.12-3.90 (m, 3H), 3.89-3.61 (m, 2H), 3.39 (br t, J=11.6 Hz, 2H), 3.10-2.80 (m, 4H), 2.60-2.39 (m, 3H), 2.3-2.1 (m, 2H), 2.02-1.87 (m, 2H), 1.83-1.72 (m, 2H), 1.70-1.61 (m, 2H).

Example 63

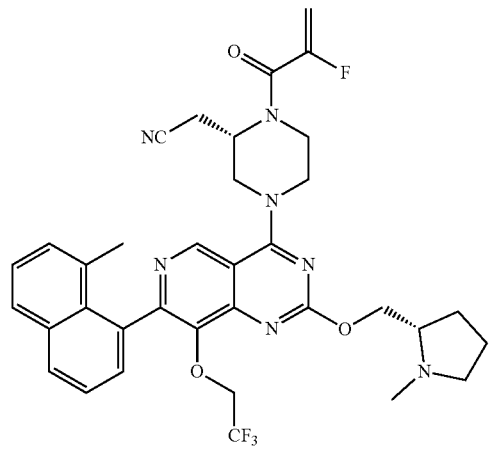

2-((S)-1-(2-fluoroacryloyl)-4-(7-(8-methylnaphthalen-1-yl)-2-(((S)-1-methylpyrrolidin-2-yl)methoxy)-8-(2,2,2-trifluoroethoxy)pyrido[4,3-d]pyrimidin-4-yl)piperazin-2-yl)acetonitrile

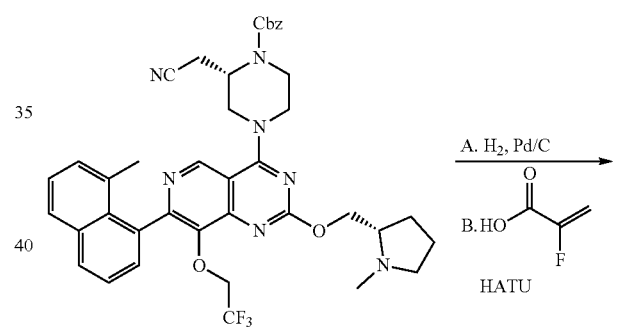

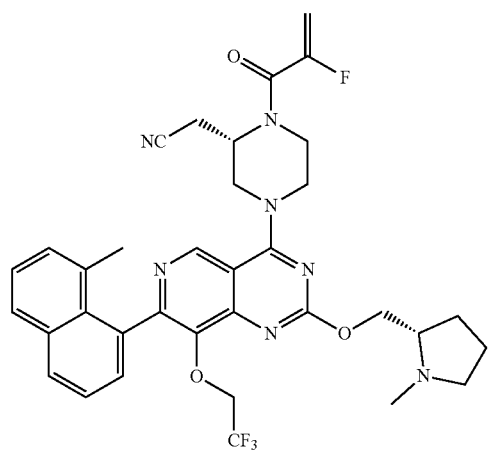 [SMILES: C=C(F)C(=O)N1CCN(c2nc(OC[C@@H]3CCCN3C)nc3c(OCC(F)(F)F)c(-c4cccc5cccc(C)c45)ncc23)C[C@@H]1CC#N]

Example 63

Step A: A mixture of benzyl (2S)-2-(cyanomethyl)-4-[7-(8-methyl-1-naphthyl)-2-[[(2S)-1-methylpyrrolidin-2-yl]methoxy]-8-(2,2,2-trifluoroethoxy)pyrido[4,3-d]pyrimidin-4-yl]piperazine-1-carboxylate (50 mg, 67.6 μmol, 1.0 equiv), Pd/C (0.01 g, 10% wt/wt) in NH₃ (3 mL, 20% in MeOH) and methanol (3.0 mL) was stirred at 15° C. for 0.5 hour under H₂ (15 psi). The system was flushed with nitrogen and was filtered and concentrated under vacuum. The residue was purified by prep-HPLC [column: Waters Xbridge 150*50 10 μm; water (0.05% ammonia hydroxide v/v)—ACN]; ACN: 27%-57%, 10 min] to afford 2-[(2S)-4-[7-(8-methyl-1-naphthyl)-2-[[(2S)-1-methylpyrrolidin-2-yl]methoxy]-8-(2,2,2-trifluoroethoxy)pyrido[4,3-d]pyrimidin-4-yl]piperazin-2-yl]acetonitrile (15.3 mg, 25.2 umol, 37% yield, 99.6% purity) as a white solid. LCMS [ESI, M/2+1, M+1]: 304, 606. ¹H NMR (400 MHz, chloroform-d): δ 9.01 (s, 1H), 7.95 (d, J=8.0 Hz, 1H), 7.80 (d, J=8.0 Hz, 1H), 7.51 (t, J=7.6 Hz, 1H), 7.44-7.36 (m, 2H), 7.26-7.23 (m, 1H), 4.73-4.59 (m, 2H), 4.58-4.45 (m, 2H), 4.45-4.30 (m, 2H), 3.62-3.46 (m, 1H), 3.35 (m, 1H), 3.26-3.05 (m, 4H), 2.77-2.68 (m, 1H), 2.67-2.53 (m, 2H), 2.49 (s, 3H), 2.35-2.26 (m, 1H), 2.13-2.04 (m, 1H), 2.01 (s, 3H), 1.93-1.75 (m, 3H).

Example 63: To a mixture of 2-[(2S)-4-[7-(8-methyl-1-naphthyl)-2-[[(2S)-1-methylpyrrolidin-2-yl]methoxy]-8-(2,2,2-trifluoroethoxy)pyrido[4,3-d]pyrimidin-4-yl]piperazin-2-yl]acetonitrile (100 mg, 165 μmol, 1.0 equiv), 2-fluoroprop-2-enoic acid (44.6 mg, 495 μmol, 3.0 equiv) and DIEA (128 mg, 991 μmol, 173 μL, 6.0 equiv) in dichloromethane (3.0 mL) was added HATU (188 mg, 495 μmol, 3 equiv). After stirring at 15° C. for 0.5 h the mixture was diluted with water (5.0 mL) and the mixture was extracted with dichloromethane (2×5.0 mL). The combined organic layer washed with brine (5.0 mL), dried over anh Na₂SO₄, filtered and concentrated under vacuum. The residue was purified by prep-HPLC [column: Waters Xbridge 150*50 10 μm; water (0.05% ammonia hydroxide v/v); ACN: 48%-78%, 10 min] to give 2-[(2S)-1-(2-fluoroprop-2-enoyl)-4-[7-(8-methyl-1-naphthyl)-2-[[(2S)-1-methylpyrrolidin-2-yl]methoxy]-8-(2,2,2-trifluoroethoxy)pyrido[4,3-d]pyrimidin-4-yl]piperazin-2-yl]acetonitrile (15.7 mg, 22.5 μmol, 14% yield, 97.1% purity) as a yellow solid. LCMS [ESI, M/2+1, M+1]: 340, 678. ¹H NMR (400 MHz, chloroform-d) δ=9.06 (d, J=3.2 Hz, 1H), 7.96 (d, J=8.4 Hz, 1H), 7.81 (d, J=8.4 Hz, 1H), 7.52 (dt, J=2.8, 7.6 Hz, 1H), 7.43-7.37 (m, 2H), 7.26-7.24 (m, 1H), 5.56-5.40 (m, 1H), 5.34-5.25 (m, 1H), 4.88 (br s, 1H), 4.69-4.22 (m, 7H), 4.04 (m, 1H), 3.76 (m, 2H), 3.15 (br s, 1H), 3.07-2.98 (m, 1H), 2.85 (m, 1H), 2.75 (br s, 1H), 2.51 (s, 3H), 2.33 (m, 1H), 2.13-2.05 (m, 1H), 2.00 (d, J=7.6 Hz, 3H), 1.89-1.77 (m, 3H).

Following the teachings of the General Reaction Schemes and Example 1-63 and using intermediates 1-61, A-1 to A-10, B1 to B26, C1 to C12 and D1 to D9, E1 to E29 and F1 to F137, Examples 64-210 were prepared and listed in Table 3.

TABLE 3

Examples 64 to 210

| Int. # | Structure | Characterization Data |
| --- | --- | --- |
| 64 | (S)-2-(4-(7-(8-chloronaphthalen-1-yl)-8-fluoro-2-((1-(tetrahydro-2H-pyran-4-yl)piperidin-4-yl)oxy)pyrido[4,3-d]pyrimidin-4-yl)-1-(2-fluoroacryloyl)piperazin-2-yl)acetonitrile | LCMS [ESI, M + 1]: 689<br>¹H NMR (400 MHz, CDCl₃) δ = 9.06 (s, 1H), 8.09-7.98 (m, 1H), 7.90 (d, J = 8.0 Hz, 1H), 7.67-7.52 (m, 3H), 7.48-7.38 (m, 1H), 5.59-5.38 (m, 1H), 5.34-5.17 (m, 2H), 4.98-4.74 (m, 1H), 4.55-4.35 (m, 2H), 4.35-4.14 (m, 1H), 4.12-3.90 (m, 3H), 3.89-3.61 (m, 2H), 3.39 (br t, J = 11.6 Hz, 2H), 3.10-2.80 (m, 4H), 2.60-2.39 (m, 3H), 2.3-2.1 (m, 2H), 2.02-1.87 (m, 2H), 1.83-1.72 (m, 2H), 1.70-1.61 (m, 2H). |

TABLE 3-continued

Examples 64 to 210

| Int. # | Structure | Characterization Data |
|---|---|---|
| 65 | 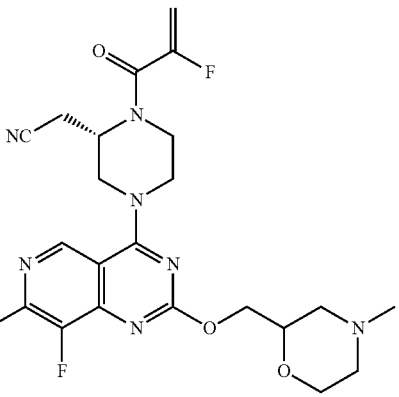<br>2-((2S)-4-(7-(8-chloronaphthalen-1-yl)-8-fluoro-2-((4-methylmorpholin-2-yl)methoxy)pyrido[4,3-d]pyrimidin-4-yl)-1-(2-fluoroacryloyl)piperazin-2-yl)acetonitrile | LCMS [ESI, M + 1]: 634<br>$^1$H NMR (400 MHz, CDCl$_3$) δ = 9.07 (s, 1H), 8.02 (d, J = 7.6 Hz, 1H), 7.90 (d, J = 8.0 Hz, 1H), 7.67-7.53 (m, 3H), 7.47-7.40 (m, 1H), 5.59-5.38 (m, 1H), 5.33-5.23 (m, 1H), 4.97-4.75 (m, 1H), 4.65-4.38 (m, 4H), 4.34-4.15 (m, 1H), 4.13-3.88 (m, 3H), 3.86-3.56 (m, 3H), 3.09-2.95 (m, 1H), 2.93-2.78 (m, 2H), 2.67 (br d, J = 11.6 Hz, 1H), 2.33 (s, 3H), 2.25-2.14 (m, 1H), 2.12-2.00 (m, 1H) |
| 66 | 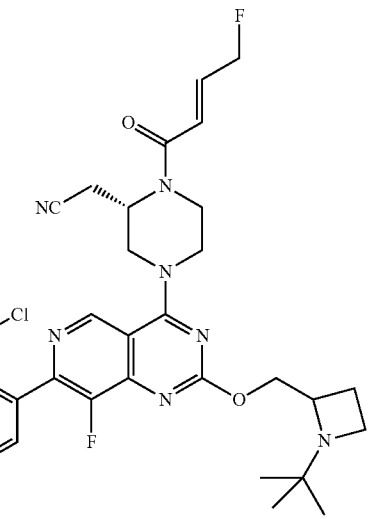<br>2-((2S)-4-(2-((1-(tert-butyl)azetidin-2-yl)methoxy)-7-(8-chloronaphthalen-1-yl)-8-fluoropyrido[4,3-d]pyrimidin-4-yl)-1-((E)-4-fluorobut-2-enoyl)piperazin-2-yl)acetonitrile | LCMS [ESI, M + 1]: 660<br>$^1$H NMR (400 MHz, CDCl$_3$) δ = 9.06 (s, 1H), 8.04-7.99 (m, 1H), 7.91-7.86 (m, 1H), 7.64-7.53 (m, 3H), 7.46-7.40 (m, 1H), 7.09-6.94 (m, 1H), 6.66-6.47 (m, 1H), 5.21-4.95 (m, 3H), 4.75-4.61 (m, 1H), 4.52-4.35 (m, 3H), 4.22-3.56 (m, 5H), 3.23-3.14 (m, 2H), 3.06-2.71 (m, 2H), 2.15-2.03 (m, 2H), 1.02 (s, 9H) |

TABLE 3-continued

Examples 64 to 210

| Int. # | Structure | Characterization Data |
|---|---|---|
| 67 | 2-((S)-4-(7-(5-chloroisoquinolin-4-yl)-8-fluoro-2-(((2S,4R)-4-methoxy-1-methylpyrrolidin-2-yl)methoxy)pyrido[4,3-d]pyrimidin-4-yl)-1-((E)-4-fluorobut-2-enoyl)piperazin-2-yl)acetonitrile | LCMS [ESI, M + 1]: 660<br>$^1$H NMR (400 MHz, CD$_3$CO$_2$D) δ = 9.66-9.47 (m, 2H), 8.63 (br d, J = 2.8 Hz, 1H), 8.32 (d, J = 8.4 Hz, 1H), 8.01-7.91 (m, 1H), 7.79 (t, J = 8.0 Hz, 1H), 7.17-6.99 (m, 1H), 6.88-6.67 (m, 1H), 5.25-5.05 (m, 3H), 5.04-4.77 (m, 3H), 4.76-4.61 (m, 1H), 4.34-3.93 (m, 6H), 3.45-3.30 (m, 4H), 3.22-3.15 (m, 3H), 3.14-2.94 (m, 2H), 2.57-2.44 (m, 1H), 2.40-2.16 (m, 2H). |
| 68 | (S)-2-(4-(7-(8-chloronaphthalen-1-yl)-2-(2-(dimethylamino)ethoxy)-8-fluoropyrido[4,3-d]pyrimidin-4-yl)-1-(2-fluoroacryloyl)piperazin-2-yl)acetamide | LCMS [ESI, M + 1]: 592<br>$^1$H NMR (400 MHz, CDCl$_3$) δ = 9.07 (s, 1H), 8.02 (dd, J = 2.0, 8.0 Hz, 1H), 7.90 (d, J = 8.0 Hz, 1H), 7.67-7.51 (m, 3H), 7.44 (td, J = 2.0, 7.6 Hz, 1H), 5.48 (dd, J = 2.0, 7.6 Hz, 1H), 5.29 (dd, J = 3.6, 16.8 Hz, 1H), 4.98-4.75 (m, 1H), 4.64 (t, J = 5.6 Hz, 2H), 4.53-4.40 (m, 2H), 4.35-3.91 (m, 2H), 3.90-3.61 (m, 2H), 3.08-2.94 (m, 1H), 2.92-2.75 (m, 3H), 2.36 (s, 6H) |
| 69 | 1-((S)-4-(7-(8-chloronaphthalen-1-yl)-8-fluoro-2-(((S)-1-methylpyrrolidin-2-yl)methoxy)pyrido[4,3-d]pyrimidin-4-yl)-3-methylpiperazin-1-yl)prop-2-en-1-one | LCMS [ESI, M + 1]: 575<br>$^1$H NMR (400 MHz, CDCl$_3$) δ = 9.01 (s, 1H), 8.07-7.98 (m, 1H), 7.89 (d, J = 8.4 Hz, 1H), 7.68-7.53 (m, 3H), 7.49-7.39 (m, 1H), 6.71-6.51 (m, 1H), 6.47-6.34 (m, 1H), 5.81 (br d, J = 10.4 Hz, 1H), 5.07-4.86 (m, 1H), 4.78-4.33 (m, 4H), 4.13-3.79 (m, 1H), 3.78-3.50 (m, 2H), 3.35-3.03 (m, 2H), 2.92-2.71 (m, 1H), 2.55 (s, 3H), 2.41-2.25 (m, 1H), 2.17-1.98 (m, 1H), 1.96-1.78 (m, 3H), 1.54-1.46 (m, 3H) |

TABLE 3-continued

Examples 64 to 210

| Int. # | Structure | Characterization Data |
|---|---|---|
| 70 | (S)-2-(4-(7-(8-chloronaphthalen-1-yl)-8-fluoro-2-((1-methylpiperidin-4-yl)oxy)pyrido[4,3-d]pyrimidin-4-yl)-1-(2-fluoroacryloyl)piperazin-2-yl)acetonitrile | LCMS [ESI, M + 1]: 618<br>$^1$H NMR (400 MHz, CD$_3$CO$_2$D) δ = 9.59-9.47 (m, 1H), 8.17 (d, J = 8.0 Hz, 1H), 8.03 (d, J = 8.0 Hz, 1H), 7.79-7.69 (m, 1H), 7.69-7.63 (m, 2H), 7.58-7.51 (m, 1H), 5.68-5.43 (m, 2H), 5.39 (dd, J = 3.6, 17.2 Hz, 1H), 5.11-4.76 (m, 2H), 4.73-4.63 (m, 1H), 4.15 (br s, 2H), 4.14-3.73 (m, 2H), 3.33 (br t, J = 11.6 Hz, 2H), 3.19-3.06 (m, 2H), 2.95-2.90 (m, 3H), 2.22 (br s, 4H) |
| 71 | 2-((2S)-4-(7-(8-chloronaphthalen-1-yl)-8-fluoro-2-((1-methylazetidin-2-yl)methoxy)pyrido[4,3-d]pyrimidin-4-yl]-1-(2-fluoroacryloyl)piperazin-2-yl)acetonitrile | LCMS [ESI, M + 1]: 604<br>$^1$H NMR (400 MHz, CDCl$_3$) δ = 9.07 (s, 1H), 8.02 (dd, J = 1.6, 7.6 Hz, 1H), 7.90 (d, J = 8.4 Hz, 1H), 7.65-7.55 (m, 3H), 7.44 (dt, J = 2.0, 7.6 Hz, 1H), 5.59-5.37 (m, 1H), 5.29 (dd, J = 3.6, 16.8 Hz, 1H), 5.08-4.75 (m, 1H), 4.61-4.43 (m, 4H), 4.36-3.92 (m, 2H), 3.89-3.61 (m, 2H), 3.45 (br d, J = 5.6 Hz, 2H), 3.09-2.96 (m, 1H), 2.94-2.81 (m, 2H), 2.41 (d, J = 1.6 Hz, 3H), 2.20-2.05 (m, 2H) |
| 72 | 2-((2S)-1-acryloyl-4-(7-(8-chloronaphthalen-1-yl)-2-((1-cyclopropylazetidin-2-yl)methoxy)-8-fluoropyrido[4,3-d]pyrimidin-4-yl)piperazin-2-yl)acetonitrile | LCMS [ESI, M + 1]: 630<br>$^1$H NMR (400 MHz, CDCl$_3$) δ = 9.07 (s, 1H), 8.02 (dd, J = 1.6, 8.0 Hz, 1H), 7.90 (d, J = 8.0 Hz, 1H), 7.69-7.52 (m, 3H), 7.49-7.39 (m, 1H), 5.60-5.38 (m, 1H), 5.29 (dd, J = 3.6, 16.8 Hz, 1H), 5.02-4.77 (m, 1H), 4.65-4.41 (m, 4H), 4.35-3.93 (m, 2H), 3.77 (br d, J = 5.2 Hz, 3H), 3.42 (br t, J = 6.8 Hz, 1H), 3.16-2.95 (m, 2H), 2.94-2.81 (m, 1H), 2.23-2.05 (m, 2H), 1.91 (br d, J = 3.6 Hz, 1H), 0.54-0.28 (m, 4H) |

TABLE 3-continued

Examples 64 to 210

| Int. # | Structure | Characterization Data |
|---|---|---|
| 73 | 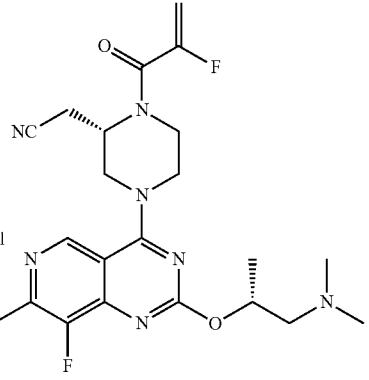<br>2-((S)-4-(7-(8-chloronaphthalen-1-yl)-2-(((R)-1-(dimethylamino)propan-2-yl)oxy)-8-fluoropyrido[4,3-d]pyrimidin-4-yl)-1-(2-fluoroacryloyl)piperazin-2-yl)acetonitrile | LCMS [ESI, M + 1]: 606<br>$^1$H NMR (400 MHz, CDCl$_3$): δ 9.08-9.05 (m, 1H), 8.05-7.99 (m, 1H), 7.90 (d, J = 8.4 Hz, 1H), 7.66-7.54 (m, 3H), 7.44 (dt, J = 2.8, 7.6 Hz, 1H), 5.68-5.57 (m, 1H), 5.57-5.39 (m, 1H), 5.35-5.23 (m, 1H), 4.95-4.75 (m, 1H), 4.54-4.40 (m, 2H), 4.35-4.11 (m, 1H), 4.10-3.91 (m, 1H), 3.91-3.59 (m, 2H), 3.10-2.96 (m, 1H), 2.94-2.71 (m, 2H), 2.46-2.39 (m, 1H), 2.34 (br d, J = 4.8 Hz, 6H), 1.46-1.40 (m, 3H) |
| 74 | 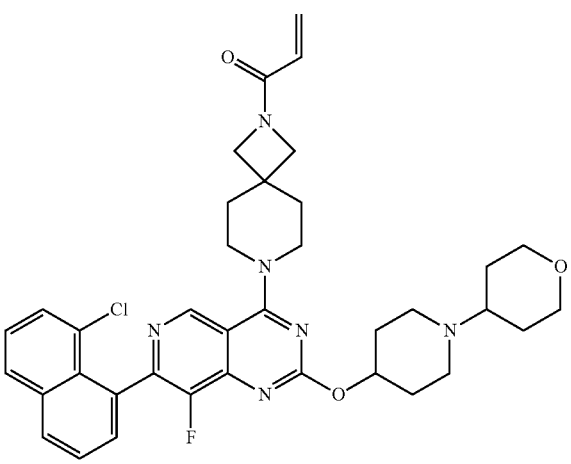<br>1-(7-(7-(8-chloronaphthalen-1-yl)-8-fluoro-2-((1-(tetrahydro-2H-pyran-4-yl)piperidin-4-yl)oxy)pyrido[4,3-d]pyrimidin-4-yl)-2,7-diazaspiro[3.5]nonan-2-yl)prop-2-en-1-one | LCMS [ESI, M + 1]: 671<br>$^1$H NMR (400 MHz, CDCl$_3$): δ 9.00 (s, 1H), 8.01 (dd, J = 1.6, 7.6 Hz, 1H), 7.89 (dd, J = 1.2, 8.0 Hz, 1H), 7.64-7.53 (m, 3H), 7.46-7.41 (m, 1H), 6.42-6.36 (m, 1H), 6.28-6.19 (m, 1H), 5.72 (dd, J = 2.0, 10.4 Hz, 1H), 5.27-5.16 (m, 1H), 4.08-3.91 (m, 8H), 3.89-3.81 (m, 2H), 3.39 (br t, J = 11.2 Hz, 2H), 3.02-2.87 (m, 2H), 2.66-2.36 (m, 3H), 2.24-1.88 (m, 8H), 1.84-1.72 (m, 2H), 1.70-1.62 (m, 2H) |

TABLE 3-continued

Examples 64 to 210

| Int. # | Structure | Characterization Data |
|---|---|---|
| 75 | 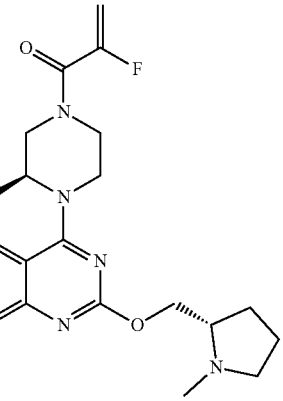<br>1-((S)-4-(7-(8-chloronaphthalen-1-yl)-8-fluoro-2-(((S)-1-methylpyrrolidin-2-yl)methoxy)pyrido[4,3-d]pyrimidin-4-yl)-3-methylpiperazin-1-yl)-2-fluoroprop-2-en-1-one | LCMS [ESI, M + 1]: 593<br>$^1$H NMR (400 MHz, CDCl$_3$): δ 9.01 (s, 1H), 8.05-7.97 (m, 1H), 7.89 (d, J = 8.0 Hz, 1H), 7.67-7.52 (m, 3H), 7.48-7.38 (m, 1H), 5.49-5.31 (m, 1H), 5.22 (dd, J = 3.6, 16.8 Hz, 1H), 5.03-4.89 (m, 1H), 4.66-4.31 (m, 4H), 4.27-3.85 (m, 1H), 3.81-3.03 (m, 4H), 2.75 (br s, 1H), 2.52 (s, 3H), 2.38-2.25 (m, 1H), 2.15-1.99 (m, 1H), 1.94-1.78 (m, 3H), 1.52 (dd, J = 6.8, 10.0 Hz, 3H) |
| 76 | 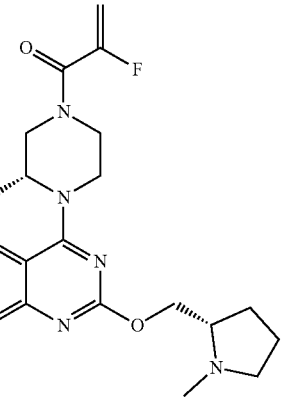<br>1-((R)-4-(7-(8-chloronaphthalen-1-yl)-8-fluoro-2-(((S)-1-methylpyrrolidin-2-yl)methoxy)pyrido[4,3-d]pyrimidin-4-yl)-3-methylpiperazin-1-yl)-2-fluoroprop-2-en-1-one | LCMS [ESI, M + 1]: 593<br>$^1$H NMR (400 MHz, CDCl$_3$): δ = 9.00 (s, 1H), 8.02 (dd, J = 2.0, 8.0 Hz, 1H), 7.90 (d, J = 8.0 Hz, 1H), 7.62-7.55 (m, 3H), 7.46-7.42 (m, 1H), 5.47-5.34 (m, 1H), 5.23 (dd, J = 3.6, 16.8 Hz, 1H), 4.99-4.94 (m, 1H), 4.61-4.35 (m, 4H), 4.27-3.85 (m, 1H), 3.78-3.10 (m, 4H), 2.74 (br s, 1H), 2.51 (s, 3H), 2.33-2.27 (m, 1H), 2.10-2.03 (m, 1H), 1.89-1.74 (m, 3H), 1.54-1.50 (m, 3H) |
| 77 | 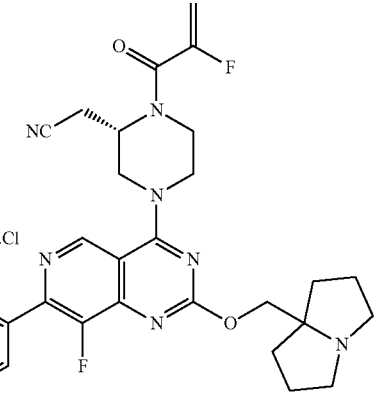<br>(S)-2-(4-(7-(8-chloronaphthalen-1-yl)-8-fluoro-2-((tetrahydro-1H-pyrrolizin-7a(5H)-yl)methoxy)pyrido[4,3-d]pyrimidin-4-yl)-1-(2-fluoroacryloyl)piperazin-2-yl)acetonitrile | LCMS [ESI, M + 1]: 644<br>$^1$H NMR (400 MHz, CDCl$_3$): δ = 9.05 (s, 1H), 8.01 (dd, J = 1.6, 7.6 Hz, 1H), 7.89 (d, J = 8.0 Hz, 1H), 7.66-7.52 (m, 3H), 7.43 (dt, J = 2.4, 7.6 Hz, 1H), 5.61-5.38 (m, 1H), 5.29 (dd, J = 3.6, 16.8 Hz, 1H), 5.07-4.65 (m, 1H), 4.60-4.39 (m, 2H), 4.37-4.25 (m, 2H), 4.23-3.30 (m, 4H), 3.16 (br d, J = 4.4 Hz, 2H), 3.08-2.97 (m, 1H), 2.95-2.83 (m, 1H), 2.72-2.62 (m, 2H), 2.08 (br dd, J = 6.4, 12.4 Hz, 2H), 1.90 (quin, J = 6.4 Hz, 4H), 1.74-1.65 (m, 2H) |

TABLE 3-continued

Examples 64 to 210

| Int. # | Structure | Characterization Data |
|---|---|---|
| 78 | 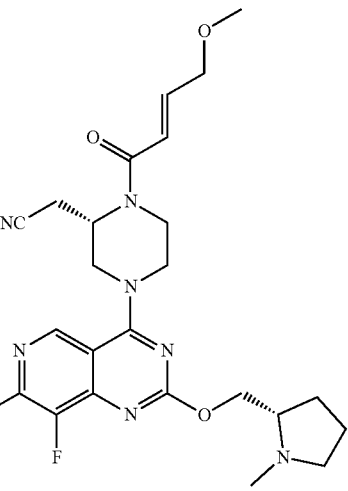<br>2-((S)-4-(7-(8-chloronaphthalen-1-yl)-8-fluoro-2-(((S)-1-methylpyrrolidin-2-yl)methoxy)pyrido[4,3-d]pyrimidin-4-yl)-1-((E)-4-methoxybut-2-enoyl)piperazin-2-yl)acetonitrile | LCMS [ESI, M + 1]: 646<br>$^1$H NMR (400 MHz, CDCl$_3$): δ 9.09 (s, 1H), 8.06-8.01 (m, 1H), 7.91 (d, J = 8.4 Hz, 1H), 7.67-7.55 (m, 3H), 7.45 (dt, J = 2.0, 7.8 Hz, 1H), 7.03 (br d, J = 14.8 Hz, 1H), 6.57 (br d, J = 15.2 Hz, 1H), 5.18-4.94 (m, 1H), 4.66-4.58 (m, 1H), 4.54-4.37 (m, 3H), 4.25-3.66 (m, 6H), 3.46 (s, 3H), 3.13 (br t, J = 7.6 Hz, 1H), 3.06-2.93 (m, 1H), 2.89-2.70 (m, 2H), 2.52 (d, J = 1.6 Hz, 3H), 2.38-2.25 (m, 1H), 2.13-2.02 (m, 1H), 1.90-1.75 (m, 3H) |
| 79 | 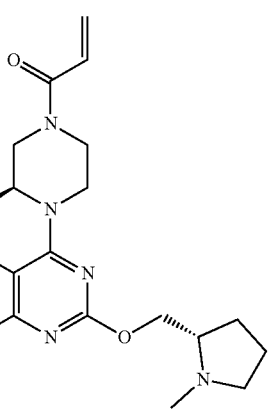<br>1-((3S)-4-(8-fluoro-7-(5-methyl-1H-indazol-4-yl)-2-(((S)-1-methylpyrrolidin-2-yl)methoxy)pyrido[4,3-d]pyrimidin-4-yl)-3-methylpiperazin-1-yl)prop-2-en-1-one | LCMS [ESI, M + 1]: 545<br>$^1$H NMR (400 MHz, CDCl$_3$): δ = 10.29 (br s, 1H), 9.11 (s, 1H), 7.82 (s, 1H), 7.54-7.48 (m, 1H), 7.41-7.34 (m, 1H), 6.71-6.52 (m, 1H), 6.45-6.36 (m, 1H), 5.85-5.77 (m, 1H), 5.07-4.87 (m, 1H), 4.78-4.43 (m, 3H), 4.40 (br dd, J = 6.4, 10.4 Hz, 1H), 4.12-3.82 (m, 1H), 3.80-3.48 (m, 2H), 3.35-3.04 (m, 2H), 2.80-2.68 (m, 1H), 2.51 (s, 3H), 2.40 (d, J = 1.2 Hz, 3H), 2.34-2.26 (m, 1H), 2.12-2.01 (m, 1H), 1.93-1.76 (m, 3H), 1.51 (br s, 3H) |

TABLE 3-continued

Examples 64 to 210

| Int. # | Structure | Characterization Data |
|---|---|---|
| 80 | 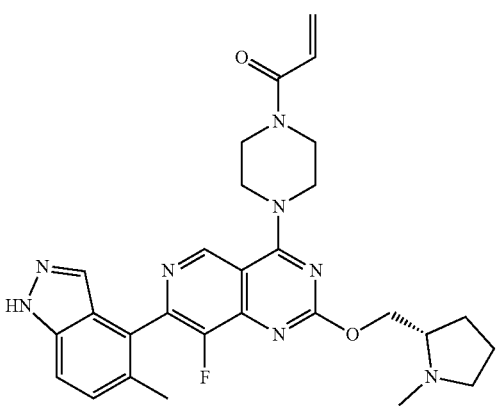<br>1-(4-(8-fluoro-7-(5-methyl-1H-indazol-4-yl)-2-(((S)-1-methylpyrrolidin-2-yl)methoxy)pyrido[4,3-d]pyrimidin-4-yl)piperazin-1-yl)prop-2-en-1-one | LCMS [ESI, M + 1]: 531<br>$^1$H NMR (400 MHz, CDCl$_3$): δ 10.35 (br s, 1H), 9.15 (s, 1H), 7.81 (s, 1H), 7.55-7.47 (m, 1H), 7.37 (d, J = 8.4 Hz, 1H), 6.61 (dd, J = 10.4, 16.8 Hz, 1H), 6.40 (dd, J = 1.6, 16.8 Hz, 1H), 5.81 (dd, J = 2.0, 10.4 Hz, 1H), 4.60 (dd, J = 4.8, 10.8 Hz, 1H), 4.41 (dd, J = 6.4, 10.8 Hz, 1H), 4.08 (br s, 4H), 4.02-3.81 (m, 4H), 3.16-3.09 (m, 1H), 2.79-2.70 (m, 1H), 2.52 (s, 3H), 2.40 (d, J = 1.2 Hz, 3H), 2.35-2.26 (m, 1H), 2.13-2.03 (m, 1H), 1.94-1.78 (m, 3H) |
| 81 | 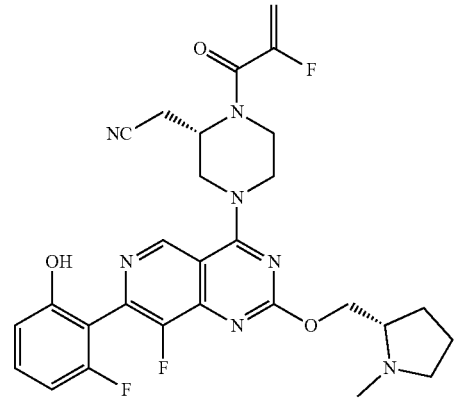<br>2-((2S)-4-(8-fluoro-7-(2-fluoro-6-hydroxyphenyl)-2-(((S)-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 568<br>$^1$H NMR (400 MHz, CDCl$_3$): δ 9.01 (s, 1H), 7.34 (dt, J = 6.4, 8.4 Hz, 1H), 6.88 (d, J = 8.4 Hz, 1H), 6.80-6.74 (m, 1H), 5.56-5.40 (m, 1H), 5.29 (dd, J = 3.6, 16.8 Hz, 1H), 4.84 (br s, 1H), 4.62 (dd, J = 4.8, 10.8 Hz, 1H), 4.54-4.38 (m, 3H), 4.34-3.96 (m, 2H), 3.92-3.61 (m, 2H), 3.18-3.10 (m, 1H), 3.03 (br dd, J = 7.2, 16.8 Hz, 1H), 2.90-2.67 (m, 2H), 2.52 (s, 3H), 2.31 (dt, J = 7.2, 9.2 Hz, 1H), 2.12-2.02 (m, 1H), 1.92-1.80 (m, 3H) |
| 82 | 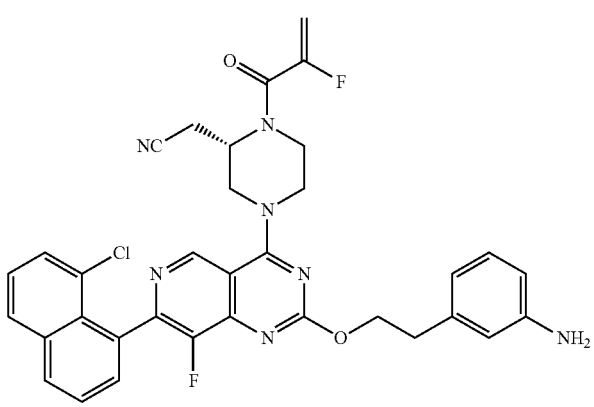<br>(S)-2-(4-(2-(3-aminophenethoxy)-7-(8-chloronaphthalen-1-yl)-8-fluoropyrido[4,3-d]pyrimidin-4-yl)-1-(2-fluoroacryloyl)piperazin-2-yl)acetonitrile | LCMS [ESI, M + 1]: 640<br>$^1$H NMR (400 MHz, CDCl$_3$): δ 9.06 (s, 1H), 8.02 (dd, J = 1.6, 8.0 Hz, 1H), 7.90 (d, J = 8.4 Hz, 1H), 7.67-7.53 (m, 3H), 7.48-7.39 (m, 1H), 7.09 (t, J = 7.6 Hz, 1H), 6.75-6.66 (m, 2H), 6.56 (dd, J = 1.6, 8.0 Hz, 1H), 5.59-5.39 (m, 1H), 5.35-5.24 (m, 1H), 5.00-4.77 (m, 1H), 4.71 (t, J = 7.6 Hz, 2H), 4.57-4.38 (m, 2H), 4.35-3.89 (m, 2H), 3.87-3.68 (m, 2H), 3.68-3.61 (m, 2H), 3.10 (t, J = 7.2 Hz, 2H), 3.06-2.95 (m, 1H), 2.91-2.79 (m, 1H) |

TABLE 3-continued

Examples 64 to 210

| Int. # | Structure | Characterization Data |
|---|---|---|
| 83 | 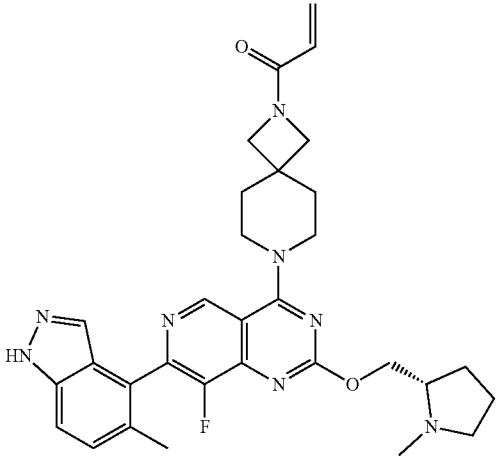<br>1-(7-(8-fluoro-7-(5-methyl-1H-indazol-4-yl)-2-(((S)-1-methylpyrrolidin-2-yl)methoxy)pyrido[4,3-d]pyrimidin-4-yl)-2,7-diazaspiro[3.5]nonan-2-yl)prop-2-en-1-one | LCMS [ESI, M + 1]: 571<br>$^1$H NMR (400 MHz, CDCl$_3$): δ 10.10 (br s, 1H), 9.11 (s, 1H), 7.82 (s, 1H), 7.52 (d, J = 8.0 Hz, 1H), 7.39 (d, J = 8.8 Hz, 1H), 6.43-6.35 (m, 1H), 6.29-6.18 (m, 1H), 5.76-5.68 (m, 1H), 4.59 (dd, J = 4.8, 10.8 Hz, 1H), 4.42-4.33 (m, 1H), 4.09-4.04 (m, 2H), 4.03-3.97 (m, 2H), 3.96-3.93 (m, 2H), 3.92-3.82 (m, 2H), 3.11 (dd, J = 6.8, 8.0 Hz, 1H), 2.78-2.69 (m, 1H), 2.51 (s, 3H), 2.40 (d, J = 1.2 Hz, 3H), 2.35-2.25 (m, 1H), 2.12-2.01 (m, 5H), 1.91-1.75 (m, 3H) |
| 84 | 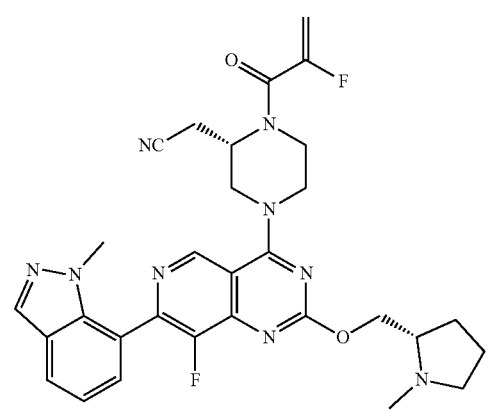<br>2-((S)-4-(8-fluoro-7-(1-methyl-1H-indazol-7-yl)-2-(((S)-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 588<br>$^1$H NMR (400 MHz, CDCl$_3$): δ 9.14 (s, 1H), 8.08 (s, 1H), 7.89-7.84 (m, 1H), 7.50 (d, J = 7.2 Hz, 1H), 7.27-7.24 (m, 1H), 5.59-5.39 (m, 1H), 5.35-5.25 (m, 1H), 4.95-4.73 (m, 1H), 4.64-4.55 (m, 1H), 4.54-4.38 (m, 3H), 4.34-3.94 (m, 2H), 3.92-3.62 (m, 5H), 3.17-3.07 (m, 1H), 3.06-2.95 (m, 1H), 2.88-2.79 (m, 1H), 2.77-2.66 (m, 1H), 2.51 (s, 3H), 2.37-2.26 (m, 1H), 2.14-2.02 (m, 1H), 1.93-1.73 (m, 3H) |

TABLE 3-continued

Examples 64 to 210

| Int. # | Structure | Characterization Data |
|---|---|---|
| 85 | 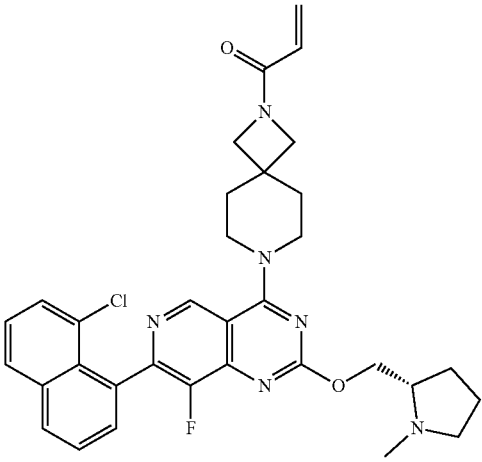<br>(S)-1-(7-(7-(8-chloronaphthalen-1-yl)-8-fluoro-2-((1-methylpyrrolidin-2-yl)methoxy)pyrido[4,3-d]pyrimidin-4-yl)-2,7-diazaspiro[3.5]nonan-2-yl)prop-2-en-1-one | LCMS [ESI, M + 1]: 601<br>$^1$H NMR (400 MHz, CDCl$_3$): δ 9.03-8.98 (m, 1H), 8.01 (dd, J = 1.8, 7.6 Hz, 1H), 7.89 (dd, J = 0.8, 8.0 Hz, 1H), 7.65-7.52 (m, 3H), 7.46-7.40 (m, 1H), 6.42-6.35 (m, 1H), 6.28-6.19 (m, 1H), 5.72 (dd, J = 1.6, 10.0 Hz, 1H), 4.58 (ddd, J = 1.6, 10.4 Hz, 1H), 4.36 (dd, J = 6.8, 10.8 Hz, 1H), 4.05-3.81 (m, 8H), 3.16-3.07 (m, 1H), 2.79-2.69 (m, 1H), 2.51 (s, 3H), 2.34-2.25 (m, 1H), 2.12-1.99 (m, 5H), 1.90-1.73 (m, 3H) |
| 86 | 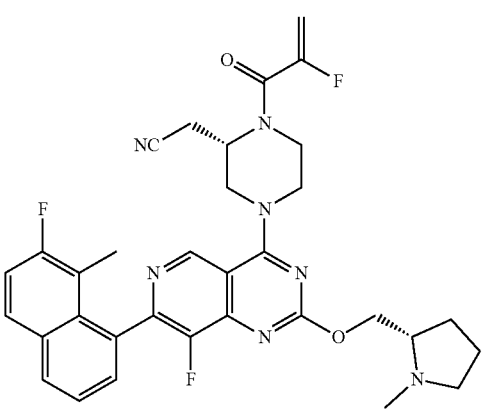<br>2-((S)-4-(8-fluoro-7-(7-fluoro-8-methylnaphthalen-1-yl)-2-(((S)-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 616<br>$^1$H NMR (400 MHz, CDCl$_3$): δ 9.09 (d, J = 2.4 Hz, 1H), 8.08-7.93 (m, 1H), 7.81 (dd, J = 6.0, 8.8 Hz, 1H), 7.52 (dd, J = 4.0, 6.0 Hz, 2H), 7.31 (t, J = 9.2 Hz, 1H), 5.62-5.39 (m, 1H), 5.30 (br d, J = 16.4 Hz, 1H), 4.98-4.78 (m, 1H), 4.67 (br s, 1H), 4.59-4.39 (m, 3H), 4.36-3.91 (m, 2H), 3.89-3.46 (m, 2H), 3.22 (br d, J = 1.2 Hz, 1H), 3.05 (br dd, J = 7.2, 16.8 Hz, 1H), 2.86 (br dd, J = 5.6, 10.4 Hz, 2H), 2.58 (br s, 3H), 2.39 (br d, J = 7.2 Hz, 1H), 2.16-2.06 (m, 1H), 1.95-1.91 (m, 3H), 1.90-1.78 (m, 3H) |

TABLE 3-continued

Examples 64 to 210

| Int. # | Structure | Characterization Data |
|---|---|---|
| 87 | 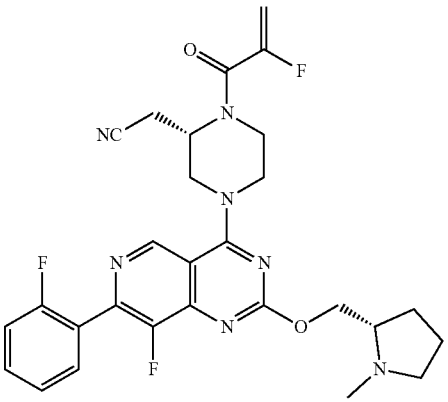<br>2-((S)-4-(8-fluoro-7-(2-fluorophenyl)-2-(((S)-1-methylpyrrolidin-2-yl)methoxy)pyrido[4,3-d]pyrimidin-4-yl)-1-(2-fluoroacryloyl)piperazin-2-yl)acetonitrile | Method C<br>LCMS [ESI, M + 1]: 522<br>$^1$H NMR (400 MHz, CDCl$_3$): δ 9.10 (s, 1H), 7.69 (td, J = 1.6, 7.2 Hz, 1H), 7.53-7.46 (m, 1H), 7.32 (td, J = 1.2, 7.6 Hz, 1H), 7.26-7.20 (m, 1H), 5.57-5.37 (dd, J = 3.6, 47.6 Hz, 1H), 5.29 (dd, J = 3.6, 16.8 Hz, 1H), 4.97-4.73 (m, 1H), 4.68-4.56 (m, 1H), 4.53-4.33 (m, 3H), 4.28-3.92 (m, 2H), 3.89-3.52 (m, 2H), 3.22-3.08 (m, 1H), 3.07-2.95 (m, 1H), 2.90-2.68 (m, 2H), 2.57-2.45 (s, 3H), 2.38-2.24 (m, 1H), 2.14-2.00 (m, 1H), 1.92-1.76 (m, 3H) |
| 88 | 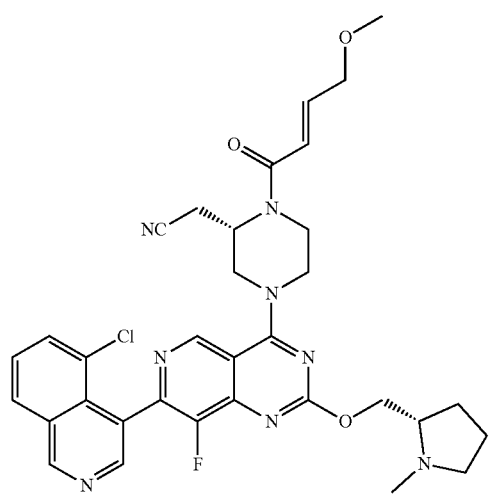<br>2-((S)-4-(7-(5-chloroisoquinolin-4-yl)-8-fluoro-2-(((S)-1-methylpyrrolidin-2-yl)methoxy)pyrido[4,3-d]pyrimidin-4-yl)-1-((E)-4-methoxybut-2-enoyl)piperazin-2-yl)acetonitrile | LCMS [ESI, M + 1]: 645<br>$^1$H NMR (400 MHz, CDCl$_3$): δ 9.39 (s, 1H), 9.10 (s, 1H), 8.59 (d, J = 11.2 Hz, 1H), 8.05 (d, J = 8.0 Hz, 1H), 7.78 (ddd, J = 1.2, 2.8, 7.6 Hz, 1H), 7.60 (dt, J = 2.0, 7.6 Hz, 1H), 7.02 (br d, J = 14.8 Hz, 1H), 6.55 (br d, J = 14.8 Hz, 1H), 5.17-4.94 (m, 1H), 4.65-4.55 (m, 1H), 4.55-4.36 (m, 3H), 4.32-3.62 (m, 6H), 3.44 (s, 3H), 3.12 (br t, J = 7.6 Hz, 1H), 3.07-2.70 (m, 3H), 2.51 (d, J = 1.6 Hz, 3H), 2.36-2.24 (m, 1H), 2.13-2.00 (m, 1H), 1.94-1.77 (m, 3H) |

TABLE 3-continued

Examples 64 to 210

| Int. # | Structure | Characterization Data |
|---|---|---|
| 89 | 2-((S)-4-(7-(5-chloroisoquinolin-4-yl)-8-fluoro-2-(((2S,4R)-4-methoxy-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 649<br>$^1$H NMR (400 MHz, CDCl$_3$): δ 9.39 (s, 1H), 9.09 (s, 1H), 8.59 (d, J = 8.8 Hz, 1H), 8.05 (d, J = 8.0 Hz, 1H), 7.81-7.74 (m, 1H), 7.60 (dt, J = 2.4, 8.0 Hz, 1H), 5.60-5.37 (m, 1H), 5.29 (dd, J = 3.6, 16.8 Hz, 1H), 4.99-4.74 (m, 1H), 4.68-4.56 (m, 1H), 4.55-4.40 (m, 3H), 4.36-3.64 (m, 5H), 3.46 (dd, J = 6.4, 10.0 Hz, 1H), 3.31 (d, J = 0.4 Hz, 3H), 3.11-2.77 (m, 3H), 2.50 (s, 3H), 2.35 (dd, J = 5.6, 10.0 Hz, 1H), 2.16-1.97 (m, 2H) |
| 90 | 2-((S)-4-(7-(5-chloroisoquinolin-4-yl)-8-fluoro-2-(((S)-1-methylpyrrolidin-2-yl)methoxy)pyrido[4,3-d]pyrimidin-4-yl)-1-((E)-4-fluorobut-2-enoyl)piperazin-2-yl)acetonitrile | LCMS [ESI, M + 1]: 633<br>$^1$H NMR (400 MHz, CDCl$_3$): δ 9.39 (s, 1H), 9.10 (s, 1H), 8.59 (d, J = 11.2 Hz, 1H), 8.06 (d, J = 8.0 Hz, 1H), 7.78 (ddd, J = 1.2, 2.4, 7.2 Hz, 1H), 7.61 (dt, J = 2.0, 7.6 Hz, 1H), 7.11-6.96 (m, 1H), 6.60 (br d, J = 14.4 Hz, 1H), 5.22-4.85 (m, 3H), 4.67-4.56 (m, 1H), 4.55-4.37 (m, 3H), 4.34-3.49 (m, 4H), 3.19-3.09 (m, 1H), 3.06-2.90 (m, 1H), 2.89-2.67 (m, 2H), 2.52 (d, J = 0.8 Hz, 3H), 2.37-2.25 (m, 1H), 2.13-2.00 (m, 1H), 1.95-1.77 (m, 3H) |

TABLE 3-continued

Examples 64 to 210

| Int. # | Structure | Characterization Data |
|---|---|---|
| 91 | 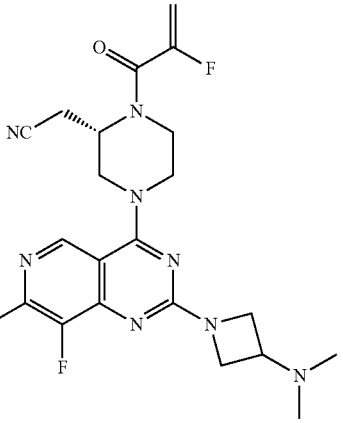<br>(S)-2-(4-(7-(8-chloronaphthalen-1-yl)-2-(3-(dimethylamino)azetidin-1-yl)-8-fluoropyrido[4,3-d]pyrimidin-4-yl)-1-(2-fluoroacryloyl)piperazin-2-yl)acetonitrile | LCMS [ESI, M + 1]: 603<br>$^1$H NMR (400 MHz, CDCl$_3$): δ 8.83 (d, J = 1.2 Hz, 1H), 7.99 (dd, J = 1.6, 7.6 Hz, 1H), 7.87 (d, J = 8.0 Hz, 1H), 7.64-7.51 (m, 3H), 7.41 (dt, J = 2.0, 7.6 Hz, 1H), 5.58-5.35 (m, 1H), 5.28 (dd, J = 3.6, 16.8 Hz, 1H), 5.06-4.73 (m, 1H), 4.50 (br t, J = 14.8 Hz, 1H), 4.40-4.25 (m, 3H), 4.21-3.97 (m, 3H), 3.81-3.45 (m, 3H), 3.28-3.17 (m, 1H), 3.05-2.92 (m, 1H), 2.91-2.79 (m, 1H), 2.24 (s, 6H) |
| 92 | 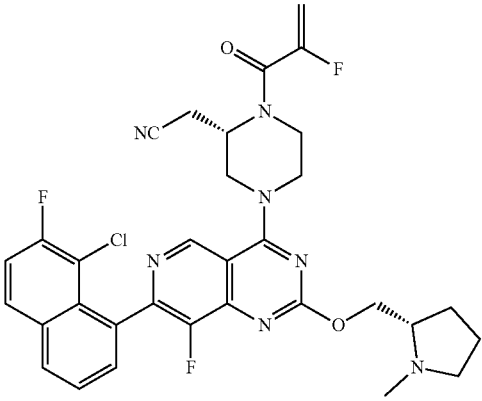<br>2-((S)-4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 636<br>$^1$H NMR (400 MHz, CDCl$_3$): δ 9.06 (s, 1H), 8.04-7.98 (m, 1H), 7.90 (dd, J = 5.6, 8.8 Hz, 1H), 7.66-7.56 (m, 2H), 7.41 (dt, J = 2.0, 8.8 Hz, 1H), 5.59-5.38 (m, 1H), 5.29 (dd, J = 3.2, 16.8 Hz, 1H), 4.98-4.77 (m, 1H), 4.60 (dd, J = 4.8, 10.8 Hz, 1H), 4.55-4.37 (m, 3H), 4.34-4.14 (m, 1H), 4.12-3.93 (m, 1H), 3.87-3.62 (m, 2H), 3.12 (br t, J = 7.6 Hz, 1H), 3.07-2.96 (m, 1H), 2.94-2.80 (m, 1H), 2.78-2.68 (m, 1H), 2.51 (s, 3H), 2.36-2.24 (m, 1H), 2.12-1.99 (m, 1H), 1.93-1.73 (m, 3H) |
| 93 | 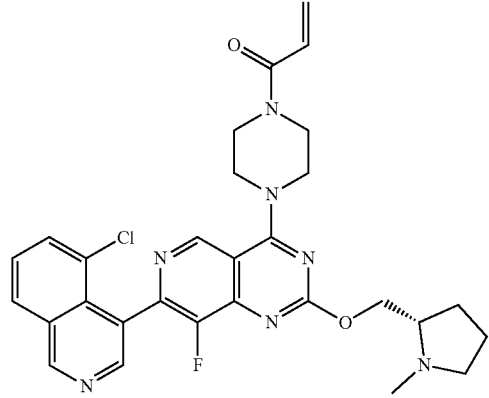<br>(S)-1-(4-(7-(5-chloroisoquinolin-4-yl)-8-fluoro-2-((1-methylpyrrolidin-2-yl)methoxy)pyrido[4,3-d]pyrimidin-4-yl)piperazin-1-yl)prop-2-en-1-one | LCMS [ESI, M + 1]: 562<br>$^1$H NMR (400 MHz, CDCl$_3$): δ 9.39 (s, 1H), 9.08 (s, 1H), 8.59 (s, 1H), 8.05 (dd, J = 0.8, 8 Hz, 1H), 7.78 (dd, J = 1.2, 7.6 Hz, 1H), 7.64-7.57 (m, 1H), 6.67-6.55 (m, 1H), 6.40 (dd, J = 1.6, 16.4 Hz, 1H), 5.81 (dd, J = 2, 10.4 Hz, 1H), 4.63-4.54 (m, 1H), 4.43-4.35 (m, 1H), 4.14-4.04 (m, 4H), 4.02-3.80 (m, 4H), 3.15-3.07 (m, 1H), 2.79-2.68 (m, 1H), 2.50 (s, 3H), 2.35-2.25 (m, 1H), 2.13-2.00 (m, 1H), 1.93-1.74 (m, 3H) |

TABLE 3-continued

Examples 64 to 210

| Int. # | Structure | Characterization Data |
|---|---|---|
| 94 | 1-(4-(7-(1,6-dimethyl-1H-indazol-7-yl)-8-fluoro-2-(((S)-1-methylpyrrolidin-2-yl)methoxy)pyrido[4,3-d]pyrimidin-4-yl)piperazin-1-yl)prop-2-en-1-one | LCMS [ESI, M + 1]: 562<br>$^1$H NMR (400 MHz, CDCl$_3$): δ 9.39 (s, 1H), 9.08 (s, 1H), 8.59 (s, 1H), 8.05 (dd, J = 0.8, 8 Hz, 1H), 7.78 (dd, J = 1.2, 7.6 Hz, 1H), 7.64-7.57 (m, 1H), 6.67-6.55 (m, 1H), 6.40 (dd, J = 1.6, 16.4 Hz, 1H), 5.81 (dd, J = 2, 10.4 Hz, 1H), 4.63-4.54 (m, 1H), 4.43-4.35 (m, 1H), 4.14-4.04 (m, 4H), 4.02-3.80 (m, 4H), 3.15-3.07 (m, 1H), 2.79-2.68 (m, 1H), 2.50 (s, 3H), 2.35-2.25 (m, 1H), 2.13-2.00 (m, 1H), 1.93-1.74 (m, 3H) |
| 95 | 2-((S)-4-(8-fluoro-7-(3-hydroxynaphthalen-1-yl)-2-(((S)-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 600<br>$^1$H NMR (400 MHz, CDCl$_3$): δ 8.92 (s, 1H), 7.73-7.66 (m, 2H), 7.41-7.34 (m, 1H), 7.23-7.17 (m, 1H), 7.15 (d, J = 2.4 Hz, 1H), 6.90-6.85 (m, 1H), 5.48-5.28 (m, 1H), 5.23 (dd, J = 3.6, 16.8 Hz, 1H), 4.94-4.80 (m, 1H), 4.75-4.46 (m, 2H), 4.37-4.24 (m, 1H), 4.19 (br d, J = 12.8 Hz, 1H), 3.63-3.16 (m, 4H), 3.09-2.83 (m, 2H), 2.82-2.69 (m, 5H), 2.52-2.43 (m, 2H), 2.19-1.94 (m, 3H) |

TABLE 3-continued

Examples 64 to 210

| Int. # | Structure | Characterization Data |
|---|---|---|
| 96 | 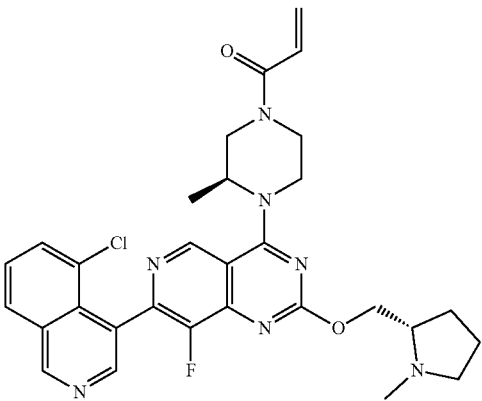<br>1-((S)-4-(7-(5-chloroisoquinolin-4-yl)-8-fluoro-2-(((S)-1-methylpyrrolidin-2-yl)methoxy)pyrido[4,3-d]pyrimidin-4-yl)-3-methylpiperazin-1-yl)prop-2-en-1-one | LCMS [ESI, M + 1]: 576<br>$^1$H NMR (400 MHz, CDCl$_3$): δ 9.39 (s, 1H), 9.03 (s, 1H), 8.59 (d, J = 7.2 Hz, 1H), 8.05 (d, J = 8.0 Hz, 1H), 7.78 (d, J = 7.6 Hz, 1H), 7.61 (t, J = 8.0 Hz, 1H), 6.72-6.50 (m, 1H), 6.46-6.35 (m, 1H), 5.81 (br d, J = 10.8 Hz, 1H), 5.07-4.89 (m, 1H), 4.79-4.33 (m, 4H), 4.14-3.51 (m, 3H), 3.34-3.04 (m, 2H), 2.79-2.66 (m, 1H), 2.51 (d, J = 1.6 Hz, 3H), 2.35-2.25 (m, 1H), 2.13-2.00 (m, 1H), 1.89-1.72 (m, 3H), 1.55-1.45 (m, 3H) |
| 97 | 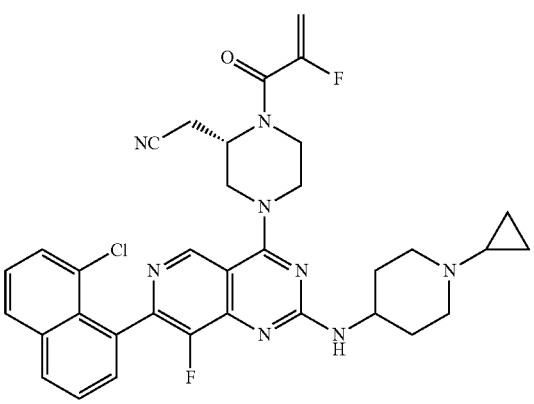<br>(S)-2-(4-(7-(8-chloronapthalen-1-yl)-2-((1-cyclopropylpiperidin-4-yl)amino)-8-fluoropyrido[4,3-d]pyrimidin-4-yl)-1-(2-fluoroacryloyl)piperazin-2-yl)acetonitrile | LCMS [ESI, M + 1]: 643<br>$^1$H NMR (400 MHz, CD$_3$CN): δ 8.88 (d, J = 5.2 Hz, 1H), 8.10 (br d, J = 8.0 Hz, 1H), 8.00 (d, J = 8.0 Hz, 1H), 7.70-7.63 (m, 1H), 7.62-7.55 (m, 2H), 7.54-7.46 (m, 1H), 6.08-5.86 (m, 1H), 5.36-5.11 (m, 2H), 5.05-4.72 (m, 1H), 4.53-4.22 (m, 2H), 4.20-3.86 (m, 2H), 3.81-3.35 (m, 3H), 3.18-2.81 (m, 4H), 2.41-2.25 (m, 2H), 2.20-2.16 (m, 2H), 1.67-1.34 (m, 3H), 0.49-0.20 (m, 4H) |
| 98 | 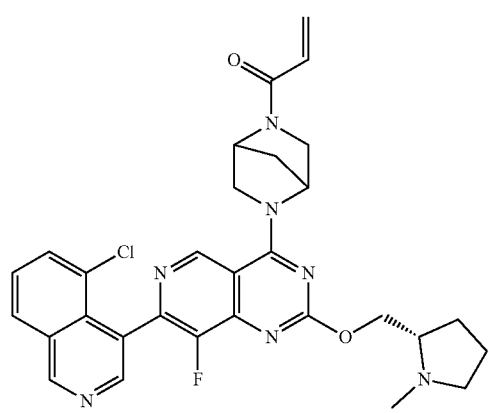<br>1-(5-(7-(5-chloroisoquinolin-4-yl)-8-fluoro-2-(((S)-1-methylpyrrolidin-2-yl)methoxy)pyrido[4,3-d]pyrimidin-4-yl)-2,5-diazabicyclo[2.2.1]heptan-2-yl)prop-2-en-1-one | LCMS [ESI, M + 1]: 574<br>$^1$H NMR (400 MHz, CDCl$_3$): δ 9.37 (s, 1H), 9.14-9.04 (m, 1H), 8.56 (d, J = 6.0 Hz, 1H), 8.03 (d, J = 8.4 Hz, 1H), 7.76 (s, 1H), 7.59 (s, 1H), 6.57-6.38 (m, 1H), 6.36-6.21 (m, 1H), 5.83-5.70 (m, 1H), 5.64-5.47 (m, 1H), 5.36-4.76 (m, 1H), 4.67-4.51 (m, 1H), 4.43-4.33 (m, 1H), 4.31-4.18 (m, 1H), 4.14-4.02 (m, 1H), 4.01-3.86 (m, 1H), 3.84-3.71 (m, 1H), 3.19-3.08 (m, 1H), 2.84-2.71 (m, 1H), 2.55-2.47 (m, 3H), 2.38-2.27 (m, 1H), 2.25-2.03 (m, 4H), 1.83 (br s, 2H) |

TABLE 3-continued

Examples 64 to 210

| Int. # | Structure | Characterization Data |
|---|---|---|
| 99 | 2-((2S)-4-(7-(1,6-dimethyl-1H-indazol-7-yl)-8-fluoro-2-(((S)-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 602<br>$^1$H NMR (400 MHz, CDCl$_3$): δ 9.17 (d, J = 2.0 Hz, 1H), 7.97 (d, J = 2.4 Hz, 1H), 7.73 (d, J = 8.4 Hz, 1H), 7.13 (dd, J = 1.6, 8.3 Hz, 1H), 5.58-5.41 (m, 1H), 5.34-5.25 (m, 1H), 4.94-4.79 (m, 1H), 4.64-4.38 (m, 4H), 4.37-3.62 (m, 4H), 3.50 (d, J = 6.4 Hz, 3H), 3.16-3.09 (m, 1H), 3.07-2.96 (m, 1H), 2.89-2.79 (m, 1H), 2.77-2.66 (m, 1H), 2.51 (s, 3H), 2.35-2.28 (m, 1H), 2.27 (d, J = 2.4 Hz, 3H), 2.13-2.00 (m, 1H), 1.93-1.71 (m, 3H) |
| 100 | 1-((S)-4-(8-fluoro-7-(2-fluorophenyl)-2-(((S)-1-methylpyrrolidin-2-yl)methoxy)pyrido[4,3-d]pyrimidin-4-yl)-3-methylpiperazin-1-yl)prop-2-en-1-one | LCMS [ESI, M + 1]: 509<br>$^1$H NMR (400 MHz, CDCl$_3$): δ 9.03 (s, 1H), 7.72-7.66 (m, 1H), 7.53-7.45 (m, 1H), 7.32 (t, J = 8.0 Hz, 1H), 7.23 (t, J = 9.2 Hz, 1H), 6.73-6.47 (m, 1H), 6.40 (dd, J = 1.2, 16 Hz, 1H), 5.80 (br d, J = 10.6 Hz, 1H), 5.01-4.83 (m, 1H), 4.78-4.33 (m, 4H), 4.10-3.78 (m, 1H), 3.76-3.45 (m, 2H), 3.30-3.00 (m, 2H), 2.78-2.67 (m, 1H), 2.51 (s, 3H), 2.35-2.24 (m, 1H), 2.12-2.00 (m, 1H), 1.91-1.73 (m, 3H), 1.48 (br d, J = 6.4 Hz, 3H) |
| 101 | (S)-2-(4-(8-fluoro-7-(3-fluoro-2-(trifluoromethyl)phenyl)-2-((tetrahydro-1H-pyrrolizin-7a(5H)-yl)methoxy)pyrido[4,3-d]pyrimidin-4-yl)-1-(2-fluoroacryloyl)piperazin-2-yl)acetonitrile | LCMS [ESI, M + 1]: 646<br>$^1$H NMR (400 MHz, CDCl$_3$): δ 9.03 (s, 1H), 7.68-7.61 (m, 1H), 7.39-7.32 (m, 1H), 7.26 (s, 1H), 5.59-5.38 (m, 1H), 5.29 (dd, J = 3.6, 16.8 Hz, 1H), 4.94-4.77 (m, 1H), 4.60-4.11 (m, 5H), 4.08-3.92 (m, 1H), 3.86-3.63 (m, 2H), 3.35-2.98 (m, 3H), 2.91-2.80 (m, 1H), 2.75-2.62 (m, 2H), 2.19-2.03 (m, 2H), 1.99-1.85 (m, 4H), 1.76-1.69 (m, 2H) |

TABLE 3-continued

Examples 64 to 210

| Int. # | Structure | Characterization Data |
|---|---|---|
| 102 | 1-(4-(7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)piperazin-1-yl)prop-2-en-1-one | LCMS [ESI, M + 1]: 605<br>$^1$H NMR (400 MHz, CDCl$_3$): δ 9.04 (s, 1H), 8.00 (dd, J = 7.6, 2.0 Hz, 1H), 7.89 (dd, J = 8.8, 5.2, Hz, 1H), 7.65-7.56 (m, 2H), 7.40 (t, J = 8.8 Hz, 1H), 6.62 (dd, J = 16.8, 10.4, Hz, 1H), 6.40 (dd, J = 16.8, 2.0, Hz, 1H), 5.81 (dd, J = 10.4, 1.6, Hz, 1H), 4.28 (s, 2H), 4.13-4.04 (m, 4H), 4.00-3.81 (m, 4H), 3.22-3.08 (m, 2H), 2.75-2.60 (m, 2H), 2.17-2.04 (m, 2H), 1.94-1.85 (m, 4H), 1.74-1.68 (m, 2H) |
| 103 | (S)-1-(4-(7-(6-amino-3-chloropyridin-2-yl)-8-fluoro-2-((1-methylpyrrolidin-2-yl)methoxy)pyrido[4,3-d]pyrimidin-4-yl)piperazin-1-yl)prop-2-en-1-one | LCMS [ESI, M + 1]: 527<br>$^1$H NMR (400 MHz, CDCl$_3$): δ 9.08 (s, 1H), 7.57 (d, J = 8.8 Hz, 1H), 6.68-6.55 (m, 2H), 6.40 (dd, J = 2.0, 16.8 Hz, 1H), 5.81 (dd, J = 2.0, 10.4 Hz, 1H), 4.65 (s, 2H), 4.58 (dd, J = 4.4, 10.8 Hz, 1H), 4.38 (dd, J = 6.8, 10.8 Hz, 1H), 4.11-4.01 (m, 4H), 3.99-3.72 (m, 4H), 3.11 (br t, J = 7.6 Hz, 1H), 2.82-2.66 (m, 1H), 2.51 (s, 3H), 2.35-2.22 (m, 1H), 2.13-1.99 (m, 1H), 1.93-1.73 (m, 3H) |
| 104 | (S)-2-(4-(7-(8-chloro-7-fluoronaphthalen-1-yl)-8-fluoro-2-(3,3,3-trifluoropropoxy)pyrido[4,3-d]pyrimidin-4-yl)-1-(2-fluoroacryloyl)piperazin-2-yl)acetonitrile | LCMS [ESI, M + 1]: 635<br>$^1$H NMR (400 MHz, CDCl$_3$): δ 9.10 (s, 1H), 8.05-7.99 (m, 1H), 7.94-7.88 (m, 1H), 7.66-7.58 (m, 2H), 7.45-7.38 (m, 1H), 5.59-5.40 (m, 1H), 5.35-5.25 (m, 1H), 4.97-4.82 (m, 1H), 4.80-4.70 (m, 2H), 4.55-4.41 (m, 2H), 4.37-4.17 (m, 1H), 4.15-3.94 (m, 1H), 3.93-3.55 (m, 2H), 3.10-2.97 (m, 1H), 2.93-2.80 (m, 1H), 2.79-2.66 (m, 2H) |

TABLE 3-continued

Examples 64 to 210

| Int. # | Structure | Characterization Data |
|---|---|---|
| 105 | 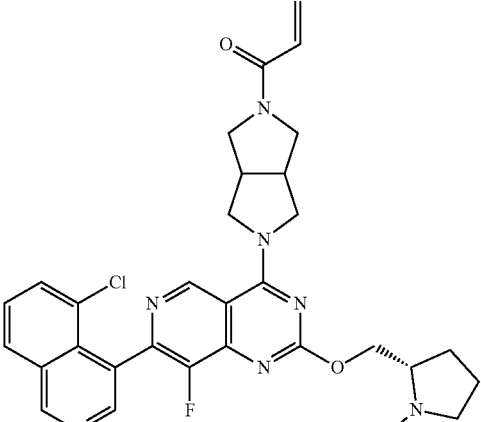<br>1-(5-(7-(5-chloroisoquinolin-4-yl)-8-fluoro-2-(((S)-1-methylpyrrolidin-2-yl)methoxy)pyrido[4,3-d]pyrimidin-4-yl)hexahydropyrrolo[3,4-c]pyrrol-2(1H)-yl)prop-2-en-1-one | LCMS [ESI, M + 1]: 588<br>$^1$H NMR (400 MHz, CDCl$_3$): δ 9.38 (s, 1H), 9.23 (s, 1H), 8.59 (s, 1H), 8.04 (dd, J = 0.8, 8.0 Hz, 1H), 7.77 (d, J = 7.6 Hz, 1H), 7.63-7.55 (m, 1H), 6.46-6.41 (m, 2H), 5.74 (dd, J = 5.2, 7.2 Hz, 1H), 4.63-4.52 (m, 1H), 4.41-4.29 (m, 3H), 4.04-3.89 (m, 4H), 3.71-3.56 (m, 2H), 3.32-3.06 (m, 3H), 2.73 (br d, J = 6.0 Hz, 1H), 2.50 (s, 3H), 2.36-2.24 (m, 1H), 2.15-2.02 (m, 1H), 1.93-1.74 (m, 3H) |
| 106 | 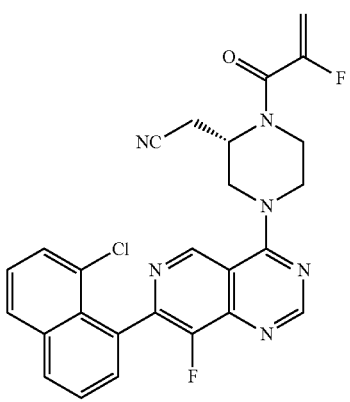<br>(S)-2-(4-(7-(8-chloronaphthalen-1-yl)-8-fluoropyrido[4,3-d]pyrimidin-4-yl)-1-(2-fluoroacryloyl)piperazin-2-yl)acetonitrile | LCMS [ESI, M + 1]: 505<br>$^1$H NMR (400 MHz, CDCl$_3$): δ 9.21 (s, 1H), 8.92 (s, 1H), 8.04 (dd, J = 1.6, 7.6 Hz, 1H), 7.91 (d, J = 8.4 Hz, 1H), 7.67-7.54 (m, 3H), 7.48-7.41 (m, 1H), 5.57-5.39 (m, 1H), 5.29 (dd, J = 3.6, 16.8 Hz, 1H), 4.99-4.78 (m, 1H), 4.59 (br d, J = 10.8 Hz, 1H), 4.54-4.44 (m, 1H), 4.40-3.57 (m, 4H), 3.07-2.94 (m, 1H), 2.91-2.76 (m, 1H) |

TABLE 3-continued

Examples 64 to 210

| Int. # | Structure | Characterization Data |
|---|---|---|
| 107 | 2-((S)-4-(7-(3-aminoisoquinolin-1-yl)-8-fluoro-2-(((S)-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 600<br>$^1$H NMR (400 MHz, CDCl$_3$): δ 9.17 (s, 1H), 7.63 (d, J = 8.8 Hz, 2H), 7.51 (t, J = 7.2 Hz, 1H), 7.21 (t, J = 7.6 Hz, 1H), 6.90 (s, 1H), 5.48 (dd, J = 2.8, 47.6 Hz, 1H), 5.29 (dd, J = 3.6, 16.8 Hz, 1H), 4.98-4.73 (m, 1H), 4.73-4.55 (m, 3H), 4.53-4.39 (m, 3H), 4.32-3.93 (m, 2H), 3.91-3.35 (m, 2H), 3.13 (br t, J = 6.4 Hz, 1H), 3.08-2.94 (m, 1H), 2.91-2.68 (m, 2H), 2.51 (s, 3H), 2.36-2.24 (m, 1H), 2.12-1.98 (m, 1H), 1.92-1.78 (m, 3H) |
| 108 | (S)-2-(1-acryloyl-4-(7-(8-chloronaphthalen-1-yl)-8-fluoropyrido[4,3-d]pyrimidin-4-yl)piperazin-2-yl)acetamide | LCMS [ESI, M + 1]: 487<br>$^1$H NMR (400 MHz, CDCl$_3$): δ 9.16 (s, 1H), 8.87 (s, 1H), 8.03 (d, J = 7.6 Hz, 1H), 7.90 (d, J = 8.0 Hz, 1H), 7.69-7.52 (m, 3H), 7.49-7.36 (m, 1H), 4.71-4.56 (m, 1H), 4.47 (br d, J = 7.6 Hz, 1H), 3.63 (q, J = 12.0 Hz, 1H), 3.35 (br s, 1H), 3.31-3.18 (m, 2H), 3.10 (br d, J = 8.8 Hz, 1H), 2.70-2.53 (m, 2H), 2.03 (br d, J = 5.6 Hz, 1H) |
| 109 | (S)-2-(1-acryloyl-4-(7-(8-chloro-7-fluoronaphthalen-1-yl)-8-fluoropyrido[4,3-d]pyrimidin-4-yl)piperazin-2-yl)acetonitrile | LCMS [ESI, M + 1]: 505<br>$^1$H NMR (400 MHz, CDCl$_3$): δ 9.22 (s, 1H), 8.92 (s, 1H), 8.06-7.99 (m, 1H), 7.91 (dd, J = 5.6, 8.8 Hz, 1H), 7.68-7.58 (m, 2H), 7.42 (dt, J = 1.6, 8.8 Hz, 1H), 6.66-6.53 (m, 1H), 6.47-6.38 (m, 1H), 5.86 (br d, J = 10.4 Hz, 1H), 5.24-4.55 (m, 2H), 4.55-4.42 (m, 1H), 4.36-3.54 (m, 4H), 3.10-2.90 (m, 1H), 2.88-2.70 (m, 1H) |

TABLE 3-continued

Examples 64 to 210

| Int. # | Structure | Characterization Data |
|---|---|---|
| 110 | 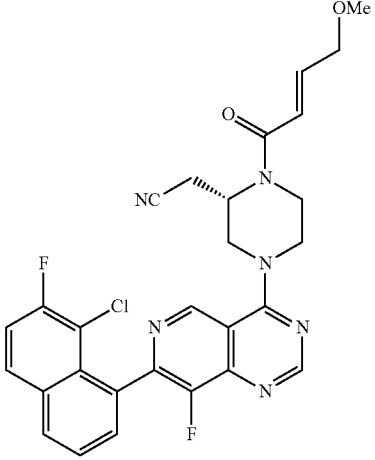<br>(S,E)-2-(4-(7-(8-chloro-7-fluoronaphthalen-1-yl)-8-fluoropyrido[4,3-d]pyrimidin-4-yl)-1-(4-methoxybut-2-enoyl)piperazin-2-yl)acetonitrile | LCMS [ESI, M + 1]: 549<br>$^1$H NMR (400 MHz, CDCl$_3$): δ 9.22 (s, 1H), 8.92 (s, 1H), 8.07-8.00 (m, 1H), 7.91 (dd, J = 5.6, 8.8 Hz, 1H), 7.69-7.58 (m, 2H), 7.42 (dt, J = 1.6, 8.8 Hz, 1H), 7.02 (br dd, J = 2.8, 15.2 Hz, 1H), 6.63-6.51 (m, 1H), 5.17-4.55 (m, 2H), 4.54-4.42 (m, 1H), 4.29-3.67 (m, 6H), 3.44 (s, 3H), 3.09-2.89 (m, 1H), 2.85-2.70 (m, 1H) |
| 111 | 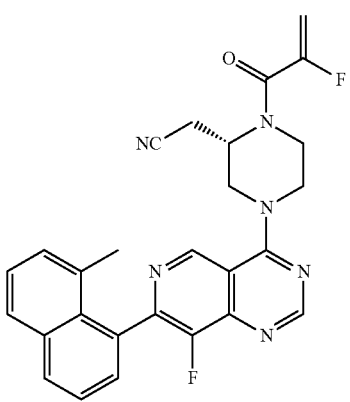<br>(S)-2-(4-(8-fluoro-7-(8-methyl-naphthalen-1-yl)pyrido[4,3-d]pyrimidin-4-yl)-1-(2-fluoroacryloyl)piperazin-2-yl)acetonitrile | LCMS [ESI, M + 1]: 485<br>$^1$H NMR (400 MHz, CDCl$_3$): δ 9.23 (s, 1H), 8.93 (s, 1H), 8.01 (d, J = 7.6 Hz, 1H), 7.83 (d, J = 8.0 Hz, 1H), 7.60-7.51 (m, 1H), 7.50-7.39 (m, 2H), 7.29 (br d, J = 6.8 Hz, 1H), 5.58-5.38 (m, 1H), 5.36-5.23 (m, 1H), 4.86 (br d, J = 1.6 Hz, 1H), 4.66-4.41 (m, 2H), 4.38-3.94 (m, 2H), 3.93-3.45 (m, 2H), 3.09-2.92 (m, 1H), 2.90-2.72 (m, 1H), 2.02 (d, J = 6.4 Hz, 3H), 1.62 (br s, 1H) |

TABLE 3-continued

Examples 64 to 210

| Int. # | Structure | Characterization Data |
|---|---|---|
| 112 | 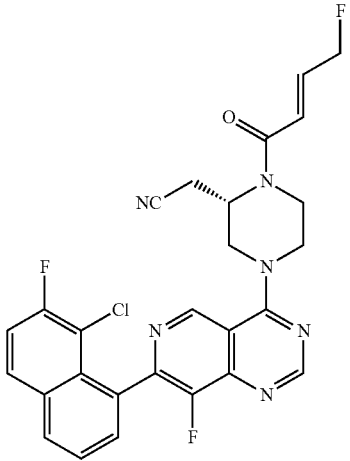<br>(S,E)-2-(4-(7-(8-chloro-7-fluoro-naphthalen-1-yl)-8-fluoropyrido[4,3-d]pyrimidin-4-yl)-1-(4-fluorobut-2-enoyl)piperazin-2-yl)acetonitrile | LCMS [ESI, M + 1]: 537<br>$^1$H NMR (400 MHz, CDCl$_3$): δ 9.22 (s, 1H), 8.92 (s, 1H), 8.05-8.00 (m, 1H), 7.91 (dd, J = 5.6, 9.2 Hz, 1H), 7.68-7.58 (m, 2H), 7.42 (dt, J = 1.6, 8.8 Hz, 1H), 7.10-6.95 (m, 1H), 6.60 (br d, J = 14.8 Hz, 1H), 5.19 (br d, J = 2.4 Hz, 1H), 5.15-4.57 (m, 3H), 4.52 (dt, J = 3.2, 9.2 Hz, 1H), 4.33-3.60 (m, 4H), 3.07-2.90 (m, 1H), 2.89-2.70 (m, 1H) |
| 113 | 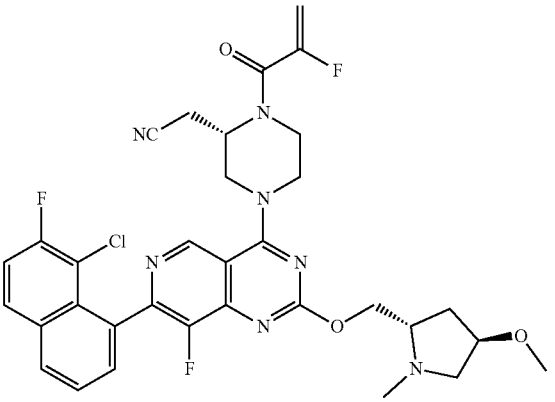<br>2-((S)-4-(7-(8-chloro-7-fluoronaphthalen-1-yl)-8-fluoro-2-(((2S,4R)-4-methoxy-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 666<br>$^1$H NMR (400 MHz, CDCl$_3$): δ 1.98-2.13 (m, 2 H) 2.35 (dd, J = 9.11, 5.93 Hz, 1 H) 2.50 (s, 3 H) 2.80-3.09 (m, 3 H) 3.31 (d, J = 1.10 Hz, 3 H) 3.47 (dd, J = 9.90, 6.11 Hz, 1 H) 3.60-3.90 (m, 2 H) 3.93-4.11 (m, 2 H) 4.13-4.35 (m, 1 H) 4.40-4.55 (m, 3 H) 4.61 (ddd, J = 11.13, 6.48, 4.52 Hz, 1 H) 4.74-5.04 (m, 1 H) 5.30 (dd, J = 16.75, 3.42 Hz, 1 H) 5.39-5.62 (m, 1 H) 7.41 (td, J = 8.68, 2.08 Hz, 1 H) 7.57-7.66 (m, 2 H) 7.90 (dd, J = 8.74, 5.56 Hz, 1 H) 7.98-8.05 (m, 1 H) 9.07 (s, 1 H) |

TABLE 3-continued

Examples 64 to 210

| Int. # | Structure | Characterization Data |
|---|---|---|
| 114 | 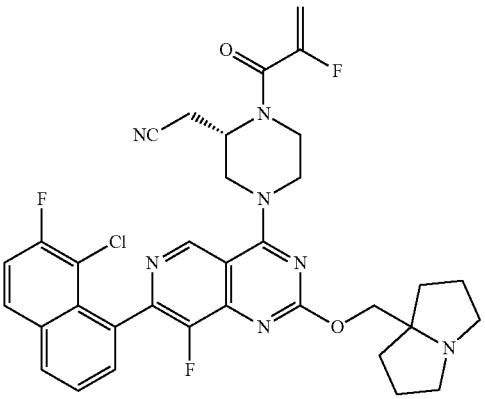<br>(S)-2-(4-(7-(8-chloro-7-fluoronaphthalen-1-yl)-8-fluoro-2-(tetrahydro-1H-pyrrolizin-7a(5H)-yl)methoxy)pyrido[4,3-d]pyrimidin-4-yl)-1-(2-fluoroacryloyl)piperazin-2-yl)acetonitrile | LCMS [ESI, M + 1]: 662<br>$^1$H NMR (400 MHz, CDCl$_3$): δ 9.05 (s, 1H), 8.00 (dd, J = 2.4, 7.2 Hz, 1H), 7.89 (dd, J = 5.6, 8.8 Hz, 1H), 7.65-7.55 (m, 2H), 7.39 (dt, J = 2.0, 8.4 Hz, 1H), 5.58-5.36 (m, 1H), 5.28 (dd, J = 3.6, 16.8 Hz, 1H), 4.98-4.76 (m, 1H), 4.60-4.41 (m, 2H), 4.41-4.31 (m, 2H), 4.26-3.68 (m, 4H), 3.34-3.19 (m, 2H), 3.15-3.03 (m, 1H), 2.97-2.84 (m, 1H), 2.77-2.66 (m, 2H), 2.19-2.07 (m, 2H), 1.98-1.87 (m, 4H), 1.80-1.66 (m, 2H) |
| 115 | 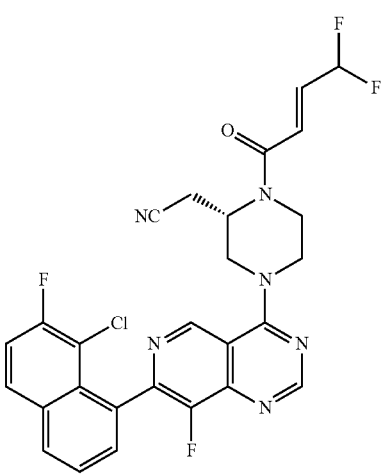<br>(S,E)-2-(4-(7-(8-chloro-7-fluoronaphthalen-1-yl)-8-fluoropyrido[4,3-d]pyrimidin-4-yl)-1-(4,4-difluorobut-2-enoyl)piperazin-2-yl)acetonitrile | LCMS [ESI, M + 1]: 555<br>$^1$H NMR (400 MHz, CDCl$_3$): δ 9.21 (br s, 1H), 8.91 (br s, 1H), 8.03 (br d, J = 6.4 Hz, 1H), 7.91 (br s, 1H), 7.63 (br s, 2H), 7.41 (br t, J = 8.4 Hz, 1H), 6.94-6.71 (m, 2H), 6.48-6.11 (m, 1H), 5.09 (br s, 1H), 4.70-4.45 (m, 2H), 4.25-3.14 (m, 4H), 3.11-2.69 (m, 2H) |

TABLE 3-continued

Examples 64 to 210

| Int. # | Structure | Characterization Data |
|---|---|---|
| 116 | 2-((S)-4-(7-(8-chloro-7-fluoronaphthalen-1-yl)-8-fluoro-2-(((2S,4R)-4-fluoro-1-isopropylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 682<br>¹H NMR (400 MHz, CDCl₃): δ 9.06 (d, J = 1.2 Hz, 1H), 7.97 (s, 1H), 7.90-7.85 (m, 1H), 7.64-7.55 (m, 2H), 7.38 (br d, J = 2.4 Hz, 1H), 5.55-5.35 (m, 1H), 5.32-5.04 (m, 2H), 4.94-4.75 (m, 1H), 4.67 (td, J = 4.0, 8.4 Hz, 1H), 4.43 (br t, J = 14.4 Hz, 2H), 4.32 (dd, J = 7.2, 10.8 Hz, 1H), 4.24-3.85 (m, 2H), 3.81-3.59 (m, 2H), 3.53 (m, 1H), 3.20 (br s, 2H), 3.05-2.77 (m, 3H), 2.42-2.25 (m, 1H), 2.10-2.00 (m, 1H), 1.10 (d, J = 6.4 Hz, 3H), 1.02 (d, J = 6.4 Hz, 3H) |
| 117 | 2-((S)-4-(7-(8-chloro-7-fluoronaphthalen-1-yl)-8-fluoro-2-(((2S,4R)-1-isopropyl-4-methoxypyrrolidin-2-yl)methoxy)pyrido[4,3-d]pyrimidin-4-yl)-1-(2-fluoroacryloyl)piperazin-2-yl)acetonitrile | LCMS [ESI, M + 1]: 694<br>¹H NMR (400 MHz, CDCl₃): δ 9.05-9.04 (m, 1H), 8.01-7.96 (m, 1H), 7.90-7.83 (m, 1H), 7.63-7.54 (m, 2H), 7.42-7.34 (m, 1H), 5.56-5.34 (m, 1H), 5.31-5.21 (m, 1H), 4.92-4.74 (m, 1H), 4.65-4.56 (m, 1H), 4.46-4.34 (m, 2H), 4.30-4.08 (m, 2H), 4.04-3.85 (m, 2H), 3.84-3.59 (m, 2H), 3.45-3.37 (m, 1H), 3.31 (s, 3H), 3.24-3.17 (m, 1H), 3.15-3.06 (m, 1H), 3.05-2.95 (m, 1H), 2.93-2.77 (m, 1H), 2.75-2.54 (m, 1H), 2.13-2.05 (m, 1H), 2.01-1.91 (m, 1H), 1.12 (d, J = 6.4 Hz, 3H), 1.03 (d, J = 6.4 Hz, 3H) |

TABLE 3-continued

Examples 64 to 210

| Int. # | Structure | Characterization Data |
|---|---|---|
| 118 | 2-((S)-4-(7-(8-chloro-7-fluoronaphthalen-1-yl)-2-(((S)-4,4-difluoro-1-isopropylpyrrolidin-2-yl)methoxy)-8-fluoropyrido[4,3-d]pyrimidin-4-yl)-1-(2-fluoroacryloyl)piperazin-2-yl)acetonitrile | LCMS [ESI, M + 1]: 700<br>$^1$H NMR (400 MHz, CDCl$_3$): δ 9.07 (s, 1H), 8.04-7.98 (m, 1H), 7.90 (ddd, J = 1.6, 5.6, 9.2 Hz, 1H), 7.65-7.57 (m, 2H), 7.41 (dt, J = 2.4, 8.8 Hz, 1H), 5.57-5.38 (m, 1H), 5.29 (dd, J = 3.2, 16.8 Hz, 1H), 4.87 (br s, 1H), 4.72-4.65 (m, 1H), 4.52-4.41 (m, 2H), 4.35 (ddd, J = 2.8, 8.0, 10.8 Hz, 1H), 4.29-3.93 (m, 2H), 3.79 (br s, 2H), 3.59-3.50 (m, 1H), 3.30-3.13 (m, 2H), 3.09-2.95 (m, 2H), 2.92-2.80 (m, 1H), 2.56-2.26 (m, 2H), 1.12 (dd, J = 1.2, 6.8 Hz, 3H), 1.03 (d, J = 6.4 Hz, 3H) |
| 119 | 1-((S)-4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-3-methylpiperazin-1-yl)prop-2-en-1-one | LCMS [ESI, M + 1]: 593<br>$^1$H NMR (400 MHz, CDCl$_3$): δ 9.01 (s, 1H), 8.03-7.97 (m, 1H), 7.89 (dd, J = 5.6, 8.8 Hz, 1H), 7.65-7.56 (m, 2H), 7.40 (t, J = 8.8 Hz, 1H), 6.72-6.50 (m, 1H), 6.47-6.35 (m, 1H), 5.81 (br d, J = 10.4 Hz, 1H), 5.10-4.68 (m, 2H), 4.63-4.56 (m, 1H), 4.55-4.44 (m, 1H), 4.39 (br dd, J = 6.4, 10.8 Hz, 1H), 4.13-3.83 (m, 1H), 3.80-3.51 (m, 2H), 3.33-3.03 (m, 2H), 2.75 (br d, J = 5.2 Hz, 1H), 2.52 (d, J = 1.2 Hz, 3H), 2.41-2.29 (m, 1H), 2.07 (dt, J = 4.4, 8.4 Hz, 1H), 2.01-1.85 (m, 3H), 1.54-1.44 (m, 3H) |
| 120 | (S)-N-(2-((7-(8-chloro-7-fluoronaphthalen-1-yl)-4-(3-(cyanomethyl)-4-(2-fluoroacryloyl)piperazin-1-yl)-8-fluoropyrido[4,3-d]pyrimidin-2-yl)oxy)ethyl)methanesulfonamide | LCMS [ESI, M + 1]: 660<br>$^1$H NMR (400 MHz, CDCl$_3$): δ 9.10 (s, 1H), 8.05-7.99 (m, 1H), 7.91 (dd, J = 5.6, 8.4 Hz, 1H), 7.66-7.57 (m, 2H), 7.41 (dt, J = 1.6, 8.8 Hz, 1H), 5.56-5.39 (m, 1H), 5.37-5.24 (m, 2H), 4.96-4.76 (m, 1H), 4.75-4.62 (m, 2H), 4.61-4.42 (m, 2H), 4.38-3.94 (m, 2H), 3.86 (br d, J = 2.8 Hz, 2H), 3.63-3.55 (m, 2H), 3.09-2.96 (m, 4H), 2.93-2.79 (m, 1H) |

… TABLE 3-continued

Examples 64 to 210

| Int. # | Structure | Characterization Data |
|---|---|---|
| 121 | 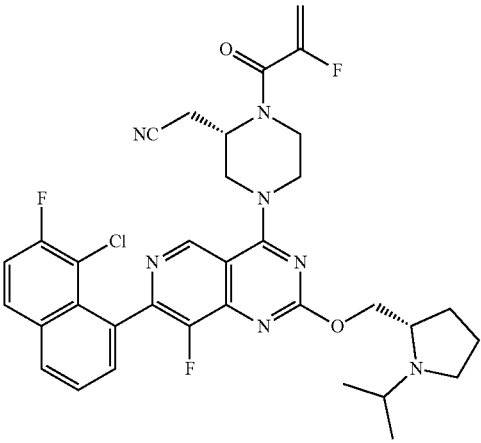<br>2-((S)-4-(7-(8-chloro-7-fluoronaphthalen-1-yl)-8-fluoro-2-(((S)-1-isopropylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 664<br>$^1$H NMR (400 MHz, CDCl$_3$): δ 8.86-8.70 (m, 1H), 8.03 (br d, J = 8.0 Hz, 1H), 7.96-7.88 (m, 1H), 7.65-7.54 (m, 2H), 7.43 (dt, J = 5.2, 8.8 Hz, 1H), 5.58-5.38 (m, 1H), 5.33-5.23 (m, 1H), 4.99-4.74 (m, 1H), 4.57-4.14 (m, 5H), 4.02-3.71 (m, 2H), 3.66-3.52 (m, 1H), 3.47-3.28 (m, 1H), 3.02-2.73 (m, 4H), 2.67-2.46 (m, 2H), 1.78-1.63 (m, 4H), 0.96-0.78 (m, 6H) |
| 122 | 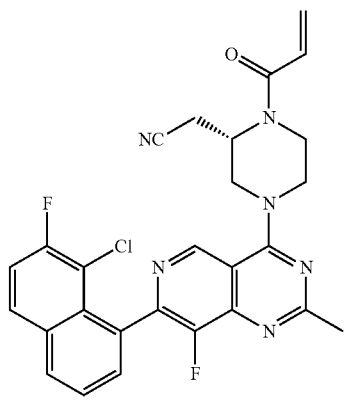<br>(S)-2-(1-acryloyl-4-(7-(8-chloro-7-fluoronaphthalen-1-yl)-8-fluoro-2-methylpyrido[4,3-d]pyrimidin-4-yl)piperazin-2-yl)acetonitrile | LCMS [ESI, M + 1]: 519<br>$^1$H NMR (400 MHz, CDCl$_3$): δ 9.15 (d, J = 2.8 Hz, 1H), 8.05-7.98 (m, 1H), 7.90 (dd, J = 8.8, 5.6 Hz, 1H), 7.66-7.57 (m, 2H), 7.41 (td, J = 8.8, 1.6 Hz, 1H), 6.67-6.53 (m, 1H), 6.48-6.38 (m, 1H), 5.86 (br d, J = 10.4 Hz, 1H), 5.24-4.89 (m, 1H), 4.82-4.57 (m, 1H), 4.53-4.40 (m, 1H), 4.22-3.55 (m, 4H), 2.99 (br d, J = 16.8, 8.0 Hz, 1H), 2.78 (d, J = 1.6 Hz, 4H) |

TABLE 3-continued

Examples 64 to 210

| Int. # | Structure | Characterization Data |
|---|---|---|
| 123 | 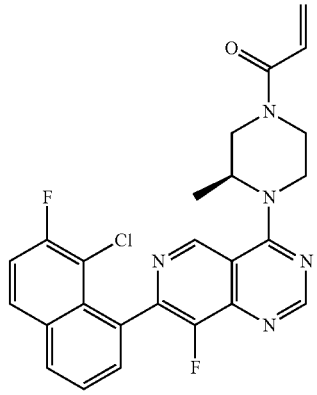<br>(S)-1-(4-(7-(8-chloro-7-fluoronaphthalen-1-yl)-8-fluoropyrido[4,3-d]pyrimidin-4-yl)-3-methylpiperazin-1-yl)prop-2-en-1-one | LCMS [ESI, M + 1]: 480<br>$^1$H NMR (400 MHz, CDCl$_3$): δ 9.17-9.12 (m, 1H), 8.88 (s, 1H), 8.05-8.00 (m, 1H), 7.91 (dd, J = 5.6, 9.2 Hz, 1H), 7.67-7.59 (m, 2H), 7.42 (t, J = 8.8 Hz, 1H), 6.71-6.53 (m, 1H), 6.46-6.38 (m, 1H), 5.82 (br d, J = 10.4 Hz, 1H), 5.11-4.93 (m, 1H), 4.83-4.42 (m, 2H), 4.16-3.85 (m, 1H), 3.83-3.51 (m, 2H), 3.36-3.07 (m, 1H), 1.55 (d, J = 6.8 Hz, 3H) |
| 124 | 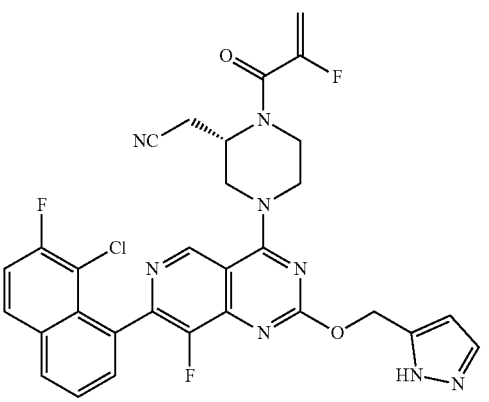<br>(S)-2-(4-(2-((1H-pyrazol-5-yl)methoxy)-7-(8-chloro-7-fluoronaphthalen-1-yl)-8-fluoropyrido[4,3-d]pyrimidin-4-yl)-1-(2-fluoroacryloyl)piperazin-2-yl)acetonitrile | LCMS [ESI, M + 1]: 619<br>$^1$H NMR (400 MHz, CDCl$_3$): δ 9.09 (s, 1H), 8.08-7.99 (m, 1H), 7.91 (dd, J = 5.6, 8.8 Hz, 1H), 7.71-7.59 (m, 2H), 7.54 (d, J = 2.0 Hz, 1H), 7.42 (dt, J = 1.6, 8.8 Hz, 1H), 6.48 (d, J = 1.2 Hz, 1H), 5.71-5.38 (m, 3H), 5.28 (td, J = 3.6, 16.8 Hz, 1H), 5.00-4.76 (m, 1H), 4.46 (br d, J = 10.0 Hz, 2H), 4.35-3.70 (m, 4H), 3.12-2.94 (m, 1H), 2.92-2.73 (m, 1H) |

TABLE 3-continued

Examples 64 to 210

| Int. # | Structure | Characterization Data |
|---|---|---|
| 125 | 2-((S)-4-(7-(8-chloronaphthalen-1-yl)-8-fluoro-2-(((S)-1-isopropylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 646<br>¹H NMR (400 MHz, CDCl₃): δ 9.06 (s, 1H), 8.07-7.99 (m, 1H), 7.90 (d, J = 8.0 Hz, 1H), 7.66-7.53 (m, 3H), 7.44 (dt, J = 2.4, 8.0 Hz, 1H), 5.59-5.40 (m, 1H), 5.29 (dd, J = 3.6, 16.8 Hz, 1H), 4.99-4.73 (m, 1H), 4.60-4.38 (m, 3H), 4.34-3.96 (m, 3H), 3.90-3.67 (m, 2H), 3.38-3.25 (m, 1H), 3.09-2.82 (m, 4H), 2.61-2.49 (m, 1H), 1.96-1.74 (m, 4H), 1.18 (br d, J = 6.0 Hz, 3H), 1.12-1.04 (m, 3H) |
| 126 | 2-((S)-4-(7-(8-chloro-7-fluoronaphthalen-1-yl)-8-fluoro-2-(((2S,4R)-4-fluoro-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 654<br>¹H NMR (400 MHz, CDCl₃): δ 9.07 (s, 1H), 8.03-7.98 (m, 1H), 7.90 (ddd, J = 0.8, 5.6, 9.2 Hz, 1H), 7.66-7.56 (m, 2H), 7.40 (td, J = 2.4, 8.8 Hz, 1H), 5.59-5.37 (m, 1H), 5.33-5.07 (m, 2H), 4.86 (br d, J = 4.4 Hz, 1H), 4.64-4.60 (m, 1H), 4.55-4.41 (m, 3H), 4.32-3.92 (m, 2H), 3.82-3.74 (m 2H), 3.64-3.49 (m, 1H), 3.14-2.96 (m, 2H), 2.92-2.79 (m, 1H), 2.72-2.56 (m, 1H), 2.54 (s, 3H), 2.40-2.25 (m, 1H), 2.15-1.95 (m, 1H) |
| 127 | (S)-2-(4-(7-(8-chloro-7-fluoronaphthalen-1-yl)-8-fluoro-2-((1-methylazetidin-3-yl)methoxy)pyrido[4,3-d]pyrimidin-4-yl)-1-(2-fluoroacryloyl)piperazin-2-yl)acetonitrile | LCMS [ESI, M + 1]: 622<br>¹H NMR (400 MHz, CDCl₃): δ 9.10 (s, 1H), 8.05-7.99 (m, 1H), 7.95-7.87 (m, 1H), 7.65-7.59 (m, 2H), 7.42 (dt, J = 2.0, 8.8 Hz, 1H), 5.58-5.40 (m, 1H), 5.30 (dd, J = 3.6, 16.8 Hz, 1H), 4.97-4.78 (m, 1H), 4.76-4.56 (m, 3H), 4.54-4.43 (m, 1H), 4.41-4.15 (m, 1H), 4.12-4.03 (m, 1H), 4.00 (br dd, J = 2.4, 4.4 Hz, 1H), 3.98-3.75 (m, 3H), 3.73-3.58 (m, 2H), 3.32-3.16 (m, 1H), 3.13-2.98 (m, 1H), 2.95-2.80 (m, 1H), 2.66 (br s, 3H) |

TABLE 3-continued

Examples 64 to 210

| Int. # | Structure | Characterization Data |
|---|---|---|
| 128 | 2-((S)-4-(7-(8-chloro-7-fluoronaphthalen-1-yl)-2-(((S)-1-ethylpyrrolidin-2-yl)methoxy)-8-fluoropyrido[4,3-d]pyrimidin-4-yl)-1-(2-fluoroacryloyl)piperazin-2-yl)acetonitrile | LCMS [ESI, M + 1]: 650<br>$^1$H NMR (400 MHz, CDCl$_3$): δ 9.10 (s, 1H), 8.05-7.99 (m, 1H), 7.95-7.87 (m, 1H), 7.65-7.59 (m, 2H), 7.42 (dt, J = 2.0, 8.8 Hz, 1H), 5.58-5.40 (m, 1H), 5.30 (dd, J = 3.6, 16.8 Hz, 1H), 4.97-4.78 (m, 1H), 4.76-4.56 (m, 3H), 4.54-4.43 (m, 1H), 4.41-4.15 (m, 1H), 4.12-4.03 (m, 1H), 4.00 (br dd, J = 2.4, 4.4 Hz, 1H), 3.98-3.75 (m, 3H), 3.73-3.58 (m, 2H), 3.32-3.16 (m, 1H), 3.13-2.98 (m, 1H), 2.95-2.80 (m, 1H), 2.66 (br s, 3H) |
| 129 | 2-((S)-4-(2-(3-((1S,4S)-2-oxa-5-azabicyclo[2.2.1]heptan-5-yl)propoxy)-7-(8-chloro-7-fluoronaphthalen-1-yl)-8-fluoropyrido[4,3-d]pyrimidin-4-yl)-1-(2-fluoroacryloyl)piperazin-2-yl)acetonitrile | LCMS [ESI, M + 1]: 678<br>$^1$H NMR (400 MHz, CDCl$_3$): δ 9.07 (s, 1H), 8.05-7.98 (m, 1H), 7.94-7.86 (m, 1H), 7.66-7.57 (m, 2H), 7.41 (dt, J = 2.0, 8.8 Hz, 1H), 5.58-5.38 (m, 1H), 5.29 (dd, J = 3.6, 16.8 Hz, 1H), 4.88 (br d, J = 2.4 Hz, 1H), 4.68-4.57 (m, 2H), 4.53-4.42 (m, 2H), 4.40 (s, 1H), 4.33-4.15 (m, 1H), 4.05 (d, J = 8.0 Hz, 2H), 3.79 (br s, 2H), 3.63 (dd, J = 1.6, 7.8 Hz, 1H), 3.55 (s, 1H), 3.09-2.95 (m, 2H), 2.93-2.73 (m, 3H), 2.56 (d, J = 10.0 Hz, 1H), 2.03 (quin, J = 6.8 Hz, 2H), 1.88 (br d, J = 9.6 Hz, 1H), 1.76-1.72 (m, 1H) |
| 130 | 2-((S)-4-(7-(8-chloro-7-fluoronaphthalen-1-yl)-8-fluoro-2-((1-isopropylazetidin-2-yl)methoxy)pyrido[4,3-d]pyrimidin-4-yl)-1-(2-fluoroacryloyl)piperazin-2-yl)acetonitrile | LCMS [ESI, M + 1]: 650<br>$^1$H NMR (400 MHz, CDCl$_3$): δ 9.06 (s, 1H), 8.01 (br d, J = 8.8 Hz, 1H), 7.90 (dd, J = 5.6, 8.8 Hz, 1H), 7.66-7.56 (m, 2H), 7.41 (br t, J = 8.8 Hz, 1H), 5.59-5.37 (m, 1H), 5.29 (br dd, J = 2.8, 16.8 Hz, 1H), 4.98-4.78 (m, 1H), 4.70 (br dd, J = 4.4, 10.8 Hz, 1H), 4.55-4.39 (m, 3H), 4.30-3.98 (m, 2H), 3.89-3.56 (m, 3H), 3.47 (br s, 1H), 3.12-2.97 (m, 1H), 2.96-2.80 (m, 2H), 2.50 (br d, J = 5.6 Hz, 1H), 2.25-2.06 (m, 2H), 1.08 (br d, J = 6.0 Hz, 3H), 0.95 (br d, J = 6.0 Hz, 3H) |

TABLE 3-continued

Examples 64 to 210

| Int. # | Structure | Characterization Data |
|---|---|---|
| 131 | 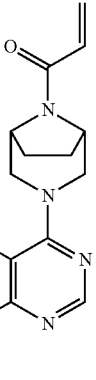<br>1-((1R,5S)-3-(7-(8-chloro-7-fluoronaphthalen-1-yl)-8-fluoropyrido[4,3-d]pyrimidin-4-yl)-3,8-diazabicyclo[3.2.1]octan-8-yl)prop-2-en-1-one | LCMS [ESI, M + 1]: 492<br>$^1$H NMR (400 MHz, CDCl$_3$): δ 9.11 (s, 1H), 8.87-8.83 (s, 1H), 8.02 (dd, J = 2.0, 7.2 Hz, 1H), 7.91 (dd, J = 5.6, 9.2 Hz, 1H), 7.66-7.58 (m, 2H), 7.41 (t, J = 8.4 Hz, 1H), 6.64-6.45 (m, 2H), 5.83 (dd, J = 2.0, 9.6 Hz, 1H), 5.03-4.50 (m, 4H), 3.98-3.55 (m, 2H), 2.14-1.80 (m, 4H) |
| 132 | 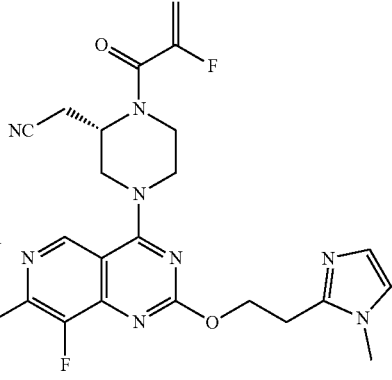<br>(S)-2-(4-(7-(8-chloro-7-fluoronaphthalen-1-yl)-8-fluoro-2-(2-(1-methyl-1H-imidazol-2-yl)ethoxy)pyrido[4,3-d]pyrimidin-4-yl)-1-(2-fluoroacryloyl)piperazin-2-yl)acetonitrile | LCMS [ESI, M + 1]: 647<br>$^1$H NMR (400 MHz, CDCl$_3$): δ 9.07 (s, 1H), 8.06-7.98 (m, 1H), 7.91 (dd, J = 5.6, 8.8 Hz, 1H), 7.67-7.56 (m, 2H), 7.41 (td, J = 2.0, 8.8 Hz, 1H), 6.94 (d, J = 1.2 Hz, 1H), 6.81 (d, J = 0.8 Hz, 1H), 5.59-5.38 (m, 1H), 5.35-5.24 (m, 1H), 5.00-4.74 (m, 3H), 4.56-4.39 (m, 2H), 4.36-3.91 (m, 2H), 3.89-3.73 (m, 2H), 3.72 (s, 3H), 3.34-3.25 (m, 2H), 3.11-2.97 (m, 1H), 2.95-2.79 (m, 1H) |
| 133 | 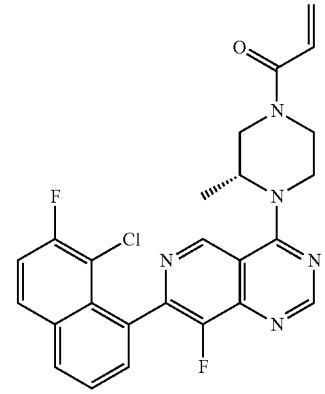<br>(R)-1-(4-(7-(8-chloro-7-fluoro-naphthalen-1-yl)-8-fluoropyrido[4,3-d]pyrimidin-4-yl)-3-methyl-piperazin-1-yl)prop-2-en-1-one | LCMS [ESI, M + 1]: 480<br>$^1$H NMR (400 MHz, CDCl$_3$) δ 9.18-9.11 (m, 1H), 8.88 (s, 1H), 8.07-7.98 (m, 1H), 7.91 (dd, J = 5.6, 8.8 Hz, 1H), 7.69-7.56 (m, 2H), 7.41 (t, J = 8.8 Hz, 1H), 6.73-6.51 (m, 1H), 6.47-6.36 (m, 1H), 5.81 (br d, J = 10.4 Hz, 1H), 4.99 (br d, J = 1.6 Hz, 1H), 4.83-4.40 (m, 2H), 4.19-3.84 (m, 1H), 3.83-3.49 (m, 2H), 3.38-3.03 (m, 1H), 1.55 (br d, J = 6.8 Hz, 3H) |

TABLE 3-continued

Examples 64 to 210

| Int. # | Structure | Characterization Data |
|---|---|---|
| 134 | 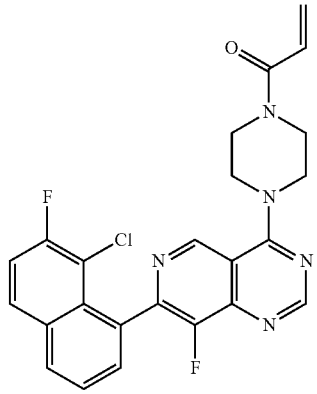<br>1-(4-(7-(8-chloro-7-fluoro-naphthalen-1-yl)-8-fluoropyrido[4,3-d]pyrimidin-4-yl)piperazin-1-yl)prop-2-en-1-one | LCMS [ESI, M + 1]: 466<br>$^1$H NMR (400 MHz, CDCl$_3$) δ 9.18-9.11 (m, 1H), 8.88 (s, 1H), 8.07-7.98 (m, 1H), 7.91 (dd, J = 5.6, 8.8 Hz, 1H), 7.69-7.56 (m, 2H), 7.41 (t, J = 8.8 Hz, 1H), 6.73-6.51 (m, 1H), 6.47-6.36 (m, 1H), 5.81 (br d, J = 10.4 Hz, 1H), 4.99 (br d, J = 1.6 Hz, 1H), 4.83-4.40 (m, 2H), 4.19-3.84 (m, 1H), 3.83-3.49 (m, 2H), 3.38-3.03 (m, 1H), 1.55 (br d, J = 6.8 Hz, 3H) |
| 135 | 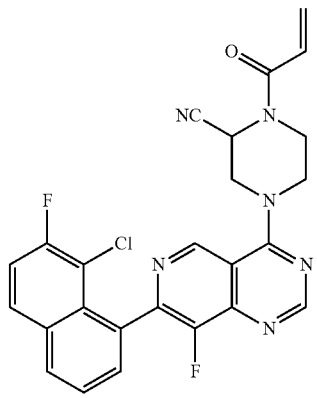<br>1-acryloyl-4-(7-(8-chloro-7-fluoronaphthalen-1-yl)-8-fluoropyrido[4,3-d]pyrimidin-4-yl)piperazine-2-carbonitrile | LCMS [ESI, M + 1]: 491<br>$^1$H NMR (400 MHz, CDCl$_3$) δ 9.31 (d, J = 10.4 Hz, 1H), 9.00 (s, 1H), 8.04 (dd, J = 1.6, 7.6 Hz, 1H), 7.92 (dd, J = 5.6, 9.2 Hz, 1H), 7.68-7.60 (m, 2H), 7.45-7.40 (m, 1H), 6.66-6.47 (m, 2H), 6.08-5.73 (m, 2H), 4.92-4.83 (m, 1H), 4.70-4.59 (m, 1H), 4.32-4.03 (m, 1H), 4.01-3.80 (m, 1H), 3.75-3.44 (m, 2H) |
| 136 | 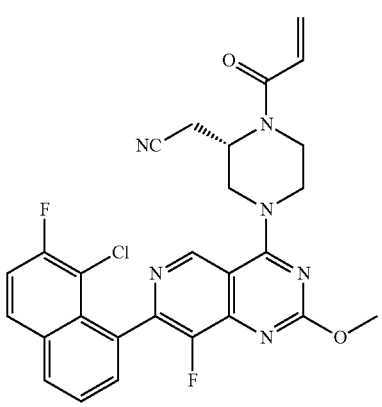<br>(S)-2-(1-acryloyl-4-(7-(8-chloro-7-fluoronaphthalen-1-yl)-8-fluoro-2-methoxypyrido[4,3-d]pyrimidin-4-yl)piperazin-2-yl)acetonitrile | LCMS [ESI, M + 1]: 535<br>$^1$H NMR (400 MHz, CDCl$_3$) δ 9.09 (s, 1H), 8.01 (br d, J = 8.8 Hz, 1H), 7.90 (br dd, J = 5.6, 8.8 Hz, 1H), 7.67-7.56 (m, 2H), 7.41 (br t, J = 8.0 Hz, 1H), 6.67-6.55 (m, 1H), 6.50-6.38 (m, 1H), 5.87 (br d, J = 10.4 Hz, 1H), 5.22-4.76 (m 1H), 4.49 (br d, J = 12.4 Hz, 2H), 4.31-3.57 (m, 7H), 3.08-2.73 (m, 2H) |

TABLE 3-continued

Examples 64 to 210

| Int. # | Structure | Characterization Data |
|---|---|---|
| 137 | 1-(4-(7-(8-chloronaphthalen-1-yl)-8-fluoropyrido[4,3-d]pyrimidin-4-yl)piperazin-1-yl)prop-2-en-1-one | LCMS [ESI, M + 1]: 448<br>¹H NMR (400 MHz, CDCl₃) δ 9.19 (s, 1H), 8.89 (s, 1H), 8.04 (dd, J = 1.6, 7.6 Hz, 1H), 7.91 (dd, J = 1.2, 8.4 Hz, 1H), 7.67-7.54 (m, 3H), 7.48-7.42 (m, 1H), 6.63 (dd, J = 10.4, 16.8 Hz, 1H), 6.41 (dd, J = 1.6, 16.8 Hz, 1H), 5.82 (dd, J = 1.6, 10.4 Hz, 1H), 4.18-4.07 (m, 4H), 4.03-3.83 (m, 4H) |
| 138 | 1-(2-(7-(8-chloro-7-fluoronaphthalen-1-yl)-8-fluoropyrido[4,3-d]pyrimidin-4-yl)-2,6-diazaspiro[3.4]octan-6-yl)prop-2-en-1-one | LCMS [ESI, M + 1]: 492<br>¹H NMR (400 MHz, CDCl₃) δ 9.04 (s, 1H), 8.81 (d, J = 1.2 Hz, 1H), 8.05-7.98 (m, 1H), 7.90 (dd, J = 1.2, 5.6, 9.2 Hz, 1H), 7.65-7.57 (m, 2H), 7.41 (t, J = 8.8 Hz, 1H), 6.54-6.36 (m, 2H), 5.80-5.70 (m, 1H), 4.59 (br s, 4H), 3.98-3.85 (m, 2H), 3.74 (t, J = 7.2 Hz, 2H), 2.41 (t, J = 6.8 Hz, 1H), 2.31 (t, J = 7.2 Hz, 1H) |
| 139 | 2-((2S)-4-(7-(8-chloro-7-fluoronaphthalen-1-yl)-2-((1-ethylazetidin-2-yl)methoxy)-8-fluoropyrido[4,3-d]pyrimidin-4-yl)-1-(2-fluoroacryloyl)piperazin-2-yl)acetonitrile | LCMS [ESI, M + 1]: 636<br>¹H NMR (400 MHz, CDCl₃) δ 9.12 (d, J = 3.2 Hz, 1H), 8.85 (d, J = 1.6 Hz, 1H), 8.30-7.98 (m, 2H), 7.65-7.60 (m, 2H), 7.40 (t, J = 8.8 Hz, 1H), 4.93 (br d, J = 7.2 Hz, 1H), 4.56-4.43 (m, 1H), 4.40-4.16 (m, 1H), 4.00 (br s, 1H), 3.78-3.64 (m, 1H), 3.32-3.12 (m, 2H), 1.51 (s, 9H), 1.46 (s, 3H) |

TABLE 3-continued

Examples 64 to 210

| Int. # | Structure | Characterization Data |
|---|---|---|
| 140 | 2-((S)-4-(7-(8-chloro-7-fluoronaphthalen-1-yl)-2-(((S)-1-cyclobutylpyrrolidin-2-yl)methoxy)-8-fluoropyrido[4,3-d]pyrimidin-4-yl)-1-(2-fluoroacryloyl)piperazin-2-yl)acetonitrile | LCMS [ESI, M + 1]: 676<br>$^1$H NMR (400 MHz, CDCl$_3$) δ 9.06 (s, 1H), 8.02-8.00 (m, 1H), 7.90 (dd, J = 5.6, 7.6 Hz, 1H), 7.63-7.59 (m, 2H), 7.43-7.38 (m, 1H), 5.55-5.42 (m, 1H), 5.29 (br dd, J = 2.8, 16.8 Hz, 1H), 4.97-4.80 (m, 1H), 4.65 (br d, J = 0.8 Hz, 1H), 4.51-4.43 (m, 2H), 4.33-4.00 (m, 3H), 3.89-3.71 (m, 2H), 3.38-3.30 (m, 1H), 3.17-3.00 (m, 3H), 2.93-2.85 (m, 1H), 2.55-2.43 (m, 1H), 2.27-1.82 (m, 10H) |
| 141 | 1-((S)-4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-2-methylpiperazin-1-yl)prop-2-en-1-one | LCMS [ESI, M + 1]: 593<br>$^1$H NMR (400 MHz, CDCl$_3$) δ 9.07 (d, J = 4.4 Hz, 1H), 8.04-7.96 (m, 1H), 7.90 (dd, J = 5.6, 9.2 Hz, 1H), 7.66-7.54 (m, 2H), 7.41 (t, J = 8.8 Hz, 1H), 6.60 (dd, J = 10.4, 16.8 Hz, 1H), 6.45-6.36 (m, 1H), 5.84-5.75 (m, 1H), 4.61 (br dd, J = 4.4, 10.8 Hz, 1H), 4.57-4.45 (m, 2H), 4.44-4.29 (m, 3H), 3.94-3.77 (m, 1H), 3.76-3.51 (m, 2H), 3.21-3.06 (m, 1H), 2.83-2.70 (m, 1H), 2.59-2.45 (m, 3H), 2.40-2.25 (m, 1H), 2.17-2.00 (m, 1H), 1.94-1.78 (m, 3H), 1.43-1.33 (m, 3H) |

TABLE 3-continued

Examples 64 to 210

| Int. # | Structure | Characterization Data |
|---|---|---|
| 142 | 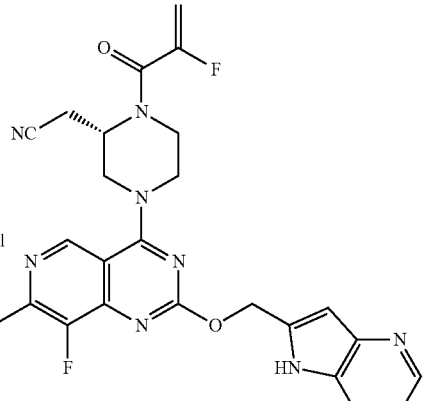<br>(S)-2-(4-(2-((1H-pyrrolo[3,2-b]pyridin-2-yl)methoxy)-7-chloro-7-fluoronaphthalen-1-yl)-8-fluoropyrido[4,3-d]pyrimidin-4-yl)-1-(2-fluoroacryloyl)piperazin-2-yl)acetonitrile | LCMS [ESI, M + 1]: 669<br>$^1$H NMR (400 MHz, CDCl$_3$) δ 9.77 (br s, 1H), 9.13 (s, 1H), 8.44 (dd, J = 1.2, 4.8 Hz, 1H), 8.06 (dd, J = 1.6, 8.0 Hz, 1H), 7.98-7.93 (m, 1H), 7.73-7.64 (m, 2H), 7.63-7.59 (m, 1H), 7.50-7.43 (m, 1H), 7.11-7.06 (m, 1H), 6.85 (s, 1H), 5.78-5.72 (m, 1H), 5.70-5.65 (m, 1H), 5.56-5.40 (m, 1H), 5.28 (dt, J = 3.2, 16.8 Hz, 1H), 4.93-4.73 (m, 1H), 4.54-4.40 (m, 2H), 4.32-4.04 (m, 2H), 3.99-3.78 (m, 2H), 3.06-2.96 (m, 1H), 2.85-2.76 (m, 1H) |
| 143 | 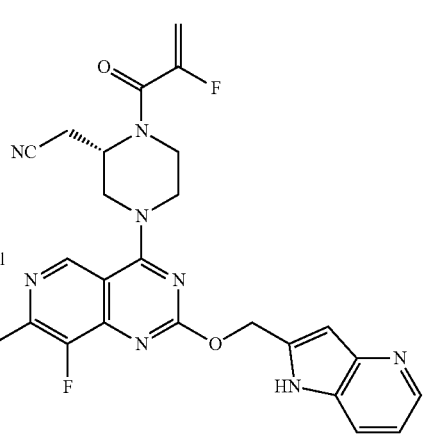<br>(S)-2-(4-(2-((1H-pyrrolo[3,2-b]pyridin-2-yl)methoxy)-7-chloro-7-fluoronaphthalen-1-yl)-8-fluoropyrido[4,3-d]pyrimidin-4-yl)-1-(2-fluoroacryloyl)piperazin-2-yl)acetonitrile | LCMS [ESI, M + 1]: 662<br>$^1$H NMR (400 MHz, CDCl$_3$) δ 9.12-9.00 (m, 1H), 8.03-7.98 (m, 1H), 7.92-7.87 (m, 1H), 7.66-7.57 (m, 2H), 7.44-7.38 (m, 1H), 5.57-5.39 (m, 1H), 5.36-5.24 (m, 1H), 4.99-4.76 (m, 1H), 4.55-4.42 (m, 2H), 4.40-4.32 (m, 1H), 4.22-4.15 (m, 1H), 4.12-3.92 (m, 1H), 3.84 (br s, 2H), 3.23 (br s, 1H), 3.09-2.97 (m, 1H), 2.94-2.81 (m, 1H), 2.44 (d, J = 1.6 Hz, 3H), 2.41 (br d, J = 2.8 Hz, 1H), 2.38-2.30 (m, 1H), 2.01-1.89 (m, 1H), 1.80 (br d, J = 9.6 Hz, 1H), 1.70-1.64 (m, 2H), 1.40-1.27 (m, 3H) |
| 144 | 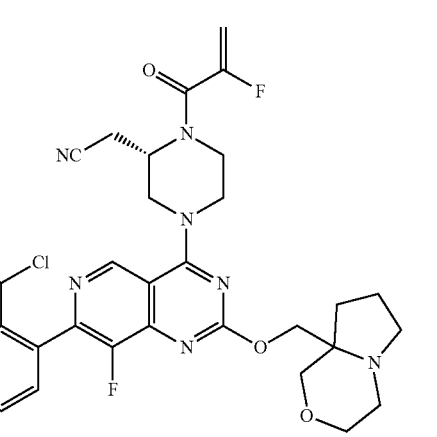<br>2-((2S)-4-(7-(8-chloro-7-fluoronaphthalen-1-yl)-8-fluoro-2-((tetrahydro-1H-pyrrolo[2,1-c][1,4]oxazin-8a(6H)-yl)methoxy)pyrido[4,3-d]pyrimidin-4-yl)-1-(2-fluoroacryloyl)piperazin-2-yl)acetonitrile | LCMS [ESI, M + 1]: 678<br>$^1$H NMR (400 MHz, CDCl$_3$) δ 9.06 (s, 1H), 8.04-7.98 (m, 1H), 7.90 (dd, J = 5.6, 8.8 Hz, 1H), 7.66-7.57 (m, 2H), 7.41 (dt, J = 2.0, 8.8 Hz, 1H), 5.60-5.38 (m, 1H), 5.30 (dd, J = 3.6, 16.8 Hz, 1H), 4.97-4.73 (m, 2H), 4.59-4.38 (m, 3H), 4.37-3.96 (m, 2H), 3.95-3.69 (m, 4H), 3.66-3.56 (m, 1H), 3.44 (d, J = 11.6 Hz, 1H), 3.36-3.23 (m, 1H), 3.20-3.09 (m, 1H), 3.08-2.96 (m, 2H), 2.94-2.81 (m, 1H), 2.80-2.70 (m, 1H), 2.02 (s, 1H), 1.90 (quin, J = 7.2 Hz, 2H), 1.59-1.54 (m, 1H) |

TABLE 3-continued

Examples 64 to 210

| Int. # | Structure | Characterization Data |
|---|---|---|
| 145 | 2-((2S)-4-(7-(8-chloro-7-fluoronaphthalen-1-yl)-8-fluoro-2-(((2R)-2-fluorotetrahydro-1H-pyrrolizin-7a(5H)-yl)methoxy)pyrido[4,3-d]pyrimidin-4-yl)-1-(2-fluoroacryloyl)piperazin-2-yl)acetonitrile | LCMS [ESI, M + 1]: 680<br>$^1$H NMR (400 MHz, CDCl$_3$) δ 9.18 (s, 1H), 8.34-8.14 (m, 2H), 7.83-7.61 (m, 3H), 5.54-5.35 (m, 2H), 5.35-5.17 (m, 1H), 5.02-4.71 (m, 1H), 4.61-4.34 (m, 2H), 4.27-4.11 (m, 2H), 4.11-3.58 (m, 4H), 3.28-3.18 (m, 1H), 3.13-3.02 (m, 1H), 3.02-2.92 (m, 1H), 2.91-2.73 (m, 1H), 2.61-2.54 (m, 2H), 2.36-2.30 (m, 1H), 2.01-1.74 (m, 4H), 1.75-1.57 (m, 1H) |
| 146 | 1-((2S,6S)-4-(7-(8-chloro-7-fluoronaphthalen-1-yl)-8-fluoropyrido[4,3-d]pyrimidin-4-yl)-2,6-dimethylpiperazin-1-yl)prop-2-en-1-one | LCMS [ESI, M + 1]: 494<br>$^1$H NMR (400 MHz, CDCl$_3$) δ 9.27 (d, J = 10.4 Hz, 1H), 8.89 (d, J = 3.2 Hz, 1H), 8.06-8.00 (m, 1H), 7.95-7.88 (m, 1H), 7.71-7.58 (m, 2H), 7.46-7.37 (m, 1H), 6.68-6.58 (m, 1H), 6.56-6.48 (m, 1H), 5.83 (dt, J = 2.0, 10.0 Hz, 1H), 4.94-4.30 (m, 4H), 4.22-4.08 (m, 2H), 1.48-1.39 (m, 6H) |
| 147 | 2-((S)-4-(7-(7,8-dichloronaphthalen-1-yl)-8-fluoro-2-(((S)-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 652<br>$^1$H NMR (400 MHz, CDCl$_3$) δ 9.06 (s, 1H), 8.02-7.96 (m, 1H), 7.83 (d, J = 8.8 Hz, 1H), 7.66-7.58 (m, 3H), 5.58-5.38 (m, 1H), 5.34-5.25 (m, 1H), 5.00-4.72 (m, 1H), 4.61 (dd, J = 4.8, 10.8 Hz, 1H), 4.55-4.38 (m, 3H), 4.32-3.94 (m, 2H), 3.88-3.67 (m, 2H), 3.15 (br t, J = 7.6 Hz, 1H), 3.08-2.97 (m, 1H), 2.86 (ddd, J = 5.6, 11.2, 16.8 Hz, 1H), 2.80-2.71 (m, 1H), 2.53 (s, 3H), 2.37-2.27 (m, 1H), 2.13-2.00 (m, 1H), 1.92-1.79 (m, 3H) |

TABLE 3-continued

Examples 64 to 210

| Int. # | Structure | Characterization Data |
|---|---|---|
| 148 | 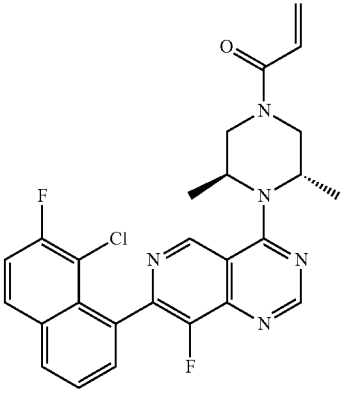<br>1-((3S,5S)-4-(7-(8-chloro-7-fluoronaphthalen-1-yl)-8-fluoropyrido[4,3-d]pyrimidin-4-yl)-3,5-dimethylpiperazin-1-yl)prop-2-en-1-one | LCMS [ESI, M + 1]: 494<br>$^1$H NMR (400 MHz, CDCl$_3$) δ 9.32 (d, J = 1.2 Hz, 1H), 9.04 (d, J = 6.0 Hz, 1H), 8.03 (dd, J = 2.0, 7.2 Hz, 1H), 7.92 (dd, J = 5.6, 9.2 Hz, 1H), 7.68-7.59 (m, 2H), 7.46-7.39 (m, 1H), 6.62 (ddd, J = 1.6, 10.4, 16.4 Hz, 1H), 6.43 (ddd, J = 1.6, 4.4, 16.4 Hz, 1H), 5.82 (dt, J = 2.4, 10.4 Hz, 1H), 4.61-4.47 (m, 2H), 4.06-3.72 (m, 4H), 1.46-1.37 (m, 6H) |
| 149 | 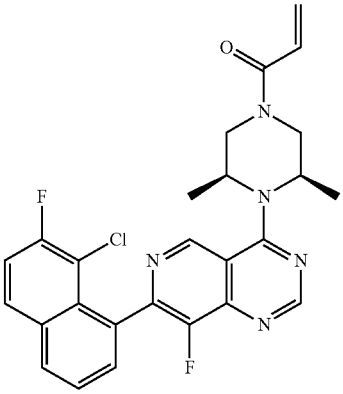<br>1-((3R,5S)-4-(7-(8-chloro-7-fluoronaphthalen-1-yl)-8-fluoropyrido[4,3-d]pyrimidin-4-yl)-3,5-dimethylpiperazin-1-yl)prop-2-en-1-one | LCMS [ESI, M + 1]: 494<br>$^1$H NMR (400 MHz, CDCl$_3$) δ 9.23 (s, 1H), 8.86 (s, 1H), 8.07-7.99 (m, 1H), 7.92 (dd, J = 5.6, 9.2 Hz, 1H), 7.68-7.57 (m, 2H), 7.42 (t, J = 8.8 Hz, 1H), 6.71-6.60 (m, 1H), 6.53-6.41 (m, 1H), 5.84 (dd, J = 1.6, 10.4 Hz, 1H), 5.32-4.99 (m, 2H), 4.60-4.39 (m, 1H), 4.00-3.86 (m, 1H), 3.72-3.55 (m, 1H), 3.34-3.20 (m, 1H), 1.66 (s, 2H), 1.64 (s, 4H) |
| 150 | 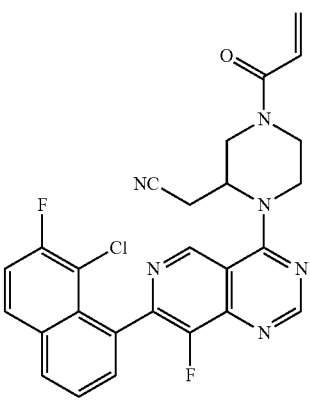<br>2-(4-acryloyl-1-(7-(8-chloro-7-fluoronaphthalen-1-yl)-8-fluoropyrido[4,3-d]pyrimidin-4-yl)piperazin-2-yl)acetonitrile | LCMS [ESI, M + 1]: 505<br>$^1$H NMR (400 MHz, CDCl$_3$) δ 9.21 (s, 1H), 8.97 (d, J = 3.6 Hz, 1H), 8.12-7.99 (m, 1H), 7.92 (dd, J = 5.6, 9.2 Hz, 1H), 7.73-7.57 (m, 2H), 7.43 (t, J = 8.8 Hz, 1H), 6.77-6.55 (m, 1H), 6.53-6.42 (m, 1H), 5.89 (br d, J = 9.6 Hz, 1H), 5.58-5.16 (m, 1H), 4.81-4.54 (m, 1H), 4.51-4.38 (m, 1H), 4.36-3.96 (m, 1H), 3.94-3.73 (m, 1H), 3.70-3.43 (m, 1H), 3.38-2.79 (m, 3H) |

TABLE 3-continued

Examples 64 to 210

| Int. # | Structure | Characterization Data |
|---|---|---|
| 151 | 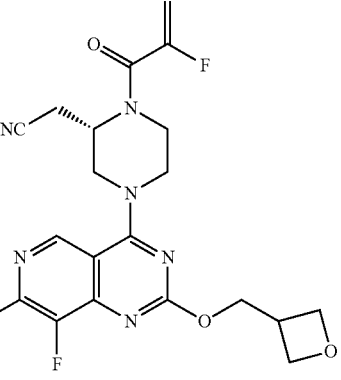<br>(S)-2-(4-(7-(8-chloro-7-fluoronaphthalen-1-yl)-8-fluoro-2-(oxetan-3-ylmethoxy)pyrido[4,3-d]pyrimidin-4-yl)-1-(2-fluoroacryloyl)piperazin-2-yl)acetonitrile | LCMS [ESI, M + 1]: 609<br>$^1$H NMR (400 MHz, CDCl$_3$) δ 9.09 (s, 1H), 8.06-7.99 (m, 1H), 7.91 (dd, J = 5.6, 8.8 Hz, 1H), 7.68-7.58 (m, 2H), 7.41 (td, J = 1.6, 8.8 Hz, 1H), 5.62-5.38 (m, 1H), 5.30 (dd, J = 3.6, 16.8 Hz, 1H), 4.96-4.82 (m, 3H), 4.79 (d, J = 6.8 Hz, 2H), 4.62 (t, J = 6.0 Hz, 2H), 4.57-4.42 (m, 2H), 4.40-3.96 (m, 2H), 3.95-3.63 (m, 2H), 3.60-3.48 (m, 1H), 3.10-2.96 (m, 1H), 2.94-2.79 (m, 1H) |
| 152 | 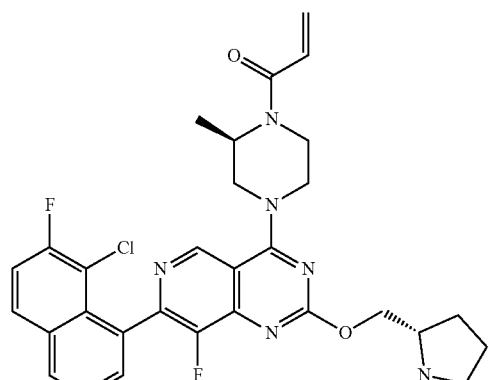<br>1-((R)-4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-2-methylpiperazin-1-yl)prop-2-en-1-one | LCMS [ESI, M + 1]: 593<br>$^1$H NMR (400 MHz, CDCl$_3$) δ 9.07 (d, J = 4.4 Hz, 1H), 8.02-7.99 (m, 1H), 7.90 (dd, J = 5.6, 8.8 Hz, 1H), 7.61 (ddd, J = 2.0, 5.6, 7.6 Hz, 2H), 7.40 (t, J = 8.8 Hz, 1H), 6.64-6.57 (m, 1H), 6.43-6.37 (m, 1H), 5.80 (d, J = 11.6 Hz, 1H), 4.76-4.21 (m, 6H), 3.95-3.48 (m, 3H), 3.12 (br t, J = 7.6 Hz, 1H), 2.76 (br d, J = 5.6 Hz, 1H), 2.51 (s, 3H), 2.34-2.27 (m, 1H), 2.12-2.03 (m, 1H), 1.92-1.76 (m, 3H), 1.45-1.36 (m, 3H) |
| 153 | 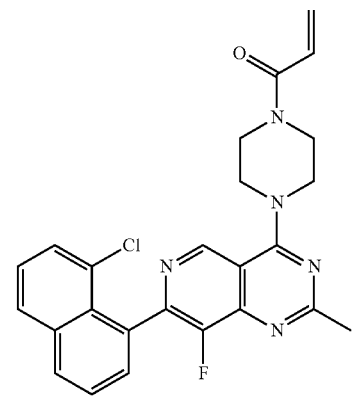<br>1-(4-(7-(8-chloronaphthalen-1-yl)-8-fluoro-2-methylpyrido[4,3-d]pyrimidin-4-yl)piperazin-1-yl)prop-2-en-1-one | LCMS [ESI, M + 1]: 462<br>$^1$H NMR (400 MHz, CDCl$_3$) δ 9.13 (s, 1H), 8.02 (dd, J = 7.6, 1.6 Hz, 1H), 7.89 (dd, J = 8.0, 1.2 Hz, 1H), 7.66-7.57 (m, 2H), 7.55 (dd, J = 7.6, 1.2 Hz, 1H), 7.47-7.40 (m, 1H), 6.62 (dd, J = 16.8, 10.4 Hz, 1H), 6.45-6.37 (m, 1H), 5.81 (dd, J = 10.4, 1.8 Hz, 1H), 4.15-4.04 (m, 4H), 4.01-3.81 (m, 4H), 2.75 (s, 3H) |

TABLE 3-continued

Examples 64 to 210

| Int. # | Structure | Characterization Data |
|---|---|---|
| 154 | (S)-2-(4-(7-(8-chloro-7-fluoronaphthalen-1-yl)-8-fluoro-2-((3-methyloxetan-3-yl)methoxy)pyrido[4,3-d]pyrimidin-4-yl)-1-(2-fluoroacryloyl)piperazin-2-yl)acetonitrile | LCMS [ESI, M + 1]: 623<br>$^1$H NMR (400 MHz, CDCl$_3$) δ 9.08 (s, 1H), 8.06-7.98 (m, 1H), 7.90 (dd, J = 5.6, 8.8 Hz, 1H), 7.66-7.58 (m, 2H), 7.41 (td, J = 1.6, 8.8 Hz, 1H), 5.59-5.39 (m, 1H), 5.30 (dd, J = 3.6, 16.8 Hz, 1H), 4.98-4.86 (m, 1H), 4.73-4.62 (m, 4H), 4.60-4.43 (m, 4H), 4.40-3.99 (m, 2H), 3.94-3.55 (m, 2H), 3.11-2.97 (m, 1H), 2.94-2.79 (m, 1H), 1.49 (s, 3H) |
| 155 | 1-((R)-4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-3-methylpiperazin-1-yl)prop-2-en-1-one | LCMS [ESI, M + 1]: 593<br>$^1$H NMR (400 MHz, CDCl$_3$) δ 9.01 (s, 1H), 8.03-7.96 (m, 1H), 7.89 (dd, J = 5.2, 8.8 Hz, 1H), 7.65-7.56 (m, 2H), 7.40 (t, J = 8.8 Hz, 1H), 6.71-6.51 (m, 1H), 6.45-6.35 (m, 1H), 5.81 (br d, J = 10.4 Hz, 1H), 5.06-4.88 (m, 1H), 4.78-4.41 (m, 4H), 4.12-3.83 (m, 1H), 3.80-3.52 (m, 2H), 3.35-3.06 (m, 2H), 3.02-2.89 (m, 1H), 2.62 (s, 3H), 2.49-2.38 (m, 1H), 2.18-2.08 (m, 1H), 2.00-1.80 (m, 3H), 1.55-1.45 (m, 3H) |
| 156 | 2-((2S)-4-(7-(8-chloro-7-fluoronaphthalen-1-yl)-8-fluoro-2-(oxetan-2-ylmethoxy)pyrido[4,3-d]pyrimidin-4-yl)-1-(2-fluoroacryloyl)piperazin-2-yl)acetonitrile | LCMS [ESI, M + 1]: 609<br>$^1$H NMR (400 MHz, CDCl$_3$) δ 9.07 (s, 1H), 8.08-7.96 (m, 1H), 7.95-7.83 (m, 1H), 7.69-7.52 (m, 2H), 7.41 (td, J = 2.0, 8.8 Hz, 1H), 5.57-5.38 (m, 1H), 5.29 (br dd, J = 3.6, 16.8 Hz, 1H), 5.24-5.16 (m, 1H), 5.01-4.82 (m, 1H), 4.80-4.65 (m, 4H), 4.58-4.42 (m, 2H), 4.34-3.95 (m, 2H), 3.93-3.59 (m, 2H), 3.09-2.97 (m, 1H), 2.94-2.65 (m, 3H) |

TABLE 3-continued

Examples 64 to 210

| Int. # | Structure | Characterization Data |
|---|---|---|
| 157 | 2-((S)-4-(7-(7,8-difluoronaphthalen-1-yl)-8-fluoro-2-(((S)-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 620<br>$^1$H NMR (400 MHz, CDCl$_3$) δ 9.11-9.05 (m, 1H), 8.02-7.96 (m, 1H), 7.77-7.70 (m, 1H), 7.69-7.57 (m, 2H), 7.46-7.37 (m, 1H), 5.59-5.38 (m, 1H), 5.34-5.24 (m, 1H), 4.98-4.78 (m, 1H), 4.65-4.58 (m, 1H), 4.51-4.39 (m, 3H), 4.34-4.15 (m, 1H), 4.11-3.94 (m, 1H), 3.85-3.72 (m, 1H), 3.19-3.10 (m, 1H), 3.09-2.98 (m, 1H), 2.92-2.82 (m, 1H), 2.80-2.71 (m, 1H), 2.58-2.49 (m, 3H), 2.38-2.27 (m, 1H), 2.13-2.00 (m, 1H), 1.93-1.73 (m, 4H) |
| 158 | 2-((S)-4-(7-(8-chloro-7-fluoronaphthalen-1-yl)-8-fluoro-2-(((R)-4-methylmorpholin-2-yl)methoxy)pyrido[4,3-d]pyrimidin-4-yl)-1-(2-fluoroacryloyl)piperazin-2-yl)acetonitrile | LCMS [ESI, M + 1]: 652<br>$^1$H NMR (400 MHz, CDCl$_3$) δ 9.07 (s, 1H), 8.04-7.98 (m, 1H), 7.90 (dd, J = 5.6, 8.8 Hz, 1H), 7.66-7.57 (m, 2H), 7.41 (br d, J = 2.0 Hz, 1H), 5.57-5.39 (m, 1H), 5.29 (dd, J = 3.4, 16.7 Hz, 1H), 4.94-4.78 (m, 1H), 4.69-4.35 (m, 5H), 4.14-4.04 (m, 2H), 3.99-3.96 (m, 1H), 3.81 (m, 3H), 3.00-2.99 (m, 2H), 2.87-2.77 (m, 2H), 2.40 (s, 3H), 2.30-2.20 (m, 2H) |

TABLE 3-continued

Examples 64 to 210

| Int. # | Structure | Characterization Data |
|---|---|---|
| 159 | 1-(6-(7-(8-chloro-7-fluoronaphthalen-1-yl)-8-fluoropyrido[4,3-d]pyrimidin-4-yl)-2,6-diazaspiro[3.3]heptan-2-yl)prop-2-en-1-one | LCMS [ESI, M + 1]: 478<br>$^1$H NMR (400 MHz, CDCl$_3$) δ 9.04 (s, 1H), 8.82 (s, 1H), 8.09-7.96 (m, 1H), 7.94-7.87 (m, 1H), 7.67-7.56 (m, 2H), 7.41 (t, J = 8.8 Hz, 1H), 6.46-6.35 (m, 1H), 6.27-6.13 (m, 1H), 5.77 (s, 1H), 4.93-4.69 (m, 4H), 4.57-4.38 (m, 4H) |
| 160 | 1-((2S,6S)-4-(7-(8-chloro-7-fluoronaphthalen-1-yl)-8-fluoropyrido[4,3-d]pyrimidin-4-yl)-2,6-dimethylpiperazin-1-yl)prop-2-en-1-one | LCMS [ESI, M + 1]: 494<br>$^1$H NMR (400 MHz, CDCl$_3$) δ 9.27 (d, J = 10.4 Hz, 1H), 8.89 (d, J = 3.2 Hz, 1H), 8.06-8.00 (m, 1H), 7.95-7.88 (m, 1H), 7.71-7.58 (m, 2H), 7.46-7.37 (m, 1H), 6.68-6.58 (m, 1H), 6.56-6.48 (m, 1H), 5.83 (dt, J = 2.0, 10.0 Hz, 1H), 4.94-4.30 (m, 4H), 4.22-4.08 (m, 2H), 1.48-1.39 (m, 6H) |
| 161 | 2-((2S)-4-(7-(8-chloro-7-fluoronaphthalen-1-yl)-2-((1,2-dimethylazetidin-2-yl)methoxy)-8-fluoropyrido[4,3-d]pyrimidin-4-yl)-1-(2-fluoroacryloyl)piperazin-2-yl)acetonitrile | LCMS [ESI, M + 1]: 636<br>$^1$H NMR (400 MHz, CDCl$_3$) δ 9.13-9.07 (m, 1H), 8.01 (dd, J = 2.8, 6.8 Hz, 1H), 7.94-7.87 (m, 1H), 7.66-7.57 (m, 2H), 7.41 (td, J = 2.0, 8.8 Hz, 1H), 5.58-5.38 (m, 1H), 5.29 (br dd, J = 3.2, 16.8 Hz, 1H), 5.10-4.94 (m, 1H), 4.92-4.62 (m, 3H), 4.57-4.45 (m, 1H), 4.28-4.05 (m, 2H), 3.98-3.62 (m, 3H), 3.31-3.08 (m, 1H), 2.97-2.78 (m, 2H), 2.75 (br d, J = 4.4 Hz, 3H), 2.37-2.18 (m, 2H), 1.77 (s, 3H) |

TABLE 3-continued

Examples 64 to 210

| Int. # | Structure | Characterization Data |
|---|---|---|
| 162 | 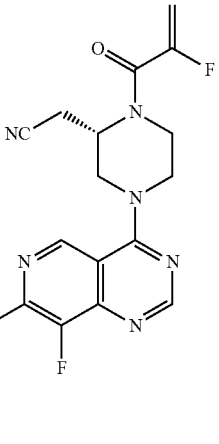<br>(S)-2-(4-(8-fluoro-7-(3-hydroxy-naphthalen-1-yl)pyrido[4,3-d]pyrimidin-4-yl)-1-(2-fluoroacryloyl)piperazin-2-yl)acetonitrile | LCMS [ESI, M + 1]: 487<br>$^1$H NMR (400 MHz, CDCl$_3$) δ 9.24 (s, 1H), 8.94 (s, 1H), 7.74 (d, J = 8.4 Hz, 1H), 7.66 (br d, J = 8.4 Hz, 1H), 7.47-7.41 (m, 1H), 7.31-7.28 (m, 2H), 7.25 (br s, 1H), 5.56-5.36 (m, 1H), 5.28 (dd, J = 3.6, 16.8 Hz, 1H), 4.89-4.71 (m, 1H), 4.57-4.34 (m, 2H), 4.22-3.37 (m, 4H), 3.04-2.90 (m, 1H), 2.85-2.68 (m, 1H) |
| 163 | 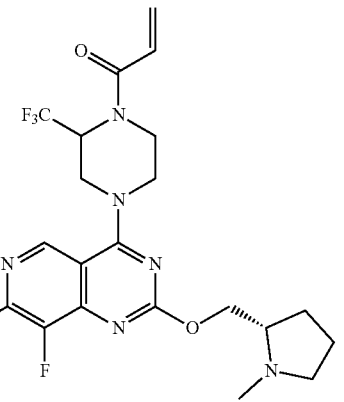<br>1-(4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-2-(trifluoromethyl)piperazin-1-yl)prop-2-en-1-one | LCMS [ESI, M + 1]: 647<br>$^1$H NMR (400 MHz, CDCl$_3$) δ 9.04 (d, J = 10.4 Hz, 1H), 8.04-7.97 (m, 1H), 7.90 (dd, J = 5.6, 8.8 Hz, 1H), 7.69-7.56 (m, 2H), 7.46-7.36 (m, 1H), 6.72-6.52 (m, 1H), 6.51-6.37 (m, 1H), 5.95-5.80 (m, 1H), 5.62-5.44 (m, 1H), 4.94-4.70 (m, 1H), 4.66-4.50 (m, 2H), 4.48-4.35 (m, 1H), 4.16-3.27 (m, 4H), 3.23-3.11 (m, 1H), 2.80-2.68 (m, 1H), 2.50 (s, 3H), 2.36-2.26 (m, 1H), 2.15-1.98 (m, 1H), 1.94-1.76 (m, 3H) |
| 164 | 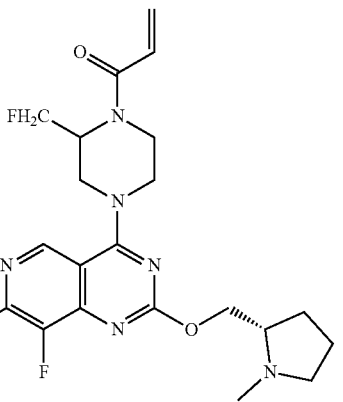<br>1-(4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-2-(fluoromethyl)piperazin-1-yl)prop-2-en-1-one | LCMS [ESI, M + 1]: 611<br>$^1$H NMR (400 MHz, CDCl$_3$) δ 9.23-9.00 (m, 1H), 8.08-7.97 (m, 1H), 7.90 (dd, J = 9.2, 5.6 Hz, 1H), 7.71-7.56 (m, 2H), 7.40 (t, J = 8.8 Hz, 1H), 6.62 (br dd, J = 16.0, 10.8 Hz, 1H), 6.41 (br d, J = 16.8 Hz, 1H), 5.83 (br d, J = 10.4 Hz, 1H), 5.35-4.35 (m, 8H), 4.19-3.33 (m, 6H), 2.91 (br s, 3H), 2.87-2.75 (m, 1H), 2.35-2.18 (m, 3H) |

TABLE 3-continued

Examples 64 to 210

| Int. # | Structure | Characterization Data |
|---|---|---|
| 165 | 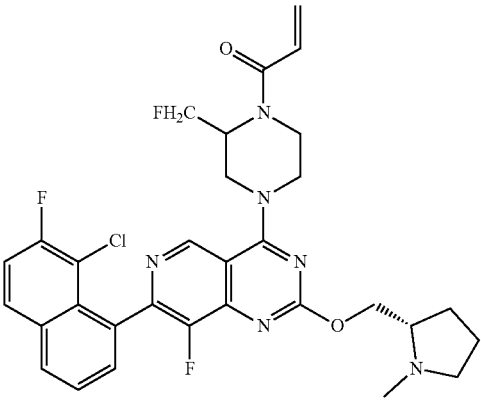<br>1-(4-(7-(8-chloro-7-fluoronaphthalen-1-yl)-8-fluoro-2-(((S)-1-methylpyrrolidin-2-yl)methoxy)pyrido[4,3-d]pyrimidin-4-yl)-2-(difluoromethyl)piperazin-1-yl)prop-2-en-1-one | LCMS [ESI, M + 1]: 629<br>$^1$H NMR (400 MHz, CDCl$_3$) δ 9.16-9.00 (m, 1H), 8.04-7.98 (m, 1H), 7.90 (dd, J = 5.6, 9.2 Hz, 1H), 7.68-7.57 (m, 2H), 7.41 (dt, J = 1.2, 8.8 Hz, 1H), 6.68-6.57 (m, 1H), 6.48-6.39 (m, 1H), 6.30-5.95 (m, 1H), 5.87 (br d, J = 10.8 Hz, 1H), 5.15-4.41 (m, 5H), 4.19-3.81 (m, 2H), 3.79-3.16 (m, 3H), 2.96-2.79 (m, 1H), 2.59 (br d, J = 3.6 Hz, 3H), 2.47-2.34 (m, 1H), 2.18-2.07 (m, 1H), 1.97-1.85 (m, 3H) |
| 166 | 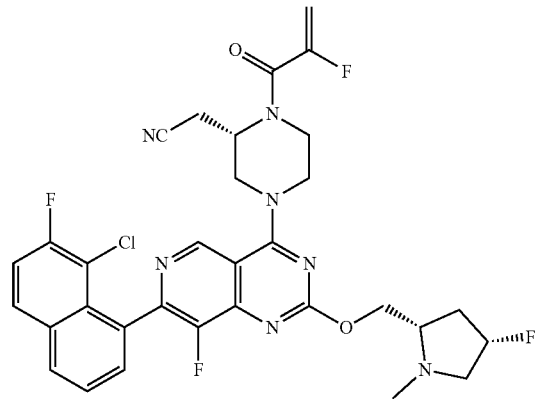<br>2-((S)-4-(7-(8-chloro-7-fluoronaphthalen-1-yl)-8-fluoro-2-(((2S,4S)-4-fluoro-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 654<br>$^1$H NMR (400 MHz, CDCl$_3$) δ 9.07 (s, 1 H) 8.06-7.98 (m, 1 H) 7.90 (ddd, J = 0.8, 5.6, 9.2 Hz, 1 H) 7.67-7.57 (m, 2 H) 7.41 (td, J = 2.0, 8.8 Hz, 1 H) 5.60-5.40 (m, 1 H) 5.29 (dd, J = 2.4, 16.8 Hz, 1 H) 5.24-5.04 (m, 1 H) 4.87 (br s, 1 H) 4.69 (ddd, J = 2.0, 4.8, 10.8 Hz, 1 H) 4.58-4.41 (m, 3 H) 4.38-3.97 (m, 2 H) 3.80 (br s, 2 H) 3.37 (ddd, J = 1.6, 11.6, 18.0 Hz, 1 H) 3.10-2.98 (m, 1 H) 2.94-2.76 (m, 2 H) 2.59-2.37 (m, 5 H) 2.22-2.04 (m, 1 H) |
| 167 | 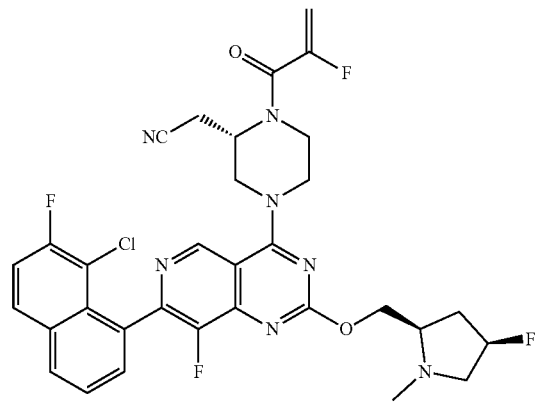<br>2-((S)-4-(7-(8-chloro-7-fluoronaphthalen-1-yl)-8-fluoro-2-(((2R,4R)-4-fluoro-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 654<br>$^1$H NMR (400 MHz, CDCl$_3$) δ 9.07 (s, 1 H) 8.12-7.83 (m, 2 H) 7.71-7.57 (m, 2 H) 7.41 (td, J = 8.8, 2.0 Hz, 1 H) 5.63-5.37 (m, 1 H) 5.29 (dd, J = 3.2, 16.4 Hz, 1 H) 5.24-5.04 (m, 1 H) 4.98-4.77 (m, 1 H) 4.67 (dt, J = 4.0, 10.8 Hz, 1 H) 4.58-4.41 (m, 3 H) 4.36-3.95 (m, 2 H) 3.92-3.61 (m, 2 H) 3.36 (br dd, J = 11.6, 18.0 Hz, 1 H) 3.10-2.97 (m, 1 H) 2.93-2.73 (m, 2 H) 2.61-2.36 (m, 5 H) 2.22-2.03 (m, 1 H) |

TABLE 3-continued

Examples 64 to 210

| Int. # | Structure | Characterization Data |
|---|---|---|
| 168 | 2-((S)-4-(7-(8-chloro-7-fluoronaphthalen-1-yl)-8-fluoro-2-(((2S,3R)-3-fluoro-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 654<br>$^{1}$H NMR (400 MHz, CDCl$_3$) δ 9.08 (s, 1H), 8.08-7.97 (m, 1H), 7.90 (dd, J = 5.2, 8.8 Hz, 1H), 7.68-7.54 (m, 2H), 7.41 (dt, J = 1.6, 8.8 Hz, 1H), 5.63-5.39 (m, 1H), 5.36-5.07 (m, 2H), 4.99-4.76 (m, 1H), 4.69-4.57 (m, 1H), 4.55-4.36 (m, 3H), 4.33-3.95 (m, 2H), 3.80 (br d, J = 2.4 Hz, 2H), 3.16-2.78 (m, 4H), 2.72-2.58 (m, 1H), 2.56 (s, 3H), 2.27-1.92 (m, 2H) |
| 169 | 2-((S)-4-(7-(8-chloro-7-fluoronaphthalen-1-yl)-8-fluoro-2-(((R)-1-methylpyrrolidin-3-yl)methoxy)pyrido[4,3-d]pyrimidin-4-yl)-1-(2-fluoroacryloyl)piperazin-2-yl)acetonitrile | LCMS [ESI, M + 1]: 636<br>$^{1}$H NMR (400 MHz, CDCl$_3$) δ 9.07 (s, 1 H), 8.07-7.98 (m, 1 H), 7.90 (dd, J = 5.6, 8.8 Hz, 1 H), 7.67-7.55 (m, 2 H), 7.47-7.35 (m, 1 H), 5.59-5.39 (m, 1 H), 5.30 (dd, J = 3.6, 16.8 Hz, 1 H), 5.01-4.81 (m, 1 H), 4.58-4.40 (m, 4 H), 4.35-3.95 (m, 2 H), 3.90-3.60 (m, 2 H), 3.09-2.97 (m, 1 H), 2.94-2.68 (m, 3 H), 2.62 (td, J = 5.6, 8.4 Hz, 1 H), 2.57-2.46 (m, 2 H), 2.37 (s, 3 H), 2.17-2.02 (m, 1 H), 1.73-1.65 (m, 1 H) |
| 170 | (S)-2-(4-(7-(8-chloro-7-fluoronaphthalen-1-yl)-2-(3-(dimethylamino)azetidin-1-yl)-8-fluoropyrido[4,3-d]pyrimidin-4-yl)-1-(2-fluoroacryloyl)piperazin-2-yl)acetonitrile | LCMS [ESI, M + 1]: 621<br>$^{1}$H NMR (400 MHz, CDCl$_3$) δ 8.83 (s, 1 H) 7.97 (br d, J = 7.6 Hz, 1 H) 7.87 (br dd, J = 8.8, 5.6 Hz, 1 H) 7.58 (q, J = 7.6 Hz, 2 H) 7.38 (br t, J = 8.8 Hz, 1 H) 5.59-5.36 (m, 1 H) 5.28 (br d, J = 13.6 Hz, 1 H) 4.93 (br d, J = 9.29 Hz, 1 H) 4.53 (br d, J = 15.04 Hz, 1 H) 4.41-4.23 (m, 4 H) 4.21-3.96 (m, 2 H) 3.62 (br s, 3 H) 3.22 (br s, 1 H) 3.06-2.94 (m, 1 H) 2.91-2.76 (m, 1 H) 2.24 (s, 6 H) |

TABLE 3-continued

Examples 64 to 210

| Int. # | Structure | Characterization Data |
|---|---|---|
| 171 | 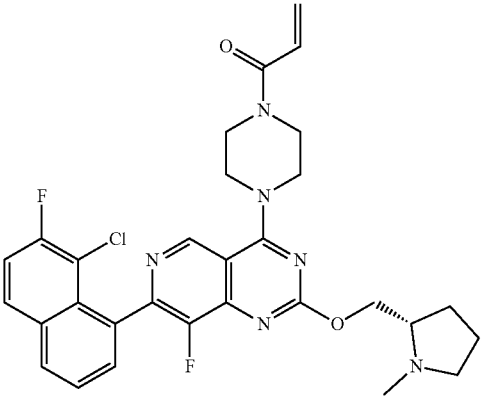<br>(S)-1-(4-(7-(8-chloro-7-fluoronaphthalen-1-yl)-8-fluoro-2-((1-methylpyrrolidin-2-yl)methoxy)pyrido[4,3-d]pyrimidin-4-yl)piperazin-1-yl)prop-2-en-1-one | LCMS [ESI, M + 1]: 579<br>$^1$H NMR (400 MHz, CDCl$_3$) δ 9.17-9.09 (m, 1 H) 8.19-8.13 (m, 1 H) 8.11-8.04 (m, 1 H) 7.72-7.63 (m, 2 H) 7.57-7.49 (m, 1 H) 6.88-6.74 (m, 1 H) 6.35-6.23 (m, 1 H) 5.88-5.76 (m, 1 H) 4.55-4.46 (m, 2 H) 4.26-4.16 (m, 4 H) 4.02-3.91 (m, 4 H) 3.17-3.04 (m, 1 H) 2.87-2.73 (m, 1 H) 2.55-2.47 (m, 3 H) 2.44-2.28 (m, 1 H) 2.18-2.04 (m, 1 H) 1.88-1.69 (m, 3 H) |
| 172 | 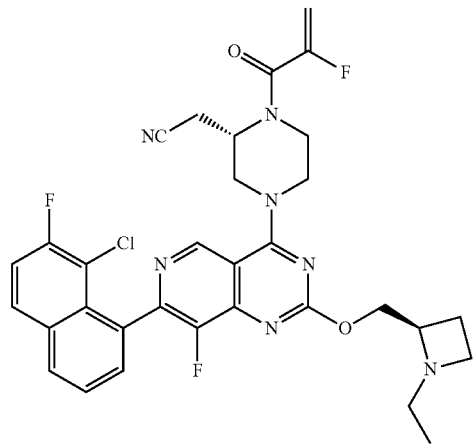<br>2-((S)-4-(7-(8-chloro-7-fluoronaphthalen-1-yl)-2-(((R)-1-ethylazetidin-2-yl)methoxy)-8-fluoropyrido[4,3-d]pyrimidin-4-yl)-1-(2-fluoroacryloyl)piperazin-2-yl)acetonitrile | LCMS [ESI, M + 1]: 636<br>$^1$H NMR (400 MHz, CDCl$_3$) δ 9.06 (s, 1H), 8.07-7.96 (m, 1H), 7.90 (dd, J = 5.6, 8.8 Hz, 1H), 7.66-7.56 (m, 2H), 7.41 (dt, J = 1.6, 8.8 Hz, 1H), 5.48 (dd, J = 3.2, 47.6 Hz, 1H), 5.29 (ddd, J = 16.0, 4.0, 16.8 Hz, 1H), 5.00-4.78 (m, 1H), 4.65-4.41 (m, 4H), 4.35-3.96 (m, 2H), 3.92-3.63 (m, 2H), 3.59-3.39 (m, 2H), 3.12-2.96 (m, 1H), 2.94-2.68 (m, 3H), 2.50-2.37 (m, 1H), 2.22-2.07 (m, 2H), 1.01 (t, J = 7.2 Hz, 3H) |

TABLE 3-continued

Examples 64 to 210

| Int. # | Structure | Characterization Data |
|---|---|---|
| 173 | 2-((S)-4-(7-(8-chloro-7-fluoronaphthalen-1-yl)-2-(((S)-1-ethylazetidin-2-yl)methoxy)-8-fluoropyrido[4,3-d]pyrimidin-4-yl)-1-(2-fluoroacryloyl)piperazin-2-yl)acetonitrile | LCMS [ESI, M + 1]: 636<br>$^1$H NMR (400 MHz, CDCl$_3$) δ 9.06 (s, 1H), 8.03-7.99 (m, 1H), 7.90 (dd, J = 5.2, 8.4 Hz, 1H), 7.66-7.57 (m, 2H), 7.41 (dt, J = 2.4, 8.8 Hz, 1H), 5.48 (dd, J = 3.2, 47.6 Hz, 1H), 5.29 (dd, J = 2.8, 16.0 Hz, 1H), 4.98-4.78 (m, 1H), 4.67-4.40 (m, 4H), 4.36-3.96 (m, 2H), 3.89-3.69 (m, 2H), 3.59-3.40 (m, 2H), 3.10-2.97 (m, 1H), 2.94-2.70 (m, 3H), 2.51-2.37 (m, 1H), 2.22-2.08 (m, 2H), 1.02 (t, J = 7.2 Hz, 3H) |
| 174 | 2-((2S)-4-(7-(8-chloro-7-fluoronaphthalen-1-yl)-8-fluoro-2-((hexahydro-1H-pyrrolizin-3-yl)methoxy)pyrido[4,3-d]pyrimidin-4-yl)-1-(2-fluoroacryloyl)piperazin-2-yl)acetonitrile | LCMS [ESI, M + 1]: 662<br>$^1$H NMR (400 MHz, CDCl$_3$) δ 9.07 (s, 1H), 8.04-8.00 (m, 1H), 7.91 (dd, J = 5.2, 8.8 Hz, 1H), 7.67-.58 (m, 2H), 7.42 (td, J = 2.0, 8.8 Hz, 1H), 5.59-5.41 (m, 1H), 5.31 (dd, J = 3.2, 16.8 Hz, 1H), 5.03-4.76 (m, 1H), 4.65-4.36 (m, 4H), 4.31-3.95 (m, 2H), 3.89-3.60 (m, 3H), 3.27-2.98 (m, 3H), 2.96-2.79 (m, 2H), 2.28-2.03 (m, 2H), 1.99-1.77 (m, 4H), 1.54-1.42 (m, 2H) |

TABLE 3-continued

Examples 64 to 210

| Int. # | Structure | Characterization Data |
|---|---|---|
| 175 | 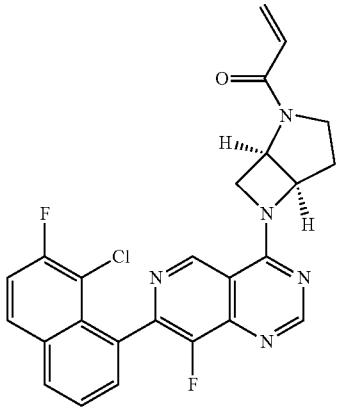<br>1-((1R,5R)-6-(7-(8-chloro-7-fluoronaphthalen-1-yl)-8-fluoropyrido[4,3-d]pyrimidin-4-yl)-2,6-diazabicyclo[3.2.0]heptan-2-yl)prop-2-en-1-one | LCMS [ESI, M + 1]: 478<br>$^1$H NMR (400 MHz, CDCl$_3$) δ 9.04 (s, 1H), 8.88-8.77 (m, 1H), 8.08-7.96 (m, 1H), 7.90 (dd, J = 6.0, 8.8 Hz, 1H), 7.67-7.56 (m, 2H), 7.40 (t, J = 8.4 Hz, 1H), 6.63-6.36 (m, 2H), 5.82 (br d, J = 10.4 Hz, 1H), 5.71-5.49 (m, 1H), 5.22-4.84 (m, 2H), 4.52-4.11 (m, 2H), 4.04-3.71 (m, 1H), 2.82-2.60 (m, 1H), 2.38-2.12 (m, 1H) |
| 176 | 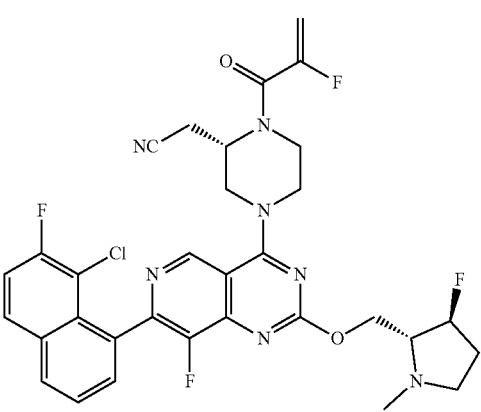<br>2-((S)-4-(7-(8-chloro-7-fluoronaphthalen-1-yl)-8-fluoro-2-(((2R,3S)-3-fluoro-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 654<br>$^1$H NMR (400 MHz, CDCl$_3$) δ 9.08 (s, 1H), 8.08-7.97 (m, 1H), 7.90 (dd, J = 5.6, 9.2 Hz, 1H), 7.70-7.55 (m, 2H), 7.41 (td, J = 2.0, 8.4 Hz, 1H), 5.62-5.39 (m, 1H), 5.35-5.08 (m, 2H), 4.99-4.77 (m, 1H), 4.75-4.60 (m, 1H), 4.58-4.38 (m, 3H), 4.35-3.93 (m, 2H), 3.91-3.61 (m, 2H), 3.34-2.95 (m, 3H), 2.92-2.80 (m, 1H), 2.79-2.51 (m, 4H), 2.28-2.01 (m, 2H) |

TABLE 3-continued

Examples 64 to 210

| Int. # | Structure | Characterization Data |
|---|---|---|
| 177 | 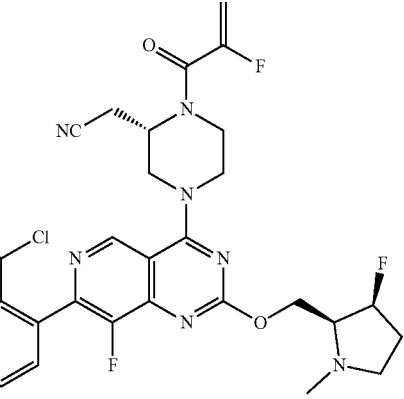<br>2-((S)-4-(7-(8-chloro-7-fluoronaphthalen-1-yl)-8-fluoro-2-(((2S,3S)-3-fluoro-1-methylpyrrolidin-2-yl)methoxy)pyrido[4,3-d]pyrimidin-4-yl)-1-(2-fluoroacryloyl)piperazin-2-yl)acetonitrile | LCMS [ESI, M + 1]: 654<br>$^1$H NMR (400 MHz, CDCl$_3$) δ 9.08 (s, 1H), 8.05-7.98 (m, 1H), 7.90 (dd, J = 5.6, 8.8 Hz, 1H), 7.68-7.57 (m, 2H), 7.41 (dt, J = 2.0, 8.8 Hz, 1H), 5.60-5.41 (m, 1H), 5.40-5.21 (m, 2H), 4.84-4.76 (m, 1H), 4.71-4.61 (m, 1H), 4.60-4.41 (m, 2H), 4.33-4.06 (m, 1H), 4.03-3.68 (m, 2H), 3.37-3.23 (m, 1H), 3.13-2.96 (m, 1H), 2.94-2.80 (m, 1H), 2.76-2.62 (m, 1H), 2.49 (s, 3H), 2.28-1.97 (m, 3H), 1.39-1.22 (m, 2H) |
| 178 | 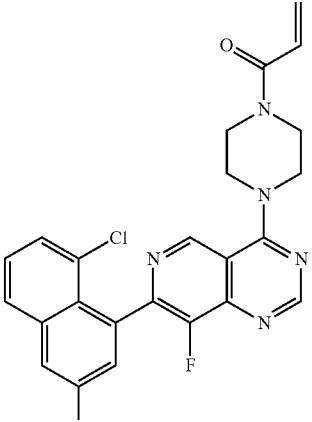<br>1-(4-(7-(8-chloro-3-hydroxynaphthalen-1-yl)-8-fluoropyrido[4,3-d]pyrimidin-4-yl)piperazin-1-yl)prop-2-en-1-one | LCMS [ESI, M + 1]: 464<br>$^1$H NMR (400 MHz, DMSO-d$_6$) δ 10.27 (br s, 1H), 9.28 (s, 1H), 8.76 (s, 1H), 7.86 (dd, J = 1.2, 8.4 Hz, 1H), 7.52-7.30 (m, 3H), 7.17 (d, J = 2.4 Hz, 1H), 6.83 (dd, J = 10.4, 16.8 Hz 1H), 6.19 (dd, J = 2.4, 16.8 Hz, 1H), 5.75 (dd, J = 2.0, 10.4 Hz, 1H), 4.21-4.04 (m, 4H), 3.99-3.75 (m, 4H) |
| 179 | 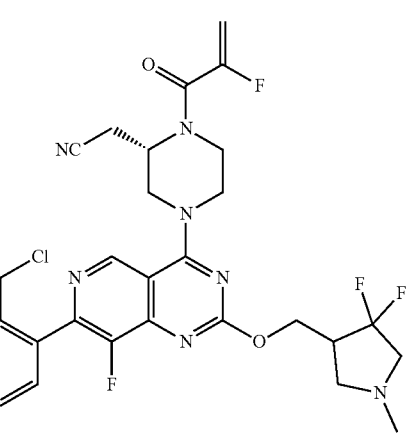<br>2-((2S)-4-(7-(8-chloro-7-fluoronaphthalen-1-yl)-2-((4,4-difluoro-1-methylpyrrolidin-3-yl)methoxy)-8-fluoropyrido[4,3-d]pyrimidin-4-yl)-1-(2-fluoroacryloyl)piperazin-2-yl)acetonitrile | 1$^{st}$ eluting isomer by chiral SFC<br>LCMS [ESI, M + 1]: 672<br>$^1$H NMR (400 MHz, DMSO-d$_6$) δ 9.08 (s, 1H), 8.04-7.98 (m, 1H), 7.94-7.72 (m, 1H), 7.66-7.57 (m, 2H), 7.41 (td, J = 1.6, 8.8 Hz, 1H), 5.60-5.37 (m, 1H), 5.29 (dd, J = 3.2, 16.8 Hz, 1H), 4.98-4.72 (m, 2H), 4.62-4.40 (m, 3H), 4.36-3.94 (m, 2H), 3.93-3.62 (m, 2H), 3.26-2.97 (m, 4H), 2.96-2.78 (m, 2H), 2.75-2.62 (m, 1H), 2.42 (s, 3H) |

TABLE 3-continued

Examples 64 to 210

| Int. # | Structure | Characterization Data |
|---|---|---|
| 180 | 2-((2S)-4-(7-(8-chloro-7-fluoronaphthalen-1-yl)-2-((4,4-difluoro-1-methylpyrrolidin-3-yl)methoxy)-8-fluoropyrido[4,3-d]pyrimidin-4-yl)-1-(2-fluoroacryloyl)piperazin-2-yl)acetonitrile | 2$^{nd}$ eluting isomer by chiral SFC<br>LCMS [ESI, M + 1]: 672<br>$^1$H NMR (400 MHz, DMSO-d$_6$) δ 9.08 (s, 1H), 8.04-7.98 (m, 1H), 7.90 (dd, J = 5.6, 9.2 Hz, 1H), 7.66-7.57 (m, 2 H), 7.40 (td, J = 2.0, 8.8 Hz, 1H) 5.44-5.37 (m, 1H), 5.29 (dd, J = 3.2, 16.8 Hz, 1H), 4.98-4.72 (m, 2H), 4.62-4.40 (m, 3H), 4.36-3.94 (m, 2H), 3.93-3.62 (m, 2H), 3.26-2.97 (m, 4H), 2.96-2.78 (m, 2H), 2.69-2.62 (m, 1H), 2.39 (s, 3H) |
| 181 | 2-((2S)-4-(7-(8-chloro-7-fluoronaphthalen-1-yl)-8-fluoro-2-(((2R)-2-fluorotetrahydro-1H-pyrrolizin-7a(5H)-yl)methoxy)pyrido[4,3-d]pyrimidin-4-yl)-1-(2-fluoroacryloyl)piperazin-2-yl)acetonitrile | LCMS [ESI, M + 1]: 680<br>$^1$H NMR (400 MHz, CDCl$_3$): δ 9.06 (s, 1H), 8.03-7.97 (m, 1H), 7.93-7.86 (m, 1H), 7.65-7.56 (m, 2H), 7.44-7.36 (m, 1H), 5.57-5.23 (m, 3H), 4.91-4.85 (m, 1H), 4.57-4.41 (m, 3H), 4.30 (d, J = 10.4 Hz, 1H), 4.20-3.95 (m, 1H), 3.84-3.78 (m, 2H), 3.53 (br dd, J = 12.0, 19.6 Hz, 1H), 3.21-3.12 (m, 1H), 3.08-2.97 (m, 1H), 2.93-2.76 (m, 2H), 2.69-2.54 (m, 2H), 2.21-2.12 (m, 1H), 2.03-1.69 (m, 5H) |

TABLE 3-continued

Examples 64 to 210

| Int. # | Structure | Characterization Data |
|---|---|---|
| 182 | 2-((S)-4-(7-(8-chloro-7-fluoronaphthalen-1-yl)-8-fluoro-2-(((S)-1-(2-fluoroethyl)pyrrolidin-2-yl)methoxy)pyrido[4,3-d]pyrimidin-4-yl)-1-(2-fluoroacryloyl)piperazin-2-yl)acetonitrile | LCMS [ESI, M + 1]: 668<br>$^1$H NMR (400 MHz, CDCl$_3$): δ 9.06 (s, 1H), 8.01 (br d, J = 7.2 Hz, 1H), 7.90 (br dd, J = 6.0, 8.4 Hz, 1H), 7.68-7.54 (m, 2H), 7.41 (br t, J = 8.8 Hz, 1H), 5.59-5.37 (m, 1H), 5.29 (br d, J = 16.8 Hz, 1H), 4.89-4.76 (m, 1H), 4.64-4.29 (m, 7H), 4.28-3.93 (m, 2H), 3.87-3.72 (m, 1H), 3.39-3.18 (m, 2H), 3.13-2.96 (m, 2H), 2.94-2.71 (m, 2H), 2.47-2.34 (m, 1H), 2.04-1.93 (m, 1H), 1.92-1.77 (m, 3H) |
| 183 | (S)-1-(4-(7-(8-chloro-7-fluoronaphthalen-1-yl)-8-fluoropyrido[4,3-d]pyrimidin-4-yl)-2-(2,2-difluoroethyl)piperazin-1-yl)prop-2-en-1-one | LCMS [ESI, M + 1]: 530<br>$^1$H NMR (400 MHz, CDCl$_3$): δ 9.71-9.50 (m, 1H), 9.05-8.91 (m, 1H), 8.27-8.12 (m, 1H), 8.06 (dd, J = 5.6, 9.2 Hz, 1H), 7.81-7.38 (m, 3H), 6.91-6.68 (m, 1H), 6.47-6.33 (m, 1H), 5.98 (br s, 1H), 5.93-5.75 (m, 1H), 5.25-4.59 (m, 3H), 3.55 (br d, J = 12.4 Hz, 4H), 2.57-2.25 (m, 2H) |

TABLE 3-continued

Examples 64 to 210

| Int. # | Structure | Characterization Data |
|---|---|---|
| 184 | 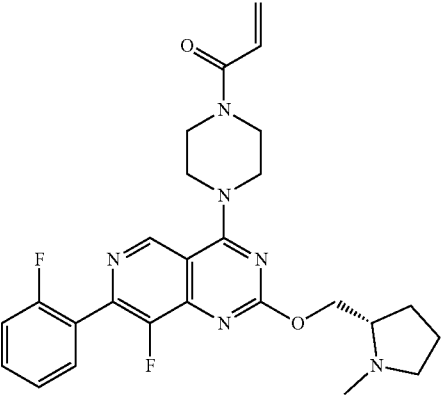<br>(S)-1-(4-(8-fluoro-7-(2-fluorophenyl)-2-((1-methylpyrrolidin-2-yl)methoxy)pyrido[4,3-d]pyrimidin-4-yl)piperazin-1-yl)prop-2-en-1-one | LCMS [ESI, M + 1]: 495<br>$^1$H NMR (400 MHz, CDCl$_3$): δ 9.08 (s, 1H), 7.69 (td, J = 2.0, 7.6 Hz, 1H), 7.52-7.45 (m, 1H), 7.32 (td, J = 1.2, 7.6 Hz, 1H), 7.26-7.19 (m, 1H), 6.61 (dd, J = 10.4, 16.8 Hz, 1H), 6.39 (dd, J = 2.0, 16.8 Hz, 1H), 5.81 (dd, J = 1.6, 10.4 Hz, 1H), 4.61 (dd, J = 4.8, 10.8 Hz, 1H), 4.40 (dd, J = 6.4, 10.8 Hz, 1H), 4.10-4.01 (m, 4H), 3.98-3.80 (m, 4H), 3.18-3.09 (m, 1H), 2.81-2.71 (m, 1H), 2.52 (s, 3H), 2.37-2.27 (m, 1H), 2.13-2.00 (m, 1H), 1.94-1.82 (m, 3H) |
| 185 | 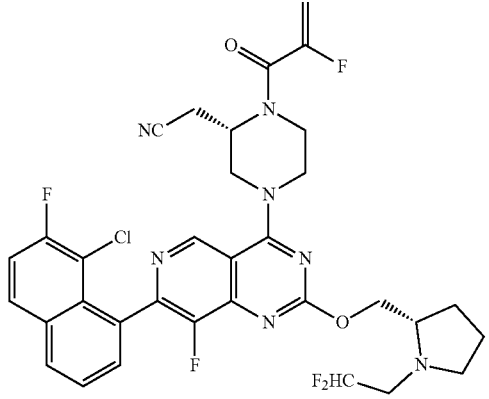<br>2-((S)-4-(7-(8-chloro-7-fluoronaphthalen-1-yl)-2-(((S)-1-(2,2-difluoroethyl)pyrrolidin-2-yl)methoxy)-8-fluoropyridin[4,3-d]pyrimidin-4-yl)-1-(2-fluoroacryloyl)piperazin-2-yl)acetonitrile | LCMS [ESI, M + 1]: 686<br>$^1$H NMR (400 MHz, CDCl$_3$): δ 9.07 (s, 1H), 8.07-7.97 (m, 1H), 7.90 (dd, J = 5.6, 8.4 Hz, 1H), 7.66-7.57 (m, 2H), 7.41 (td, J = 2.0, 8.8 Hz, 1H), 6.09-5.73 (m, 1H), 5.55-5.40 (m, 1H), 5.29 (dd, J = 2.8, 16.8 Hz, 1H), 5.01-4.74 (m, 1H), 4.61-4.42 (m, 3H), 4.40-4.33 (m, 1H), 4.32-3.93 (m, 2H), 3.91-3.64 (m, 2H), 3.48-3.30 (m, 1H), 3.29-3.23 (m, 1H), 3.18-3.09 (m, 1H), 3.07-2.97 (m, 1H), 2.96-2.79 (m, 2H), 2.54-2.44 (m, 1H), 2.08-1.97 (m, 1H), 1.93-1.73 (m, 3H) |
| 186 | 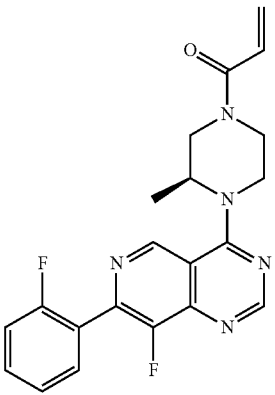<br>(S)-1-(4-(8-fluoro-7-(2-fluorophenyl)pyrido[4,3-d]pyrimidin-4-yl)-3-methyl-piperazin-1-yl)prop-2-en-1-one | LCMS [ESI, M + 1]: 396<br>$^1$H NMR (400 MHz, CDCl$_3$): δ 9.17 (s, 1H), 8.87 (s, 1H), 7.72 (td, J = 1.6, 7.2 Hz, 1H), 7.55-7.48 (m, 1H), 7.34 (td, J = 1.2, 7.6 Hz, 1H), 7.26-7.22 (m, 1H), 6.70-6.51 (m, 1H), 6.41 (dd, J = 2.4, 16.8 Hz, 1H), 5.81 (dd, J = 1.6, 10.4 Hz, 1H), 5.04-4.86 (m, 1H), 4.78-4.43 (m, 2H), 4.11-3.81 (m, 1H), 3.77-3.51 (m, 2H), 3.29-3.01 (m, 1H), 1.52 (br d, J = 5.2 Hz, 3H) |

TABLE 3-continued

Examples 64 to 210

| Int. # | Structure | Characterization Data |
|---|---|---|
| 187 | 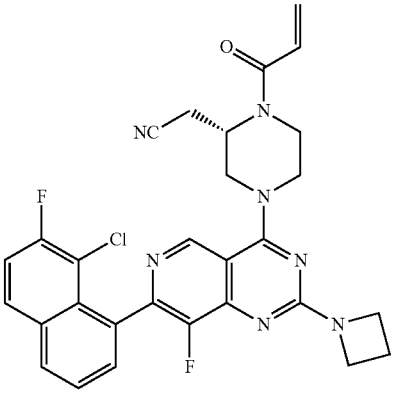<br>(S)-2-(1-acryloyl-4-(2-(azetidin-1-yl)-7-(8-chloro-7-fluoronaphthalen-1-yl)-8-fluoropyrido[4,3-d]pyrimidin-4-yl)piperazin-2-yl)acetonitrile | LCMS [ESI, M + 1]: 560<br>$^1$H NMR (400 MHz, CDCl$_3$): δ 8.83 (d, J = 1.6 Hz, 1H), 7.97 (dd, J = 2.0, 7.6 Hz, 1H), 7.87 (dd, J = 5.6, 9.2 Hz, 1H), 7.64-7.54 (m, 2H), 7.38 (td, J = 2.0, 8.8 Hz, 1H), 6.72-6.53 (m, 1H), 6.47-6.36 (m, 1H), 5.85 (br d, J = 10.8 Hz, 1H), 5.23-4.62 (m, 1H), 4.59-3.95 (m, 7H), 3.94-3.31 (m, 3H), 3.02-2.89 (m, 1H), 2.88-2.75 (m, 1H), 2.47-2.35 (m, 2H) |
| 188 | 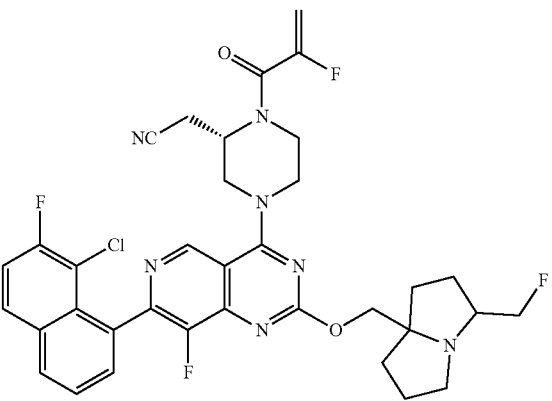<br>2-((2S)-4-(7-(8-chloro-7-fluoronaphthalen-1-yl)-8-fluoro-2-((3-(fluoromethyl)tetrahydro-1H-pyrrolizin-7a(5H)-yl)methoxy)pyrido[4,3-d]pyrimidin-4-yl)-1-(2-fluoroacryloyl)piperazin-2-yl)acetonitrile | LCMS [ESI, M + 1]: 694<br>$^1$H NMR (400 MHz, CDCl$_3$): δ 9.07 (s, 1H), 8.06-7.97 (m, 1H), 7.90 (dd, J = 5.2, 8.8 Hz, 1H), 7.67-7.56 (m, 2H), 7.41 (dt, J = 2.0, 8.8 Hz, 1H), 5.62-5.40 (m, 1H), 5.30 (dd, J = 2.4, 16.8 Hz, 1H), 4.98-4.58 (m, 3H), 4.57-4.40 (m, 2H), 4.39-3.93 (m, 3H), 3.92-3.55 (m, 2H), 3.34-2.97 (m, 5H), 2.95-2.77 (m, 1H), 2.18-2.06 (m, 1H), 2.04-1.74 (m, 7H) |
| 189 | 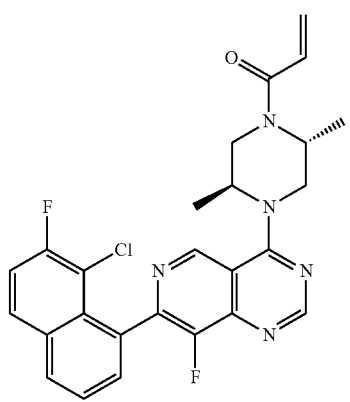<br>1-((2R,5S)-4-(7-(8-chloro-7-fluoronaphthalen-1-yl)-8-fluoropyrido[4,3-d]pyrimidin-4-yl)-2,5-dimethylpiperazin-1-yl)prop-2-en-1-one | LCMS [ESI, M + 1]: 694<br>$^1$H NMR (400 MHz, CDCl$_3$): δ 9.07 (s, 1H), 8.06-7.97 (m, 1H), 7.90 (dd, J = 5.2, 8.8 Hz, 1H), 7.67-7.56 (m, 2H), 7.41 (dt, J = 2.0, 8.8 Hz, 1H), 5.62-5.40 (m, 1H), 5.30 (dd, J = 2.4, 16.8 Hz, 1H), 4.98-4.58 (m, 3H), 4.57-4.40 (m, 2H), 4.39-3.93 (m, 3H), 3.92-3.55 (m, 2H), 3.34-2.97 (m, 5H), 2.95-2.77 (m, 1H), 2.18-2.06 (m, 1H), 2.04-1.74 (m, 7H) |

TABLE 3-continued

Examples 64 to 210

| Int. # | Structure | Characterization Data |
|---|---|---|
| 190 | 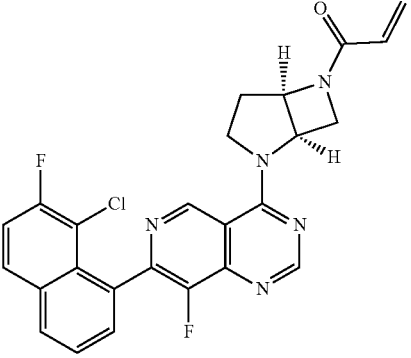<br>1-((1R,5R)-2-(7-(8-chloro-7-fluoro-naphthalen-1-yl)-8-fluoropyrido[4,3-d]pyrimidin-4-yl)-2,6-diazabicyclo[3.2.0]heptan-6-yl)prop-2-en-1-one | LCMS [ESI, M + 1]: 478<br>$^1$H NMR (400 MHz, CDCl$_3$) δ 9.38-9.11 (m, 1H), 8.83 (d, J = 2.0 Hz, 1H), 8.02 (dd, J = 2.4, 7.2 Hz, 1H), 7.91 (dd, J = 5.6, 8.8 Hz, 1H), 7.70-7.57 (m, 2H), 7.41 (t, J = 8.8 Hz, 1H), 6.56-6.09 (m, 2H), 5.87-5.70 (m, 1H), 5.50-5.17 (m, 2H), 4.98-4.49 (m, 2H), 4.37-4.14 (m, 1H), 4.13-3.87 (m, 1H), 2.92-2.46 (m, 1H), 2.40-2.17 (m, 1H) |
| 191 | 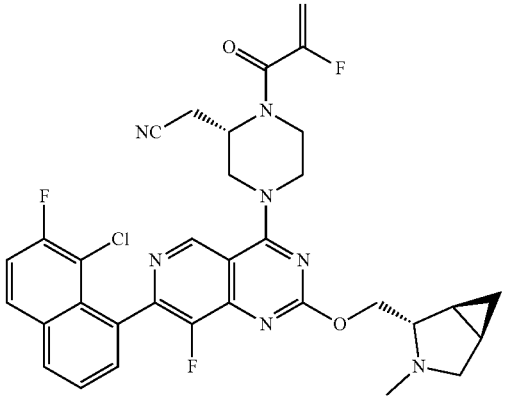<br>2-((S)-4-(7-(8-chloro-7-fluoronaphthalen-1-yl)-8-fluoro-2-(((1S,2S,5R)-3-methyl-3-azabicyclo[3.1.0]hexan-2-yl)methoxy)pyrido[4,3-d]pyrimidin-4-yl)-1-(2-fluoroacryloyl)piperazin-2-yl)acetonitrile | LCMS [ESI, M + 1]: 648<br>$^1$H NMR (400 MHz, CDCl$_3$): δ 9.07 (s, 1 H), 8.07-7.95 (m, 1H), 7.90 (dd, J = 5.6, 9.2 Hz, 1H), 7.68-7.55 (m, 2H), 7.45-7.36 (m, 1H), 5.58-5.40 (m, 1H), 5.28 (dd, J = 3.2, 16.4 Hz 1H), 4.96-4.79 (m, 1H), 4.69-4.60 (m, 1H), 4.56-4.42 (m, 2H), 4.41-4.35 (m, 1H), 4.29-3.96 (m, 2H), 3.93-3.68 (m, 2H), 3.27 (t, J = 5.6 Hz, 1H), 3.13-2.98 (m, 2H), 2.95-2.83 (m, 1H), 2.72 (br d, J = 9.2 Hz, 1H), 2.49 (d, J = 1.6 Hz, 3H), 1.56-1.42 (m, 2H), 0.67-0.61 (m, 1H), 0.52-0.47 (m, 1H) |
| 192 | 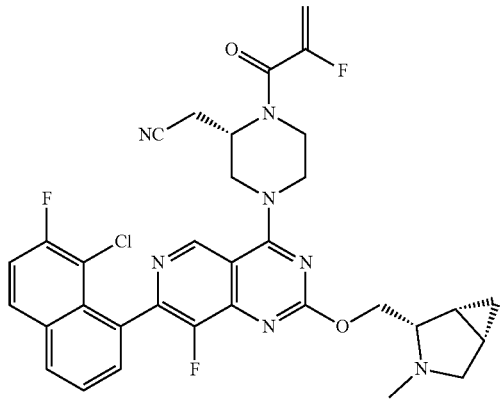<br>2-((S)-4-(7-(8-chloro-7-fluoronaphthalen-1-yl)-8-fluoro-2-(((1R,2S,5S)-3-methyl-3-azabicyclo[3.1.0]hexan-2-yl)methoxy)pyrido[4,3-d]pyrimidin-4-yl)-1-(2-fluoroacryloyl)piperazin-2-yl)acetonitrile | LCMS [ESI, M + 1]: 648<br>$^1$H NMR (400 MHz, CDCl$_3$): δ 9.07 (s, 1H), 8.04-7.98 (m, 1H), 7.90 (dd, J = 5.6, 8.8 Hz, 1H), 7.67-7.57 (m, 2H), 7.42 (dt, J = 2.0, 8.8 Hz, 1H), 5.58-5.40 (m, 1H), 5.29 (dd, J = 2.8, 16.8 Hz, 1H), 4.96-4.82 (m, 1H), 4.69 (br d, J = 7.2 Hz, 1H), 4.56-4.37 (m, 3H), 4.32-3.96 (m, 1H), 4.30-3.94 (m, 1H), 3.85-3.72 (m, 2H), 3.14 (br d, J = 6.4 Hz, 1H), 3.09-2.82 (m, 3H), 2.58-2.54 (m, 1H), 2.43 (s, 3H), 1.74-1.67 (m, 1H), 1.48-1.41 (m, 1H), 0.84-0.75 (m, 1H), 0.42-0.36 (m, 1H) |

TABLE 3-continued

Examples 64 to 210

| Int. # | Structure | Characterization Data |
|---|---|---|
| 193 | 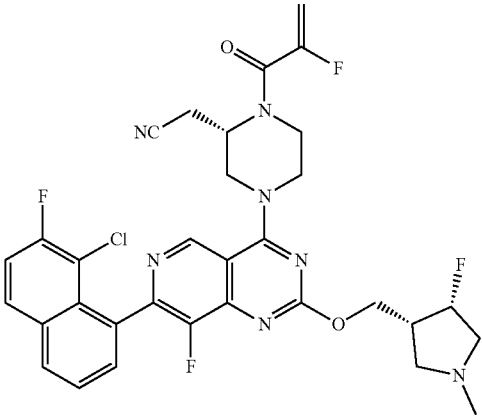<br>2-((S)-4-(7-(8-chloro-7-fluoronaphthalen-1-yl)-8-fluoro-2-(((3R,4S)-4-fluoro-1-methylpyrrolidin-3-yl)methoxy)pyrido[4,3-d]pyrimidin-4-yl)-1-(2-fluoroacryloyl)piperazin-2-yl)acetonitrile | LCMS [ESI, M + 1]: 654<br>$^1$H NMR (400 MHz, CDCl$_3$) δ 9.07 (s, 1H), 8.05-7.96 (m, 1H), 7.90 (br dd, J = 5.6, 8.4 Hz, 1H), 7.66-7.56 (m, 2H), 7.41 (br t, J = 8.8 Hz, 1H), 5.57-5.38 (m, 1H), 5.38-5.19 (m, 2H), 4.97-4.72 (m, 2H), 4.64-4.41 (m, 3H), 4.33-3.90 (m, 2H), 3.82-3.63 (m, 2H), 3.14-2.66 (m, 7H), 2.43 (s, 3H) |
| 194 | 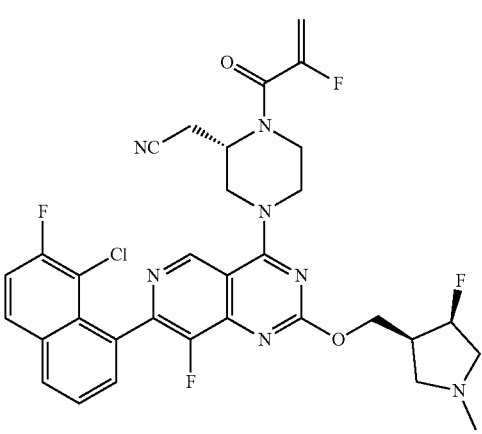<br>2-((S)-4-(7-(8-chloro-7-fluoronaphthalen-1-yl)-8-fluoro-2-(((3S,4R)-4-fluoro-1-methylpyrrolidin-3-yl)methoxy)pyrido[4,3-d]pyrimidin-4-yl)-1-(2-fluoroacryloyl)piperazin-2-yl)acetonitrile | LCMS [ESI, M + 1]: 654<br>$^1$H NMR (400 MHz, CDCl$_3$) δ 9.07 (s, 1H), 8.04-7.98 (m, 1H), 7.90 (dd, J = 5.6, 8.8 Hz, 1H), 7.67-7.56 (m, 2H), 7.41 (td, J = 1.6, 8.8 Hz, 1H), 5.58-5.40 (m, 1H), 5.39-5.19 (m, 2H), 4.94-4.72 (m, 2H), 4.61-4.41 (m, 3H), 4.33-3.94 (m, 2H), 3.89-3.74 (m, 2H), 3.16-2.65 (m, 7H), 2.44 (s, 3H) |

TABLE 3-continued

Examples 64 to 210

| Int. # | Structure | Characterization Data |
|---|---|---|
| 195 | 2-((S)-4-(7-(8-chloro-7-fluoronaphthalen-1-yl)-8-fluoro-2-(((1S,3R,4R)-2-(2-fluoroethyl)-2-azabicyclo[2.2.1]heptan-3-yl)methoxy)pyrido[4,3-d]pyrimidin-4-yl)-1-(2-fluoroacryloyl)piperazin-2-yl)acetonitrile | LCMS [ESI, M + 1]: 694<br>$^1$H NMR (400 MHz, CDCl$_3$) δ 9.06 (s, 1H), 8.05-7.97 (m, 1H), 7.94-7.87 (m, 1H), 7.68-7.55 (m, 2 H), 7.41 (td, J = 2.0, 8.8 Hz, 1H), 5.61-5.38 (m, 1H), 5.29 (dd, J = 2.8, 16.8 Hz, 1H), 4.96-4.80 (m, 1H), 4.77-4.38 (m, 5H), 4.35-3.91 (m, 3H), 3.88-3.72 (m, 2H), 3.48-3.33 (m, 1H), 3.14-2.78 (m, 4H), 2.58-2.49 (m, 1H), 2.47 (br d, J = 2.4 Hz, 1H), 1.99-1.80 (m, 2H), 1.74-1.63 (m, 1H), 1.49-1.36 (m, 1H), 1.34-1.26 (m, 2H) |
| 196 | 2-((S)-4-(7-(8-chloro-7-fluoronaphthalen-1-yl)-2-(((1S,3R,4R)-2-(2,2-difluoroethyl)-2-azabicyclo[2.2.1]heptan-3-yl)methoxy)-8-fluoropyrido[4,3-d]pyrimidin-4-yl)-1-(2-fluoroacryloyl)piperazin-2-yl)acetonitrile | LCMS [ESI, M + 1]: 712<br>$^1$H NMR (400 MHz, CDCl$_3$) δ 9.06 (s, 1H), 8.06-7.96 (m, 1H), 7.89 (dd, J = 5.6, 8.8 Hz, 1H), 7.68-7.54 (m, 2H), 7.40 (td, J = 2.4, 8.8 Hz, 1H), 6.15-5.76 (m, 1H), 5.59-5.37 (m, 1H), 5.28 (dd, J = 3.2, 16.8 Hz, 1H), 4.94-4.76 (m, 1H), 4.52-4.47 (m, 2H), 4.37 (ddd, J = 1.6, 4.8, 10.8 Hz, 1H), 4.33-3.90 (m, 3H), 3.82-3.65 (m, 2H), 3.34 (s, 1H), 3.10-2.93 (m, 3H), 2.92-2.78 (m, 1H), 2.56-2.51 (m, 1H), 2.44 (br s, 1H), 1.92-1.78 (m, 2H), 1.73-1.64 (m, 1H), 1.48-1.37 (m, 1H), 1.36-1.26 (m, 2H) |

TABLE 3-continued

Examples 64 to 210

| Int. # | Structure | Characterization Data |
|---|---|---|
| 197 | 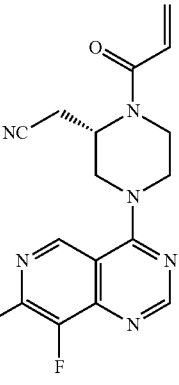<br>(S)-2-(1-acryloyl-4-(8-fluoro-7-(7-fluoronaphthalen-1-yl)pyrido[4,3-d]pyrimidin-4-yl)piperazin-2-yl)acetonitrile | LCMS [ESI, M + 1]: 471<br>$^1$H NMR (400 MHz, CDCl$_3$) δ 9.37-9.29 (m, 1H), 8.96-8.92 (m, 1H), 8.05-7.99 (m, 1H), 7.99-7.93 (m, 1H), 7.79-7.72 (m, 1H), 7.64-7.57 (m, 1H), 7.51-7.44 (m, 1H), 7.37-7.30 (m, 1H), 6.67-6.54 (m, 1H), 6.49-6.38 (m, 1H), 5.87 (br d, J = 10.4 Hz, 1H), 5.20-4.88 (m, 1H), 4.67-4.47 (m, 2H), 3.88 (br s, 4H), 3.10-2.72 (m, 2H) |
| 198 | 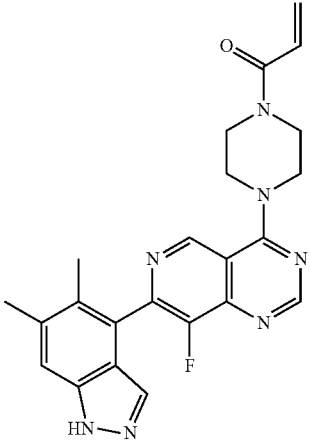<br>1-(4-(7-(5,6-dimethyl-1H-indazol-4-yl)-8-fluoropyrido[4,3-d]pyrimidin-4-yl)piperazin-1-yl)prop-2-en-1-one | LCMS [ESI, M + 1]: 432<br>$^1$H NMR (400 MHz, CDCl$_3$) δ 9.31 (s, 1H), 8.91 (s, 1H), 7.73 (s, 1H), 7.43 (s, 1H), 6.76-6.57 (m, 1H), 6.44 (d, J = 1.6 Hz, 1H), 5.85-5.79 (m, 1H), 4.23-4.09 (m, 4H), 4.05-3.79 (m, 4H), 2.50 (s, 3H), 2.25 (d, J = 1.6 Hz, 3H) |
| 199 | 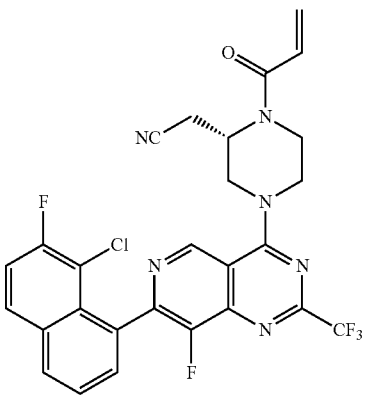<br>(S)-2-(1-acryloyl-4-(7-(8-chloro-7-fluoronaphthalen-1-yl)-8-fluoro-2-(trifluoromethyl)pyrido[4,3-d]pyrimidin-4-yl)piperazin-2-yl)acetonitrile | LCMS [ESI, M + 1]: 573<br>$^1$H NMR (400 MHz, CDCl$_3$) δ 9.31 (d, J = 2.4 Hz, 1H), 8.11-7.99 (m, 1H), 7.93 (dd, J = 5.6, 8.8 Hz, 1H), 7.71-7.59 (m, 2H), 7.43 (dt, J = 2.0, 8.8 Hz, 1H), 6.68-6.54 (m, 1H), 6.50-6.39 (m, 1H), 5.96-5.83 (m, 1H), 5.14-4.83 (m, 1H), 4.77-4.52 (m, 2H), 4.50-3.85 (m, 4H), 3.19-2.92 (m, 1H), 2.90-2.66 (m, 1H) |

TABLE 3-continued

Examples 64 to 210

| Int. # | Structure | Characterization Data |
|---|---|---|
| 200 | 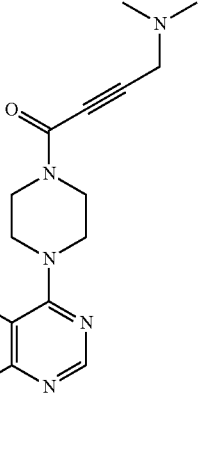<br>1-(4-(7-(8-chloro-7-fluoronaphthalen-1-yl)-8-fluoropyrido[4,3-d]pyrimidin-4-yl)piperazin-1-yl)-4-(dimethylamino)but-2-yn-1-one | LCMS [ESI, M + 1]: 521<br>$^1$H NMR (400 MHz, CDCl$_3$) δ 9.18 (s, 1H), 8.91 (s, 1H), 8.03 (dd, J = 1.6, 7.6 Hz, 1H), 7.92 (dd, J = 5.6, 9.2 Hz, 1H), 7.67-7.59 (m, 2H), 7.42 (t, J = 8.8 Hz, 1H), 4.16-4.03 (m, 6H), 3.96-3.90 (m, 2H), 3.50 (s, 2H), 2.37 (s, 6H) |
| 201 | 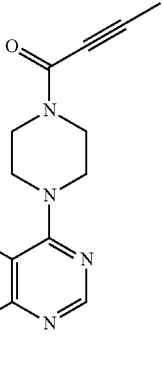<br>1-(4-(7-(8-chloro-7-fluoronaphthalen-1-yl)-8-fluoropyrido[4,3-d]pyrimidin-4-yl)piperazin-1-yl)but-2-yn-1-one | LCMS [ESI, M + 1]: 478<br>$^1$H NMR (400 MHz, CDCl$_3$) δ 9.18 (s, 1H), 8.91 (s, 1H), 8.03 (dd, J = 2.0, 7.6 Hz, 1H), 7.92 (dd, J = 5.6, 9.2 Hz, 1H), 7.68-7.58 (m, 2H), 7.42 (t, J = 8.8 Hz, 1H), 4.17-3.97 (m, 6H), 3.95-3.86 (m, 2H), 2.07 (s, 3H) |

TABLE 3-continued

Examples 64 to 210

| Int. # | Structure | Characterization Data |
|---|---|---|
| 202 | 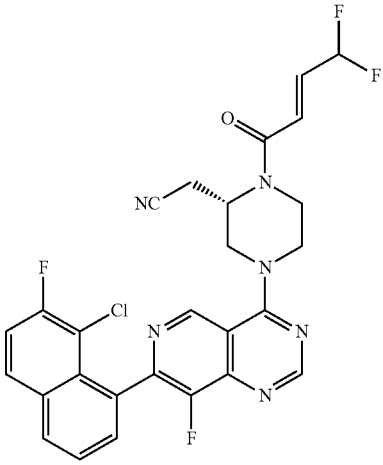<br>(S,E)-2-(4-(7-(8-chloro-7-fluoronaphthalen-1-yl)-8-fluoropyrido[4,3-d]pyrimidin-4-yl)-1-(4,4-difluorobut-2-enoyl)piperazin-2-yl)acetonitrile | LCMS [ESI, M + 1]: 516<br>$^1$H NMR (400 MHz, CDCl$_3$) δ 9.24-9.13 (m, 1H), 8.91 (d, J = 4.8 Hz, 1H), 8.09-7.97 (m, 1H), 7.95-7.85 (m, 1H), 7.69-7.55 (m, 2H), 7.42 (dt, J = 3.2, 8.8 Hz, 1H), 6.29-6.73 (m, 2H), 6.50-6.13 (m, 1H), 4.14 (br d, J = 2.4 Hz, 4H), 4.04-3.81 (m, 4H) |
| 203 | 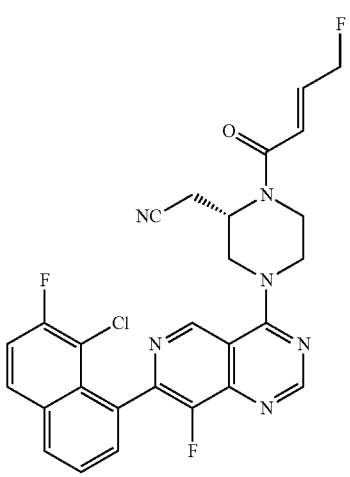<br>(S,E)-2-(4-(7-(8-chloro-7-fluoronaphthalen-1-yl)-8-fluoropyrido[4,3-d]pyrimidin-4-yl)-1-(4-fluorobut-2-enoyl)piperazin-2-yl)acetonitrile | LCMS [ESI, M + 1]: 498<br>$^1$H NMR (400 MHz, CDCl$_3$) δ 9.19 (s, 1H), 8.92-8.88 (m, 1H), 8.03 (dd, J = 2.0, 7.6 Hz, 1H), 7.91 (dd, J = 5.6, 9.2 Hz, 1H), 7.67-7.59 (m, 2H), 7.42 (t, J = 8.8 Hz, 1H), 7.08-6.94 (m, 1H), 6.62 (dd, J = 1.6, 15.6 Hz, 1H), 5.21-5.06 (m, 2H), 4.20-4.09 (m, 4H), 4.05-3.86 (m, 4H) |

TABLE 3-continued

Examples 64 to 210

| Int. # | Structure | Characterization Data |
|---|---|---|
| 204 | 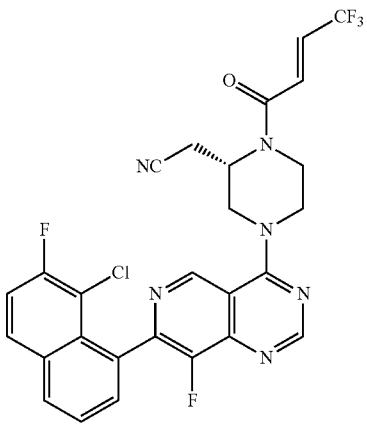<br>(S,E)-2-(4-(7-(8-chloro-7-fluoronaphthalen-1-yl)-8-fluoropyrido[4,3-d]pyrimidin-4-yl)-1-(4,4,4-trifluorobut-2-enoyl)piperazin-2-yl)acetonitrile | LCMS [ESI, M + 1]: 534<br>$^1$H NMR (400 MHz, CDCl$_3$) δ 9.19 (s, 1H), 8.92 (s, 1H), 8.03 (dd, J = 2.0, 7.6 Hz, 1H), 7.91 (dd, J = 5.6, 9.2 Hz, 1H), 7.70-7.58 (m, 2H), 7.42 (t, J = 8.8 Hz, 1H), 7.02 (dd, J = 2.0, 1.5 Hz, 1H), 6.94-6.76 (m, 1H), 4.15 (br d, J = 3.6 Hz, 4H), 4.05-3.81 (m, 4H) |
| 205 | 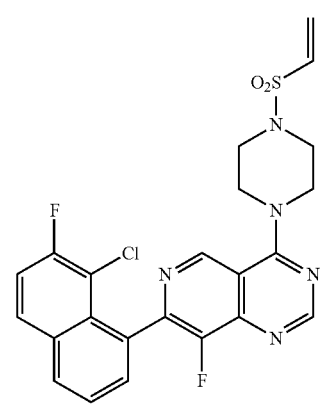<br>7-(8-chloro-7-fluoronaphthalen-1-yl)-8-fluoro-4-(4-(vinylsulfonyl)piperazin-1-yl)pyrido[4,3-d]pyrimidine | LCMS [ESI, M + 1]: 502<br>$^1$H NMR (400 MHz, CDCl$_3$) δ 9.14 (s, 1H), 8.90 (s, 1H), 8.03 (dd, J = 2.4, 7.2 Hz, 1H), 7.92 (dd, J = 5.6, 8.8 Hz, 1H), 7.67-7.58 (m, 2H), 7.42 (t, J = 8.8 Hz, 1H), 6.53-6.43 (m, 1H), 6.38-6.31 (m, 1H), 6.15 (d, J = 9.6 Hz, 1H), 4.24-4.10 (m, 4H), 3.43 (t, J = 5.2 Hz, 4H) |
| 206 | 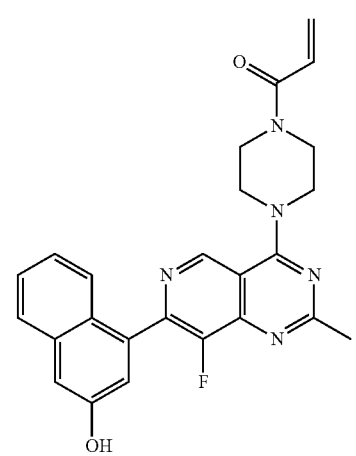<br>1-(4-(8-fluoro-7-(3-hydroxynaphthalen-1-yl)-2-methylpyrido[4,3-d]pyrimidin-4-yl)piperazin-1-yl)prop-2-en-1-one | LCMS [ESI, M + 1]: 444<br>$^1$H NMR (400 MHz, CDCl$_3$) δ 9.28 (s, 1H), 7.77 (d, J = 8.4 Hz, 1H), 7.54 (br d, J = 8.8 Hz, 1H), 7.43 (dt, J = 1.2, 7.6 Hz, 1H), 7.33-7.21 (m, 3H), 6.82 (dd, J = 10.8, 16.8 Hz, 1H), 6.30 (dd, J = 2.0, 16.8 Hz, 1H), 5.87-5.78 (m, 1H), 4.30-4.16 (m, 4H), 3.95 (br s, 4H), 2.68 (s, 3H) |

TABLE 3-continued

Examples 64 to 210

| Int. # | Structure | Characterization Data |
|---|---|---|
| 207 | (S)-2-(4-(7-(8-chloro-7-fluoronaphthalen-1-yl)-8-fluoro-2-((2-methyl-1,2,3,4-tetrahydroisoquinolin-5-yl)oxy)pyrido[4,3-d]pyrimidin-4-yl)-1-(2-fluoroacryloyl)piperazin-2-yl)acetonitrile | LCMS [ESI, M + 1]: 684<br>$^1$H NMR (400 MHz, CDCl$_3$) δ 9.07 (d, J = 3.2 Hz, 1H), 8.01 (dd, J = 2.8, 6.8 Hz, 1H), 7.90 (ddd, J = 1.6, 5.6, 9.0 Hz, 1H), 7.66-7.56 (m, 2H), 7.41 (dt, J = 2.4, 8.8 Hz, 1H), 7.23 (dt, J = 2.0, 8.0 Hz, 1H), 7.05-6.96 (m, 2H), 5.59-5.36 (m, 1H), 5.27 (td, J = 1.6, 18.8 Hz, 1H), 4.81-4.53 (m, 1H), 4.49-4.04 (m, 3H), 4.00-3.48 (m, 5H), 2.92-2.51 (m, 6H), 2.48 (s, 3H) |
| 208 | 2-((2S)-4-(7-(8-chloro-7-fluoronaphthalen-1-yl)-8-fluoro-2-((3-methoxy-1,2-dimethylazetidin-2-yl)methoxy)pyrido[4,3-d]pyrimidin-4-yl)-1-(2-fluoroacryloyl)piperazin-2-yl)acetonitrile | LCMS [ESI, M + 1]: 666<br>$^1$H NMR (400 MHz, CDCl$_3$) δ 9.05 (s, 1H), 8.02-7.96 (m, 1H), 7.89 (ddd, J = 1.2, 5.6, 9.2 Hz, 1H), 7.64-7.55 (m, 2H), 7.39 (dt, J = 2.4, 8.8 Hz, 1H), 5.56-5.38 (m, 1H), 5.28 (dd, J = 3.2, 16.8 Hz, 1H), 5.00-4.75 (m, 1H), 4.67-4.57 (m, 2H), 4.57-4.41 (m, 2H), 4.37-3.87 (m, 2H), 3.77 (br dd, J = 4.4, 6.0 Hz, 3H), 3.39 (t, J = 7.2 Hz, 1H), 3.32 (d, J = 1.6 Hz, 3H), 3.27-3.21 (m, 1H), 3.07-2.97 (m, 1H), 2.95-2.80 (m, 1H), 2.35 (d, J = 0.8 Hz, 3H), 1.42 (d, J = 1.6 Hz, 3H) |

TABLE 3-continued

Examples 64 to 210

| Int. # | Structure | Characterization Data |
|---|---|---|
| 209 | 2-((S)-4-(7-(8-chloro-7-fluoronaphthalen-1-yl)-2-(((S)-1-cyclopropylpyrrolidin-2-yl)methoxy)-8-fluoropyrido[4,3-d]pyrimidin-4-yl)-1-(2-fluoroacryloyl)piperazin-2-yl)acetonitrile | LCMS [ESI, M + 1]: 662<br>$^1$H NMR (400 MHz, CDCl$_3$) δ 9.07 (s, 1H), 8.03-7.98 (m, 1H), 7.93-7.87 (m, 1H), 7.66-7.57 (m, 2H), 7.41 (td, J = 1.6, 8.8 Hz, 1H), 5.58-5.40 (m, 1H), 5.34-5.25 (m, 1H), 5.00-4.69 (m, 2H), 4.54-3.97 (m, 5H), 3.91-3.54 (m, 2H), 3.30-2.97 (m, 3H), 2.94-2.80 (m, 1H), 2.60 (br s, 1H), 2.17-2.03 (m, 1H), 1.93-1.75 (m, 4H), 0.79-0.21 (m, 4H) |
| 210 | 2-((S)-4-(7-(8-chloro-7-fluoronaphthalen-1-yl)-2-(((S)-4,4-difluoro-1-methylpyrrolidin-2-yl)methoxy)-8-fluoropyrido[4,3-d]pyrimidin-4-yl)-1-(2-fluoroacryloyl)piperazin-2-yl)acetonitrile | LCMS [ESI, M + 1]: 672<br>$^1$H NMR (400 MHz, CDCl$_3$) δ 9.09 (s, 1H), 8.07-7.98 (m, 1H), 7.95-7.87 (m, 1H), 7.66-7.56 (m, 2H), 7.41 (dt, J = 2.4, 8.8 Hz, 1H), 5.58-5.39 (m, 1H), 5.30 (dd, J = 3.6, 17.2 Hz, 1H), 4.97-4.79 (m, 1H), 4.72-4.60 (m, 1H), 4.58-4.42 (m, 3H), 4.34-4.00 (m, 2H), 3.90-3.69 (m, 2H), 3.44 (dt, J = 5.6, 11.6 Hz, 1H), 3.11-2.98 (m, 2H), 2.92-2.80 (m, 1H), 2.71 (dt, J = 12.0, 16.8 Hz, 1H), 2.61-2.52 (m, 1H), 2.50 (s, 3H), 2.43-2.27 (m, 1H) |

Example 211

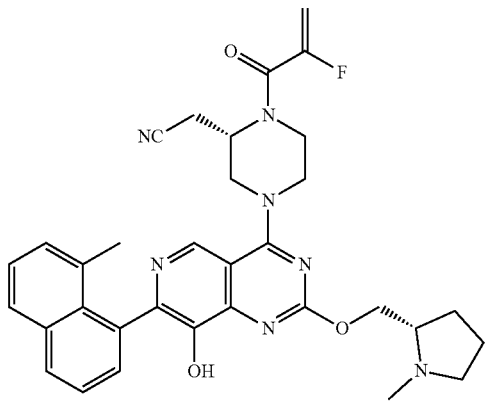 [SMILES: C=C(F)C(=O)N1CCN(c2nc(OC[C@@H]3CCCN3C)nc3c(O)c(-c4cccc5cccc(C)c45)ncc23)C[C@@H]1CC#N]

2-((S)-1-(2-fluoroacryloyl)-4-(8-hydroxy-7-(8-methylnaphthalen-1-yl)-2-(((S)-1-methylpyrrolidin-2-yl)methoxy)pyrido[4,3-d]pyrimidin-4-yl)piperazin-2-yl)acetonitrile

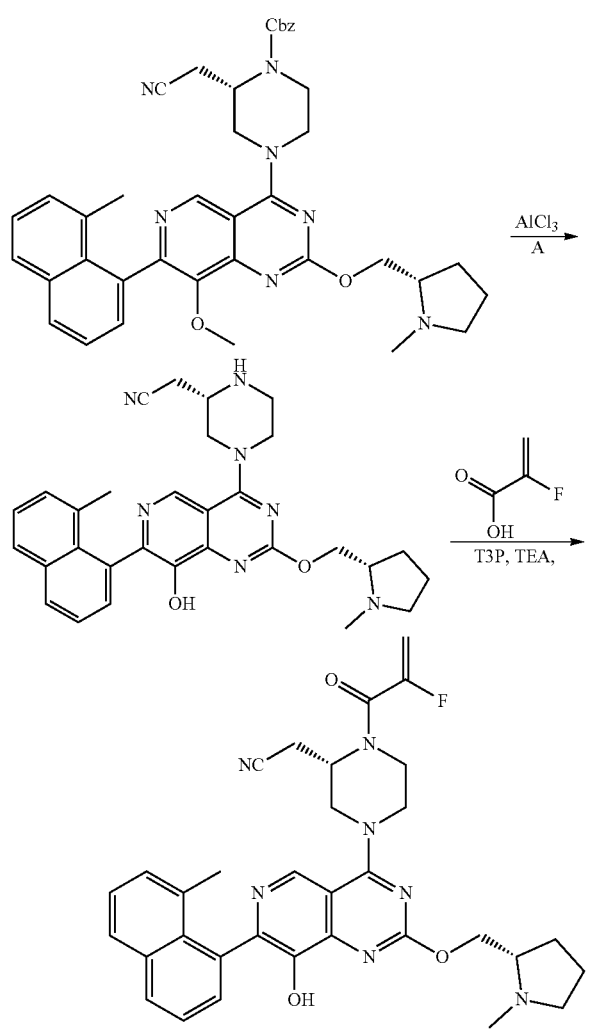

Example 211

Step A: To a solution of benzyl (2S)-2-(cyanomethyl)-4-[8-methoxy-7-(8-methyl-1-naphthyl)-2-[[(2S)-1-methylpyrrolidin-2-yl]methoxy]pyrido[4,3-d]pyrimidin-4-yl]piperazine-1-carboxylate (0.1 g, 149 umol, 1.0 equiv) and AlCl₃ (119 mg, 893 μmol, 48.8 μL, 6.0 equiv) in toluene (2.0 mL) was stirred at 60° C. for 2 h. Subsequently, the mixture was diluted with water (5.0 mL), neutralized with NaHCO₃ (200 mg), and was extracted with ethyl acetate (3×5.0 mL). The combined organic layer was washed with brine (5.0 mL), dried over anh Na₂SO₄, filtered and concentrated under vacuum. The residue was purified by reversed phase flash chromatography [water (FA, 0.1%)/acetonitrile] and prep-HPLC [column: Xtimate C18 150*25 mm*5 μm; water (0.05% ammonia hydroxide v/v); ACN: 30%-60%, 10 min] to afford 2-[(2S)-4-[8-hydroxy-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (3.43 mg, 6.53 μmol, 4.4% yield, 99.7% purity) as an off-white solid. LCMS [ESI, M+1]: 524. ¹H NMR (400 MHz, chloroform-d): δ 8.96 (s, 1H), 7.91 (d, J=8.0 Hz, 1H), 7.83 (d, J=8.4 Hz, 1H), 7.66 (dd, J=1.2, 7.2 Hz, 1H), 7.56-7.51 (m, 2H), 7.34 (dd, J=1.6, 8.4 Hz, 1H), 4.65-4.50 (m, 3H), 4.35 (dd, J=6.8, 10.4 Hz, 1H), 3.62-3.53 (m, 1H), 3.40-3.32 (m, 1H), 3.28-3.21 (m, 2H), 3.18-3.09 (m, 2H), 2.78 (br s, 1H), 2.68-2.56 (m, 2H), 2.52 (s, 3H), 2.44 (s, 3H), 2.37-2.29 (m, 1H), 2.14-2.07 (m, 1H), 1.93-1.81 (m, 3H).

Example 211: To a mixture of 2-[(2S)-4-[8-hydroxy-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (30 mg, 57.3 μmol, 1.0 equiv), 2-fluoroprop-2-enoic acid (10.3 mg, 115 μmol, 2.0 equiv), and TEA (46.4 mg, 458 μmol, 63.8 μL, 8.0 equiv) in ethyl acetate (2.0 mL) was added T3P (219 mg, 344 μmol, 204 μL, 50% solution in ethyl acetate, 6.0 equiv). After stirring at room temperature for 0.5 h, the mixture was diluted with H₂O (5.0 mL) and was extracted with ethyl acetate (2×5.0 mL). The combined organic layer was washed with brine (5.0 mL), dried over anh Na₂SO₄, filtered and concentrated under vacuum. The residue was purified by reversed phase flash chromatography [water (FA, 0.1%)/acetonitrile] and prep-HPLC [column: Xtimate C18 150*25 mm*5 μm; water (0.05% ammonia hydroxide v/v); ACN: 30%-60%, 10 min] to give 2-[(2S)-1-(2-fluoroprop-2-enoyl)-4-[8-hydroxy-7-(8-methyl-1-naphthyl)-2-[[(2S)-1-methylpyrrolidin-2-yl]methoxy]pyrido[4,3-d]pyrimidin-4-yl]piperazin-2-yl]acetonitrile (5.75 mg, 9.49 μmol, 17% yield, 98.3% purity) as a yellow solid. LCMS [ESI, M+1]: 596. ¹H NMR (400 MHz, chloroform-d): δ 9.00 (s, 1H), 7.92 (d, J=8.4 Hz, 1H), 7.83 (d, J=8.4 Hz, 1H), 7.66 (d, J=6.8 Hz, 1H), 7.57-7.51 (m, 2H), 7.34 (d, J=8.0 Hz, 1H), 5.59-5.40 (m, 1H), 5.30 (dd, J=3.6, 16.8 Hz, 1H), 4.87 (br s, 1H), 4.64-4.47 (m, 3H), 4.37 (dd, J=6.4, 10.4 Hz, 1H), 4.14 (br s, 1H), 3.84 (br s, 2H), 3.21-2.98 (m, 2H), 2.96-2.61 (m, 3H), 2.53 (s, 3H), 2.43 (s, 3H), 2.39-2.30 (m, 1H), 2.15-2.08 (m, 1H), 1.96-1.81 (m, 3H).

Example 212

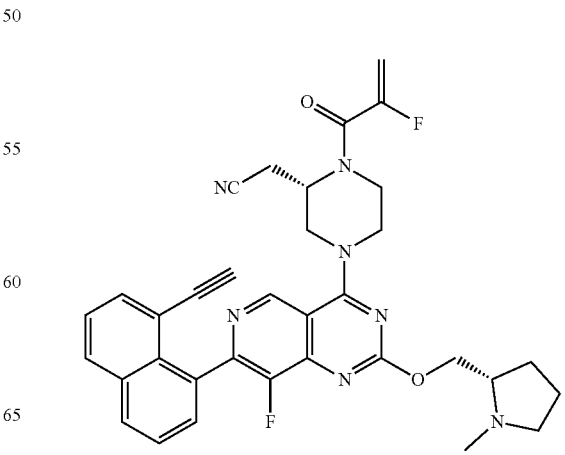

2-((S)-4-(7-(8-ethynylnaphthalen-1-yl)-8-fluoro-2-(((S)-1-methylpyrrolidin-2-yl)methoxy)pyrido[4,3-d]pyrimidin-4-yl)-1-(2-fluoroacryloyl)piperazin-2-yl)acetonitrile

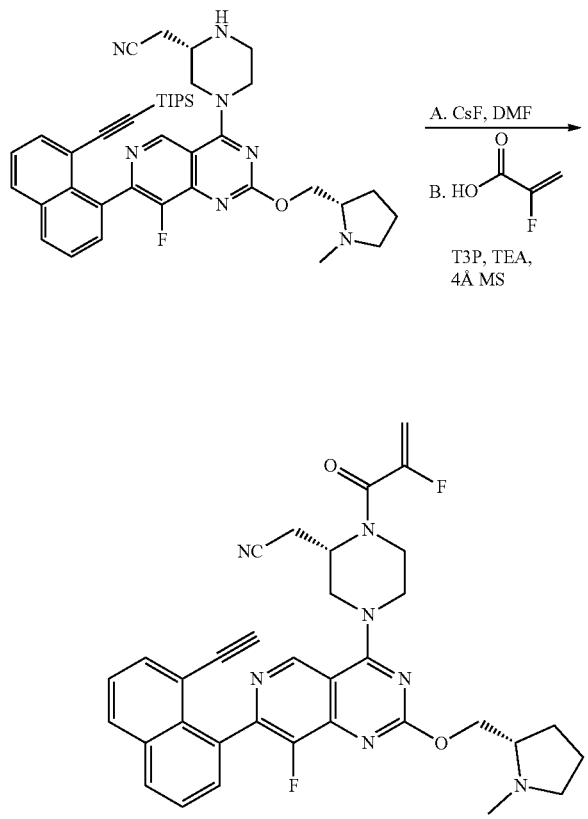

Example 212

Step A: A mixture of 2-((S)-4-(8-fluoro-2-(((S)-1-methylpyrrolidin-2-yl)methoxy)-7-(8-((triisopropylsilyl)ethynyl)naphthalen-1-yl)pyrido[4,3-d]pyrimidin-4-yl)piperazin-2-yl)acetonitrile (100 mg, crude) and CsF (110 mg, 723 µmol, 26.6 µL) in DMF (2 mL) was stirred at room temperature for 3 h. Subsequently, the mixture was diluted with ethyl acetate (5.0 mL), washed with brine (2.0 mL), dried over anh Na₂SO₄, filtered and concentrated under vacuum. The residue was purified by column chromatography (Al₂O₃, ethyl acetate/methanol, 10:1) and prep-HPLC [column: Xtimate C18 150*25 mm*5 µm; water (0.05% ammonia hydroxide v/v); ACN: 32%-52%, 10 min] to give 2-((S)-4-(7-(8-ethynylnaphthalen-1-yl)-8-fluoro-2-(((S)-1-methylpyrrolidin-2-yl)methoxy)pyrido[4,3-d]pyrimidin-4-yl)piperazin-2-yl)acetonitrile (16.2 mg, 30.1 µmol, 24% yield over two steps) as a yellow solid. LCMS [ESI, M+1]: 536. ¹H NMR (400 MHz, chloroform-d): δ 9.01 (s, 1H), 7.99 (br dd, J=7.6, 12.4 Hz, 2H), 7.77 (br d, J=6.8 Hz, 1H), 7.68-7.57 (m, 2H), 7.54-7.43 (m, 1H), 4.66-4.49 (m, 2H), 4.46-4.34 (m, 2H), 3.63-3.47 (m, 1H), 3.36 (br s, 1H), 3.28-3.04 (m, 4H), 2.77-2.54 (m, 4H), 2.50 (br s, 3H), 2.36-2.23 (m, 1H), 2.05 (br s, 2H), 1.93-1.74 (m, 3H).

Example 212: To a mixture of 2-((S)-4-(7-(8-ethynylnaphthalen-1-yl)-8-fluoro-2-(((S)-1-methylpyrrolidin-2-yl)methoxy)pyrido[4,3-d]pyrimidin-4-yl)piperazin-2-yl)acetonitrile (40 mg, 74.7 µmol, 1.0 equiv), 2-fluoroprop-2-enoic acid (20.2 mg, 224 µmol, 3.0 equiv), TEA (90.7 mg, 896 µmol, 125 µL, 12 equiv) and 4 Å molecular sieve (20 mg) in ethyl acetate (2 mL) was added T3P (285 mg, 448 µmol, 266 µL, 50% in ethyl acetate, 6.0 equiv). After stirring at 15° C. for 0.5 hour, the mixture was diluted with ethyl acetate (5.0 mL), washed with water (3.0 mL), dried over anh Na₂SO₄, filtered and concentrated under vacuum. The residue was purified by prep-HPLC [column: Xtimate C18 150*25 mm*5 µm; water (0.05% ammonia hydroxide v/v); ACN: 43%-73%, 10 min] to afford 2-((S)-4-(7-(8-ethynylnaphthalen-1-yl)-8-fluoro-2-(((S)-1-methylpyrrolidin-2-yl)methoxy)pyrido[4,3-d]pyrimidin-4-yl)-1-(2-fluoroacryloyl)piperazin-2-yl)acetonitrile (3.35 mg, 5.47 µmol, 7.3% yield, 99.2% purity) as an off-white solid. LCMS [ESI, M+1]: 608. ¹H NMR (400 MHz, chloroform-d): δ 9.06 (d, J=10.8 Hz, 1H), 8.03-7.96 (m, 2H), 7.77 (d, J=7.2 Hz, 1H), 7.66-7.57 (m, 2H), 7.48 (t, J=7.6 Hz, 1H), 5.56-5.39 (m, 1H), 5.28 (dd, J=4.0, 16.8 Hz, 1H), 4.85 (br s, 1H), 4.60 (dt, J=4.8, 10.8 Hz, 1H), 4.54-4.38 (m, 3H), 4.16 (br s, 2H), 3.82 (br s, 2H), 3.13 (br s, 1H), 3.09-2.93 (m, 1H), 2.91-2.84 (m, 1H), 2.73-2.60 (m, 2H), 2.52 (d, J=3.6 Hz, 3H), 2.31 (br d, J=8.8 Hz, 1H), 2.12-2.01 (m, 1H), 1.92-1.70 (m, 3H).

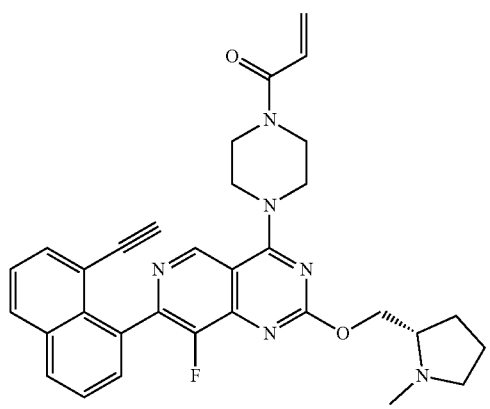 [SMILES: C#Cc1cccc2cccc(-c3ncc4c(N5CCN(C(=O)C=C)CC5)nc(OC[C@@H]5CCCN5C)nc4c3F)c12]

Example 213

(S)-1-(4-(7-(8-ethynylnaphthalen-1-yl)-8-fluoro-2-((1-methylpyrrolidin-2-yl)methoxy)pyrido[4,3-d]pyrimidin-4-yl)piperazin-1-yl)prop-2-en-1-one

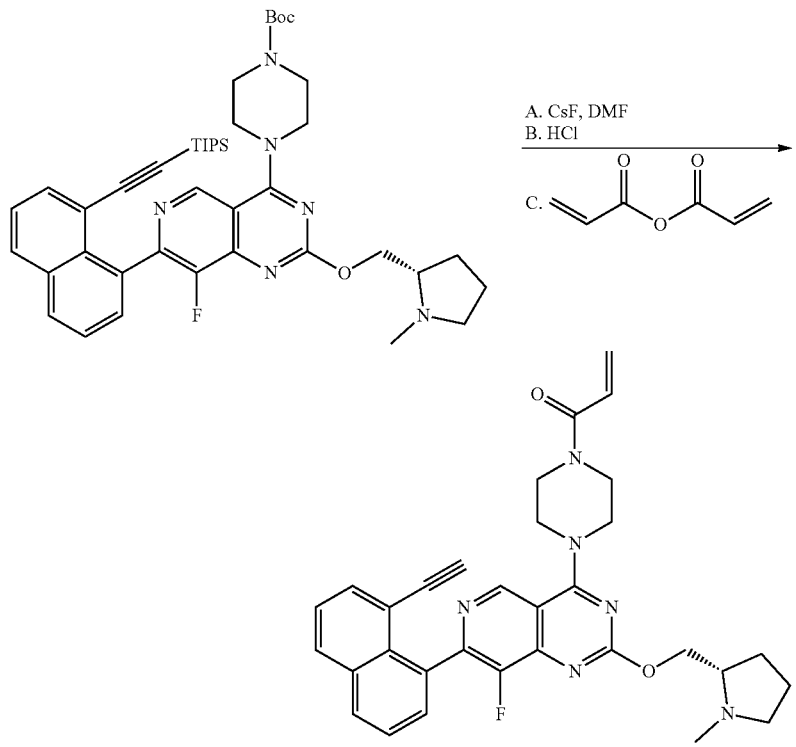

Example 213

Step A: To a solution of tert-butyl (S)-4-(8-fluoro-2-((1-methylpyrrolidin-2-yl)methoxy)-7-(8-((triisopropylsilyl)ethynyl)naphthalen-1-yl)pyrido[4,3-d]pyrimidin-4-yl)piperazine-1-carboxylate (80.0 mg, 106 μmol, 1.00 equiv) in DMF (2.0 mL) was added cesium fluoride (80.7 mg, 531 μmol, 19.6 μL, 5.00 equiv). The mixture was stirred at 25° C. for 0.5 hours. The reaction mixture was diluted with water (2.0 mL) and was extracted with ethyl acetate (3×2 mL). The combined organic layer was washed with brine (2×2 mL), dried over anh magnesium sulfate and filtered. The solvent was removed in vacuo to give tert-butyl (S)-4-(7-(8-ethynylnaphthalen-1-yl)-8-fluoro-2-((1-methylpyrrolidin-2-yl)methoxy)pyrido[4,3-d]pyrimidin-4-yl)piperazine-1-carboxylate (70 mg, crude) as a yellow solid. LCMS [ESI, M+1]: 597.3.

Step B: To a solution of tert-butyl (S)-4-(7-(8-ethynylnaphthalen-1-yl)-8-fluoro-2-((1-methylpyrrolidin-2-yl)methoxy)pyrido[4,3-d]pyrimidin-4-yl)piperazine-1-carboxylate (70.0 mg, 117 μmol, 1.00 equiv) in MeCN (0.5 mL) was added HCl in dioxane (4 M, 0.5 mL). The mixture was stirred at 25° C. for 10 min prior to dilution with satd aq sodium bicarbonate (3.0 mL). The mixture was extracted with ethyl acetate (3×5 mL) and the combined organic layer was washed with brine (2×5 mL), dried over anh magnesium sulfate and filtered. The solvent was removed in vacuo to give (S)-7-(8-ethynylnaphthalen-1-yl)-8-fluoro-24(1-methylpyrrolidin-2-yl)methoxy)-4-(piperazin-1-yl)pyrido[4,3-d]pyrimidine (50 mg, crude) as a yellow solid. $^1$H NMR (400 MHz, CDCl$_3$) δ=9.01 (s, 1H), 8.02-7.94 (m, 2H), 7.78-7.75 (m, 1H), 7.64-7.59 (m, 2H), 7.49-7.44 (m, 1H), 4.63-4.56 (m, 1H), 4.43-4.34 (m, 1H), 4.10-3.96 (m, 4H), 3.18-3.06 (m, 5H), 2.82-2.73 (m, 1H), 2.58 (d, J=2.4 Hz, 1H), 2.52 (s, 3H), 2.36-2.28 (m, 1H), 2.13-2.01 (m, 1H), 1.89-1.78 (m, 4H).

Example 213: To a solution of (S)-7-(8-ethynylnaphthalen-1-yl)-8-fluoro-2-((1-methylpyrrolidin-2-yl)methoxy)-4-(piperazin-1-yl)pyrido[4,3-d]pyrimidine (47 mg, 94.6 μmol, 1.00 equiv) in ethyl acetate (1.0 mL) at 0° C. was added TEA (28.7 mg, 284 μmol, 39.5 μL, 3.00 equiv) and prop-2-enoyl prop-2-enoate (17.9 mg, 142 μmol, 1.50 equiv). The mixture was stirred at this temperature for 15 minutes and was then concentrated under reduced pressure to give a residue. The crude product was purified by prep-HPLC [column: Xtimate C18 150*25 mm*5 μm; water (0.05% ammonia hydroxide v/v); ACN: 28%-58%, 10 min] to afford (5)-1-(4-(7-(8-ethynylnaphthalen-1-yl)-8-fluoro-2-((1-methylpyrrolidin-2-yl)methoxy)pyrido[4,3-d]pyrimidin-4-yl)piperazin-1-yl)prop-2-en-1-one (18.4 mg, 35% yield) as a yellow solid. $^1$H NMR (400 MHz, CDCl$_3$): δ 9.05 (s, 1H), 8.02-7.95 (m, 2H), 7.80-7.75 (m, 1H), 7.65-7.58 (m, 2H), 7.50-7.44 (m, 1H), 6.66-6.57 (m, 1H), 6.44-6.36 (m, 1H), 5.84-5.78 (m, 1H), 4.64-4.55 (m, 1H), 4.45-4.37 (m, 1H), 4.10-4.04 (m, 4H), 3.99-3.84 (m, 4H), 3.18-3.10 (m, 1H), 2.81-2.71 (m, 1H), 2.57 (d, J=2.8 Hz, 1H), 2.52 (s, 3H), 2.37-2.25 (m, 1H), 2.13-2.01 (m, 1H), 1.91-1.81 (m, 3H); LCMS [ESI, M+1]: 551.3.

Example 214

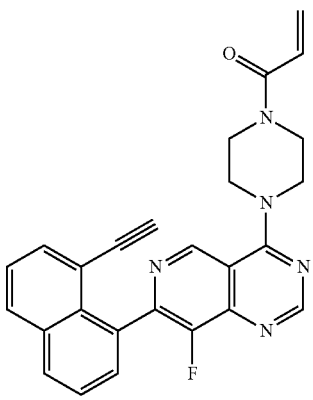 [SMILES: C#Cc1cccc2cccc(-c3ncc4c(N5CCN(C(=O)C=C)CC5)ncnc4c3F)c12]

1-(4-(7-(8-ethynylnaphthalen-1-yl)-8-fluoropyrido[4,3-d]pyrimidin-4-yl)piperazin-1-yl)prop-2-en-1-one

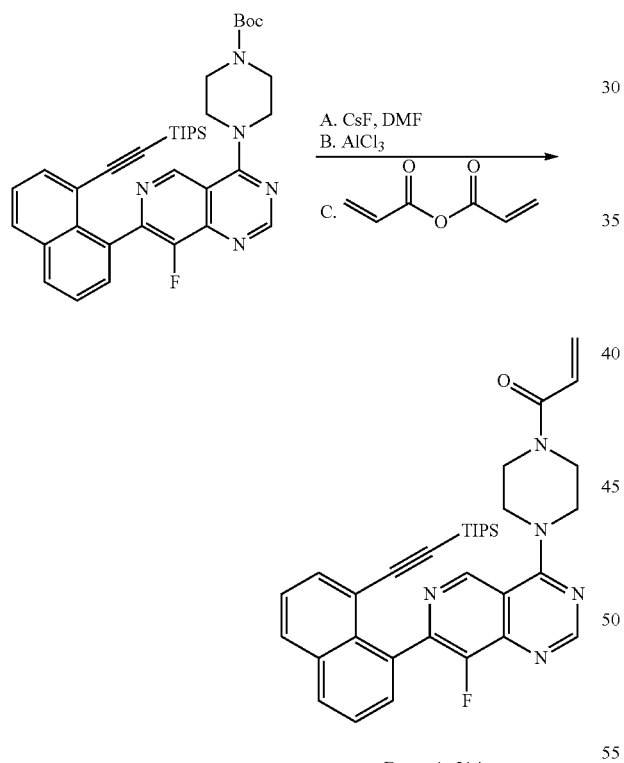

Example 214

Step A: To a mixture of tert-butyl 4-(8-fluoro-7-(8-(((triisopropylsilyl)ethynyl)naphthalen-1-yl)pyrido[4,3-d]pyrimidin-4-yl)piperazine-1-carboxylate (230 mg, 359 μmol, 1 equiv) in DMF (5 mL) was added CsF (546 mg, 3.59 mmol, 10 equiv) in one portion at 25° C. The mixture was stirred at 25° C. for 30 minutes. The mixture was poured into water (20 mL) and was extracted with ethyl acetate (3×30 mL). The combined organic phase was washed with brine (30 mL), dried with anhydrous Na$_2$SO$_4$, filtered and concentrated in vacuum. The residue was purified by prep-HPLC [column: Phenomenex Gemini-NX C18 75*30 mm*3 μm; water (0.1% FA); ACN: 55%-85%, 10 min] to afford tert-butyl 4-(7-(8-ethynylnaphthalen-1-yl)-8-fluoropyrido[4,3-d]pyrimidin-4-yl)piperazine-1-carboxylate (140 mg, 261 μmol, 73% yield) as a yellow solid. LCMS [ESI, M+1]: 484.

Step B: To a mixture of 4-(7-(8-ethynylnaphthalen-1-yl)-8-fluoropyrido[4,3-d]pyrimidin-4-yl)piperazine-1-carboxylate (40 mg, 82.7 μmol, 1 equiv) in MeCN (2 mL) was added AlCl$_3$ (33.1 mg, 248 μmol, 3 equiv) in one portion at 25° C. The mixture was stirred at 25° C. for 30 minutes. The mixture was filtered and concentrated in vacuum. The residue was purified by prep-HPLC [column: Waters Xbridge 150*25 mm*5 μm; water (0.05% ammonia hydroxide v/v); ACN: 23%-50%, 10 min] to afford 7-(8-ethynylnaphthalen-1-yl)-8-fluoro-4-(piperazin-1-yl)pyrido[4,3-d]pyrimidine (14.7 mg, 37.6 μmol, 20% yield) as a yellow solid. $^1$H NMR (400 MHz, DMSO-d$_6$): δ 9.16 (s, 1H), 8.70 (s, 1H), 8.19-8.13 (m, 2H), 7.75-7.69 (m, 2H), 7.65-7.62 (m, 1H), 7.61-7.55 (m, 1H), 4.01-3.92 (m, 4H), 3.69 (s, 1H), 3.32 (br s, 1H), 2.92 (t, J=4.8 Hz, 4H); LCMS (ESI, M+1): 384.

Example 214: To a mixture of 7-(8-ethynylnaphthalen-1-yl)-8-fluoro-4-(piperazin-1-yl)pyrido[4,3-d]pyrimidine (65 mg, 170 μmol, 1 equiv) and prop-2-enoyl prop-2-enoate (64.1 mg, 508 μmol, 3 equiv) in DCM (1 mL) at 0° C. was added TEA (51.5 mg, 509 μmol, 70.8 3 equiv) in one portion. The mixture was stirred at 0° C. for 10 min and was concentrated in vacuum. The residue was purified by pre-HPLC [column: Waters Xbridge 150*25 mm*5 μm; water (0.05% ammonia hydroxide v/v); ACN: 26%-56%, 10 min] to afford 1444748-ethynylnaphthalen-1-yl)-8-fluoropyrido[4,3-d]pyrimidin-4-yl)piperazin-1-yl)prop-2-en-1-one (22.1 mg, 49.6 μmol, 29% yield) as a yellow solid. $^1$H NMR (400 MHz, DMSO-d$_6$): δ 9.25 (s, 1H), 8.76 (s, 1H), 8.18-8.13 (m, 2H), 7.75-7.69 (m, 2H), 7.64 (dd, J=1.2, 6.8 Hz, 1H), 7.60-7.55 (m, 1H), 6.84 (dd, J=10.4, 16.8 Hz, 1H), 6.19 (dd, J=2.4, 16.8 Hz, 1H), 5.78-5.73 (m, 1H), 4.17-4.05 (m, 4H), 3.94-3.75 (m, 4H), 3.68 (s, 1H). LCMS (ESI, M+1): 438.

Example 215

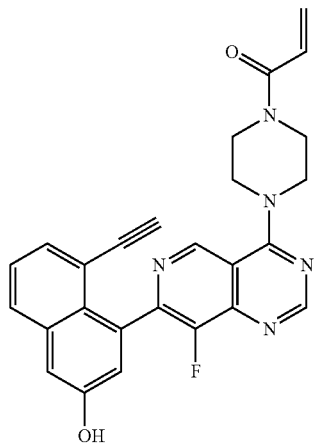 [SMILES: C#Cc1cccc2cc(O)cc(-c3ncc4c(N5CCN(C(=O)C=C)CC5)ncnc4c3F)c12]

1-(4-(7-(8-ethynyl-3-hydroxynaphthalen-1-yl)-8-fluoropyrido[4,3-d]pyrimidin-4-yl)piperazin-1-yl)prop-2-en-1-one

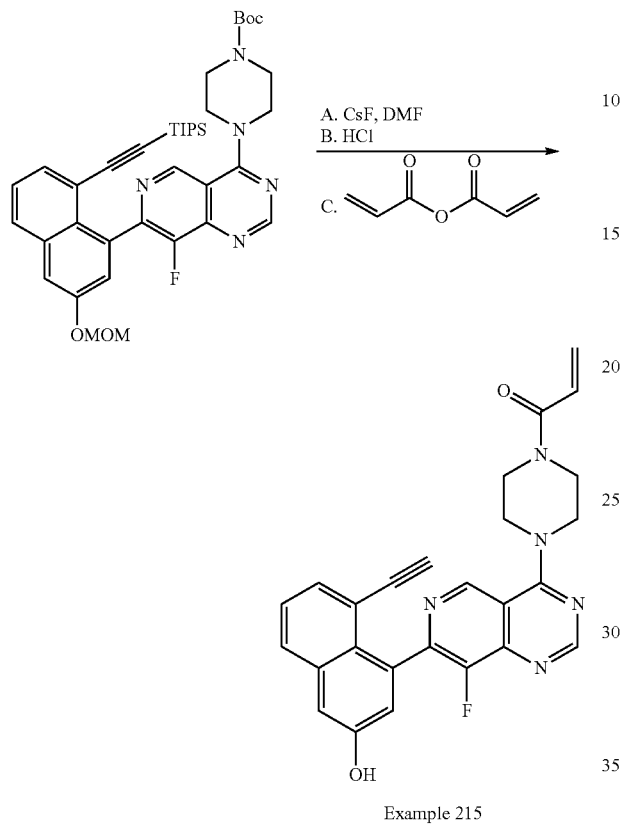

Example 215

Step A: To a mixture of tert-butyl 4-(8-fluoro-7-(3-(methoxymethoxy)-8-((triisopropylsilyl)ethynyl)naphthalen-1-yl)pyrido[4,3-d]pyrimidin-4-yl)piperazine-1-carboxylate (120 mg, 172 µmol, 1.00 equiv) in DMF (3.00 mL) was added CsF (234 mg, 1.54 mmol, 9.00 equiv). The mixture was stirred at 20° C. for 1 h and was diluted with H$_2$O (30 mL) and extracted with ethyl acetate (60 mL). The organic layer was washed with brine (20 mL), dried over anh Na$_2$SO$_4$, filtered and concentrated under reduced pressure to give a residue. The residue was purified by prep-TLC (SiO$_2$, petroleum ether/ethyl acetate, 1:1, R$_f$=0.24) to afford tert-butyl 4-(7-(8-ethynyl-3-(methoxymethoxy)naphthalen-1-yl)-8-fluoropyrido [4,3-d]pyrimidin-4-yl)piperazine-1-carboxylate (90.0 mg, 166 µmol, 96% yield) a light yellow solid. LCMS [ESI, M+1]: 544.2.

Step B: To a mixture of tert-butyl 4-(7-(8-ethynyl-3-(methoxymethoxy)naphthalen-1-yl)-8-fluoropyrido[4,3-d]pyrimidin-4-yl)piperazine-1-carboxylate (50.0 mg, 91.9 µmol, 1 equiv) in ethyl acetate (0.5 mL) was added HCl in ethyl acetate (4 M, 23.0 µL, 1.0 equiv). The mixture was stirred at 20° C. for 1 h and was concentrated under reduced pressure afford 5-ethynyl-4-(8-fluoro-4-(piperazin-1-yl)pyrido[4,3-d]pyrimidin-7-yl)naphthalen-2-ol (40.0 mg, crude, 50% purity, HCl salt) as a light yellow solid. LCMS [ESI, M+1]: 400.1. LCMS [ESI, M+1]: 436.1 (impurity).

Example 215: To a mixture of 5-ethynyl-4-(8-fluoro-4-(piperazin-1-yl)pyrido[4,3-d]pyrimidin-7-yl)naphthalen-2-ol (40.0 mg, 55.1 µmol, 1.00 equiv, HCl salt) in DCM (2 mL) at 0° C. was added TEA (22.3 mg, 220 µmol, 30.7 µL, 4.0 equiv) and 5-prop-2-enoyl prop-2-enoate (10.1 mg, 79.8 µmol, 1.45 equiv). The mixture was stirred at 0° C. for 0.5 hour and was then diluted with H$_2$O (10 mL) and extracted with DCM (30 mL). The organic layer was concentrated under reduced pressure to give a residue. The residue was purified by prep-HPLC [column: YMC-Actus Triart C18 100*30 mm*5 µm; water (10 mM NH$_4$HCO$_3$); ACN: 15%-45%, 10 min] to afford 1-(4-(7-(8-ethynyl-3-hydroxynaphthalen-1-yl)-8-fluoropyrido[4,3-d]pyrimidin-4-yl)piperazin-1-yl)prop-2-en-1-one (7.82 mg, 16.62 µmol, 30% yield, 96.4% purity) as a light yellow solid. $^1$H NMR (400 MHz, CDCl$_3$) δ 9.14 (s, 1H), 8.87 (s, 1H), 7.76 (br d, J=8.4 Hz, 2H), 7.57 (d, J=6.8 Hz, 1H), 7.43-7.34 (m, 1H), 7.29 (d, J=2.4 Hz, 1H), 7.24 (d, J=2.4 Hz, 1H), 6.63-6.57 (m, 1H), 6.41 (dd, J=1.6, 16.8 Hz, 1H), 5.82 (dd, J=1.2, 10.4 Hz, 1H), 4.11 (br t, J=5.2 Hz, 4H), 4.02-3.75 (m, 4H), 2.46 (s, 1H). LCMS [ESI, M+1]: 454.1.

Example 216

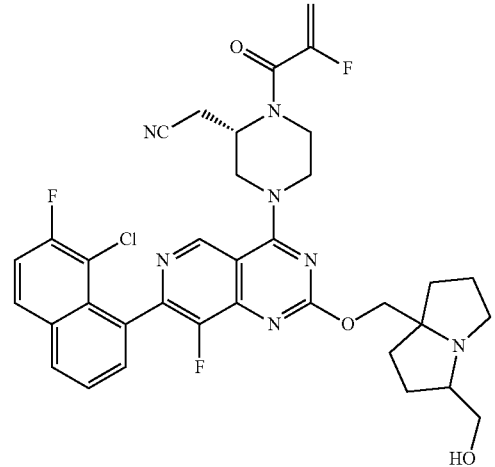 [SMILES: C=C(F)C(=O)N1CCN(c2nc(OCC34CCCN3C(CO)CC4)nc3c(F)c(-c4cccc5ccc(F)c(Cl)c45)ncc23)C[C@@H]1CC#N]

2-((2 S)-4-(7-(8-chloro-7-fluoronaphthalen-1-yl)-8-fluoro-2-((3-(hydroxymethyl)tetrahydro-1H-pyrrolizin-7a(5H)-yl)methoxy)pyrido[4,3-d]pyrimidin-4-yl)-1-(2-fluoroacryloyl)piperazin-2-yl)acetonitrile

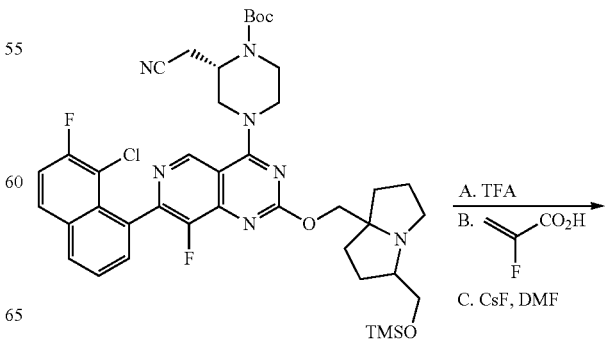

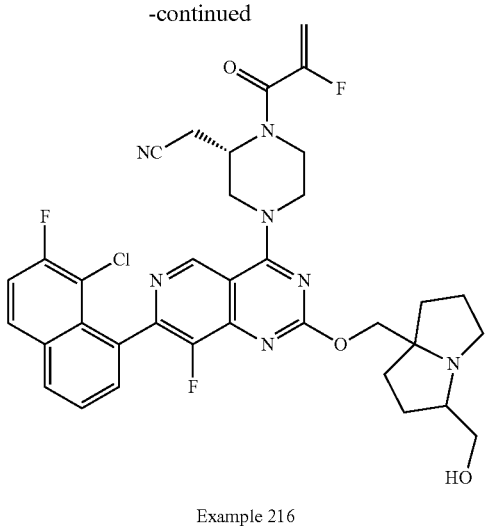

Example 216

Step A: To a solution of tert-butyl (2S)-4-(2-((3-(((tert-butyldimethylsilyl)oxy)methyl)tetrahydro-1H-pyrrolizin-7a(5H)-yl)methoxy)-7-(8-chloro-7-fluoronaphthalen-1-yl)-8-fluoropyrido[4,3-d]pyrimidin-4-yl)-2-(cyanomethyl)piperazine-1-carboxylate (50.0 mg, 53.3 μmol, 1.0 equiv) in dichloromethane (1.0 mL) at 0° C. was added TFA (1.54 g, 13.5 mmol, 1.0 mL, 253 equiv). The mixture was stirred at 0° C. for 0.5 hour and was then diluted with water (4.0 mL). The pH was adjusted to about 8 using solid NaHCO₃ and the mixture was extracted with ethyl acetate (3×5 mL). The combined organic layer was dried over anhydrous sodium sulfate and filtered. The filtrate was concentrated under reduced pressure to afford 2-((2S)-4-(2-((3-(((tert-butyldimethylsilyl)oxy)methyl)tetrahydro-1H-pyrrolizin-7a(5H)-yl)methoxy)-7-(8-chloro-7-fluoronaphthalen-1-yl)-8-fluoropyrido[4,3-d]pyrimidin-4-yl)piperazin-2-yl)acetonitrile (40.0 mg, crude) as a yellow solid. R$_f$=0.20 [petroleum ether/ethyl acetate/ethanol (2% NH₄OH), 4:3:1]. LCMS [ESI, M+1]: 734.

Step B: To a mixture of 2-((2S)-4-(2-((3-(((tert-butyldimethylsilyl)oxy)methyl)tetrahydro-1H-pyrrolizin-7a(5H)-yl)methoxy)-7-(8-chloro-7-fluoronaphthalen-1-yl)-8-fluoropyrido[4,3-d]pyrimidin-4-yl)piperazin-2-yl)acetonitrile (40.0 mg, 41.9 μmol, 1.0 equiv) and 2-fluoroprop-2-enoic acid (11.3 mg, 126 μmol, 3 equiv) in ethyl acetate (1.0 mL) at 0° C. was added TEA (63.7 mg, 629 μmol, 87.6 μL, 15.0 equiv) and T3P (107 mg, 168 μmol, 99.8 μL, 50% in EtOAc, 4.0 equiv). The mixture was stirred at 0° C. for 0.25 h and then was diluted with water (5.0 mL) and extracted with ethyl acetate (3×8 mL). The combined organic layer was dried over anhydrous sodium sulfate and filtered. The filtrate was concentrated under reduced pressure to afford 2-((2S)-4-(2-((3-(((tert-butyldimethylsilyl)oxy)methyl)tetrahydro-1H-pyrrolizin-7a(5H)-yl)methoxy)-7-(8-chloro-7-fluoronaphthalen-1-yl)-8-fluoropyrido[4,3-d]pyrimidin-4-yl)-1-(2-fluoroacryloyl)piperazin-2-yl)acetonitrile (34.0 mg, crude) as a yellow solid. R$_f$=0.30 [petroleum ether/ethyl acetate/ethanol (2% NH₄OH), 4:3:1]. LCMS [ESI, M+1]: 80.

Example 216: To a solution of 2-((2S)-4-(2-((3-(((tert-butyldimethylsilyl)oxy)methyl)tetrahydro-1H-pyrrolizin-7a(5H)-yl)methoxy)-7-(8-chloro-7-fluoronaphthalen-1-yl)-8-fluoropyrido[4,3-d]pyrimidin-4-yl)-1-(2-fluoroacryloyl)piperazin-2-yl)acetonitrile (34.0 mg, 42.2 μmol, 1.0 equiv) in DMF (0.5 mL) was added CsF (19.2 mg, 126 umol, 3.0 equiv). The mixture was stirred at 25° C. for 10 h. Subsequently, TFA (770 mg, 6.75 mmol, 0.5 mL, 160 equiv) was added and the mixture was stirred at 25° C. for 0.5 hour. The mixture was diluted with water (4.0 mL) and the pH was adjusted to about 8 using solid NaHCO₃. The resulting mixture was extracted with ethyl acetate (3×5 mL). The combined organic layer was dried over anhydrous sodium sulfate and filtered. The filtrate was concentrated under reduced pressure. The residue was purified by prep-HPLC [column: Waters Xbridge C18 150*50 mm*10 μm; water (10 mM NH₄HCO₃); ACN: 24%-54%, 10 min] to afford 2-((2S)-4-(7-(8-chloro-7-fluoronaphthalen-1-yl)-8-fluoro-2-((3-(hydroxymethyl)tetrahydro-1H-pyrrolizin-7a(5H)-yl)methoxy)pyrido[4,3-d]pyrimidin-4-yl)-1-(2-fluoroacryloyl)piperazin-2-yl)acetonitrile (4.59 mg, 15% yield) as a white solid. R$_f$=0.05 [petroleum ether/ethyl acetate/ethanol (2% NH₄OH), 4:3:1]. ¹H NMR (400 MHz, CDCl₃) δ 9.05 (s, 1H), 8.01 (dd, J=2.4, 7.2 Hz, 1H), 7.90 (dd, J=5.6, 8.4 Hz, 1H), 7.67-7.56 (m, 2H), 7.40 (dt, J=2.0, 8.8 Hz, 1H), 5.58-5.38 (m, 1H), 5.29 (dd, J=3.2, 16.4 Hz, 1H), 5.01-4.74 (m, 1H), 4.73-4.54 (m, 1H), 4.52-4.44 (m, 1H), 4.43-4.13 (m, 3H), 3.93-3.69 (m, 4H), 3.55-3.35 (m, 1H), 3.15-2.98 (m, 2H), 2.94-2.81 (m, 1H), 2.79-2.69 (m, 1H), 2.32-2.18 (m, 1H), 2.08-1.87 (m, 5H), 1.67-1.56 (m, 3H). LCMS [ESI, M+1]: 692.

Example 217

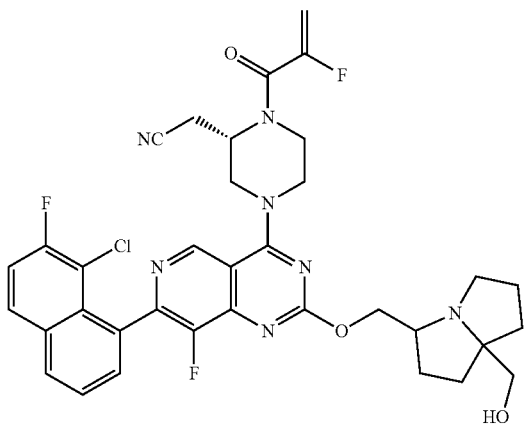 [SMILES: C=C(F)C(=O)N1CCN(c2nc(OCC3CCC4(CO)CCCN34)nc3c(F)c(-c4cccc5ccc(F)c(Cl)c45)ncc23)C[C@@H]1CC#N]

2-((2S)-4-(7-(8-chloro-7-fluoronaphthalen-1-yl)-8-fluoro-2-((7a-(hydroxymethyl)hexahydro-1H-pyrrolizin-3-yl)methoxy)pyrido[4,3-d]pyrimidin-4-yl)-1-(2-fluoroacryloyl)piperazin-2-yl)acetonitrile

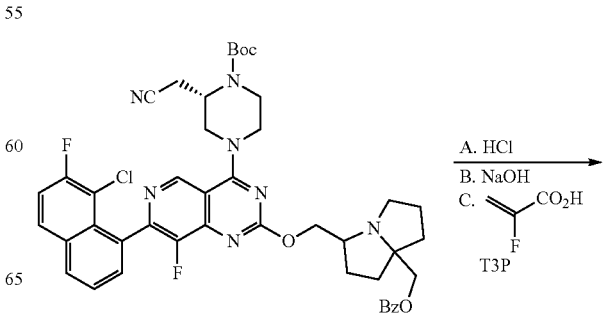

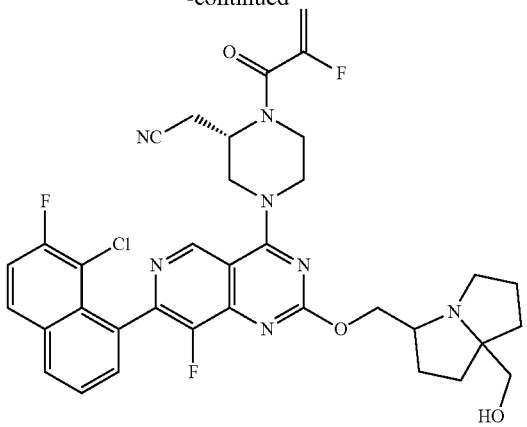

Example 217

Step A: To a solution of tert-butyl (2S)-4-(2-((7a-((benzoyloxy)methyl)hexahydro-1H-pyrrolizin-3-yl)methoxy)-7-(8-chloro-7-fluoronaphthalen-1-yl)-8-fluoropyrido[4,3-d]pyrimidin-4-yl)-2-(cyanomethyl)piperazine-1-carboxylate (93.0 mg, 113 μmol, 1.0 equiv) in CH₃CN (1.0 mL) at 0° C. was added HCl in dioxane (4 M, 1.0 mL, 35.4 equiv). The mixture was stirred at 0° C. for 0.5 hour and was then diluted with water (5.0 mL) and the pH was adjusted to 10 using solid Na₂CO₃. The resulting mixture was extracted with ethyl acetate (3×8 mL). The combined organic layer was dried over anhydrous sodium sulfate and filtered. The filtrate was concentrated under reduced pressure to afford (3-(((7-(8-chloro-7-fluoronaphthalen-1-yl)-4-((S)-3-(cyanomethyl)piperazin-1-yl)-8-fluoropyrido[4,3-d]pyrimidin-2-yl)oxy)methyl)tetrahydro-1H-pyrrolizin-7a(5H)-yl)methyl benzoate (75 mg, 92% yield) as a yellow solid. R$_f$=0.20 (dichloromethane/methanol, 10:1).

Step B: To a solution of (3-(((7-(8-chloro-7-fluoronaphthalen-1-yl)-4-((S)-3-(cyanomethyl)piperazin-1-yl)-8-fluoropyrido[4,3-d]pyrimidin-2-yl)oxy)methyl)tetrahydro-1H-pyrrolizin-7a(5H)-yl)methyl benzoate (50.0 mg, 69.0 μmol, 1.0 equiv) in CH₃CN (2.0 mL) was added NaOH (27.6 mg, 690 μmol, 10.0 equiv) in H₂O (2.0 mL). The mixture was stirred at 25° C. for 1 h and was then diluted with water (8.0 mL) and extracted with ethyl acetate (3×15 mL). The combined organic layer was dried over anhydrous sodium sulfate and filtered. The filtrate was concentrated under reduced pressure to afford 2-((2S)-4-(7-(8-chloro-7-fluoronaphthalen-1-yl)-8-fluoro-2-((7a-(hydroxymethyl)hexahydro-1H-pyrrolizin-3-yl)methoxy)pyrido[4,3-d]pyrimidin-4-yl)piperazin-2-yl)acetonitrile (50.0 mg, crude) as a yellow solid. LCMS [ESI, M+1]: 620.

Example 217: To a solution of 2-((2S)-4-(7-(8-chloro-7-fluoronaphthalen-1-yl)-8-fluoro-2-((7a-(hydroxymethyl)hexahydro-1H-pyrrolizin-3-yl)methoxy)pyrido[4,3-d]pyrimidin-4-yl)piperazin-2-yl)acetonitrile (50.0 mg, 80.6 μmol, 1.0 equiv) and 2-fluoroprop-2-enoic acid (21.8 mg, 242 μmol, 3.0 equiv) in ethyl acetate (1.0 mL) at 0° C. was added T3P (205 mg, 322 μmol, 192 μL, 50% in EtOAc, 4.0 equiv) and TEA (122 mg, 1.21 mmol, 168 μL, 15.0 equiv). The mixture was stirred at 0° C. for 10 min and was then diluted with water (10.0 mL) and extracted with ethyl acetate (3×15 mL). The combined organic layer was dried over anhydrous sodium sulfate and filtered. The filtrate was concentrated under reduced pressure to dryness. The residue was purified by prep-HPLC [column: Waters Xbridge C18 150*50 mm*10 μm; water (10 mM NH₄HCO₃); ACN: 24%-54%, 10 min] to afford 2-((2S)-4-(7-(8-chloro-7-fluoronaphthalen-1-yl)-8-fluoro-2-((7a-(hydroxymethyl)hexahydro-1H-pyrrolizin-3-yl)methoxy)pyrido[4,3-d]pyrimidin-4-yl)-1-(2-fluoroacryloyl)piperazin-2-yl)acetonitrile (5.90 mg, 9.9% yield) as a yellow solid. R$_f$=0.20 (dichloromethane/methanol, 10:1); ¹H NMR (400 MHz, CDCl₃): δ 9.08 (s, 1H), 8.07-7.98 (m, 1H), 7.90 (dd, J=5.6, 8.8 Hz, 1H), 7.71-7.57 (m, 2H), 7.41 (dt, J=2.0, 8.8 Hz, 1H), 5.61-5.39 (m, 1H), 5.29 (dd, J=3.6, 16.8 Hz, 1H), 5.02-4.81 (m, 1H), 4.79-4.65 (m, 2H), 4.62-4.41 (m, 2H), 4.34-3.94 (m, 2H), 3.90-3.54 (m, 3H), 3.47-3.34 (m, 2H), 3.20-3.00 (m, 2H), 2.94-2.78 (m, 2H), 2.06 (ddd, J=3.2, 6.4, 9.2 Hz, 2H), 1.85-1.57 (m, 6H). LCMS [ESI, M+1]: 694.

Example 218

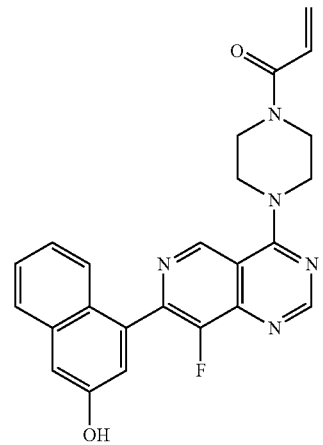 [SMILES: C=CC(=O)N1CCN(c2ncnc3c(F)c(-c4cc(O)cc5ccccc45)ncc23)CC1]

1-(4-(8-fluoro-7-(3-hydroxynaphthalen-1-yl)pyrido[4,3-d]pyrimidin-4-yl)piperazin-1-yl)prop-2-en-1-one

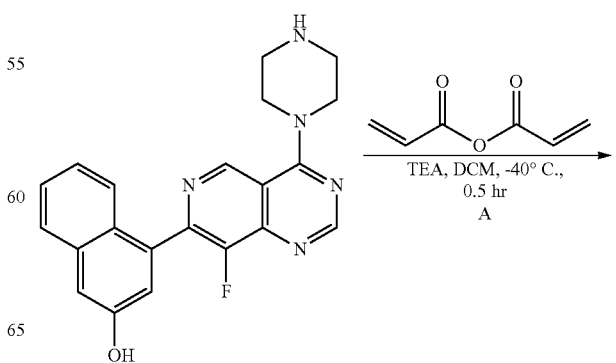

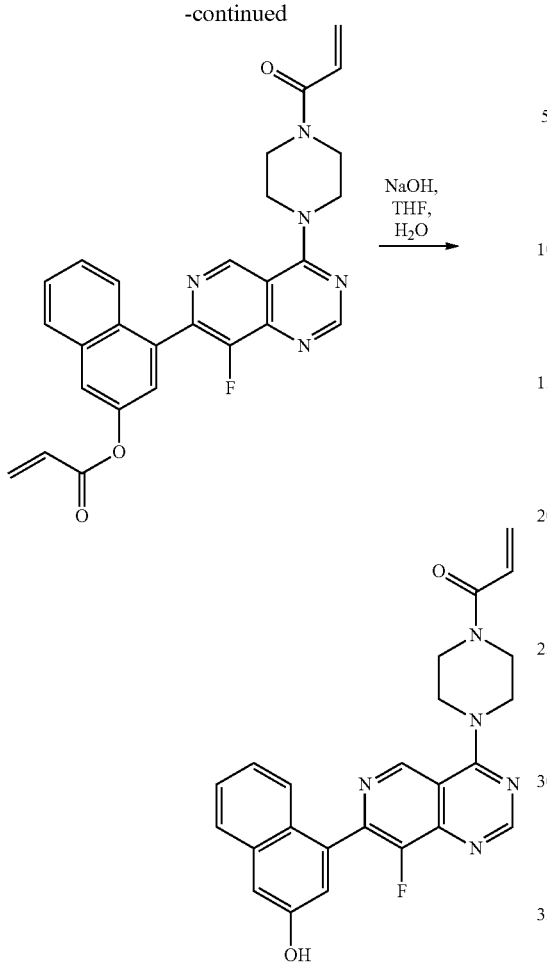

Example 218

NH₄HCO₃); ACN: 18%-48%,10 min] to give 1-(4-(8-fluoro-7-(3-hydroxynaphthalen-1-yl)pyrido[4,3-d]pyrimidin-4-yl)piperazin-1-yl)prop-2-en-1-one (6.50 mg, 15.1 µmol, 24% yield) as a white solid. $^1$H NMR (400 MHz, CDCl₃): δ 9.21 (s, 1H), 8.86 (s, 1H), 7.72 (d, J=8.4 Hz, 1H), 7.65 (d, J=8.4 Hz, 1H), 7.45-7.39 (m, 1H), 7.36 (d, J=2.0 Hz, 1H), 7.29 (d, J=2.8 Hz, 1H), 7.27-7.24 (m, 1H), 6.62-6.52 (m, 1H), 6.44-6.36 (m, 1H), 5.84-5.78 (m, 1H), 4.12-4.04 (m, 4H), 3.95-3.71 (m, 4H). LCMS [ESI, M+1]: 430.

Example 219

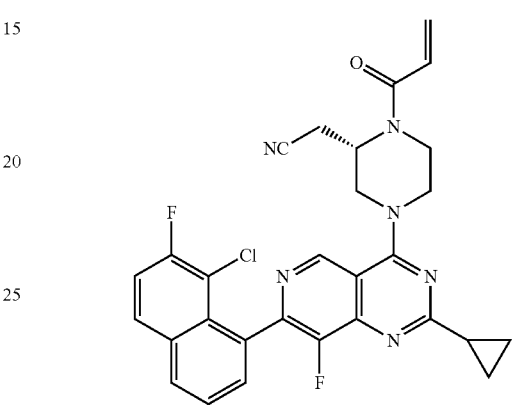

(S)-2-(1-acryloyl-4-(7-(8-chloro-7-fluoronaphthalen-1-yl)-2-cyclopropyl-8-fluoropyrido[4,3-d]pyrimidin-4-yl)piperazin-2-yl)acetonitrile Step A; To a solution of 4-(8-fluoro-4-(piperazin-1-yl)pyrido[4,3-d]pyrimidin-7-yl)naphthalen-2-ol (130 mg, 346 µmol, 1.0 equiv), 4 Å MS (200 mg) and TEA (140 mg, 1.39 mmol, 4.0 equiv) in DCM (10 mL) at −40° C. was added prop-2-enoyl prop-2-enoate (48.0 mg, 381 µmol, 1.1 equiv). The reaction mixture was stirred at −40° C. for 0.5 h and was quenched with water (10 mL) at −40° C., diluted with DCM (15 mL) and separated. The aqueous layer was extracted with DCM mL (15 mL×2). The combined organic layer was dried over anh Na₂SO₄ and concentrated under reduced pressure to dryness. The residue was purified by prep-HPLC [column: Waters Xbridge C18 150*50 mm*10 µm; water (10 mM NH₄HCO₃); ACN: 30%-60%, 10 min] to afford 4-(4-(4-acryloylpiperazin-1-yl)-8-fluoropyrido[4,3-d]pyrimidin-7-yl)naphthalen-2-yl acrylate (45 mg, 63.29 µmol, 18% yield) as a white solid. LCMS [ESI, M+1]: 484.

Example 218: To a solution of 4-(4-(4-acryloylpiperazin-1-yl)-8-fluoropyrido[4,3-d]pyrimidin-7-yl)naphthalen-2-yl acrylate (30.0 mg, 62.0 µmol, 1.0 equiv) in THF (5 mL) was added a solution of NaOH (4.96 mg, 124.10 µmol, 2.0 equiv) in H₂O (1 mL) at 25° C. The reaction mixture was stirred at 25° C. for 0.5 h and was then diluted with water (5 mL) at 25° C. The mixture was extracted with ethyl acetate (5 mL×2). The combined organic layer was dried over Na₂SO₄ and concentrated under reduced pressure to give a residue. The residue was purified by prep-HPLC [column: Waters Xbridge C18 150*50 mm*10 µm; water (10 mM

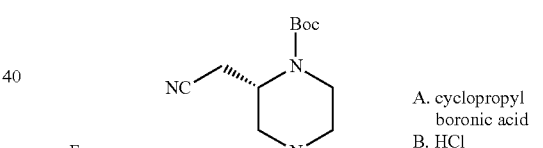

A. cyclopropyl boronic acid
B. HCl
C. acryloyl chloride

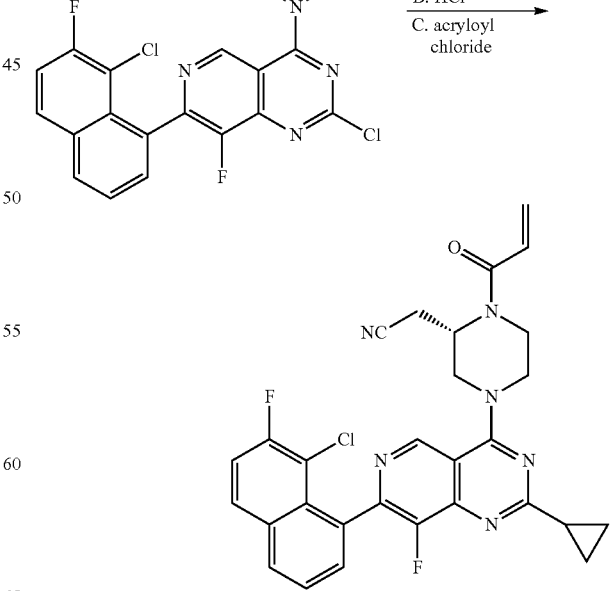

Example 219

Step A: To a solution of tert-butyl (S)-4-(2-chloro-7-(8-chloro-7-fluoronaphthalen-1-yl)-8-fluoropyrido[4,3-d]pyrimidin-4-yl)-2-(cyanomethyl)piperazine-1-carboxylate (300 mg, 512 μmol, 1.0 equiv) and cyclopropylboronic acid (264 mg, 3.07 mmol, 6.0 equiv) in dioxane (2 mL) was added K$_3$PO$_4$ (326 mg, 1.54 mmol, 3.0 equiv) and Pd(dppf)Cl$_2$ (56.2 mg, 76.9 μmol, 0.15 equiv). The mixture was stirred at 90° C. for 3 h and was concentrated under reduced pressure to provide a residue. The residue was diluted with H$_2$O (10 mL) and extracted with ethyl acetate (3×10 mL). The combined organic layer was washed with brine (50 mL), dried over anh Na$_2$SO$_4$, filtered and concentrated under vacuum. The residue was purified by reversed phase flash chromatography (C18, 0.1% FA in water, 0-40% ACN) to afford tert-butyl (S)-4-(7-(8-chloro-7-fluoronaphthalen-1-yl)-2-cyclopropyl-8-fluoropyrido[4,3-d]pyrimidin-4-yl)-2-(cyanomethyl)piperazine-1-carboxylate (180 mg, 55% yield) as a yellow solid. LCMS [ESI, M+1]: 591.1.

Step B: To a solution of tert-butyl (S)-4-(7-(8-chloro-7-fluoronaphthalen-1-yl)-2-cyclopropyl-8-fluoropyrido[4,3-d]pyrimidin-4-yl)-2-(cyanomethyl)piperazine-1-carboxylate (140 mg, 237 μmol, 1.0 equiv) in MeCN (0.5 mL) was added HCl in dioxane (4 M, 1.5 mL). The mixture was stirred at 0° C. for 1 h and was then diluted with H$_2$O (10 mL) and the pH was adjusted to 7 with solid NaHCO$_3$. The mixture was extracted with ethyl acetate (3×10 mL). The combined organic layer was washed with brine (20 mL), dried over anh Na$_2$SO$_4$, filtered and concentrated under reduced pressure to afford (S)-2-(4-(7-(8-chloro-7-fluoronaphthalen-1-yl)-2-cyclopropyl-8-fluoropyrido[4,3-d]pyrimidin-4-yl)piperazin-2-yl)acetonitrile (120 mg, crude) as a yellow solid. LCMS [ESI, M+1]: 491.1.

Example 219: To a solution of (S)-2-(4-(7-(8-chloro-7-fluoronaphthalen-1-yl)-2-cyclopropyl-8-fluoropyrido[4,3-d]pyrimidin-4-yl)piperazin-2-yl)acetonitrile (120 mg, 244 umol 1.0 eq) in DCM (2 mL) at −40° C. was added TEA (74.2 mg, 733 μmol, 102 μL, 3.0 equiv) and prop-2-enoyl chloride (44.2 mg, 489 μmol, 39.9 μL, 2 equiv). The mixture was stirred at −40° C. for 0.5 hour. Subsequently, the reaction mixture was concentrated under reduced pressure. The residue was diluted with H$_2$O (10 mL) and extracted with ethyl acetate (3×10 mL). The combined organic layer was washed with brine (50 mL), dried over anh Na$_2$SO$_4$, filtered and concentrated under reduced pressure to give a residue. The residue was purified by prep-HPLC [column: Waters Xbridge 150*25 mm*5 μm; water (10 mM NH$_4$HCO$_3$); ACN: 34%-64%, 10 min] to afford (S)-2-(1-acryloyl-4-(7-(8-chloro-7-fluoronaphthalen-1-yl)-2-cyclopropyl-8-fluoropyrido[4,3-d]pyrimidin-4-yl)piperazin-2-yl)acetonitrile (30.8 mg, 23% over two steps) as a white solid. $^1$H NMR (400 MHz, CDCl$_3$): δ 9.09 (d, J=0.8 Hz, 1H), 8.05-7.97 (m, 1H), 7.90 (dd, J=5.6, 8.8 Hz, 1H), 7.66-7.56 (m, 2H), 7.40 (td, J=2.0, 8.8 Hz, 1H), 6.71-6.52 (m, 1H), 6.50-6.36 (m, 1H), 5.86 (br d, J=10.0 Hz, 1H), 5.28-4.74 (m, 1H), 4.63-4.38 (m, 2H), 4.32-3.45 (m, 4H), 3.07-2.90 (m, 1H), 2.88-2.73 (m, 1H), 2.48-2.31 (m, 1H), 1.32-1.23 (m, 2H), 1.22-1.10 (m, 2H). LCMS [ESI, M+1]: 545.1.

Examples 220

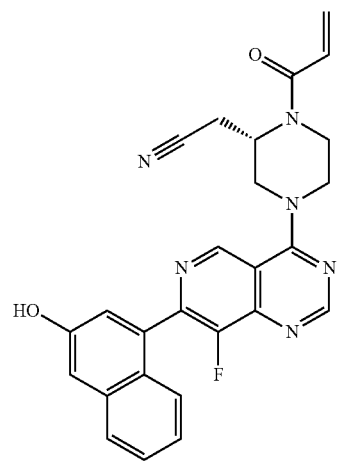

(S)-2-(1-acryloyl-4-(8-fluoro-7-(3-hydroxynaphthalen-1-yl)pyrido[4,3-d]pyrimidin-4-yl)piperazin-2-yl)acetonitrile

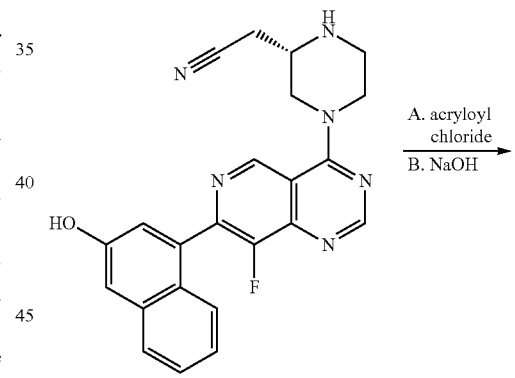

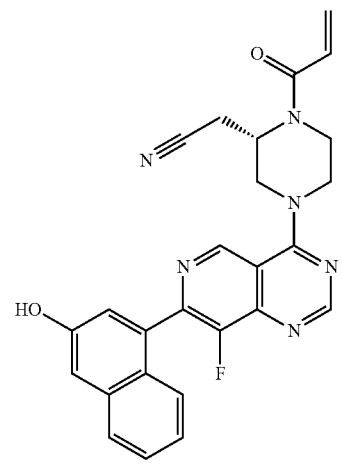

Example 220

Step A: To a solution of (S)-2-(4-(8-fluoro-7-(3-hydroxynaphthalen-1-yl)pyrido[4,3-d]pyrimidin-4-yl)piperazin-2-yl)acetonitrile (140 mg, 338 µmol, 1.0 equiv) and TEA (273 mg, 2.70 mmol, 376 µL, 8.0 equiv) in dichloromethane (2 mL) at 0° C. was added prop-2-enoyl chloride (61.2 mg, 676 µmol, 55.1 µL, 2.0 equiv). The mixture was stirred at 0° C. for 0.5 h and was diluted with water (5 mL) and extracted with ethyl acetate (3×5 mL). The combined organic layer was dried over anh $Na_2SO_4$, filtered and concentrated to afford (S)-4-(4-(4-acryloyl-3-(cyanomethyl)piperazin-1-yl)-8-fluoropyrido[4,3-d]pyrimidin-7-yl)naphthalen-2-yl acrylate (180 mg, crude) as a yellow solid. LCMS [ESI, M+1]: 523.2.

Example 220: To a solution of (S)-4-(4-(4-acryloyl-3-(cyanomethyl)piperazin-1-yl)-8-fluoropyrido[4,3-d]pyrimidin-7-yl)naphthalen-2-yl acrylate (180 mg, 345 µmol, 1.0 equiv) in THF (3 mL) was added a solution of NaOH (27.6 mg, 689 µmol, 2.0 equiv) in $H_2O$ (1 mL). The mixture was stirred at 20° C. for 0.5 h and was diluted with water (5 mL) and extracted with ethyl acetate (3×5 mL). The organic layer was dried over anh $Na_2SO_4$, filtered and concentrated. The residue was purified by prep-HPLC [column: Waters Xbridge C18 150*50 mm*1 µm; water (10 mM $NH_4HCO_3$); ACN: 20%-50%, 10 min] to afford (S)-2-(1-acryloyl-4-(8-fluoro-7-(3-hydroxynaphthalen-1-yl)pyrido[4,3-d]pyrimidin-4-yl)piperazin-2-yl)acetonitrile (35 mg, 22% yield over three steps) as an off-white solid. $^1$H NMR (400 MHz, $CDCl_3$): δ 9.20 (s, 1H), 8.91 (s, 1H), 7.71 (d, J=8.4 Hz, 1H), 7.65 (br d, J=8.0 Hz, 1H), 7.42 (t, J=7.2 Hz, 1H), 7.27-7.22 (m, 3H), 6.56-6.44 (m, 1H), 6.43-6.33 (m, 1H), 5.83 (br d, J=10.4 Hz, 1H), 5.12-4.71 (m, 1H), 4.62-3.21 (m, 6H), 3.03-2.82 (m, 1H), 2.68 (br dd, J=4.4, 16.8 Hz, 1H). LCMS [ESI, M+1]: 469.2.

Examples 221-245 were prepared following the teachings of the General Reaction Schemes, Examples 1-220 above and the Intermediates disclosed herein. Examples 221-245 are listed in Table 4.

TABLE 4

Examples 221-244

| Ex. # | Structure | Characterization Data |
|---|---|---|
| 221 | (E)-1-((1R,5R)-6-(7-(8-chloro-7-fluoronaphthalen-1-yl)-8-fluoropyrido[4,3-d]pyrimidin-4-yl)-2,6-diazabicyclo[3.2.0]heptan-2-yl)-4-fluorobut-2-en-1-one | LCMS [ESI, M + 1]: 510<br>$^1$H NMR (400 MHz, $CDCl_3$): δ 9.05 (s, 1H), 8.84 (s, 1H), 8.05-7.98 (m, 1H), 7.93-7.86 (m, 1H), 7.65-7.56 (m, 2H), 7.41 (t, J = 8.8 Hz, 1H), 7.13-6.98 (m, 1H), 6.60-6.34 (m, 1H), 5.73-5.49 (m, 1H), 5.23-4.91 (m, 4H), 4.52-4.15 (m, 2H), 4.02-3.69 (m, 1H), 2.85-2.62 (m, 1H), 2.38-2.26 (m, 1H) |

TABLE 4-continued

Examples 221-244

| Ex. # | Structure | Characterization Data |
|---|---|---|
| 222 | 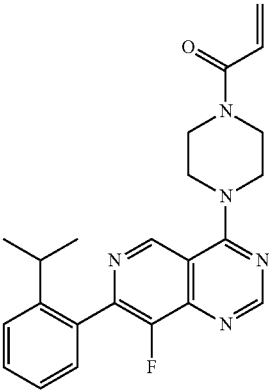<br>1-(4-(8-fluoro-7-(2-isopropylphenyl)pyrido[4,3-d]pyrimidin-4-yl)piperazin-1-yl)prop-2-en-1-one | LCMS [ESI, M + 1]: 406<br>$^1$H NMR (400 MHz, CDCl$_3$): δ 9.20 (s, 1H), 8.86 (s, 1H), 7.50-7.44 (m, 2H), 7.36-7.29 (m, 2H), 6.60 (dd, J = 10.4, 16.8 Hz, 1H), 6.43-6.35 (m, 1H), 5.80 (dd, J = 1.6, 10.4 Hz, 1H), 4.17-4.05 (m, 4H), 4.00-3.79 (m, 4H), 2.92 (td, J = 6.8, 13.6 Hz, 1H), 1.19 (d, J = 6.8 Hz, 6H) |
| 223 | 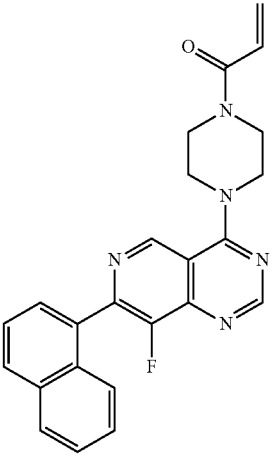<br>1-(4-(8-fluoro-7-(naphthalen-1-yl)pyrido[4,3-d]pyrimidin-4-yl)piperazin-1-yl)prop-2-en-1-one | LCMS [ESI, M + 1]: 414<br>$^1$H NMR (400 MHz, chloroform-d): δ = 9.30 (s, 1H), 8.91 (s, 1H), 8.06-7.92 (m, 2H), 7.81 (br d, J = 8.8 Hz, 1H), 7.76-7.69 (m, 1H), 7.67-7.60 (m, 1H), 7.58-7.44 (m, 2H), 6.7-6.55 (m, 1H), 6.44-6.38(m, 1H), 5.82 (dd, J = 1.8, 10.5 Hz, 1H), 4.24-4.08 (m, 4H), 4.05-3.81 (m, 4H) |
| 224 | 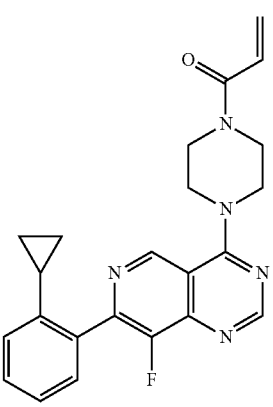<br>1-(4-(7-(2-cyclopropylphenyl)-8-fluoropyrido[4,3-d]pyrimidin-4-yl)piperazin-1-yl)prop-2-en-1-one | LCMS [ESI, M + 1]: 404<br>$^1$H NMR (400 MHz, CDCl$_3$): δ 9.22 (s, 1H), 8.86 (s, 1H), 7.45-7.37 (m, 2H), 7.34-7.28 (m, 1H), 7.09 (d, J = 7.6 Hz, 1H), 6.61 (dd, J = 10.4, 16.8 Hz, 1H), 6.39 (dd, J = 1.6, 16.8 Hz, 1H), 5.80 (dd, J = 1.6, 10.4 Hz, 1H), 4.10 (dd, J = 4.0, 6.4 Hz, 4H), 3.99-3.79 (m, 4H), 1.99-1.86 (m, 1H), 0.83-0.73 (m, 2H), 0.69-0.56 (m, 2H) |

TABLE 4-continued

Examples 221-244

| Ex. # | Structure | Characterization Data |
|---|---|---|
| 225 | 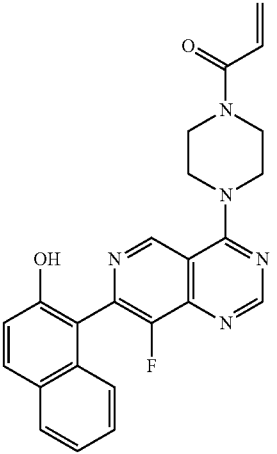<br>1-(4-(8-fluoro-7-(2-hydroxynaphthalen-1-yl)pyrido[4,3-d]pyrimidin-4-yl)piperazin-1-yl)prop-2-en-1-one | LCMS [ESI, M + 1]: 430<br>$^1$H NMR (400 MHz, CDCl$_3$): δ = 9.91 (s, 1H), 9.23 (s, 1H), 8.90 (s, 1H), 7.93 (d, J = 8.8 Hz, 1H), 7.85 (d, J = 7.6 Hz, 1H), 7.63 (t, J = 8.0 Hz, 1H), 7.49-7.35 (m, 2H), 7.31 (d, J = 7.2 Hz, 1H), 6.70-6.54 (m, 1H), 6.48-6.35 (m, 1H), 5.83 (dd, J = 1.6, 10.4 Hz, 1H), 4.29-3.81 (m, 8H) |
| 226 | 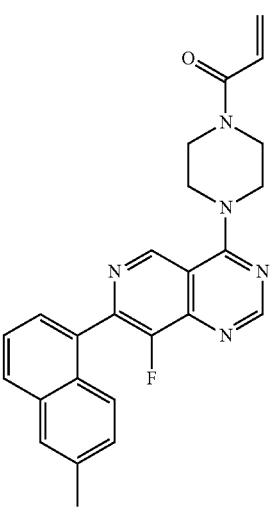<br>1-(4-(8-fluoro-7-(3-methylnaphthalen-1-yl)pyrido[4,3-d]pyrimidin-4-yl)piperazin-1-yl)prop-2-en-1-one | LCMS [ESI, M + 1]: 428<br>$^1$H NMR (400 MHz, CDCl$_3$): δ 9.30 (s, 1H), 8.90 (s, 1H), 7.90-7.83 (m, 1H), 7.78 (s, 1H), 7.75-7.70 (m, 1H), 7.56 (s, 1H), 7.53-7.46 (m, 1H), 7.45-7.36 (m, 1H), 6.66-6.56 (m, 1H), 6.47-6.38 (m, 1H), 5.83 (dd, J = 2.0, 10.4 Hz, 1H), 4.26-4.14 (m, 4H), 4.06-3.82 (m, 4H), 2.59 (s, 3H) |

TABLE 4-continued

Examples 221-244

| Ex. # | Structure | Characterization Data |
|---|---|---|
| 227 | 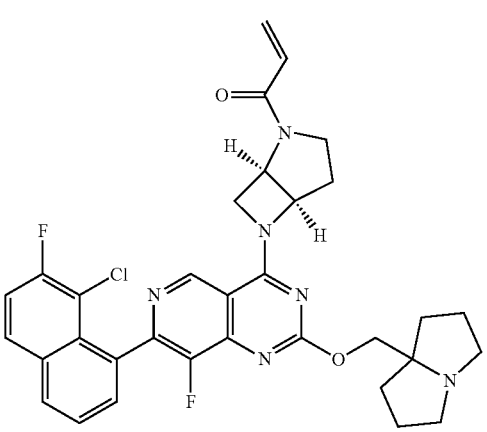<br>1-((1R,5R)-6-(7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)-2,6-diazabicyclo[3.2.0]heptan-2-yl)prop-2-en-1-one | LCMS [ESI, M + 1]: 617<br>$^1$H NMR (400 MHz, CDCl$_3$): δ 8.86 (s, 1H), 8.00-7.94 (m, 1H), 7.86 (dd, J = 5.6, 8.8 Hz, 1H), 7.62-7.53 (m, 2H), 7.37 (t, J = 8.8 Hz, 1H), 6.60-6.33 (m, 2H), 5.80 (br d, J = 10.0 Hz, 1H), 5.69-5.44 (m, 1H), 5.22-4.77 (m, 2H), 4.50-3.63 (m, 6H), 3.22-3.03 (m, 2H), 2.77-2.67 (m, 1H), 2.64 (td, J = 6.8, 10.0 Hz, 2H), 2.30-2.18 (m, 1H), 2.14-2.03 (m, 3H), 1.90-1.87 (m, 2H), 1.71-1.61 (m, 2H) |
| 228 | 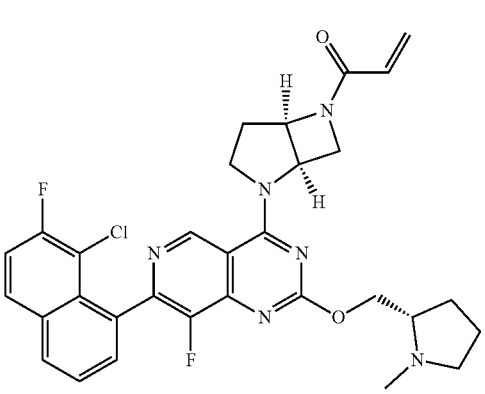<br>1-((1R,5R)-2-(7-(8-chloro-7-fluoronaphthalen-1-yl)-8-fluoro-2-(((S)-1-methylpyrrolidin-2-yl)methoxy)pyrido[4,3-d]pyrimidin-4-yl)-2,6-diazabicyclo[3.2.0]heptan-6-yl)prop-2-en-1-one | LCMS [ESI, M + 1]: 591<br>$^1$H NMR (400 MHz, CDCl$_3$): δ 9.34-8.92 (m, 1H), 8.00 (dd, J = 2.4, 7.2 Hz, 1H), 7.89 (dd, J = 5.6, 9.2 Hz, 1H), 7.68-7.56 (m, 2H), 7.40 (t, J = 8.8 Hz, 1H), 6.53-6.07 (m, 2H), 5.85-5.68 (m, 1H), 5.47-5.17 (m, 2H), 4.97-4.46 (m, 3H), 4.39 (ddd, J = 3.6, 6.4, 10.4 Hz, 1H), 4.29-3.87 (m, 2H), 3.18 (br t, J = 7.6 Hz, 1H), 2.88-2.69 (m, 2H), 2.55 (s, 3H), 2.42-2.31 (m, 1H), 2.29-2.17 (m, 1H), 2.14-2.08 (m, 1H), 1.89-1.75 (m, 3H) |

TABLE 4-continued

Examples 221-244

| Ex. # | Structure | Characterization Data |
|---|---|---|
| 229 | 2-((S)-4-(7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-1-(2-fluoroacryloyl)piperazin-2-yl)acetonitrile | LCMS [ESI, M + 1]: 680<br>¹H NMR (400 MHz, CDCl₃): δ 9.06 (s, 1H), 8.04-7.97 (m, 1H), 7.90 (ddd, J = 1.2, 5.2, 8.8 Hz, 1H), 7.65-7.57 (m, 2H), 7.44-7.37 (m, 1H), 5.58-5.40 (m, 1H), 5.38-5.19 (m, 2H), 4.99-4.73 (m, 1H), 4.62-4.41 (m, 2H), 4.38-4.12 (m, 3H), 4.09-3.89 (m, 1H), 3.87-3.58 (m, 2H), 3.33-3.22 (m, 2H), 3.21-3.14 (m, 1H), 3.07-2.94 (m, 2H), 2.91-2.80 (m, 1H), 2.33-2.25 (m, 1H), 2.24-2.10 (m, 2H), 2.02-1.86 (m, 3H) |
| 230 | (S)-N-(2-((7-(8-chloro-7-fluoronaphthalen-1-yl)-4-(3-(cyanomethyl)-4-(2-fluoroacryloyl)piperazin-1-yl)-8-fluoropyrido[4,3-d]pyrimidin-2-yl)oxy)ethyl)isobutyramide | LCMS [ESI, M + 1]: 652<br>¹H NMR (400 MHz, CDCl₃): δ 9.10 (s, 1H), 8.11-7.96 (m, 1H), 7.91 (dd, J = 5.6, 8.8 Hz, 1H), 7.66-7.58 (m, 2H), 7.42 (dt, J = 1.6, 8.8 Hz, 1H), 6.35-6.26 (m, 1H), 5.59-5.40 (m, 1H), 5.38-5.24 (m, 1H), 4.94-4.78 (m, 1H), 4.68-4.59 (m, 2H), 4.57 (br s, 2H), 4.41-3.94 (m, 2H), 3.93-3.64 (m, 4H), 3.12-2.82 (m, 2H), 2.37 (td, J = 6.8, 13.6 Hz, 1H), 1.14 (d, J = 6.8 Hz, 6H) |
| 231 | 1-((1R,5R)-2-(7-(8-chloro-7-fluoronaphthalen-1-yl)-8-fluoro-2-methylpyrido[4,3-d]pyrimidin-4-yl)-2,6-diazabicyclo[3.2.0]heptan-6-yl)prop-2-en-1-one | LCMS [ESI, M + 1]: 492<br>¹H NMR (400 MHz, CDCl₃): δ 9.20 (br d, J = 14.0 Hz, 1H), 8.01 (dd, J = 2.4, 7.2 Hz, 1H), 7.90 (dd, J = 5.6, 9.2 Hz, 1H), 7.67-7.56 (m, 2H), 7.40 (t, J = 8.8 Hz, 1H), 6.53-6.37 (m, 1H), 6.36-6.13 (m, 1H), 5.84-5.70 (m, 1H), 5.49-5.18 (m, 2H), 5.00-4.72 (m, 1H), 4.70-4.48 (m, 1H), 4.31-4.12 (m, 1H), 4.11-3.88 (m, 1H), 2.86-2.73 (m, 1H), 2.71 (s, 3H), 2.36-2.16 (m, 1H) |

TABLE 4-continued

Examples 221-244

| Ex. # | Structure | Characterization Data |
|---|---|---|
| 232 | 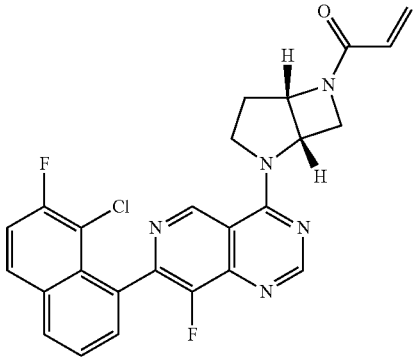<br>1-((1S,5S)-2-(7-(8-chloro-7-fluoronaphthalen-1-yl)-8-fluoropyrido[4,3-d]pyrimidin-4-yl)-2,6-diazabicyclo[3.2.0]heptan-6-yl)prop-2-en-1-one | LCMS [ESI, M + 1]: 478<br>$^1$H NMR (400 MHz, CDCl$_3$): δ 9.38-9.12 (m, 1H), 8.83 (s, 1H), 8.02 (dd, J = 2.0, 7.6 Hz, 1H), 7.91 (dd, J = 5.6, 9.2 Hz, 1H), 7.68-7.57 (m, 2H), 7.41 (t, J = 8.8 Hz, 1H), 6.57-6.11 (m, 2H), 5.87-5.69 (m, 1H), 5.51-5.18 (m, 2H), 5.00-4.49 (m, 2H), 4.37-3.86 (m, 2H), 2.91-2.48 (m, 1H), 2.38-2.19 (m, 1H) |
| 233 | 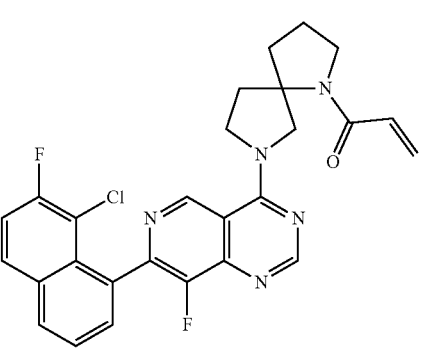<br>1-(7-(7-(8-chloro-7-fluoronaphthalen-1-yl)-8-fluoropyrido[4,3-d]pyrimidin-4-yl)-1,7-diazaspiro[4.4]nonan-1-yl)prop-2-en-1-one | LCMS [ESI, M + 1]: 506<br>$^1$H NMR (400 MHz, CDCl$_3$): δ 9.35 (d, J = 15.6 Hz, 1H), 8.79 (s, 1H), 8.04-7.94 (m, 1H), 7.92-7.82 (m, 1H), 7.68-7.57 (m, 2H), 7.44-7.35 (m, 1H), 6.56-6.45 (m, 1H), 6.42-6.33 (m, 1H), 5.77-5.67 (m, 1H), 5.08-4.63 (m, 1H), 4.48-4.24 (m, 1H), 4.19-3.92 (m, 1H), 3.91-3.62 (m, 3H), 3.54-3.35 (m, 1H), 2.23-1.82 (m, 5H) |
| 234 | 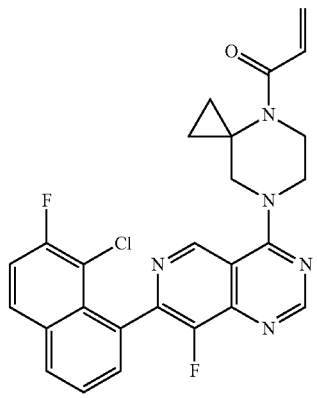<br>1-(7-(7-(8-chloro-7-fluoronaphthalen-1-yl)-8-fluoropyrido[4,3-d]pyrimidin-4-yl)-4,7-diazaspiro[2.5]octan-4-yl)prop-2-en-1-one | LCMS [ESI, M + 1]: 492<br>$^1$H NMR (400 MHz, CDCl$_3$): δ 9.11 (s, 1H), 8.85 (s, 1H), 8.03-8.01 (dd, J = 1.6, 7.2 Hz, 1H), 7.93-7.89 (dd, J = 5.6, 9.2 Hz, 1H), 7.67-7.59 (m, 2H), 7.44-7.39 (t, J = 8.4 Hz, 1H), 6.98-6.68 (m, 1H), 6.47-6.42 (dd, J = 1.6, 16.8 Hz, 1H), 5.83-5.77 (m, 1H), 4.20 (br s, 2H), 4.10-3.97 (m, 4H), 1.15 (br s, 4H) |

TABLE 4-continued

Examples 221-244

| Ex. # | Structure | Characterization Data |
|---|---|---|
| 235 | 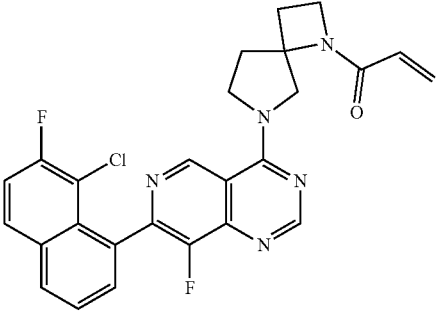<br>1-(6-(7-(8-chloro-7-fluoronaphthalen-1-yl)-8-fluoropyrido[4,3-d]pyrimidin-4-yl)-1,6-diazaspiro[3.4]octan-1-yl)prop-2-en-1-one | LCMS [ESI, M + 1]: 492<br>$^{1}$H NMR (400 MHz, CDCl$_3$): δ 9.40-9.37 (br d, J = 9.2 Hz, 1H), 8.80-8.79 (d, J = 2.8 Hz, 1H), 8.04-7.99 (dd, J = 2.0, 7.6 Hz, 1H), 7.91-7.87 (dd, J = 5.6, 9.2 Hz, 1H), 7.69-7.57 (m, 2H), 7.42-7.38 (dt, J = 1.6, 8.4 Hz, 1H), 6.44-6.33 (m, 1H), 6.25-6.11 (m, 1H), 5.76-5.67 (m, 1H), 4.87-4.68 (m, 1H), 4.67-4.43 (m, 1H), 4.26-4.19 (m, 2H), 4.19-4.03 (m, 2H), 3.09-2.93 (m, 1H), 2.60-2.39 (m, 2H), 2.38-2.19 (m, 1H) |
| 236 | 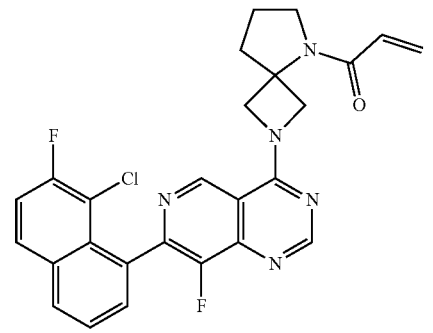<br>1-(2-(7-(8-chloro-7-fluoronaphthalen-1-yl)-8-fluoropyrido[4,3-d]pyrimidin-4-yl)-2,5-diazaspiro[3.4]octan-5-yl)prop-2-en-1-one | LCMS [ESI, M + 1]: 492<br>$^{1}$H NMR (400 MHz, CDCl$_3$): δ 9.05 (s, 1H), 8.79 (s, 1H), 8.05-7.95 (m, 1H), 7.89 (dd, J = 5.6, 8.8 Hz, 1H), 7.67-7.55 (m, 2H), 7.45-7.35 (m, 1H), 6.55-6.36 (m, 2H), 5.82-5.72 (m, 1H), 5.70-5.55 (m, 1H), 5.36-5.15 (m, 1H), 4.67-4.43 (m, 1H), 4.40-4.19 (m, 1H), 3.78-3.65 (m, 2H), 2.48-2.34 (m, 2H), 2.09-1.95 (m, 2H) |
| 237 | 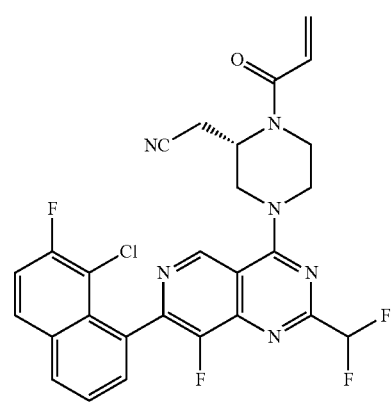<br>(S)-2-(1-acryloyl-4-(7-(8-chloro-7-fluoronaphthalen-1-yl)-2-(difluoromethyl)-8-fluoropyrido[4,3-d]pyrimidin-4-yl)piperazin-2-yl)acetonitrile | LCMS [ESI, M + 1]: 555<br>$^{1}$H NMR (400 MHz, CDCl$_3$): δ 9.27 (d, J = 3.6 Hz, 1H), 8.07-8.01 (m, 1H), 7.92 (dd, J = 4.8, 8.4 Hz, 1H), 7.66-7.60 (m, 2H), 7.43 (td, J = 2.0, 8.8 Hz, 1H), 7.39-7.39 (m, 1H), 6.63-6.40 (m, 2H), 5.88 (d, J = 10.4 Hz, 1H), 5.11-4.98 (m, 1H), 4.72-4.66 (m, 1H), 4.64-4.51 (m, 1H), 4.40-3.73 (m, 4H), 3.12-2.94 (m, 1H), 2.90-2.72 (m, 1H) |

US 11,548,888 B2

TABLE 4-continued

Examples 221-244

| Ex. # | Structure | Characterization Data |
|---|---|---|
| 238 | 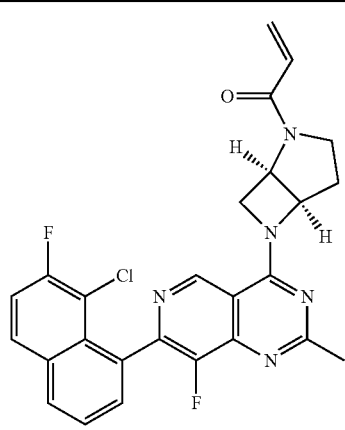<br>1-((1R,5R)-6-(7-(8-chloro-7-fluoronaphthalen-1-yl)-8-fluoro-2-methylpyrido[4,3-d]pyrimidin-4-yl)-2,6-diazabicyclo[3.2.0]heptan-2-yl)prop-2-en-1-one | LCMS [ESI, M + 1]: 492<br>$^1$H NMR (400 MHz, CDCl$_3$): δ 9.01-8.94 (m, 1H), 8.02-7.96 (m, 1H), 7.88 (dd, J = 5.2, 9.2 Hz, 1H), 7.63-7.54 (m, 2H), 7.39 (t, J = 8.8 Hz, 1H), 6.62-6.39 (m, 2H), 5.81 (br d, J = 10.4 Hz, 1H), 5.70-5.47 (m, 1H), 5.13 (br d, J = 2.8 Hz, 1H), 4.99-4.79 (m, 1H), 4.49-4.35 (m, 1H), 4.22-4.11 (m, 1H), 4.00-3.68 (m, 1H), 2.70 (s, 4H), 2.32-2.08 (m, 1H) |
| 239 | 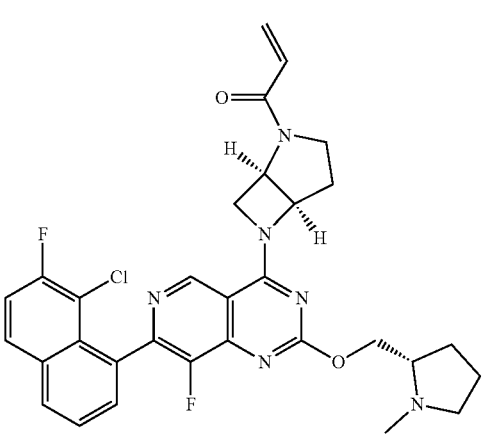<br>1-((1R,5R)-6-(7-(8-chloro-7-fluoronaphthalen-1-yl)-8-fluoro-2-(((S)-1-methylpyrrolidin-2-yl)methoxy)pyrido[4,3-d]pyrimidin-4-yl)-2,6-diazabicyclo[3.2.0]heptan-2-yl)prop-2-en-1-one | LCMS [ESI, M + 1]: 591<br>$^1$H NMR (400 MHz, CDCl$_3$): δ 8.95-8.83 (m, 1H), 8.03-7.95 (m, 1H), 7.88 (dd, J = 5.6, 8.8 Hz, 1H), 7.63-7.55 (m, 2H), 7.39 (t, J = 8.8 Hz, 1H), 6.62-6.34 (m, 2H), 5.81 (br d, J = 10.4 Hz, 1H), 5.70-5.49 (m, 1H), 5.19-4.74 (m, 2H), 4.63 (dd, J = 4.8, 10.8 Hz, 1H), 4.50-4.10 (m, 3H), 4.00-3.67 (m, 1H), 3.15 (br t, J = 7.6 Hz, 1H), 2.84-2.59 (m, 2H), 2.53 (s, 3H), 2.39-2.26 (m, 2H), 1.91-1.71 (m, 4H) |

TABLE 4-continued

Examples 221-244

| Ex. # | Structure | Characterization Data |
|---|---|---|
| 240 | 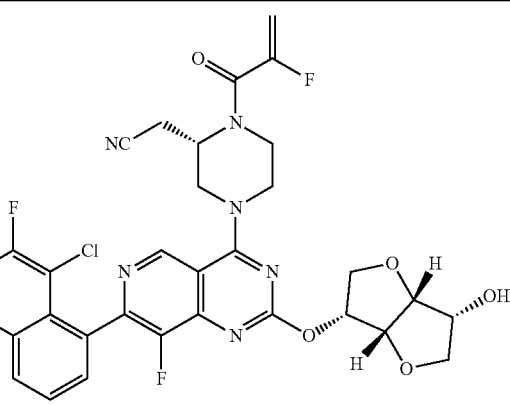<br>2-((S)-4-(7-(8-chloro-7-fluoronaphthalen-1-yl)-8-fluoro-2-(((3R,3aR,6R,6aR)-6-hydroxyhexahydrofuro[3,2-b]furan-3-yl)oxy)pyrido[4,3-d]pyrimidin-4-yl)-1-(2-fluoroacryloyl)piperazin-2-yl)acetonitrile | LCMS [ESI, M + 1]: 667<br>$^1$H NMR (400 MHz, CDCl$_3$): δ 9.09 (s, 1H), 8.10-7.96 (m, 1H), 7.91 (ddd, J = 1.2, 5.6, 9.2 Hz, 1H), 7.66-7.57 (m, 2H), 7.41 (dt, J = 2.0, 8.8 Hz, 1H), 5.67-5.58 (m, 1H), 5.57-5.41 (m, 1H), 5.29 (dd, J = 3.2, 16.8 Hz, 1H), 5.06-4.98 (m, 1H), 4.96-4.74 (m, 1H), 4.60 (td, J = 5.2, 7.2 Hz, 1H), 4.54-4.41 (m, 2H), 4.33 (ddd, J = 6.8, 9.2, 12.8 Hz, 3H), 4.15-3.94 (m, 3H), 3.91-3.62 (m, 3H), 3.11-2.95 (m, 1H), 2.94-2.78 (m, 1H), 2.69 (br d, J = 8.0 Hz, 1H) |
| 241 | 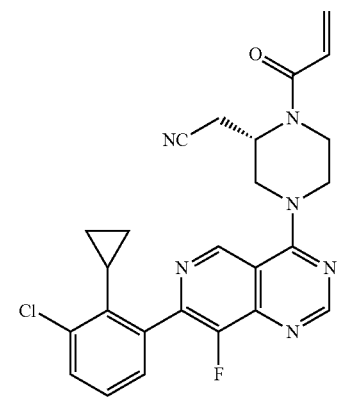<br>(S)-2-(1-acryloyl-4-(7-(3-chloro-2-cyclopropylphenyl)-8-fluoropyrido[4,3-d]pyrimidin-4-yl)piperazin-2-yl)acetonitrile | LCMS [ESI, M + 1]: 477<br>$^1$H NMR (400 MHz, CDCl$_3$): δ 9.23 (s, 1H), 8.90 (s, 1H), 7.51 (d, J = 8.0 Hz, 1H), 7.45-7.37 (m, 1H), 7.35-7.28 (m, 1H), 6.59 (br dd, J = 10.4, 16.0 Hz, 1H), 6.45-6.37 (m, 1H), 5.86 (br d, J = 10.4 Hz, 1H), 5.14-4.92 (m, 1H), 4.62-4.45 (m, 2H), 4.23-3.70 (m, 4H), 3.05-2.71 (m, 2H), 2.19-1.96 (m, 1H), 0.71 (br d, J = 7.6 Hz, 2H), 0.13 (br s, 2H) |
| 242 | 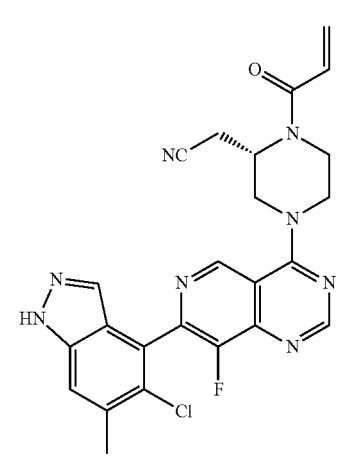<br>2-((2S)-1-acryloyl-4-(7-(5-chloro-6-methyl-1H-indazol-4-yl)-8-fluoropyrido[4,3-d]pyrimidin-4-yl)piperazin-2-yl)acetonitrile | LCMS [ESI, M + 1]: 491<br>$^1$H NMR (400 MHz, CDCl$_3$): δ 10.38-10.09 (m, 1H), 9.33 (s, 1H), 8.94 (s, 1H), 7.75 (d, J = 4.0 Hz, 1H), 7.54 (s, 1H), 6.69-6.53 (m, 1H), 6.50-6.39 (m, 1H), 5.87 (br d, J = 10.0 Hz, 1H), 5.21-4.44 (m, 3H), 4.32-3.72 (m, 4H), 3.12-2.70 (m, 2H), 2.67-2.53 (m, 3H) |

TABLE 4-continued

Examples 221-244

| Ex. # | Structure | Characterization Data |
|---|---|---|
| 243 | 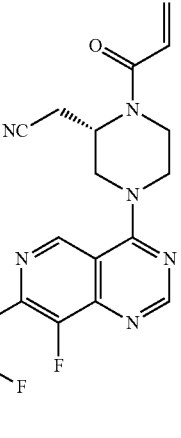<br>2-((2S)-1-acryloyl-4-(7-(2-amino-3,5-dichloro-6-fluorophenyl)-8-fluoropyrido[4,3-d]pyrimidin-4-yl)piperazin-2-yl)acetonitrile | LCMS [ESI, M + 1]: 504<br>$^1$H NMR (400 MHz, CDCl$_3$): δ 9.25 (s, 1H), 8.92 (s, 1H), 7.46 (d, J = 7.2 Hz, 1H), 6.66-6.53 (m, 1H), 6.50-6.38 (m, 1H), 5.92-5.83 (m, 1H), 4.95 (br s, 3H), 4.65-4.46 (m, 2H), 4.25-3.96 (m, 2H), 3.95-3.71 (m, 2H), 3.03-2.85 (m, 1H), 2.81-2.65 (m, 1H) |
| 244 | 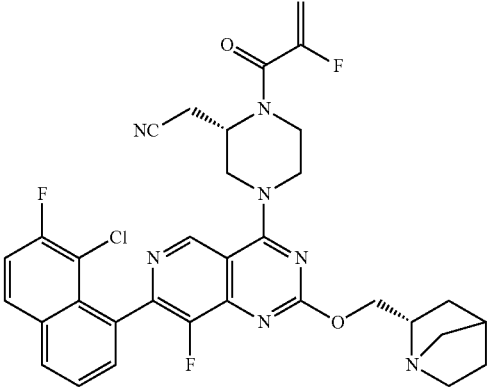<br>2-((2S)-4-(2-(((2S)-1-azabicyclo[2.2.1]heptan-2-yl)methoxy)-7-(8-chloro-7-fluoronaphthalen-1-yl)-8-fluoropyrido[4,3-d]pyrimidin-4-yl)-1-(2-fluoroacryloyl)piperazin-2-yl)acetonitrile | LCMS [ESI, M + 1]: 648<br>$^1$H NMR (400 MHz, CDCl$_3$): δ 9.07 (s, 1H), 8.04-7.97 (m, 1H), 7.90 (dd, J = 5.6, 8.8 Hz, 1H), 7.67-7.56 (m, 2H), 7.41 (dt, J = 2.0, 8.8 Hz, 1H), 5.57-5.38 (m, 1H), 5.28 (dd, J = 3.6, 16.8 Hz, 1H), 4.96-4.77 (m, 1H), 4.76-4.58 (m, 2H), 4.57-4.41 (m, 2H), 4.34-3.96 (m, 2H), 3.93-3.65 (m, 3H), 3.33-3.15 (m, 1H), 3.06 (br dd, J = 7.2, 17.2 Hz, 1H), 2.96-2.81 (m, 2H), 2.81-2.73 (m, 1H), 2.72-2.61 (m, 2H), 2.04-1.88 (m, 1H), 1.80-1.64 (m, 1H), 1.31-1.13 (m, 1H), 0.90 (ddd, J = 2.8, 6.0, 8.8 Hz, 1H) |

Example 245

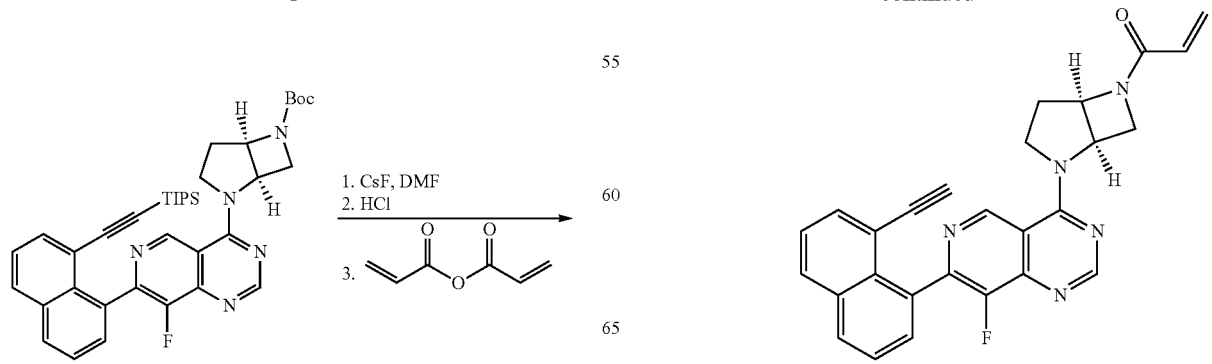

713

To a mixture of tert-butyl (1R,5R)-2-(8-fluoro-7-(8-((triisopropylsilyl)ethynyl)naphthalen-1-yl)pyrido[4,3-d]pyrimidin-4-yl)-2,6-diazabicyclo[3.2.0]heptane-6-carboxylate (180 mg, 276 µmol, 1.0 equiv) in DMF (3.0 mL) was added CsF (419 mg, 2.76 mmol, 10.0 equiv). The mixture was stirred at 25° C. for 30 min and was then diluted with water (5.0 mL). The aqueous phase was extracted with ethyl acetate (3×10 mL). The combined organic phase was washed with brine (15 mL), dried with anhydrous Na₂SO₄, filtered and concentrated at reduced pressure. The crude product was purified by reversed-phase flash [water (0.1% FA)/acetonitrile] to afford tert-butyl (1R,5R)-2-(7-(8-ethynylnaphthalen-1-yl)-8-fluoropyrido[4,3-d]pyrimidin-4-yl)-2,6-diazabicyclo[3.2.0]heptane-6-carboxylate (90 mg, 65% yield) as a yellow solid. LCMS [ESI, M+1]: 496.

To a mixture of tert-butyl (1R,5R)-2-(7-(8-ethynylnaphthalen-1-yl)-8-fluoropyrido[4,3-d]pyrimidin-4-yl)-2,6-diazabicyclo[3.2.0]heptane-6-carboxylate (80 mg, 161 µmol, 1.0 equiv) in MeCN (4.0 mL) was added HCl (4 M in dioxane, 8.00 mL, 198 equiv). The mixture was stirred at 0° C. for 30 min and was diluted with satd aq Na₂CO₃ (0.5 mL) and further neutralized with solid sodium bicarbonate. The resultant mixture was purified directly by reversed-phase flash chromatography [water (0.1% FA)/acetonitrile] to provide 4-((1R,5R)-2,6-diazabicyclo[3.2.0]heptan-2-yl)-7-(8-ethynylnaphthalen-1-yl)-8-fluoropyrido[4,3-d]pyrimidine (40 mg, 61% yield) as a yellow solid. LCMS [ESI, M+1]: 396.

To a mixture of 4-((1R,5R)-2,6-diazabicyclo[3.2.0]heptan-2-yl)-7-(8-ethynylnaphthalen-1-yl)-8-fluoropyrido[4,3-d]pyrimidine (30 mg, 75.9 µmol, 1.0 equiv) in DCM (1.5 mL) at −40° C. was added Et₃N (61.4 mg, 607 µmol, 84.5 µL, 8.0 equiv) followed by prop-2-enoyl prop-2-enoate (28.7 mg, 228 µmol, 3.0 equiv) in DCM (0.5 mL). The solution was stirred at this temperature for 30 min prior to being diluted with water (3.0 mL). The aqueous phase was extracted with DCM (3×5 mL). The combined organic phase was washed with brine (5.0 mL), dried over anhydrous Na₂SO₄, filtered and concentrated at reduced pressure. The residue was purified by prep-HPLC [Waters Xbridge 150× 25 mm×5 µm; A: water (0.05% ammonium hydroxide), B: ACN, B %: 22%-52%] to afford 1-((1R,5R)-2-(7-(8-ethynylnaphthalen-1-yl)-8-fluoropyrido[4,3-d]pyrimidin-4-yl)-2,6-diazabicyclo[3.2.0]heptan-6-yl)prop-2-en-1-one (13 mg, 38% yield) as a yellow solid. ¹H NMR (400 MHz, CDCl₃): δ 9.38-9.16 (m, 1H), 8.85 (s, 1H), 8.08-7.98 (m, 2H), 7.79 (d, J=7.2 Hz, 1H), 7.69-7.61 (m, 2H), 7.53-7.43 (m, 1H), 6.59-6.39 (m, 1H), 6.38-6.15 (m, 1H), 5.88-5.72 (m, 1H), 5.44-5.12 (m, 2H), 4.94-4.53 (m, 2H), 4.39-4.13 (m, 1H), 4.13-3.91 (m, 1H), 2.91-2.57 (m, 1H), 2.53 (d, J=6.4 Hz, 1H), 2.36-2.21 (m, 1H). LCMS [ESI, M+1]: 450.

Example 246

714

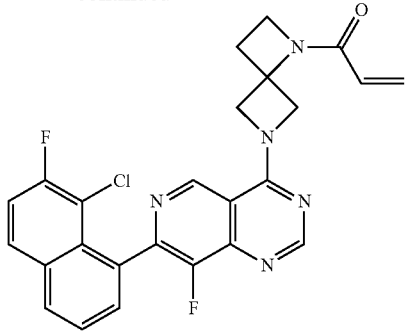

To a solution of 1-(6-(7-(8-chloro-7-fluoronaphthalen-1-yl)-8-fluoropyrido[4,3-d]pyrimidin-4-yl)-1,6-diazaspiro[3.3]heptan-1-yl)-2,2,2-trifluoroethan-1-one (50 mg, 96.2 µmol, 1.0 equiv) in MeOH (2.5 mL) was added Cs₂CO₃ (31.3 mg, 96.2 µmol, 1.0 equiv) and water (0.063 mL) at 25° C. The mixture was stirred at 40° C. for 2.5 h and was subsequently concentrated at reduced pressure. The residue was taken up in ethyl acetate and was dried over anh Na₂SO₄, filtered and concentrated at reduced pressure to provide 7-(8-chloro-7-fluoronaphthalen-1-yl)-8-fluoro-4-(1,6-diazaspiro[3.3]heptan-6-yl)pyrido[4,3-d]pyrimidine (55 mg, crude) as a yellow solid. LCMS [ESI, M+1]: 424.

To a solution of 7-(8-chloro-7-fluoronaphthalen-1-yl)-8-fluoro-4-(1,6-diazaspiro[3.3]heptan-6-yl)pyrido[4,3-d]pyrimidine (55 mg, 130 µmol, 1.0 equiv) in DCM (1.0 mL) at −40° C. was added TEA (39.4 mg, 390 µmol, 54.2 µL, 3.0 equiv) followed by the dropwise addition of a solution of prop-2-enoyl prop-2-enoate (24.5 mg, 195 µmol, 1.5 equiv) in dichloromethane (0.2 mL). Stirring was continued at this temperature for 30 min prior to the addition of methanol (0.2 mL) and water (2.0 mL). The aqueous phase was extracted with ethyl acetate (3×2.0 mL). The combined organic layers were dried over anh Na₂SO₄, filtered and concentrated at reduced pressure. The resultant residue was purified by prep-HPLC [Waters Xbridge C18 150 mm×50 mm×10 µm, A: water (10 mM NH₄HCO₃), B: ACN; B %: 30%-60%). The desired fractions were lyophilized to provide 1-(6-(7-(8-chloro-7-fluoronaphthalen-1-yl)-8-fluoropyrido[4,3-d]pyrimidin-4-yl)-1,6-diazaspiro[3.3]heptan-1-yl)prop-2-en-1-one (12.6 mg, 18% over two steps) as a yellow solid. LCMS [ESI, M+1]: 478. ¹H NMR (400 MHz, CDCl₃): δ 9.04 (s, 1H), 8.80 (s, 1H), 8.01-7.99 (dd, J=2.8, 6.4 Hz, 1H), 7.87-7.91 (dd, J=5.6, 9.2 Hz, 1H), 7.63-7.59 (m, 2H), 7.42-7.40 (t, J=8.8 Hz, 1H), 6.45-6.40 (dd, J=1.6, 16.8 Hz, 1H), 6.23-6.15 (m, 1H), 5.78-5.75 (dd, J=1.6, 10.4 Hz, 1H), 5.70-5.14 (m, 2H), 4.88-4.46 (m, 2H), 4.26-4.22 (t, J=7.2 Hz, 2H), 2.74-2.70 (t, J=7.6 Hz, 2H).

Example 247

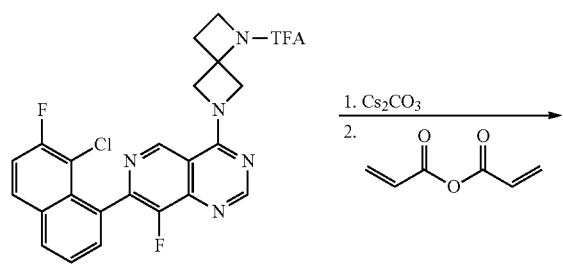

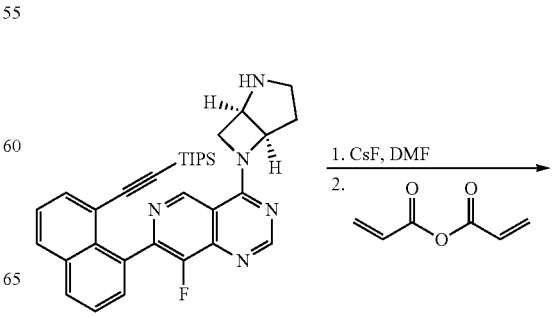

-continued

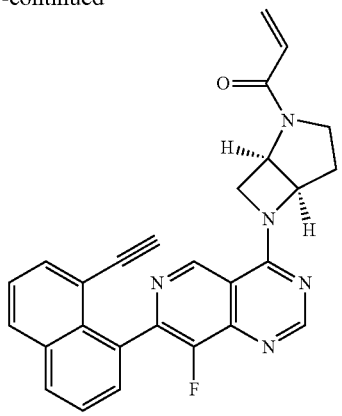

To a solution of 4-((1R,5R)-2,6-diazabicyclo[3.2.0]heptan-6-yl)-8-fluoro-7-(8-(((triisopropylsilyl)ethynyl)naphthalen-1-yl)pyrido[4,3-d]pyrimidine (430 mg, 779 μmol, 1.0 equiv) in DMF (20.0 mL) was added CsF (1.18 g, 7.79 mmol, 10 equiv) at 25° C. The mixture was stirred at 25° C. for 1 h prior to being diluted with water (20 mL) and extracted with DCM (3×30 mL). The combined organic layer was separated, dried over anh sodium sulfate, filtered and concentrated at reduced pressure to afford 4-((1R,5R)-2,6-diazabicyclo[3.2.0]heptan-6-yl)-7-(8-ethynylnaphthalen-1-yl)-8-fluoropyrido[4,3-d]pyrimidine (417 mg, crude) as a yellow solid. LCMS [ESI, M+1]: 396.

To a solution of 4-((1R,5R)-2,6-diazabicyclo[3.2.0]heptan-6-yl)-7-(8-ethynylnaphthalen-1-yl)-8-fluoropyrido[4,3-d]pyrimidine (417 mg, 1.05 mmol, 1.0 equiv) in DCM (40.0 mL) at −40° C. was added DIEA (678 mg, 5.25 mmol, 914 μL, 5.0 equiv) and prop-2-enoyl prop-2-enoate (265 mg, 2.10 mmol, 2.0 equiv). The mixture was stirred for 30 min at this temperature prior to being diluted with water (30 mL). The organic layer was separated, dried over anh sodium sulfate, filtered and concentrated at reduced pressure. The resultant residue was purified by prep-HPLC (Waters Xbridge 150 mm×25 mm×5 μm, A: water (0.05% ammonium hydroxide), B: ACN, B %: 24%-54%) to afford 1-((1R,5R)-6-(7-(8-ethynylnaphthalen-1-yl)-8-fluoropyrido[4,3-d]pyrimidin-4-yl)-2,6-diazabicyclo[3.2.0]heptan-2-yl)prop-2-en-1-one (75.9 mg, 22% over two steps) as a yellow solid. LCMS [ESI, M+1]: 450. $^1$H NMR (400 MHz, CDCl$_3$): δ 9.09-9.00 (m, 1H), 8.82-8.74 (m, 1H), 8.00 (dd, J=8.0, 16.4 Hz, 2H), 7.80-7.71 (m, 1H), 7.66-7.55 (m, 2H), 7.48 (t, J=7.6 Hz, 1H), 6.62-6.33 (m, 2H), 5.86-5.77 (m, 1H), 5.75-5.51 (m, 1H), 5.26-4.88 (m, 2H), 4.57-4.10 (m, 2H), 4.06-3.70 (m, 1H), 2.86-2.57 (m, 2H), 2.41-2.11 (m, 1H).

Following teachings of the General Reaction Schemes and Examples 1-247, the following compounds listed in Table 5 were prepared:

TABLE 5

Compounds 248-287

| Ex. # | Structure | Data |
|---|---|---|
| 248 | 1-((1R,5R)-6-(2-chloro-7-(8-chloro-7-fluoronaphthalen-1-yl)-8-fluoropyrido[4,3-d]pyrimidin-4-yl)-2,6-diazabicyclo[3.2.0]heptan-2-yl)prop-2-en-1-one | LCMS [ESI, M + 1]: 508.4<br>$^1$H NMR (400 MHz, CDCl$_3$): δ 8.99 (s, 1H), 8.01 (dd, J = 2.4, 7.2 Hz, 1H), 7.90 (dd, J = 5.6, 9.2 Hz, 1H), 7.69-7.54 (m, 2H), 7.41 (t, J = 8.8 Hz, 1H), 6.67-6.32 (m, 2H), 5.94-5.77 (m, 1H), 5.74-5.45 (m, 1H), 5.32-4.80 (m, 2H), 4.60-4.35 (m, 1H), 4.29-4.09 (m, 1H), 4.06-3.67 (m, 1H), 2.96-2.59 (m, 1H), 2.46-2.11 (m, 1H) |

TABLE 5-continued

Compounds 248-287

| Ex. # | Structure | Data |
|---|---|---|
| 249 | 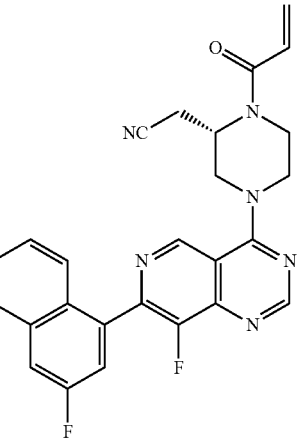<br>(S)-2-(1-acryloyl-4-(8-fluoro-7-(3-fluoronaphthalen-1-yl)pyrido[4,3-d]pyrimidin-4-yl)piperazin-2-yl)acetonitrile | LCMS [ESI, M + 1]: 471<br>$^1$H NMR (400 MHz, CDCl$_3$): δ 9.33 (s, 1H), 8.94 (s, 1H), 7.90 (d, J = 8.4 Hz, 1H), 7.76 (dd, J = 1.2, 8.4 Hz, 1H), 7.64 (dd, J = 2.4, 9.2 Hz, 1H), 7.59-7.50 (m, 2H), 7.47-7.41 (m, 1H), 6.66-6.53 (m, 1H), 6.48-6.39 (m, 1H), 5.87 (br d, J = 10.4 Hz, 1H), 5.16-4.88 (m, 1H), 4.66-4.47 (m, 2H), 4.28-3.99 (m, 2H), 3.87 (br s, 2H), 3.08-2.90 (m, 1H), 2.78 (br dd, J = 5.2, 16.8 Hz, 1H) |
| 250 | 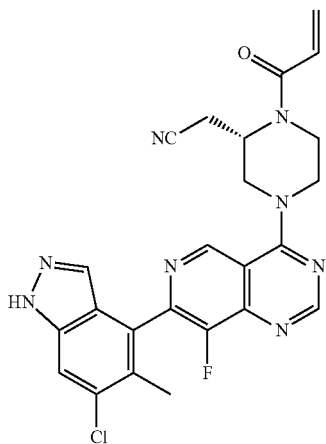<br>2-((2S)-1-acryloyl-4-(7-(6-chloro-5-methyl-1H-indazol-4-yl)-8-fluoropyrido[4,3-d]pyrimidin-4-yl)piperazin-2-yl)acetonitrile | LCMS [ESI, M + 1]: 491<br>$^1$H NMR (400 MHz, CDCl$_3$): δ 10.35-9.92 (m, 1H), 9.41-9.29 (m, 1H), 9.02-8.88 (m, 1H), 7.78-7.74 (m, 1H), 7.73-7.72 (m, 1H), 6.69-6.54 (m, 1H), 6.48-6.38 (m, 1H), 5.92-5.78 (m, 1H), 5.23-4.86 (m, 1H), 4.71-4.45 (m, 2H), 4.16 (br s, 2H), 3.90 (br s, 2H), 3.09-2.89 (m, 1H), 2.85-2.71 (m, 1H), 2.39 (d, J = 1.6 Hz, 3H) |

TABLE 5-continued

Compounds 248-287

| Ex. # | Structure | Data |
|---|---|---|
| 251 | 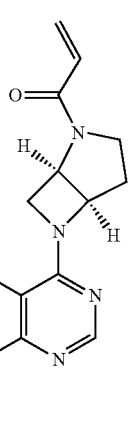<br>1-((1R,5R)-6-(7-(5-chloroisoquinolin-4-yl)-8-fluoropyrido[4,3-d]pyrimidin-4-yl)-2,6-diazabicyclo[3.2.0]heptan-2-yl)prop-2-en-1-one | LCMS [ESI, M + 1]: 461<br>$^1$H NMR (400 MHz, CDCl$_3$): δ 9.40 (s, 1H), 9.07 (d, J = 1.6 Hz, 1H), 8.89-8.78 (m, 1H), 8.58 (d, J = 4.8 Hz, 1H), 8.06 (d, J = 8.0 Hz, 1H), 7.82-7.72 (m, 1H), 7.67-7.57 (m, 1H), 6.64-6.38 (m, 2H), 5.82 (dd, J = 2.0, 10.0 Hz, 1H), 5.74-5.46 (m, 1H), 5.23-4.83 (m, 2H), 4.45 (br d, J = 7.2 Hz, 1H), 4.18 (br t, J = 9.6 Hz, 1H), 3.94 (dt, J = 4.0, 10.8 Hz, 1H), 2.86-2.56 (m, 1H), 2.40-2.11 (m, 1H) |
| 252 | 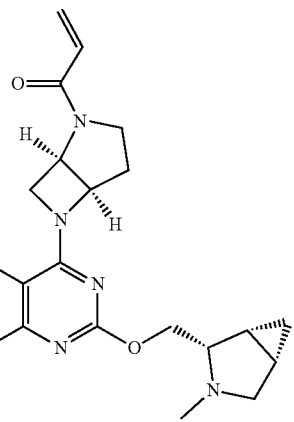<br>1-((1R,5R)-6-(7-(8-chloro-7-fluoronaphthalen-1-yl)-8-fluoro-2-(((1R,2S,5S)-3-methyl-3-azabicyclo[3.1.0]hexan-2-yl)methoxy)pyrido[4,3-d]pyrimidin-4-yl)-2,6-diazabicyclo[3.2.0]heptan-2-yl)prop-2-en-1-one | LCMS [ESI, M + 1]: 603<br>$^1$H NMR (400 MHz, CDCl$_3$): δ 8.90 (s, 1H), 8.03-7.95 (m, 1H), 7.88 (dd, J = 5.2, 8.8 Hz, 1H), 7.64-7.55 (m, 2H), 7.39 (t, J = 8.8 Hz, 1H), 6.64-6.35 (m, 2H), 5.82 (br d, J = 10.0 Hz, 1H), 5.73-5.50 (m, 1H), 5.25-4.80 (m, 2H), 4.66 (br dd, J = 2.8, 10.0 Hz, 1H), 4.53-4.10 (m, 3H), 4.02-3.68 (m, 1H), 3.12 (d, J = 8.8 Hz, 1H), 3.03-2.89 (m, 1H), 2.83-2.62 (m, 1H), 2.58-2.48 (m, 1H), 2.40 (d, J = 2.4 Hz, 3H), 2.32-2.08 (m, 1H), 1.79-1.67 (m, 1H), 1.47-1.37 (m, 1H), 0.79-0.69 (m, 1H), 0.41-0.29 (m, 1H) |

TABLE 5-continued

Compounds 248-287

| Ex. # | Structure | Data |
|---|---|---|
| 253 | 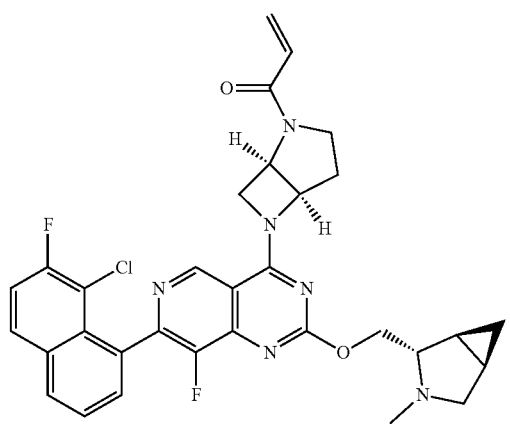 1-((1R,5R)-6-(7-(8-chloro-7-fluoronaphthalen-1-yl)-8-fluoro-2-(((1S,2S,5R)-3-methyl-3-azabicyclo[3.1.0]hexan-2-yl)methoxy)pyrido[4,3-d]pyrimidin-4-yl)-2,6-diazabicyclo[3.2.0]heptan-2-yl)prop-2-en-1-one | LCMS [ESI, M + 1]: 603<br>$^1$H NMR (400 MHz, CDCl$_3$): δ 8.94-8.86 (s, 1H), 8.03-7.95 (m, 1H), 7.89 (dd, J = 5.6, 9.2 Hz, 1H), 7.62-7.56 (m, 2H), 7.39 (t, J = 8.8 Hz, 1H), 6.68-6.34 (m, 2H), 5.81 (br d, J = 10.4 Hz, 1H), 5.72-5.50 (m, 1H), 5.23-4.77 (m, 2H), 4.74-4.59 (m, 1H), 4.53-4.10 (m, 3H), 4.02-3.68 (m, 1H), 3.28 (br t, J = 5.2 Hz, 1H), 3.05 (br dd, J = 3.2, 9.2 Hz, 1H), 2.84-2.60 (m, 2H), 2.49 (d, J = 2.4 Hz, 3H), 2.37-2.09 (m, 1H), 1.57-1.43 (m, 2H), 0.70-0.57 (m, 1H), 0.53-0.43 (m, 1H) |
| 254 | 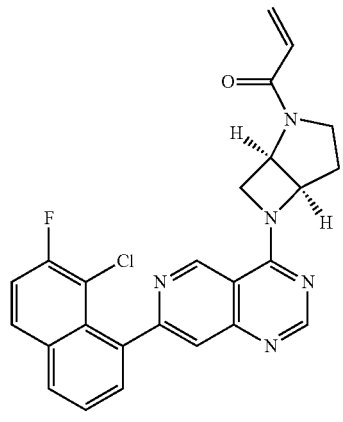 1-((1R,5R)-6-(7-(8-chloro-7-fluoronaphthalen-1-yl)pyrido[4,3-d]pyrimidin-4-yl)-2,6-diazabicyclo[3.2.0]heptan-2-yl)prop-2-en-1-one | LCMS [ESI, M + 1]: 460<br>$^1$H NMR (400 MHz, CDCl$_3$): δ $^1$H NMR (400 MHz, CDCl$_3$) δ 9.23-9.18 (m, 1H), 8.80-8.75 (m, 1H), 7.98-7.96 (dd, J = 2.4, 7.2 Hz, 1H), 7.90-7.87 (dd, J = 5.6, 9.2 Hz, 1H), 7.85-7.79 (m, 1H), 7.61-7.53 (m, 2H), 7.42-7.38 (t, J = 8.8 Hz, 1H), 6.63-6.38 (m, 2H), 5.85-5.78 (m, 1H), 5.70-5.49 (m, 1H), 5.21-4.84 (m, 2H), 4.50-4.13 (m, 2H), 4.02-3.70 (m, 1H), 2.78-2.60 (m, 1H), 2.35-2.12 (m, 1H) |

TABLE 5-continued

Compounds 248-287

| Ex. # | Structure | Data |
|---|---|---|
| 255 | 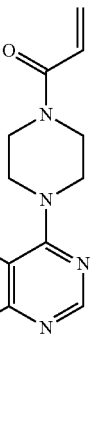<br>1-(4-(7-(3-chloronaphthalen-1-yl)-8-fluoropyrido[4,3-d]pyrimidin-4-yl)piperazin-1-yl)prop-2-en-1-one | LCMS [ESI, M + 1]: 448<br>$^1$H NMR (400 MHz, CDCl$_3$): δ 9.29 (s, 1H), 8.92 (s, 1H), 8.00 (d, J = 2.0 Hz, 1H), 7.88 (d, J = 8.4 Hz, 1H), 7.76 (dd, J = 1.2, 8.4 Hz, 1H), 7.69 (d, J = 1.6 Hz, 1H), 7.57 (ddd, J = 1.2, 6.8, 8.4 Hz, 1H), 7.51-7.45 (m, 1H), 6.63 (dd, J = 10.4, 16.8 Hz, 1H), 6.42 (dd, J = 2.0, 16.8 Hz, 1H), 5.83 (dd, J = 2.0, 10.4 Hz, 1H), 4.20-4.11 (m, 4H), 4.04-3.83 (m, 4H) |
| 256 | 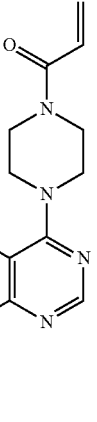<br>4-(4-(4-acryloylpiperazin-1-yl)-8-fluoropyrido[4,3-d]pyrimidin-7-yl)-2-naphthonitrile | LCMS [ESI, M + 1]: 439<br>$^1$H NMR (400 MHz, CDCl$_3$): δ 9.30 (s, 1H), 8.93 (s, 1H), 8.40 (s, 1H), 8.06-8.00 (m, 1H), 7.88-7.82 (m, 2H), 7.72-7.62 (m, 2H), 6.69-6.58 (m, 1H), 6.42 (dd, J = 2.0, 16.8 Hz, 1H), 5.83 (dd, J = 2.0, 10.4 Hz, 1H), 4.22-4.11 (m, 4H), 4.06-3.82 (m, 4H) |
| 257 | 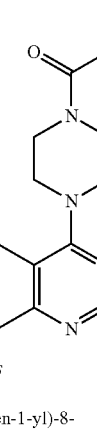<br>1-(4-(7-(6-chloronaphthalen-1-yl)-8-fluoropyrido[4,3-d]pyrimidin-4-yl)piperazin-1-yl)prop-2-en-1-one | LCMS [ESI, M + 1]: 448<br>$^1$H NMR (400 MHz, CDCl$_3$): δ 9.29 (s, 1H), 8.91 (s, 1H), 7.98-7.91 (m, 2H), 7.78 (dd, J = 1.6, 9.2 Hz, 1H), 7.75-7.70 (m, 1H), 7.69-7.63 (m, 1H), 7.42 (dd, J = 2.0, 9.2 Hz, 1H), 6.63 (dd, J = 10.4, 16.8 Hz, 1H), 6.42 (dd, J = 1.6, 16.8 Hz, 1H), 5.83 (dd, J = 1.6, 10.4 Hz, 1H), 4.15 (dd, J = 4.0, 6.4 Hz, 4H), 4.02-3.83 (m, 4H) |

TABLE 5-continued

Compounds 248-287

| Ex. # | Structure | Data |
|---|---|---|
| 258 | 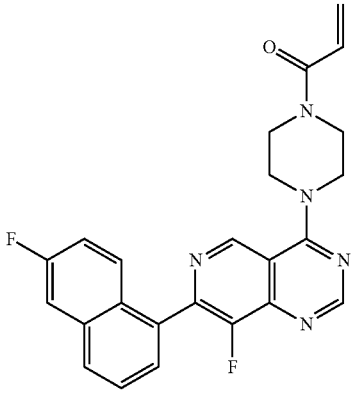<br>1-(4-(8-fluoro-7-(6-fluoronaphthalen-1-yl)pyrido[4,3-d]pyrimidin-4-yl)piperazin-1-yl)prop-2-en-1-one | LCMS [ESI, M + 1]: 432<br>$^1$H NMR (400 MHz, CDCl$_3$): δ 9.29 (s, 1H), 8.94-8.88 (m, 1H), 7.96 (dd, J = 1.2, 7.6 Hz, 1H), 7.86-7.80 (m, 1H), 7.70-7.63 (m, 2H), 7.57 (dd, J = 2.4, 9.6 Hz, 1H), 6.62 (dd, J = 10.4, 16.8 Hz, 1H), 6.41 (dd, J = 1.6, 16.8 Hz, 1H), 5.85-5.79 (m, 1H), 4.18-4.11 (m, 4H), 4.02-3.84 (m, 4H) |
| 259 | 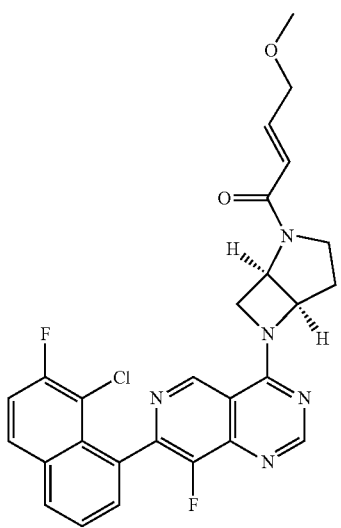<br>(E)-1-((1R,5R)-6-(7-(8-chloro-7-fluoronaphthalen-1-yl)-8-fluoropyrido[4,3-d]pyrimidin-4-yl)-2,6-diazabicyclo[3.2.0]heptan-2-yl)-4-methoxybut-2-en-1-one | LCMS [ESI, M + 1]: 522<br>$^1$H NMR (400 MHz, CDCl$_3$): δ 9.04 (d, J = 2.0 Hz, 1H), 8.84-8.82 (m, 1H), 8.04-7.99 (m, 1H), 7.92-7.88 (dd, J = 5.6, 8.8 Hz, 1H), 7.63-7.59 (m, 2H), 7.43-7.39 (t, J = 8.8 Hz, 1H), 7.10-6.99 (m, 1H), 6.54-6.31 (m, 1H), 5.71-5.48 (m, 1H), 5.24-4.86 (m, 2H), 4.48-4.40 (m, 1H), 4.27-4.11 (m, 3H), 4.02-3.70 (m, 1H), 3.44 (s, 3H), 2.80-2.58 (m, 1H), 2.36-2.08 (m, 1H) |

TABLE 5-continued

Compounds 248-287

| Ex. # | Structure | Data |
|---|---|---|
| 260 | 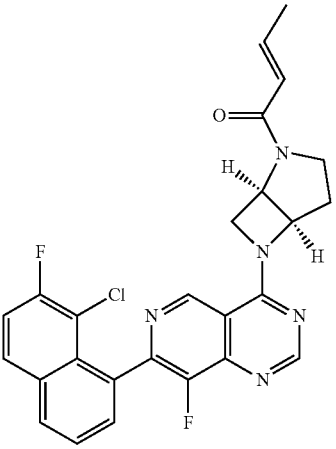<br>(E)-1-((1R,5R)-6-(7-(8-chloro-7-fluoronaphthalen-1-yl)-8-fluoropyrido[4,3-d]pyrimidin-4-yl)-2,6-diazabicyclo[3.2.0]heptan-2-yl)but-2-en-1-one | LCMS [ESI, M + 1]: 492<br>$^1$H NMR (400 MHz, CDCl$_3$): δ 9.04-9.03 (d, J = 2.0 Hz, 1H), 8.83-8.82 (d, J = 6.0 Hz, 1H), 8.04-7.98 (m, 1H), 7.92-7.88 (dd, J = 5.6, 9.2 Hz, 1H), 7.63-7.59 (m, 2H), 7.43-7.38 (t, J = 8.8 Hz, 1H), 7.10-7.00 (qd, J = 7.2, 14.8 Hz, 1H), 6.32-6.02 (m, 1H), 5.70-5.46 (m, 1H), 5.24-4.85 (m, 2H), 4.51-4.08 (m, 2H), 4.00-3.60 (m, 1H), 2.82-2.55 (m, 1H), 2.35-2.07 (m, 1H), 1.96-1.94 (d, J = 6.8 Hz, 3H) |
| 261 | 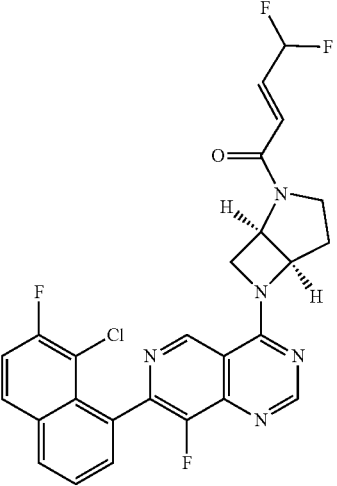<br>(E)-1-((1R,5R)-6-(7-(8-chloro-7-fluoronaphthalen-1-yl)-8-fluoropyrido[4,3-d]pyrimidin-4-yl)-2,6-diazabicyclo[3.2.0]heptan-2-yl)-4,4-difluorobut-2-en-1-one | LCMS [ESI, M + 1]: 528<br>$^1$H NMR (400 MHz, CDCl$_3$): δ 9.06-8.98 (m, 1H), 8.87-8.81 (m, 1H), 8.06-7.98 (m, 1H), 7.90 (dd, J = 5.6, 9.2 Hz, 1H), 7.65-7.56 (m, 2H), 7.41 (t, J = 8.8 Hz, 1H), 6.97-6.83 (m, 1H), 6.80-6.53 (m, 1H), 6.47-6.14 (m, 1H), 5.55 (br t, J = 5.6 Hz, 1H), 5.21-4.88 (m, 2H), 4.56-4.31 (m, 1H), 4.25-4.11 (m, 1H), 4.08-3.71 (m, 1H), 2.85-2.54 (m, 1H), 2.38-2.12 (m, 1H) |

TABLE 5-continued

Compounds 248-287

| Ex. # | Structure | Data |
|---|---|---|
| 262 | 1-((1R,5R)-6-(7-(8-chloro-7-fluoronaphthalen-1-yl)-2-(((S)-4,4-difluoro-1-methylpyrrolidin-2-yl)methoxy)-8-fluoropyrido[4,3-d]pyrimidin-4-yl)-2,6-diazabicyclo[3.2.0]heptan-2-yl)prop-2-en-1-one | LCMS [ESI, M + 1]: 627<br>$^1$H NMR (400 MHz, CDCl$_3$): δ 8.91 (s, 1H), 7.99 (br d, J = 4.8 Hz, 1H), 7.89 (br d, J = 5.2 Hz, 1H), 7.63-7.55 (m, 2H), 7.40 (t, J = 8.8 Hz, 1H), 6.50 (d, J = 1.6 Hz, 2H), 5.87-5.76 (m, 1H), 5.72-5.48 (m, 1H), 5.21-4.77 (m, 2H), 4.71-4.58 (m, 1H), 4.54-4.34 (m, 2H), 4.23-3.89 (m, 1H), 3.88-3.53 (m, 1H), 3.50-3.32 (m, 1H), 3.13-2.98 (m, 1H), 2.79-2.52 (m, 3H), 2.50 (s, 3H), 2.43-2.20 (m, 2H) |
| 263 | (E)-1-((1R,5R)-6-(7-(8-chloro-7-fluoronaphthalen-1-yl)-8-fluoropyrido[4,3-d]pyrimidin-4-yl)-2,6-diazabicyclo[3.2.0]heptan-2-yl)-4,4,4-trifluorobut-2-en-1-one | LCMS [ESI, M + 1]: 546<br>$^1$H NMR (400 MHz, CDCl$_3$): δ 9.04-9.03 (d, J = 2.0 Hz, 1H), 8.89-8.82 (m, 1H), 8.07-7.98 (m, 1H), 7.92-7.89 (dd, J = 5.6, 9.2 Hz, 1H), 7.65-7.57 (m, 2H), 7.43-7.39 (m, 1H), 6.99-5.79 (br d, J = 19.2 Hz, 2H), 5.76-5.52 (m, 1H), 5.21-4.88 (m, 2H), 4.56-4.16 (m, 2H), 4.09-3.74 (m, 1H), 2.90-2.65 (m, 1H), 2.41-2.12 (m, 1H) |

TABLE 5-continued

Compounds 248-287

| Ex. # | Structure | Data |
|---|---|---|
| 264 | 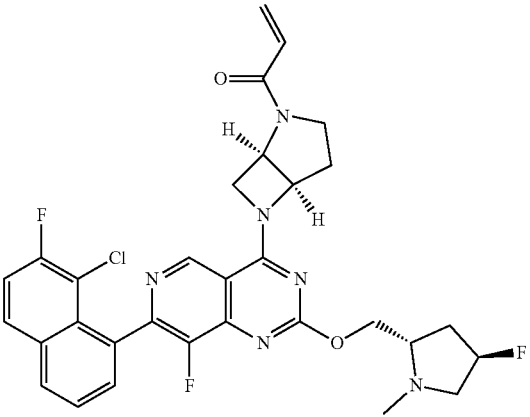<br>1-((1R,5R)-6-(7-(8-chloro-7-fluoronaphthalen-1-yl)-8-fluoro-2-(((2S,4R)-4-fluoro-1-methylpyrrolidin-2-yl)methoxy)pyrido[4,3-d]pyrimidin-4-yl)-2,6-diazabicyclo[3.2.0]heptan-2-yl)prop-2-en-1-one | LCMS [ESI, M + 1]: 609<br>$^1$H NMR (400 MHz, CDCl$_3$): δ 8.90 (s, 1H), 8.05-7.94 (m, 1H), 7.89 (dd, J = 5.6, 8.8 Hz, 1H), 7.60 (s, 2H), 7.44-7.35 (m, 1H), 6.49 (d, J = 2.0 Hz, 2H), 5.85-5.77 (m, 1H), 5.72-5.46 (m, 1H), 5.30-5.05 (m, 2H), 5.00-4.73 (m, 1H), 4.70-4.58 (m, 1H), 4.50-4.30 (m, 2H), 4.16 (br t, J = 10.0 Hz, 1H), 3.76 (br s, 1H), 3.63-3.49 (m, 1H), 3.17-3.04 (m, 1H), 2.82-2.55 (m, 2H), 2.54 (d, J = 0.8 Hz, 3H), 2.42-1.89 (m, 3H) |
| 265 | 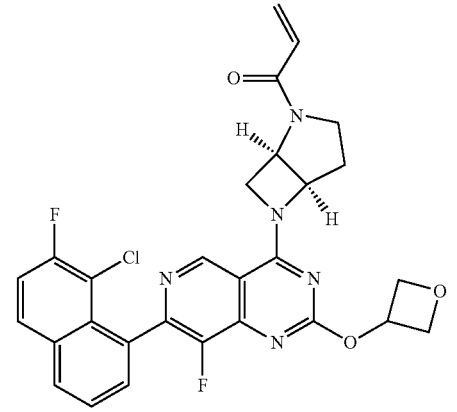<br>1-((1R,5R)-6-(7-(8-chloro-7-fluoronaphthalen-1-yl)-8-fluoro-2-(oxetan-3-yloxy)pyrido[4,3-d]pyrimidin-4-yl)-2,6-diazabicyclo[3.2.0]heptan-2-yl)prop-2-en-1-one | LCMS [ESI, M + 1]: 550<br>$^1$H NMR (400 MHz, CDCl$_3$): δ 8.92 (s, 1H), 8.05-7.96 (m, 1H), 7.89 (dd, J = 5.6, 9.2 Hz, 1H), 7.65-7.57 (m, 2H), 7.40 (t, J = 8.8 Hz, 1H), 6.65-6.36 (m, 2H), 5.87-5.70 (m, 2H), 5.68-5.48 (m, 1H), 5.24-5.11 (m, 1H), 5.00 (t, J = 7.2 Hz, 2H), 4.96-4.83 (m, 3H), 4.53-4.35 (m, 1H), 4.24-4.13 (m, 1H), 4.03-3.70 (m, 1H), 2.81-2.59 (m, 1H), 2.40-2.13 (m, 1H) |
| 266 | 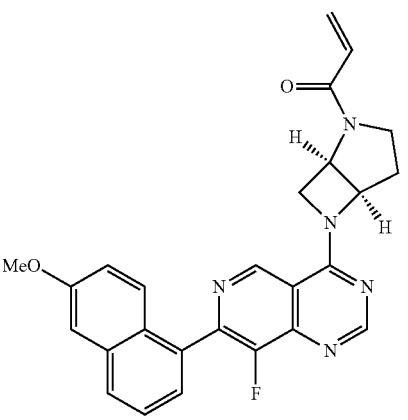<br>1-((1R,5R)-6-(8-fluoro-7-(6-methoxynaphthalen-1-yl)pyrido[4,3-d]pyrimidin-4-yl)-2,6-diazabicyclo[3.2.0]heptan-2-yl)prop-2-en-1-one | LCMS [ESI, M + 1]: 456<br>$^1$H NMR (400 MHz, CDCl$_3$): δ 9.12 (s, 1H), 8.87-8.74 (m, 1H), 7.88 (d, J = 8.0 Hz, 1H), 7.65 (br d, J = 9.2 Hz, 1H), 7.60-7.49 (m, 2H), 7.22 (d, J = 2.4 Hz, 1H), 7.12 (dd, J = 2.8, 9.2 Hz, 1H), 6.61-6.33 (m, 2H), 5.81 (dd, J = 1.6, 10.0 Hz, 1H), 5.69-5.44 (m, 1H), 5.21-4.81 (m, 2H), 4.51-4.09 (m, 2H), 3.94 (s, 3H), 3.91-3.68 (m, 1H), 2.79-2.58 (m, 1H), 2.39-2.10 (m, 1H) |

TABLE 5-continued

Compounds 248-287

| Ex. # | Structure | Data |
|---|---|---|
| 267 | 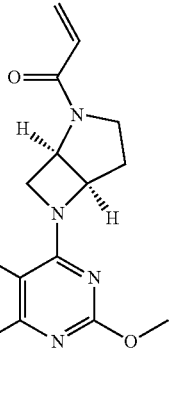<br>1-((1R,5R)-6-(7-(8-chloro-7-fluoronaphthalen-1-yl)-8-fluoro-2-methoxypyrido[4,3-d]pyrimidin-4-yl)-2,6-diazabicyclo[3.2.0]heptan-2-yl)prop-2-en-1-one | LCMS [ESI, M + 1]: 508<br>$^1$H NMR (400 MHz, CDCl$_3$): δ 8.91 (s, 1H), 7.99 (dd, J = 3.6, 5.6 Hz, 1H), 7.89 (dd, J = 5.6, 9.2 Hz, 1H), 7.65-7.55 (m, 2H), 7.40 (t, J = 8.8 Hz, 1H), 6.69-6.32 (m, 2H), 5.81 (br d, J = 10.4 Hz, 1H), 5.71-5.47 (m, 1H), 5.20-4.80 (m, 2H), 4.53-4.35 (m, 1H), 4.20-4.12 (m, 1H), 4.11 (s, 3H), 4.02-3.67 (m, 1H), 2.83-2.57 (m, 1H), 2.36-2.08 (m, 1H) |
| 268 | 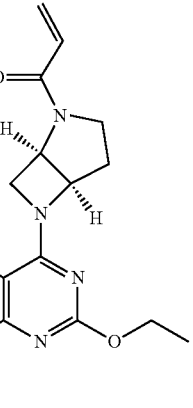<br>1-((1R,5R)-6-(7-(8-chloro-7-fluoronaphthalen-1-yl)-2-ethoxy-8-fluoropyrido[4,3-d]pyrimidin-4-yl)-2,6-diazabicyclo[3.2.0]heptan-2-yl)prop-2-en-1-one | LCMS [ESI, M + 1]: 522<br>$^1$H NMR (400 MHz, CDCl$_3$): δ 8.90 (s, 1H), 7.99 (dd, J = 3.2, 6.4 Hz, 1H), 7.88 (dd, J = 5.6, 9.2 Hz, 1H), 7.66-7.53 (m, 2H), 7.39 (t, J = 8.8 Hz, 1H), 6.67-6.30 (m, 2H), 5.81 (br d, J = 10.4 Hz, 1H), 5.73-5.48 (m, 1H), 5.26-4.80 (m, 2H), 4.57 (q, J = 7.2 Hz, 2H), 4.50-4.12 (m, 2H), 4.06-3.66 (m, 1H), 2.86-2.57 (m, 1H), 2.39-2.05 (m, 1H), 1.47 (t, J = 7.2 Hz, 3H) |
| 269 | 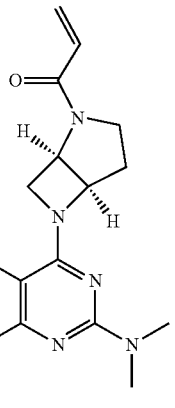<br>1-((1R5R)-6-(7-(8-chloro-7-fluoronaphthalen-1-yl)-2-(dimethylamino)-8-fluoropyrido[4,3-d]pyrimidin-4-yl)-2,6-diazabicyclo[3.2.0]heptan-2-yl)prop-2-en-1-one | LCMS [ESI, M + 1]: 521<br>$^1$H NMR (400 MHz, CDCl$_3$): δ 8.72-8.64 (m, 1H), 7.95 (dd, J = 1.6, 7.6 Hz, 1H), 7.86 (dd, J = 5.6, 9.2 Hz, 1H), 7.62-7.52 (m, 2H), 7.37 (t, J = 8.8 Hz, 1H), 6.63-6.34 (m, 2H), 5.84-5.76 (m, 1H), 5.60-5.41 (m, 1H), 5.13-5.08 (m, 1H), 5.12-5.04 (m, 1H), 4.91-4.70 (m, 1H), 4.49-4.08 (m, 2H), 4.02-3.71 (m, 1H), 3.29 (br s, 6H), 2.77-2.56 (m, 1H), 2.27-2.01 (m, 1H) |

TABLE 5-continued

Compounds 248-287

| Ex. # | Structure | Data |
|---|---|---|
| 270 | 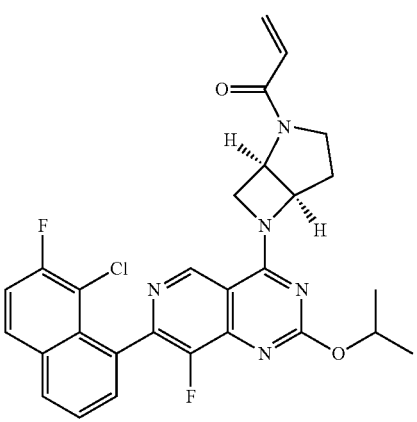<br>1-((1R,5R)-6-(7-(8-chloro-7-fluoronaphthalen-1-yl)-8-fluoro-2-isopropoxypyrido[4,3-d]pyrimidin-4-yl)-2,6-diazabicyclo[3.2.0]heptan-2-yl)prop-2-en-1-one | LCMS [ESI, M + 1]: 536<br>$^1$H NMR (400 MHz, CDCl$_3$): δ 8.89 (s, 1H), 7.98 (dd, J = 2.8, 6.8 Hz, 1H), 7.88 (dd, J = 5.6, 9.2 Hz, 1H), 7.63-7.55 (m, 2H), 7.39 (t, J = 8.8 Hz, 1H), 6.63-6.34 (m, 2H), 5.85-5.76 (m, 1H), 5.71-5.44 (m, 2H), 5.22-4.78 (m, 2H), 4.50-4.09 (m, 1H), 4.01-3.71 (m, 1H), 2.80-2.56 (m, 1H), 2.34-2.08 (m, 1H), 1.66 (br s, 1H), 1.50-1.39 (m, 6H) |
| 271 | 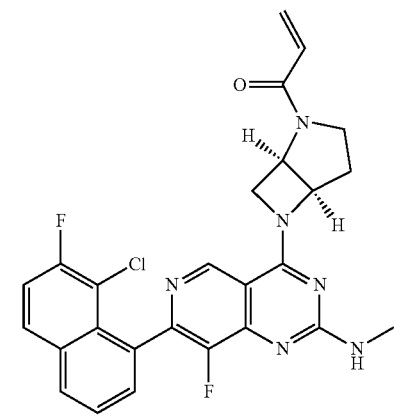<br>1-((1R,5R)-6-(7-(8-chloro-7-fluoronaphthalen-1-yl)-8-fluoro-2-(methylamino)pyrido[4,3-d]pyrimidin-4-yl)-2,6-diazabicyclo[3.2.0]heptan-2-yl)prop-2-en-1-one | LCMS [ESI, M + 1]: 507<br>$^1$H NMR (400 MHz, CDCl$_3$): δ 8.79-8.65 (m, 1H), 7.96 (dd, J = 2.0, 7.2 Hz, 1H), 7.86 (dd, J = 5.6, 9.2 Hz, 1H), 7.63-7.52 (m, 2H), 7.38 (t, J = 8.8 Hz, 1H), 6.64-6.34 (m, 2H), 5.81 (br d, J = 10.0 Hz, 1H), 5.61-5.37 (m, 1H), 5.34-5.04 (m, 1H), 4.93-4.74 (m, 1H), 4.49-4.09 (m, 2H), 4.03-3.69 (m, 1H), 3.10 (br s, 3H), 2.81-2.51 (m, 1H), 2.29-2.04 (m, 1H) |
| 272 | 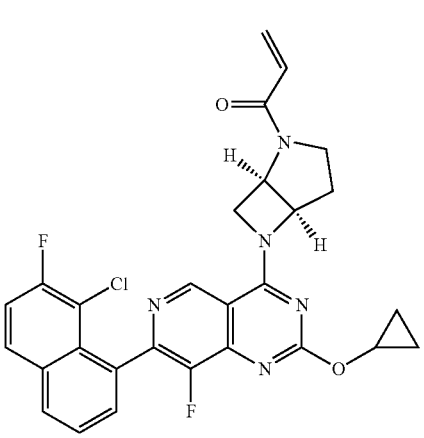<br>1-((1R,5R)-6-(7-(8-chloro-7-fluoronaphthalen-1-yl)-2-cyclopropoxy-8-fluoropyrido[4,3-d]pyrimidin-4-yl)-2,6-diazabicyclo[3.2.0]heptan-2-yl)prop-2-en-1-one | LCMS [ESI, M + 1]: 534<br>$^1$H NMR (400 MHz, CDCl$_3$): δ 8.91 (s, 1H), 7.99 (dd, J = 3.2, 6.4 Hz, 1H), 7.89 (dd, J = 5.6, 9.2 Hz, 1H), 7.64-7.57 (m, 2H), 7.40 (t, J = 8.8 Hz, 1H), 6.70-6.25 (m, 2H), 5.81 (br d, J = 10.0 Hz, 1H), 5.73-5.45 (m, 1H), 5.26-4.79 (m, 2H), 4.61-4.35 (m, 2H), 4.16 (br t, J = 9.6 Hz, 1H), 4.03-3.69 (m, 1H), 2.84-2.63 (m, 1H), 2.35-2.13 (m, 1H), 0.97-0.88 (m, 2H), 0.87-0.77 (m, 2H) |

… TABLE 5-continued

Compounds 248-287

| Ex. # | Structure | Data |
|---|---|---|
| 273 | 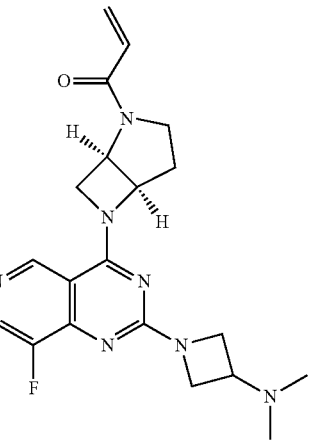 1-((1R,5R)-6-(7-(8-chloro-7-fluoronaphthalen-1-yl)-2-(3-(dimethylamino)azetidin-1-yl)-8-fluoropyrido[4,3-d]pyrimidin-4-yl)-2,6-diazabicyclo[3.2.0]heptan-2-yl)prop-2-en-1-one | LCMS [ESI, M + 1]: 576<br>$^1$H NMR (400 MHz, CDCl$_3$): δ δ 8.80-8.72 (m, 1H), 7.97 (dd, J = 4.0, 6.0 Hz, 1H), 7.87 (dd, J = 5.6, 9.2 Hz, 1H), 7.62-7.53 (m, 2H), 7.38 (t, J = 8.8 Hz, 1H), 6.63-6.34 (m, 2H), 5.84-5.77 (m, 1H), 5.62-5.39 (m, 1H), 5.14-4.74 (m, 2H), 4.58-4.38 (m, 4H), 4.37-4.27 (m, 1H), 4.13 (br t, J = 10.0 Hz, 1H), 4.01-3.68 (m, 2H), 2.70 (br s, 6H), 2.67-2.51 (m, 1H), 2.27-2.14 (m, 1H) |
| 274 | 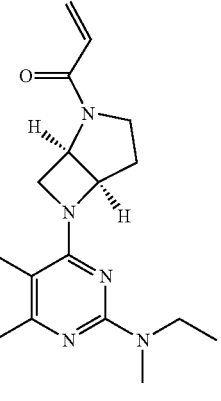 1-((1R,5R)-6-(7-(8-chloro-7-fluoronaphthalen-1-yl)-2-(ethyl(methyl)amino)-8-fluoropyrido[4,3-d]pyrimidin-4-yl)-2,6-diazabicyclo[3.2.0]heptan-2-yl)prop-2-en-1-one | LCMS [ESI, M + 1]: 535<br>$^1$H NMR (400 MHz, CDCl$_3$): δ 8.77-8.64 (m, 1H), 8.00-7.81 (m, 2H), 7.66-7.51 (m, 2H), 7.37 (t, J = 8.8 Hz, 1H), 6.66-6.32 (m, 2H), 5.88-5.73 (m, 1H), 5.64-5.36 (m, 1H), 5.17-4.66 (m, 2H), 4.53-4.09 (m, 2H), 4.03-3.64 (m, 3H), 3.37-3.17 (m, 3H), 2.74-2.51 (m, 1H), 2.33-2.06 (m, 1H), 1.27-1.20 (m, 3H) |
| 275 | 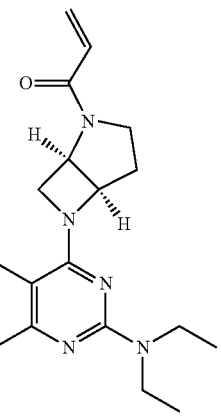 1-((1R,5R)-6-(7-(8-chloro-7-fluoronaphthalen-1-yl)-2-(diethylamino)-8-fluoropyrido[4,3-d]pyrimidin-4-yl)-2,6-diazabicyclo[3.2.0]heptan-2-yl)prop-2-en-1-one | LCMS [ESI, M + 1]: 549<br>$^1$H NMR (400 MHz, CDCl$_3$): δ 8.73-8.63 (m, 1H), 8.01-7.80 (m, 2H), 7.64-7.49 (m, 2H), 7.37 (t, J = 8.8 Hz, 1H), 6.67-6.28 (m, 2H), 5.85-5.75 (m, 1H), 5.60-5.37 (m, 1H), 5.14-4.70 (m, 2H), 4.50-4.09 (m, 2H), 4.01-3.60 (m, 5H), 2.75-2.52 (m, 1H), 2.28-2.04 (m, 1H), 1.25 (br t, J = 6.8 Hz, 6H) |

TABLE 5-continued

Compounds 248-287

| Ex. # | Structure | Data |
|---|---|---|
| 276 | 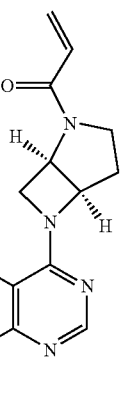<br>1-((1R,5R)-6-(7-(benzo[b]thiophen-4-yl)-8-fluoropyrido[4,3-d]pyrimidin-4-yl)-2,6-diazabicyclo[3.2.0]heptan-2-yl)prop-2-en-1-one | LCMS [ESI, M + 1]: 432<br>$^1$H NMR (400 MHz, CDCl$_3$): δ 9.12 (s, 1H), 8.85-8.80 (m, 1H), 8.03 (d, J = 8.0 Hz, 1H), 7.73 (br d, J = 7.6 Hz, 1H), 7.57-7.47 (m, 3H), 6.62-6.37 (m, 2H), 5.86-5.79 (m, 1H), 5.68-5.48 (m, 1H), 5.23-4.81 (m, 2H), 4.51-4.13 (m, 2H), 3.99-3.69 (m, 1H), 2.81-2.61 (m, 1H), 2.36-2.12 (m, 1H) |
| 277 | 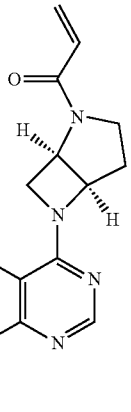<br>1-((1R,5R)-6-(7-(3-chloro-2-cyclopropylphenyl)-8-fluoropyrido[4,3-d]pyrimidin-4-yl)-2,6-diazabicyclo[3.2.0]heptan-2-yl)prop-2-en-1-one | LCMS [ESI, M + 1]: 450<br>$^1$H NMR (400 MHz, CDCl$_3$): δ 9.04 (s, 1H), 8.83-8.76 (m, 1H), 7.49 (d, J = 7.6 Hz, 1H), 7.39-7.35 (m, 1H), 7.33-7.28 (m, 1H), 6.62-6.35 (m, 2H), 5.86-5.74 (m, 1H), 5.70-5.45 (m, 1H), 5.24-4.84 (m, 2H), 4.56-4.08 (m, 2H), 3.99-3.67 (m, 1H), 2.80-2.59 (m, 1H), 2.40-2.12 (m, 1H), 2.10-1.98 (m, 1H), 0.69 (br d, J = 6.4 Hz, 2H), 0.11 (br s, 2H) |
| 278 | 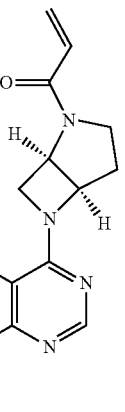<br>1-((1R,5R)-6-(7-(benzo[b]thiophen-7-yl)-8-fluoropyrido[4,3-d]pyrimidin-4-yl)-2,6-diazabicyclo[3.2.0]heptan-2-yl)prop-2-en-1-one | LCMS [ESI, M + 1]: 432<br>$^1$H NMR (400 MHz, CDCl$_3$): δ 9.22-9.14 (m, 1H), 8.14 (d, J = 7.6 Hz, 1H), 7.97 (d, J = 7.6 Hz, 1H), 7.60-7.53 (m, 2H), 7.44 (d, J = 5.6 Hz, 1H), 6.63-6.36 (m, 2H), 5.80-5.77 (m, 1H), 5.70-5.65 (m, 1H), 5.45-4.80 (m, 2H), 5.23-4.81 (m, 2H), 4.45-4.22 (m, 2H), 3.99-3.69 (m, 1H), 2.81-2.65 (m, 1H), 2.36-2.20 (m, 1H) |

TABLE 5-continued

Compounds 248-287

| Ex. # | Structure | Data |
|---|---|---|
| 279 | 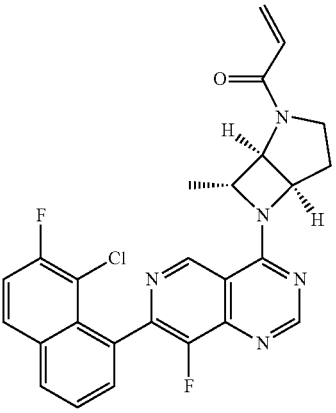<br>1-((1R,5R,7R)-6-(7-(8-chloro-7-fluoronaphthalen-1-yl)-8-fluoropyrido[4,3-d]pyrimidin-4-yl)-7-methyl-2,6-diazabicyclo[3.2.0]heptan-2-yl)prop-2-en-1-one | LCMS [ESI, M + 1]: 492<br>$^1$H NMR (400 MHz, CDCl$_3$): δ 9.10-8.86 (m, 1H), 8.82 (s, 1H), 8.00 (d, J = 7.6 Hz, 1H), 7.89 (dd, J = 5.6, 9.2 Hz, 1H), 7.67-7.55 (m, 2H), 7.39 (t, J = 8.8 Hz, 1H), 6.66-6.31 (m, 2H), 5.88-5.75 (m, 1H), 5.74-5.40 (m, 1H), 4.92-4.42 (m, 2H), 4.41-3.60 (m, 2H), 2.79-2.39 (m, 1H), 2.37-2.04 (m, 1H), 1.74-1.68 (m, 3H) |
| 280 | 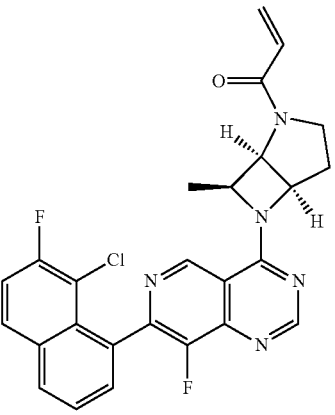<br>1-((1R,5R,7S)-6-(7-(8-chloro-7-fluoronaphthalen-1-yl)-8-fluoropyrido[4,3-d]pyrimidin-4-yl)-7-methyl-2,6-diazabicyclo[3.2.0]heptan-2-yl)prop-2-en-1-one | LCMS [ESI, M + 1]: 492<br>$^1$H NMR (400 MHz, CDCl$_3$): δ 9.12 (dd, J = 2.0, 3.6 Hz, 1H), 8.87-8.78 (m, 1H), 8.00 (dd, J = 2.4, 6.8 Hz, 1H), 7.89 (dd, J = 5.6, 8.8 Hz, 1H), 7.65-7.55 (m, 2H), 7.39 (t, J = 8.8 Hz, 1H), 6.66-6.29 (m, 2H), 5.86-5.77 (m, 1H), 5.65-5.40 (m, 1H), 5.30-4.94 (m, 2H), 4.57-4.16 (m, 1H), 3.95-3.66 (m, 1H), 2.80-2.59 (m, 1H), 2.47-2.22 (m, 1H), 1.54-1.49 (m, 3H) |
| 281 | 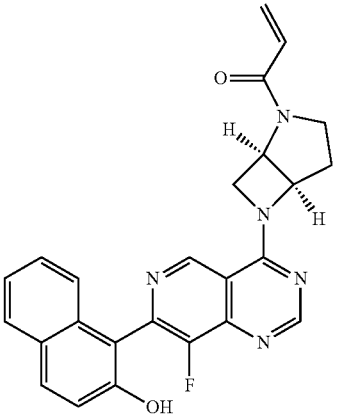<br>1-((1R,5R)-6-(8-fluoro-7-(2-hydroxynaphthalen-1-yl)pyrido[4,3-d]pyrimidin-4-yl)-2,6-diazabicyclo[3.2.0]heptan-2-yl)prop-2-en-1-one | LCMS [ESI, M + 1]: 442.0<br>$^1$H NMR (400 MHz, CDCl$_3$): δ 9.78-9.37 (m, 1H), 9.11 (s, 1H), 8.88-8.78 (m, 1H), 7.96-7.89 (m, 1H), 7.84 (d, J = 7.6 Hz, 1H), 7.61-7.50 (m, 1H), 7.49-7.34 (m, 2H), 7.33-7.28 (m, 1H), 6.63-6.36 (m, 2H), 5.87-5.78 (m, 1H), 5.71-5.46 (m, 1H), 5.23-4.84 (m, 2H), 4.55-4.12 (m, 2H), 3.98-3.69 (m, 1H), 2.83-2.61 (m, 1H), 2.38-2.11 (m, 1H) |

TABLE 5-continued

Compounds 248-287

| Ex. # | Structure | Data |
|---|---|---|
| 282 | 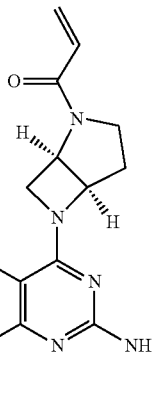<br>1-((1R,5R)-6-(2-amino-7-(8-chloro-7-fluoronaphthalen-1-yl)-8-fluoropyrido[4,3-d]pyrimidin-4-yl)-2,6-diazabicyclo[3.2.0]heptan-2-yl)prop-2-en-1-one | LCMS [ESI, M + 1]: 493<br>$^1$H NMR (400 MHz, CDCl$_3$): δ 8.78-8.70 (m, 1H), 8.01-7.92 (m, 1H), 7.86 (dd, J = 5.6, 9.2 Hz, 1H), 7.62-7.52 (m, 2H), 7.37 (t, J = 8.8 Hz, 1H), 6.62-6.28 (m, 2H), 5.82-5.75 (m, 1H), 5.73-5.47 (m, 2H), 5.47-5.37 (m, 1H), 5.15-4.72 (m, 2H), 4.47-4.08 (m, 2H), 4.01-3.64 (m, 1H), 2.75-2.52 (m, 1H), 2.28-2.02 (m, 1H) |
| 283 | 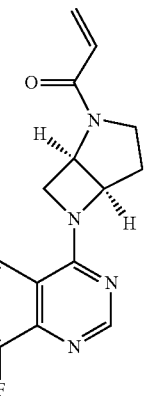<br>1-((1R,5R)-6-(8-fluoro-7-(8-methylnaphthalen-1-yl)pyrido[4,3-d]pyrimidin-4-yl)-2,6-diazabicyclo[3.2.0]heptan-2-yl)prop-2-en-1-one | LCMS [ESI, M + 1]: 440<br>$^1$H NMR (400 MHz, CDCl$_3$): δ 9.04 (s, 1H), 8.86-8.79 (m, 1H), 7.99 (d, J = 8.0 Hz, 1H), 7.82 (d, J = 8.0 Hz, 1H), 7.54 (t, J = 7.6 Hz, 1H), 7.48-7.38 (m, 2H), 7.29 (br s, 1H), 6.63-6.33 (m, 2H), 5.82 (dd, J = 2.4, 10.0 Hz, 1H), 5.69-5.46 (m, 1H), 5.22-4.82 (m, 2H), 4.58-4.09 (m, 2H), 4.01-3.65 (m, 1H), 2.82-2.60 (m, 1H), 2.36-2.12 (m, 1H), 2.01 (s, 3H) |
| 284 | 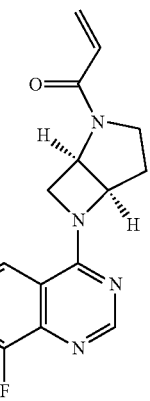<br>1-((1R,5R)-6-(7-(8-chloronaphthalen-1-yl)-8-fluoropyrido[4,3-d]pyrimidin-4-yl)-2,6-diazabicyclo[3.2.0]heptan-2-yl)prop-2-en-1-one | LCMS [ESI, M + 1]: 460<br>$^1$H NMR (400 MHz, CDCl$_3$): δ 9.08-9.01 (m, 1H), 8.85-8.79 (m, 1H), 8.03 (d, J = 8.0 Hz, 1H), 7.90 (d, J = 8.4 Hz, 1H), 7.66-7.60 (m, 1H), 7.59-7.52 (m, 2H), 7.47-7.40 (m, 1H), 6.64-6.35 (m, 2H), 5.82 (dd, J = 1.6, 10.0 Hz, 1H), 5.70-5.48 (m, 1H), 5.22-4.84 (m, 2H), 4.51-4.12 (m, 2H), 4.01-3.69 (m, 1H), 2.81-2.60 (m, 1H), 2.36-2.11 (m, 1H) |

TABLE 5-continued

Compounds 248-287

| Ex. # | Structure | Data |
|---|---|---|
| 285 | 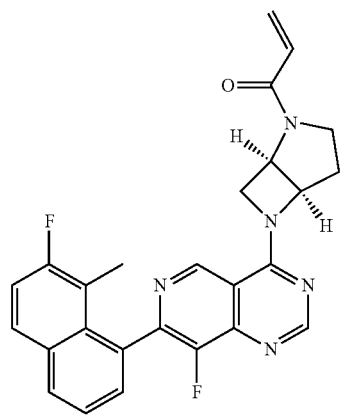<br>1-((1R,5R)-6-(8-fluoro-7-(7-fluoro-8-methylnaphthalen-1-yl)pyrido[4,3-d]pyrimidin-4-yl)-2,6-diazabicyclo[3.2.0]heptan-2-yl)prop-2-en-1-one | LCMS [ESI, M + 1]: 458.1<br>$^1$H NMR (400 MHz, CDCl$_3$): δ 9.05 (s, 1H), 8.90-8.77 (m, 1H), 7.97 (dd, J = 3.2, 6.4 Hz, 1H), 7.81 (dd, J = 6.0, 8.8 Hz, 1H), 7.59-7.46 (m, 2H), 7.31 (t, J = 9.2 Hz, 1H), 6.64-6.35 (m, 2H), 5.94-5.75 (m, 1H), 5.72-5.43 (m, 1H), 5.29-4.85 (m, 2H), 4.55-4.12 (m, 2H), 4.04-3.65 (m, 1H), 2.88-2.59 (m, 1H), 2.47-2.12 (m, 1H), 1.87 (s, 3H) |
| 286 | 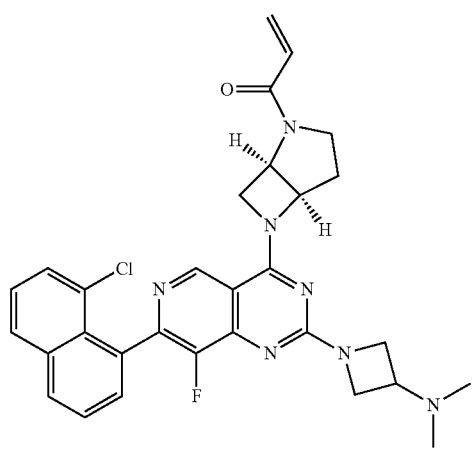<br>1-((1R,5R)-6-(7-(8-chloronaphthalen-1-yl)-2-(3-(dimethylamino)azetidin-1-yl)-8-fluoropyrido[4,3-d]pyrimidin-4-yl)-2,6-diazabicyclo[3.2.0]heptan-2-yl)prop-2-en-1-one | LCMS [ESI, M + 1]: 558.1<br>$^1$H NMR (400 MHz, CDCl$_3$): δ |
| 287 | 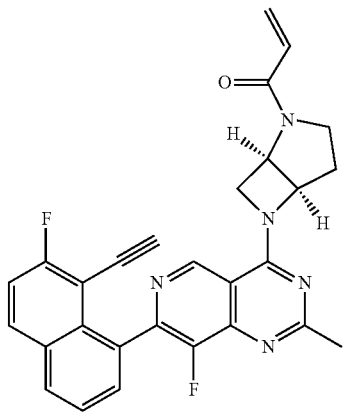<br>1-((1R,5R)-6-(7-(8-ethynyl-7-fluoronaphthalen-1-yl)-8-fluoro-2-methylpyrido[4,3-d]pyrimidin-4-yl)-2,6-diazabicyclo[3.2.0]heptan-2-yl)prop-2-en-1-one | LCMS [ESI, M + 1]: 482.2<br>$^1$H NMR (400 MHz, CDCl$_3$): δ |

Example 288

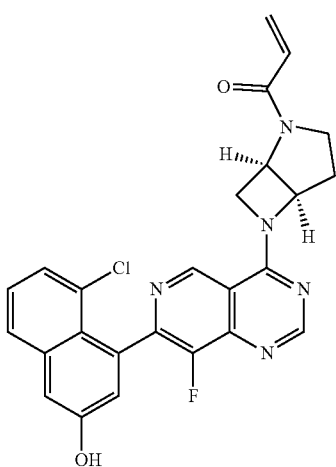 [SMILES: C=CC(=O)N1CC[C@@H]2[C@H]1CN2c1ncnc2c(F)c(-c3cc(O)cc4cccc(Cl)c34)ncc12]

1-((1R,5R)-6-(7-(8-chloro-3-hydroxynaphthalen-1-yl)-8-fluoropyrido[4,3-d]pyrimidin-4-yl)-2,6-diazabicyclo[3.2.0]heptan-2-yl)prop-2-en-1-one

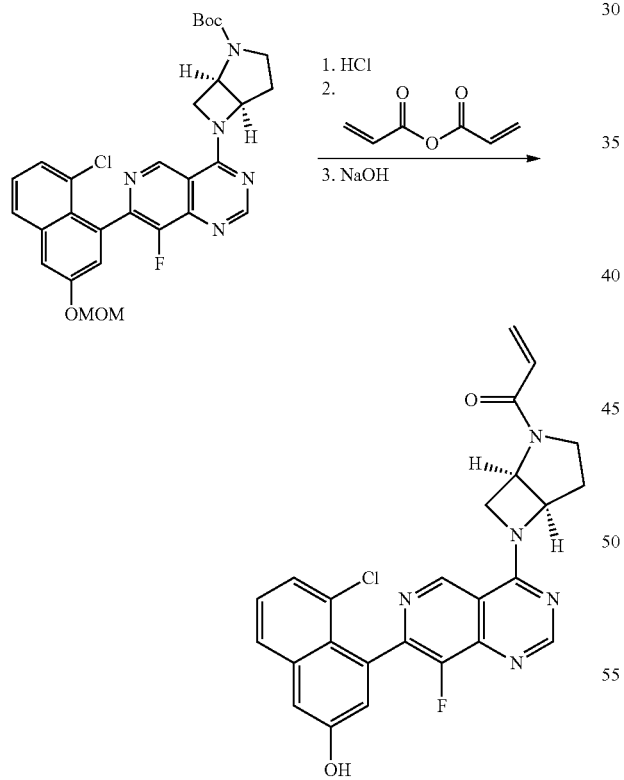

To a solution of tert-butyl (1R,5R)-6-(7-(8-chloro-3-(methoxymethoxy)naphthalen-1-yl)-8-fluoropyrido[4,3-d]pyrimidin-4-yl)-2,6-diazabicyclo[3.2.0]heptane-2-carboxylate (65.0 mg, 115 μmol, 1.0 equiv) in CH₃CN (1.0 mL) at 0° C. was added HCl (4 M in dioxane, 1.0 mL). The mixture was stirred at 0° C. for 20 min and then was concentrated under reduced pressure to afford 4-(4-((1R,5R)-2,6-diazabicyclo[3.2.0]heptan-6-yl)-8-fluoropyrido[4,3-d]pyrimidin-7-yl)-5-chloronaphthalen-2-ol (53.0 mg, HCl salt) as a yellow solid. LCMS [ESI, M+1]: 422.

To a solution of 4-(4-((1R,5R)-2,6-diazabicyclo[3.2.0]heptan-6-yl)-8-fluoropyrido[4,3-d]pyrimidin-7-yl)-5-chloronaphthalen-2-ol (53.0 mg, 116 μmol, 1.0 equiv, HCl salt) in dichloromethane (1.0 mL) at 0° C. was added TEA (96.6 μL, 694 μmol, 6.0 equiv) and acrylic anhydride (43.7 mg, 347 μmol, 3.0 equiv). The mixture was stirred at 0° C. for 10 min prior to being diluted with water (8.0 mL). The mixture was extracted with ethyl acetate (3×10 mL). The combined organic layer was dried over anhydrous sodium sulfate, filtered and concentrated to provide 4-(4-((1R,5R)-2-acryloyl-2,6-diazabicyclo[3.2.0]heptan-6-yl)-8-fluoropyrido[4,3-d]pyrimidin-7-yl)-5-chloronaphthalen-2-yl acrylate (61 mg) as a yellow solid. R$_f$=0.20 [petroleum ether/ethyl acetate/ethanol (2% NH₄OH), 4:3:1]; LCMS [ESI, M+1]: 530.

To a solution of 4-(4-((1R,5R)-2-acryloyl-2,6-diazabicyclo[3.2.0]heptan-6-yl)-8-fluoropyrido[4,3-d]pyrimidin-7-yl)-5-chloronaphthalen-2-yl acrylate (61.0 mg, 115 μmol, 1.0 equiv) in H₂O (0.5 mL) and THF (0.5 mL) was added NaOH (46.0 mg, 1.15 mmol, 10.0 equiv). The mixture was stirred at 25° C. for 0.5 h and then diluted water (8.0 mL). The pH was adjusted to around 7 using solid NH₄Cl and the mixture was extracted with ethyl acetate (3×10 mL). The combined organic layer was dried over anhydrous sodium sulfate, filtered and concentrated to provide the crude material. The residue was purified by prep-HPLC [Phenomenex Gemini NX-C18 (75×30 mm×3 μm); A: water (10 mM NH₄HCO₃), B: ACN; B %: 16%-46% over 8 min) to afford 1-((1R,5R)-6-(7-(8-chloro-3-hydroxynaphthalen-1-yl)-8-fluoropyrido[4,3-d]pyrimidin-4-yl)-2,6-diazabicyclo[3.2.0]heptan-2-yl)prop-2-en-1-one (7.93 mg, 14% yield) as a yellow solid. R$_f$=0.10 [petroleum ether/ethyl acetate/ethanol (2% NH₄OH), 4:3:1]; ¹H NMR (400 MHz, CDCl₃): δ 10.43-9.25 (m, 1H), 9.13-8.84 (m, 1H), 8.81-8.63 (m, 1H), 7.67-7.47 (m, 1H), 7.30-7.27 (m, 1H), 7.26-7.12 (m, 3H), 6.65-6.13 (m, 2H), 5.87-5.70 (m, 1H), 5.56-4.52 (m, 3H), 4.43-4.21 (m, 1H), 4.16-3.94 (m, 1H), 3.91-3.54 (m, 1H), 2.73-2.44 (m, 1H), 2.29-2.03 (m, 1H); LCMS [ESI, M+1]: 476.

Example 289

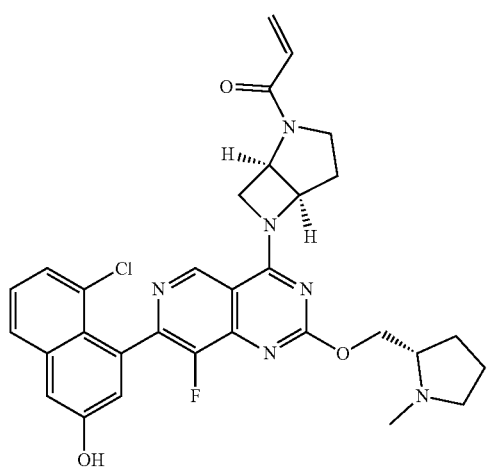 [SMILES: C=CC(=O)N1CC[C@@H]2[C@H]1CN2c1nc(OC[C@@H]2CCCN2C)nc2c(F)c(-c3cc(O)cc4cccc(Cl)c34)ncc12]

1-((1R, 5R)-6-(7-(8-chloro-3-hydroxynaphthalen-1-yl)-8-fluoro-2-(((S)-1-methylpyrrolidin-2-yl)methoxy)pyrido[4,3-d]pyrimidin-4-yl)-2,6-diazabicyclo[3.2.0]heptan-2-yl)prop-2-en-1-one
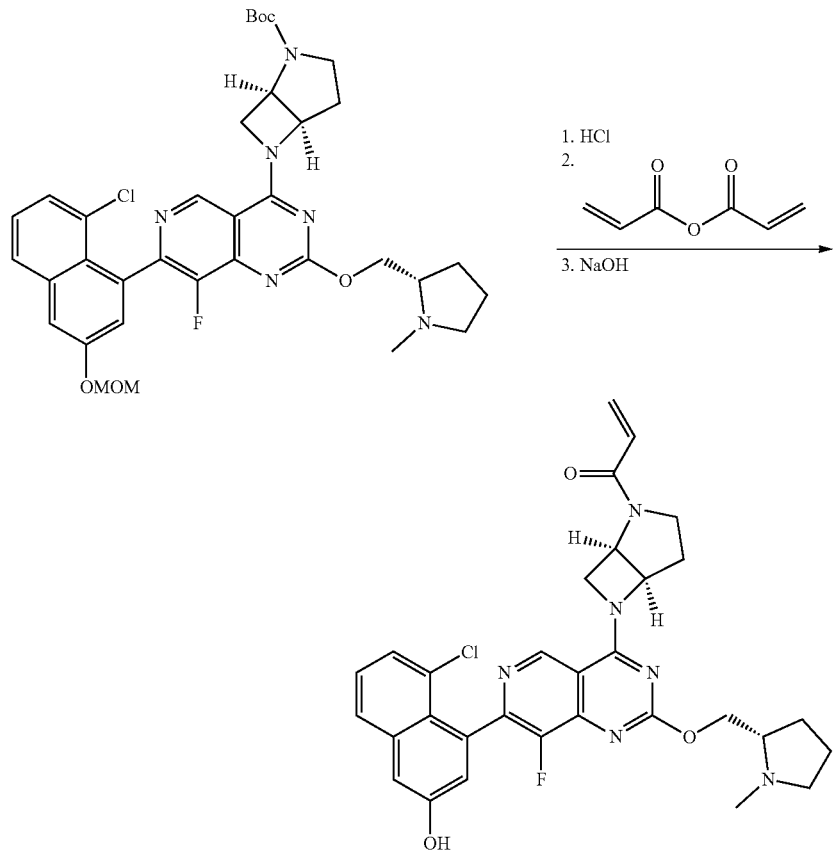
Procedure as Ex 288: LCMS [ESI, M+1]: 589.2; $^1$H NMR (400 MHz, CDCl$_3$): δ 8.88-8.51 (m, 1H), 7.61-7.41 (m, 1H), 7.27-7.00 (m, 4H), 6.56-6.16 (m, 2H), 5.83-5.64 (m, 1H), 5.44-4.87 (m, 2H), 4.84-4.43 (m, 3H), 4.41-4.13 (m, 3H), 4.04-3.51 (m, 3H), 3.19 (br d, J=2.4 Hz, 1H), 2.92-2.69 (m, 1H), 2.63-2.47 (m, 3H), 2.36 (br s, 1H), 2.15-1.87 (m, 3H).
Example 290
1-((1R, 5R)-6-(7-(8-ethynyl-7-fluoronaphthalen-1-yl)-8-fluoropyrido[4,3-d]pyrimidin-4-yl)-2,6-diazabicyclo[3.2.0]heptan-2-yl)prop-2-en-1-one
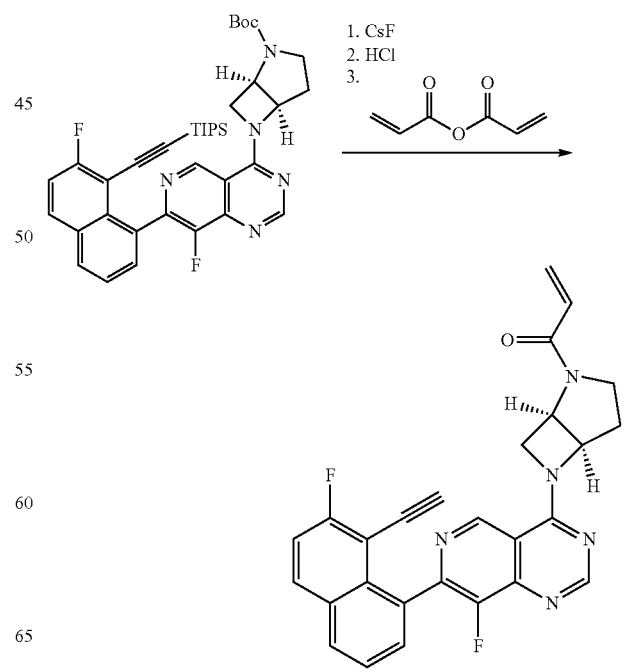
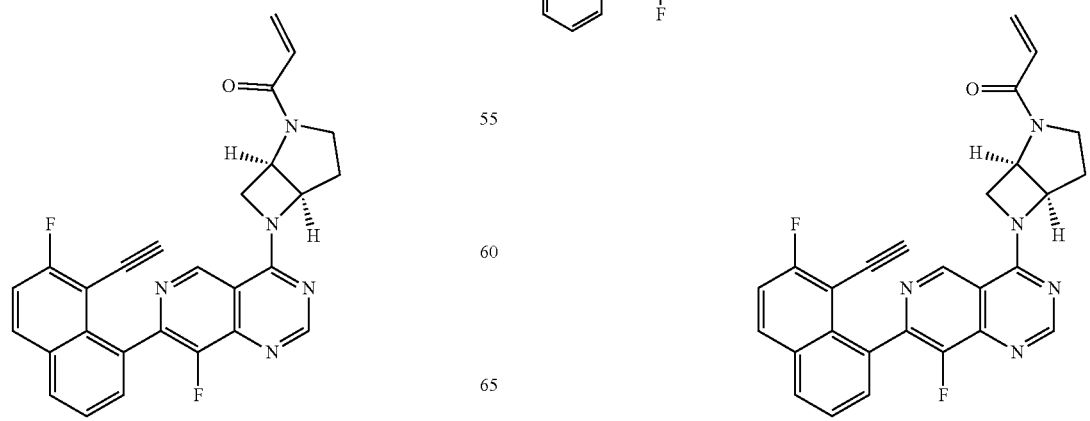

751

To a solution of tert-butyl (1R,5R)-6-(8-fluoro-7-(7-fluoro-8-((triisopropylsilyl)ethynyl)naphthalen-1-yl)pyrido[4,3-d]pyrimidin-4-yl)-2,6-diazabicyclo[3.2.0]heptane-2-carboxylate (150 mg, 224 μmol, 1.0 equiv) in DMF (1.5 mL) was added CsF (340 mg, 2.24 mmol, 10 equiv). The mixture allowed to stir at room temperature for 1 h prior to being filtered. The filtrate (in DMF) was purified by reversed phase flash chromatography [water (0.1% FA) in acetonitrile] to provide tert-butyl (1R,5R)-6-(7-(8-ethynyl-7-fluoronaphthalen-1-yl)-8-fluoropyrido[4,3-d]pyrimidin-4-yl)-2,6-diazabicyclo[3.2.0]heptane-2-carboxylate as a yellow solid. LCMS [ESI, M+1]: 514.2.

To a solution of tert-butyl (1R,5R)-6-(7-(8-ethynyl-7-fluoronaphthalen-1-yl)-8-fluoropyrido[4,3-d]pyrimidin-4-yl)-2,6-diazabicyclo[3.2.0]heptane-2-carboxylate (50.0 mg, 97.4 μmol, 1.0 equiv) in ACN (0.18 mL) was added HCl (4 M in dioxane, 365 μL, 15 equiv). The mixture was allowed to stir for 30 min prior to being concentrated under vacuum to afford 4-((1R,5R)-2,6-diazabicyclo[3.2.0]heptan-6-yl)-7-(8-ethynyl-7-fluoronaphthalen-1-yl)-8-fluoropyrido[4,3-d]pyrimidine (50 mg, crude, bis-HCl salt) as a yellow solid. LCMS [ESI, M+1]: 414.0.

To a solution of 4-((1R,5R)-2,6-diazabicyclo[3.2.0]heptan-6-yl)-7-(8-ethynyl-7-fluoronaphthalen-1-yl)-8-fluoropyrido[4,3-d]pyrimidine (43.0 mg, 88 μmol, 0.85 equiv, bis-HCl salt) in DCM (1.0 mL) at −40° C. was added TEA (57.9 μL, 416 μmol, 4.0 equiv) and prop-2-enoyl prop-2-enoate (15.7 mg, 125 μmol, 1.2 eq). The mixture was allowed to stir at this temperature for 30 min prior to being diluted with methanol (0.5 mL) and water (40 mL). The aqueous phase was extracted with ethyl acetate (2×40 mL). Combined organic layer was dried over anh Na$_2$SO$_4$, filtered and concentrated at reduced pressure. The resultant residue was purified by prep-HPLC [Waters Xbridge 150×25 mm×5 μm; A: water (10 mM NH$_4$HCO$_3$), B: ACN; B %: 25%-55%, 10 min] to afford 1-((1R,5R)-6-(7-(8-ethynyl-7-fluoronaphthalen-1-yl)-8-fluoropyrido[4,3-d]pyrimidin-4-yl)-2,6-diazabicyclo[3.2.0]heptan-2-yl)prop-2-en-1-one (13.8 mg, 35% over two steps) as a yellow solid. R$_f$=0.50 (10:1, dichloromethane/methanol); LCMS [ESI, M+1]: 468.5; $^1$H NMR (400 MHz, CDCl$_3$): δ 9.10-9.03 (m, 1H), 8.87-8.81 (m, 1H), 8.05-7.96 (m, 1H), 7.67-7.59 (m, 2H), 7.42-7.34 (m, 1H), 6.65-6.41 (m, 2H), 5.90-5.80 (m, 1H), 5.74-5.50 (m, 1H), 5.26-4.79 (m, 2H), 4.56-4.13 (m, 2H), 4.07-3.70 (m, 1H), 2.86-2.62 (m, 2H), 2.41-2.13 (m, 1H).

Example 291

752

1-((1R,5R)-6-(7-(8-ethynyl-3-hydroxynaphthalen-1-yl)-8-fluoropyrido[4,3-d]pyrimidin-4-yl)-2,6-diazabicyclo[3.2.0]heptan-2-yl)prop-2-en-1-one

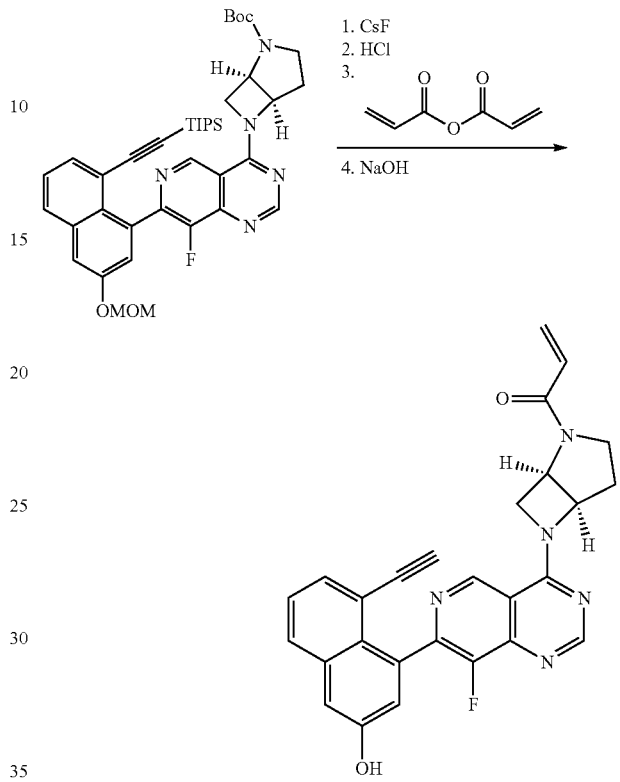

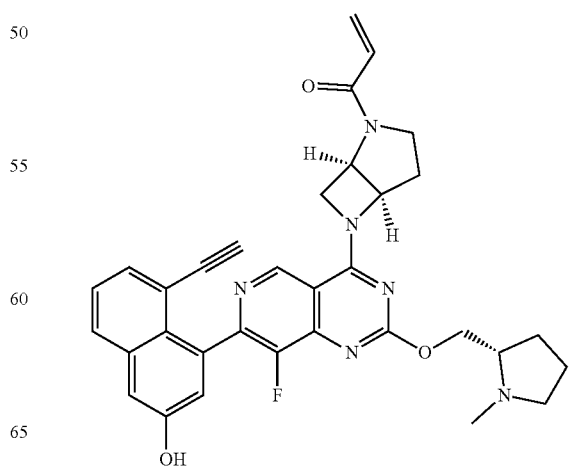

Procedure as Ex 290 (Steps 1-3)/288 (Step 3): LCMS [ESI, M+1]: 466; $^1$H NMR (400 MHz, CDCl$_3$): δ 9.05-8.88 (m, 1H), 8.81-8.69 (m, 1H), 7.69 (br t, J=9.2 Hz, 1H), 7.49 (br d, J=4.4 Hz, 1H), 7.35-7.28 (m, 1H), 7.26-7.12 (m, 2H), 6.66-6.24 (m, 2H), 5.88-5.71 (m, 1H), 5.63-5.32 (m, 1H), 5.16-4.56 (m, 2H), 4.46-4.24 (m, 1H), 4.19-4.00 (m, 1H), 3.96-3.60 (m, 1H), 2.76-2.50 (m, 1H), 2.48-2.40 (m, 1H), 2.32-1.96 (m, 1H).

Example 292

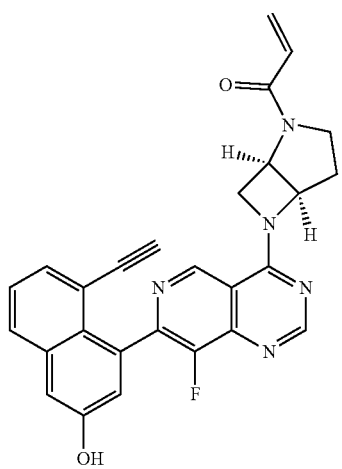 [SMILES: C#Cc1cccc2cc(O)cc(-c3ncc4c(N5C[C@@H]6[C@H]5CCN6C(=O)C=C)ncnc4c3F)c12]

1-(((1R,5R)-6-(7-(8-ethynyl-3-hydroxynaphthalen-1-yl)-8-fluoro-2-(((S)-1-methylpyrrolidin-2-yl)methoxy)pyrido[4,3-d]pyrimidin-4-yl)-2,6-diazabicyclo[3.2.0]heptan-2-yl)prop-2-en-1-one
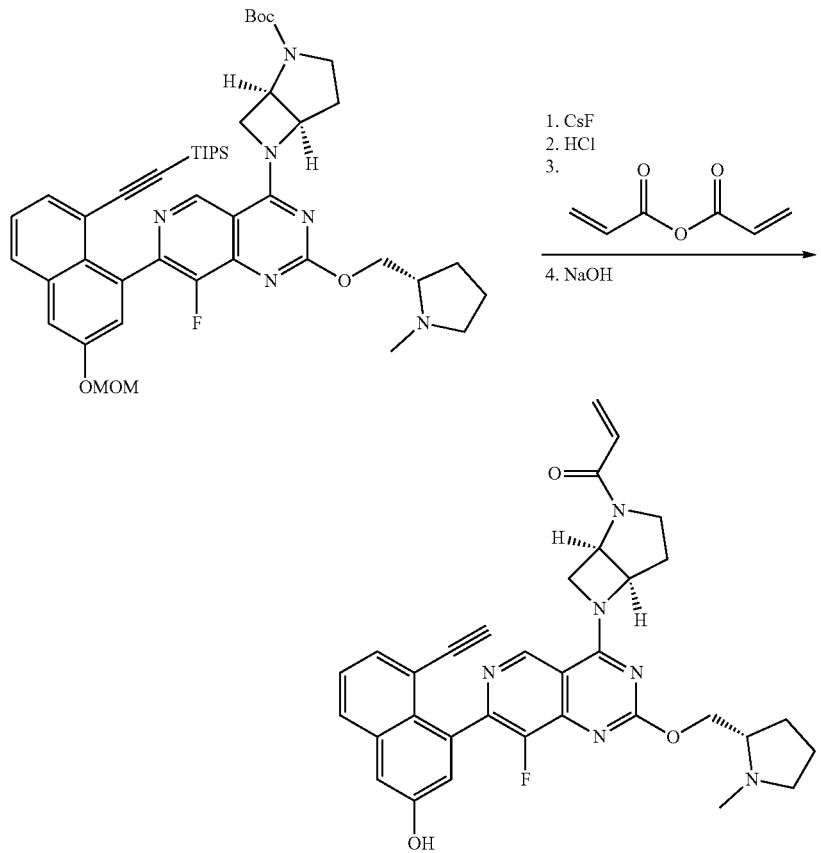
Procedure as Ex 290 (Steps 1-3)/288 (Step 3): LCMS [ESI, M+1]: 579.3; $^1$H NMR (400 MHz, CDCl$_3$): δ 8.84-8.60 (m, 1H), 7.76-7.61 (m, 1H), 7.56-7.46 (m, 1H), 7.32-7.28 (m, 1H), 7.27-7.13 (m, 2H), 6.59-6.13 (m, 2H), 5.84-5.67 (m, 1H), 5.51-4.93 (m, 1H), 4.91-4.49 (m, 2H), 4.44-3.84 (m, 3H), 3.80-3.53 (m, 1H), 3.28-3.13 (m, 1H), 2.86-2.74 (m, 1H), 2.62-2.28 (m, 8H), 2.14-1.99 (m, 2H), 1.96-1.85 (m, 2H).
Example 293
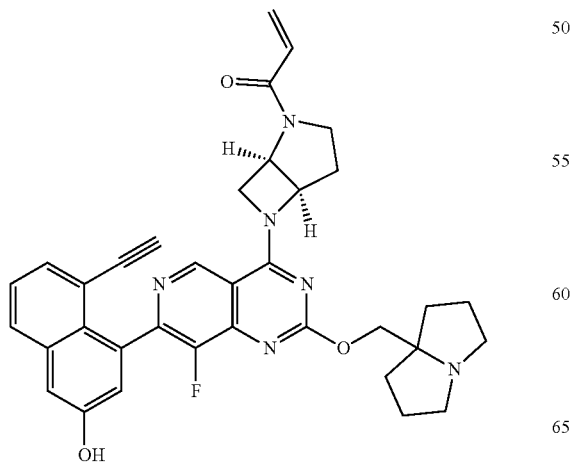

1-((1R, 5R)-6-(7-(8-ethynyl-3-hydroxynaphthalen-1-yl)-8-fluoro-2-((tetrahydro-1H-pyrrolizin-7a(5H)-yl)methoxy)pyrido[4,3-d]pyrimidin-4-yl)-2,6-diazabicyclo[3.2.0]heptan-2-yl)prop-2-en-1-one
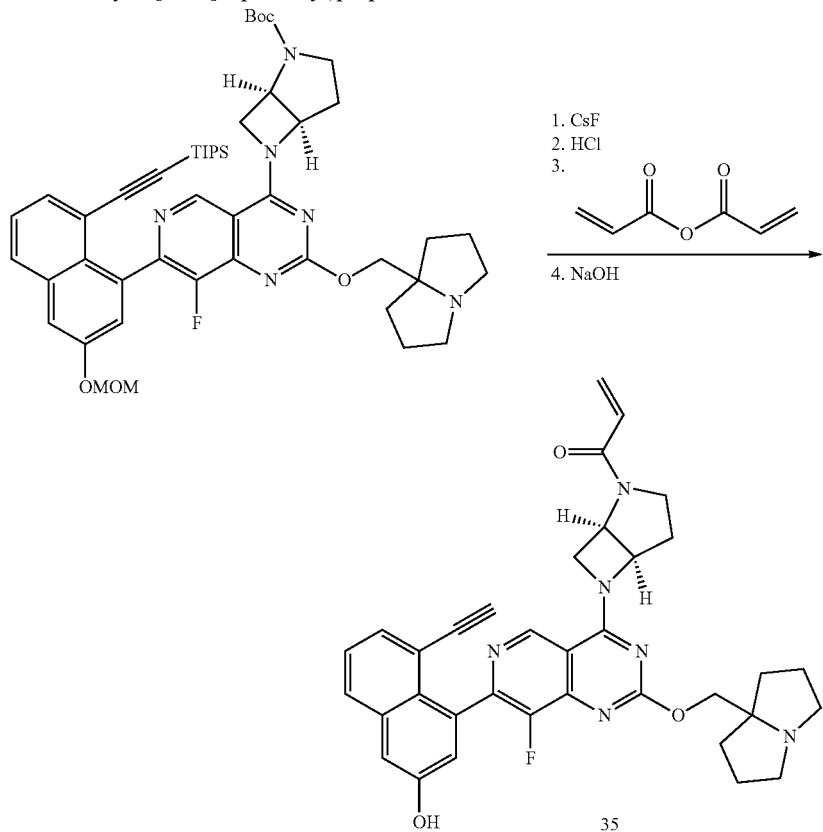
Procedure as Ex 290 (Steps 1-3)/288 (Step 3): LCMS [ESI, M+1]: 605; ¹H NMR (400 MHz, CDCl₃) δ 8.82-8.52 (m, 1H), 7.63 (br d, J=8.0 Hz, 1H), 7.52-7.41 (m, 1H), 7.32-7.27 (m, 1H), 7.25-6.93 (m, 2H), 6.58-6.05 (m, 2H), 5.88-5.61 (m, 1H), 5.47-4.80 (m, 2H), 4.70-4.00 (m, 6H), 3.99-3.46 (m, 2H), 3.43-3.20 (m, 2H), 2.83-2.66 (m, 2H), 2.60-2.51 (m, 1H), 2.51-2.27 (m, 1H), 2.21-2.09 (m, 2H), 2.07-1.92 (m, 3H), 1.78-1.67 (m, 2H).
Example 294
1-((1R,5R)-6-(7-(3-chloro-8-ethynylnaphthalen-1-yl)-8-fluoropyrido[4,3-d]pyrimidin-4-yl)-2,6-diazabicyclo[3.2.0]heptan-2-yl)prop-2-en-1-one
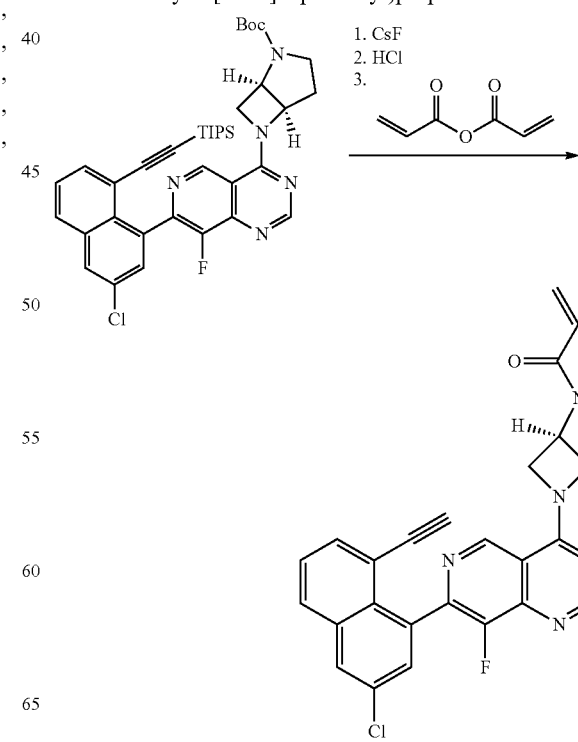
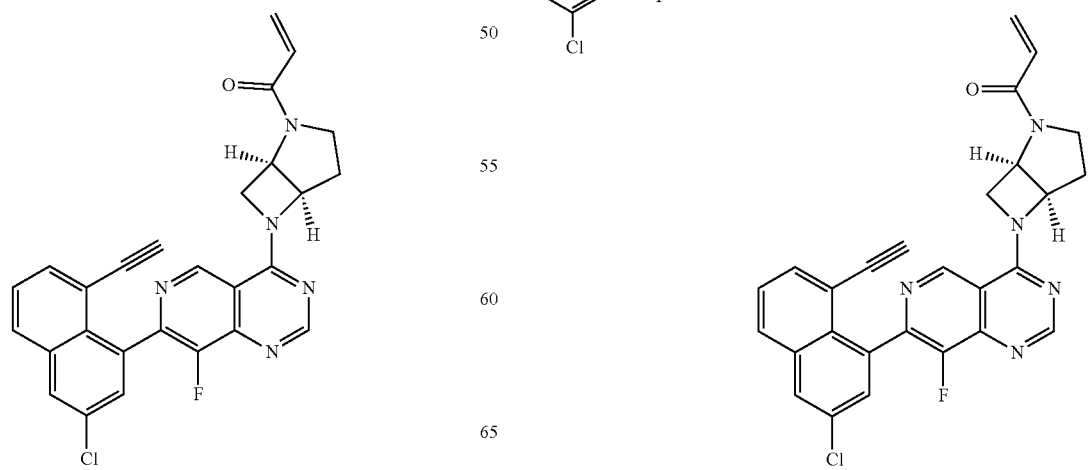

Procedure as Ex 290: LCMS [ESI, M+1]: 484; ¹H NMR (400 MHz, CDCl₃) δ 9.07-8.99 (m, 1H), 8.85-8.79 (m, 1H), 8.02-7.97 (m, 1H), 7.89 (d, J=8.0 Hz, 1H), 7.77-7.72 (m, 1H), 7.57-7.47 (m, 2H), 6.64-6.35 (m, 2H), 5.88-5.78 (m, 1H), 5.71-5.48 (m, 1H), 5.23-4.81 (m, 2H), 4.53-4.14 (m, 2H), 4.03-3.69 (m, 1H), 2.80-2.60 (m, 1H), 2.58-2.49 (m, 1H), 2.38-2.13 (m, 1H).

Following the teachings of the General Reaction Schemes and Examples 1-294, Examples 295-298 were prepared as shown in Table 6:

TABLE 6

Examples 295 to 298

| Ex. # | Structure | Data |
|---|---|---|
| 295 | 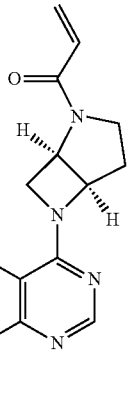<br>1-((1R,5R)-6-(7-(5-ethynylisoquinolin-4-yl)-8-fluoropyrido[4,3-d]pyrimidin-4-yl)-2,6-diazabicyclo[3.2.0]heptan-2-yl)prop-2-en-1-one | LCMS [ESI, M + 1]: 451<br>¹H NMR (400 MHz, CDCl₃) δ 9.39 (s, 1H), 9.06 (s, 1H), 8.89-8.76 (m, 1H), 8.60 (s, 1H), 8.13 (d, J = 8.4 Hz, 1H), 7.96 (br d, J = 7.2 Hz, 1H), 7.64 (t, J = 8.0 Hz, 1H), 6.67-6.34 (m, 2H), 5.83 (dd, J = 2.0, 10.0 Hz, 1H), 5.72-5.50 (m, 1H), 5.24-4.85 (m, 2H), 4.52-4.13 (m, 2H), 4.02-3.71 (m, 1H), 2.83-2.63 (m, 1H), 2.62-2.55 (m, 1H), 2.39-2.14 (m, 1H) |
| 296 | 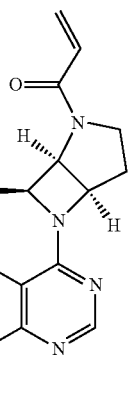<br>1-((1R,5R,7S)-6-(7-(8-ethynyl-7-fluoronaphthalen-1-yl)-8-fluoropyrido[4,3-d]pyrimidin-4-yl)-7-methyl-2,6-diazabicyclo[3.2.0]heptan-2-yl)prop-2-en-1-one | LCMS [ESI, M + 1]: 481.2<br>¹H NMR (400 MHz, CDCl₃) δ 9.09 (dd, J = 2.0, 9.2 Hz, 1H), 8.71 (dd, J = 2.8, 4.0 Hz, 1H), 8.28-8.19 (m, 2H), 7.75-7.58 (m, 3H), 6.86-6.59 (m, 1H), 6.30-6.19 (m, 1H), 5.82-5.50 (m, 2H), 5.16-5.00 (m, 2H), 4.33-4.19 (m, 1H), 4.09-4.01 (m, 1H), 3.83-3.50 (m, 1H), 1.39-1.32 (m, 3H);<br>¹H NMR (400 MHz, CDCl₃) δ 9.16-9.12 (m, 1H), 8.86-8.82 (m, 1H), 8.04-7.95 (m, 2H), 7.67-7.58 (m, 2H), 7.37 (t, J = 8.8 Hz, 1H), 6.67-6.32 (m, 2H), 5.87-5.80 (m, 1H), 5.63-5.41 (m, 1H), 5.34-4.96 (m, 2H), 4.59-4.19 (m, 1H), 3.94-3.68 (m, 1H), 2.87-2.80 (m, 1H), 2.79-2.63 (m, 1H), 2.47-2.23 (m, 1H), 1.54-1.50 (m, 3H) |

TABLE 6-continued

Examples 295 to 298

| Ex. # | Structure | Data |
|---|---|---|
| 297 | 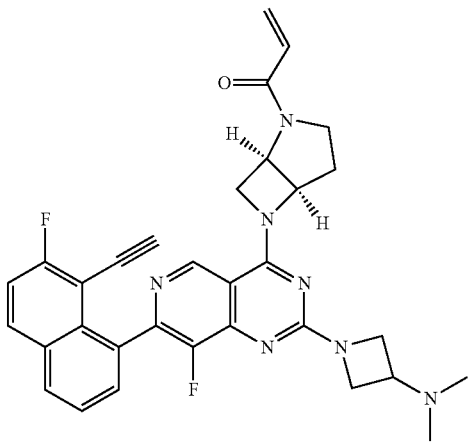<br>1-((1R,5R)-6-(2-(3-(dimethylamino)azetidin-1-yl)-7-(8-ethynyl-7-fluoronaphthalen-1-yl)-8-fluoropyrido[4,3-d]pyrimidin-4-yl)-2,6-diazabicyclo[3.2.0]heptan-2-yl)prop-2-en-1-one | LCMS [ESI, M + 1]: 566<br>$^1$H NMR (400 MHz, CDCl$_3$): δ 8.71-8.65 (m, 1H), 7.96-7.88 (m, 2H), 7.61-7.51 (m, 2H), 7.31 (t, J = 8.8 Hz, 1H), 6.66-6.30 (m, 2H), 5.83-5.75 (m, 1H), 5.57-5.39 (m, 1H), 5.14-4.67 (m, 2H), 4.46-3.96 (m, 6H), 3.94-3.66 (m, 1H), 3.18 (quin, J = 6.0 Hz, 1H), 2.95-2.87 (m, 1H), 2.74-2.51 (m, 1H), 2.23 (s, 6H), 2.20-2.02 (m, 1H) |
| 298 | 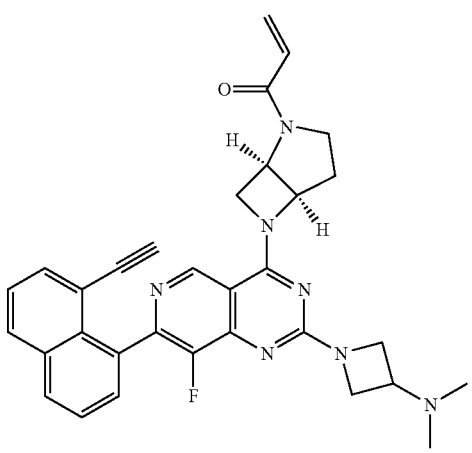<br>1-((1R,5R)-6-(2-(3-(dimethylamino)azetidin-1-yl)-7-(8-ethynylnaphthalen-1-yl)-8-fluoropyrido[4,3-d]pyrimidin-4-yl)-2,6-diazabicyclo[3.2.0]heptan-2-yl)prop-2-en-1-one | LCMS [ESI, M + 1]: 548<br>$^1$H NMR (400 MHz, CDCl$_3$): δ 8.78-8.66 (m, 1H), 7.94 (t, J = 8.8 Hz, 2H), 7.73 (dd, J = 1.2, 7.2 Hz, 1H), 7.63-7.51 (m, 2H), 7.43 (t, J = 7.7 Hz, 1H), 6.63-6.32 (m, 2H), 5.85-5.72 (m, 1H), 5.62-5.36 (m, 1H), 5.15-4.70 (m, 2H), 4.46-4.08 (m, 6H), 3.99-3.67 (m, 1H), 3.54-3.32 (m, 1H), 2.74-2.62 (m, 2H), 2.44 (br s, 6H), 2.24-2.15 (m, 1H) |

Example 299

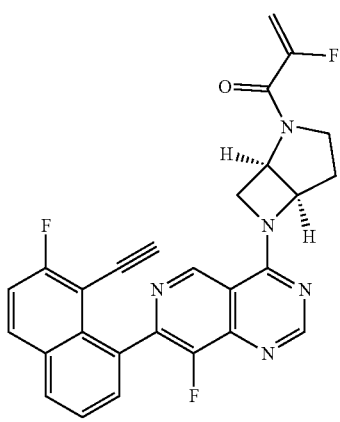 [SMILES: C#Cc1c(F)ccc2cccc(-c3ncc4c(N5C[C@@H]6[C@H]5CCN6C(=O)C(=C)F)ncnc4c3F)c12]

1-((1R,5R)-6-(7-(8-ethynyl-7-fluoronaphthalen-1-yl)-8-fluoropyrido[4,3-d]pyrimidin-4-yl)-2,6-diazabicyclo[3.2.0]heptan-2-yl)-2-fluoroprop-2-en-1-one To a solution of 4-((1R,5R)-2,6-diazabicyclo[3.2.0]heptan-6-yl)-7-(8-ethynyl-7-fluoronaphthalen-1-yl)-8-fluoropyrido[4,3-d]pyrimidine (100 mg, 241 µmol, 1.0 equiv) in ethyl acetate (0.5 mL) at 25° C. was added 4 Å MS (100 mg, 242 µmol) followed by the dropwise addition of TEA (269 µL, 1.94 mmol, 8.0 equiv). The mixture was stirred for 10 min and cooled to −40° C. prior to the dropwise addition of 2-fluoroprop-2-enoic acid (65.3 mg, 726 µmol, 3.0 equiv) in ethyl acetate (0.5 mL). To the resultant mixture at −40° C. was added dropwise T3P (719 µL, 1.21 mmol, 50% in EtOAc, 5.0 equiv) and stirring was continued at this temperature for 30 min. An additional portion of 2-fluoroprop-2-enoic acid (65.4 mg, 726 µmol, 3.0 equiv) and T3P (719 µL 1.21 mmol, 50% in EtOAc, 5.0 equiv) was added dropwise at −40° C. The resulting mixture was stirred for an additional 30 min at this temperature. The reaction mixture was concentrated under reduced pressure. The residue was diluted with satd aq NaHCO₃ (2 mL) and extracted with ethyl acetate (3×5 mL). The combined organic layer was washed with brine (5 mL×1), dried over anh Na₂SO₄, filtered and concentrated. The residue was purified by prep-HPLC [column: Waters Xbridge 150×25 mm×5 µm; A: water (10 mM NH₄HCO₃), B: ACN, B %: 27%-57%, 10 min] to afford 1-((1R,5R)-6-(7-(8-ethynyl-7-fluoronaphthalen-1-yl)-8-fluoropyrido[4,3-d]pyrimidin-4-yl)-2,6-diazabicyclo[3.2.0]heptan-2-yl)-2-fluoroprop-2-en-1-one (26 mg, 22% yield). ¹H NMR (400 MHz, CDCl₃): δ 9.05 (d, J=3.6 Hz, 1H), 8.83 (s, 1H), 8.08-7.92 (m, 2H), 7.68-7.57 (m, 2H), 7.36 (t, J=8.8 Hz, 1H), 5.75-5.49 (m, 2H), 5.31-4.86 (m, 3H), 4.62-4.24 (m, 2H), 4.08-3.72 (m, 1H), 2.84-2.79 (m, 1H), 2.78-2.60 (m, 1H), 2.37-2.11 (m, 1H); LCMS [ESI, M+1]: 486.1.

Example 300

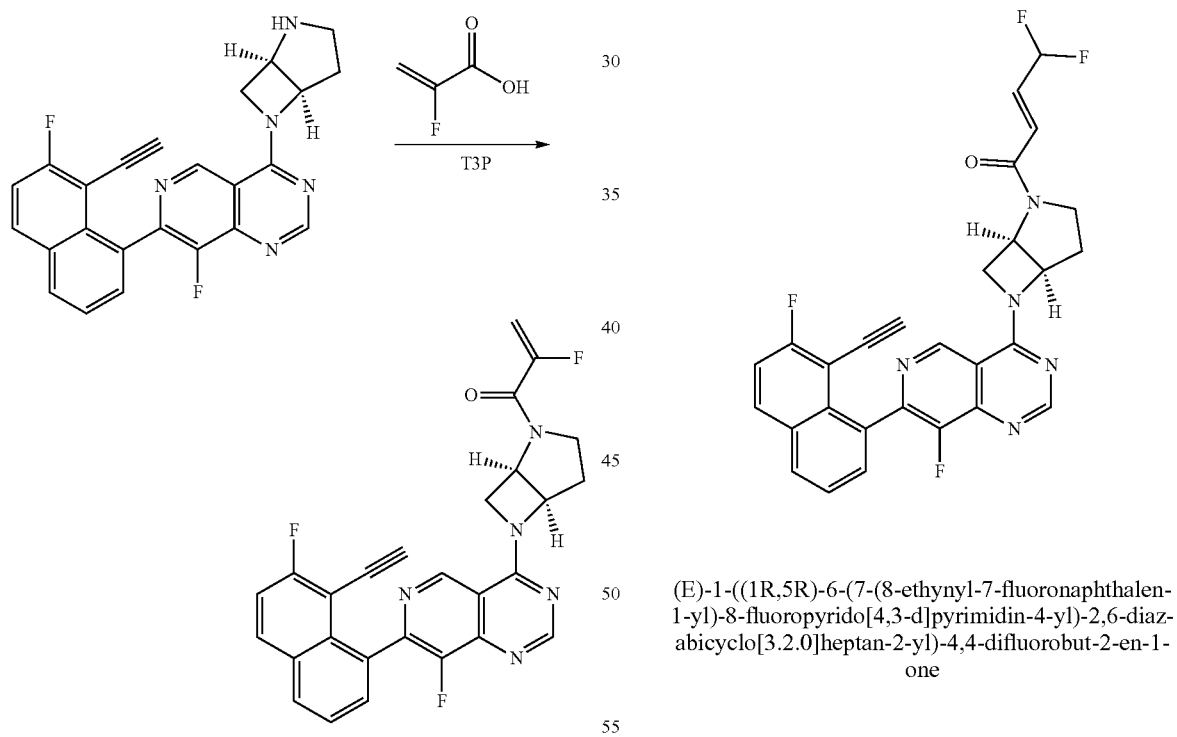

(E)-1-((1R,5R)-6-(7-(8-ethynyl-7-fluoronaphthalen-1-yl)-8-fluoropyrido[4,3-d]pyrimidin-4-yl)-2,6-diazabicyclo[3.2.0]heptan-2-yl)-4,4-difluorobut-2-en-1-one

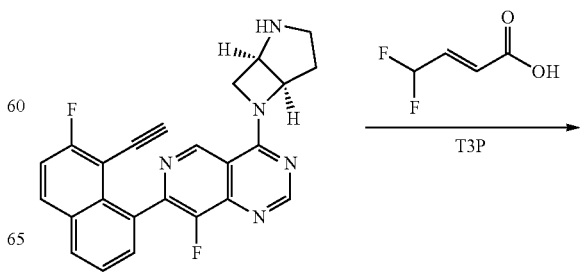

-continued

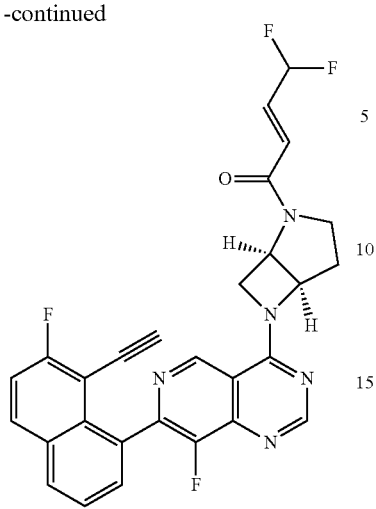

Procedure as Ex 55: LCMS [ESI, M+1]: 518; ¹H NMR (400 MHz, CDCl₃) δ 9.02 (d, J=2.8 Hz, 1H), 8.85-8.76 (m, 1H), 8.04-7.88 (m, 2H), 7.69-7.53 (m, 2H), 7.34 (t, J=8.8 Hz, 1H), 6.98-6.81 (m, 1H), 6.79-6.50 (m, 1H), 6.47-6.09 (m, 1H), 5.71-5.48 (m, 1H), 5.22-4.82 (m, 2H), 4.56-4.10 (m, 2H), 4.06-3.68 (m, 1H), 2.91-2.52 (m, 2H), 2.42-2.10 (m, 1H).

Example 301

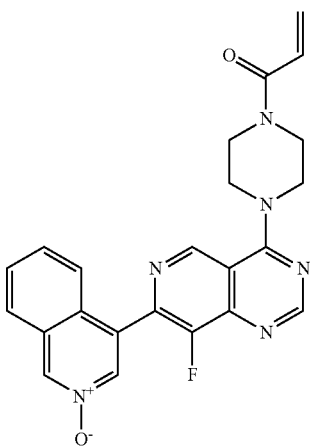

4-(4-(4-acryloylpiperazin-1-yl)-8-fluoropyrido[4,3-d]pyrimidin-7-yl)isoquinoline 2-oxide

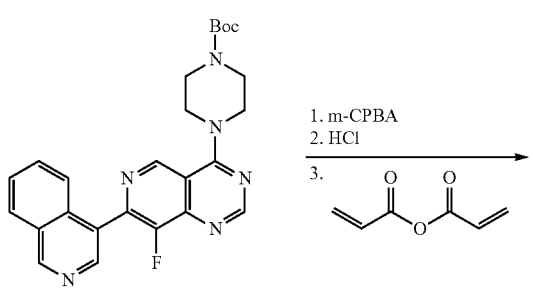

-continued

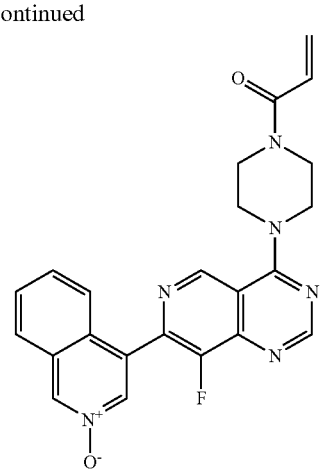

To a mixture of tert-butyl 4-(8-fluoro-7-(isoquinolin-4-yl)pyrido[4,3-d]pyrimidin-4-yl)piperazine-1-carboxylate (426 mg, 675.31 μmol, 1.0 equiv) in DCM (3.0 mL) at 0° C. was added m-CPBA (146 mg, 675 μmol, 80% purity, 1.0 equiv). The mixture was warmed to room temperature and stirred for 1 h. An additional portion of m-CPBA (146 mg, 675 μmol, 80% purity, 1.0 equiv) was added and the mixture was stirred for 24 h. The mixture was diluted with saturated NaHCO₃ (6.0 mL) and was extracted with ethyl acetate (3×10 mL). The combined organic layer was dried with anhydrous Na₂SO₄, filtered and concentrated under reduced pressure to provide the crude residue. The crude product was purified by reversed phase flash chromatography to give 4-(4-(4-(tert-butoxycarbonyl)piperazin-1-yl)-8-fluoropyrido[4,3-d]pyrimidin-7-yl)isoquinoline 2-oxide (123 mg, 37% yield) as a brown solid. LCMS [ESI, M+1]: 477.

To a mixture of 4-(4-(4-(tert-butoxycarbonyl)piperazin-1-yl)-8-fluoropyrido[4,3-d]pyrimidin-7-yl)isoquinoline 2-oxide in ACN (0.5 mL) at 0° C. was added HCl (4 M in dioxane, 1 mL, 19.1 equiv) in one portion. The mixture was stirred at 0° C. for 30 min and was concentrated under reduced pressure to give 4-(8-fluoro-4-(piperazin-1-yl)pyrido[4,3-d]pyrimidin-7-yl)isoquinoline 2-oxide (100 mg, HCl salt) as a yellow solid.

Example 302

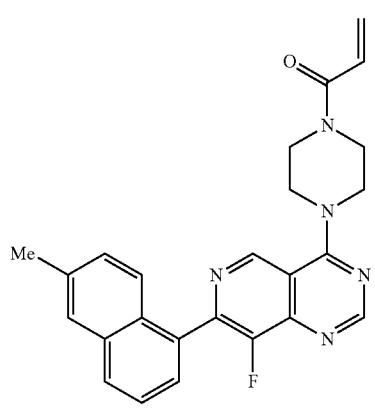

1-(4-(8-fluoro-7-(6-methylnaphthalen-1-yl)pyrido[4,3-d]pyrimidin-4-yl)piperazin-1-yl)prop-2-en-1-one

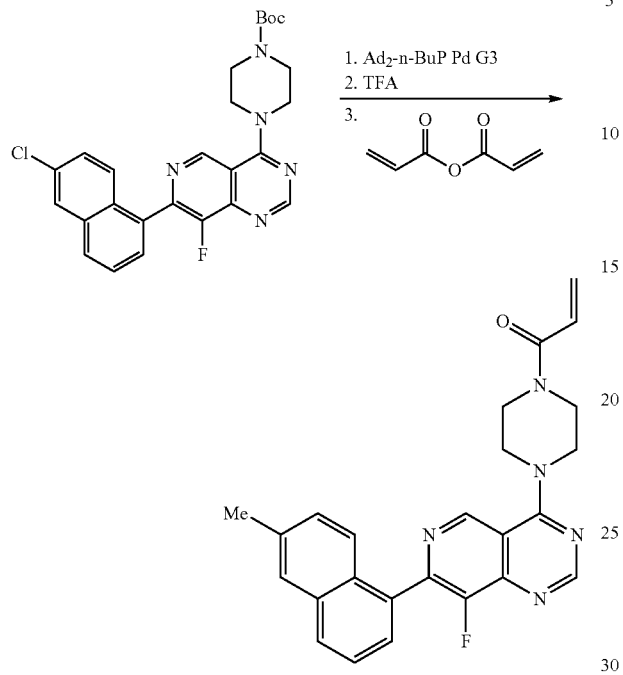

To a solution of tert-butyl 4-(7-(6-chloronaphthalen-1-yl)-8-fluoropyrido[4,3-d]pyrimidin-4-yl)piperazine-1-carboxylate (100 mg, 202 µmol, 1.0 equiv) in THF (5 mL) was added MeB(OH)$_2$ (60.6 mg, 1.01 mmol, 5.0 equiv) Ad$_2$-n-BuP Pd G3 (cataCXium® A Pd G3) (29.5 mg, 40.5 µmol, 0.2 equiv) and K$_3$PO$_4$ (258 mg, 1.21 mmol, 6.0 equiv). The mixture was stirred at 60° C. for 12 h under N$_2$. After 12 hours, another portion of MeB(OH)$_2$ (60.6 mg, 1.01 mmol, 5.0 equiv), Ad$_2$-n-BuP Pd G3 (cataCXium® A Pd G3) (29.5 mg, 40.5 µmol, 0.2 equiv) and aq K$_3$PO$_4$ (1.5 M, 810 µL, 6.0 equiv) in THF (5 mL) was added. The mixture was stirred at 60° C. for an additional 12 h. The mixture was diluted with water (5 mL) and extracted with ethyl acetate (3×5 mL). The combined organic layer was washed with brine (5 mL), dried over anh Na$_2$SO$_4$, filtered and concentrated to dryness. The residue was purified by column chromatography (SiO$_2$, petroleum ether/ethyl acetate, 1:0 to 1:1) to provide tert-butyl 4-(8-fluoro-7-(6-methylnaphthalen-1-yl)pyrido[4,3-d]pyrimidin-4-yl)piperazine-1-carboxylate (57 mg, 56% yield) as a yellow solid. LCMS [ESI, M+1]: 474.2.

To a solution of tert-butyl 4-(8-fluoro-7-(6-methylnaphthalen-1-yl)pyrido[4,3-d]pyrimidin-4-yl)piperazine-1-carboxylate (50.0 mg, 105 µmol, 1.0 equiv) in DCM (0.5 mL) was added TFA (0.50 mL, 1.0 equiv). The mixture was stirred at 0° C. for 10 min, was concentrated and diluted with water (1 mL). The mixture was diluted with saturated NaHCO$_3$ aqueous solution and extracted with DCM (3×1 mL). The combined organic phase was washed with brine (1 mL), dried over anh Na$_2$SO$_4$, filtered and concentrated to afford 8-fluoro-7-(6-methylnaphthalen-1-yl)-4-(piperazin-1-yl)pyrido[4,3-d]pyrimidine (90 mg, crude) as a yellow solid. LCMS [ESI, M+1]: 374.2.

To a solution of 8-fluoro-7-(6-methylnaphthalen-1-yl)-4-(piperazin-1-yl)pyrido[4,3-d]pyrimidine (85.0 mg, 228 µmol, 1.0 equiv) in DCM (2 mL) at −40° C. was added DIEA (198 µL, 1.14 mmol, 5.0 equiv) and acrylic anhydride (71.8 mg, 569 µmol, 2.5 equiv). The mixture was stirred at −40° C. for 20 min prior to being diluted with saturated aq NH$_4$Cl (3 ml) and extracted with ethyl acetate (3×5 mL). The combined organic layer was washed with brine (5 mL), dried over anh Na$_2$SO$_4$. The mixture was filtered and concentrated under reduced pressure. The residue was purified by prep-HPLC [Waters Xbridge 150×25 mm×5 µm; A: water (10 mM NH$_4$HCO$_3$), B %: ACN, 33%-63%,10 min] to afford 1-(4-(8-fluoro-7-(6-methylnaphthalen-1-yl)pyrido[4,3-d]pyrimidin-4-yl)piperazin-1-yl)prop-2-en-1-one (15.0 mg, 35% over two steps) as a white solid. $^1$H NMR (400 MHz, CDCl$_3$): δ 9.29 (s, 1H), 8.95-8.85 (m, 1H), 7.93 (d, J=8.0 Hz, 1H), 7.74-7.57 (m, 4H), 7.32 (dd, J=1.6, 8.8 Hz, 1H), 6.63 (dd, J=10.4, 16.8 Hz, 1H), 6.41 (dd, J=1.6, 16.8 Hz, 1H), 5.82 (dd, J=1.6, 10.4 Hz, 1H), 4.18-4.10 (m, 4H), 4.01-3.83 (m, 4H), 2.54 (s, 3H); LCMS [ESI, M+1]: 428.2.

Example 303

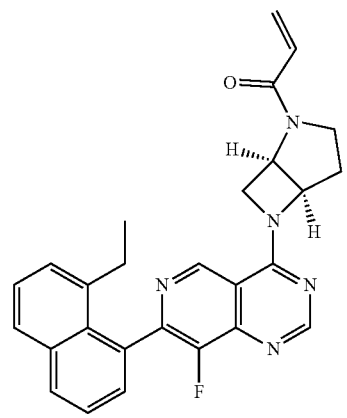 [SMILES: C=CC(=O)N1CC[C@@H]2[C@H]1CN2c1ncnc2c(F)c(-c3cccc4cccc(CC)c34)ncc12]

1-((1R, 5R)-6-(7-(8-ethylnaphthalen-1-yl)-8-fluoropyrido[4,3-d]pyrimidin-4-yl)-2,6-diazabicyclo[3.2.0]heptan-2-yl)prop-2-en-1-one

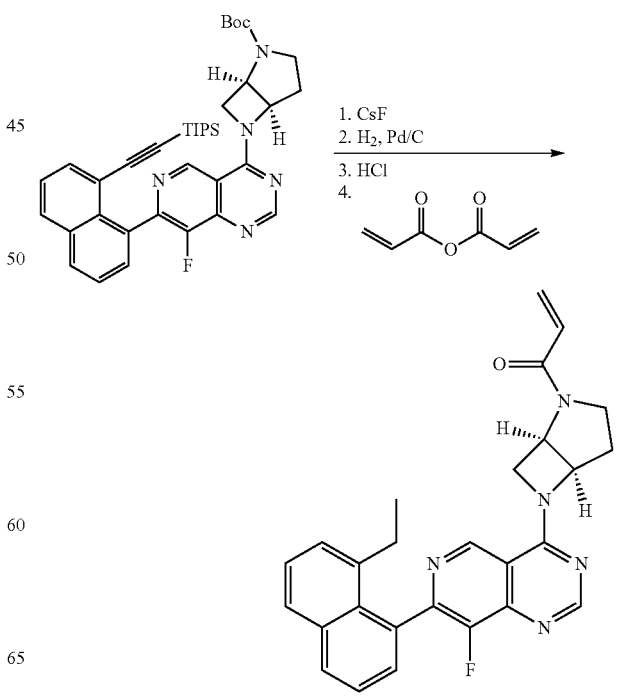

To a solution of tert-butyl (1R,5R)-6-(8-fluoro-7-(8-((tri-isopropylsilyl)ethynyl)naphthalen-1-yl)pyrido[4,3-d]pyrimidin-4-yl)-2,6-diazabicyclo[3.2.0]heptane-2-carboxylate (530 mg, 813 μmol, 1.0 equiv) in DMF (6.00 mL) was added CsF (1.24 g, 8.13 mmol, 10 equiv) and the mixture was stirred at 25° C. for 1 h. The reaction mixture was diluted with water (20 mL) and extracted with ethyl acetate (3×30 mL). The combined organic layer was washed with brine (3×30 mL), dried over anhydrous sodium sulfate and filtered. The filtrate was concentrated under reduced pressure to afford tert-butyl (1R,5R)-6-(7-(8-ethynylnaphthalen-1-yl)-8-fluoropyrido[4,3-d]pyrimidin-4-yl)-2,6-diazabicyclo[3.2.0]heptane-2-carboxylate (400 mg, 99% yield) as a yellow solid. LCMS [ESI, M+1]: 496.

To a solution of tert-butyl (1R,5R)-6-(7-(8-ethynylnaphthalen-1-yl)-8-fluoropyrido[4,3-d]pyrimidin-4-yl)-2,6-diazabicyclo[3.2.0]heptane-2-carboxylate (400 mg, 807 μmol, 1.0 equiv) in MeOH (40.0 mL) was added Pd/C (300 mg, 10% purity). The suspension was evacuated and purged with H₂ several times. The mixture was stirred under H₂ (15 psi) at 25° C. for 2 h. The vessel was flushed with nitrogen, the mixture was filtered and the filter cake was washed with THF (40 mL). The filtrate was concentrated under reduced pressure to provide tert-butyl (1R,5R)-6-(7-(8-ethylnaphthalen-1-yl)-8-fluoropyrido[4,3-d]pyrimidin-4-yl)-2,6-diazabicyclo[3.2.0]heptane-2-carboxylate (550 mg) as a brown solid. LCMS [ESI, M+1]: 500.

To a solution of tert-butyl (1R,5R)-6-(7-(8-ethylnaphthalen-1-yl)-8-fluoropyrido[4,3-d]pyrimidin-4-yl)-2,6-diazabicyclo[3.2.0]heptane-2-carboxylate (550 mg, 1.10 mmol, 1.0 equiv) in MeCN (2.00 mL) was added HCl (4 M in dioxane, 1.93 mL, 7.0 equiv). The mixture was stirred at 0° C. for 30 min. The mixture was diluted with water (3 mL) and solid Na₂CO₃ was added until the pH was about 10. The mixture was extracted with ethyl acetate (3 mL×3). The combined organic layer was dried over anhydrous sodium sulfate, filtered and concentrated to dryness to afford 4-((1R,5R)-2,6-diazabicyclo[3.2.0]heptan-6-yl)-7-(8-ethylnaphthalen-1-yl)-8-fluoropyrido[4,3-d]pyrimidine (450 mg) as a brown solid. LCMS [ESI, M+1]: 400.

To a solution of 4-((1R,5R)-2,6-diazabicyclo[3.2.0]heptan-6-yl)-7-(8-ethylnaphthalen-1-yl)-8-fluoropyrido[4,3-d]pyrimidine (440 mg, 1.10 mmol, 1.0 equiv) in dichloromethane (2.00 mL) was added DIEA (959 μL, 5.51 mmol, 5.0 equiv) and acrylic anhydride (125 mg, 991 μmol, 0.90 equiv). The mixture was stirred at −40° C. for 10 min. The mixture was directly loaded on a column and purified (SiO₂, petroleum ether/ethyl acetate/Et₀H/NH₄OH, 10:1:0:0 to 4:3:1:0.1) and again by prep-HPLC [Waters Xbridge 150×25 mm×5 um; A: water (10 mM NH₄HCO₃), B %: ACN; B: 27%-57%, 9 min] to afford 1-((1R,5R)-6-(7-(8-ethylnaphthalen-1-yl)-8-fluoropyrido[4,3-d]pyrimidin-4-yl)-2,6-diazabicyclo[3.2.0]heptan-2-yl)prop-2-en-1-one (111 mg, 22% yield) as an off-white solid. HPLC: 99.8% purity; SFC: Chiralpak AD-3 50×4.6 mm I.D., 3 um, 40% MeOH (0.05% DEA) in CO₂, 3 mL/min, 35° C., $t_R$=1.869 min; ¹H NMR (400 MHz, CDCl₃): δ 9.04 (s, 1H), 8.86-8.81 (m, 1H), 8.00 (d, J=8.0 Hz, 1H), 7.82 (d, J=8.0 Hz, 1H), 7.53 (t, J=7.6 Hz, 1H), 7.48 (t, J=7.6 Hz, 1H), 7.40 (br dd, J=7.2, 18.4 Hz, 2H), 6.70-6.30 (m, 2H), 5.87-5.78 (m, 1H), 5.68-5.47 (m, 1H), 5.23-4.77 (m, 2H), 4.56-4.11 (m, 2H), 4.05-3.65 (m, 1H), 2.87-2.57 (m, 1H), 2.44-2.08 (m, 3H), 0.95 (t, J=7.6 Hz, 3H); LCMS [ESI, M+1]: 454.

Example 304

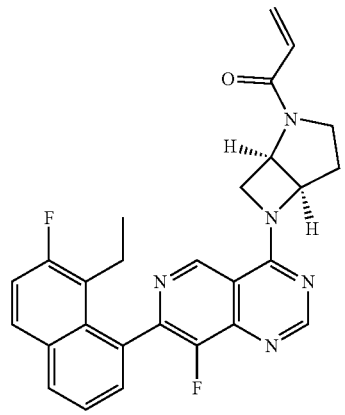 [SMILES: C=CC(=O)N1CC[C@@H]2[C@H]1CN2c1ncnc2c(F)c(-c3cccc4ccc(F)c(CC)c34)ncc12]

1-((1R,5R)-6-(7-(8-ethyl-7-fluoronaphthalen-1-yl)-8-fluoropyrido[4,3-d]pyrimidin-4-yl)-2,6-diazabicyclo[3.2.0]heptan-2-yl)prop-2-en-1-one

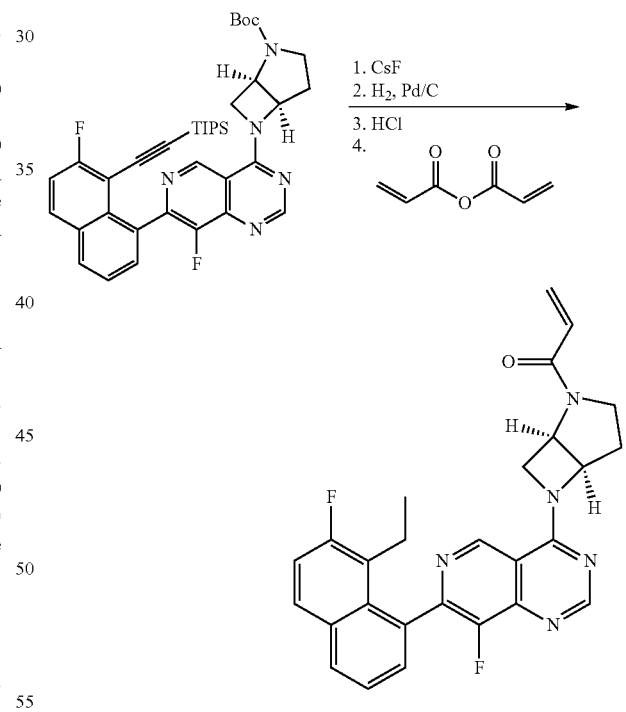

Procedure as Ex 303: White solid; R$_f$=0.30 (dichloromethane/methanol=10/1); HPLC: 97.2% purity; SFC: Chiralpak IC-3 (50×4.6 mm I.D., 3 um), 60% MeOH/40% ACN (0.05% DEA) in CO₂, 3 mL/min, 35° C.; ¹H NMR (400 MHz, CDCl₃): δ 9.04 (s, 1H), 8.92-8.79 (m, 1H), 7.97 (d, J=8.0 Hz, 1H), 7.81 (dd, J=6.0, 8.8 Hz, 1H), 7.57-7.38 (m, 2H), 7.31 (t, J=9.2 Hz, 1H), 6.66-6.31 (m, 2H), 5.82 (br d, J=10.4 Hz, 1H), 5.71-5.45 (m, 1H), 5.23-4.81 (m, 2H), 4.53-4.10 (m, 2H), 4.05-3.69 (m, 1H), 2.83-2.60 (m, 1H), 2.58-2.43 (m, 1H), 2.38-2.10 (m, 2H), 0.92-0.76 (m, 3H); LCMS [ESI, M+1]: 472.2.

Example A

KRas G12C Modification Assay

This Example illustrates a procedure that may be employed to demonstrate that exemplary compounds of the present invention covalently bind to KRas G12C using a LCMS assay to detect a covalent adduct of the exemplary compound and KRAS G12C.

The protein concentration of GDP-loaded K-Ras (1-169) G12C, C51S, C80L, C118S and GTP-loaded K-Ras (1-169) G12C, C51S, C80L, C118S, Q61H is adjusted to 2 µM in K-Ras Assay Buffer (25 mM HEPES, 150 mM NaCl, 5 mM $MgCl_2$, and 10 mM Octyl β-glucopyranoside at pH 7.5). A 10 µL aliquot of each protein solution is then transferred to a 384 well microtiter plate. Initial compound stocks are generated at fifty times their desired final assay concentration in DMSO.

Exemplary compounds of Formula (I) are diluted 25-fold into K-Ras Assay Buffer to a final of two times their final concentration. A 10 µL aliquot of each diluted compound solution is then added to each of the protein solutions in the microtiter plate to initiate reaction. Typical final compound concentrations are 3.0, 5.0 and 25.0 µM. At each time point, the reactions are quenched with 20 µL of a 25 mM acetic acid solution. Usual assay endpoints are 15, 180 and 1440 minutes. Once all reactions are quenched, the plates are heat sealed and the samples were injected into a LC/MS system for data acquisition.

Data collection may take place on an Agilent 6520 Q-TOF Accurate Mass Spectrometer. Samples are injected in their liquid phase onto a C-3 reverse phase column to remove assay buffer and prepare the samples for mass spectrometer. The proteins are eluted from the column using an acetonitrile gradient and fed directly into the mass analyzer. Initial raw data analysis may take place in Agilent MassHunter software immediately post data acquisition.

Raw data analysis of the intact protein is exclusively a deconvolution of the multiple charge states of each protein in solution using a maximum entropy deconvolution provided in Mass Hunter. To minimize complexity, only the data over limited mass ranges are considered for analysis, with a minimum of one Dalton mass step intervals. The heights of all masses identified during raw data analysis are exported to be further analyzed in Spotfire® data analysis software.

Final data analysis is a multistep process in the Spotfire® data analysis software package. Briefly, each protein mass is calculated as a percent of the total signal of that sample, that percentage is then normalized to the percentage of signal of the protein in the absence of reactive compounds. Those normalized signals are reported as normalized percent of control (POC). An increased POC value indicates a compound that displays a higher degree of modification at a given condition compared to other compounds under the same conditions. The exemplary compounds of Formula (I) are tested at 5 µM concentration for 3 hours.

Example B

Inhibition of KRas G12C-Dependent Cell Growth

This Example illustrates that exemplary compounds of the present invention inhibit the growth of tumor cell lines that express KRas G12C.

The cellular inhibition of KRAs G12C by exemplary compounds of the present invention was determined by measuring the amount of a downstream marker of KRas activity, phosphorylated ERK ("Phospho-ERK").

NCI-H358 cells (ATCC CRL-5807) express KRas G12C and were grown in RPMI medium supplemented with 10% fetal bovine serum, penicillin/streptomycin and 10 mM HEPES. Cells were plated in poly-D-Lysine coated 96-well plates at a concentration of 50,000 cells/well and allowed to attach for 8-12 hours. Diluted compounds were then added at a final concentration of 0.5% DMSO. After 3 hours, the medium was removed, 150 µL of 4% formaldehyde was added and the plates were incubated for 20 minutes. The plates were washed with PBS, and permeabilized using 150 µL of ice cold 100% methanol for 10 minutes. Non-specific antibody binding to the plates was blocked using 100 µL Licor Blocking Buffer (Li-Cor Biotechnology, Lincoln Nebr.) for 1 hour at room temperature. Positive control samples and samples lacking cells were parallel processed with test samples as standards.

The amount Phospho-ERK was determined using an antibody specific for the phosphorylated form of ERK and compared to the amount of GAPDH. Primary antibodies used for detection were added as follows: Phospho-ERK (Cell Signaling cs9101) diluted 1:500 and GAPDH (Millipore MAB374) diluted 1:5000 in Licor block+0.05% Tween 20. The plates were incubated for 2 hours at room temperature. The plates were washed with PBS+0.05% Tween 20.

Secondary antibodies used to visualize primary antibodies were added as follows: Anti-rabbit-680 diluted 1:1000 and Anti-mouse-800 diluted 1:1000 in Licor Block+0.05% Tween 20 and incubated for 1 hour at room temperature. The plates were washed with PBS+0.05% Tween 20. A 100 µL aliquot of PBS was added to each well and the plates were read on a LICOR AERIUS plate reader.

The pERK(Thr202/Tyr204) signal was normalized with the GAPDH signal and percent of DMSO control values were calculated. $IC_{50}$ values were generated using a 4 parameter fit of the dose response curve. The results for exemplary compounds of Formula (I) are shown in Table 7.

TABLE 7

Inhibition of KRas G12C-mediated Cell Proliferation by Exemplary Compounds

| Example No. | $IC_{50}$ |
|---|---|
| 1 | 1917 |
| 2 | 325 |
| 3 | 16000 |
| 4 | 3430 |
| 5 | 45 |
| 6 | 300 |
| 7 | 7 |
| 8 | 132 |
| 9 | 142 |
| 10 | 2 |
| 11 | 84 |
| 12 | 31 |
| 13 | 127 |
| 14 | 119 |
| 15 | 50 |
| 16 | 118 |
| 17 | 59 |
| 18 | 50 |
| 19 | 2 |
| 20 | 3 |
| 21 | 105 |
| 22 | 38 |
| 23 | 18 |
| 24 | 109 |
| 25 | 13 |

TABLE 7-continued

Inhibition of KRas G12C-mediated Cell Proliferation by Exemplary Compounds

| Example No. | IC$_{50}$ |
|---|---|
| 26 | 55 |
| 27 | 30 |
| 28 | 260 |
| 29 | 85 |
| 30 | 131 |
| 31 | 33 |
| 32 | 137 |
| 33 | 79 |
| 34 | 45 |
| 35 | 27 |
| 36 | 44 |
| 37 | 168 |
| 38 | 338 |
| 39 | 544 |
| 40 | 496 |
| 41 | 216 |
| 42 | 18 |
| 43 | 4 |
| 44 | 15 |
| 45 | 205 |
| 46 | 94 |
| 47 | 30 |
| 48 | 270 |
| 49 | 62 |
| 50 | 53 |
| 51 | 19 |
| 52 | 23 |
| 53 | 17 |
| 54 | 14 |
| 55 | 90 |
| 56 | 28 |
| 57 | 58 |
| 58 | 330 |
| 59 | 60 |
| 60 | 127 |
| 61 | 70 |
| 62 | 18 |
| 63 | 2845 |
| 64 | 376 |
| 65 | 36 |
| 66 | 12 |
| 67 | 21 |
| 68 | 86 |
| 69 | 58 |
| 70 | 456 |
| 71 | 13 |
| 72 | 31 |
| 73 | 593 |
| 74 | 1352 |
| 75 | 1186 |
| 76 | 3000 |
| 77 | 2 |
| 78 | 13 |
| 79 | 675 |
| 80 | 2522 |
| 81 | 1101 |
| 82 | 618 |
| 83 | 3500 |
| 84 | 765 |
| 85 | 519 |
| 86 | 14 |
| 87 | 4376 |
| 88 | 77 |
| 89 | 28 |
| 90 | 26 |
| 91 | 29 |
| 92 | 11 |
| 93 | 366 |
| 94 | 360 |
| 95 | 14 |
| 96 | 200 |
| 97 | 2519 |
| 98 | 10000 |
| 99 | 444 |
| 100 | 10000 |
| 101 | 43 |
| 102 | 12 |
| 103 | 10000 |
| 104 | 699 |
| 105 | 10000 |
| 106 | 1541 |
| 107 | 156 |
| 108 | 37 |
| 109 | 21 |
| 110 | 725 |
| 111 | 3918 |
| 112 | 218 |
| 113 | 13 |
| 114 | 2 |
| 115 | 76 |
| 116 | 31 |
| 117 | 18 |
| 118 | 329 |
| 119 | 39 |
| 120 | 976 |
| 121 | 63 |
| 122 | 32 |
| 123 | 3963 |
| 124 | 1766 |
| 125 | 42 |
| 126 | 15 |
| 127 | 243 |
| 128 | 15 |
| 129 | 73 |
| 130 | 26 |
| 131 | 10000 |
| 132 | 145 |
| 133 | 10000 |
| 134 | 10000 |
| 135 | 6050 |
| 136 | 92 |
| 137 | 3350 |
| 138 | 7171 |
| 139 | 37 |
| 140 | 14 |
| 141 | 50 |
| 142 | 1251 |
| 143 | 13 |
| 144 | 35 |
| 145 | 2 |
| 146 | 10000 |
| 147 | 23 |
| 148 | 6283 |
| 149 | 10000 |
| 150 | 10000 |
| 151 | 256 |
| 152 | 322 |
| 153 | 10000 |
| 154 | 221 |
| 155 | 585 |
| 156 | 134 |
| 157 | 23 |
| 158 | 68 |
| 159 | 10000 |
| 160 | 10000 |
| 161 | 11 |
| 162 | 590 |
| 163 | 110 |
| 164 | 153 |
| 165 | 158 |
| 166 | 26 |
| 167 | 60 |
| 168 | 65 |
| 169 | 60 |
| 170 | 19 |

TABLE 7-continued

Inhibition of KRas G12C-mediated Cell Proliferation by Exemplary Compounds

| Example No. | IC$_{50}$ |
|---|---|
| 171 | 22 |
| 172 | 18 |
| 173 | 31 |
| 174 | 20 |
| 175 | 134 |
| 176 | 30 |
| 177 | 51 |
| 178 | 63 |
| 179 | 224 |
| 180 | 362 |
| 181 | 4 |
| 182 | 27 |
| 183 | 10000 |
| 184 | 10000 |
| 185 | 145 |
| 186 | 10000 |
| 187 | 74 |
| 188 | 29 |
| 189 | 10000 |
| 190 | 10000 |
| 191 | 15 |
| 192 | 38 |
| 193 | 67 |
| 194 | 64 |
| 195 | 31 |
| 196 | 1727 |
| 197 | 165 |
| 198 | 8000 |
| 199 | 3396 |
| 200 | 410 |
| 201 | 10000 |
| 202 | 10000 |
| 203 | 10000 |
| 204 | 10000 |
| 205 | 10000 |
| 206 | 1685 |
| 207 | 6847 |
| 208 | 4 |
| 209 | 46 |
| 210 | 49 |
| 211 | 2 |
| 212 | 7 |
| 213 | 62 |
| 214 | 2108 |
| 215 | 31 |
| 216 | 121 |
| 217 | 11 |
| 218 | 711 |
| 219 | 538 |
| 220 | 22 |
| 221 | 1931 |
| 222 | 10000 |
| 223 | 10000 |
| 224 | 10000 |
| 225 | 4927 |
| 226 | 10000 |
| 227 | 5 |
| 228 | 230 |
| 229 | 1 |
| 230 | 1848 |
| 231 | 4283 |
| 232 | 10000 |
| 233 | 10000 |
| 234 | 10000 |
| 235 | 10000 |
| 236 | 10000 |
| 237 | 230 |
| 238 | 379 |
| 239 | 5 |
| 240 | 10000 |
| 241 | 111 |
| 242 | 187 |
| 243 | 1205 |
| 244 | 88 |
| 245 | 4044 |
| 246 | 6470 |
| 247 | 105 |
| 248 | 993 |
| 249 | 1248 |
| 250 | 91 |
| 251 | 799 |
| 252 | 29 |
| 253 | 35 |
| 254 | 2163 |
| 255 | 10000 |
| 256 | 10000 |
| 257 | 10000 |
| 258 | 10000 |
| 259 | 9000 |
| 260 | 10000 |
| 261 | 486 |
| 262 | 114 |
| 263 | 1142 |
| 264 | 20 |
| 265 | 1491 |
| 266 | 10000 |
| 267 | 330 |
| 268 | 1130 |
| 269 | 4490 |
| 270 | 3781 |
| 271 | 1067 |
| 272 | 1467 |
| 273 | 16 |
| 274 | 10000 |
| 275 | 10000 |
| 276 | 6613 |
| 277 | 553 |
| 278 | 10000 |
| 279 | 408 |
| 280 | 90 |
| 281 | 2340 |
| 282 | 287 |
| 283 | 2430 |
| 284 | 557 |
| 285 | 782 |
| 286 | |
| 287 | |
| 288 | 15 |
| 289 | 40 |
| 290 | 30 |
| 291 | 2 |
| 292 | 20 |
| 293 | 65 |
| 294 | 2152 |
| 295 | 418 |
| 296 | 23 |
| 297 | 4 |
| 298 | 24 |
| 299 | 1332 |
| 300 | 235 |
| 301 | 10000 |
| 302 | 10000 |
| 303 | 714 |
| 304 | 456 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:
1. A compound, wherein the compound is:
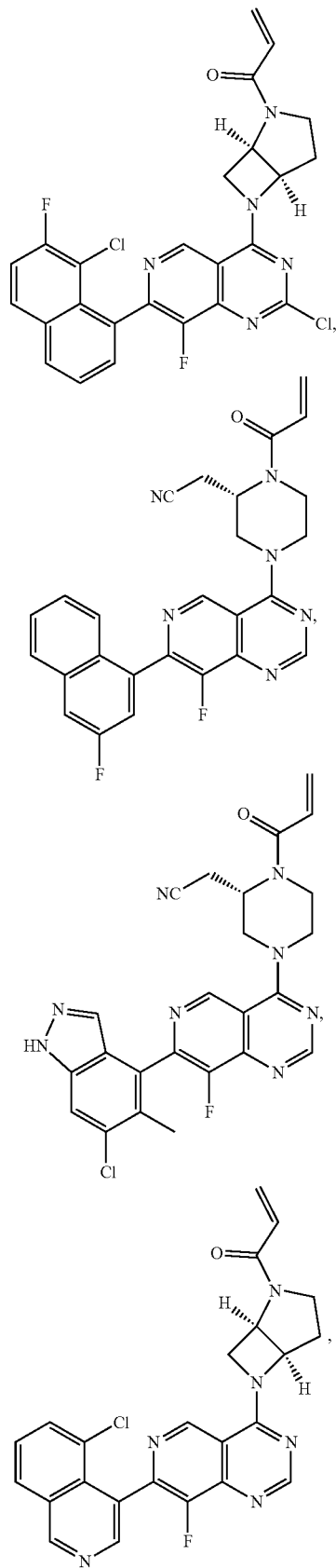
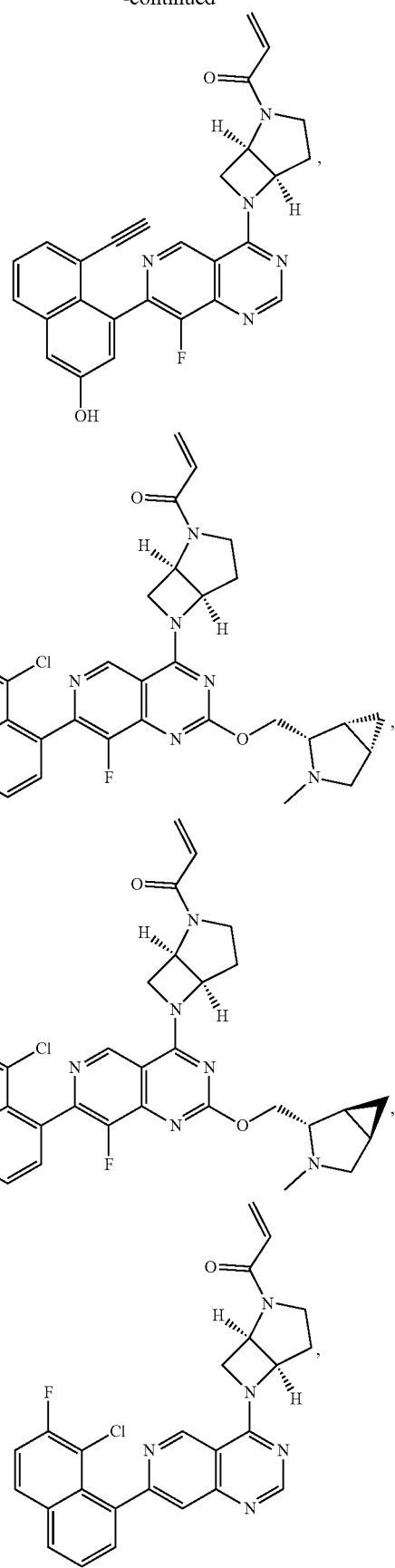

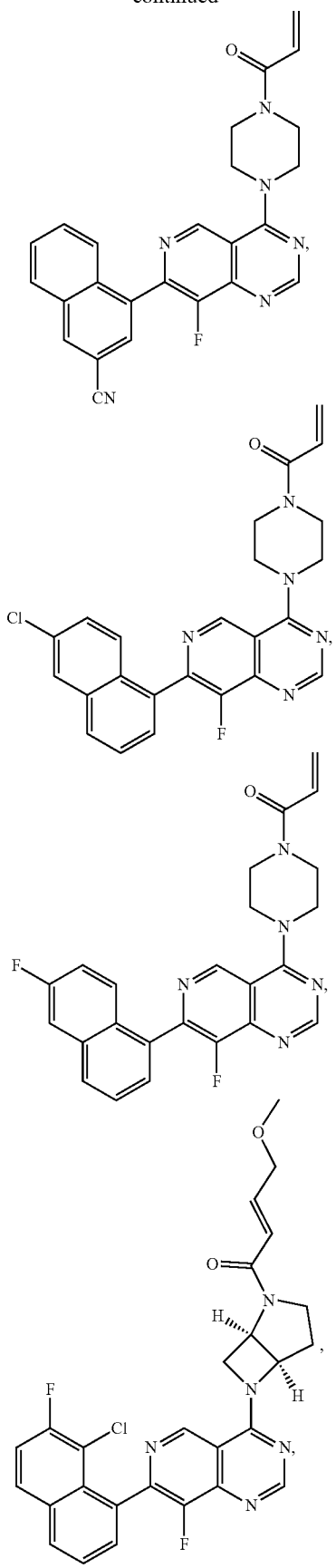
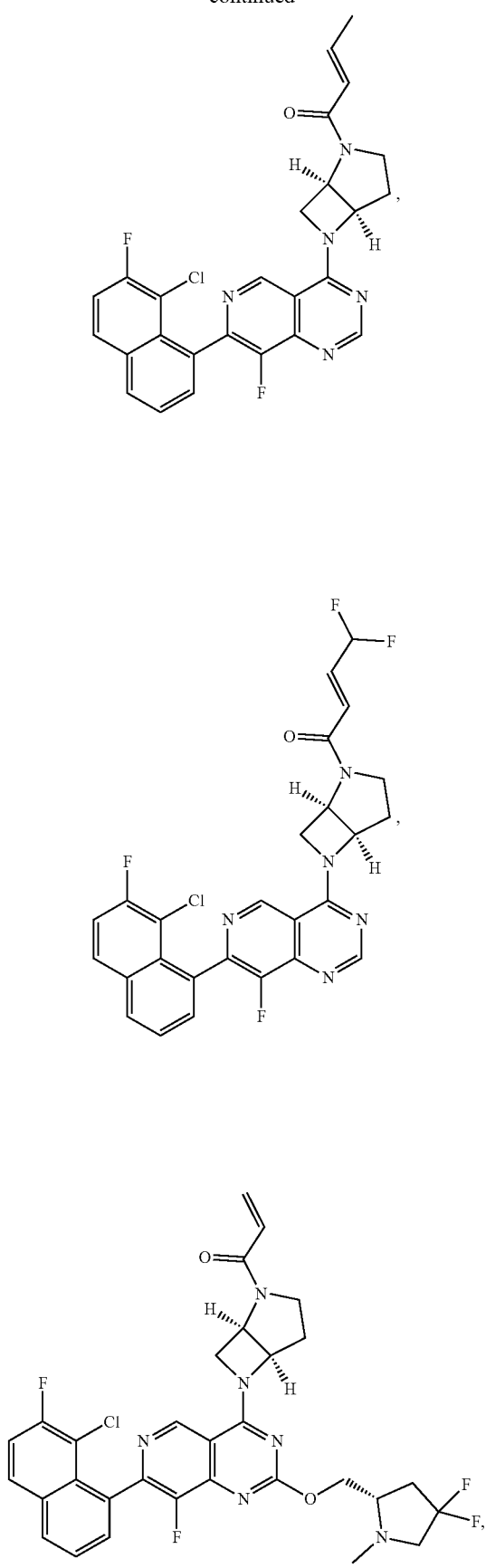

779
-continued
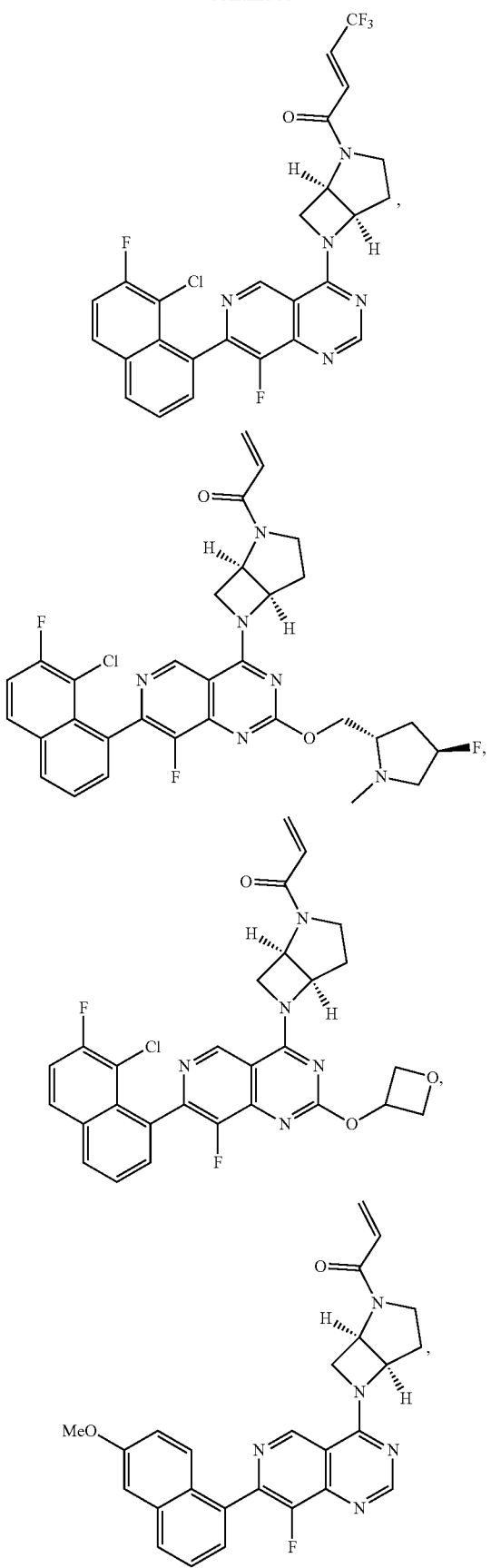
780
-continued
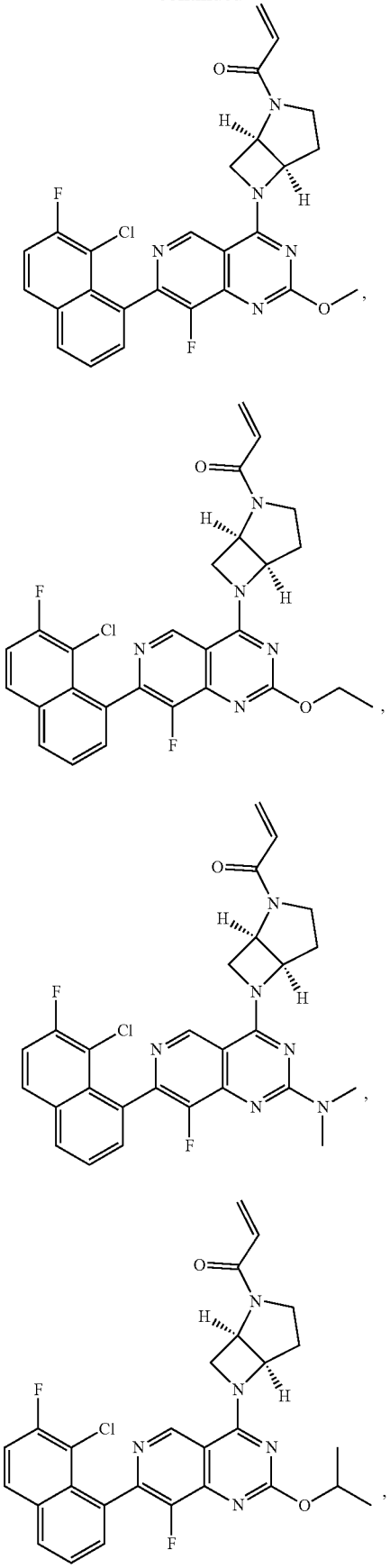

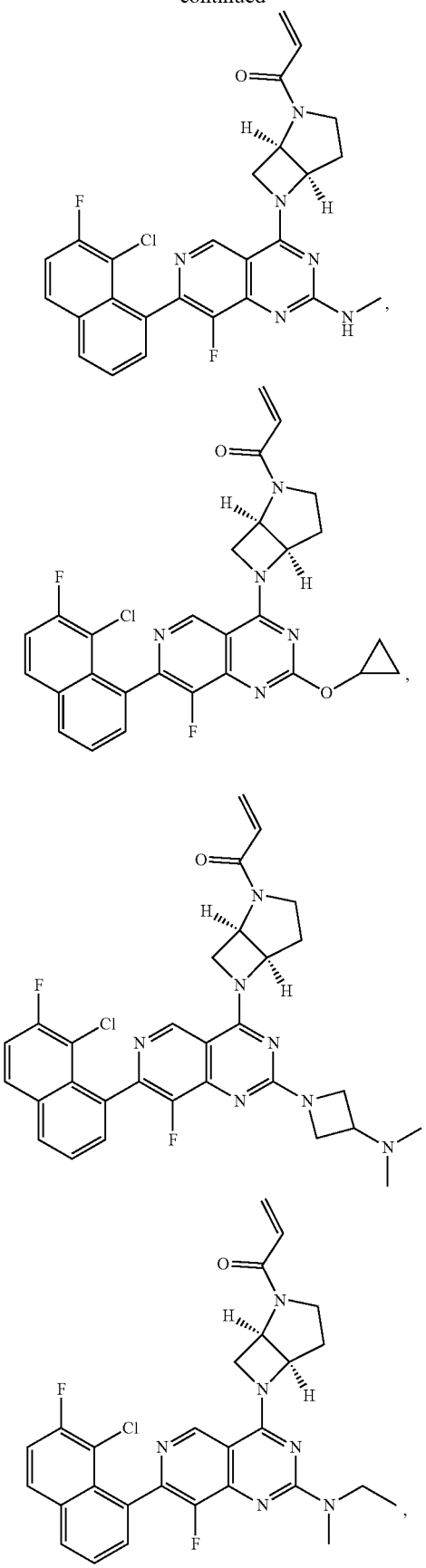
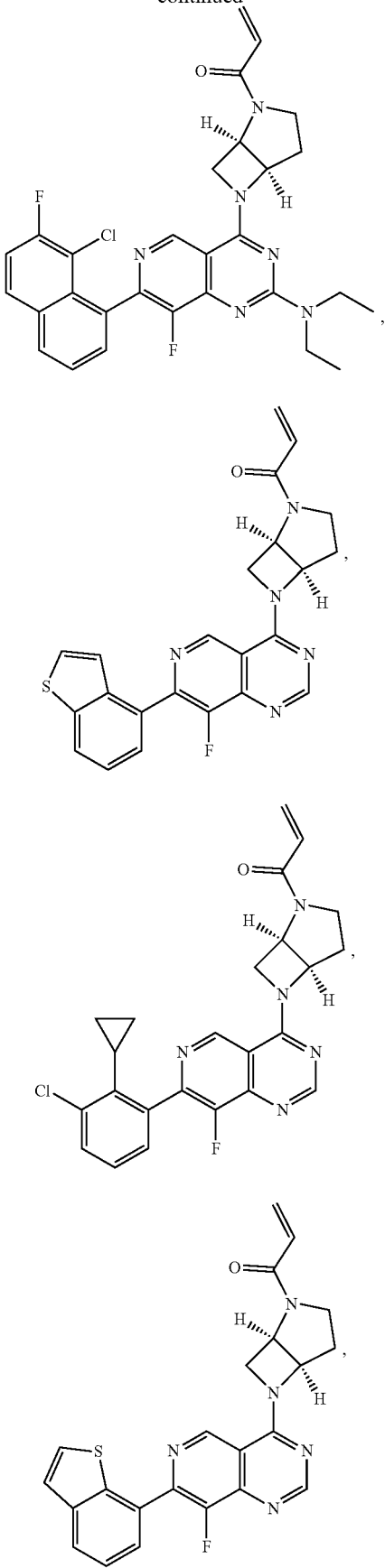

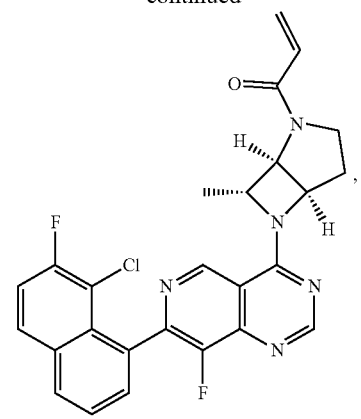
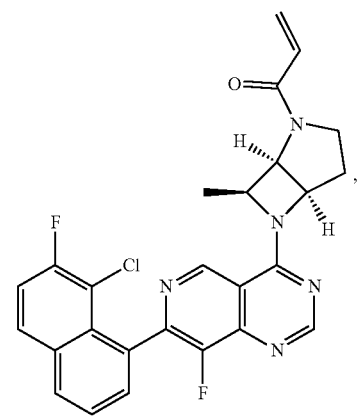
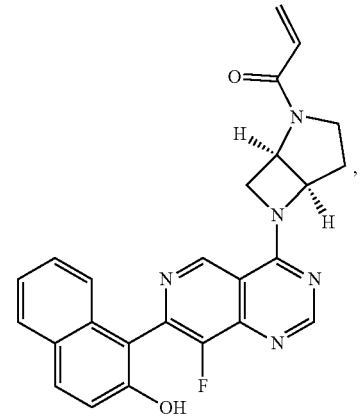
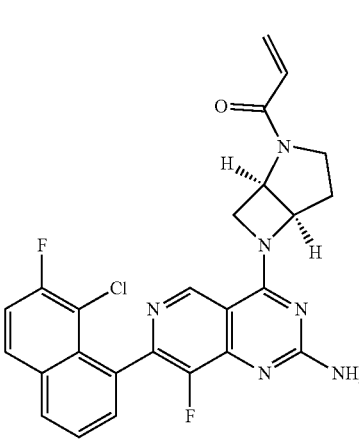
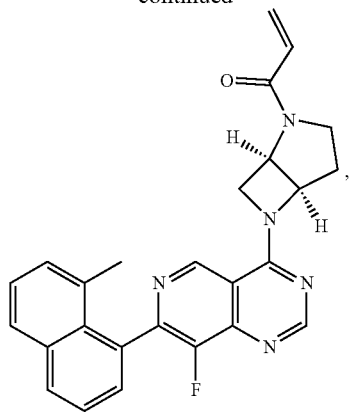
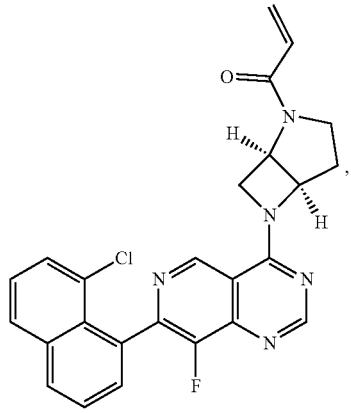
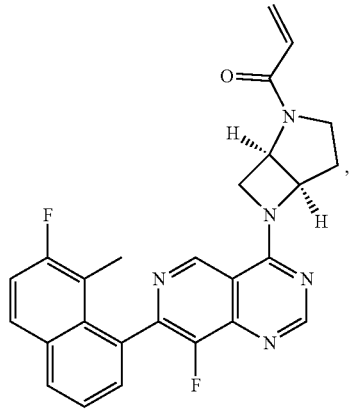
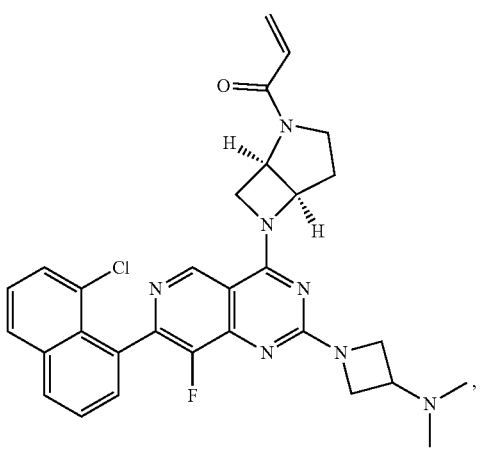

785
-continued
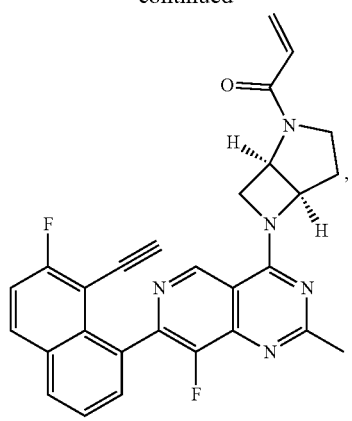
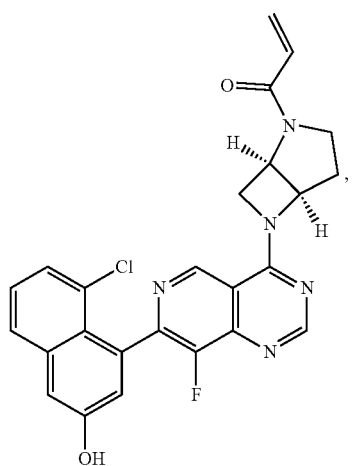
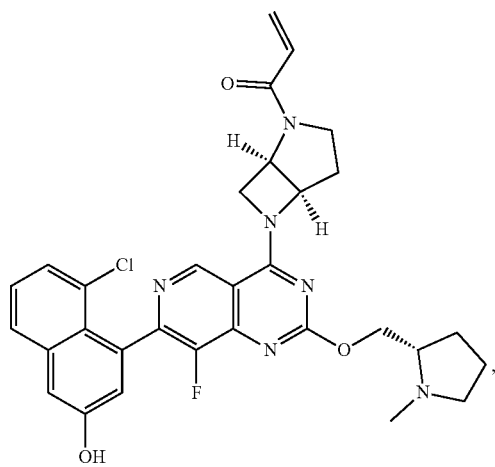
786
-continued
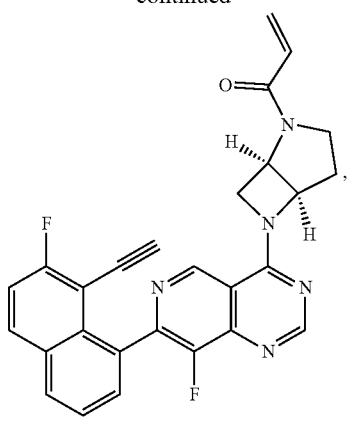
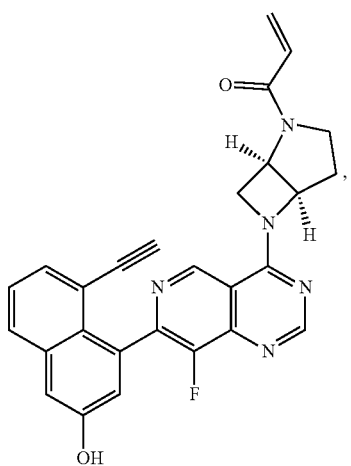
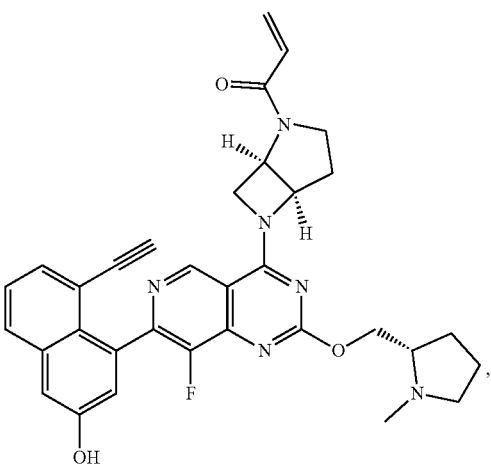

787
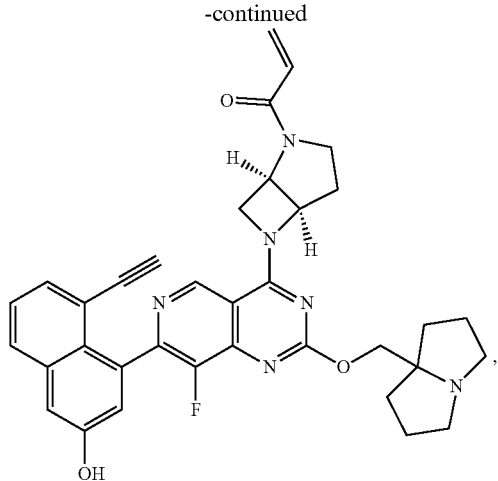
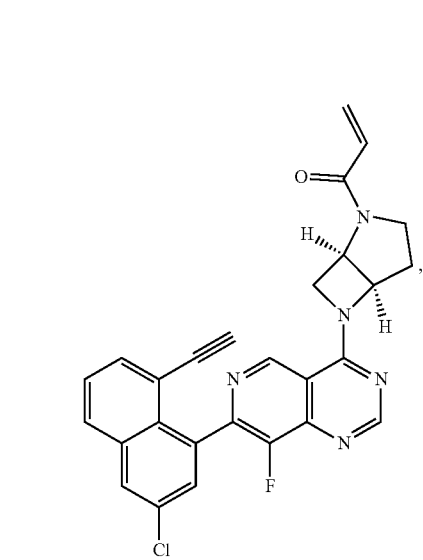
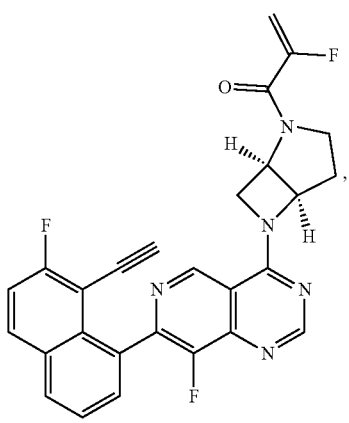
788
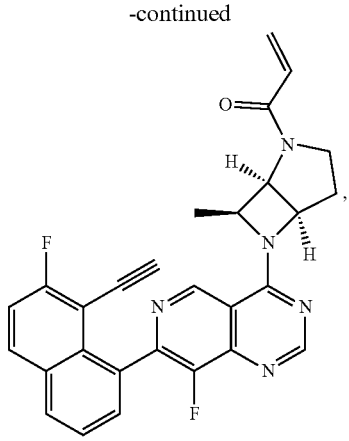
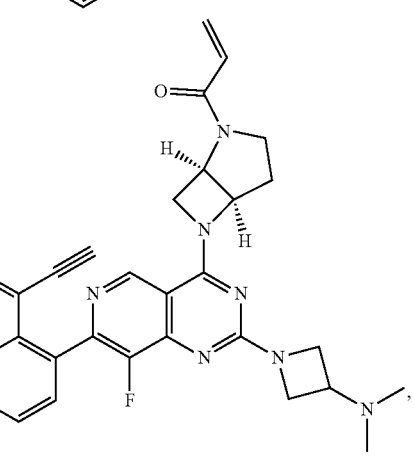
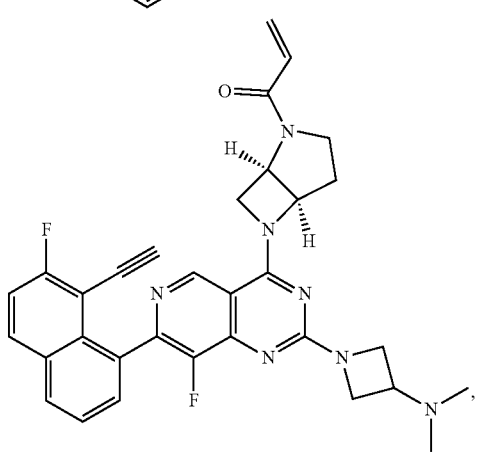
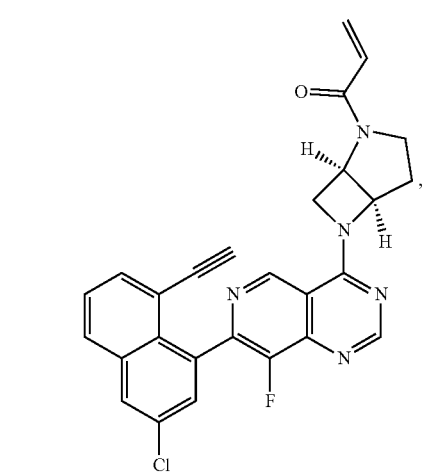

-continued

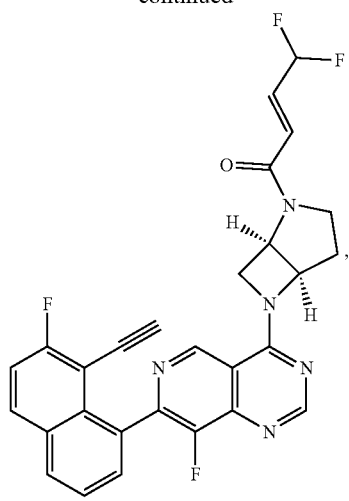

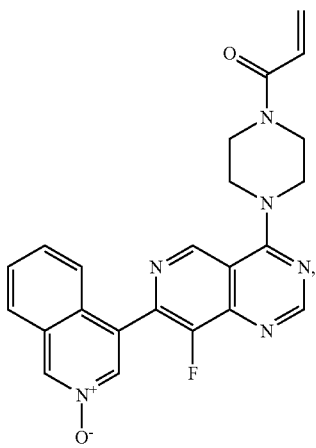

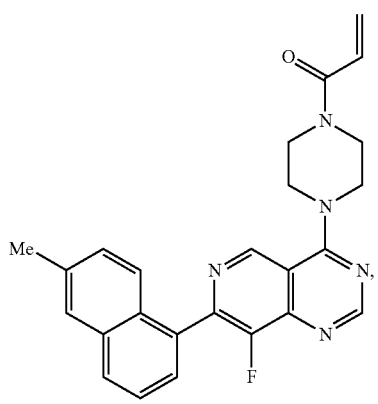

-continued

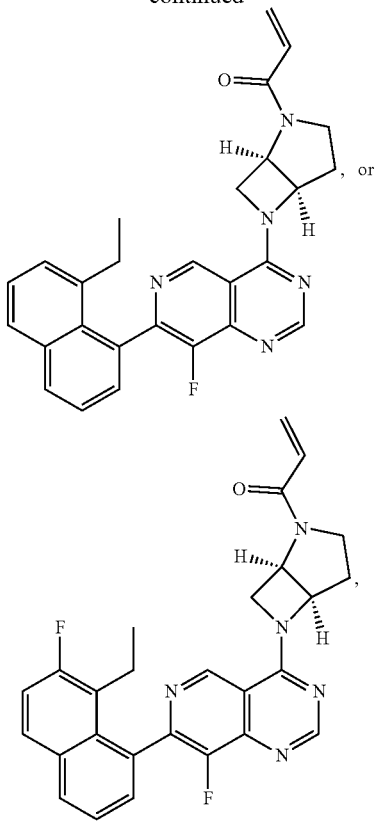

or a pharmaceutically acceptable salt thereof.

2. A pharmaceutical composition, comprising a therapeutically effective amount of a compound of claim 1, and a pharmaceutically acceptable excipient.

3. A method for inhibiting KRas G12C activity in a cell, comprising contacting the cell in which inhibition of KRas G12C activity is desired with an effective amount of a compound of claim 1, pharmaceutically acceptable salts thereof or pharmaceutical compositions containing the compound of claim 1, or pharmaceutically acceptable salt thereof.

4. A method for treating a KRas G12C-associated cancer comprising administering to a patient having a KRas G12C-associated cancer a therapeutically effective amount of a compound of claim 1, or a pharmaceutically acceptable salt thereof, alone or combined with a pharmaceutically acceptable carrier, excipient or diluents.

5. The method of claim 4, wherein the therapeutically effective amount of the compound is between about 0.01 to 100 mg/kg per day.

6. The method of claim 4, wherein the therapeutically effective amount of the compound is between about 0.1 to 50 mg/kg per day.

7. The method of claim 4, wherein the KRas G12C-associated cancer is selected from the group consisting of Cardiac: sarcoma selected from angiosarcoma, fibrosarcoma, rhabdomyosarcoma, and liposarcoma, myxoma, rhabdomyoma, fibroma, lipoma and teratoma; Lung: bronchogenic carcinoma selected from squamous cell, undifferentiated small cell, undifferentiated large cell, and adenocarcinoma, alveolar carcinoma, bronchiolar carcinoma, bronchial adenoma, sarcoma, lymphoma, chondromatous hamartoma, mesothelioma, and non-small cell lung cancer; Gastrointestinal: esophagus selected from squamous cell carcinoma, adenocarcinoma, leiomyosarcoma, and lymphoma, stomach selected from carcinoma, lymphoma, and leiomyosarcoma, pancreas selected from ductal adenocarcinoma, insulinoma, glucagonoma, gastrinoma, carcinoid tumors, and vipoma, small bowel selected from adenocarcinoma, lymphoma, carcinoid tumors, Kaposi's sarcoma, leiomyoma, hemangioma, lipoma, neurofibroma, and fibroma, large bowel selected from adenocarcinoma, tubular adenoma, villous adenoma, hamartoma, and leiomyoma; Genitourinary tract: kidney selected from adenocarcinoma, Wilm's tumor (nephroblastoma), lymphoma, and leukemia, bladder and urethra selected from squamous cell carcinoma, transitional cell carcinoma, and adenocarcinoma, prostate selected from adenocarcinoma and sarcoma, testis selected from seminoma, teratoma, embryonal carcinoma, teratocarcinoma, choriocarcinoma, sarcoma, interstitial cell carcinoma, fibroma, fibroadenoma, adenomatoid tumors, and lipoma; Liver: hepatoma, cholangiocarcinoma, hepatoblastoma, angiosarcoma, hepatocellular adenoma, and hemangioma; Biliary tract: gall bladder carcinoma, ampullary carcinoma, cholangiocarcinoma; Bone: osteogenic sarcoma, fibrosarcoma, malignant fibrous histiocytoma, chondrosarcoma, Ewing's sarcoma, malignant lymphoma, multiple myeloma, malignant giant cell tumor chordoma, osteochondroma, benign chondroma, chondroblastoma, chondromyxofibroma, osteoid osteoma and giant cell tumors; Nervous system: skull selected from osteoma, hemangioma, granuloma, xanthoma, and osteitis deformans, meninges selected from meningioma, meningiosarcoma and gliomatosis, brain selected from astrocytoma, medulloblastoma, glioma, ependymoma, germinoma, glioblastoma multiform, oligodendroglioma, schwannoma, retinoblastoma, congenital tumors and spinal cord neurofibroma; Gynecological: uterus selected from endometrial carcinoma, granulosa-thecal cell tumors, Sertoli-Leydig cell tumors, dysgerminoma, and malignant teratoma, vulva selected from squamous cell carcinoma, intraepithelial carcinoma, adenocarcinoma, fibrosarcoma, and melanoma, vagina selected from clear cell carcinoma, squamous cell carcinoma, botryoid sarcoma, fallopian tubes; Hematologic: blood selected from myeloid leukemia, acute lymphoblastic leukemia, chronic lymphocytic leukemia, myeloproliferative diseases, multiple myeloma, and myelodysplastic syndrome, Hodgkin's disease, non-Hodgkin's lymphoma; Skin: malignant melanoma, basal cell carcinoma, squamous cell carcinoma, Kaposi's sarcoma, moles dysplastic nevi, lipoma, angioma, dermatofibroma; and Adrenal glands: neuroblastoma.

8. The method of claim 7, wherein the cancer is non-small cell lung cancer.

9. A method for treating cancer in a patient in need thereof, the method comprising (a) determining that the cancer is associated with a KRas G12C mutation; and (b) administering to the patient a therapeutically effective amount of a compound of claim 1 or a pharmaceutically acceptable salt thereof, or a pharmaceutical composition thereof.

\* \* \* \* \*